(12) United States Patent
Wang et al.

(10) Patent No.: US 10,927,092 B2
(45) Date of Patent: *Feb. 23, 2021

(54) GLUCOSYLCERAMIDE SYNTHASE INHIBITORS FOR THE TREATMENT OF DISEASES

(71) Applicant: BioMarin Pharmaceutical Inc., Novato, CA (US)

(72) Inventors: Bing Wang, San Jose, CA (US); Daniel Chu, Santa Clara, CA (US); Alexander James Bridges, Saline, MI (US)

(*) Notice: Subject to any disclaimer, the term of this patent is extended or adjusted under 35 U.S.C. 154(b) by 7 days.

This patent is subject to a terminal disclaimer.

(21) Appl. No.: 16/264,505

(22) Filed: Jan. 31, 2019

(65) Prior Publication Data

US 2019/0263775 A1 Aug. 29, 2019

Related U.S. Application Data

(63) Continuation of application No. 15/023,337, filed as application No. PCT/US2014/056555 on Sep. 19, 2014, now Pat. No. 10,227,323.

(Continued)

(51) Int. Cl.

| | | |
|---|---|---|
| *C07D 213/10* | (2006.01) |
| *C07D 307/78* | (2006.01) |
| *C07D 319/14* | (2006.01) |
| *C07D 319/18* | (2006.01) |
| *C07D 405/14* | (2006.01) |
| *C07D 309/10* | (2006.01) |
| *C07D 311/12* | (2006.01) |
| *C07D 333/16* | (2006.01) |
| *C07D 231/56* | (2006.01) |
| *C07D 333/62* | (2006.01) |
| *C07D 235/06* | (2006.01) |
| *C07D 405/12* | (2006.01) |
| *C07D 407/12* | (2006.01) |
| *C07D 409/12* | (2006.01) |
| *C07D 413/12* | (2006.01) |
| *C07D 417/12* | (2006.01) |
| *C07D 205/04* | (2006.01) |
| *C07D 265/30* | (2006.01) |
| *C07D 277/22* | (2006.01) |
| *C07D 209/04* | (2006.01) |
| *C07D 277/62* | (2006.01) |
| *C07D 295/12* | (2006.01) |
| *C07D 213/46* | (2006.01) |
| *C07D 213/64* | (2006.01) |
| *C07D 307/79* | (2006.01) |
| *C07B 59/00* | (2006.01) |

(Continued)

(52) U.S. Cl.
CPC .......... *C07D 319/18* (2013.01); *C07B 59/002* (2013.01); *C07D 205/04* (2013.01); *C07D 209/04* (2013.01); *C07D 211/46* (2013.01); *C07D 213/46* (2013.01); *C07D 213/56* (2013.01); *C07D 213/61* (2013.01); *C07D 213/64* (2013.01); *C07D 215/06* (2013.01); *C07D 231/56* (2013.01); *C07D 235/06* (2013.01); *C07D 235/08* (2013.01); *C07D 265/30* (2013.01); *C07D 277/22* (2013.01); *C07D 277/30* (2013.01); *C07D 277/62* (2013.01); *C07D 295/12* (2013.01); *C07D 295/13* (2013.01); *C07D 305/08* (2013.01); *C07D 307/79* (2013.01); *C07D 307/81* (2013.01); *C07D 309/10* (2013.01); *C07D 309/12* (2013.01); *C07D 311/12* (2013.01); *C07D 311/58* (2013.01); *C07D 333/16* (2013.01); *C07D 333/24* (2013.01); *C07D 333/60* (2013.01); *C07D 333/62* (2013.01); *C07D 405/06* (2013.01); *C07D 405/12* (2013.01); *C07D 405/14* (2013.01); *C07D 407/12* (2013.01); *C07D 409/12* (2013.01); *C07D 413/12* (2013.01); *C07D 417/12* (2013.01); *C07D 471/04* (2013.01); *C07D 471/08* (2013.01); *C07D 487/08* (2013.01); *C07D 491/056* (2013.01); *C07B 2200/05* (2013.01); *C07B 2200/07* (2013.01)

(58) Field of Classification Search
CPC ... C07D 231/10; C07D 307/78; C07D 319/14
See application file for complete search history.

(56) References Cited

U.S. PATENT DOCUMENTS 6,407,064 B2 6/2002 Masuda et al.
6,835,831 B2 12/2004 Hirth
(Continued)

FOREIGN PATENT DOCUMENTS

CN 101888840 A 11/2010
EP 0782992 B1 7/1997
(Continued)

OTHER PUBLICATIONS

Jimbo et al., "Development of a New Inhibitor of Glucosylceramide Synthase," Journal of Biochemistry, vol. 127, 485-491, 2000.
(Continued)

*Primary Examiner* — Samira J Jean-Louis
(74) *Attorney, Agent, or Firm* — Jun He Law Offices P.C.; James J. Zhu

(57) ABSTRACT

Described herein are compounds of Formula I, methods of making such compounds, pharmaceutical compositions and medicaments containing such compounds, and methods of using such compounds to treat or prevent diseases or conditions associated with the enzyme glucosylceramide synthase (GCS).

14 Claims, No Drawings

Related U.S. Application Data

(60) Provisional application No. 61/880,752, filed on Sep. 20, 2013.

(51) Int. Cl.

| | | |
|---|---|---|
| C07D 211/46 | (2006.01) |
| C07D 213/56 | (2006.01) |
| C07D 213/61 | (2006.01) |
| C07D 215/06 | (2006.01) |
| C07D 235/08 | (2006.01) |
| C07D 277/30 | (2006.01) |
| C07D 295/13 | (2006.01) |
| C07D 305/08 | (2006.01) |
| C07D 307/81 | (2006.01) |
| C07D 309/12 | (2006.01) |
| C07D 311/58 | (2006.01) |
| C07D 333/24 | (2006.01) |
| C07D 333/60 | (2006.01) |
| C07D 405/06 | (2006.01) |
| C07D 471/04 | (2006.01) |
| C07D 471/08 | (2006.01) |
| C07D 487/08 | (2006.01) |
| C07D 491/056 | (2006.01) |

(56) References Cited

U.S. PATENT DOCUMENTS

| | | |
|---|---|---|
| 7,041,831 B2 | 5/2006 | Hirth |
| 7,265,228 B2 | 9/2007 | Hirth et al. |
| 7,763,738 B2 | 7/2010 | Hirth et al. |
| 8,304,447 B2 | 11/2012 | Siegel et al. |
| 8,389,517 B2 | 3/2013 | Ibraghimov-Beskrovnaya et al. |
| 10,227,323 B2 | 3/2019 | Wang et al. |
| 2010/0256216 A1 | 10/2010 | Siegel et al. |
| 2012/0322787 A1 | 12/2012 | Siegel et al. |
| 2013/0095089 A1 | 4/2013 | Larsen et al. |
| 2016/0229830 A1 | 8/2016 | Wang et al. |

FOREIGN PATENT DOCUMENTS

| | | |
|---|---|---|
| EP | 1106609 B1 | 6/2001 |
| JP | 10324671 B2 | 12/1998 |
| JP | 10338636 B2 | 12/1998 |
| JP | 2010540638 A | 12/2010 |
| JP | 2011529500 A | 12/2011 |
| JP | 2012504608 A | 2/2012 |
| WO | 96/39137 A1 | 12/1996 |
| WO | 99/64035 A1 | 12/1999 |
| WO | 00/67746 A1 | 11/2000 |
| WO | 02/080920 A1 | 10/2002 |
| WO | 03/008399 A1 | 1/2003 |
| WO | 03/045928 A1 | 6/2003 |
| WO | 03/057874 A1 | 7/2003 |
| WO | 2004/080960 A2 | 9/2004 |
| WO | 2005/068426 A1 | 7/2005 |
| WO | 2006/053043 A2 | 5/2006 |
| WO | 2006/081252 A2 | 8/2006 |
| WO | 2006/081276 A1 | 8/2006 |
| WO | 2007/134086 A2 | 11/2007 |
| WO | 2008/011483 A2 | 1/2008 |
| WO | 2008/011487 A2 | 1/2008 |
| WO | 2008/012555 A2 | 1/2008 |
| WO | 2008/109286 A1 | 9/2008 |
| WO | 2008/150486 A2 | 12/2008 |
| WO | 2009/011880 A2 | 1/2009 |
| WO | 2009/045503 A1 | 4/2009 |
| WO | 2009/058216 A1 | 5/2009 |
| WO | 2009/117150 A2 | 9/2009 |
| WO | 2010/014554 A1 | 2/2010 |
| WO | 2010/035032 A1 | 4/2010 |
| WO | 2010/039256 A1 | 4/2010 |
| WO | 2013/059119 A1 | 4/2013 |
| WO | 2014/150043 A1 | 9/2014 |

OTHER PUBLICATIONS

Husain at al., "Syn-Selective additions to Garner aldehyde: synthesis of a potent glucosylceramide synthase inhibitor," Tetrahedron Letters, vol. 43, 8621-8623, 2002.

Larsen at al., "Property-based design of a glucosylceramide synthase inhibitor that reduces glucosylceramide in the brain," Journal of Lipid Research, vol. 53, 282-290, 2012.

GLUCOSYLCERAMIDE SYNTHASE INHIBITORS FOR THE TREATMENT OF DISEASES

CROSS REFERENCE

The present application is a continuation of U.S. application Ser. No. 15/023,337, filed Mar. 18, 2016, which is a U.S. National Stage filing under 35 U.S.C. § 371 of International Application No. PCT/US2014/056555, filed Sep. 19, 2014, which claims the benefit of priority of U.S. Provisional Application No. 61/880,752, filed Sep. 20, 2013, the contents of each of which applications are incorporated herein by reference in their entireties.

FIELD

Described herein are compounds, methods of making such compounds, pharmaceutical compositions and medicaments containing such compounds, and methods of using such compounds to treat or prevent diseases or conditions associated with the enzyme glucosylceramide synthase (GCS).

BACKGROUND

Glucosylceramide synthase (GCS) is a key enzyme which catalyzes the initial glycosylation step in the biosynthesis of glucosylceramide-based glycosphingolipids (GSLs) namely via the transfer of glucose from UDP-glucose (UDP-Glc) to ceramide to form glucosylceramide. GCS is a transmembrane, type III integral protein localized in the cis/medial golgi. Glycosphingolipids (GSLs) are believed to be integral in many cell membrane events, including cellular interactions, signaling, and trafficking. Synthesis of GSL structures has been shown (*Proc. Natl. Acad. Sci USA* 1999, 96(16), 9142-9147) to be essential for embryonic development and for the differentiation of some tissues. Ceramide plays a central role in sphingolipid metabolism, and downregulation of GCS activity has been shown to have marked effects on the sphingolipid pattern with diminished expression of glycosphingolipids. Sphingolipids have a role in physiological as well as pathological cardiovascular conditions. In particular, sphingolipids and their regulating enzymes appear to play a role in adaptive responses to chronic hypoxia in the neonatal rat heart (*Prostaglandins & Other Lipid Mediators* 2005, 78(1-4), 249-263).

GCS inhibitors have been proposed for the treatment of a variety of diseases (see, for example, WO2005068426). Such diseases include glycolipid storage diseases (e.g., Tay Sachs, Sandhoffs, GM1 gangliosidosis and Fabry diseases), diseases associated with glycolipid accumulation (e.g., Gaucher disease), diseases that cause renal hypertrophy or hyperplasia such as diabetic nephropathy, diseases that cause hyperglycemia or hyperinsulinemia, cancers in which glycolipid synthesis is abnormal, infectious diseases caused by organisms which use cell surface glycolipids as receptors, infectious diseases in which synthesis of glucosylceramide is essential or important, diseases in which excessive glycolipid synthesis occurs (e.g., atherosclerosis, polycystic kidney disease, and renal hypertrophy), neuronal disorders, neuronal injury, inflammatory diseases or disorders associated with macrophage recruitment and activation (e.g., rheumatoid arthritis, Crohn's disease, asthma and sepsis), pain (see WO2008011483—neuropathic pain, inflammatory pain, headache pain, somatic pain, visceral pain, referred pain), cognitive disorders (see WO2008/109286—agnosia; amnesia; aphasia; an apraxia; delirium; dementia including AIDS dementia complex, Binswanger's disease, dementia with Lewy Bodies, frontotemporal dementia, mild cognitive impairment, multi-infarct dementia, Pick's disease, semantic dementia, senile dementia, and vascular dementia; and learning disorders including Asperger's syndrome, attention deficit disorder, attention deficit hyperactivity disorder, autism, childhood disintegrative disorder, and Rett syndrome), neurodegenerative disorders (such as Alzheimer's disease, corticobasal degeneration, Creutzfeldt-Jacob disease, frontotemporal lobar degeneration, Huntington disease, multiple sclerosis, normal pressure hydrocephalus, organic chronic brain syndrome, Parkinson's disease, Pick disease, progressive supranuclear palsy, and senile dementia (Alzheimer type), glomerular disease, and diabetes mellitus and obesity (see WO 2006053043). Renal hypertrophy induced by diabetes is associated with enhanced synthesis of glycosphingolipids such as glucosylceramide and ganglioside GM3 which accumulate in the kidney of rats (*J. Clin. Invest.* 1993, 91(3), 797).

It has been shown that overexpression of GCS is implicated in multi-drug resistance and disrupts ceramide-induced apoptosis. For example, Turzanski et al. (*Experimental Hematology* 2005, 33(1), 62-72) have shown that ceramide induces apoptosis in acute myeloid leukemia (AML) cells and that P-glycoprotein (p-gp) confers resistance to ceramide-induced apoptosis, with modulation of the ceramide-glucosylceramide pathway making a marked contribution to this resistance in TF-I cells. Thus, GCS inhibitors can be useful for treatment of proliferative disorders (such as cancer) by inducing apoptosis in diseased cells.

Sandhoff (or type 2 GM2 gangliosidosis) is caused by a deficiency in (3-hexosaminidase A and B activity which leads to an accumulation of the ganglioside GM2 and other glycolipids causing damage to the central nervous system and eventually is lethal (*PLoS One* 2011, 6(6), e21758). Tay-Sachs disease (or GM2 gangliosidosis) is caused by a deficiency in (1-hexosaminidase A which lead to an accumulation of gangliosides in the brain's nerve cells eventually leading to their premature death. Intravenous injection of the missing enzyme(s) is not a viable option as of the enzymes does cross the blood-brain barrier (*Genetics in Medicine* 2009, 1(6), 425). Glucosylceramide synthase is a key enzyme in the synthesis of glucosylceramide and other glycosphingolipids. Its inhibition can decrease the amount of the glycosphingolipids which accumulate in Sandhoff disease.

Fabry disease is caused by loss of activity of the lysosomal hydrolase α-galactosidase which leads to an accumulation of glycosphingolipids (particularly globotriaosylceramide) causing pain, renal disease and failure, cerebral vascular disease, and myocardial infarction (*Kidney International* 2000, 57, 446). One treatment strategy is to provide the defective enzyme to the patient; however, enzyme replacement therapy can only slow the progression of the disease and is not a cure. An alternative or complementary strategy is one where glucosylceramide synthase, a key enzyme in the synthesis of glycosphingolipids, is inhibited with a small molecule thus decreasing the amount of globotriaosylceramide and other glucosylceramide-based lipids that need to be broken down by hydrolase α-galactosidase.

Gaucher disease is caused by a defect in the enzyme lysosomal glucocerebrosidase which is responsible for catalyzing the breakdown of glucosylceramide which then accumulates in tissues of affected people (*J. Org. Chem.* 2007, 72(4), 1088) causing liver malfunction, skeletal disorders, painful bone lesions, hypersplenism, pancytopenia, and neurological symptoms (convulsions, hypertonia, mental retardation, apnea, dementia, and ocular muscle apraxia). One treatment strategy is to provide the defective enzyme to the patient; however, enzyme replacement therapy is not suitable for all patients and does not address the neurological manifestations of the disease for those with type 2 and type 3. An alternative or complementary strategy is one where glucosylceramide synthase is inhibited with small molecules thus decreasing the amount of glucosylceramide that needs to be broken down by glucocerebrosidase.

Nonalcoholic fatty liver disease (NALD) is a disease where fat accumulates in the liver of people who drink little or no alcohol and results in inflammation and scarring of the liver which can progress to liver failure. Inhibition of glucosylceramide synthase in ob/ob mice lowered glucose levels, lowered liver/body weight ratio, decreased the accumulation of triglycerides, and prevented and reversed steatosis (*Hepatology* 2009, 50(1), 85-93). Thus GCS inhibitors are useful for the prevention and treatment of NALD.

Polycystic kidney disease (PKD) is a genetic disease characterized by noncancerous cysts which are filled with fluid and cause the kidneys to enlarge which can result in a decrease in quality of life (e.g., headaches, high blood pressure, back and side pain, colon problems, mitral valve prolapsed, and kidney stones) and can be life-threatening (e.g. kidney failure, aneurysm in the brain, and high blood pressure which can lead to heart disease and stroke). PKD can also damage the liver, spleen, pancreas, vasculature, testes, seminal vesicles, and intestines. Glucosylceramide and ganglioside GM3 levels in the kidney are higher than in normal tissue (*Nat Med* 2010, 16(7), 788). Thus, blocking the synthesis of glucosylceramide with an inhibitor of GCS can be useful in the treatment of PKD to reduce new cyst formation (partial or complete inhibition of cystogenesis), reduce cyst mass, reduce the size and number of cysts, and/or reduce the severity of the symptoms associated. All current treatments for PKD address symptoms and do not treat the underlying cause of the disease (*Nat Med* 2010, 16(7), 788).

SUMMARY OF THE INVENTION

In one aspect, provided is a compound of Formula I:

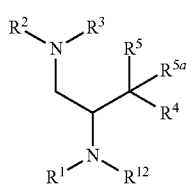

Formula I where
$R^1$ is —C(O)C($R^6$)($R^{6a}$)$R^{1a}$ or —C(O)C($R^6$)($R^{6a}$)—$X^1$—$R^{1a}$;
$X^1$ is alkylene, alkenylene, or cycloalkylene;
$R^{1a}$ is alkyl, heterocycloalkyl, aryl or heteroaryl each of which is optionally substituted with 1, 2, or 3 $R^7$ groups;
$R^2$ and $R^3$ together with the nitrogen to which they are attached form a 3-10 membered heterocycloalkyl ring, optionally substituted with 1, 2, 3, 4, 5, 6, 7, or 8 $R^8$;
$R^4$ is aryl or heteroaryl each of which is optionally substituted with 1, 2, 3, or 4 $R^9$ groups;
$R^5$ is —OH, and $R^{5a}$ is hydrogen;

$R^6$ and $R^{6a}$ are halo; $R^6$ and $R^{6a}$ are deuterium; or $R^6$ and $R^{6a}$ together with the carbon to which they are attached form C(=NOH) or C(O);
each $R^7$, when present, is independently nitro, cyano, amino, alkylamino, dialkylamino, halo, haloalkyl, alkyl, alkenyl, alkynyl, hydroxy, alkoxy, haloalkoxy, alkoxycarbonyl, aminocarbonyl, alkylaminocarbonyl, dialkylaminocarbonyl, cycloalkyl, heterocycloalkyl, phenyl, phenylalkyl, phenyloxy, heteroaryl, heteroarylalkyl, or heteroaryloxy; where the phenyl and the heteroaryl, either alone or as part of another group, are independently optionally substituted with 1, 2 or 3 $R^{7a}$;
each $R^{7a}$, when present, is independently selected from cyano, halo, alkyl, alkenyl, haloalkyl, hydroxyalkyl, and cycloalkyl;
each $R^8$, when present, is independently deuterium, amino, alkylamino, dialkylamino, alkyl, hydroxy, alkoxy, halo, haloalkyl, or cycloalkyl; or two $R^8$ together with the carbon to which they are attached form C(O);
each $R^9$, when present, is independently cyano, nitro, amino, alkylamino, dialkylamino, halo, haloalkyl, alkyl, hydroxy, alkoxy, alkenyloxy, hydroxyalkyloxy, haloalkoxy, cycloalkylthio, cycloalkyloxy, cycloalkylalkyloxy, heterocycloalkyl, heterocycloalkyloxy, heterocycloalkylalkyloxy, or phenyl; where the heterocycloalkyl and the phenyl, either alone or as part of another group, are independently optionally substituted with 1 or 2 $R^{9a}$;
each $R^{9a}$, when present, is independently selected from alkyl, hydroxy, alkoxy, halo, haloalkyl, haloalkoxy, alkoxycarbonyl, amino, alkylamino, and dialkylamino; and
$R^{12}$ is hydrogen or $C_{1-5}$ alkyl;
optionally a tautomer, a single stereoisomer or mixture of stereoisomers thereof and additionally optionally a pharmaceutically acceptable salt thereof.

In a further aspect, provided is a pharmaceutical composition comprising 1) a compound of Formula I optionally as a tautomer, a single stereoisomer or mixture of stereoisomers thereof and additionally optionally as a pharmaceutically acceptable salt thereof, and 2) a pharmaceutically acceptable excipient or pharmaceutically acceptable carrier.

In a further aspect, provided is a method of treating a disease or disorder comprising administering a compound of Formula I, optionally as a tautomer, a single stereoisomer or mixture of stereoisomers thereof and additionally optionally as a pharmaceutically acceptable salt thereof, or the pharmaceutical composition thereof additionally comprising a pharmaceutically acceptable excipient or pharmaceutically acceptable carrier.

In a further aspect, it is provided a method of making a compound of Formula I, comprising
a) treating an intermediate of formula 100

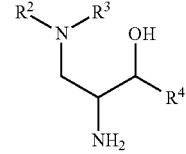

100 or a salt thereof, where $R^2$, $R^3$, $R^4$, and all other groups are as defined in the Summary of the Invention or as in any of the embodiments described herein; with an intermediate of formula $R^1$C(O)OH using standard amide coupling conditions to yield a Compound of Formula I where $R^5$ is hydroxy and $R^{5a}$ is hydrogen and $R^1$ is as defined in the Summary of the Invention or as in any of the embodiments described herein; and b) optionally separating individual isomers.

DETAILED DESCRIPTION

Abbreviations

| Abbreviation | Meaning |
|---|---|
| ACN | acetonitrile |
| aq | aqueous |
| Boc | tert-butoxycarbonyl |
| CBz | |
| conc | concentrated |
| DAST | diethylaminosulfur trifluoride |
| DIPEA | diisoproylethylamine |
| DCM | dichloromethane |
| DIBAL | diisobutylaluminum hydride |
| DMF | dimethylformamide |
| DMP | Dess-Martin periodinane |
| DMSO | dimethyl sulfoxide |
| EDCI | 1-ethyl-3-(3-dimethylaminopropyl)carbodiimide |
| h | hours |
| HATU | O-(7-azabenzotriazol-1-yl)-N,N,N',N'-tetramethyluronium hexafluorophosphate |
| HOBt | hydroxybenzotriazole |
| mg | milligram |
| mHz | megahertz |
| mL | milliliter |
| μL | microliter |
| Ms | mesyl |
| NBS | N-bromosuccinimide |
| NMR | nuclear magnetic resonance |
| PE | petroleum ether |
| rt or RT | room temperature |
| sat | saturated |
| TBAF | tetra-n-butylammonium fluoride |
| TBDMS | tert-butyldimethylsilyl |
| TBS | tert-butyl-silyl |
| TEA | triethylamine |
| TFA | trifluoroacetic acid |
| THF | tetrahydrofuran |
| TLC | thin layer chromatography |

Definitions

To facilitate understanding of the disclosure set forth herein, a number of terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

As used throughout this application and the appended claims, the following terms have the following meanings:

"About" preceding a numerical value refers to a range of values±10% of the value specified.

"Acceptable" with respect to a formulation, composition or ingredient, as used herein, means having no persistent detrimental effect on the general health of the subject being treated.

"Alkoxy" means an —OR group where R is alkyl, as defined herein. In some embodiments, alkoxy includes, but are not limited to, methoxy, ethoxy, propoxy, 2-propoxy, butoxy, tert-butoxy, pentyloxy, and hexyloxy.

"Alkoxycarbonyl" means a —C(O)R group where R is alkoxy, as defined herein.

"Alkenyl" means a straight or branched hydrocarbon radical having from 2 to 8 carbon atoms and at least one double bond. "Lower alkenyl" means an alkenyl group having one to six carbon atoms. In some embodiments, alkenyl includes ethenyl, propenyl, 1-but-3-enyl, 1-pent-3-enyl, 1-hex-5-enyl and the like.

"Alkenylene" means a divalent alkenyl group, as defined herein.

"Alkenyloxy" means an —OR group where R is alkenyl, as defined herein.

"Alkyl" means a straight or branched saturated hydrocarbon radical containing from 1-10 carbon atoms, in another example 1-6 carbon atoms. In some embodiments, alkyl includes, but is not limited to, methyl, ethyl, n-propyl, iso-propyl, n-butyl, sec-butyl, tert-butyl, n-pentyl, isopentyl, neopentyl, n-hexyl, 3-methylhexyl, 2,2-dimethylpentyl, 2,3-dimethylhexyl, n-heptyl, n-octyl, n-nonyl, and n-decyl.

"Alkylamino" means a —NHR radical where R is alkyl as defined herein, or an N-oxide derivative thereof. In some embodiments, alkylamino includes methylamino, ethylamino, n-, iso-propylamino, n-, iso-, tert-butylamino, or methylamino-N-oxide, and the like.

"Alkylaminoalkyl" means an alkyl group substituted with one or two alkylamino groups, as defined herein.

"Alkylaminocarbonyl" means a —C(O)NHR group where R is alkyl, as defined herein.

"Alkylene" means a divalent alkyl group, as defined herein.

"Alkynyl" means a straight or branched hydrocarbon radical having from 2 to 8 carbon atoms and at least one triple bond.

"Amino" means —NH$_2$.

"Aminoalkyl" means an alkyl group substituted with at least one, for example one, two, or three, amino groups.

"Aminocarbonyl" means a —C(O)NH$_2$ group.

"Aryl" means a monovalent six- to fourteen-membered, mono- or bi-carbocyclic ring, wherein the monocyclic ring is aromatic and at least one of the rings in the bicyclic ring is aromatic. In some embodiments, the examples of aryl include phenyl, naphthyl, and indanyl, and the like.

"Carboxy" means a —C(O)OH group.

"Cycloalkyl" means a monocyclic or fused bicyclic, saturated or partially unsaturated (but not aromatic), hydrocarbon radical of three to ten carbon ring atoms. Fused bicyclic hydrocarbon radical includes bridged rings. Cycloalkyl includes spirocycloalkyl rings. Unless stated otherwise, the valency of the group may be located on any atom of any ring within the radical, valency rules permitting. One or two ring carbon atoms may be replaced by a —C(O)—, —C(S)—, or —C(=NH)— group.

In some embodiments, cycloalkyl includes but is not limited to:

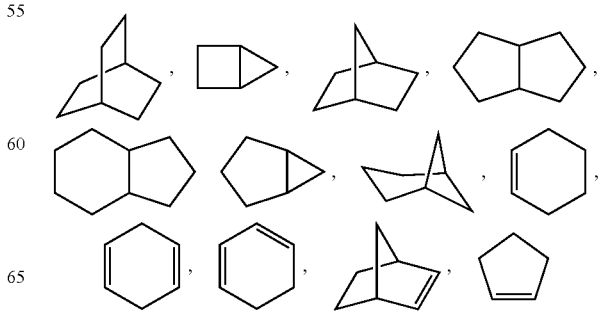

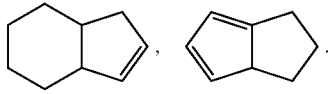

"Cycloalkylene" means a divalent cycloalkyl group, as defined herein.

"Cycloalkylalkyl" means an alkyl group, as defined herein, substituted with at least one, in another example 1 or 2, cycloalkyl groups as defined herein.

"Cycloalkylalkyloxy" means an —OR group where R is a cycloalkylalkyl group as defined herein.

"Cycloalkyloxy" means an —OR group where R is cycloalkyl, as defined herein.

"Cycloalkylthio" means an —SR group where R is cycloalkyl, as defined herein.

"Dialkylamino" means an —NRR' radical where R and R' are independently alkyl as defined herein, or an N-oxide derivative, or a protected derivative thereof. In some embodiments, dialkylamino includes dimethylamino, diethylamino, N,N-methylpropylamino or N,N-methylethylamino, and the like.

"Dialkylaminoalkyl" means an alkyl group substituted with at least one, for example one or two, dialkylamino group(s), as defined herein.

"Dialkylaminocarbonyl" means a —C(O)NRR' group where R and R' are alkyl, as defined herein.

"Haloalkoxy" means an alkoxy group, as defined herein, substituted with one or more halo atoms, in another example by 1, 2, or 3 halo atoms.

"Haloalkyl" means an alkyl group substituted with one or more halo atoms, in another example by 1, 2, 3, 4, 5, or 6 halo atoms, in another example by 1, 2, or 3 halo atoms. In some embodiments, haloalkyl includes, but is not limited to, trifluoromethyl, chloromethyl, and the like.

"Heteroaryl" means monocyclic, fused bicyclic, or fused tricyclic, radical of 5 to 14 ring atoms containing one or more, in another example one, two, three, or four ring heteroatoms independently selected from —O—, —S(O)$_n$— (n is 0, 1, or 2), —N—, —N(H)—, and N-oxide, and the remaining ring atoms being carbon, wherein the ring comprising a monocyclic radical is aromatic and wherein at least one of the fused rings comprising a bicyclic or tricyclic radical is aromatic (but does not have to be a ring which contains a heteroatom, e.g. 2,3-dihydrobenzo[b][1,4]dioxin-6-yl). One or two ring carbon atoms of any nonaromatic rings comprising a bicyclic or tricyclic radical may be replaced by a —C(O)—, —C(S)—, or —C(=NH)— group. Fused bicyclic radical includes bridged ring systems. Unless stated otherwise, the valency may be located on any atom of any ring of the heteroaryl group, valency rules permitting.

In some embodiments, heteroaryl includes, but is not limited to, triazolyl, tetrazolyl, pyrrolyl, imidazolyl, thienyl, furanyl, pyrazolyl, oxazolyl, isooxazolyl, oxadiazolyl, thiadiazolyl, indolyl, 2,3-dihydro-1H-indolyl (including, for example, 2,3-dihydro-1H-indol-2-yl or 2,3-dihydro-1H-indol-5-yl, and the like), indazolyl, phthalimidyl, benzimidazolyl, benzoxazolyl, benzofuranyl, benzothienyl, benzopyranyl, benzothiazolyl, pyridinyl, pyrazinyl, pyrimidinyl, pyridazinyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), pyrrolo[1,2-b]pyridazinyl, imidazo[1,2-a]pyridinyl, thiazolyl, benzo[d][1,3]dioxolyl, 2,3-dihydrobenzo[b][1,4]dioxinyl, furo[2,3-d]thiazolyl, thieno[2,3-d]oxazolyl, thieno[3,2-b]furanyl, furo[2,3-d]pyrimidinyl, furo[3,2-b]pyridinyl, furo[3,2-c]pyridinyl, 6,7-dihydro-5H-cyclopenta[b]pyridinyl, and 7,8-dihydro-6H-cyclopenta[g]quinoxalinyl; and derivatives, N-oxide and protected derivatives thereof.

"Heteroarylalkyl" means an alkyl group, as defined herein, substituted with one or two heteroaryl groups, as defined herein.

"Heteroaryloxy" means an —OR group where R is heteroaryl as defined herein.

"Heterocycloalkyl" means a saturated or partially unsaturated (but not aromatic) monovalent monocyclic group of 3 to 9 ring atoms or a saturated or partially unsaturated (but not aromatic) monovalent fused bicyclic group of 5 to 12 ring atoms in which one or more heteroatoms, for example one, two, three, or four ring heteroatoms, independently selected from —O—, —S(O)$_n$— (n is 0, 1, or 2), —N=, —NH—, and N-oxide, the remaining ring atoms being carbon. One or two ring carbon atoms may be replaced by a —C(O)—, —C(S)—, or —C(=NH)— group. Fused bicyclic radical includes bridged ring systems. Unless otherwise stated, the valency of the group may be located on any atom of any ring within the radical, valency rules permitting. Heterocycloalkyl includes spiroheterocycloalkyl rings.

In some embodiments, heterocycloalkyl includes, but is not limited to, azetidinyl, pyrrolidinyl, 2-oxopyrrolidinyl, 2,5-dihydro-1H-pyrrolinyl, 2,5-dioxo-1H-pyrrolyl, 2,5-dioxo-pyrrolidinyl, 2,5-dihydro-1H-pyrrolyl, piperidinyl, 2-oxopiperidinyl, 4-piperidonyl, morpholinyl, piperazinyl, 2-oxopiperazinyl, dioxopiperazinyl, pyranyl, tetrahydropyranyl, tetrahydrothiopyranyl, 1,3-dioxinyl, 1,3-dioxanyl, 1,4-dioxinyl, 1,4-dioxanyl, thiomorpholinyl, thiamorpholinyl, perhydroazepinyl, pyrazolidinyl, imidazolinyl, imidazolidinyl, 2,4-dioxo-imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydroindolyl, octahydroisoindolyl, decahydroisoquinolyl, tetrahydrofuryl, 2-azaspiro[3.3]heptanyl, 7-azabicyclo[2.2.1]heptanyl, and 8-azabicyclo[3.2.1]octanyl, and the derivatives thereof and N-oxide (for example 1-oxido-pyrrolidin-1-yl) or a protected derivative thereof.

"Heterocycloalkylalkyl" means an alkyl group substituted with at least one, in another example 1 or 2, heterocycloalkyl groups, as defined herein.

"Heterocycloalkylalkyloxy" means an —OR group where R is an heterocycloalkylalkyl group, as defined herein.

"Heterocycloalkyloxy" means an —OR group where R is heterocycloalkyl, as defined herein.

"Hydroxyalkyl" means an alkyl group, as defined herein, substituted with 1, 2, or 3 hydroxy groups.

"Hydroxyalkyloxy" means an —OR group where R is hydroxyalkyl, as defined herein.

"Phenylalkyl" means an alkyl group, as defined herein, substituted with one or two phenyl groups.

"Phenyloxy" means an —OR group where R is phenyl.

The term "protecting group" refers to a removable group which modifies the reactivity of a functional group, for example, a hydroxyl, ketone or amine, against undesirable reaction during synthetic procedures and to be later removed. Examples of hydroxy-protecting groups include, but not limited to, methylthiomethyl, tert-dimethylsilyl, tert-butyldiphenylsilyl, ethers such as methoxymethyl, and esters including acetyl, benzoyl, and the like. Examples of ketone protecting groups include, but not limited to, ketals, oximes, O-substituted oximes for example O-benzyl oxime, O-phenylthiomethyl oxime, 1-isopropoxycyclohexyl oxime, and the like. Examples of amine protecting groups include, but are not limited to, tert-butoxycarbonyl (Boc) and carbobenzyloxy (Cbz).

"Stereoisomers" include (but are not limited to) geometric isomers, enantiomers, diastereomers, and mixtures of geometric isomers, enantiomers or diastereomers. In some embodiments, individual stereoisomers of compounds are prepared synthetically from commercially available starting materials which contain asymmetric or chiral centers or by preparation of racemic mixtures followed by resolution. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic column.

As used herein, "amelioration" of the symptoms of a particular disorder by administration of a particular compound or pharmaceutical composition refers to any lessening of severity, delay in onset, slowing of progression, or shortening of duration, whether permanent or temporary, lasting or transient that can be attributed to or associated with administration of the compound or composition.

The term "carrier" includes pharmaceutically inert, inorganic or organic carriers for the production of pharmaceutical compositions. Lactose, corn starch, or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active ingredient no carriers are, however, usually required in the case of soft gelatin capsules, other than the soft gelatin itself. Suitable carriers for the production of solutions and syrups are, for example, water, polyols, glycerol, vegetable oils and the like. Suitable carriers for suppositories are, for example, natural or hardened oils, waxes, fats, semi-liquid or liquid polyols and the like.

The term "diluent" refers to chemical compounds that are used to dilute the compound of interest prior to delivery. Diluents include chemicals used to stabilize compounds because they provide a more stable environment. Salts dissolved in buffered solutions (which also can provide pH control or maintenance) are utilized as diluents in some or any embodiments, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

"Excipient" or "pharmaceutically acceptable excipient" means a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy*, 21st ed.; Lippincott Williams & Wilkins: Philadelphia, Pa., 2005; *Handbook of Pharmaceutical Excipients*, 6th ed.; Rowe et al., Eds.; The Pharmaceutical Press and the American Pharmaceutical Association: 2009; *Handbook of Pharmaceutical Additives*, 3rd ed.; Ash and Ash Eds.; Gower Publishing Company: 2007; *Pharmaceutical Preformulation and Formulation*, 2nd ed.; Gibson Ed.; CRC Press LLC: Boca Raton, Fla., 2009.

"Pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt s not specifically limited as far as it can be used in medicaments. Examples of a salt that the compound of the present invention forms with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

"Subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

"Treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. Often, the beneficial effects that a subject derives from a therapeutic agent do not result in a complete cure of the disease, disorder or condition.

Embodiments

The following paragraphs present a number of embodiments of the compounds disclosed herein. In each instance the embodiment includes both the recited compound(s) as well as a single stereoisomer or mixture of stereoisomers thereof, as well as a pharmaceutically acceptable salt thereof. The compounds include the N-oxides or pharmaceutically acceptable salts thereof. In some situations, the compounds exist as tautomers. All tautomers are included within the scope of the compounds presented herein.

The compounds described herein, as well as their corresponding pharmaceutically acceptable salts thereof, can exist in isotopically-labeled form, in which one or more atoms of the compounds are replaced by an atom having the same atomic number but an atomic mass different from the atomic mass usually found in nature. Examples of isotopes that can be incorporated into compounds of the invention include isotopes of hydrogen, carbon, nitrogen, oxygen, phosphorous, sulfur, fluorine, and chloride, such as $^2$H (deuterium), $^3$H (tritium), $^{13}$C, $^{14}$C, $^{15}$N, $^{17}$O, $^{18}$O, $^{31}$P, $^{32}$P, $^{35}$S, $^{18}$F, and $^{36}$Cl, respectively. Isotopically labeled compounds of the present invention, as well as pharmaceutically acceptable salts thereof, generally can be prepared by carrying out the procedures disclosed in the Schemes and/or in the Examples and Preparations herein, by substituting a readily available isotopically labeled reagent for a non-isotopically labeled reagent.

In the compounds of the invention, unless otherwise stated, any atom not specifically designated as a particular isotope is meant to represent any stable isotope of that atom at is natural abundance. When a position is designated as "H" or "hydrogen," the position is to be understood to have hydrogen at is naturally abundant isotopic composition, with the understanding that some variation of natural isotopic abundance occurs in a synthesized compound depending upon the origin of chemical materials used in the synthesis. When a particular position is designated as "D" or "deuterium," it is to be understood that the abundance of deuterium at that position is substantially greater than the natural abundance of deuterium, with is 0.015%, and typically has at least 50% deuterium incorporation at that position.

The methods disclosed herein also include methods of treating diseases by administering deuterated compounds of the invention or other isotopically-labeled compounds of the invention alone or as pharmaceutical compositions. In some of these situations, substitution of hydrogen atoms with heavier isotopes such as deuterium can afford certain therapeutic advantages resulting from greater metabolic stability (for example, increased in vivo half-life or reduced dosage requirements). Moreover, certain isotopically-labeled compounds, for example those into which radioactive isotopes such as $^3$H and $^{14}$C are incorporated, are useful in drug and/or substrate tissue distribution assays such as positron emission tomography (PET). Tritiated ($^3$H) and carbon-14 ($^{14}$C) isotopes are useful for these embodiments.

In one aspect, provided is a compound of Formula I:

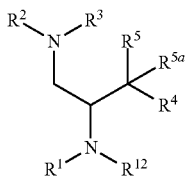

Formula I where
$R^1$ is —C(O)C($R^6$)($R^{6a}$)$R^{1a}$ or —C(O)C($R^6$)($R^{6a}$)—$X^1$—$R^{1a}$;
$X^1$ is alkylene, alkenylene, or cycloalkylene;
$R^{1a}$ is alkyl, cycloalkyl, heterocycloalkyl, aryl or heteroaryl each of which is optionally substituted with 1, 2, or 3 $R^7$ groups;
$R^2$ is hydrogen, hydroxy, or alkyl; and $R^3$ is alkyl, aminoalkyl, alkylaminoalkyl, or dialkylaminoalkyl; $R^2$ and $R^3$ together with the nitrogen to which they are attached form a 3-10 membered heterocycloalkyl ring, optionally substituted with 1, 2, 3, 4, 5, 6, 7, or 8 $R^8$;
$R^4$ is aryl or heteroaryl each of which is optionally substituted with 1, 2, 3, or 4 $R^9$ groups;
$R^5$ is halo, —OH, —OTBS, —N$_3$, —NH$_2$, —NH(OCH$_3$), —NHC(O)CH$_3$, or —NHC(O)H; and $R^{5a}$ is hydrogen, alkyl, or deuterium; or $R^5$ and $R^{5a}$ together with the carbon to which they are attached form C(O) or —C(NOH);
$R^6$ is halo or deuterium; and $R^{6a}$ is hydrogen, halo, or deuterium; or $R^6$ and $R^{6a}$ together with the carbon to which they are attached form C(=NOR$^{10}$) or —C(O);
each $R^7$, when present, is independently nitro, cyano, amino, alkylamino, dialkylamino, halo, haloalkyl, alkyl, alkenyl, alkynyl, hydroxy, alkoxy, haloalkoxy, carboxy, alkoxycarbonyl, aminocarbonyl, alkylaminocarbonyl, dialkylaminocarbonyl, cycloalkyl, heterocycloalkyl, phenyl, phenylalkyl, phenyloxy, heteroaryl, heteroarylalkyl, or heteroaryloxy; where the phenyl and the heteroaryl, either alone or as part of another group, are independently optionally substituted with 1, 2 or 3 $R^{7a}$;
each $R^{7a}$, when present, is independently selected from cyano, halo, alkyl, alkenyl, haloalkyl, hydroxyalkyl, and cycloalkyl;
each $R^8$, when present, is independently deuterium, amino, alkylamino, dialkylamino, alkyl, hydroxy, alkoxy, halo, haloalkyl, or cycloalkyl; or two $R^8$ together with the carbon to which they are attached form C(O);
each $R^9$, when present, is independently cyano, nitro, amino, alkylamino, dialkylamino, halo, haloalkyl, alkyl, —NR$^{11}$C(O)NR$^{11a}$R$^{11b}$, hydroxy, alkoxy, alkenyloxy, hydroxyalkyloxy, haloalkoxy, cycloalkylthio, cycloalkyloxy, cycloalkylalkyloxy, heterocycloalkyl, heterocycloalkyloxy, heterocycloalkylalkyloxy, or phenyl; where the heterocycloalkyl and the phenyl, either alone or as part of another group, are independently optionally substituted with 1 or 2 $R^{9a}$;
each $R^{9a}$, when present, is independently selected from alkyl, hydroxy, alkoxy, halo, haloalkyl, haloalkoxy, alkoxycarbonyl, amino, alkylamino, and dialkylamino;
$R^{10}$ is hydrogen, alkyl, or phenyl;
$R^{11}$, $R^{11a}$, and $R^{11b}$ are independently hydrogen, alkyl, or cycloalkyl; and
$R^{12}$ is hydrogen or C$_{1-5}$ alkyl;
optionally a tautomer, a single stereoisomer or mixture of stereoisomers thereof and additionally optionally a pharmaceutically acceptable salt thereof.

In some or any embodiments, the compound of Formula I is that where

R$^1$ is —C(O)C(R$^6$)(R$^{6a}$)R$^{1a}$ or —C(O)C(R$^6$)(R$^{6a}$)—X$^1$—R$^{1a}$;

X$^1$ is alkylene, alkenylene, or cycloalkylene;

R$^{1a}$ is alkyl, heterocycloalkyl, aryl or heteroaryl each of which is optionally substituted with 1, 2, or 3 R$^7$ groups;

R$^2$ and R$^3$ together with the nitrogen to which they are attached form a 3-10 membered heterocycloalkyl ring, optionally substituted with 1, 2, 3, 4, 5, 6, 7, or 8 R$^8$;

R$^4$ is aryl or heteroaryl each of which is optionally substituted with 1, 2, 3, or 4 R$^9$ groups;

R$^5$ is —OH, and R$^{5a}$ is hydrogen;

R$^6$ and R$^{6a}$ are halo; R$^6$ and R$^{6a}$ are deuterium; or R$^6$ and R$^{6a}$ together with the carbon to which they are attached form C(=NOH) or C(O);

each R$^7$, when present, is independently nitro, cyano, amino, alkylamino, dialkylamino, halo, haloalkyl, alkyl, alkenyl, alkynyl, hydroxy, alkoxy, haloalkoxy, alkoxycarbonyl, aminocarbonyl, alkylaminocarbonyl, dialkylaminocarbonyl, cycloalkyl, heterocycloalkyl, phenyl, phenylalkyl, phenyloxy, heteroaryl, heteroarylalkyl, or heteroaryloxy; where the phenyl and the heteroaryl, either alone or as part of another group, are independently optionally substituted with 1, 2 or 3 R$^{7a}$;

each R$^{7a}$, when present, is independently selected from cyano, halo, alkyl, alkenyl, haloalkyl, hydroxyalkyl, and cycloalkyl;

each R$^8$, when present, is independently deuterium, amino, alkylamino, dialkylamino, alkyl, hydroxy, alkoxy, halo, haloalkyl, or cycloalkyl; or two R$^8$ together with the carbon to which they are attached form C(O);

each R$^9$, when present, is independently cyano, nitro, amino, alkylamino, dialkylamino, halo, haloalkyl, alkyl, hydroxy, alkoxy, alkenyloxy, hydroxyalkyloxy, haloalkoxy, cycloalkylthio, cycloalkyloxy, cycloalkylalkyloxy, heterocycloalkyl, heterocycloalkyloxy, heterocycloalkylalkyloxy, or phenyl; where the heterocycloalkyl and the phenyl, either alone or as part of another group, are independently optionally substituted with 1 or 2 R$^{9a}$;

each R$^{9a}$, when present, is independently selected from alkyl, hydroxy, alkoxy, halo, haloalkyl, haloalkoxy, alkoxycarbonyl, amino, alkylamino, and dialkylamino; and R$^{12}$ is hydrogen or C$_{1-5}$ alkyl;

optionally a tautomer, a single stereoisomer or mixture of stereoisomers thereof and additionally optionally a pharmaceutically acceptable salt thereof.

In some or any embodiments, the compound of Formula I is that where

R$^1$ is —C(O)C(R$^6$)(R$^{6a}$)R$^{1a}$ or —C(O)C(R$^6$)(R$^{6a}$)—X$^1$—R$^{1a}$;

X$^1$ is alkylene, alkenylene, or cycloalkylene;

R$^{1a}$ is alkyl, heterocycloalkyl, aryl or heteroaryl each of which is optionally substituted with 1, 2, or 3 R$^7$ groups;

R$^2$ and R$^3$ together with the nitrogen to which they are attached form a 4-5 membered monocyclic heterocycloalkyl ring or a 7-8 membered bicyclic heterocycloalkyl; each of which is optionally substituted with 1 or 2 R$^8$;

R$^4$ is aryl or heteroaryl each of which is optionally substituted with 1, 2, or 3 R$^9$ groups;

R$^5$ is —OH, and R$^{5a}$ is hydrogen;

R$^6$ and R$^{6a}$ are halo; or R$^6$ and R$^{6a}$ together with the carbon to which they are attached form C(=NOH) or C(O);

each R$^7$, when present, is independently nitro, cyano, halo, haloalkyl, alkyl, alkenyl, alkynyl, cycloalkyl, heterocycloalkyl, phenyl, phenylalkyl, phenyloxy, heteroaryl, heteroarylalkyl, or heteroaryloxy; where the phenyl and the heteroaryl, either alone or as part of another group, are independently optionally substituted with 1, 2 or 3 R$^{7a}$;

each R$^{7a}$, when present, is independently selected from cyano, halo, alkyl, alkenyl, haloalkyl, hydroxyalkyl, and cycloalkyl;

each R$^8$, when present, is independently amino, alkylamino, dialkylamino, alkyl, halo, or cycloalkyl; or two R$^8$ together with the carbon to which they are attached form C(O);

each R$^9$, when present, is independently cyano, nitro, amino, alkylamino, dialkylamino, halo, haloalkyl, alkyl, hydroxy, alkoxy, alkenyloxy, hydroxyalkyloxy, haloalkoxy, cycloalkylthio, cycloalkyloxy, cycloalkylalkyloxy, heterocycloalkyl, heterocycloalkyloxy, heterocycloalkylalkyloxy, or phenyl; where the heterocycloalkyl and the phenyl, either alone or as part of another group, are independently optionally substituted with 1 or 2 R$^{9a}$;

each R$^{9a}$, when present, is independently selected from alkyl, hydroxy, alkoxy, halo, haloalkyl, haloalkoxy, alkoxycarbonyl, amino, alkylamino, and dialkylamino; and R$^{12}$ is hydrogen or CH$_3$;

optionally a tautomer, a single stereoisomer or mixture of stereoisomers thereof and additionally optionally a pharmaceutically acceptable salt thereof.

In some or any embodiments, the compound of Formula I is that where

R$^1$ is —C(O)C(R$^6$)(R$^{6a}$)R$^{1a}$ or —C(O)C(R$^6$)(R$^{6a}$)—X$^1$—R$^{1a}$;

X$^1$ is alkylene or alkenylene;

R$^{1a}$ is heterocycloalkyl, aryl or heteroaryl each of which is optionally substituted with 1 or 2 R$^7$ groups;

R$^2$ and R$^3$ together with the nitrogen to which they are attached form a 4-5 membered monocyclic heterocycloalkyl ring or a 7-8 membered bicyclic heterocycloalkyl; each of which is optionally substituted with 1 or 2 R$^8$;

R$^4$ is aryl or heteroaryl each of which is optionally substituted with 1, 2, or 3 R$^9$ groups;

R$^5$ is —OH, and R$^{5a}$ is hydrogen;

R$^6$ and R$^{6a}$ are halo; or R$^6$ and R$^{6a}$ together with the carbon to which they are attached form C(=NOH) or C(O);

each R$^7$, when present, is independently cyano, halo, haloalkyl, alkyl, alkynyl, cycloalkyl, heterocycloalkyl, phenyl, phenylalkyl, phenyloxy, heteroaryl, or heteroaryloxy; where the phenyl and the heteroaryl, either alone or as part of another group, are independently optionally substituted with 1 or 2 R$^{7a}$;

each R$^{7a}$, when present, is independently selected from cyano, halo, alkyl, alkenyl, haloalkyl, hydroxyalkyl, and cycloalkyl;

each R$^8$, when present, is independently amino, alkyl, or halo; or two R$^8$ together with the carbon to which they are attached form C(O);

each R$^9$, when present, is independently amino, halo, haloalkyl, alkyl, alkoxy, alkenyloxy, hydroxyalkyloxy, haloalkoxy, cycloalkylthio, cycloalkyloxy, heterocycloalkyloxy, heterocycloalkylalkyloxy, or phenyl; where the heterocycloalkyl and the phenyl, either alone or as part of another group, are independently optionally substituted with 1 or 2 R$^{9a}$;

each R$^{9a}$, when present, is independently selected from alkyl or halo;

R$^{10}$ is hydrogen or CH$_3$;

R$^{12}$ is hydrogen; and optionally a tautomer, a single stereoisomer or mixture of stereoisomers thereof and additionally optionally a pharmaceutically acceptable salt thereof.

In some or any embodiments, the compound of Formula I is that where $R^1$ is —C(O)C($R^6$)($R^{6a}$)$R^{1a}$ or —C(O)C($R^6$)($R^{6a}$)—$X^1$—$R^{1a}$;

$X^1$ is alkylene;

$R^{1a}$ is heterocycloalkyl, aryl or heteroaryl each of which is optionally substituted with 1, 2, or 3 $R^7$ groups;

$R^2$ and $R^3$ together with the nitrogen to which they are attached form a 4-5 membered monocyclic heterocycloalkyl ring or a 7-8 membered bicyclic heterocycloalkyl; each of which is optionally substituted with 1 or 2 $R^8$;

$R^4$ is aryl or heteroaryl each of which is optionally substituted with 1, 2, or 3 $R^9$ groups;

$R^5$ is —OH, and $R^{5a}$ is hydrogen;

$R^6$ and $R^{6a}$ are halo; or $R^6$ and $R^{6a}$ together with the carbon to which they are attached form or C(O);

each $R^7$, when present, is independently nitro, cyano, halo, haloalkyl, alkyl, alkenyl, alkynyl, cycloalkyl, heterocycloalkyl, phenyl, phenylalkyl, phenyloxy, heteroaryl, heteroarylalkyl, or heteroaryloxy; where the phenyl and the heteroaryl, either alone or as part of another group, are independently optionally substituted with 1, 2 or 3 $R^{7a}$;

each $R^{7a}$, when present, is independently selected from cyano, halo, alkyl, alkenyl, haloalkyl, hydroxyalkyl, and cycloalkyl;

each $R^8$, when present, is independently amino, alkylamino, dialkylamino, alkyl, or halo;

each $R^9$, when present, is independently amino, alkylamino, dialkylamino, halo, haloalkyl, alkyl, hydroxy, alkoxy, alkenyloxy, hydroxyalkyloxy, haloalkoxy, cycloalkylthio, cycloalkyloxy, cycloalkylalkyloxy, heterocycloalkyl, heterocycloalkyloxy, heterocycloalkylalkyloxy, or phenyl; where the heterocycloalkyl and the phenyl, either alone or as part of another group, are independently optionally substituted with 1 or 2 $R^{9a}$;

each $R^{9a}$, when present, is independently selected from alkyl and halo; and $R^{12}$ is hydrogen or $CH_3$;

optionally a tautomer, a single stereoisomer or mixture of stereoisomers thereof and additionally optionally a pharmaceutically acceptable salt thereof.

In another aspect, provided is a compound of Formula II:

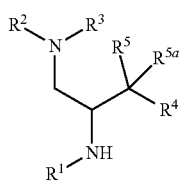

Formula II where $R^1$ is —C(O)C($R^6$)($R^{6a}$)$R^{1a}$ or —C(O)C($R^6$)($R^{6a}$)—$X^1$—$R^{1a}$;

$X^1$ is alkylene, alkenylene, or cycloalkylene;

$R^{1a}$ is alkyl, cycloalkyl, heterocycloalkyl, aryl or heteroaryl each of which is optionally substituted with 1, 2, or 3 $R^7$ groups;

$R^2$ is hydrogen, hydroxy, or alkyl; and $R^3$ is alkyl, aminoalkyl, alkylaminoalkyl, or dialkylaminoalkyl; or $R^2$ and $R^3$ together with the nitrogen to which they are attached form a 3-10 membered heterocycloalkyl ring which is optionally substituted with 1, 2, 3, or 4 $R^8$;

$R^4$ is aryl or heteroaryl each of which is optionally substituted with 1, 2, or 3 $R^9$ groups;

$R^5$ is halo, —OH, —OTBS, —$N_3$, —$NH_2$, —NH(OCH$_3$), —NHC(O)CH$_3$, or —NHC(O)H and $R^{5a}$ is hydrogen, alkyl, or deuterium; or $R^5$ and $R^{5a}$ together with the carbon to which they are attached form C(O) or C(NOH);

$R^6$ is halo or deuterium; and $R^{6a}$ is hydrogen, halo, or deuterium; or $R^6$ and $R^{6a}$ together with the carbon to which they are attached form C(NOR$^{10}$) or —C(O);

each $R^7$, when present, is independently nitro, cyano, amino, alkylamino, dialkylamino, halo, haloalkyl, alkyl, hydroxy, alkoxy, haloalkoxy, carboxy, alkoxycarbonyl, aminocarbonyl, alkylaminocarbonyl, dialkylaminocarbonyl, or heteroaryl;

each $R^8$, when present, is independently deuterium, amino, alkylamino, dialkylamino, alkyl, hydroxy, alkoxy, halo, haloalkyl, or cycloalkyl;

each $R^9$, when present, is independently cyano, nitro, amino, alkylamino, dialkylamino, halo, haloalkyl, alkyl, —NR$^{11}$C(O)NR$^{11a}$R$^{11b}$, hydroxy, alkoxy, haloalkoxy, cycloalkyloxy, cycloalkylalkyloxy, heterocycloalkyloxy, or heterocycloalkylalkyloxy which is optionally substituted with 1 or 2 hydroxy;

$R^{10}$ is hydrogen, alkyl, or phenyl;

$R^{11}$, $R^{11a}$, and $R^{11b}$ are independently hydrogen, alkyl, or cycloalkyl; and optionally a tautomer, a single stereoisomer or mixture of stereoisomers thereof and additionally optionally a pharmaceutically acceptable salt thereof.

In some or any embodiments, the compound of Formula I or II is that where $R^1$ is —C(O)C($R^6$)($R^{6a}$)$R^{1a}$; and all other groups are as defined in the Summary of the Invention or any of the embodiments described herein. In some or any embodiments, the compound of Formula I or II is that where $R^1$ is —C(O)C($R^6$)($R^{6a}$)$R^{1a}$; $R^6$ and $R^{6a}$ are halo; and all other groups are as defined in the Summary of the Invention or any of the embodiments described herein. In some or any embodiments, the compound of Formula I or II is that where $R^1$ is —C(O)CF$_2$R$^{1a}$; and all other groups are as defined in the Summary of the Invention or any of the embodiments described herein. In some or any embodiments, the compound of Formula I or II is that where $R^1$ is —C(O)C($R^6$)($R^{6a}$)$R^{1a}$; $R^6$ is halo and $R^{6a}$ is hydrogen; and all other groups are as defined in the Summary of the Invention or any of the embodiments described herein. In some or any embodiments, the compound of Formula I or II is that where $R^1$ is —C(O)C(H)(F)R$^{1a}$; and all other groups are as defined in the Summary of the Invention or any of the embodiments described herein. In some or any embodiments, the compound of Formula I or II is that where $R^1$ is —C(O)CD$_2$R$^{1a}$; and all other groups are as defined in the Summary of the Invention or any of the embodiments described herein. In some or any embodiments, the compound of Formula I or II is that where $R^1$ is —C(O)C($R^6$)($R^{6a}$)$R^{1a}$; $R^6$ and $R^{6a}$ together with the carbon to which they are attached form C(=NOR$^{10}$); and all other groups are as defined in the Summary of the Invention or any of the embodiments described herein. In some or any embodiments, the compound of Formula I or II is that where $R^1$ is —C(O)C($R^6$)($R^{6a}$)$R^{1a}$; $R^6$ and $R^{6a}$ together with the carbon to which they are attached form C(O); and all other groups are as defined in the Summary of the Invention or any of the embodiments described herein.

In some or any embodiments, the compound of Formula I or II is that where $R^1$ is —C(O)C($R^6$)($R^{6a}$)—$X^1$—$R^{1a}$; and all other groups are as defined in the Summary of the Invention or any of the embodiments described herein. In some or any embodiments, the compound of Formula I or II is that where $R^1$ is —C(O)C($R^6$)($R^{6a}$)—$X^1$—$R^{1a}$; $R^6$ and $R^{6a}$ are halo; and all other groups are as defined in the Summary of the Invention or any of the embodiments described herein. In some or any embodiments, the compound of Formula I or II is that where $R^1$ is —C(O)CF$_2$—$X^1$—$R^{1a}$; and all other groups are as defined in the Summary of the Invention or any of the embodiments described herein.

In some or any embodiments, the compound of Formula I or II is that where $R^1$ is —C(O)C($R^6$)($R^{6a}$)—$X^1$—$R^{1a}$; $X^1$ is alkylene; and all other groups are as defined in the Summary of the Invention or any of the embodiments described herein. In some or any embodiments, the compound of Formula I or II is that where $R^1$ is —C(O)C($R^6$)($R^{6a}$)—CH$_2$—$R^{1a}$; and all other groups are as defined in the Summary of the Invention or any of the embodiments described herein. In some or any embodiments, the compound of Formula I or II is that where $R^1$ is —C(O)C($R^6$)($R^{6a}$)—CH$_2$CH$_2$CH$_2$—$R^{1a}$; and all other groups are as defined in the Summary of the Invention or any of the embodiments described herein. In some or any embodiments, the compound of Formula I or II is that where $R^1$ is —C(O)C($R^6$)($R^{6a}$)—$X^1$—$R^{1a}$; $X^1$ is alkenylene; and all other groups are as defined in the Summary of the Invention or any of the embodiments described herein. In some or any embodiments, the compound of Formula I or II is that where $R^1$ is —C(O)C($R^6$)($R^{6a}$)—$X^1$—$R^{1a}$; $X^2$ is —CH═CH— or —C(CH$_2$)CH$_2$—; and all other groups are as defined in the Summary of the Invention or any of the embodiments described herein.

In some or any embodiments, the compound of Formula I or II is that where $R^1$ is —C(O)C($R^6$)($R^{6a}$)—$X^1$—$R^{1a}$ which is —C(O)C(halo)$_2$CH$_2$$R^{1a}$, —C(O)C(halo)$_2$CH$_2$CH$_2$$R^{1a}$, —C(O)C(O)CH$_2$CH$_2$$R^{1a}$, —C(O)C(═NOH)CH$_2$CH$_2$$R^{1a}$, —C(O)C(═NOCH$_3$)CH$_2$CH$_2$$R^{1a}$, —C(O)C(halo)$_2$-CH═CH$R^{1a}$, or —C(O)C(halo)$_2$-C(═CH$_2$)CH$_2$$R^{1a}$; and all other groups are as defined in the Summary of the Invention or any of the embodiments described herein. In some or any embodiments, the compound of Formula I or II is that where $R^1$ is —C(O)C($R^6$)($R^{6a}$)—$X^1$—$R^{1a}$ which is —C(O)CF$_2$CH$_2$$R^{1a}$, —C(O)CF$_2$CH$_2$CH$_2$$R^{1a}$, —C(O)CF$_2$—CH═CH$R^{1a}$, or —C(O)CF$_2$—C(═CH$_2$)CH$_2$$R^{1a}$; and all other groups are as defined in the Summary of the Invention or any of the embodiments described herein.

In some or any embodiments, the compound of Formula I or II is that where $R^1$ is —C(O)C($R^6$)($R^{6a}$)$R^{1a}$; $R^6$ and $R^{6a}$ together with the carbon to which they are attached form C(O); and all other groups are as defined in the Summary of the Invention or any of the embodiments described herein.

In some or any embodiments, the compound of Formula I or II is that where $R^{1a}$ is alkyl optionally substituted with 1, 2, or 3 $R^7$ groups; and all other groups are as defined in the Summary of the Invention or any of the embodiments described herein. In some or any embodiments, the compound of Formula I or II is that where $R^{1a}$ is methyl; and all other groups are as defined in the Summary of the Invention or any of the embodiments described herein.

In some or any embodiments, the compound of Formula I or II is that where $R^{1a}$ is aryl optionally substituted with 1, 2, or 3 $R^7$ groups; and all other groups are as defined in the Summary of the Invention or any of the embodiments described herein. In some or any embodiments, the compound of Formula I or II is that where $R^{1a}$ is naphthyl optionally substituted with 1 or 2 $R^7$ groups; and all other groups are as defined in the Summary of the Invention or any of the embodiments described herein. In some or any embodiments, the compound of Formula I or II is that where $R^{1a}$ is naphthyl optionally substituted with 1 or 2 $R^7$ groups and each $R^7$, when present, is halo; and all other groups are as defined in the Summary of the Invention or any of the embodiments described herein. In some or any embodiments, the compound of Formula I or II is that where $R^{1a}$ is indanyl optionally substituted with 1 or 2 $R^7$ groups; and all other groups are as defined in the Summary of the Invention or any of the embodiments described herein. In some or any embodiments, the compound of Formula I or II is that where $R^{1a}$ is indanyl optionally substituted with 1 or 2 $R^7$ groups and each $R^7$, when present, is independently heteroaryl (in another example pyridinyl) or halo; and all other groups are as defined in the Summary of the Invention or any of the embodiments described herein. In some or any embodiments, the compound of Formula I or II is that where $R^{1a}$ is phenyl optionally substituted with 1, 2, or 3 $R^7$ groups; and all other groups are as defined in the Summary of the Invention or any of the embodiments described herein. In some or any embodiments, the compound of Formula I or II is that where $R^{1a}$ is phenyl optionally substituted with 1 or 2 $R^7$ groups and each $R^7$, when present, is independently halo, haloalkoxy, or heteroaryl (in another example pyridinyl); and all other groups are as defined in the Summary of the Invention or any of the embodiments described herein. In some or any embodiments, the compound of Formula I or II is that where $R^{1a}$ is phenyl optionally substituted with 1 or 2 $R^7$ groups and each $R^7$, when present, is independently aryl or heteroaryl; and all other groups are as defined in the Summary of the Invention or any of the embodiments described herein. In some or any embodiments, the compound of Formula I or II is that where $R^{1a}$ is phenyl optionally substituted with 1 or 2 $R^7$ groups and each $R^7$, when present, is independently phenyl or heteroaryl; and all other groups are as defined in the Summary of the Invention or any of the embodiments described herein.

In some or any embodiments, the compound of Formula I or II is that where $R^{1a}$ is heteroaryl optionally substituted with 1, 2, or 3 $R^7$ groups; and all other groups are as defined in the Summary of the Invention or any of the embodiments described herein. In some or any embodiments, the compound of Formula I or II is that where $R^{1a}$ is fused bicyclic heteroaryl optionally substituted with 1, 2, or 3 $R^7$ groups; and all other groups are as defined in the Summary of the Invention or any of the embodiments described herein. In some or any embodiments, the compound of Formula I or II is that where $R^{1a}$ is benzofuranyl, benzothienyl, indolyl, benzimidazolyl, 6,7-dihydro-5H-cyclopenta[b]pyridinyl, benzothiazolyl, furo[3,2-c]pyridinyl, pyrrolo[1,2-b]pyridazinyl, imidazo[1,2-a]pyridinyl, furo[3,2-b]pyridinyl, furo[2,3-d]pyrimidinyl, thieno[3,2-b]furanyl, thieno[2,3-d]oxazolyl, or furo[2,3-d]thiazolyl, each of which is optionally substituted with 1 or 2 $R^7$ groups; and all other groups are as defined in the Summary of the Invention or any of the embodiments described herein. In some or any embodiments, the compound of Formula I or II is that where $R^{1a}$ is benzofuranyl, benzothienyl, indolyl, benzimidazolyl, 6,7-dihydro-5H-cyclopenta[b]pyridinyl, or benzothiazolyl, each of which is optionally substituted with 1 or 2 $R^7$ groups; and all other groups are as defined in the Summary of the Invention or any of the embodiments described herein. In some or any embodiments, the compound of Formula I or II is that where $R^{1a}$ is benzofuranyl optionally substituted with 1 or 2 $R^7$ groups; and all other groups are as defined in the Summary of the Invention or any of the embodiments described herein.

In some or any embodiments, the compound of Formula I or II is that where $R^{1a}$ is fused bicyclic heteroaryl optionally substituted with 1, 2, or 3 $R^7$ groups where each $R^7$, when present, is independently halo, alkyl, or haloalkyl; and all other groups are as defined in the Summary of the Invention or any of the embodiments described herein. In some or any embodiments, the compound of Formula I or II is that where $R^{1a}$ is fused bicyclic heteroaryl optionally substituted with 1, 2, or 3 $R^7$ groups where each $R^7$, when present, is independently chloro, bromo, fluoro, methyl, or trifluoromethyl; and all other groups are as defined in the Summary of the Invention or any of the embodiments described herein.

In some or any embodiments, the compound of Formula I or II is that where $R^{1a}$ is fused tricyclic heteroaryl optionally substituted with 1, 2, or 3 $R^7$ groups; and all other groups are as defined in the Summary of the Invention or any of the embodiments described herein. In some or any embodiments, the compound of Formula I or II is that where $R^{1a}$ is 7,8-dihydro-6H-cyclopenta[g]quinoxalinyl; and all other groups are as defined in the Summary of the Invention or any of the embodiments described herein.

In some or any embodiments, the compound of Formula I or II is that where each $R^7$, when present, is independently optionally substituted with 1, 2 or 3 $R^{7a}$ groups, where each $R^{7a}$, when present, is independently cyano, halo, alkyl, alkenyl, haloalkyl, hydroxyalkyl, and cycloalkyl; and all other groups are as defined in the Summary of the Invention or any of the embodiments described herein. In some or any embodiments, the compound of Formula I or II is that where each $R^7$, when present, is aryl or heteroaryl, either alone or as part of another group, such aryl or heteroaryl is independently optionally substituted with 1, 2 or 3 $R^{7a}$ groups, as described herein. In some or any embodiments, the compound of Formula I or II is that where each $R^7$, when present, is phenyl or heteroaryl, either alone or as part of another group, such phenyl or heteroaryl is independently optionally substituted with 1, 2 or 3 $R^{7a}$ groups, as described herein.

In some or any embodiments, the compound of Formula I or II is that where $R^2$ is hydrogen, hydroxy, or alkyl; and $R^3$ is alkyl, aminoalkyl, alkylaminoalkyl, or dialkylaminoalkyl; and all other groups are as defined in the Summary of the Invention or any of the embodiments described herein. In some or any embodiments, the compound of Formula I or II is that where $R^2$ is hydroxy and $R^3$ is alkyl; and all other groups are as defined in the Summary of the Invention or any of the embodiments described herein.

In some or any embodiments, the compound of Formula I or II is that where $R^2$ and $R^3$ together with the nitrogen to which they are attached form a 3-10 membered heterocycloalkyl ring which is optionally substituted with 1, 2, 3, or 4 $R^8$; and all other groups are as defined in the Summary of the Invention or any of the embodiments described herein. In some or any embodiments, the compound of Formula I or II is that where $R^2$ and $R^3$ together with the nitrogen to which they are attached form a 4-8 membered heterocycloalkyl ring which is optionally substituted with 1, 2, 3, or 4 $R^8$; and all other groups are as defined in the Summary of the Invention or any of the embodiments described herein. In some or any embodiments, the compound of Formula I or II is that where $R^2$ and $R^3$ together with the nitrogen to which they are attached form azetidinyl, pyrrolidinyl, 2-azabicyclo[2.2.1]heptanyl, 7-azabicyclo[2.2.1]heptanyl, 2-azaspiro[3.3]heptanyl, 1-oxidopyrrolidinyl, piperidinyl, piperazinyl, or 8-azabicyclo[3.2.1]octanyl, each of which is optionally substituted with 1 or 2 $R^8$; and all other groups are as defined in the Summary of the Invention or any of the embodiments described herein. In some or any embodiments, the compound of Formula I or II is that where $R^2$ and $R^3$ together with the nitrogen to which they are attached form pyrrolidinyl optionally substituted with 1, 2, 3, or 4 $R^8$; and all other groups are as defined in the Summary of the Invention or any of the embodiments described herein. In some or any embodiments, the compound of Formula I or II is that where $R^2$ and $R^3$ together with the nitrogen to which they are attached form pyrrolidinyl optionally substituted with 1 or 2 $R^8$; and all other groups are as defined in the Summary of the Invention or any of the embodiments described herein. In some or any embodiments, the compound of Formula I or II is that where $R^2$ and $R^3$ together with the nitrogen to which they are attached form pyrrolidinyl optionally substituted with 1, 2, 3, or 4 $R^8$ where each $R^8$, when present, is independently deuterium, amino, alkyl, halo, or cycloalkyl; and all other groups are as defined in the Summary of the Invention or any of the embodiments described herein. In some or any embodiments, the compound of Formula I or II is that where $R^2$ and $R^3$ together with the nitrogen to which they are attached form unsubstituted pyrrolidinyl; and all other groups are as defined in the Summary of the Invention or any of the embodiments described herein. In some or any embodiments, the compound of Formula I or II is that where $R^2$ and $R^3$ together with the nitrogen to which they are attached form azetidinyl optionally substituted with 1 or 2 $R^8$; and all other groups are as defined in the Summary of the Invention or any of the embodiments described herein. In some or any embodiments, the compound of Formula I or II is that where $R^2$ and $R^3$ together with the nitrogen to which they are attached form azetidinyl optionally substituted with 1 or 2 $R^8$ where each $R^8$, when present, is independently alkyl; and all other groups are as defined in the Summary of the Invention or any of the embodiments described herein.

In some or any embodiments, the compound of Formula I or II is that where $R^2$ and $R^3$ together with the nitrogen to which they are attached form a 3-10 membered heterocycloalkyl ring which is optionally substituted with 1, 2, 3, or 4 $R^8$ where each $R^8$, when present, is independently deuterium, amino, alkyl, halo, or cycloalkyl; and all other groups are as defined in the Summary of the Invention or any of the embodiments described herein. In some or any embodiments, the compound of Formula I or II is that where $R^2$ and $R^3$ together with the nitrogen to which they are attached form a 3-10 membered heterocycloalkyl ring which is optionally substituted with 1, 2, 3, or 4 $R^8$ where each $R^8$, when present, is independently deuterium, amino, methyl, fluoro, or cyclopropyl; and all other groups are as defined in the Summary of the Invention or any of the embodiments described herein. In some or any embodiments, the compound of Formula I or II is that where $R^2$ and $R^3$ together with the nitrogen to which they are attached form a 3-10 membered heterocycloalkyl ring which is optionally substituted with 1 or 2 $R^8$ where each $R^8$, when present, is independently amino, methyl, fluoro, or cyclopropyl; and all other groups are as defined in the Summary of the Invention or any of the embodiments described herein.

In some or any embodiments, the compound of Formula I or II is that where $R^4$ is aryl optionally substituted with 1, 2, or 3 $R^9$ groups; and all other groups are as defined in the Summary of the Invention or any of the embodiments described herein. In some or any embodiments, the compound of Formula I or II is that where $R^4$ is phenyl optionally substituted with 1, 2, or 3 $R^9$ groups; and all other groups are as defined in the Summary of the Invention or any of the embodiments described herein. In some or any embodiments, the compound of Formula I or II is that where $R^4$ is phenyl optionally substituted with 1, 2, or 3 $R^9$ groups where each $R^9$, when present, is independently halo, alkyl, haloalkyl, haloalkoxy, cycloalkyloxy, heterocycloalkyloxy, or heterocycloalkylalkyloxy which is optionally substituted with one hydroxy; and all other groups are as defined in the Summary of the Invention or any of the embodiments described herein. In some or any embodiments, the compound of Formula I or II is that where $R^4$ is phenyl optionally substituted with 1 or 2 $R^9$ groups where each $R^9$, when present, is independently bromo, chloro, fluoro, methoxy, difluoromethyl, trifluoromethyl, trifluoromethoxy, cyclopropyloxy, tetrahydrofuranyloxy, or tetrahydropyranylmethyl which is optionally substituted with one hydroxy; and all other groups are as defined in the Summary of the Invention or any of the embodiments described herein. In some or any embodiments, the compound of Formula I or II is that where $R^4$ is phenyl optionally substituted with 2 $R^9$ groups one of which is halo, and one of which is alkoxy; and all other groups are as defined in the Summary of the Invention or any of the embodiments described herein.

In some or any embodiments, the compound of Formula I or II is that where $R^4$ is heteroaryl optionally substituted with 1, 2, or 3 $R^9$ groups; and all other groups are as defined in the Summary of the Invention or any of the embodiments described herein. In some or any embodiments, the compound of Formula I or II is that where $R^4$ is pyridinyl, 1H-indazolyl, benzofuranyl, 2,3-dihydrobenzo[b][1,4]dioxin-6-yl, or quinolinyl each of which is optionally substituted with 1 or 2 $R^9$ groups; and all other groups are as defined in the Summary of the Invention or any of the embodiments described herein. In some or any embodiments, the compound of Formula I or II is that where $R^4$ is pyridinyl, 1H-indazolyl, benzofuranyl, 2,3-dihydrobenzo[b][1,4]dioxin-6-yl, or quinolinyl; $R^9$, when present, is halo, alkyl, alkoxy, haloalkoxy, cycloalkyloxy, or heterocycloalkylalkyloxy which is optionally substituted with one hydroxy; and all other groups are as defined in the Summary of the Invention or any of the embodiments described herein. In some or any embodiments, the compound of Formula I or II is that where $R^4$ is pyridinyl, 1H-indazolyl, benzofuranyl, 2,3-dihydrobenzo[b][1,4]dioxin-6-yl, or quinolinyl; $R^9$, when present, is chloro, fluoro, methyl, methoxy, isopropoxy, 2,2,2-trifluoroethoxy, cyclopropyloxy, or tetrahydropyranylmethyl which is optionally substituted with one hydroxy; and all other groups are as defined in the Summary of the Invention or any of the embodiments described herein. In some or any embodiments, the compound of Formula I or II is that where $R^4$ is unsubstituted 2,3-dihydrobenzo[b][1,4]dioxin-6-yl; and all other groups are as defined in the Summary of the Invention or any of the embodiments described herein.

In some or any embodiments, the compound of Formula I or II is that where $R^5$ is $R^5$ is halo, —OH, —OTBS, —$N_3$, —$NH_2$, —NH(OCH$_3$), —NHC(O)CH$_3$, or —NHC(O)H and $R^{5a}$ is hydrogen, alkyl, or deuterium; or $R^5$ and $R^{5a}$ together with the carbon to which they are attached form C(O) or C(NOH); and all other groups are as defined in the Summary of the Invention or any of the embodiments described herein. In some or any embodiments, the compound of Formula I or II is that where $R^5$ is —OH, —$NH_2$, —NH(OCH$_3$), —NHC(O)CH$_3$, or —NHC(O)H and $R^{5a}$ is hydrogen, alkyl, or deuterium; or $R^5$ and $R^{5a}$ together with the carbon to which they are attached form C(O) or —C(NOH); and all other groups are as defined in the Summary of the Invention or any of the embodiments described herein. In some or any embodiments, the compound of Formula I or II is that where $R^5$ is OH and $R^{5a}$ is hydrogen; and all other groups are as defined in the Summary of the Invention or any of the embodiments described herein. In some or any embodiments, the compound of Formula I or II is that where $R^5$ is —$NH_2$ and $R^{5a}$ is hydrogen; and all other groups are as defined in the Summary of the Invention or any of the embodiments described herein. In some or any embodiments, the compound of Formula I or II is that where $R^5$ is OH and $R^{5a}$ is deuterium; and all other groups are as defined in the Summary of the Invention or any of the embodiments described herein. In some or any embodiments, the compound of Formula I or II is that where $R^5$ is —NH(OCH$_3$) and $R^{5a}$ is hydrogen; and all other groups are as defined in the Summary of the Invention or any of the embodiments described herein. In some or any embodiments, the compound of Formula I or II is that where $R^5$ is OH and $R^{5a}$ is alkyl; and all other groups are as defined in the Summary of the Invention or any of the embodiments described herein. In some or any embodiments, the compound of Formula I or II is that where $R^5$ is —NHC(O)H and $R^{5a}$ is hydrogen; and all other groups are as defined in the Summary of the Invention or any of the embodiments described herein. In some or any embodiments, the compound of Formula I or II is that where $R^5$ and $R^{5a}$ together with the carbon to which they are attached form C(O); and all other groups are as defined in the Summary of the Invention or any of the embodiments described herein. In some or any embodiments, the compound of Formula I or II is that where $R^5$ and $R^{5a}$ together with the carbon to which they are attached form C(NOH); and all other groups are as defined in the Summary of the Invention or any of the embodiments described herein. In some or any embodiments, the compound of Formula I or II is that where $R^5$ is OH and $R^{5a}$ is hydrogen, $R^5$ is —$NH_2$ and $R^{5a}$ is hydrogen, $R^5$ is OH and $R^{5a}$ is deuterium, $R^5$ is —NH(OCH$_3$) and $R^{5a}$ is hydrogen, $R^5$ is OH and $R^{5a}$ is alkyl, $R^5$ is —NHC(O)H and $R^{5a}$ is hydrogen, $R^5$ and $R^{5a}$ together with the carbon to which they are attached form C(O), or $R^5$ and $R^{5a}$ together with the carbon to which they are attached form C(NOH); and all other groups are as defined in the Summary of the Invention or any of the embodiments described herein.

In some or any embodiments, the compound of Formula I or II is that where $R^{10}$ is hydrogen; and all other groups are as defined in the Summary of the Invention or any of the embodiments described herein. In some or any embodiments, the compound of Formula I or II is that where $R^{10}$ is alkyl; and all other groups are as defined in the Summary of the Invention or any of the embodiments described herein. In some or any embodiments, the compound of Formula I or II is that where $R^{10}$ is methyl; and all other groups are as defined in the Summary of the Invention or any of the embodiments described herein. In some or any embodiments, the compound of Formula I or II is that where $R^{10}$ is phenyl; and all other groups are as defined in the Summary of the Invention or any of the embodiments described herein.

In some or any embodiments, the compound of Formula I is according to Formula I(a):

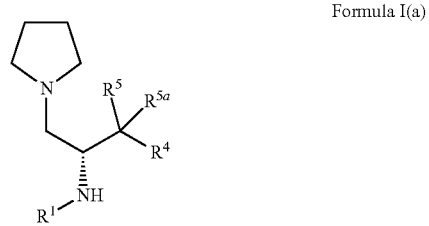

Formula I(a)

where all groups are as defined in the Summary of the Invention or as defined in any of the above embodiments. In another embodiment, the compound of Formula I(a) is that where $R^{5a}$ is hydrogen; and all other groups are as defined in the Summary of the Invention or as defined in any of the embodiments described herein. In another embodiment, the compound of Formula I(a) is that where $R^5$ is OH; and all other groups are as defined in the Summary of the Invention or as defined in any of the embodiments described herein. In another embodiment, the compound of Formula I(a) is that where $R^1$ is —C(O)C($R^6$)($R^{6a}$)$R^{1a}$; and all other groups are as defined in the Summary of the Invention or as defined in any of the embodiments described herein. In another embodiment, the compound of Formula I(a) is that where $R^4$ is heteroaryl optionally substituted with 1, 2, or 3 $R^9$ groups; and all other groups are as defined in the Summary of the Invention or as defined in any of the embodiments described herein. In another embodiment, the compound of Formula I(a) is that where $R^4$ is aryl optionally substituted with 1, 2, or 3 $R^9$ groups; and all other groups are as defined in the Summary of the Invention or as defined in any of the embodiments described herein. In another embodiment, the compound of Formula I(a) is that where $R^2$ and $R^3$ together with the nitrogen to which they are attached form a 3-10 membered heterocycloalkyl ring which is optionally substituted with 1, 2, or 3 $R^8$; and all other groups are as defined in the Summary of the Invention or as defined in any of the embodiments described herein.

In some or any embodiments, the compound of Formula I is according to Formula I(b) or I(c):

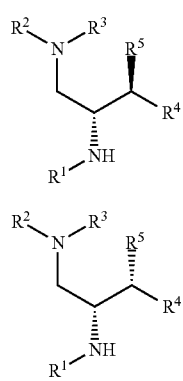

Formula I(b)

Formula I(c)

where all groups are as defined in the Summary of the Invention or as defined in any of the embodiments described herein. In another embodiment, the compound of Formula I(b) or I(c) is that where $R^5$ is OH; and all other groups are as defined in the Summary of the Invention or as defined in any of the embodiments described herein. In another embodiment, the compound of Formula I(b) or I(c) is that where $R^1$ is —C(O)C($R^6$)($R^{6a}$)$R^{1a}$; and all other groups are as defined in the Summary of the Invention or as defined in any of the embodiments described herein. In another embodiment, the compound of Formula I(b) or I(c) is that where $R^1$ is —C(O)C($R^6$)($R^{6a}$)$R^{1a}$; $R^{1a}$ is unsubstituted indanyl; and all other groups are as defined in the Summary of the Invention or as defined in any of the embodiments described herein. In another embodiment, the compound of Formula I(b) or I(c) is that where $R^4$ is heteroaryl optionally substituted with 1, 2, or 3 $R^9$ groups; and all other groups are as defined in the Summary of the Invention or as defined in any of the embodiments described herein. In another embodiment, the compound of Formula I(b) or I(c) is that where $R^4$ is aryl optionally substituted with 1, 2, or 3 $R^9$ groups; and all other groups are as defined in the Summary of the Invention or as defined in any of the embodiments described herein. In another embodiment, the compound of Formula I(b) or I(c) is that where $R^2$ and $R^3$ together with the nitrogen to which they are attached form a 3-10 membered heterocycloalkyl ring which is optionally substituted with 1, 2, or 3 $R^8$; and all other groups are as defined in the Summary of the Invention or as defined in any of the embodiments described herein.

In some or any embodiments, the compound of Formula I is according to Formula I(d):

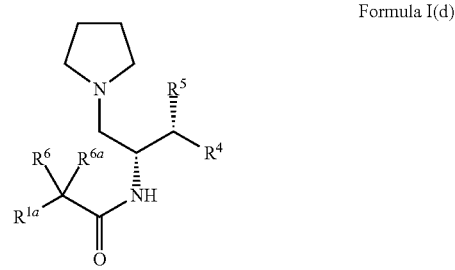

Formula I(d)

where all groups are as defined in the Summary of the Invention or as defined in any of the embodiments described herein. In another embodiment, the compound of Formula I(d) is that where $R^5$ is OH; and all other groups are as defined in the Summary of the Invention or as defined in any of the embodiments described herein. In another embodiment, the compound of Formula I(d) is that where $R^4$ is heteroaryl optionally substituted with 1, 2, or 3 $R^9$ groups; and all other groups are as defined in the Summary of the Invention or as defined in any of the embodiments described herein. In another embodiment, the compound of Formula I(d) is that where $R^4$ is aryl optionally substituted with 1, 2, or 3 $R^9$ groups; and all other groups are as defined in the Summary of the Invention or as defined in any of the embodiments described herein. In another embodiment, the compound of Formula I(d) is that where $R^2$ and $R^3$ together with the nitrogen to which they are attached form a 3-10 membered heterocycloalkyl ring which is optionally substituted with 1, 2, or 3 $R^8$; and all other groups are as defined in the Summary of the Invention or as defined in any of the embodiments described herein. In another embodiment, the compound of Formula I(d) is that where $R^6$ and $R^{6a}$ are halo; and all other groups are as defined in the Summary of the Invention or as defined in any of the embodiments described herein. In another embodiment, the compound of Formula I(d) is that where $R^{1a}$ is heteroaryl optionally substituted with 1, 2, or 3 $R^7$ groups; and all other groups are as defined in the Summary of the Invention or as defined in any of the embodiments described herein. In another embodiment, the compound of Formula I(d) is that where at least one $R^7$ is halo; and all other groups are as defined in the Summary of the Invention or as defined in any of the embodiments described herein.

In some or any embodiments, the compound of Formula I is according to Formula I(e):

Formula I(e)

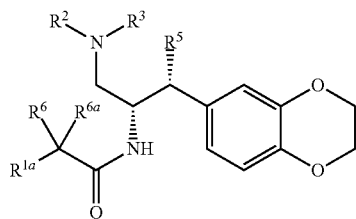

where all groups are as defined in the Summary of the Invention or as defined in any of the embodiments described herein. In another embodiment, the compound of Formula I(e) is that where $R^5$ is OH; and all other groups are as defined in the Summary of the Invention or as defined in any of the embodiments described herein. In another embodiment, the compound of Formula I(e) is that where $R^2$ and $R^3$ together with the nitrogen to which they are attached form a 3-10 membered heterocycloalkyl ring which is optionally substituted with 1, 2, or 3 $R^8$; and all other groups are as defined in the Summary of the Invention or as defined in any of the embodiments described herein. In another embodiment, the compound of Formula I(e) is that where $R^6$ and $R^{6a}$ are halo; and all other groups are as defined in the Summary of the Invention or as defined in any of the embodiments described herein. In another embodiment, the compound of Formula I(e) is that where $R^{1a}$ is heteroaryl optionally substituted with 1, 2, or 3 $R^7$ groups; and all other groups are as defined in the Summary of the Invention or as defined in any of the embodiments described herein. In another embodiment, the compound of Formula I(e) is that where at least one $R^7$ is halo; and all other groups are as defined in the Summary of the Invention or as defined in any of the embodiments described herein.

In some or any embodiments, the compound of Formula I is according to Formula I(f):

Formula I(f)

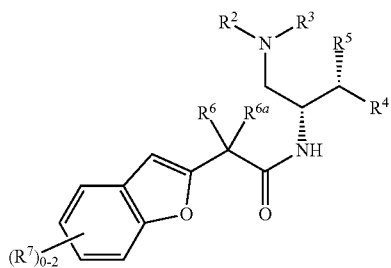

where all groups are as defined in the Summary of the Invention or as defined in any of the embodiments described herein. In another embodiment, the compound of Formula I(f) is that where $R^5$ is OH; and all other groups are as defined in the Summary of the Invention or as defined in any of the embodiments described herein. In another embodiment, the compound of Formula I(f) is that where $R^2$ and $R^3$ together with the nitrogen to which they are attached form a 3-10 membered heterocycloalkyl ring which is optionally substituted with 1, 2, or 3 $R^8$; and all other groups are as defined in the Summary of the Invention or as defined in any of the embodiments described herein. In another embodiment, the compound of Formula I(f) is that where $R^6$ and $R^{6a}$ are halo; and all other groups are as defined in the Summary of the Invention or as defined in any of the embodiments described herein. In another embodiment, the compound of Formula I(f) is that where at least one $R^7$ is halo; and all other groups are as defined in the Summary of the Invention or as defined in any of the embodiments described herein. In another embodiment, the compound of Formula I(f) is that where $R^4$ is heteroaryl optionally substituted with 1, 2, or 3 $R^9$ groups; and all other groups are as defined in the Summary of the Invention or as defined in any of the embodiments described herein. In another embodiment, the compound of Formula I(f) is that where $R^4$ is aryl optionally substituted with 1, 2, or 3 $R^9$ groups; and all other groups are as defined in the Summary of the Invention or as defined in any of the embodiments described herein.

In some or any embodiments, the compound of Formula I is according to Formula I(g):

Formula I(g)

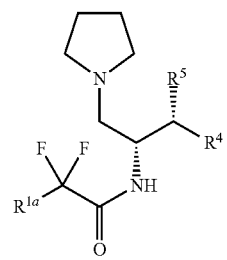

where all groups are as defined in the Summary of the Invention or as defined in any of the embodiments described herein. In another embodiment, the compound of Formula I(g) is that where $R^5$ is OH; and all other groups are as defined in the Summary of the Invention or as defined in any of the embodiments described herein. In another embodiment, the compound of Formula I(g) is that where $R^4$ is heteroaryl optionally substituted with 1, 2, or 3 $R^9$ groups; and all other groups are as defined in the Summary of the Invention or as defined in any of the embodiments described herein. In another embodiment, the compound of Formula I(g) is that where $R^4$ is unsubstituted 2,3-dihydrobenzo[b][1,4]dioxinyl; and all other groups are as defined in the Summary of the Invention or as defined in any of the embodiments described herein. In another embodiment, the compound of Formula I(g) is that where $R^4$ is aryl optionally substituted with 1, 2, or 3 $R^9$ groups; and all other groups are as defined in the Summary of the Invention or as defined in any of the embodiments described herein. In another embodiment, the compound of Formula I(g) is that where $R^{1a}$ is heteroaryl optionally substituted with 1, 2, or 3 $R^7$ groups; and all other groups are as defined in the Summary of the Invention or as defined in any of the embodiments described herein. In another embodiment, the compound of Formula I(g) is that where at least one $R^7$ is halo; and all other groups are as defined in the Summary of the Invention or as defined in any of the embodiments described herein. In another embodiment, the compound of Formula I(g) is that where $R^{1a}$ is benzofuranyl optionally substituted with 1, 2, or 3 $R^7$ groups; and all other groups are as defined in the Summary of the Invention or as defined in any of the embodiments described herein.

In some or any embodiments, the compound of Formula I is according to Formula I(s):

Formula I(s)

where all groups are as defined in the Summary of the Invention or as defined in any of the embodiments described herein. In another embodiment, the compound of Formula I(s) is that where $R^5$ is OH; and all other groups are as defined in the Summary of the Invention or as defined in any of the embodiments described herein. In another embodiment, the compound of Formula I(s) is that where $R^4$ is heteroaryl optionally substituted with 1, 2, or 3 $R^9$ groups; and all other groups are as defined in the Summary of the Invention or as defined in any of the embodiments described herein. In another embodiment, the compound of Formula I(s) is that where $R^4$ is unsubstituted 2,3-dihydrobenzo[b][1,4]dioxinyl; and all other groups are as defined in the Summary of the Invention or as defined in any of the embodiments described herein. In another embodiment, the compound of Formula I(s) is that where $R^4$ is aryl optionally substituted with 1, 2, or 3 $R^9$ groups; and all other groups are as defined in the Summary of the Invention or as defined in any of the embodiments described herein. In another embodiment, the compound of Formula I(s) is that where $R^{1a}$ is heteroaryl optionally substituted with 1, 2, or 3 $R^7$ groups; and all other groups are as defined in the Summary of the Invention or as defined in any of the embodiments described herein. In another embodiment, the compound of Formula I(s) is that where at least one $R^7$ is halo; and all other groups are as defined in the Summary of the Invention or as defined in any of the embodiments described herein. In another embodiment, the compound of Formula I(s) is that where $R^{1a}$ is benzofuranyl optionally substituted with 1, 2, or 3 $R^7$ groups; and all other groups are as defined in the Summary of the Invention or as defined in any of the embodiments described herein.

In another embodiment, the compound of Formula I(s) is that where $R^{1a}$ is benzothiophene optionally substituted with 1, 2, or 3 $R^7$ groups; and all other groups are as defined in the Summary of the Invention or as defined in any of the embodiments described herein. In another embodiment, the compound of Formula I(s) is that where $R^{1a}$ is aryl optionally substituted with 1, 2, or 3 $R^7$ groups; and all other groups are as defined in the Summary of the Invention or as defined in any of the embodiments described herein. In another embodiment, the compound of Formula I(s) is that where $R^{1a}$ is phenyl optionally substituted with 1, 2, or 3 $R^7$ groups; and all other groups are as defined in the Summary of the Invention or as defined in any of the embodiments described herein. In another embodiment, the compound of Formula I(s) is that where at least one $R^7$ is halo; and all other groups are as defined in the Summary of the Invention or as defined in any of the embodiments described herein. In another embodiment, the compound of Formula I(s) is that where $R^7$ is phenyl or heteroaryl optionally substituted with at least one $R^{7a}$; and all other groups are as defined in the Summary of the Invention or as defined in any of the embodiments described herein. In another embodiment, the compound of Formula I(s) is that where at least one $R^{7a}$ is halo; and all other groups are as defined in the Summary of the Invention or as defined in any of the embodiments described herein.

In some or any embodiments, the compound of Formula I is according to Formula I(t):

Formula I(t)

where all groups are as defined in the Summary of the Invention or as defined in any of the embodiments described herein. In another embodiment, the compound of Formula I(t) is that where $R^5$ is OH; and all other groups are as defined in the Summary of the Invention or as defined in any of the embodiments described herein. In another embodiment, the compound of Formula I(t) is that where $R^4$ is heteroaryl optionally substituted with 1, 2, or 3 $R^9$ groups; and all other groups are as defined in the Summary of the Invention or as defined in any of the embodiments described herein. In another embodiment, the compound of Formula I(t) is that where $R^4$ is unsubstituted 2,3-dihydrobenzo[b][1,4]dioxinyl; and all other groups are as defined in the Summary of the Invention or as defined in any of the embodiments described herein. In another embodiment, the compound of Formula I(t) is that where $R^4$ is aryl optionally substituted with 1, 2, or 3 $R^9$ groups; and all other groups are as defined in the Summary of the Invention or as defined in any of the embodiments described herein. In another embodiment, the compound of Formula I(t) is that where $R^{1a}$ is heteroaryl optionally substituted with 1, 2, or 3 $R^7$ groups; and all other groups are as defined in the Summary of the Invention or as defined in any of the embodiments described herein. In another embodiment, the compound of Formula I(t) is that where at least one $R^7$ is halo; and all other groups are as defined in the Summary of the Invention or as defined in any of the embodiments described herein. In another embodiment, the compound of Formula I(t) is that where $R^{1a}$ is benzofuranyl optionally substituted with 1, 2, or 3 $R^7$ groups; and all other groups are as defined in the Summary of the Invention or as defined in any of the embodiments described herein.

In some or any embodiments, the compound of Formula I is according to Formula I(u):

Formula I(u)

where all groups are as defined in the Summary of the Invention or as defined in any of the embodiments described herein. In another embodiment, the compound of Formula I(u) is that where $R^5$ is OH; and all other groups are as defined in the Summary of the Invention or as defined in any of the embodiments described herein. In another embodiment, the compound of Formula I(u) is that where $R^4$ is heteroaryl optionally substituted with 1, 2, or 3 $R^9$ groups; and all other groups are as defined in the Summary of the Invention or as defined in any of the embodiments described herein. In another embodiment, the compound of Formula I(u) is that where $R^4$ is unsubstituted 2,3-dihydrobenzo[b][1,4]dioxinyl; and all other groups are as defined in the Summary of the Invention or as defined in any of the embodiments described herein. In another embodiment, the compound of Formula I(u) is that where $R^4$ is aryl optionally substituted with 1, 2, or 3 $R^9$ groups; and all other groups are as defined in the Summary of the Invention or as defined in any of the embodiments described herein. In another embodiment, the compound of Formula I(u) is that where $R^{1a}$ is heteroaryl optionally substituted with 1, 2, or 3 $R^7$ groups; and all other groups are as defined in the Summary of the Invention or as defined in any of the embodiments described herein. In another embodiment, the compound of Formula I(u) is that where at least one $R^7$ is halo; and all other groups are as defined in the Summary of the Invention or as defined in any of the embodiments described herein. In another embodiment, the compound of Formula I(u) is that where $R^{1a}$ is benzofuranyl optionally substituted with 1, 2, or 3 $R^7$ groups; and all other groups are as defined in the Summary of the Invention or as defined in any of the embodiments described herein.

In some or any embodiments, the compound of Formula I is according to Formula I(v), Formula I(v'), or Formula I(v"):

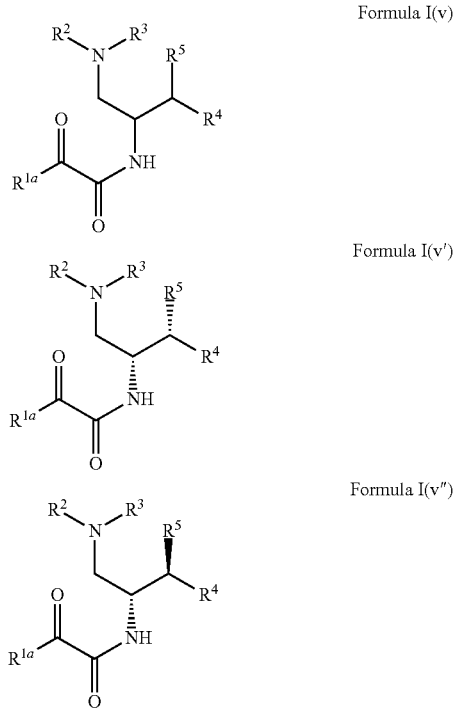

Formula I(v)

Formula I(v')

Formula I(v")

where all groups are as defined in the Summary of the Invention or as defined in any of the embodiments described herein. In another embodiment, the compound of Formula I(v), Formula I(v'), or Formula I(v") is that where $R^2$ and $R^3$ together with the nitrogen to which they are attached form a 3-10 membered heterocycloalkyl ring which is optionally substituted with 1, 2, or 3 $R^8$; and all other groups are as defined in the Summary of the Invention or as defined in any of the embodiments described herein. In another embodiment, the compound of Formula I(v), Formula I(v'), or Formula I(v") is that where $R^5$ is OH; and all other groups are as defined in the Summary of the Invention or as defined in any of the embodiments described herein. In another embodiment, the compound of Formula I(v), Formula I(v'), or Formula I(v") is that where $R^4$ is heteroaryl optionally substituted with 1, 2, or 3 $R^9$ groups; and all other groups are as defined in the Summary of the Invention or as defined in any of the embodiments described herein. In another embodiment, the compound of Formula I(v), Formula I(v'), or Formula I(v") is that where $R^4$ is unsubstituted 2,3-dihydrobenzo[b][1,4]dioxinyl; and all other groups are as defined in the Summary of the Invention or as defined in any of the embodiments described herein. In another embodiment, the compound of Formula I(v), Formula I(v'), or Formula I(v") is that where $R^4$ is aryl optionally substituted with 1, 2, or 3 $R^9$ groups; and all other groups are as defined in the Summary of the Invention or as defined in any of the embodiments described herein. In another embodiment, the compound of Formula I(v), Formula I(v'), or Formula I(v") is that where at least one $R^9$ is halo; and all other groups are as defined in the Summary of the Invention or as defined in any of the embodiments described herein. In another embodiment, the compound of Formula I(v), Formula I(v'), or Formula I(v") is that where at least one $R^9$ is alkoxy; and all other groups are as defined in the Summary of the Invention or as defined in any of the embodiments described herein. In another embodiment, the compound of Formula I(v), Formula I(v'), or Formula I(v") is that where $R^{1a}$ is heteroaryl optionally substituted with 1, 2, or 3 $R^7$ groups; and all other groups are as defined in the Summary of the Invention or as defined in any of the embodiments described herein. In another embodiment, the compound of Formula I(v), Formula I(v'), or Formula I(v") is that where $R^{1a}$ is benzofuranyl optionally substituted with 1, 2, or 3 $R^7$ groups; and all other groups are as defined in the Summary of the Invention or as defined in any of the embodiments described herein. In another embodiment, the compound of Formula I(v), Formula I(v'), or Formula I(v") is that where $R^{1a}$ is benzothiophene optionally substituted with 1, 2, or 3 $R^7$ groups; and all other groups are as defined in the Summary of the Invention or as defined in any of the embodiments described herein. In another embodiment, the compound of Formula I(v), Formula I(v'), or Formula I(v") is that where $R^{1a}$ is aryl optionally substituted with 1, 2, or 3 $R^7$ groups; and all other groups are as defined in the Summary of the Invention or as defined in any of the embodiments described herein. In another embodiment, the compound of Formula I(v), Formula I(v'), or Formula I(v") is that where $R^{1a}$ is phenyl optionally substituted with 1, 2, or 3 $R^7$ groups; and all other groups are as defined in the Summary of the Invention or as defined in any of the embodiments described herein. In another embodiment, the compound of Formula I(v), Formula I(v'), or Formula I(v") is that where at least one $R^7$ is halo; and all other groups are as defined in the Summary of the Invention or as defined in any of the embodiments described herein. In another embodiment, the compound of Formula I(v), Formula I(v'), or Formula I(v″) is that where $R^7$ is phenyl or heteroaryl optionally substituted with at least one $R^{7a}$; and all other groups are as defined in the Summary of the Invention or as defined in any of the embodiments described herein. In another embodiment, the compound of Formula I(v), Formula I(v′), or Formula I(v″) is that where at least one $R^{7a}$ is halo; and all other groups are as defined in the Summary of the Invention or as defined in any of the embodiments described herein.

In some or any embodiments, the compound of Formula I is according to Formula I(w), Formula I(w′), or Formula I(w″):

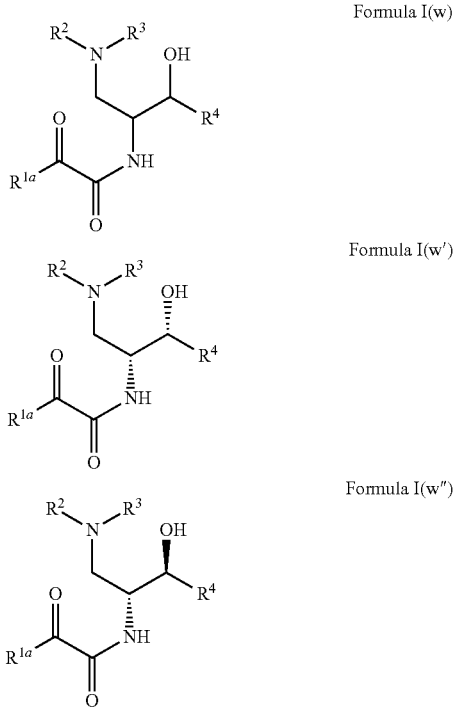

where all groups are as defined in the Summary of the Invention or as defined in any of the embodiments described herein. In another embodiment, the compound of Formula I(w), Formula I(w′), or Formula I(w″) is that where $R^2$ and $R^3$ together with the nitrogen to which they are attached form a 3-10 membered heterocycloalkyl ring which is optionally substituted with 1, 2, or 3 $R^8$; and all other groups are as defined in the Summary of the Invention or as defined in any of the embodiments described herein. In another embodiment, the compound of Formula I(w), Formula I(w′), or Formula I(w″) is that where $R^4$ is heteroaryl optionally substituted with 1, 2, or 3 $R^9$ groups; and all other groups are as defined in the Summary of the Invention or as defined in any of the embodiments described herein. In another embodiment, the compound of Formula I(w), Formula I(w′), or Formula I(w″) is that where $R^4$ is unsubstituted 2,3-dihydrobenzo[b][1,4]dioxinyl; and all other groups are as defined in the Summary of the Invention or as defined in any of the embodiments described herein. In another embodiment, the compound of Formula I(w), Formula I(w′), or Formula I(w″) is that where $R^4$ is aryl optionally substituted with 1, 2, or 3 $R^9$ groups; and all other groups are as defined in the Summary of the Invention or as defined in any of the embodiments described herein. In another embodiment, the compound of Formula I(w), Formula I(w′), or Formula I(w″) is that where at least one $R^9$ is halo; and all other groups are as defined in the Summary of the Invention or as defined in any of the embodiments described herein. In another embodiment, the compound of Formula I(w), Formula I(w′), or Formula I(w″) is that where at least one $R^9$ is alkoxy; and all other groups are as defined in the Summary of the Invention or as defined in any of the embodiments described herein. In another embodiment, the compound of Formula I(w), Formula I(w′), or Formula I(w″) is that where $R^{1a}$ is heteroaryl optionally substituted with 1, 2, or 3 $R^7$ groups; and all other groups are as defined in the Summary of the Invention or as defined in any of the embodiments described herein. In another embodiment, the compound of Formula I(w), Formula I(w′), or Formula I(w″) is that where $R^{1a}$ is benzofuranyl optionally substituted with 1, 2, or 3 $R^7$ groups; and all other groups are as defined in the Summary of the Invention or as defined in any of the embodiments described herein. In another embodiment, the compound of Formula I(w), Formula I(w′), or Formula I(w″) is that where $R^{1a}$ is benzothiophene optionally substituted with 1, 2, or 3 $R^7$ groups; and all other groups are as defined in the Summary of the Invention or as defined in any of the embodiments described herein. In another embodiment, the compound of Formula I(w), Formula I(w′), or Formula I(w″) is that where $R^{1a}$ is aryl optionally substituted with 1, 2, or 3 $R^7$ groups; and all other groups are as defined in the Summary of the Invention or as defined in any of the embodiments described herein. In another embodiment, the compound of Formula I(w), Formula I(w′), or Formula I(w″) is that where $R^{1a}$ is phenyl optionally substituted with 1, 2, or 3 $R^7$ groups; and all other groups are as defined in the Summary of the Invention or as defined in any of the embodiments described herein. In another embodiment, the compound of Formula I(w), Formula I(w′), or Formula I(w″) is that where at least one $R^7$ is halo; and all other groups are as defined in the Summary of the Invention or as defined in any of the embodiments described herein. In another embodiment, the compound of Formula I(w), Formula I(w′), or Formula I(w″) is that where $R^7$ is phenyl or heteroaryl optionally substituted with at least one $R^{7a}$; and all other groups are as defined in the Summary of the Invention or as defined in any of the embodiments described herein. In another embodiment, the compound of Formula I(w), Formula I(w′), or Formula I(w″) is that where at least one $R^{7a}$ is halo; and all other groups are as defined in the Summary of the Invention or as defined in any of the embodiments described herein.

In some or any embodiments, the compound of Formula I is according to Formula I(x), Formula I(x′), or Formula I(x″):

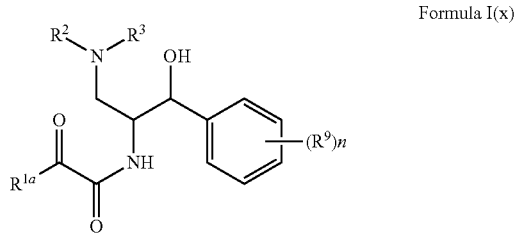

33

-continued

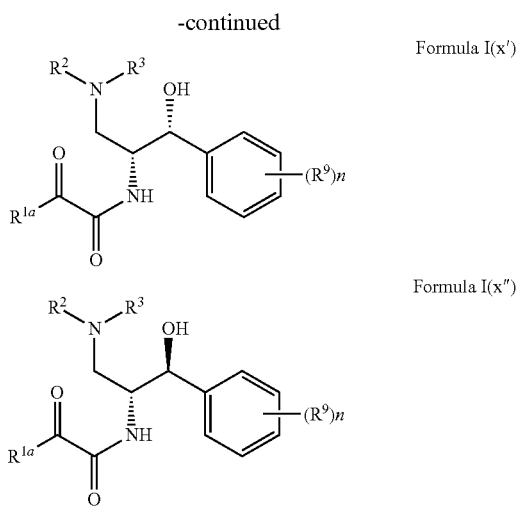

Formula I(x')

Formula I(x")

where all groups are as defined in the Summary of the Invention or as defined in any of the embodiments described herein. In another embodiment, the compound of Formula I(x), Formula I(x'), or Formula I(x") is that where $R^2$ and $R^3$ together with the nitrogen to which they are attached form a 3-10 membered heterocycloalkyl ring which is optionally substituted with 1, 2, or 3 $R^8$; and all other groups are as defined in the Summary of the Invention or as defined in any of the embodiments described herein. In another embodiment, the compound of Formula I(x), Formula I(x'), or Formula I(x") is that where at least one $R^9$ is halo; and all other groups are as defined in the Summary of the Invention or as defined in any of the embodiments described herein. In another embodiment, the compound of Formula I(x), Formula I(x'), or Formula I(x") is that where at least one $R^9$ is alkoxy; and all other groups are as defined in the Summary of the Invention or as defined in any of the embodiments described herein. In another embodiment, the compound of Formula I(v), Formula I(v'), or Formula I(v") is that where there are 2 $R^9$ groups, where one $R^9$ is halo and one $R^9$ is alkoxy, preferably cyclopropyloxy; and all other groups are as defined in the Summary of the Invention or as defined in any of the embodiments described herein. In another embodiment, the compound of Formula I(x), Formula I(x'), or Formula I(x") is that where $R^{1a}$ is heteroaryl optionally substituted with 1, 2, or 3 $R^7$ groups; and all other groups are as defined in the Summary of the Invention or as defined in any of the embodiments described herein. In another embodiment, the compound of Formula I(x), Formula I(x'), or Formula I(x") is that where $R^{1a}$ is benzofuranyl optionally substituted with 1, 2, or 3 $R^7$ groups; and all other groups are as defined in the Summary of the Invention or as defined in any of the embodiments described herein. In another embodiment, the compound of Formula I(x), Formula I(x'), or Formula I(x") is that where $R^{1a}$ is benzothiophene optionally substituted with 1, 2, or 3 $R^7$ groups; and all other groups are as defined in the Summary of the Invention or as defined in any of the embodiments described herein. In another embodiment, the compound of Formula I(x), Formula I(x'), or Formula I(x") is that where $R^{1a}$ is aryl optionally substituted with 1, 2, or 3 $R^7$ groups; and all other groups are as defined in the Summary of the Invention or as defined in any of the embodiments described herein. In another embodiment, the compound of Formula I(x), Formula I(x'), or Formula I(x") is that where $R^{1a}$ is phenyl optionally substituted with 1, 2, or 3 $R^7$ groups; and all other

34 groups are as defined in the Summary of the Invention or as defined in any of the embodiments described herein. In another embodiment, the compound of Formula I(x), Formula I(x'), or Formula I(x") is that where at least one $R^7$ is halo; and all other groups are as defined in the Summary of the Invention or as defined in any of the embodiments described herein. In another embodiment, the compound of Formula I(x), Formula I(x'), or Formula I(x") is that where $R^7$ is phenyl or heteroaryl optionally substituted with at least one $R^{7a}$; and all other groups are as defined in the Summary of the Invention or as defined in any of the embodiments described herein. In another embodiment, the compound of Formula I(x), Formula I(x'), or Formula I(x") is that where at least one $R^{7a}$ is halo; and all other groups are as defined in the Summary of the Invention or as defined in any of the embodiments described herein.

In some or any embodiments, the compound of Formula I is according to Formula I(y), Formula I(y'), or Formula I(y"):

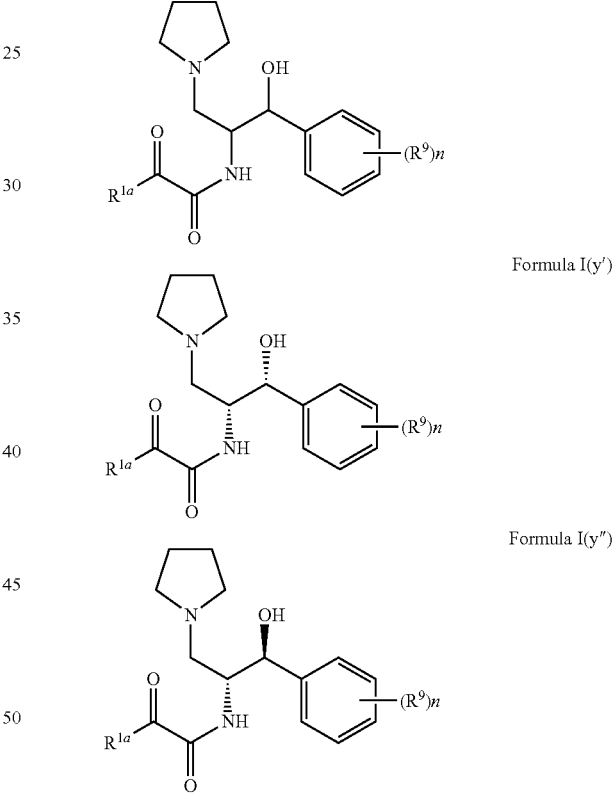

Formula I(y)

Formula I(y')

Formula I(y")

where all groups are as defined in the Summary of the Invention or as defined in any of the embodiments described herein. In another embodiment, the compound of Formula I(y), Formula I(y'), or Formula I(y") is that where at least one $R^9$ is halo; and all other groups are as defined in the Summary of the Invention or as defined in any of the embodiments described herein. In another embodiment, the compound of Formula I(y), Formula I(y'), or Formula I(y") is that where at least one $R^9$ is alkoxy; and all other groups are as defined in the Summary of the Invention or as defined in any of the embodiments described herein. In another embodiment, the compound of Formula I(v), Formula I(v'), or Formula I(v") is that where there are 2 $R^9$ groups, where one R$^9$ is halo and one R$^9$ is alkoxy, preferably cyclopropyloxy; and all other groups are as defined in the Summary of the Invention or as defined in any of the embodiments described herein. In another embodiment, the compound of Formula I(y), Formula I(y'), or Formula I(y") is that where R$^{1a}$ is heteroaryl optionally substituted with 1, 2, or 3 R$^7$ groups; and all other groups are as defined in the Summary of the Invention or as defined in any of the embodiments described herein. In another embodiment, the compound of Formula I(y), Formula I(y'), or Formula I(y") is that where R$^{1a}$ is benzofuranyl optionally substituted with 1, 2, or 3 R$^7$ groups; and all other groups are as defined in the Summary of the Invention or as defined in any of the embodiments described herein. In another embodiment, the compound of Formula I(y), Formula I(y'), or Formula I(y") is that where R$^{1a}$ is benzothiophene optionally substituted with 1, 2, or 3 R$^7$ groups; and all other groups are as defined in the Summary of the Invention or as defined in any of the embodiments described herein. In another embodiment, the compound of Formula I(y), Formula I(y'), or Formula I(y") is that where R$^{1a}$ is aryl optionally substituted with 1, 2, or 3 R$^7$ groups; and all other groups are as defined in the Summary of the Invention or as defined in any of the embodiments described herein. In another embodiment, the compound of Formula I(y), Formula I(y'), or Formula I(y") is that where R$^{1a}$ is phenyl optionally substituted with 1, 2, or 3 R$^7$ groups; and all other groups are as defined in the Summary of the Invention or as defined in any of the embodiments described herein. In another embodiment, the compound of Formula I(y), Formula I(y'), or Formula I(y") is that where at least one R$^7$ is halo; and all other groups are as defined in the Summary of the Invention or as defined in any of the embodiments described herein. In another embodiment, the compound of Formula I(y), Formula I(y'), or Formula I(y") is that where R$^7$ is phenyl or heteroaryl optionally substituted with at least one R$^{7a}$; and all other groups are as defined in the Summary of the Invention or as defined in any of the embodiments described herein. In another embodiment, the compound of Formula I(y), Formula I(y'), or Formula I(y") is that where at least one R$^{7a}$ is halo; and all other groups are as defined in the Summary of the Invention or as defined in any of the embodiments described herein.

In some or any embodiments, the compound of Formula I is according to Formula I(z), Formula I(z'), or Formula I(z"):

Formula I(z)

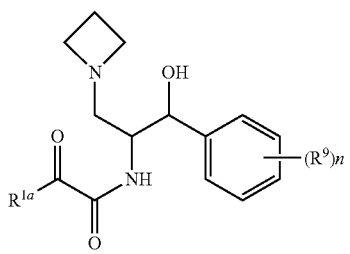

Formula I(z')

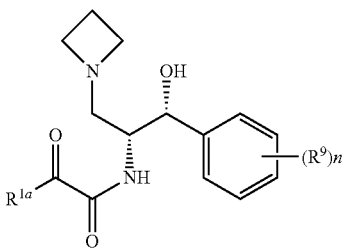

Formula I(z")

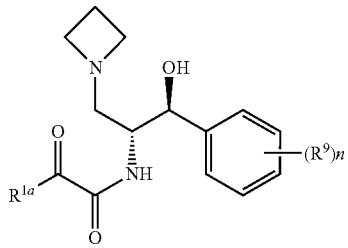

where all groups are as defined in the Summary of the Invention or as defined in any of the embodiments described herein. In another embodiment, the compound of Formula I(z), Formula I(z'), or Formula I(z") is that where at least one R$^9$ is halo; and all other groups are as defined in the Summary of the Invention or as defined in any of the embodiments described herein. In another embodiment, the compound of Formula I(z), Formula I(z'), or Formula I(z") is that where at least one R$^9$ is alkoxy; and all other groups are as defined in the Summary of the Invention or as defined in any of the embodiments described herein. In another embodiment, the compound of Formula I(v), Formula I(v'), or Formula I(v") is that where there are 2 R$^9$ groups, where one R$^9$ is halo and one R$^9$ is alkoxy, preferably cyclopropyloxy; and all other groups are as defined in the Summary of the Invention or as defined in any of the embodiments described herein. In another embodiment, the compound of Formula I(z), Formula I(z'), or Formula I(z") is that where R$^{1a}$ is heteroaryl optionally substituted with 1, 2, or 3 R$^7$ groups; and all other groups are as defined in the Summary of the Invention or as defined in any of the embodiments described herein. In another embodiment, the compound of Formula I(z), Formula I(z'), or Formula I(z") is that where R$^{1a}$ is benzofuranyl optionally substituted with 1, 2, or 3 R$^7$ groups; and all other groups are as defined in the Summary of the Invention or as defined in any of the embodiments described herein. In another embodiment, the compound of Formula I(z), Formula I(z'), or Formula I(z") is that where R$^{1a}$ is benzothiophene optionally substituted with 1, 2, or 3 R$^7$ groups; and all other groups are as defined in the Summary of the Invention or as defined in any of the embodiments described herein. In another embodiment, the compound of Formula I(z), Formula I(z'), or Formula I(z") is that where R$^{1a}$ is aryl optionally substituted with 1, 2, or 3 R$^7$ groups; and all other groups are as defined in the Summary of the Invention or as defined in any of the embodiments described herein. In another embodiment, the compound of Formula I(z), Formula I(z'), or Formula I(z") is that where R$^{1a}$ is phenyl optionally substituted with 1, 2, or 3 R$^7$ groups; and all other groups are as defined in the Summary of the Invention or as defined in any of the embodiments described herein. In another embodiment, the compound of Formula I(z), Formula I(z'), or Formula I(z") is that where at least one R$^7$ is halo; and all other groups are as defined in the Summary of the Invention or as defined in any of the embodiments described herein. In another embodiment, the compound of Formula I(z), Formula I(z'), or Formula I(z") is that where R$^7$ is phenyl or heteroaryl optionally substituted with at least one R$^{7a}$; and all other groups are as defined in the Summary of the Invention or as defined in any of the embodiments described herein. In another embodiment, the compound of Formula I(z), Formula I(z'), or Formula I(z") is that where at least one R$^{7a}$ is halo; and all other groups are as defined in the Summary of the Invention or as defined in any of the embodiments described herein.

In some or any embodiments, the compound of Formula I is according to Formula I(aa), Formula I(ab), Formula I(ac), Formula I(ad), or Formula I(ae):

Formula I(aa)

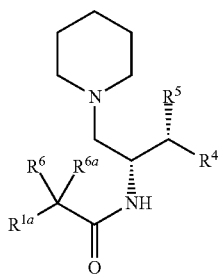

Formula I(ab)

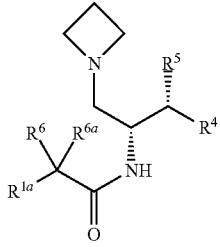

Formula I(ac)

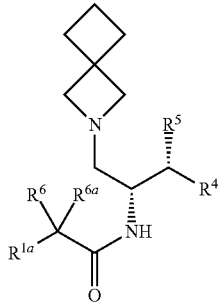

Formula I(ad)

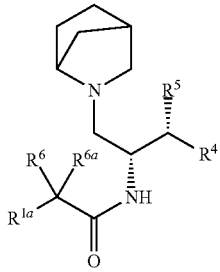

Formula I(ae)

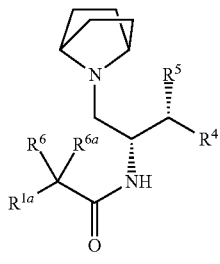

where all groups are as defined in the Summary of the Invention or as defined in any of the embodiments described herein. In another embodiment, the compound of Formula I(aa), Formula I(ab), Formula I(ac), Formula I(ad), or Formula I(ae) is that where $R^5$ is OH; and all other groups are as defined in the Summary of the Invention or as defined in any of the embodiments described herein. In another embodiment, the compound of Formula I(aa), Formula I(ab), Formula I(ac), Formula I(ad), or Formula I(ae) is that where $R^4$ is heteroaryl optionally substituted with 1, 2, or 3 $R^9$ groups; and all other groups are as defined in the Summary of the Invention or as defined in any of the embodiments described herein. In another embodiment, the compound of Formula I(aa), Formula I(ab), Formula I(ac), Formula I(ad), or Formula I(ae) is that where $R^4$ is aryl optionally substituted with 1, 2, or 3 $R^9$ groups; and all other groups are as defined in the Summary of the Invention or as defined in any of the embodiments described herein. In another embodiment, the compound of Formula I(aa), Formula I(ab), Formula I(ac), Formula I(ad), or Formula I(ae) is that where $R^2$ and $R^3$ together with the nitrogen to which they are attached form a 3-10 membered heterocycloalkyl ring which is optionally substituted with 1, 2, or 3 $R^8$; and all other groups are as defined in the Summary of the Invention or as defined in any of the embodiments described herein. In another embodiment, the compound of Formula I(aa), Formula I(ab), Formula I(ac), Formula I(ad), or Formula I(ae) is that where $R^6$ and $R^{6a}$ are halo; and all other groups are as defined in the Summary of the Invention or as defined in any of the embodiments described herein. In another embodiment, the compound of Formula I(aa), Formula I(ab), Formula I(ac), Formula I(ad), or Formula I(ae) is that where $R^{1a}$ is heteroaryl optionally substituted with 1, 2, or 3 $R^7$ groups; and all other groups are as defined in the Summary of the Invention or as defined in any of the embodiments described herein. In another embodiment, the compound of Formula I(aa), Formula I(ab), Formula I(ac), Formula I(ad), or Formula I(ae) is that where at least one $R^7$ is halo; and all other groups are as defined in the Summary of the Invention or as defined in any of the embodiments described herein.

In some or any embodiments, the compound of Formula I is according to Formula I(af), Formula I(ag), Formula I(ah), Formula I(ai), Formula I(aj), or Formula I(ak):

Formula I(af)

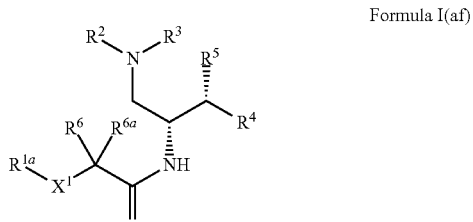

Formula I(ag)

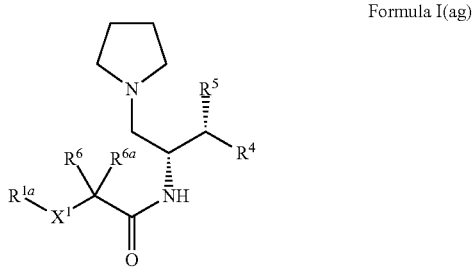

-continued

Formula I(ah)
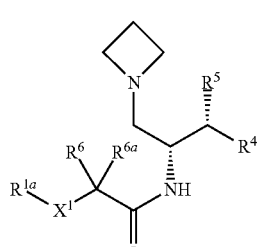

Formula I(ai)
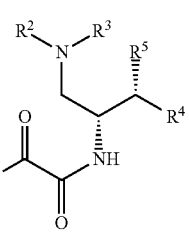

Formula I(aj)
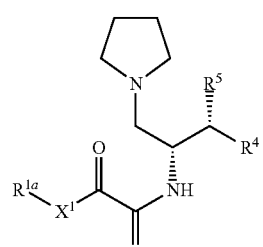

Formula I(ak)
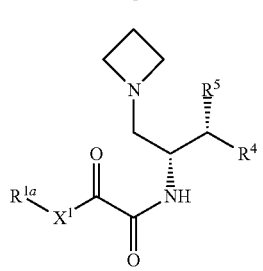

where all groups are as defined in the Summary of the Invention or as defined in any of the embodiments described herein. In another embodiment, the compound of Formula I(af), Formula I(ag), Formula I(ah), Formula I(ai), Formula I(aj), or Formula I(ak) is that where $X^1$ is alkylene or alkenylene; and all other groups are as defined in the Summary of the Invention or as defined in any of the embodiments described herein. In another embodiment, the compound of Formula I(af), Formula I(ag), Formula I(ah), Formula I(ai), Formula I(aj), or Formula I(ak) is that where $R^5$ is OH; and all other groups are as defined in the Summary of the Invention or as defined in any of the embodiments described herein. In another embodiment, the compound of Formula I(af), Formula I(ag), Formula I(ah), Formula I(ai), Formula I(aj), or Formula I(ak) is that where $R^4$ is heteroaryl optionally substituted with 1, 2, or 3 $R^9$ groups; and all other groups are as defined in the Summary of the Invention or as defined in any of the embodiments described herein. In another embodiment, the compound of Formula I(af), Formula I(ag), Formula I(ah), Formula I(ai), Formula I(aj), or Formula I(ak) is that where $R^4$ is aryl optionally substituted with 1, 2, or 3 $R^9$ groups; and all other groups are as defined in the Summary of the Invention or as defined in any of the embodiments described herein. In another embodiment, the compound of Formula I(af) or Formula I(ai) is that where $R^2$ and $R^3$ together with the nitrogen to which they are attached form a 3-10 membered heterocycloalkyl ring which is optionally substituted with 1, 2, or 3 $R^8$; and all other groups are as defined in the Summary of the Invention or as defined in any of the embodiments described herein. In another embodiment, the compound of Formula I(af), Formula I(ag), or Formula I(ah), is that where $R^6$ and $R^{6a}$ are halo; and all other groups are as defined in the Summary of the Invention or as defined in any of the embodiments described herein. In another embodiment, the compound of Formula I(af), Formula I(ag), Formula I(ah), Formula I(ai), Formula I(aj), or Formula I(ak) is that where $R^{1a}$ is aryl or heteroaryl optionally substituted with 1, 2, or 3 $R^7$ groups; and all other groups are as defined in the Summary of the Invention or as defined in any of the embodiments described herein. In another embodiment, the compound of Formula I(af), Formula I(ag), Formula I(ah), Formula I(ai), Formula I(aj), or Formula I(ak) is that where at least one $R^7$ is halo; and all other groups are as defined in the Summary of the Invention or as defined in any of the embodiments described herein.

In some or any embodiments, the compound of Formula I is according to Formula I(al), Formula I(am), Formula I(an), or Formula I(ao):

Formula I(al)
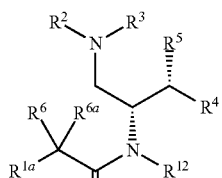

Formula I(am)
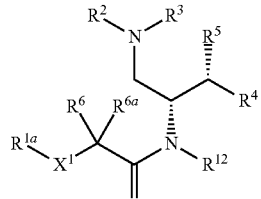

Formula I(an)
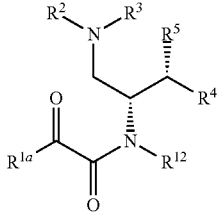

Formula I(ao)
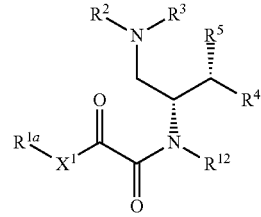

where all groups are as defined in the Summary of the Invention or as defined in any of the embodiments described herein. In another embodiment, the compound of Formula I(am) or Formula I(ao) is that where $X^1$ is alkylene or alkenylene; and all other groups are as defined in the Summary of the Invention or as defined in any of the embodiments described herein. In another embodiment, the compound of Formula I(al), Formula I(am), Formula I(an), or Formula I(ao) is that where $R^5$ is OH; and all other groups are as defined in the Summary of the Invention or as defined in any of the embodiments described herein. In another embodiment, the compound of Formula I(al), Formula I(am), Formula I(an), or Formula I(ao) is that where $R^4$ is heteroaryl optionally substituted with 1, 2, or 3 $R^9$ groups; and all other groups are as defined in the Summary of the Invention or as defined in any of the embodiments described herein. In another embodiment, the compound of Formula I(al), Formula I(am), Formula I(an), or Formula I(ao) is that where $R^4$ is aryl optionally substituted with 1, 2, or 3 $R^9$ groups; and all other groups are as defined in the Summary of the Invention or as defined in any of the embodiments described herein. In another embodiment, the compound of Formula I(al), Formula I(am), Formula I(an), or Formula I(ao) is that where $R^2$ and $R^3$ together with the nitrogen to which they are attached form a 3-10 membered heterocycloalkyl ring which is optionally substituted with 1, 2, or 3 $R^8$; and all other groups are as defined in the Summary of the Invention or as defined in any of the embodiments described herein. In another embodiment, the compound of Formula I(al) or Formula I(am) is that where $R^6$ and $R^{6a}$ are halo; and all other groups are as defined in the Summary of the Invention or as defined in any of the embodiments described herein. In another embodiment, the compound of Formula I(al), Formula I(am), Formula I(an), or Formula I(ao) is that where $R^{1a}$ is aryl or heteroaryl optionally substituted with 1, 2, or 3 $R^7$ groups; and all other groups are as defined in the Summary of the Invention or as defined in any of the embodiments described herein. In another embodiment, the compound of Formula I(al), Formula I(am), Formula I(an), or Formula I(ao) is that where at least one $R^7$ is halo; and all other groups are as defined in the Summary of the Invention or as defined in any of the embodiments described herein. In another embodiment, the compound of Formula I(al), Formula I(am), Formula I(an), or Formula I(ao) is that where at least one $R^{12}$ is $CH_3$; and all other groups are as defined in the Summary of the Invention or as defined in any of the embodiments described herein.

In some or any embodiments, the compound is that of any one of Examples 1-74.

In some or any embodiments, the compound is that of any one of Examples 77-383.

In some or any embodiments, the compound is that of any one of Examples 384-478.

In some or any embodiments, the compound is selected from Table 1.

In some or any embodiments, the compound is selected from Table 2.

In some or any embodiments, the compound is selected from Table 3.

In some or any embodiments, the compound is selected from Table 1, where $R^{1a}$ is aryl, which is optionally substituted with 1, 2, or 3 $R^7$ groups.

In some or any embodiments, the compound is selected from Table 1, where $R^{1a}$ is heterocycloalkyl, which is optionally substituted with 1, 2, or 3 $R^7$ groups.

In some or any embodiments, the compound is selected from Table 1, where $R^{1a}$ is heteroaryl, which is optionally substituted with 1, 2, or 3 $R^7$ groups.

In some or any embodiments, the compound is selected from Table 1, where $R^2$ and $R^3$ together with the nitrogen to which they are attached form a 4-5 membered monocyclic heterocycloalkyl ring, which is optionally substituted with 1 or 2 $R^8$.

In some or any embodiments, the compound is selected from Table 1, where $R^2$ and $R^3$ together with the nitrogen to which they are attached form a 7-8 membered bicyclic heterocycloalkyl ring, which is optionally substituted with 1 or 2 $R^8$.

In some or any embodiments, the compound is selected from Table 1, where $R^4$ is aryl, which is optionally substituted with 1, 2, or 3 $R^9$ groups.

In some or any embodiments, the compound is selected from Table 1, where $R^4$ is heteroaryl, which is optionally substituted with 1, 2, or 3 $R^9$ groups.

In some or any embodiments, the compound is selected from Table 1, where $R^5$ is —OH.

In some or any embodiments, the compound is selected from Table 1, where $R^6$ and $R^{6a}$ together with the carbon to which they are attached form C(O).

In some or any embodiments, the compound is selected from Table 2, where $R^{1a}$ is heterocycloalkyl, which is optionally substituted with 1, 2, or 3 $R^7$ groups.

In some or any embodiments, the compound is selected from Table 2, where $R^{1a}$ is heteroaryl, which is optionally substituted with 1, 2, or 3 $R^7$ groups.

In some or any embodiments, the compound is selected from Table 2, where $R^2$ and $R^3$ together with the nitrogen to which they are attached form a 4-5 membered monocyclic heterocycloalkyl ring, which is optionally substituted with 1 or 2 $R^8$.

In some or any embodiments, the compound is selected from Table 2, where $R^2$ and $R^3$ together with the nitrogen to which they are attached form a 7-8 membered bicyclic heterocycloalkyl ring, which is optionally substituted with 1 or 2 $R^8$.

In some or any embodiments, the compound is selected from Table 2, where $R^4$ is aryl, which is optionally substituted with 1, 2, or 3 $R^9$ groups.

In some or any embodiments, the compound is selected from Table 2, where $R^4$ is heteroaryl, which is optionally substituted with 1, 2, or 3 $R^9$ groups.

In some or any embodiments, the compound is selected from Table 2, where $R^5$ is —OH.

In some or any embodiments, the compound is selected from Table 2, where $R^6$ and $R^{6a}$ together with the carbon to which they are attached form C(O).

In some or any embodiments, the compound is selected from Table 3, where $R^{1a}$ is heterocycloalkyl, which is optionally substituted with 1, 2, or 3 $R^7$ groups.

In some or any embodiments, the compound is selected from Table 3, where $R^{1a}$ is heteroaryl, which is optionally substituted with 1, 2, or 3 $R^7$ groups.

In some or any embodiments, the compound is selected from Table 3, where $R^2$ and $R^3$ together with the nitrogen to which they are attached form a 4-5 membered monocyclic heterocycloalkyl ring, which is optionally substituted with 1 or 2 $R^8$.

In some or any embodiments, the compound is selected from Table 3, where $R^2$ and $R^3$ together with the nitrogen to which they are attached form a 7-8 membered bicyclic heterocycloalkyl ring, which is optionally substituted with 1 or 2 $R^8$.

In some or any embodiments, the compound is selected from Table 3, where $R^4$ is aryl, which is optionally substituted with 1, 2, or 3 $R^9$ groups.

In some or any embodiments, the compound is selected from Table 3, where $R^4$ is heteroaryl, which is optionally substituted with 1, 2, or 3 $R^9$ groups.

In some or any embodiments, the compound is selected from Table 3, where $R^5$ is —OH.

In some or any embodiments, the compound is selected from Table 3, where $R^6$ and $R^{6a}$ together with the carbon to which they are attached form C(O).

In some or any embodiments, provided is a pharmaceutical composition comprising 1) a Compound of Formula I, I(a), I(b), I(c), I(d), I(e), I(f), I(g), I(h), I(j), I(k), I(m), I(n), I(p), I(q), I(r), I(s), I(t), I(u), I(v), I(v'), I(v''), I(w), I(w'), I(w''), I(x), I(x'), I(x''), I(y), I(y'), I(y''), I(z), I(z'), I(z''), I(aa), I(ab), I(ac), I(ad), I(ae), I(af), I(ag), I(ah), I(ai), I(aj), I(ak), I(al), I(am), I(an), or I(ao) or a compound in Table 1, 2, or 3, optionally as a tautomer, a single stereoisomer or mixture of stereoisomers thereof and additionally optionally as a pharmaceutically acceptable salt thereof, and 2) a pharmaceutically acceptable excipient or pharmaceutically acceptable carrier.

Pharmaceutical Composition/Formulation

In some or any embodiments, optionally in combination with any or all of the above various embodiments, provided herein is a pharmaceutical composition comprising of a compound of Formula I, I(a), I(b), I(c), I(d), I(e), I(f), I(g), I(h), I(j), I(k), I(m), I(n), I(p), I(q), I(r), I(s), I(t), I(u), I(v), I(v'), I(v''), I(w), I(w'), I(w''), I(x), I(x'), I(x''), I(y), I(y'), I(y''), I(z), I(z'), I(z''), I(aa), I(ab), I(ac), I(ad), I(ae), I(af), I(ag), I(ah), I(ai), I(aj), I(ak), I(al), I(am), I(an), or I(ao), or a compound of Table 1, 2, or 3, or stereoisomers, or a pharmaceutically acceptable salt, and one or more pharmaceutically acceptable carrier(s), excipient(s), binder(s) or diluent(s). The pharmaceutical compositions can, moreover, contain preservatives, solubilizers, stabilizers, wetting agents, emulsifiers, sweeteners, colorants, flavorants, salts for varying the osmotic pressure, buffers, coating agents or antioxidants.

In some or any embodiments, disclosed herein is a pharmaceutical composition comprising a compound, pharmaceutically acceptable salt, pharmaceutically acceptable N-oxide, pharmaceutically active metabolite, pharmaceutically acceptable prodrug, or pharmaceutically acceptable solvate of any of the compounds disclosed herein. In some embodiments, the pharmaceutical compositions further comprises a pharmaceutically acceptable diluent, excipient or binder.

In some or any embodiments, pharmaceutical compositions are formulated in any manner, including using one or more physiologically acceptable carriers comprising excipients and/or auxiliaries which facilitate processing of the active compounds into pharmaceutical preparations. In some embodiments, proper formulation is dependent upon the route of administration chosen. In various embodiments, any techniques, carriers, and excipients are used as suitable.

A pharmaceutical composition, as used herein, refers to a mixture of a compound described herein with other chemical components, such as carriers, stabilizers, diluents, dispersing agents, suspending agents, thickening agents, and/or excipients. In some or any embodiments, a pharmaceutical composition facilitates administration of the compound to an organism. In some embodiments, practicing the methods of treatment or use provided herein, includes administering or using a pharmaceutical composition comprising a therapeutically effective amount of a compound provided herein. In specific embodiments, the methods of treatment provided for herein include administering such a pharmaceutical composition to a mammal having a disease or condition to be treated. In one embodiment, the mammal is a human. In some embodiments, the therapeutically effective amount varies widely depending on the severity of the disease, the age and relative health of the subject, the potency of the compound used and other factors. In various embodiments, the compounds described herein are used singly or in combination with one or more therapeutic agents as components of mixtures.

In a some or any embodiment, it is provided a method of forming a composition, comprising providing a compound and forming the composition. In some embodiments, the composition further comprises a pharmaceutically acceptable carrier. In some embodiments of the composition, optionally in combination with any or all of the above various embodiments, the composition is formulated in a formulation for local or systemic delivery. Examples of such formulations are formulations for oral administration, injection, topical administration, pulmonary administration, or implant. In some or any embodiments, the compound is according to any of the various embodiments described above or below.

In some or any embodiments, the pharmaceutical compositions provided herein are formulated for intravenous injections. In certain aspects, the intravenous injection formulations provided herein are formulated as aqueous solutions, and, in some embodiments, in physiologically compatible buffers such as Hank's solution, Ringer's solution, or physiological saline buffer. In certain embodiments, the pharmaceutical compositions provided herein are formulated for transmucosal administration. In some aspects, transmucosal formulations include penetrants appropriate to the barrier to be permeated. In certain embodiments, the pharmaceutical compositions provided herein are formulated for other parenteral injections, appropriate formulations include aqueous or nonaqueous solutions, and in one embodiment, with physiologically compatible buffers or excipients.

In some or any embodiments, the pharmaceutical compositions provided herein are formulated for oral administration. In certain aspects, the oral formulations provided herein comprise compounds described herein that are formulated with pharmaceutically acceptable carriers or excipients. Such carriers enable the compounds described herein to be formulated as tablets, powders, pills, dragees, capsules, liquids, gels, syrups, elixirs, slurries, suspensions and the like, for oral ingestion by a patient to be treated.

In some or any embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. I(f) desired, disintegrating agents are optionally added, such as the cross-linked croscarmellose sodium, polyvinylpyrrolidone, agar, or alginic acid or a salt thereof such as sodium alginate.

In some or any embodiments, provided herein is a pharmaceutical composition formulated as dragee cores with suitable coatings. In some or any embodiments, concentrated sugar solutions are used in forming the suitable coating, and optionally contain gum arabic, talc, polyvinylpyrrolidone, carbopol gel, polyethylene glycol, and/or titanium dioxide, lacquer solutions, and suitable organic solvents or solvent mixtures. In some embodiments, dyestuffs and/or pigments are added to tablets, dragees and/or the coatings thereof for, e.g., identification or to characterize different combinations of active compound doses.

In some or any embodiments, pharmaceutical preparations which are used include orally include push-fit capsules made of gelatin, as well as soft, sealed capsules made of gelatin and a plasticizer, such as glycerol or sorbitol. In some embodiments, the push-fit capsules contain the active ingredients in admixture with filler such as lactose, binders such as starches, and/or lubricants such as talc or magnesium stearate and, optionally, stabilizers. In some or any embodiments, in soft capsules, the active compounds are dissolved or suspended in suitable liquids, such as fatty oils, liquid paraffin, or liquid polyethylene glycols. In addition, stabilizers are optionally added. In some or any embodiments, the formulations for oral administration are in dosages suitable for such administration.

In some or any embodiments, the pharmaceutical compositions provided herein are formulated for buccal or sublingual administration. In some or any embodiments, buccal or sublingual compositions take the form of tablets, lozenges, or gels formulated in a conventional manner. In some or any embodiments, parenteral injections involve bolus injection or continuous infusion. In some embodiments, formulations for injection are presented in unit dosage form, e.g., in ampoules or in multi-dose containers, with an added preservative. In some embodiments, the pharmaceutical composition described herein is in a form suitable for parenteral injection as a sterile suspensions, solutions or emulsions in oily or aqueous vehicles, and optionally contains formulatory agents such as suspending, stabilizing and/or dispersing agents. Pharmaceutical formulations for parenteral administration include aqueous solutions of the active compounds in water-soluble form. In some embodiments, suspensions of the active compounds are prepared as appropriate oily injection suspensions. Suitable lipophilic solvents or vehicles include fatty oils such as sesame oil, or synthetic fatty acid esters, such as ethyl oleate or triglycerides, or liposomes. In some or any embodiments, aqueous injection suspensions contain substances which increase the viscosity of the suspension, such as sodium carboxymethyl cellulose, sorbitol, or dextran. Optionally, the suspensions also contain suitable stabilizers or agents which increase the solubility of the compounds to allow for the preparation of highly concentrated solutions. In alternative embodiments, the active ingredient is in powder form for constitution with a suitable vehicle, e.g., sterile pyrogen-free water, before use.

In some embodiments, the compounds described herein are administered topically. In specific embodiments, the compounds described herein are formulated into a variety of topically administrable compositions, such as solutions, suspensions, lotions, gels, pastes, medicated sticks, balms, creams or ointments. Such pharmaceutical compounds optionally contain solubilizers, stabilizers, tonicity enhancing agents, buffers and/or preservatives.

In some or any embodiments, the pharmaceutical compositions provided herein are formulated for transdermal administration of compounds described herein. In some embodiments, administration of such compositions employs transdermal delivery devices and transdermal delivery patches. In some or any embodiments, the compositions are lipophilic emulsions or buffered, aqueous solutions, dissolved and/or dispersed in a polymer or an adhesive. Such patches include those constructed for continuous, pulsatile, or on demand delivery of pharmaceutical agents. In some embodiments, transdermal delivery of the compounds described herein is accomplished by use of iontophoretic patches and the like. In some or any embodiments, transdermal patches provide controlled delivery of the compounds provided herein, such as, for example, compounds of Formula (I). In some or any embodiments, the rate of absorption is slowed by using rate-controlling membranes or by trapping the compound within a polymer matrix or gel. Conversely, absorption enhancers are optionally used to increase absorption. Absorption enhancer and carrier include absorbable pharmaceutically acceptable solvents that assist in passage of the compound through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In some or any embodiments, the pharmaceutical compositions provided herein are formulated for administration by inhalation. In some or any embodiments, in such pharmaceutical compositions formulated for inhalation, the compounds described herein are in a form as an aerosol, a mist or a powder. In some embodiments, pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In certain aspects of a pressurized aerosol, the dosage unit is determined by providing a valve to deliver a metered amount. In some or any embodiments, capsules and cartridges of, such as, by way of example only, gelatin for use in an inhaler or insufflator is formulated containing a powder mix of the compound described herein and a suitable powder base such as lactose or starch.

In some embodiments, the compounds described herein are formulated in rectal compositions such as enemas, rectal gels, rectal foams, rectal aerosols, suppositories, jelly suppositories, or retention enemas. In some or any embodiments, rectal compositions optionally contain conventional suppository bases such as cocoa butter or other glycerides, as well as synthetic polymers such as polyvinylpyrrolidone, PEG, and the like. In some or any suppository forms of the compositions, a low-melting wax such as, but not limited to, a mixture of fatty acid glycerides, optionally in combination with cocoa butter is first melted.

In various embodiments provided herein, the pharmaceutical compositions are formulated in a conventional manner using one or more physiologically acceptable carriers comprising excipients and auxiliaries which facilitate processing of the active compounds into pharmaceutically acceptable preparations. In some or any embodiments, proper formulation is dependent upon the route of administration chosen. In various embodiments, any of the techniques, carriers, and excipients is used as suitable. In some embodiments, pharmaceutical compositions comprising a compound described herein are manufactured in a conventional manner, such as, by way of example only, by means of conventional mixing, dissolving, granulating, dragee-making, levigating, emulsifying, encapsulating, entrapping or compression processes.

In some or any embodiments, the pharmaceutical compositions include at least one pharmaceutically acceptable carrier, diluent or excipient and a compound described herein described herein as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds described herein exist as tautomers. All tautomers are included within the scope of the compounds presented herein. Additionally, included herein are the solvated and unsolvated forms of the compounds described herein. Solvated compounds include those that are solvated with pharmaceutically acceptable solvents such as water, ethanol, and the like. The solvated forms of the compounds presented herein are also considered to be disclosed herein. In some embodiments, the pharmaceutical compositions described herein include other medicinal or pharmaceutical agents, carriers, adjuvants, such as preserving, stabilizing, wetting or emulsifying agents, solution promoters, salts for regulating the osmotic pressure, and/or buffers. In additional embodiments, the pharmaceutical compositions described herein also contain other therapeutically valuable substances.

Methods for the preparation of compositions containing the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. In various embodiments, the compositions are in liquid solutions or suspensions, solid forms suitable for solution or suspension in a liquid prior to use, or as emulsions. These compositions optionally contain minor amounts of nontoxic, auxiliary substances, such as wetting or emulsifying agents, pH buffering agents, and so forth.

In some embodiments, a composition comprising a compound described herein takes the form of a liquid where the agents are present in solution, in suspension or both. In some embodiments, when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

Useful aqueous suspension optionally contain one or more polymers as suspending agents. Useful polymers include water-soluble polymers such as cellulosic polymers, e.g., hydroxypropyl methylcellulose, and water-insoluble polymers such as cross-linked carboxyl-containing polymers. Useful compositions optionally comprise an mucoadhesive polymer, selected for example from carboxymethylcellulose, carbomer (acrylic acid polymer), poly (methylmethacrylate), polyacrylamide, polycarbophil, acrylic acid/butyl acrylate copolymer, sodium alginate and dextran.

Useful compositions optionally include solubilizing agents to aid in the solubility of a compound described herein. The term "solubilizing agent" generally includes agents that result in formation of a micellar solution or a true solution of the agent. Solubilizing agents include certain acceptable nonionic surfactants, for example polysorbate 80, and ophthalmically acceptable glycols, polyglycols, e.g., polyethylene glycol 400, and glycol ethers.

Useful compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Useful compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Certain useful compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Some useful compositions optionally include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Certain useful compositions optionally one or more antioxidants to enhance chemical stability where required. Suitable antioxidants include, by way of example only, ascorbic acid and sodium metabisulfite.

In some embodiments, aqueous suspension compositions are packaged in single-dose non-reclosable containers. In alternative embodiments, multiple-dose reclosable containers are used, in which case it is typical to include a preservative in the composition.

In various embodiments, any delivery system for hydrophobic pharmaceutical compounds is employed. Liposomes and emulsions are examples of delivery vehicles or carriers for hydrophobic drugs. In some or any embodiments, certain organic solvents such as N-methylpyrrolidone are employed. In some embodiments, the compounds are delivered using a sustained-release system, such as semipermeable matrices of solid hydrophobic polymers containing the therapeutic agent. Various sustained-release materials are utilized in the embodiments herein. In some or any embodiments, sustained-release capsules release the compounds for a few weeks up to over 100 days. In some embodiments, depending on the chemical nature and the biological stability of the therapeutic reagent, additional strategies for protein stabilization are employed.

In some or any embodiments, the formulations or compositions described herein benefit from and/or optionally comprise antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Methods of Dosing and Treatment Regimens

In some or any embodiments, the method can be conducted in living bodies of mammals. In such a case, the compounds may be administered to the mammals.

In some or any embodiments, the compounds described herein are used in the preparation or manufacture of medicaments for the treatment of diseases or conditions that are mediated by the enzyme GCS or in which inhibition of the enzyme GCS ameliorates the disease or condition. In some embodiments, a method for treating any of the diseases or conditions described herein in a subject in need of such treatment, involves administration of pharmaceutical compositions containing at least one compound described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

In some or any embodiments, provided is a method of treating or ameliorating a medical condition, comprising administering to a subject in need thereof a compound according to any of the various embodiments described herein or a pharmaceutical composition according to any of the various embodiments described herein.

In some or any embodiments, provided herein is a method of treating or ameliorating a disease ameliorated by the inhibition of GCS comprising administering to a subject in need of treatment a therapeutically-effective amount of a compound of Formula I, I(a), I(b), I(c), I(d), I(e), I(f), I(g), I(h), I(j), I(k), I(m), I(n), I(p), I(q), I(r), I(s), I(t), I(u), I(v), I(v'), I(v''), I(w), I(w'), I(w''), I(x), I(x'), I(x''), I(y), I(y'), I(y''), I(z), I(z'), I(z''), I(aa), I(ab), I(ac), I(ad), I(ae), I(af), I(ag), I(ah), I(ai), I(aj), I(ak), I(al), I(am), I(an), or I(ao), or a compound in Table 1, 2, or 3, optionally as a tautomer, a single stereoisomer or mixture of stereoisomers thereof and additionally optionally as a pharmaceutically acceptable salt thereof. In some or any embodiments, the disease is selected from glycolipid storage diseases (e.g., Tay Sachs, Sandhoffs, GM1 gangliosidosis and Fabry diseases); diseases associated with glycolipid accumulation (e.g., Gaucher disease); diseases that cause renal hypertrophy or hyperplasia such as diabetic nephropathy; diseases that cause hyperglycemia or hyperinsulemia; cancers in which glycolipid synthesis is abnormal; infectious diseases caused by organisms which use cell surface glycolipids as receptors or in which synthesis of glucosylceramide is essential or important; a metabolic disorder such as atherosclerosis, polycystic kidney disease, renal hypertrophy, diabetes mellitus, and obesity; cancer such as breast cancer, renal adenocarcinoma, brain cancer, neuroblastoma, lung cancer, intestinal cancer, pancreas and prostate cancer; neuronal disorders; neuronal injury; inflammatory diseases or disorders (e.g., rheumatoid arthritis, Crohn's disease, asthma and sepsis), and diabetes mellitus and obesity In any of the aforementioned embodiments are further embodiments that include single administrations of the effective amount of the compound, including further embodiments in which the compound is administered to the subject (i) once; (ii) multiple times over the span of one day; (iii) continually; or (iv) continuously.

In any of the aforementioned embodiments are further embodiments in which administration is enteral, parenteral, or both, and wherein:
(a) the effective amount of the compound is systemically administered to the subject;
(b) the effective amount of the compound is administered orally to the subject;
(c) the effective amount of the compound is intravenously administered to the subject;
(d) the effective amount of the compound administered by inhalation;
(e) the effective amount of the compound is administered by nasal administration;
(f) the effective amount of the compound is administered by injection to the subject;
(g) the effective amount of the compound is administered topically (dermal) to the subject;
(h) the effective amount of the compound is administered by ophthalmic administration; and/or
(i) the effective amount of the compound is administered rectally to the subject.

In some or any embodiments, the compositions containing the compound(s) described herein are administered for prophylactic and/or therapeutic treatments. In some or any therapeutic applications, the compositions are administered to a patient already suffering from a disease or condition, in an amount sufficient to cure or at least partially arrest the symptoms of the disease or condition. In some embodiments, amounts effective for this use will depend on the severity and course of the disease or condition, previous therapy, the patient's health status, weight, and response to the drugs, and the judgment of the treating physician. In certain instances, it is considered appropriate for the caregiver to determine such therapeutically effective amounts by routine experimentation (including, but not limited to, a dose escalation clinical trial).

In some or any prophylactic applications, compositions containing the compounds described herein are administered to a patient susceptible to or otherwise at risk of a particular disease, disorder or condition. In some embodiments, the amount administered is defined to be a "prophylactically effective amount or dose." In some or any embodiments of this use, the precise amounts of compound administered depend on the patient's state of health, weight, and the like. In some embodiments, it is considered appropriate for the caregiver to determine such prophylactically effective amounts by routine experimentation (e.g., a dose escalation clinical trial). In some or any embodiments, when used in a patient, effective amounts for this use will depend on the severity and course of the disease, disorder or condition, previous therapy, the patient's health status and response to the drugs, and the judgment of the treating physician.

In some or any embodiments are further embodiments that include multiple administrations of the effective amount of the compound, including further embodiments wherein:
(i) the compound is administered in a single dose;
(ii) the time between multiple administrations is every 6 hours;
(iii) the compound is administered to the subject every 8 hours.

In further or alternative embodiments, the method includes a drug holiday, wherein the administration of the compound is temporarily suspended or the dose of the compound being administered is temporarily reduced; at the end of the drug holiday, dosing of the compound is resumed. In some embodiments, the length of the drug holiday varies from 2 days to 1 year.

In certain instances, a patient's condition does not improve or does not significantly improve following administration of a compound or composition described herein and, upon the doctor's discretion the administration of the compounds is optionally administered chronically, that is, for an extended period of time, including throughout the duration of the patient's life in order to ameliorate or otherwise control or limit the symptoms of the patient's disease or condition.

In certain cases wherein the patient's status does improve or does not substantially improve, upon the doctor's discretion the administration of the compounds are optionally given continuously; alternatively, the dose of drug being administered is optionally temporarily reduced or temporarily suspended for a certain length of time (i.e., a "drug holiday"). In some or any embodiments, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes a reduction from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

In some or any embodiments, once improvement of the patient's conditions has occurred, a maintenance dose is administered if necessary. In some embodiments, the dosage, e.g., of the maintenance dose, or the frequency of administration, or both, are reduced, as a function of the symptoms, to a level at which the improved disease, disorder or condition is retained. In some or any embodiments, however, patients are optionally given intermittent treatment on a long-term basis upon any recurrence of symptoms.

In some or any embodiments, the amount of a given agent that corresponds to an effective amount varies depending upon factors such as the particular compound, disease or condition and its severity, the identity (e.g., weight) of the subject or host in need of treatment. In some embodiments, the effective amount is, nevertheless, determined according to the particular circumstances surrounding the case, including, e.g., the specific agent that is administered, the route of administration, the condition being treated, and the subject or host being treated. In some or any embodiments, however, doses employed for adult human treatment is in the range of about 0.02 to about 5000 mg per day, in a specific embodiment about 1 to about 1500 mg per day. In various embodiments, the desired dose is conveniently presented in a single dose or as divided doses administered simultaneously (or over a short period of time) or at appropriate intervals, for example as two, three, four or more sub-doses per day.

In some or any embodiments, the pharmaceutical compositions described herein are in a unit dosage form suitable for single administration of precise dosages. In some instances, in unit dosage form, the formulation is divided into unit doses containing appropriate quantities of one or more compound. In some or any embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. In alternative embodiments, multiple-dose reclosable containers are used, in which case it is typical to include a preservative in the composition. By way of example only, formulations for parenteral injection are, in some embodiments, presented in unit dosage form, which include, but are not limited to ampoules, or in multi-dose containers, with an added preservative.

In some or any embodiments, the daily dosages appropriate for the compounds described herein described herein are from about 0.01 to about 2.5 mg/kg per body weight. In some embodiments, an indicated daily dosage in the larger subject, including, but not limited to, humans, is in the range from about 0.5 mg to about 100 mg, conveniently administered in divided doses, including, but not limited to, up to four times a day or in extended release form. In some or any embodiments, suitable unit dosage forms for oral administration comprise from about 1 to about 50 mg active ingredient. The foregoing ranges are merely suggestive, as the number of variables in regard to an individual treatment regime is large, and considerable excursions from these recommended values are not uncommon. In some or any embodiments, the dosages are altered depending on a number of variables, not limited to the activity of the compound used, the disease or condition to be treated, the mode of administration, the requirements of the individual subject, the severity of the disease or condition being treated, and the judgment of the practitioner.

In some or any embodiments, toxicity and therapeutic efficacy of such therapeutic regimens are determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. In some or any embodiments, compounds exhibiting high therapeutic indices are preferred. In some embodiments, the data obtained from cell culture assays and animal studies is used in formulating a range of dosage for use in human. In specific embodiments, the dosage of such compounds lies within a range of circulating concentrations that include the $ED_{50}$ with minimal toxicity. In some or any embodiments, the dosage varies within this range depending upon the dosage form employed and the route of administration utilized.

Kits/Articles of Manufacture

Articles of manufacture, comprising packaging material, a compound provided herein that is effective for modulating the activity of the enzyme GCS, or for treatment, prevention or amelioration of one or more symptoms of a GCS-mediated disease or condition, within the packaging material, and a label that indicates that the compound or composition, or pharmaceutically acceptable salt, pharmaceutically acceptable N-oxide, pharmaceutically active metabolite, pharmaceutically acceptable prodrug, or pharmaceutically acceptable solvate thereof, is used for modulating the activity of GCS, or for treatment, prevention or amelioration of one or more symptoms of GCS-mediated disease or condition, are provided.

For use in the therapeutic applications described herein, kits and articles of manufacture are also described herein. In various embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes.

In some embodiments, the containers are formed from a variety of materials such as glass or plastic.

In some embodiments, the articles of manufacture provided herein contain packaging materials. Packaging materials for use in packaging pharmaceutical products include, but are not limited to, blister packs, bottles, tubes, inhalers, pumps, bags, vials, containers, syringes, bottles, and any packaging material suitable for a selected formulation and intended mode of administration and treatment.

In some embodiments, the container(s) described herein comprise one or more compounds described herein, optionally in a composition or in combination with another agent as disclosed herein. The container(s) optionally have a sterile access port (for example in some embodiments the container is an intravenous solution bag or a vial having a stopper pierceable by a hypodermic injection needle). Such kits optionally comprise a compound with an identifying description or label or instructions relating to its use in the methods described herein.

In some embodiments, a kit will comprises one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions is optionally included.

In some or any embodiments, a label is on or associated with the container. In some embodiments, a label is on a container when letters, numbers or other characters forming the label are attached, molded or etched into the container itself; a label is associated with a container when it is present within a receptacle or carrier that also holds the container, e.g., as a package insert. In some or any embodiments, a label indicates that the contents are to be used for a specific therapeutic application. In some embodiments, the label indicates directions for use of the contents, such as in the methods described herein.

In some or any embodiments, the pharmaceutical compositions are presented in a pack or dispenser device which contains one or more unit dosage forms containing a compound provided herein. In some embodiments, the pack contains a metal or plastic foil, such as a blister pack. The pack or dispenser device is optionally accompanied by instructions for administration. In some embodiments, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. In some or any embodiments, such notice is, for example, the labeling approved by the U.S. Food and Drug Administration for prescription drugs, or the approved product insert. In some embodiments, compositions containing a compound provided herein are formulated in a compatible pharmaceutical carrier and are placed in an appropriate container labeled for treatment of an indicated condition.

Any combination of the groups described above for the various variables is contemplated herein.

PREPARATION OF COMPOUNDS

The following are illustrative examples of how the compounds can be prepared and tested. Although the examples can represent only some embodiments, it should be understood that the following examples are illustrative and not limiting.

In a further aspect, it is provided a method of making a compound, comprising synthesizing a compound as any of the various embodiments described above or below. Examples of the method are further described in the Examples.

Compounds disclosed herein are commercially available or can be readily prepared from commercially available starting materials according to established methodology in the art of organic synthesis. General methods of synthesizing the compound can be found in, e.g., Stuart Warren and Paul Wyatt, Workbook for Organic Synthesis: The Disconnection Approach, second Edition, Wiley, 2010. Synthesis of some of the compounds are exemplified in detail below.

In some embodiments, individual stereoisomers of compounds are prepared synthetically from commercially available starting materials which contain asymmetric or chiral centers or by preparation of racemic mixtures followed by resolution. These methods of resolution are exemplified by (1) attachment of a mixture of enantiomers to a chiral axillary, separation of the resulting mixture of diastereomers by recrystallization or chromatography and liberation of the optically pure product from the auxiliary or (2) direct separation of the mixture of optical enantiomers on chiral chromatographic column.

Materials were obtained from commercial suppliers and were used without further purification. Air or moisture sensitive reactions were conducted under argon atmosphere using oven-dried glassware and standard syringe/septa techniques. $^1$H NMR spectra were measured at 400 MHz unless stated otherwise and data were reported as follows in ppm (δ) from the internal standard (TMS, 0.0 ppm): chemical shift (multiplicity, integration, coupling constant in Hz).

General Scheme 1

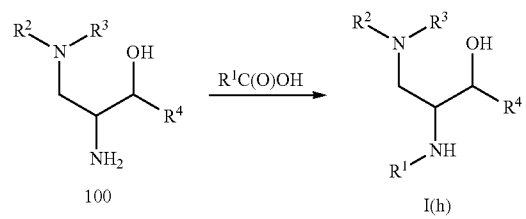

A Compound of Formula I(h) (where all groups are as defined in the Summary of the Invention for a compound of Formula I or according to any of the embodiments disclosed herein) can be prepared according to General Scheme 1.

A Compound of Formula I(h) can be prepared using standard amide coupling conditions. More specifically, an intermediate of formula 100, which can be prepared using procedures disclosed herein or are known to one of ordinary skill in the art, is treated with in a solvent such as DMF, DCM or THF, optionally in the presence of a base such as DIPEA or TEA, and in the presence of a coupling agent such as EDCI and/or HOBt to yield a compound of Formula I(h). The mixture can optionally be purified using procedures known to one of ordinary skill in the art. Alternatively, the intermediate of formula R$^1$C(O)OH can be treated with a chlorinating agent such as oxalyl chloride in a solvent such as DMF followed by treatment with the intermediate of formula 100 to yield a compound of Formula I(h). The mixture can optionally be purified using procedures known to one of ordinary skill in the art.

General Scheme 2

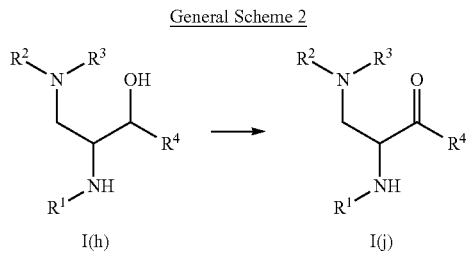

A Compound of Formula I(j) (where all groups are as defined in the Summary of the Invention for a compound of Formula I or according to any of the embodiments disclosed herein) can be prepared according to General Scheme 2. A Compound of Formula I(h) is treated with a base such as NMP, in the presence of NHCO$_3$, and in a solvent such as DCM to yield a Compound of Formula I(j).

General Scheme 3

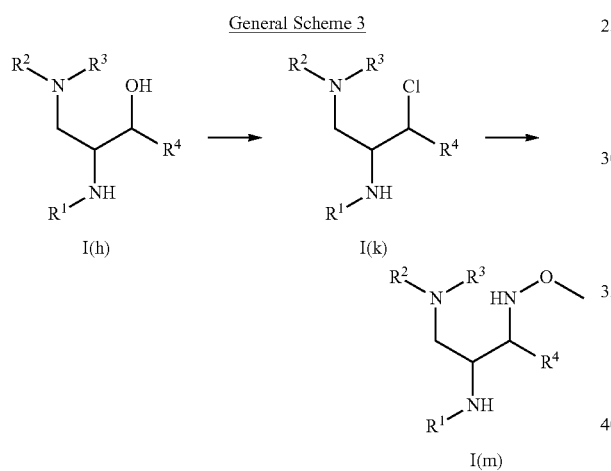

A Compound of Formula I(k) or I(m) (where all groups are as defined in the Summary of the Invention for a compound of Formula I or according to any of the embodiments disclosed herein) can be prepared according to General Scheme 3. A Compound of Formula I(h) is treated with a chlorinating agent such as SOCl$_2$ in a solvent such as DCM to yield a Compound of Formula I(k). A Compound of Formula I(m) is prepared by treating a Compound of Formula I(k) with NH$_2$OCH$_3$ in a solvent such as MeOH.

General Scheme 4

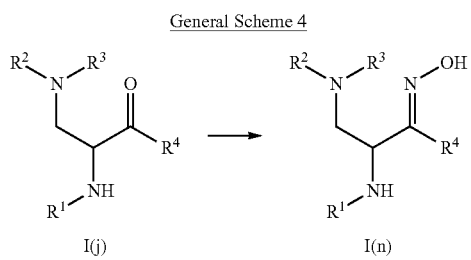

A Compound of Formula I(n) (where all groups are as defined in the Summary of the Invention for a compound of Formula I or according to any of the embodiments disclosed herein) can be prepared according to General Scheme 4. A Compound of Formula I(j) is treated with hydroxylamine in a solvent such as MeOH to yield a Compound of Formula I(n).

General Scheme 5

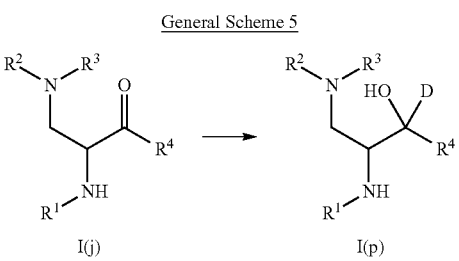

A Compound of Formula I(p) (where all groups are as defined in the Summary of the Invention for a compound of Formula I or according to any of the embodiments disclosed herein) can be prepared according to General Scheme 5. A Compound of Formula I(j) is treated with NaBD$_4$ in a deuterated solvent such as CD$_3$OD to yield a Compound of Formula I(p).

General Scheme 6

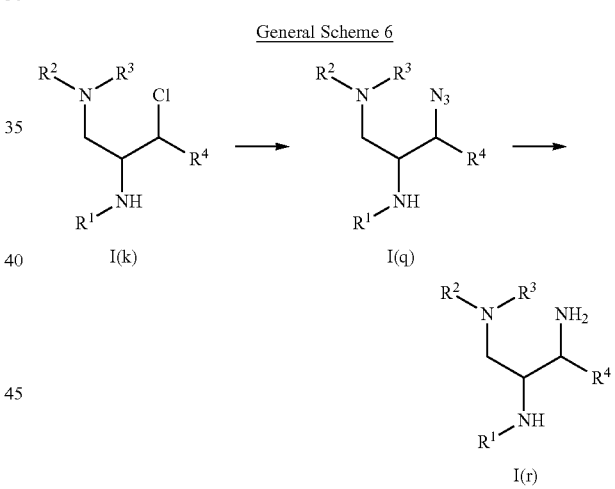

A Compound of Formula I(q) or I(r) (where all groups are as defined in the Summary of the Invention for a compound of Formula I or according to any of the embodiments disclosed herein) can be prepared according to General Scheme 6. A Compound of Formula I(k) is treated with NaN$_3$ in a solvent such as DMF and heated to about 50° C. to yield a Compound of Formula I(q) which can be optionally worked up before proceeding to the next step. The Compound of Formula I(q) is then treated with PPh$_3$ in a solvent such as THF to yield the Compound of Formula I(r).

In some or any embodiments of General Schemes 1-6, intermediate of formula 100 or the Compound of Formula I(h), I(j), or I(k) is that where R$^2$ and R$^3$ together with the nitrogen to which they are attached form a 3-10-membered ring which is optionally substituted with 1, 2, or 3 R$^8$ groups.

General Scheme 7

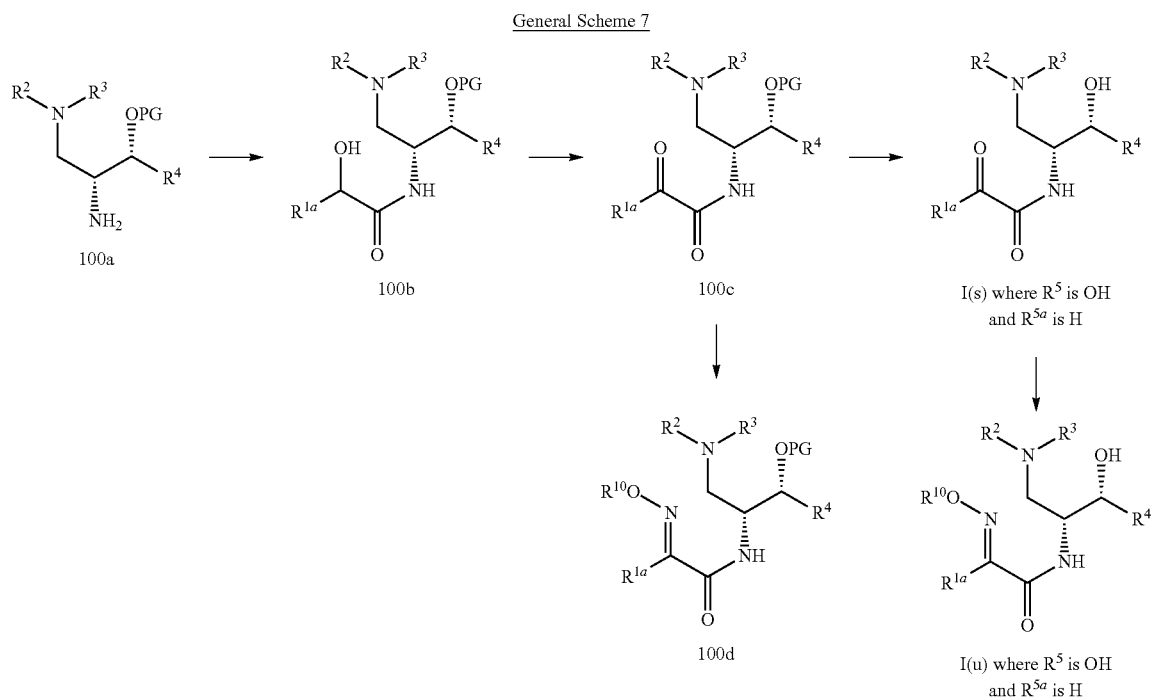

A Compound of Formula I(s) (where $R^5$ is hydroxy and $R^{5a}$ is hydrogen and all groups are as defined in the Summary of the Invention for a compound of Formula I or according to any of the embodiments disclosed herein) can be prepared according to General Scheme 7.

An intermediate of formula 100b can be prepared using standard amide coupling conditions. More specifically, an intermediate of formula 100a, which can be prepared using procedures disclosed herein or are known to one of ordinary skill in the art, is treated with in a solvent such as DMF, DCM or THF, optionally in the presence of a base such as DIPEA or TEA, and in the presence of a coupling agent such as EDCI and/or HOBt to yield an intermediate of formula 100c (e.g., a compound of Formula I(s) where $R^5$ is —OTBS and $R^{5a}$ is hydrogen). The protecting group in intermediate of formula 100c is then removed in the presence of TBAF in a solvent such as THF. The mixture can optionally be purified using procedures known to one of ordinary skill in the art. Alternatively, a Compound of Formula I(s) (where $R^5$ is hydroxy and $R^{5a}$ is hydrogen and all groups are as defined in the Summary of the Invention for a compound of Formula I or according to any of the embodiments disclosed herein) can be prepared by treating an intermediate of formula 100a with $R^{1a}C(O)C(O)OH$ using standard amide coupling procedures described herein or known to one of ordinary skill in the art. The mixture can optionally be purified using procedures known to one of ordinary skill in the art.

A Compound of Formula I(u) (where $R^5$ is hydroxy and $R^{5a}$ is hydrogen and all groups are as defined in the Summary of the Invention for a compound of Formula I or according to any of the embodiments disclosed herein) can be prepared according to General Scheme 7. The intermediate of formula 100c is treated with an intermediate of formula $R^{1a}ONH_2$ in the presence of sodium acetate in a solvent such as ethanol or methanol to yield an intermediate of formula 100d (e.g., a compound of Formula I(u) where $R^5$ is —OTBS and $R^{5a}$ is hydrogen and all groups are as defined in the Summary of the Invention for a compound of Formula I or according to any of the embodiments disclosed herein). The intermediate of formula 100d is treated with TBAF in a solvent such as THF to yield a Compound of Formula I(u). The mixture can optionally be purified using procedures known to one of ordinary skill in the art. Alternatively, the Compound of Formula I(s) (where $R^5$ is hydroxy and $R^{5a}$ is hydrogen and all groups are as defined in the Summary of the Invention for a compound of Formula I or according to any of the embodiments disclosed herein) is treated with an intermediate of formula $R^{1a}ONH_2$ in a solvent such as ethanol or methanol to yield a Compound of Formula I(u). The mixture can optionally be purified using procedures known to one of ordinary skill in the art.

SYNTHETIC EXAMPLES

Intermediate A

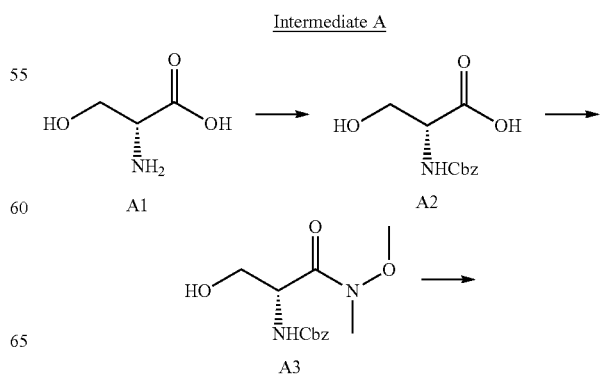

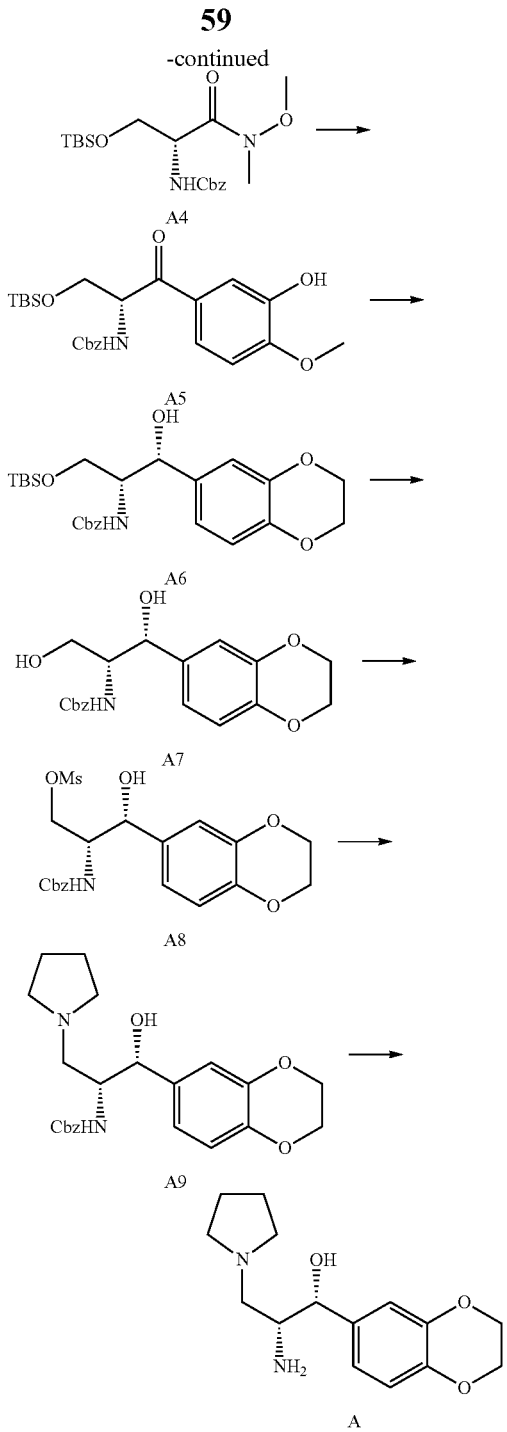

Benzyl chloroformate (50 mL, 50 w.t. % solution in toluene, 148 mmol) was added to a solution of (R)-2-amino-3-hydroxypropanoic acid (A1) (10.5 g, 100 mmol) in sat. aq NaHCO$_3$ solution (400 mL). The mixture was stirred vigorously for 4 h at 20° C., and the aqueous solution was extracted with ether (400 mL×2). The aqueous phase was acidified with conc. hydrochloric acid to pH=2 and extracted with ethyl acetate (300 mL×3). The combined organic phase was dried with Na$_2$SO$_4$ and concentrated to afford crude product Compound A2 (20 g, yield 84%) as a white solid. LC-MS (m/z): 240 [M+1]$^+$; $^1$H-NMR (DMSO-d$_6$, 400 MHz) peaks: δ (ppm) 3.653 (m, 2H), 4.051 (m, 1H), 4.884 (m, 1H), 5.038 (s, 2H), 7.303-7.373 (m, 6H), 12.658 (s, 1H).

To a mixture of EDCl.HCl (2.4 g, 12.5 mmol), HOBt (1.7 g, 12.5 mmol), DIPEA (2.7 g, 20 mmol) in DCM (50 mL) was added Compound A2 (1 g, 4 mmol) and N,O-dimethylhydroxylamine hydrochloride (1.2 g, 12.5 mmol). The mixture was stirred at rt overnight. The mixture was washed with hydrochloric acid solution (1 M, 50 mL×2), saturated aqueous NaHCO$_3$ (20 mL), brine (20 mL), and dried over Na$_2$SO$_4$. The crude product was purified by silica gel column chromatography (ethyl acetate in petroleum, 30% v/v) to give Compound A3 (826 mg, yield 70%) as a colorless liquid. LC-MS (m/z): 283 [M+1]$^+$; $^1$H-NMR (CDCl$_3$, 400 MHz) peaks: δ (ppm) 3.113 (s, 3H), 3.673 (s, 3H), 3.743 (t, J=4.8 Hz, 2H), 4.766 (m, 1H), 4.959-5.044 (m, 2H), 6.046 (d, J=8.0 Hz, 1H), 7.200-7.254 (m 5H).

TBDMS-Cl (800 mg, 5.31 mmol) in THF (10 mL) was added dropwise to a solution of Compound A3 (500 mg, 1.77 mmol) and imidazole (602 mg, 8.86 mmol) in THF (20 mL) at 0° C. The mixture was stirred at rt for 2 h, and then filtered. The filtrate was washed with 1N HCl (50 mL×2) and brine (50 mL), and dried over Na$_2$SO$_4$. The crude product was purified with silica gel column chromatography (ethyl acetate in petroleum, 13% v/v) to give Compound A4 (526 mg, yield 75%) as a colorless liquid. LC-MS (m/z): 396 [M+1]$^+$; $^1$H-NMR (CDCl$_3$, 400 MHz) peaks: δ (ppm) 0.012 (s, 3H), 0.085 (s, 6H), 0.852 (s, 9H), 3.211 (s, 3H), 3.756 (s, 3H), 3.794-3.896 (m, 2H), 4.809 (m, 1H), 5.085 (q, J=11.2 Hz, 2H), 5.662 (d, J=8.8 Hz, 1H), 7.286-7.351 (m 5H).

To a solution of 6-bromo-2,3-dihydrobenzo[b][1,4]dioxine (4.9 g, 23 mmol) in THF (100 mL) was added n-BuLi (1.6 M, 15 mL) at −60° C. under N$_2$ and stirred for 0.5 h, before a solution of Compound A4 (3 g, 7.6 mmol) in THF (50 mL) was added slowly. The mixture was stirred at −60° C. for 1 h, and followed by addition of a saturate NH$_4$Cl solution. The mixture was extracted with ethyl acetate (100 mL×2), brine (100 mL), and then dried over Na$_2$SO$_4$. The crude product was purified by column chromatography on silica gel (ethyl acetate in petroleum, 10% v/v) to give Compound A5 (3 g, yield 84%) as a colorless liquid. LC-MS (m/z): 472 [M+1]$^+$; $^1$H-NMR (CDCl$_3$, 400 MHz) peaks: δ (ppm) 0.000 (s, 3H), 0.024 (s, 3H), 0.892 (s, 9H), 4.024-4.116 (m, 1H), 4.402-4.465 (m, 4H), 5.262 (s, 2H), 5.421 (m, 1H), 6.066 (d, J=8.0 Hz, 1H), 7.043 (d, J=8.0 Hz, 1H), 7.444-7.505 (m, 5H), 7.618-7.639 (m, 2H).

Compound A5 (2 g, 4.2 mmol) was dissolved in THF (30 mL) and the solution was cooled down to −70° C. under nitrogen atmosphere. L-Selectride (8.5 mL, 1M solution in THF, 8.5 mmol) was added dropwise while keeping the temperature at −70° C. After an hour, the reaction was quenched with saturate NH$_4$Cl solution and extracted with ethyl acetate (50 mL×2). The extract was dried over Na$_2$SO$_4$ to yield a crude product which was purified by column chromatography on silica gel (ethyl acetate in petroleum, 10% v/v) to afford Compound A6 (1.4 g, yield 70%) as a colorless oil. LC-MS (m/z): 474 [M+1]$^+$; $^1$H-NMR (CDCl$_3$, 400 MHz) peaks: δ (ppm) 0.08 (m, 6H), 0.85 (s, 9H), 3.71 (m, 1H), 3.77 (m, 2H), 4.18 (s, 4H), 4.88 (m, 1H), 4.50 (m, 2H), 5.36 (d, J=7.6 Hz, 1H), 6.76 (s, 2H), 6.83 (s, 1H), 7.28 (m, 5H).

To a solution of Compound A6 (1.4 g, 3 mmol) in THF (50 mL) was added a solution of TBAF (155 mg, 0.6 mmol) in THF (5 mL) at 0° C., then the mixture was stirred at rt overnight. After removal of solvent by evaporation, water (50 mL) was added to the mixture which was then extracted with ethyl acetate (2×50 mL), washed with brine (1×100 mL), and dried over Na$_2$SO$_4$ to obtained Compound A7 (1 g, crude). LC-MS (m/z): 342 [M+1]$^+$; $^1$H-NMR (CDCl$_3$, 400 MHz) peaks: δ (ppm) 3.620-3.737 (m, 3H), 3.772-3.814 (m, 1H), 4.014 (s, 1H), 4.224 (s, 4H), 4.867 (m, 1H), 5.024 (s, 2H), 5.607 (d, J=8.8 Hz, 1H), 6.809 (s, 2H), 6.888 (s, 1H), 7.24 (m, 5H).

To a solution of Compound A7 (3.6 g, 10 mmol) in THF (50 mL) was added Et₃N (3 g, 30 mmol), and then the mixture was cooled to −15° C. before adding MsCl (0.8 mL) slowly. The mixture was stirred at −15° C. about half an hour. The reaction mixture was taken up with water (30 mL), extracted with ethyl acetate (30 mL×3), dried over anhydrous sodium sulfate, and evaporated to get Compound A8. To a solution of the resulting mesylate intermediate (A8) in THF (50 mL) was added pyrrolidine (5.7 g, 80 mmol), K₂CO₃ (11 g, 80 mmol) and NaI (3 g). The mixture was heated at 50° C. overnight. After filtration and evaporation, the crude product was purified by column chromatography on silica gel (methanol in dichloromethane, 5% v/v) to give Compound A9 (2.5 g, yield 61%) as a colorless oil. LC-MS (m/z): 413 [M+1]⁺; ¹H-NMR (CDCl₃, 400 MHz) peaks: δ (ppm) 1.756 (m, 4H), 2.534 (m, 1H), 2.660 (m, 4H), 2.877 (m, 1H), 4.019 (m, 1H), 4.236 (s, 4H), 4.924 (d, J=2.8 Hz, 1H), 5.043 (s, 2H), 5.079 (m, 1H), 6.7756-6.892 (m, 3H), 7.266-7.361 (m, 5H).

To a solution of Compound A9 (2.5 g, 6.1 mmol) in methanol (20 mL) was added Pd(OH)₂ (250 mg), and then the mixture was stirred at rt under H₂ overnight. The mixture was filtered and the filtrate was evaporated to dryness to give Intermediate A (1.7 g). LC-MS (m/z): 279 [M+1]⁺; ¹H-NMR (CDCl₃, 400 MHz) peaks: δ (ppm) 1.70 (m, 4H), 2.53 (m, 6H), 3.05 (m, 1H), 4.18 (s, 4H), 4.47 (d, J=3.6 Hz, 1H), 6.75 (m, 3H).

Intermediate B

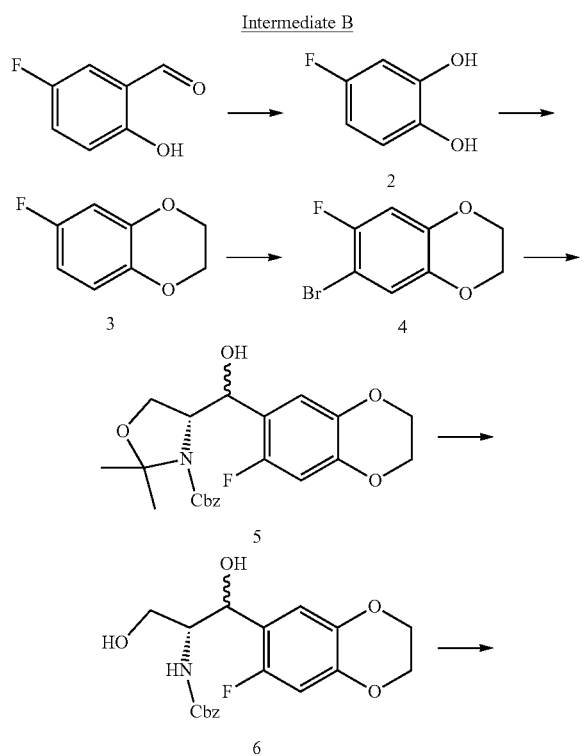

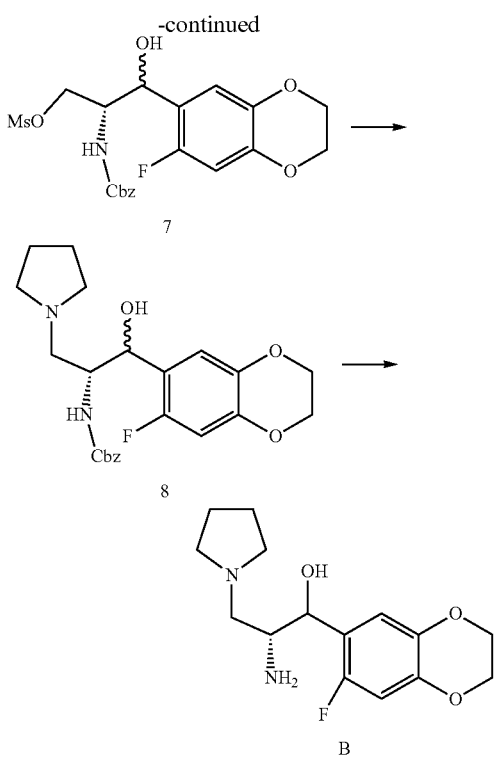

To a solution of 5-fluoro-2-hydroxybenzaldehyde (14.0 g, 0.1 mol) in THF (150 mL) was added dropwise sat. aq. NaOH solution (0.05 N, 300 mL, 15 mmol) at 0° C., followed by 30% H₂O₂ solution (40 mL). After stirred for 2 h at rt, the second portion of 30% H₂O₂ (40 mL) was added dropwise and stirred for additional 4 h. The reaction mixture was cooled to 0° C. and pH was adjusted to 10-11 using aq. NaOH solution (2 N, 60 mL). The mixture was stirred for 0.5 h before it was quenched with conc. HCl at 0° C. to pH 2~3. The mixture was extracted with DCM (150 mL×3) and washed with brine (150 mL×1), dried over sodium sulfate, and evaporated to dryness to yield Compound B1 (12.8 g, yield 100%) as a yellow oil. ¹H-NMR (DMSO-d₆, 400 MHz) major characteristic peaks: δ (ppm) 6.38-6.56 (m, 1H), 6.53-6.56 (m, 1H), 6.66-6.70 (m, 1H), 8.83 (s, 1H), 9.30 (s, 1H).

A mixture of Compound B1 (12.8 g, 0.1 mol), Cs₂CO₃ (81.5 g, 0.25 mol) in DMF (200 mL) was first stirred for 0.5 h at 40° C. and then 1,2-dibromoethane (11.7 mL, 0.135 mol) was added and the mixture was stirred for 16 h at 80° C. After it was cooled down to rt, the mixture was filtered and the cake was washed with ethyl acetate (100 mL). The filtrate was diluted with water (400 mL) and extracted with ethyl acetate (200 mL×3). The combined organic layer was washed with water (200 mL×5) and brine (200 ml×1), dried over sodium sulfate, concentrated, and purified by column chromatography on silica gel (ethyl acetate/PE=1/20, v/v) to get Compound B2 (4.3 g, yield 30%) as a yellow oil. ¹H-NMR (CDCl₃, 400 MHz) major characteristic peaks: δ (ppm) 4.20-4.25 (m, 4H), 6.51-6.56 (m, 1H), 6.58-6.61 (m, 1H), 6.76-6.80 (m, 1H).

To a solution of Compound B2 (4.1 g, 26.5 mmol) and NBS (7.1 g, 40 mmol) in ACN (30 mL) was added TFA (302 mg, 2.65 mmol) at rt and the mixture was kept at rt with stirring overnight. Upon removal of the solvents, the residue was purified by column chromatography on silica gel (ethyl acetate/PE=1/25, v/v) to yield Compound B3 (4.9 g, yield 79%) as a white solid. $^1$H NMR (CDCl$_3$, 400 MHz) major characteristic peaks: δ (ppm) 4.21-4.26 (m, 4H), 6.67-6.69 (d, J=9.2 Hz, 1H), 7.02-7.04 (d, J=6.8 Hz, 1H).

To a solution of Compound B3 (700 mg, 53.7 mmol) in THF (10 mL) was added n-BuLi (2.5M, 1.24 mL, 3.1 mmol) at −60° C. under N$_2$. After 30 min, a solution of (R)-benzyl 4-formyl-2,2-dimethyloxazolidine-3-carboxylate (263 mg, 1 mmol) in THF (3 mL). The mixture was stirred at −60° C. under N$_2$ for an additional 30 min, before it was quenched with saturated aqueous NH$_4$Cl solution (20 mL). The mixture was extracted with ethyl acetate (20 mL×3), washed with brine (20 mL×1), dried over anhydrous Na$_2$SO$_4$, and purified by column chromatography on silica (ethyl acetate in petroleum, 30% v/v) to yield Compound B4 (120 mg, yield 29%) as a white foam. LCMS (m/z): 440 [M+1]$^+$; $^1$H-NMR (CDCl$_3$, 400 MHz) major characteristic peaks: δ (ppm) 1.41-1.70 (m, 6H), 3.63-3.94 (m, 1.5H), 4.09 (m, 0.5H), 4.19 (m, 4H), 4.29-4.41 (m, 1H), 4.95-4.98 (m, 1H), 5.09-5.22 (m, 2H), 6.54 (m, 1H), 6.98 (m, 1H), 7.35 (m, 5H).

To a solution of Compound B4 (2 g, 4.8 mmol) in THF (20 mL) was added 3 N HCl (8 mL) and stirred at 50° C. for 6 h. The mixture was diluted with water (50 mL), extracted with ethyl acetate (30 mL×3), washed with brine (30 mL×1), dried over anhydrous Na$_2$SO$_4$, and concentrated to obtain Compound B5 (1.8 g, yield 100%) as a yellow oil. LCMS (m/z): 400 [M+23]$^+$.

To a solution of Compound B5 (1.8 g, 4.8 mmol) and Et$_3$N (1 mL, 7.2 mmol) in THF (40 mL) was added MsCl (1.44 mL) at −50° C. Stirred at this temperature for 2 h under N$_2$, the reaction was quenched with sat. aqueous NaHCO$_3$ solution (50 mL). It was extracted with ethyl acetate (50 mL×3), washed with brine (30 mL×1), dried with anhydrous Na$_2$SO$_4$, purified with a silica gel column (MeOH in DCM, 3% v/v) to give Compound B6 (1.2 g, yield 55%) as a colorless oil. LCMS (m/z): 478 [M+23]$^+$; $^1$H-NMR (CDCl$_3$, 400 MHz) major characteristic peaks: δ (ppm) 2.94-3.09 (m, 3H), 4.13-4.55 (m, 7H), 5.00-5.31 (m, 4H), 6.56-6.60 (m, 1H), 6.94-6.98 (m, 1H), 7.27-7.37 (m, 5H).

To a solution of Compound B6 (1.2 g, 2.6 mmol) in THF (40 mL) was added pyrrolidine (2 mL, 23.7 mmol) and stirred at 50° C. overnight. After the mixture was cooled down, the mixture was diluted with water (100 mL), extracted with ethyl acetate (50 mL×3), washed with water (100 mL×3), brine (100 mL×1), dried over anhydrous Na$_2$SO$_4$, and purified using silica gel column chromatography (MeOH in DCM, 4% v/v) to obtain Compound B7 (0.4 g, 36%) as a white solid. LCMS (m/z): 431 [M+1]$^+$.

To a solution of Compound B7 (400 mg, 0.93 mmol) in EtOH (20 mL) and water (2 mL) was added LiOH.H$_2$O (120 mg, 2.79 mmol). The mixture was stirred at reflux for 4 h, followed by addition of water (50 mL). The mixture was extracted with ethyl acetate (30 mL×3), washed with brine (50 mL×1), dried over anhydrous Na$_2$SO$_4$, and concentrated to give Intermediate B (300 mg, yield 100%) as a yellow solid. LCMS (m/z): 297 [M+1]$^+$.

Intermediate C

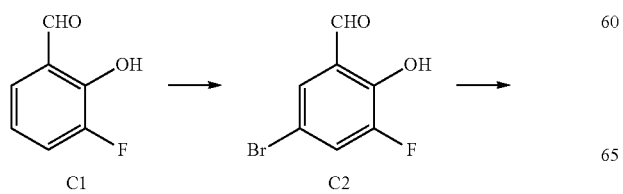

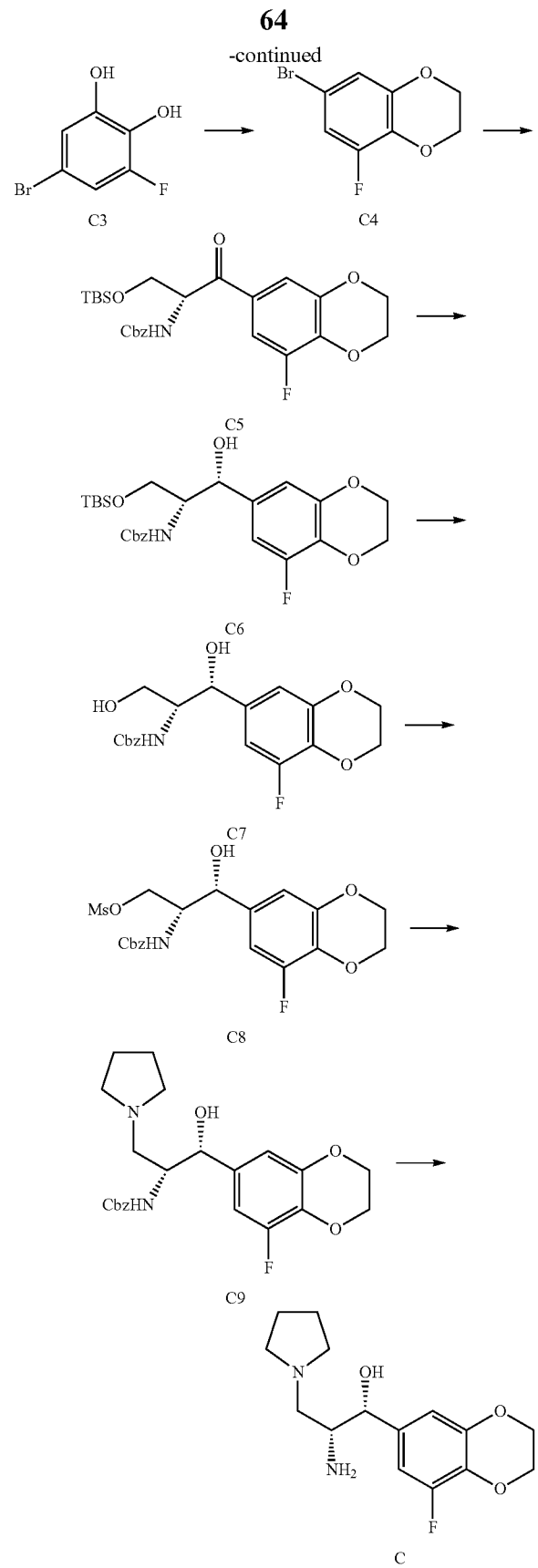

To a solution of Compound C1 (50 g, 357 mmol) in ACN (400 mL) was added NBS (60.08 g, 360 mmol) and HC(O)

O—NH₄+(2.47 mg, 39 mmol) at rt and then the mixture was stirred at rt for 2 h. After removal of the solvent and diluted with ethyl acetate (200 mL), the mixture was washed with brine, dried over anhydrous Na₂SO₄, and concentrated to give Compound C2 (78 g, yield 100%) as a yellow solid. ¹H-NMR (CDCl₃, 400 MHz) major characteristic peaks: δ (ppm) 7.48-7.23 (m, 2H), 9.87 (s, 1H), 10.89 (s, 1H).

To a solution of Compound C2 (40 g, 183 mmol) in THF (260 mL) was added dropwise aq. NaOH solution (0.05 N, 720 mL, 37 mmol) at 0° C., and then 30% H₂O₂ solution (90 mL). The mixture was stirred for 2 h at rt and followed by the addition of a second portion of 30% H₂O₂ (90 mL). After stirred for 4 h, it was cooled to 0° C. and aq. NaOH solution (2 N, 112 mL) was added until pH10~11 was reached, and then the mixture was stirred for 0.5 h and quenched with conc. HCl at 0° C. to pH2~3. It was extracted with dichloromethane (250 mL×3) and washed with brine (300 mL×2), dried over Na₂SO₄, and concentrated to give Compound C3 (37 g, yield 98%) as a yellow oil. LC-MS (m/z): 205 [M−1]⁻.

To a mixture of Compound C3 (30 g, 146 mol), K₂CO₃ (60.3 g, 437 mol) in DMF (450 mL) was added 1,2-dibromoethane 63 mL, 730 mol). The mixture was stirred at 80° C. for 4 h. After cooled to rt, it was filtered and the cake was washed with ethyl acetate (100 mL). The filtrate was diluted with water (900 mL) and extracted with ethyl acetate (400 mL×3). The organic layer was washed with water (900 mL×5) and brine (900 ml×1), dried, concentrated, and purified by column chromatography on silica gel (ethyl acetate in petroleum, 5% v/v) to afford Compound C4 (20.4 g, yield 60%) as a colorless oil. ¹H-NMR (CDCl₃, 400 MHz) major characteristic peaks: δ (ppm) 4.35 (s, 4H), 6.91 (t, J=8 Hz, 2H), 7.33 (s, 1H).

To a solution of Compound C4 (10.5 g, 45 mmol) in THF (300 mL) was added n-BuLi (2.4 M, 20 mL, 46.5 mmol) at −60° C. under N₂ and it was stirred at under this condition for 0.5 h. It was added a solution of Compound A4 (6 g, 15 mmol) in THF (10 mL). The mixture was stirred at −60° C. under N₂ for 20 min, quenched with saturated aqueous NH₄Cl solution (200 mL), extracted with ethyl acetate (200 mL×3), washed with brine (200 mL×1), dried over anhydrous Na₂SO₄, and purified by column chromatography on silica gel (ethyl acetate in petroleum, 10% v/v) to obtain Compound C5 (4.87 g, yield 66%) as a colorless oil. LC-MS (m/z): 490 [M+1]⁺.

To a solution of Compound C5 (4 g, 8.1 mmol) in THF (50 mL) was added L-Selectride (16.3 mL) at −60° C. under N₂. The mixture was stirred under the same condition for 1 h before quenched with saturated aqueous NH₄Cl solution (50 mL). It was extracted with ethyl acetate (50 mL×3), washed with brine, dried over anhydrous Na₂SO₄, and purified by column chromatography on silica gel (ethyl acetate in petroleum, 9% v/v) to yield Compound C6 (4 g, yield 100%) as a colorless oil. LC-MS (m/z): 474 [M+1-18]⁺; ¹H-NMR (CDCl₃, 400 MHz) major characteristic peaks: δ (ppm) 3.77-3.83 (m, 2H), 4.28 (t, J=8 Hz, 4H), 4.92-5.05 (m, 2H), 5.11 (m, 1H), 5.38-5.57 (m, 1H), 6.67-6.74 (m, 2H), 7.29-7.36 (m, 5H).

To a solution of Compound C6 (4.15 g, 8.4 mmol) in THF (150 mL) was added TBAF (1.1 g, 4.2 mmol) at 0° C. and it was stirred at rt overnight. The mixture was added water (100 mL), extracted with ethyl acetate (50 mL×3), washed with brine (100 mL×2), dried over anhydrous Na₂SO₄, and concentrated to give Compound C7 (3.18 g, yield 100%) as a colorless oil. LC-MS (m/z): 360 [M+1-18]⁺; ¹H-NMR (CDCl₃, 400 MHz) major characteristic peaks: δ (ppm) 4.14-4.16 (m, 6H), 4.91 (s, 2H), 4.98 (s, 1H), 5.47 (d, J=8 Hz, 2H), 6.55-6.63 (m, 2H), 7.17-7.26 (m, 5H).

To a solution of Compound C7 (3.18 g, 8.4 mmol) and Et₃N (3.5 mL, 25.3 mmol) in THF (80 mL) was added MsCl (0.71 mL, 9.3 mmol) at −40° C. and the mixture was stirred at −40° C. for 4 h. It was added water (100 mL), extracted with ethyl acetate (50 mL×3), washed with brine (100 mL×1), dried over anhydrous Na₂SO₄, and purified by column chromatography on silica gel (ethyl acetate in petroleum, 30% v/v) to give Compound C8 (1.35 g, yield 35%) as a colorless oil. LC-MS (m/z): 438 [M+1-18]⁺.

To a solution of Compound C8 (1 g, 3 mmol) in THF (20 mL) was added pyrrolidine (2.66 mL, 30 mmol). The mixture was stirred at 60° C. overnight. It was added water (20 mL), extracted with ethyl acetate (10 mL×3), washed with brine (30 mL×1), dried over anhydrous Na₂SO₄ and concentrated in vacuum to give Compound C9 (900 mg, crude) as a yellow oil. LC-MS (m/z): 431 [M+1]⁺.

To a solution of Compound C9 (900 mg, 2.1 mmol) in EtOH/water (20 mL, 9:1, v/v) was added LiOH.H₂O (264 mg, 6.3 mmol). The mixture was refluxed for 36 h and then diluted with water (20 mL). It was extracted with ethyl acetate (20 mL×3). The combined organic layers were dried over anhydrous Na₂SO₄ and concentrated in vacuum to give Intermediate C (800 mg, crude) as a yellow oil. LC-MS (m/z): 297 [M+1]⁺.

Intermediate D

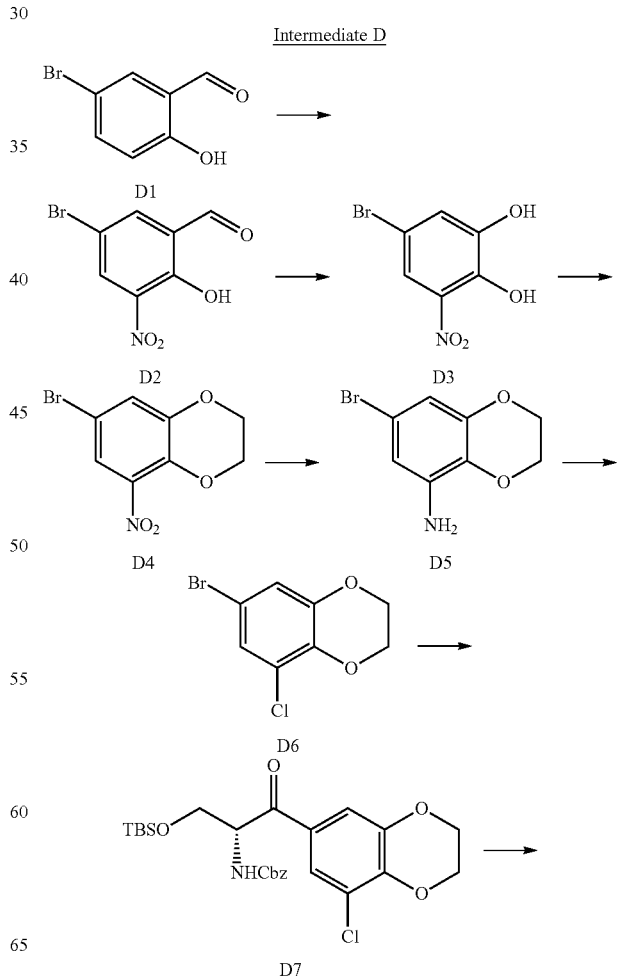

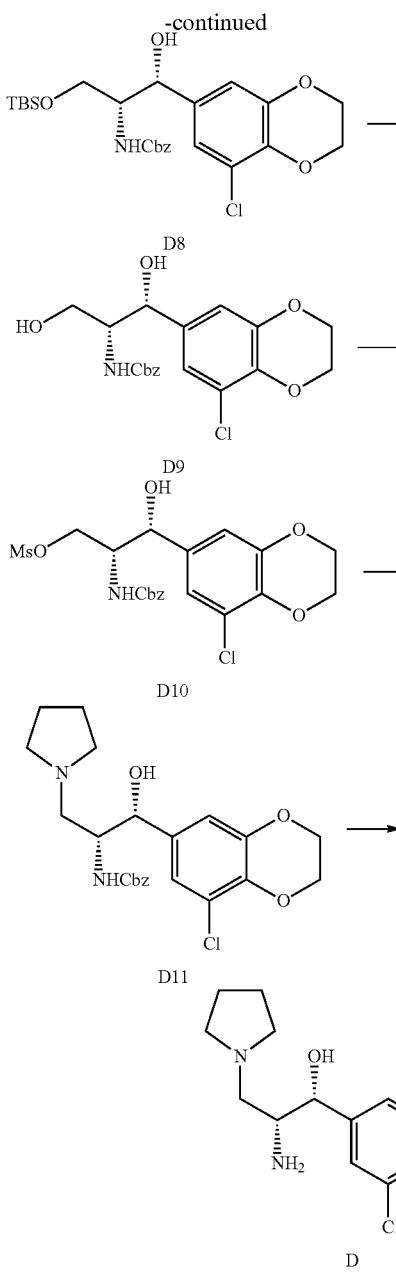

over Na$_2$SO$_4$, and concentrated to give Compound D3 (37 g, yield 98%) as a yellow solid. LC-MS (m/z): 232 [M−1]$^−$; $^1$H-NMR (CDCl$_3$, 400 MHz) major characteristic peaks: δ (ppm) 7.17 (s, 1H), 7.48 (s, 1H), 10.59 (s, 2H).

To a mixture of Compound D3 (32 g, 137 mol) and K$_2$CO$_3$ (73 g, 549 mol) in DMF (500 mL) was added 1,2-dibromoethane (147 mL, 343 mol). The mixture was stirred at 80° C. for 4 h. After cooling to rt, the mixture was filtered and the cake was washed with ethyl acetate (100 mL). The filtrate was diluted with water (900 mL) and extracted with ethyl acetate (400 mL×3). The organic layer was washed with water (900 mL×5) and brine (900 ml×1), dried, concentrated, and purified by column chromatography on silica gel (ethyl acetate in petroleum, 5% v/v) to yield Compound D4 (30 g, yield 84%) as a colorless oil. $^1$H-NMR (CDCl$_3$, 400 MHz) major characteristic peaks: δ (ppm) 4.35 (s, 4H), 6.91 (t, J=8 Hz, 2H), 7.33 (s, 1H).

To a solution of Compound D4 (11 g, 42.5 mmol) in EtOH (200 mL) was added HCl (7 mL). Fe (7.1 g, 127 mmol) was added over 0.5 h. Then HCl was added to reach pH 3-4. The mixture was stirred at 100° C. for 2 h. After cooling to rt, 10% NaOH aq was added dropwise until pH 10~11. The mixture was filtered and the cake was washed with THF. The filtrate was condensed and extracted with ethyl acetate (100 mL×3), washed with brine (200 mL×1), dried over anhydrous Na$_2$SO$_4$, concentrated, and purified by column chromatography on silica gel (ethyl acetate in petroleum, 20% v/v) to obtain Compound D5 (9 g, yield 93%) as a white solid. LC-MS (m/z): 230 [M+1]$^+$; $^1$H-NMR (CDCl$_3$, 400 MHz) major characteristic peaks: δ (ppm) 4.23-4.27 (m, 4H), 6.46 (d, J=8 Hz, 2H).

A solution of D5 (3.3 g, 14.7 mmol) in H$_2$O (15 mL) and concentrated HCl (4 mL, 48 mmol) was cooled to 5° C. A solution of NaNO$_2$ (1.09 g, 15.8 mmol) in H$_2$O (7 mL) was added dropwise. The brown solution of the diazionium salt was then added dropwise to a solution of CuCl (2.96 g, 28.4 mmol) in concentrated HCl (5 mL), maintaining the internal temperature around 10° C. The mixture was then diluted with H$_2$O (120 ml) and the solution was stirred for an additional 1 h at rt. The product was extracted into ethyl acetate (50 mL×3), washed with brine (200 mL×1), dried over anhydrous Na$_2$SO$_4$, concentrated, and purified by column chromatography on silica gel (ethyl acetate in petroleum, 20% v/v) to obtain Compound D6 (1.9 g, yield 53%) as a white solid. $^1$H-NMR (CDCl$_3$, 400 MHz) major characteristic peaks: δ (ppm) 4.26 (t, J=8 Hz, 2H), 4.34 (t, J=8 Hz, 2H), 6.95 (s, 1H), 7.08 (s, 1H).

To a solution of Compound D6 (8.05 g, 32 mmol) in THF (300 mL) was added n-BuLi (2.4 M, 14 mL, 29.4 mmol) at −60° C. under N$_2$ and stirred for 0.5 h. Then it was added a solution of Compound A6 (4.3 g, 11 mmol) in THF (10 mL). The mixture was stirred at −60° C. under N$_2$ for 20 min, quenched with saturated aqueous NH$_4$Cl solution (200 mL), extracted with ethyl acetate (200 mL×3), washed with brine (200 mL×1), dried over anhydrous Na$_2$SO$_4$, purified by column chromatography on silica gel (ethyl acetate in petroleum, 10% v/v) to yield Compound D7 (4.87 g, yield 66%) as a colorless oil. LC-MS (m/z): 506 [M+1]$^+$.

To a solution of Compound D7 (4.5 g, 8.8 mmol) in THF (50 mL) was added L-selectride (17.7 mL) at −60° C. under N$_2$. After stirred for 1 h, the mixture was quenched with saturated aqueous NH$_4$Cl solution (50 mL), extracted with ethyl acetate (50 mL×3), washed with brine, dried over anhydrous Na$_2$SO$_4$, and purified by column chromatography on silica gel (ethyl acetate in petroleum, 20% v/v) to give Compound D8 (3.8 g, yield 85%) as a white solid. LC-MS (m/z): 490 [M+1−18]$^+$; $^1$H-NMR (CDCl$_3$, 400 MHz) major To a solution of Compound D1 (80 g, 266 mmol) in CH$_3$CO$_2$H (400 ml) was added fuming HNO$_3$ (24 mL) at 10° C. and the mixture was stirred at 32° C. for 1 h. Water (200 mL) was added and the mixture filtered. The filtrate was washed with water to remove CH$_3$CO$_2$H and was dried to give Compound D2 (80 g, yield 82%) as a yellow solid. LC-MS (m/z): 244 [M−1]$^−$.

To a solution of Compound D2 (40 g, 163 mmol) in THF (260 mL) was added dropwise aq. NaOH solution (0.05 N, 640 mL, 33 mmol) at 0° C. and 30% H$_2$O$_2$ solution (80 mL). The mixture was stirred for 2 h at rt. The second portion of 30% H$_2$O$_2$ (80 mL) was added dropwise and the mixture was stirred for 4 h. After cooling to 0° C., aq. NaOH solution (2 N, 98 mL) was added dropwise until pH10~11. The mixture was stirred for 0.5 h and quenched with conc. HCl at 0° C. until pH 2~3. The mixture was extracted with dichloromethane (250 mL×3) and washed with brine (300 mL×2), dried characteristic peaks: δ (ppm) 0.90 (s, 9H), 3.77-3.85 (m, 2H), 4.25 (s, 2H), 4.34 (s, 2H), 4.90 (s, 1H), 5.01-5.12 (m, 2H), 5.40 (d, J=8 Hz, 1H), 6.80 (s, 1H), 6.97 (s, 1H), 7.32-7.36 (m, 5H).

To a solution of Compound D8 (3.8 g, 7.5 mmol) in THF (150 mL) was added TBAF (1 g, 3.8 mmol) at 0° C. and it was stirred at rt overnight. The mixture was added water (100 mL), extracted with ethyl acetate (50 mL×3), washed with brine (100 mL×2), dried over anhydrous Na$_2$SO$_4$, and concentrated to yield D9 (2.81 g, yield 100%) as a colorless oil. LC-MS (m/z): 376 [M+1-18]$^+$; $^1$H-NMR (CDCl$_3$, 400 MHz) major characteristic peaks: δ (ppm) 3.72-3.80 (m, 2H), 4.23 (s, 2H), 4.31 (s, 2H), 4.69-4.86 (m, 1H), 5.02-5.15 (m, 2H), 5.51 (d, J=8 Hz, 1H), 6.75-6.96 (m, 2H), 7.29-7.36 (m, 5H).

To a solution of Compound D9 (1.4 g, 3.6 mmol) and TEA (1.5 mL, 10.8 mmol) in THF (30 mL) was added MsCl (0.31 mL, 3.9 mmol) at −40° C. After stirring at −0° C. for 4 h, water (50 mL) was added and the product was extracted into ethyl acetate (50 mL×3) which was washed with brine (100 mL×1) and dried over anhydrous Na$_2$SO$_4$. The product was purified by column chromatography on silica gel (ethyl acetate in petroleum, 50% v/v) to give Compound D10 (756 mg, yield 45%) as a white solid. LC-MS (m/z): 454 [M+1-18]$^+$.

To a solution of Compound D10 (756 mg, 1.6 mmol) in THF (20 mL) was added pyrrolidine (1.4 mL, 16 mmol). The mixture was stirred at 60° C. overnight. It was added water (20 mL), extracted with ethyl acetate (10 mL×3), washed with brine (30 mL×1), dried over anhydrous Na$_2$SO$_4$, and concentrated in vacuum to give crude product Compound D11 (715 mg, crude) as a white solid. LC-MS (m/z): 447 [M+1]$^+$.

To a solution of Compound D11 (714 mg, 1.6 mmol) in EtOH/water (24 mL, 2:1, v/v) was added LiOH.H$_2$O (672 mg, 16 mmol). The mixture was refluxed for 24 h before added water (20 mL). It was extracted with ethyl acetate (20 mL×3). The combined organic layers were dried over anhydrous Na$_2$SO$_4$ and concentrated in vacuum to give crude product Intermediate D (620 mg, crude) as a yellow oil. LC-MS (m/z): 313 [M+1]$^+$.

Intermediate E

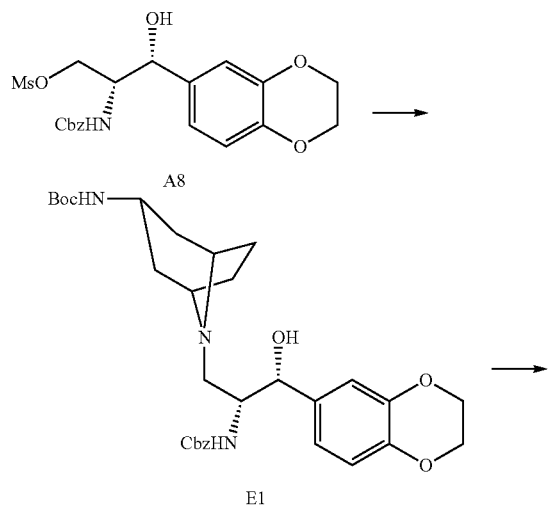

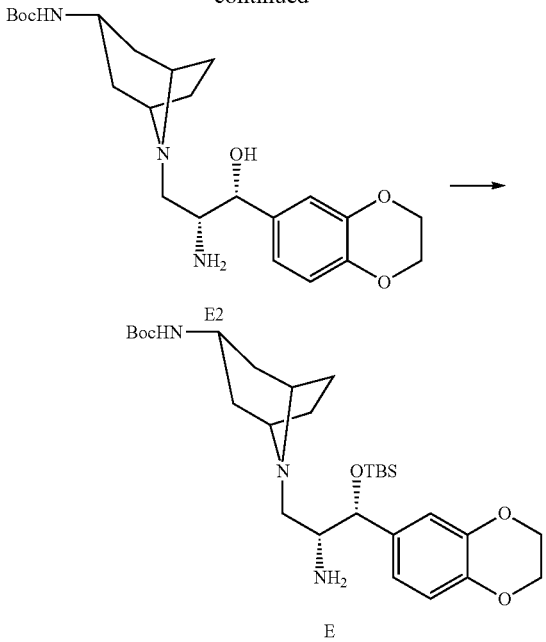

A suspension of Compound A8 (1.00 g, 2.29 mmol), tert-butyl-8-azabicyclo[3.2.1]octan-3-ylcarbamate (1.96 g, 6.86 mmol) and K$_2$CO$_3$ (1.58 g, 11.45 mmol) in ACN (30 mL) was stirred at 60° C. overnight. The mixture was diluted with ethyl acetate (150 mL) and evaporated to give Compound E1 (1.20 g, yield 92%) as a colorless oil. LCMS (m/z): 568 [M+1]$^+$.

A mixture of Compound E1 (1.20 g, 2.12 mmol) and NaOH (423 mg, 10.58 mmol) in H$_2$O/EtOH (10/50 mL) was stirred at 80° C. overnight. The mixture was diluted with ethyl acetate (150 mL), washed with water and brine, and purified by prep-HPLC to yield Compound E2 (980 mg, yield 100%) as a colorless oil. LCMS (m/z): 433 [M+1]$^+$.

To a solution of Compound E2 (980 mg, 2.26 mmol) and imidazole (461 mg, 6.78 mmol) in THF (10 mL) was added TBDMSCl (678 mg, 4.53 mmol) at rt. The mixture was stirred at rt for 2 h. It was diluted with ethyl acetate (150 mL), washed with water and brine, dried with anhydrous Na$_2$SO$_4$, and evaporated to afford Intermediate E (1.10 g, yield 89%) as a colorless oil, which was used for next step directly. LCMS (m/z): 548 [M+1]$^+$.

Example 1

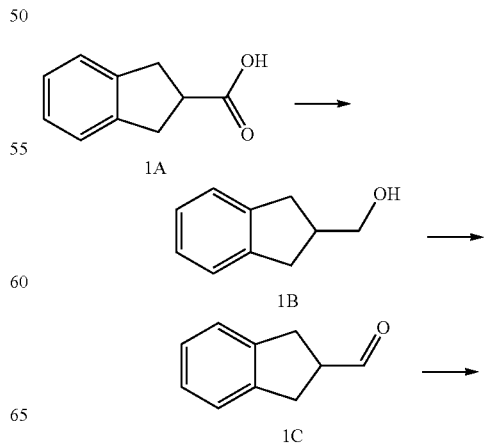

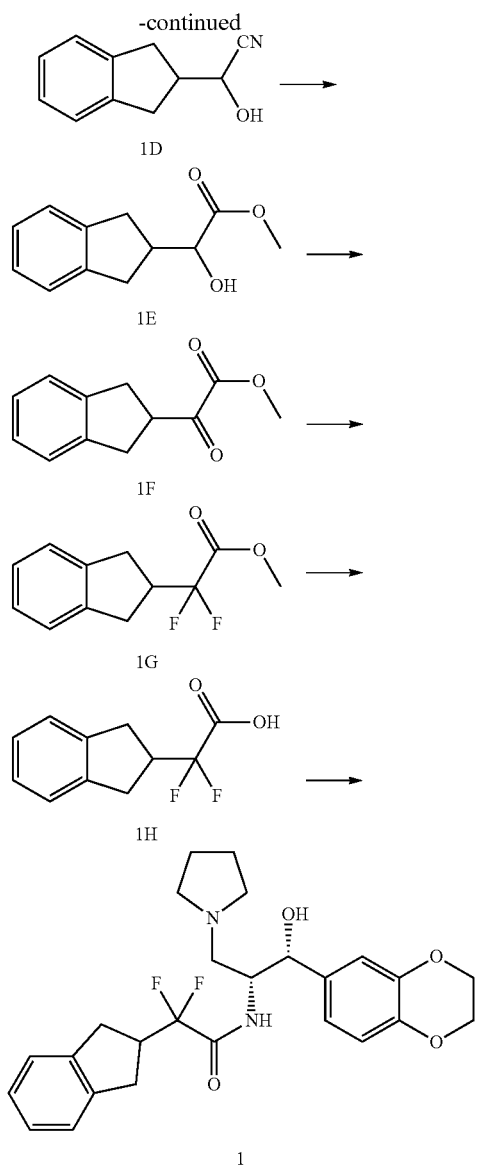

stirring, the organic phase was collected and the aqueous phase was extracted with diethyl ether (10 mL×3). The combined organic layers were dried and evaporated to give a crude product which was purified by column chromatography on silica gel (ethyl acetate in petroleum ether, from 1% to 4% v/v) to afford Compound 1C (190 mg, yield 96%) as a yellow oil. $^1$H-NMR (CDCl$_3$, 400 MHz) major characteristic peaks: δ (ppm) 3.05-3.23 (m, 5H), 7.06-7.15 (m, 4H), 9.67 (s, 1H).

Compound 1C (292 mg, 2 mmol) was added to a solution of sodium metabisulfite (196 mg, 4 mmol) in water (3 mL). The mixture was vigorously stirred for 2 h at rt and after the addition of sodium cyanide (380 mg, 2 mmol), and then stirred for 1 h. The mixture was extracted with diethyl ether (20 mL×3). The combined organic layers were washed with brine (20 mL), dried over Na$_2$SO$_4$, and concentrated to give a crude product 1D (316 mg, yield 91%) as a yellow oil. $^1$H-NMR (CDCl$_3$, 400 MHz) major characteristic peaks: δ (ppm) 2.89-3.01 (m, 3H), 3.14-3.24 (m, 2H), 4.41-4.43 (d, J=8 Hz, 1H), 7.16-7.26 (m, 4H).

A solution of Compound 1D (300 mg, 1.7 mmol) in HCl/MeOH (3 M, 2 mL) was heated to reflux for 18 h. The mixture was concentrated by evaporation and purified by column chromatography on silica gel to give Compound 1E (116 mg, yield 32%). $^1$H-NMR (CDCl$_3$, 400 MHz) major characteristic peaks: δ (ppm) 2.85-3.01 (m, 6H), 3.75 (s, 3H), 4.28 (s, 1H), 7.11-7.19 (m, 4H).

A solution of Compound 1E (550 mg, 2.70 mmol) and Dess-Martin reagents (1.3 g, 3.2 mmol) in dichloromethane (20 mL) was stirred at rt for 4 h. The suspension was diluted with diethyl ether (60 mL) before being slowly poured into a saturated solution of sodium hydrogen carbonate (20 mL) in which contained a pre-dissolved sodium thiosulfate pentahydrate (1.6 g, 6.4 mmol). After 15 min of vigorous stirring, the organic phase was collected and the aqueous phase was extracted with diethyl ether (10 mL×3). The combined organic layers were dried and evaporated to give a crude product 1F (500 mg, yield 92%) as a yellow oil. $^1$H-NMR (CDCl$_3$, 400 MHz) major characteristic peaks: δ (ppm) 3.24-3.26 (d, J=4 Hz, 4H), 3.89-3.91 (m, 3H), 4.01-4.05 (m, 1H), 7.14-7.20 (m, 4H).

To a stirred solution of Compound 1F (200 mg, 1 mmol) in DCM (4 mL) was added DAST (0.8 mL, 6 mmol) at 0° C. The resulting mixture was stirred at rt for 24 h. The mixture was poured into crash ice slowly with stirring. The mixture was stirred for 30 min, and then extracted with DCM (10 mL×3). The combined organic layers were washed with brine (20 mL), dried over Na$_2$SO$_4$, and concentrated to give a crude product. The crude product was purified by prep-TLC (petroleum ether as the eluent) to give Compound 1G (80 mg, yield 36%). $^1$H-NMR (CDCl$_3$, 400 MHz) major characteristic peaks: δ (ppm) 2.98-3.19 (m, 5H), 3.74 (s, 3H), 7.07-7.17 (m, 4H).

To a stirred solution of Compound 1G (140 mg, 0.6 mmol) in EtOH (2 mL) and H$_2$O (2 mL) was added LiOH.H$_2$O (50 mg, 1.2 mmol) in ice bath. The resulting mixture was stirred at rt for 2 h and followed by acidification to pH 2 with 2 M HCl. The mixture was extracted with EtOAc (20 mL×2). The combined organic layers were dried over Na$_2$SO$_4$, and concentrated to give Compound 1H (130 mg, yield 100%) as yellow oil. LC-MS (m/z): 211 [M−1]$^-$; H-NMR (CDCl$_3$, 400 MHz) major characteristic peaks: δ (ppm) 3.09-3.12 (m, 5H), 7.13-7.18 (m, 4H).

To a stirred mixture of Compound 1H (31.8 mg, 0.15 mmol) and Intermediate A (62.55 mg, 0.23 mmol) in DMF (3 mL) was added HOBt (30 mg, 0.25 mmol) and EDCI (43.2 mg, 0.23 mmol). The resulting mixture was stirred at To a stirred solution of Compound 1A (2.75 g, 17 mmol) in DCM (40 mL) was added THF-borane (1 M, 20 mL, 20 mmol) at −78° C. The resulting mixture was allowed to warm up to rt over 1 h. To the mixture was added MeOH (8 mL) and it was heated to reflux for 2 h. Diluted with aq. NaHCO$_3$ (20 mL), the mixture was poured into crash ice slowly with stirring. The mixture was then extracted with EtOAc (20 mL×3). The combined organic layers were dried over Na$_2$SO$_4$ and concentrated to give the crude product which was purified by column chromatography on silica gel (ethyl acetate in petroleum ether, from 1% to 25% v/v) to yield compound 1B (2.4 g, yield 96%) as a white solid. $^1$H-NMR (CDCl$_3$, 400 MHz) major characteristic peaks: δ (ppm) 1.79-2.75 (m, 3H), 3.01-3.08 (m, 2H), 3.61-3.64 (m, 2H), 7.10-7.23 (m, 4H).

A solution of Compound 1B (200 mg, 1.4 mmol) and Dess-Martin reagent (688 mg, 1.6 mmol) in dichloromethane (20 mL) was stirred at rt for 4 h. The resulting solution was poured into a saturated solution of sodium hydrogen carbonate (20 mL) in which beforehand sodium thiosulfate pentahydrate had been dissolved. After 15 min of vigorous rt overnight. The mixture was diluted with water (15 mL), and extracted with EtOAc (15 mL×3). The combined organic layers were washed with brine (15 mL), dried over $Na_2SO_4$, and concentrated to give a crude product. The crude product was purified by prep-HPLC to afford trifluoroacetic acid salt of Compound 1 (11.1 mg, yield 15.5%) as a white solid. LC-MS (m/z): 473 [M+1]$^+$; $^1$H-NMR (CDCl$_3$, 400 MHz) major characteristic peaks: δ (ppm) 1.62 (s, 4H), 2.16 (s, 4H), 2.58-2.64 (m, 2H), 2.85-3.09 (m, 4H), 3.52-3.57 (m, 1H), 3.52-3.57 (m, 1H), 4.11-4.21 (m, 4H), 4.39-4.41 (m, 1H), 5.16 (s, 1H), 6.80-6.90 (m, 3H), 7.13-7.15 (t, J=4 Hz, 4H), 7.37-7.39 (d, J=8 Hz, 1H).

Example 2

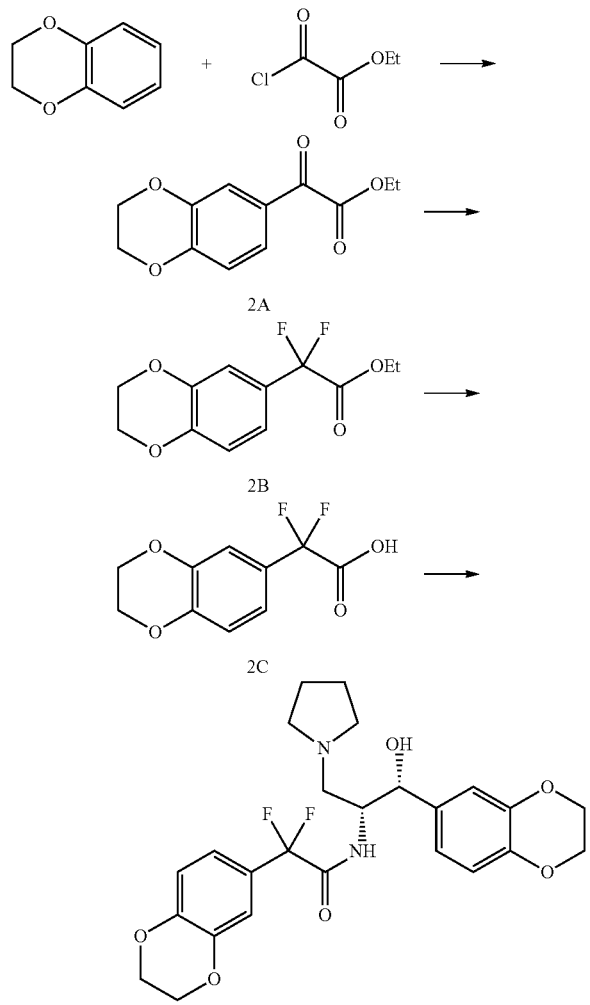

To a stirred suspension of AlCl$_3$ (26.7 g, 200 mmol) in DCM (100 mL) was added dropwise ethyl 2-chloro-2-oxoacetate (27.3 g, 200 mL) at 0° C. After stirred at 0° C. for 30 min, 2, 3-dihydrobenzo[b][1,4]dioxine (13.6 g, 100 mmol) was added dropwise at 0° C. to the mixture. The resulting mixture was stirred at rt for 3 h, poured into ice water (300 mL), and then extracted with DCM (150 mL×3). The combined organic layers were washed with aq. NaHCO$_3$ (200 mL), brine (200 mL), dried over Na$_2$SO$_4$, and concentrated to give a crude product. The crude product was purified by column chromatography on silica gel (ethyl acetate in petroleum ether, from 5% to 10% v/v) to yield Compound 2A (18 g, yield 76%) as a yellow solid. LC-MS (m/z): 162 [M+1]$^+$, $^1$H-NMR (CDCl$_3$, 400 MHz) major characteristic peaks: δ (ppm) 1.40-1.43 (t, J=7.2 Hz, 3H), 4.28-4.33 (m, 2H), 4.34-4.36 (m, 2H), 4.40-4.45 (m, 2H), 6.94-6.96 (dd, J=7.6, 1.6 Hz, 1H), 7.54-7.56 (m, 2H).

To a stirred solution of Compound 2A (4.72 g, 20 mmol) in DCM (50 mL) was added DAST (16.1 g, 100 mmol) at 0° C. The resulting mixture was stirred at rt for 24 h and poured into crash ice slowly with stirring. The mixture was stirred for 30 min, and then extracted with DCM (40 mL×3). The combined organic layers were washed with brine (20 mL), dried over Na$_2$SO$_4$, and concentrated to give crude product. The crude product was purified by column chromatography on silica gel (ethyl acetate in petroleum ether, from 0% to 3% v/v) to afford Compound 2B (4.28 g, yield 83%) as a yellow oil. LC-MS (m/z): 259 [M+1]$^+$, $^1$H-NMR (CDCl$_3$, 400 MHz) major characteristic peaks: δ (ppm) 1.29-1.33 (t, J=7.2 Hz, 3H), 4.26-4.32 (m, 6H), 6.90-6.92 (d, J=8.0 Hz, 1H), 7.07-7.12 (dd, J=7.6, 2.4 Hz, 1H), 7.12-7.13 (d, J=2.0 Hz, 1H).

To a stirred solution of Compound 2B (4.28 g, 16.59 mmol) in THF (20 mL) and H$_2$O (20 mL) was added LiOH.H$_2$O (1.393 g, 33.18 mmol) in an ice bath. The resulting mixture was stirred at rt for 16 h. THF was removed under reduced pressure. The residue was diluted with water (20 mL), acidified to pH 2 with 2 M HCl, and then extracted with EtOAc (20 mL×3). The combined organic layers were dried over Na$_2$SO$_4$ and concentrated to give Compound 2C (3.8 g, yield 98%) as light yellow solid. LC-MS (m/z): 211 [M−19]$^+$; H-NMR (CDCl$_3$, 400 MHz) major characteristic peaks: δ (ppm) 4.28-4.30 (t, J=4.4 Hz, 4H), 6.98-7.04 (m, 3H).

To a stirred mixture of Compound 2C (23 mg, 0.1 mmol) and Intermediate A (41.7 mg, 0.15 mmol) in DMF (1 mL) was added HOBt (20 mg, 0.15 mmol) and EDCI (30 mg, 0.15 mmol). The resulting mixture was stirred at rt overnight. The mixture was diluted with water (10 mL) and extracted with EtOAc (10 mL×3). The combined organic layers were washed with brine (10 mL), dried over Na$_2$SO$_4$, and concentrated to give crude product. The crude product was purified by prep-HPLC to give trifluoroacetic acid salt of Compound 2 (18.9 mg, yield 39%) as a white solid. LC-MS (m/z): 491 [M+1]$^+$; $^1$H-NMR (CDCl$_3$, 400 MHz) major characteristic peaks: δ (ppm) 2.07 (s, 3H), 2.86 (s, 1H), 3.00 (s, 1H), 3.46 (s, 2H), 3.76 (s, 2H), 4.20-4.25 (m, 8H), 4.37 (s, 1H), 5.05 (s, 1H), 6.72-6.81 (m, 4H), 6.91 (s, 1H), 7.65 (s, 1H), 11.67 (s, 1H).

Example 3

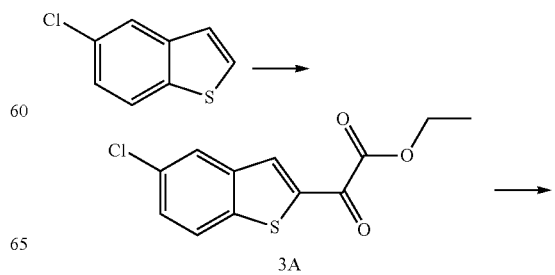

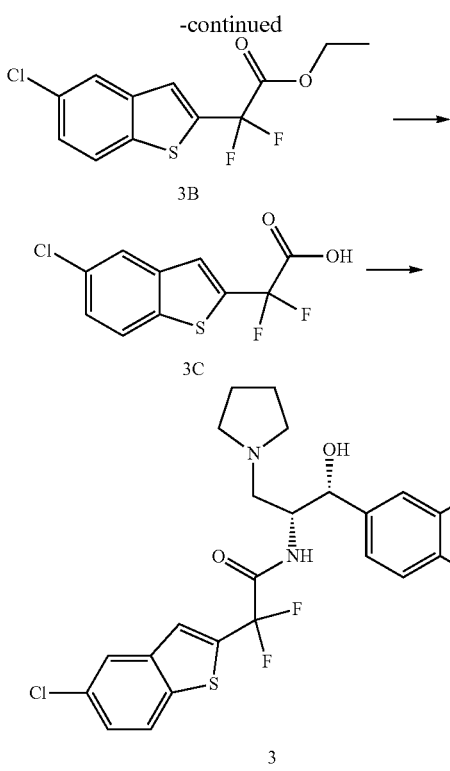

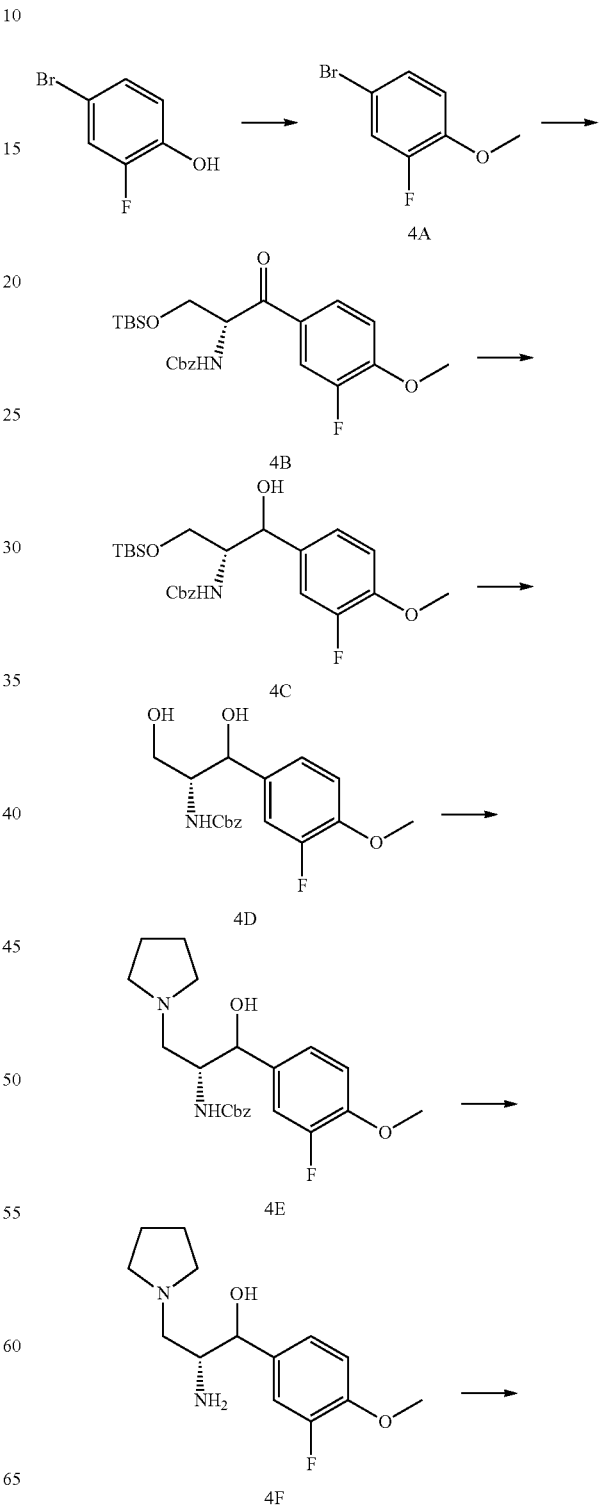

by prep-HPLC to afford Compound 3 (50 mg, yield 33%) as a white solid. LCMS: 523 [M+1]⁺; ¹H-NMR (CDCl₃, 400 MHz) major characteristic peaks: δ (ppm) 2.14 (br s, 4H), 2.59 (br s, 4H), 2.89-3.03 (m, 2H), 3.45-3.51 (m, 2H), 3.82 (br s, 2H), 4.00-4.16 (m, 4H), 4.44 (br s, 1H), 5.15 (s, 1H), 6.72-6.82 (m, 3H), 7.10 (s, 1H), 3.37 (d, J=10.4 Hz, 1H), 7.70-7.78 (m, 2H), 11.95 (s, 1H).

Example 4

To a solution of 5-chlorobenzo[b]thiophene (2.00 g, 11.83 mmol) in THF (50 mL) was added dropwise n-BuLi in THF (5.20 mL, 13.01 mmol) at −78° C. Then it was stirred at −50° C. for 1 h. Diethyl oxalate (4.32 g, 29.58 mmol) was added to the mixture quickly at −78° C. The mixture was stirred at −50° C. for 1 h. It was quenched with acetic acid, diluted with ethyl acetate (200 mL), washed with water and brine, dried with anhydrous Na₂SO₄, and evaporated to give a residue which was washed with petroleum ether to obtain Compound 3A (2.60 g, yield 82%) as a light yellow solid. LCMS: 269 [M+1]⁺; ¹H-NMR (CDCl₃, 400 MHz) major characteristic peaks: δ (ppm) 1.46 (t, J=7.6 Hz, 3H), 4.45-4.51 (m, 2H), 7.48 (d, J=8.8 Hz, 1H), 7.82 (d, J=8.8 Hz, 1H), 7.92 (s, 1H), 8.37 (s, 1H).

To a solution of Compound 3A (600 mg, 2.25 mmol) in DCM (120 mL) was added dropwise DAST (1.5 mL, 11.19 mmol) at rt. The mixture was stirred at rt overnight. It was then quenched with ice, diluted with ethyl acetate (150 mL), washed with water and brine, dried with anhydrous Na₂SO₄, and evaporated to yield Compound 3B (420 mg, yield 64%) as a yellow oil. LCMS: 291 [M+1]⁺; ¹H-NMR (CDCl₃, 400 MHz) major characteristic peaks: δ (ppm) 1.37 (t, J=7.2 Hz, 3H), 4.35-4.41 (m, 2H), 7.38 (d, J=8.8 Hz, 1H), 7.58 (s, 1H), 7.77-7.82 (m, 2H).

A solution of Compound 3B (420 mg, 1.45 mmol) and LiOH·H₂O (122 mg, 2.90 mmol) in THF/MeOH/H₂O (10/10/5 mL) was stirred at rt for 2 h. The mixture was adjusted to pH 2 with conc. HCl, diluted with ethyl acetate (150 mL), washed with water and brine, dried with anhydrous Na₂SO₄, and evaporated to give Compound 3C (400 mg, yield 100%) as a white solid. LCMS: 261 [M−1]⁻.

A mixture of Intermediate A (80 mg, 0.29 mmol), Compound 3C (94 mg, 0.34 mmol), EDCI (84 mg, 0.44 mmol), HOBt (59 mg, 0.44 mmol) and DIPEA (0.2 mL) in DCM (5 mL) was stirred at rt overnight. Then it was diluted with ethyl acetate (150 mL) washed with water and brine, purified

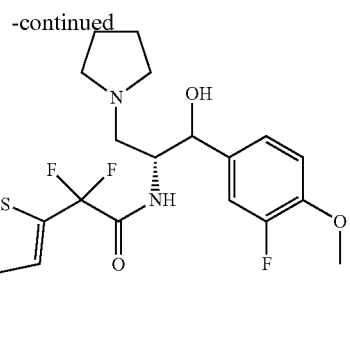

4

To a solution of 4-bromo-2-fluorophenol (15 g, 78.5 mmol) in DMF (200 mL) was added $K_2CO_3$ (32.25 g, 235.6 mmol), $CH_3I$ (12.3 mL, 96.3 mmol). The mixture was stirred at rt overnight. Water (500 mL) was added to the mixture and the mixture was extracted with ethyl acetate (200 mL×3), dried over anhydrous $Na_2SO_4$, and purified by column chromatography on silica gel (petroleum 100%) to obtain Compound 4A (11.3 g, 70%) as a colorless oil. $^1$H-NMR (CDCl$_3$, 400 MHz) major characteristic peaks: δ (ppm) 3.86 (s, 3H), 6.83 (t, J=8.8 Hz, 1H), 7.20 (m, 2H).

To a solution of Compound 4A (11 g, 53.7 mmol) in THF (250 mL) was added n-BuLi (2.5M, 22.2 mL, 55.5 mmol) at −60° C. under $N_2$. The mixture was stirred at −0° C. under $N_2$ for 0.5 h. Then it was added a solution of Intermediate A4 (7.1 g, 17.9 mmol) in THF (50 mL). The mixture was stirred at −60° C. under $N_2$ for another 5 min before quenched with saturated aqueous $NH_4Cl$ solution (200 mL). The mixture was extracted with ethyl acetate (200 mL×3), washed with brine (200 mL×1), dried over anhydrous $Na_2SO_4$, and purified by column chromatography on silica (ethyl acetate in petroleum, 9% v/v) to yield Compound 4B (7.1 g, 86%) as a colorless oil. LCMS: 462 [M+1]$^+$; $^1$H-NMR (CDCl$_3$, 400 MHz) major characteristic peaks: δ (ppm) −0.14 (s, 3H), −0.12 (s, 3H), 0.75 (s, 9H), 3.89 (m, 1H), 3.96 (m, 4H), 5.13 (s, 2H), 5.29 (m, 1H), 5.89 (m, 1H), 7.01 (m, 1H), 7.35 (m, 5H), 7.73 (m, 2H).

To a solution of Compound 4B (7.1 g, 15.4 mmol) in THF (100 mL) was added L-Selectride (31 mL) at −60° C. under $N_2$ and stirred at −60° C. under $N_2$ for 1 h. The mixture was quenched with saturated aqueous $NH_4Cl$ solution (100 mL) and extracted with ethyl acetate (100 mL×3), washed with brine, dried over anhydrous $Na_2SO_4$, and then purified by column chromatography on silica gel (ethyl acetate in petroleum, 9% v/v) to give Compound 4C (6.7 g, 94%) as a colorless oil. LCMS: 446 [M+1-18]$^+$; $^1$H-NMR (CDCl$_3$, 400 MHz) major characteristic peaks: δ (ppm) 0.03 (m, 6H), 0.90 (d, 9H), 3.68 (m, 1H), 3.88 (m, 5H), 4.89 (m, 1H), 5.04 (m, 2H), 5.39 (m, 1H), 6.88 (m, 1H), 7.03 (m, 1H), 7.12 (m, 1H), 7.30 (m, 5H).

To a solution of Compound 4C (6.7 g, 13.6 mmol) in THF (250 mL) was added TBAF (1.8 g, 6.8 mmol) at 0° C. and stirred at rt overnight. The mixture was added water (200 mL), extracted with ethyl acetate (100 mL×3), washed with brine (200 mL×1), dried over anhydrous $Na_2SO_4$, concentrated to obtain Compound 4D (5 g, 98%) as a yellow oil. LCMS: 332 [M+1-18]$^+$.

To a solution of Compound 4D (5 g, 14.3 mmol) and TEA (6 mL, 42.9 mmol) in THF (80 mL) was added MsCl (1.2 mL) at −60° C. and stirred at −60° C. for 2 h. The mixture was added pyrrolidine (12 mL, 143 mmol) and stirred at 50° C. overnight. After the mixture was cooled down, water (200 mL) was added. The mixture was extracted with ethyl acetate (100 mL×3). The combined organic layers were washed with brine (200 mL×1), and dried over anhydrous $Na_2SO_4$. The crude product was purified by prep-HPLC to obtain Compound 4E (1.9 g, 33%) as a colorless oil. LCMS: 403 [M+1]$^+$; $^1$H-NMR (CDCl$_3$, 400 MHz) major characteristic peaks: δ (ppm) 1.78 (m, 4H), 2.64 (m, 6H), 3.88 (m, 4H), 5.03 (m, 4H), 6.89 (m, 1H), 6.70 (m, 1H), 7.11 (m, 1H), 7.28 (m, 5H).

To a solution of Compound 4E (1.9 g, 4.7 mmol) in MeOH (30 mL) was added Pd(OH)$_2$ (660 mg, 4.7 mmol). The mixture was stirred at rt overnight under $H_2$. The mixture was filtered and the filtrate was concentrated to obtain Compound 4F (1.2 g, 95%) as a colorless oil. LCMS: 269 [M+1]$^+$.

To a mixture of Compound 4F (194 mg, 0.74 mmol) in DCM (10 mL) was added EDCI (213 mg, 1.1 mmol), HOBt (150 mg, 1.11 mmol) and Compound 3C (200 mg, 0.74 mmol) and stirred at rt for overnight. Then it was added water (50 mL), extracted with DCM (20 mL×3), dried over anhydrous $Na_2SO_4$, purified by prep-HPLC to give 4 (50 mg, 14%) as a white solid. LCMS: 514 [M+1]$^+$; $^1$H-NMR (DMSO-d$_6$, 400 MHz) major characteristic peaks: δ (ppm) 1.88 (m, 2H), 2.02 (m, 2H), 3.12 (m, 2H), 3.49 (s, 3H), 3.56 (m, 4H), 4.28 (m, 1H), 4.48 (d, J=9.2 Hz, 1H), 6.06 (br, 1H), 6.71 (t, J=8.8 Hz, 1H), 6.93 (d, J=8 Hz, 1H), 7.05 (dd, 1H), 7.20 (s, 1H), 7.52 (dd, 1H), 7.95 (d, J=2.4 Hz, 1H), 8.07 (d, J=8.4 Hz, 1H), 9.23 (m, 1H), 9.78 (br, 1H).

Example 5

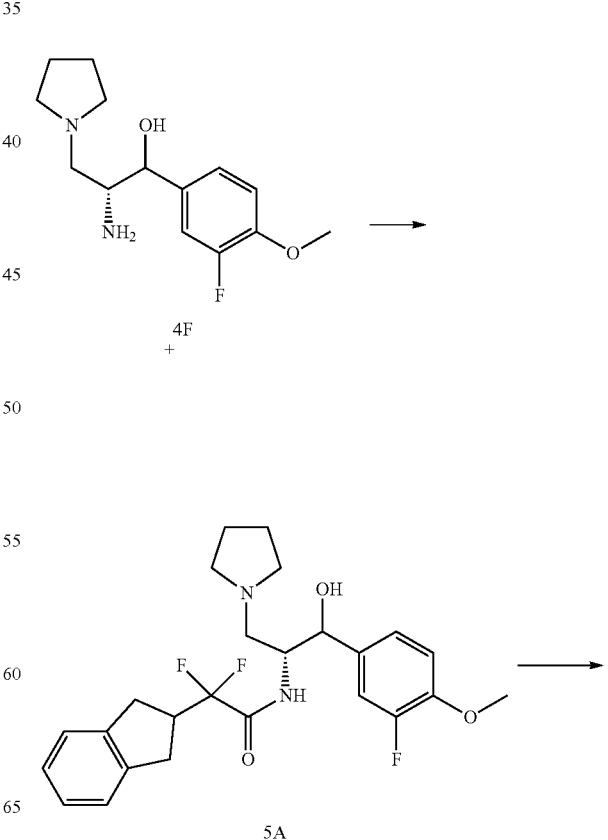

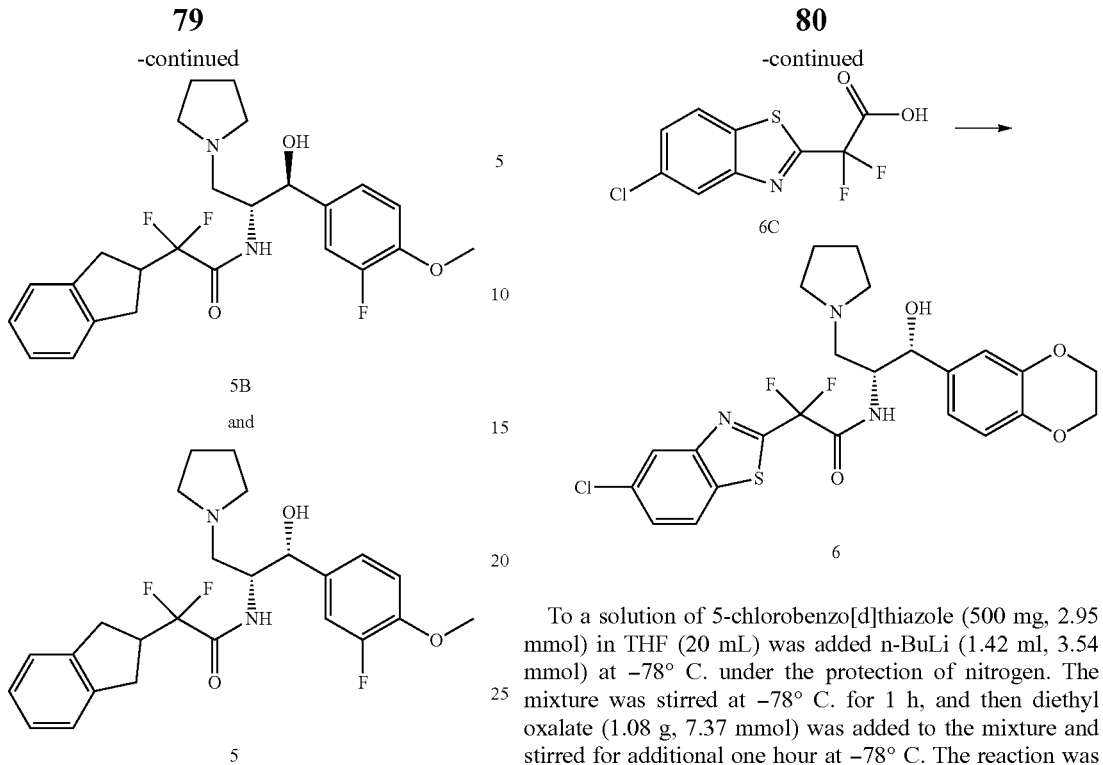

To a mixture of Compound 4F (157 mg, 0.74 mmol) in DCM (10 mL) was added EDCI (213 mg, 1.11 mmol), HOBt (150 mg, 1.11 mmol) and Compound 1H (200 mg, 0.74 mmol) and stirred at rt overnight. Water (50 mL) was added to the mixture, which was then extracted with DCM (20 mL×3). The combined organic phases were dried over anhydrous Na$_2$SO$_4$ and evaporated to remove solvents. The residues were purified by prep-HPLC to yield 5 (30 mg, yield 9%) as a white solid. LCMS: 463 [M+1]$^+$; $^1$H-NMR (DMSO-d$_6$, 400 MHz) major characteristic peaks: δ (ppm) 1.88 (m, 2H), 2.03 (m, 2H), 3.10 (m, 2H), 3.54 (m, 5H), 3.76 (s, 3H), 4.31 (m, 1H), 4.50 (d, J=7.2 Hz, 1H), 6.09 (br, 1H), 7.13 (m, 7H), 8.86 (d, J=8.8 Hz, 1H), 9.51 (br, 1H).

Example 6

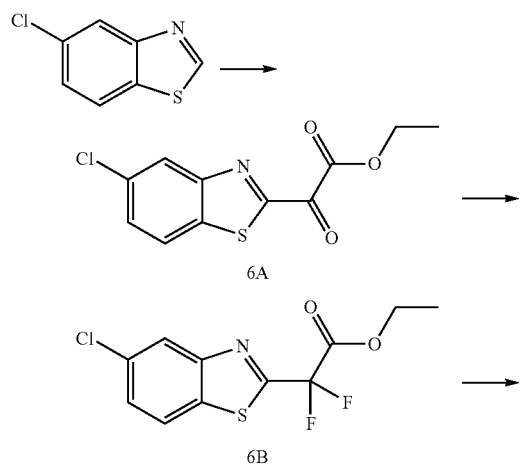

To a solution of 5-chlorobenzo[d]thiazole (500 mg, 2.95 mmol) in THF (20 mL) was added n-BuLi (1.42 ml, 3.54 mmol) at −78° C. under the protection of nitrogen. The mixture was stirred at −78° C. for 1 h, and then diethyl oxalate (1.08 g, 7.37 mmol) was added to the mixture and stirred for additional one hour at −78° C. The reaction was quenched with sat. aqueous NH$_4$Cl. The organic phase was separated and washed with brine, dried over anhydrous Na$_2$SO$_4$, and purified with column chromatography on silica gel (ethyl acetate in petroleum 20% v/v) to give Compound 6A (200 mg, yield 25%) as a yellow solid. LCMS (m/z): 288 [M+18]$^+$; $^1$H-NMR (CDCl$_3$, 400 MHz) major characteristic peaks: δ (ppm) 1.46 (t, J=7.2 Hz, 3H), 4.54 (q, J=7.2 Hz, 2H), 7.57 (dd, J=2.0, 8.8 Hz, 1H), 7.95 (d, J=8.8 Hz, 1H), 8.27 (d, J=2.0 Hz, 1H).

To a solution of Compound 6A (170 mg, 0.63 mmol) in DCM (10 mL) was added DAST (305 mg, 1.89 mmol) at 0° C. under N$_2$ and stirred at 15° C. overnight. The reaction mixture was poured into 100 mL of ice-water and extracted with DCM (50 mL×3). The combined organic phase was washed with brine, and dried over anhydrous Na$_2$SO$_4$, and purified by column chromatography on silica gel (ethyl acetate in petroleum, 9% v/v) to yield Compound 6B (105 mg, yield 52%) as a yellow oil. LCMS (m/z): 292 [M+1]$^+$; $^1$H-NMR (CDCl$_3$, 400 MHz) major characteristic peaks: δ (ppm) 1.27 (t, J=7.2 Hz, 3H), 4.43 (q, J=7.2 Hz, 2H), 7.72 (dd, J=2.0, 8.8 Hz, 1H), 8.36 (m, 2H).

To a solution of Compound 6B (105 mg, 0.36 mmol) in THF/MeOH/water (6 mL, 1:1:1, v/v) was added LiOH.H$_2$O (15 mg). The mixture was stirred at 25° C. for 2 h. After removal of the solvents and adjust pH to 7 with 1 N HCl, the mixture was diluted with ethyl acetate (100 mL), washed with water, brine, and dried over anhydrous Na$_2$SO$_4$. The crude product was used for next step without further purification. Compound 6C (95 mg, yield 99%) was obtained as a yellow oil. LCMS (m/z): 264 [M+1]$^+$; $^1$H-NMR (CDCl$_3$, 400 MHz) major characteristic peaks: δ (ppm) 7.51 (dd, J=1.6, 8.8 Hz, 1H), 7.90 (d, J=8.84 Hz, 1H), 8.14 (d, J=1.6 Hz, 1H).

To a mixture of Compound 6C (95 mg, 0.36 mmol) in DCM (10 mL) was added EDCI (104 mg, 0.54 mmol), HOBt (73 mg, 0.54 mmol) and Intermediate A (100 mg, 0.36 mmol) and stirred at 25° C. overnight. Diluted with water (5 mL), the mixture was extracted with DCM (20 mL×3). The organic phase was dried over anhydrous Na$_2$SO$_4$ and purified with prep-HPLC to afford Compound 6 (10 mg, yield 6%) as a colorless oil. LCMS (m/z): 524 [M+1]+; 1H-NMR (CDCl3, 400 MHz) major characteristic peaks: δ (ppm) 1.91 (m, 4H), 2.75 (m, 2H), 2.93-3.01 (m, 6H), 3.23 (m, 2H), 4.24 (s, 4H), 4.63 (d, J=9.6 Hz, 1H), 6.80 (m, 2H), 7.41 (d, J=8.4 Hz, 1H), 7.83 (d, J=8.8 Hz, 1H), 7.93 (d, J=2.0 Hz, 1H).

Example 7

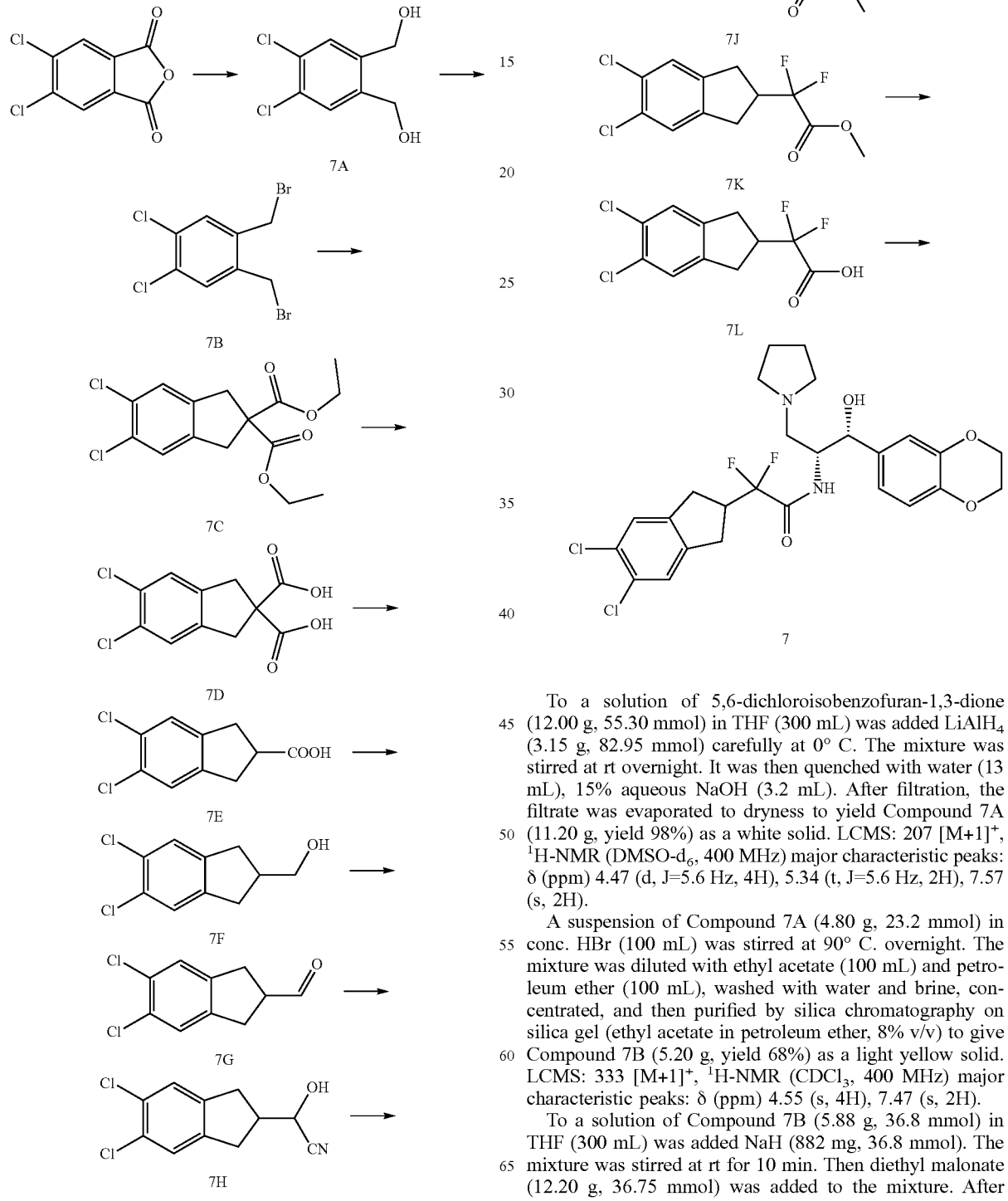

To a solution of 5,6-dichloroisobenzofuran-1,3-dione (12.00 g, 55.30 mmol) in THF (300 mL) was added LiAlH4 (3.15 g, 82.95 mmol) carefully at 0° C. The mixture was stirred at rt overnight. It was then quenched with water (13 mL), 15% aqueous NaOH (3.2 mL). After filtration, the filtrate was evaporated to dryness to yield Compound 7A (11.20 g, yield 98%) as a white solid. LCMS: 207 [M+1]+, 1H-NMR (DMSO-d6, 400 MHz) major characteristic peaks: δ (ppm) 4.47 (d, J=5.6 Hz, 4H), 5.34 (t, J=5.6 Hz, 2H), 7.57 (s, 2H).

A suspension of Compound 7A (4.80 g, 23.2 mmol) in conc. HBr (100 mL) was stirred at 90° C. overnight. The mixture was diluted with ethyl acetate (100 mL) and petroleum ether (100 mL), washed with water and brine, concentrated, and then purified by silica chromatography on silica gel (ethyl acetate in petroleum ether, 8% v/v) to give Compound 7B (5.20 g, yield 68%) as a light yellow solid. LCMS: 333 [M+1]+, 1H-NMR (CDCl3, 400 MHz) major characteristic peaks: δ (ppm) 4.55 (s, 4H), 7.47 (s, 2H).

To a solution of Compound 7B (5.88 g, 36.8 mmol) in THF (300 mL) was added NaH (882 mg, 36.8 mmol). The mixture was stirred at rt for 10 min. Then diethyl malonate (12.20 g, 36.75 mmol) was added to the mixture. After stirring for 20 min, an additional portion of NaH (882 mg, 36.8 mmol) was added. After stirring at rt overnight, the mixture was evaporated to dryness to give Compound 7C (12.6 g, yield 100%) as a white solid. LCMS: 331 [M+1]+.

A mixture of Compound 7C (12.6 g, 38.2 mmol) and LiOH.H$_2$O (5.80 g, 0.15 mol) in THF/MeOH/H$_2$O (100/100/50 mL) was stirred at rt overnight. The mixture was condensed by removal of solvents and adjusted to pH 1 with conc. HCl. The precipitate was filtered to obtain Compound 7D (11.2 g, yield 100%) as a white solid. LCMS: 273 [M−1]−, $^1$H-NMR (DMSO-d$_6$, 400 MHz) major characteristic peaks: δ (ppm) 3.47 (s, 4H), 7.57 (s, 2H), 13.16 (s, 2H).

A mixture of Compound 7D (4.80 g, 17.5 mmol) and NaCl (4.80 g) in DMSO (100 mL) was stirred at 130° C. for 5 h. Diluted with ethyl acetate (200 mL), the mixture was washed with water and brine, dried with anhydrous Na$_2$SO$_4$, and evaporated to dryness to give Compound 7E (3.40 g, yield 84%) as a white solid. LCMS: 229 [M−1]−, $^1$H-NMR (DMSO-d$_6$, 400 MHz) major characteristic peaks: δ (ppm) 3.12-3.23 (m, 4H), 3.34-3.42 (m, 1H), 7.55 (s, 2H), 12.45 (s, 1H).

To a solution of Compound 7E (3.40 g, 1.47 mmol) in THF (100 mL) was added LiAlH$_4$ (554 mg, 1.47 mmol). The mixture was stirred at rt overnight. After being quenched with water (2.4 mL) and aqueous NaOH (15%, 0.56 mL), the precipitate was filtered off and the filtrate was evaporated to give Compound 7F (2.80 g, yield 88%) as a white solid. LCMS: 217 [M+1]+; $^1$H-NMR (DMSO-d$_6$, 400 MHz) major characteristic peaks: δ (ppm) 2.50-2.60 (m, 1H), 2.89-2.95 (m, 2H), 3.32 (s, 4H), 4.65-4.68 (m, 1H), 7.44 (s, 2H).

To a solution of Compound 7F (2.80 g, 12.96 mmol) in DCM (100 mL) was added DMP (6.60 g, 15.6 mmol). The mixture was stirred at rt for 2 h. The solids were filtered off and the filtrate was diluted with ethyl acetate (200 mL), washed with water and brine, and purified by silica gel chromatography (ethyl acetate in PE, 15% v/v) to give Compound 7G (2.10 g, yield 76%) as a light yellow solid. LCMS: 215 [M+1]+; $^1$H-NMR (DMSO-d$_6$, 400 MHz) major characteristic peaks: δ (ppm) 3.06-3.12 (m, 2H), 3.19-3.24 (m, 2H), 3.37-3.44 (m, 1H), 7.51 (s, 2H), 9.68 (s, 1H).

A suspension of Compound 7G (2.70 g, 12.6 mmol) and Na$_2$O$_5$S$_2$ (1.24 g, 25.2 mmol) in EtOH/H$_2$O (20/20 mL) was stirred at rt for 2 h before NaCN (1.24 g, 25.24 mmol) was added. The mixture was stirred at rt overnight. It was diluted with ethyl acetate (200 mL), washed with water and brine, purified by silica gel chromatography (ethyl acetate in petroleum ether, 30% v/v) to yield Compound 7H (2.10 g, yield 69%) as a white solid. LCMS: 242 [M+1]+; $^1$H-NMR (DMSO-d$_6$, 400 MHz) major characteristic peaks: δ (ppm) 2.79-2.87 (m, 3H), 3.01-3.08 (m, 2H), 4.57 (t, J=6.8 Hz, 1H), 6.60 (d, J=6.4 Hz, 1H), 7.50 (s, 2H).

A solution of Compound 7H (2.10 g, 8.71 mmol) in MeOH (100 mL) was stirred at rt overnight in the presence of HCl gas. After the addition of water (20 mL), the mixture was stirred at rt for 2 h and then diluted with ethyl acetate (200 mL), washed with water and brine, dried with anhydrous Na$_2$SO$_4$. Removal of solvents by evaporation gave Compound 7I (1.80 g, yield 75%) as a white solid. LCMS: 275 [M+1]+; $^1$H-NMR (DMSO-d$_6$, 400 MHz) major characteristic peaks: δ (ppm) 2.76-2.92 (m, 5H), 3.63 (s, 3H), 4.08 (t, J=5.6 Hz, 1H), 5.65 (d, J=6.0 Hz, 1H), 7.44 (s, 2H).

To a solution of Compound 7I (1.00 g, 3.65 mmol) in DCM (30 mL) was added DMP (1.55 g, 3.65 mmol). The mixture was stirred at rt for 2 h. It was then diluted with ethyl acetate (200 mL), washed with water and brine, and purified by silica gel chromatography (ethyl acetate in petroleum ether, 25% v/v) to afford Compound 7J (880 mg, yield 87%) as a white solid. LCMS: 273 [M+1]+.

To a solution of Compound 7J (272 mg, 1.00 mmol) in DCM (10 mL) was added DAST (0.66 mL, 5.00 mmol). The mixture was stirred at 25° C. overnight. It was then diluted with ethyl acetate (150 mL), washed with water and brine, and purified by silica gel chromatography (ethyl acetate in PE, 10% v/v) to yield Compound 7K (210 mg, yield 71%) as a white solid. LCMS: 295 [M+1]+.

A mixture of Compound 7K (120 mg, 0.41 mmol) and LiOH.H$_2$O (52 mg, 1.23 mmol) in THF/MeOH/H$_2$O (5/5/2 mL) was stirred at rt for 2 h. After removal of solvents, the residues were purified by prep-HPLC to give Compound 7L (90 mg, yield 78%) as a white solid. LCMS: 279 [M−1]−.

A mixture of Intermediate A (100 mg, 0.36 mmol), Compound 7L (100 mg, 0.36 mmol), EDCI (103 mg, 0.54 mmol), HOBt (73 mg, 0.54 mmol) and Et$_3$N (0.2 mL) in DCM (5 mL) was stirred at 25° C. overnight. It was diluted with ethyl acetate (150 mL), washed with water and brine, and purified by prep-HPLC to afford 7 (50 mg, yield 37%) as a white solid. LCMS: 541 [M+1]+; $^1$H-NMR (CDCl$_3$, 400 MHz) major characteristic peaks: δ (ppm) 2.14 (br s, 4H), 2.52-2.59 (m, 2H), 2.65-2.87 (m, 3H), 2.93-3.11 (m, 3H), 3.38-3.50 (m, 2H), 3.82 (br s, 2H), 4.14-4.25 (m, 4H), 4.42 (br s, 1H), 5.12 (s, 1H), 6.80-6.88 (m, 3H), 7.21 (s, 2H), 7.45 (br s, 1H), 11.99 (s, 1H).

Example 8

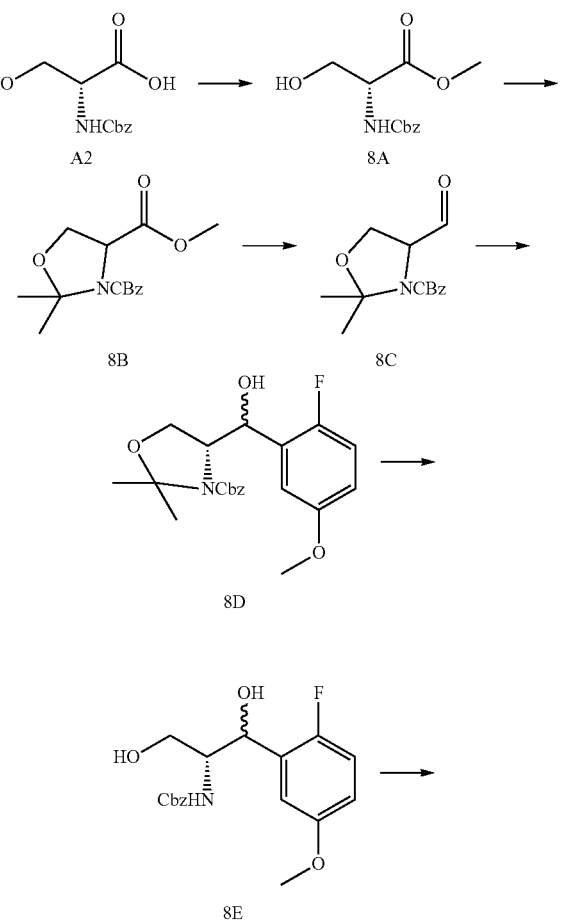

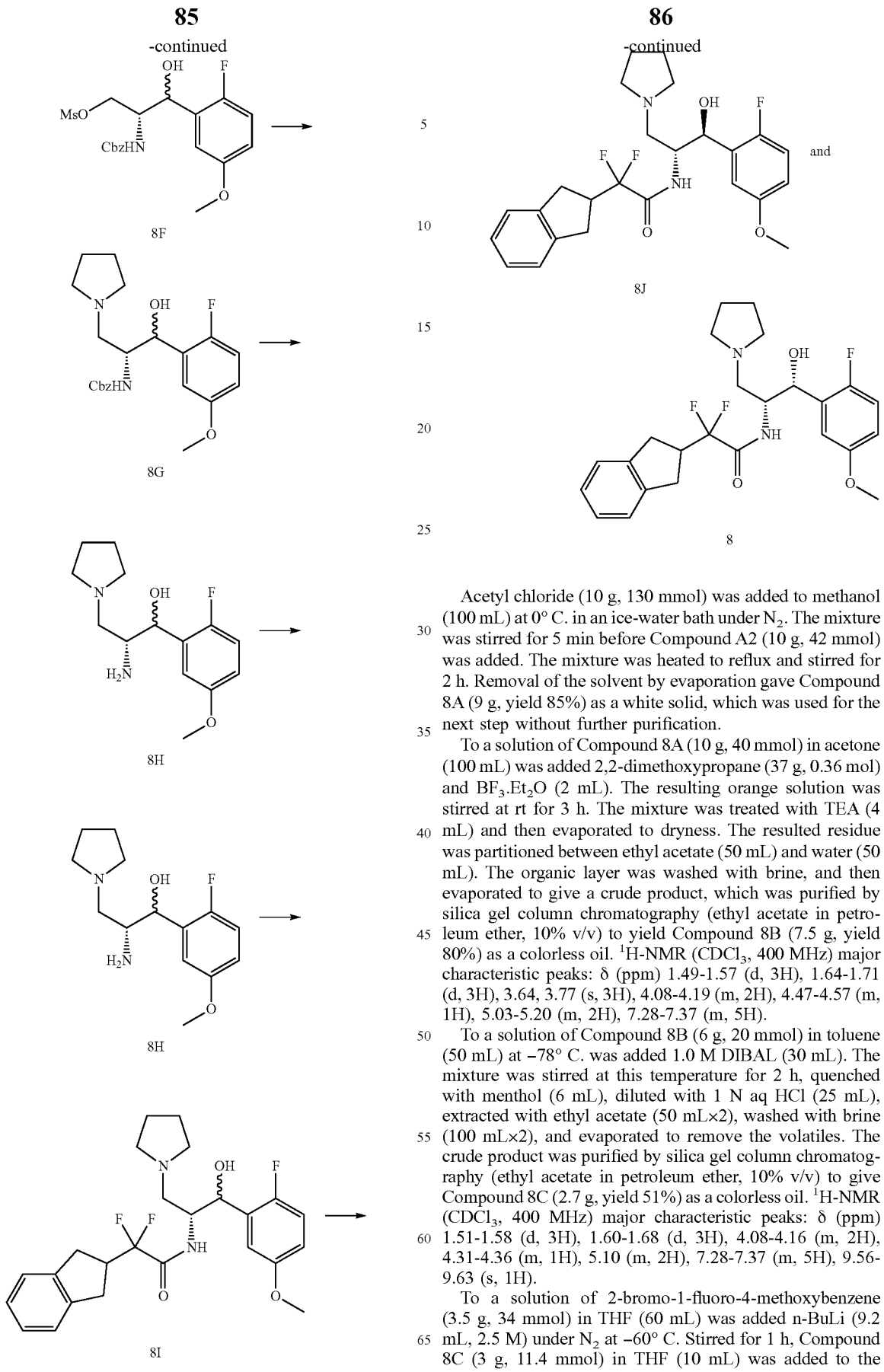

Acetyl chloride (10 g, 130 mmol) was added to methanol (100 mL) at 0° C. in an ice-water bath under $N_2$. The mixture was stirred for 5 min before Compound A2 (10 g, 42 mmol) was added. The mixture was heated to reflux and stirred for 2 h. Removal of the solvent by evaporation gave Compound 8A (9 g, yield 85%) as a white solid, which was used for the next step without further purification.

To a solution of Compound 8A (10 g, 40 mmol) in acetone (100 mL) was added 2,2-dimethoxypropane (37 g, 0.36 mol) and $BF_3.Et_2O$ (2 mL). The resulting orange solution was stirred at rt for 3 h. The mixture was treated with TEA (4 mL) and then evaporated to dryness. The resulted residue was partitioned between ethyl acetate (50 mL) and water (50 mL). The organic layer was washed with brine, and then evaporated to give a crude product, which was purified by silica gel column chromatography (ethyl acetate in petroleum ether, 10% v/v) to yield Compound 8B (7.5 g, yield 80%) as a colorless oil. $^1$H-NMR ($CDCl_3$, 400 MHz) major characteristic peaks: δ (ppm) 1.49-1.57 (d, 3H), 1.64-1.71 (d, 3H), 3.64, 3.77 (s, 3H), 4.08-4.19 (m, 2H), 4.47-4.57 (m, 1H), 5.03-5.20 (m, 2H), 7.28-7.37 (m, 5H).

To a solution of Compound 8B (6 g, 20 mmol) in toluene (50 mL) at −78° C. was added 1.0 M DIBAL (30 mL). The mixture was stirred at this temperature for 2 h, quenched with menthol (6 mL), diluted with 1 N aq HCl (25 mL), extracted with ethyl acetate (50 mL×2), washed with brine (100 mL×2), and evaporated to remove the volatiles. The crude product was purified by silica gel column chromatography (ethyl acetate in petroleum ether, 10% v/v) to give Compound 8C (2.7 g, yield 51%) as a colorless oil. $^1$H-NMR ($CDCl_3$, 400 MHz) major characteristic peaks: δ (ppm) 1.51-1.58 (d, 3H), 1.60-1.68 (d, 3H), 4.08-4.16 (m, 2H), 4.31-4.36 (m, 1H), 5.10 (m, 2H), 7.28-7.37 (m, 5H), 9.56-9.63 (s, 1H).

To a solution of 2-bromo-1-fluoro-4-methoxybenzene (3.5 g, 34 mmol) in THF (60 mL) was added n-BuLi (9.2 mL, 2.5 M) under $N_2$ at −60° C. Stirred for 1 h, Compound 8C (3 g, 11.4 mmol) in THF (10 mL) was added to the mixture. After stirring for an additional 3 h at rt, the mixture was diluted with sat. aq. NH₄Cl (40 mL), extracted with ethyl acetate (50 mL×2), washed with brine (100 mL×2), and then evaporated to give a crude product, which was purified by silica gel column chromatography (ethyl acetate in petroleum ether, 30% v/v) to yield Compound 8D (1.8 g, yield 41%) as colorless oil. LC-MS (m/z): 390 [M+1]⁺.

A solution of Compound 8D (0.39 g, 1 mmol) in THF (10 mL) and 1 N aq HCl (2 mL) was stirred at rt for 5 h. The mixture was quenched with water (10 mL), extracted with ethyl acetate (20 mL×2), washed with brine (30 mL×2), and evaporated to remove solvents. The crude product was purified by silica gel column chromatography (ethyl acetate in petroleum ether, 50% v/v) to give Compound 8E (283 mg, yield 81%) as a colorless oil. LC-MS (m/z): 350 [M+1]⁺.

To a solution of Compound 8E (1 g, 2.9 mmol) in THF (25 mL) was added triethylamine (0.44 g, 4.4 mmol) and MsCl (0.4 g, 3.5 mmol) under N₂ at −40° C. The mixture was stirred at this temperature for 3 h before quenched with water (40 mL). It was extracted with ethyl acetate (50 mL×3), washed with brine (100 mL×2), and evaporated to give a crude product, which was purified by silica gel column chromatography (ethyl acetate in petroleum ether, 50% v/v) to yield Compound 8F (0.85 g, yield 69%) as a colorless oil. LC-MS (m/z): 410 [M+17]⁺.

To a solution of Compound 8F (0.8 g, 2.3 mmol) in THF (25 mL) was added pyrrolidine (1.5 g, 21 mmol). The mixture was stirred at 60° C. overnight, quenched with water (40 mL), extracted with ethyl acetate (50 mL×3), washed with brine (100 mL×2), and evaporated to remove solvents. The crude product was purified by column chromatography on silica gel (ethyl acetate in petroleum ether, 50% v/v) to give Compound 8G (0.5 g, 54%) as colorless oil. LC-MS (m/z): 403 [M+1]⁺.

A solution of Compound 8G (0.5 g, 1.2 mmol) and LiOH.H₂O (157 mg, 3.6 mmol) in ethanol (20 mL) was heated to reflux overnight. The mixture was quenched with water (40 mL), extracted with ethyl acetate (50 mL×3), washed with brine (100 mL×2), and evaporated to yield Compound 8H (0.3 g, 93%) as a colorless oil. LC-MS (m/z): 269 [M+1]⁺.

To a solution of Compound 8H (0.2 g, 0.75 mmol) in dichloromethane (15 mL) was added Compound 1H (191 mg, 0.9 mmol), EDCI (216 mg, 1.13 mmol), HOBt (152 mg, 1.13 mmol). The mixture was stirred at rt overnight, quenched with water (20 mL), extracted with DCM (20 mL×2), washed with brine (50 mL×2), and evaporated. The crude product was purified by prep-HPLC to give 8I and followed by chiral-prep-HPLC to afford two isomers 8J (5 mg) as a white solid and 8K (105 mg) as a white solid. For 8J: LC-MS (m/z): 463 [M+1]⁺, ¹H-NMR (CDCl₃, 400 MHz) major characteristic peaks: δ (ppm) 1.87 (m, 4H), 2.80 (m, 3H), 2.86 (m, 2H), 2.96 (m, 3H), 3.10 (m, 3H), 3.72 (s, 3H), 3.81 (s, 1H), 4.34 (s, 1H), 5.46 (s, 1H), 6.80 (m, 1H), 6.96 (m, 2H), 7.14 (m, 5H). For 8K: LC-MS (m/z): 463 [M+1]⁺; ¹H-NMR (CDCl₃, 400 MHz) major characteristic peaks: δ (ppm) 1.84 (s, 4H), 2.80 (m, 7H), 3.02 (m, 3H), 3.18 (m, 1H), 3.81 (s, 3H), 4.21 (s, 1H), 5.16 (m, 1H), 6.81 (m, 1H), 6.94 (m, 1H), 7.16 (m, 5H).

Example 9

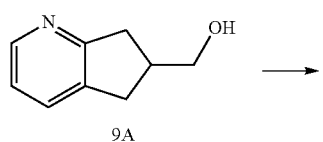

9A

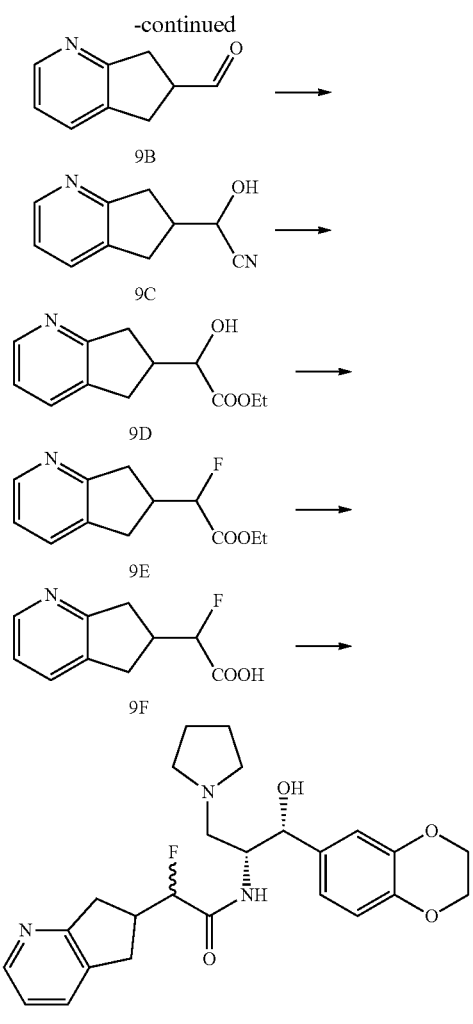

9

To a solution of Compound 9A (2.18 g, 15 mmol) in DCM (50 mL) was added DMP (7.44 g, 18 mmol). The mixture was stirred at rt for 2 h, followed by filtration. The filtrate was washed with sat. aq. NaHCO₃ (50 mL×2), extracted with DCM (50 mL×2), washed with brine (1×50 mL), dried over Na₂SO₄, concentrated, and purified by column chromatography on silica gel (ethyl acetate in petroleum ether, 10% v/v) to give Compound 9B (1.2 g, yield 56%) as a white solid. LC-MS (m/z): 148 [M+1]⁺; ¹H-NMR (CDCl₃, 400 MHz) major characteristic peaks: δ (ppm) 3.17 (m, 1H), 3.38 (m, 4H), 7.09 (m, 1H), 7.53 (d, J=8.0 Hz, 1H), 8.39 (d, J=4.4 Hz, 1H), 9.82 (s, 1H).

Compound 9B (1.2 g, 8.2 mmol) was added to a solution of sodium metabisulfate (1.55 g, 8.2 mmol) in water (35 mL). The mixture was vigorously stirred for 2 h at rt before the addition of NaCN (800 mg, 16 mmol). Stirred overnight, the mixture was diluted with water (30 mL) and THF (10 mL). The mixture was extracted with ethyl acetate (100 mL×2), washed with brine (100 mL×1), dried over Na₂SO₄, and concentrated to give Compound 9C (1.15 g, yield 81%) as a white solid. LC-MS (m/z): 175 [M+1]⁺; ¹H-NMR (DMSO-d₆, 400 MHz) major characteristic peaks: δ (ppm) 2.86 (m, 3H), 3.08 (m, 2H), 4.62 (m, 1H), 6.63 (t, J=3.2 Hz, 1H), 7.13 (t, J=7.2 Hz, 1H), 7.60 (d, J=7.6 Hz, 1H), 8.29 (d, J=4.8 Hz, 1H).

A solution of Compound 9C (1.15 g, 6.6 mmol) in EtOH (20 mL) was bubbled with a gentle stream of HCl (gas)

(dried over conc. H$_2$SO$_4$) for 5 h at 0° C. The mixture was added water (20 mL), stirred at rt for 2 h, and then adjusted pH to 7 with dilute NaOH (2M). It was extracted with DCM (50 mL×2), washed with brine (50 mL×1), dried over Na$_2$SO$_4$, concentrated, and purified by silica gel column chromatography (ethyl acetate in petroleum ether, 50% v/v) to yield Compound 9D (1 g, yield 69%) as a colorless oil. LC-MS (m/z): 222 [M+1]$^+$; $^1$H-NMR (CDCl$_3$, 400 MHz) major characteristic peaks: δ (ppm) 1.29 (m, 3H), 3.055 (m, 5H), 4.24 (m, 3H), 7.03 (m, 1H), 7.46 (m, 1H), 8.33 (d, J=4.4 Hz, 1H)

To a solution of Compound 9D (500 mg, 2.26 mmol) in DCM (20 mL) was added DAST (1.1 g, 6.78 mmol) at 0° C., then the mixture was stirred at rt overnight. The mixture was poured into ice-water, added sat. aq NaHCO$_3$ (20 mL), extracted with DCM (50 mL×2), washed with brine (50 mL×1), dried over Na$_2$SO$_4$ and evaporated. The crude product was purified by silica gel column chromatography (ethyl acetate in petroleum ether, 50% v/v) to render Compound 9E (170 mg, yield 34%) as a colorless oil. LC-MS (m/z): 224 [M+1]$^+$; $^1$H-NMR (CDCl$_3$, 400 MHz) major characteristic peaks: δ (ppm) 1.29 (t, J=7.2 Hz, 3H), 3.12 (m, 5H), 4.26 (q, J=7.2 Hz, 2H), 5.01 (m, 1H), 7.06 (m, 1H), 7.49 (d, J=7.6 Hz, 1H), 8.35 (d, J=5.2 Hz, 1H).

To a solution of Compound 9E (170 mg, 0.76 mmol) in EtOH (5 mL) was added LiOH (96 mg, 2.29 mmol) in water (5 mL). The mixture was stirred at rt overnight and concentrated to remove EtOH. After adjusted pH to 7 with diluted aq HCl, a lyophilization of the solution led to Compound 9F (148 mg, crude), which was used for the next step without further purification. LC-MS (m/z): 196 [M+1]$^+$.

A mixture of Compound 9F (100 mg, 0.51 mmol), EDCI (148 mg, 0.77 mmol), HOBt (105 mg, 0.77 mmol), DIPEA (198 mg, 1.54 mmol), Intermediate A (142 mg, 0.51 mmol) in THF (20 mL) was stirred at rt overnight. After addition of aq sat. NaHCO$_3$, the mixture was extracted with ethyl acetate (50 mL×2), washed with brine (50 mL×1), dried over Na$_2$SO$_4$, and concentrated. The crude product was purified by prep-HPLC to give Compound 9 (39 mg, yield 18%) as a white solid. LC-MS (m/z): 456 [M+1]$^+$; $^1$H-NMR (CDCl$_3$, 400 MHz) major characteristic peaks: δ (ppm) 1.73 (s, 4H), 2.86 (m, 11H), 4.16 (m, 5H), 4.76 (s, 0.5H), 4.87 (m, 1H), 4.98 (s, 0.5H), 6.75 (m, 4H), 6.95 (m, 1H), 7.35 (m, 1H), 8.24 (m, 1H).

Example 10

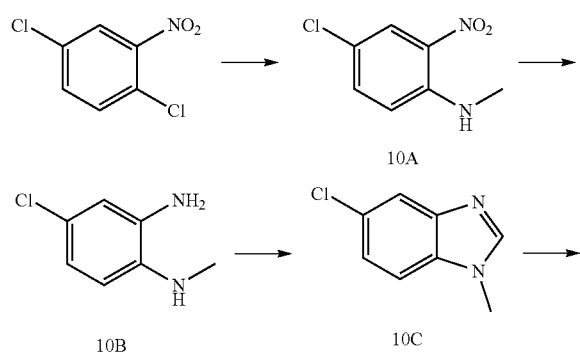

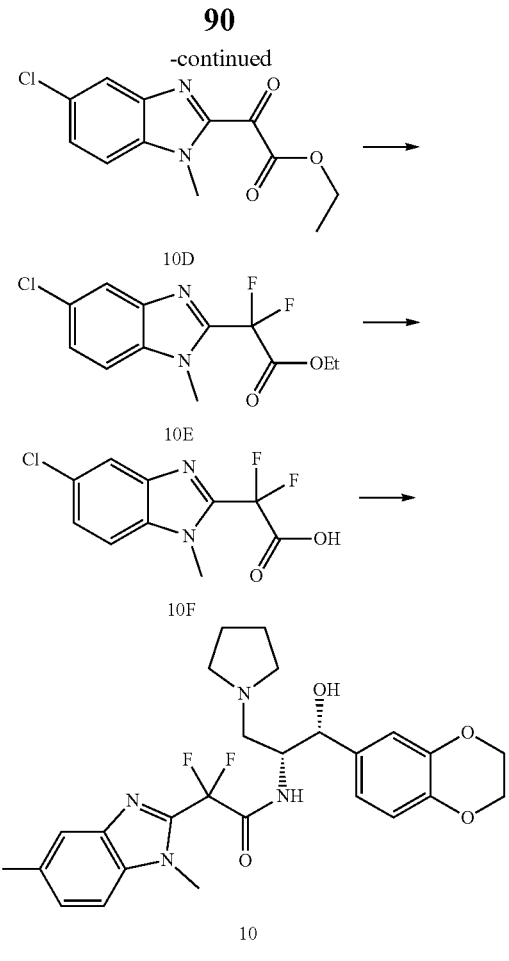

A solution of 1, 4-dichloro-2-nitrobenzene (5 g, 26 mmol) in 30% methylamine alcohol solution (50 mL) was stirred at 50° C. for 4 h. The mixture was quenched with water (50 mL) and extracted with ethyl acetate (80 mL×3). The organic layer was washed with brine (150 mL×2) and then evaporated to give Compound 10A (4 g, yield 84%) as a red solid. LC-MS (m/z): 187 [M+1]$^+$, $^1$H-NMR (CDCl$_3$, 400 MHz) major characteristic peaks: δ (ppm) 2.95 (d, J=4.8 Hz, 3H), 7.04 (d, J=9.2 Hz, 1H), 7.59 (d, J=9.2 Hz, 1H), 8.05 (s, 1H), 8.24 (s, 1H).

To a solution of Compound 10A (3 g, 16 mmol) in ethanol (100 mL) was added 10 N aq HCl (2 mL) and Fe (9 g, 0.16 mmol). The mixture was stirred at 80° C. overnight. After filtration, the filtrate was washed with 3 N aq NaOH (50 mL), extracted with ethyl acetate (100 mL×2), and dried over Na$_2$SO$_4$. Filtration and solvent evaporation led to crude Compound 10B (2.7 g, crude) as a red solid, which was used to next step without purified. LC-MS (m/z): 157 [M+1]$^+$.

To a solution of Compound 10B (2.5 g, 16 mmol) in methanol (50 mL) was added triethoxymethane (2.8 g, 19 mmol) and sulfamic acid (155 mg, 1.6 mmol). The mixture was stirred at rt for 5 h. After removal of solvents, the mixture was diluted with water (30 mL) and extracted with ethyl acetate (50 mL×3). The organic layer was dried over Na$_2$SO$_4$. Filtration and evaporation of solvents gave a crude product Compound 10C (2.3 g, crude) as a red solid, which was used to next step without purification. LC-MS (m/z): 167 [M+1]$^+$, $^1$H-NMR (CDCl$_3$, 400 MHz) major characteristic peaks: δ (ppm) 3.84 (s, 3H), 7.30 (d, J=8.4 Hz, 1H), 7.61 (d, J=8.8 Hz, 1H), 7.70 (s, 1H), 8.25 (s, 1H).

Ethyl oxalyl chloride (2.7 g, 20 mmol) was added dropwise over 20 mins to a stirred solution of Compound 10C (2.5 g, 15 mmol) in dichloromethane (60 mL) at −20° C. Then DIPEA (3.9 g, 30 mmol) was added and the mixture was warmed to rt and kept stirring overnight. The mixture was quenched with water (50 mL) and extracted with dichloromethane (50 mL×2). The organic layer was dried over $Na_2SO_4$ before filtered and concentrated, giving a crude product. The crude product was purified by column chromatography on silica gel (ethyl acetate in petroleum ether, 30% v/v) to give Compound 10D (3.3 g, yield 83%) as yellow solid. LC-MS (m/z): 267 [M+1]$^+$.

To a solution of Compound 10D (1.5 g, 5.6 mmol) in dichloromethane (30 mL) was added DAST (2.7 g, 17 mmol). The mixture was stirred at rt overnight, quenched with water (30 mL), and extracted with dichloromethane (50 mL×2). After dried over $Na_2SO_4$, the organic layer was filtered and concentrated to give the crude product Compound 10E (0.9 g, crude) as a colorless oil, which was used for the next step without purification. LC-MS (m/z): 289 [M+1]$^+$.

To a solution of Compound 10E (1 g, 3.5 mmol) in methanol (20 mL) and $H_2O$ (10 mL) was added $LiOH \cdot H_2O$ (294 mg, 7 mmol). The mixture was stirred at rt for 5 h, quenched with water (30 mL), and extracted with ethyl acetate (50 mL×2). The organic layer was dried over $Na_2SO_4$. Filtration and removal of solvents led to the crude product Compound 10F (0.4 g, crude) as a colorless oil, which was used for the next step without purification. LC-MS (m/z): 261 [M+1]$^+$, $^1$H-NMR (CDCl$_3$, 400 MHz) δ (ppm) 3.97 (s, 3H), 7.47 (d, J=10.4 Hz, 1H), 7.78 (d, J=8.8 Hz, 1H), 7.86 (s, 1H).

To a solution of Intermediate A (0.16 g, 0.58 mmol) in dichloromethane (15 mL) was added Compound 10F (150 mg, 0.58 mmol), EDCI (167 mg, 0.87 mmol), HOBt (116 mg, 0.87 mmol). The mixture was stirred at rt overnight, quenched with water (20 mL), extracted with dichloromethane (20 mL×2), washed with brine (50 mL×2), and evaporated. The crude product was purified by prep-HPLC to afford Compound 10 (29 mg, yield 9.6%) as a white solid. LC-MS (m/z): 521 [M+1]$^+$, $^1$H-NMR (CDCl$_3$, 400 MHz) major characteristic peaks: δ (ppm) 1.95 (m, 4H), 3.47 (m, 6H), 3.89 (s, 3H), 4.16 (s, 4H), 4.42 (s, 1H), 4.69 (s, 1H), 5.91 (s, 1H), 6.57 (d, J=8.8 Hz, 1H), 6.79 (d, J=10.4 Hz, 1H), 6.81 (s, 1H), 7.50 (d, J=11.2 Hz, 1H), 7.80 (d, J=10.8 Hz, 2H), 8.96 (d, J=9.2 Hz, 1H), 9.37 (s, 1H).

Example 11

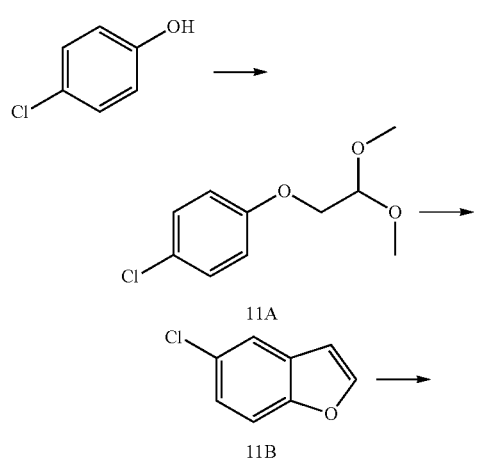

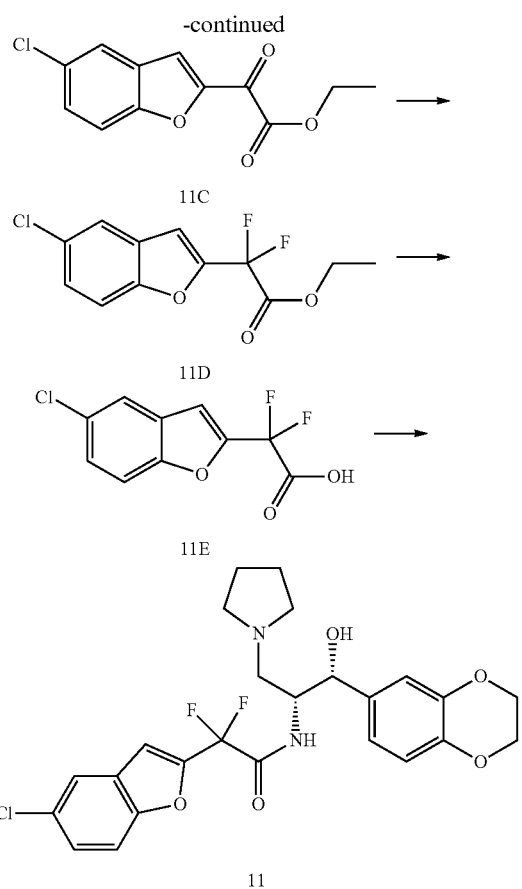

A mixture of 4-chlorophenol (10 g, 78 mmol), 2-bromo-1,1-dimethoxyethane (13.1 g, 78 mmol), $K_2CO_3$ (14 g, 101 mmol), KI (100 mg) in DMF (50 mL) was stirred at reflux for 3 h. The mixture was cooled to rt and filtered. The filtrate was added water (200 mL), extracted with ethyl acetate (100 mL×2), washed with water (100 mL×3), brine (100 mL×1), dried over $Na_2SO_4$, concentrated, and purified by column chromatography on silica gel (ethyl acetate in petroleum ether, 10% v/v) to yield Compound 11A (15 g, yield 89%) as a colorless liquid. $^1$H-NMR (CDCl$_3$, 400 MHz) major characteristic peaks: δ (ppm) 3.45 (s, 6H), 3.96 (d, J=5.2 Hz, 2H), 4.70 (t, J=5.6 Hz, 1H), 6.85 (d, J=8.8 Hz, 2H), 7.21 (d, J=8.8 Hz, 2H).

A solution of polyphosphoric acid (90 g) in toluene was heated to 90° C. To this solution was added Compound 11A (15.4 g, 71 mmol) in toluene (20 mL), followed by stirring at 90° C. for 3 h. The mixture was poured into ice and stirred for 30 min. It was extracted with ethyl acetate (2×100 mL), washed with brine (100 mL×1), dried over $Na_2SO_4$, concentrated and purified by column chromatography on silica gel (petroleum ether, 100% v/v) to yield Compound 11B (4.5 g, yield 50%) as a red liquid. $^1$H-NMR (CDCl$_3$, 400 MHz) major characteristic peaks: δ (ppm) 6.72 (m, 1H), 7.24 (dd, $J_1$, $J_2$=8.8, 2.4 Hz, 1H), 7.42 (d, J=8.8 Hz, 1H), 7.56 (d, J=2.0 Hz, 1H), 7.63 (d, J=2.4 Hz, 1H).

To a solution of Compound 11B (4.5 g, 30 mmol) in THF (20 mL) was added n-BuLi (14 mL) at −78° C. under $N_2$. Stirred for 30 min, to the mixture was added diethyl oxalate (10.8 g, 74 mmol). The mixture was stirred at −78° C. for 1 h before the addition of aq sat. $NH_4Cl$. It was extracted with ethyl acetate (50 mL×2), washed with sat. $NaHCO_3$ (50 mL×2), brine (50 mL×1), dried over $Na_2SO_4$, concentrated and purified by silica gel column chromatography (ethyl acetate in petroleum ether, 20% v/v) to give Compound 11C (3.5 g, yield 47%) as a yellow solid. $^1$H NMR (DMSO-d$_6$, 400 MHz) major characteristic peaks: δ (ppm) 1.37 (t, J=6.8 Hz, 3H), 4.41 (q, J=6.8 Hz, 2H), 7.64 (m, 1H), 7.82 (d, J=8.8 Hz, 1H), 8.03 (d, J=2.4 Hz, 1H), 8.19 (s, 1H).

To a solution of Compound 11C (1 g, 3.95 mmol) in DCM (50 mL) was added DAST (3.18 g, 18 mmol) at 0° C., then the mixture was stirred at rt overnight. The reaction was quenched by addition of ice-water and sat. aq NaHCO$_3$ (20 mL). It was then extracted with DCM (50 mL×2), washed with brine (50 mL×1), dried over Na$_2$SO$_4$, and evaporated to remove solvents. The crude product was purified by silica gel column chromatography (ethyl acetate in petroleum ether, 10% v/v) to yield Compound 11D (700 mg, yield 65%) as a yellow liquid. $^1$H-NMR (CDCl$_3$, 400 MHz) major characteristic peaks: δ (ppm) 1.37 (t, J=6.8 Hz, 3H), 4.41 (q, J=6.8 Hz, 2H), 7.10 (s, 1H), 7.36 (m, 1H), 7.47 (d, J=8.8 Hz, 1H), 7.62 (d, J=2.0 Hz, 1H).

To a solution of Compound 11D (120 mg, 0.44 mmol) in EtOH (5 mL) was added LiOH (46 mg, 1.09 mmol) in water (5 mL). The mixture was stirred at rt overnight, followed by removal of EtOH. It was adjusted to pH 7 with diluted HCl and freeze-dried to give Compound 11E (100 mg, crude) which was used for the next step without further purification. LC-MS (m/z): 245 [M−1]$^−$.

A mixture of Compound 11E (100 mg, 0.41 mmol), EDCI (117 mg, 0.61 mmol), HOBt (83 mg, 0.61 mmol), Intermediate A (115 mg, 0.41 mmol) in DCM (20 mL) was stirred at rt overnight. The reaction was quenched by addition of sat. NaHCO$_3$. The resulting mixture was extracted with DCM (50 mL×2), washed with brine (50 mL×1), dried over Na$_2$SO$_4$, and evaporated to dryness. The crude product was purified by prep-HPLC to give Compound 11 (49 mg, yield 24%) as a white solid. LC-MS (m/z): 507 [M+1]$^+$; $^1$H-NMR (CDCl$_3$, 400 MHz) major characteristic peaks: δ (ppm) 2.13 (s, 4H), 2.91 (m, 2H), 3.48 (s, 2H), 3.84 (s, 2H), 4.15 (m, 4H), 4.46 (m, 1H), 5.13 (s, 1H), 6.77 (s, 3H), 6.84 (s, 1H), 7.35 (m, 1H), 7.42 (d, J=8.8 Hz, 1H), 7.58 (d, J=2.0 Hz, 1H), 7.43 (d, J=7.6 Hz, 1H), 11.68 (s, 1H).

Example 12

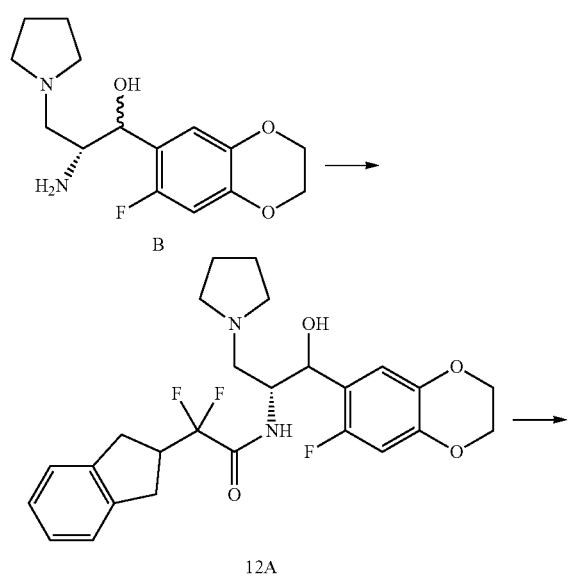

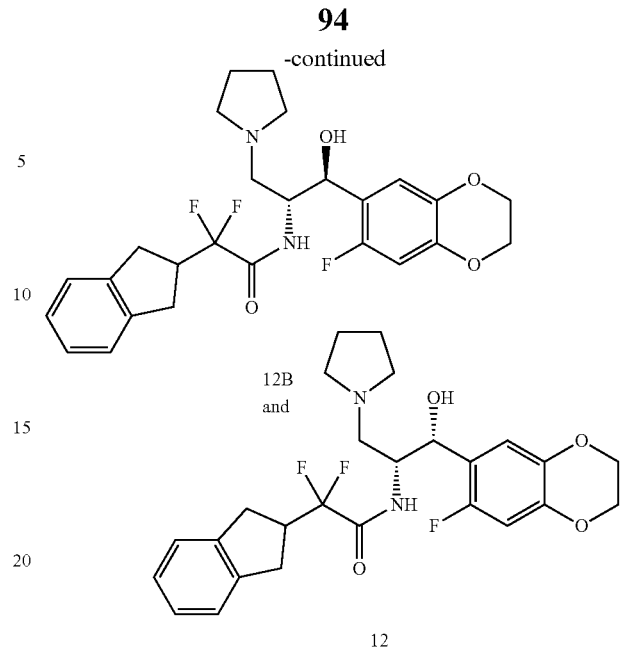

To a mixture of Intermediate B (300 mg, 1 mmol) in DCM (15 mL) was added EDCI (400 mg, 2 mmol), HOBt (264 mg, 2 mmol) and Compound 1H (300 mg, 1.5 mmol) and stirred at rt overnight. The reaction mixture was poured into water (50 mL), extracted with DCM (20 mL×3), dried over anhydrous Na$_2$SO$_4$, and purified by prep-HPLC to afford a crude product 12A (100 mg, yield 20%) as a white solid. The chiral resolution on Compound 12A was achieved using chiral-prep-HPLC to give Compound 12B (70 mg) and 12 (1.2 mg). For Compound 12B, LCMS: 491 [M+1]$^+$; $^1$H-NMR (CDCl$_3$, 400 MHz) major characteristic peaks: δ (ppm) 1.82 (m, 4H), 2.82 (m, 7H), 3.04 (m, 3H), 3.19 (m, 1H), 4.16 (m, 1H), 4.26 (m, 4H), 5.05 (m, 1H), 6.56 (d, J=10.8 Hz, 1H), 6.69 (m, 1H), 7.06 (d, J=7.2 Hz, 1H), 7.16 (m, 4H). For Compound 12, LCMS: 491 [M+1]$^+$; $^1$H-NMR (CDCl$_3$, 400 MHz) major characteristic peaks: δ (ppm) 2.23 (m, 4H), 2.67 (m, 1H), 2.82 (m, 1H), 2.97 (m, 2H), 3.12 (m, 2H), 3.65 (m, 1H), 3.81 (m, 1H), 3.89 (m, 1H), 4.03 (m, 1H), 4.12 (m, 1H), 4.18 (m, 1H), 4.47 (m, 1H), 5.43 (m, 1H), 6.60 (d, J=11.2 Hz, 1H), 7.08 (d, J=7.2 Hz, 1H), 7.16 (m, 5H).

Example 13

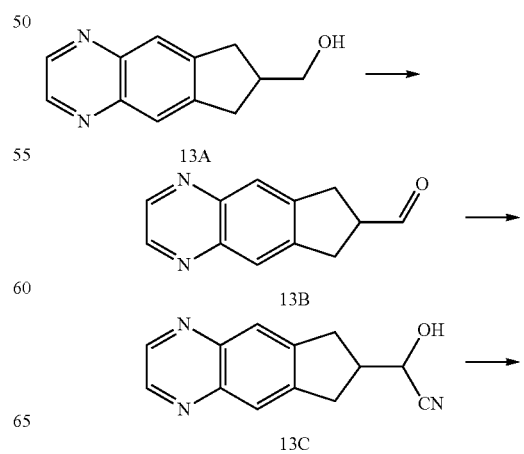

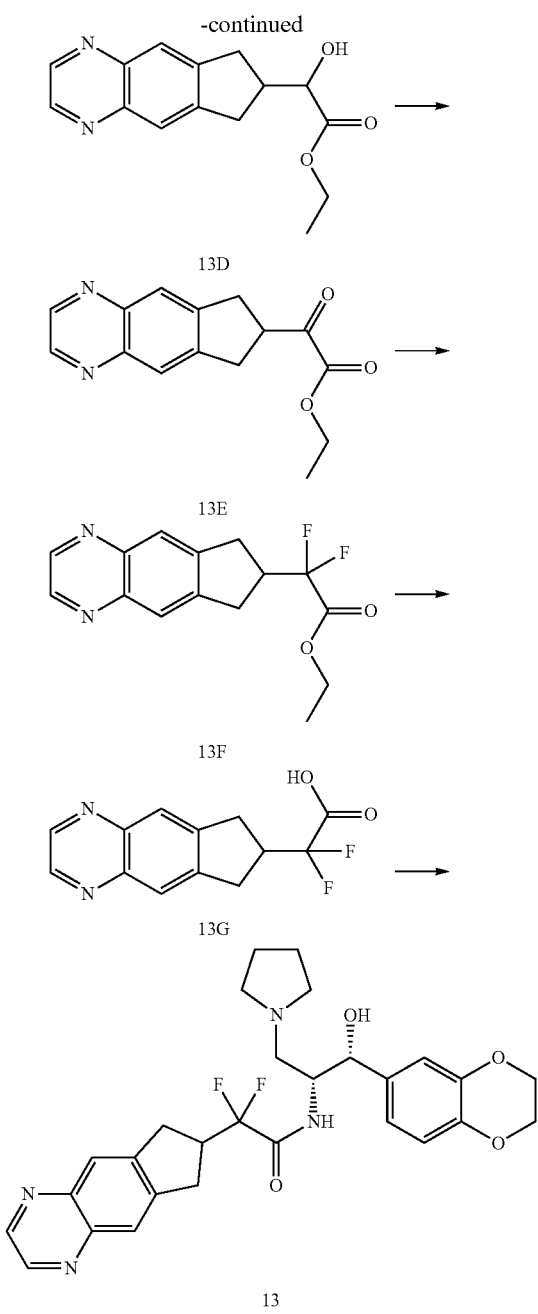

13D

13E

13F

13G

13

To a solution of Compound 13A (2.00 g, 10 mmol) in DCM (50 mL) was added DMP (7.44 g, 18 mmol). The mixture was stirred at rt for 2 h and filtered. The filtrate was washed with sat. aq NaHCO$_3$ (50 mL×2), extracted with DCM (50 mL×2), washed with brine (50 mL), dried over Na$_2$SO$_4$, concentrated, and purified by silica gel column chromatography (ethyl acetate in petroleum ether, 10% v/v) to get Compound 13B (1.2 g, yield 56%) as a white solid. LC-MS (m/z): 199 [M+1]$^+$.

Compound 13B (1.13 g, 5 mmol) was added to a solution of sodium metabisulfate (1.55 g, 8.2 mmol) in water (35 mL). The mixture was vigorously stirred for 2 h at rt, before the addition of NaCN (800 mg, 16 mmol). After stirred overnight, the reaction mixture was poured to a mixture of water (30 mL) and THF (10 mL). It was then extracted with ethyl acetate (100 mL×2), washed with brine (00 mL), dried over Na$_2$SO$_4$, and concentrated to give Compound 13C (1.15 g, 81%) as a white solid. LC-MS (m/z): 226 [M+1]$^+$.

To a solution of Compound 13C (1.15 g, 5 mmol) in EtOH (20 mL) was bubbled with a gentle stream of HCl (gas) (dried over con. H$_2$SO$_4$) at 0° C. for 5 h. Water (20 mL) was added to the mixture and stirred at rt for 2 h. It was adjusted to pH=7 with diluted NaOH (2M), extracted with DCM (50 mL×2), washed with brine (50 mL), dried over Na$_2$SO$_4$, concentrated, and purified by silica gel column chromatography (ethyl acetate in petroleum ether, 50% v/v) to get Compound 13D (1 g, yield 69%) as a colorless oil. LC-MS (m/z): 273 [M+1]$^+$.

To a solution of Compound 13D (2.72 g, 10 mmol) in DCM (50 mL) was added DMP (7.44 g, 18 mmol). The mixture was stirred at rt for 2 h and filtered. The filtrate was washed with sat. aq NaHCO$_3$ (50 mL×2), extracted with DCM (50 mL×2), washed with brine (50 mL), dried over Na$_2$SO$_4$, concentrated, and purified by column chromatography on silica gel (ethyl acetate in petroleum ether, 10% v/v) to get Compound 13E (1.2 g, yield 56%) as a white solid. LC-MS (m/z): 271 [M+1]$^+$.

To a solution of Compound 13E (540 mg, 2 mmol) in DCM (20 mL) was added DAST (1.1 g, 6.78 mmol) at 0° C., then the mixture was stirred at rt overnight. The reaction mixture was quenched by pouring into ice-water. After neutralized with sat. NaHCO$_3$ (20 mL), the mixture was extracted with DCM (2×50 mL), washed with brine (1×50 mL), dried over Na$_2$SO$_4$, and evaporated to dryness. The crude product was purified by silica gel column chromatography (ethyl acetate in petroleum ether, 50% v/v) to yield Compound 13F (170 mg, yield 34%) as a colorless oil. LC-MS (m/z): 293 [M+1]$^+$.

To a solution of Compound 13F (293 mg, 1 mmol) in EtOH (5 mL) was added LiOH (96 mg, 2.29 mmol) in water (5 mL). The mixture was stirred at rt overnight, concentrated to remove EtOH, and adjusted to pH 7 with diluted HCl. It was then lyophilized to give Compound 13G (148 mg, crude), which was used for the next step without further purification. LC-MS (m/z): 265 [M+1]$^+$.

A mixture of Compound 13G (132 mg, 0.51 mmol), EDCI (148 mg, 0.77 mmol), HOBt (105 mg, 0.77 mmol), DIPEA (198 mg, 1.54 mmol), Intermediate A (142 mg, 0.51 mmol) in THF (20 mL) was stirred at rt overnight. After the addition of sat. aq NaHCO$_3$, the mixture was extracted with ethyl acetate (50 mL×2), washed with brine (50 mL), dried over Na$_2$SO$_4$, and evaporated to dryness. The crude product was purified by prep-HPLC to give Compound 13 (39 mg, yield 18%) as a white solid. LC-MS (m/z): 525 [M+1]$^+$; $^1$H-NMR (CDCl$_3$, 400 MHz) major characteristic peaks: δ (ppm) 1.84 (m, 4H), 2.75 (m, 4H), 3.03 (m, 6H), 4.22 (m, 6H), 5.11 (m, 1H), 6.90 (m, 4H), 7.85 (s, 2H), 8.76 (s, 2H).

Example 14

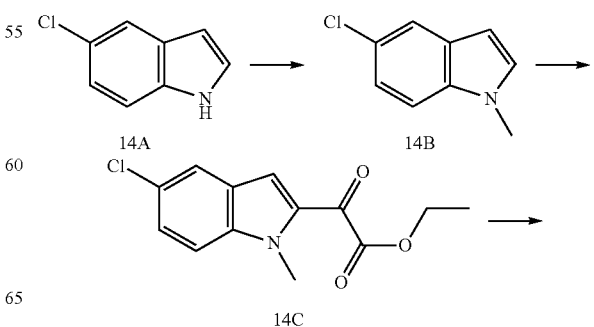

14A

14B

14C

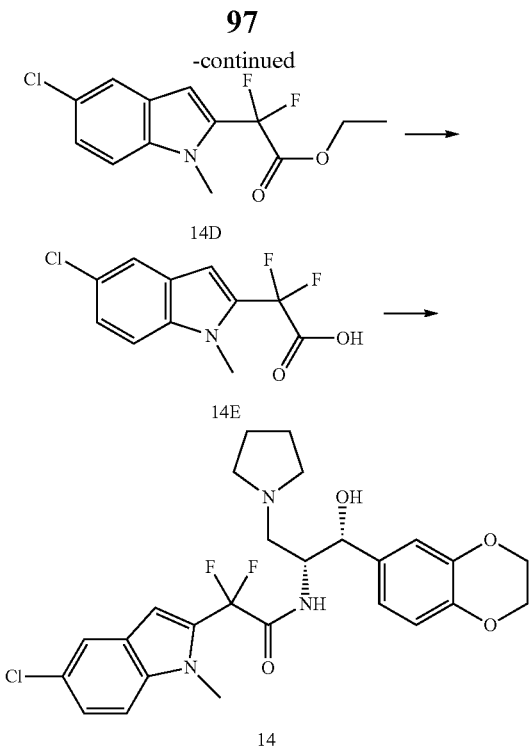

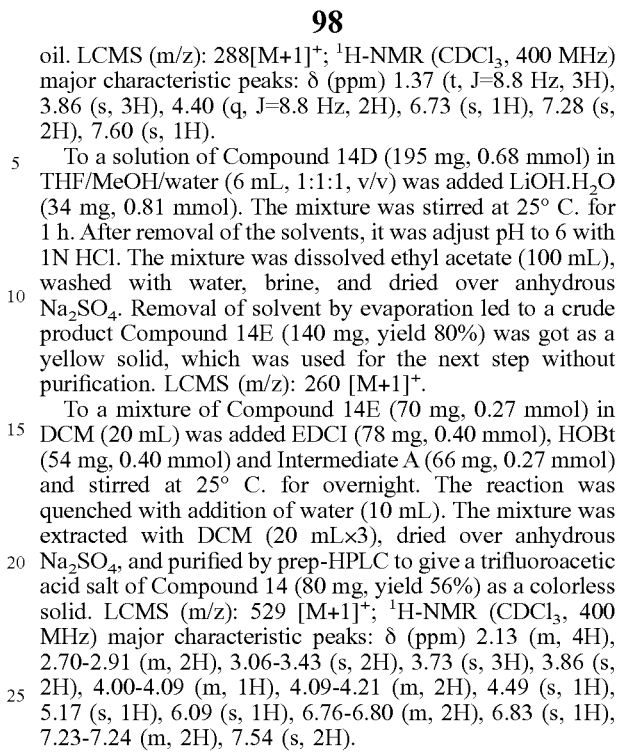

To a solution of Compound 14A (1.21 g, 8 mmol) in THF (20 mL) was added NaH (480 mg, 12 mmol) under N₂ atmosphere. The mixture was stirred at 0° C. for 1 h. CH₃I (0.47 mL, 16 mmol) was added. The mixture was stirred at 25° C. for additional 2 h. It was diluted with NH₄Cl (30 mL) and extracted with EtOAc (30 mL×3). The combined organic layers were washed with brine (60 mL), dried over Na₂SO₄, and concentrated to give a crude product, which was purified by column chromatography on silica gel (ethyl acetate in petroleum 10% v/v) to yield Compound 14B (1.2 g, yield 90%) as a red oil. LCMS (m/z): 166 [M+1]⁺. ¹H-NMR (CDCl₃, 400 MHz) major characteristic peaks: δ (ppm) 3.76 (s, 3H), 6.40 (d, J=3.2 Hz, 1H), 7.05 (d, J=3.2 Hz, 1H), 7.16 (dd, J=1.6, 8.4 Hz, 1H), 7.20 (d, J=8.4 Hz, 1H), 7.57 (d, J=1.6 Hz, 1H).

To a solution of Compound 14B (1.04 g, 6 mmol) in THF (20 mL) was added n-BuLi (3 ml, 8 mmol) at −78° C. under the protection of nitrogen. Then it was allowed to warm up to rt over one hour. At this point, diethyl oxalate (2.1 mL, 16 mmol) was added to the mixture at −78° C. and then it was allowed to warm up to rt over one hour. The mixture was quenched with sat. aq NH₄Cl. The organic phase was washed with brine, dried over anhydrous Na₂SO₄, and purified by silica gel column chromatography (ethyl acetate in petroleum 3% to 10% v/v) to afford Compound 14C (1.38 g, yield 86%) as a yellow solid. LCMS (m/z): 266 [M+1]⁺; ¹H-NMR (CDCl₃, 400 MHz) major characteristic peaks: δ (ppm) 1.45 (t, J=7.2 Hz, 3H), 4.08 (s, 3H), 4.45 (q, J=7.2 Hz, 1H), 7.33 (d, J=8.4 Hz, 1H), 7.39 (dd, J=1.6, 8.4 Hz, 1H), 7.53 (s, 1H), 7.69 (d, J=1.6 Hz, 1H).

To a solution of Compound 14C (530 mg, 2 mmol) in DCM (20 mL) was added DAST (1.6 mL, 12 mmol) at 0° C. under N₂ and stirred at 25° C. overnight. It was poured into 50 mL of ice-water and extracted with DCM (20 mL×3). The combined organic phase was washed with brine, and dried over anhydrous Na₂SO₄, and purified by silica gel column chromatography (ethyl acetate in petroleum, 10% v/v) to yield Compound 14D (195 mg, yield 33%) as yellow oil. LCMS (m/z): 288[M+1]⁺; ¹H-NMR (CDCl₃, 400 MHz) major characteristic peaks: δ (ppm) 1.37 (t, J=8.8 Hz, 3H), 3.86 (s, 3H), 4.40 (q, J=8.8 Hz, 2H), 6.73 (s, 1H), 7.28 (s, 2H), 7.60 (s, 1H).

To a solution of Compound 14D (195 mg, 0.68 mmol) in THF/MeOH/water (6 mL, 1:1:1, v/v) was added LiOH.H₂O (34 mg, 0.81 mmol). The mixture was stirred at 25° C. for 1 h. After removal of the solvents, it was adjust pH to 6 with 1N HCl. The mixture was dissolved ethyl acetate (100 mL), washed with water, brine, and dried over anhydrous Na₂SO₄. Removal of solvent by evaporation led to a crude product Compound 14E (140 mg, yield 80%) was got as a yellow solid, which was used for the next step without purification. LCMS (m/z): 260 [M+1]⁺.

To a mixture of Compound 14E (70 mg, 0.27 mmol) in DCM (20 mL) was added EDCI (78 mg, 0.40 mmol), HOBt (54 mg, 0.40 mmol) and Intermediate A (66 mg, 0.27 mmol) and stirred at 25° C. for overnight. The reaction was quenched with addition of water (10 mL). The mixture was extracted with DCM (20 mL×3), dried over anhydrous Na₂SO₄, and purified by prep-HPLC to give a trifluoroacetic acid salt of Compound 14 (80 mg, yield 56%) as a colorless solid. LCMS (m/z): 529 [M+1]⁺; ¹H-NMR (CDCl₃, 400 MHz) major characteristic peaks: δ (ppm) 2.13 (m, 4H), 2.70-2.91 (m, 2H), 3.06-3.43 (s, 2H), 3.73 (s, 3H), 3.86 (s, 2H), 4.00-4.09 (m, 1H), 4.09-4.21 (m, 2H), 4.49 (s, 1H), 5.17 (s, 1H), 6.09 (s, 1H), 6.76-6.80 (m, 2H), 6.83 (s, 1H), 7.23-7.24 (m, 2H), 7.54 (s, 2H).

Example 15

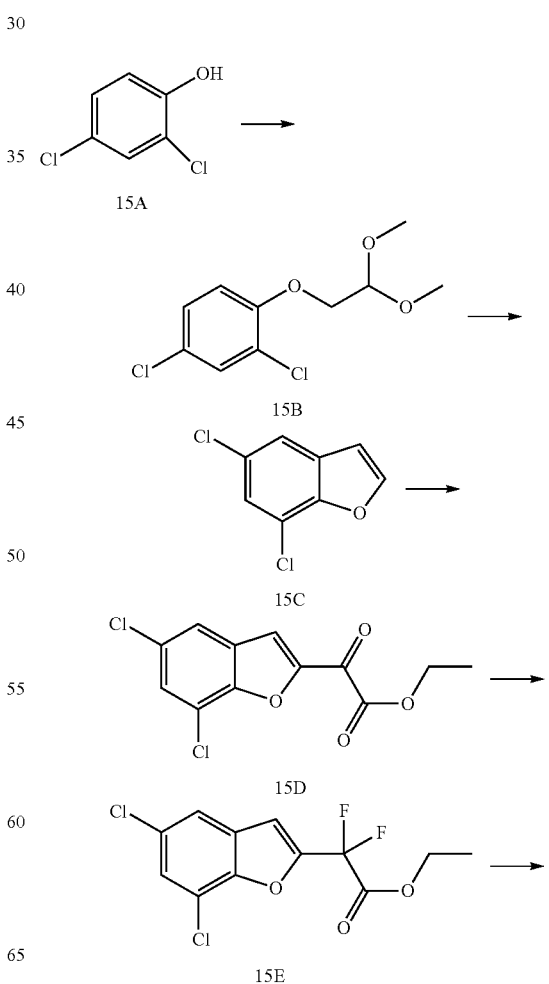

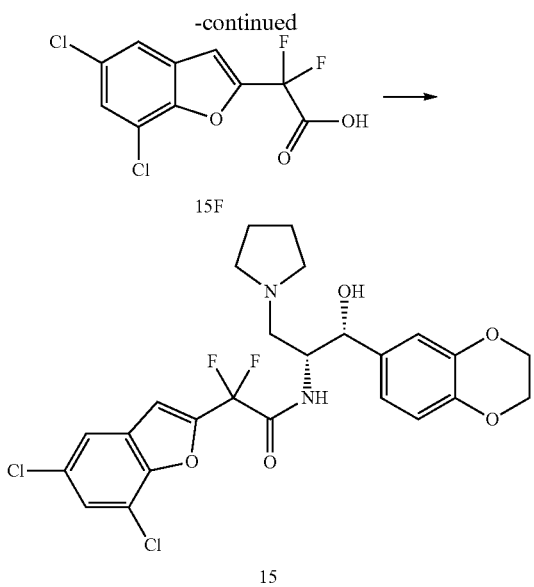

A mixture of Compound 15A (12.64 g, 78 mmol), 2-bromo-1,1-dimethoxyethane (13.6 g, 79 mmol), $K_2CO_3$ (14 g, 101 mmol), KI (100 mg) in DMF (50 mL) was stirred at reflux for 3 h, and then cooled to rt, and filtered. The filtrate was diluted with water (200 mL), extracted with ethyl acetate (100 mL×2), washed with water (100 mL×3), brine (100 mL×1), dried over $Na_2SO_4$, concentrated, and purified by silica gel column chromatography (ethyl acetate in petroleum ether, 10% v/v) to yield Compound 15B (17.2 g, yield 88%) as a red liquid. $^1$H-NMR (CDCl$_3$, 400 MHz) major characteristic peaks: δ (ppm) 3.49 (s, 6H), 4.02 (d, J=5.2 Hz, 2H), 4.73 (t, J=5.6 Hz, 1H), 6.86 (d, J=8.8 Hz, 1H), 7.15-7.18 (dd, J=2.8, 8.8 Hz, 1H), 7.36 (d, J=2.8 Hz, 1H).

A solution of polyphosphoric acid (90 g) in toluene was stirred to 90° C., then to the solution was added Compound 15B (15 g, 60 mmol) in toluene (20 mL). The mixture was stirred at 90° C. for 3 h before it was poured into ice and stirred for 30 min. It was then extracted with ethyl acetate (100 mL×2), washed with brine (100 mL×1), dried over $Na_2SO_4$, concentrated, and purified by silica gel column chromatography (petroleum ether, 100% v/v) to give Compound 15C (2.6 g, yield 23%) as a white solid. $^1$H-NMR (CDCl$_3$, 400 MHz) major characteristic peaks: δ (ppm) 6.76 (d, J=2.4 Hz, 1H), 7.30 (d, J=2.0 Hz, 1H), 7.46 (d, J=2.0 Hz, 1H), 7.69 (d, J=2.4 Hz, 1H).

To a solution of Compound 15C (1.6 g, 8.6 mmol) in THF (10 mL) was added n-BuLi (4.2 mL) at −78° C. under $N_2$. After stirred for 30 min, to the mixture was added diethyl oxalate (10.8 g, 74 mmol). It was stirred at −78° C. for 1 h before it was quenched by addition of aq sat. NH$_4$Cl. The mixture was sequentially extracted with ethyl acetate (50 mL×2), washed with sat. NaHCO$_3$ (50 mL×2), brine (50 mL×1), dried over $Na_2SO_4$, concentrated, and purified by silica gel column chromatography (ethyl acetate in petroleum ether, 20% v/v) to yield Compound 15D (1.64 g, yield 67%) as a yellow solid. $^1$H-NMR (CDCl$_3$, 400 MHz) major characteristic peaks: δ (ppm) 1.46 (t, J=7.2 Hz, 3H), 4.48 (q, J=7.2 Hz, 2H), 7.54 (m, 1H), 7.66 (d, J=1.6 Hz, 1H), 8.04 (s, 1H).

To a solution of Compound 15D (500 mg, 1.75 mmol) in DCM (15 mL) was added DAST (1.15 g, 8.74 mmol) at 0° C. The mixture was stirred at rt overnight before it was poured into ice-water, and followed by addition of aq sat. aq NaHCO$_3$ (20 mL). The resulted mixture was extracted with DCM (50 mL×2), washed with brine (50 mL×1), dried over $Na_2SO_4$, and concentrated to give a crude product, which was purified by silica gel column chromatography (ethyl acetate in petroleum ether, 10% v/v) to afford Compound 15E (269 mg, yield 50%) as a red liquid. $^1$H-NMR (CDCl$_3$, 400 MHz) major characteristic peaks: δ (ppm) 1.37 (t, J=6.8 Hz, 3H), 4.44 (q, J=7.2 Hz, 2H), 7.14 (s, 1H), 7.41 (m, 1H), 7.54 (m, 1H).

To a solution of Compound 15E (260 mg, 0.88 mmol) in EtOH (0.5 mL) was added LiOH (46 mg, 1.09 mmol) in water (0.5 mL). The mixture was stirred at rt overnight, evaporated to remove EtOH, and neutralized with diluted HCl. This aqueous solution was lyophilized to yield a crude Compound 15F (193 mg), which was used for the next step without further purification. LC-MS (m/z): 279 [M−1]$^-$.

A mixture of Compound 15F (70 mg, 0.25 mmol), EDCI.HCl (71 mg, 0.37 mmol), HOBt (50 mg, 0.37 mmol), Intermediate A (61 mg, 0.25 mmol) in DCM (10 mL) was stirred at 28° C. overnight. The reaction was quenched by addition of aq sat. NaHCO$_3$. The mixture was extracted with DCM (50 mL×2), washed with brine (50 mL×1), dried over $Na_2SO_4$, and concentrated to give a crude product, which was purified by prep-HPLC to afford Compound 15 (46.3 mg, yield 23%) as a white solid. LC-MS (m/z): 541 [M+1]$^+$; $^1$H-NMR (CDCl$_3$, 400 MHz) major characteristic peaks: δ (ppm) 2.12-2.17 (m, 4H), 2.93-2.99 (m, 2H), 3.45-3.55 (m, 2H), 3.82-3.92 (m, 3H), 4.10-4.16 (m, 4H), 4.52 (s, 1H), 5.05 (s, 1H), 6.70-6.83 (m, 4H), 7.40 (s, 1H), 7.49 (s, 1H), 7.94-7.96 (d, J=8.0 Hz, 1H), 11.53 (s, 1H).

Example 16

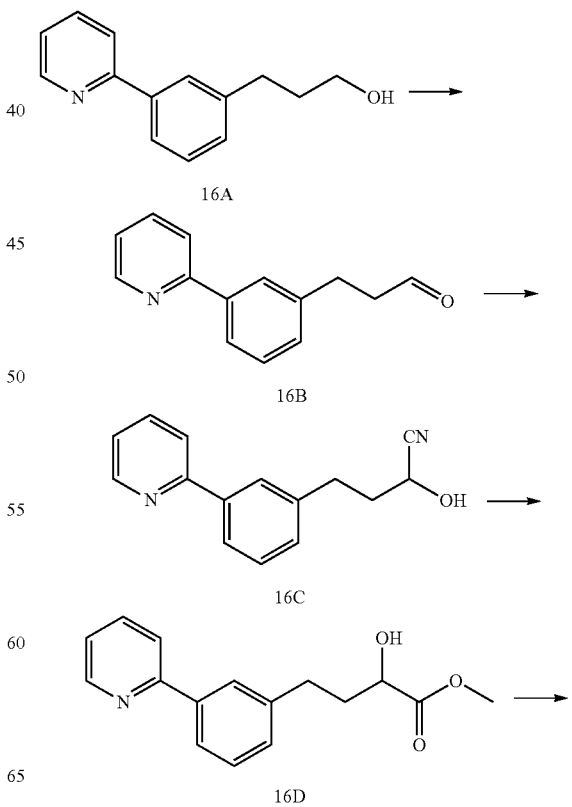

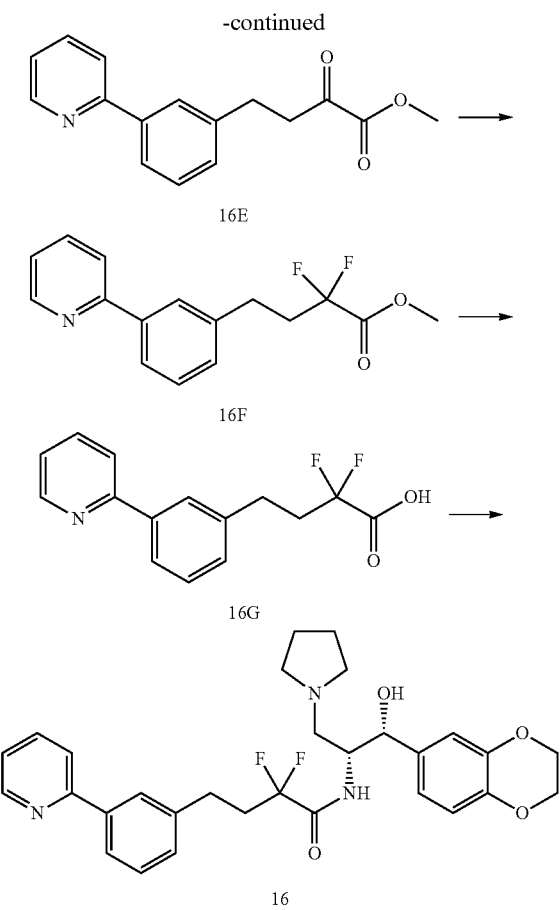

(ppm) 1.96-2.06 (m, 1H), 2.14-2.23 (m, 1H), 2.83-2.90 (m, 2H), 3.75 (s, 3H), 4.21-4.24 (m, 1H), 7.21-7.29 (m, 1H), 7.40 (t, J=7.6 Hz, 1H), 7.22-7.80 (m, 3H), 7.87 (s, 1H), 8.70 (s, 1H).

To a solution of Compound 16D (800 mg, 2.95 mmol) in DCM (20 mL) was added DMP (1.50 g, 3.54 mmol). The mixture was stirred at rt for 2 h. It was then diluted with ethyl acetate (150 mL), filtered to remove solid, washed with water and brine, dried with anhydrous $Na_2SO_4$, and purified by silica gel column chromatography (ethyl acetate in PE, 30% v/v) to yield Compound 16E (300 mg, yield 38%) as a colorless oil. LCMS (m/z): 270 [M+1]$^+$, $^1$H-NMR (CDCl$_3$, 400 MHz) major characteristic peaks: δ (ppm) 3.07 (t, J=7.2 Hz, 2H), 3.28 (t, J=7.2 Hz, 2H), 3.86 (m, 3H), 7.25-7.35 (m, 2H), 7.43 (t, J=7.2 Hz, 1H), 7.78-7.93 (m, 4H), 8.74 (s, 1H).

To a solution of Compound 16E (400 mg, 1.48 mmol) in DCM (15 mL) was added DAST (1.23 g, 7.43 mmol) at rt. The mixture was stirred at rt overnight. It was then diluted with ethyl acetate (150 mL), washed with saturated NaHCO$_3$, waster and brine, purified by silica gel column chromatography (ethyl acetate in petroleum ether, 40% v/v) to afford Compound 16F (120 mg, yield 28%) as a white solid. LCMS (m/z): 292 [M+1]$^+$.

A mixture of Compound 16F (120 mg, 0.41 mmol) and LiOH.H$_2$O (52 mg, 1.24 mmol) in THF/MeOH/H$_2$O (5/5/2 mL) was stirred at rt for 2 h. It was adjusted to pH 6 with 1 M HCl and purified by prep-HPLC to give Compound 16G (80 mg, yield 70%) as white solid. LCMS (m/z): 278 [M+1]$^+$; $^1$H-NMR (CDCl$_3$, 400 MHz) major characteristic peaks: δ (ppm) 2.40-2.53 (m, 2H), 2.89-2.93 (m, 2H), 7.26-7.37 (m, 2H), 7.42 (t, J=7.2 Hz, 1H), 7.73-7.88 (m, 4H), 8.72 (s, 1H).

A solution of Intermediate A (80 mg, 0.29 mmol), Compound 16G (80 mg, 0.29 mmol), EDCI (83 mg, 0.44 mmol) and HOBt (59 mg, 0.44 mmol) in DCM (5 mL) was stirred at rt overnight. It was then diluted with ethyl acetate (150 mL), washed with water and brine, and purified by prep-HPLC to afford Compound 16 (50 mg, yield 32%) as a white solid. LCMS (m/z): 538 [M+1]$^+$; $^1$H-NMR (CDCl$_3$, 400 MHz) major characteristic peaks: δ (ppm) 1.58 (br s, 2H), 1.86 (s, 4H), 2.21-2.42 (m, 3H), 2.56-2.64 (m, 1H), 2.75-2.85 (m, 3H), 3.02 (s, 2H), 3.88-4.06 (m, 4H), 4.21 (s, 1H), 5.12 (s, 1H), 6.78-6.87 (m, 4H), 7.14 (d, J=7.6, 1H), 7.39 (t, J=7.6 Hz, 1H), 7.72-7.82 (m, 4H), 8.69 (s, 1H).

The mixture of Compound 16A (4.10 g, 19.25 mmol) in DCM (100 mL) was added DMP (9.79 g, 23.09 mmol) at rt. After stirred at rt for 1 h the mixture was diluted with ethyl acetate (200 mL), filtered to remove solid, washed with water and brine, and purified by silica gel chromatography (ethyl acetate in petroleum ether, 20% v/v) to give Compound 16B (3.10 g, yield 76%) as a colorless oil. LCMS (m/z): 212 [M+1]$^+$, $^1$H-NMR (CDCl$_3$, 400 MHz) major characteristic peaks: δ (ppm) 2.90 (t, J=9.2 Hz, 2H), 3.06 (t, J=9.2 Hz, 2H), 7.25-7.32 (m, 2H), 7.43 (t, J=12.8 Hz, 1H), 7.78-7.93 (m, 4H), 8.74 (s, 1H), 9.86 (s, 1H).

A mixture of Compound 16B (3.00 g, 14.22 mmol) and 2NaO$_5$S$_2$ (2.70 g, 14.22 mmol) in H$_2$O/dioxane (50/10 mL) was stirred at rt for 2 h. After the addition of NaCN (1.39 g, 28.43 mmol), the mixture was stirred at rt overnight. It was diluted with ethyl acetate (200 mL), washed with water and brine, and purified by silica gel column chromatography (ethyl acetate in petroleum ether, 50% v/v) to yield Compound 16C (2.00 g, yield 59%) as a colorless oil. LCMS (m/z): 239 [M+1]$^+$; $^1$H-NMR (CDCl$_3$, 400 MHz) major characteristic peaks: δ (ppm) 2.05-2.26 (m, 2H), 2.83-2.96 (m, 2H), 4.36 (t, J=6.8 Hz, 1H), 4.97 (s, 1H), 7.22-7.31 (m, 2H), 7.41 (t, J=7.6 Hz, 1H), 7.69-7.82 (m, 4H), 8.68 (s, 1H).

A solution of Compound 16C (2.00 g, 8.40 mmol) in MeOH (50 mL) was stirred at rt for 6 h with HCl gas bubbling. The reaction was quenched with H$_2$O (10 mL) and stirred at rt for 1 h. It was diluted with ethyl acetate (150 mL), washed with water and brine, dried with anhydrous NaSO$_4$, and evaporated to give Compound 16D (1.90 g, yield 83%) as colorless oil. LCMS (m/z): 272 [M+1]$^+$; $^1$H-NMR (CDCl$_3$, 400 MHz) major characteristic peaks: δ

Example 17

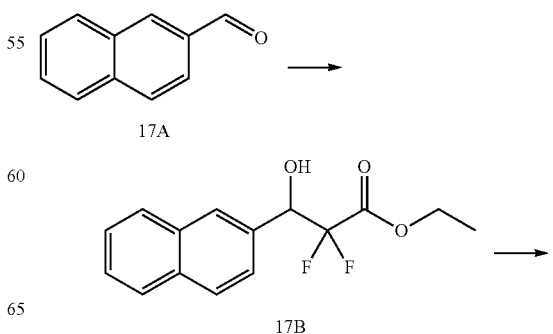

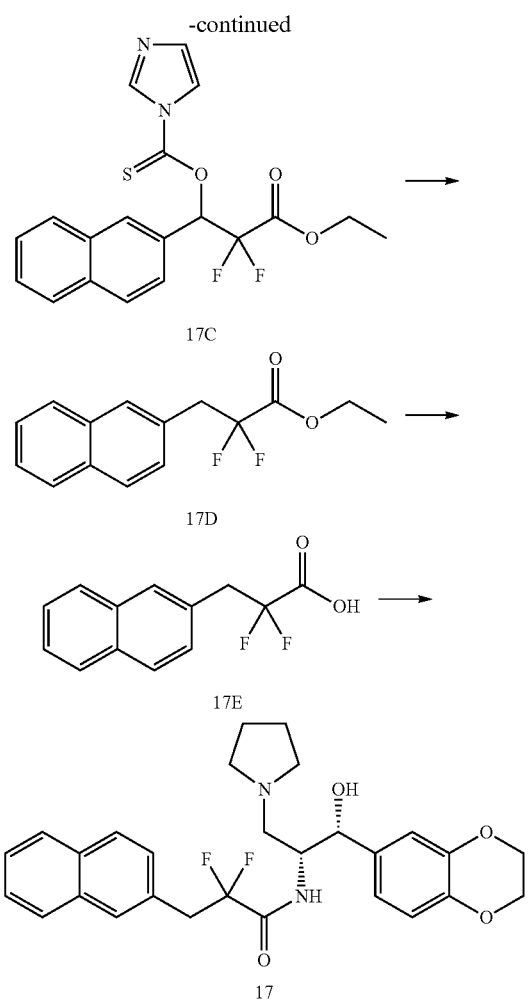

17C

17D

17E

17 dropwise the Compound 17C (310 mg, 0.79 mmol) in toluene (10 ml). After stirred for 3 h at 110° C., the reaction mixture was cooled to rt and concentrated in vacuum to give a crude product Compound 17D (500 mg, crude) as a yellow oil. It was used for the next step without purification. LCMS (m/z): 265 [M+1]$^+$.

To a solution of Compound 17D (500 mg, 0.79 mmol) in THF/MeOH/water (3 mL, 1:1:1, v/v) was added LiOH.H$_2$O (60 mg, 1.5 mmol). The mixture was stirred at 25° C. for 1 h. After the addition of water (20 mL), the mixture was extracted with ethyl acetate (20 mL×2). The water phrase was adjusted pH to 6 with 1 N HCl and extracted with ethyl acetate (20 mL×2). The combined organic layers were dried over anhydrous Na$_2$SO$_4$ and concentrated in vacuum to give a crude product Compound 17E (169 mg, yield 80%) as a white solid. LCMS (m/z): 235 [M−1]$^−$; $^1$H-NMR (DMSO-d$_6$, 400 MHz) major characteristic peaks: δ (ppm) 3.59 (t, J=17.2 Hz, 2H), 7.42 (d, J=8 Hz, 1H), 7.52 (d, J=8 Hz, 1H), 7.82 (s, 1H), 7.90 (t, J=8 Hz, 3H), 14.75 (s, 1H).

To a mixture of Compound 17E (67 mg, 0.25 mmol) in DCM (10 mL) was added EDCI (72 mg, 0.38 mmol), HOBt (51 mg, 0.38 mmol) and Intermediate A (61 mg, 0.25 mmol) and stirred at 25° C. overnight. After the addition of water (10 mL), the mixture was extracted with DCM (20 mL×3), dried over anhydrous Na$_2$SO$_4$, and purified by prep-HPLC to afford trifluoroacetic acid salt of Compound 17 (47 mg, yield 27%) as a white solid. LCMS (m/z): 496 [M+1]$^+$; $^1$H-NMR (CDCl$_3$, 400 MHz) major characteristic peaks: δ (ppm) 1.62-2.03 (m, 4H), 2.53 (s, 1H), 2.95 (s, 1H), 3.33-3.56 (m, 4H), 3.94 (s, 2H), 4.19 (s, 4H), 4.25 (s, 1H), 4.89 (s, 1H), 6.60 (d, J=8 Hz, 1H), 6.71 (d, J=8 Hz, 1H), 6.78 (s, 1H), 7.34 (t, J=8 Hz, 2H), 7.48 (d, J=8 Hz, 2H), 7.70 (s, 1H), 7.77-7.83 (m, 3H), 11.31 (s, 1H).

Example 18

To a solution of Compound 17A (3.12 g, 20 mmol) in anhydrous tetrahydrofuran (80 mL) was added zinc (2.1 g, 26 mmol). The mixture was heated at 75° C. under N$_2$ atmosphere and ethyl 2-bromo-2,2-difluoroacetate (3.2 mL, 29 mmol) was slowly added. The mixture was heated under the same conditions for 2 h. After cooling, it was filtered. The filtrate was concentrated to give a crude product which was purified by column chromatography on silica gel (ethyl acetate in petroleum 5% to 20% v/v) to yield Compound 17B (3.9 g, yield 70%) as a white solid. LCMS (m/z): 281 [M+1]$^+$. $^1$H-NMR (CDCl$_3$, 400 MHz) major characteristic peaks: δ (ppm) 1.26 (t, J=7.2 Hz, 3H), 4.30 (q, J=7.2 Hz, 2H), 5.34 (q, J=8 Hz, 1H), 7.50-7.56 (m, 3H), 7.83-7.88 (m, 3 3H), 7.91 (s, 1H)

To a solution of Compound 17B (280 mg, 1 mmol) in DCM (20 mL) was added dropwise N,N'-thiocarbonyldiimidazole (25.0 g, 126 mmol) in DCM (10 mL) at 72° C. After stirring for 3 h, the reaction mixture was cooled to rt and concentrated in vacuum to give a crude product. It was purified by silica gel column chromatography (ethyl acetate in petroleum 5% to 20% v/v) to afford Compound 17C (310 mg, yield 79%) as a yellow oil. LCMS (m/z): 391 [M+1]$^+$; $^1$H-NMR (CDCl$_3$, 400 MHz) major characteristic peaks: δ (ppm) 1.24 (t, J=7.2 Hz, 3H), 4.30 (q, J=7.2 Hz, 2H), 6.98 (m, 1H), 7.10 (s, 1H), 7.53-7.55 (m, 3H), 7.70 (s, 1H), 7.84-7.90 (m, 3H), 7.94 (s, 1H), 8.43 (s, 1H).

To a solution of n-Bu$_3$SnH (922 mg, 1.59 mmol) and AIBN (2 mg, cat.) in refluxing toluene (10 ml) was added

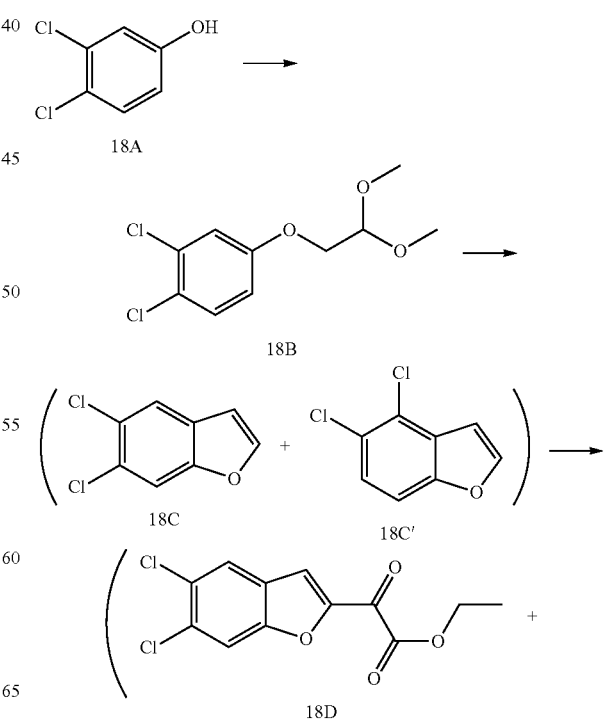

18A

18B 18C    18C'

18D

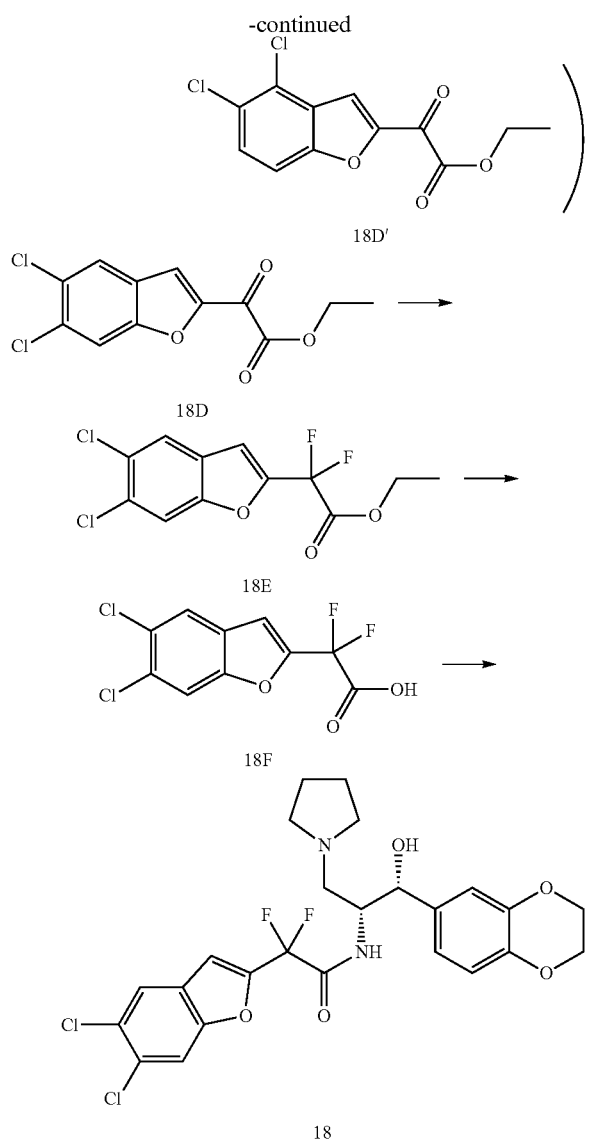

A mixture of Compound 18A (30 g, 184 mmol), 2-bromo-1,1-dimethoxyethane (37 g, 221 mmol), K$_2$CO$_3$ (38 g, 276 mmol), KI (600 mg) in DMF (150 mL) was stirred at reflux overnight. Cooling to rt, it was filtered. The filtrate was diluted with water (500 mL), extracted with ethyl acetate (250 mL×2), washed with water (250 mL×3) and brine (250 mL), dried over Na$_2$SO$_4$, and evaporated to dryness to yield a crude Compound 18B (46 g, yield 100%), which was used for the next step without further purification.

A solution of polyphosphoric acid (75 g) in toluene was stirred to 90° C., then to the solution was added Compound 18B (46 g) in toluene (20 mL). The mixture was stirred at 90° C. for 4 h, then poured into ice, and stirred for 30 min. Cooling to rt, the mixture was extracted with ethyl acetate (100 mL×2), washed with brine (100 mL), dried over Na$_2$SO$_4$, concentrated, and purified by silica gel column chromatography (petroleum ether, 100% v/v) to yield a mixture of Compound 18C and Compound 18C' (7 g, yield 21%) as a white solid. $^1$H-NMR (CDCl$_3$, 400 MHz) major characteristic peaks: δ (ppm) 6.69 (d, J=1.6 Hz, 1H), 6.84 (d, J=1.6 Hz, 1H), 7.34 (s, 2H), 7.61 (s, 1H), 7.62 (d, J=2.0 Hz, 1H), 7.65 (s, 1H).

To a solution of Compound 18C and 18C' (8 g, 42.8 mmol) in THF (60 mL) was added n-BuLi (20 mL) at −78° C. under N$_2$. After stirred for 30 min, diethyl oxalate (6 g, 51 mmol) was added to the mixture and it was stirred at −78° C. for 1 h, followed by the addition of aq sat. NH$_4$Cl. The resulting mixture was extracted with ethyl acetate (100 mL×2), washed with aq sat. NaHCO$_3$ (100 mL×2), brine (100 mL), dried over Na$_2$SO$_4$, concentrated, and purified by silica gel column chromatography (ethyl acetate in petroleum ether, 20% v/v) to give Compound 18D (2.5 g, yield 19%) and Compound 18D' (250 mg, yield 1.9%) as a yellow solid. Compound 18D: LC-MS (m/z): 287 [M1]$^−$; $^1$H-NMR (DMSO-d$_6$, 400 MHz) major characteristic peaks: δ (ppm) 1.45 (t, J=6.8 Hz, 3H), 4.45 (q, J=6.8 Hz, 2H), 6.79 (d, J=2.4 Hz, 1H), 7.70 (d, J=2.4 Hz, 1H), 7.83 (s, 1H). Compound 18D': LC-MS (m/z): 287 [M+1]$^−$; $^1$H-NMR (DMSO-d$_6$, 400 MHz) major characteristic peaks: δ (ppm) 1.47 (t, J=6.8 Hz, 3H), 4.50 (q, J=8.8 Hz, 2H), 7.47 (d, J=2.4 Hz, 1H), 7.58 (d, J=8.8 Hz, 1H), 8.12 (s, 1H).

To a solution of Compound 18D (750 mg, 2.6 mmol) in DCM (50 mL) was added DAST (2.5 g, 15.7 mmol) at 0° C. and the mixture was stirred at rt overnight. It was poured into ice-water, followed by addition of aq sat. aq NaHCO$_3$ (20 mL). The resulted mixture was extracted with DCM (50 mL×2), washed with brine (50 mL), dried over Na$_2$SO$_4$, and concentrated. The crude product was purified by silica gel column chromatography (ethyl acetate in petroleum ether, 10% v/v) to render Compound 18E (350 mg, yield 51%) as a yellow liquid. $^1$H-NMR (CDCl$_3$, 400 MHz) major characteristic peaks: δ (ppm) 1.26 (t, J=6.8 Hz, 3H), 4.31 (q, J=6.8 Hz, 2H), 6.71 (d, J=1.6 Hz, 1H), 7.66 (d, J=1.6 Hz, 1H), 7.76 (s, 1H).

To a solution of Compound 18E (150 mg, 0.5 mmol) in THF (20 mL) was added LiOH (24 mg, 0.6 mmol) in water (5 mL) and the mixture was stirred at rt 3 h. It was concentrated by removal of EtOH and adjusted to pH 7 with diluted HCl. Lyophilization of the solution led to Compound 18F (124 mg, crude), which was used for the next step without further purification. LC-MS (m/z): 280 [M−1]$^−$; $^1$H-NMR (DMSO-d$_6$, 400 MHz) major characteristic peaks: δ (ppm) 7.17 (s, 1H), 8.24 (s, 1H), 8.26 (s, 1H).

A mixture of Compound 18F (124 mg, 0.44 mmol), EDCI (117 mg, 0.61 mmol), HOBt (83 mg, 0.61 mmol), Intermediate A (115 mg, 0.41 mmol) in DCM (20 mL) was stirred at rt overnight. To the mixture was added dropwise aq sat. NaHCO$_3$. It was then extracted with DCM (50 mL×2), washed with brine (50 mL), dried over Na$_2$SO$_4$, and concentrated. The crude product was purified by prep-HPLC to give Compound 18 (78 mg, yield 26%) as a white solid. LC-MS (m/z): 541 [M+1]$^+$; $^1$H-NMR (CDCl$_3$, 400 MHz) major characteristic peaks: δ (ppm) 2.13 (s, 4H), 2.89 (m, 2H), 3.09 (brs, 1H), 3.37 (brs, 1H), 3.62 (brs, 1H), 3.87 (brs, 2H), 4.25 (s, 4H), 4.36 (m, 1H), 5.21 (s, 1H), 6.75 (s, 1H), 6.83 (s, 2H), 6.89 (s, 1H), 7.62 (d, J=2 Hz, 1H), 7.68 (d, J=2 Hz, 1H), 7.80 (s, 1H), 11.41 (s, 1H).

Example 19

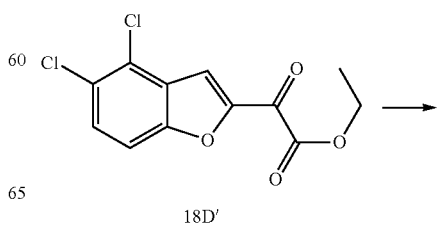

3.56-3.62 (m, 1H), 3.78 (s, 1H), 3.94-3.80 (m, 2H), 4.11-4.15 (m, 4H) 4.48 (s, 1H), 5.03 (s, 1H), 6.69-6.77 (m, 2H), 6.80 (s, 1H), 7.35-7.38 (d, J=9.2 Hz, 1H), 7.44-7.46 (d, J=8.8 Hz, 1H), 8.02-8.04 (d, J=8.8 Hz, 1H), 11.70 (s, 1H).

Example 20

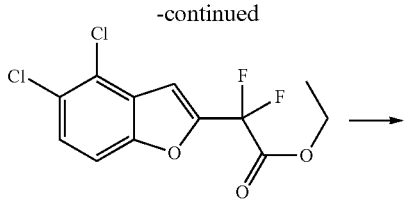

19A

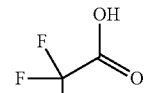

19B

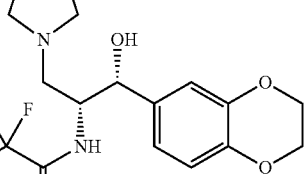

19

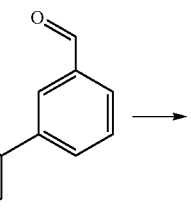

20A

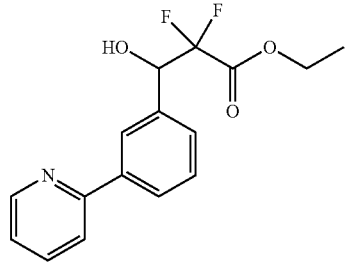

20B

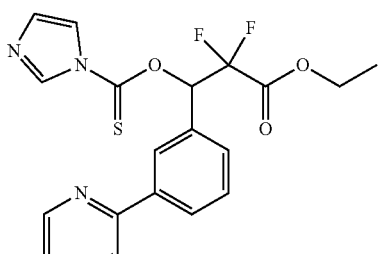

20C

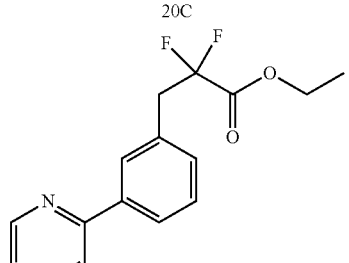

20D

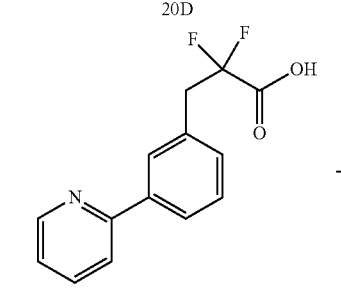

20E

To a solution of Compound 18D' (240 mg, 0.84 mmol) in DCM (11 mL) was added DAST (740 mg, 4.59 mmol) at 0° C. and the mixture was stirred at rt overnight. The reaction was quenched by pouring the mixture into ice-water, and followed with addition of sat. aq NaHCO$_3$ (20 mL). It was extracted with DCM (50 mL×2), washed with brine (50 mL×1), dried over Na$_2$SO$_4$, and concentrated. The crude product was purified by silica gel column chromatography (ethyl acetate in petroleum ether, 10% v/v) to render Compound 19A (245 mg, yield 94.8%) as a yellow liquid. $^1$H-NMR (CDCl$_3$, 400 MHz) major characteristic peaks: δ (ppm) 1.35-1.40 (m, 3H), 4.35-4.44 (m, 2H), 7.23 (s, 1H), 7.40-7.42 (d, J=8.8 Hz, 1H), 7.46-7.48 (d, J=8.8 Hz, 1H).

To a solution of Compound 19A (245 mg, 0.795 mmol) in THF (10 mL) was added LiOH (63 mg, 1.49 mmol) in water (5 mL) and the mixture was stirred at rt for 4 h. The mixture was concentrated by removal of solvent and then adjusted pH to 6 with diluted HCl. Lyophilization of the solution gave rise to Compound 19B (210 mg, crude), which was used for the next step without further purification. LC-MS (m/z): 279 [M−1]$^−$.

A mixture of Compound 19B (135 mg, 0.48 mmol), EDCI (135 mg, 0.70 mmol), HOBt (94 mg, 0.69 mmol), Intermediate A (130 mg, 0.47 mmol) in DCM (20 mL) was stirred at rt overnight. The mixture was diluted with aq sat. NaHCO$_3$, extracted with DCM (50 mL×2), washed with brine (50 mL×1), dried over Na$_2$SO$_4$, and concentrated. The crude product was purified by prep-HPLC to give 19 (83 mg, yield 32%) as a white solid. LC-MS (m/z): 541.2 [M+1]$^+$; $^1$H-NMR (CDCl$_3$, 400 MHz) major characteristic peaks: δ (ppm) 2.11 (s, 4H), 2.91-2.99 (m, 2H), 3.41-3.42 (m, 1H),

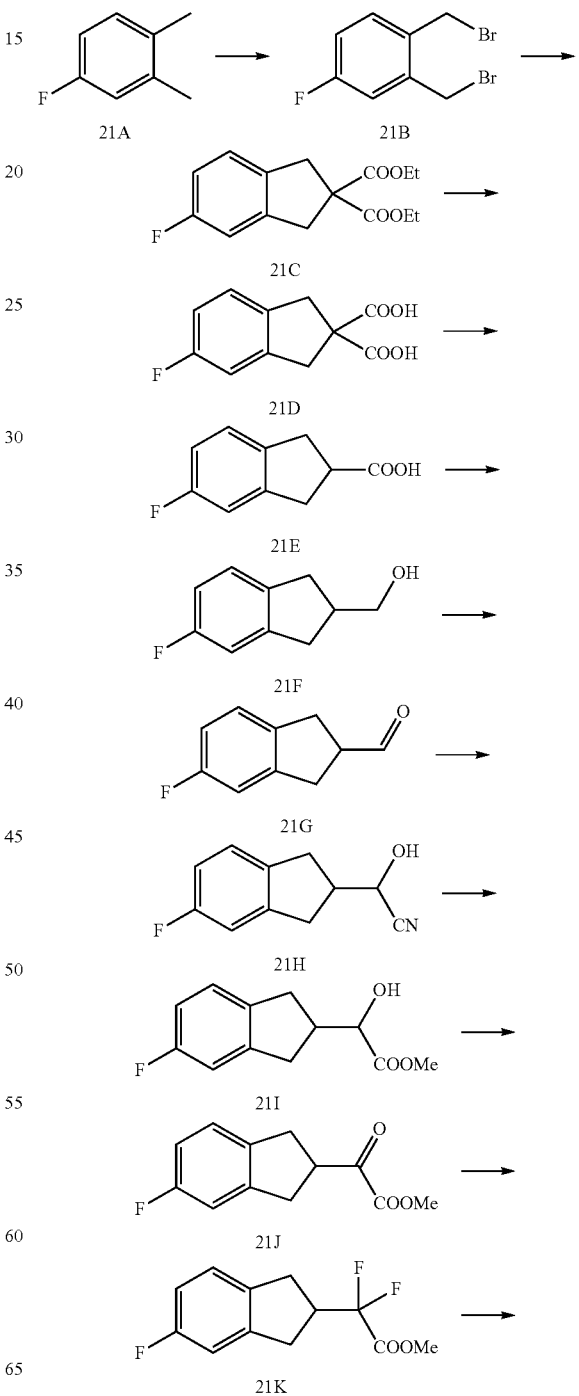

To a solution of Compound 20A (2.2 g, 12 mmol) in anhydrous tetrahydrofuran (80 mL) was added zinc (1.01 g, 15.6 mmol). The mixture was heated at 75° C. under $N_2$ atmosphere and ethyl 2-bromo-2, 2-difluoroacetate (1.9 mL, 15 mmol) was slowly added. The mixture was heated under the same conditions for 2 h. After cooling, it was filtered. The filtrate was concentrated to give a crude product, which was purified by silica gel column chromatography (ethyl acetate in petroleum ether, 20% v/v) to afford Compound 20B (1.9 g, yield 58%) as a colorless oil. LCMS (m/z): 309 [M+1]$^+$.

To a solution of Compound 20B (500 mg, 1.63 mmol) in DCM (20 mL) was added dropwise N,N'-thiocarbonyldiimidazole (349 mg, 1.95 mmol) in DCM (10 mL) at 72° C. After 3 h, the reaction mixture was cooled to rt and concentrated in vacuum to give a crude product. It was purified by silica gel column chromatography (ethyl acetate in petroleum ether, 20% v/v) to render Compound 20C (590 mg, yield 87%) as a colorless oil. LCMS (m/z): 418 [M+1]$^+$; $^1$H-NMR (CDCl$_3$, 400 MHz) major characteristic peaks: δ (ppm) 1.26 (t, J=6.8 Hz, 3H), 4.31 (q, J=6.8 Hz, 2H), 6.92 (m, 1H), 7.09 (s, 1H), 7.28 (m, 1H), 7.60 (m, 2H), 7.70-7.81 (m, 3H), 8.07 (d, J=7.2 Hz, 1H), 8.13 (s, 1H), 8.41 (s, 1H), 8.70 (d, J=4.4 Hz, 1H).

To a solution of n-Bu$_3$SnH (821 mg, 2.8 mmol) and AIBN (2 mg, cat.) in refluxing toluene (10 ml) was added dropwise the Compound 20C (590 mg, 1.4 mmol) in toluene (10 ml). After stirred for 3 h at 110° C., the reaction mixture was cooled to rt and concentrated in vacuum to purified by silica gel column chromatography (ethyl acetate in petroleum ether, 20% v/v) to afford Compound 20D (200 mg, yield 50%) as a colorless oil. LCMS (m/z): 392 [M+1]$^+$.

To a solution of Compound 20D (100 mg, 0.34 mmol) in THF/MeOH/water (3 mL, 1:1:1, v/v) was added LiOH.H$_2$O (36 mg, 1.5 mmol). The mixture was stirred at 25° C. for 1 h. After the completion of the reaction, water (20 mL) was added. It was extracted with ethyl acetate (20 mL×2). The aqueous phrase was adjusted pH to 6 with 1 N HCl and extracted with ethyl acetate (20 mL×2). The combined organic layers were dried over anhydrous Na$_2$SO$_4$ and concentrated in vacuum to give crude product Compound 20E (90 mg, crude) as a yellow solid. LCMS (m/z): 264 [M+1]$^+$.

To a mixture of Compound 20E (80 mg, 0.3 mmol) in DCM (10 mL) was added EDCI (88 mg, 0.45 mmol), HOBt (62 mg, 0.45 mmol) and Intermediate A (85 mg, 0.3 mmol) and stirred at 25° C. overnight. After the addition of water (10 mL), the mixture was extracted with DCM (20 mL×3), dried over anhydrous Na$_2$SO$_4$, purified by prep-HPLC to render Compound 20 (35 mg, yield 22%) as a white solid. LCMS (m/z): 524 [M+1]$^+$; $^1$H-NMR (CDCl$_3$, 400 MHz) major characteristic peaks: δ (ppm) 1.99 (s, 4H), 2.72 (m, 2H), 3.19 (s, 1H), 3.42-3.66 (m, 6H), 4.20 (s, 4H), 4.40 (s, 1H), 4.77 (s, 1H), 4.89 (s, 1H), 6.68 (m, 1H), 6.76 (m, 2H), 7.45-7.54 (m, 2H), 7.70 (m, 1H), 7.77-7.85 (m, 3H), 7.99 (d, J=8.0 Hz, 1H), 8.28 (t, J=7.6 Hz, 1H), 8.90 (s, 1H), 11.43 (s, 1H).

Example 21

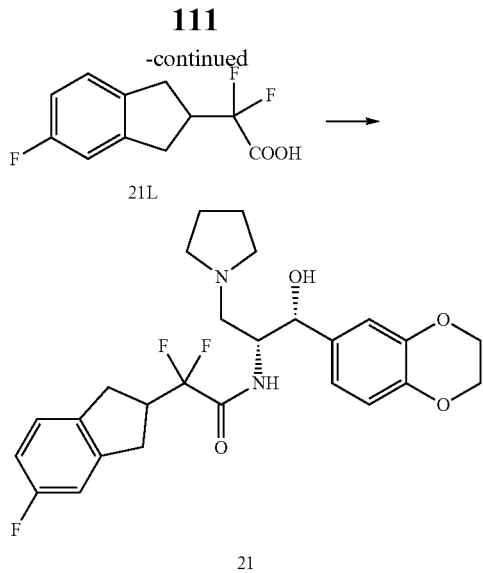

To a solution of Compound 21A (2.5 g, 20 mmol) in CCl$_4$ (100 mL) was added NBS (7.12 g, 40 mmol), BPO (100 mg) and it was stirred at reflux overnight. The mixture was purified by column chromatography on silica gel (ethyl acetate in petroleum ether, 10% v/v) to render Compound 21B (2.34 g, yield 41%) as a colorless oil. $^1$H-NMR (CDCl$_3$, 400 MHz) major characteristic peaks: δ (ppm) 4.60 (s, 2H), 4.62 (s, 2H), 6.98 (m, 1H), 7.08 (m, 1H), 7.33 (m, 1H).

To a solution of diethyl malonate (1.52 mL, 10 mmol) in THF (100 mL) was added NaH (60%, 400 mg, 10 mmol) at 0° C. and stirred at 0° C. for 15 min. To the mixture was added Compound 21B (2.8 g, 10 mmol) at 0° C. and stirred for 15 min and then followed by addition of NaH (60%, 400 mg, 10 mmol) at 0° C. The mixture was stirred at rt for 2 h and was filtered to remove the salt. The filtrate was concentrated and purified by flash column (ethyl acetate in petroleum ether, 10% v/v) to give Compound 21C (2.2 g, yield 79%) as a colorless oil. LC-MS (m/z): 281 [M+1]$^+$; $^1$H-NMR (CDCl$_3$, 400 MHz) major characteristic peaks: δ (ppm) 1.26 (t, J=7.0 Hz, 6H), 3.53 (s, 2H), 3.56 (s, 2H), 4.20 (m, 4H), 6.87 (m, 2H), 7.12 (m, 1H).

To a solution of Compound 2lB (2.2 g, 7.9 mmol) in ethanol (30 mL) was added a solution of LiOH (1.26 g, 31.4 mmol) in water (30 mL) and stirred at rt overnight. The mixture was concentrated to remove ethanol, acidified with conc. aqueous HCl solution, extracted with ethyl acetate (100 mL×3) and concentrated to render Compound 21D (1 g, yield 62%) as a yellow solid. LC-MS (m/z): 247 [M+23]$^+$; $^1$H-NMR (DMSO-d$_6$, 400 MHz) major characteristic peaks: δ (ppm) 3.38 (s, 2H), 3.42 (s, 2H), 6.93 (m, 1H), 7.05 (m, 1H), 7.21 (m, 1H), 12.93 (s, 2H).

To a solution of Compound 21D (1 g, 4.5 mmol) in DMSO (15 mL) was added NaCl (1 g). The mixture was stirred at 130° C. for 6 h. After the addition of ethyl acetate (100 mL), the mixture was washed with water (200 mL×3) and brine (200 mL×1), dried over anhydrous Na$_2$SO$_4$, and concentrated to yield Compound 21E (0.6 g, yield 74%) as a brown solid. $^1$H-NMR (DMSO-d$_6$, 400 MHz) major characteristic peaks: δ (ppm) 3.08 (m, 4H), 3.29 (m, 1H), 6.92 (m, 1H), 7.03 (m, 1H), 7.21 (m, 1H), 12.37 (s, 1H).

To a solution of Compound 21E (0.6 g, 3.3 mmol) in DCM (10 mL) was added B$_2$H$_6$ in THF solution (1M, 4 mL, 4 mmol) at −78° C. under N$_2$ and stirred at rt for 1 h. MeOH (2 mL) was added to the mixture and it was stirred at the same temperature overnight. After removal of the solvents, the residues were purified with flash column chromatography (ethyl acetate in petroleum ether, 35% v/v) to give Compound 21F (250 mg, yield 46%) as a yellow oil. $^1$H-NMR (CDCl$_3$, 400 MHz) major characteristic peaks: δ (ppm) 2.70 (m, 3H), 3.04 (m, 2H), 3.65 (d, J=6.4 Hz, 2H), 6.80 (m, 1H), 6.87 (m, 1H), 7.11 (m, 1H).

To a solution of Compound 21F (6.3 g, 38 mmol) in DCM (300 mL) was added DMP (19 g, 45.5 mmol) at 0° C. and it was stirred at rt for 3 h. The mixture was concentrated and purified by flash column chromatography (ethyl acetate in petroleum ether, 20% v/v) to give Compound 21G (6 g, yield 96%) as a yellow oil. $^1$H-NMR (CDCl$_3$, 400 MHz) major characteristic peaks: δ (ppm) 3.23 (m, 5H), 6.88 (m, 2H), 7.15 (m, 1H), 9.77 (d, J=0.8 Hz, 1H).

To a solution of Na$_2$S$_2$O$_5$ (3.6 g, 73.2 mmol) in water (100 mL) was added Compound 21G (6 g, 36.6 mmol) and it was stirred at rt for 2 h and followed by the addition of NaCN (3.6 g, 73.2 mmol). The mixture was stirred at rt overnight. It was extracted with ethyl acetate (100 mL×3), dried over anhydrous Na$_2$SO$_4$, purified by flash column chromatography (ethyl acetate in petroleum, 30% v/v) to give Compound 21H (3.3 g, 47%) as a colorless oil. $^1$H-NMR (CDCl$_3$, 400 MHz) major characteristic peaks: δ (ppm) 2.96 (m, 3H), 3.16 (m, 2H), 4.45 (m, 1H), 6.86 (m, 2H), 7.14 (m, 1H).

To a solution of Compound 21H (3.3 g, 17.3 mmol) in MeOH (100 mL) was bubbled with a gentle stream of HCl gas (dried over conc. H$_2$SO$_4$) for 6 h and was allowed to stand overnight at 4° C. To the mixture was added water (50 mL) and it was stirred at rt for 3 h. Saturated aqueous NaHCO$_3$ solution was added to adjust pH>7, the mixture was then extracted with ethyl acetate (100 mL×3), washed with brine (100 mL×1), dried over anhydrous Na$_2$SO$_4$, and purified by flash column chromatography (ethyl acetate in petroleum ether, 25% v/v) to give Compound 21I (1.9 g, yield 49%) as a yellow oil. $^1$H-NMR (CDCl$_3$, 400 MHz) major characteristic peaks: δ (ppm) 2.90 (m, 5H), 3.77 (d, J=2.4 Hz, 3H), 4.27 (d, J=3.6 Hz, 1H), 6.81 (m, 2H), 7.07 (m, 1H).

To a solution of Compound 21I (1.9 g, 8.5 mmol) in DCM (100 mL) was added DMP (5.4 g, 12.7 mmol) at 0° C. and it was stirred at rt for 3 h. After removal of the solvent, the residues were purified by flash column chromatography (ethyl acetate in petroleum ether, 10% v/v) to give Compound 21J (1.7 g, yield 90%) as a colorless oil. $^1$H-NMR (CDCl$_3$, 400 MHz) major characteristic peaks: δ (ppm) 3.19 (m, 4H), 3.91 (s, 3H), 4.07 (m, 1H), 6.83 (m, 2H), 7.10 (m, 1H).

To a solution of Compound 21J (444 mg, 2 mmol) in DCM (10 mL) was added DAST (1 mL, 8 mmol) and it was stirred at 25° C. overnight. The mixture was purified by flash column chromatography (ethyl acetate in petroleum ether, 2% v/v) to give 21K (300 mg, 61%) as a yellow oil. LC-MS (m/z): 225 [M−19]$^+$.

To a solution of Compound 21K (300 mg, 1.23 mmol) in MeOH (5 mL) was added a solution of LiOH (100 mg, 2.46 mmol) in water (5 mL) and it was stirred at rt overnight. The mixture was acidified using 1M aqueous HCl solution, extracted with ethyl acetate (10 mL×3), dried over anhydrous Na$_2$SO$_4$, and concentrated to give Compound 21L (200 mg, yield 35%) as a colorless oil. LC-MS (m/z): 229 [M−1]$^-$.

To a solution of Compound 21L (230 mg, 0.87 mmol) in DCM (10 mL) was added EDCI (250 mg, 1.3 mmol), HOBt (175 mg, 1.3 mmol), Intermediate A (240 mg, 0.87 mmol) and it was stirred at rt overnight. The mixture was diluted with DCM (20 mL), washed with water (50 mL×2) and brine (50 mL×1), dried over anhydrous Na$_2$SO$_4$, concentrated, and purified by prep-HPLC to give Compound 21 (20 mg, yield 5%) as a white solid. LC-MS (m/z): 491 [M+1]$^+$; $^1$H-NMR (CDCl$_3$, 400 MHz) major characteristic peaks: δ (ppm) 2.15 (br, 4H), 2.61 (m, 2H), 2.91 (m, 5H), 3.38 (br, 1H), 3.54 (br, 1H), 3.88 (s, 2H), 4.20 (m, 4H), 4.44 (s, 1H), 5.20 (s, 1H), 6.83 (m, 4H), 6.90 (m, 1H), 7.05 (m, 1H), 7.39 (m, 1H), 11.42 (s, 1H).

Example 22

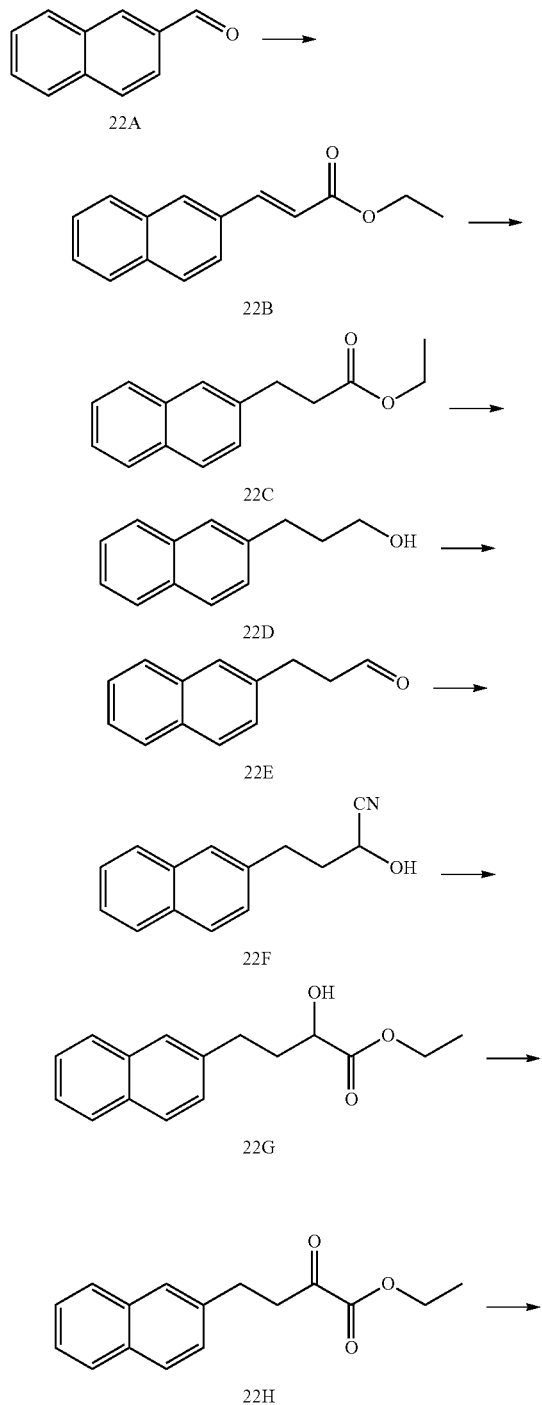

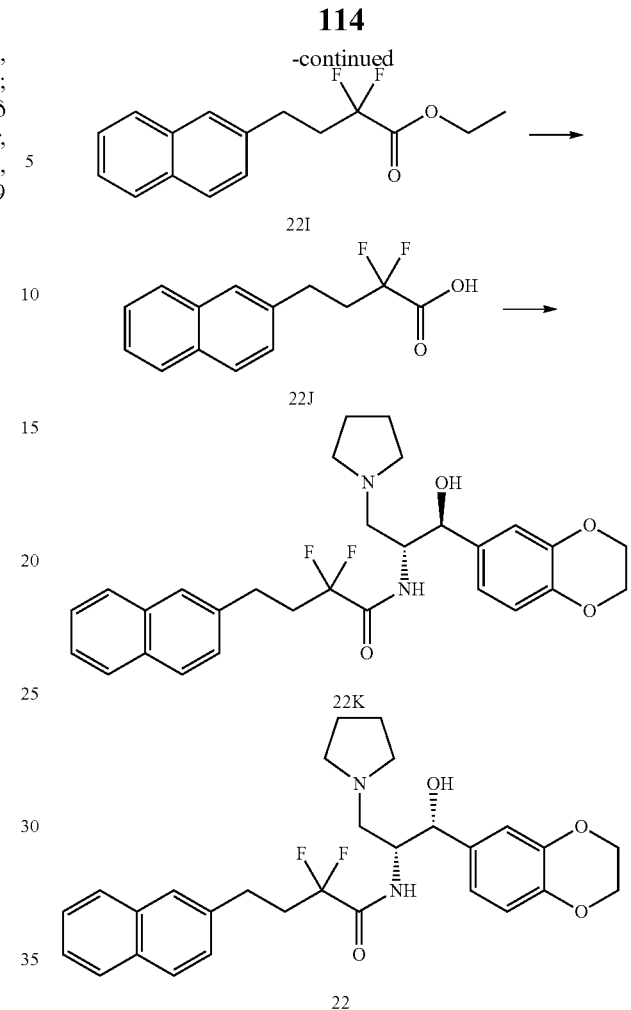

To a solution of ethyl 2-(diethoxyphosphoryl)acetate (7.2 g, 32 mmol) in THF (150 mL) was added NaH (1.3 g, 32 mmol) at 0° C. under N$_2$ and it was stirred at this temperature for 30 min, followed by the addition of Compound 22A (5 g, 32 mmol) in THF (15 mL). Stirred at 40° C. for 1 h, the mixture was first cooled down to rt, and then added water, extracted with ethyl acetate (50 mL×2), washed with brine (50 mL×1), dried over Na$_2$SO$_4$, concentrated, and purified by silica gel column chromatography (ethyl acetate in petroleum ether, 20% v/v) to give Compound 22B (7 g, yield 97%). LC-MS (m/z): 227 [M+1]$^+$; $^1$H-NMR (CDCl$_3$, 400 MHz) major characteristic peaks: δ (ppm) 1.36 (t, J=6.8 Hz, 3H), 4.28 (q, J=7.2 Hz, 2H), 6.54 (d, J=16 Hz, 1H), 7.5 (m, 2H), 7.65 (d, J=10 Hz, 1H), 7.82 (m, 4H), 7.91 (s, 1H).

To a solution of Compound 22B (7 g, 31 mmol) in methanol (50 mL) and THF (30 mL) was added Pd/C (700 mg) and it was stirred at 25° C. for 4 h under H$_2$. The mixture was filtered, and the filtrate was concentrated to render Compound 22C (7 g, crude), which was used for the next step without further purification. LC-MS (m/z): 229 [M+1]$^+$.

To a solution of AlLiH$_4$ (1.16 g, 31 mmol) in THF (100 mL) was added Compound 22C (7 g, 31 mmol) in THF (20 mL) at −60° C. under N$_2$ and the mixture was stirred for 2 h, and then allowed the temperature raised to rt. Sodium sulfate was added to the mixture. After filtration, the filtrate was purified by silica gel column chromatography (ethyl acetate in petroleum ether, 20% v/v) to yield the Compound 22D (5.6 g, yield 98%) as a white solid. LC-MS (m/z): 169

[M–18]+; 1H-NMR (CDCl3, 400 MHz) major characteristic peaks: δ (ppm) 1.06 (s, 1H), 1.97 (m, 2H), 2.87 (d, J=7.6 Hz, 2H), 3.70 (d, J=6.4 Hz, 2H), 7.33 (d, J=8.4 Hz, 1H), 7.43 (m, 2H), 7.63 (s, 1H), 7.78 (m, 3H).

To a solution of Compound 22D (3 g, 16 mmol) in DCM (100 mL) was added DMP (8.2 g, 19 mmol) and the mixture was stirred at rt for 2 h, and then filtered. The filtrate was washed with aq sat. NaHCO3 (2×50 mL), extracted with DCM (2×50 mL), washed with brine (1×50 mL), dried over Na2SO4, concentrated, and purified by silica gel column chromatography (ethyl acetate in petroleum ether, 20% v/v) to afford Compound 22E (2.6 g, yield 88%) as a colorless oil. 1H-NMR (CDCl3, 400 MHz) major characteristic peaks: δ (ppm) 2.87 (d, J=7.2 Hz, 2H), 3.12 (d, J=7.6 Hz, 2H), 7.33 (d, J=8.4 Hz, 1H), 7.44 (m, 2H), 7.63 (s, 1H), 7.79 (m, 3H), 9.86 (s, 1H).

Compound 22E (2.6 g, 14 mmol) was added to a solution of sodium metabisulfate (2.7 g, 14 mmol) in water (100 mL). The mixture was vigorously stirred for 2 h at rt, and after the addition of NaCN (1.4 mg, 28 mmol) it was stirred overnight. The mixture was added water (30 mL) and THF (10 mL), extracted with ethyl acetate (100 mL×2), washed with brine (100 mL×1), dried over Na2SO4, concentrated to yield Compound 22F (2 g, 66% yield). LC-MS (m/z): 212 [M+1]+; 1H-NMR (DMSO-d6, 400 MHz)□□ major characteristic peaks: δ (ppm) 2.25 (m, 2H), 2.99 (m, 2H), 4.43 (t, J=6.8 Hz, 1H), 7.33 (d, J=8.8 Hz, 1H), 7.44 (m, 2H), 7.65 (s, 1H), 7.81 (m, 3H).

To a solution of Compound 22F (2.0 g, 9.5 mmol) in EtOH (30 mL) at 0° C. was bubbled with a gentle stream of HCl (gas) (dried over con. H2SO4) for 5 h. The mixture was added water (20 mL), stirred at rt for 2 h, and adjusted pH to 7 with diluted NaOH (2 M). It was extracted with DCM (100 mL×2), washed with brine (50 mL×1), dried over Na2SO4, concentrated, and purified by silica gel column chromatography (ethyl acetate in petroleum ether, 33% v/v) to render Compound 22G (1.56 g, yield 64%) as a yellow oil. LC-MS (m/z): 259 [M+1]+; 1H-NMR (CDCl3, 400 MHz) major characteristic peaks: δ (ppm) 1.27 (t, J=7.6 Hz, 1H), 2.03 (m, 1H), 2.22 (m, 1H), 2.92 (m, 2H), 4.20 (m, 3H), 7.35 (d, J=9.2 Hz, 1H), 7.44 (m, 2H), 7.65 (s, 1H), 7.79 (m, 3H).

To a solution of Compound 22G (500 mg, 1.94 mmol) in DCM (20 mL) was added DMP (986 mg, 2.3 mmol) and the mixture was stirred at rt for 2 h and then filtered. The filtrate was washed with aq sat. NaHCO3 (50 mL×2) and aq sat. Na2S2O3 (50 mL×2), extracted with DCM (50 mL×2), washed with brine (50 mL×1), dried over Na2SO4, and concentrated to yield Compound 22H (450 mg, yield 91%) as a yellow oil. LC-MS (m/z): 239 [M–18]+.

To a solution of Compound 22H (450 mg, 1.76 mmol) in DCM (20 mL) was added DAST (1.4 g, 8.8 mmol) at 0° C. and the mixture was stirred at rt overnight. The reaction mixture was poured into ice-water, extracted with DCM (50 mL×2), washed with brine (50 mL×1), dried over Na2SO4, and concentrated. The crude product was purified by silica gel column chromatography (ethyl acetate in petroleum ether, 20% v/v) to yield Compound 22I (450 mg, yield 92%) as a colorless oil. LC-MS (m/z): 279 [M+1]+; 1H-NMR (CDCl3, 400 MHz) major characteristic peaks: δ (ppm) 1.31 (t, J=7.2 Hz, 1H), 2.47 (m, 2H), 2.98 (m, 2H), 4.27 (q, J=7.2 Hz, 2H), 7.31 (d, J=8.4 Hz, 1H), 7.45 (m, 2H), 7.63 (s, 1H), 7.77 (m, 3H).

To a solution of Compound 22I (450 mg, 1.6 mmol) in EtOH (5 mL) was added LiOH (136 mg, 3.2 mmol) in water (5 mL) and the mixture was stirred at rt overnight. After concentration by evaporation, the mixture was adjusted to pH 2 with diluted HCl, extracted with DCM (20 mL×2), washed with brine (20 mL×1), dried over Na2SO4, and concentrated to give Compound 22J (250 mg, yield 62%), which was used for the next step without further purification. LC-MS (m/z): 251 [M+1]+.

A mixture of Compound 22J (100 mg, 0.4 mmol), EDCI (115 mg, 0.6 mmol), HOBt (82 mg, 0.6 mmol), Intermediate A (110 mg, 0.4 mmol) in DCM (20 mL) was stirred at rt overnight. The reaction mixture was diluted with water, extracted with DCM (50 mL×2), washed with brine (50 mL×1), dried over Na2SO4, and concentrated. The crude product was purified first by prep-HPLC, followed by chiral-prep-HPLC to give Compound 22K (24 mg, yield 12%) as a white solid and Compound 22 (22 mg, yield 11%) as a white solid. For Compound 22K: LC-MS (m/z): 511 [M+1]+; 1H-NMR (CDCl3, 400 MHz) major characteristic peaks: δ (ppm) 1.81 (s, 4H), 2.46 (m, 3H), 2.70 (m, 5H), 2.98 (d, J=3.6 Hz, 2H), 3.94 (m, 4H), 4.20 (s, 1H), 5.07 (s, 1H), 6.82 (m, 4H), 7.22 (m, 1H), 7.45 (m, 2H), 7.54 (s, 1H), 7.77 (m, 3H). For Compound 22: LC-MS (m/z): 511 [M+1]+; 1H-NMR (CDCl3, 400 MHz) major characteristic peaks: δ (ppm) 1.89 (s, 4H), 2.36 (m, 2H), 2.88 (m, 4H), 2.99 (m, 3H), 3.19 (s, 1H), 4.04 (m, 4H), 4.25 (s, 1H), 4.77 (d, J=5.6 Hz, 1H), 6.86 (m, 3H), 7.28 (m, 1H), 7.44 (m, 2H), 7.59 (s, 1H), 7.78 (m, 3H).

Example 23

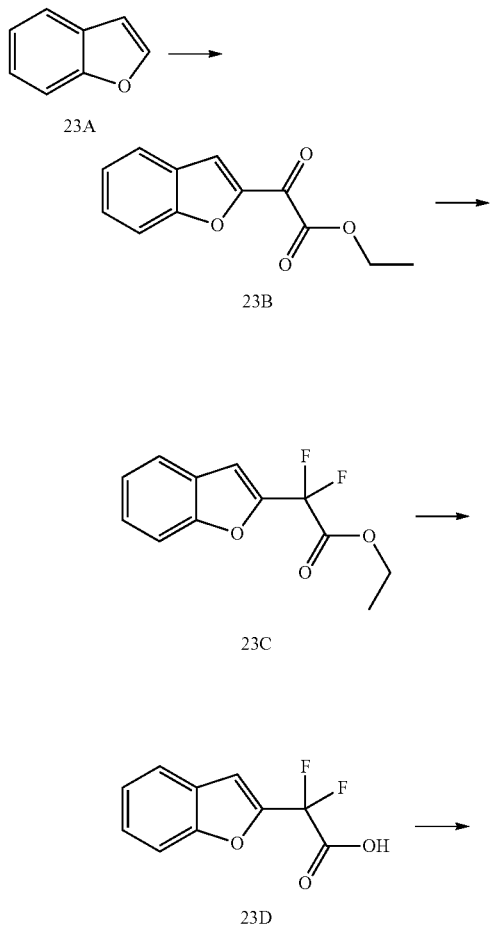

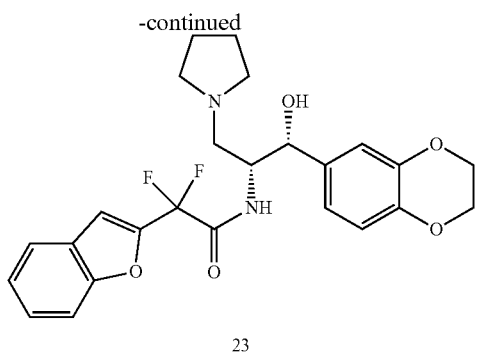

23

To a solution of Compound 23A (2.36 g, 20.0 mmol) in tetrahydrofuran (30 mL) stirring at −70° C. (CO₂, acetone bath) was added n-BuLi (8.0 mL, 20.0 mmol, 1.6 M in hexanes). The reaction was stirred for 30 min (yellow color) and added dropwise via a cannulated needle into a solution of diethyl oxalate (2.92 g, 20.0 mmol) in tetrahydrofuran (20 mL) stirring at −70° C. The reaction mixture was stirred for 1 h and then quenched with saturated aqueous ammonium chloride solution. The mixture was warmed to rt, diluted with dichloromethane, and washed with 0.1 N HCl. The organic layer was separated, dried over anhydrous magnesium sulfate, filtered, and evaporated under reduced pressure. The residue was purified by chromatography on silica gel (ethyl acetate in petroleum ether, 10% v/v) to provide Compound 23B (1.10 g, yield 25%). $^1$H-NMR (CDCl₃, 400 MHz) major characteristic peaks: δ (ppm) 1.46 (t, J=7.2 Hz, 3H), 4.87 (q, J=7.2 Hz, 2H), 7.35-7.37 (m, 1H), 7.55-7.57 (m, 1H), 7.61-7.64 (m, 1H), 7.77-7.78 (m, 1H), 8.09-8.10 (m, 1H).

To a solution of Compound 23B (800 mg, 3.67 mmol) in CH₂Cl₂ (10 mL) was added DAST (1.77 g, 11.01 mmol). The reaction mixture was stirred for 10 h and then poured into ice-water, extracted with CH₂Cl₂. The combined organic layers were dried over Na₂SO₄, filtered, evaporated to give desired product Compound 23C (860 mg, yield 97%). $^1$H-NMR (CDCl₃, 400 MHz) major characteristic peaks: δ (ppm) 1.35-1.40 (m, 3H), 4.33-4.43 (m, 2H), 7.14-7.15 (m, 1H), 7.31-7.33 (m, 1H), 7.38-7.42 (m, 1H), 7.54-7.56 (m, 1H), 7.64-7.66 (m, 1H).

To a solution of Compound 23C (480 mg, 2 mmol) in THF (2 mL) was added LiOH·H₂O (3 mmol, 126 mg), H₂O (2 mL) and MeOH (2 mL). The reaction mixture was stirred for 3 h at 25° C., neutralized with 1 N HCl, and evaporated to dryness. The residue was dissolved in H₂O and extracted with ethyl acetate. The organic layer was dried over Na₂SO₄, filtered, evaporated to give Compound 23D (290 mg, yield 68%). LCMS (m/z): 213 [M+1]⁺.

To a solution of Compound 23D (88 mg, 0.41 mmol) in DCM (10 mL) was added Intermediate A (114 mg, 0.41 mmol), HOBt (82 mg, 0.61 mmol) and EDCI (116 mg, 0.61 mmol). The mixture was stirred for 3 h at 25° C., washed with brine, dried over Na₂SO₄, filtered, evaporated, and purified by prep-HPLC to give Compound 23 (30 mg, yield 15%) as a white solid. LC-MS (m/z): 473 [M+1]⁺; $^1$H-NMR (MeOD-d₄, 400 MHz) major characteristic peaks: δ (ppm) 1.77-1.78 (m, 4H), 2.55-2.64 (m, 4H), 2.74-2.75 (m, 2H), 4.08-4.14 (m, 4H), 4.35-4.36 (m, 1H), 4.79 (d, J=4.0 Hz, 1H), 6.66-6.68 (m, 1H), 6.76-6.78 (m, 1H), 6.83-6.84 (m, 1H), 7.00 (s, 1H), 7.30-7.34 (m, 1H), 7.41-7.45 (m, 1H), 7.55-7.57 (m, 1H), 7.66-7.68 (m, 1H), 7.81-7.83 (m, 1H).

Example 24

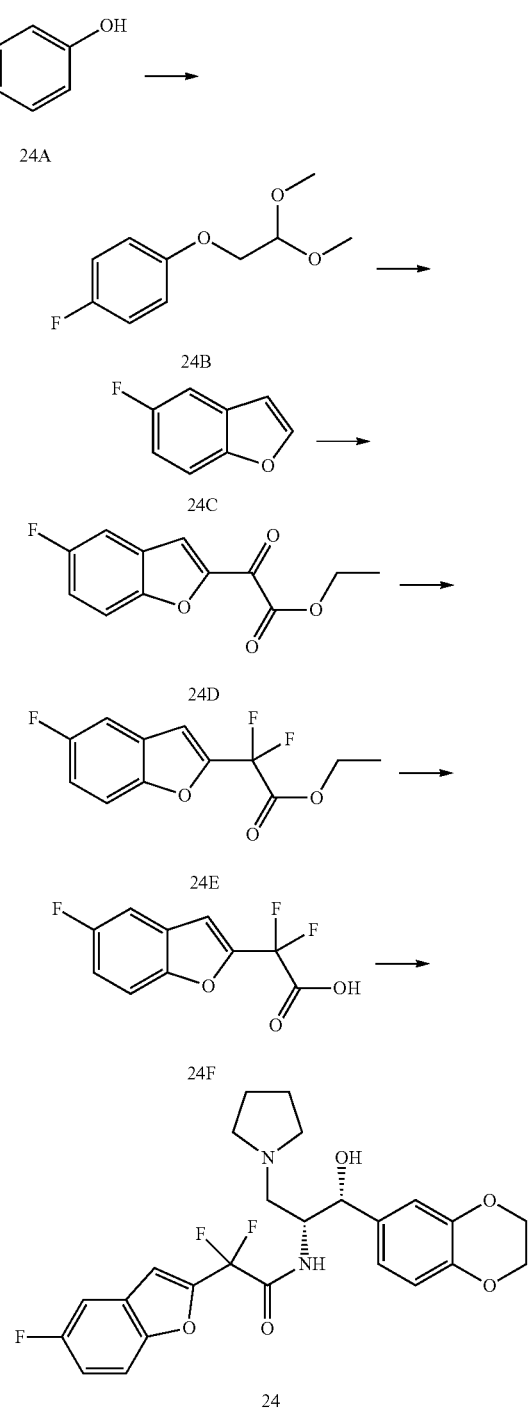

A mixture of Compound 24A (10 g, 89 mmol), 2-bromo-1,1-dimethoxyethane (15 g, 89 mmol), K₂CO₃ (18.4 g, 134 mmol), KI (100 mg) in DMF (100 mL) was stirred at reflux for 3 h, then cooled to rt, and filtered. The filtrate was added water (200 mL), extracted with ethyl acetate (100 mL×2), washed with water (100 mL×3), brine (100 mL×1), dried over Na₂SO₄, concentrated, and purified by silica gel column chromatography (ethyl acetate in petroleum ether, 10% v/v) to render Compound 24B (15 g, yield 85%) as a colorless liquid. $^1$H-NMR (CDCl$_3$, 400 MHz) major characteristic peaks: δ (ppm) 3.46 (s, 6H), 3.96 (d, J=5.2 Hz, 2H), 4.71 (t, J=5.6 Hz, 1H), 6.90 (m, 2H), 7.26 (m, 2H).

A solution of polyphosphoric acid (90 g) in toluene was stirred to 90° C., then to the solution was added Compound 24B (15 g, 75 mmol) in toluene (20 mL) and the mixture was stirred at 90° C. for 3 h, then poured into ice, and stirred for 30 min. It was extracted with ethyl acetate (100 mL×2), washed with brine (100 mL×1), dried over Na$_2$SO$_4$, concentrated, and purified by column chromatography on silica gel (petroleum ether, 100% v/v) to yield Compound 24C (4.5 g, yield 44%) as a red liquid. $^1$H-NMR (CDCl$_3$, 400 MHz) major characteristic peaks: δ (ppm) 6.742-6.746 (m, 1H), 6.994-7.035 (m, 1H), 7.24-7.26 (m, 1H), 7.41-7.44 (m, 1H), 7.651-7.655 (d, J=1.6 Hz, 1H).

To a solution of Compound 24C (4.5 g, 33 mmol) in THF (20 mL) was added n-BuLi (15 mL) at −78° C. under N$_2$ and the mixture was stirred for 30 min, before the addition of diethyl oxalate (10.8 g, 74 mmol). The mixture was stirred at −78° C. for 1 h, and quenched with addition of aq sat. NH$_4$Cl. It was extracted with ethyl acetate (2×50 mL), washed with sat. NaHCO$_3$ (50 mL×2), brine (50 mL), dried over Na$_2$SO$_4$, concentrated, and purified by column chromatography on silica gel (ethyl acetate in petroleum ether, 20% v/v) to give Compound 24D (2.5 g, yield 32%) as a yellow solid.

To a solution of Compound 24D (1 g, 4.2 mmol) in DCM (50 mL) was added DAST (3.18 g, 18 mmol) at 0° C. and the mixture was stirred at rt overnight, poured into ice-water, and added sat. aq NaHCO$_3$ (20 mL). The mixture was extracted with DCM (50 mL×2), washed with brine (50 mL×1), dried over Na$_2$SO$_4$, and concentrated. The crude product was purified by silica gel column chromatography (ethyl acetate in petroleum ether, 10% v/v) to yield Compound 24E (600 mg, yield 55%) as a yellow liquid.

To a solution of Compound 24E (120 mg, 0.46 mmol) in EtOH (5 mL) was added LiOH (46 mg, 1.09 mmol) in water (5 mL) and the mixture was stirred at rt overnight, concentrated to remove EtOH, and adjusted to pH 7 with diluted HCl. Lyophilization of the solution provided Compound 24F (60 mg, crude), which was used for the next step without further purification. LC-MS (m/z): 229 [M−1]$^-$.

A mixture of Compound 24F (60 mg, 0.26 mmol), EDCI (75 mg, 0.39 mmol), HOBt (53 mg, 0.39 mmol), Intermediate A (72 mg, 0.41 mmol) in DCM (10 mL) was stirred at rt overnight. After quenched with sat. NaHCO$_3$, the mixture was extracted with DCM (2×50 mL), washed with brine (1×50 mL), dried over Na$_2$SO$_4$, concentrated. The crude product was purified by prep-HPLC to give Compound 24 (2 mg, yield 2%) as a white solid. LC-MS (m/z): 491 [M+1]$^+$; $^1$H-NMR (CDCl$_3$, 400 MHz) major characteristic peaks: δ (ppm) 1.85 (m, 4H), 3.07 (m, 2H), 3.43 (m, 4H), 4.15 (s, 4H), 4.45 (s, 1H), 4.70 (s, 1H), 5.90 (s, 1H), 6.67 (m, 2H), 6.79 (s, 1H), 7.02 (s, 1H), 7.36 (s, 1H), 7.56 (s, 1H), 7.73 (s, 1H), 8.85 (s, 1H), 9.49 (s, 1H).

Example 25

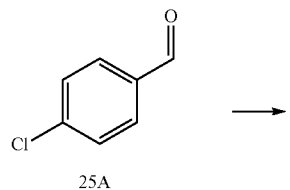

25A

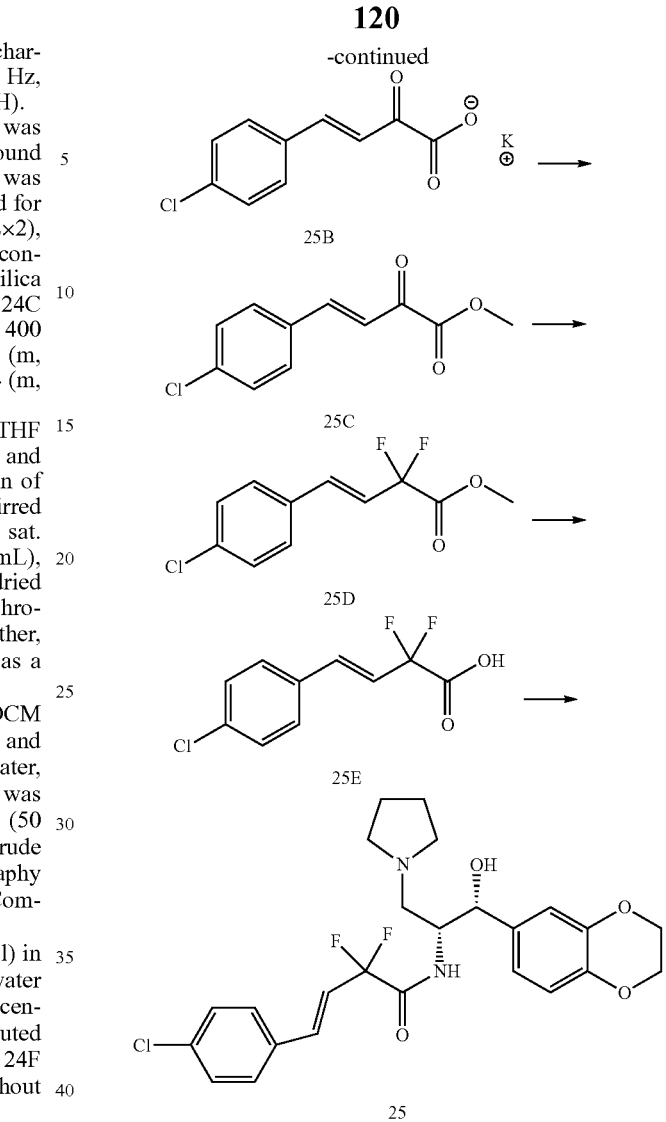

Compound 25A (5.64 g, 40 mmol) and 2-oxopropanoic acid (3.52 g, 40 mmol) were dissolved in MeOH (4 mL). To this solution, KOH (3.95 g, 60 mmol) in MeOH (10 mL) was added. The mixture was stirred at rt for 5 h. The precipitate was isolated by filtration. Compound 25B (8.5 g, yield 85%) was obtained as a yellow solid. LCMS (m/z): 211 [M+1]$^+$.

Acetyl chloride (3.84 mL) was added dropwise to MeOH (23 mL) at 0° C. Then Compound 25B (3.98 mg, 16 mmol) was added to the mixture. The mixture was heated to reflux overnight. After evaporation, the mixture was diluted with water, extracted by ethyl acetate and dried over anhydrous Na$_2$SO$_4$. After evaporation to dryness, the residue was recrystallized from EtOH. Compound 25C (1.34 g, yield 37%) was obtained as a yellow solid. LCMS (m/z): 247 [M+1]$^+$; $^1$H-NMR (CDCl$_3$, 400 MHz) major characteristic peaks: δ (ppm) 3.94 (s, 3H), 7.36 (d, J=16 Hz, 1H), 7.40 (d, J=8.4 Hz, 2H), 7.57 (d, J=8.4 Hz, 2H), 7.82 (d, J=16.4 Hz, 1H).

To the solution of Compound 25C (225 mg, 1 mmol) in CH$_2$Cl$_2$ (5 mL) was added DAST (483.6 mg, 3 mmol) at 0° C. The mixture was stirred at rt overnight. After evaporation, the residue was purified by silica gel column chromatography (ethyl acetate in petroleum, 5% v/v). Compound 25D was obtained as a yellow solid (150 mg, 60%). LCMS (m/z): 227 [M−19]$^+$.

To the solution of compound 25D (86 mg, 0.35 mmol) in MeOH (5 mL) and H₂O (1.5 mL) was added LiOH.H₂O (74 mg, 1.75 mmol) at 0° C. The mixture was stirred for an hour at rt. After evaporation of the solvent, the residue was diluted with water and the mixture was adjusted to pH 4 with 1 M HCl. The resulted mixture was extracted with ethyl acetate and dried over anhydrous Na₂SO₄. After evaporation, Compound 25E was obtained as a yellow solid (63 mg, yield 77%). LCMS (m/z): 231 [M−1]⁻; ¹H-NMR (CDCl₃, 400 MHz) major characteristic peaks: δ (ppm) 6.27-6.31 (m, 1H), 7.08 (d, J=16.4 Hz, 1H), 7.34-7.40 (m, 4H).

To the solution of Compound 25E (63 mg, 0.27 mmol), Intermediate A (75 mg, 0.27 mmol) in DCM (4 mL) was added EDCI (52 mg, 0.27 mmol). The mixture was stirred at rt overnight. After evaporation, the crude was purified by prep-HPLC to give Compound 25 (11 mg, yield 6.7%) as a white solid. LCMS (m/z): 493 [M+1]⁺; ¹H-NMR (CDCl₃, 400 MHz) major characteristic peaks: δ (ppm) 2.02 (m, 4H), 2.71-2.85 (m, 2H), 3.09 (m, 2H), 3.60-3.89 (m, 3H), 4.15 (s, 4H), 4.34 (s, 1H), 4.91 (s, 1H), 6.19-6.23 (m, 1H), 6.78-7.00 (m, 4H), 7.30-7.35 (m, 4H), 8.72 (s, 1H), 11.7 (s, 1H).

Example 26

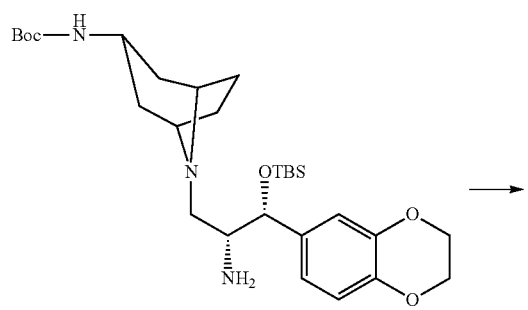

Intermediate E

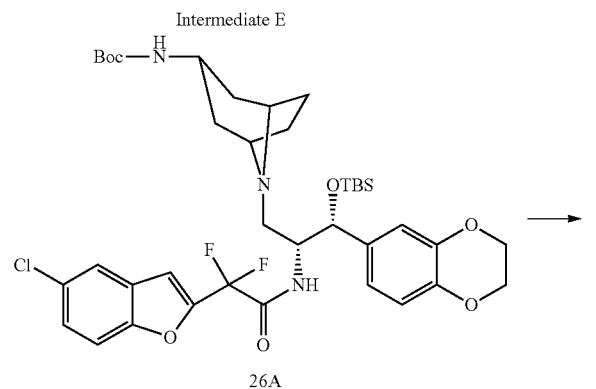

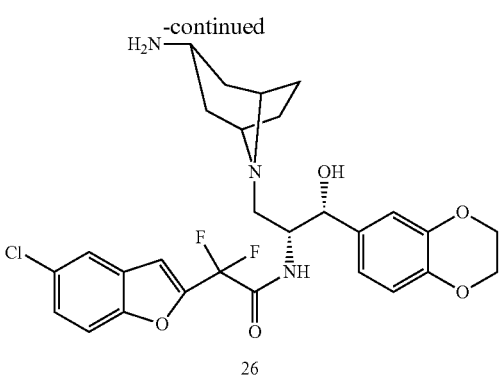

A solution of Compound 11E (100 mg, 0.41 mmol), Intermediate C (222 mg, 0.41 mmol), EDCI (118 mg, 0.62 mmol) and HOBt (84 mg, 0.62 mmol) in DCM (20 mL) was stirred at rt overnight. The mixture was diluted with ethyl acetate (150 mL), washed with water and brine, dried over anhydrous Na₂SO₄, and evaporated to render Compound 26A (200 mg, yield 63%) as a yellow oil, which was used for next step directly. LCMS (m/z): 776 [M+1]⁺.

A mixture of Compound 26A (200 mg, 0.23 mmol) and Bu₄NF (20 mg) in THF (10 mL) was stirred at 25° C. overnight. It was then diluted with ethyl acetate (150 mL), washed with water and brine, dried with anhydrous Na₂SO₄, evaporated, and purified by prep-HPLC to yield Compound 26B (103 mg, yield 68%) as colorless oil. LCMS (m/z): 662 [M+1]⁺.

A solution of Compound 26B (103 mg, 0.16 mmol) and TFA (0.5 mL) in DCM (5 mL) was stirred at rt for 2 h. The reaction was quenched with saturated aqueous NaHCO₃, diluted with ethyl acetate (150 mL), washed with water and brine, dried with anhydrous Na₂SO₄, evaporated, and purified by prep-HPLC to afford Compound 26 (30 mg, yield 33%) as a white solid. LCMS (m/z): 562 [M+1]⁺; ¹H-NMR (DMSO-d₆, 400 MHz) major characteristic peaks: δ (ppm) 1.92-2.16 (m, 7H), 3.26-3.60 (m, 6H), 4.05-4.20 (m, 5H), 4.51 (s, 1H), 6.00-6.13 (m, 1H), 6.68-6.84 (m, 3H), 7.51-7.54 (m, 1H), 7.72 (t, J=8.4 Hz, 1H), 7.80 (d, J=17.6 Hz, 1H), 8.15 (br s, 2H).

Example 27

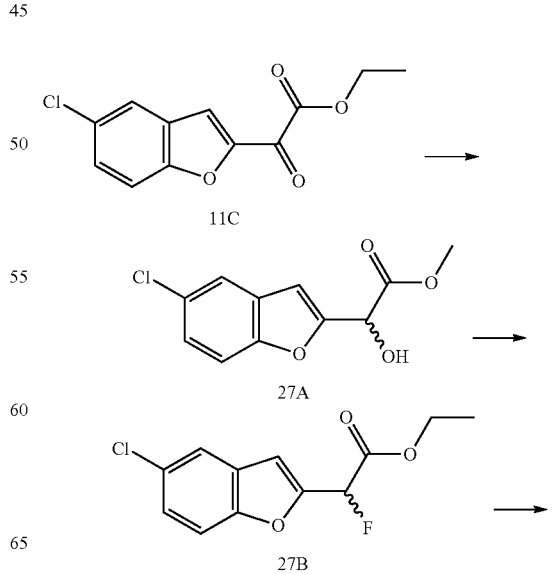

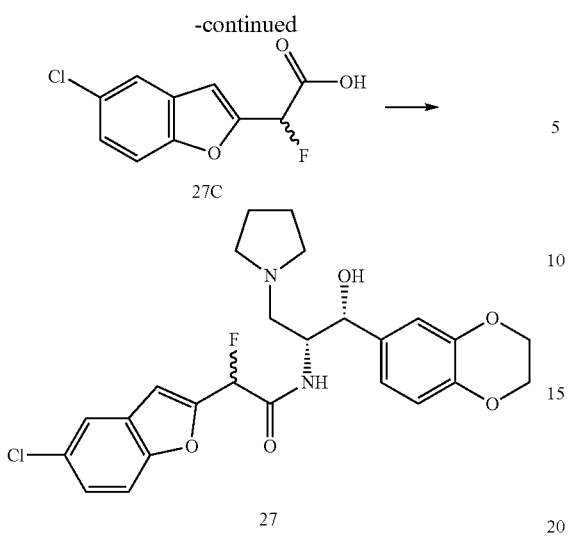

(m, 3H), 3.83-3.90 (m, 2H), 4.16-4.22 (m, 3H), 4.45-4.64 (m, 1H), 4.88-5.08 (m, 1H), 5.72-5.96 (m, 1H), 6.76-6.95 (m, 3H), 7.28-7.38 (m, 1H), 7.49-7.56 (m, 1H), 7.75-8.70 (m, 1H), 11.11-11.80 (m, 1H).

Example 28

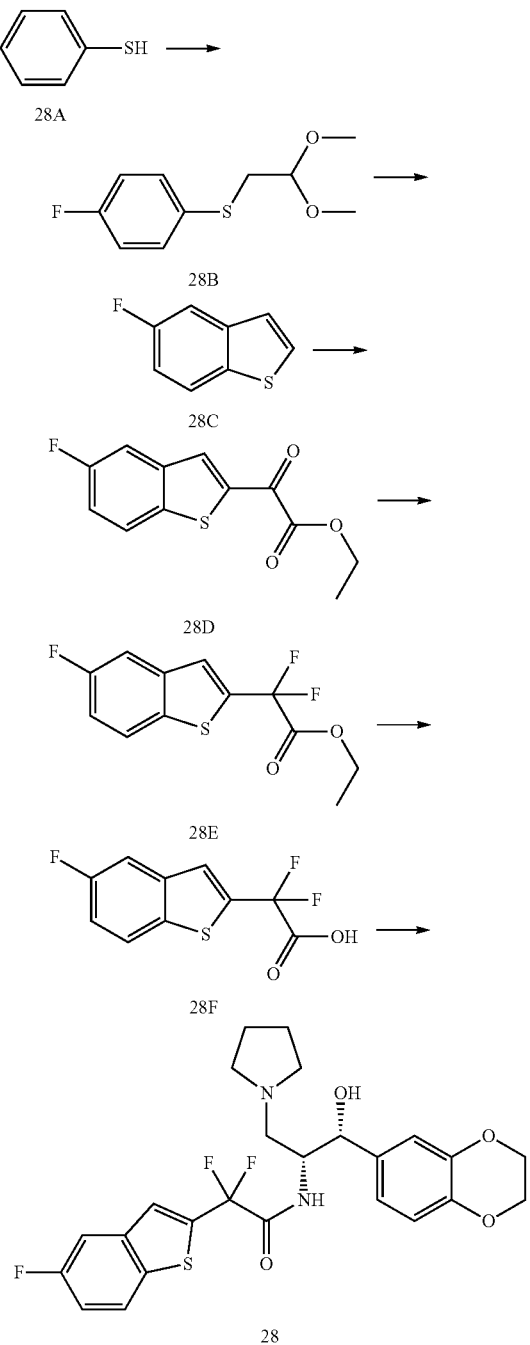

To a solution of Compound 11C (564 mg, 2.24 mmol) in dichloromethane, under an atmosphere of nitrogen at 76° C. was added diisobutylaluminum hydride (2.95 ml, 2.95 mmol). The solution was stirred at 76° C. for 45 min, and then allowed to warm to rt. A mixture of water/methanol (10 mL, 1/1 v/v) was added dropwise. The two layers were separated and the aqueous phase was extracted with dichloromethane. The combined organic extracts were dried, evaporated and purified on silica gel column (ethyl acetate/ PE) to give Compound 27A (153 mg, yield 27%) as a yellow solid. $^1$H-NMR (CDCl$_3$, 400 MHz) major characteristic peaks: δ (ppm) 1.25-1.29 (m, 3H), 4.27-4.35 (m, 2H), 5.29 (s, 1H), 6.72 (s, 1H), 7.242-7.248 (d, J=2.4 Hz, 1H), 7.261-7.269 (d, J=3.2 Hz, 1H), 7.38-7.40 (d, J=8.4 Hz, 1H). 7.534-7.538 (d, J=2.4 Hz, 1H).

To a solution of Compound 27A (184 mg, 0.72 mmol) in DCM (8 mL) was added DAST (380 mg, 2.36 mmol) at 0° C. and the mixture was stirred at rt overnight. It was poured into ice-water, extracted with DCM (2×50 mL), washed with brine (1×50 mL), dried over Na$_2$SO$_4$, and concentrated. The crude product was purified by silica gel column chromatography (ethyl acetate in petroleum ether, 10% v/v) to afford Compound 27B (70 mg, yield 37.9%) as a yellow liquid. $^1$H-NMR (CDCl$_3$, 400 MHz) major characteristic peaks: δ (ppm) 1.30-1.34 (m, 3H), 4.33-4.37 (m, 2H), 5.85-5.97 (d, J=47.6 Hz, 1H), 6.89-6.90 (d, J=4.0 Hz, 1H), 7.30-7.33 (d, J=8.8 Hz, 1H), 7.43-7.45 (d, J=8.8 Hz, 1H), 7.583-7.588 (d, J=2.0 Hz, 1H).

To a solution of Compound 27B (70 mg, 0.273 mmol) in THF (5 mL) was added LiOH (22 mg, 0.52 mmol) in water (2.5 mL) and the mixture was stirred at rt for 4 h. It was concentrated and adjusted to pH 6 with diluted HCl. Lyophilization of the solution led to Compound 27C (210 mg, crude), which was used for the next step without further purification. LC-MS (m/z): 227 [M−1]$^-$.

A mixture of Compound 27C (66 mg, 0.29 mmol), EDCI (80.8 mg, 0.42 mmol), HOBt (56 mg, 0.42 mmol), Intermediate A (77.8 mg, 0.28 mmol) in DCM (12 mL) was stirred at rt overnight. It was diluted with sat. aq NaHCO$_3$, extracted with DCM (2×50 mL), washed with brine (1×50 mL), dried over Na$_2$SO$_4$, and concentrated. The crude product was purified by prep-HPLC to give Compound 27 (15 mg, yield 10.6%) as a white solid. LC-MS (m/z): 489.1 [M+1]$^+$; $^1$H-NMR (CDCl$_3$, 400 MHz) major characteristic peaks: δ (ppm) 2.03-2.08 (m, 4H), 2.48 (s, 6H), 2.73-3.50

To 4-fluorothiophenol 28A (1.28 g, 10 mmol) in anhydrous acetone (40 mL), under nitrogen at rt was added potassium carbonate (1.38 g, 10 mmol). To the mixture was slowly added bromoacetaldehyde diethyl acetal (1.69 g, 10 mmol). The reaction mixture was stirred at rt overnight. The potassium carbonate was filtered off and washed thoroughly with acetone. The filtrate was then concentrated and the oily residue diluted with H₂O and extracted with ethyl acetate. The ethyl acetate extracts were washed with 0.5 M KOH, H₂O and brine, dried over anhydrous magnesium sulfate, filtered and concentrated. Purification by column chromatography on silica gel (ethyl acetate in petroleum ether, 10% v/v) afforded Compound 28B (1.54 g, yield 71%). ¹H-NMR (CDCl₃, 400 MHz) major characteristic peaks: δ (ppm) 3.05 (d, J=6.4 Hz, 2H), 3.32 (s, 6H), 4.49 (t, J=6.4 Hz, 1H), 6.97-7.01 (m, 2H), 7.38-7.42 (m, 2H).

To a 3-neck 100 mL flask was introduced polyphosphoric acid (5 g) and anhydrous chlorobenzene (30 ml). The mixture was stirred under nitrogen at reflux. Compound 28B (1.54 g, 7.1 mmol) was then added over 5 min period in 2 mL of chlorobenzene. Within 30 min the reaction mixture turned relatively dark and it was kept under reflux for 3 h. The mixture was cooled down to rt and the chlorobenzene layer decanted. The black tar was suspended in H₂O (50 mL) and stirred for about 30 min. The aqueous layer was extracted with CH₂Cl₂. The organic extracts were pooled with the chlorobenzene layer, treated with brine, dried over anhydrous magnesium sulfate, filtered and concentrated. Purification by column chromatography on silica gel (petroleum ether, 100% v/v) afforded Compound 28C (470 mg, yield 43%). ¹H-NMR (MeOD-d₄, 400 MHz) major characteristic peaks: δ (ppm) 7.11-7.16 (m, 1H), 7.34-7.35 (m, 1H), 7.53-7.56 (m, 1H), 7.66-7.67 (m, 1H), 7.86-7.89 (m, 1H).

Compound 28C (470 mg, 3.1 mmol) was added to THF (10 mL) followed by addition of n-BuLi (1.24 mL, 3.1 mmol) at rt. The reaction mixture was stirred at rt for 60 min. Diethyl oxalate (905 mg, 6.2 mmol) was added to THF (30 mL) −78° C. To this solution, 5-fluorobenzo[b]thiophene anion solution was added dropwise and the reaction was stirred at −78° C. for 20 min. It was quenched with saturated aqueous NH₄Cl (30 mL) and extracted with ethyl acetate (30 mL×3). The organic extracts were concentrated in vacuum and purified by column chromatography on silica gel (ethyl acetate in petroleum ether, 10% v/v) to give the Compound 28D (450 mg, yield 57%) as an orange oil. ¹H-NMR (CDCl₃, 400 MHz) major characteristic peaks: δ (ppm) 1.36 (t, J=7.2 Hz, 3H), 4.36 (q, J=7.2 Hz, 2H), 7.25-7.30 (m, 1H), 7.65-7.68 (m, 1H), 7.87-7.91 (m, 1H), 7.77-7.78 (m, 1H), 8.35 (s, 1H).

To a solution of Compound 28D (450 mg, 1.78 mmol) in CH₂Cl₂ (10 mL) was added DAST (2.86 g, 17.8 mmol). The reaction mixture was stirred for 10 h before poured into ice-water and extracted with CH₂Cl₂ (50 mL×2). The combined organic layers were dried over Na₂SO₄, filtered, and evaporated to give Compound 28E (88 mg, yield 18%). ¹H-NMR (CDCl₃, 400 MHz) major characteristic peaks: δ (ppm) 1.34 (t, J=7.2 Hz, 3H), 4.40 (q, J=7.2 Hz, 2H), 7.26-7.31 (m, 1H), 7.64-7.67 (m, 1H), 7.72 (s, 1H), 7.94-7.98 (m, 1H).

To a solution of Compound 28E (88 mg, 0.32 mmol) in THF (2 mL) was added LiOH.H₂O (20 mg, 0.48 mmol), H₂O (2 mL) and MeOH (2 mL). The reaction mixture was stirred for 3 hours at 25° C., and then neutralized with 1 N HCl, It was evaporated to dryness, the resulted residue was dissolved in H₂O and extracted with ethyl acetate. The organic layer was dried over Na₂SO₄, filtered, and evaporated to give Compound 28F (80 mg, yield 100%). LCMS (m/z): 245 [M−1]⁻.

To a solution of Compound 28F (80 mg, 0.32 mmol) in DCM (10 mL) was added Intermediate A (88 mg, 0.32 mmol), HOBt (65 mg, 0.48 mmol) and EDCI (92 mg, 0.48 mmol). The mixture was stirred overnight at 25° C., then washed with brine, dried over Na₂SO₄, filtered, evaporated, and purified by prep-HPLC to give Compound 28 (31 mg, yield 19%) as a white solid. LC-MS (m/z): 507 [M+1]⁺; ¹H-NMR (CDCl₃, 400 MHz) major characteristic peaks: δ (ppm) 2.11-2.17 (m, 4H), 2.89-3.01 (m, 2H), 3.494-3.51 (m, 2H), 3.79-3.81 (m, 2H), 4.03-4.13 (m, 4H), 4.45-4.47 (m, 1H), 5.08 (s, 1H), 6.72-6.74 (m, 1H), 6.82 (s, 1H), 7.17-7.19 (m, 2H), 7.43-7.46 (m, 1H), 7.73-7.77 (m, 1H), 7.85-7.87 (m, 1H), 7.66-7.68 (m, 1H), 11.94 (br, 1H).

Example 29

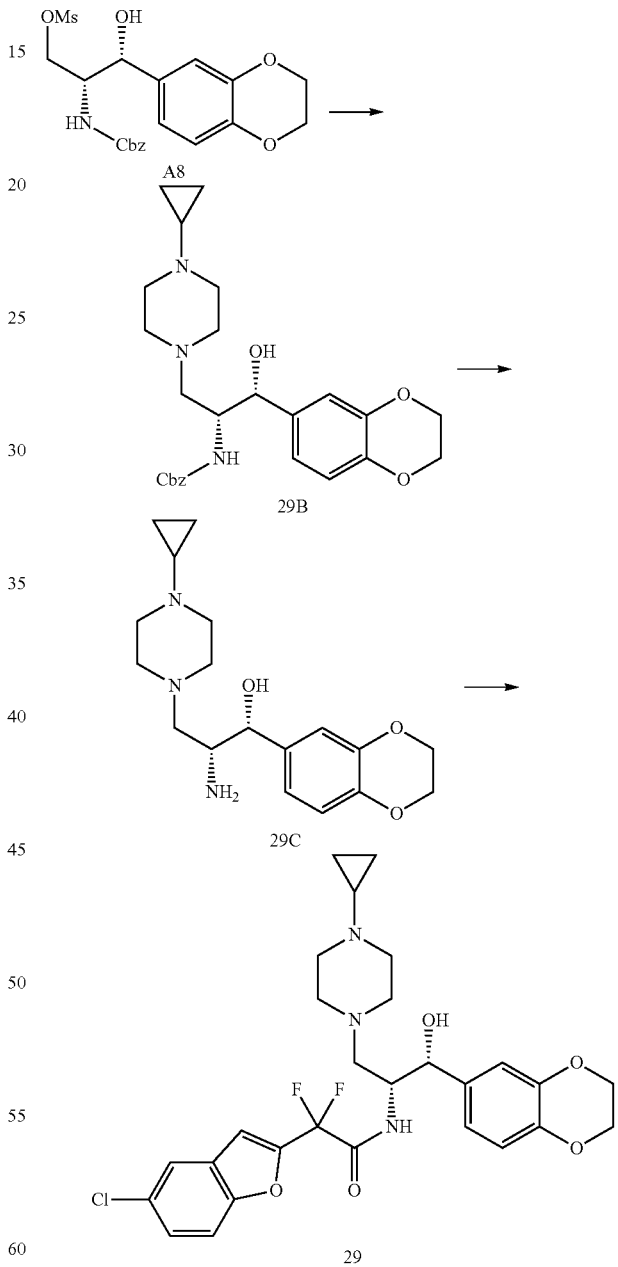

To a solution of Compound A8 (406 mg, 0.93 mmol) in CH₃CN (15 mL) was added 1-cyclopropylpiperazine (350 mg, 2.80 mmol), K₂CO₃ (387 mg, 2.80 mmol) and NaI (100 mg). The mixture was heated at 82° C. for 2 h. It was cooled to rt and filtered. The filtrate was concentrated in vacuum to give a crude product Compound 29B (450 mg, crude) as a yellow oil. LCMS (m/z): 468 [M+1]⁺.

To a solution of Compound 29B (450 mg, 0.96 mmol) in EtOH/water (10 mL, 9:1, v/v) was added LiOH.H$_2$O (126 mg, 2.88 mmol). After refluxed overnight, water (20 mL) was added to the mixture. It was extracted with ethyl acetate (20 mL×3). The combined organic layers were dried over anhydrous Na$_2$SO$_4$ and concentrated in vacuum to give a crude product Compound 29C (350 mg, crude) as a yellow oil. LCMS (m/z): 334 [M+1]⁺.

To a mixture of Compound 29C (100 mg, 0.30 mmol) in DCM (10 mL) was added EDCI (86 mg, 0.45 mmol), HOBt (61 mg, 0.45 mmol) and Intermediate A (88 mg, 0.30 mmol) and stirred at 25° C. for 2 h. Water (10 mL) was added to the mixture, which was then extracted with DCM (20 mL×3), dried over anhydrous Na$_2$SO$_4$, and purified by prep-HPLC to yield a trifluoroacetic acid salt of Compound 29 (33 mg, yield 20%) as a white solid. LCMS (m/z): 562 [M+1]⁺; $^1$H-NMR (CDCl$_3$, 400 MHz) major characteristic peaks: δ (ppm) 0.87 (d, J=8 Hz, 2H), 1.17 (s, 2H), 2.45 (s, 1H), 3.28 (d, J=16 Hz, 1H), 3.49-3.63 (m, 10H), 4.12-4.16 (m, 4H), 4.54 (s, 1H), 4.84 (s, 1H), 6.78-6.86 (m, 4H), 7.35 (d, J=8 Hz, 1H), 7.44 (d, J=8 Hz, 1H), 7.59 (s, 1H), 8.23 (d, J=8 Hz, 1H).

Example 30

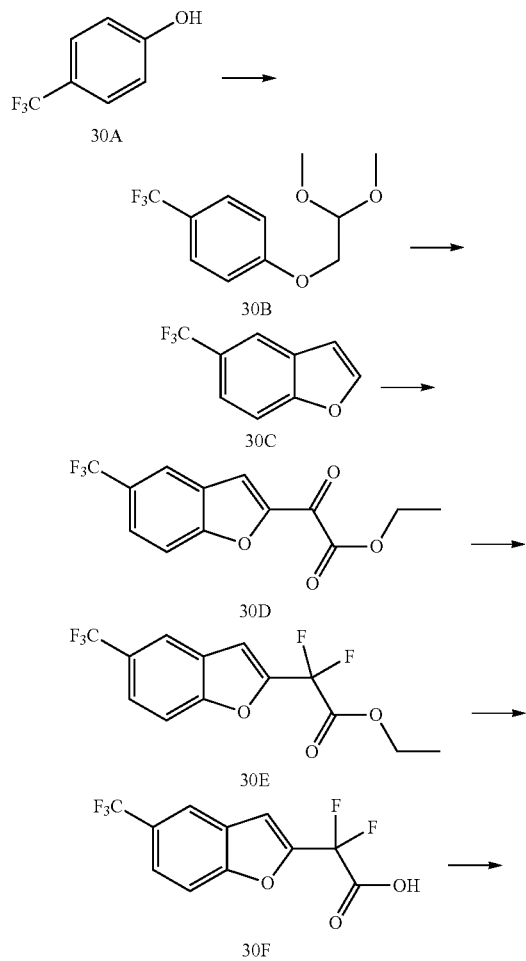

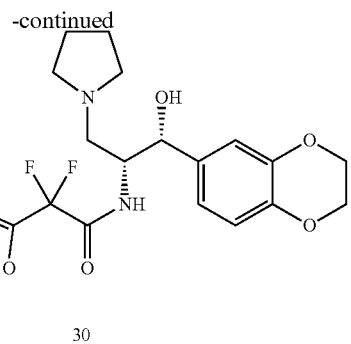

30

A mixture of Compound 30A (10 g, 62 mmol), 2-bromo-1,1-dimethoxyethane (18.2 g, 108 mmol), Cs$_2$CO$_3$ (28 g, 86 mmol), NaI (100 mg) in DMF (10 mL) was stirred at 65° C. overnight. It was then cooled to rt and filtered. The filtrate was added water (200 mL), and extracted with ethyl acetate (100 mL×3). The combined extracts were washed with water (100 mL×3), brine (100 mL×1), and dried over Na$_2$SO$_4$. Filtration and concentration of the mixture gave rise to Compound 30B (10 g, yield 67%) as a yellow liquid. $^1$H-NMR (CDCl$_3$, 400 MHz) major characteristic peaks: δ (ppm) 3.46 (s, 6H), 4.03-4.05 (d, J=5.2 Hz, 2H), 4.72-4.74 (t, J=4.8 Hz, 1H), 6.98-6.99 (d, J=8.8 Hz, 2H), 7.53-7.55 (d, J=8.8 Hz, 2H).

A solution of polyphosphoric acid (8.1 g, 24 mmol) in toluene (10 mL) was added compound 30B (5 g, 20 mmol) in toluene (10 mL) and the mixture was stirred at 80° C. for 2 h. It was then poured into ice, stirred for 30 min, and extracted with DCM (50 mL×3). The combined extracts were washed with brine (50 mL×1), dried over Na$_2$SO$_4$, concentrated, and purified by column chromatography on silica gel (petroleum, 100% v/v) to afford Compound 30C (690 mg, yield 19%) as a yellow solution in petroleum. $^1$H-NMR (CDCl$_3$, 400 MHz) major characteristic peaks: δ (ppm) 6.79 (s, 1H), 7.54 (m, 2H), 7.67 (s, 1H), 7.87 (s, 1H).

To a solution of Compound 30C (690 mg, 3.71 mmol) in petroleum ether from last step and anhydrous THF (10 mL) was added n-BuLi (2.5 M in hexane, 1.78 mL) at −78° C. under N$_2$. After stirred for 30 min, to the mixture was added diethyl oxalate (2.7 g, 18.5 mmol). Stirred at −78° C. for 1 h, it was quenched with sat. aq NH$_4$Cl, and extracted with ethyl acetate (50 mL×2). The combined extracts were washed with brine (50 mL×1), dried over Na$_2$SO$_4$, concentrated and recrystallized from MeOH (3 mL) to afford Compound 30D (500 g, yield 47%) as a yellow solid. $^1$H-NMR (CDCl$_3$, 400 MHz) major characteristic peaks: δ (ppm) 1.35-1.38 (t, J=7.2 Hz, 3H), 4.37-4.43 (q, J=7.6 Hz, 2H), 7.93-8.03 (m, 2H), 8.34 (s, 1H), 8.42-8.44 (m, 1H).

To a solution of Compound 30D (500 mg, 1.75 mmol) in DCM (10 mL) was added DAST (1.41 g, 8.76 mmol) at 0° C. and the mixture was stirred at rt for 1 h. It was poured into ice-water, added sat. NaHCO$_3$ (20 mL), and extracted with DCM (50 mL×2). The combined extracts were washed with brine (50 mL×1), dried over Na$_2$SO$_4$, and concentrated. The crude product was purified by column chromatography on silica gel (ethyl acetate in petroleum, 4% v/v) to render Compound 30E (200 mg, yield 62%) as a yellow liquid. $^1$H-NMR (CDCl$_3$, 400 MHz) major characteristic peaks: δ (ppm) 1.36-1.39 (t, J=7.2 Hz, 3H), 4.39-4.45 (q, J=7.2 Hz, 2H), 7.23 (s, 1H), 7.63-7.68 (m, 2H), 7.96 (s, 1H).

To a solution of Compound 30E (170 mg, 0.55 mmol) in EtOH (2 mL) was added LiOH.H$_2$O (28 mg, 0.66 mmol) in water (0.5 mL) and the mixture was stirred at rt overnight.

It was then adjusted pH to 4-5 with 1 N HCl, and extracted with ethyl acetate (50 mL×3). The combined extracts were washed with brine (20 mL), dried over Na$_2$SO$_4$, and concentrated to give Compound 30F (150 mg, yield 100%) as a yellow solid. LC-MS (m/z): 279 [M−1]$^-$.

A mixture of Compound 30F (60 mg, 0.21 mmol), EDCI (61 mg, 0.31 mmol), HOBt (48 mg, 0.31 mmol), Intermediate A (59 mg, 0.21 mmol) in DCM (5 mL) was stirred at 28° C. overnight before quenched with sat. aq NaHCO$_3$. The mixture was extracted with DCM (50 mL×2). The combined extracts were washed with brine (50 mL×1), dried over Na$_2$SO$_4$, and concentrated. The crude product was purified by prep-HPLC to give Compound 30 (5 mg, yield 4%) as a white solid. LC-MS (m/z): 541 [M+1]$^+$; $^1$H-NMR (CDCl$_3$, 400 MHz) major characteristic peaks: δ (ppm) 2.13 (m, 4H), 2.70-3.02 (m, 2H), 3.49-3.54 (m, 2H), 3.83 (m, 2H), 4.13-4.18 (m, 4H), 4.50 (m, 1H), 5.10 (s, 1H), 6.75-6.84 (m, 4H), 7.60-7.67 (m, 2H), 7.88-7.92 (m, 2H), 11.96 (s, 1H).

Example 31

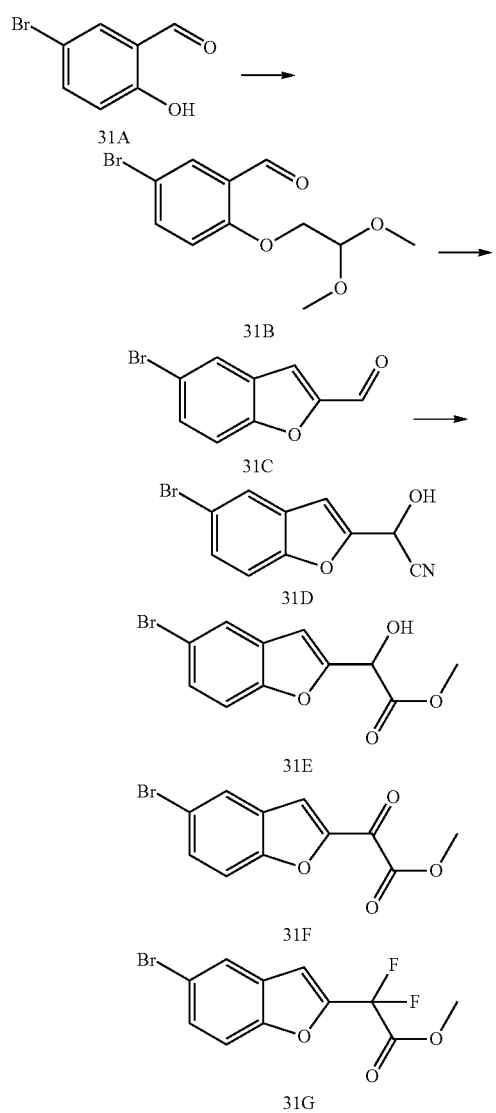

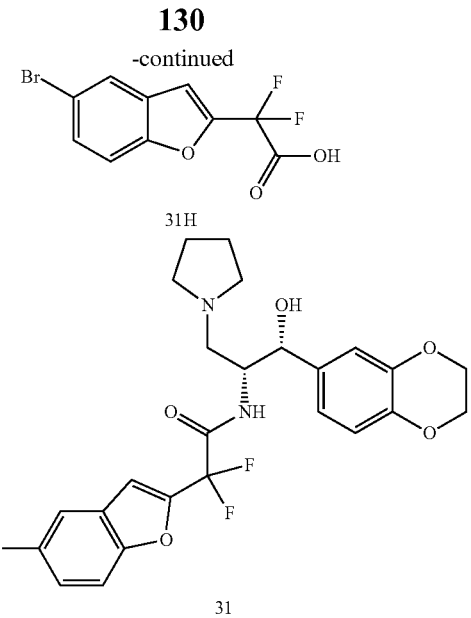

A mixture of Compound 31A (3.00 g, 14.93 mmol), 2-bromo-1,1-dimethoxyethane (2.77 g, 16.42 mmol) and K$_2$CO$_3$ (4.12 g, 29.86 mmol) in DMF (26 mL) was stirred at 150° C. for 2 h. It was evaporated to remove DMF. The residue was diluted with ethyl acetate (200 mL), washed with water and brine, dried with anhydrous Na$_2$SO$_4$, and evaporated to render Compound 31B (3.80 g, yield 88%) as a white solid. $^1$H-NMR (CDCl$_3$, 400 MHz) major characteristic peaks: δ (ppm) 4.10 (d, J=5.2 Hz, 2H), 4.75 (t, J=5.2 Hz, 1H), 6.89 (d, J=9.2 Hz, 1H), 7.61-7.64 (m, 1H), 7.93 (s, 1H), 10.42 (s, 1H).

A mixture of Compound 31B (2.00 g, 6.90 mmol) in Acetic acid (50 mL) was stirred at 120° C. overnight. The mixture was evaporated to remove Acetic acid, diluted with ethyl acetate (200 mL), washed with water and brine, dried with anhydrous Na$_2$SO$_4$, and evaporated to yield Compound 31C (1.26 g, yield 81%) as a white solid. $^1$H-NMR (CDCl$_3$, 400 MHz) major characteristic peaks: δ (ppm) 7.49-7.52 (m, 2H), 7.60-7.64 (m, 1H), 7.90 (s, 1H), 9.89 (s, 1H).

To a solution of Compound 31C (2.00 g, 8.93 mmol) and NaCN (1.31 g, 26.78 mmol) in MeOH (100 mL) was added Acetic acid (1.61 g, 26.78 mmol). The mixture was stirred at rt overnight. It was then quenched with sat. aq NaHCO$_3$ solution, diluted with ethyl acetate (200 mL), washed with water and brine, and purified by silica gel column chromatography (ethyl acetate in petroleum, 30% v/v) to provide Compound 31D (1.60 g, yield 71%) as a colorless oil. LCMS: 252 [M+1]$^+$; $^1$H-NMR (DMSO-d$_6$, 400 MHz) major characteristic peaks: δ (ppm) 6.10 (d, J=6.8 Hz, 1H), 7.06 (s, 1H), 7.48-7.54 (m, 2H), 7.65 (d, J=8.8 Hz, 1H), 7.93 (s, 1H).

A solution of Compound 31D (1.00 g, 3.98 mmol) in MeOH (20 mL) was stirred at rt overnight with bubbling of HCl gas. The reaction was quenched with H$_2$O (100 mL) and stirred at rt for 2 h. It was evaporated to remove MeOH, diluted with ethyl acetate (150 mL), washed with water and brine, dried with anhydrous Na$_2$SO$_4$, and evaporated to render Compound 31E (900 mg, yield 82%) as a white solid. LCMS: 285 [M+1]$^+$; $^1$H-NMR (DMSO-d$_6$, 400 MHz) major characteristic peaks: δ (ppm) 3.69 (s, 3H), 5.41 (d, J=6.4 Hz, 1H), 6.52 (t, J=6.4 Hz, 1H), 6.90 (s, 1H), 7.43-7.47 (m, 1H), 7.55-7.58 (m, 1H), 7.86 (s, 1H).

A suspension of Compound 31E (400 mg, 1.40 mmol) and DMP (712 mg, 1.68 mmol) in DCM (20 mL) was stirred at rt overnight. It was quenched with saturated aq Na₂S₂O₃, diluted with ethyl acetate (150 mL), washed with water and brine, and purified by silica gel column chromatography eluted with ethyl acetate in petroleum (from 10% to 20%, v/v) to give Compound 31F (180 mg, yield 46%) as a white solid. LCMS: 283 [M+1]⁺; ¹H-NMR (DMSO-d₆, 400 MHz) major characteristic peaks: δ (ppm) 3.92 (s, 3H), 7.77 (m, 2H), 8.19 (d, J=7.6 Hz, 2H).

To a solution of Compound 31F (500 mg, 1.77 mmol) in DCM (5 mL) was added DAST (1.42 g, 8.85 mmol). The mixture was stirred at rt overnight. The mixture was purified by column chromatography on silica gel eluted with ethyl acetate in petroleum (10%, v/v) to yield Compound 31G (300 mg, yield 55%) as a white solid. ¹H-NMR (DMSO-d₆, 400 MHz) major characteristic peaks: δ (ppm) 3.95 (s, 3H), 7.55 (s, 1H), 7.65 (d, J=9.2 Hz, 1H), 7.74 (d, J=9.6 Hz, 1H), 8.01 (s, 1H).

A mixture of Compound 31G (300 mg, 0.98 mmol) and LiOH.H₂O (123 mg, 2.94 mmol) in MeOH/H₂O (10 mL/2 mL) was stirred at rt for 2 h. The mixture was evaporated to remove MeOH. The residue was adjusted to pH 3 with 1 N HCl and filtered to afford Compound 31H (200 mg, yield 70%) as a white solid. LCMS: 289 [M−1]⁻.

A solution of Intermediate A (95 mg, 0.34 mmol), Compound 31H (100 mg, 0.34 mmol), EDCI (98 mg, 0.51 mmol) and HOBt (67 mg, 0.51 mmol) in DCM (5 mL) was stirred at rt overnight. The mixture was diluted with ethyl acetate (150 mL), washed with water and brine, dried with anhydrous Na₂SO₄, and purified by prep-HPLC to afford Compound 31 (100 mg, yield 53%) as a white solid. LCMS: 551 [M+1]⁺; ¹H-NMR (CDCl₃, 400 MHz) major characteristic peaks: δ (ppm) 2.12 (br s, 4H), 2.89-3.02 (m, 2H), 3.48 (s, 2H), 3.81 (br s, 3H), 4.07-4.19 (m, 4H), 4.45-4.52 (m, 1H), 5.09 (s, 1H), 6.73-6.76 (m, 3H), 6.83 (s, 1H), 7.38 (d, J=8.8 Hz, 1H), 7.39-7.50 (m, 1H), 7.74 (s, 1H), 7.83 (s, 1H).

Example 32

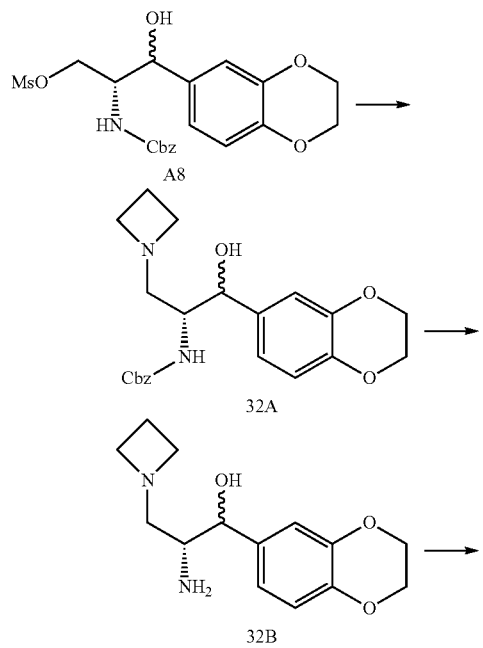

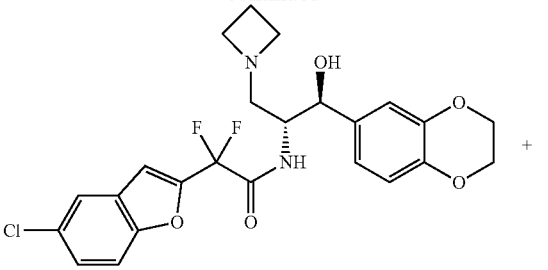

32C

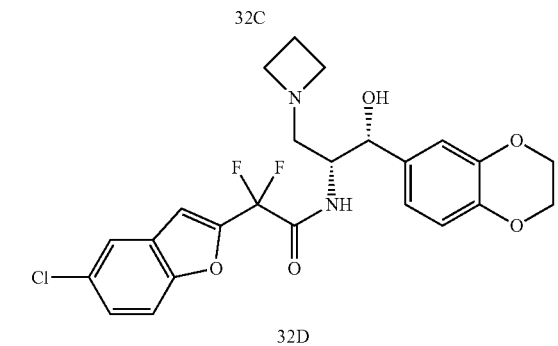

32D

To a solution of Compound A8 (437 mg, 1 mmol) in ACN (20 mL) was added azetidine (171 mg, 3 mmol), K₂CO₃ (414 mg, 3 mmol) and NaI (449 mg, 3 mmol). The mixture was heated at 82° C. overnight. It was cooled to rt and filtered. The filtration was concentrated in vacuum to give crude product Compound 32A (330 mg, crude) as a yellow oil. LCMS (m/z): 399 [M+1]⁺.

To a solution of Compound 32A (330 mg, 0.83 mmol) in EtOH/water (10 mL, 9:1, v/v) was added LiOH.H₂O (104 mg, 2.48 mmol). The mixture was refluxed overnight. After reaction, water (20 mL) was added. It was extracted with ethyl acetate (20 mL×3). The combined organic layers were dried over anhydrous Na₂SO₄ and concentrated in vacuum to give a crude product Compound 32B (170 mg, crude) as a yellow oil. LCMS (m/z): 265 [M+1]⁺.

To a mixture of Compound 32B (150 mg, 0.57 mmol) in DCM (20 mL) was added EDCI (164 mg, 0.85 mmol), HOBt (115 mg, 0.85 mmol) and Compound 11E (140 mg, 0.57 mmol) and stirred at 25° C. overnight. It was added water (10 mL), extracted with DCM (20 mL×3), dried over anhydrous Na₂SO₄, and purified by prep-HPLC and followed by prep-chiral-HPLC to render trifluoroacetic acid salts of Compound 32C (10 mg, yield 3.6%) as a white solid and Compound 32D (5 mg, yield 1.8%) as a white solid. For Compound 32C, LCMS (m/z): 493 [M+1]⁺; ¹H-NMR (CDCl₃, 400 MHz) major characteristic peaks: δ (ppm) 2.42 (s, 1H), 2.66 (s, 2H), 3.50-3.61 (m, 2H), 4.06-4.14 (m, 6H), 4.23-4.30 (m, 3H), 4.12-4.16 (m, 4H), 4.63 (d, J=8 Hz, 1H), 6.56 (s, 1H), 6.73 (d, J=8 Hz, 1H), 6.80-6.85 (m, 3H), 7.37 (d, J=8 Hz, 1H), 7.45 (d, J=8 Hz, 1H), 7.61 (s, 1H); For Compound 32D, LCMS (m/z): 493 [M+1]⁺; ¹H-NMR (CDCl₃, 400 MHz) major characteristic peaks: δ (ppm) 2.40 (s, 1H), 2.70 (s, 1H), 3.38 (s, 1H), 3.47 (d, J=8 Hz, 2H), 4.10-4.17 (m, 5H), 4.20-4.30 (m, 3H), 4.89-4.90 (d, J=4 Hz, 1H), 6.75 (s, 3H), 6.82 (s, 1H), 7.36 (d, J=8 Hz, 1H), 7.45 (d, J=8 Hz, 1H), 7.60 (s, 1H).

Example 33

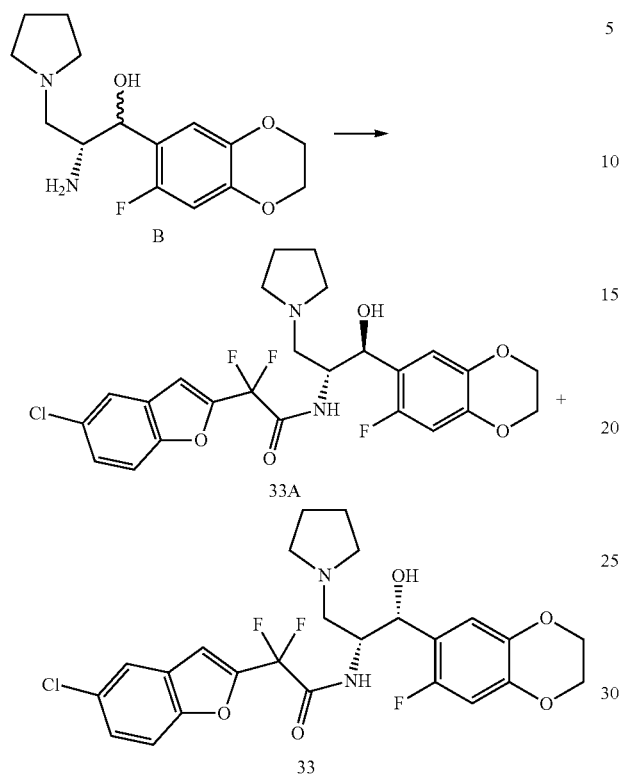

To a solution of Intermediate B (300 mg, 1 mmol) in DCM (15 mL) was added EDCI (288 mg, 1.5 mmol), HOBt (200 mg, 1.5 mmol), and Compound 11E (247 mg, 1 mmol). It was stirred at rt overnight. The mixture was added DCM (20 mL), washed with water (50 mL×2), brine (50 mL×1), and dried over anhydrous $Na_2SO_4$. The residue was purified by prep-HPLC, followed by prep-chiral-HPLC to give Compound 33A (70 mg, yield 13%) as a white foam and Compound 33 (65 mg, yield 12%) as a white foam. For Compound 33A, LC-MS (m/z): 525 [M+1]$^+$; $^1$H-NMR (CDCl$_3$, 400 MHz) major characteristic peaks: δ (ppm) 2.09 (s, 4H), 2.87 (d, J=39.6 Hz, 2H), 3.34 (s, 1H), 3.81 (s, 3H), 4.11 (m, 4H), 4.60 (s, 1H), 5.12 (s, 1H), 6.45 (d, J=10.8 Hz, 1H), 6.91 (m, 2H), 7.32 (m, 1H), 7.41 (d, J=8.8 Hz, 1H), 7.57 (d, J=2.4 Hz, 1H), 8.49 (d, J=6.8 Hz, 1H), 10.65 (s, 1H). For Compound 33, LC-MS (m/z): 525 [M+1]$^+$; $^1$H-NMR (CDCl$_3$, 400 MHz) major characteristic peaks: δ (ppm) 2.09 (s, 4H), 2.84 (d, J=44 Hz, 2H), 3.29 (d, J=10.8 Hz, 1H), 3.73 (m, 3H), 4.12 (m, 4H), 4.58 (s, 1H), 5.14 (d, J=5.2 Hz, 1H), 6.47 (d, J=10.8 Hz, 1H), 6.94 (m, 2H), 7.32 (m, 1H), 7.42 (d, J=8.8 Hz, 1H), 7.58 (d, J=1.6 Hz, 1H), 8.60 (d, J=8 Hz, 1H), 11.06 (s, 1H).

Example 34

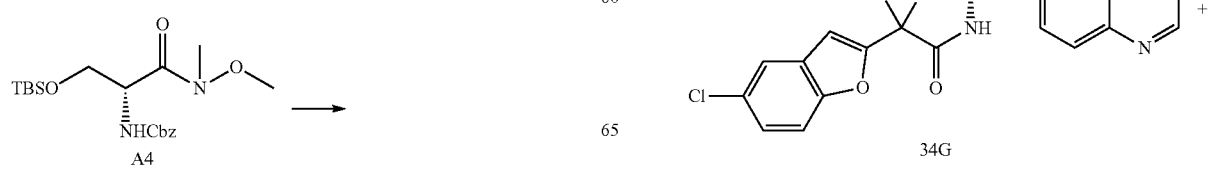

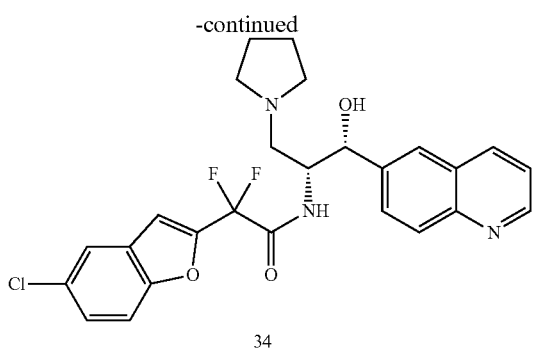

34

To a solution of 6-bromoquinoline (7.9 g, 38 mmol) in THF (200 mL) was added n-BuLi (15 mL) at −60° C. under N₂ and after stirred for 0.5 h, Compound A4 (5 g, 13 mmol) in THF (10 mL) was added slowly. The reaction mixture was maintained at this temperature with stirring for 1 h, and then added saturate aq NH₄Cl, extracted with ethyl acetate (100 mL×2), brine (100 mL), and dried over Na₂SO₄. The crude product was purified by column chromatography on silica gel (ethyl acetate in petroleum, 10% v/v) to give Compound 34A (4.4 g, yield 75%) as a colorless liquid. LC-MS (m/z): 465 [M+1]⁺; ¹H-NMR (CDCl₃, 400 MHz) major characteristic peaks: δ (ppm) 0.00 (s, 3H), 0.04 (s, 3H), 0.89 (s, 9H), 4.22 (m, 2H), 5.33 (s, 2H), 5.40 (s, 1H), 7.55 (m, 5H), 8.37 (m, 4H), 8.66 (s, 1H), 9.20 (m, 1H).

Compound 34A (4.4 g, 9.5 mmol) was dissolved in THF (60 mL) and cooled down −80° C. under nitrogen atmosphere. L-Selectride (20 mL of 1M solution in THF, 18.9 mmol) was added dropwise while keeping the temperature at −80° C. After an hour, the reaction was quenched with saturate aq NH₄Cl solution and the mixture was extracted with ethyl acetate (50 mL×2), washed with brine (100 mL), and dried over Na₂SO₄. The crude product was purified by column chromatography on silica gel (ethyl acetate in petroleum, 10% v/v) to render Compound 34B (3 g, yield 68%) as a colorless liquid. LC-MS (m/z): 466 [M+1]⁺; ¹H-NMR (CDCl₃, 400 MHz) major characteristic peaks: δ (ppm) 0.03 (m, 6H), 0.92 (m, 9H), 4.10 (m, 3H), 4.96 (m, 1H), 5.12 (s, 1H), 7.20 (s, 1H), 7.35 (m, 2H), 7.41 (m, 1H), 7.62 (m, 1H), 7.88 (m, 1H), 8.18 (m, 2H), 8.91 (s, 1H).

Compound 34B (3 g, 6.4 mmol) was dissolved in THF (50 mL) at 0° C., to this solution was added TBAF (839 mg, 3.2 mmol) at 0° C. The mixture was stirred at rt overnight. It was condensed by evaporation of solvent, added water (50 mL), and extracted with ethyl acetate (50 mL×2), washed with brine (100 mL), dried over Na₂SO₄, and concentrated. The residue was suspended in a mixture of ethyl acetate in petroleum (10% v/v). Filtration gave Compound 34C (1.7 g, yield 75%) as a white solid. LC-MS (m/z): 466 [M+1]⁺; ¹H-NMR (CDCl₃, 400 MHz) major characteristic peaks: δ (ppm) 3.72 (m, 3H), 4.89 (m, 4H), 5.63 (m, 1H), 6.80 (m, 1H), 7.15 (m, 5H), 7.52 (m, 1H), 7.74 (m, 1H), 7.89 (s, 1H), 7.93 (m, 1H), 8.32 (m, 1H), 8.87 (s, 1H).

Compound 34C (1 g, 2.8 mmol) was dissolved in THF (20 mL), to the mixture was added TEA (860 mg, 8.5 mmol). The mixture was cooled to −15° C., to the mixture was added MsCl (360 mg, 3.1 mmol) slowly. Stirred at this temperature for 30 min, the mixture was diluted with water, extracted with ethyl acetate (50 mL×2), washed with brine (50 mL), dried over Na₂SO₄, and concentrated to yield Compound 34D (1.2 g, crude), which was used for the next step without further purification. LC-MS (m/z): 431 [M+1]⁺.

To a solution of Compound 34D (1.2 g, 2.8 mmol) in THF (20 mL) was added pyrrolidine (2 g, 28 mmol). The reaction mixture was allowed to warm up to rt and then heated at 50° C. overnight. The rude product was purified by column chromatography on silica gel (methanol in dichloromethane, 5% v/v) to give 34E (1 g, yield 91%). LC-MS (m/z): 406 [M+1]⁺; ¹H-NMR (CDCl₃, 400 MHz) major characteristic peaks: δ (ppm) 1.88 (m, 4H), 2.77 (s, 2H), 2.86 (m, 4H), 3.63 (m, 1H), 4.15 (m, 1H), 4.94 (s, 1H), 5.04 (s, 1H), 7.15 (s, 1H), 7.24 (m, 4H), 7.39 (m, 1H), 7.68 (m, 1H), 7.85 (m, 1H), 8.08 (m, 2H), 8.90 (m, 1H).

To a solution of Compound 34E (1 g, 2.5 mmol) in methanol (20 mL) was added Pd(OH)₂ (100 mg) and the mixture was stirred at rt under H₂ overnight. Filtration and evaporation of the mixture gave Compound 34F (400 mg, yield 60%). LC-MS (m/z): 272 [M+1]⁺.

A mixture of Compound 11E (182 mg, 0.74 mmol), EDCI (212 mg, 1.1 mmol), HOBt (150 mg, 1.1 mmol), Compound 34F (200 mg, 0.74 mmol) in DCM (20 mL) was stirred at rt overnight. After added water, the mixture was extracted with DCM (50 mL×2), washed with brine (50 mL), dried over Na₂SO₄, and concentrated. The crude product was purified by prep-HPLC and followed by chiral-prep-HPLC to give Compound 34G (46 mg, yield 13%) as a white solid and Compound 34 (58 mg, yield 16%) as a white solid. For Compound 34G, LC-MS (m/z): 500 [M+1]⁺. ¹H-NMR (CDCl₃, 400 MHz) major characteristic peaks: δ (ppm) 2.08 (s, 4H), 2.90 (m, 2H), 3.52 (m, 1H), 3.64 (m, 2H), 3.94 (t, J=16.8 Hz, 1H), 4.71 (m, 2H), 5.14 (d, J=7.2 Hz, 1H), 6.79 (s, 1H), 7.20 (m, 1H), 7.23 (s, 1H), 7.38 (s, 1H), 7.66 (m, 1H), 8.06 (m, 2H), 8.22 (d, J=8.8 Hz, 1H), 8.52 (d, J=8.4 Hz, 1H), 8.88 (d, J=4.0 Hz, 1H), 9.43 (d, J=8.4 Hz, 1H), 11.56 (s, 1H); For Compound 34, LC-MS (m/z): 500 [M+1]⁺. ¹H-NMR (CDCl₃, 400 MHz) major characteristic peaks: δ (ppm) 2.16 (s, 2H), 3.05 (s, 2H), 3.74 (s, 3H), 4.32 (s, 4H), 4.81 (s, 1H), 5.43 (s, 1H), 6.70 (s, 1H), 7.17 (m, 1H), 7.24 (m, 1H), 7.34 (m, 1H), 7.66 (m, 1H), 7.90 (d, J=8.8 Hz, 1H), 8.05 (s, 1H), 8.23 (m, 1H), 8.45 (d, J=8.4 Hz, 1H), 8.96 (d, J=4.4 Hz, 1H), 11.80 (s, 1H).

Example 35

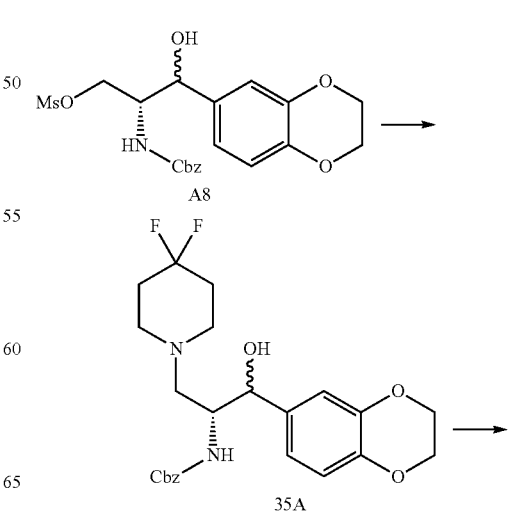

-continued

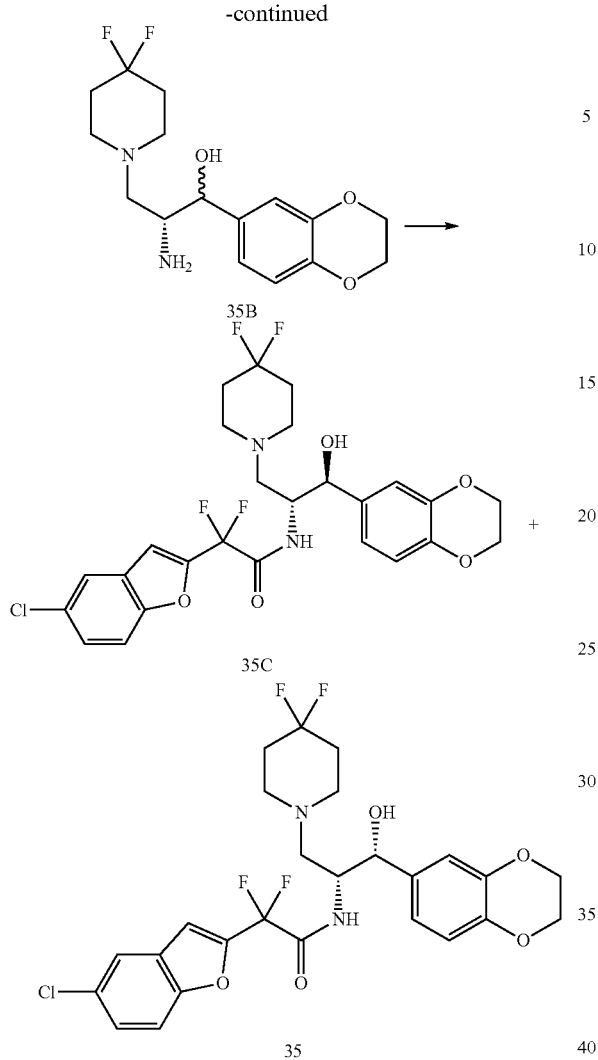

Compound 35C, LCMS (m/z): 557 [M+1]+; 1H-NMR (CDCl3, 400 MHz) major characteristic peaks: δ (ppm) 2.32 (s, 4H), 3.16 (dd, J=4.12 Hz, 2H), 3.81 (t, J=12 Hz, 1H), 4.14-4.20 (m, 5H), 4.55 (s, 1H), 4.89 (d, J=4 Hz, 1H), 6.77-6.84 (m, 2H), 6.89 (d, J=8 Hz, 2H), 7.32-7.37 (m, 1H), 7.42 (d, J=8 Hz, 1H), 7.60 (s, 1H), 8.93 (d, J=8 Hz, 1H); For Compound 35, LCMS (m/z): 557 [M+1]+; 1H NMR (CDCl3, 400 MHz) major characteristic peaks: δ (ppm) 2.38 (s, 4H), 3.33 (dd, J=4, 12 Hz, 2H), 3.52-3.58 (m, 2H), 4.07-4.21 (m, 5H), 4.56 (s, 1H), 4.98 (s, 1H), 6.75 (s, 2H), 6.82 (s, 2H), 7.35 (d, J=8 Hz, 1H), 7.43 (d, J=8 Hz, 1H), 7.59 (s, 1H), 7.94 (d, J=8 Hz, 1H).

Example 36

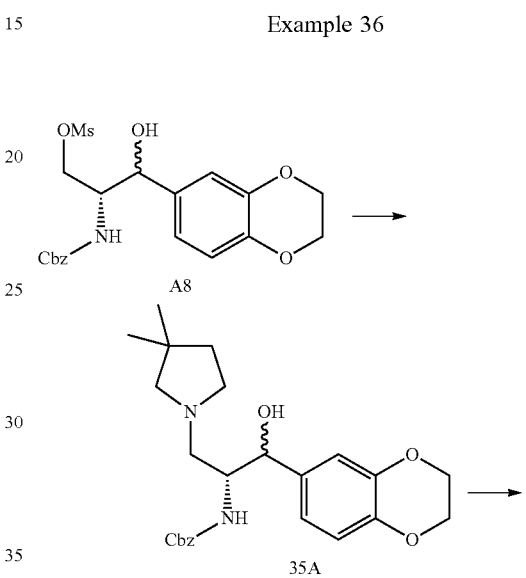

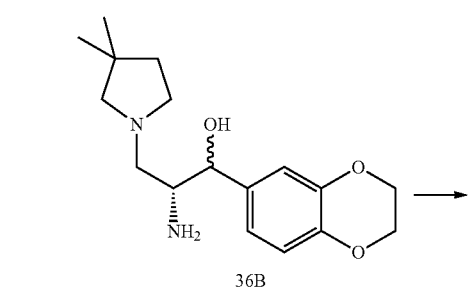

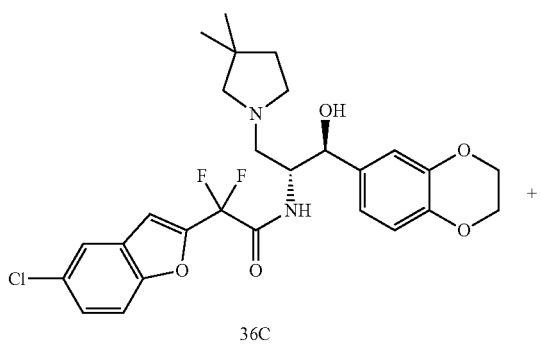

To a solution of Compound A8 (847 mg, 2 mmol) in ACN (20 mL) was added 4,4-difluoropiperidine (628 mg, 4 mmol), K2CO3 (414 mg, 3 mmol) and NaI (449 mg, 3 mmol). The mixture was heated at 82° C. overnight. It was cooled to rt, filtered and added ethyl acetate (30 mL). It was washed with brine, dried over anhydrous Na2SO4 and concentrated in vacuum to give a crude product Compound 35A (900 mg, crude) as a colorless solid. LCMS (m/z): 463 [M+1]+.

To a solution of Compound 35A (100 mg, 0.22 mmol) in EtOH/water (10 mL, 9:1, v/v) was added LiOH.H2O (28 mg, 0.66 mmol). The mixture was refluxed overnight, cooled down to rt, and added water (20 mL). It was extracted with ethyl acetate (20 mL×3). The combined organic layers were dried over anhydrous Na2SO4 and concentrated in vacuum to give crude product Compound 35B (70 mg, crude) as a yellow oil. LCMS (m/z): 329 [M+1]+.

To a mixture of Compound 35B (70 mg, 0.20 mmol) in DCM (10 mL) was added EDCI (57 mg, 0.30 mmol), HOBt (40 mg, 0.30 mmol) and Compound 11E (49 mg, 0.2 mmol) and stirred at 25° C. overnight. It was diluted with water (10 mL), extracted with DCM (20 mL×3), dried over anhydrous Na2SO4, and purified by chiral-prep-HPLC to give Compound 35C (6.5 mg, yield 4.5%) as a white solid and Compound 35 (16.5 mg, yield 11.5%) as a white solid. For

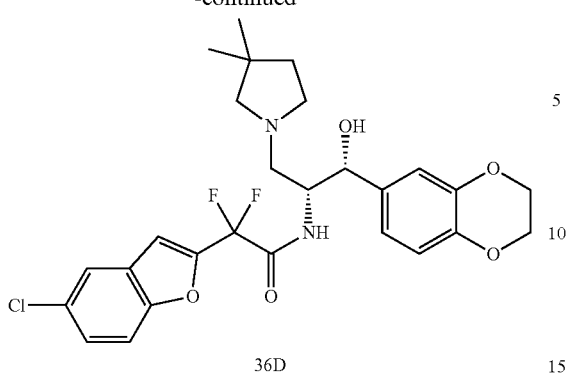

36D

To a solution of 3,3-dimethylpyrrolidine (645 mg, 4.79 mmol) in THF (15 mL) was added Compound A8 (520 mg, 1.19 mmol) and TEA (1 mL). The reaction mixture was stirred at 85° C. overnight. The solvents were removed and the residue was purified by prep-HPLC to afford the Compound 36A (110 mg, yield 21%). LCMS: 441 [M+1]$^+$.

To a solution of Compound 36A (110 mg, 0.25 mmol) in MeOH (5 mL) was added Pd(OH)$_2$ (15 mg). The reaction mixture was stirred at rt overnight, then filtered and evaporated to give Compound 36B (80 mg, yield 100%). LCMS: 307 [M+1]$^+$.

A solution of Compound 36B (80 mg, 0.26 mmol), Compound 11E (64.5 mg, 0.26 mmol), HOBT (53 mg, 0.39 mmol), EDCI (75 mg, 0.39 mmol) in DCM (10 mL) was stirred at rt overnight. After added water (50 mL), the mixture was extracted with DCM (50 mL×2). The combined organic phases were dried over Na$_2$SO$_4$, filtered, evaporated, and purified by chiral-prep-HPLC to give Compound 36C (13.8 mg, yield 10%) as a white solid and Compound 36D (10.4 mg, yield 7.5%) as a white solid. For Compound 36C, LCMS (m/z): 535 [M+1]$^+$; $^1$H-NMR (CDCl$_3$, 400 MHz) major characteristic peaks: δ (ppm) 1.09-1.31 (m, 6H), 1.84-1.94 (d, J=20 Hz, 2H), 2.46-2.52 (m, 1H), 2.90-3.01 (m, 1H), 3.13-3.27 (m, 2H), 3.55-3.96 (m, 2H), 4.16-4.19 (m, 4H), 4.43 (s, 1H), 4.90 (s, 1H), 6.76-6.78 (m, 1H), 6.82-6.91 (m, 3H), 7.31-7.34 (m, 1H), 7.42-7.44 (m, 1H), 7.58-7.59 (m, 1H), 9.07-9.38 (m, 1H), 11.85 (s, 1H); For Compound 36D, LCMS (m/z): 535 [M+1]$^+$; $^1$H NMR (CDCl$_3$, 400 MHz) major characteristic peaks: δ (ppm) 1.19-1.24 (m, 6H), 1.90-2.00 (d, J=20 Hz, 2H), 2.65-2.83 (m, 1H), 3.07-3.09 (m, 1H), 3.42 (s, 1H), 3.54 (s, 2H), 3.88 (s, 1H), 4.06-4.20 (m, 4H), 4.44 (s, 1H), 5.08-5.12 (m, 1H), 6.72-6.75 (m, 3H), 6.83 (s, 1H), 7.32-7.35 (m, 1H), 7.40-7.43 (m, 1H), 7.57-7.58 (m, 1H), 7.70-7.988 (m, 1H), 11.78-12.01 (m, 1H).

Example 37

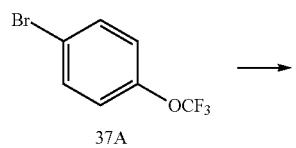

37A

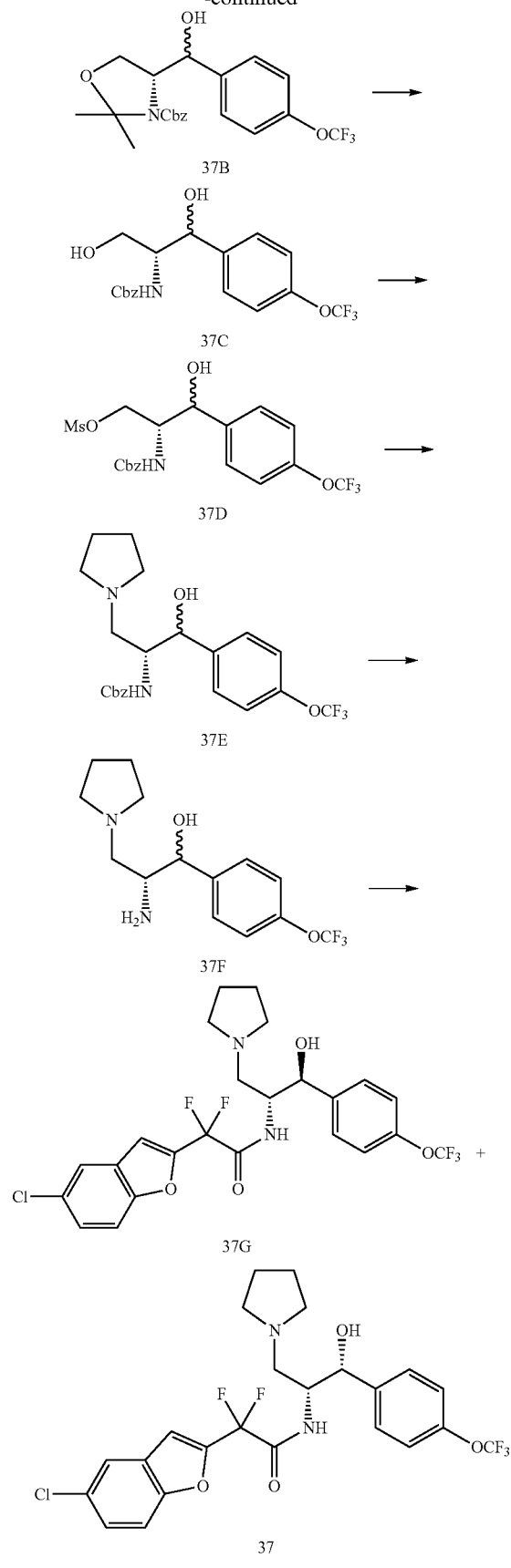

To a solution of Compound 37A (2 g, 8.3 mmol) in THF (30 mL) was added n-BuLi (4 mL, 2.5 M) under N₂ at −60° C. The mixture was stirred for 1 h, Compound 8C (2.2 g, 8.3 mmol) in THF (10 mL) was added. Stirred at rt for 15 min, the mixture was diluted with aq NH₄Cl (40 mL), extracted with ethyl acetate (50 mL×2), washed with brine (100 mL×2), and evaporated to dryness. The crude product was purified by column chromatography on silica gel (ethyl acetate in petroleum ether, 30% v/v) to give Compound 37B (1.4 g, yield 40%) as colorless oil. LC-MS (m/z): 426 [M+1]⁺.

A solution of Compound 37B (1 g, 2.4 mmol) in THF (10 mL) and 1 N aq HCl (5 mL) was stirred at rt for 5 h. The mixture was quenched with water (10 mL), extracted with ethyl acetate (20 mL×2), washed with brine (30 mL×2), and evaporated to dryness. The crude product was purified by column chromatography silica gel (ethyl acetate in petroleum ether, 50% v/v) to afford Compound 37C (693 mg, yield 75%) as colorless oil. LC-MS (m/z): 386 [M+1]⁺.

To a solution of Compound 37C (0.5 g, 1.3 mmol) in THF (10 mL) was added triethylamine (0.26 g, 2.6 mmol) and MsCl (164 mg, 1.4 mmol) under N₂ at −40° C. The mixture was stirred at this temperature for 3 h, quenched with water (20 mL), extracted with ethyl acetate (30 mL×2), washed with brine (50 mL×2), and evaporated to dryness. The crude product was purified by column chromatography on silica gel (ethyl acetate in petroleum ether, 50% v/v) to yield Compound 37D (0.42 g, yield 70%) as colorless oil. LC-MS (m/z): 464 [M−17]⁺.

To a solution of Compound 37D (0.4 g, 0.86 mmol) in THF (10 mL) was added pyrrolidine (0.61 g, 8.6 mmol). The mixture was stirred at 60° C. overnight, quenched with water (20 mL), extracted with ethyl acetate (30 mL×3), washed with brine (100 mL×2), and evaporated to dryness. The crude product was purified by column chromatography on silica gel (ethyl acetate in petroleum ether, 50% v/v) to give Compound 37E (0.2 g, yield 53%) as a colorless oil. LC-MS (m/z): 439 [M+1]⁺.

A solution of Compound 37E (0.2 g, 0.46 mmol) and LiOH.H₂O (57 mg, 1.4 mmol) in ethanol (10 mL) was heated to reflux overnight. The mixture was quenched with water (10 mL), extracted with ethyl acetate (20 mL×3), washed with brine (50 mL×2), and evaporated to dryness to give Compound 37F (126 mg, yield 90%) as a colorless oil. LC-MS (m/z): 305 [M+1]⁺.

To a solution of Compound 37F (0.1 g, 0.33 mmol) in dichloromethane (10 mL) was added Compound 11E (81 mg, 0.33 mmol), EDCI (95 mg, 0.5 mmol), HOBt (68 mg, 0.5 mmol). The mixture was stirred at rt overnight, quenched with water (20 mL), extracted with dichloromethane (20 mL×2), washed with brine (50 mL×2), and evaporated to dryness. The crude product was purified by prep-HPLC and followed Chiral-HPLC to give two isomers Compound 37G (11 mg) as a white solid and Compound 37 (6 mg) as a white solid. For Compound 37G, LC-MS (m/z): 533 [M+1]⁺, ¹H-NMR (DMSO-d₆, 400 MHz) major characteristic peaks: δ (ppm) 1.88 (m, 4H), 3.11 (m, 2H), 3.52 (m, 4H), 4.31 (m, 1H), 4.60 (m, 1H), 6.22 (s, 1H), 6.84 (s, 1H), 7.12 (m, 2H), 7.38 (m, 2H), 7.52 (m, 1H), 7.67 (m, 1H), 7.78 (m, 1H), 9.28 (m, 1H), 9.82 (s, 1H). For Compound 37, LC-MS (m/z): 533 [M+1]⁺, ¹H-NMR (DMSO-d₆, 400 MHz) major characteristic peaks: δ (ppm) 1.87 (m, 4H), 3.10 (m, 2H), 3.50 (m, 4H), 4.51 (m, 1H), 4.89 (m, 1H), 6.11 (s, 1H), 7.05 (m, 3H), 7.39 (m, 2H), 7.54 (m, 1H), 7.73 (m, 1H), 7.82 (m, 1H), 8.94 (m, 1H), 9.63 (s, 1H).

Example 38

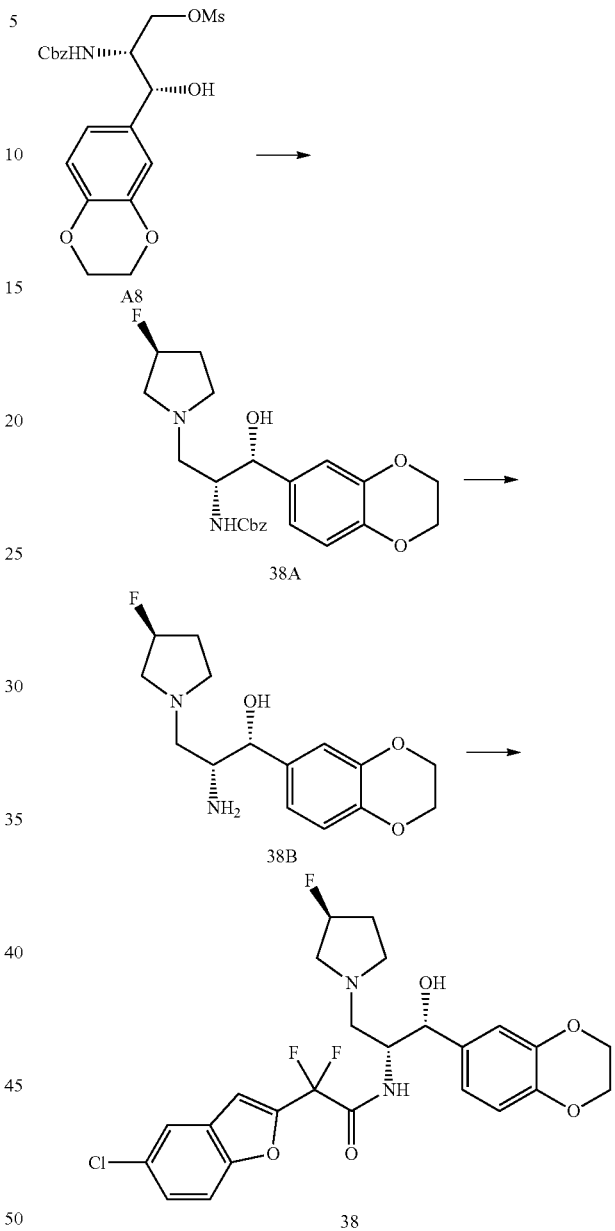

To a solution of (S)-3-fluoropyrrolidine (650 mg, 5.2 mmol) in CH₃CN (50 mL) was added Na₂CO₃ (717 mg, 5.2 mmol) and it was stirred at rt for 30 min. Compound A6 (756 mg, 1.73 mmol) was added and the reaction mixture was heated to reflux overnight. It was poured into ice-water, extracted with ethyl acetate (100 mL×2), washed with brine (100 mL×1), dried over Na₂SO₄, and evaporated to dryness. The crude product was purified by prep-HPLC to afford the Compound 38A (270 mg, yield 36%) as a yellow liquid. LCMS: 431 [M+1]⁺.

To a solution of Compound 38A (170 mg, 0.55 mmol) in EtOH (2 mL) was added LiOH.H₂O (79 mg, 1.89 mmol) in water (1 mL) and the mixture was stirred at reflux overnight. It was quenched with H₂O (50 mL), extracted by ethyl acetate (50 mL×3), washed with brine (20 mL), dried over Na$_2$SO$_4$, and evaporated to dryness to give Compound 38B (200 mg, 100%) as a yellow oil. LC-MS (m/z): 297 [M+1]$^-$.

A mixture of Compound 11E (165 mg, 0.67 mmol), EDCI.HCl (192 mg, 0.99 mmol), HOBt (135 mg, 0.99 mmol), Compound 38B (200 mg, 0.67 mmol) in DCM (10 mL) was stirred at 28° C. overnight. The reaction was quenched with sat. aq NaHCO$_3$ (100 mL). The mixture was extracted with DCM (50 mL×2), washed with brine (50 mL×1), dried over Na$_2$SO$_4$, and evaporated to dryness. The crude product was purified by prep-HPLC to give Compound 38 (100 mg, yield 28%) as a white solid. LC-MS (m/z): 525 [M+1]$^+$; $^1$H-NMR (CDCl$_3$, 400 MHz) major characteristic peaks: δ (ppm) 2.04-2.49 (m, 2H), 3.21-3.97 (m, 6H), 4.06-4.20 (m, 4H), 4.52 (s, 1H), 5.04 (s, 1H), 5.32-5.45 (d, J=52.4 Hz, 1H), 6.70-6.83 (m, 4H), 7.33-7.44 (m, 2H), 7.58 (s, 1H), 7.74-7.76 (d, J=7.6 Hz, 1H).

Example 39

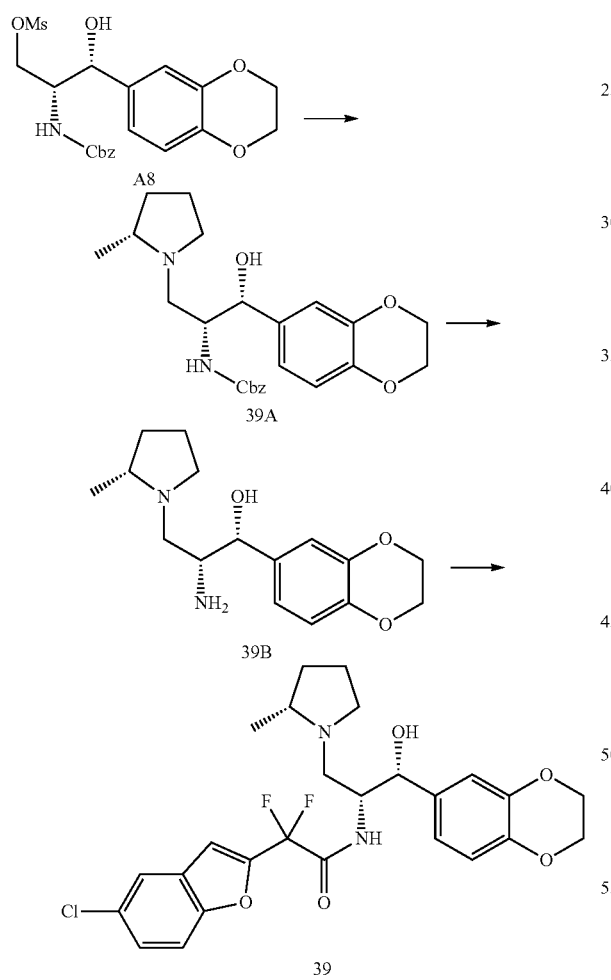

To a solution of Compound A8 (514 mg, 1.16 mmol) in THF (15 mL) was added (R)-2-methylpyrrolidine (400 mg, 4.7 mmol) and Et$_3$N (0.5 mL). The reaction mixture was stirred at 85° C. overnight. After the removal of solvents, the residue was purified by prep-HPLC to afford the Compound 39A (150 mg, yield 30%) as a white solid. LCMS: 427 [M+1]$^+$.

To a solution of Compound 39A (150 mg, 0.35 mmol) in MeOH (5 mL) was added Pd(OH)$_2$ (15 mg). The reaction mixture was stirred in the presence of H$_2$ at rt overnight. Filtration and evaporation of the solution led to Compound 39B (102 mg, yield 100%) as the colorless oil. LCMS: 293 [M+1]$^+$.

A solution of Compound 39B (102 mg, 0.35 mmol), Compound 11E (86.3 mg, 0.35 mmol), HOBt (71.4 mg, 0.52 mmol), EDCI (100 mg, 0.52 mmol) in DCM (10 mL) was stirred at rt overnight. It was added water (50 mL), extracted with DCM (50 mL×2), dried over Na$_2$SO$_4$, filtered, and evaporated to dryness. The residue was purified by prep-HPLC to give desired product Compound 39 (8.7 mg, yield 5%) as the colorless oil. LCMS (m/z): 521 [M+1]$^+$; $^1$H-NMR (CDCl$_3$, 400 MHz) major characteristic peaks: δ (ppm) 1.25-1.49 (m, 3H), 1.97-2.11 (m, 2H), 2.25-2.26 (m, 2H), 2.96-3.19 (m, 3H), 3.75-3.80 (m, 1H), 4.01 (s, 1H), 4.04-4.19 (m, 4H), 4.46 (s, 1H), 5.23 (s, 1H), 6.64 (s, 1H), 6.69-6.79 (m, 2H), 6.84 (s, 1H), 7.31-7.35 (m, 1H), 7.40-7.43 (m, 1H), 7.53-7.57 (m, 2H), 11.48 (s, 1H).

Example 40

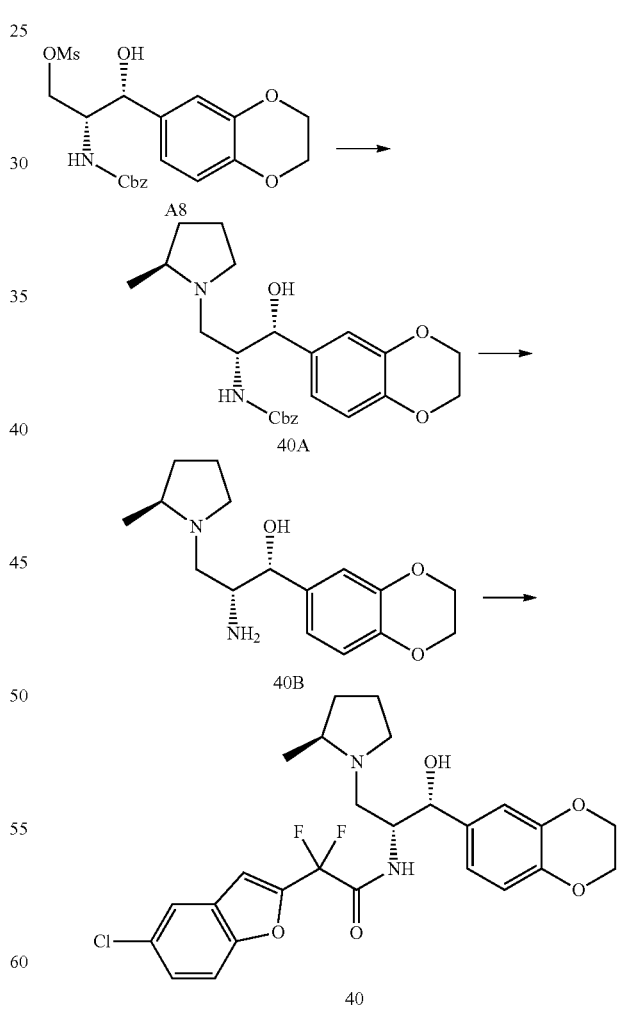

To a solution of (S)-2-methylpyrrolidine hydrochloride (540 mg, 4.4 mmol) in CH$_3$CN (10 mL) was added Na$_2$CO$_3$ (600 mg, 4.4 mmol). Stirred at rt for 30 min, Compound A8 (437 mg, 1 mmol) was added. The reaction mixture was stirred at reflux overnight. It was poured into ice-water, extracted with ethyl acetate (100 mL×2), washed with brine (100 mL×1), dried over Na$_2$SO$_4$, and concentrated to afford the mixture of Compound 40A (300 mg) as a yellow oil. LCMS: 427 [M+1]$^+$.

To a solution of Compound 40A (300 mg) in EtOH (10 mL) was added LiOH.H$_2$O (197 mg, 4.7 mmol) in water (5 mL) and the mixture was stirred reflux overnight. It was quenched in H$_2$O (50 mL) and the mixture was extracted by ethyl acetate (50 mL×3), washed with brine (20 mL), dried over Na$_2$SO$_4$, and concentrated to render Compound 40B (326 mg, yield 100%) as a yellow oil. LC-MS (m/z): 293 [M+1]$^+$.

A mixture of Compound 40B (326 mg, 1.12 mmol), EDCI.HCl (233 mg, 1.66 mmol), HOBt (164 mg, 1.66 mmol), Compound 11E (200 mg, 1.12 mmol) in DCM (10 mL) was stirred at 28° C. overnight. After quenched with sat. aq NaHCO$_3$ (100 mL), the mixture was extracted with DCM (50 mL×2), washed with brine (50 mL×1), dried over Na$_2$SO$_4$, and concentrated. The crude product was purified by prep-HPLC to give Compound 40 (126 mg, yield 18%) as a white solid. LC-MS (m/z): 525 [M+1]$^+$; $^1$H-NMR (DMSO-d$_6$, 400 MHz) major characteristic peaks: δ (ppm) 1.31-1.33 (d, J=6.4 Hz, 3H), 1.59-1.65 (m, 1H), 1.90-2.00 (m, 2H), 2.16-2.21 (m, 1H), 3.21-3.26 (m, 1H), 3.42-3.61 (m, 4H), 4.06-4.16 (m, 4H), 4.45-4.47 (m, 1H), 4.66-4.67 (m, 1H), 5.91 (s, 1H), 6.62-6.77 (m, 3H), 7.01 (s, 1H), 7.52-7.55 (m, 1H), 7.75-7.77 (d, J=8.8 Hz, 1H), 7.83-7.85 (m, 1H), 8.92-8.99 (m, 2H).

Example 41

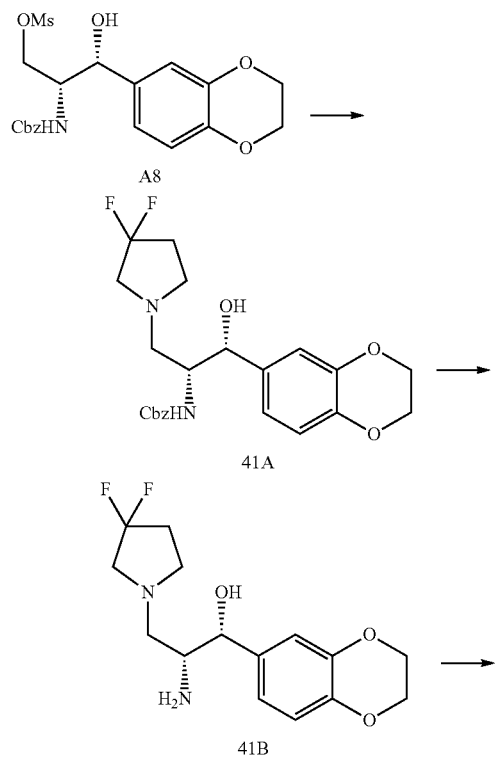

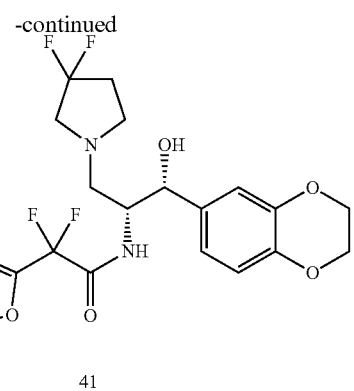

To a solution of 3,3-difluoropyrrolidine (384 mg, 3 mmol) in CH$_3$CN (20 mL) was added Compound A8 (437 mg, 1 mmol), K$_2$CO$_3$ (414 mg, 3 mmol) and NaI (449 mg, 3 mmol). The mixture was heated at 82° C. overnight. It was cooled to rt, filtered and concentrated in vacuum to give a crude product Compound 41A (250 mg, crude) as a yellow oil. LCMS (m/z): 449 [M+1]$^+$.

To a solution of Compound 41A (200 mg, 0.45 mmol) in EtOH/water (10 mL, 9:1, v/v) was added LiOH.H$_2$O (93.6 mg, 2.23 mmol). The mixture was refluxed overnight. The mixture was diluted with water (20 mL) and then extracted with ethyl acetate (20 mL×3), dried over anhydrous Na$_2$SO$_4$, and concentrated in vacuum to give a crude Compound 41B (170 mg, crude) as a yellow oil. LCMS (m/z): 315 [M+1]$^+$.

To a mixture of Compound 41B (150 mg, 0.47 mmol) in DCM (20 mL) was added EDCI (164 mg, 0.85 mmol), HOBt (115 mg, 0.85 mmol) and Compound 11E (140 mg, 0.57 mmol) and stirred at 25° C. overnight. After the addition of water (10 mL), the mixture was extracted with DCM (20 mL×3), dried over anhydrous Na$_2$SO$_4$, and purified by prep-HPLC to afford Compound 41 (40 mg) as a white solid. LCMS (m/z): 543 [M+1]$^+$; $^1$H-NMR (CDCl$_3$, 400 MHz) major characteristic peaks: δ (ppm) 2.59 (s, 2H), 3.44 (s, 1H), 3.60-3.74 (m, 4H), 4.07-4.15 (m, 4H), 4.46 (s, 1H), 4.99 (s, 1H), 6.73-6.80 (m, 4H), 7.32-7.35 (m, 1H), 7.40-7.43 (d, 1H), 7.57 (d, 1H), 7.78 (s, 1H).

Example 42

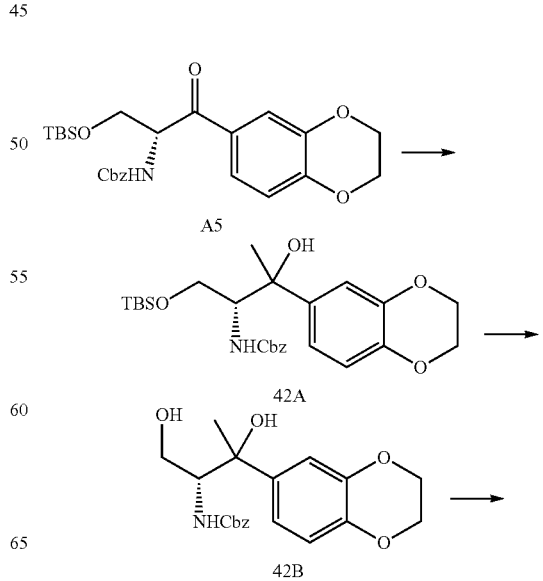

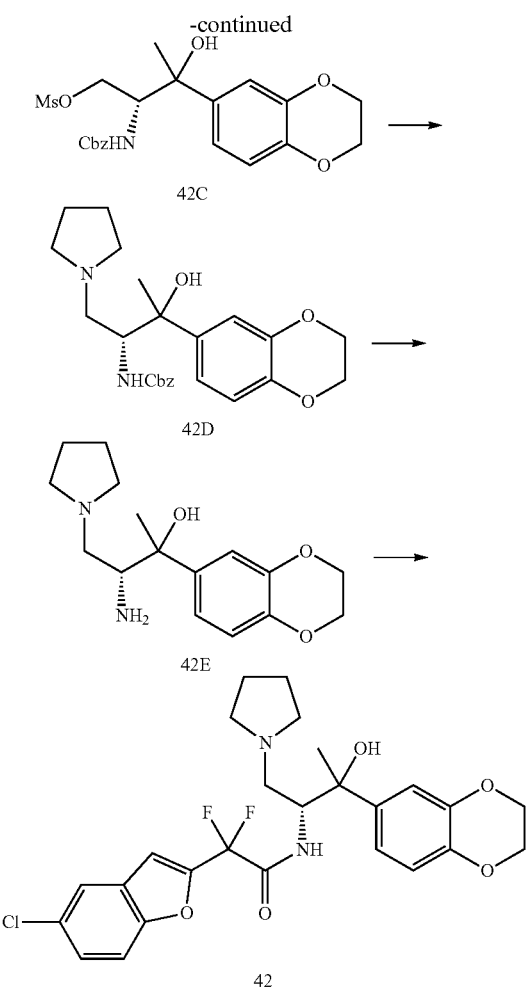

Compound A5 (4.64 g, 9.85 mmol) was dissolved in anhydrous THF (100 mL) and cooled down −30° C. under nitrogen atmosphere. CH₃MgBr (9.85 mL, 3M solution in ether, 29.55 mmol) was added dropwise while keeping the temperature at −30° C. Then the reaction was warmed to rt and stirred for 3 hrs. The reaction was quenched with saturate aq NH₄Cl solution and extracted with ethyl acetate (50 mL×3). The combined organic phases were washed water, brine, and dried over Na₂SO₄. The crude product was purified by column chromatography on silica gel (ethyl acetate in petroleum, 10% v/v) to give Compound 42A (3.76 g, yield 78%) as a white solid. LC-MS (m/z): 193 [M+1]⁺; ¹H-NMR (CDCl₃, 400 MHz) major characteristic peaks: δ (ppm) −0.09 (s, 3H), −0.05 (s, 3H), 0.84 (s, 9H), 1.42 (s, 3H), 3.51 (dd, J=2.0, 10.4 Hz, 1H), 3.53 (dd, J=2.0, 10.4 Hz, 1H), 3.91 (d, J=7.2 Hz, 1H), 3.71 (m, 1H), 4.26 (s, 4H), 4.45 (m, 1H), 5.16 (s, 2H), 5.72 (d, J=7.2 Hz, 1H), 6.85 (m, 2H), 6.95 (s, 1H), 7.38 (m, 5H).

To a solution of Compound 42A (5.9 g, 12.11 mmol) in THF (120 mL) was added a solution of TBAF (1.58 g, 6.06 mmol) in THF (10 mL) at 0° C. and the mixture was stirred at 25° C. overnight. The mixture was condensed by removal of solvent and added water (50 mL). It was extracted with ethyl acetate (50 mL×3), washed with brine (100 mL×1), dried over Na₂SO₄. The crude product was purified by column chromatography on silica gel (methanol in dichloromethane, 3% v/v) to give Compound 42B (3.2 g, yield 71%) as a yellow oil. LC-MS (m/z): 356 [M−17]⁺; ¹H-NMR (CDCl₃, 400 MHz) major characteristic peaks: δ (ppm) 1.49 (s, 3H), 3.34 (s, 1H), 3.58 (m, 2H), 3.91 (d, J=8.8 Hz, 1H), 4.25 (s, 4H), 5.15 (s, 2H), 5.79 (d, J=8.8 Hz, 1H), 6.85 (m, 2H), 6.96 (s, 1H), 7.38 (m, 5H).

To a solution of Compound 42B (3.2 g, 8.58 mmol) in THF (80 mL) was added Et₃N (2.6 g, 25.7 mmol) and the mixture was cooled to −40° C., MsCl (0.7 mL, 9.01 mmol) was added slowly and kept with stirring at −40° C. about 0.5 h. Pyrrolidine (5.48 g, 77.2 mmol) was added to −40° C. The reaction mixture was allowed to warm up to rt and then heated to 50° C. overnight. The mixture was added water (50 mL), extracted with ethyl acetate (50 mL×3), washed with brine (100 mL×1), and dried over Na₂SO₄. The crude product was purified by column chromatography on silica gel (methanol in dichloromethane, 3% v/v) to give Compound 42C (2.52 g, yield 77%) as a white syrup. LC-MS (m/z): 356 [M−17]⁺; ¹H-NMR (CDCl₃, 400 MHz) major characteristic peaks: δ (ppm) 1.40 (s, 3H), 1.69 (m, 4H), 2.35 (m, 1H), 2.57 (m, 1H), 4.16 (m, 1H), 4.27 (s, 4H), 5.15 (s, 2H), 5.59 (d, J=10.2 Hz, 1H), 6.86 (m, 2H), 6.98 (s, 1H), 7.38 (m, 5H).

To a solution of Compound 42C (2.52 g, 5.92 mmol) in methanol (60 mL) was added Pd(OH)₂ (250 mg) and then the mixture was stirred at 25° C. under H₂ overnight. It was filtered and evaporated to render Compound 42D (1.82 g, crude). LC-MS (m/z): 356 [M−17]⁺.

To a solution of compound 42D (200 mg, 0.68 mmol) and Compound 11E (168 mg, 0.68 mmol) in DCM (210 mL) was added EDCI (197 mg, 1.03 mmol) and HOBt (139 mg, 1.03 mmol) under N₂. The mixture was stirred at 25° C. overnight. When TLC showed the starting material was consumed, water was added to the mixture. It was then extracted with DCM (50 mL×3). The combined organic layers were washed with brine, dried over sodium sulfate, and concentrated to give a crude product. The crude product was purified by prep-HPLC to give Compound 42 (145 mg, yield 41%) as a white solid. LC-MS (m/z): 521 (M+1)⁺, ¹H-NMR (CDCl₃, 400 MHz) major characteristic peaks: δ (ppm) 1.52 (s, 3H), 1.99-2.06 (m, 4H), 2.60-2.74 (m, 4H), 3.60-3.69 (m, 2H), 3.88 (t, J=7.2 Hz, 1H), 4.03 (m, 2H), 4.27 (s, 4H), 4.61 (t, J=7.2 Hz, 1H), 6.86 (d, J=8.4 Hz, 1H), 6.93 (d, J=8.4 Hz, 1H), 7.03 (s, 1H), 7.15 (s, 1H), 7.34 (d, J=8.4 Hz, 1H), 7.44 (d, J=8.4 Hz, 1H), 7.62 (s, 1H), 9.19 (d, J=8.4 Hz, 1H), 11.20 (s, 1H).

Example 43

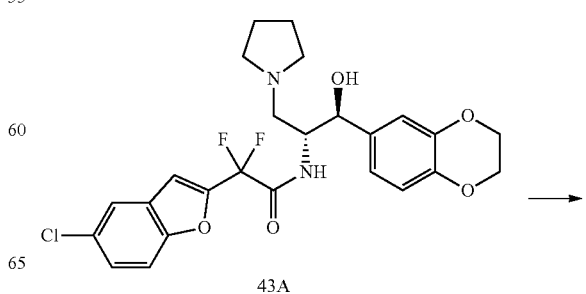

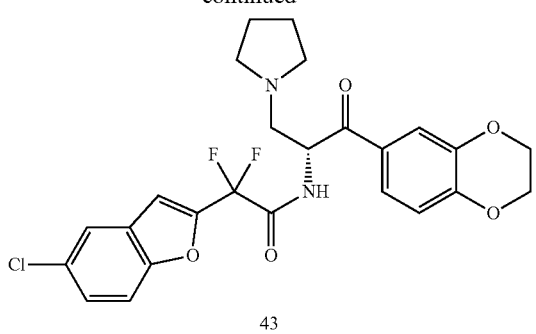

43

To a stirred solution of Compound 43A (100 mg, 0.2 mmol), NaHCO₃ (33 mg, 0.4 mmol) and NMP (126 mg, 0.3 mmol) in DCM (5 mL) was stirred at rt for 2 h. The mixture was diluted with saturation aq NaHSO₃ (15 mL) and extracted with EtOAc (15 mL×3). The combined organic layers were washed with saturate aq NaHSO₃ (15 mL), brine (15 mL), dried over Na₂SO₄, and concentrated to give a crude product. The crude product was purified by prep-HPLC to afford Compound 43 (17 mg, yield 14%) as a white solid. LC-MS (m/z): 505 [M+1]⁺; ¹H-NMR (CDCl₃, 400 MHz) major characteristic peaks: δ (ppm) 2.13 (s, 4H), 2.95-2.96 (m, 2H), 3.58-3.61 (m, 2H), 3.89-3.99 (m, 2H), 4.06-4.23 (m, 4H), 5.47 (s, 1H), 6.70-6.72 (d, J=9 Hz, 2H), 6.86 (s, 1H), 7.30-7.33 (m, 4H), 7.54 (s, 1H), 9.66-9.68 (d, J=8 Hz, 1H).

Example 44

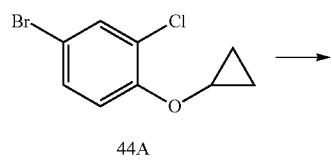

44A

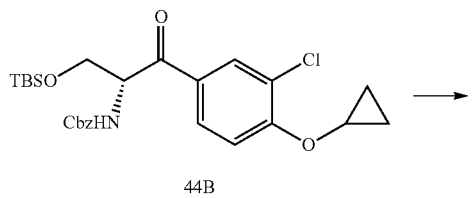

44B

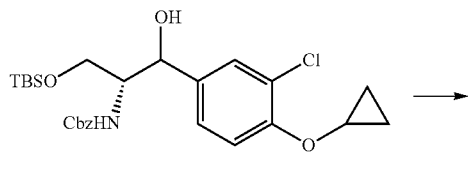

44C

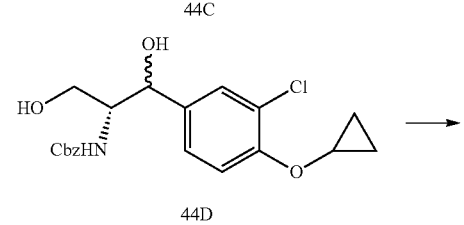

44D

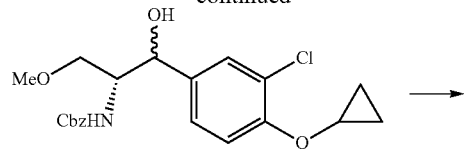

44E

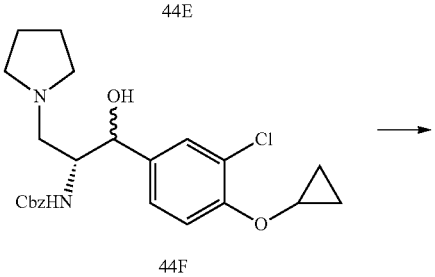

44F

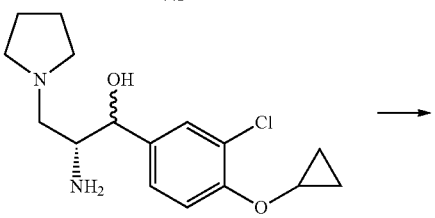

44G

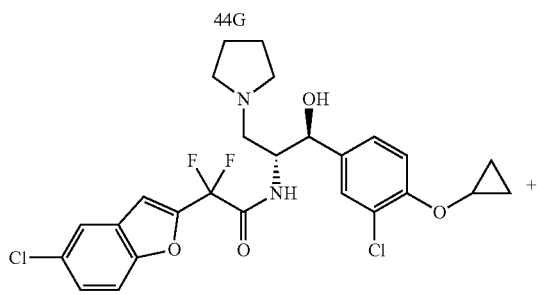

44H

44

To a solution of Compound 44A (3.73 g, 15.1 mmol) in THF (200 mL) was added n-BuLi (6.1 mL) at −60° C. under N₂ and it was stirred for 0.5 h, and then added slowly Compound A4 (2 g, 5.06 mmol) in THF (10 mL). The mixture was stirred at −60° C. for 1 h. After the addition of saturate aq NH₄Cl solution, the mixture was extracted with ethyl acetate (100 mL×2), brine (100 mL), and dried over Na₂SO₄. The crude product was purified by column chromatography on silica gel (ethyl acetate in petroleum, 10% v/v) to yield Compound 44B (1.2 g, yield 47%) as a colorless oil. LC-MS (m/z): 504.2 [M+1]⁺.

Compound 44B (714 mg, 1.42 mmol) was dissolved in THF (9 mL) and cooled down −80° C. under nitrogen atmosphere. L-Selectride (3 mL of 1M solution in THF, 18.9 mmol) was added dropwise while keeping the temperature at −80° C. After an hour, the reaction was quenched with saturate aq NH₄Cl solution and extracted with ethyl acetate (50 mL×2), washed with brine (100 mL), and dried over Na₂SO₄. The crude product was purified by column chromatography on silica gel (10% ethyl acetate in petroleum) to give Compound 44C (350 g, yield 49%) as a colorless oil. LC-MS (m/z): 488.2 [M−17]⁺.

A solution of Compound 44C (2.08 g, 4.11 mmol) in THF (40 mL) was added TBAF (537 mg, 2.06 mmol) at 0° C. and the mixture was stirred at rt overnight. The mixture was condensed and then added water (50 mL). It was extracted with ethyl acetate (50 mL×2), washed with brine (100 mL), dried over Na₂SO₄, and concentrated. The residue was suspended in a mixture solution of ethyl acetate in petroleum (10% v/v). Filtration gave Compound 44D (1 g, yield 65%) as a white solid. LC-MS (m/z): 374.1 [M+1]⁺.

A solution of Compound 44D (0.9 g, 2.3 mmol) in THF (60 mL) was added Et₃N (700 mg, 6.9 mmol) and the mixture was cooled to −15° C., to the mixture was added MsCl (467 mg, 4.1 mmol) slowly. The mixture was stirred at −15° C. about half an hour, and then diluted water. It was extracted with ethyl acetate (50 mL×2), washed with brine (50 mL), dried over Na₂SO₄, and concentrated to give Compound 44E (1.12 g, crude), which was used for the next step without further purification. LC-MS (m/z): 452.1 [M+1]⁺.

To a solution of Compound 44E (1.12 g, 2.83 mmol) in THF (60 mL) was added pyrrolidine (2 g, 28 mmol). The reaction mixture was allowed to warm up to rt and then heated at 50° C. overnight. The crude product was purified by column chromatography on silica gel (methanol in dichloromethane, 5% v/v) to render Compound 44F (0.5 g, yield 50%). LC-MS (m/z): 445 [M+1]⁺.

To a solution of Compound 44F (520 mg, 1.17 mmol) in ethanol (12 mL) and water (2 mL) was added LiOH·H₂O (197 mg, 4.68 mmol). The mixture was stirred at 80° C. overnight, diluted water, extracted with DCM (50 mL×2), washed with brine (50 mL), dried over Na₂SO₄, and concentrated to give Compound 44G (360 mg, crude), which was used for the next step without further purification. LC-MS (m/z): 311.1 [M+1]⁺.

A mixture of Compound 11E (149 mg, 0.60 mmol), EDCI (175 mg, 0.9 mmol), HOBt (150 mg, 1.1 mmol), Compound 44G (188 mg, 0.60 mmol) in DCM (10 mL) was stirred at rt overnight. The mixture was added water, extracted with DCM (50 mL×2), washed with brine (50 mL), dried over Na₂SO₄, and concentrated. The crude product was purified by prep-HPLC and followed by chiral-prep-HPLC to give Compound 44H (23 mg, yield 7%) as a white solid and Compound 44 (22 mg, yield 7%) as a white solid. For Compound 44H, LC-MS (m/z): 539.1 [M+1]⁺; ¹H-NMR (CDCl₃, 400 MHz) major characteristic peaks: δ (ppm) 0.72-0.79 (m, 4H), 2.06 (s, 4H), 2.78-3.20 (m, 6H), 3.60-3.93 (m, 4H), 4.50 (s, 1H), 4.93-4.95 (d, J=5.6 Hz, 1H), 6.83 (s, 1H), 7.10-7.12 (d, J=8.4 Hz, 1H), 7.20-7.22 (d, J=8.0 Hz, 1H), 7.30-7.33 (dd, J=2.0, 8.8 Hz, 1H), 7.40-7.42 (m, 2H), 7.56-7.57 (d, J=2.0 Hz, 1H), 9.07-9.09 (d, J=8.0 Hz, 1H). For Compound 44, LC-MS (m/z): 539.1 [M+1]⁺; ¹H NMR (CDCl₃, 400 MHz) major characteristic peaks: δ (ppm) 0.72-0.77 (m, 4H), 2.08-2.14 (d, J=24.4 Hz, 4H), 2.94-3.02 (d, J=34.4 Hz, 5H), 3.53-3.58 (m, 3H), 3.81-3.82 (d, J=2.4 Hz, 2H), 4.48-4.50 (d, J=9.6 Hz, 1H), 5.14 (s, 1H), 6.71 (s, 1H), 7.04-7.06 (d, J=8.4 Hz, 1H), 7.12-7.14 (d, J=8.4 Hz, 1H), 7.32-7.41 (m, 3H), 7.56 (s, 1H), 7.88-7.90 (d, J=7.2 Hz, 1H).

Example 45

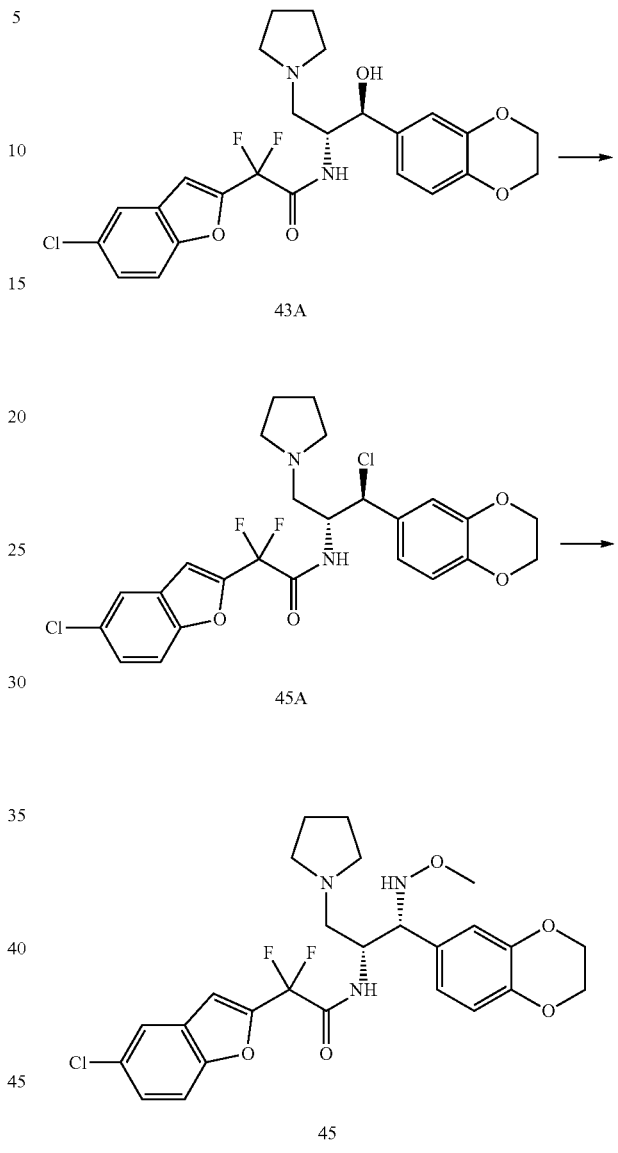

To a solution of Compound 43A (100 mg, 0.2 mmol) in DCM (10 mL) was added SOCl₂ (0.1 mL). The mixture was stirred at 25° C. for 3 h, and concentrated to afford the Compound 45A (105 mg) as a yellow liquid. LCMS (m/z): 525 [M+1]⁺.

A solution of NH₂OCH₃ in MeOH (30%, m/v, 1 mL) was added to the Compound 45A (105 mg, 0.2 mmol). The mixture was stirred at 25° C. for 3 h. After reaction, the mixture was concentrated. The crude product was purified by prep-HPLC to give Compound 45 (15 mg, yield 15%) as a white solid. LC-MS (m/z): 536 [M+1]⁺; ¹H-NMR (CDCl₃, 400 MHz) major characteristic peaks: δ (ppm) 1.82 (m, 4H), 2.72 (m, 5H), 2.91-2.96 (m, 1H), 3.76 (s, 3H), 4.06-4.07 (m, 1H), 4.23-4.27 (m, 4H), 4.94 (d, J=2.4 Hz, 1H), 5.26-5.28 (d, J=10.8 Hz, 1H), 6.72 (s, 1H), 6.75-6.81 (m, 2H), 6.86 (s, 1H), 7.31-7.34 (m, 1H), 7.43-7.45 (m, 1H), 7.55-7.56 (m, 1H).

Example 46

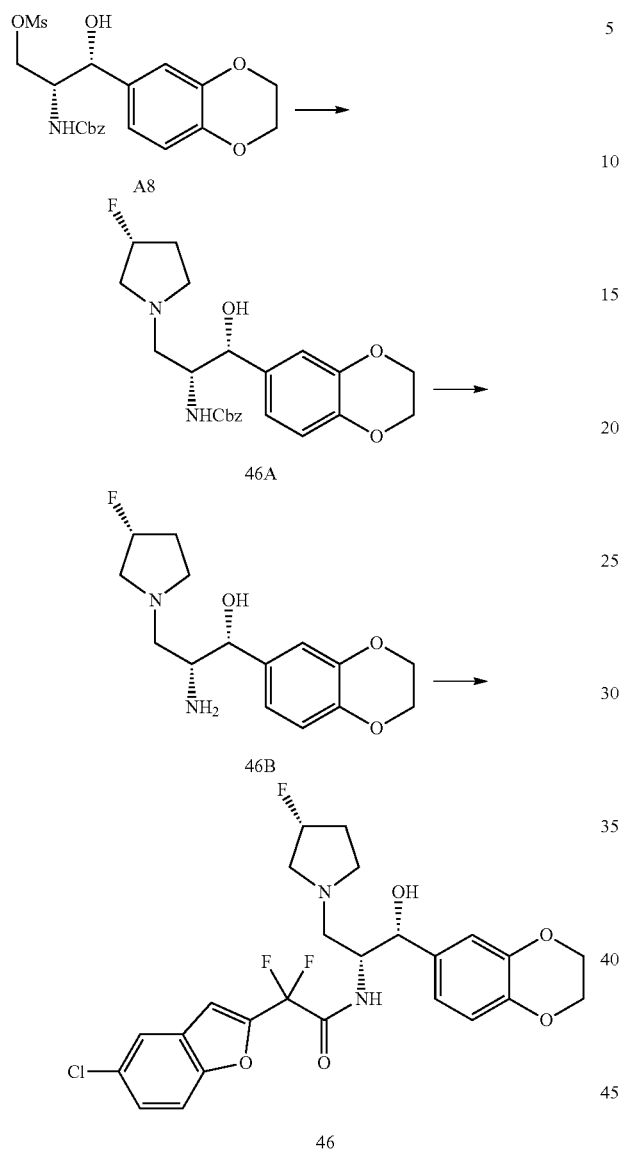

To a solution of (R)-3-fluoropyrrolidine (174 mg, 1.38 mmol) in CH₃CN (10 mL) was added K₂CO₃ (190 mg, 1.38 mmol). Stirred at rt for 30 min, Compound A8 (200 mg, 0.46 mmol) was added. The reaction mixture was stirred at reflux overnight. It was poured into ice-water, extracted with ethyl acetate (100 mL×2), washed with brine (100 mL×1), dried over Na₂SO₄, and concentrated to give a crude Compound 46A (200 mg, 100%), which was used for the next step without further purification. LC-MS (m/z): 431 [M+1]⁺.

To a solution of Compound 46A (200 mg, 0.62 mmol) in EtOH (10 mL) was added LiOH.H₂O (130 mg, 3.1 mmol) in water (10 mL) and the mixture was stirred at reflux overnight. It was poured into H₂O (50 mL), extracted with ethyl acetate (50 mL×3), washed with brine (20 mL), dried over Na₂SO₄, and concentrated to yield a crude Compound 46B (170 mg, yield 100%) as a yellow oil. LC-MS (m/z): 297 [M+1]⁺.

A mixture of Compound 11E (140 mg, 0.57 mmol), EDCI (160 mg, 0.84 mmol), HOBt (113 mg, 0.84 mmol) and Compound 46B (170 mg, 0.57 mmol) in DCM (20 mL) was stirred at 28° C. overnight. The mixture was added sat. NaHCO₃ (100 mL), extracted with DCM (50 mL×2), washed with brine (50 mL×1), dried over Na₂SO₄, and concentrated. The crude product was purified by prep-HPLC to give Compound 46 (60 mg, 20%) as a white solid. LC-MS (m/z): 525 [M+1]⁺; ¹H-NMR (CDCl₃, 400 MHz) major characteristic peaks: δ (ppm) 2.08-2.39 (m, 2H), 3.19-3.86 (m, 6H), 4.03-4.14 (m, 4H), 4.49 (s, 1H), 4.71 (s, 1H), 5.38-5.54 (d, J=48.4 Hz, 1H), 5.91 (s, 1H), 6.64-6.72 (m, 3H), 6.96-6.99 (m, 1H), 7.52-7.55 (m, 1H), 7.71-7.83 (m, 2H), 8.82-8.89 (m, 1H), 10.33 (s, 1H).

Example 47

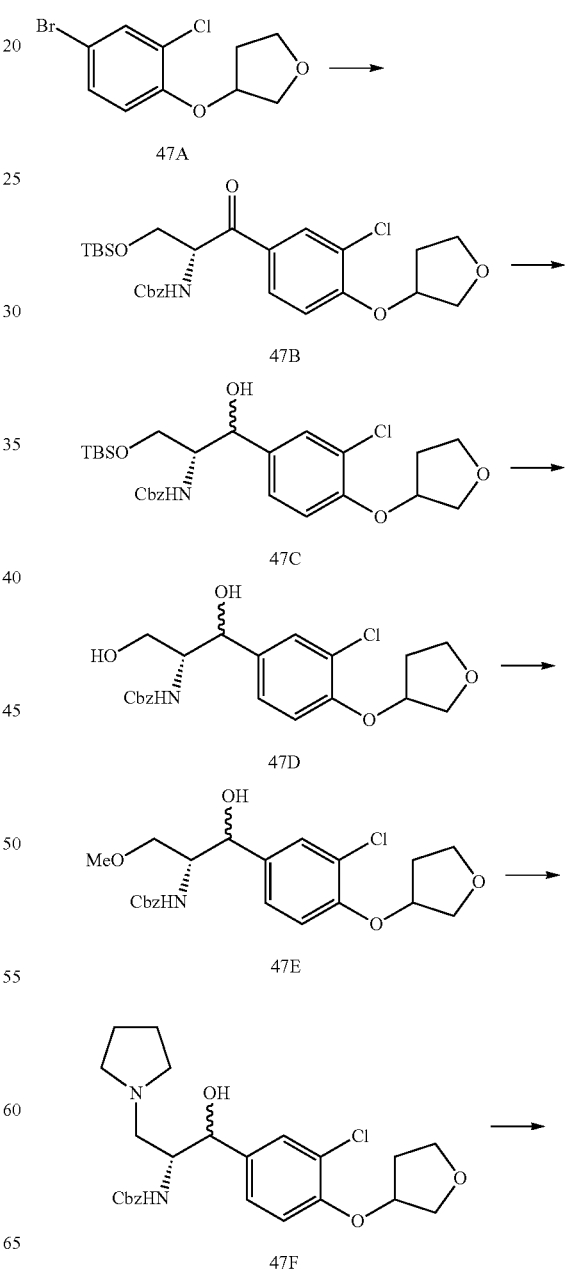

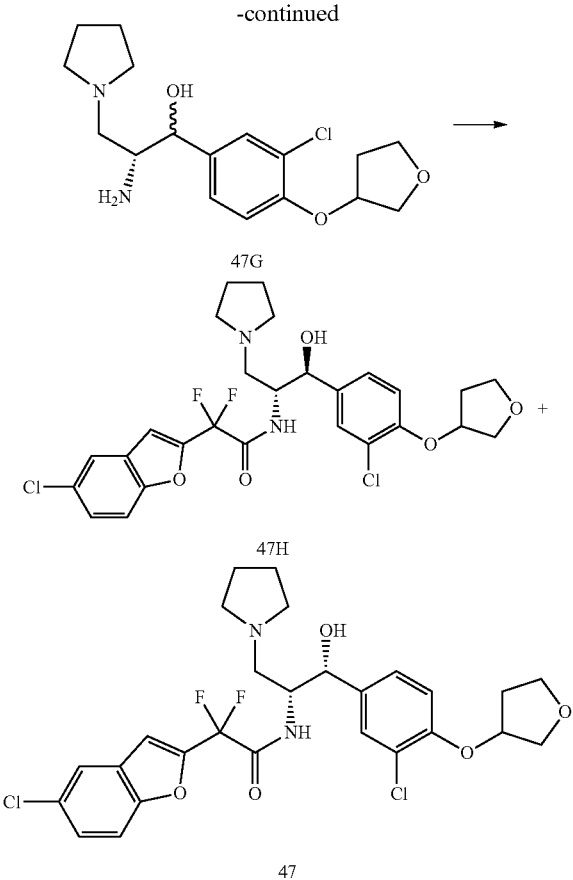

47G

47H

47

To a solution of Compound 47A (12.6 g, 45.5 mmol) in THF (300 mL) was added n-BuLi (18.3 mL) at −60° C. under $N_2$ and it was stirred for 0.5 h, and then slowly added A4 (6 g, 15.2 mmol) in THF (40 mL). The mixture was stirred at −60° C. for 1 h, and followed by the addition of saturate aq $NH_4Cl$ solution. It was extracted with ethyl acetate (300 mL×2), brine (200 mL), dried over $Na_2SO_4$. The crude product was purified by column chromatography on silica gel (ethyl acetate in petroleum, 10 v/v) to give Compound 47B (4 g, yield 50%) as a colorless oil. LC-MS (m/z): 534.2 [M+1]$^+$.

Compound 47B (4.05 g, 7.6 mmol) was dissolved in THF (48 mL) and cooled down to −80° C. under nitrogen atmosphere. L-Selectride (16 mL of 1M solution in THF, 15 mmol) was added dropwise while keeping the temperature at −80° C. After an hour, the reaction was quenched with saturate aq $NH_4Cl$ solution and then extracted with ethyl acetate (200 mL×2), washed with brine (200 mL), and dried over $Na_2SO_4$. The crude product was purified by column chromatography on silica gel (ethyl acetate in petroleum, 10% v/v) to give Compound 47C (3.2 g, 79%) as a colorless oil. LC-MS (m/z): 518.2 [M−17]$^+$.

A solution of Compound 47C (3.2 g, 5.98 mmol) in THF (40 mL) was added TBAF (780 mg, 3 mmol) at 0° C. The mixture was stirred at rt overnight, condensed by removal of solvents, and added water (150 mL). It was extracted with ethyl acetate (250 mL×2), washed with brine (100 mL), dried over $Na_2SO_4$, concentrated. The residue was suspended in a solution of ethyl acetate in petroleum (10% v/v). filtration of the suspension gave Compound 47D (2.25 g, yield 89%) as a white solid. LC-MS (m/z): 422.1 [M+1]$^+$.

A solution of Compound 47D (2.25 g, 5.34 mmol) in THF (120 mL) was added $Et_3N$ (1.63 g, 16 mmol) and MsCl (1.08 g, 9.43 mmol) slowly at −15° C. The mixture was stirred about half an hour, and then diluted water, extracted with ethyl acetate (200 mL×2), washed with brine (150 mL), dried over $Na_2SO_4$, and concentrated to render Compound 47E (2.3 g, crude), which was used for the next step without further purification. LC-MS (m/z): 482 [M−17]$^+$.

To a solution of Compound 47E (2.3 g, 4.61 mmol) in THF (60 mL) was added pyrrolidine (3.5 g, 49 mmol). The reaction mixture was allowed to warm up to rt and then heated at 50° C. overnight. The crude product was purified by column chromatography on silica gel (methanol in dichloromethane, 5% v/v) to give Compound 47F (0.52 g, yield 23.8%). LC-MS (m/z): 475 [M+1]$^+$.

To a solution of Compound 47F (520 mg, 1.1 mmol) in ethanol (12 mL) and water (2 mL) was added $LiOH \cdot H_2O$ (197 mg, 4.68 mmol). The mixture was stirred at 80° C. overnight, and then diluted water, extracted with DCM (150 mL×2), washed with brine (150 mL), dried over $Na_2SO_4$, and concentrated to afford Compound 47G (360 mg, crude), which was used for the next step without further purification. LC-MS (m/z): 341.2 [M+1]$^+$.

A mixture of Compound 11E (149 mg, 0.60 mmol), EDCI (175 mg, 0.9 mmol), HOBt (150 mg, 1.1 mmol), Compound 47G (206 mg, 0.60 mmol) in DCM (10 mL) was stirred at rt overnight. The mixture was added water, extracted with DCM (150 mL×2), washed with brine (100 mL), dried over $Na_2SO_4$, and concentrated. The crude product was purified by prep-HPLC and followed by chiral-prep-HPLC to give Compound 47H (13 mg, yield 4%) as a white solid and Compound 47 (31 mg, 10.5%) as a white solid. For Compound 47H, LC-MS (m/z): 569.2 [M+1]$^+$; $^1$H NMR (CDCl$_3$, 400 MHz) major characteristic peaks: δ (ppm) 2.05-2.81 (m, 6H), 2.78-2.89 (m, 5H), 3.21-3.22 (d, J=4.0 Hz, 1H), 3.62 (s, 1H), 3.75 (S, 1H), 3.90-4.02 (m, 5H), 4.50 (s, 1H), 4.77 (s, 1H), 4.90 (s, 1H), 6.63-6.66 (dd, J$_1$=5.2 Hz, J$_2$=8.0 Hz, 1H), 6.80-6.81 (d, J=4.8 Hz, 1H), 7.17-7.19 (d, J=8.0 Hz, 1H), 7.30-7.32 (m, 1H), 7.38-7.41 (dd, J$_1$=3.2 Hz, J$_2$=8.0 Hz, 1H), 7.44-7.46 (d, J=6.4 Hz, 1H), 7.55-7.56 (m, 1H), 9.14 (s, 1H), 11.57 (s, 1H). For Compound 47, LC-MS (m/z): 569.2 [M+1]$^+$; $^1$H NMR (CDCl$_3$, 400 MHz) major characteristic peaks: δ (ppm) 2.02-2.11 (m, 6H), 2.97-3.02 (m, 2H), 3.50 (s, 1H), 3.69-4.12 (m, 9H), 4.56 (m, 1H), 4.71 (s, 1H), 5.10 (s, 1H), 6.55-6.57 (d, J=8.0 Hz, 1H), 6.63-6.65 (d, J=7.6 Hz, 1H), 7.09-7.11 (d, J=7.2 Hz, 1H), 7.31-7.40 (m, 3H), 7.55 (Is, 1H), 8.06 (s, 1H), 11.48 (s, 1H).

Example 48

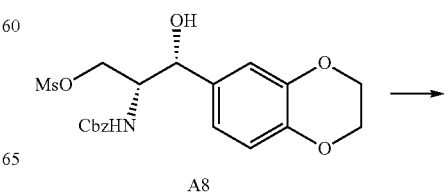

A8

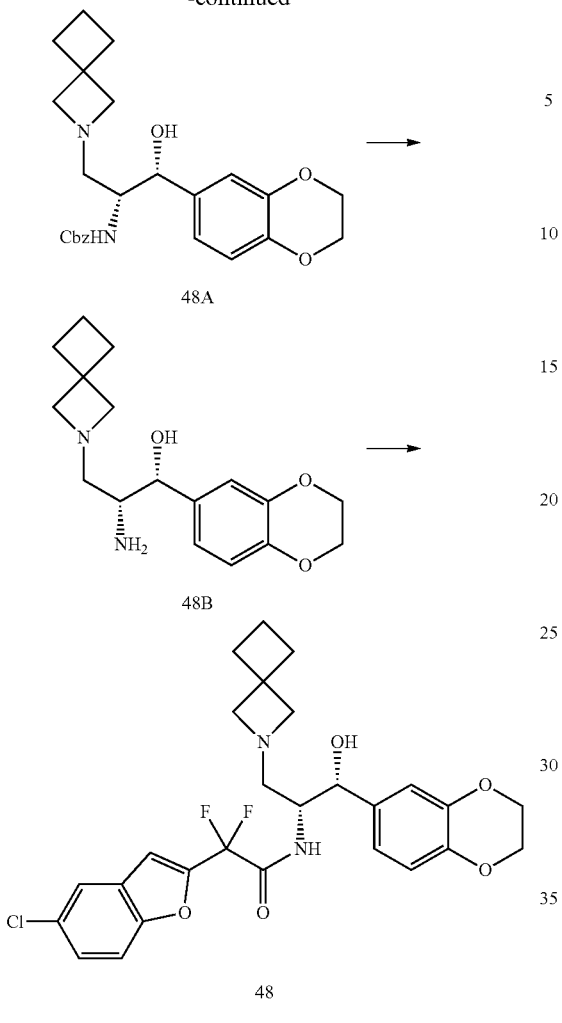

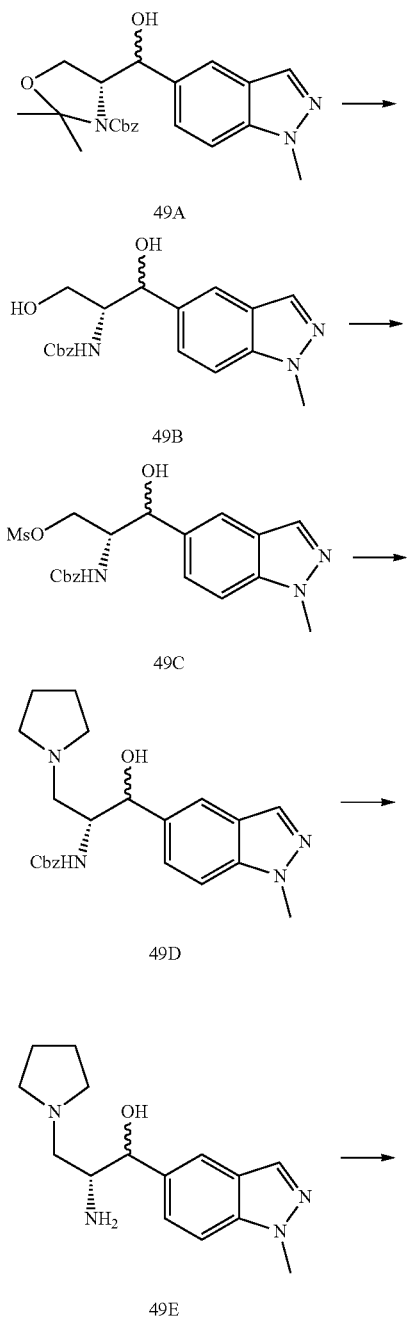

4.06-4.19 (m, 4H), 4.28-4.38 (m, 3H), 5.01 (s, 1H), 6.74-6.81 (m, 4H), 7.34-7.7.36 (m, 1H), 7.42-7.44 (m, 1H), 7.58-7.58 (m, 1H), 7.84-7.86 (m, 1H), 12.29-12.30 (m, 1H).

Example 49

To a solution of 2-azaspiro [3.3] heptane (100 mg, 1.0 mmol) in CH$_3$CN (10 mL) was added K$_2$CO$_3$ (414 mg, 3.0 mmol) and Compound A6 (437 mg, 1.0 mmol). The reaction mixture was stirred at reflux overnight. It was poured into ice-water, extracted with ethyl acetate (20 mL×2), washed with brine (20 mL×1), dried over Na$_2$SO$_4$, and concentrated to afford the Compound 48A (180 mg, yield 40%) as a yellow liquid. LC-MS (m/z): 439 [M+1]$^+$.

To a solution of Compound 48A (180 mg, 0.4 mmol) in EtOH (3 mL) was added LiOH.H$_2$O (84 mg, 2.0 mmol) in water (1 mL) and the mixture was stirred at reflux overnight. The mixture was diluted with H$_2$O (30 mL), extracted by ethyl acetate (30 mL×3), washed with brine (20 mL), dried by Na$_2$SO$_4$, and concentrated to render Compound 48B (100 mg, yield 80%) as a yellow oil. LC-MS (m/z): 305 [M+1]$^+$.

A mixture of Compound 11E (81 mg, 0.3 mmol), EDCI (76 mg, 0.4 mmol), HOBt (54 mg, 0.4 mmol), Compound 48B (100 mg, 0.3 mmol) in DCM (5 mL) was stirred at 28° C. overnight. After the addition of sat. aq NaHCO$_3$ (100 mL), the mixture was extracted with DCM (30 mL×2), washed with brine (30 mL×1), dried over Na$_2$SO$_4$, and concentrated. The crude product was purified by prep-HPLC to give Compound 48 (14 mg, yield 8%) as a white solid. LC-MS (m/z): 533 [M+1]$^+$; $^1$H-NMR (CDCl$_3$, 400 MHz) major characteristic peaks: δ (ppm) 1.83-1.88 (m, 2H), 2.15 (s, 2H), 2.34 (s, 2H), 3.34 (s, 2H), 3.78-3.84 (m, 2H),

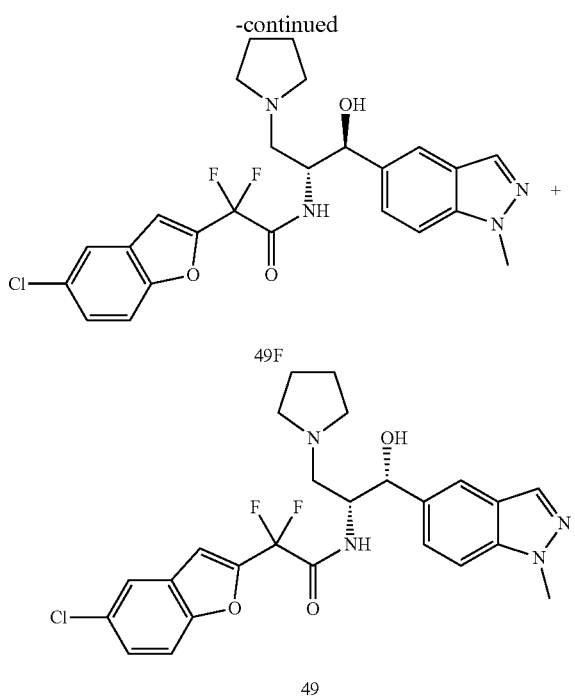

To a solution of 5-bromo-1-methyl-1H-indazole (3.2 g, 15 mmol) in THF (50 mL) was added n-BuLi (7.2 mL, 2.5 M) under $N_2$ at -60° C. The mixture was stirred for 1 h, Compound 8C (1.3 g, 5 mmol) in THF (10 mL) was added. After stirred at rt for 3 h, the mixture was diluted with aq $NH_4Cl$ (40 mL) solution, extracted with ethyl acetate (50 mL×2), washed with brine (100 mL×2), and evaporated. The crude product was purified by column chromatography on silica gel (ethyl acetate in petroleum ether, 30% v/v) to give Compound 49A (1.0 g, yield 51%) as a colorless oil. LC-MS (m/z): 396 [M+1]$^+$.

A solution of Compound 49A (0.5 g, 1.3 mmol) in THF (20 mL) and 1 N aq HCl (4 mL) was stirred at rt for 5 h. The mixture was quenched with water (10 mL), extracted with ethyl acetate (20 mL×2), washed with brine (30 mL×2), and evaporated to remove the solvents. The crude product was purified by column chromatography on silica gel (ethyl acetate in petroleum ether, 50% v/v) to give Compound 49B (374 mg, yield 81%) as a colorless oil. LC-MS (m/z): 356 [M+1]$^+$.

To a solution of Compound 49B (1 g, 2.8 mmol) in THF (25 mL) was added triethylamine (0.44 g, 4.4 mmol) and MsCl (0.4 g, 3.5 mmol) under $N_2$ at -40° C. The mixture was stirred at this temperature for 3 h, quenched with water (40 mL), extracted with ethyl acetate (50 mL×3), washed with brine (100 mL×2), NS evaporated to dryness. The crude product was purified by column chromatography on silica gel (ethyl acetate in petroleum ether, 50% v/v) to give Compound 49C (0.87 g, yield 72%) as a colorless oil. LC-MS (m/z): 416 [M-17]$^+$.

To a solution of Compound 49C (0.8 g, 1.8 mmol) in THF (25 mL) was added pyrrolidine (1.3 g, 18 mmol). The mixture was stirred at 60° C. overnight, quenched with water (40 mL), extracted with ethyl acetate (50 mL×3), washed with brine (100 mL×2), and evaporated to dryness. The crude product was purified by column chromatography on silica gel (ethyl acetate in petroleum ether, 50% v/v) to give Compound 49D (0.4 g, yield 55%) as colorless oil. LC-MS (m/z): 409 [M+1]$^+$.

A solution of Compound 49D (0.4 g, 1 mmol) and LiOH.H$_2$O (157 mg, 3.6 mmol) in ethanol (20 mL) was heated to reflux overnight. After the addition of water (40 mL), the mixture was extracted with ethyl acetate (50 mL×3), washed with brine (100 mL×2), evaporated to give Compound 49E (247 mg, yield 90%) as a colorless oil. LC-MS (m/z): 275 [M+1]$^+$.

To a solution of Compound 49E (0.2 g, 0.73 mmol) in dichloromethane (15 mL) was added Compound 11E (222 mg, 0.9 mmol), EDCI (216 mg, 1.13 mmol), HOBt (152 mg, 1.13 mmol). The mixture was stirred at rt overnight, quenched with water (20 mL), extracted with dichloromethane (20 mL×2), washed with brine (50 mL×2), and evaporated to dryness. The crude product was purified by prep-HPLC and followed by chira-prepl-HPLC to give two isomers Compound 49F (5 mg) as white solid and Compound 49 (5 mg) as white solid. For Compound 49F, LC-MS (m/z): 503 [M+1]$^+$, $^1$H-NMR (DMSO-d$_6$, 400 MHz) major characteristic peaks: δ (ppm) 1.88 (m, 4H), 3.14 (m, 2H), 3.58 (m, 2H), 3.68 (m, 1H), 3.92 (s, 3H), 4.44 (m, 1H), 4.66 (m, 1H), 6.12 (s, 2H), 7.47 (m, 5H), 7.63 (s, 1H), 7.92 (s, 1H), 9.27 (s, 1H), 9.70 (s, 1H); For Compound 49, LC-MS (m/z): 503 [M+1]$^+$, $^1$H-NMR (DMSO-d$_6$, 400 MHz) major characteristic peaks: δ (ppm) 2.0 (m, 6H), 3.17 (m, 3H), 3.50 (m, 3H), 3.98 (m, 4H), 4.60 (s, 1H), 4.96 (s, 1H), 6.05 (s, 1H), 6.69 (s, 1H), 7.57 (m, 9H), 7.88 (s, 1H), 8.92 (s, 1H), 9.65 (s, 1H).

Example 50

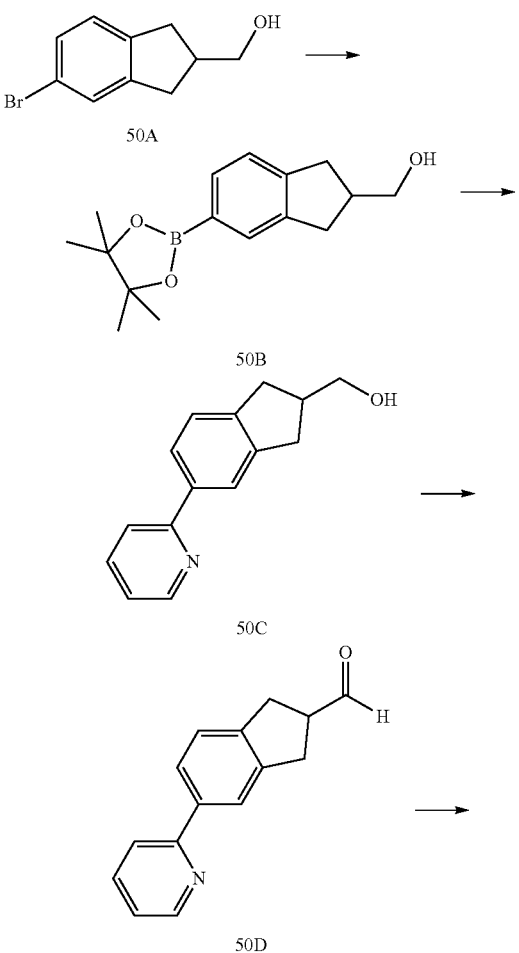

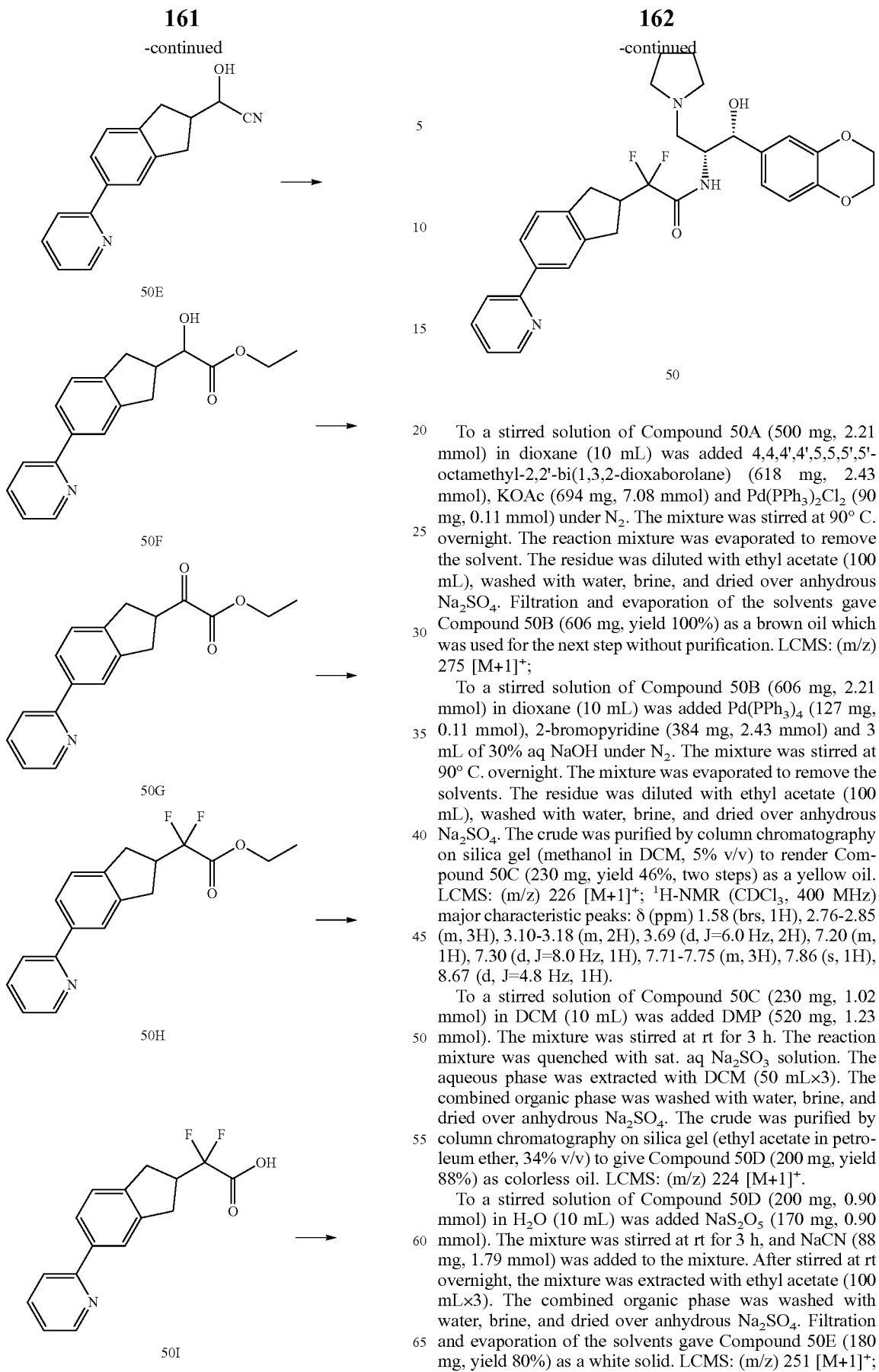

To a stirred solution of Compound 50A (500 mg, 2.21 mmol) in dioxane (10 mL) was added 4,4,4',4',5,5,5',5'-octamethyl-2,2'-bi(1,3,2-dioxaborolane) (618 mg, 2.43 mmol), KOAc (694 mg, 7.08 mmol) and Pd(PPh$_3$)$_2$Cl$_2$ (90 mg, 0.11 mmol) under N$_2$. The mixture was stirred at 90° C. overnight. The reaction mixture was evaporated to remove the solvent. The residue was diluted with ethyl acetate (100 mL), washed with water, brine, and dried over anhydrous Na$_2$SO$_4$. Filtration and evaporation of the solvents gave Compound 50B (606 mg, yield 100%) as a brown oil which was used for the next step without purification. LCMS: (m/z) 275 [M+1]$^+$;

To a stirred solution of Compound 50B (606 mg, 2.21 mmol) in dioxane (10 mL) was added Pd(PPh$_3$)$_4$ (127 mg, 0.11 mmol), 2-bromopyridine (384 mg, 2.43 mmol) and 3 mL of 30% aq NaOH under N$_2$. The mixture was stirred at 90° C. overnight. The mixture was evaporated to remove the solvents. The residue was diluted with ethyl acetate (100 mL), washed with water, brine, and dried over anhydrous Na$_2$SO$_4$. The crude was purified by column chromatography on silica gel (methanol in DCM, 5% v/v) to render Compound 50C (230 mg, yield 46%, two steps) as a yellow oil. LCMS: (m/z) 226 [M+1]$^+$; $^1$H-NMR (CDCl$_3$, 400 MHz) major characteristic peaks: δ (ppm) 1.58 (brs, 1H), 2.76-2.85 (m, 3H), 3.10-3.18 (m, 2H), 3.69 (d, J=6.0 Hz, 2H), 7.20 (m, 1H), 7.30 (d, J=8.0 Hz, 1H), 7.71-7.75 (m, 3H), 7.86 (s, 1H), 8.67 (d, J=4.8 Hz, 1H).

To a stirred solution of Compound 50C (230 mg, 1.02 mmol) in DCM (10 mL) was added DMP (520 mg, 1.23 mmol). The mixture was stirred at rt for 3 h. The reaction mixture was quenched with sat. aq Na$_2$SO$_3$ solution. The aqueous phase was extracted with DCM (50 mL×3). The combined organic phase was washed with water, brine, and dried over anhydrous Na$_2$SO$_4$. The crude was purified by column chromatography on silica gel (ethyl acetate in petroleum ether, 34% v/v) to give Compound 50D (200 mg, yield 88%) as colorless oil. LCMS: (m/z) 224 [M+1]$^+$.

To a stirred solution of Compound 50D (200 mg, 0.90 mmol) in H$_2$O (10 mL) was added NaS$_2$O$_5$ (170 mg, 0.90 mmol). The mixture was stirred at rt for 3 h, and NaCN (88 mg, 1.79 mmol) was added to the mixture. After stirred at rt overnight, the mixture was extracted with ethyl acetate (100 mL×3). The combined organic phase was washed with water, brine, and dried over anhydrous Na$_2$SO$_4$. Filtration and evaporation of the solvents gave Compound 50E (180 mg, yield 80%) as a white solid. LCMS: (m/z) 251 [M+1]$^+$; $^1$H-NMR (CDCl$_3$, 400 MHz) major characteristic peaks: δ

(ppm) 2.86-3.03 (m, 3H), 3.15-3.18 (m, 3H), 4.28 (d, J=4.2 Hz, 1H), 7.30 (m, 2H), 7.65-7.69 (m, 2H), 7.77-7.80 (m, 2H), 8.70 (d, J=2.8 Hz, 1H).

A solution of Compound 50E (1.88 g, 7.52 mmol) in ethanol (80 mL) was bubbled with a gentle stream of HCl gas (dried over conc H$_2$SO$_4$) for 6 h and left to stand overnight at 4° C. The mixture was added water (30 mL) and stirred at 80° C. for 2 h. After cooled down to rt, the mixture was extracted with ethyl acetate (100 mL×3). The combined organic phase was washed with water, brine, and dried over anhydrous Na$_2$SO$_4$, and purified by column chromatography on silica gel (methanol in dichloromethane, 3% v/v) to yield Compound 50F (1.17 g, yield 52%) as a yellow solid. LCMS: (m/z) 298 [M+1]$^+$.

To a stirred solution of Compound 50F (210 mg, 0.71 mmol) in DCM (11 mL) was added NaHCO$_3$ (119 mg, 1.41 mmol), and DMP (360 mg, 0.85 mmol) at 0° C. The mixture was stirred at 0° C. for one hour. The reaction mixture was quenched with sat. aq Na$_2$SO$_3$ solution. The aqueous phase was extracted with DCM (50 mL×3). The combined organic phase was washed with water, brine, and dried over anhydrous Na$_2$SO$_4$. The crude was purified by column chromatography on silica gel (methanol in dichloromethane, 3% v/v) to afford Compound 50G (180 mg, yield 86%) as yellow oil. LCMS: (m/z) 224 [M+1]$^+$.

To a stirred solution of Compound 50G (233 mg, 0.79 mmol) in DCM (10 mL) was added DAST (720 mg, 4.47 mmol). The mixture was stirred at rt overnight. After cooled down to rt, the mixture was poured into water and then extracted with ethyl acetate (100 mL×3). The combined organic phase was washed with water, brine, and dried over anhydrous Na$_2$SO$_4$, purified by column chromatography on silica gel (methanol in dichloromethane, 5% v/v) to give Compound 50H (140 mg, yield 56%) as a yellow oil. LCMS: (m/z) 318 [M+1]$^+$.

To a stirred solution of Compound 50H (140 mg, 0.44 mmol) in THF (10 mL) was added LiOH.H$_2$O (37 mg, 0.88 mmol) and water (2 mL). The mixture was stirred at rt for 3 h. The mixture was acidified to pH 1 with 1M HCl and evaporated. The aqueous phase was extracted with ethyl acetate (50 mL×3). The combined organic phase was washed with water, brine, and dried over anhydrous Na$_2$SO$_4$, concentrated to give Compound 50I (110 mg, yield 86%) as a yellow oil. LCMS: (m/z) 290 [M+1]$^+$.

To a solution of Compound 50I (110 mg, 0.38 mmol) in DCM (10 mL) was added EDCI (110 mg, 0.57 mmol), HOBt (77 mg, 0.57 mmol), Intermediate A (106 mg, 0.38 mmol). Then it was stirred at rt overnight. The mixture was added DCM (20 mL), washed with water (50 mL×2) and brine (50 mL×1), dried over anhydrous Na$_2$SO$_4$, concentrated, and purified by prep-HPLC twice to give Compound 50 (1.6 mg, yield 1%) as a colorless oil. LC-MS (m/z): 550 [M+1]$^+$; $^1$H-NMR (CDCl$_3$, 400 MHz) major characteristic peaks: δ (ppm) 1.95 (m, 4H), 2.68-2.96 (m, 5H), 3.29-3.38 (m, 2H), 3.76 (s, 2H), 4.11 (s, 4H), 4.37 (s, 1H), 5.08 (m, 1H), 5.28 (s, 1H), 6.79-6.85 (m, 3H), 7.30 (s, 1H), 7.47 (m, 1H), 7.65 (m, 3H), 7.92 (m, 1H), 8.24 (m, 1H), 8.96 (m, 1H), 11.79 (s, 1H).

Example 51

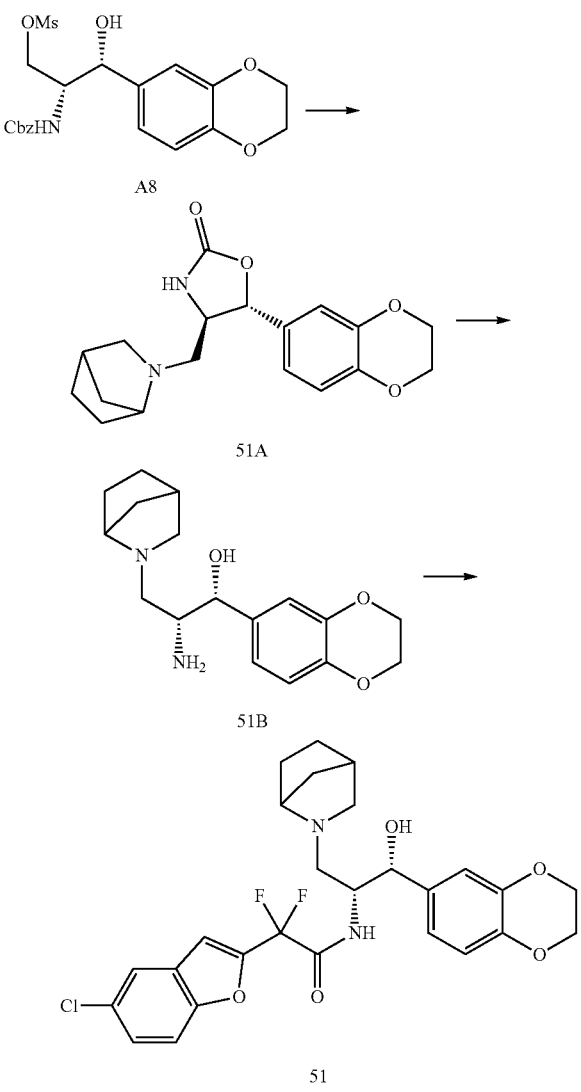

To a solution of 2-azabicyclo [2.2.1] heptane (132 mg, 1 mmol) in MeCN (10 mL) was added K$_2$CO$_3$ (69 mg, 0.5 mmol) and Compound A8 (219 mg, 0.5 mmol). The mixture was stirred at 70° C. for 48 h. After evaporation to remove solvents, the residue was dissolved in H$_2$O, extracted with ethyl acetate; the combined organic layers were dried over anhydrous Na$_2$SO$_4$. After filtration and evaporation, a crude Compound 51A (210 mg) was obtained as an oil, which was used for the next step directly. LCMS (m/z): 331 [M+1]$^+$.

To a solution of Compound 51A (210 mg, 0.64 mmol) in EtOH (9 mL) and H$_2$O (9 mL) was added LiOH.H$_2$O (267 mg, 6.4 mmol). The reaction mixture was refluxed for 24 h. After removal of the solvents, the residue was dissolved in H$_2$O, extracted with ethyl acetate, and dried over Na$_2$SO$_4$ to give Compound 51B (190 mg), which was used for the next step without purification. LCMS (m/z): 305 [M+1]$^+$.

To a solution of Compound 51B (91 mg, 0.3 mmol) in DCM (12 mL) was added Compound 11E (111 mg, 0.45 mmol), HOBt (61 mg, 0.45 mmol) and EDCI (86 mg, 0.45 mmol). The mixture was stirred for 12 h at 25° C. The mixture was washed with brine and dried over anhydrous Na$_2$SO$_4$. After filtration and evaporation, the residue was purified by prep-HPLC to give Compound 51 (38 mg, yield 19%) as a white solid. LC-MS (m/z): 507 [M+1]$^+$; $^1$H-NMR (CDCl$_3$, 400 MHz) major characteristic peaks: δ (ppm) 1.52-1.90 (m, 4H), 2.04-2.24 (m, 1H), 2.57-2.98 (m, 2H), 3.30-3.72 (m, 3H), 4.07-4.50 (m, 8H), 5.01-5.16 (m, 1H), 6.68-6.83 (m, 4H), 7.33-7.35 (m, 1H), 7.42-7.44 (m, 1H), 7.57 (d, J=1.2 Hz, 1H), 8.02-8.17 (m, 1H), 10.21-10.33 (m, 1H).

Example 52

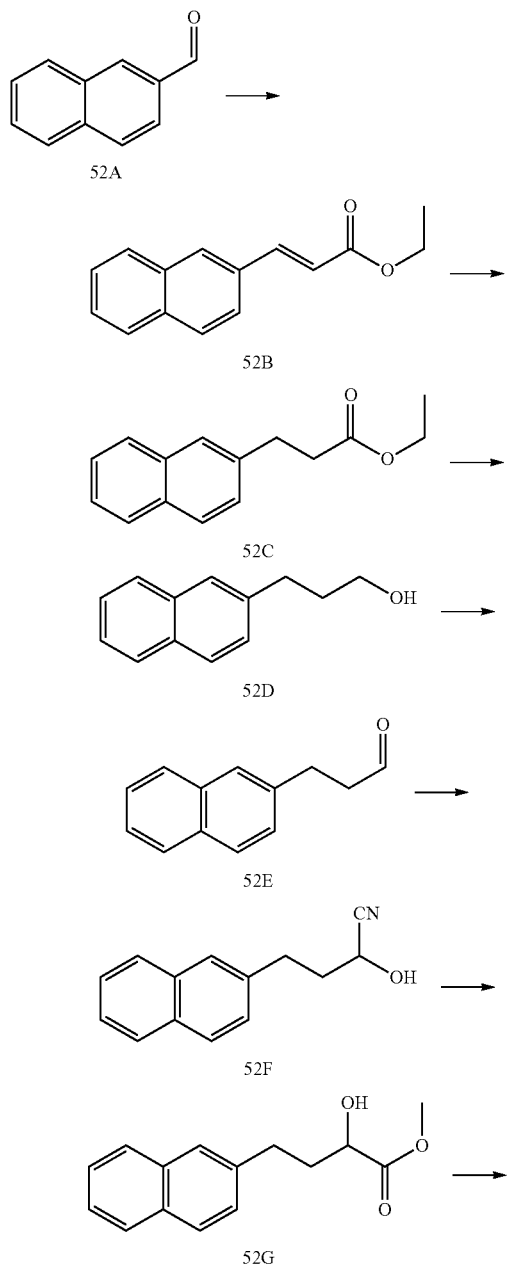

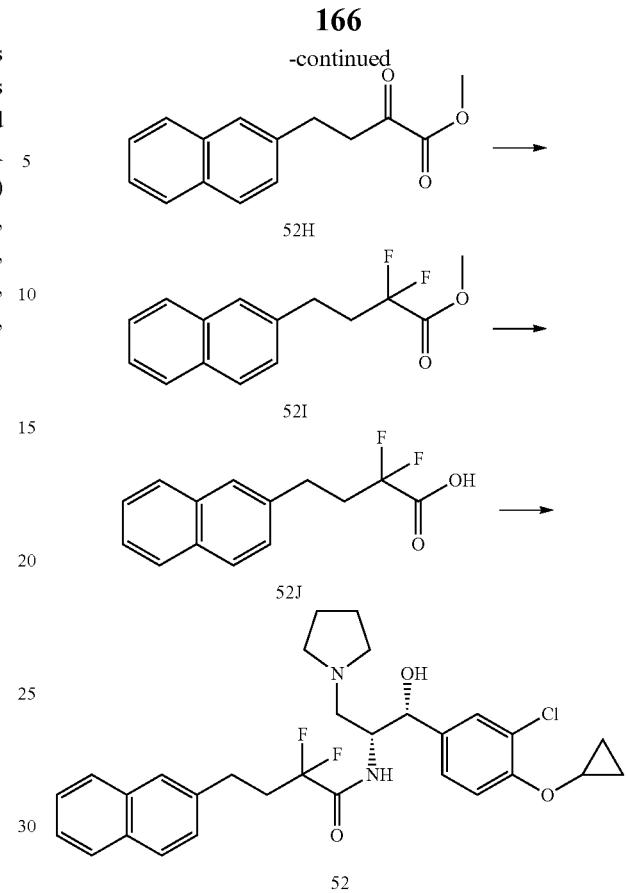

To a solution of ethyl 2-(diethoxyphosphoryl) acetate (10.77 g, 48.08 mmol) in THF (50 mL) was added t-BuOK (5.38 g, 48.08 mmol) at room temperature. After stirred for 30 min, Compound 52A (5.00 g, 32.05 mmol) was added. The mixture was stirred at room temperature overnight. It was diluted with ethyl acetate (200 mL), washed with water and brine, and purified with silica gel column chromatography (ethyl acetate in petroleum ether, 10% v/v) to render Compound 52B (6.60 g, yield 91%) as a colorless oil. LC-MS (m/z): 227 [M+1]$^+$; $^1$H-NMR (CDCl$_3$, 400 MHz) major characteristic peaks: δ (ppm) 1.36 (t, J=7.2 Hz, 3H), 426-4.32 (m, 2H), 6.55 (d, J=15.6 Hz, 1H), 7.5-7.53 (m, 2H), 7.65-7.69 (m, 1H), 7.83-7.87 (m, 4H).

A suspension of Pd/C (1.00 g, 10%) and Compound 52B (7.30 g, 32.0 mmol) in MeOH (100 mL) was stirred at room temperature overnight under H$_2$. The mixture was filtered to remove Pd/C. The filtrate was evaporated to yield Compound 52C (7.30 g, yield 100%) as a colorless oil. LC-MS (m/z): 229 [M+1]$^+$; $^1$H-NMR (CDCl$_3$, 400 MHz) major characteristic peaks: δ (ppm) 1.23 (t, J=7.2 Hz, 3H), 2.71 (t, J=7.6 Hz, 2H), 3.12 (t, J=8.4 Hz, 2H), 4.10-4.16 (m, 2H), 7.34 (d, J=7.6 Hz, 1H), 7.40-7.47 (m, 2H), 7.64 (s, 1H), 7.76-7.81 (m, 3H).

To a solution of Compound 52C (7.30 g, 32.02 mmol) in dry THF (80 mL) was added LiAlH$_4$ (1.20 g, 32.0 mmol) at 0° C. Then it was warmed to room temperature and stirred for 2 h. It was added with Na$_2$SO$_4$.10H$_2$O and filtered to remove the solid. The filtrate was evaporated to give Compound 52D (6.10 g, yield 100%) as a colorless oil. LC-MS (m/z): 187 [M+1]$^+$; $^1$H-NMR (CDCl$_3$, 400 MHz) major characteristic peaks: δ (ppm) 1.95-2.02 (m, 2H), 2.88 (t, J=8.0 Hz, 2H), 3.72 (t, J=6.8 Hz, 2H), 7.33 (d, J=7.2 Hz, 1H), 7.39-7.47 (m, 2H), 7.63 (s, 1H), 7.76-7.81 (m, 3H).

A mixture of Compound 52D (16 g, 86 mmol) in DCM (300 mL) was added DMP (43 g, 103 mmol) at room temperature. Then it was stirred at room temperature for 1 h. The mixture was diluted with EA (400 mL), filtered to remove solid, washed with water and brine, and purified by silica gel column chromatography (ethyl acetate in petroleum ether, 20% v/v) to afford Compound 52E (14 g, yield 88%) as a colorless oil. LC-MS (m/z): 185 [M+1]+.

A mixture of Compound 52E (8.00 g, 43.4 mmol) and 2NaO$_5$S$_2$ (8.3 g, 43.4 mmol) in water/dioxane (100/20 mL) was stirred at room temperature for 2 h. Then NaCN (4 g, 86.95 mmol) was added. The mixture was stirred at room temperature overnight. It was diluted with ethyl acetate (200 mL), washed with water and brine, and purified by silica gel column chromatography (ethyl acetate in petroleum ether, 50% v/v) to give Compound 52F (6.6 g, yield 72%) as a colorless oil. LC-MS (m/z): 212 [M+1]+; $^1$H-NMR (DMSO-d$_6$, 400 MHz) major characteristic peaks: δ (ppm) 2.07-2.13 (m, 2H), 2.87-2.91 (m, 2H), 4.50-4.55 (m, 1H), 6.48-6.49 (d, J=4 Hz, 1H), 7.40-7.51 (m, 3H), 7.73 (s, 1H), 7.85-7.89 (m, 3H).

A solution of Compound 52F (6.6 g, 31.27 mmol) in MeOH (150 mL) was bubbled with a gentle stream of HCl gas at room temperature for 6 h. Then it was quenched with H$_2$O (30 mL) and stirred at room temperature for 1 h. The mixture was diluted with ethyl acetate (300 mL), washed with water and brine, dried with anhydrous Na$_2$SO$_4$, and evaporated to give Compound 52G (6.7 g, yield 87%) as colorless oil. LC-MS (m/z): 245 [M+1]+; $^1$H-NMR (DMSO-d$_6$, 400 MHz) major characteristic peaks: δ (ppm) 1.91-2.03 (m, 2H), 2.81-2.85 (t, J=8 Hz, 2H), 3.64 (s, 3H), 5.54-5.55 (m, 1H), 7.37-7.39 (m, 1H), 7.42-7.50 (m, 2H), 7.69 (s, 1H), 7.83-7.87 (t, J=8 Hz, 3H).

To a solution of Compound 52G (6.7 g, 27.46 mmol) in DCM (50 mL) was added DMP (14 g, 33 mmol). The mixture was stirred at room temperature for 2 h. Then it was diluted with ethyl acetate (150 mL), filtered to remove the solid, washed with water and brine, dried over anhydrous Na$_2$SO$_4$, and purified by silica gel column chromatography (ethyl acetate in petroleum ether, 30% v/v) to yield Compound 52H (5 g, yield 75%) as a colorless oil. LC-MS (m/z): 243 [M+1]+; $^1$H-NMR (DMSO-d$_6$, 400 MHz) major characteristic peaks: δ (ppm) 2.98-3.02 (t, J=8 Hz, 2H), 3.24-3.28 (t, J=8 Hz, 2H), 3.77 (s, 3H), 7.39-7.48 (m, 3H), 7.71 (s, 1H), 7.82-7.87 (m, 3H).

To a solution of Compound 52H (2.0 g, 8.26 mmol) in DCM (50 mL) was added DAST (3 mL, 41.3 mmol) at room temperature. The mixture was stirred at room temperature overnight. Then it was diluted with ethyl acetate (150 mL), washed with saturated NaHCO$_3$, water and brine, and purified by silica gel column chromatography (ethyl acetate in petroleum ether, 40% v/v) to afford Compound 52I (2.0 g, yield 91%) as a white solid. LC-MS (m/z): 265 [M+1]+.

A mixture of Compound 52I (2.5 g, 4.47 mmol) and LiOH.H$_2$O (1.2 g, 28.4 mmol) in THF/MeOH/H$_2$O (10/10/4 mL) was stirred at room temperature for 2 h. Then it was adjusted to pH 6 with 1 M HCl aq solution. The mixture was diluted with ethyl acetate (150 mL), washed with water and brine, dried with anhydrous Na$_2$SO$_4$, and purified by silica gel column chromatography (ethyl acetate in petroleum ether, 30% v/v) to give Compound 52J (1.8 g, yield 75%) as a white solid. LC-MS (m/z): 251 [M+1]+; $^1$H-NMR (DMSO-d$_6$, 400 MHz) major characteristic peaks: δ (ppm) 2.45-2.49 (m, 2H), 2.88-2.92 (m, 2H), 7.42-7.50 (m, 3H), 7.76 (s, 1H), 7.84-7.88 (m, 3H).

A solution of Compound 11E (200 mg, 0.64 mmol), Compound 52J (241 mg, 0.96 mmol), EDCI (183 mg, 0.96 mmol) and HOBt (130 mg, 0.96 mmol) in DCM (15 mL) was stirred at room temperature overnight. Then it was diluted with ethyl acetate (150 mL), washed with water and brine, and purified by prep-HPLC to afford Compound 52 (108 mg, yield 30%) as a white solid. LC-MS (m/z): 543 [M+1]+; $^1$H-NMR (DMSO-d$_6$, 400 MHz) major characteristic peaks: δ (ppm) 0.41-0.44 (m, 2H), 0.54-0.59 (m, 2H), 1.87-1.88 (m, 2H), 2.01 (s, 2H), 2.16-2.27 (m, 2H), 2.49-2.71 (m, 2H), 3.10-3.15 (m, 2H), 3.46-3.61 (m, 5H), 4.47-4.48 (m, 1H), 4.82 (s, 1H), 6.01-6.02 (m, 1H), 7.24-7.34 (m, 3H), 7.38 (s, 1H), 7.45-7.51 (m, 2H), 7.65 (s, 1H), 7.83-7.89 (m, 3H), 8.41-8.44 (m, 1H), 9.52 (s, 1H).

Example 53

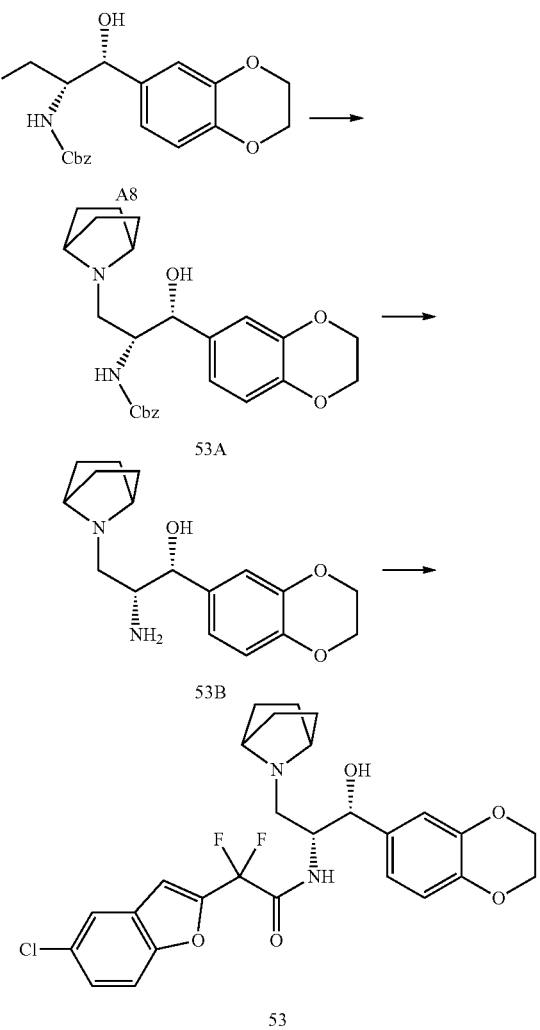

To a solution of Compound A8 (500 mg, 1.1 mmol) in THF (20 mL) was added 7-azabicyclo [2.2.1] heptane (1.1 g, 11 mmol) and stirred at 50° C. for 16 h. The mixture was added water (50 mL) and extracted with ethyl acetate (30 mL×3). The organic layer was washed with water (50 mL×3), brine (50 mL×1), dried over anhydrous Na$_2$SO$_4$, and concentrated to give Compound 53A (600 mg, crude) as a colorless oil. LCMS: 439 [M+1]+.

A mixture of Compound 53A (660 mg, crude), LiOH.H$_2$O (150 mg) in EtOH (30 mL) and H$_2$O (5 mL) was stirred at 100° C. for 16 h. The mixture was concentrated and added water (50 mL), and then extracted with DCM (30 mL×3), dried over anhydrous Na$_2$SO$_4$, and concentrated to give Compound 53B (400 mg, crude) as a colorless oil. LCMS: 305 [M+1]$^+$.

To a solution of Compound 11E (250 mg), EDCI (290 mg), HOBt (200 mg, 0.75 mmol) in DCM (10 mL) was added Compound 53B (400 mg, crude). The mixture was stirred at 25° C. for 24 h, added water (50 mL), extracted with DCM (30 mL×3), dried over anhydrous Na$_2$SO$_4$, and purified by prep-HPLC to give Compound 53 (15 mg, yield 2%) as a colorless oil. LCMS: 533 [M+1]$^+$; $^1$H-NMR (CDCl$_3$, 400 MHz) major characteristic peaks: δ (ppm) 1.69 (m, 4H), 2.14 (m, 4H), 3.35 (br, 1H), 3.47 (br, 1H), 4.11 (m, 5H), 4.49 (br, 2H), 5.06 (s, 1H), 6.78 (m, 4H), 7.33 (m, 1H), 7.41 (m, 1H), 7.58 (m, 1H), 8.10 (br, 1H), 10.58 (br, 1H).

Example 54

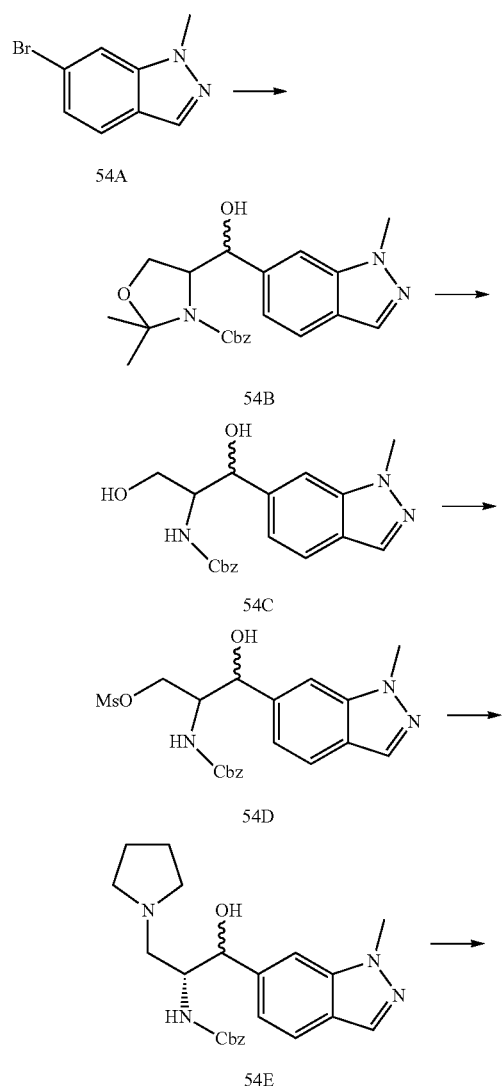

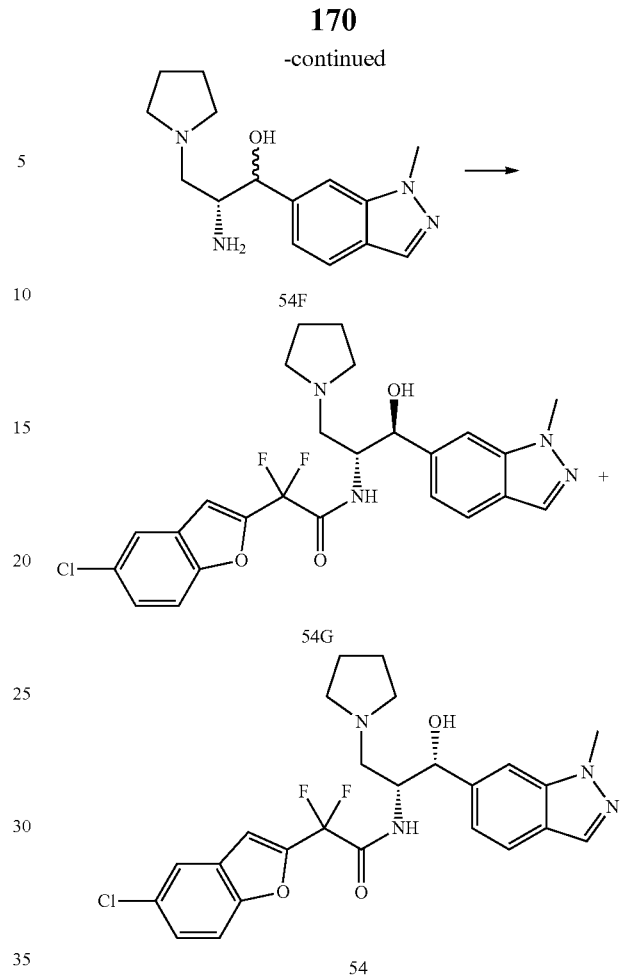

To a solution of Compound 54A (14.1 g, 19.4 mmol) in THF (15 mL) was added n-BuLi (8.1 mL, 19.4 mmol) carefully at −68° C. The mixture was stirred at −68° C. for 15 min, and then Compound 8C (1.70 g, 6.48 mmol) in THF (10 mL) was added. The mixture was stirred at −68° C. for 15 min before quenched with saturated aq NH$_4$Cl. It was diluted with ethyl acetate (100 mL), washed with water and brine, dried with anhydrous Na$_2$SO$_4$, and evaporated to give Compound 54B (1.90 g, yield 79%) as a light yellow oil. LC-MS (m/z): 396 [M+1]$^+$.

A mixture of Compound 54B (1.90 g, 4.81 mmol) in THF (5 mL) and hydrochloric acid (6 M, 5 mL) was stirred at 20° C. overnight. It was diluted with ethyl acetate (200 mL), washed with water and brine, purified by silica gel chromatography eluted with MeOH in DCM (from 0% to 5%, v/v) to render Compound 54C (500 mg, yield 48%) as a colorless oil. LC-MS (m/z): 356 [M+1]$^+$.

To a solution of Compound 54C (520 mg, 1.46 mmol) in THF (50 mL) was added dropwise MsCl (184 mg, 161 mmol) at −40° C. The mixture was stirred at −30° C. for 2 h. It was quenched with ice-water, diluted with ethyl acetate (200 mL), washed with water and brine, dried with anhydrous Na$_2$SO$_4$, and evaporated to give Compound 54D (500 mg, yield 79%) as a colorless oil. LC-MS (m/z): 434 [M+1]$^+$.

A mixture of Compound 54D (500 mg, 1.15 mmol) and pyrrolidine (3 mL) in THF (20 mL) was stirred at 50° C. overnight. It was evaporated to remove THF. The residue was diluted with ethyl acetate (150 mL), washed with water and brine, purified by silica gel chromatography (methanol in dichloromethane, from 0% to 8% v/v) to yield Compound 54E (120 mg) as a colorless oil. LC-MS (m/z): 409 [M+1]⁺.

A mixture of Compound 54E (120 mg, 0.29 mmol) in EtOH/H$_2$O (10/2 mL) was stirred at 85° C. overnight. It was diluted with ethyl acetate (150 mL), washed with water and brine, and purified by silica gel chromatography (methanol in dichloromethane, from 0% to 10% v/v) to give Compound 54F (90 mg, yield 100%) as a colorless oil. LC-MS (m/z): 275 [M+1]⁺.

The mixture of Compound 54F (90 mg, 0.33 mmol), EDCI (95 mg, 0.50 mmol), HOBt (68 mg, 0.50 mmol) and Compound 11E (81 mg, 0.33 mmol) in DCM (5 mL) was stirred at 20° C. overnight. It was diluted with ethyl acetate (150 mL), washed with water and brine, and purified by prep-HPLC to afford Compound 54G (20 mg) as a white solid and Compound 54 (15 mg) as a white solid. For Compound 54G, LC-MS (m/z): 503 [M+1]⁺; ¹H-NMR (MeOD, 400 MHz) major characteristic peaks: δ (ppm) 2.07 (s, 2H), 2.21 (s, 2H), 3.13-3.26 (m, 2H), 3.52-3.58 (m, 1H), 3.77-3.89 (m, 3H), 3.91 (s, 3H), 4.61-4.67 (m, 1H), 4.82 (d, J=5.2 Hz, 1H), 6.34 (s, 1H), 7.21-7.27 (m, 2H), 7.35-7.38 (m, 2H), 7.47 (s, 2H), 7.58 (d, J=8.8 Hz, 1H), 7.87 (s, 1H). For Compound 54, LC-MS (m/z): 503 [M+1]⁺; ¹H-NMR (MeOD, 400 MHz) major characteristic peaks: δ (ppm) 2.05 (s, 2H), 2.20 (s, 2H), 3.17-3.26 (m, 2H), 3.64-3.82 (m, 4H), 3.85 (s, 3H), 4.80 (d, J=5.2 Hz, 1H), 5.16 (s, 1H), 6.34 (s, 1H), 7.18-7.21 (m, 1H), 7.32-7.34 (m, 1H), 7.38-7.40 (m, 2H), 7.55-7.60 (m, 2H), 7.91 (s, 1H).

Example 55

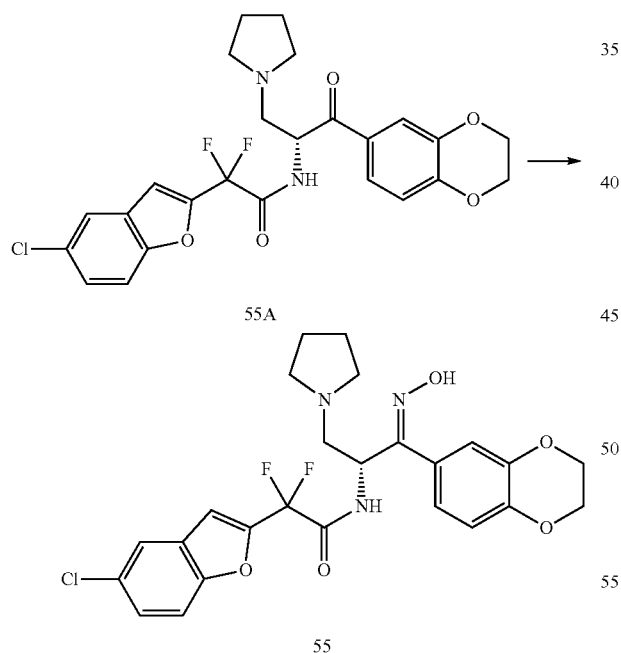

A solution of Compound 55A (100 mg, 0.2 mmol), hydroxylamine hydrochloride (41 mg, 0.6 mmol) in MeOH (5 mL) was stirred at 25° C. for 16 h. The mixture was diluted with saturation aq NaHCO$_3$ (15 mL) and extracted with EtOAc (15 mL×3). The combined organic layers were washed with brine (15 mL), dried over Na$_2$SO$_4$, and concentrated to give a crude product. The crude product was purified by prep-HPLC to give a trifluoroacetic acid salt of Compound 55 (1.6 mg, yield 1.3%) as a white solid. LC-MS (m/z): 520 [M+1]⁺; ¹H-NMR (CDCl$_3$, 400 MHz) major characteristic peaks: δ (ppm) 1.82 (s, 4H), 2.00-2.22 (m, 2H), 2.65-2.75 (m, 3H), 2.92-2.97 (m, 1H), 4.18-4.24 (m, 4H), 5.33-5.47 (m, 2H), 6.82-6.84 (m, 1H), 6.95 (s, 1H), 7.13-7.14 (m, 2H), 7.33-7.34 (m, 1H), 7.40-7.43 (m, 1H), 7.54-7.55 (m, 1H).

Example 56

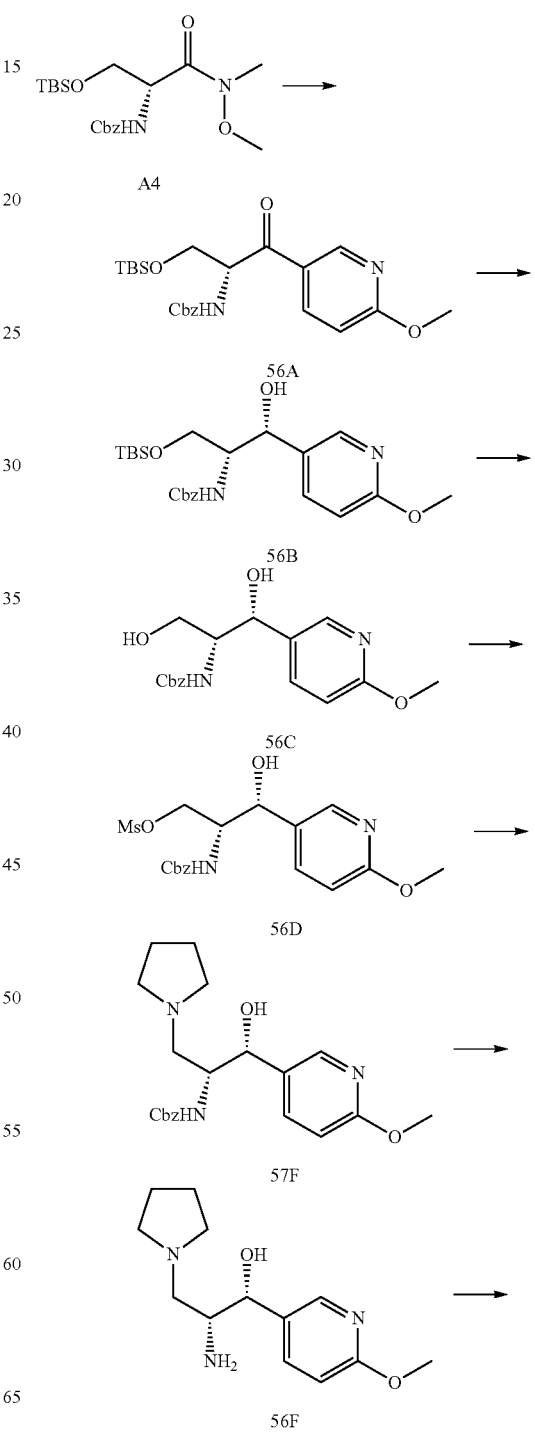

-continued

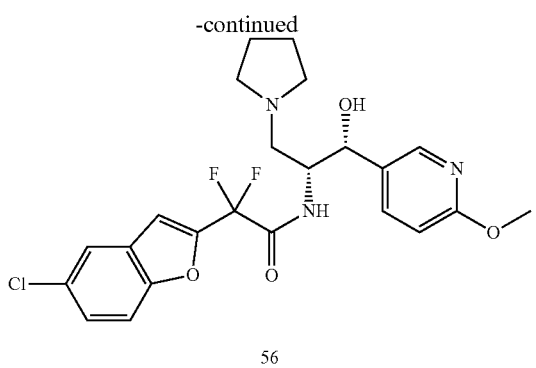

56

To a solution of 5-bromo-2-methoxypyridine (10 g, 53.2 mmol) in THF (200 mL) was added n-BuLi (2.5 M, 22 mL) at −60° C. under N₂. It was stirred for 0.5 h, and then a solution of Compound A4 (7.02 g, 17.7 mmol) in THF (50 mL) was added. The reaction mixture was stirred at −60° C. for an additional 1 h, before quenched with saturate aq NH₄Cl solution. It was extracted with ethyl acetate (100 mL×2), brine (100 mL), and dried over Na₂SO₄. The crude product was purified by column chromatography on silica gel (ethyl acetate in petroleum, 10% v/v) to give Compound 56A (7.5 g, yield 95%) as a colorless liquid. LC-MS (m/z): 445[M+1]⁺; ¹H-NMR (CDCl₃, 400 MHz) major characteristic peaks: δ (ppm) −0.13 (s, 3H), −0.11 (s, 3H), 0.75 (s, 9H), 3.88-3.92 (m, 1H), 3.99-4.00 (m, 1H), 4.02 (s, 3H), 5.14 (s, 2H), 5.29 (t, J=3.6 Hz, 1H), 5.93 (d, J=6.8 Hz, 1H), 6.81 (d, J=8.8 Hz, 1H), 7.37-7.38 (m, 5H), 8.13 (dd, J=2.0, 8.8 Hz, 1H), 8.80 (d, J=2.0 Hz, 1H).

Compound 56A (7.5 g, 16.9 mmol) was dissolved in anhydrous THF (500 mL) and cooled down −80° C. under nitrogen atmosphere. L-Selectride (33.8 mL, 1M solution in THF, 33.8 mmol) was added dropwise to the solution while keeping the temperature at −80° C. The reaction was stirred at −80° C. for 0.5 h before quenched with saturate aq NH₄Cl solution. It was extracted with ethyl acetate (100 mL×3). The combined organic phases were washed water and brine, and dried over Na₂SO₄. The crude product was purified by column chromatography on silica gel (ethyl acetate in petroleum, 20% v/v) to give Compound 56B (5.1 g, yield 68%) as a colorless oil. LC-MS (m/z): 447 [M+1]⁺; ¹H-NMR (CDCl₃, 400 MHz) major characteristic peaks: δ (ppm) −0.08 (s, 6H), 0.92 (s, 9H), 3.68 (m, 1H), 3.84 (m, 3H), 3.94 (s, 3H), 5.05 (m, 3H), 5.46 (d, J=7.6 Hz, 1H), 6.71 (d, J=8.4 Hz, 1H), 7.32-7.34 (m, 5H), 7.59 (d, J=8.4 Hz, 1H), 8.14 (s, 1H).

To a solution of Compound 56B (5.1 g, 11.4 mmol) in THF (120 mL) was added a solution of TBAF (1.49 g, 5.7 mmol) in THF (10 mL) at 0° C. The mixture was stirred at 25° C. overnight, and then evaporated to reduce the volume, added water (50 mL), extracted with ethyl acetate (100 mL×3), washed with brine, and dried over Na₂SO₄. The crude product was purified by column chromatography on silica gel (methanol in dichloromethane, 5% v/v) to give Compound 56C (3.42 g, yield 52%) as a colorless oil. LC-MS (m/z): 333 [M+1]⁺.

To a solution of Compound 56C (3.42 g, 8.58 mmol) in THF (100 mL) was added Et₃N (3.12 g, 30.9 mmol). The mixture was cooled to −40° C., and then MsCl (1.30 g, 11.3 mmol) was added slowly. It was stirred at −40° C. about half an hour before added pyrrolidine (3.78 g, 53.2 mmol). The reaction mixture was allowed to warm up to rt and then heated to 50° C. Stirred overnight, the mixture was added water (50 mL), extracted with ethyl acetate (50 mL×3), washed with brine (100 mL), and dried over Na₂SO₄. The crude product was purified by column chromatography on silica gel (methanol in dichloromethane, 3% v/v) and flash column (reverse-phase, 0.05% NH₄OH/MeOH, v/v) to give Compound 56D (800 mg, yield 39%) as white syrup. LC-MS (m/z): 386 [M+1]⁺.

To a solution of Compound 56D (400 mg, 1.04 mmol) in methanol (10 mL) was added Pd(OH)₂ (40 mg). The mixture was stirred at 25° C. under H₂ overnight. It was filtered and evaporated to give Compound 56E (260 mg, crude). LC-MS (m/z): 252 [M+1]⁺.

To a solution of Compound 56E (260 mg, 1.04 mmol) and Compound 11E (255 mg, 1.04 mmol) in DCM (10 mL) was added EDCI (298 mg, 1.55 mmol) and HOBt (210 mg, 1.55 mmol) under N₂. The mixture was stirred at 25° C. overnight. TLC showed the starting material was consumed completely; water was added to the mixture and then extracted with DCM (50 mL×3). The combined organic layers were washed with brine, dried over sodium sulfate, and concentrated to give a crude product. The crude product was purified by prep-HPLC to give Compound 56 (98.6 mg, yield 19%) as a white solid. LC-MS (m/z): 480 [M+1]⁺, ¹H-NMR (CDCl₃, 400 MHz) major characteristic peaks δ (ppm): 2.10 (s, 4H), 3.03 (s, 2H), 3.58-3.72 (m, 4H), 3.86 (s, 3H), 4.26 (s, 1H), 5.24 (m, 1H), 6.71 (s, 1H), 6.84 (s, 1H), 7.33 (d, J=8.4 Hz, 1H), 7.40 (d, J=8.4 Hz, 1H), 7.55 (s, 1H), 7.86 (s, 1H), 8.38 (m, 2H), 11.43 (s, 1H).

Example 57

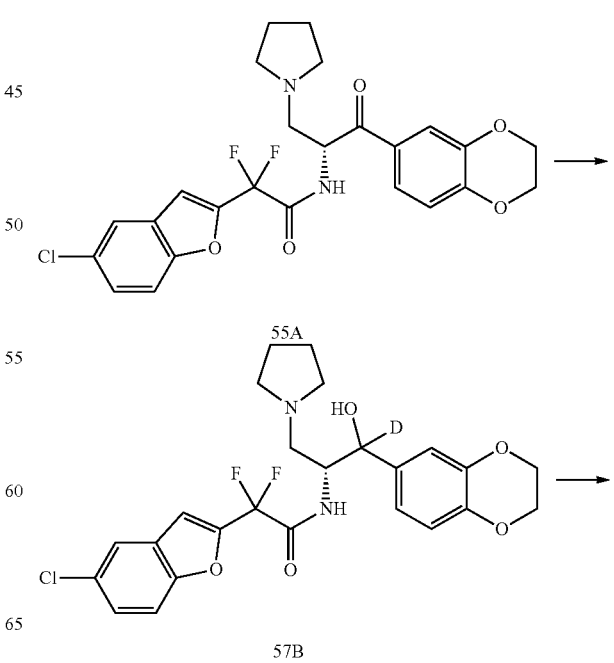

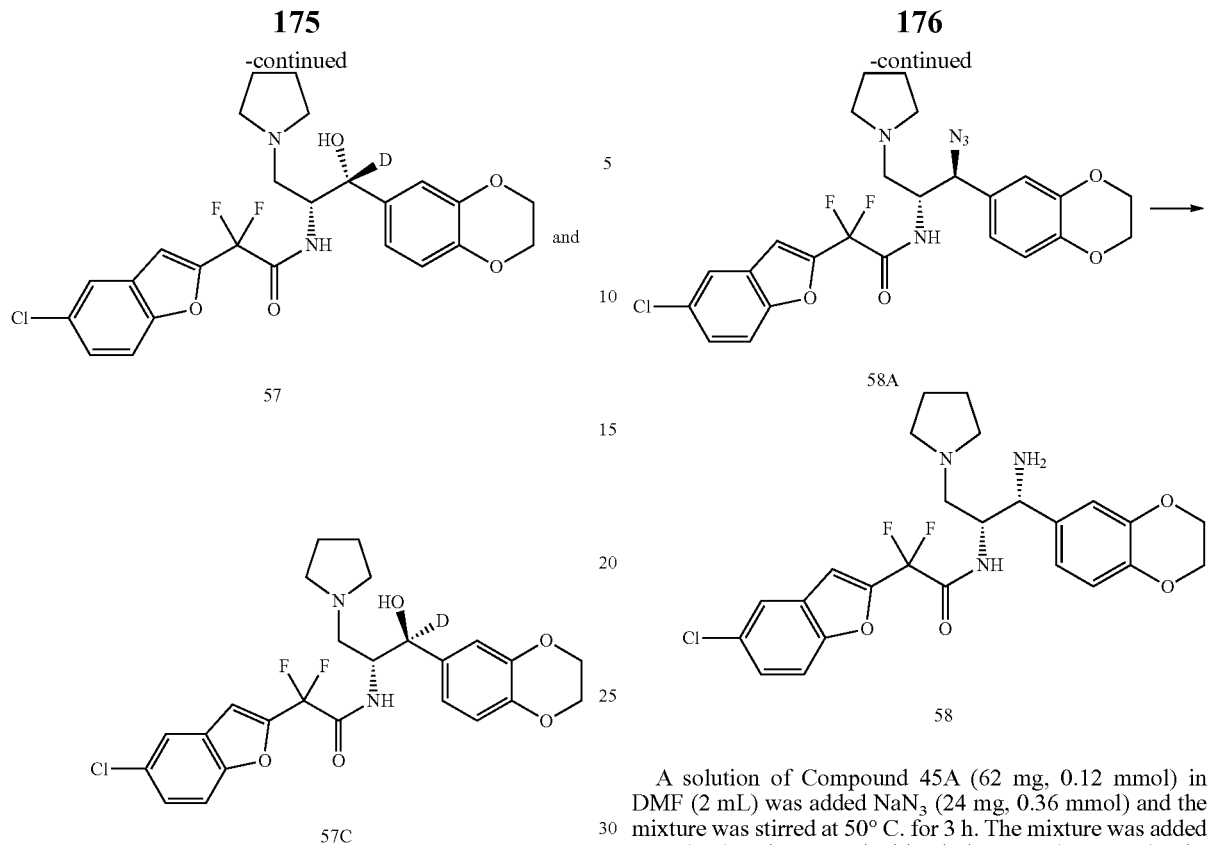

57

57C

To a solution of Compound 55A was dissolved in CD₃OD (5 mL) was added NaBD₄ (13 mg, 0.32 mmol) at −30° C. under nitrogen atmosphere. The reaction was warmed to 0° C. and kept stirring for 1 h. After quenched with 2% CD₃COOD in D₂O, the mixture was extracted with dichloromethane (50 mL×3) and washed with D₂O. The crude product was purified by prep-HPLC to give Compound 57 (20 mg, yield 25%) as a white solid. LC-MS (m/z): 508 [M+1]⁺; ¹H-NMR (CDCl₃, 400 MHz) major characteristic peaks: δ (ppm) 2.13 (s, 4H), 3.01 (s, 2H), 3.49 (s, 2H), 3.81 (s, 2H), 4.12-4.17 (m, 4H), 4.47-4.49 (m, 1H), 6.76 (m, 2H), 6.84 (s, 1H), 7.35 (dd, J=2.0, 8.8 Hz, 1H), 7.44 (d, J=8.8 Hz, 1H), 7.45 (s, 1H), 7.90 (d, J=2.0 Hz, 1H), 11.95 (s, 1H).

Example 58

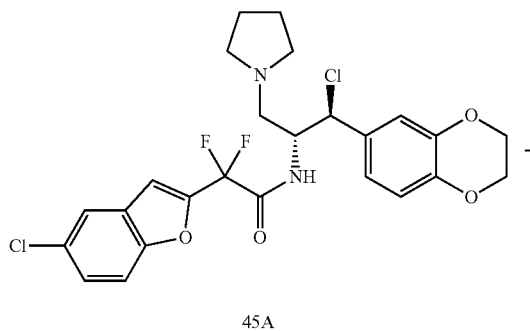

45A

58A

58

A solution of Compound 45A (62 mg, 0.12 mmol) in DMF (2 mL) was added NaN₃ (24 mg, 0.36 mmol) and the mixture was stirred at 50° C. for 3 h. The mixture was added H₂O (mL) and extracted with ethyl acetate (50 mL×3). The combined organic layer was washed with brine, and concentrated to give Compound 58A (40 mg, yield 63%) as a white solid. LC-MS (m/z): 532 [M+1]⁺.

To a solution of Compound 58A (40 mg, 0.075 mmol) in THF (1 mL) was added PPh₃ (21 mg, 0.08 mmol), the mixture was stirred at 20° C. for 18 h. It was added H₂O (mL) and stirred for 2 h and concentrated. The crude product was purified by prep-HPLC to give Compound 58 (5 mg, yield 13%) as a white solid. LC-MS (m/z): 506 [M+1]⁺; ¹H-NMR (CDCl₃, 400 MHz) major characteristic peaks: δ (ppm) 1.79-1.81 (m, 4H), 2.40-2.45 (m, 1H), 2.56-2.64 (m, 6H), 3.34-3.38 (m, 1H), 4.14-4.34 (m, 5H), 4.90-4.91 (m, 2H), 6.75-6.84 (m, 3H), 7.07 (s, 1H), 7.32-7.35 (m, 1H), 7.45-7.58 (m, 1H), 7.59 (s, 1H), 9.66-9.67 (m, 1H).

Example 59

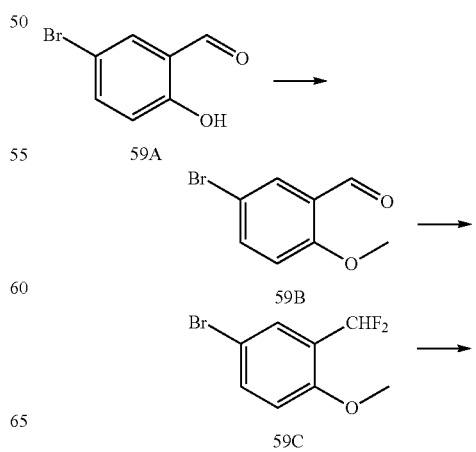

59A

59B

59C

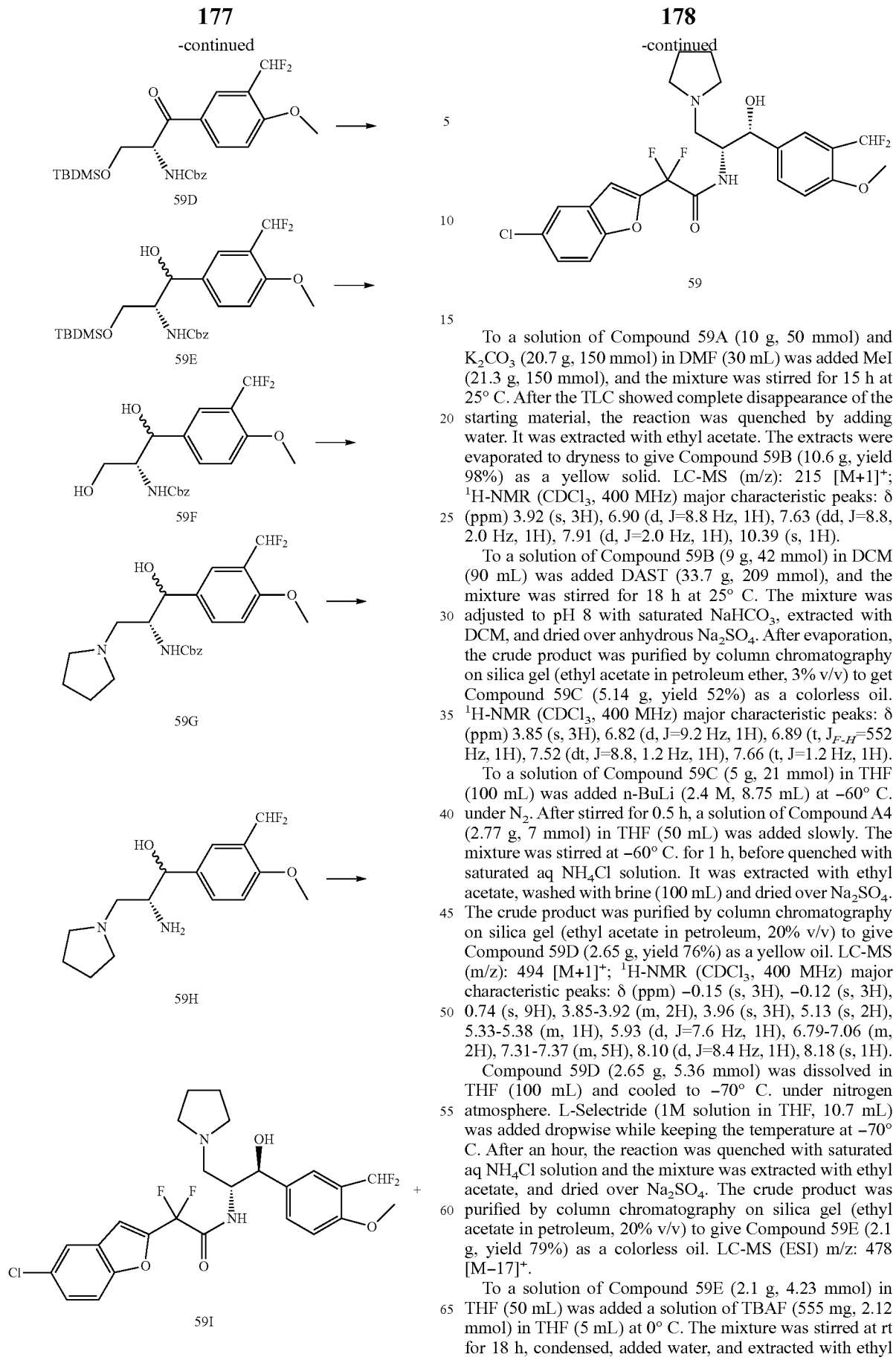

To a solution of Compound 59A (10 g, 50 mmol) and K₂CO₃ (20.7 g, 150 mmol) in DMF (30 mL) was added MeI (21.3 g, 150 mmol), and the mixture was stirred for 15 h at 25° C. After the TLC showed complete disappearance of the starting material, the reaction was quenched by adding water. It was extracted with ethyl acetate. The extracts were evaporated to dryness to give Compound 59B (10.6 g, yield 98%) as a yellow solid. LC-MS (m/z): 215 [M+1]⁺; ¹H-NMR (CDCl₃, 400 MHz) major characteristic peaks: δ (ppm) 3.92 (s, 3H), 6.90 (d, J=8.8 Hz, 1H), 7.63 (dd, J=8.8, 2.0 Hz, 1H), 7.91 (d, J=2.0 Hz, 1H), 10.39 (s, 1H).

To a solution of Compound 59B (9 g, 42 mmol) in DCM (90 mL) was added DAST (33.7 g, 209 mmol), and the mixture was stirred for 18 h at 25° C. The mixture was adjusted to pH 8 with saturated NaHCO₃, extracted with DCM, and dried over anhydrous Na₂SO₄. After evaporation, the crude product was purified by column chromatography on silica gel (ethyl acetate in petroleum ether, 3% v/v) to get Compound 59C (5.14 g, yield 52%) as a colorless oil. ¹H-NMR (CDCl₃, 400 MHz) major characteristic peaks: δ (ppm) 3.85 (s, 3H), 6.82 (d, J=9.2 Hz, 1H), 6.89 (t, J_{F-H}=552 Hz, 1H), 7.52 (dt, J=8.8, 1.2 Hz, 1H), 7.66 (t, J=1.2 Hz, 1H).

To a solution of Compound 59C (5 g, 21 mmol) in THF (100 mL) was added n-BuLi (2.4 M, 8.75 mL) at −60° C. under N₂. After stirred for 0.5 h, a solution of Compound A4 (2.77 g, 7 mmol) in THF (50 mL) was added slowly. The mixture was stirred at −60° C. for 1 h, before quenched with saturated aq NH₄Cl solution. It was extracted with ethyl acetate, washed with brine (100 mL) and dried over Na₂SO₄. The crude product was purified by column chromatography on silica gel (ethyl acetate in petroleum, 20% v/v) to give Compound 59D (2.65 g, yield 76%) as a yellow oil. LC-MS (m/z): 494 [M+1]⁺; ¹H-NMR (CDCl₃, 400 MHz) major characteristic peaks: δ (ppm) −0.15 (s, 3H), −0.12 (s, 3H), 0.74 (s, 9H), 3.85-3.92 (m, 2H), 3.96 (s, 3H), 5.13 (s, 2H), 5.33-5.38 (m, 1H), 5.93 (d, J=7.6 Hz, 1H), 6.79-7.06 (m, 2H), 7.31-7.37 (m, 5H), 8.10 (d, J=8.4 Hz, 1H), 8.18 (s, 1H).

Compound 59D (2.65 g, 5.36 mmol) was dissolved in THF (100 mL) and cooled to −70° C. under nitrogen atmosphere. L-Selectride (1M solution in THF, 10.7 mL) was added dropwise while keeping the temperature at −70° C. After an hour, the reaction was quenched with saturated aq NH₄Cl solution and the mixture was extracted with ethyl acetate, and dried over Na₂SO₄. The crude product was purified by column chromatography on silica gel (ethyl acetate in petroleum, 20% v/v) to give Compound 59E (2.1 g, yield 79%) as a colorless oil. LC-MS (ESI) m/z: 478 [M−17]⁺.

To a solution of Compound 59E (2.1 g, 4.23 mmol) in THF (50 mL) was added a solution of TBAF (555 mg, 2.12 mmol) in THF (5 mL) at 0° C. The mixture was stirred at rt for 18 h, condensed, added water, and extracted with ethyl acetate. The combined organic layers were washed with brine and dried over Na₂SO₄. The crude product was purified by flash column chromatography on silica gel (MeOH in H₂O, 40% v/v) to give Compound 59F (760 mg, yield 47%) as a colorless oil. LC-MS (m/z): 364 [M–17]⁺.

To a solution of Compound 59F (0.76 g, 2 mmol) in THF (50 mL) was added Et₃N (0.6 g, 6 mmol) at –40° C. MsCl (241 mg, 2.09 mmol) was added slowly and the mixture was stirred at –20° C. for 7 h. Pyrrolidine (1.13 g, 16 mmol) were added and the reaction mixture was allowed to warm up to rt and then heated to 50° C. for 15 h. The crude product was purified by column chromatography silica gel (methanol in dichloromethane, 5% v/v) to give Compound 59G (270 mg, yield 31%) as colorless oil. LC-MS (m/z): 435 [M+1]⁺.

To a solution of Compound 59G (270 mg, 0.62 mmol) in methanol (20 mL) was added Pd(OH)₂ (27 mg) and the mixture was stirred at 25° C. under H₂ for 24 h. The mixture was filtered and evaporated to render Compound 59H (260 mg, yield 98%) as a white solid. LC-MS (m/z): 301 [M+1]⁺.

The mixture of Compound 59H (180 mg, 0.6 mmol), EDCI (173 mg, 0.9 mmol), HOBt (122 mg, 0.9 mmol) and Compound 11E (178 mg, 0.72 mmol) in DCM (15 mL) was stirred for 16 h at 25° C. The mixture was washed with saturated aq NaHCO₃ and brine. After evaporation, the residues were purified by prep-HPLC to afford Compound 59I (64 mg, yield 11%) as the white solid and Compound 59 (59 mg, yield 10%) as the white solid. For Compound 59I, LC-MS (m/z): 529 [M+1]⁺; ¹H-NMR (CDCl₃, 400 MHz) major characteristic peaks: δ (ppm) 2.07-2.19 (m, 4H), 2.77-2.91 (m, 2H), 3.21-3.24 (m, 1H), 3.63-3.64 (m, 1H), 3.76 (s, 3H), 3.80-3.82 (m, 1H), 3.88-3.90 (m, 1H), 4.52 (s, 1H), 5.02 (s, 1H), 6.72-7.00 (m, 3H), 7.31-7.34 (m, 1H), 7.40-7.42 (m, 2H), 7.52-7.62 (m, 2H), 9.15 (d, J=4.8 Hz, 1H), 11.78 (s, 1H). For Compound 59, LC-MS (m/z): 529 [M+1]⁺; ¹H-NMR (CDCl₃, 400 MHz) major characteristic peaks: δ (ppm) 2.13 (s, 4H), 2.88-3.04 (m, 2H), 3.53-3.63 (m, 2H), 3.71 (s, 3H), 3.74-3.81 (m, 2H), 4.60 (s, 1H), 5.19 (s, 1H), 6.65-6.98 (m, 3H), 7.32-7.39 (m, 3H), 7.51-7.53 (m, 2H), 7.95 (d, J=6.4 Hz, 1H), 11.69 (s, 1H).

Example 60

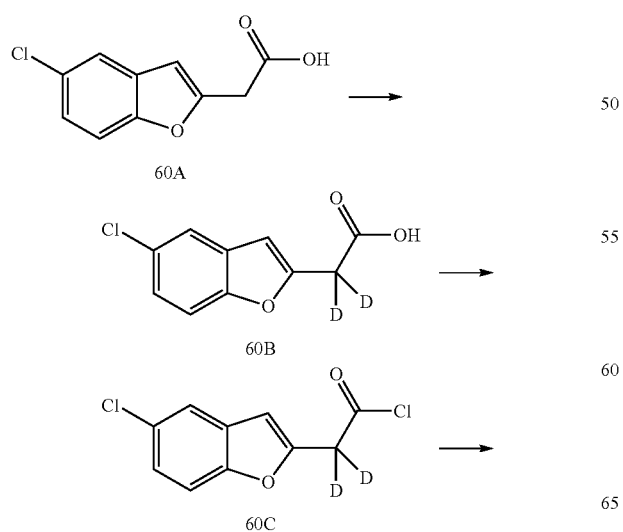

60A

60B

60C

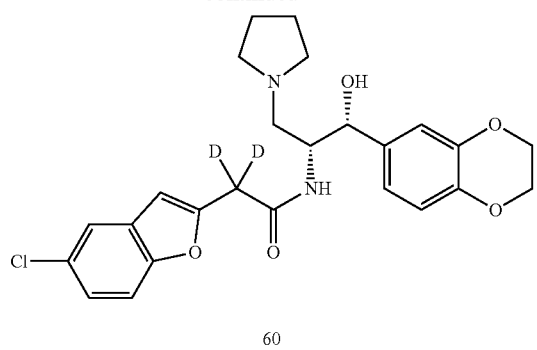

60

A solution of Compound 60A (21 mg, 0.1 mmol) and K₂CO₃ (55 mg, 0.4 mmol) in D₂O (3 mL) was stirred at 110° C. for 16 h under N₂. The mixture was acidified by the addition of 1M HCl solution, extracted with DCM (20 mL×2), dried over anhydrous Na₂SO₄, and concentrated to yield Compound 60B (15 mg, yield 71%) as a white solid. LC-MS (m/z): 167 [M–45]⁻; ¹H-NMR (CDCl₃, 400 MHz) major characteristic peaks: δ (ppm) 6.63 (s, 1H), 7.21 (m, 1H), 7.35 (d, J=8.8 Hz, 1H), 7.50 (d, J=2.0 Hz, 1H).

A mixture of Compound 60B (100 mg, 0.47 mmol) in SOCl₂ (3 mL) was stirred at 25° C. for 2 h. The mixture was concentrated to give Compound 60C (100 mg, crude) as a yellow oil which was used for the next step without further purification.

Intermediate A was dissolved in CD₃OD and the solvent evaporated. To a solution of Intermediate A (100 mg, 0.36 mmol) in DCM (3 mL) was added Compound 60C solution (100 mg, 0.43 mmol). The mixture was stirred at 25° C. for 0.5 h. The mixture was added water (30 mL), extracted with DCM (30 mL×3), dried over anhydrous Na₂SO₄, and purified by prep-HPLC to give Compound 60 (19 mg, yield 9%) as a white foam. LC-MS (m/z): 473 [M+1]⁺; ¹H-NMR (CDCl₃, 400 MHz) major characteristic peaks: δ (ppm) 2.03 (m, 4H), 2.82 (m, 2H), 3.16 (m, 1H), 3.48 (m, 1H), 3.73 (br, 2H), 4.14 (m, 4H), 4.45 (m, 1H), 4.84 (d, J=2.4 Hz, 1H), 6.41 (s, 1H), 6.64 (s, 2H), 6.76 (s, 1H), 7.18 (m, 1H), 7.32 (d, J=8.4 Hz, 1H), 7.45 (d, J=2.0 Hz, 1H), 7.53 (d, J=8.8 Hz, 1H), 11.42 (br, 1H).

Example 61

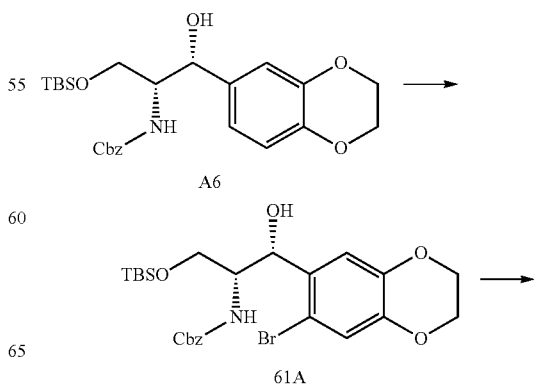

A6

61A

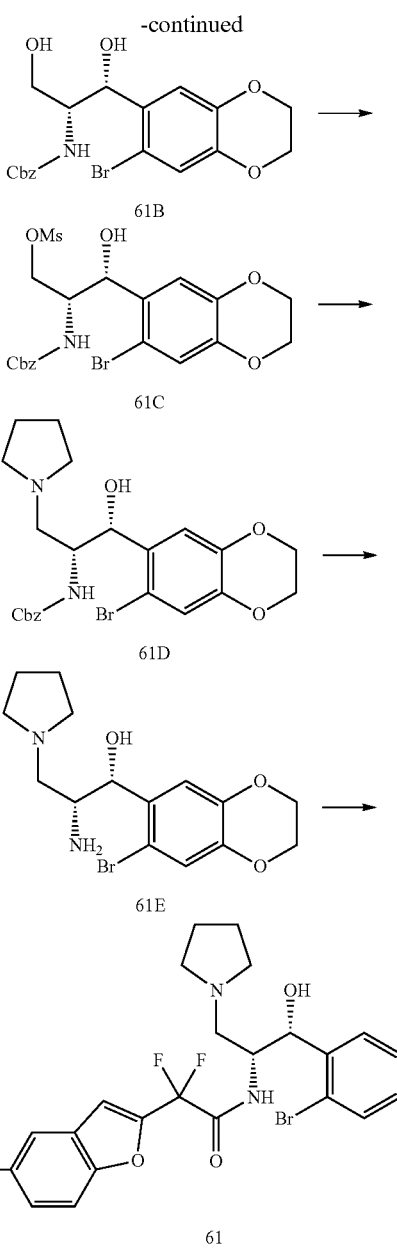

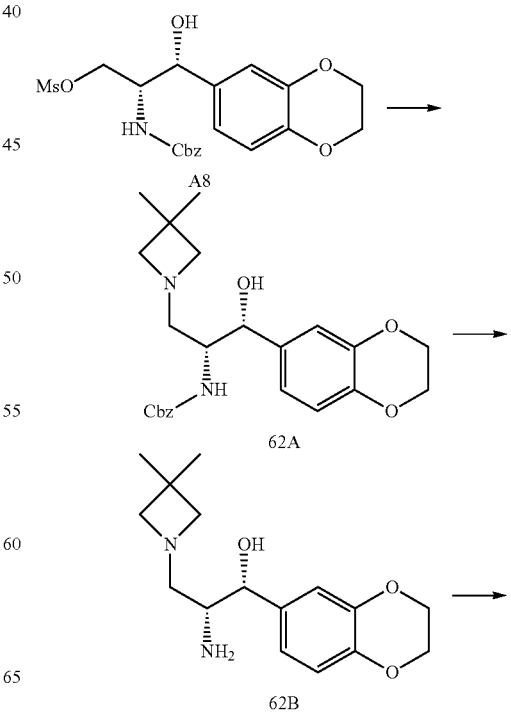

mixture was cooled to −15° C., added MsCl (207 mg, 1.8 mmol) slowly, and stirred at −15° C. for half an hour. It was diluted with water, extracted with ethyl acetate (50 mL×2), washed with brine (50 mL), dried over $Na_2SO_4$, and concentrated to render Compound 61C (700 mg, yield 83%), which was used for the next step without further purification. LC-MS (m/z): 498 $[M-18]^+$.

To a solution of Compound 61C (700 mg, 1.36 mmol) in THF (20 mL) was added and pyrrolidine (1 g, 13.6 mmol). The reaction mixture was allowed to warm up to rt and then heated at 50° C. overnight. After cooled to rt and added water (20 mL), the mixture was extracted with ethyl acetate (50 mL×2), washed with water (50 ml×3) and brine (50 mL), dried over $Na_2SO_4$, and concentrated to give Compound 61D (600 mg, crude). LC-MS (m/z): 491 $[M+1]^+$.

To a solution of Compound 61D (600 mg, 1.22 mmol) in EtOH (20 mL) and $H_2O$ (2 mL) was added LiOH (154 mg, 3.67 mmol) and then the mixture was stirred at 100° C. overnight. After cooled to rt and added water (50 mL), the mixture was extracted with DCM (50 mL×2), washed with brine (50 mL), dried over $Na_2SO_4$, and concentrated to yield Compound 61E (200 mg, yield 50%) as a yellow liquid. LC-MS (m/z): 357 $[M+1]^+$.

A mixture of Compound 11E (166 mg, 0.67 mmol), EDCI (216 mg, 1.12 mmol), HOBt (216 mg, 1.12 mmol), and Compound 61E (200 mg, 0.56 mmol) in DCM (20 mL) was stirred at rt overnight. The mixture was added water, extracted with DCM (50 mL×2), washed with brine (50 mL), dried over $Na_2SO_4$, and concentrated. The crude product was purified by prep-HPLC to give Compound 61 (130 mg, yield 40%) as a white solid. LC-MS (m/z): 585 $[M+1]^+$; $^1$H-NMR (CDCl$_3$, 400 MHz) major characteristic peaks: δ (ppm) 2.15 (s, 4H), 2.95 (s, 1H), 3.10 (s, 1H), 2.57 (m, 2H), 3.87 (m, 2H), 3.94 (m, 2H), 4.04 (m, 1H), 4.13 (m, 1H), 4.68 (d, J=7.2 Hz, 1H), 5.31 (s, 1H), 6.79 (s, 1H), 7.01 (s, 1H), 7.08 (s, 1H), 7.33 (m, 1H), 7.44 (d, J=8.8 Hz, 1H), 7.56 (d, J=1.6 Hz, 1H), 7.67 (d, J=8.4 Hz, 1H), 11.79 (s, 1H).

Example 62

To a solution of Compound A6 (1 g, 2 mmol) in $CH_3CN$ (15 mL) was added NBS (564 mg, 3.2 mmol) and the mixture was stirred at 50° C. for 1.5 h. It was cooled to rt, diluted with DCM (50 mL), washed with water (100 mL×3) and brine (100 mL), dried over $Na_2SO_4$, and concentrated to give Compound 61A (1.2 g, crude) as a yellow solid. LC-MS (m/z): 534 $[M-18]^+$.

To a solution of Compound 61A (1 g, 2.1 mmol) in THF (20 mL) was added TBAF (275 mg, 1.05 mmol) at 0° C. The mixture was stirred at rt overnight, evaporated to remove solvent, and added water (50 mL). It was extracted with ethyl acetate (50 mL×2), washed with brine (100 mL), dried over $Na_2SO_4$, concentrated and, purified by column chromatography on silica gel (33% ethyl acetate in petroleum) to give Compound 61B (720 mg, yield 80%) as a white solid. LC-MS (m/z): 420 $[M-18]^+$.

To a solution of Compound 61B (720 mg, 1.6 mmol) in THF (20 mL) was added $Et_3N$ (500 mg, 4.94 mmol). The

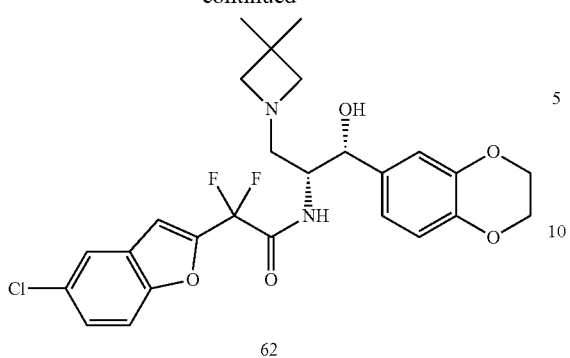

62

To a solution of Compound A8 (437 mg, 1 mmol) in CH₃CN (20 mL) was added 3,3-dimethylazetidine (363 mg, 3 mmol), K₂CO₃ (414 mg, 3 mmol), and NaI (449 mg, 3 mmol). The mixture was heated at 82° C. overnight. It was cooled to rt, filtered and concentrated in vacuum to give a crude Compound 62A (426 mg, crude) as a yellow oil. LC-MS (m/z): 427 [M+1]⁺.

To a solution of Compound 62A (426 mg, 1 mmol) in EtOH/water (20 mL, 9:1, v/v) was added LiOH.H₂O (420 mg, 10 mmol). The mixture was refluxed for 36 h. It was added water (20 mL) and extracted with ethyl acetate (20 mL×3). The combined organic layers were dried over anhydrous Na₂SO₄ and concentrated in vacuum to yield Compound 62B (300 mg, crude) as a yellow oil. LC-MS (m/z): 293 [M+1]⁺.

To a mixture of Compound 62B (292 mg, 1 mmol) in DCM (20 mL) was added EDCI (288 mg, 1.5 mmol), HOBt (202 mg, 1.5 mmol) and Compound 11E (246 mg, 1 mmol). It was stirred at 25° C. overnight, added water (10 mL), extracted with DCM (20 mL×3), dried over anhydrous Na₂SO₄, and purified by prep-HPLC to afford a trifluoroacetic acid salt of Compound 62 (139 mg, yield 27%) as a white solid. LC-MS (m/z): 521 [M+1]⁺; ¹H-NMR (CDCl₃, 400 MHz) major characteristic peaks: δ (ppm) 1.30 (s, 3H), 1.43 (s, 3H), 3.50 (s, 2H), 3.64 (t, J=12 Hz, 2H), 4.05-4.19 (m, 6H), 4.30 (s, 1H), 5.01 (s, 1H), 6.73 (s, 3H), 6.8 (s, 1H), 7.34 (d, J=8 Hz, 1H), 7.42 (d, J=8 Hz, 1H), 7.58 (s, 1H), 7.89 (d, J=8 Hz, 1H), 12.23 (s, 1H).

Example 63

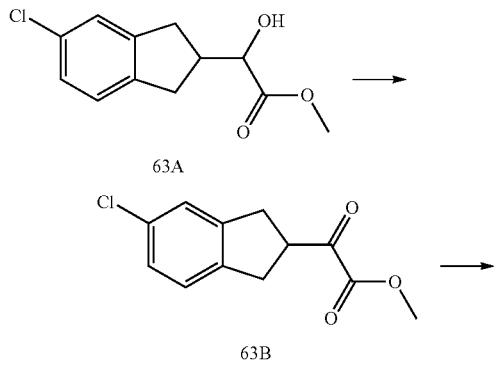

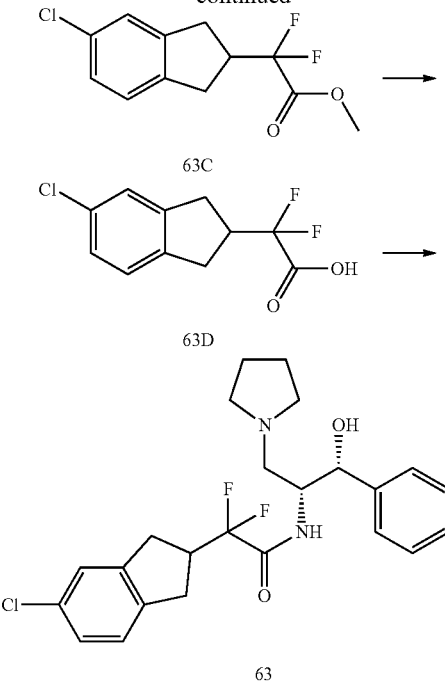

To a solution of Compound 63A (3.00 g, 12.50 mmol) in DCM (100 mL) was added DMP (6.36 g, 15.00 mmol) carefully. The mixture was stirred at 25° C. overnight. The mixture was quenched with aq Na₂S₂O₃ solution, diluted with ethyl acetate (200 mL), washed with water and brine, and purified with silica gel column chromatography (ethyl acetate in petroleum ether, from 0% to 20% v/v) to render Compound 63B (2.10 g, yield 70%) as a white solid. LC-MS (m/z): 239 [M+1]⁺; ¹H-NMR (CDCl₃, 400 MHz) major characteristic peaks: δ (ppm) 3.06-3.11 (m, 3H), 3.15-3.30 (m, 1H), 3.84 (s, 3H), 3.90-3.93 (m, 0.5H), 4.06-4.10 (m, 0.5H), 7.10-7.20 (m, 3H).

To a solution of Compound 63B (200 mg, 1.26 mmol), in DCM (5 mL) was added DAST (1.01 g, 6.30 mmol) dropwise at 20° C. The mixture was stirred at 20° C. overnight. The mixture was diluted with ethyl acetate (100 mL), washed with water and brine, and purified by silica gel column chromatography (dichloromethane in petroleum ether, from 0% to 8% v/v) to yield Compound 63C (280 mg, yield 85%) as a colorless oil. LC-MS (m/z): 261 [M+1]⁺; ¹H-NMR (CDCl₃, 400 MHz) major characteristic peaks: δ (ppm) 3.06-3.11 (m, 3H), 3.15-3.30 (m, 1H), 3.84 (s, 3H), 3.90-3.93 (m, 0.5H), 4.06-4.10 (m, 0.5H), 7.10-7.20 (m, 3H).

A mixture of Compound 63C (280 mg, 1.08 mmol) and LiOH.H₂O (136 mg, 3.24 mmol) in THF/MeOH/H₂O (10/10/5 mL) was stirred at 20° C. overnight. The mixture was acidified to pH 2 with dilute HCl and extracted with DCM. Then organic phase washed with water and brine, dried over anhydrous Na₂SO₄, and evaporated to give Compound 63D (230 mg, yield 86%) as white solid. LC-MS (m/z): 465 [M−1]⁻.

A mixture of Compound 63D (89 mg, 0.36 mmol), Compound 11E (100 mg, 0.36 mmol), EDCI (104 mg, 0.54 mmol) and HOBt (73 mg, 0.54 mmol) in DCM (10 mL) was stirred at 25° C. overnight. The mixture was diluted with ethyl acetate (150 mL), washed with water and brine, and purified by prep-HPLC to afford Compound 63 (100 mg, yield 55%) as a white solid. LC-MS (m/z): 507 [M+1]⁺; ¹H-NMR (DMSO-d₆, 400 MHz) major characteristic peaks: δ (ppm) 1.88 (br s, 2H), 2.01 (br s, 2H), 2.50-2.83 (m, 4H), 3.00-3.16 (m, 3H), 3.50-3.55 (m, 5H), 4.13-4.20 (m, 4H), 4.42-4.50 (m, 1H), 4.74 (br s, 1H), 5.88 (s, 1H), 6.78-6.84 (m, 3H), 7.20-7.26 (m, 3H), 8.40 (d, J=8.8 Hz, 1H), 9.50 (s, 1H).

Example 64

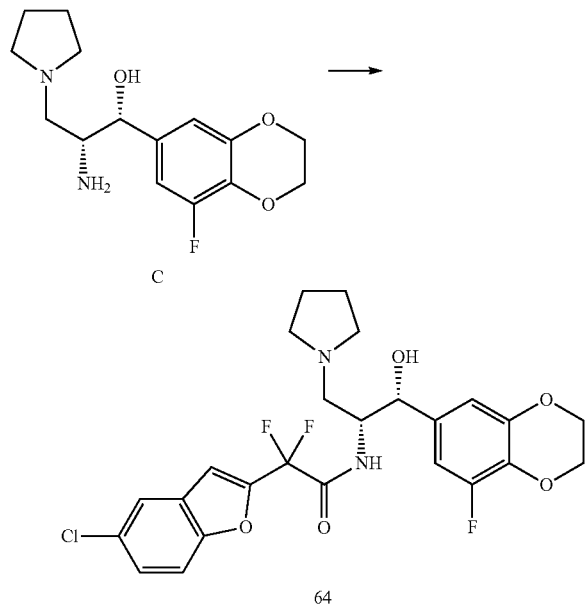

To a solution of Intermediate C (292 mg, 1 mmol) in DCM (20 mL) was added EDCI (288 mg, 1.5 mmol), HOBt (202 mg, 1.5 mmol) and Compound 11E (246 mg, 1 mmol) and it was stirred at 25° C. overnight. The mixture was added water (10 mL), extracted with dichloromethane (20 mL×3), dried over anhydrous Na₂SO₄, and purified by prep-HPLC to afford a trifluoroacetic acid salt of Compound 64 (120 mg, yield 19%) as a white solid. LC-MS (m/z): 525 [M+1]⁺; ¹H-NMR (CDCl₃, 400 MHz) major characteristic peaks: δ (ppm) 2.14 (s, 4H), 2.91-3.03 (m, 2H), 3.50 (d, J=4 Hz, 2H), 3.82 (s, 2H), 4.11-4.19 (m, 4H), 4.44 (d, J=4 Hz, 1H), 5.07 (s, 1H), 6.61 (s, 1H), 6.70 (d, J=12 Hz, 1H), 6.86 (s, 1H), 7.34 (d, J=12 Hz, 1H), 7.43 (d, J=12 Hz, 1H), 7.58 (s, 1H), 7.80 (d, J=8 Hz, 1H), 11.76 (s, 1H).

Example 65

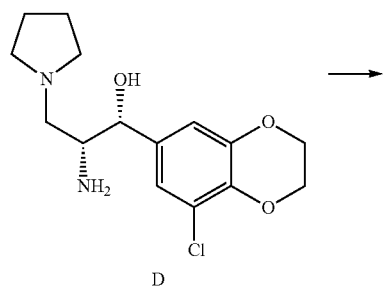

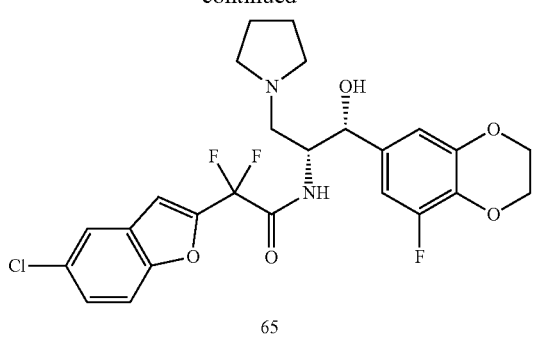

To a solution of Intermediate D (250 mg, 0.8 mmol) in dichloromethane (20 mL) was added EDCI (230 mg, 1.2 mmol), HOBt (162 mg, 1.2 mmol) and Compound 11E (196 mg, 0.8 mmol). The mixture was stirred at 25° C. overnight, added water (10 mL), extracted with dichloromethane (20 mL×3), dried over anhydrous Na₂SO₄, and purified by prep-HPLC to afford a trifluoroacetic acid salt of Compound 65 (75 mg, yield 14%) as a white solid. LC-MS (m/z): 541[M+1]⁺; ¹H-NMR (CDCl₃, 400 MHz) major characteristic peaks: δ (ppm) 2.13 (s, 4H), 3.01 (s, 2H), 3.51 (s, 2H), 3.80 (s, 2H), 4.06 (s, 2H), 4.20 (s, 2H), 4.47 (d, J=4 Hz, 1H), 5.06 (s, 1H), 6.74 (s, 1H), 6.80 (s, 1H), 6.94 (s, 1H), 7.34 (d, J=12 Hz, 1H), 7.43 (d, J=12 Hz, 1H), 7.58 (s, 1H), 7.80 (d, J=8 Hz, 1H), 11.76 (s, 1H).

Example 66

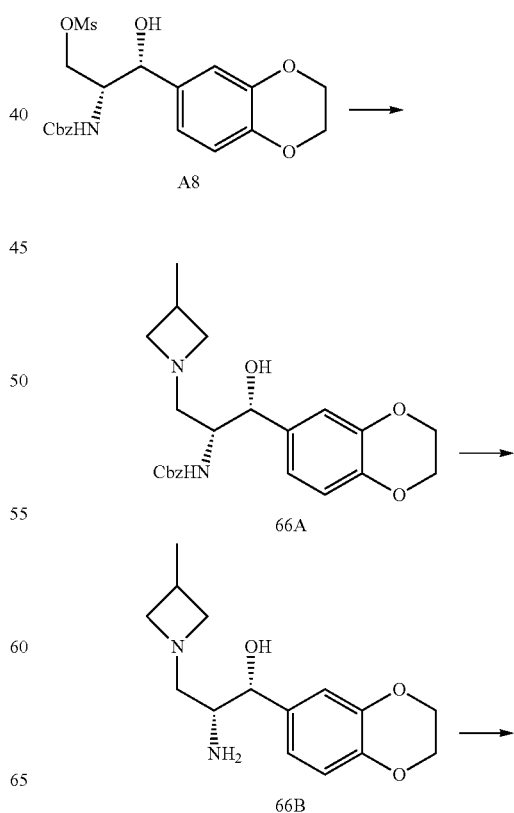

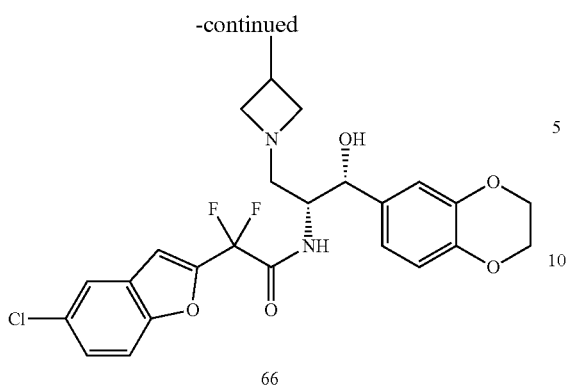

66

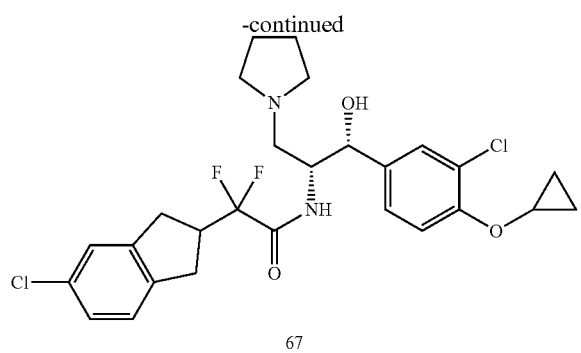

67

To a solution of Compound A8 (437 mg, 1 mmol) in CH₃CN (20 mL) was added 3-methylazetidine hydrochloride (321 mg, 3 mmol), K₂CO₃ (414 mg, 3 mmol) and NaI (449 mg, 3 mmol). The mixture was heated at 82° C. overnight. It was cooled to rt, filtered, and concentrated in vacuum to give crude Compound 66A (426 mg, crude) as a yellow oil. LC-MS (m/z): 413 [M+1]⁺.

To a solution of Compound 66A (412 mg, 1 mmol) in EtOH/water (20 mL, 9:1, v/v) was added LiOH.H₂O (420 mg, 10 mmol). The mixture was refluxed for 24 h and water (20 mL) was added. It was extracted with ethyl acetate (20 mL×3). The combined organic layers were dried over anhydrous Na₂SO₄ and concentrated in vacuum to give crude Compound 66B (280 mg, crude) as a yellow oil. LC-MS (m/z): 278 [M+1]⁺.

To a mixture of Compound 66B (140 mg, 0.5 mmol) in DCM (10 mL) was added EDCI (144 mg, 0.75 mmol), HOBt (100 mg, 0.75 mmol), and Compound 11E (123 mg, 0.5 mmol) and stirred at 30° C. overnight. It was added water (10 mL), extracted with DCM (20 mL×3), dried over anhydrous Na₂SO₄, and purified by prep-HPLC to give a trifluoroacetic acid salt of Compound 66 (20 mg, yield 6%) as a white solid. LC-MS (m/z): 507 [M+1]⁺; ¹H-NMR (CDCl₃, 400 MHz) major characteristic peaks: δ (ppm) 1.23-1.38 (m, 3H), 2.92 (s, 1H), 3.15 (s, 1H), 3.49 (s, 3H), 4.01-4.15 (m, 5H), 4.30 (s, 1H), 4.43 (s, 1H), 5.00 (s, 1H), 6.73 (s, 3H), 6.80 (s, 1H), 7.34 (d, J=8 Hz, 1H), 7.42 (d, J=8 Hz, 1H), 7.58 (s, 1H), 7.85 (s, 1H), 12.34 (s, 1H).

Example 67

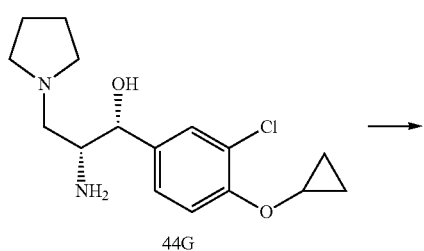

44G

A mixture of Compound 11E (100 mg, 0.41 mmol), EDCI.HCl (118 mg, 0.62 mmol), HOBt (81 mg, 0.62 mmol), Compound 44G (126 mg, 0.41 mmol) in DCM (5 mL) was stirred at 28° C. overnight. The mixture was added dropwise sat. aq NaHCO₃, and then extracted with DCM (50 mL×2), washed with brine (50 mL×1), dried over Na₂SO₄, and concentrated. The crude product was purified by prep-HPLC to give Compound 67 (62 mg, yield 28%) as a white solid. LC-MS: 539 [M+1]⁺; ¹H-NMR (DMSO-d₆, 400 MHz) major characteristic peaks: δ (ppm) 0.62 (m, 2H), 081 (m, 2H), 1.88 (m, 2H), 2.03 (m, 2H), 2.60-2.65 (m, 2H), 2.76-2.80 (m, 2H), 3.06-3.20 (m, 3H), 3.41-3.54 (m, 4H), 3.88 (s, 1H), 5.53 (s, 1H), 8.84 (s, 1H), 6.00 (s, 1H), 7.15-7.21 (m, 3H), 7.27-7.31 (m, 1H), 7.36-7.40 (m, 2H), 8.45 (d, J=9.2 Hz, 1H).

Example 68

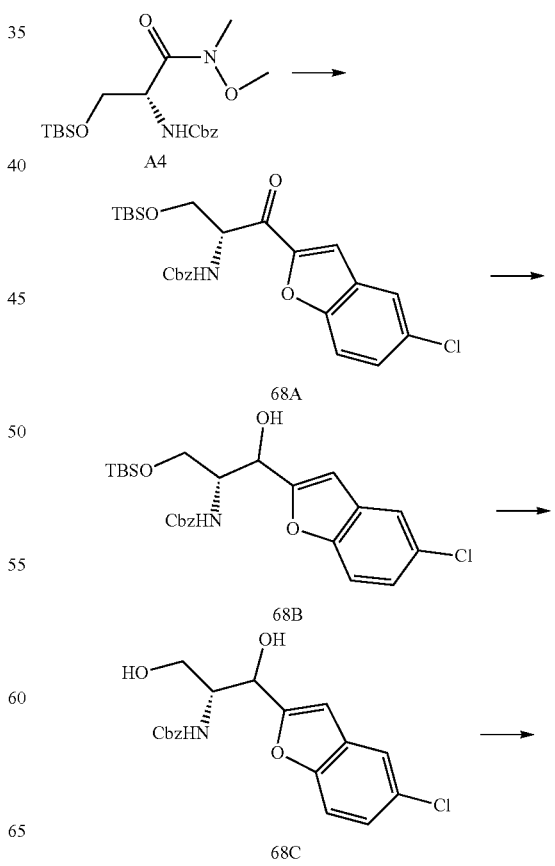

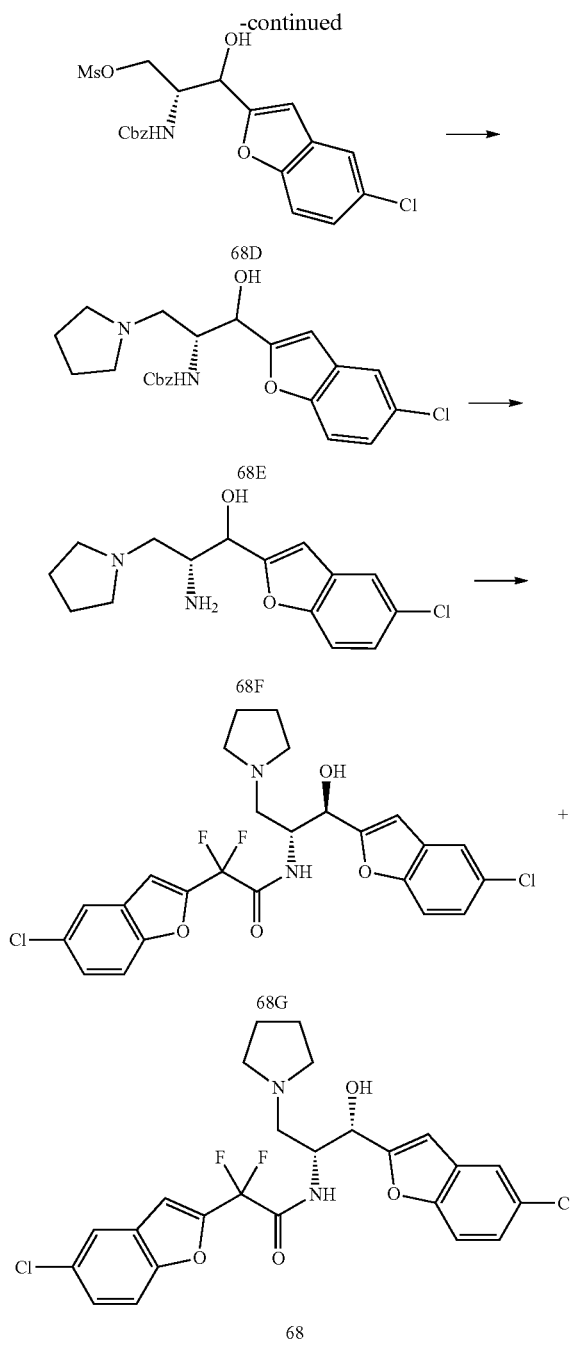

1H), 5.87 (d, J=7.6 Hz, 1H), 7.32-7.38 (m, 5H), 7.45-7.57 (m, 3H), 7.70 (d, J=2.0 Hz, 1H).

A solution of Compound 68A (3.48 g, 7.14 mmol) in THF (200 mL) was added L-selectride (1M solution in THF, 14.3 mL) dropwise at −70° C. under nitrogen atmosphere. After stirred for one hour, the reaction was quenched with saturated aq NH$_4$Cl solution and the mixture was extracted with ethyl acetate and dried over Na$_2$SO$_4$. The crude product was purified by column chromatography on silica gel (ethyl acetate in petroleum, 20% v/v) to give Compound 68B (3.41 g, yield 97%) as a colorless oil. LC-MS (m/z): 472 [M−17]$^+$.

To a solution of Compound 68B (3.41 g, 6.95 mmol) in THF (100 mL) was added a solution of TBAF (0.91 mg, 3.48 mmol) in THF (10 mL) at 0° C. After stirred at rt for 18 h, the mixture was evaporated to remove solvent. The residue was taken up with water, extracted with ethyl acetate, washed with brine, and dried over Na$_2$SO$_4$. The crude was purified by flash column chromatography on silica gel (MeOH in DCM, 5% v/v) to render Compound 69C (2.01 g, yield 76%) as a white solid. LC-MS (m/z): 358 [M−17]$^+$.

To a solution of Compound 68C (2.01 g, 5.35 mmol) in THF (100 mL) was added Et$_3$N (1.62 g, 16.01 mmol) at −40° C. MsCl (646 mg, 5.62 mmol) was added slowly and the mixture was stirred at −20° C. for 4 h. After evaporation, Compound 68D (2.28 g, yield 100%) was obtained as yellow oil, which was used for the next step without purification.

To a solution of Compound 68D (2.28 g, 5.35 mmol) in THF (100 mL) was added pyrrolidine (3.03 g, 42.8 mmol). The reaction mixture was heated at 50° C. for 15 h. After evaporation, the crude product was purified by column chromatography on silica gel (methanol in dichloromethane, 5% v/v) to give Compound 68E (940 mg) as a colorless oil. LC-MS (m/z): 429 [M+H]$^+$.

To a solution of Compound 68E (310 mg, 0.72 mmol) in ethanol (10 mL) and H$_2$O (10 mL) was added LiOH (152 mg, 3.61 mmol). The mixture was refluxed for 4 h. After evaporation, the mixture was extracted by DCM, and washed by brine, and dried over anhydrous Na$_2$SO$_4$. After filtration and evaporation, Compound 69F (210 mg, yield 98%) was obtained as a yellow oil. LC-MS (m/z): 295 [M+1]$^+$.

A mixture of Compound 68F (210 mg, 0.71 mmol), EDCI (204 mg, 1.07 mmol), HOBt (145 mg, 1.07 mmol) and Compound 11E (210 mg, 0.85 mmol) in DCM (10 mL) was stirred at 25° C. for 16 h. The mixture was washed by saturated NaHCO$_3$ and brine. After evaporation, the crude was purified by prep-HPLC and followed by chiral-prep-HPLC to afford Compound 68G (77 mg, yield 17%) as a white solid and Compound 68 (82 mg, yield 18%) as a white solid. For Compound 68G, LCMS (m/z): 523 [M+1]$^+$; $^1$H-NMR (CDCl$_3$, 400 MHz) major characteristic peaks: δ (ppm) 2.07 (s, 4H), 2.82-2.91 (m, 2H), 3.26-3.29 (m, 1H), 3.70-3.95 (m, 3H), 4.82 (s, 1H), 5.02 (d, J=4.0 Hz, 1H), 6.68 (s, 1H), 6.91 (s, 1H), 7.19-7.21 (m, 1H), 7.28-7.33 (m, 3H), 7.35 (d, J=2.0 Hz, 1H), 7.50 (d, J=1.2 Hz, 1H), 9.18 (d, J=7.2 Hz, 1H), 11.70 (s, 1H). For Compound 68, LC-MS (m/z): 523 [M+1]$^+$; $^1$H-NMR (CDCl$_3$, 400 MHz) major characteristic peaks: δ (ppm) 2.13 (s, 4H), 2.94-3.06 (m, 2H), 3.61 (s, 2H), 3.85 (s, 2H), 4.81 (d, J=6.0 Hz, 1H), 5.33 (s, 1H), 6.64 (s, 2H), 7.06-7.09 (m, 1H), 7.14-7.15 (m, 1H), 7.19-7.21 (m, 1H), 7.28-7.31 (m, 2H), 7.39-7.40 (m, 1H), 7.96 (d, J=7.2 Hz, 1H), 11.78 (s, 1H).

To a solution of Compound 11B (4.59 g, 30 mmol) in THF (125 mL) was added n-BuLi (2.4 M, 12.5 mL) at −60° C. under N$_2$ and stirred for 0.5 h and then a solution of Compound A4 (3.97 g, 10 mmol) in THF (50 mL) was added slowly. The mixture was stirred at −60° C. for 1 h, before quenched by addition of saturate aq NH$_4$Cl solution The mixture was extracted with ethyl acetate, brine, and dried over Na$_2$SO$_4$. The crude product was purified by column chromatography on silica gel (ethyl acetate in petroleum, 5% v/v) to give Compound 68A (3.48 g, yield 71%) as a yellow oil. LC-MS (m/z): 488 [M+1]$^+$; $^1$H-NMR (CDCl$_3$, 400 MHz) major characteristic peaks: δ (ppm) −0.11 (s, 3H), −0.08 (s, 3H), 0.75 (s, 9H), 4.99 (dd, J=4.4, 10.0 Hz, 1H), 4.19 (dd, J=3.6, 10.0 Hz, 1H), 5.14 (s, 2H), 5.26-5.30 (m,

Example 69

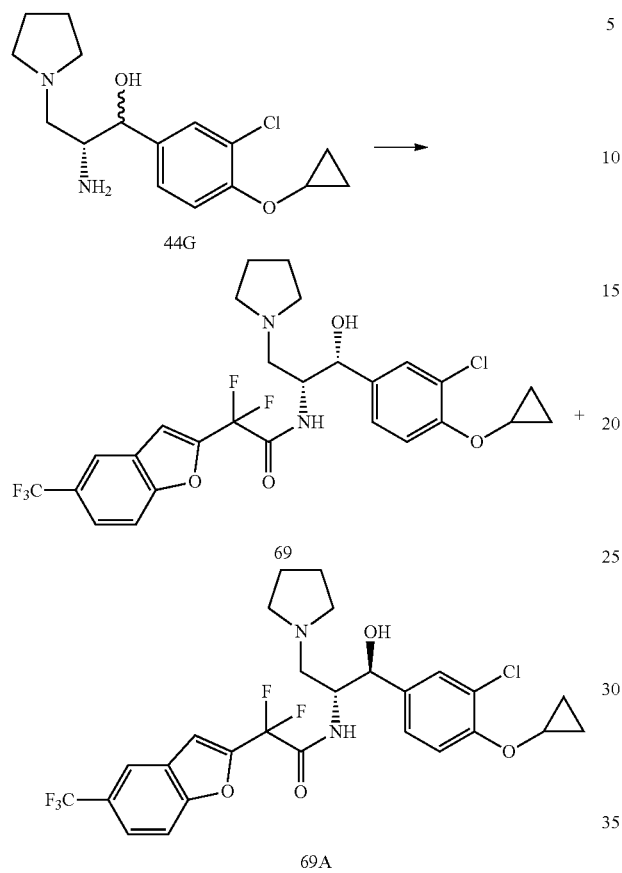

A mixture of Compound 33F (150 mg, 0.54 mmol), EDCI.HCl (154 mg, 0.81 mmol), HOBt (109 mg, 0.81 mmol), Compound 44G (166 mg, 0.54 mmol) in DCM (5 mL) was stirred at 28° C. overnight. The reaction was quenched with addition of sat. aq NaHCO$_3$ and the mixture was extracted with DCM (50 mL×2), washed with brine (50 mL×1), dried over Na$_2$SO$_4$, and concentrated. The crude product was purified by prep-HPLC to give Compound 70 (42 mg, yield 14.1%) as a white solid and Compound 69A (42 mg, yield 14.1%) as a white solid. For Compound 69, LC-MS (m/z): 573 [M+1]$^+$; $^1$H-NMR (DMSO-d$_6$, 400 MHz) major characteristic peaks: δ (ppm) 0.52-0.61 (m, 2H), 0.73-0.76 (m, 2H), 1.89 (br s, 2H), 2.02 (br s, 2H), 3.08-3.21 (m, 2H), 3.50 (s, 4H), 3.67-3.72 (m, 1H), 4.53 (s, 1H), 4.82 (s, 1H), 6.04 (s, 1H), 7.02 (s, 1H), 7.13 (d, J=8.8 Hz, 1H), 7.21 (d, J=8.8 Hz, 1H), 7.32 (s, 1H), 7.86 (s, 1H), 7.93 (d, J=8.8 Hz, 1H), 8.16 (s, 1H), 8.93 (d, J=9.2 Hz, 1H), 9.66 (s, 1H). For Compound 69A, LC-MS (m/z): 573 [M+1]$^+$; $^1$H-NMR (DMSO-d$_6$, 400 MHz) major characteristic peaks: δ (ppm) 0.46-0.54 (m, 2H), 0.70-0.74 (m, 2H), 1.89 (br s, 2H), 2.04 (br s, 2H), 3.15 (s, 2H), 3.38-3.48 (m, 4H), 3.60-3.65 (m, 1H), 4.13-4.37 (s, 1H), 4.52 (s, 1H), 6.09 (s, 1H), 6.73 (s, 1H), 7.14 (d, J=8.8 Hz, 1H), 7.23 (d, J=8.8 Hz, 1H), 7.82-7.90 (m, 2H), 8.09 (s, 1H), 9.27 (d, J=9.2 Hz, 1H), 9.62 (s, 1H).

Example 70

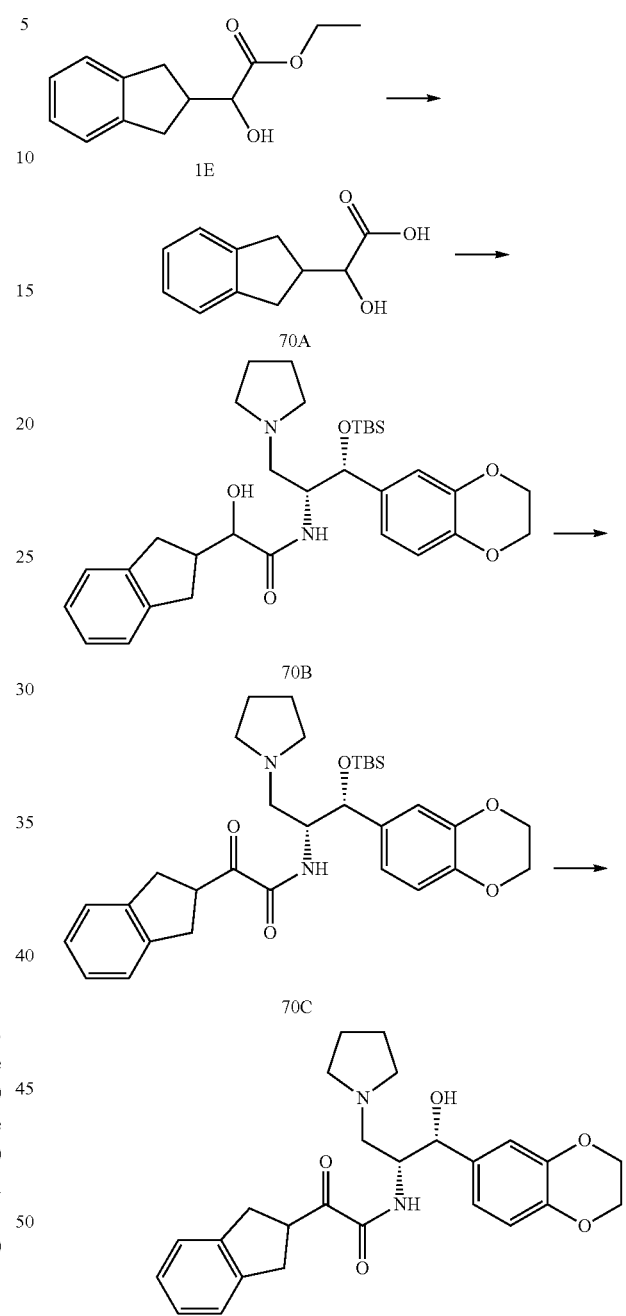

To a stirred solution of Compound 1E (500 mg, 2.27 mmol) in THF (8 mL) was added LiOH.H$_2$O (99 mg, 2.27 mmol) and water (2 mL). The mixture was stirred at room temperature for 3 h. After reaction, the mixture was adjusted pH to 1 with 1 M HCl and concentrated by evaporation. The aqueous phase was extracted with ethyl acetate (50 mL×3). The combined organic phase was washed with water and brine, dried over anhydrous Na$_2$SO$_4$, and concentrated to render Compound 70A (403 mg, yield 92%) as a yellow solid. LCMS: (m/z) 193 [M+1]$^+$; $^1$H-NMR (CDCl$_3$, 400

MHz) major characteristic peaks: δ (ppm) 2.97 (m, 3H), 3.07-3.09 (m, 2H), 4.39 (d, J=4.4 Hz, 1H), 7.15-7.19 (m, 4H).

To a solution of (1R,2R)-1-((tert-butyldimethylsilyl)oxy)-1-(2,3-dihydrobenzo[b][1,4]dioxin-6-yl)-3-(pyrrolidin-1-yl)propan-2-amine (392 mg, 1.0 mmol) in DCM (20 mL) was added EDCI (288 mg, 1.5 mmol), HOBt (202 mg, 1.5 mmol) and Compound 70A (192 mg, 1.0 mmol). The mixture was stirred at room temperature overnight and diluted with DCM (20 mL). It was washed with water (50 mL×2), brine (50 mL×1), dried over anhydrous Na$_2$SO$_4$, concentrated, and purified by silica gel column chromatography (methanol in dichloromethane, 5% v/v) to give Compound 70B (360 mg, yield 64%) as a yellow oil. LC-MS (m/z): 567 [M+1]$^+$.

To a stirred solution of Compound 70B (360 mg, 0.64 mmol) in DCM (20 mL) was added DMP (324 mg, 0.76 mmol). The mixture was stirred at room temperature overnight. It was quenched with sat. aq Na$_2$SO$_3$ solution and then concentrate by evaporation. The aqueous phase was extracted with DCM (50 mL×3). The combined organic phase was washed with water, brine, and dried over anhydrous Na$_2$SO$_4$. Filtration and evaporation to dryness gave Compound 70C (210 mg, yield 60%) as a yellow oil. LCMS: (m/z) 565 [M+1]$^+$.

To a solution of Compound 70C (210 mg, 0.37 mmol) in THF (20 mL) was added TBAF (195 mg, 0.74 mmol). The mixture was stirred at room temperature overnight, quenched with sat. aq NH$_4$Cl solution, and concentrated by evaporation. The aqueous phase was extracted with DCM (50 mL×3). The combined organic phase was washed with water, brine, and dried over anhydrous Na$_2$SO$_4$. Removal of solvent led to a crude product, which was purified by prep-HPLC to give Compound 70 (12 mg, yield 7%) as a yellow solid. LC-MS (m/z): 451 [M+1]$^+$; $^1$H-NMR (CDCl$_3$, 400 MHz) major characteristic peaks: δ (ppm) 2.07 (s, 4H), 2.87 (m, 3H), 3.21 (m, 4H), 3.82 (m, 3H), 4.08 (m, 1H), 4.21 (s, 4H), 4.45 (m, 2H), 4.96 (m, 1H), 6.76-6.82 (m, 3H), 7.14 (m, 4H), 7.86 (s, 1H), 11.11 (s, 1H).

Example 71

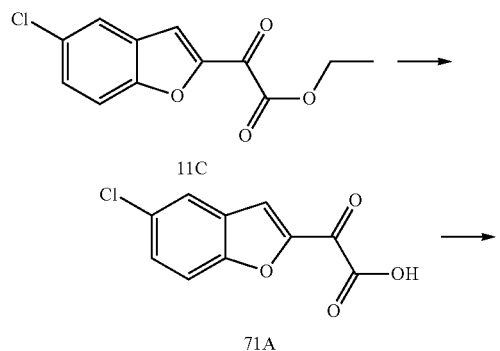

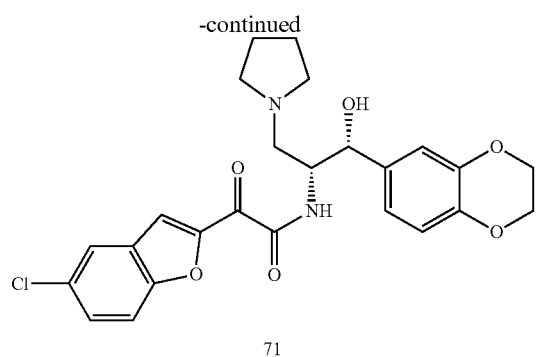

To a solution of Compound 11C (300 mg, 1.19 mmol) in EtOH (5 mL) was added LiOH (43 mg, 1.78 mmol) in water (5 mL). The mixture was stirred at room temperature overnight. After removal of EtOH by evaporation, the mixture was adjusted to pH 7 with diluted HCl. lyophilization of the solution gave Compound 71A (200 mg, crude), which was used for the next step without further purification. LC-MS (m/z): 223 [M−1]$^−$.

A mixture of Compound 71A (100 mg, 0.45 mmol), EDCI (130 mg, 0.68 mmol), HOBt (91 mg, 0.68 mmol), Intermediate A (125 mg, 0.45 mmol) in DCM (10 mL) was stirred at room temperature overnight. After addition of sat. aq NaHCO$_3$, the mixture was extracted with DCM (50 mL×2), washed with brine (50 mL), dried over Na$_2$SO$_4$, and concentrated. The crude product was purified by prep-HPLC to give Compound 71 (68 mg, yield 31%) as a white solid. LC-MS (m/z): 485 [M+1]$^+$; $^1$H-NMR (DMSO-d$_6$, 400 MHz) major characteristic peaks: δ (ppm) 1.84 (m, 4H), 3.13 (m, 2H), 3.51 (m, 4H), 4.18 (s, 4H), 4.42 (s, 1H), 4.70 (s, 1H), 5.92 (s, 1H), 6.80 (m, 3H), 7.65 (m, 1H), 7.81 (m, 1H), 8.05 (s, 1H), 8.19 (m, 1H), 8.59 (s, 1H), 9.18 (s, 1H).

Example 72

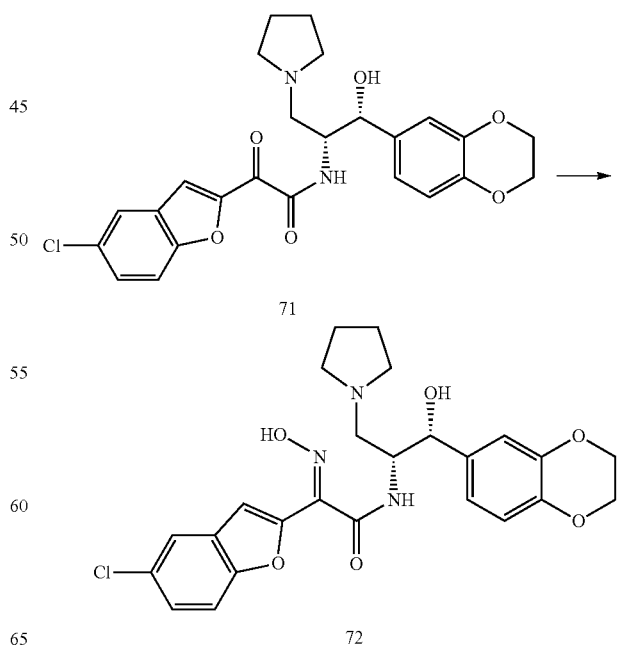

A mixture of Compound 71 (20 mg, 0.042 mmol) and saturated hydroxylamine solution in methanol (5 mL) was stirred at 70° C. for 5 h. After addition of sat. aq NH₄Cl (10 mL), the mixture was extracted with DCM (10 mL×2), washed with brine (30 mL), dried over Na₂SO₄, and concentrated. The crude product was purified by prep-HPLC to give Compound 72 (3 mg, yield 14%) as a white solid. LC-MS (m/z): 500 [M+1]⁺; ¹H-NMR (DMSO-d₆, 400 MHz) major characteristic peaks: δ (ppm) 1.92 (m, 4H), 3.11 (m, 2H), 3.55 (m, 4H), 4.21 (s, 4H), 4.58 (s, 1H), 4.80 (s, 1H), 5.95 (s, 1H), 6.46 (s, 1H), 6.87 (m, 3H), 7.40 (m, 1H), 7.64 (m, 2H), 8.84 (m, 1H), 10.07 (s, 1H), 12.42 (s, 1H).

Example 73

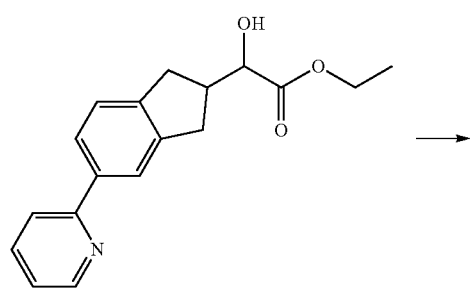

50F

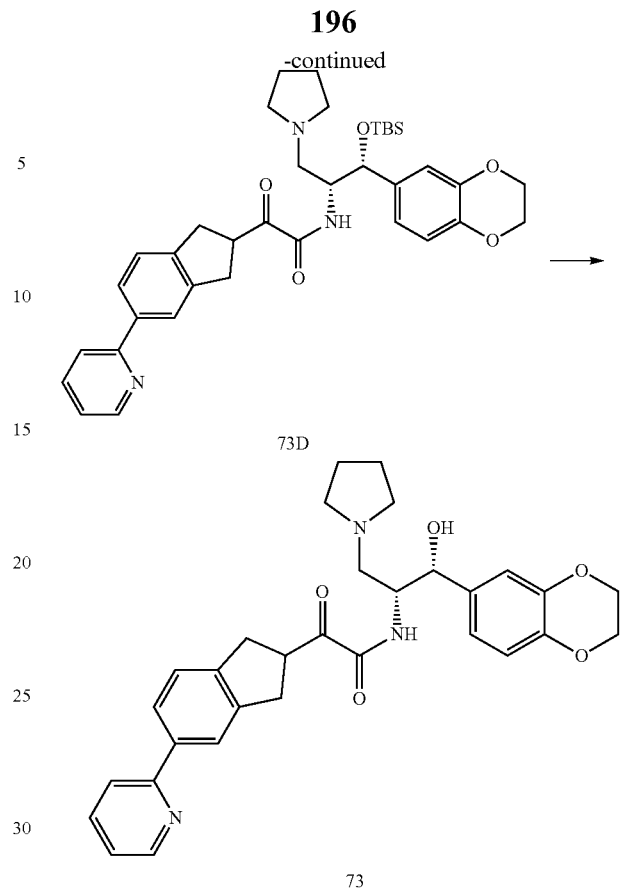

73D

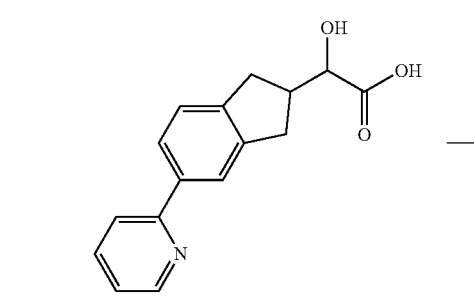

73A

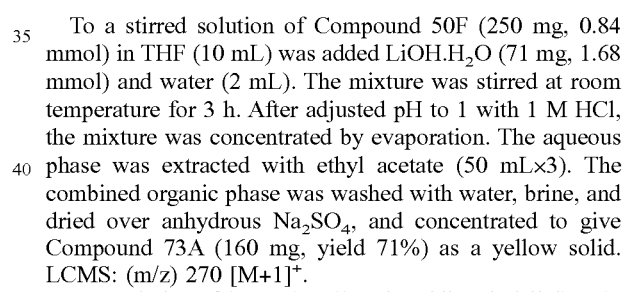

73

To a stirred solution of Compound 50F (250 mg, 0.84 mmol) in THF (10 mL) was added LiOH.H₂O (71 mg, 1.68 mmol) and water (2 mL). The mixture was stirred at room temperature for 3 h. After adjusted pH to 1 with 1 M HCl, the mixture was concentrated by evaporation. The aqueous phase was extracted with ethyl acetate (50 mL×3). The combined organic phase was washed with water, brine, and dried over anhydrous Na₂SO₄, and concentrated to give Compound 73A (160 mg, yield 71%) as a yellow solid. LCMS: (m/z) 270 [M+1]⁺.

To a solution of (1R,2R)-1-((tert-butyldimethylsilyl)oxy)-1-(2,3-dihydrobenzo[b][1,4]dioxin-6-yl)-3-(pyrrolidin-1-yl) propan-2-amine (233 mg, 0.59 mmol) in DCM (10 mL) was added EDCI (171 mg, 0.89 mmol), HOBt (120 mg, 0.89 mmol) and Compound 73A (160 mg, 0.59 mmol). The mixture was stirred at 25° C. overnight. After diluted with DCM (20 mL), it was washed with water (50 mL×2), brine (50 mL×1), dried over anhydrous Na₂SO₄, concentrated, and purified by column chromatography on silica gel (methanol in dichloromethane, 5% v/v) to give Compound 73B (120 mg, yield 31%) as a yellow oil. LC-MS (m/z): 644 [M+1]⁺.

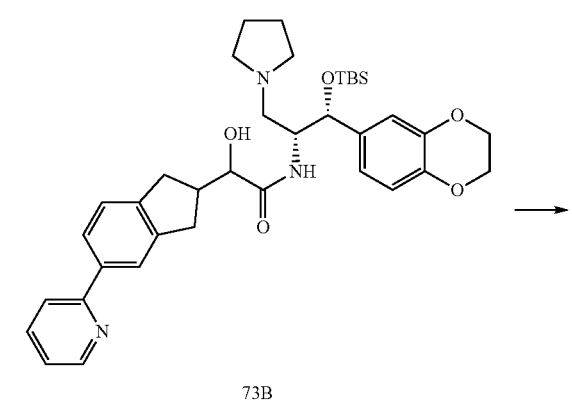

73B

To a stirred solution of Compound 73B (120 mg, 0.19 mmol) in DCM (10 mL) was added DMP (97 mg, 0.23 mmol) and NaHCO₃ (31 mg, 0.37 mmol). The mixture was stirred at 25° C. overnight. After addition with sat. aq Na₂SO₃ solution, the mixture was concentrated by evaporation. The aqueous phase was extracted with DCM (50 mL×3). The combined organic phase was washed with water, brine, and dried over anhydrous Na₂SO₄. Filtration and evaporation of the solution to dryness gave Compound 73C (110 mg, yield 92%) as a colorless oil. LCMS (m/z): 642 [M+1]⁺.

To a solution of Compound 73C (110 mg, 0.17 mmol) in THF (10 mL) was added TBAF (22 mg, 0.09 mmol). The mixture was stirred at 25° C. overnight and followed by quenched with sat. aq NH₄Cl solution. The aqueous phase was extracted with DCM (50 mL×3). The combined organic phase was washed with water, brine, and dried over anhydrous Na₂SO₄. After removal of the solvents, the crude product was purified by prep-HPLC twice to give Compound 73 (5.9 mg, yield 7%) as a white solid. LC-MS (m/z): 528 [M+1]⁺; ¹H-NMR (CDCl₃, 400 MHz) major characteristic peaks: δ (ppm) 1.72 (m, 2H), 1.85 (m, 3H), 1.94-1.97 (m, 1H), 2.31 (s, 1H), 2.53 (s, 1H), 2.77 (m, 3H), 2.92-3.12 (m, 3H), 3.26-3.28 (m, 3H), 4.23-4.24 (m, 5H), 4.62 (d, J=4.8 HZ, 0.36H), 5.03 (m, 0.64H), 6.62-6.72 (m, 1H), 6.79-6.85 (m, 2H), 7.21 (m, 1H), 7.29-7.34 (m, 1H), 7.70-7.72 (m, 3H), 7.83-7.86 (m, 1H), 8.66 (m, 1H).

Example 74

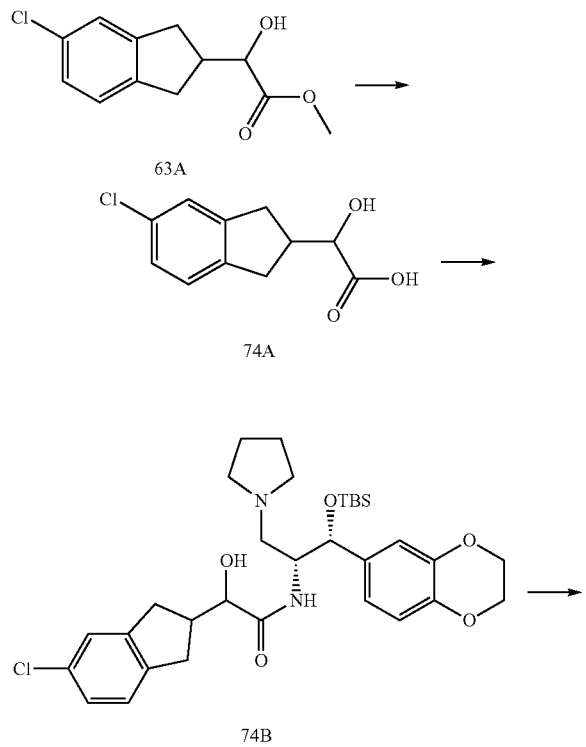

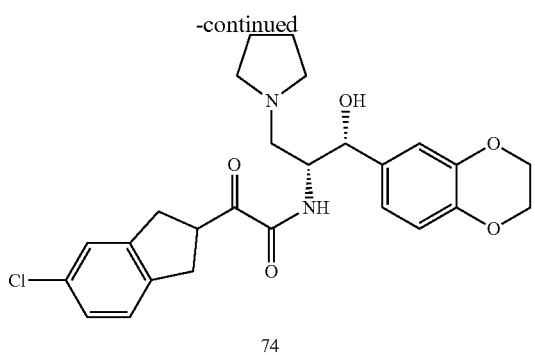

A mixture of Compound 63A (1.10 g, 4.58 mmol) and LiOH.H₂O (577 mg, 13.75 mmol) in THF/MeOH/H₂O (20/20/10 mL) was stirred at 25° C. for 3 h. It was diluted with ice-water (150 mL) and adjusted to pH 1 with conc. HCl. Filtration to collect the solid gave Compound 74A (900 mg, yield 87%) as a white solid. ¹H-NMR (DMSO-d₆, 400 MHz) major characteristic peaks: δ (ppm) 2.75-2.91 (m, 5H), 3.96 (s, 1H), 7.12-7.24 (m, 3H).

A mixture of Compound 74A (100 mg, 0.44 mmol), EDCI (127 mg, 0.66 mmol), HOBt (89 mg, 0.66 mmol) and (1R,2R)-1-(tert-butyldimethylsilyloxy)-1-(2,3-dihydrobenzo[b][1,4]dioxin-6-yl)-3-(pyrrolidin-1-yl)propan-2-amine (173 mg, 0.44 mmol) in DCM (10 mL) was stirred at 25° C. overnight. It was diluted with ethyl acetate (150 mL), washed with water and brine, and purified by silica gel column chromatography (methanol in dichloromethane, from 0% to 8% v/v) to give Compound 74B (230 mg, yield 87%) as a white solid. LC-MS (m/z): 601 [M+1]⁺.

A mixture of Compound 74B (200 mg, 0.33 mmol) and DMP (212 mg, 0.50 mmol) in DCM (10 mL) was stirred at 25° C. overnight. The mixture was diluted with ethyl acetate (150 mL), washed with water and brine, and purified by silica gel column chromatography (methanol in dichloromethane, from 0% to 8% v/v) to afford Compound 74C (160 mg, yield 80%) as a colorless oil. LC-MS (m/z): 599 [M+1]⁺.

A mixture of Compound 74C (160 mg, 0.27 mmol) and Bu₄NF (50 mg) in THF (20 mL) was stirred at 25° C. overnight. The mixture was diluted with ethyl acetate (150 mL), washed with water and brine, and purified by prep-HPLC to yield Compound 74 (60 mg, yield 46%) as a white solid. LC-MS (m/z): 485 [M+1]⁺; ¹H-NMR (CDCl₃, 400 MHz) major characteristic peaks: δ (ppm) 1.72 (br s, 4H), 1.87-1.96 (m, 2H), 2.30 (br s, 1H), 2.54-2.65 (m, 2H), 2.95-3.03 (m, 3H), 3.12-3.25 (m, 3H), 3.49-3.56 (m, 1H), 4.59 (s, 5H), 4.60 (d, J=8.0 Hz, 1H), 5.09 (s, 1H), 6.57-6.63 (m, 1H), 6.77-6.85 (m, 2H), 7.10-7.17 (m, 4H).

Example 75

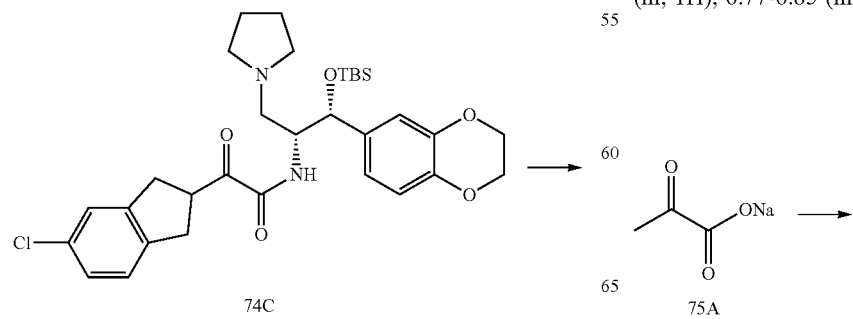

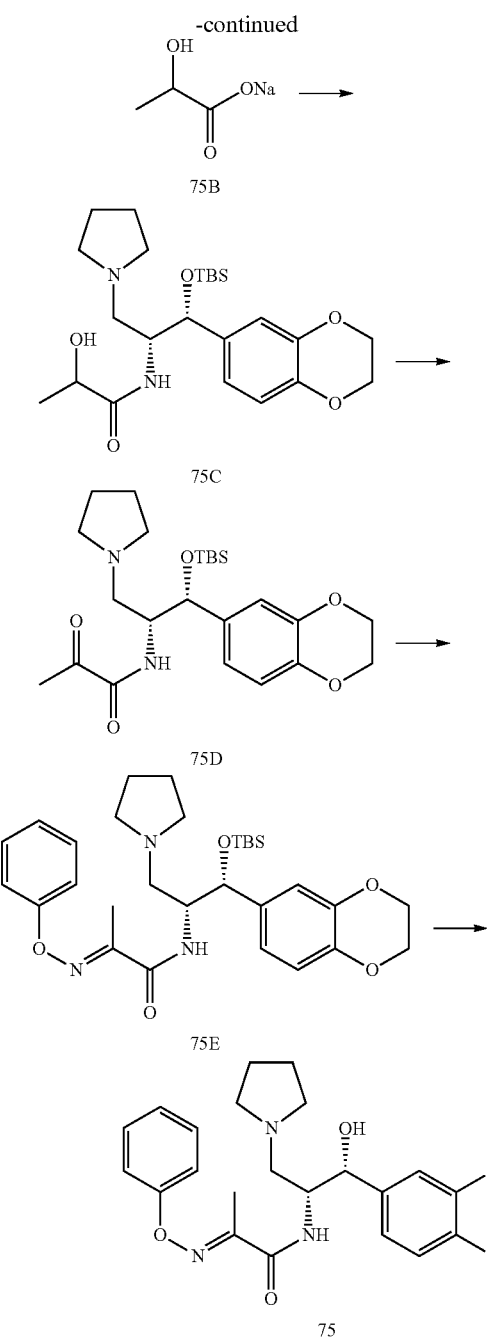

romethane, from 0% to 8% v/v) to yield Compound 75C (180 mg, yield 76%) as colorless oil. LC-MS (m/z): 465 [M+1]$^+$.

To a solution of Compound 75C (470 mg, 1.01 mmol) in DCM (10 mL) was added DMP (478 mg, 1.11 mmol) at 20° C. The mixture was stirred at 20° C. overnight. The mixture was quenched with Na$_2$S$_2$O$_3$ aqueous solution, diluted with ethyl acetate (200 mL), washed with water and brine, dried with anhydrous Na$_2$SO$_4$, and purified by silica gel column chromatography (methanol in dichloromethane, from 0% to 8% v/v) to afford Compound 75D (320 mg, yield 68%) as colorless oil. LC-MS (m/z): 463 [M+1]$^+$.

A mixture of Compound 75D (150 mg, 0.32 mmol), sodium acetate (53 mg, 0.64 mmol) and O-phenylhydroxylamine hydrochloride (91 mg, 0.64 mmol) in EtOH (10 mL) was stirred at 85° C. for 3 h. Purification by prep-HPLC gave Compound 75E (100 mg, yield 56%) as a colorless oil. LC-MS (m/z): 554 [M+1]$^+$.

A mixture of Compound 75E (100 mg, 0.23 mmol) and Bu$_4$NF (10 mg) in THF (10 mL) was stirred at 20° C. overnight. The mixture was diluted with ethyl acetate (150 mL), washed with water and brine, and purified by prep-HPLC to give Compound 75 (22 mg, yield 22%) as a white solid. LC-MS (m/z): 440 [M+1]$^+$; $^1$H-NMR (MeOD, 400 MHz) major characteristic peaks: δ (ppm) 1.99-2.06 (m, 2H), 2.17 (s, 5H), 3.14-3.23 (m, 2H), 3.43-3.49 (m, 1H), 3.59-3.68 (m, 2H), 3.80-3.87 (m, 1H), 4.21 (s, 4H), 4.50-4.55 (m, 1H), 4.83 (s, 1H), 6.80 (d, J=8.0 Hz, 1H), 6.87-6.90 (m, 1H), 6.96 (s, 1H), 7.12-7.16 (m, 1H), 7.30-7.33 (m, 2H), 7.38-7.42 (m, 2H).

Example 76

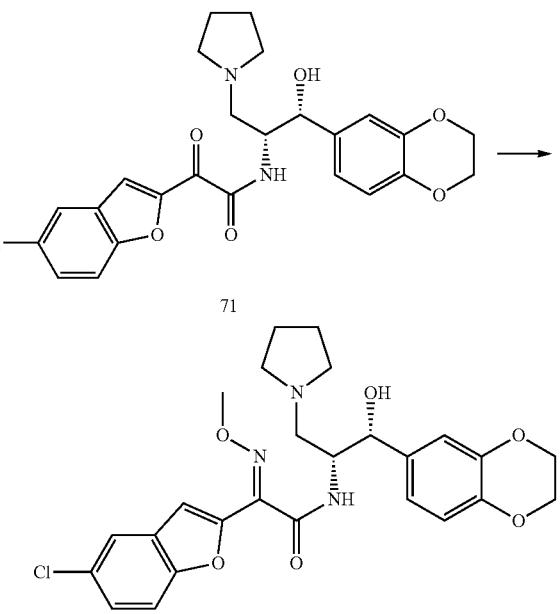

A mixture of 75A (1.00 g, 9.09 mmol) and Pd/C (1.00 g, 10%) in MeOH (20 mL) was stirred at 25° C. overnight in the presence of H$_2$. Then mixture was filtered to remove Pd/C. The filtrate was evaporated to render Compound 75B (1.00 g, yield 100%) as a white solid. LC-MS (m/z): 89 [M−1]$^−$.

A mixture of Compound 75B (57 mg, 0.51 mmol), (1R,2R)-1-(tert-butyldimethylsilyloxy)-1-(2,3-dihydrobenzo[b][1,4]dioxin-6-yl)-3-(pyrrolidin-1-yl)propan-2-amine (200 mg, 0.51 mmol), EDCI (147 mg, 0.76 mmol) and HOBt (103 mg, 0.76 mmol) in DMSO (5 mL) was stirred at 20° C. overnight. It was diluted with ethyl acetate (200 mL), washed with water and brine, and purified by silica gel column chromatography (methanol in dichlo- A mixture of Compound 71 (30 mg, 0.062 mmol), O-methylhydroxylamine (29 mg, 0.62 mmol) in methanol (5 mL) was stirred at 60° C. for 5 h. After addition of sat. aq NH$_4$Cl (10 mL), the mixture was extracted with DCM (10 mL×2), washed with brine (30 mL×1), dried over Na$_2$SO$_4$, and concentrated. The crude product was purified by prep- HPLC to give Compound 76 (10 mg, yield: 31%) as a white solid. LC-MS (m/z): 514 [M+1]⁺; ¹H-NMR (DMSO-d₆, 400 MHz) major characteristic peaks: δ (ppm) 1.88 (m, 4H), 3.10 (m, 2H), 3.61 (m, 4H), 3.96 (m, 3H), 4.20 (m, 4H), 4.48 (m, 1H), 4.83 (m, 1H), 5.98 (s, 1H), 6.44 (s, 1H), 6.91 (m, 3H), 7.61 (m, 1H), 8.40 (m, 1H), 9.61 (m, 1H).

Example 77

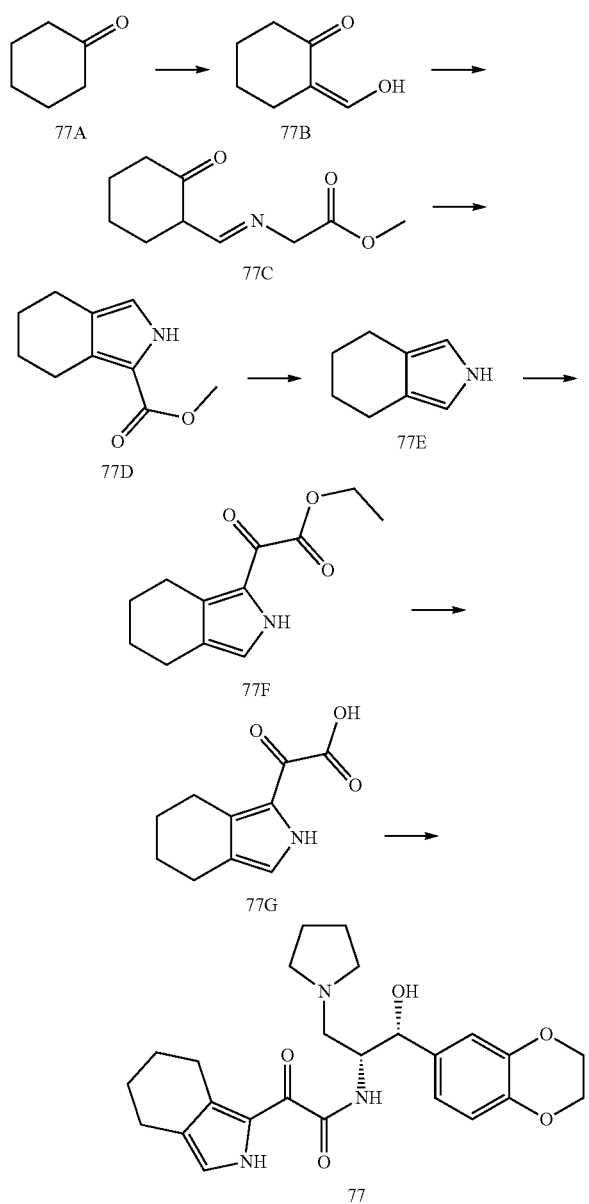

A mixture of NaH (60%, 20 g, 500 mmol), THF (3 L), EtOH (2.5 mL) was cooled to 0° C., ethyl formate (55.5 g, 750 mmol) and Compound 77A (49 g, 500 mmol) were added. The mixture was stirred for 6 hrs, and stood for 24 hrs. After the addition of EtOH (10 mL), the mixture was stirred for 1 hr, added water (1 L) and EA (1 L), washed with water (500 mL×2). The aqueous layer was acidified with 6 N HCl, extracted with EA (300 mL×2), washed with brine (300 mL×1), dried over anhydrous Na₂SO₄, and purified by column chromatography on silica (ethyl acetate in Petroleum ether, 10% v/v) to give Compound 77B.

To a solution of Compound 77B (23 g, 183 mmol) in MeOH (300 mL) was added 2-aminoacetate hydrochloride (23 g, 183 mmol) and NEt₃ (18.4 g, 183 mmol). The mixture was stirred at 25° C. for 16 hrs. The mixture was concentrated and added water (100 mL), extracted with DCM (100 mL×3), washed with brine (100 mL×1), dried over anhydrous Na₂SO₄, concentrated to give Compound 77C.

To a solution of NaOMe (6.86 g, 127 mmol) in MeOH (200 mL) was added Compound 77C (25 g, 127 mmol). The mixture was stirred at 90° C. for 3 hrs. The mixture was poured into water (500 mL), extracted with EA (100 mL×3), washed with water (50 mL×1), dried over anhydrous Na₂SO₄, purified by column chromatography (dichloromethane, 100% v/v) to give Compound 77D.

A mixture of Compound 77D (1 g, 5.6 mmol) and KOH (0.6 g, 11.2 mmol) in ethane-1,2-diol (20 mL) was stirred at 200° C. for 3 hrs. The mixture was cooled down, added DCM (50 mL), washed with water (50 mL×3), brine (50 mL×1), dried over anhydrous Na₂SO₄, purified by FCC (ethyl acetate in petroleum ether, 0-20% v/v) to give Compound 77E.

To a solution of Compound 77E (200 mg, 1.7 mmol) and NEt₃ (550 mg, 5.1 mmol) in DCM (20 mL) was added ethyl 2-chloro-2-oxoacetate (455 mg, 3.4 mmol) and stirred at 25° C. for 3 hrs. The mixture was added DCM (50 mL), washed with water (50 mL×3), brine (50 mL×1), dried over anhydrous Na₂SO₄, purified by FCC (ethyl acetate in petroleum ether, 0-20% v/v) to give Compound 77F.

To a solution of Compound 77F (350 mg, 1.58 mmol) in EtOH (30 mL) and H₂O (3 mL) was added LiOH.H₂O (133 mg, 3.17 mmol) and stirred at 25° C. for 10 min, concentrated and added water (30 mL), extracted with DCM (20 mL×2). The aqueous layer was acidified via the addition of 1 N HCl, extracted with DCM (20 mL×3), dried over anhydrous Na₂SO₄, concentrated to give Compound 77G.

To a solution of Compound 77G (100 mg, 0.5 mmol), EDCI (144 mg, 0.75 mmol), HOBt (100 mg, 0.75 mmol) in DCM (10 mL) was added Intermediate A (140 mg, 0.5 mmol). The mixture was stirred at 25° C. for 24 hrs, added water (50 mL), extracted with DCM (30 mL×3), dried over anhydrous Na₂SO₄, purified by prep-HPLC to give Compound 77. LCMS: 454 [M+H]⁺; ¹H NMR (CDCl₃, 400 MHz) δ (ppm) 1.73 (m, 4H), 2.10 (m, 5H), 2.51 (m, 2H), 2.84 (m, 2H), 2.97 (br, 1H), 3.40 (m, 2H), 3.92 (m, 2H), 4.21 (s, 4H), 4.44 (s, 1H), 5.10 (s, 1H), 6.80 (m, 3H), 6.88 (s, 1H), 8.20 (br, 1H), 11.02 (br, 1H), 11.49 (br, 1H).

Example 78

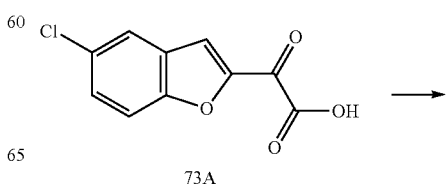

-continued

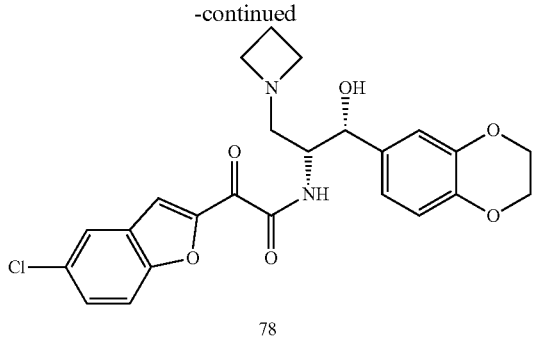

78

A mixture of Compound 73A (200 mg, 0.75 mmol), EDCI (218 mg, 1.13 mmol), HOBt (154 mg, 1.13 mmol), Intermediate F (168 mg, 0.75 mmol) in DCM (20 mL) was stirred at room temperature overnight. Then added water, extracted with DCM (50 mL×2), washed with brine (50 mL), dried over Na$_2$SO$_4$, concentrated. The crude product was purified by pre-HPLC to give Compound 78. LC-MS (ESI) m/z: 471 [M+H]$^+$; $^1$H NMR (CDCl$_3$, 400 MHz) δ (ppm) 2.43 (m, 2H), 3.14 (s, 3H), 3.58 (m, 2H), 4.13 (s, 4H), 4.41 (m, 2H), 4.99 (s, 1H), 6.83 (m, 3H), 7.44 (s, 2H), 7.67 (s, 1H), 8.01 (s, 1H), 8.19 (s, 1H), 10.96 (s, 1H).

Example 79

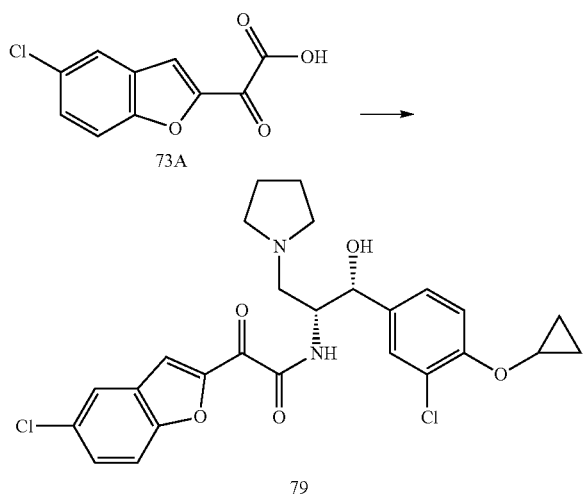

A mixture of Compound 73A (254 mg, 1.13 mmol), EDCI.HCl (325 mg, 1.69 mmol), HOBt (230 mg, 1.69 mmol) and Intermediate I (350 mg, 1.13 mmol) in DCM (25 mL) was stirred at room temperature overnight. Then the mixture was treated with water, extracted with DCM (150 mL×2), washed with brine (100 mL×1), dried over Na$_2$SO$_4$ and concentrated. The crude product was purified with Prep-HPLC to provide Compound 79. LC-MS (ESI) m/z: 517.0 [M+H]$^+$; $^1$H NMR (CDCl$_3$, 400 MHz) δ (ppm) 0.74-0.76 (d, J=5.2 Hz, 4H), 2.15 (s, 4H), 2.98-2.99 (m, 3H), 3.66 (s, 1H), 3.68-3.77 (m, 2H), 3.91 (s, 2H), 4.53 (s, 1H), 5.14 (s, 1H), 7.17-7.22 (m, 2H), 7.35 (s, 1H), 7.43-7.49 (m, 2H), 7.685-7.688 (d, J=1.2 Hz, 1H), 8.11-8.18 (m, 2H), 11.77 (s, 1H).

Example 80

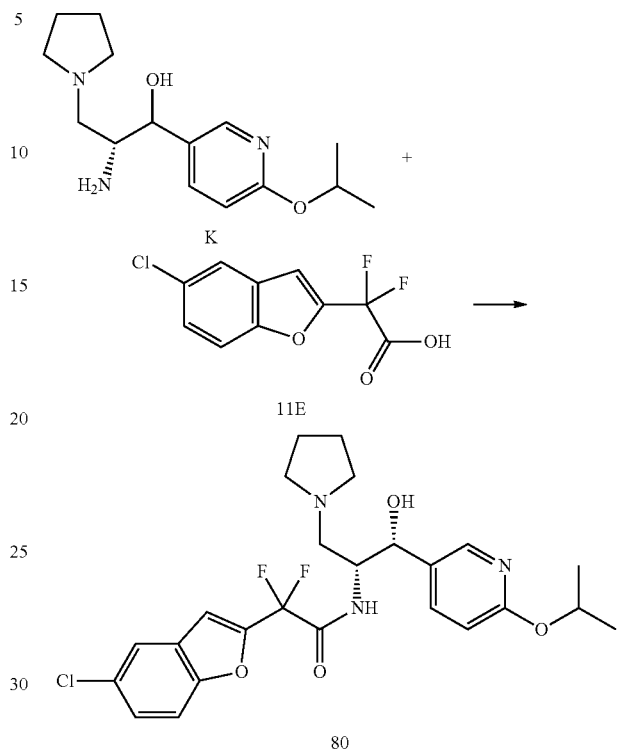

To a solution of Intermediate K (200 mg, 0.72 mmol) and Compound 11E (176 mg, 0.72 mmol) in DCM (10 mL) was added EDCI.HCl (207 mg, 1.08 mmol) and HOBt (146 mg, 1.08 mmol) under N$_2$. The mixture was stirred at 30° C. overnight. TLC and LC-MS showed the starting material was consumed completely, then water (3 mL) was added to the mixture and then extracted with DCM (50 mL×3). The combined organic layers were washed with brine (5 mL×2), dried over anhydrous Na$_2$SO$_4$, and concentrated to provide the crude product. The crude product was purified with Prep-HPLC to provide a racemic mixture (45 mg, Yield: 12%) as a white solid, which was further purified by chiral HPLC (AD-H, 0.1% DEA in methanol) to furnish Compound 80. LC-MS (ESI) m/z: 508 [M+H]$^+$, $^1$H NMR (MeOD, 400 MHz) δ (ppm) 1.29 (m, 6H), 1.83 (s, 4H), 2.69-2.73 (m, 4H), 2.91 (d, J=6.8 Hz, 2H), 4.41 (m, 1H), 4.93 (d, J=3.6 Hz, 1H), 5.08 (m, 1H), 6.56 (d, J=8.4 Hz, 1H), 7.07 (s, 1H), 7.45 (dd, J=2.4, 8.8 Hz, 1H), 7.59 (d, J=8.8 Hz, 1H), 7.63 (dd, J=2.4, 8.8 Hz, 1H), 7.71 (d, J=2.0 Hz, 1H), 8.09 (d, J=2.8 Hz, 1H).

Example 82

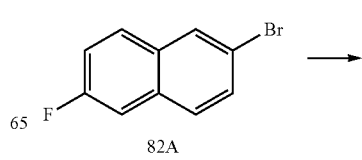

-continued

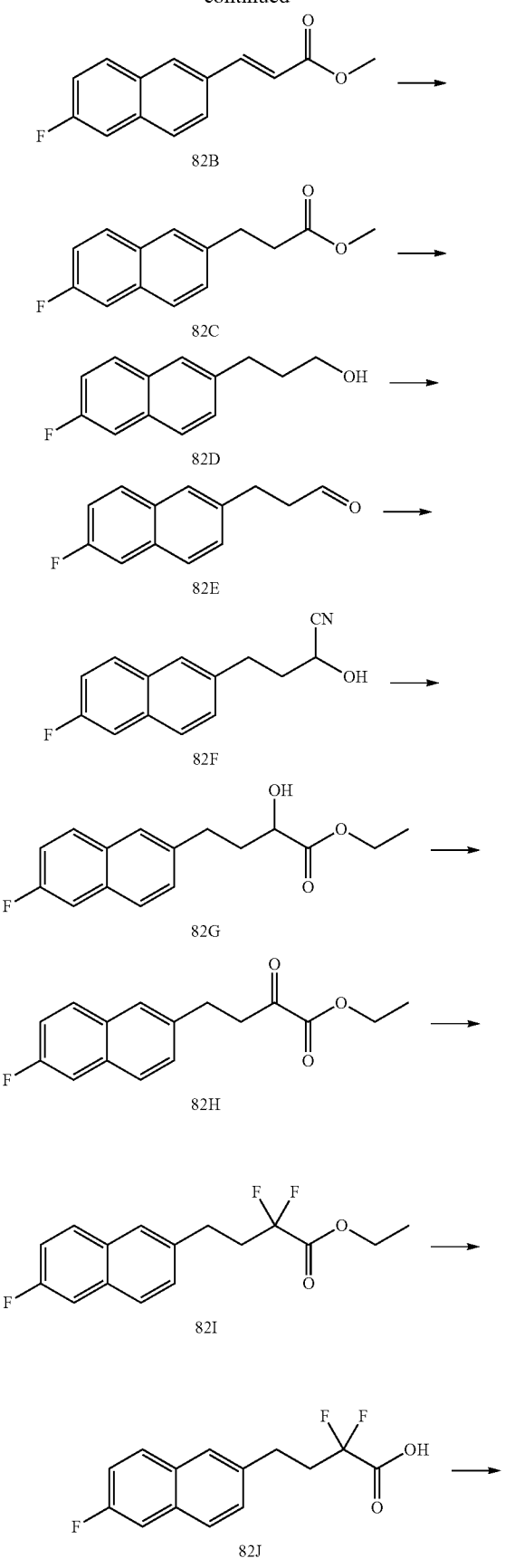

-continued

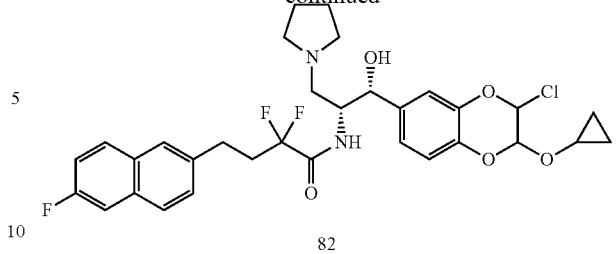

A mixture of Compound 82A (20 g, 89 mmol), methyl acrylate (23 g, 268 mmol) Pd(PPh₃)₂Cl₂ (3 g, 45 mmol) and K₂CO₃ (30 g, 223 mmol) in DMF (100 mixture was stirred at 100° C. for 12 h, then cooled to room temperature, then filtered. The filtrate was treated with water, extracted with DCM (100 mL×2), washed with water (100 mL×3), brine (100 mL), dried over Na₂SO₄, and concentrated to furnish the solid, then the solid was washed with PE, filtered to furnish the crude Compound 82B.

To a solution of Compound 82B (17 g, 74 mmol) in MeOH (200 mL) and THF (80 mL) was added Pd/C (2 g), then the mixture was stirred at room temperature for 12 h under H₂, then filtered. The filtrate was concentrated to furnish the crude Compound 82C.

To a solution of LiAlH₄ (3 g, 73 mmol) in THF (100 mL) was added dropwise Compound 82C (17 g, 73 mmol) in THF (50 mL) at −78° C. under N₂, then the mixture was stirred at −78° C. for 30 min, then quenched with Na₂SO₄.10H₂O and filtered. The filtrate was concentrated to furnish the crude Compound 82D.

To a solution of Compound 82D (13 g, 64 mmol) in DCM (100 mL) was added DMP (32 g, 76 mmol) at 0° C., then the mixture was stirred at room temperature for 2 h, then filtered. The filtrate was concentrated and the residue was purified with column chromatography (ethyl acetate in petroleum, 10% v/v) to furnish Compound 82E.

Compound 82E (25 g, 0.12 mol) was added to a solution of Na₂S₂O₅ (24 g, 0.12 mol) in water (300 mL), then the mixture was stirred for 2 h at room temperature. And after the addition of NaCN (12 g, 0.24 mol) for 15 h, the mixture was diluted with EA (50 mL), extracted with EA (100 mL×2), washed with sat. NaHCO₃ (100 mL×2), brine (100 mL), dried over Na₂SO₄, and concentrated to furnish the crude product Compound 82F.

To a solution of Compound 82F (5 g, 22 mmol) in EtOH (50 mL) was bubbled a gentle stream of HCl gas (dried over con. H₂SO₄) at 0° C. for 5 h. Then the mixture was treated with water slowly at 0° C., stirred at room temperature for 2 h, then extracted with DCM (100 mL×2), washed with brine (100 mL), dried over Na₂SO₄, concentrated and purified with column chromatography (ethyl acetate in petroleum, 10% v/v) to furnish Compound 82G.

To a solution of Compound 82G (4 g, 14.5 mmol) in DCM (100 mL) was added DMP (7.4 g, 17.4 mmol), then the mixture was stirred at room temperature for 1 h, then filtered. The filtrate was concentrated and the residue was purified with column chromatography (10% ethyl acetate in petroleum) to furnish Compound 82H.

To a solution of Compound 82H (2 g, 7.3 mmol) in DCM (50 mL) was added DAST (5.9 g, 36 mmol), then the mixture was stirred at room temperature for 12 h, poured into ice water, extracted with DCM (50 mL×2), washed with brine (50 mL), dried over Na₂SO₄, concentrated and purified with column chromatography (10% ethyl acetate in petroleum) to furnish Compound 821.

To a solution of Compound 821 (1.8 g, 6.07 mmol) in THF (30 mL) was added LiOH (383 mg, 9.1 mmol) in water (2 mL), then the mixture was stirred at room temperature for 2 h, then evaporated to remove solvent. The mixture was treated with water, adjusted PH to 2 with diluted HCl, then extracted with EA (50 mL×2), washed with brine (50 mL), dried over Na$_2$SO$_4$, and concentrated to furnish the Compound 82J.

To a solution of Compound 82J (173 mg, 0.64 mmol) in DCM (50 mL) was added EDCI.HCl (186 mg, 0.97 mmol), HOBt (132 mg, 0.97 mmol), and (1R,2R)-2-amino-1-(3-chloro-4-cyclopropoxyphenyl)-3-(pyrrolidin-1-yl)propan-1-ol (200 mg, 0.97 mmol), then the mixture was stirred at room temperature overnight. The mixture was treated with water (50 mL), extracted with DCM (50 mL×2), washed with brine (50 mL), dried over Na$_2$SO$_4$ and concentrated. The crude product was purified with Prep-HPLC to provide Compound 82. LC-MS (ESI) m/z: 561 [M+H]$^+$; $^1$H NMR (CDCl$_3$, 400 MHz) δ (ppm) 0.56 (m, 4H), 2.13 (m, 4H), 2.41 (m, 2H), 2.60 (m, 2H), 2.90 (m, 2H), 3.43 (s, 3H), 3.81 (s, 2H), 4.47 (s, 1H), 5.16 (s, 1H), 7.16 (m, 3H), 7.40 (m, 2H), 7.49 (s, 1H), 7.56 (s, 1H), 7.68 (s, 1H), 7.75 (m, 1H), 7.79 (m, 1H), 11.99 (s, 1H).

Example 83

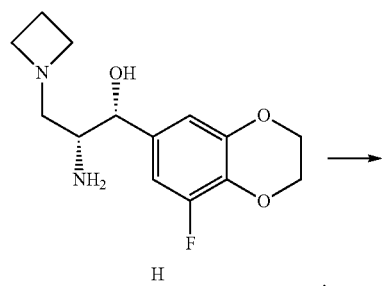

To a mixture of Compound 11E (106 mg, 0.3 mmol) in dichloromethane (20 mL) was added EDCI.HCl (86 mg, 0.45 mmol), HOBt (61 mg, 0.45 mmol) and Intermediate H (74 mg, 0.3 mmol). It was stirred at 30° C. for 5 h. Then it was treated with water (20 mL), extracted with dichloromethane (20 mL×3), dried over anhydrous Na$_2$SO$_4$, evaporated and purified with Prep-HPLC to furnish trifluoroacetic acid salt of Compound 83. LC-MS (ESI) m/z: 493 [M+H]$^+$; $^1$H NMR (CDCl$_3$, 400 MHz) δ (ppm) 2.42 (s, 1H), 2.60 (s, 1H), 3.55-3.58 (m, 2H), 4.05-4.13 (m, 4H), 4.24 (s, 1H), 4.41 (t, J=8 Hz, 1H), 4.80 (s, 1H), 6.64 (s, 1H), 6.72 (d, J=12 Hz, 1H), 6.90 (s, 1H), 7.43 (d, J=8 Hz, 1H), 7.46 (d, J=8 Hz, 1H), 7.70 (s, 1H).

Example 84

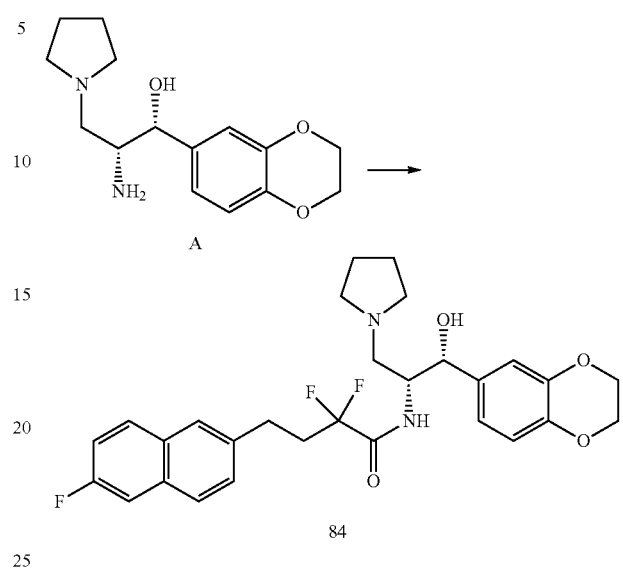

A mixture of Intermediate A (100 mg, 0.36 mmol), Compound 82J (96 mg, 0.36 mmol), EDCI.HCl (104 mg, 0.54 mmol) and HOBt (73 mg, 0.54 mmol) in DCM (20 mL) was stirred at room temperature overnight. The mixture was treated with water (50 mL), extracted with DCM (50 mL×2), washed with brine (50 mL), dried over Na$_2$SO$_4$ and concentrated. The crude product was purified with Prep-HPLC to provide Compound 84. LC-MS (ESI) m/z: 529 [M+H]$^+$; $^1$H NMR (CDCl$_3$, 400 MHz) δ (ppm) 2.09 (s, 4H), 2.22 (m, 2H), 2.49 (m, 1H), 2.65 (m, 1H), 3.45 (m, 4H), 3.89 (m, 4H), 4.48 (s, 1H), 5.05 (s, 1H), 6.80 (s, 2H), 6.90 (s, 1H), 7.24 (m, 2H), 7.41 (m, 1H), 7.52 (s, 1H), 7.79 (m, 2H), 7.76 (m, 1H), 11.76 (s, 1H).

Example 85

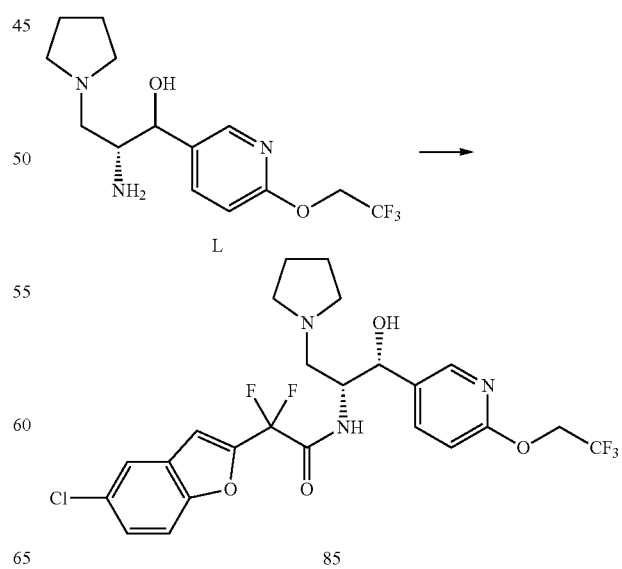

To a solution of Intermediate L (200 mg, 0.63 mmol) and 11E (185 mg, 0.75 mmol) in DCM (10 mL) was added EDCI.HCl (181 mg, 0.94 mmol) and HOBt (127 mg, 0.94 mmol) under N₂. The mixture was stirred at 30° C. overnight. TLC and LC-MS showed the starting material was consumed completely, and sat. NaHCO₃ (3 mL) was added to the mixture and then extracted with DCM (50 mL×3). The combined organic layers were washed with brine (5 mL×2), dried over anhydrous Na₂SO₄, and concentrated to provide the crude product. The crude product was purified with Prep-HPLC to provide Compound 85. LC-MS (ESI) m/z: 548 [M+H]⁺, ¹H NMR (MeOD, 400 MHz) δ (ppm) 2.08-2.22 (m, 4H), 3.25 (m, 2H), 3.65-3.77 (m, 4H), 4.55-4.57 (m, 1H), 4.67-4.72 (m, 2H), 6.71 (d, J=2.8 Hz, 1H), 6.62 (d, J=8.4 Hz, 1H), 7.02 (s, 1H), 7.48 (dd, J=2.0, 8.8 Hz, 1H), 7.59 (d, J=9.2 Hz, 1H), 7.71 (dd, J=2.4, 8.4 Hz, 1H), 7.75 (d, J=2.0, Hz, 1H), 8.15 (d, J=2.4 Hz, 1H).

Example 86

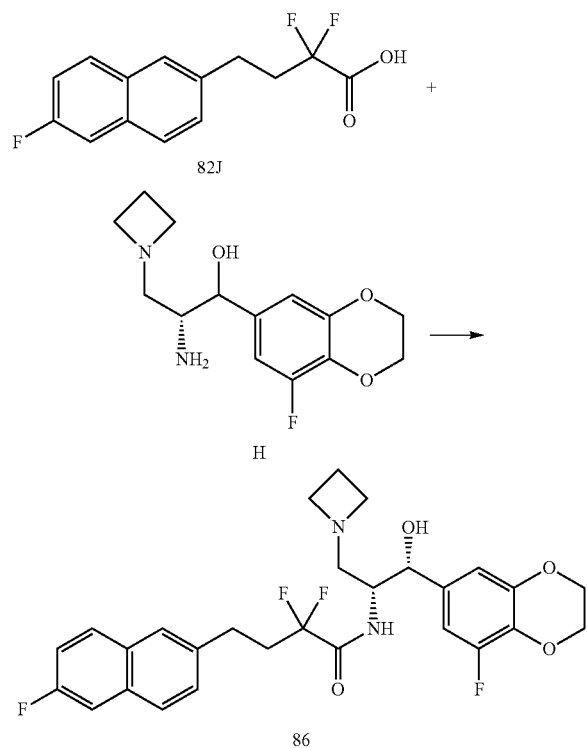

To a mixture of Compound 82J (99 mg, 0.35 mmol) in dichloromethane (10 mL) was added EDCI.HCl (99 mg, 0.52 mmol), HOBt (71 mg, 0.52 mmol) and Intermediate H (94 mg, 0.35 mmol). It was stirred at 30° C. for 2 h. Then it was treated with water (20 mL), extracted with dichloromethane (20 mL×3), dried over anhydrous Na₂SO₄, evaporated and purified with Prep-HPLC to furnish trifluoroacetic acid salt of Compound 86. LC-MS (ESI) m/z: 533 [M+H]⁺; ¹H NMR (CDCl₃, 400 MHz) of Compound δ (ppm) 2.18-2.68 (m, 6H), 3.56-3.59 (m, 2H), 3.72-3.95 (m, 4H), 4.25-4.45 (m, 4H), 4.46 (m, 1H), 4.85-4.86 (d, J=2.8 Hz, 1H), 6.75-6.82 (m, 2H), 7.28-7.34 (m, 2H), 7.49-7.52 (m, 1H), 7.63 (s, 1H), 7.79-7.90 (m, 2H).

Example 87

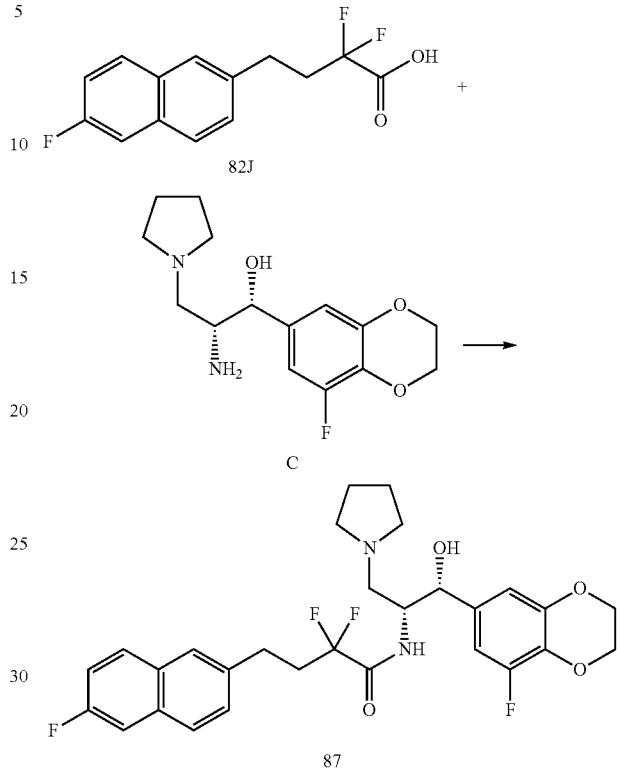

To a mixture of Compound 82J (80 mg, 0.3 mmol) in dichloromethane (10 mL) was added EDCI.HCl (86 mg, 0.45 mmol), HOBt (61 mg, 0.45 mmol) and Intermediate C (118 mg, 0.4 mmol) and the resultant mixture was stirred at 30° C. for 15 h. Then it was treated with water (20 mL), extracted with dichloromethane (20 mL×3), dried over anhydrous Na₂SO₄, evaporated and purified with Prep-HPLC to furnish trifluoroacetic acid salt of Compound 87. LC-MS (ESI) m/z: 557 [M+H]⁺; ¹H NMR (CDCl₃, 400 MHz) δ (ppm) 2.12-2.31 (m, 3H), 2.45-2.52 (m, 1H), 2.62-2.70 (m, 1H), 2.90 (s, 1H), 3.01-3.11 (m, 5H), 3.46 (m, 2H), 3.79-3.98 (m, 6H), 4.45 (s, 1H), 5.50 (s, 1H), 6.68-6.74 (m, 2H), 7.22-7.24 (m, 1H), 7.39 (d, J=12 Hz, 1H), 7.53-7.58 (m, 2H), 7.70 (d, J=12 Hz, 1H), 7.76 (t, J=8 Hz, 1H), 11.62 (s, 1H).

Example 88

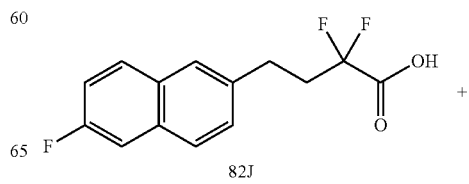

-continued

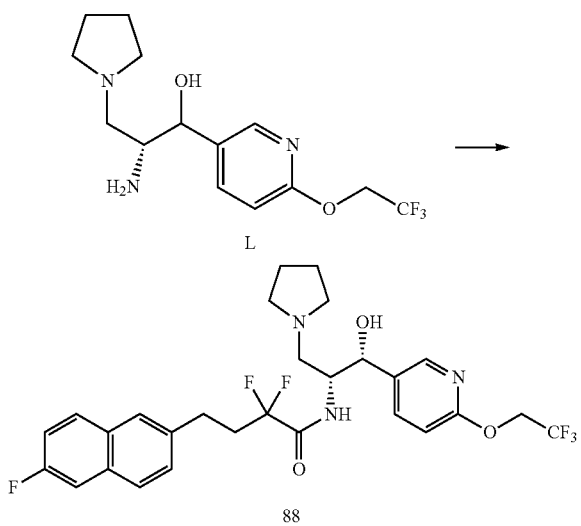

To a solution of Intermediate L (238 mg, 0.75 mmol) and Compound 82J (200 mg, 0.75 mmol) in DCM (10 mL) was added EDCI.HCl (216 mg, 1.12 mmol) and HOBt (152 mg, 1.12 mmol) under $N_2$. The mixture was stirred at 30° C. overnight. TLC and LC-MS showed the starting material was consumed completely, then sat. $NaHCO_3$ (5 mL) was added to the mixture and then extracted with DCM (50 mL×3). The combined organic layers were washed with water (5 mL), brine (5 mL), dried over anhydrous sodium sulphate, and concentrated to offer crude product. The crude product was purified with Prep-HPLC to offer Compound 88. LC-MS (ESI) m/z: 548 [M+H]$^+$; $^1$H NMR (MeOD, 400 MHz) δ (ppm) 2.06 (m, 2H), 2.17-2.26 (m, 4H), 2.49-2.56 (m, 1H), 2.67-2.75 (m, 1H), 3.20-3.26 (m, 2H), 3.57-3.61 (m, 1H), 3.67-3.73 (m, 3H), 4.29-4.34 (m, 1H), 4.58-4.67 (m, 2H), 5.02 (d, J=2.8 Hz, 1H), 6.86 (d, J=8.4 Hz, 1H), 7.27-7.33 (m, 2H), 7.49 (dd, J=2.4, 10.0 Hz, 1H), 7.64 (s, 1H), 7.79-7.88 (m, 3H), 8.25 (d, J=2.4 Hz, 1H).

Example 89

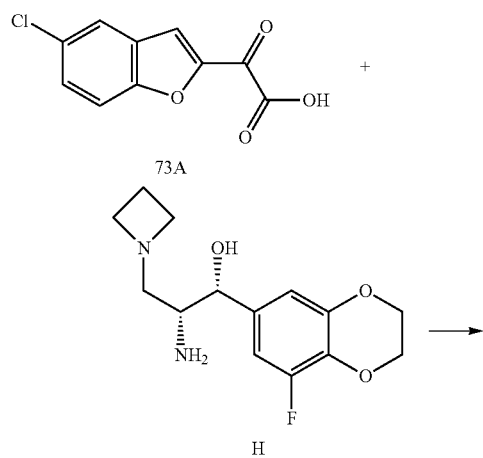

-continued

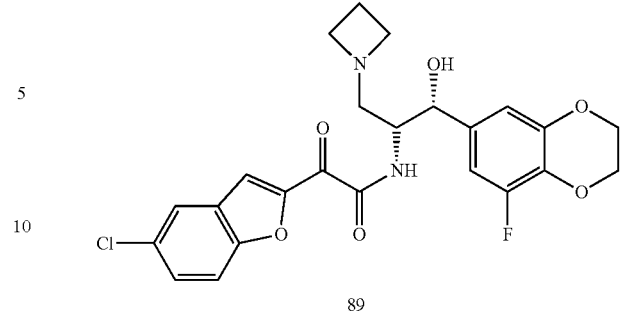

To a solution of Compound 73A (114 mg, 0.5 mmol), HATU (285 mg, 0.75 mmol) in DCM (5 mL) was added Intermediate H (141 mg, 0.5 mmol). Then the reaction was stirred at room temperature for 1.5 h. Then the mixture was treated with water, extracted with DCM (25 mL×2), washed with brine (50 mL), dried over sodium sulphate and concentrated. The crude product was purified with purified with Prep-HPLC and chiral HPLC (OJ-H, ethanol-DEA), followed by Prep-HPLC to furnish trifluoroacetic acid salt of Compound 89. LC-MS (ESI) m/z: 489 [M+H]$^+$; $^1$H NMR (CDCl$_3$, 400 MHz) δ (ppm) 2.41 (m, 2H), 3.31-3.50 (m, 1H), 4.13-4.23 (m, 10H), 4.79-4.80 (d, J=2.8 Hz, 1H), 6.63-6.68 (m, 2H), 7.42-7.48 (m, 2H), 7.65-7.66 (s, 1H), 8.10-8.11 (s, 1H).

Example 90

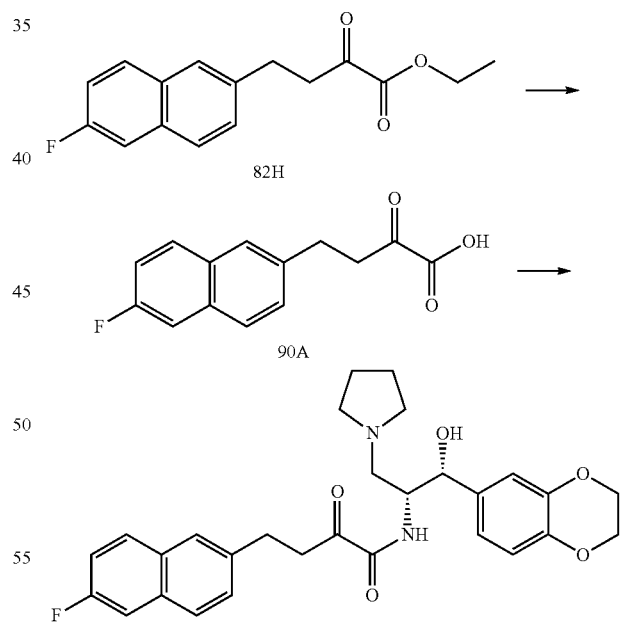

To a solution of Compound 82H (1.1 g, 4.0 mmol) in THF (50 mL) was added LiOH (252 mg, 6.0 mmol) in water (5 mL) at −10° C., then the mixture was stirred at −10° C. for 30 min, then added ice water, adjusted pH 2 with diluted HCl, extracted with EtOAc (50 mL×2). The organic layer was concentrated to form a solid, washed with PE, filtered to furnish Compound 90A.

A mixture of Compound 90A (177 mg, 0.72 mmol), Intermediate A (200 mg, 0.72 mmol), EDCI.HCl (207 mg, 1.08 mmol), HOBt (147 mg, 1.08 mmol) in DMF (20 mL) was stirred at room temperature overnight, then purified with Prep-HPLC to offer Compound 90. LC-MS (ESI) m/z: 507 [M+H]$^+$; $^1$H NMR (CDCl$_3$, 400 MHz) δ (ppm) 2.05 (s, 4H), 2.85 (m, 6H), 3.22 (s, 2H), 3.65 (s, 1H), 3.83 (s, 1H), 4.18 (s, 4H), 4.40 (s, 1H), 4.92 (s, 1H), 6.77 (s, 2H), 6.84 (s, 1H), 7.30 (m, 1H), 7.38 (m, 2H), 7.59 (s, 1H), 7.73 (m, 3H), 11.58 (s, 1H).

Example 91

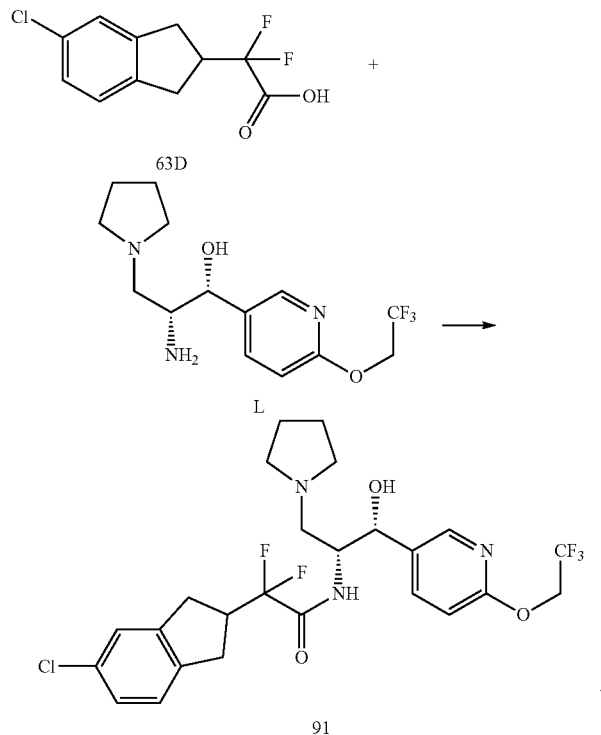

The solution of Compound 63D (60 mg, 0.24 mmol), Intermediate L (77 mg, 0.24 mmol), EDCI.HCl (68 mg, 0.36 mmol) and HOBt (49 mg, 0.36 mmol) in DCM (5 mL) was stirred at 25° C. for 16 h. Then it was diluted with EA (150 mL), washed with water (50 mL×3) and brine (50×2 mL), dried over sulphate, evaporated and purified with Prep-HPLC to furnish Compound 91. LC-MS (ESI) m/z: 548 [M+H]$^+$; $^1$H NMR (MeOD, 400 MHz) δ 2.06 (br s, 2H), 2.19 (br s, 2H), 2.68-2.76 (m, 3H), 2.84-2.92 (m, 2H), 2.97-3.07 (m, 2H), 2.56-3.69 (m, 3H), 3.75 (br s, 1H), 4.65-4.72 (m, 2H), 4.74-4.83 (m, 1H), 5.02 (s, 1H), 6.91 (d, J=8.8 Hz, 1H), 7.10-7.15 (m, 3H), 7.83 (d, J=8.8 Hz, 1H), 8.24 (s, 1H).

Example 92

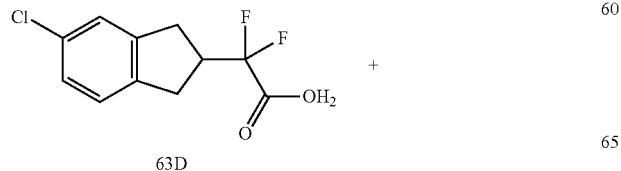

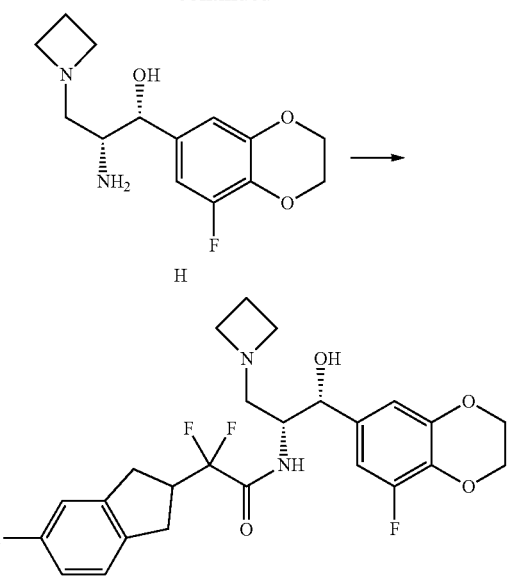

To a mixture of Compound 63D (59 mg, 0.24 mmol) and Intermediate H (59 mg, 0.2 mmol) in dichloromethane (9 mL) was added EDCI.HCl (58 mg, 0.3 mmol), HOBt (41 mg, 0.3 mmol). It was stirred at 30° C. for 2 h. Then it was treated with water (20 mL), extracted with dichloromethane (20 mL×3), dried over anhydrous sodium sulphate, evaporated and purified with Prep-HPLC to furnish trifluoroacetic acid salt of Compound 92. LC-MS (ESI) m/z: 511 [M+H]$^+$; $^1$H NMR (CDCl$_3$, 400 MHz) δ (ppm) 2.38-3.07 (m, 7H), 3.48 (s, 2H), 3.96-4.39 (m, 9H), 5.00 (s, 1H), 6.65-6.73 (m, 2H), 7.03-7.12 (m, 3H), 7.50-7.52 (d, J=4 Hz, 1H), 12.33 (br, 1H).

Example 93

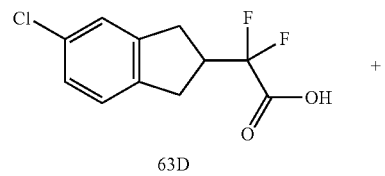

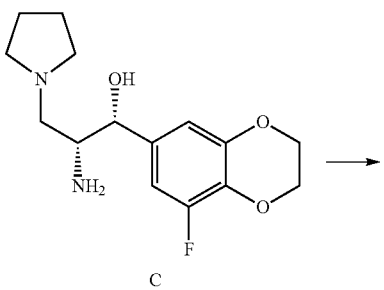

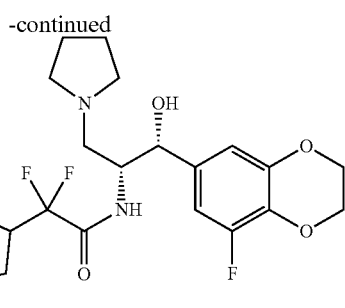

93

To a mixture of Compound 63D (118 mg, 0.48 mmol) in dichloromethane (10 mL) was added EDCI.HCl (115 mg, 0.60 mmol), HOBt (81 mg, 0.60 mmol) and Intermediate C (118 mg, 0.4 mmol). It was stirred at 30° C. for 2 h. Then it was treated with water (20 mL), extracted with dichloromethane (20 mL×3), dried over anhydrous sodium sulphate, evaporated and purified with Prep-HPLC to furnish trifluoroacetic acid salt of Compound 93. LC-MS (ESI) m/z: 525 [M+H]$^+$; $^1$H NMR (CDCl$_3$, 400 MHz) δ (ppm) 2.12 (s, 4H), 2.57-2.66 (m, 2H), 2.80-2.93 (m, 5H), 3.47 (s, 2H), 3.77 (s, 2H), 4.16-4.24 (m, 4H), 4.44 (s, 1H), 5.06 (s, 1H), 6.68-6.75 (m, 2H), 7.03-7.11 (m, 3H), 7.58 (s, 1H), 11.69 (s, 1H).

Example 94

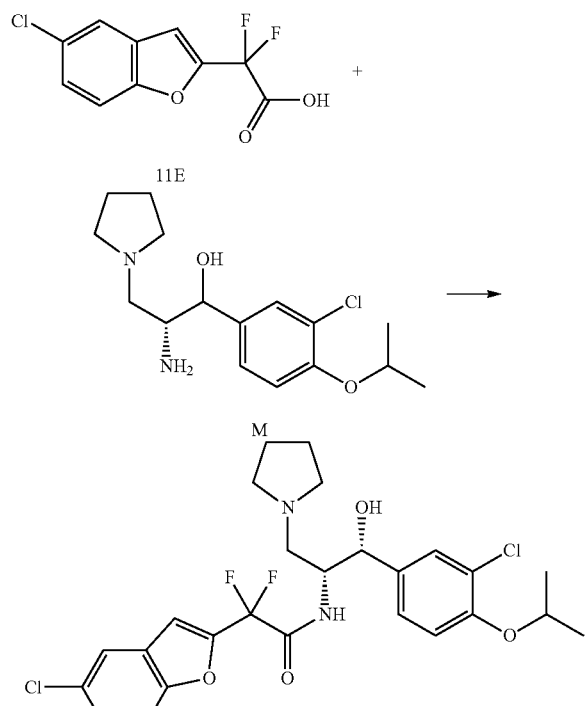

94

A mixture of Intermediate M (150 mg, 0.48 mmol), EDCI.HCl (138 mg, 0.72 mmol), HOBt (97 mg, 0.72 mmol) and Compound 11E (142 mg, 0.58 mmol) in DCM (15 mL) was stirred for 18 h at 25° C. Then the mixture was washed with saturated NaHCO$_3$ (15 mL) and brine (15 mL), dried over anhydrous sodium sulphate. After evaporation, the crude compound was purified with Prep-HPLC to furnish Compound 94. LC-MS (ESI) m/z: 541 [M+H]$^+$; $^1$H NMR (CDCl$_3$, 400 MHz) δ (ppm) 1.26-1.34 (m, 6H), 2.11 (m, 4H), 2.93-3.01 (m, 4H), 3.52-3.55 (m, 1H), 3.79 (m, 1H), 4.37-4.43 (m, 1H), 4.52 (m, 1H), 5.13 (s, 1H), 6.67 (s, 1H), 6.71 (d, J=4.4 Hz, 1H), 7.10 (d, J=8.4 Hz, 1H), 7.32-7.43 (m, 3H), 7.94 (d, J=6.4 Hz, 1H), 11.80 (s, 1H).

Example 95

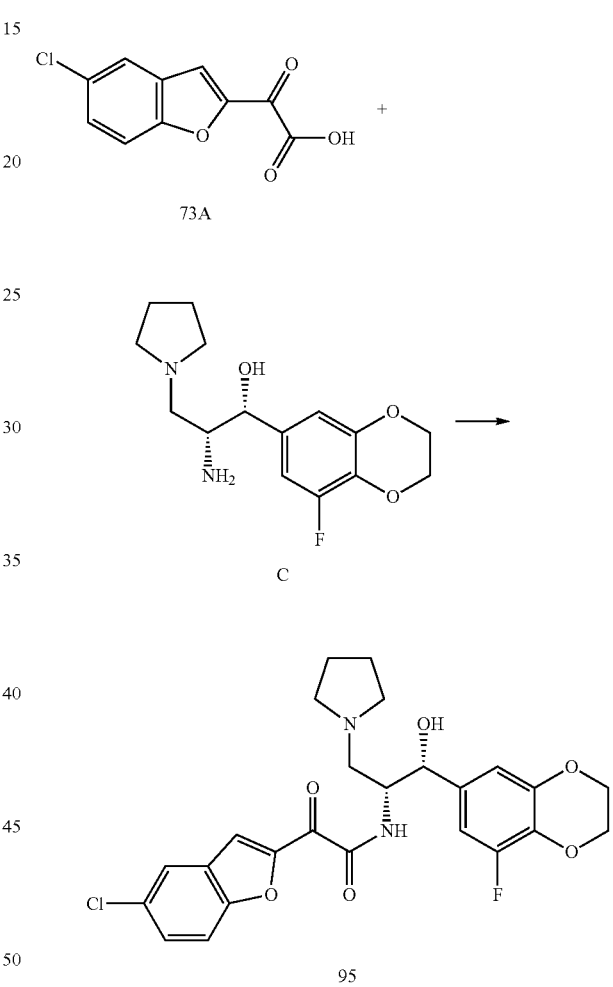

95

To a mixture of Compound 73A (180 mg, 0.8 mmol) in dichloromethane (20 mL) was added HATU (456 mg, 1.2 mmol), DMF (0.1 mL) and Intermediate C (237 mg, 0.8 mmol). It was stirred at 30° C. for 2 h. Then it was treated with water (20 mL), extracted with dichloromethane (20 mL×3), dried over anhydrous sodium sulphate, evaporated and purified with Prep-HPLC to furnish the mixture. Then the mixture was further purified with chiral separation, Prep-HPLC to furnish trifluoroacetic acid salt of Compound 95. LC-MS (ESI) m/z: 503 [M+H]$^+$; $^1$H NMR (CDCl$_3$, 400 MHz) δ (ppm) 2.18 (s, 4H), 2.95-3.08 (m, 2H), 3.52 (s, 2H), 3.93 (s, 2H), 4.23 (s, 4H), 4.47 (s, 1H), 5.13 (s, 1H), 6.73 (d, J=12 Hz, 2H), 7.46-7.53 (m, 2H), 7.70 (s, 1H), 7.99 (s, 1H), 8.25 (s, 1H), 11.86 (s, 1H).

Example 96

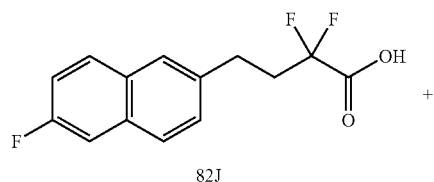
82J
+

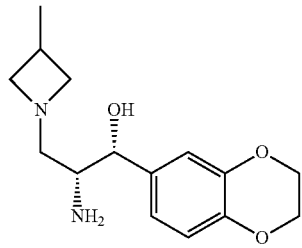
66B

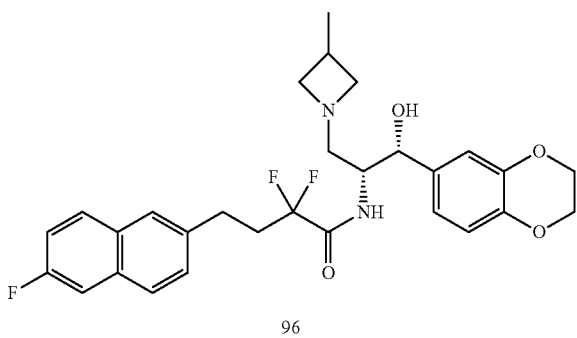
96

A mixture of Compound 82J (80 mg, 0.3 mmol), EDCI.HCl (86 mg, 0.45 mmol), HOBt (61 mg, 0.45 mmol) and Compound 66B (83 mg, 0.3 mmol) in DCM (10 mL) was stirred at room temperature for 5 h. Then the reaction mixture was treated with water (20 mL), extracted with DCM (50 mL×2), washed with brine (50 mL), dried over sodium sulphate and concentrated under vacuum. The residue was purified with Prep-HPLC to offer Compound 96. LC-MS (ESI) m/z: 529 [M+H]$^+$; $^1$H NMR (CDCl$_3$, 400 MHz) δ (ppm) 1.21-1.35 (m, 3H), 2.21 (s, 2H), 2.47 (s, 1H), 2.61 (s, 1H), 3.10 (s, 2H), 3.39-3.49 (m, 3H), 3.81-3.96 (m, 5H), 4.30-4.38 (m, 2H), 4.98 (s, 1H), 6.78-6.86 (m, 3H), 7.25 (d, J=8 Hz, 1H), 7.51 (s, 1H), 7.68-7.77 (m, 3H), 12.13 (s, 1H).

Example 97

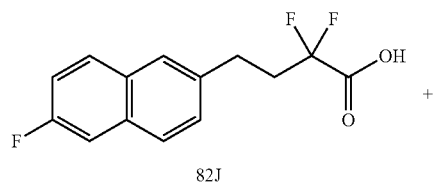
82J
+

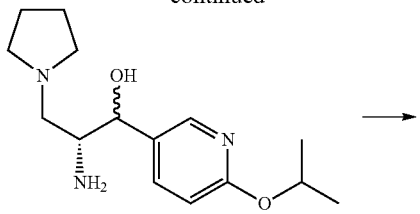
K

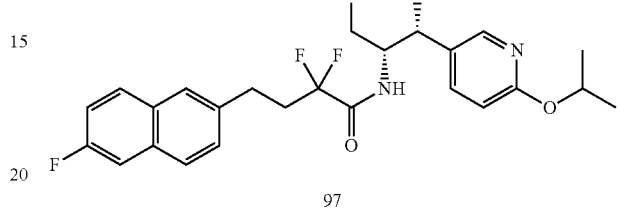
97

A mixture of Intermediate K (200 mg, 0.72 mmol), 82J (192 mg, 0.72 mmol), EDCI.HCl (206 mg, 1.07 mmol), HOBt (146 mg, 1.07 mmol) in DCM (20 mL) was stirred at 25° C. for 4 h, added water, extracted with DCM (50 mL×2), washed with brine (50 mL), dried over sodium sulphate, concentrated, and purified with Prep-HPLC to offer Compound 97. LC-MS (ESI) m/z: 529 [M+H]$^+$. $^1$H NMR (CDCl$_3$, 400 MHz) δ (ppm) 1.20-1.23 (m, 6H), 2.07 (s, 4H), 2.23-2.28 (m, 2H), 2.64-2.69 (m, 2H), 3.00 (s, 2H), 3.62-3.82 (m, 4H), 4.63 (s, 1H), 4.94 (s, 1H), 5.26 (s, 1H), 6.85 (s, 1H), 7.19-7.23 (m, 2H), 7.36-7.39 (m, 1H), 7.52 (s, 1H), 7.65-7.74 (m, 2H), 8.04 (s, 2H), 8.41 (s, 1H), 11.54 (s, 1H).

Example 98

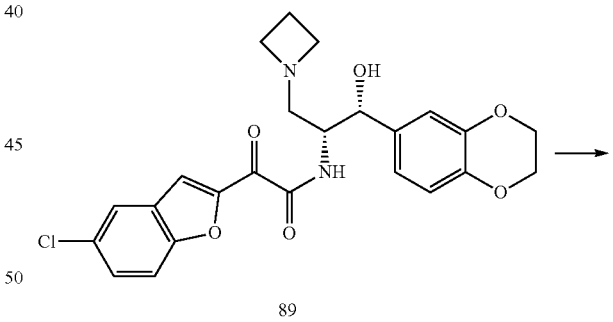
89

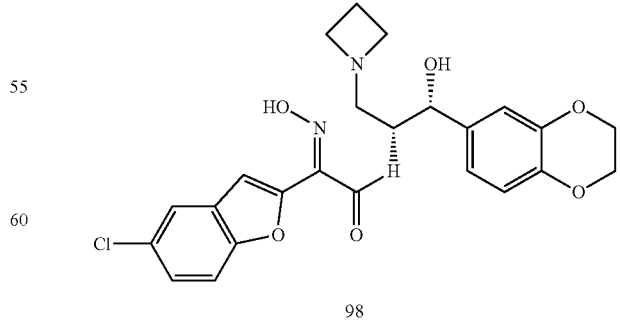
98

To a solution of 89 (12 mg, 0.025 mmol) in MeOH (6 mL) was added hydroxylamine hydrochloride (34 mg, 0.5 mmol)

at 30° C., then the reaction was stirred at 55° C. for 4 h. Then it was purified with Prep-HPLC to furnish Compound 98. LC-MS (ESI) m/z: 504 [M+H]$^+$; $^1$H NMR (MeOD, 400 MHz) δ (ppm) 2.21-2.61 (m, 2H), 3.37-3.41 (m, 2H), 4.12-4.18 (m, 9H), 4.74-4.79 (m, 1H), 6.36 (s, 1H), 6.63-6.71 (m, 2H), 7.26-7.27 (m, 1H), 7.28-7.54 (m, 3H).

Example 99

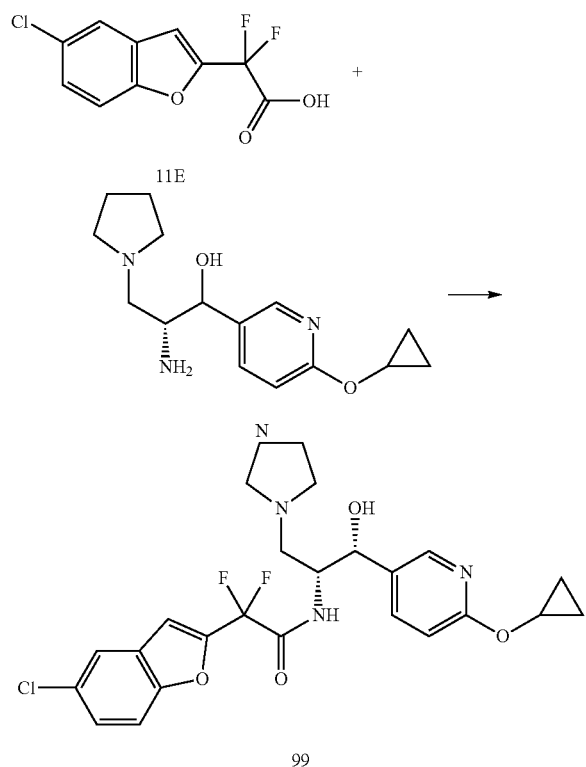

To a solution of Intermediate N (110 mg, 0.397 mmol) in CH$_2$Cl$_2$ (5 mL) was added Compound 11E (97 mg, 0.397 mmol), EDCI.HCl (113 mg, 0.595 mmol) and HOBt (80 mg, 0.595 mmol). The reaction mixture was stirred for 10 hours at 30° C. The solvent was removed under reduced pressure, and the residue was purified successively by prep. TLC (MeOH in CH$_2$Cl$_2$, 10% v/v) and chiral HPLC (co-solvent MeOH (0.1% DEA), column, AD-H 4.6*250 mm, 5 um) to offer desired product Compound 99. LC-MS (ESI) m/z: 506 [M+H]$^+$; $^1$H NMR (CDCl$_3$, 400 MHz) δ (ppm) 0.73-0.79 (m, 4H), 1.78-1.82 (m, 4H), 2.64-2.67 (m, 2H), 2.74-2.76 (m, 2H), 2.97-3.07 (m, 2H), 4.07-4.10 (m, 1H), 4.23 (br, 1H), 5.17 (s, 1H), 6.68 (d, J=8.4 Hz, 1H), 6.87 (s, 1H), 7.32-7.35 (m, 1H), 7.41-7.44 (m, 1H), 7.53-7.58 (m, 2H), 8.21 (d, J=2.0 Hz, 1H).

Example 100

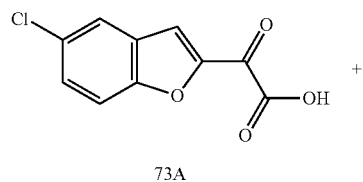

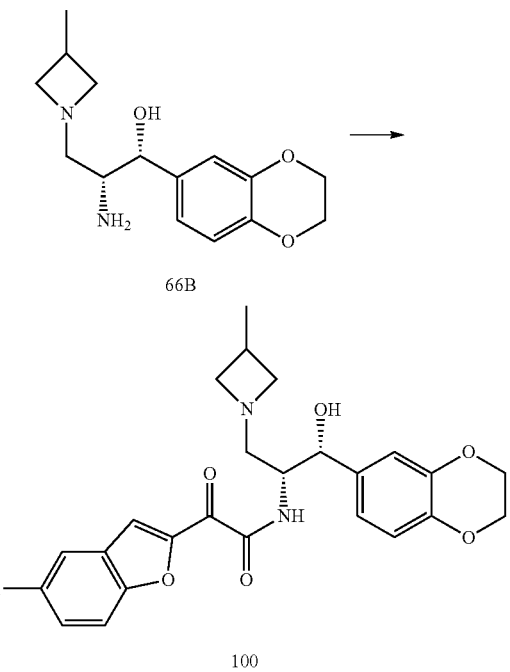

A mixture of Compound 73A (145 mg, 0.65 mmol), HATU (370 mg, 0.97 mmol), and Compound 66B (180 mg, 0.65 mmol) in DCM (20 mL) and DMF (2 mL) was stirred at room temperature for 2 h. Then the reaction mixture was treated with water (20 mL), extracted with DCM (50 mL×2), washed with brine (50 mL), dried over sodium sulphate and concentrated. The crude product was purified with Prep-HPLC to offer Compound 100. LC-MS (ESI) m/z: 485 [M+H]$^+$; $^1$H NMR (CDCl$_3$, 400 MHz) δ (ppm) 1.25-1.37 (m, 3H), 2.31-2.45 (m, 1H), 3.01-3.15 (m, 1H), 3.47-3.59 (m, 3H), 4.08-4.16 (m, 5H), 4.33 (s, 1H), 4.51 (s, 1H), 5.01 (s, 1H), 6.78-6.85 (m, 3H), 7.43-7.49 (m, 2H), 7.69 (s, 1H), 7.95 (s, 1H), 8.24 (s, 1H), 11.32 (s, 1H).

Example 101

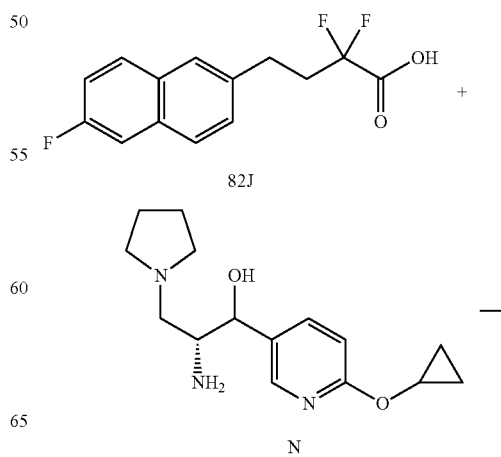

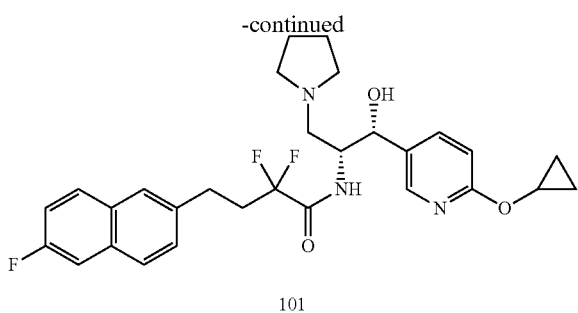

101

A mixture of Intermediate N (100 mg, 0.36 mmol), Compound 82J (96 mg, 0.36 mmol), EDCI.HCl (104 mg, 0.54 mmol), HOBt (74 mg, 0.54 mmol) in DCM (20 mL) was stirred at 25° C. overnight, added water, extracted with DCM (50 mL×2), Brine (50 mL), dried over sodium sulphate, concentrated and purified with Prep-HPLC to offer Compound 101. LC-MS (ESI) m/z: 528 [M+H]$^+$; $^1$H NMR (CDCl$_3$, 400 MHz) δ (ppm) 0.67-0.72 (m, 4H), 2.06 (s, 4H), 2.17-2.27 (m, 2H), 2.57-2.71 (m, 2H), 3.04 (s, 2H), 3.53-3.67 (m, 3H), 3.88 (s, 2H), 4.67 (s, 1H), 5.23 (s, 1H), 6.01 (s, 1H), 7.10 (s, 1H), 7.19-7.24 (m, 2H), 7.37-7.39 (m, 1H), 7.51 (s, 1H), 7.66-7.68 (m, 1H), 7.70-7.74 (m, 1H), 8.10 (s, 2H), 8.50 (s, 1H), 11.31 (s, 1H).

Example 102

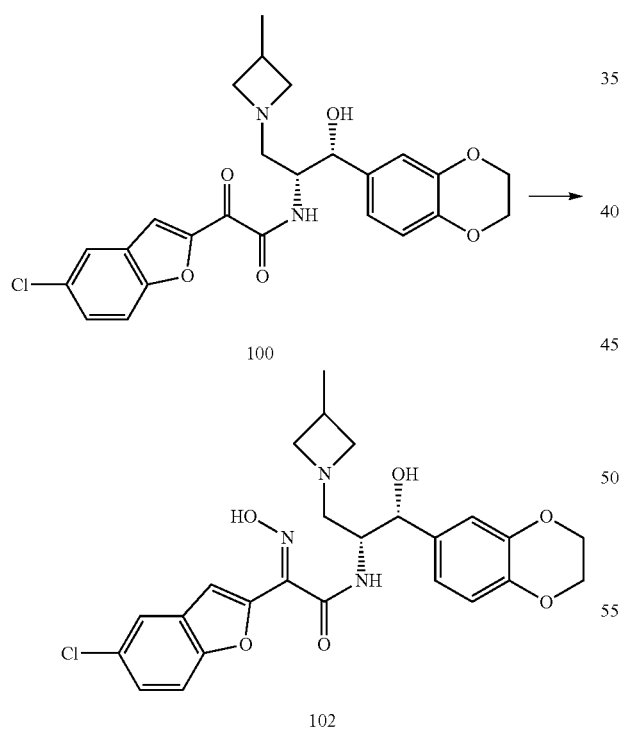

A mixture of 100 (12 mg, 0.025 mmol) and hydroxylamine hydrochloride (17 mg, 0.25 mmol) in MeOH (3 mL) was stirred at room temperature for 4 h. Then it was purified with Prep-HPLC directly to offer Compound 102. LC-MS (ESI) m/z: 500 [M+H]$^+$; $^1$H NMR (MeOD, 400 MHz) δ (ppm) 1.26-1.35 (m, 3H), 3.12 (s, 1H), 3.45-3.52 (m, 2H), 3.78-4.14 (m, 4H), 4.38-4.52 (m, 5H), 4.86-4.93 (m, 1H), 6.23 (s, 1H), 6.80-6.94 (m, 3H), 7.29 (s, J=8 Hz, 1H), 7.34-7.41 (m, 1H), 7.44-7.62 (m, 2H).

Example 103

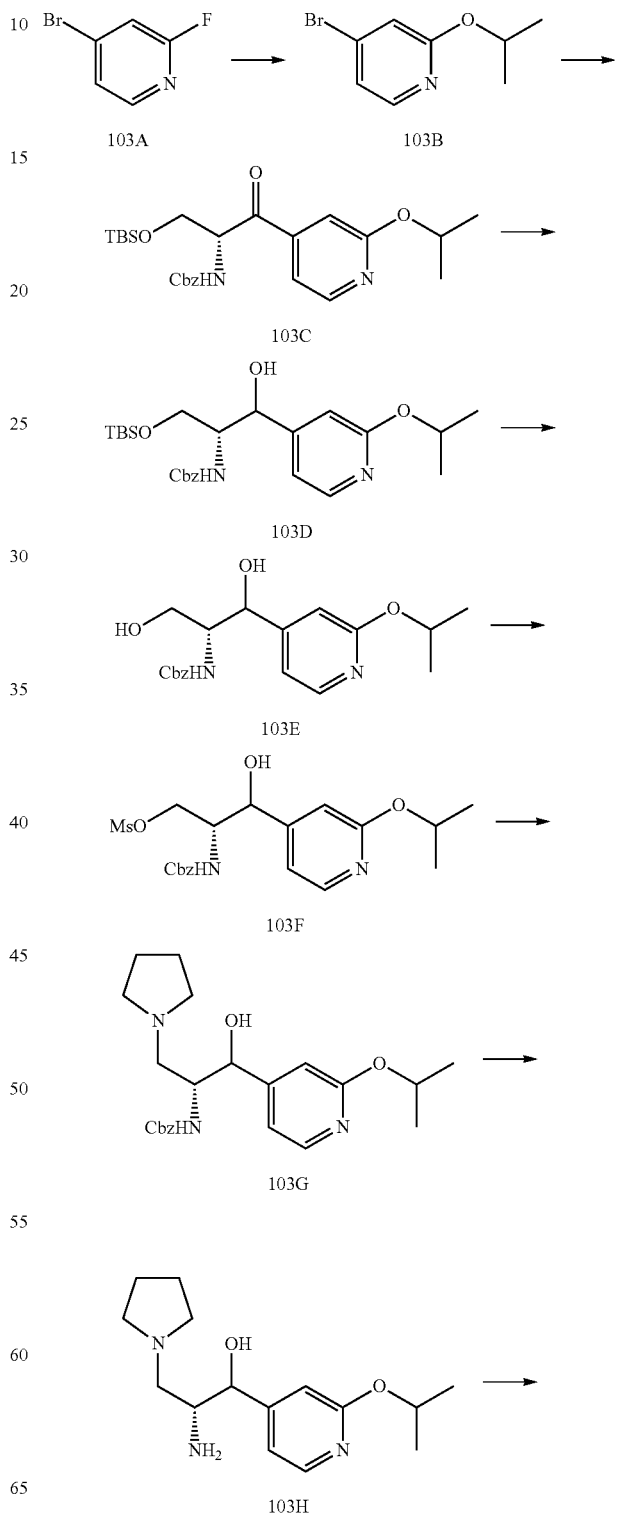

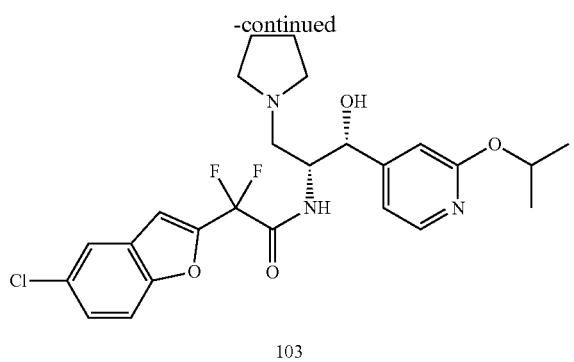

103

60% NaH (1.04 g, 26 mmol) was added in two portions to isopropyl alcohol (30 mL) at room temperature (about 30° C.) under $N_2$. The mixture was stirred at 60° C. for 30 min. Compound 103A (2 g, 11.36 mmol) was added in two portions and the mixture was stirred at reflux 4 h and at 80° C. overnight. The solution was concentrated in vacuo. Water (100 mL) and ethyl acetate (200 mL) were added and the layers were separated. The aqueous layer was extracted with ethyl acetate (50 mL×3). The combined organic layers were washed with water (10 mL×2), brine (10 mL×2) and dried over anhydrous sodium sulphate. After filtration the solvent was removed in vacuo. The crude product was subjected to flash chromatography (silica, ethyl acetate in petroleum, 0-10% v/v) to offer Compound 103B.

To a solution of Compound 103B (13 g, 60 mmol) in THF (300 mL) was added n-BuLi (2.4 M, 25 mL) at −60° C. under $N_2$ and the resultant mixture was stirred for 0.5 h, then a solution of Compound A4 (8 g, 20 mmol) in THF (50 mL) was added, then the mixture was stirred at −60° C. for 1 h. After reaction monitored by LC-MS and TLC, added saturated $NH_4Cl$ solution (50 mL), extracted with ethyl acetate (100 mL×3), washed with brine (100 mL×2), and dried over anhydrous sodium sulphate. The crude product was purified with column chromatography (ethyl acetate in petroleum, 0-20% v/v) to offer Compound 103C.

Compound 103C (472 mg, 1 mmol) was dissolved in anhydrous THF (10 mL) and cooled down to −70° C. under nitrogen atmosphere. L-Selectride (2 mL, 1M solution in THF, 2 mmol) was added dropwise while keeping the temperature at −70° C. Then the reaction was stirred for 0.5 h at −70° C. After reaction was monitored by TLC, the reaction was quenched with saturated $NH_4Cl$ solution (30 mL) and extracted with ethyl acetate (30 mL×3). The combined organic phases were washed water (30 mL), brine (30 mL×2), and dried over anhydrous sodium sulphate. The crude product was purified with column chromatography (ethyl acetate in petroleum, 0-20% v/v) to offer Compound 103D.

To a solution of Compound 103D (2.1 g, 4.4 mmol) in THF (40 mL) was added a solution of TBAF (0.58 g, 2.2 mmol) in THF (10 mL) at 0° C., then the mixture was stirred at 30° C. overnight. After the reaction was monitored by TLC and LC-MS. THF was evaporated. Then the residue was treated with water (50 mL) and extracted with ethyl acetate (50 mL×3), washed with brine (50 mL), and dried over anhydrous sodium sulphate. The crude product was purified with flash column (silica, methanol in dichloromethane, 0-10% v/v) to offer Compound 103E.

To a solution of Compound 103E (1.2 g, 3.3 mmol) in dry DCM (20 mL) was added $Et_3N$ (1 mL) under $N_2$, then the mixture was cooled to −40° C., MsCl (0.31 mL, 4 mmol) was added slowly. Then the mixture was stirred at −40° C. about an hour. After reaction was monitored by TLC, the mixture was treated with water (10 mL) and extracted with DCM (50 mL×3), washed with brine (50 mL), dried over anhydrous sodium sulphate. The crude product was purified with flash column (silica, methanol in dichloromethane, 0-30% v/v) to offer Compound 103F.

To a solution of Compound 103F (1 g, 2.3 mmol) in THF (40 mL) was added pyrrolidine (2 mL) under $N_2$, then the mixture was stirred at 50° C. for 16 h. After reaction monitored by LC-MS, the mixture was treated with water (50 mL) and extracted with EA (50 mL×3), washed with brine (50 mL×2), dried over anhydrous sodium sulphate. The crude product was purified with column chromatography (methanol in dichloromethane, 0-10% v/v) to offer Compound 103G.

To a solution of Compound 103G (400 mg, 0.97 mmol) in EtOH (20 mL) and water (5 mL) was added $LiOH.H_2O$ (163 mg, 3.87 mmol). The mixture was stirred at 90° C. overnight, concentrated and added water (50 mL), extracted with DCM (30 mL×3), dried over anhydrous sodium sulphate, and concentrated to furnish the product Compound 103H.

To a solution of Compound 103H (140 mg, 0.5 mmol) and Compound 11E (123 mg, 0.5 mmol) in DMF (5 mL) was added EDCI.HCl (144 mg, 0.75 mmol) and HOBt (101 mg, 0.75 mmol) under $N_2$. The mixture was stirred at 30° C. overnight. TLC and LC-MS showed the starting material was consumed completely, EA (50 mL) was added to the mixture and then washed with water (50 mL×3), brine (50 mL×1), dried over anhydrous sodium sulphate, and concentrated to offer crude product. The crude product was purified with Prep-HPLC to offer a mixture (50 mg, 20%) as a white solid, then the mixture was separated by Chiral-HPLC (Co-solvent EtOH (0.1% DEA), column OJ-H 250*4.6 mm 5 um) to offer Compound 103.

Example 104

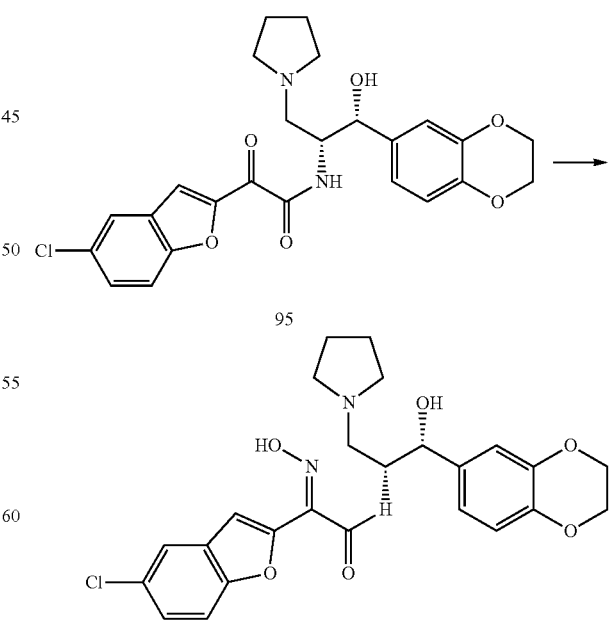

A mixture of 95 (18 mg, 0.036 mmol) and hydroxylamine hydrochloride (25 mg, 0.36 mmol) in MeOH (3 mL) was stirred at room temperature for 8 h. Then it was purified with Prep-HPLC directly to offer Compound 104. LC-MS (ESI) m/z: 518 [M+H]$^+$; $^1$H NMR (MeOD, 400 MHz) δ (ppm) 2.06-2.18 (m, 4H), 3.24 (s, 2H), 3.48-3.83 (m, 4H), 4.15-4.34 (m, 4H), 4.59-4.77 (m, 1H), 4.91 (d, J=4 Hz, 1H), 6.39 (s, 1H), 6.80-6.89 (m, 2H), 7.35-7.60 (m, 3H), 7.67-7.71 (m, 1H).

Example 105

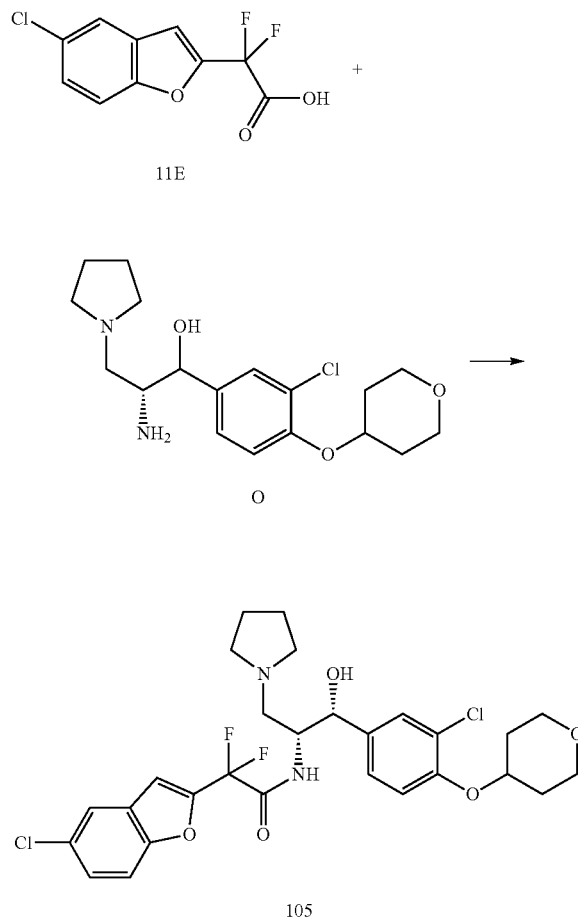

The mixture of Intermediate O (120 mg, 0.34 mmol), EDCI.HCl (98 mg, 0.51 mmol), HOBt (69 mg, 0.51 mmol) and Compound 11E (101 mg, 0.41 mmol) in DCM (15 mL) was stirred for 18 h at 25° C. Then the mixture was washed with saturated NaHCO$_3$ (10 mL) and brine (10 mL), dried over anhydrous sodium sulphate. After evaporation, the crude compound was purified with Prep-HPLC to furnish Compound 105. LC-MS (ESI) m/z: 583 [M+H]$^+$; $^1$H NMR (CDCl$_3$, 400 MHz) δ (ppm) 1.75-1.84 (m, 2H), 1.96-2.14 (m, 6H), 2.77-2.87 (m, 2H), 3.17-3.20 (m, 1H), 3.55-3.60 (m, 3H), 3.76 (m, 1H), 3.88-4.02 (m, 3H), 4.41-4.48 (m, 2H), 4.95 (d, J=4.8 Hz, 1H), 6.79 (d, J=8.4 Hz, 1H), 6.87 (s, 1H), 7.19 (dd, J=8.4, 1.6 Hz, 1H), 7.32 (dd, J=8.8, 2.0 Hz, 1H), 7.42 (d, J=9.2 Hz, 1H), 7.46 (d, J=1.6 Hz, 1H), 7.58 (d, J=2.0 Hz, 1H), 9.23 (d, J=8.0 Hz, 1H), 11.87 (s, 1H).

Example 106

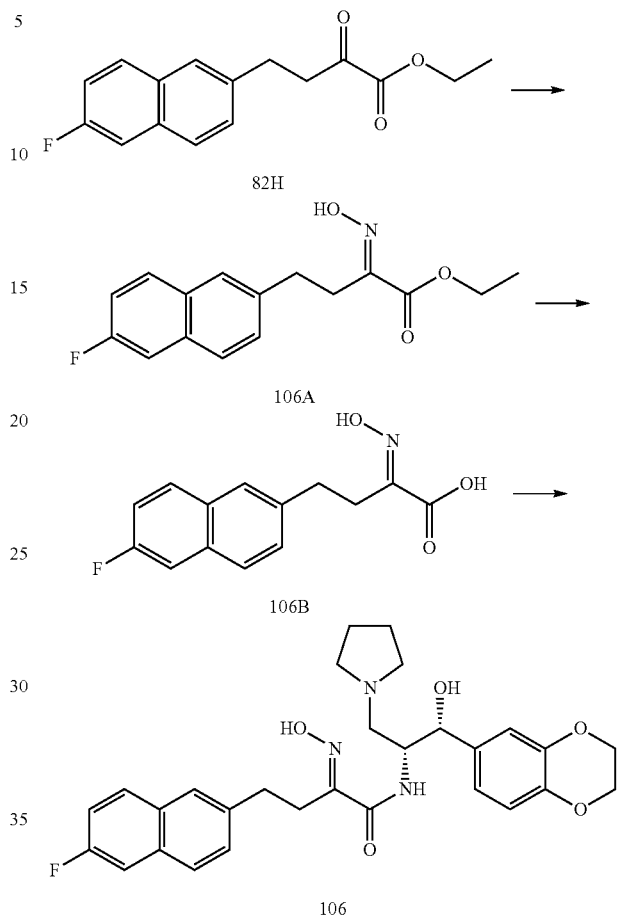

To a solution of Compound 82H (310 mg, 1.13 mmol) in ethanol (10 mL) was added hydroxylamine hydrochloride (102 mg, 1.47 mmol) and K$_2$CO$_3$ (203 mg, 1.47 mmol), then the mixture was stirred at 25° C. for 12 h and filtered. The filtrate was concentrated to furnish the Compound 106A. LC-MS (ESI) m/z: 290 [M+H]$^+$; $^1$H NMR (CDCl$_3$, 400 MHz) δ (ppm) 1.25 (t, J=6.8 Hz, 3H), 2.98 (s, 4H), 4.17-4.23 (m, 2H), 7.18-7.26 (m, 1H), 7.37-7.41 (m, 2H), 7.63 (s, 1H), 7.70-7.73 (m, 2H).

To a solution of Compound 106A (1500 mg, 0.52 mmol) in THF (15 mL) was added LiOH (65 mg, 1.55 mmol) in water (2 mL), then the mixture was stirred at 25° C. for 12 h, then added water, diluted with EA (20 mL), adjusted to PH=2 with diluted HCl, extracted with EA (50 mL×2), brine (50 mL), dried over sodium sulphate, and concentrated to furnish crude Compound 106B.

A mixture of Compound 106B (135 mg, 0.52 mmol), Intermediate A, EDCI.HCl (149 mg, 0.77 mmol), HOBt (106 mg, 0.77 mmol) in DMF (8 mL) was stirred at 25° C. overnight, purified with Prep-HPLC to offer Compound 106. LC-MS (ESI) m/z: 522 [M+H]$^+$; $^1$H NMR (CDCl$_3$, 400 MHz) δ (ppm) 1.97 (s, 4H), 2.83-2.87 (m, 6H), 3.09 (s, 1H), 3.49 (s, 1H), 3.72 (s, 2H), 4.14 (s, 4H), 4.48 (s, 1H), 4.84 (s, 1H), 6.74-6.79 (m, 2H), 6.87 (s, 1H), 7.16-7.23 (m, 1H), 7.36-7.40 (m, 2H), 7.61 (s, 1H), 7.65-7.67 (m, 1H), 7.71-7.75 (m, 1H), 11.17 (s, 1H).

Example 107

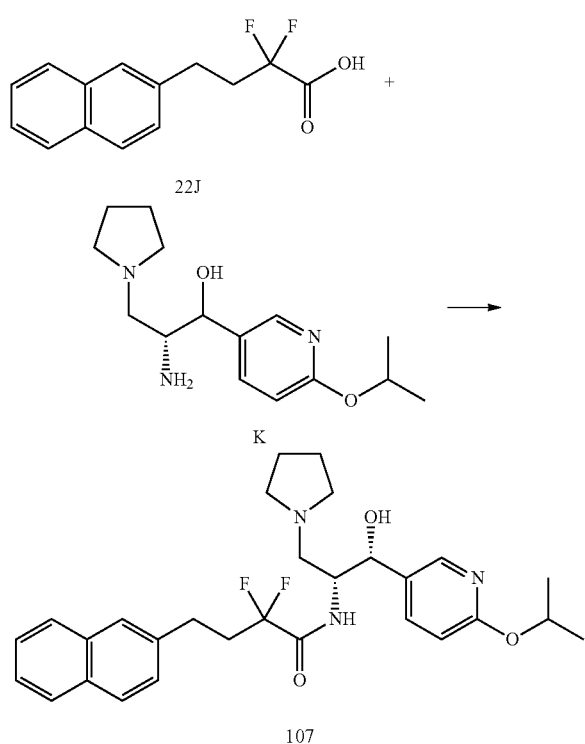

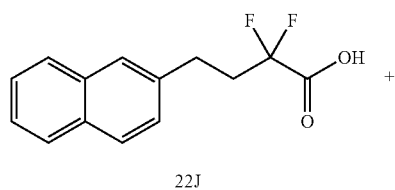

To a solution of Intermediate K (167 mg, 0.60 mmol) and Compound 22J (150 mg, 0.60 mmol) in DMF (10 mL) was added EDCI.HCl (173 mg, 0.90 mmol) and HOBt (122 mg, 0.90 mmol) under $N_2$. The mixture was stirred at 25° C. overnight. TLC and LC-MS showed the starting material was consumed completely, sat. $NaHCO_3$ (5 mL) was added to the mixture and then extracted with EA (50 mL×3). The combined organic layers were washed with water (5 mL), brine (5 mL), dried over anhydrous sodium sulphate, and concentrated to offer crude product. The crude product was purified with Prep-HPLC to offer Compound 107. LC-MS (ESI) m/z: 512 [M+H]+, $^1$H NMR (MeOD, 400 MHz) δ (ppm) 0.97 (d, J=6.0 Hz, 3H), 1.06 (d, J=6.4 Hz, 3H), 1.98-2.01 (m, 2H), 2.13-2.25 (m, 4H), 2.49-2.57 (m, 1H), 2.65-2.73 (m, 1H), 3.13-3.21 (m, 2H), 3.52-3.56 (m, 1H), 3.61-3.67 (m, 3H), 4.61 (d, J=10.0 Hz, 1H), 4.82-4.85 (m, 1H), 4.97 (d, J=2.4 Hz, 1H), 6.79-6.81 (m, 1H), 7.24 (dd, J=8.4, 1.6 Hz, 1H), 7.38-7.44 (m, 2H), 7.57 (s, 1H), 7.75-7.79 (m, 3H), 7.82-7.85 (m, 1H), 8.17 (s, 1H).

Example 108

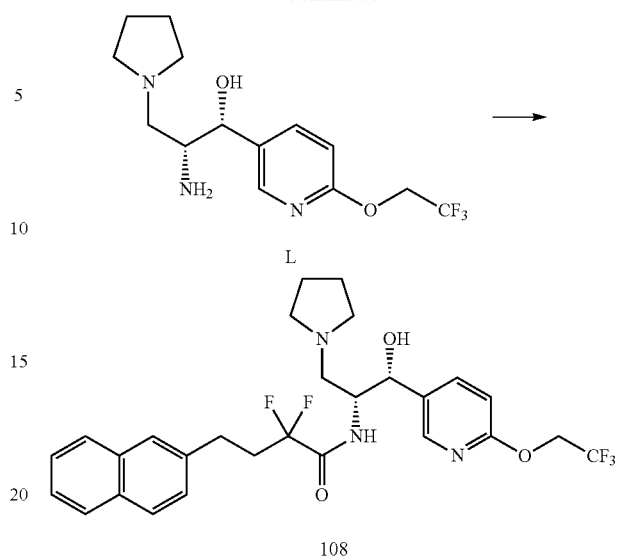

The solution of Intermediate L (230 mg, 0.72 mmol), Compound 22J (150 mg, 0.60 mmol), EDCI.HCl (172 mg, 0.90 mmol) and HOBt (122 mg, 0.90 mmol) in DCM (10 mL) was stirred at room temperature overnight. Then it was diluted with EA (150 mL), washed with water (50 mL×3) and brine (50×2 mL), dried over sulphate, evaporated and purified with Prep-HPLC to offer Compound 108. LC-MS (ESI) m/z: 552 [M+H]+; $^1$H NMR (CDCl$_3$, 400 MHz) δ (ppm) 2.02-2.16 (m, 4H), 2.09-2.36 (m, 2H), 2.53-2.60 (m, 2H), 2.77-2.99 (m, 2H), 3.34-3.40 (m, 2H), 3.67-3.77 (m, 2H), 4.42-4.47 (m, 2H), 4.54-4.60 (m, 1H), 5.18 (s, 1H), 6.80-6.82 (m, 1H), 7.19-7.21 (m, 1H), 7.43-7.46 (m, 2H), 7.53 (s, 1H), 7.61-7.63 (m, 2H), 7.75-7.80 (m, 3H), 8.14 (s, 1H), 11.88 (s, 1H).

Example 109

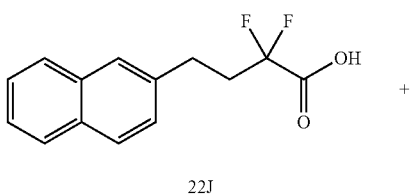

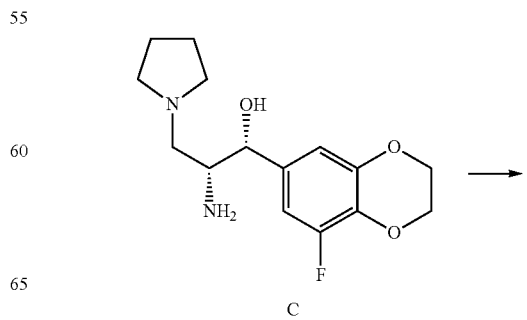

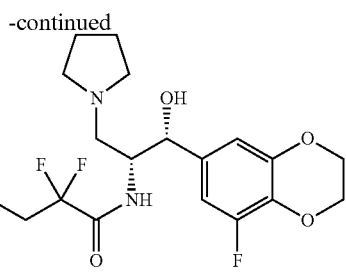

109

A mixture of Compound 22J (100 mg, 0.40 mmol), EDCI.HCl (115 mg, 0.60 mmol) and HOBt (81 mg, 0.60 mmol) in Dichloromethane (20 mL) was stirred at 30° C. for 15 min. Intermediate C (148 mg, 0.50 mmol) was added. The reaction was stirred at 30° C. for 15 h. It was treated with water (20 mL), extracted with dichloromethane (20 mL×3). The organic layer was washed with water (50 mL×2) and brine (50 mL), dried over anhydrous sodium sulphate, evaporated and purified with Prep-HPLC to furnish Compound 109. LC-MS (ESI) m/z: 529 [M+H]$^+$; $^1$H NMR (CDCl$_3$, 400 MHz) δ (ppm) 2.10 (m, 4H), 2.27 (s, 1H), 2.45-2.54 (m, 1H), 2.63-2.71 (m, 1H), 2.84 (s, 1H), 2.98 (s, 1H), 3.42 (s, 2H), 3.77-3.95 (m, 6H), 4.43 (s, 1H), 5.04 (s, 1H), 6.68-6.73 (m, 2H), 7.22-7.24 (m, 1H), 7.41-7.47 (m, 2H), 7.54 (s, 2H), 7.75-7.80 (m, 3H), 11.59 (s, 1H).

Example 110

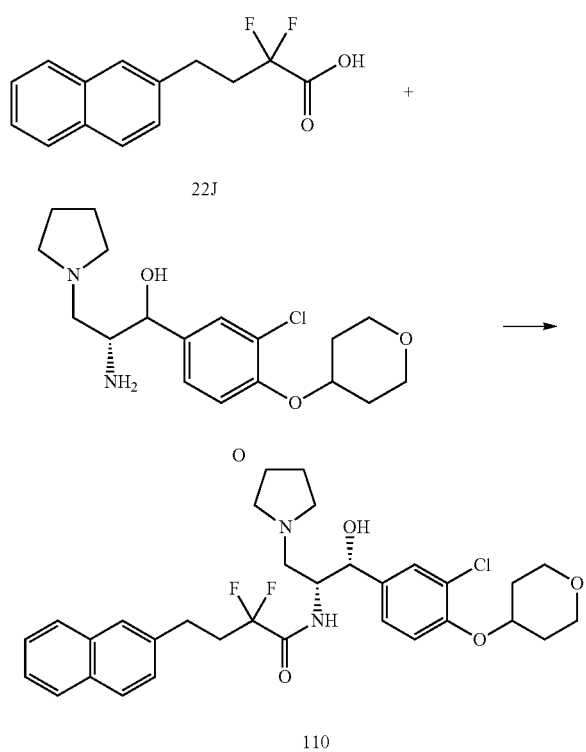

The mixture of Intermediate 0 (120 mg, 0.34 mmol), EDCI.HCl (98 mg, 0.51 mmol), HOBt (69 mg, 0.51 mmol) and Compound 22J (103 mg, 0.41 mmol) in DCM (15 mL) was stirred for 3 h at 25° C. Then the mixture was washed with saturated NaHCO$_3$ (10 mL) and brine (10 mL), dried over anhydrous sodium sulphate. After evaporation, the crude compound was purified with Prep-HPLC to furnish Compound 110. LC-MS (ESI) m/z: 587 [M+H]$^+$; $^1$H NMR (CDCl$_3$, 400 MHz) δ (ppm) 1.57 (m, 2H), 1.71 (m, 2H), 2.10 (m, 4H), 2.23-2.33 (m, 2H), 2.44-2.68 (m, 2H), 2.81-2.95 (m, 2H), 3.32-3.42 (m, 4H), 3.77-3.79 (m, 4H), 4.21 (m, 1H), 4.45 (m, 1H), 5.12 (s, 1H), 6.82 (d, J=8.0 Hz, 1H), 7.14-7.22 (m, 2H), 7.41-7.48 (m, 3H), 7.59 (s, 1H), 7.63 (s, 1H), 7.74-7.80 (m, 3H), 11.7 (s, 1H).

Example 111

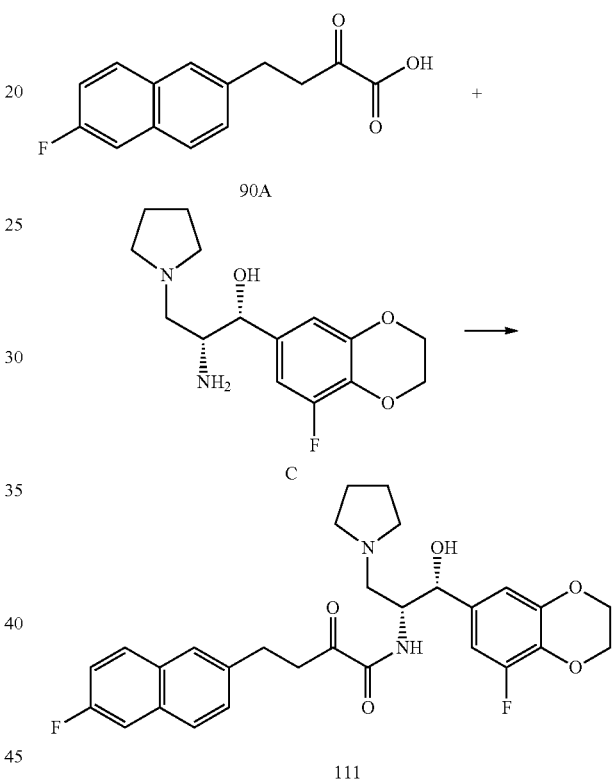

A mixture of Compound 90A (160 mg, 0.65 mmol), HATU (370 mg, 0.97 mmol) and DMF (0.5 mL) in Dichloromethane (20 mL) was stirred at 30° C. for 15 min. Intermediate C (192 mg, 0.65 mmol) was added. The reaction was stirred at 30° C. for 4 h. Then water (20 mL) was added to reaction mixture. The resulting mixture was extracted with dichloromethane (20 mL×3), dried over anhydrous sodium sulphate, evaporated and purified with Prep-HPLC to furnish trifluoroacetic acid salt of Compound 111. LC-MS (ESI) m/z: 525 [M+H]$^+$; $^1$H NMR (CDCl$_3$ & MeOD, 400 MHz) δ (ppm) 1.97-2.05 (m, 4H), 2.93-2.97 (m, 3H), 3.12-3.16 (m, 3H), 3.09-3.33 (m, 1H), 3.47 (t, J=12 Hz, 1H), 3.62 (s, 1H), 3.76 (s, 1H), 4.14-4.18 (m, 4H), 4.23-4.27 (m, 1H), 4.74 (s, 1H), 6.60-6.65 (m, 2H), 7.16 (t, J=8 Hz, 1H), 7.27 (d, J=8 Hz, 1H), 7.34 (d, J=12 Hz, 1H), 7.56 (s, 1H), 7.61-7.71 (m, 2H).

Example 112

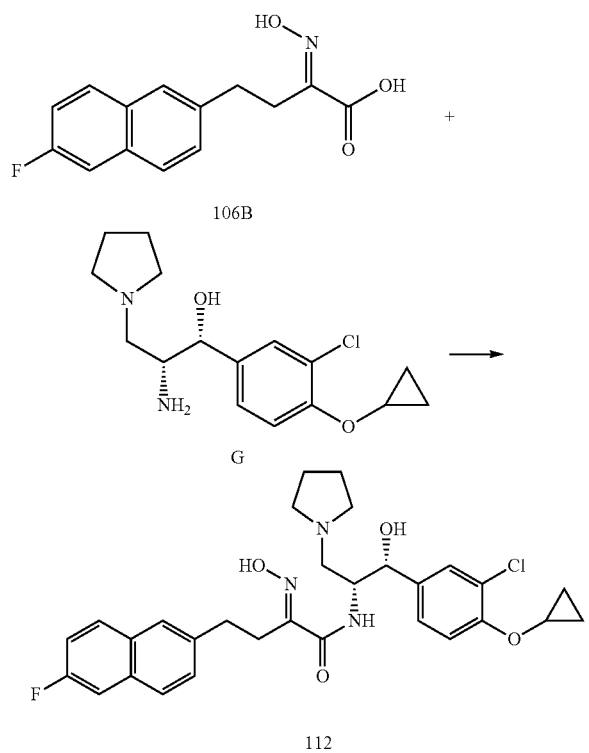

A mixture of Compound 106B (150 mg, 0.57 mmol), Intermediate G (178 mg, 0.57 mmol), EDCI.HCl (165 mg, 0.86 mmol), HOBt (117 mg, 0.86 mmol) in DMF (5 mL) was stirred at 25° C. for 12 h, purified with Prep-HPLC to offer Compound 112. LC-MS (ESI) m/z: 529 [M+H]$^+$. $^1$H NMR (CDCl$_3$, 400 MHz) δ (ppm) 0.72 (s, 4H), 1.97 (s, 4H), 2.77-2.82 (m, 7H), 3.66 (s, 4H), 4.52 (s, 1H), 4.92 (s, 1H), 7.16-7.21 (m, 3H), 7.34-7.38 (m, 3H), 7.57 (s, 1H), 7.63-7.65 (m, 1H), 7.68-7.72 (m, 2H), 8.15 (s, 1H), 10.90 (s, 1H).

Example 113

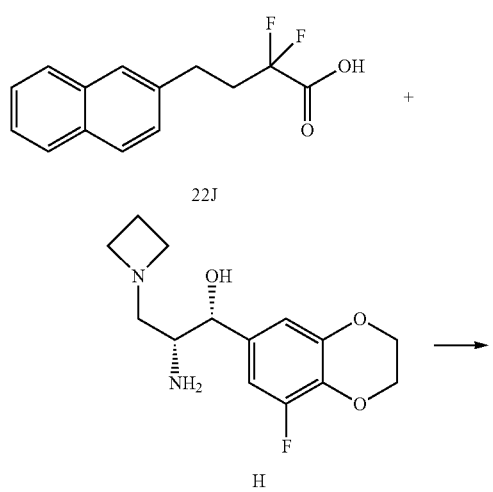

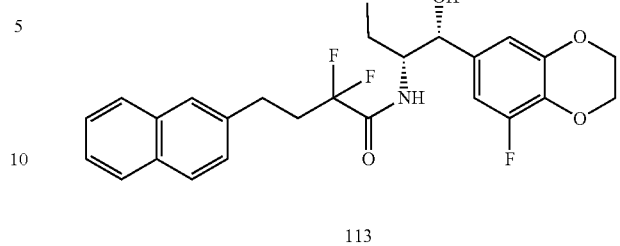

To a solution of Compound 22J (100 mg, 0.40 mmol) in Dichloromethane (20 mL) was added EDCI.HCl (115 mg, 0.60 mmol), HOBt (81 mg, 0.60 mmol), and the resultant mixture was stirred at 30° C. for 15 min. then Intermediate H (140 mg, 0.50 mmol) was added. The reaction was stirred at 30° C. for 15 h. It was poured into ice water (20 mL), extracted with dichloromethane (20 mL×3). The organic layer was washed with water (50 mL×2) and brine (30 mL), dried over anhydrous sodium sulphate, evaporated and purified with Prep-HPLC to furnish Compound 113. LC-MS (ESI) m/z: 515 [M+H]$^+$; $^1$H NMR (CDCl$_3$, 400 MHz) δ (ppm) 2.56-2.66 (m, 6H), 3.43 (s, 2H), 3.82-3.95 (m, 6H), 4.18-4.45 (m, 3H), 4.98 (s, 1H), 6.66-6.72 (m, 2H), 7.21-7.25 (m, 1H), 7.43-7.54 (m, 4H), 7.75-7.81 (m, 3H), 12.25 (s, 1H).

Example 114

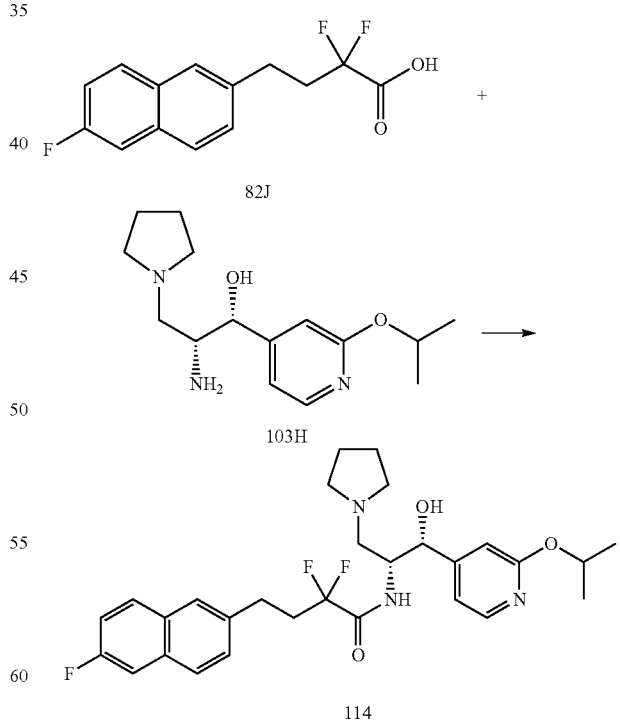

To a solution of Intermediate 103H (140 mg, 0.5 mmol) and Compound 82J (134 mg, 0.5 mmol) in DCM (5 mL) was added EDCI.HCl (144 mg, 0.75 mmol) and HOBt (101 mg, 0.75 mmol) under N$_2$. The mixture was stirred at 30° C.

overnight. TLC and LC-MS showed the starting material was consumed completely, EA (50 mL) was added to the mixture and then washed with water (50 mL×3), brine (50 mL×1), dried over anhydrous sodium sulphate, and concentrated to offer crude product. The crude product was purified with Prep-HPLC to offer a mixture (50 mg, Yield: 57%) as a white solid, then the mixture was separated by Chiral-HPLC (Co-solvent EtOH (0.1% DEA), column OZ-H 250*4.6 mm 5 um) to offer Compound 114. LC-MS (ESI) m/z: 530 [M+H]$^+$, $^1$H NMR (CDCl$_3$, 400 MHz) δ (ppm) 1.12 (d, J=6.0 Hz, 3H), 1.20 (d, J=6.4 Hz, 3H), 2.00 (m, 4H), 2.26 (m, 2H), 2.50 (m, 1H), 2.67 (m, 1H), 3.14 (m, 4H), 3.30 (m, 1H), 3.47 (m, 1H), 4.47 (m, 1H), 5.11 (m, 2H), 6.73 (s, 1H), 6.82 (m, 1H), 7.21 (m, 2H), 7.41 (m, 1H), 7.51 (m, 2H), 7.68 (d, J=8.4 Hz, 1H), 7.74 (m, 1H), 8.05 (d, J=5.2 Hz, 1H). Co-solvent: EtOH (0.1% DEA), column: OZ-H 250*4.6 mm 5 um, Rt: 3.56 min.

Example 115

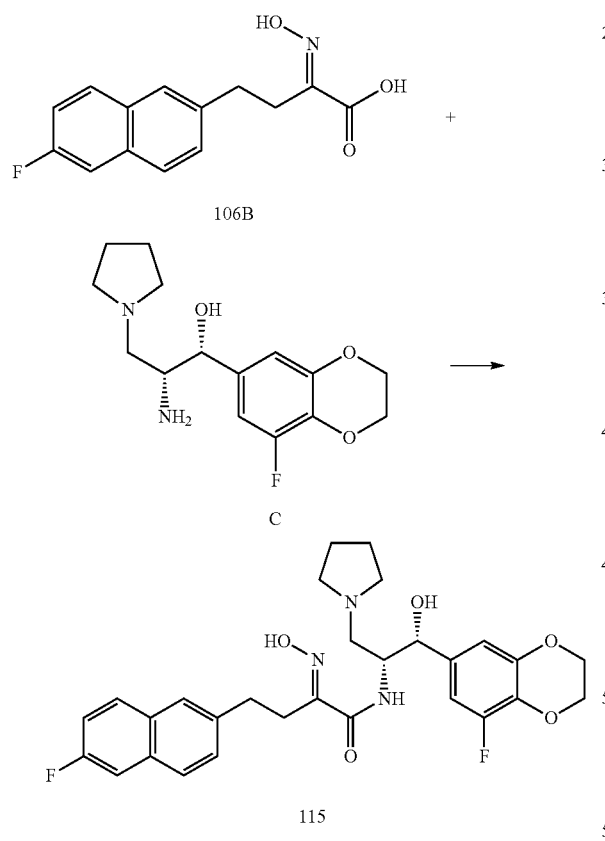

A mixture of Intermediate C (200 mg, 0.67 mmol), Compound 106B (176 mg, 0.67 mmol), EDCI.HCl (194 mg, 1.01 mmol), HOBt (137 mg, 1.01 mmol) in DMF (5 mL) was stirred at 25° C. for 12 h, purified with Prep-HPLC to offer Compound 115. LC-MS (ESI) m/z: 540 [M+H]$^+$, $^1$H NMR (CDCl$_3$, 400 MHz) δ (ppm) 1.99 (s, 4H), 2.84 (s, 6H), 3.14 (s, 1H), 3.45 (s, 1H), 3.74 (s, 2H), 4.19 (s, 4H), 4.45 (s, 1H), 4.87 (s, 1H), 6.66-6.69 (m, 2H), 7.18-7.23 (m, 1H), 7.35-7.40 (m, 2H), 7.59-7.71 (m, 3H), 7.73-7.75 (m, 1H), 11.19 (s, 1H).

Example 116

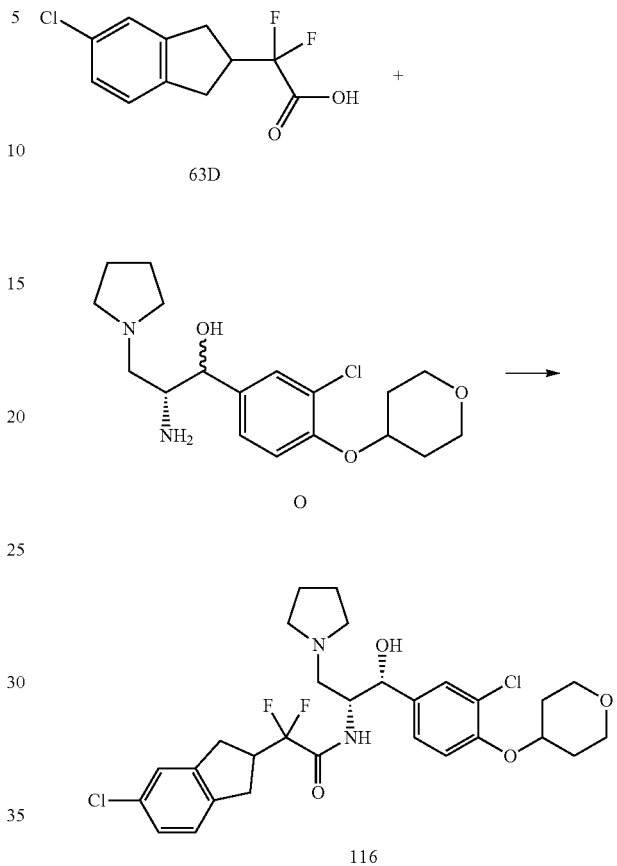

The mixture of Compound 63D (150 mg, 0.42 mmol), EDCI.HCl (121 mg, 0.63 mmol), HOBt (85 mg, 0.63 mmol) and Intermediate O (152 mg, 0.62 mmol) in DCM (15 mL) was stirred for 16 h at 25° C. Then the mixture was washed with saturated NaHCO$_3$ (10 mL) and brine (10 mL), dried over anhydrous sodium sulphate. After evaporation, the crude compound was purified with Prep-HPLC to furnish Compound 116. LC-MS (ESI) m/z: 583 [M+H]$^+$; $^1$H NMR (CDCl$_3$, 400 MHz) δ (ppm) 1.84 (m, 2H), 1.99 (m, 2H), 2.16 (m, 4H), 2.45 (d, J=8.8 Hz, 1H), 7.55 (d, J=8.8 Hz, 1H), 2.83-3.04 (m, 5H), 3.43-3.58 (m, 4H), 3.82 (m, 2H), 4.01 (m, 2H), 4.48-4.54 (m, 2H), 5.18 (s, 1H), 6.91-6.93 (m, 1H), 7.04-7.11 (m, 3H), 7.18-7.19 (m, 1H), 7.43 (s, 1H), 7.50 (s, 1H), 11.75 (s, 1H).

Example 117

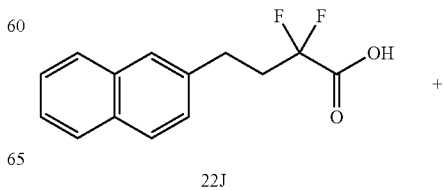

-continued

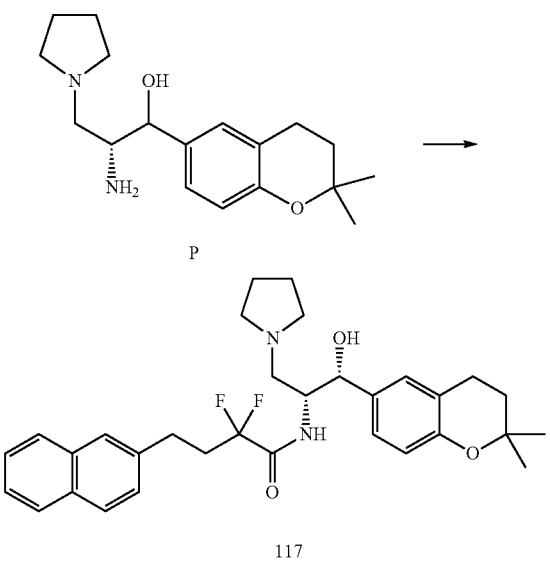

A mixture of Compound 22J (188 mg, 0.618 mmol), Intermediate P (155 mg, 0.618 mmol), EDCI.HCl (176 mg, 0.927 mmol) and HOBt (125 mg, 0.927 mmol) in DCM (10 mL) was stirred at 25° C. for 16 h. Then it was diluted with ethyl acetate (100 mL), washed with water (50 mL×3) and brine (50 mL×2), dried over anhydrous sodium sulfate, concentrated, and purified with prep-HPLC to furnish Compound 117. LC-MS (ESI) m/z: 537 [M+H]$^+$; $^1$H-NMR (DMSO-d$_6$, 400 MHz) δ (ppm) 1.03 (s, 3H), 1.05 (s, 3H), 1.47-1.52 (m, 2H), 1.83-1.82 (m, 2H), 1.98-2.02 (m, 2H), 2.27-2.29 (m, 2H), 2.53-2.60 (m, 2H), 2.63-2.76 (m, 2H), 3.06-3.40 (m, 2H), 3.43-3.48 (m, 4H), 4.52 (s, 1H), 4.72 (s, 1H), 5.82 (s, 4H), 6.63 (d, J=8.8 Hz, 1H), 7.00-7.12 (m, 2H), 7.35 (d, J=8.8 Hz, 1H), 7.45-7.52 (m, 2H), 7.68 (s, 1H), 7.84-7.90 (m, 3H), 8.35 (d, J=8.8 Hz, 1H), 9.49 (s, 1H).

Example 118

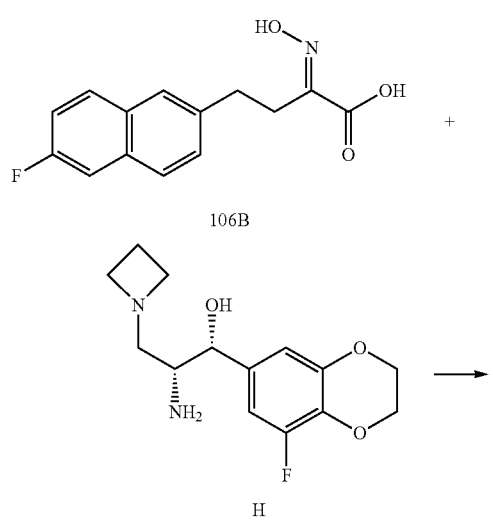

-continued

A mixture of Intermediate H (200 mg, 0.71 mol), EDCI.HCl (204, 1.06 mmol), HOBt (145, 1.01 mmol) and Compound 106B (185 mg, 0.71 mol) in DMF (5 mL) was stirred at room temperature overnight. Then the reaction mixture was purified with prep-HPLC to give Compound 118. LC-MS (ESI) m/z: 526 [M+H]$^+$; $^1$H-NMR (CDCl$_3$, 400 MHz) δ (ppm) 2.15 (s, 1H), 2.50 (m, 1H), 2.81-2.90 (m, 4H), 3.27-3.37 (m, 2H), 3.76 (s, 3H), 4.15-4.17 (m, 5H), 4.29 (s, 1H), 4.82 (s, 1H), 6.61-6.64 (m, 2H), 7.18-7.22 (m, 1H), 7.34-7.39 (m, 2H), 7.52 (s, 1H), 7.59 (s, 1H), 7.65-7.67 (m, 1H), 7.71-7.74 (m, 1H), 11.37 (s, 1H).

Example 119

A mixture of Intermediate P (150 mg, 0.490 mmol), Compound 11E (121 mg, 0.490 mmol), EDCI.HCl (140 mg, 0.740 mmol) and HOBt (100 mg, 0.740 mmol) in DCM/Et$_3$N (10/0.5 mL) was stirred at 25° C. for 16 h. Then it was diluted with ethyl acetate (100 mL), washed with water (50 mL×3) and brine (50 mL×2), dried over anhydrous sodium sulfate, concentrated, and purified with prep-HPLC to furnish Compound 119. LC-MS (ESI) m/z: 533 [M+H]+; 1H-NMR (DMSO-d6, 400 MHz) δ (ppm) 1.24 (s, 6H), 1.62-1.67 (m, 2H), 1.84-1.90 (m, 2H), 2.00 (s, 2H), 2.57-2.60 (m, 2H), 3.06-3.18 (m, 2H), 3.41-3.47 (m, 4H), 4.46-4.51 (m, 1H), 4.72 (s, 1H), 5.82 (s, 1H), 5.58 (d, J=8.4 Hz, 1H), 6.82 (s, 1H), 6.95-7.00 (m, 2H), 7.53 (d, J=6.8 Hz, 1H), 7.74 (d, J=8.4 Hz, 1H), 7.82 (s, 1H), 8.86 (d, J=9.2 Hz, 1H), 9.48 (s, 1H).

Example 120

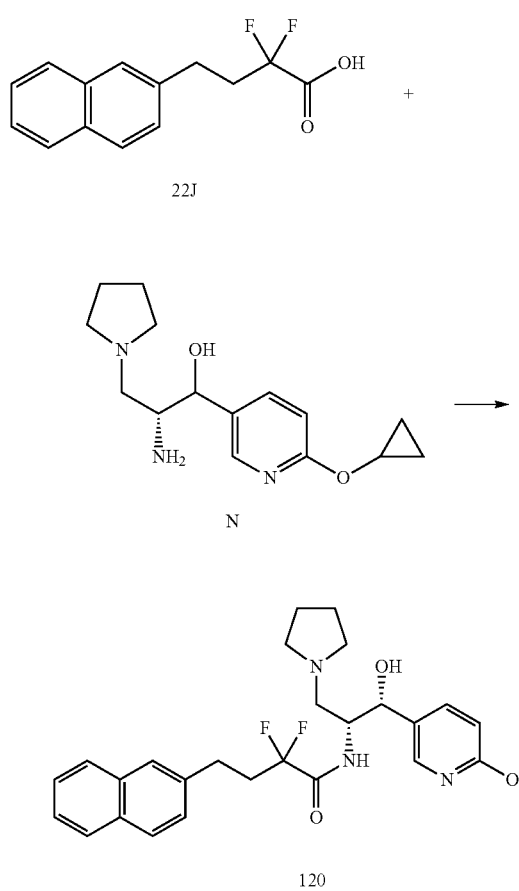

To a solution of Intermediate N (130 mg, 0.52 mmol) in dichloromethane (5 mL) was added Compound 22J (120 mg, 0.433 mmol), EDCI.HCl (149 mg, 0.7794 mmol), and HOBt (107 mg, 0.7794 mmol). The mixture was stirred at 30° C. for 2 h. The mixture was evaporated in vacuo to furnish the crude compound. The crude compound was purified with prep-HPLC to furnish a white solid (83 mg, yield 37%), which was separated by chiral HPLC (co-solvent IPA (0.5% DEA), column AD-H 250*4.6 mm 5 um) to give Compound 120. LC-MS (ESI) m/z: 510 [M+H]+; 1H-NMR (MeOD, 400 MHz) δ (ppm) 0.46-0.61 (m, 4H), 1.78-1.80 (m, 4H), 2.26-2.30 (m, 2H), 2.56-2.63 (m, 5H), 2.73-2.81 (m, 3H), 3.76-3.79 (m, 1H), 4.36 (brs, 1H), 4.96 (d, J=2.8 Hz, 1H), 6.88-6.89 (m, 1H), 7.27-7.29 (m, 1H), 7.41-7.45 (m, 2H), 7.59 (s, 1H), 7.75-7.81 (m, 4H), 8.16 (s, 1H). Co-solvent: IPA (0.5% DEA), column: AD-H 250*4.6 mm 5 um, Rt: 3.51 min.

Example 121

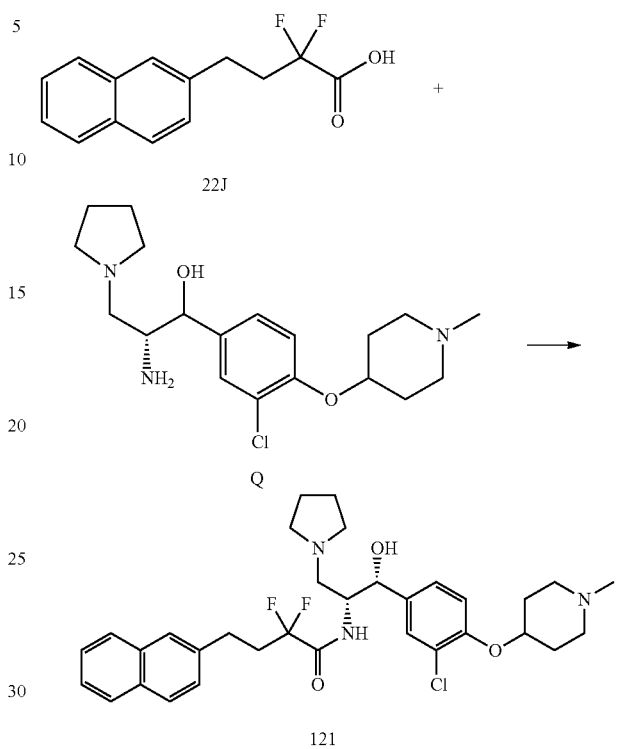

A mixture of Intermediate Q (150 mg, 0.41 mmol), EDCI.HCl (118 mg, 0.62 mmol), HOBt (84 mg, 0.62 mmol) and Compound 22J (103 mg, 0.41 mmol) in DCM (5 mL) was stirred for 18 h at 25° C. Then the mixture was washed with water (50 mL) and brine (50 mL) and dried over anhydrous sodium sulfate. After evaporation, the crude product was purified with prep-HPLC to furnish Compound 121. LC-MS (ESI) m/z: 600 [M+H]+; 1H-NMR (MEOD, 400 MHz) δ (ppm) 1.65-2.11 (m, 11H), 2.49-3.20 (m, 10H), 3.54-3.66 (m, 4H), 4.31 (s, 1H), 4.58-4.61 (d, J=10 Hz, 1H), 4.91 (s, 1H), 6.93-6.95 (m, 1H), 7.19-7.30 (m, 2H), 7.39-7.52 (m, 4H), 7.74-7.76 (m, 3H).

Example 122

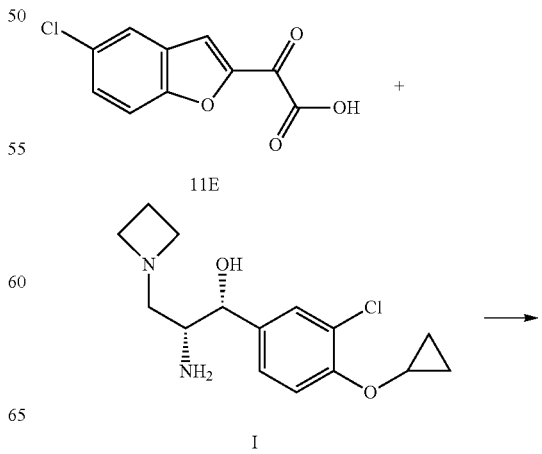

-continued

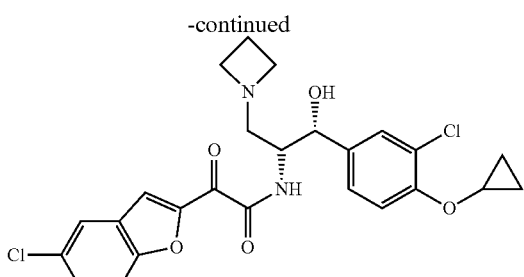

122

A mixture of Intermediate I (117 mg, 0.4 mmol), EDCI.HCl (114 mg, 0.59 mmol), HOBt (78 mg, 0.59 mmol) and Compound 11E (88.5 mg, 0.4 mmol) in DCM (15 mL) was stirred at room temperature overnight. Then the reaction mixture was treated with water (20 mL), extracted with DCM (50 mL×2), washed with brine (50 mL), dried over anhydrous sodium sulfate, and concentrated. The crude product was purified with prep-HPLC to give Compound 122. LC-MS (ESI) m/z: 503 [M+H]$^+$; $^1$H-NMR (CDCl$_3$, 400 MHz) δ (ppm) 0.67-0.75 (m, 4H), 2.35-2.36 (m, 1H), 2.64 (s, 1H), 3.48 (s, 1H), 3.59-3.69 (m, 2H), 4.0 (s, 2H), 4.35-4.63 (m, 5H), 4.99 (s, 1H), 7.09-7.11 (m, 1H), 7.30 (s, 1H), 7.35-7.40 (m, 2H), 7.60 (s, 1H), 8.04-8.06 (d, J=8.0 Hz, 1H), 8.21 (s, 1H), 11.38 (s, 1H).

Example 123

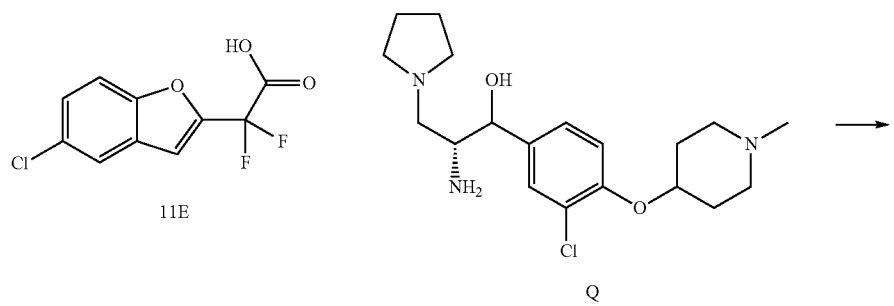

A mixture of Intermediate Q (150 mg, 0.41 mmol), EDCI.HCl (118 mg, 0.62 mmol), HOBt (84 mg, 0.62 mmol) and Compound 11E (101 mg, 0.41 mmol) in DCM (5 mL) was stirred for 18 h at 25° C. Then the mixture was washed with water (50 mL) and brine (50 mL), and dried over anhydrous sodium sulfate. After evaporation, the crude product was purified with prep-HPLC to furnish Compound 123. LC-MS (ESI) m/z: 596 [M+H]$^+$; $^1$H-NMR (MeOD, 400 MHz) δ (ppm) 2.06-2.28 (m, 8H), 2.92 (s, 3H), 3.13-3.32 (m, 4H), 3.42-3.76 (m, 6H), 4.60-4.68 (m, 2H), 4.96 (s, 1H), 6.69-6.78 (m, 1H), 6.87-6.95 (m, 1H), 7.27-7.29 (m, 1H), 7.28 (s, 2H), 7.57-7.59 (m, 1H), 7.74 (m, 1H).

Example 124

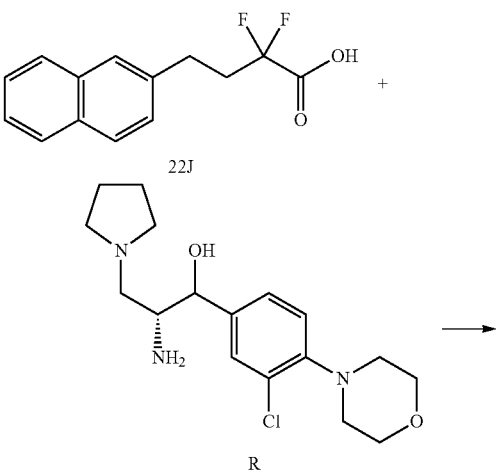

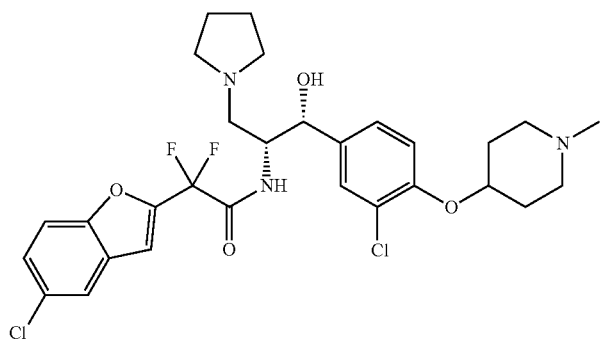

123

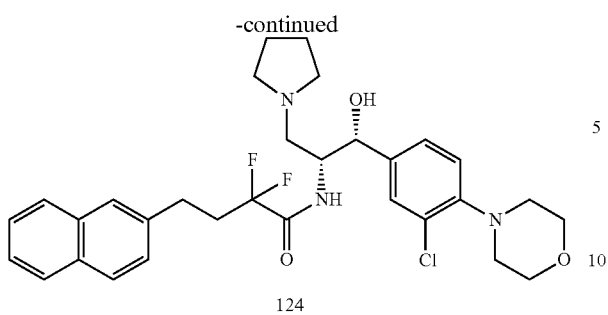

124

A mixture of Intermediate R (180 mg, 0.530 mmol), Compound 22J (132 mg, 0.530 mmol), EDCI.HCl (153 mg, 0.800 mmol) and HOBt (108 mg, 0.800 mmol) in DCM (10 mL) was stirred at 25° C. for 16 h. Then it was diluted with ethyl acetate (100 mL), washed with water (200 mL) and brine (200 mL), dried over anhydrous sodium sulfate, concentrated, and purified with prep-HPLC to furnish Compound 124. LC-MS (ESI) m/z: 572 [M+H]$^+$; $^1$H-NMR (DMSO-d$_6$, 400 MHz) δ (ppm) 1.86-1.90 (m, 2H), 2.00-2.19 (m, 4H), 2.50-2.68 (m, 6H), 3.07-3.20 (m, 2H), 3.34-3.40 (m, 4H), 3.42-3.49 (m, 4H), 4.47-4.53 (m, 1H), 4.83 (s, 2H), 6.03 (s, 1H), 6.98 (d J=8.4 Hz, 1H), 7.25-7.34 (m, 2H), 7.38 (s, 1H), 7.45-7.53 (m, 2H), 7.66 (s, 1H), 7.84-7.90 (m, 3H), 8.42 (d, J=8.4 Hz, 1H).

Example 125

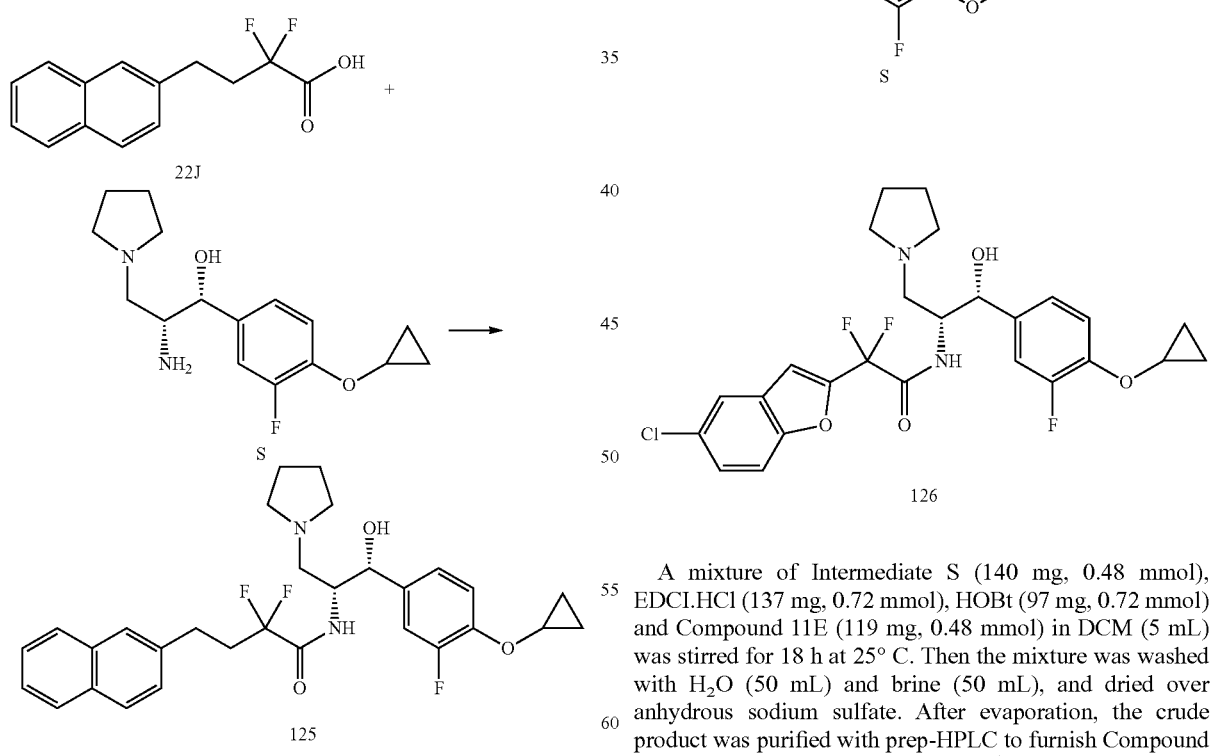

A mixture of Intermediate S (140 mg, 0.48 mmol), EDCI.HCl (137 mg, 0.72 mmol), HOBt (97 mg, 0.72 mmol) and Compound 22J (120 mg, 0.48 mmol) in DCM (5 mL) was stirred for 18 h at 25° C. Then the mixture was washed with H$_2$O (50 mL) and brine (50 mL), and dried over anhydrous sodium sulfate. After evaporation, the crude product was purified with prep-HPLC to furnish Compound 125. LC-MS (ESI) m/z: 527 [M+H]$^+$; $^1$H-NMR (CDCl$_3$, 400 MHz) δ (ppm) 0.51-0.52 (m, 4H), 2.08 (s, 4H), 2.22-2.47 (m, 2H), 2.49-2.53 (m, 1H), 2.62-2.69 (m, 1H), 2.81-2.95 (m, 2H), 3.41-3.42 (m, 3H), 3.76 (s, 2H), 4.46-4.47 (m, 1H), 5.12 (s, 1H), 7.05-7.22 (m, 4H), 7.41-7.47 (m, 2H), 7.52 (s, 1H), 7.59-7.61 (d, J=8.0 Hz, 1H), 7.74-7.79 (m, 3H), 11.7 (s, 1H).

Example 126

A mixture of Intermediate S (140 mg, 0.48 mmol), EDCI.HCl (137 mg, 0.72 mmol), HOBt (97 mg, 0.72 mmol) and Compound 11E (119 mg, 0.48 mmol) in DCM (5 mL) was stirred for 18 h at 25° C. Then the mixture was washed with H$_2$O (50 mL) and brine (50 mL), and dried over anhydrous sodium sulfate. After evaporation, the crude product was purified with prep-HPLC to furnish Compound 126. LC-MS (ESI) m/z: 523 [M+H]$^+$; $^1$H-NMR (CDCl$_3$, 400 MHz) δ (ppm) 0.66-0.74 (m, 4H), 2.11 (s, 4H), 2.95-3.02 (m, 2H), 3.41-3.65 (m, 5H), 4.47 (s, 1H), 5.10 (s, 1H), 6.74 (s, 1H), 6.68-7.15 (m, 3H), 7.32-7.35 (m, 1H), 7.39-7.41 (d, J=8.8 Hz, 1H), 7.55 (d, J=1.6 Hz, 1H), 7.99 (d, J=6.0 Hz, 1H), 11.45 (s, 1H).

Example 127

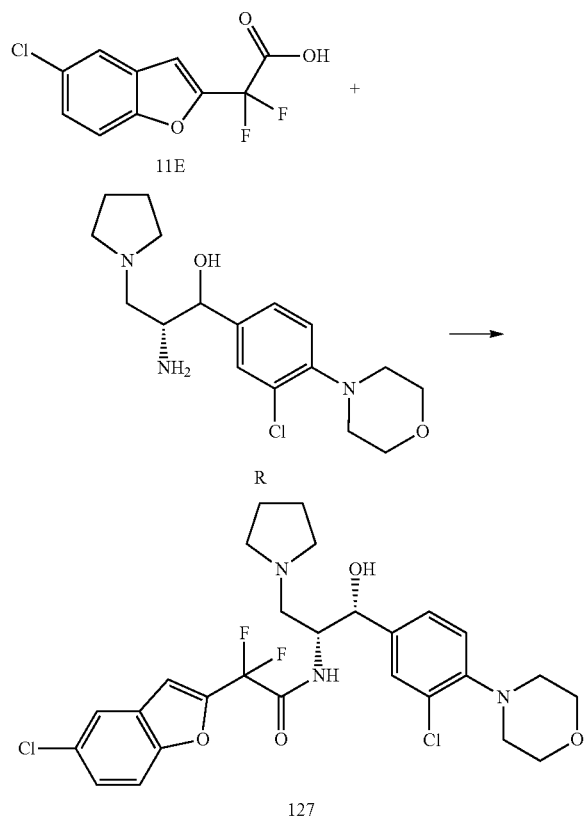

A mixture of Intermediate R (150 mg, 0.442 mmol), Compound 11E (109 mg, 0.442 mmol), EDCI.HCl (127 mg, 0.663 mmol) and HOBt (90 mg, 0.663 mmol) in DCM/Et$_3$N (10/0.3 mL) was stirred at 25° C. for 16 h. Then it was diluted with ethyl acetate (100 mL), washed with water (200 mL) and brine (200 mL), dried over anhydrous sodium sulfate, concentrated, and purified with prep-HPLC to furnish Compound 127. LC-MS (ESI) m/z: 568 [M+H]$^+$; $^1$H-NMR (MeOD, 400 MHz) δ (ppm) 2.06 (s, 2H), 2.20 (s, 2H), 2.75-2.88 (m, 4H), 3.17-3.22 (m, 2H), 3.58-3.70 (m, 4H), 3.75-3.83 (m, 4H), 4.65-4.69 (m, 1H), 4.93 (s, 1H), 6.68 (s, 1H), 6.82 (d, J=8.0 Hz, 1H), 7.24 (d, J=8.0 Hz, 1H), 7.42-7.48 (m, 2H), 7.59 (d, J=8.0 Hz, 1H), 7.79 (s, 1H).

Example 128

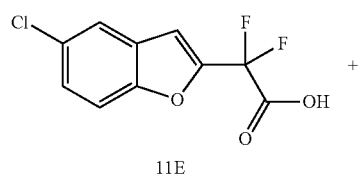

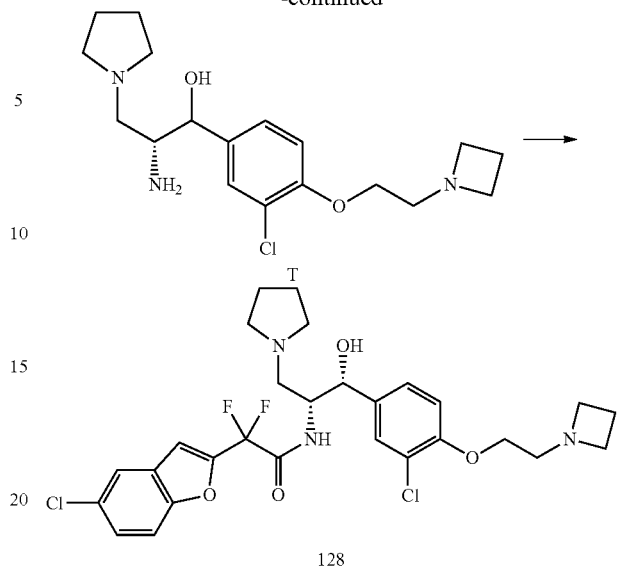

To a solution of Intermediate T (100 mg, 0.28 mmol) and Compound 11E (69 mg, 0.28 mmol) in DMF (10 mL) was added EDCI.HCl (82 mg, 0.42 mmol) and HOBt (58 mg, 0.42 mmol) under nitrogen. The mixture was stirred at 25° C. overnight. TLC and LC-MS showed the starting material was consumed completely, sat. sodium bicarbonate (3 mL) was added to the mixture and then extracted with EA (50 mL×3). The combined organic layers were washed with water (5 mL×3) and brine (5 mL), dried over anhydrous sodium sulfate, and concentrated to offer the crude product. The crude product was purified with prep-HPLC to offer Compound 128. LC-MS (ESI) m/z: 582 [M+H]$^+$. $^1$H-NMR (CDCl$_3$, 400 MHz) δ (ppm) 2.16-2.17 (m, 4H), 2.39-2.44 (m, 1H), 2.75-2.83 (m, 1H), 2.92-3.01 (m, 2H), 3.45-3.54 (m, 4H), 3.76 (s, 2H), 4.14-4.16 (m, 4H), 4.44-4.53 (m, 3H), 5.08 (d, J=2.8 Hz, 1H), 6.62 (d, J=8.4 Hz, 1H), 6.81 (s, 1H), 7.12 (dd, J=2.0, 8.8 Hz, 1H), 7.34-7.38 (m, 2H), 7.43 (d, J=8.8 Hz, 1H), 7.58 (d, J=2.0, 1H), 8.08 (d, J=8.8 Hz, 1H), 11.95 (brs, 1H), 13.25 (brs, 1H).

Example 129

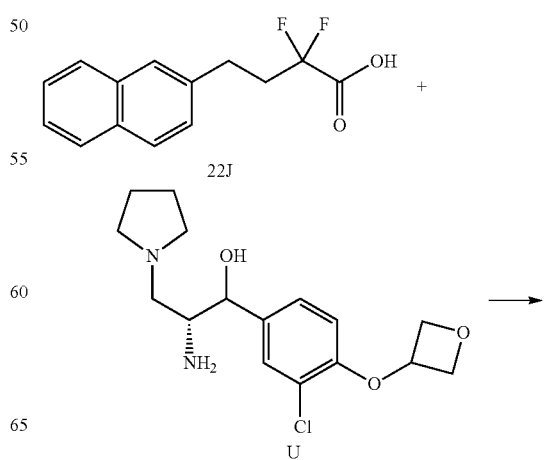

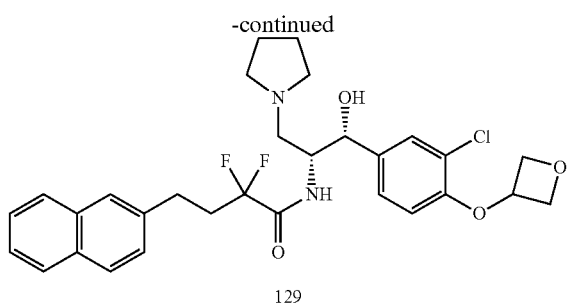

129

A mixture of Intermediate U (108 mg, 0.33 mmol), EDCI.HCl (96 mg, 0.50 mmol), HOBt (67 mg, 0.50 mmol) and Compound 22J (84 mg, 0.33 mmol) in DCM (15 mL) was stirred at room temperature for 4 hours. Then the reaction mixture was treated with water (20 mL), extracted with DCM (50 mL×2), washed with brine (50 mL), dried over sodium sulfate, and concentrated. The crude product was purified with prep-HPLC to furnish Compound 129. LC-MS (ESI) m/z: 559 [M+H]$^+$; $^1$H-NMR (CDCl$_3$, 400 MHz) δ (ppm) 2.04-2.40 (m, 7H), 2.52-2.59 (m, 1H), 2.85-2.97 (m, 2H), 3.34-3.77 (m, 4H), 4.46-4.60 (m, 6H), 5.11 (s, 1H), 6.24-6.26 (d, J=8.0 Hz, 1H), 7.14-7.20 (m, 2H), 7.42-7.48 (m, 4H), 7.60-7.63 (m, 1H), 7.75-7.81 (m, 3H).

Example 130

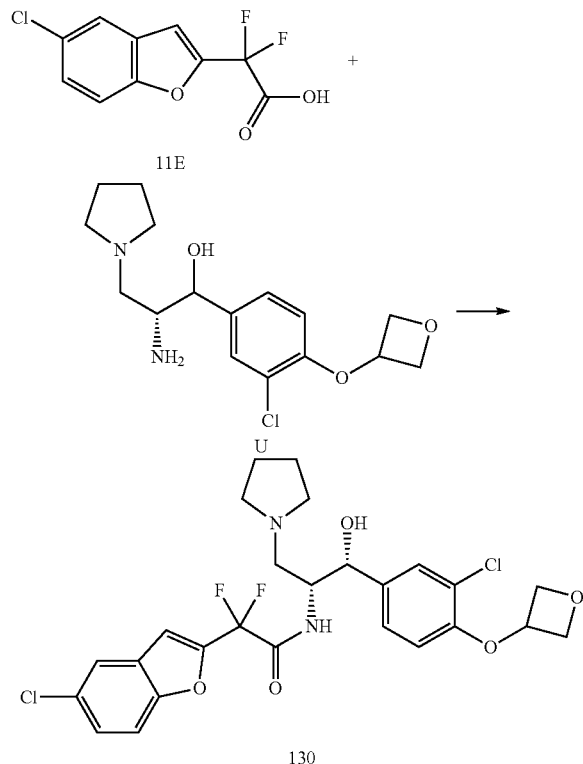

A mixture of Intermediate U (108 mg, 0.33 mmol), EDCI.HCl (96 mg, 0.50 mmol), HOBt (67 mg, 0.50 mmol) and Compound 11E (82 mg, 0.33 mmol) in DCM (15 mL) was stirred at room temperature for 4 hours. Then the reaction mixture was treated with water (20 mL), extracted with DCM (50 mL×2), washed with brine (50 mL), dried over sodium sulfate, and concentrated. The crude product was purified with prep-HPLC to furnish Compound 130. LC-MS (ESI) m/z: 555 [M+H]$^+$; $^1$H-NMR (CDCl$_3$, 400 MHz) δ (ppm) 2.13 (s, 4H), 2.96-3.09 (m, 2H), 3.22-3.88 (m, 4H), 4.52 (s, 1H), 4.67-4.74 (m, 2H), 4.91-4.96 (m, 3H), 5.12 (s, 1H), 6.18-6.20 (d, J=8.4 Hz, 1H), 6.72 (s, 1H), 7.06-7.08 (m, 1H), 7.33-7.42 (m, 3H), 7.58 (s, 1H), 7.96 (m, 1H), 11.65 (s, 1H).

Example 131

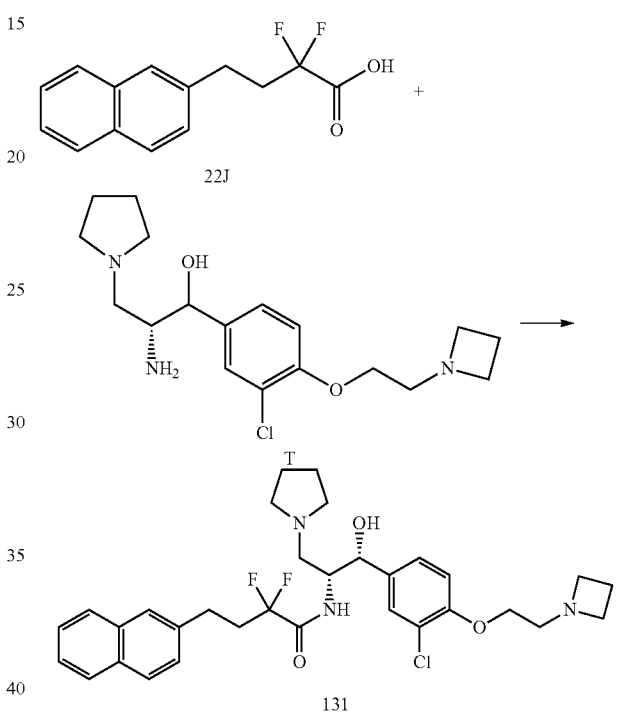

To a solution of Intermediate T (100 mg, 0.28 mmol) and Compound 22J (71 mg, 0.28 mmol) in DCM (10 mL) was added EDCI.HCl (81 mg, 0.42 mmol) and HOBt (57 mg, 0.42 mmol) under nitrogen. The mixture was stirred at 25° C. overnight. TLC and LC-MS showed the starting material was consumed completely, then sat. sodium bicarbonate (5 mL) was added to the mixture and then extracted with EA (50 mL×3). The combined organic layers were washed with water (5 mL) and brine (5 mL), dried over anhydrous sodium sulfate, and concentrated to offer the crude product. The crude product was purified with prep-HPLC to offer Compound 131. LC-MS (ESI) m/z: 586 [M+H]$^+$. $^1$H-NMR (MeOD, 400 MHz) δ (ppm) 2.03-2.22 (m, 8H), 2.34-2.42 (m, 1H), 2.51-2.59 (m, 1H), 2.90-3.01 (m, 2H), 3.15-3.17 (m, 1H), 3.23-3.24 (m, 1H), 3.54-3.58 (m, 1H), 3.63-3.68 (m, 3H), 3.74-3.78 (m, 2H), 3.82-3.93 (m, 2H), 4.01-4.04 (m, 2H), 4.64 (d, J=10.4 Hz, 1H), 4.96 (d, J=2.4 Hz, 1H), 6.89 (d, J=8.4 Hz, 1H), 7.24 (dd, J=2.0, 8.4 Hz, 1H), 7.34 (dd, J=2.0, 8.4 Hz, 1H), 7.46-7.52 (m, 3H), 7.57 (s, 1H), 7.81-7.88 (m, 3H).

Example 132

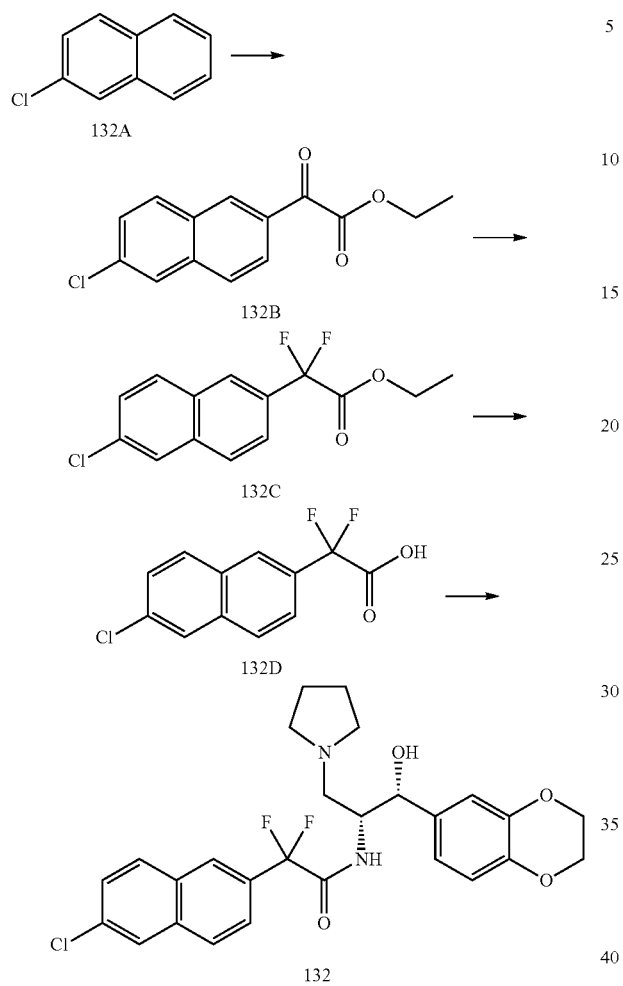

To a suspension of aluminum trichloride (1.61 g, 12 mmol) and ethyl chloroacetate (1.63 g, 12 mmol) in dichloromethane (60 mL) was added Compound 132A (1.62 g, 10 mmol) in dichloromethane (15 mL) dropwise at room temperature overnight. After 24 h a solution of ice water (100 mL) and saturated sodium bicarbonate solution (100 mL) was added dropwise. The aqueous layer was extracted with dichloromethane (50 mL×3). The combined organics were washed with brine (200 mL), dried over anhydrous sodium sulfate, filtered, and concentrated. The residue was purified with flash column chromatography on silica gel (ethyl acetate in petroleum ether, 2% v/v) to give the Compound 132B.

To a solution of Compound 132B (2.62 g, 10 mmol) in dichloromethane (350 mL) was added DAST (4 mL) at room temperature. The reaction mixture was stirred at room temperature. After 14 h, the mixture was poured into ice water (50 mL) and extracted with dichloromethane (50 mL×2). The combined organics were washed with brine (200 mL), dried over anhydrous sodium sulfate, filtered, and concentrated. Purification by silica gel chromatography (ethyl acetate in petroleum ether, 2% v/v) gave the Compound 132C.

To a solution of Compound 132C (284 mg, 1 mmol) in ethanol/water (16 mL) was added LiOH H$_2$O (84 mg, 2 mmol). The mixture was stirred at room temperature overnight. After the completion of the reaction, the mixture was adjusted to pH 2 with aqueous HCl solution (3 N, 40 mL) and extracted with ethyl acetate (20 mL×3). The combined organic layers were washed with brine (200 mL), dried over anhydrous sodium sulfate, and concentrated to furnish Compound 132D.

To a solution of 132D (256 mg, 1 mmol) in DCM (30 mL) was added Intermediate A (278 mg, 1 mmol), EDCI.HCl (286 mg, 1.5 mmol), HOBt (202 mg, 1.5 mmol), and DIPEA (1 mL). The mixture was stirred at room temperature overnight. The reaction mixture was diluted by DCM (30 mL), washed with brine (50 mL), dried over sodium sulfate, and concentrated to furnish the crude product, which was purified with prep-HPLC to furnish Compound 132. LC-MS (ESI) m/z: 517 [M+H]$^+$, $^1$H-NMR (CDCl$_3$, 400 MHz) δ (ppm) 1.65-1.68 (m, 4H), 2.53-2.63 (m, 4H), 2.86-2.88 (m, 2H), 4.02-4.15 (m, 5H), 4.94-4.95 (m, 1H), 6.66-6.69 (m, 3H), 6.89-6.70 (m, 1H), 7.33-7.40 (m, 2H), 7.64-7.79 (m, 4H).

Example 133

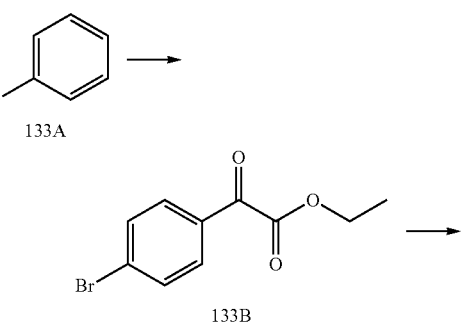

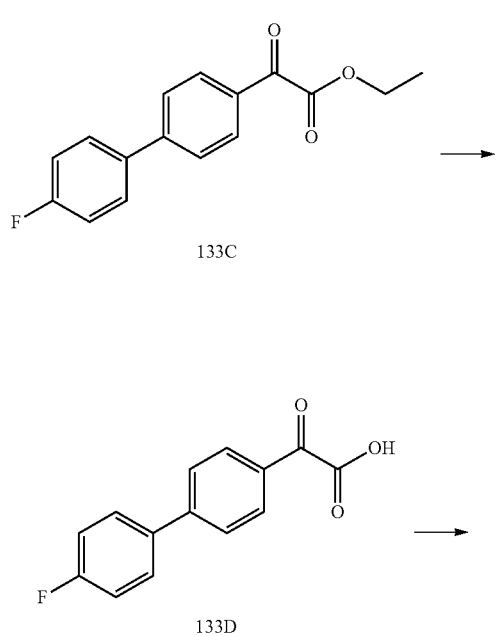

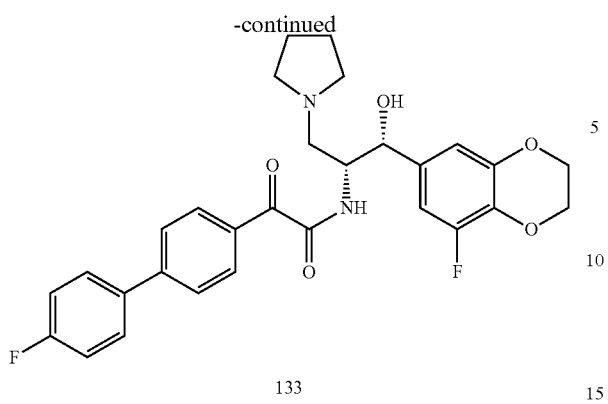

133

To a stirred suspension of AlCl₃ (8.5 g, 64 mmol) in dichloromethane (40 mL) was added dropwise ethyl 2-chloro-2-oxoacetate (8.7 g, 64 mmol) at −10° C. The mixture was stirred at −10° C. for 15 minutes. Compound 133A (5 g, 32 mmol) was added dropwise at −10° C. The resulting mixture was stirred at 20° C. for 15 hours. The mixture was poured into ice water (100 mL) to quench the reaction and extracted with dichloromethane (50 mL×3). The combined organic layers were washed with saturated sodium bicarbonate solution (200 mL) and brine (200 mL), dried over anhydrous sodium sulfate, and concentrated to give a crude compound. The crude product was purified with flash column chromatography on silica gel (petroleum ether) to furnish Compound 133B.

A mixture of Compound 133B (3.7 g, 14.4 mmol), 4-fluorophenylboronic acid (2.4 g, 17.3 mmol), Pd(PPh₃)₄ (497 mg, 0.4 mmol) and K₃PO₄ in toluene (40 mL) was heated to reflux, stirred for 3 h, and filtered. The filtrate was concentrated to give a crude compound. The crude product was purified with flash column chromatography on silica gel (ethyl acetate in petroleum ether, 10% v/v) to give Compound 133C.

To a solution of Compound 133C (1.1 g, 4 mmol) in THF/water (30 mL, 15:1, v/v) was added LiOH H₂O (250 mg, 6 mmol). The mixture was stirred at −10° C. for 3 h. After the reaction was completed, it was adjusted to pH 6 with 3 N HCl and extracted with ethyl acetate (20 mL×3). The combined organic layers were concentrated in vacuo to give Compound 133D.

A mixture of Compound 133D (195 mg, 0.8 mmol), Intermediate C (237 mg, 0.8 mmol), HATU (456 mg, 1.2 mmol) and in dichloromethane (20 mL) was stirred at 30° C. for 15 h. Then it was treated with water (20 mL), extracted with dichloromethane (20 mL×3), dried over anhydrous sodium sulfate, concentrated in vacuum and purified with prep-HPLC to furnish Compound 133. LC-MS (ESI) m/z: 524 [M+H]⁺; ¹H-NMR (CDCl₃, 400 MHz) δ (ppm) 2.14 (s, 5H), 3.11 (s, 2H), 3.51 (s, 1H), 3.79 (s, 1H), 3.93 (s, 2H), 4.16-4.21 (m, 4H), 4.52 (s, 1H), 5.04 (s, 1H), 6.72 (t, J=8 Hz, 2H), 7.14 (t, J=8 Hz, 2H), 7.54-7.57 (m, 4H), 7.82 (d, J=8 Hz, 1H), 8.08 (d, J=8 Hz, 2H), 9.21 (s, 1H).

Example 134

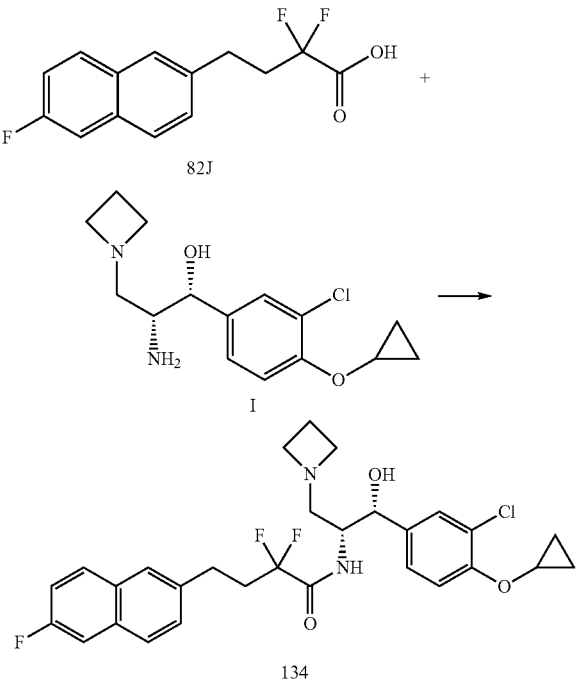

A mixture of Intermediate I (100 mg, 0.33 mmol), EDCI.HCl (97 mg, 0.51 mmol), HOBt (69 mg, 0.51 mmol) and Compound 82J (91 mg, 0.33 mmol) in DMF (5 mL) was stirred at room temperature overnight. Then the reaction mixture was purified with prep-HPLC to offer Compound 134. LC-MS (ESI) m/z: 547 [M+H]⁺; ¹H-NMR (CDCl₃, 400 MHz) δ (ppm) 0.47-0.55 (m, 4H), 2.22 (s, 2H), 2.40 (s, 2H), 2.56 (s, 2H), 3.40-3.50 (m, 3H), 3.96 (s, 2H), 4.34 (s, 3H), 5.05 (s, 1H), 7.15-7.22 (m, 4H), 7.37-7.42 (m, 2H), 7.48 (s, 1H), 7.61 (s, 1H), 7.68-7.71 (m, 1H), 7.75-7.79 (s, 1H), 12.13 (s, 1H).

Example 135

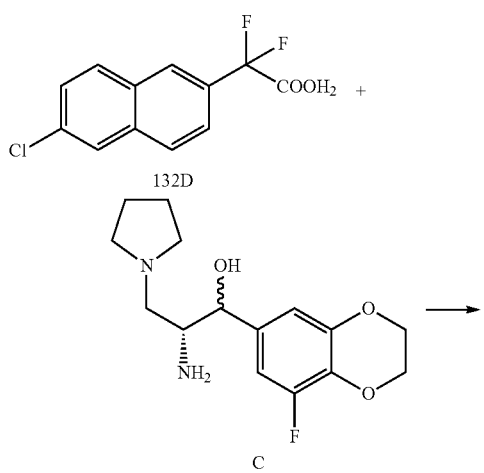

251

-continued

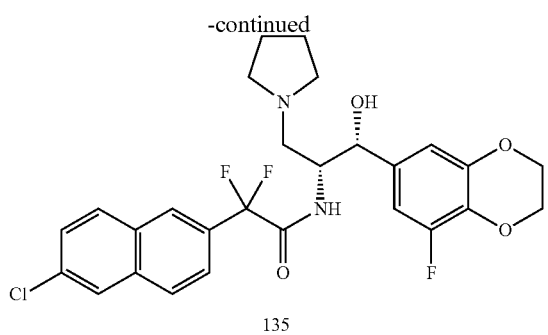

135

A mixture of Compound 132D (256 mg, 1 mmol), Intermediate C (296 mg, 1 mmol), EDCI.HCl (286 mg, 1.5 mmol) and HOBt (202 mg, 1.5 mmol) in DCM (30 mL) was stirred at 25° C. for 16 h. Then it was diluted with DCM (70 mL), washed with water (50 mL×3) and brine (50 mL×2), dried over anhydrous sodium sulfate, concentrated, and purified with prep-HPLC to furnish Compound 135. LC-MS (ESI) m/z: 535 [M+H]$^+$; $^1$H-NMR (CDCl$_3$, 400 MHz) δ (ppm) 2.10-2.11 (m, 4H), 2.86-3.01 (m, 4H), 3.49-3.51 (m, 2H), 4.05-4.10 (m, 4H), 4.37-4.39 (m, 1H), 5.03 (s, 1H), 6.51 (s, 1H), 6.68 (d, J=2 Hz, 1H), 7.42 (d, J=4.4 Hz, 1H), 7.47-7.50 (m, 1H), 7.75 (d, J=2 Hz, 1H), 7.74-7.84 (m, 3H), 7.90 (s, 1H), 11.84 (s, 1H).

Example 136

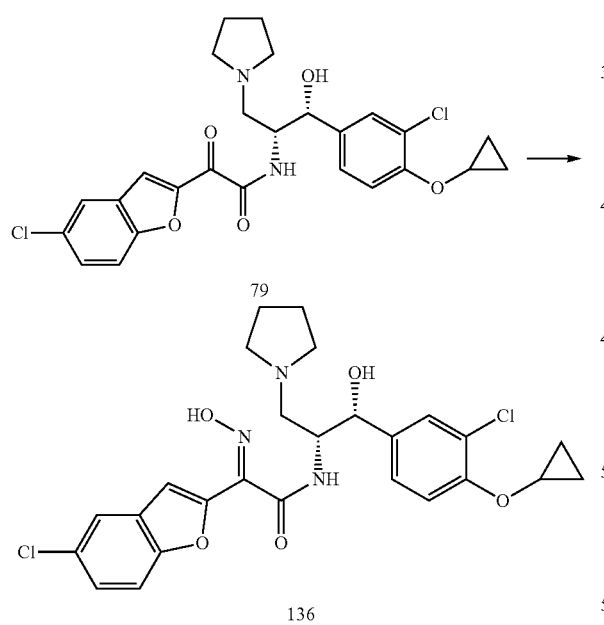

A mixture of Compound 79 (38 mg, 0.74 mmol), hydroxylamine hydrochloride (138 mg, 2 mmol) and methanol (9 mL) was stirred at 50° C. overnight. Then the mixture was purified with prep-HPLC to offer Compound 136. LC-MS (ESI) m/z: 532.1 [M+H]$^+$; $^1$H-NMR (MeOD, 400 MHz) δ (ppm) 0.74-0.86 (m, 4H), 2.05-2.19 (m, 4H), 3.25-3.30 (m, 1H), 3.52-3.58 (m, 1H), 3.72-3.76 (m, 1H), 3.84-3.89 (m, 3H), 4.81-4.85 (m, 1H), 5.02 (d, J=2.4 Hz, 1H), 5.97 (s, 1H), 7.32-7.36 (m, 1H), 7.40 (s, 2H), 7.44-7.47 (d, J=8.4 Hz, 2H), 7.54-7.56 (m, 2H).

252

Example 137

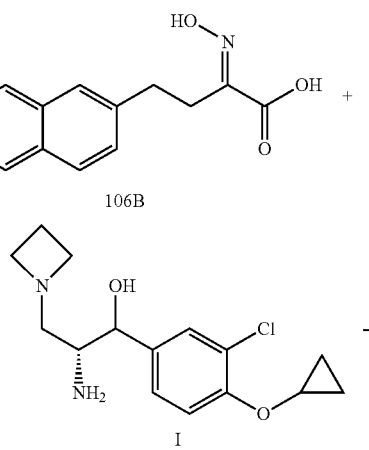

A mixture of Intermediate I (100 mg, 0.33 mmol), EDCI.HCl (97 mg, 0.51 mmol), HOBt (69 mg, 0.51 mmol) and Compound 106B (88 mg, 0.33 mmol) in DMF (5 mL) was stirred at room temperature overnight. Then the reaction mixture was purified with prep-HPLC to offer Compound 137. LC-MS (ESI) m/z: 540 [M+H]$^+$; $^1$H-NMR (CDCl$_3$, 400 MHz) δ (ppm) 0.71-0.72 (m, 4H), 1.26 (s, 1H), 2.11 (s, 1H), 2.46 (s, 1H), 2.78-2.82 (m, 4H), 3.22 (s, 1H), 3.65 (s, 3H), 4.10-4.18 (m, 2H), 4.33 (s, 1H), 4.83 (s, 1H), 7.10-7.22 (m, 3H), 7.32-7.38 (m, 3H), 7.58 (s, 1H), 7.62-7.65 (m, 1H), 7.71-7.75 (m, 1H), 11.02 (s, 1H).

Example 138

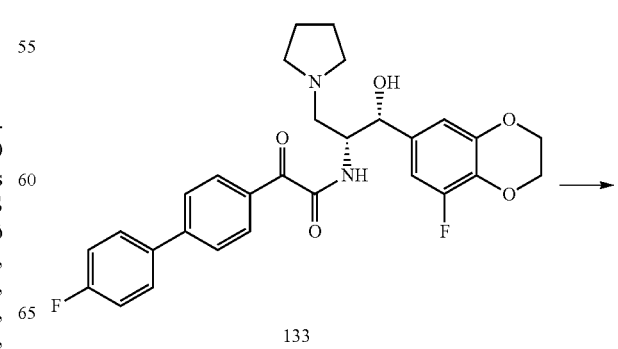

133

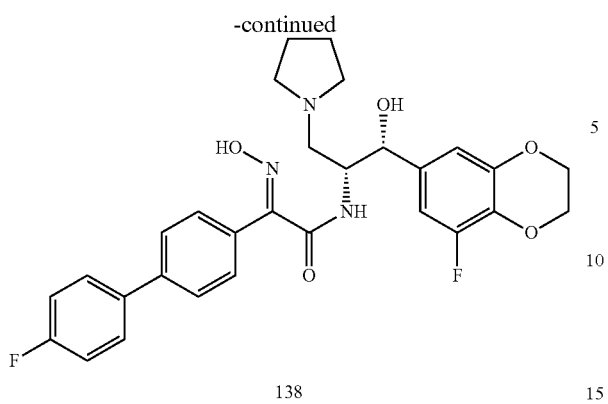

138

A mixture of Compound 133 (41 mg, 0.078 mmol) and hydroxylamine hydrochloride (109 mg, 1.56 mmol) in MeOH (10 mL) was stirred at room temperature for 4 h. Then it was purified with prep-HPLC directly to offer Compound 138. LC-MS (ESI) m/z: 538 [M+H]$^+$; $^1$H-NMR (MeOD, 400 MHz) δ (ppm) 2.02 (s, 2H), 2.20 (s, 2H), 3.12-3.28 (m, 2H), 3.45-3.87 (m, 4H), 4.26-4.60 (m, 5H), 4.78-4.82 (m, 1H), 6.82 (t, J=12 Hz, 2H), 7.17-7.42 (m, 4H), 7.53-7.68 (m, 4H).

Example 139

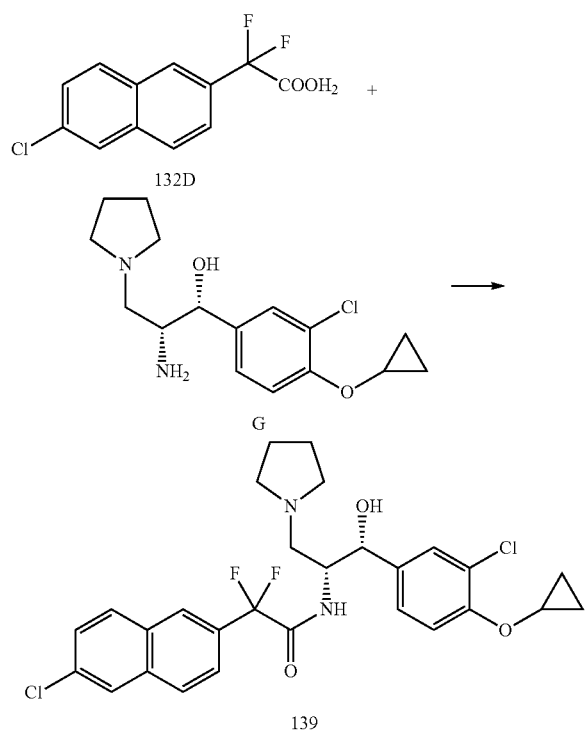

A mixture of Compound 132D (256 mg, 1 mmol), Intermediate G (296 mg, 1 mmol), EDCI.HCl (286 mg, 1.5 mmol) and HOBt (202 mg, 1.5 mmol) in DCM (30 mL) was stirred at 25° C. for 16 h. Then it was diluted with DCM (70 mL), washed with water (50 mL×3) and brine (50 mL×2), dried over anhydrous sodium sulfate, concentrated, and purified with prep-HPLC to furnish Compound 139. LC-MS (ESI) m/z: 549 [M+H]$^+$; $^1$H-NMR (CDCl$_3$, 400 MHz) δ (ppm) 0.69-0.71 (m, 4H), 1.65-1.68 (m, 4H), 2.34-2.37 (m, 4H), 2.64-2.68 (m, 2H), 3.51-3.52 (m, 1H), 4.15 (s, 1H), 5.09 (s, 1H), 6.91-6.92 (m, 1H), 7.12-7.13 (m, 2H), 7.35 (s, 1H), 6.94 (m, 1H), 7.50-7.52 (t, J=4.8 Hz, 2H), 7.78-7.86 (m, 3H), 7.96 (s, 1H).

Example 140

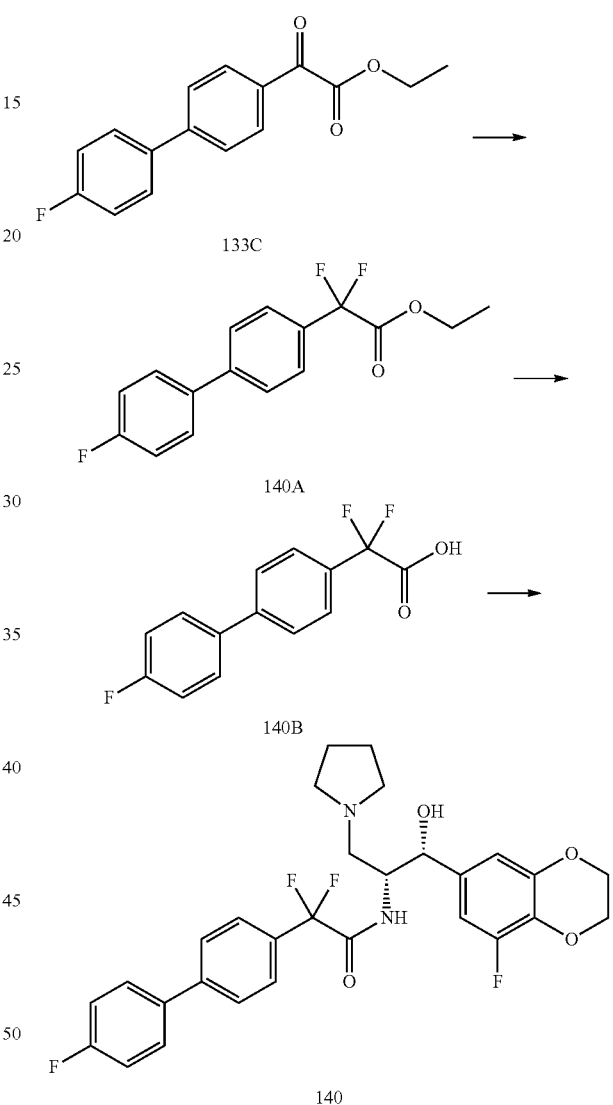

To a solution of Compound 133C (1.78 g, 6.54 mmol) in dry dichloromethane (40 mL) was added DAST (2.2 mL, 16.36 mmol). Then the mixture was stirred at 25° C. for 14 h. After the reaction was completed, dichloromethane (25 mL) was added. The organic layer was washed with water (50 mL), followed by aq. sodium bicarbonate (30 mL) and brine (50 mL), dried over sodium sulfate and concentrated to provide the crude product. The crude product was purified with flash column chromatography on silica gel (ethyl acetate in petroleum ether, 20% v/v) to provide Compound 140A.

To a solution of Compound 140A (2.3 g, 7.8 mmol) in THF/water/MeOH (30 mL, 1:1:1, v/v) was added LiOH.H₂O (493 mg, 11.7 mmol). The mixture was stirred at 28° C. for 1 h. After the reaction was completed, it was adjusted to pH to 6 with 2 N HCl and extracted with ethyl acetate (60 mL×3). The combined organic layers were concentrated in vacuum to provide the crude product Compound 140B.

To a solution of Compound 140B (133 mg, 0.5 mmol), Intermediate C (156 mg, 0.53 mmol), and EDCI.HCl (144 mg, 0.75 mmol) in dichloromethane (20 mL) was added HOBt (102 mg, 0.75 mmol) at 19° C., then the reaction was stirred at 19° C. for 4 h. Then it was treated with water (20 mL), extracted with dichloromethane (20 mL×3), dried over anhydrous sodium sulfate, concentrated in vacuum and purified with prep-HPLC to furnish Compound 140. LC-MS (ESI) m/z: 545 [M+H]⁺; ¹H-NMR (MeOD, 400 MHz) δ (ppm) 2.12 (m, 4H), 2.90-3.10 (m, 2H), 3.45-3.48 (m, 2H), 3.75-3.85 (m, 2H), 4.11-4.12 (m, 4H), 4.15-4.22 (m, 1H), 4.90-4.91 (d, J=2.8 Hz, 1H), 6.57-6.67 (m, 2H), 7.14-7.19 (m, 2H), 7.43-7.46 (m, 2H), 7.55-7.61 (m, 4H).

Example 141

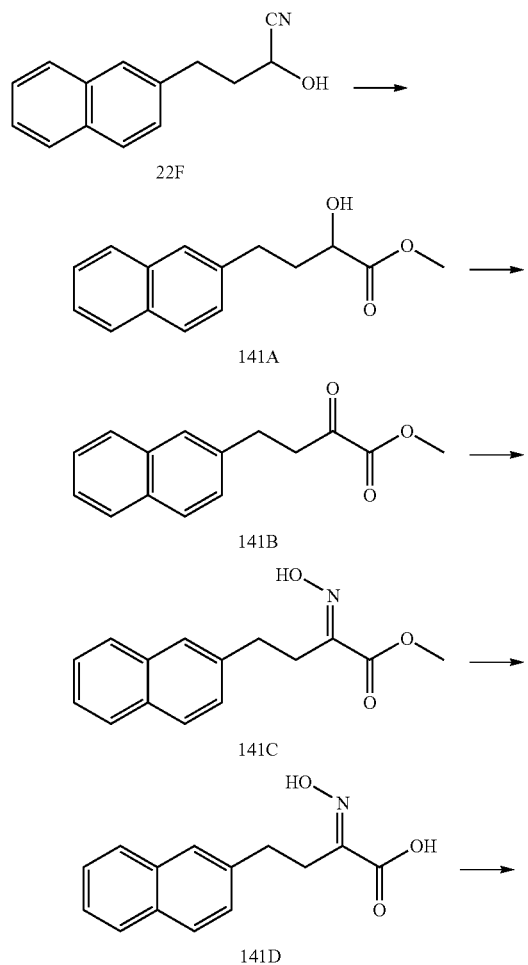

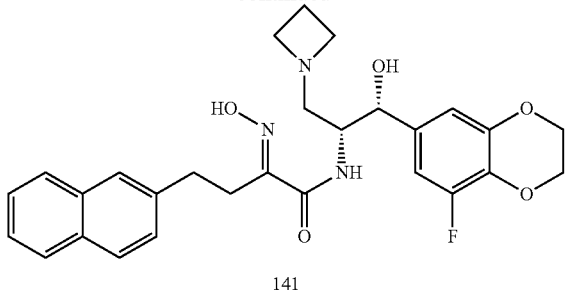

141

A solution of Compound 22F (6.6 g, 31.27 mmol) in methanol (150 mL) was stirred under HCl gas at room temperature for 6 h. It was quenched with water (30 mL) and stirred at room temperature for 1 h. After removal of solvent, the residue was dissolved in ethyl acetate (200 mL), washed with water (50 mL×3) and brine (50 mL), dried over anhydrous sodium sulfate, and concentrated to give Compound 141A.

A solution of Compound 141A (6.7 g, 27.46 mmol) and Dess-Martin periodinane (14 g, 33 mmol) in DCM (50 mL) was stirred at room temperature for 2 h. After removal of solvent, the residue was dissolved in ethyl acetate (200 mL), washed with water (50 mL×3) and brine (50 mL), dried over anhydrous sodium sulfate, and concentrated to give a residue. The crude product was purified with flash column chromatography on silica gel (ethyl acetate in petroleum ether, from 20% to 30% v/v) to afford Compound 141B.

A solution of Compound 141B (2.0 g, 8.26 mmol) in EtOH (20 mL) was added potassium carbonate (1.48 g, 10.7 mmol) and hydroxylamine hydrochloride (0.74 g, 10.7 mmol) at room temperature, then stirred at room temperature overnight. Then it was filtered and concentrated to obtain Compound 141C.

A mixture of Compound 141C (2.0 g, 7.78 mmol) and LiOH.H₂O (1.0 g, 23.3 mmol) in THF/MeOH/H₂O (10/10/4 mL) was stirred at room temperature for 3 h. The solution was concentrated to remove organic solvent, then it was adjusted to PH 6 with 3 M HCl (5 mL), filtered and washed with PE (100 mL), dried to obtain Compound 141D.

To a solution of Compound 141D (72 mg, 0.3 mmol) and Intermediate H (90 mg, 0.3 mmol) in DMF was added EDCI.HCl (86 mg, 0.45 mmol), followed by HOBt (62 mg, 0.45 mmol). Then the reaction was stirred at room temperature for 15 hours. Then the reaction mixture was treated with water (40 mL), extracted with DCM (100 mL×2), washed with brine (50 mL), dried over sodium sulfate, and concentrated. The crude product was purified with prep-HPLC to furnish Compound 141. LC-MS (ESI) m/z: 508 [M+H]⁺; ¹H-NMR (MeOD, 400 MHz) δ (ppm) 2.15-2.20 (m, 1H), 2.41-2.55 (m, 1H), 3.15-3.27 (m, 2H), 3.65-3.90 (m, 2H), 4.12-4.15 (m, 3H), 4.24 (s, 4H), 4.75-4.76 (d, J=2.8 Hz, 1H), 6.65-6.71 (m, 2H), 7.36-7.46 (m, 3H), 7.64 (s, 1H), 7.75-7.82 (m, 3H).

Example 142

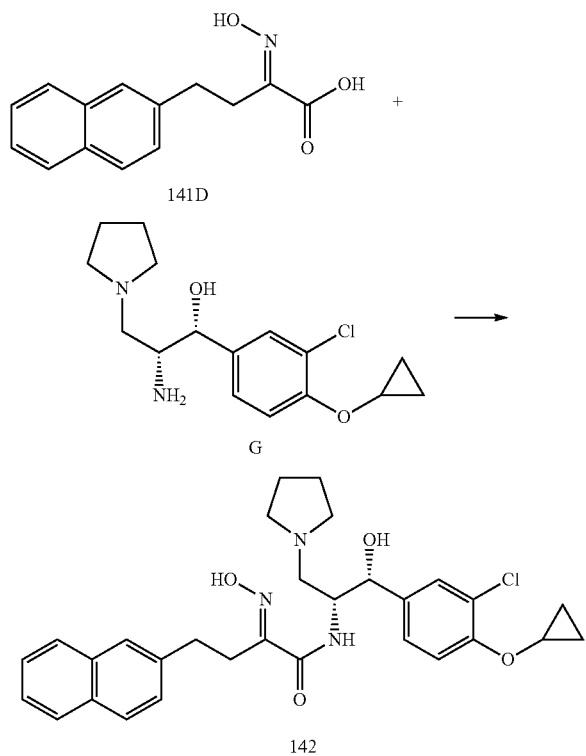

A mixture of Compound 141D (150 mg, 0.62 mmol), EDCI.HCl (178 mg, 0.93 mmol), HOBt (126 mg, 0.92 mmol) and Intermediate G (230 mg, 0.7 mmol) in DMF (8 mL) was stirred at room temperature overnight. Then the reaction mixture was purified with prep-HPLC to provide Compound 142. LC-MS (ESI) m/z: 536.2 [M+H]$^+$; $^1$H-NMR (MeOD, 400 MHz) δ (ppm) 0.63-0.73 (m, 4H), 1.95-2.09 (m, 4H), 2.65-3.14 (m, 7H), 3.43-3.47 (m, 1H), 3.55-3.58 (m, 2H), 3.70-3.77 (m, 2H), 4.47-4.50 (m, 1H), 4.84-4.85 (d, J=2.4 Hz, 1H), 7.25-7.32 (m, 3H), 7.40-7.45 (m, 3H), 7.74 (s, 1H), 7.76-7.80 (m, 3H).

Example 143

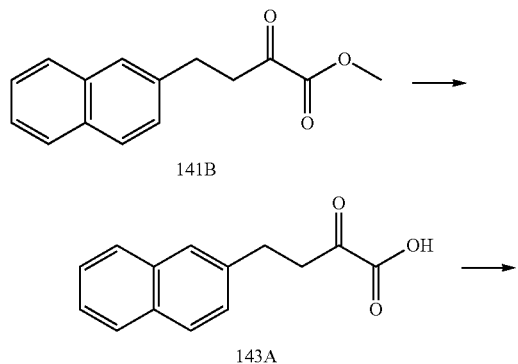

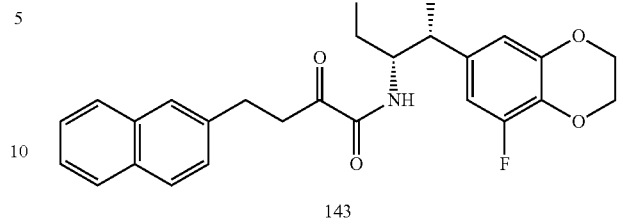

A mixture of Compound 141B (2.0 g, 8.26 mmol) and LiOH.H$_2$O (1.0 g, 24.8 mmol) in THF/MeOH/H$_2$O (10/10/4 mL) was stirred at room temperature for 5 h. The mixture was adjusted to pH 6 with aqueous HCl solution (6 N, 1.0 mL). After removal of solvent the residue was dissolved in ethyl acetate (100 mL), washed with water (50 mL×2) and brine (30 mL), dried over anhydrous sodium sulfate, and concentrated to give a residue. The crude product was purified with flash column chromatography on silica gel (ethyl acetate in petroleum ether, from 10% to 30% v/v) to afford Compound 143A.

A mixture of Compound 143A (90 mg, 0.4 mmol), Intermediate C (118 mg, 0.4 mmol), and HATU (228 mg, 0.6 mmol) in dichloromethane (10 mL) was stirred at 30° C. for 15 h. Then it was treated with water (20 mL), extracted with dichloromethane (20 mL×3), dried over anhydrous sodium sulfate, concentrated in vacuum and purified with prep-HPLC to furnish Compound 143. LC-MS (ESI) m/z: 506 [M+H]$^+$; $^1$H-NMR (DMSO-d$_6$, 400 MHz) δ (ppm) 1.77 (s, 2H), 1.93 (s, 2H), 2.87-2.96 (m, 2H), 3.00-3.10 (m, 4H), 3.21-3.27 (m, 4H), 4.18-4.30 (m, 5H), 4.61 (s, 1H), 5.95 (s, 1H), 6.67 (t, J=12 Hz, 2H), 7.36 (d, J=8 Hz, 1H), 7.40-7.47 (m, 2H), 7.67 (s, 1H), 7.78-7.84 (m, 3H), 8.14 (d, J=12 Hz, 1H), 9.03 (s, 1H).

Example 144

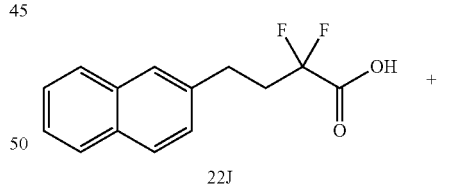

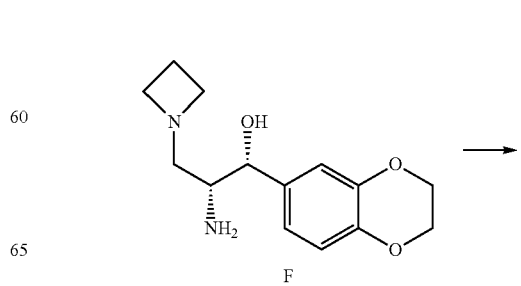

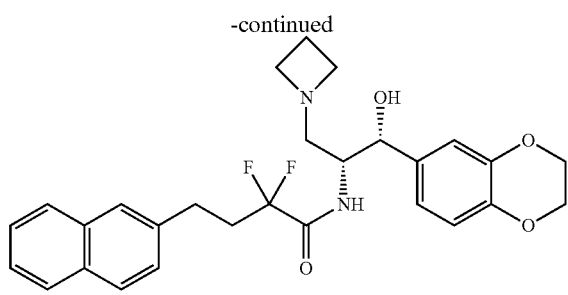

144

A mixture of Compound 22J (0.1 g, 0.4 mmol), Intermediate F (0.11 g, 0.4 mmol), DIPEA (0.10 g, 0.8 mmol), EDCI.HCl (0.11 g, 0.6 mmol) and HOBt (0.08 g, 0.6 mmol) in DCM (2 mL) was stirred at 25° C. for 16 h. Then the mixture was diluted with ethyl acetate (30 mL), washed with water (10 mL×2) and brine (10 mL), dried over sodium sulfate, concentrated, and purified with prep-HPLC to furnish Compound 144. LC-MS (ESI) m/z: 497 [M+H]$^+$; $^1$H-NMR (MeOD, 400 MHz) δ (ppm) 2.15-2.22 (m, 2H), 2.41-2.71 (m, 4H), 3.54-3.63 (m, 3H), 3.77-3.89 (m, 3H), 4.20-4.23 (m, 4H), 4.39-4.42 (m, 1H), 4.85 (d, J=3.2 Hz, 1H), 6.77-6.79 (m, 1H), 6.84-6.90 (m, 2H), 7.26-7.29 (m, 1H), 7.44-7.48 (m, 2H), 7.59 (s, 1H), 7.80-7.83 (m, 3H).

Example 145

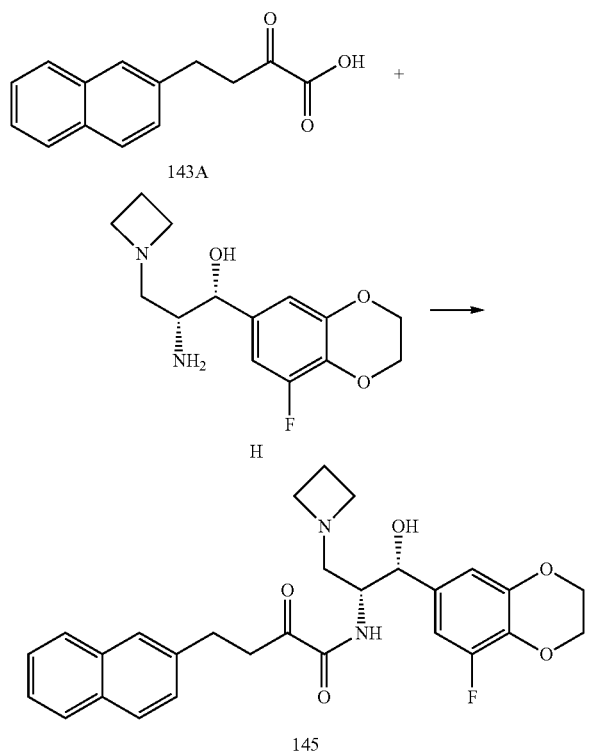

To a solution of Compound 143A (90 mg, 0.4 mmol) in dry dichloromethane (8 mL) and DMF (2 mL) was added HATU (228 mg, 0.6 mmol), followed by Intermediate H (90 mg, 0.3 mmol) in DMF. Then EDCI.HCl (86 mg, 0.45 mmol) and HOBt (62 mg, 0.45 mmol) was added. The reaction was stirred at room temperature for 15 hours, filtered, and evaporated to furnish the crude product in DMF (3 mL). It was purified with prep-HPLC to furnish Compound 145. LC-MS (ESI) m/z: 493 [M+H]$^+$; $^1$H-NMR (DMSO-d$_6$, 400 MHz) δ (ppm) 2.20-2.35 (m, 2H), 2.90-3.00 (m, 2H), 3.12-3.35 (m, 4H), 3.80-4.20 (m, 5H), 4.25 (s, 4H), 4.62 (s, 1H), 5.96 (s, 1H), 6.65-6.74 (m, 2H), 7.38-7.51 (m, 3H), 7.71 (s, 1H), 7.82-7.88 (m, 3H), 8.09-8.12 (d, J=9.6 Hz, 1H), 9.35 (br, 1H).

Example 146

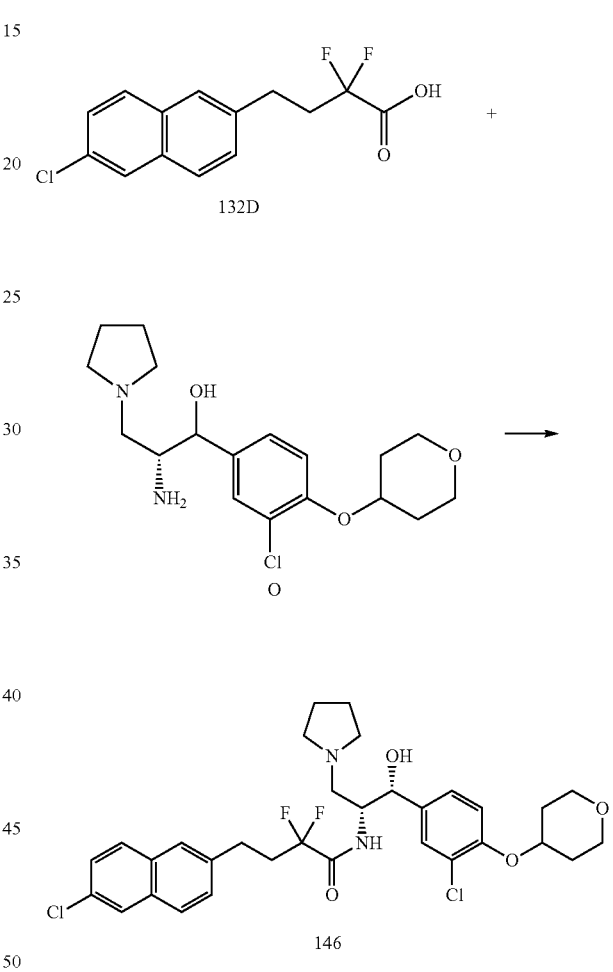

A mixture of Intermediate 0 (120 mg, 0.34 mmol), EDCI.HCl (98 mg, 0.51 mmol), HOBt (69 mg, 0.51 mmol) and Compound 132D (120 mg, 0.34 mmol) in DCM (10 mL) was stirred h at 25° C. for 12. Then the mixture was washed with saturated sodium bicarbonate (15 mL) and brine (15 mL), and dried over anhydrous sodium sulfate. After evaporation, the crude product was purified with prep-HPLC to furnish Compound 146. LC-MS (ESI) m/z: 593 [M+H]$^+$; $^1$H-NMR (CDCl$_3$, 400 MHz) δ (ppm) 1.63-1.70 (m, 2H), 1.78-1.84 (m, 2H), 2.03 (m, 4H), 2.83 (m, 1H), 2.93 (m, 1H), 3.71-3.92 (m, 8H), 4.17-4.22 (m, 1H), 4.37 (m, 1H), 5.00 (s, 1H), 6.48 (d, J=8.4 Hz, 1H), 6.91 (d, J=8.4 Hz, 1H), 7.25 (s, 1H), 7.31 (d, J=9.2 Hz, 1H), 7.41 (dd, J=8.8, 2.0 Hz, 1H), 7.65 (d, J=8.8 Hz, 1H), 7.72 (d, J=8.8 Hz, 1H), 7.76 (m, 1H), 7.82-7.86 (m, 2H), 11.44 (s, 1H).

Example 147

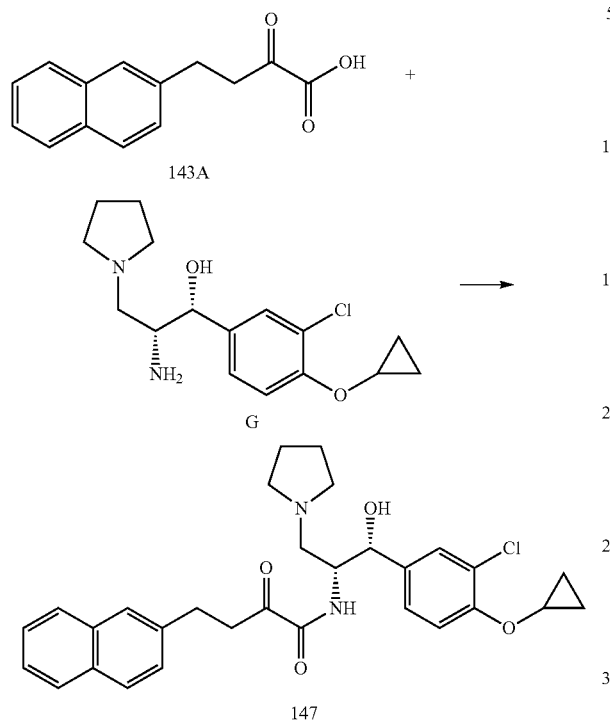

A mixture of Compound 143A (152 mg, 0.67 mmol), HATU (456 mg, 1.2 mmol), DCM (16 mL) and Intermediate G (248 mg, 0.8 mmol) in DMF (6 mL) was stirred at room temperature overnight. Then the reaction mixture was treated with water (20 mL), extracted with DCM (50 mL×2), washed with brine (50 mL), dried over anhydrous sodium sulfate, and concentrated. The crude product was purified with prep-HPLC to provide Compound 147. LC-MS (ESI) m/z: 521.3 [M+H]$^+$; $^1$H-NMR (DMSO-d$_6$, 400 MHz) δ (ppm) 0.63-0.78 (m, 4H), 1.82-1.98 (m, 4H), 2.94-3.12 (m, 5H), 3.21-3.24 (m, 1H), 3.46-3.49 (m, 3H), 3.83-3.86 (m, 2H), 4.31-4.36 (m, 1H), 4.74 (d, J=2.8 Hz, 1H), 6.01 (s, 1H), 7.21-7.24 (m, 1H), 7.30-7.40 (m, 3H), 7.45-7.50 (m, 2H), 7.70 (s, 1H), 7.82-7.88 (m, 3H), 8.20 (d, J=9.6 Hz, 1H), 9.38 (s, 1H).

Example 148

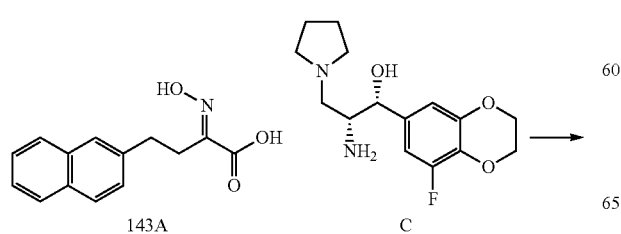

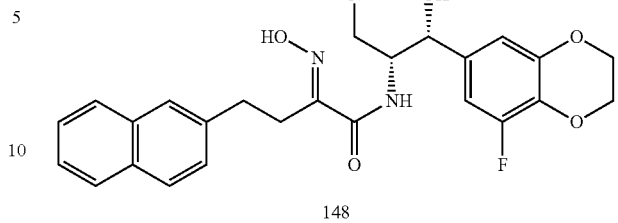

A mixture of Compound 143A (97 mg, 0.4 mmol), Intermediate C (118 mg, 0.4 mmol), HOBt (81 mg, 0.6 mmol), and EDCI.HCl (115 mg, 0.6 mmol) in DMF (10 mL) was stirred at 30° C. for 8 h. The mixture was purified with prep-HPLC directly to furnish Compound 148. LC-MS (ESI) m/z: 522 [M+H]$^+$; $^1$H-NMR (MeOD, 400 MHz) δ (ppm) 1.93 (s, 2H), 2.09 (s, 2H), 2.68-2.95 (m, 4H), 3.04-3.17 (m, 2H), 3.40-3.44 (m, 1H), 3.54 (t, J=12 Hz, 2H), 3.69 (s, 1H), 4.14-4.21 (m, 4H), 4.44-4.49 (m, 1H), 4.75 (s, 1H), 6.74 (d, J=12 Hz, 2H), 7.33 (d, J=8 Hz, 1H), 7.38-7.45 (m, 2H), 7.62 (s, 1H), 7.70 (d, J=8 Hz, 0.5H), 7.70-7.85 (m, 3H).

Example 149

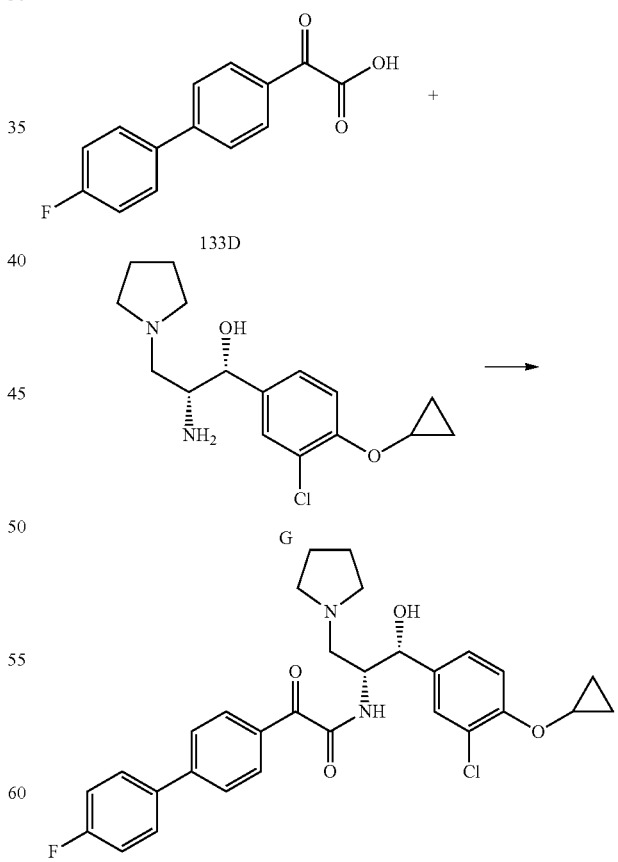

A mixture of Compound 133D (230 mg, 0.94 mmol), HATU (515 mg, 1.36 mmol), and Intermediate G (324 mg, 1.05 mmol) in DCM (25 mL) was stirred at room temperature overnight. Then the reaction mixture was treated with water (20 mL), extracted with DCM (50 mL×2), washed with brine (50 mL), dried over anhydrous sodium sulfate, and concentrated. The crude product was purified with prep-HPLC to provide Compound 149. LC-MS (ESI) m/z: 537.2 [M+H]⁺; ¹H-NMR (MeOD, 400 MHz) δ (ppm) 0.69-0.83 (m, 4H), 1.82-1.98 (m, 4H), 2.94-3.12 (m, 5H), 3.21-3.24 (m, 1H), 3.46-3.49 (m, 3H), 2.04-2.08 (m, 3H), 2.19-2.22 (m, 2H), 3.23-3.33 (m, 1H), 3.58-3.75 (m, 4H), 3.82-3.86 (m, 2H), 4.70-4.73 (m, 2H), 5.01 (s, 1H), 7.23-7.27 (m, 2H), 7.39 (d, J=0.8 Hz, 1H), 7.64-7.70 (m, 4H), 7.73-7.76 (m, 2H).

Example 150

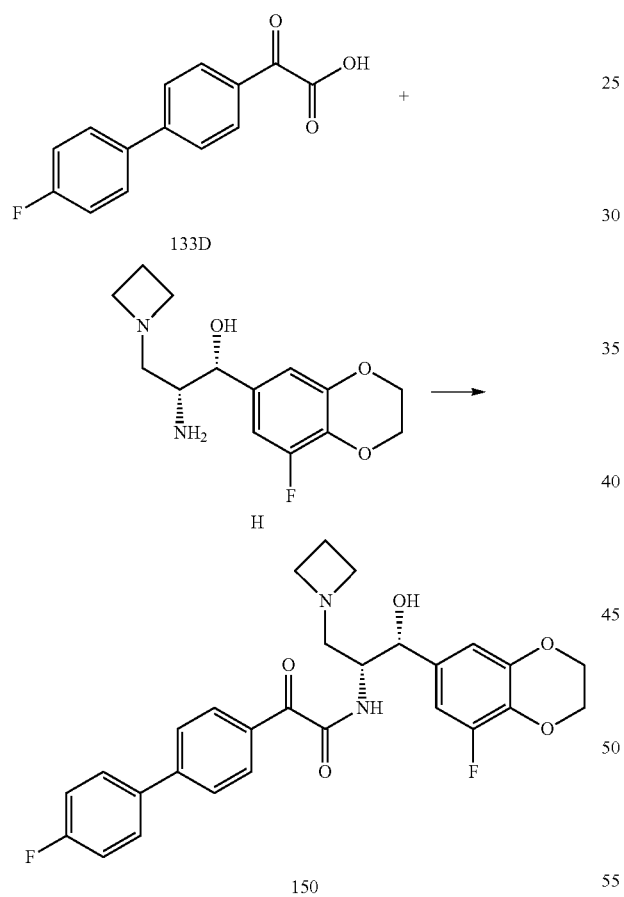

A mixture of Compound 133D (195 mg, 0.8 mmol), Intermediate H (225 mg, 0.8 mmol), and HATU (456 mg, 1.2 mmol) in dichloromethane (20 mL) was stirred at 30° C. for 8 h. Then it was treated with water (20 mL), extracted with dichloromethane (20 mL×3), dried over anhydrous sodium sulfate, concentrated in vacuum and purified with prep-HPLC to furnish Compound 150. LC-MS (ESI) m/z: 509 [M+H]⁺; ¹H-NMR (CDCl₃, 400 MHz) δ (ppm) 2.47 (s, 2H), 3.46-3.65 (m, 2H), 4.12-4.34 (m, 9H), 4.89 (s, 1H), 6.69 (d, J=12 Hz, 2H), 7.12 (t, J=8 Hz, 2H), 7.55 (t, J=8 Hz, 4H), 7.90 (d, J=8 Hz, 2H).

Example 151

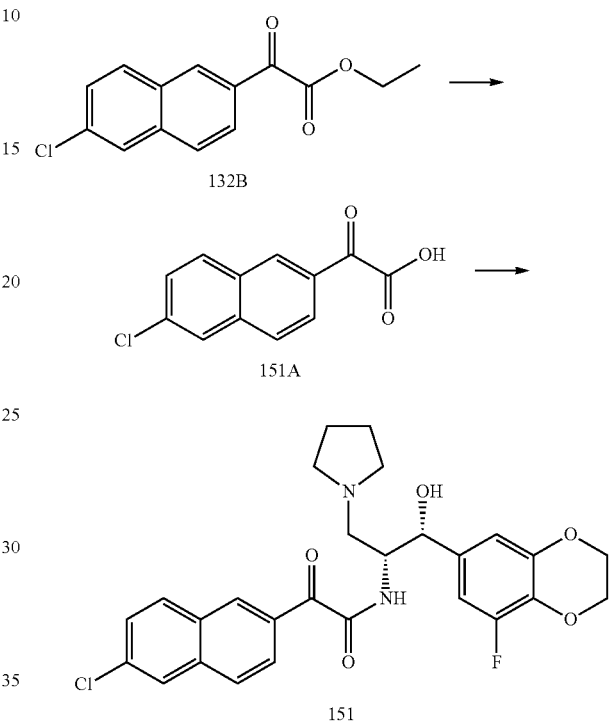

To a solution of Compound 132B (262 mg, 1 mmol) in ethanol/water (16 mL, 15/1 v/v) was added LiOH H₂O (84 mg, 2 mmol). The mixture was stirred at room temperature overnight. After the completion of the reaction, the mixture was adjusted to pH 2 with aqueous HCl solution (3 N, 40 mL) and extracted with ethyl acetate (20 mL×3). The combined organic layers were washed with brine (200 mL), dried over anhydrous sodium sulfate, and concentrated to yield the Compound 151A.

To a solution of Compound 151A (170 mg, 0.73 mmol) and Intermediate C (216 mg, 0.73 mmol) in dichloromethane (6 mL) was added HATU (414 mg, 1.09 mmol) at 25° C. Then the reaction was stirred at 25° C. for 15 hours. Then the reaction mixture was treated with water (40 mL), extracted with DCM (10 mL×2), washed with brine (10 mL), dried over sodium sulfate, and concentrated. The crude product was purified with prep-HPLC to furnish Compound 151. LC-MS (ESI) m/z: 513 [M+H]⁺; ¹H-NMR (MeOD, 400 MHz) δ (ppm) 2.05-2.07 (m, 2H), 2.22-2.25 (m, 1H), 3.20-3.22 (m, 2H), 3.58-3.95 (m, 4H), 4.05-4.24 (m, 4H), 4.56-4.59 (d, J=10.4 Hz, 1H), 4.95-4.96 (d, J=2.4 Hz, 1H), 6.75-6.81 (m, 2H), 7.52-7.55 (dd, J=2.0 Hz, J=8.4 Hz, 1H), 7.79-7.97 (m, 4H), 8.49 (s, 1H).

Example 152

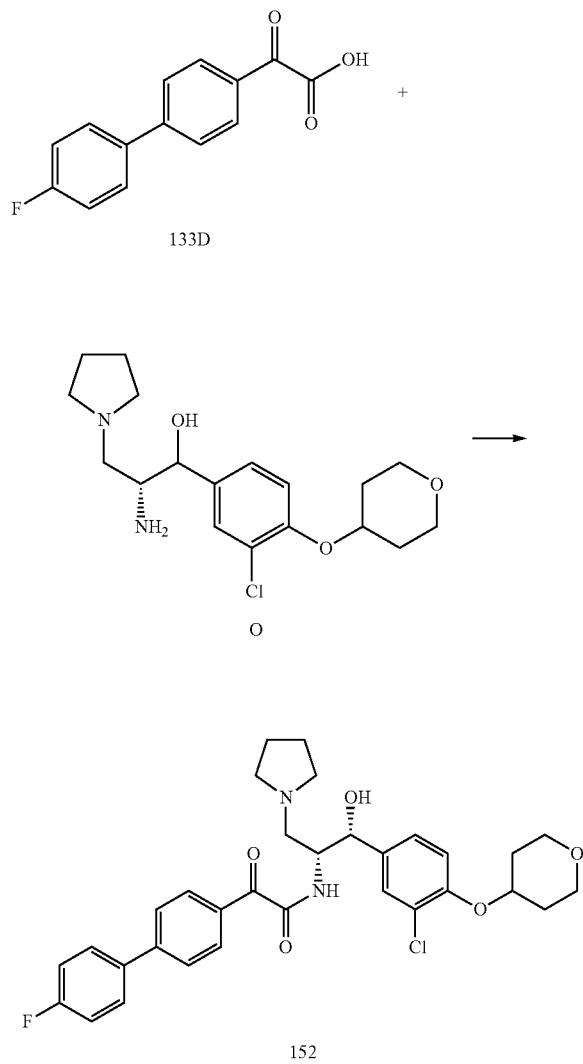

A mixture of Compound 133D (82.5 mg, 0.34 mmol), HATU (193.8 mg, 0.51 mmol) and Intermediate O (120 mg, 0.34 mmol) in DCM (10 mL) was stirred for 12 h at 25° C. Then the mixture was washed with water (15 mL) and brine (15 mL), and dried over anhydrous sodium sulfate. After evaporation, the crude product was purified with prep-HPLC to furnish Compound 152. LC-MS (ESI) m/z: 581 [M+H]$^+$; $^1$H-NMR (CDCl$_3$, 400 MHz) δ (ppm) 1.68-1.75 (s, 2H), 1.88-1.90 (s, 2H), 2.08-2.15 (m, 4H), 3.14-3.26 (m, 4H), 3.47-3.52 (m, 2H), 3.87-3.91 (m, 4H), 4.41-4.45 (m, 1H), 4.55-4.57 (m, 1H), 5.08 (s, 1H), 6.85 (d, J=17.2 Hz, 1H), 7.10-7.14 (m, 2H), 7.20-7.22 (m, 1H), 7.40 (s, 1H), 7.50-7.54 (m, 4H), 7.90-7.94 (m, 3H), 9.01 (s, 1H).

Example 153

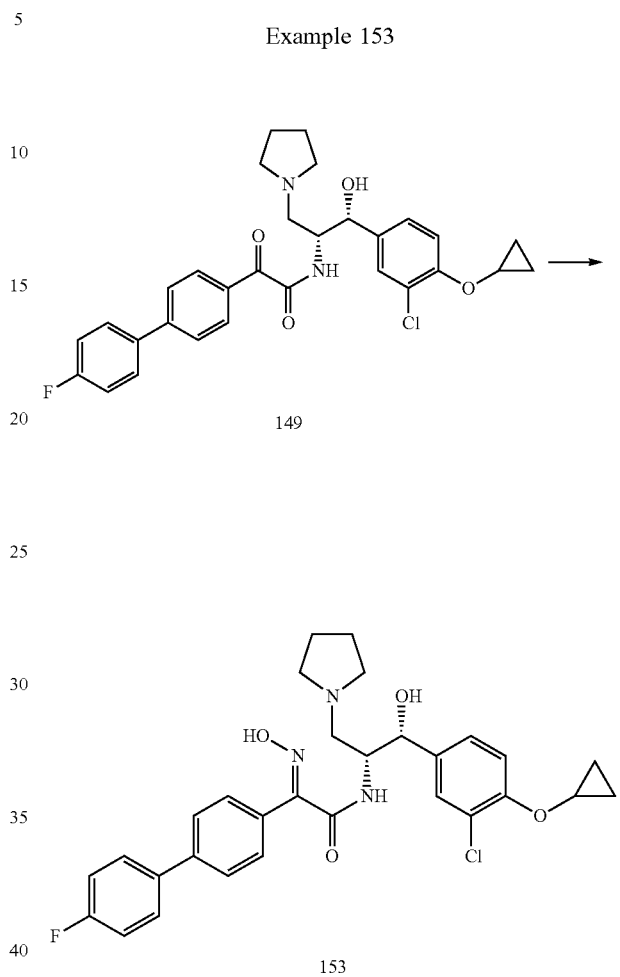

A mixture of 149 (36 mg, 0.07 mmol) and hydroxylamine hydrochloride (69 mg, 1.0 mmol) in methanol (6 mL) was stirred at 50° C. for 16 hours. Then the reaction mixture was purified with prep-HPLC to provide Compound 153. LC-MS (ESI) m/z: 552.1 [M+H]$^+$; $^1$H-NMR (MeOD, 400 MHz) δ (ppm) 0.72-0.83 (m, 4H), 1.82-1.98 (m, 4H), 2.94-3.12 (m, 5H), 3.21-3.24 (m, 1H), 3.46-3.49 (m, 3H), 2.04-2.08 (m, 3H), 2.04-2.21 (m, 4H), 3.20-3.33 (m, 2H), 3.59-3.89 (m, 5H), 4.83-4.87 (m, 1H), 5.03 (d, J=2.4 Hz, 1H), 7.09 (d, J=8.8 Hz, 2H), 7.38-7.42 (m, 2H), 7.48-7.52 (m, 3H), 7.66-7.69 (m, 2H).

Example 154

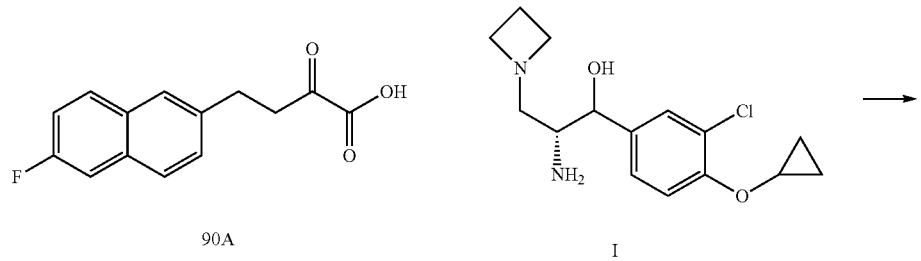

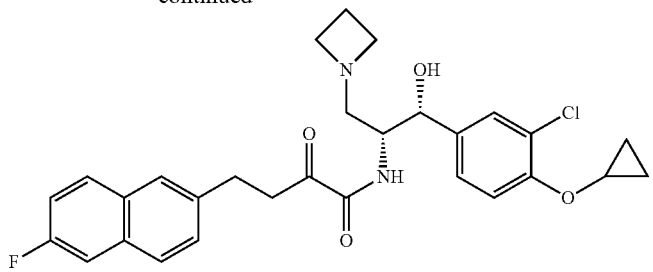

154

A mixture of Intermediate I (145 mg, 0.49 mmol), HATU (278 mg, 0.73 mmol), and Compound 90A (100 mg, 0.406 mmol) in DMF (3 mL) and DCM (6 mL) was stirred at 25° C. overnight. Then the reaction mixture was concentrated to remove DCM. The residue was purified with prep-HPLC to provide Compound 154. LC-MS (ESI) m/z: 525 [M+H]$^+$; $^1$H-NMR (DMSO-d$_6$, 400 MHz) δ (ppm) 0.61-0.65 (m, 2H), 0.76-0.81 (m, 2H), 2.16-2.25 (m, 1H), 2.31-2.39 (m, 1H), 2.93-2.98 (m, 2H), 3.05-3.14 (m, 1H), 3.20-3.42 (m, 3H), 3.84-3.88 (m, 1H), 3.92-3.99 (m, 2H), 4.05-4.18 (m, 3H), 4.69 (s, 1H), 5.97 (s, 1H), 7.21 (d, J=8.8 Hz, 1H), 7.31-7.33 (m, 2H), 7.39-7.45 (m, 2H), 7.66 (d, J=12.8 Hz, 1H), 7.75 (s, 1H), 7.84 (d, J=8.8 Hz, 1H), 7.91-7.94 (m, 1H), 8.13 (d, J=9.6 Hz, 1H), 9.34 (s, 1H).

Example 155

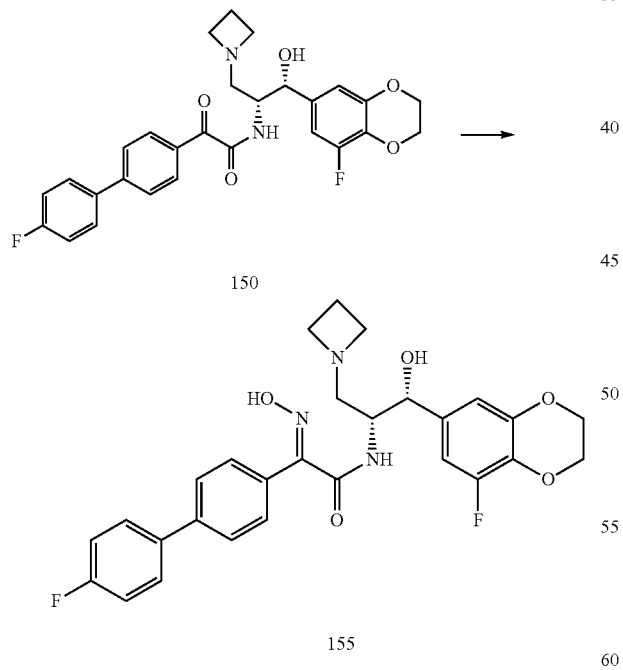

A mixture of 150 (90 mg, 0.18 mmol) and hydroxylamine hydrochloride (248 mg, 3.54 mmol) in MeOH (10 mL) was stirred at room temperature for 4 h. Then it was purified with prep-HPLC directly to provide Compound 155. LC-MS (ESI) m/z: 523 [M+H]$^+$; $^1$H-NMR (MeOD, 400 MHz) δ (ppm) 2.44 (s, 1H), 2.56-2.66 (m, 1H), 3.53-3.67 (m, 2H), 4.18-4.45 (m, 9H), 4.45 (s, 0.5H), 4.81 (s, 0.5H), 6.77-6.83 (m, 2H), 7.17-7.23 (m, 3H), 7.40-7.69 (m, 5H).

Example 156

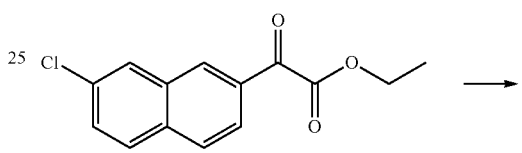

156A

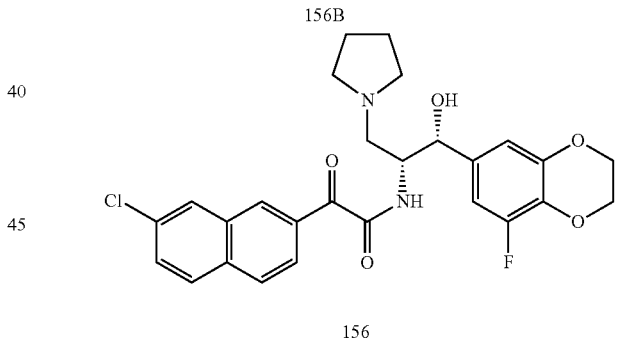

156

To a solution of Compound 156A (100 mg, 0.38 mmol) in THF/water (8 mL, 15:1, v/v) was added LiOH.H$_2$O (25 mg, 0.58 mmol). The mixture was stirred at −10° C. for 1 h. After the reaction was completed, it was adjusted to pH to 6 with 3 N HCl and extracted with ethyl acetate (15 mL×3). The combined organic layers were concentrated in vacuum without dryness to provide the desired product Compound 156B.

To a solution of Compound 156B (85 mg, 0.36 mmol) and Intermediate C (108 mg, 0.36 mmol) in dichloromethane (3 mL) was added HATU (207 mg, 0.54 mmol) at 25° C. Then the reaction was stirred at 25° C. for 15 hours. Then the reaction mixture was treated with water (20 mL), extracted with DCM (10 mL×2), washed with brine (10 mL), dried over sodium sulfate, and concentrated. The crude product was purified with prep-HPLC to furnish Compound 156. LC-MS (ESI) m/z: 513 [M+H]$^+$; $^1$H-NMR (MeOD, 400

MHz) δ (ppm) 2.05-2.17 (m, 4H), 3.11-4.12 (m, 6H), 4.17-4.31 (m, 4H), 4.55-4.57 (m, 1H), 4.95 (d, J=2.0 Hz, 1H), 6.75-6.83 (m, 2H), 7.48-7.56 (m, 2H), 7.75-7.98 (m, 4H), 8.55 (d, J=9.2 Hz, 1H).

Example 157

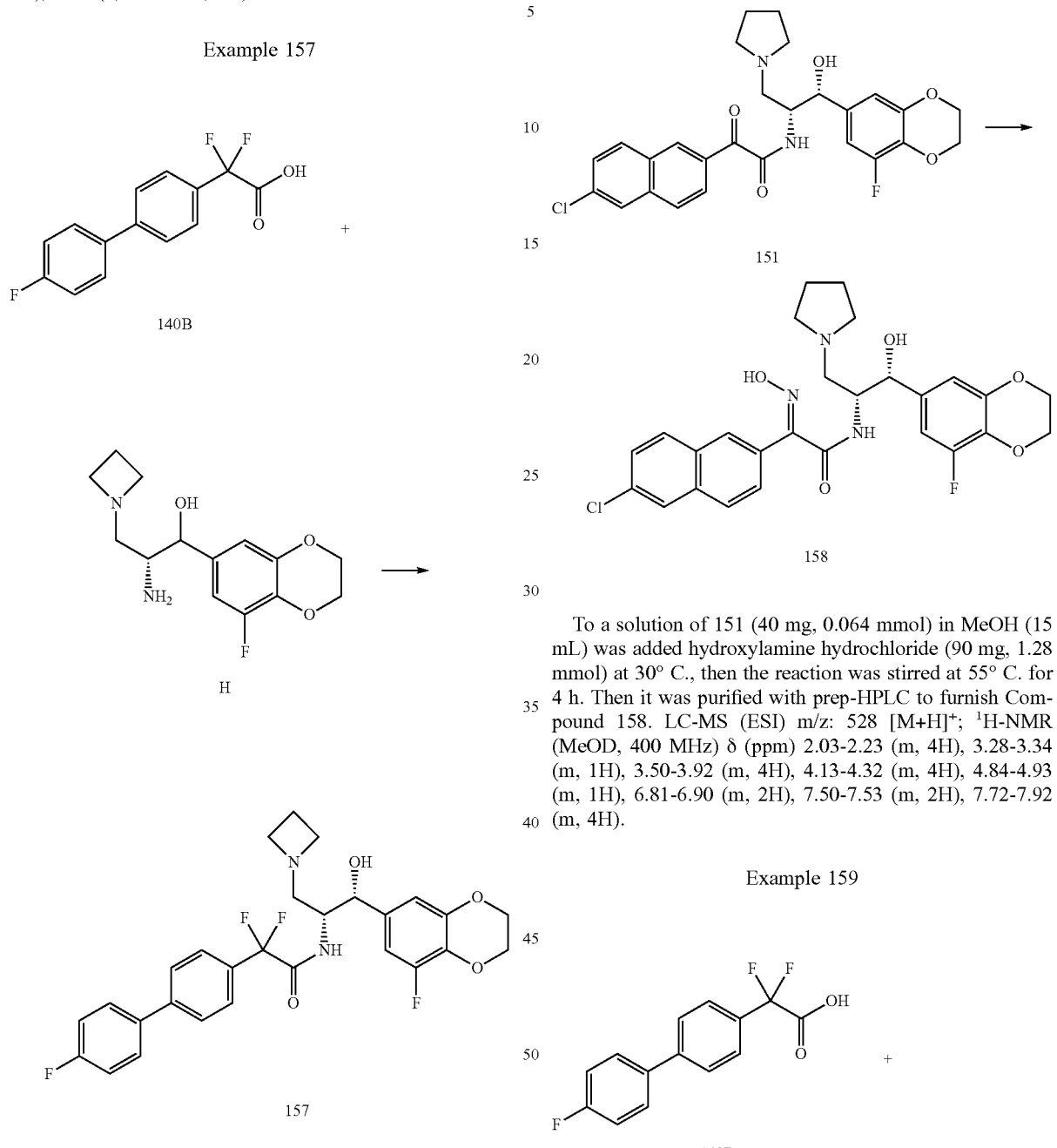

To a solution of Compound 140B (67 mg, 0.25 mmol), Intermediate H (78 mg, 0.26 mmol), and EDCI.HCl (72 mg, 0.375 mmol) in dichloromethane (10 mL) was added HOBt (51 mg, 0.375 mmol) at 19° C., then the reaction was stirred at 19° C. for 4 h. Then it was treated with water (20 mL), extracted with dichloromethane (20 mL×3), dried over anhydrous sodium sulfate, concentrated in vacuum and purified with prep-HPLC to furnish Compound 157. LC-MS (ESI) m/z: 531 [M+H]$^+$; $^1$H-NMR (MeOD, 400 MHz) δ (ppm) 2.29-2.38 (m, 2H), 2.72 (br, 1H), 4.08-4.37 (m, 10H), 4.91 (s, 1H), 6.54-6.66 (m, 2H), 7.12-7.17 (m, 2H), 7.41 (d, J=8.4 Hz, 2H), 7.53-7.58 (m, 4H).

Example 158

To a solution of 151 (40 mg, 0.064 mmol) in MeOH (15 mL) was added hydroxylamine hydrochloride (90 mg, 1.28 mmol) at 30° C., then the reaction was stirred at 55° C. for 4 h. Then it was purified with prep-HPLC to furnish Compound 158. LC-MS (ESI) m/z: 528 [M+H]$^+$; $^1$H-NMR (MeOD, 400 MHz) δ (ppm) 2.03-2.23 (m, 4H), 3.28-3.34 (m, 1H), 3.50-3.92 (m, 4H), 4.13-4.32 (m, 4H), 4.84-4.93 (m, 1H), 6.81-6.90 (m, 2H), 7.50-7.53 (m, 2H), 7.72-7.92 (m, 4H).

Example 159

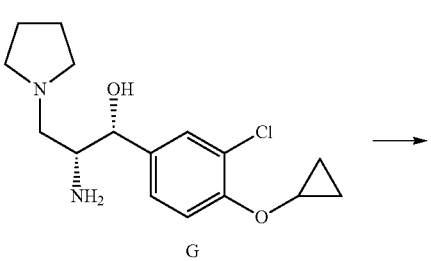

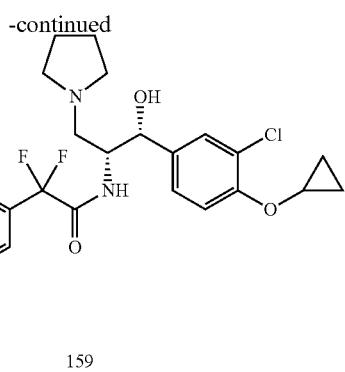

159

A mixture of Compound 140B (172 mg, 0.64 mmol), EDCI.HCl (186 mg, 0.97 mmol), HOBt (132 mg, 0.97 mmol) and Intermediate G (200 mg, 0.64 mmol) in DCM (15 mL) was stirred at room temperature overnight. Then the reaction mixture was treated with water (20 mL), extracted with DCM (50 mL×2), washed with brine (50 mL), dried over anhydrous sodium sulfate, and concentrated. The crude product was purified with prep-HPLC to provide Compound 159. LC-MS (ESI) m/z: 559.2 [M+H]$^+$; $^1$H-NMR (MeOD, 400 MHz) δ (ppm) 0.49-0.61 (m, 4H), 2.03-2.04 (m, 4H), 3.15-3.30 (m, 2H), 3.53-3.81 (m, 5H), 4.63 (d, J=10.4 Hz, 1H), 7.04 (d, J=8.4 Hz, 1H), 7.11-7.13 (m, 1H), 7.21-7.25 (m, 2H), 7.34-7.36 (m, 3H), 7.63 (d, J=8.0 Hz, 2H), 7.71-7.75 (m, 2H).

Example 160

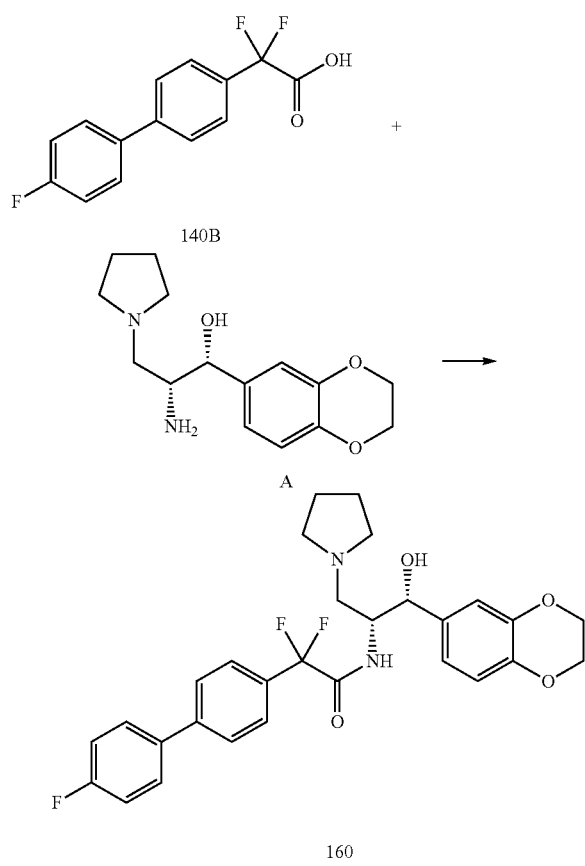

160

A mixture of Compound 140B (0.10 g, 0.4 mmol), Intermediate A (0.10 g, 0.4 mmol), DIPEA (0.1 g, 0.8 mmol), EDCI.HCl (0.10 g, 0.6 mmol) and HOBt (0.08 g, 0.6 mmol) in DCM (2 mL) was stirred at 25° C. for 16 h. Then the mixture was diluted with ethyl acetate (30 mL), washed with water (10 mL×2) and brine (10 mL), dried over sodium sulfate, concentrated, and purified with prep-HPLC to furnish Compound 160. LC-MS (ESI) m/z: 527 [M+H]$^+$; $^1$H-NMR (MeOD, 400 MHz) δ (ppm) 2.01-2.25 (m, 4H), 3.15-3.22 (m, 2H), 3.52-3.66 (m, 3H), 3.77-3.79 (m, 1H), 4.07 (s, 4H), 4.56-4.58 (m, 1H), 4.83 (d, J=3.2 Hz, 1H), 6.63-6.65 (m, 1H), 6.72-6.77 (m, 2H), 7.20-7.25 (m, 2H), 7.43-7.45 (m, 2H), 7.65-7.73 (m, 4H).

Example 161

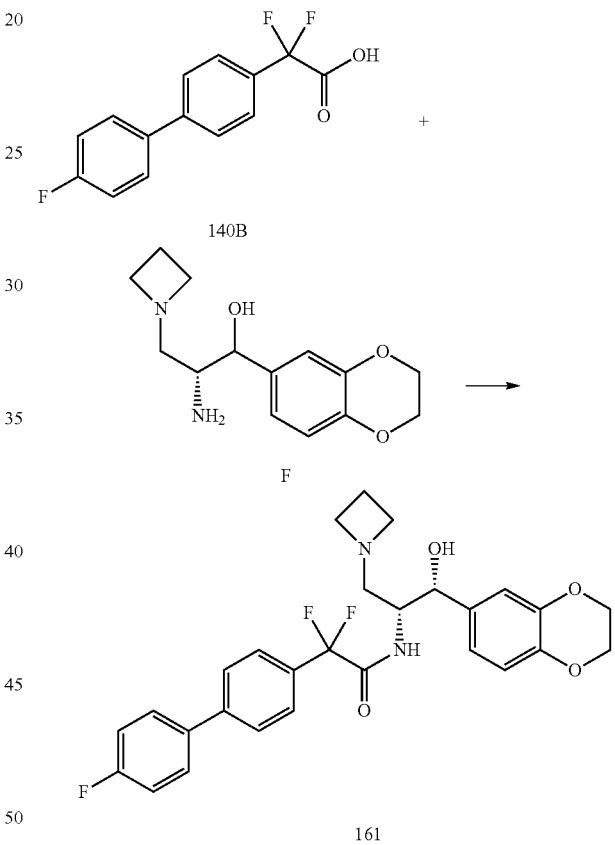

161

A mixture of Compound 140B (0.10 g, 0.4 mmol), Intermediate F (0.10 g, 0.4 mmol), DIPEA (0.1 g, 0.8 mmol), EDCI.HCl (0.10 g, 0.6 mmol) and HOBt (0.08 g, 0.6 mmol) in DCM (2 mL) was stirred at 25° C. for 16 h. Then the mixture was diluted with ethyl acetate (30 mL), washed with water (10 mL×2) and brine (10 mL), dried over sodium sulfate, concentrated, and purified with prep-HPLC to furnish Compound 161. LC-MS (ESI) m/z: 513 [M+H]$^+$; $^1$H-NMR (MeOD, 400 MHz) δ (ppm) 2.38-2.62 (m, 2H), 3.53-3.56 (m, 2H), 4.08 (s, 4H), 4.19-4.26 (m, 4H), 4.36-4.38 (m, 1H), 4.80 (d, J=3.2 Hz, 1H), 6.64-6.77 (m, 3H), 7.21-7.25 (m, 2H), 7.41-7.43 (m, 2H), 7.65-7.73 (m, 4H).

Example 162

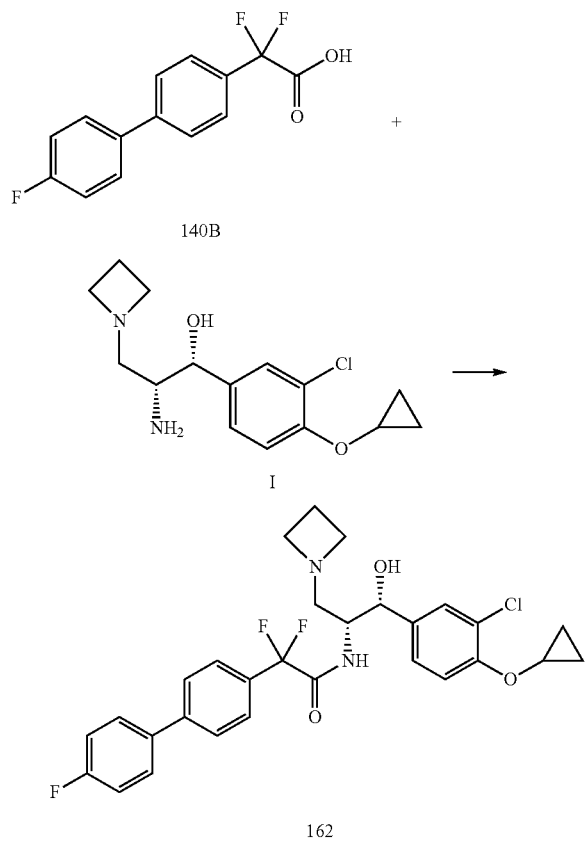

A mixture of Compound 140B (172 mg, 0.64 mmol), EDCI.HCl (186 mg, 0.97 mmol), HOBt (132 mg, 0.97 mmol) and Intermediate I (191 mg, 0.64 mmol) in DCM (15 mL) was stirred at room temperature overnight. Then the reaction mixture was treated with water (20 mL), extracted with DCM (50 mL×2), washed with brine (50 mL), dried over anhydrous sodium sulfate, and concentrated. The crude product was purified with prep-HPLC to provide Compound 162. LC-MS (ESI) m/z: 545.1 [M+H]$^+$; $^1$H-NMR (MeOD, 400 MHz) δ (ppm) 0.49-0.64 (m, 4H), 2.43-2.61 (m, 2H), 3.54-3.62 (m, 3H), 4.21-4.47 (m, 6H), 7.06 (d, J=8.4 Hz, 1H), 7.11-7.13 (m, 1H), 7.21-7.25 (m, 2H), 7.32-7.36 (m, 3H), 7.61-7.64 (m, 3H), 7.71-7.74 (m, 2H).

Example 163

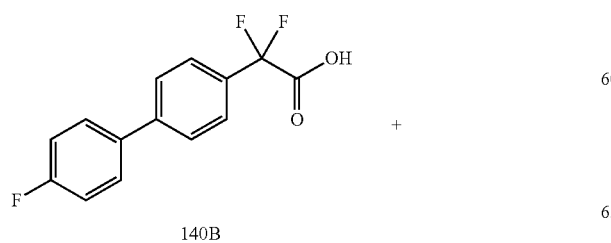

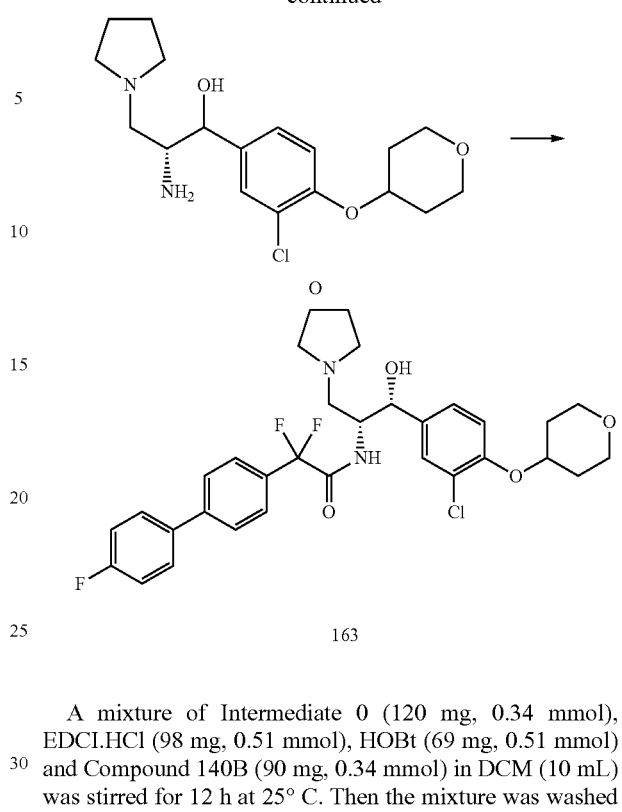

A mixture of Intermediate O (120 mg, 0.34 mmol), EDCI.HCl (98 mg, 0.51 mmol), HOBt (69 mg, 0.51 mmol) and Compound 140B (90 mg, 0.34 mmol) in DCM (10 mL) was stirred for 12 h at 25° C. Then the mixture was washed with saturated sodium bicarbonate (15 mL) and brine (15 mL), and dried over anhydrous sodium sulfate. After evaporation, the crude product was purified with prep-HPLC to furnish Compound 163. LC-MS (ESI) m/z: 603 [M+H]$^+$; $^1$H-NMR (CDCl$_3$, 400 MHz) δ (ppm) 1.65-1.75 (m, 2H), 1.85-1.89 (m, 2H), 2.13 (m, 4H), 2.91-3.03 (m, 2H), 3.49-3.54 (m, 4H), 3.76-3.94 (m, 4H), 4.40 (m, 2H), 5.16 (s, 1H), 6.78 (d, J=8.8 Hz, 1H), 7.07-7.15 (m, 3H), 7.31-7.37 (m, 3H), 7.50-7.57 (m, 4H), 7.69 (d, J=4.8 Hz, 1H), 11.80 (s, 1H).

Example 164

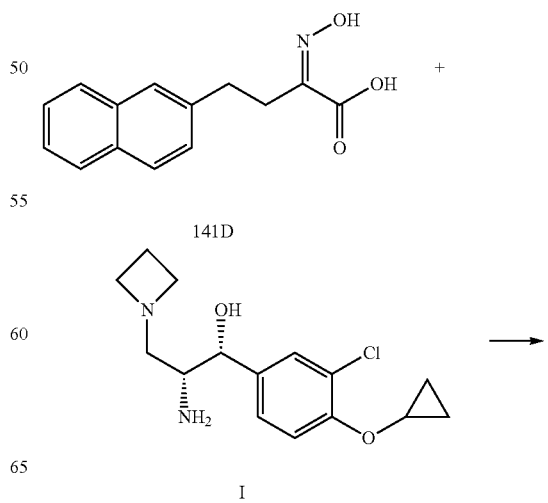

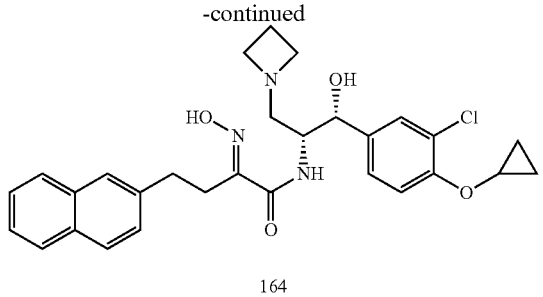

164

A solution of Compound 141D (150 mg, 0.60 mmol), Intermediate I (182 mg, 0.6 mmol), EDCI.HCl (171 mg, 0.9 mmol), HOBt (121 mg, 0.9 mmol), and DIPEA (0.2 mL, 2.40 mmol) in DCM (10 mL) and DMF (10 mL) was stirred at room temperature overnight under nitrogen. Then it was evaporated and purified with prep-HPLC to furnish Compound 164. LC-MS (ESI) m/z: 522 [M+H]$^+$; $^1$H-NMR (MeOD, 400 MHz) δ (ppm) 0.64-0.75 (m, 4H), 2.21-2.48 (m, 2H), 2.64-2.80 (m, 2H), 2.82-2.98 (m, 2H), 3.38-3.55 (m, 2H), 3.73-3.80 (m, 1H), 3.80-3.89 (m, 2H), 4.06-4.19 (m, 2H), 4.21-4.32 (m, 1H), 4.80-4.83 (m, 1H), 7.22-7.27 (m, 1H), 7.30-7.34 (m, 2H), 7.38-7.47 (m, 3H), 7.58-7.62 (m, 1H), 7.74-7.83 (m, 3H).

Example 165

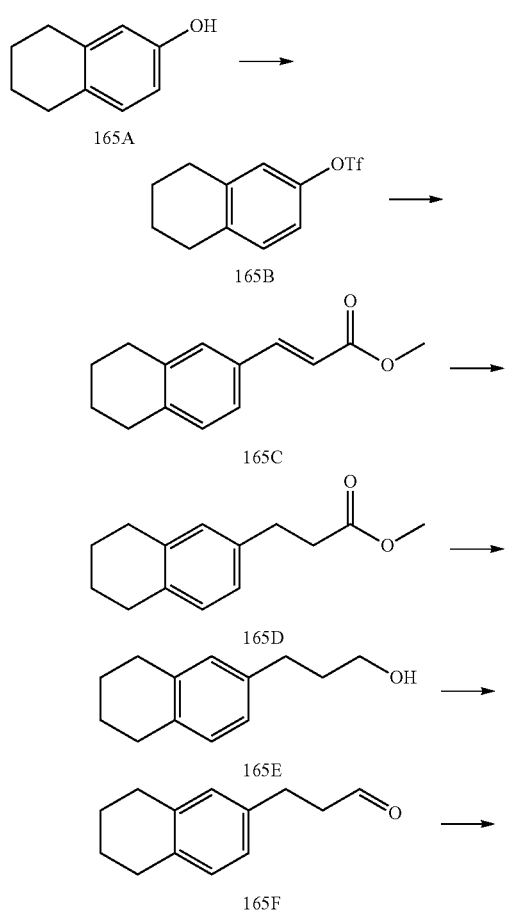

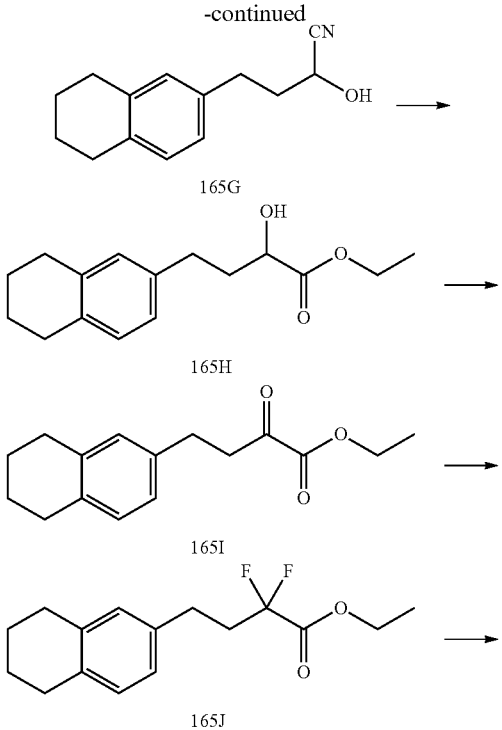

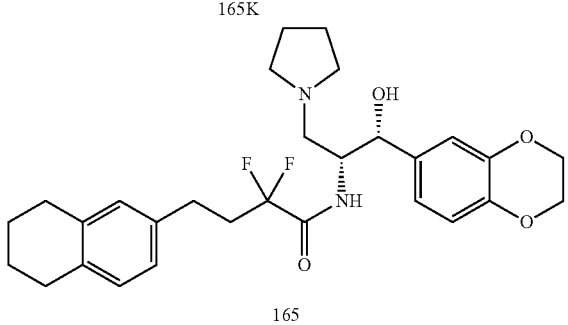

165

To a cooled solution of Compound 165A (10 g, 67 mmol), 2,6-dimethylpyridine (10.8 g, 101 mmol), and DMAP (1.65 mmol, 13 mmol) in DCM (100 mL) was added dropwise Tf$_2$O (30.5 g, 108 mmol) at 0° C. The resulting mixture was stirred at room temperature overnight, diluted with DCM, and washed with diluted HCl. The mixture was extracted with DCM (50 mL×2), washed with sat. sodium bicarbonate (50 mL) and brine (50 mL), dried over anhydrous sodium sulfate, concentrated, and purified with flash column chromatography on silica gel (ethyl acetate in petroleum ether, 5% v/v) to afford Compound 165B.

A mixture of Compound 165B (18 g, 64 mmol), methyl acrylate (16.6 g, 193 mmol), Pd(PPh$_3$)$_2$Cl$_2$ (2.26 g, 3.2 mmol), and K$_2$CO$_3$ (22 g, 161 mmol) in DMF (100 mL) was stirred at 100° C. for 12 h. The mixture was cooled to room temperature, and filtered. The filtrate was treated with water (50 mL), extracted with DCM (100 mL×2), washed with water (100 mL×3) and brine (100 mL), dried over anhydrous sodium sulfate, concentrated, and purified with flash column chromatography on silica gel (ethyl acetate in petroleum ether, 5% v/v) to afford Compound 165C.

To a solution of Compound 165C (11 g, 51 mmol) in methanol (150 mL) was added Pd/C (1.1 g). The resulting mixture was stirred at room temperature for 12 h under $H_2$ and filtered. The filtrate was concentrated to give a crude Compound 165D.

To a solution of AlLiH$_4$ (1.2 g, 31 mmol) in THF (25 mL) was added Compound 165D (6.76 g, 31 mmol) in THF (20 mL) dropwise under nitrogen at −78° C. The mixture was stirred at −78° C. for 2 h and quenched with Na$_2$SO$_4$.10H$_2$O. The filtrate was concentrated to afford the crude Compound 165E.

To a solution of Compound 165E (5.2 g, 27 mmol) in DCM (100 mL) was added Dess-Martin periodinane (13.9 g, 33 mmol) at 0° C. The resulting mixture was stirred at room temperature for 2 h and filtered. The filtrate was concentrated and the resulting residue was purified with flash column chromatography on silica gel (ethyl acetate in petroleum ether, 5% v/v) to afford Compound 165F.

Compound 165F (4 g, 22 mmol) was added to a solution of Na$_2$S$_2$O (4.11 g, 22 mmol) in water (150 mL). The resultant mixture was stirred for 2 h at room temperature, and NaCN (2.1 g, 43 mmol) was added. After stirring for 15 h, the mixture was diluted with ethyl acetate (50 mL), extracted with ethyl acetate (100 mL×2), washed with sat. sodium bicarbonate (100 mL×2) and brine (100 mL), dried over anhydrous sodium sulfate, concentrated, and purified with flash column chromatography on silica gel (ethyl acetate in petroleum ether, 10% v/v) to afford Compound 165G.

To a solution of Compound 165G (4.4 g, 20 mmol) in ethanol (50 mL) at 0° C. was bubbled a gentle stream of HCl gas (dried over con. H$_2$SO$_4$) for 5 h. The mixture was treated with water slowly at 0° C. and stirred at room temperature for 2 h. The mixture was extracted with DCM (100 mL×2), washed with brine (100 mL), dried over anhydrous sodium sulfate, concentrated, and purified with flash column chromatography on silica gel (ethyl acetate in petroleum ether, 10% v/v) to afford Compound 165H.

To a solution of Compound 165H (2 g, 7.6 mmol) in DCM (20 mL) was added Dess-Martin periodinane (3.88 g, 9.1 mmol). The mixture was stirred at room temperature for 2 h and filtered. The filtrate was concentrated and the resulting residue was purified with flash column chromatography on silica gel (ethyl acetate in petroleum ether, 10% v/v) to afford Compound 165J.

To a solution of Compound 165J (1.7 g, 6.5 mmol) in DCM (20 mL) was added DAST (5.3 g, 33 mmol). The mixture was stirred at room temperature for 12 h and poured into ice water. The mixture was extracted with DCM (50 mL×2), washed with brine (50 mL), dried over anhydrous sodium sulfate, concentrated, and purified with flash column chromatography on silica gel (ethyl acetate in petroleum ether, 10% v/v) to afford Compound 165J.

To a solution of Compound 165J (1.7 g, 6.0 mmol) in THF (50 mL) was added LiOH.H$_2$O (758 mg, 18 mmol) in water (5 mL). The resulting mixture was stirred at room temperature for 2 h and evaporated to remove solvent. The mixture was treated with water (50 mL), adjusted to pH 2 with diluted HCl, extracted with ethyl acetate (50 mL×2), washed with brine (50 mL), dried over anhydrous sodium sulfate, and concentrated to afford the Compound 165K.

A mixture of Compound 165K (164 mg, 0.65 mmol), Intermediate A (150 mg, 0.54 mmol), EDCI.HCl (155 mg, 0.81 mmol), and HOBt (110 mg, 0.81 mmol) in DCM (10 mL) was stirred at 25° C. overnight. Then the reaction mixture was concentrated to remove DCM. The residue was purified with prep-HPLC to provide Compound 165. LC-MS (ESI) m/z: 515 [M+H]$^+$; $^1$H-NMR (CDCl$_3$, 400 MHz) δ (ppm) 1.77 (s, 4H), 2.11-2.13 (m, 5H), 2.20-2.29 (m, 1H), 2.72 (s, 4H), 2.87 (s, 3H), 3.03 (s, 1H), 3.44-3.46 (m, 2H), 3.83 (s, 2H), 3.98-4.05 (m, 4H), 4.42-4.44 (m, 1H), 5.08 (s, 1H), 6.78-6.82 (m, 4H), 6.87 (s, 1H), 6.96 (d, J=7.6 Hz, 1H), 7.48 (d, J=8.0 Hz, 1H), 11.76 (s, 1H).

Example 166

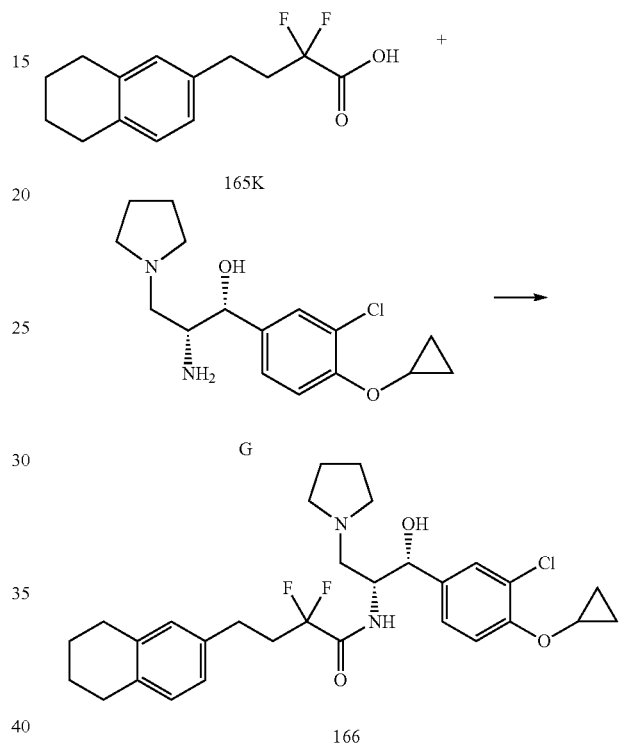

A mixture of Intermediate G (200 mg, 0.64 mmol), Compound 165K (164 mg, 0.64 mmol), EDCI.HCl (188 mg, 0.97 mmol), and HOBt (131 mg, 0.97 mmol) in DCM (10 mL) was stirred at 25° C. overnight. Then the reaction mixture was concentrated to remove DCM. The residue was purified with prep-HPLC to provide Compound 165. LC-MS (ESI) m/z: 547 [M+H]$^+$; $^1$H-NMR (CDCl$_3$, 400 MHz) δ (ppm) 0.63-0.69 (m, 4H), 1.77 (s, 4H), 2.14-2.16 (m, 5H), 2.33-2.40 (m, 1H), 2.71 (s, 4H), 2.91-2.93 (m, 1H), 3.04 (s, 1H), 3.50 (s, 5H), 3.82 (s, 2H), 4.47-4.48 (m, 1H), 5.13 (s, 1H), 6.75-6.78 (m, 2H), 6.95 (d, J=7.6 Hz, 1H), 7.16-7.21 (m, 2H), 7.36 (s, 1H), 7.53 (d, J=8.0 Hz, 1H), 11.60 (s, 1H).

Example 167

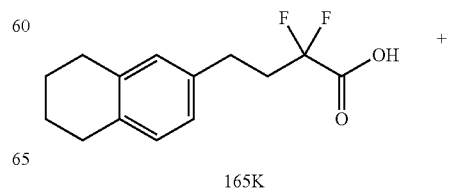

279
-continued

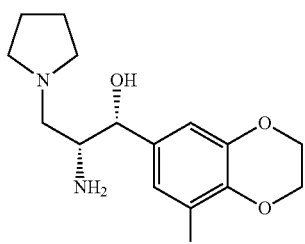
C

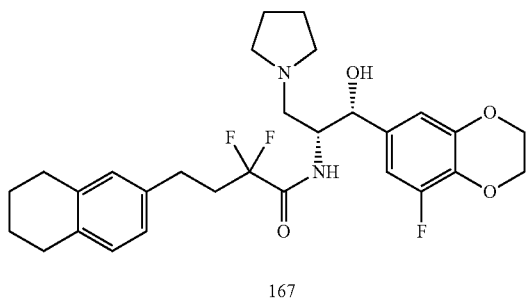
167

A mixture of Intermediate C (200 mg, 0.67 mmol), Compound 165K (172 mg, 0.67 mmol), EDCI.HCl (197 mg, 1.01 mmol), and HOBt (136 mg, 1.01 mmol) in DCM (10 mL) was stirred at 25° C. overnight. Then the reaction mixture was concentrated to remove DCM. The residue was purified with prep-HPLC to provide Compound 167. LC-MS (ESI) m/z: 533 [M+H]$^+$; $^1$H-NMR (CDCl$_3$, 400 MHz) δ (ppm) 1.75-1.78 (m, 4H), 2.15-2.21 (m, 6H), 2.38-2.44 (m, 1H), 2.71 (s, 4H), 2.91 (s, 1H), 3.05-3.13 (m, 3H), 3.48 (s, 2H), 3.83 (s, 2H), 4.00-4.06 (m, 3H), 4.44-4.45 (m, 1H), 5.07 (s, 1H), 6.67-6.72 (m, 2H), 6.78-6.82 (m, 2H), 6.96 (d, J=8.0 Hz, 1H), 7.45 (d, J=8.4 Hz, 1H), 11.70 (s, 1H).

Example 168

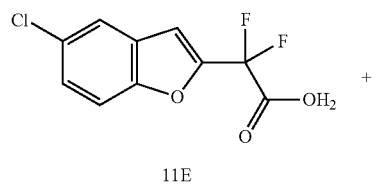
11E

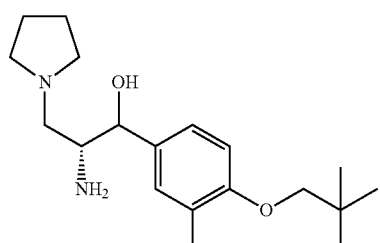
V

280
-continued

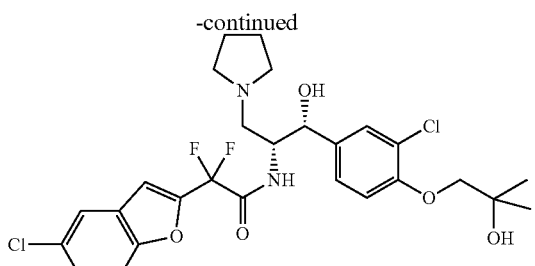
168

To a solution of Intermediate V (100 mg, 0.29 mmol) and Compound 11E (72 mg, 0.29 mmol) in DMF (10 mL) was added EDCI.HCl (84 mg, 0.44 mmol) and HOBt (59 mg, 0.44 mmol) under nitrogen. The mixture was stirred at 25° C. overnight. TLC and LC-MS showed the starting material was consumed completely, sat. sodium bicarbonate (5 mL) was added to the mixture and then extracted with EA (50 mL×3). The combined organic layers were washed with water (5 mL×3) and brine (5 mL), and dried over anhydrous sodium sulfate, and concentrated to provide the crude product. The crude product was purified with prep-HPLC to provide Compound 168. LC-MS (ESI) m/z: 571 [M+H]$^+$; $^1$H-NMR (MeOD, 400 MHz) δ (ppm) 1.31 (s, 6H), 1.98-2.00 (m, 2H), 2.14-2.15 (m, 2H), 3.15-3.23 (m, 2H), 3.59-3.67 (m, 5H), 3.72-3.75 (m, 1H), 4.60-4.62 (m, 1H), 4.90 (d, J=2.4 Hz, 1H), 6.72 (d, J=8.4 Hz, 1H), 6.74 (s, 1H), 7.19 (d, J=8.4 Hz, 1H), 7.39-7.41 (m, 2H), 7.53 (d, J=9.2, 1H), 7.68 (d, J=2.0 Hz, 1H).

Example 169

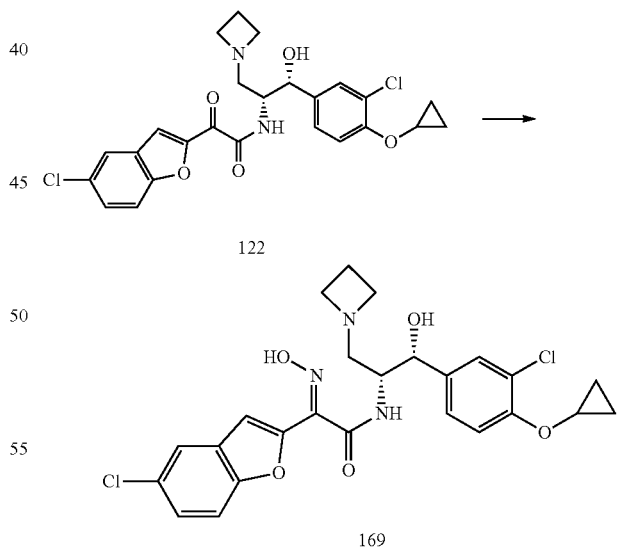
122

169

A mixture of 122 (40.8 mg, 0.08 mmol), hydroxylamine hydrochloride (76 mg, 1.1 mmol) and methanol (9 mL) was stirred at 50° C. for overnight. Then the mixture was purified with prep-HPLC to provide Compound 169. LC-MS (ESI) m/z: 518.1 [M+H]$^+$; $^1$H-NMR (MeOD, 400 MHz) δ (ppm) 0.75-0.85 (m, 4H), 2.15-2.29 (m, 2H), 3.58-3.69 (m, 2H), 3.83-3.86 (m, 1H), 4.25-4.42 (m, 4H), 4.65-4.67 (m, 1H), 4.99 (d, J=2.0 Hz, 1H), 5.86 (s, 1H), 7.32-7.35 (m, 1H), 7.38 (s, 2H), 7.44-7.46 (d, J=8.8 Hz, 1H), 7.52-7.54 (m, 2H).

Example 170

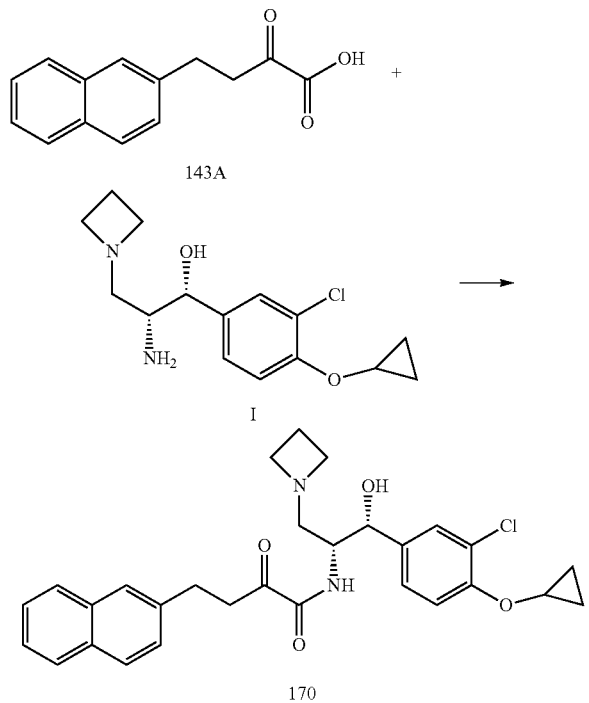

A solution of Compound 143A (114 mg, 0.5 mmol), Intermediate I (148 mg, 0.5 mmol), and HATU (684 mg, 0.9 mmol) in DCM (16 mL) and DMF (6 mL) was stirred at room temperature overnight under nitrogen. Then it was evaporated and purified with prep-HPLC to furnish Compound 170. LC-MS (ESI) m/z: 507 [M+H]+; 1H-NMR (MeOD, 400 MHz) δ (ppm) 0.10-0.90 (m, 4H), 1.77-2.05 (m, 2H), 2.05-2.43 (m, 3H), 2.85-3.21 (m, 2H), 3.45-3.76 (m, 2H), 4.08-4.41 (m, 5H), 4.88 (m, 1H), 7.12-7.14 (m, 2H), 7.21-7.51 (m, 4H), 7.65-7.87 (m, 4H).

Example 171

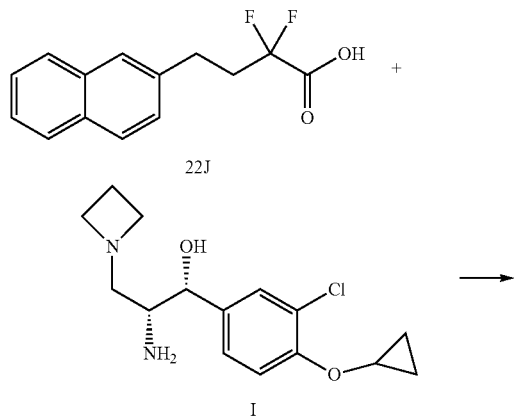

-continued

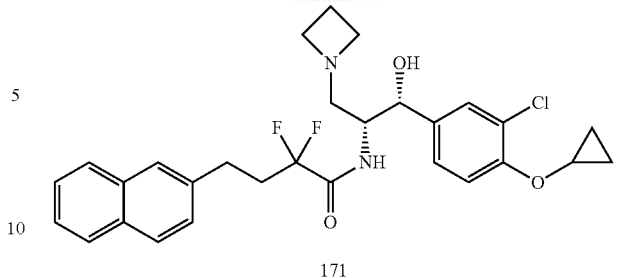

A solution of Intermediate I (150 mg, 0.60 mmol), Compound 22J (148 mg, 0.5 mmol), EDCI.HCl (143 mg, 0.75 mmol), HOBt (101 mg, 0.75 mmol), and DIPEA (0.1 mL, 1.20 mmol) in DCM (20 mL) was stirred at room temperature overnight under nitrogen. Then it was evaporated, and purified with prep-HPLC to furnish a mixture (100 mg, yield 38%) as a white solid, then the mixture was further separated with chiral HPLC (co-solvent: MeOH (0.5% DEA), column OZ-H (250*4.6 mm 5 um)) and prep-HPLC to provide Compound 171. LC-MS (ESI) m/z: 529 [M+H]+; 1H-NMR (MeOD, 400 MHz) δ (ppm) 0.29-0.44 (m, 4H), 2.11-2.17 (m, 2H), 2.37-2.41 (m, 2H), 2.57-2.65 (m, 2H), 3.26-3.27 (m, 1H), 3.57-3.60 (m, 2H), 4.19-4.32 (m, 4H), 4.45-4.47 (m, 1H), 4.92-4.93 (m, 1H), 7.17-7.19 (m, 1H), 7.23-7.25 (m, 1H), 7.29-7.32 (m, 1H), 7.43-7.49 (m, 3H), 7.55 (s, 1H), 7.79-7.83 (m, 3H).

Example 172

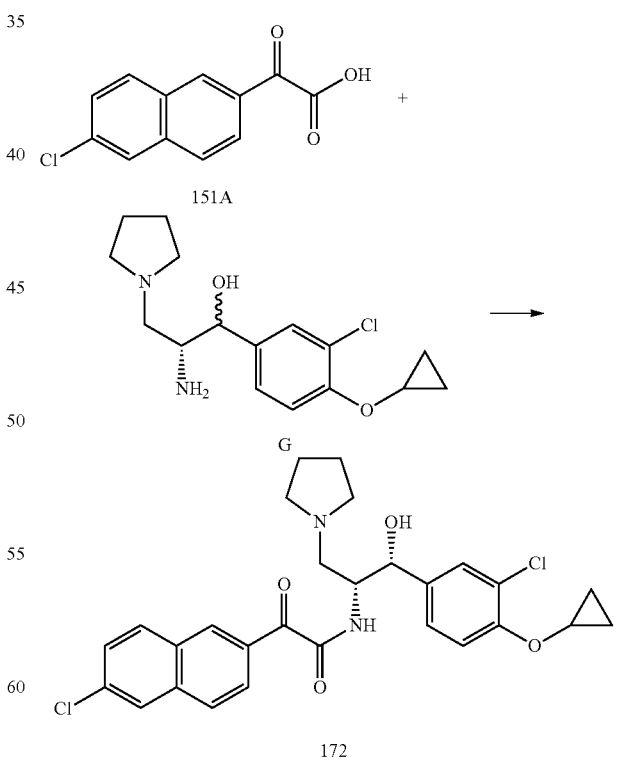

A mixture of Compound 151A (137 mg, 0.59 mmol), HATU (445 mg, 1.17 mmol), DMF (4 mL), and Intermediate G (218 mg, 0.70 mmol) in DCM (16 mL) was stirred at room temperature overnight. The reaction mixture was treated with water (20 mL), extracted with DCM (50 mL×2), washed with brine (50 mL), dried over anhydrous sodium sulfate, and concentrated. The crude product was purified with prep-HPLC to afford Compound 172. LC-MS (ESI) m/z: 527 [M+H]+; 1H-NMR (CD3OD, 400 MHz): δ (ppm) 0.54-0.79 (m, 4H), 2.04-2.22 (m, 5H), 3.23-3.26 (m, 1H), 3.58-3.82 (m, 6H), 4.70-4.73 (m, 1H), 4.99 (d, J=2.8 Hz, 1H), 7.30 (d, J=8.4 Hz, 1H), 7.37-7.41 (m, 1H), 7.50 (d, J=2.0 Hz, 1H), 7.57-7.59 (m, 1H), 7.88-7.93 (m, 3H), 7.99 (d, J=1.2 Hz, 1H), 8.29 (s, 1H).

Example 173

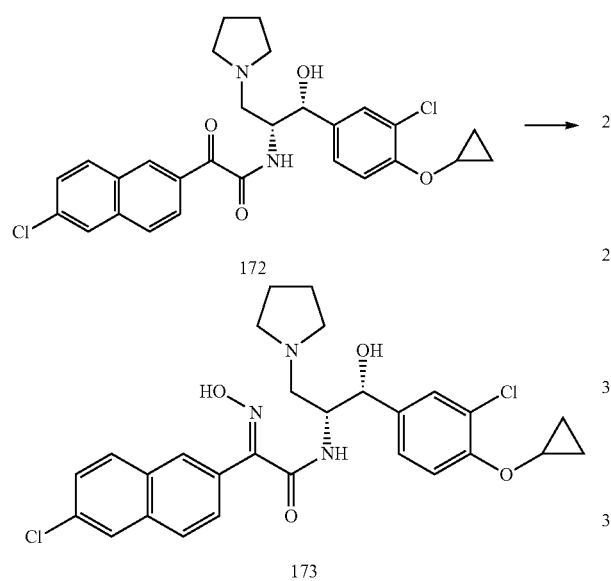

A mixture of 172 (40.8 mg, 0.08 mmol), hydroxylamine hydrochloride (76 mg, 1.1 mmol) and methanol (9 mL) was stirred at 50° C. overnight. Then the mixture was purified with prep-HPLC to provide Compound 173. LC-MS (ESI) m/z: 542.1 [M+H]+; 1H-NMR (MeOD, 400 MHz) δ (ppm) 0.69-0.84 (m, 4H), 2.02-2.22 (m, 4H), 3.21-3.29 (m, 1H), 3.62-3.80 (m, 5H), 4.70-4.73 (m, 1H), 5.01 (d, J=2.8 Hz, 1H), 7.32-7.34 (m, 1H), 7.39-7.43 (m, 1H), 7.45-7.49 (m, 1H), 7.51-7.53 (m, 1H), 7.63-7.85 (m, 3H), 7.88-7.90 (m, 1H).

Example 174

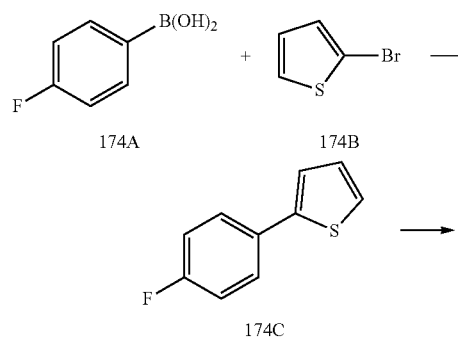

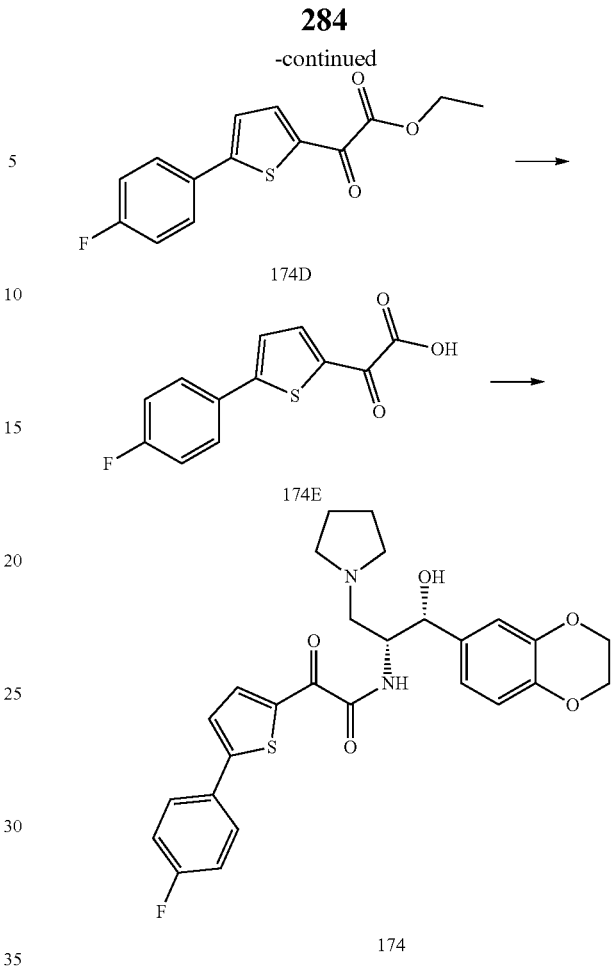

To a stirred solution of Compound 174A (2.0 g, 15.4 mmol) in dioxane (60 mL) and water (20 mL) was added Pd(PPh3)2Cl2 (1.08 g, 1.54 mmol), Compound 174B (3.0 g, 18.5 mmol) and Na2CO3 (6.53 g, 61.6 mmol) under nitrogen. The mixture was stirred at 80° C. overnight. After the reaction was completed, it was evaporated to remove the solvent. The residue was diluted with EA (200 mL), washed with water (5 mL) and brine (5 mL), and dried over anhydrous sodium sulfate. The crude product was purified with flash column chromatography on silica gel (petroleum in ethyl acetate, 3% v/v) to furnish Compound 174C.

To a solution of Compound 174C (890 mg, 5.0 mmol) in dry THF (50 mL) was added dropwise LDA (2.0 M, 3.0 mL, 6.0 mmol) under nitrogen at −70° C. After stirring for 30 min., diethyl oxalate (2.19 g, 15.0 mmol) was added as soon as possible. Then the mixture was stirred at −70° C. for about 1 h. Then the mixture was quenched with sat. NH4Cl (10 mL), extracted with ethyl acetate (50 mL×3), washed with water (5 mL) and brine (5 mL), and dried over sodium sulfate. The crude product was purified with flash column chromatography on silica gel (petroleum in ethyl acetate, 10% v/v) to furnish Compound 174D.

To a solution of Compound 174D (500 mg, 1.8 mmol) in THF (6 mL) was added dropwise a solution of LiOH.H2O (83 mg, 1.98 mmol) in water (1.5 mL) slowly at −30° C. Then the mixture was stirred at −30° C. about 0.5 h. It was adjusted to pH 3 with HCl (1 N), and extracted with DCM (100 mL×3). The organic phase was dried over sodium sulfate, filtered and concentrated to furnish the Compound 174E.

To a solution of Compound 174E (360 mg, 1.44 mmol) in DMF (15 mL) was added HATU (821 mg, 2.16 mmol). After stirring for two hours at 25° C., Intermediate A (400 mg, 1.44 mmol) was added and the resultant mixture was stirred overnight at 25° C. TLC and LC-MS showed the starting material was consumed completely, and sat. sodium bicarbonate (5 mL) was added to the mixture and then extracted with EA (50 mL×3). The combined organic layers were washed with water (5 mL×3) and brine (5 mL), and dried over anhydrous sodium sulfate, and concentrated to provide the crude product. The crude product was purified with prep-HPLC to provide Compound 174. LC-MS (ESI) m/z: 511 [M+H]$^+$; $^1$H-NMR (MeOD, 400 MHz) δ (ppm) 1.97-2.02 (m, 2H), 2.13-2.17 (m, 2H), 3.16-3.23 (m, 2H), 3.40-3.44 (m, 1H), 3.60-3.70 (m, 2H), 3.76-3.82 (m, 1H), 4.11-4.18 (m, 4H), 4.46-4.51 (m, 1H), 4.82 (d, J=3.6 Hz, 1H), 6.77 (d, J=8.0 Hz, 1H), 6.85 (dd, J=2.0, 8.4 Hz, 1H), 6.89 (d, J=1.6 Hz, 1H), 7.21 (t, J=8.8 Hz, 2H), 7.49 (d, J=4.4 Hz, 1H), 7.78-7.82 (m, 2H), 8.15 (d, J=4.4 Hz, 1H).

Example 175

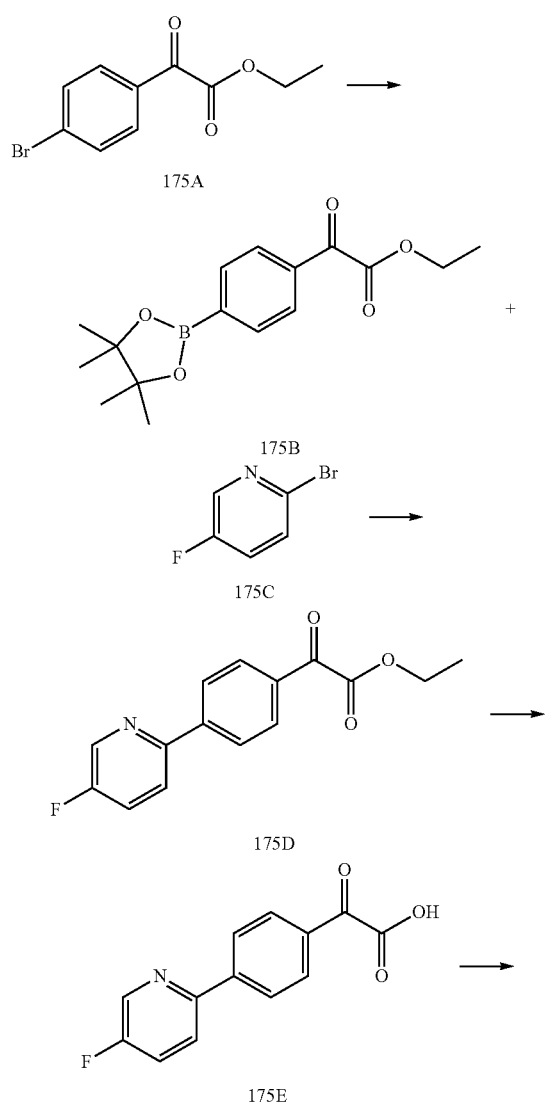

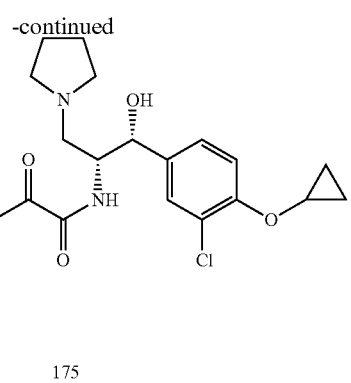

175

To a solution of Compound 175A (5.12 g, 20 mmol) in dioxane (75 mL) was added 4,4,4',4',5,5,5',5'-octamethyl-2,2'-bi(1,3,2-dioxaborolane) (6.10 g, 24 mmol), Pd(dppf)Cl$_2$ (902 mg, 1 mmol) and KOAc (5.9 g, 60 mmol). The reaction mixture was heated to 90° C. for 2.5 h, then the solution was cooled to r.t and filtered. The filtrate was concentrated to offer the crude product. The crude product was purified with flash column chromatography on silica gel (ethyl acetate in petroleum ether, 50% v/v) to offer Compound 175B.

A mixture of Compound 175B (730 mg, 2.4 mmol), Compound 175C (350 mg, 2 mmol), Pd(PPh$_3$)$_4$ (116 mg, 0.1 mmol) and K$_3$PO$_4$ (1.27 g, 6 mmol) in toluene (20 mL) was heated to reflux, stirred for 3 h and filtered. The filtrate was concentrated to offer the crude product. The crude product was purified with flash column chromatography on silica gel (ethyl acetate in petroleum ether, 20% v/v) to offer Compound 175D.

To a solution of Compound 175D (119 mg, 0.44 mmol) in THF/water (11 mL, 15:1, v/v) was added LiOH.H$_2$O (28 mg, 0.66 mmol). The mixture was stirred at −10° C. for 1 h. After the reaction, it was adjusted to pH 6 with 3 N HCl and extracted with ethyl acetate (20 mL×3). The combined organic layers were concentrated in vacuum without dryness to offer the crude product Compound 175E.

A mixture of Compound 175E (100 mg, 0.408 mmol), Intermediate G (124 mg, 0.408 mmol) and HATU (233 mg, 0.612 mmol) in dichloromethane (2 mL) and DMF (2 mL) was stirred at 25° C. for 15 h. Then it was treated with water (20 mL), extracted with dichloromethane (20 mL×3), dried over anhydrous sodium sulfate, concentrated in vacuum and purified with prep-HPLC to obtain Compound 175. LC-MS (m/z): 538 [M+1]$^+$; $^1$H-NMR (CD$_3$OD, 400 MHz) δ (ppm) 0.79-0.84 (m, 4H), 2.11-2.14 (m, 4H), 3.01-3.19 (m, 2H), 3.42-3.90 (m, 5H), 4.55-4.57 (m, 1H), 4.79 (m, 1H), 7.28-7.32 (m, 2H), 7.41-7.62 (m, 2H), 7.82-7.86 (m, 1H), 7.95-8.01 (m, 4H), 8.57 (d, J=3.2 Hz, 1H).

Example 176

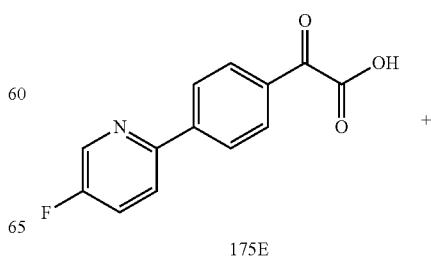

287

-continued

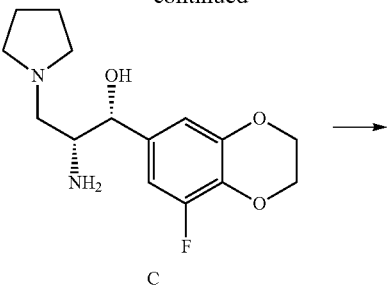

C

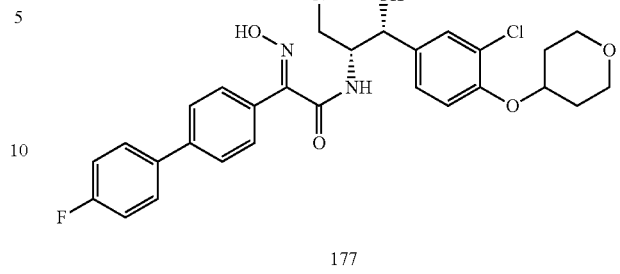

176

A mixture of Compound 175E (98 mg, 0.4 mmol), Intermediate C (118 mg, 0.4 mmol), and HATU (228 mg, 0.6 mmol) in DMF (10 mL) was stirred at 30° C. for 8 h. Then it was treated with water (20 mL), extracted with dichloromethane (20 mL×3), dried over anhydrous sodium sulfate, concentrated in vacuum and purified with prep-HPLC to obtain Compound 176. LC-MS (m/z): 524 [M+1]$^+$; $^1$H-NMR (CD$_3$OD, 400 MHz) δ (ppm) 2.04 (s, 2H), 2.19 (s, 2H), 3.18-3.30 (m, 2H), 3.48-3.57 (m, 1H), 3.65-3.74 (m, 2H), 3.78-3.84 (m, 1H), 4.19-4.34 (m, 5H), 4.65 (d, J=8 Hz, 1H), 6.81 (d, J=12 Hz, 1H), 7.69-7.76 (m, 1H), 7.90 (d, J=8 Hz, 2H), 8.02-8.05 (m, 1H), 8.11 (d, J=8 Hz, 2H), 8.60 (s, 1H).

Example 177

288

-continued

177

A mixture of 152 (30 mg, 0.04 mmol) and NH$_2$OH.HCl (27.6 mg, 0.4 mmol) in MeOH (3 mL) was stirred for 4 h at 55° C. After filtration, the filtrate was purified with prep-HPLC to furnish Compound 177. LC-MS (m/z): 596 [M+1]$^+$; $^1$H-NMR (CD$_3$OD, 400 MHz) major characteristic peaks: δ (ppm) 172-1.81 (m, 2H), 1.98-2.08 (m, 2H), 3.30 (m, 1H), 3.51-3.74 (m, 4H), 3.88-3.99 (m, 4H), 4.65-4.70 (m, 1H), 5.03 (s, 1H), 7.09-7.11 (m, 2H), 7.15-7.23 (m, 3H), 7.35 (dd, J=8.4, 2.0 Hz, 1H), 7.49 (d, J=8.4 Hz, 2H), 7.55 (d, J=2.0 Hz, 1H), 7.66-7.70 (m, 2H).

Example 178

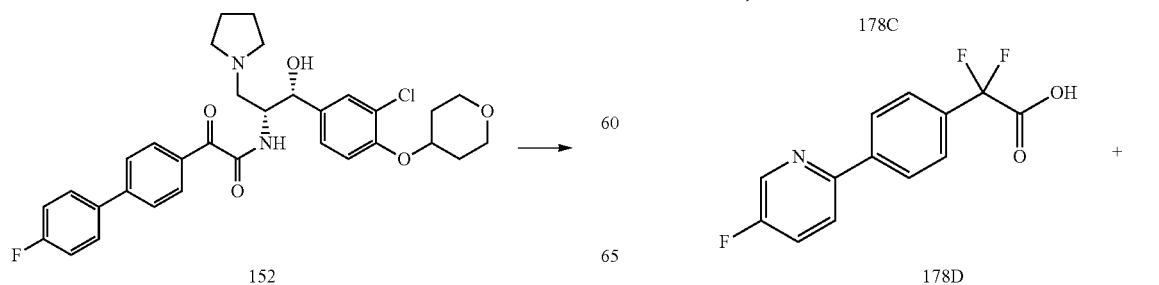

152

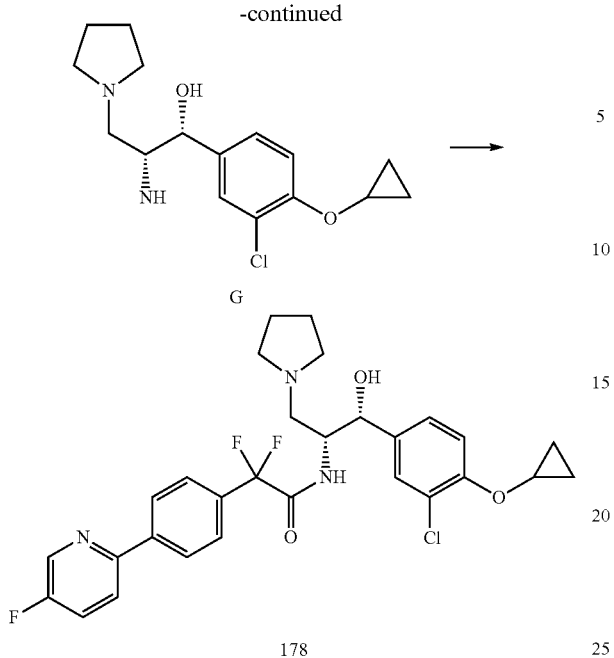

To a solution of Compound 178A (2.56 g, 10 mmol) in dry dichloromethane (50 mL) was added DAST (3.30 mL, 25 mmol). Then the mixture was stirred at 25° C. for 14 h. After the reaction, dichloromethane (25 mL) was added, then the organic layer was washed with water (50 mL), followed by addition of aq. sodium bicarbonate (30 mL) and brine (50 mL), dried over sodium sulfate and concentrated to offer the crude product. The crude product was purified with flash column chromatography on silica gel (ethyl acetate in petroleum ether, 20% v/v) to offer Compound 178B.

To a solution of Compound 178B (2.58 g, 9.3 mmol) in dioxane (45 mL) was added 4,4,4',4',5,5,5',5'-octamethyl-2,2'-bi(1,3,2-dioxaborolane) (2.82 g, 11.1 mmol), Pd(dppf)Cl$_2$ (409 mg, 0.5 mmol) and KOAc (2.72 g, 27.8 mmol). The reaction mixture was heated to 90° C. for 2.5 h, then the solution was cooled to r.t and filtered. The filtrate was concentrated to offer the crude product. The crude product was purified with flash column chromatography on silica gel (ethyl acetate in petroleum ether, 10% v/v) to offer Compound 178C.

To a solution of Compound 178C (717 mg, 2.2 mmol), 2-bromo-5-fluoropyridine (350 mg, 2 mmol), and K$_3$CO$_3$ (828 mg, 6 mmol) in dioxane (20 mL) and water (2 mL) was added Pd(dppf)Cl$_2$ (82 mg, 0.1 mmol) at 25° C. under nitrogen. Then the mixture was heated to reflux, stirred for 3 h and filtered. The filtrate was concentrated to offer the crude product. Water (10 mL) was added, and the mixture was extracted with ethyl acetate (100 mL). Then 2 N HCl was added to the aqueous layer, adjusted to pH=6-7, then extracted with THF in ethyl acetate (20% v/v, 35 mL×3). The organic layers were dried over anhydrous sodium sulfate, filtered, and evaporated to obtain Compound 178D.

A mixture of Compound 178D (88 mg, 0.33 mmol), Intermediate G (105 mg, 0.34 mmol), EDCI.HCl (96 mg, 0.49 mmol), and HOBt (67 mg, 0.49 mmol) in dichloromethane (2 mL) and DMF (2 mL) was stirred at 25° C. for 5 h. Then it was treated with water (20 mL), extracted with dichloromethane (20 mL×3), dried over anhydrous sodium sulfate, concentrated in vacuum and purified with prep-HPLC to obtain Compound 178. LC-MS (m/z): 560 [M+1]$^+$; $^1$H-NMR (CDCl$_3$, 400 MHz) δ (ppm) 0.63-0.69 (m, 4H), 2.13 (br, 2H), 3.03-3.05 (br, 2H), 3.36-3.61 (m, 5H), 4.51 (d, J=8.0 Hz, 1H), 4.95 (d, J=3.2 Hz, 1H), 7.08 (s, 2H), 7.34 (s, 1H), 7.41-7.44 (m, 2H), 7.58-7.62 (m, 1H), 7.83-7.95 (m, 3H), 8.54 (d, J=3.2 Hz, 1H).

Example 179

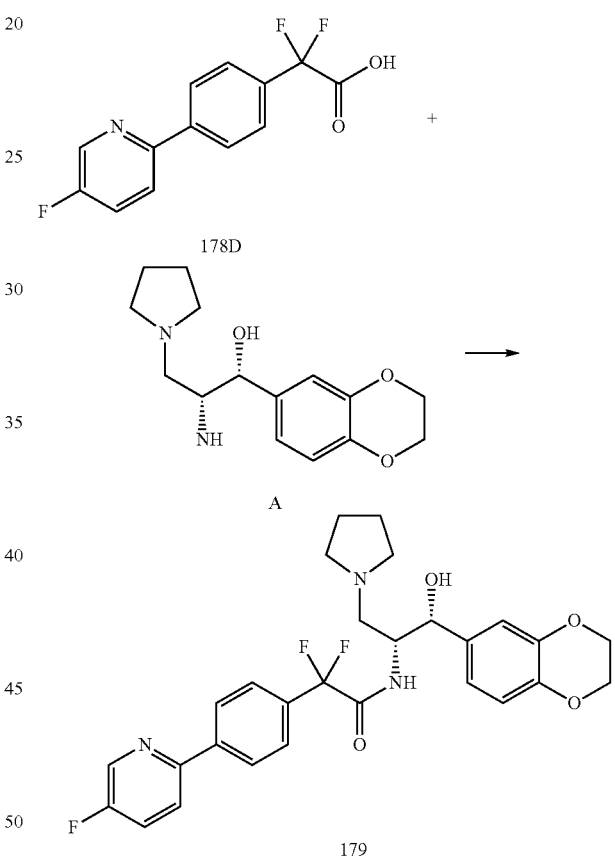

A mixture of Compound 178D (88 mg, 0.33 mmol), Intermediate A (100 mg, 0.35 mmol), EDCI.HCl (96 mg, 0.49 mmol), and HOBt (67 mg, 0.49 mmol) in dichloromethane (15 mL) and DMF (2 mL) was stirred at 25° C. for 15 h. Then it was treated with water (20 mL), extracted with dichloromethane (20 mL×3), dried over anhydrous sodium sulfate, concentrated in vacuum and purified with prep-HPLC to obtain Compound 179. LC-MS (m/z): 528 [M+1]$^+$; $^1$H-NMR (CD$_3$OD, 400 MHz) δ (ppm) 2.09-2.14 (m, 4H), 2.81-2.84 (m, 2H), 3.41-3.45 (m, 2H), 3.72-3.88 (m, 2H), 4.15 (s, 4H), 4.41 (m, 1H), 5.06 (d, J=2.0 Hz, 1H), 6.73-6.80 (m, 3H), 7.43-7.52 (m, 3H), 7.72-7.76 (m, 2H), 7.92 (d, J=8.4 Hz, 2H), 8.56 (d, J=2.8 Hz, 1H), 11.79 (brs, 1H).

Example 180

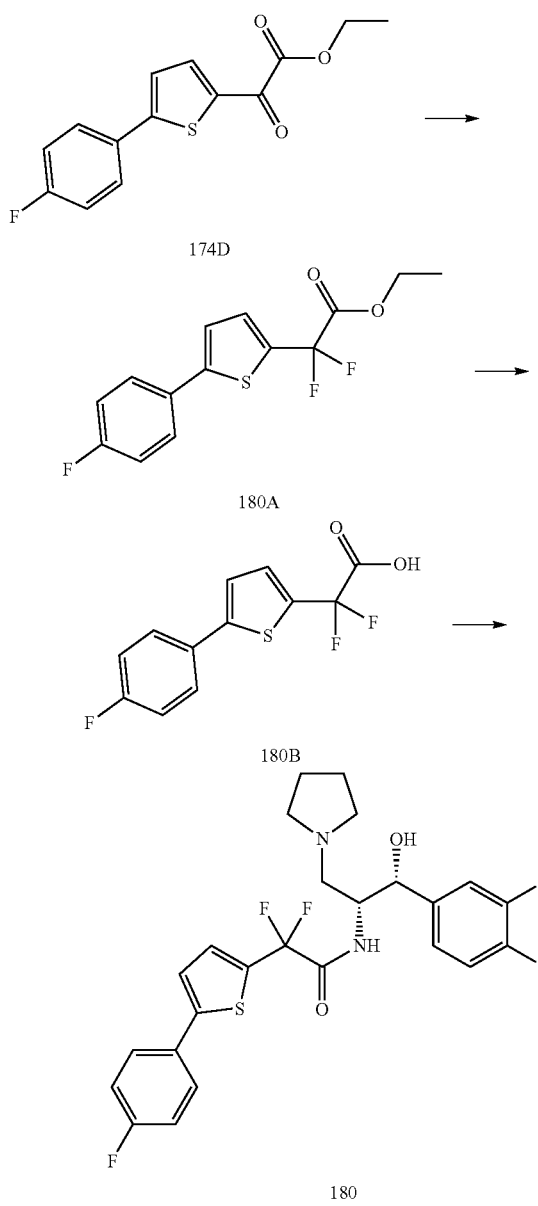

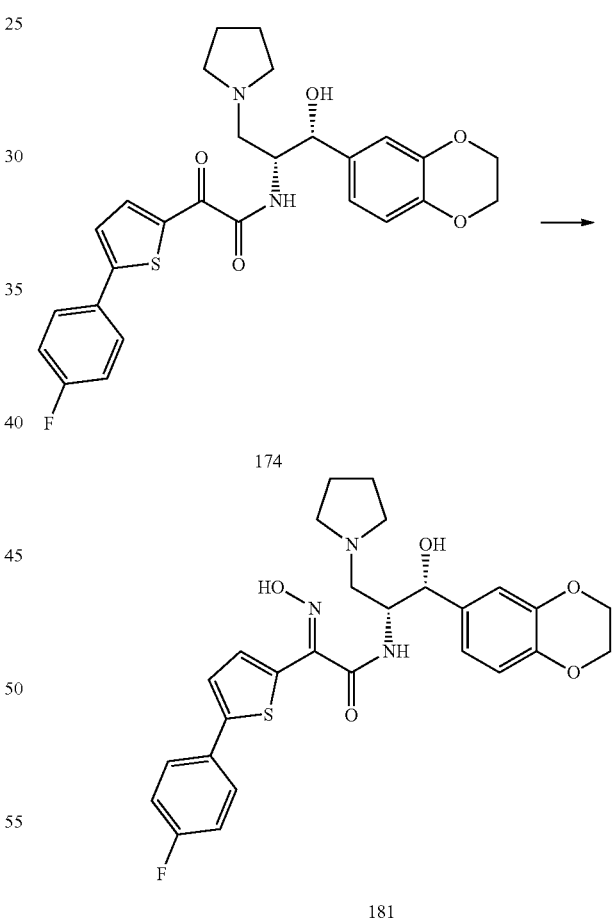

To a solution of Compound 174D (290 mg, 1.07 mmol) in DCM (5 mL) was added DAST (1 mL, excess) at room temperature and the resultant mixture was stirred at 30° C. overnight. Poured into ice-water (100 mL) and extracted with DCM (50 mL×3). The combined organic phase was washed with water (5 mL) and brine (5 mL), and dried over anhydrous sodium sulfate. The crude product was purified with flash column chromatography on silica gel (ethyl acetate in petroleum ether, 10% v/v) to obtain Compound 180A.

To a solution of Compound 180A (130 mg, 0.43 mmol) in THF/water (6 mL, 4:1, v/v) was added LiOH.H$_2$O (73 mg, 1.73 mmol). The mixture was stirred at 25° C. for 2 h. After the reaction, it was adjusted to pH 3 with HC (1 N) and separated. The organic phase was dried over sodium sulfate. Filtered and concentrated to furnish the Compound 180C.

To a mixture of Compound 180C (98 mg, 0.36 mmol) in DMF (10 mL) was added EDCI.HCl (104 mg, 0.54 mmol), HOBt (73 mg, 0.54 mmol) and Compound (A) (100 mg, 0.36 mmol) under nitrogen. The mixture was stirred at 25° C. overnight. TLC and LC-MS showed the starting material was consumed completely. Then sat. sodium bicarbonate (5 mL) was added to the mixture which was extracted with EA (50 mL×3). The combined organic layers were washed with water (5 mL×3) and brine (5 mL), dried over anhydrous sodium sulfate, and concentrated to offer the crude product. The crude product was purified with prep-HPLC to offer Compound 180. LC-MS (m/z): 533 [M+1]$^+$; $^1$H-NMR (CD$_3$OD, 400 MHz) major characteristic peaks: δ (ppm) 1.96-2.00 (m, 2H), 2.11-2.14 (m, 2H), 3.11-3.20 (m, 2H), 3.46-3.50 (m, 1H), 3.56-3.62 (m, 2H), 3.71-3.77 (m, 1H), 4.01 (s, 4H), 4.50-4.53 (m, 1H), 4.79 (d, J=3.2 Hz, 1H), 6.59 (d, J=8.4 Hz, 1H), 6.70 (dd, J=2.0, 8.4 Hz, 1H), 6.74 (d, J=2.4 Hz, 1H), 7.04 (d, J=3.6 Hz, 1H), 7.15 (t, J=8.4 Hz, 2H), 7.23 (d, J=4.0 Hz, 1H), 7.63-7.67 (m, 2H).

Example 181

To a solution of 174 (50 mg, 0.08 mmol) in MeOH (10 mL) was added hydroxylamine hydrochloride (112 mg, 1.6 mmol). The mixture was stirred overnight at 25° C. LC-MS showed the starting material was consumed completely, and the solvent was evaporated. The crude product was purified with prep-HPLC to offer Compound 181. LC-MS (m/z): 526 [M+1]$^+$; $^1$H-NMR (CD$_3$OD, 400 MHz) major characteristic peaks: δ (ppm) 1.97-2.00 (m, 2H), 2.13-2.15 (m, 2H), 3.14-3.23 (m, 2H), 3.42-3.46 (m, 1H), 3.57-3.63 (m, 2H), 3.74-3.81 (m, 1H), 4.15-4.20 (m, 4H), 4.57-4.69 (m, 1H), 4.70 (d, J=2.8 Hz, 1H), 6.74-6.86 (m, 2H), 6.90-6.94 (m, 1H), 7.10-7.15 (m, 2H), 7.27 (d, J=4.0 Hz, 1H), 7.51 (d, J=4.0 Hz, 1H), 7.61-7.69 (m, 2H).

Example 182

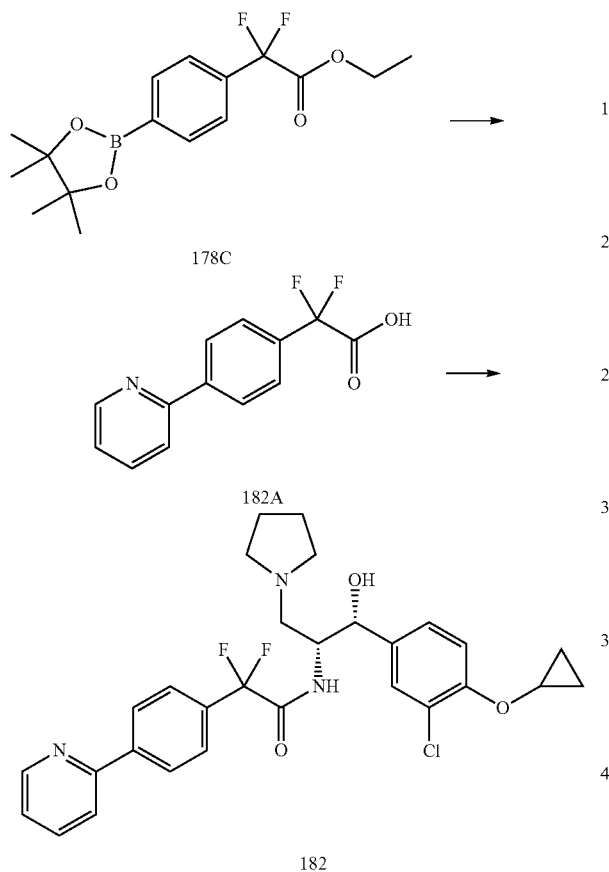

A mixture of Compound 178C (1.3 g, 4 mmol), 2-bromopyridine (628 mg, 4 mmol), Pd(dppf)₂Cl₂ (160 mg, 0.2 mmol), and Na₂CO₃ (1.27 g, 12 mmol) in dioxane (30 mL) and water (4 mL) was stirred under nitrogen at 100° C. for 3 h. The reaction mixture was cooled to room temperature and diluted with ethyl acetate (50 mL). The mixture was filtered and the filtrate was treated with water (50 mL), extracted with ethyl acetate (50 mL×2), then the water layer was adjusted to pH 3 by aqueous HCl solution (3 N), and extracted with ethyl acetate (50 mL×2). The ethyl acetate layer was washed with water (50 mL×2), dried over sodium sulfate, filtered, and concentrated to furnish the Compound 182A.

A mixture of Compound 182A (90 mg, 0.36 mmol), EDCI.HCl (103 mg, 0.54 mmol), HOBT (73 mg, 0.54 mmol), and Intermediate G (111 mg, 0.36 mmol) in DCM (5 mL) was stirred at 10° C. for 18 h. Then the mixture was diluted by ethyl acetate (50 mL), washed with sat. sodium bicarbonate solution (50 mL×2) and brine (50 mL), and dried over anhydrous sodium sulfate. After evaporation, the crude product was purified with prep-HPLC to furnish Compound 182. LC-MS (m/z): 542 [M+1]⁺; ¹H-NMR (CD₃OD, 400 MHz) major characteristic peaks: δ (ppm) 0.48-0.59 (m, 4H), 2.03-2.24 (m, 4H), 3.17-3.26 (m, 2H), 3.54-3.81 (m, 5H), 4.62 (d, J=9.2 Hz, 1H), 4.94-4.96 (m, 1H), 7.00-7.03 (m, 1H), 7.09-7.11 (m, 1H), 7.34-7.36 (m, 1H), 7.47-7.59 (m, 3H), 8.02-8.14 (m, 4H), 8.71-8.74 (m, 1H).

Example 183

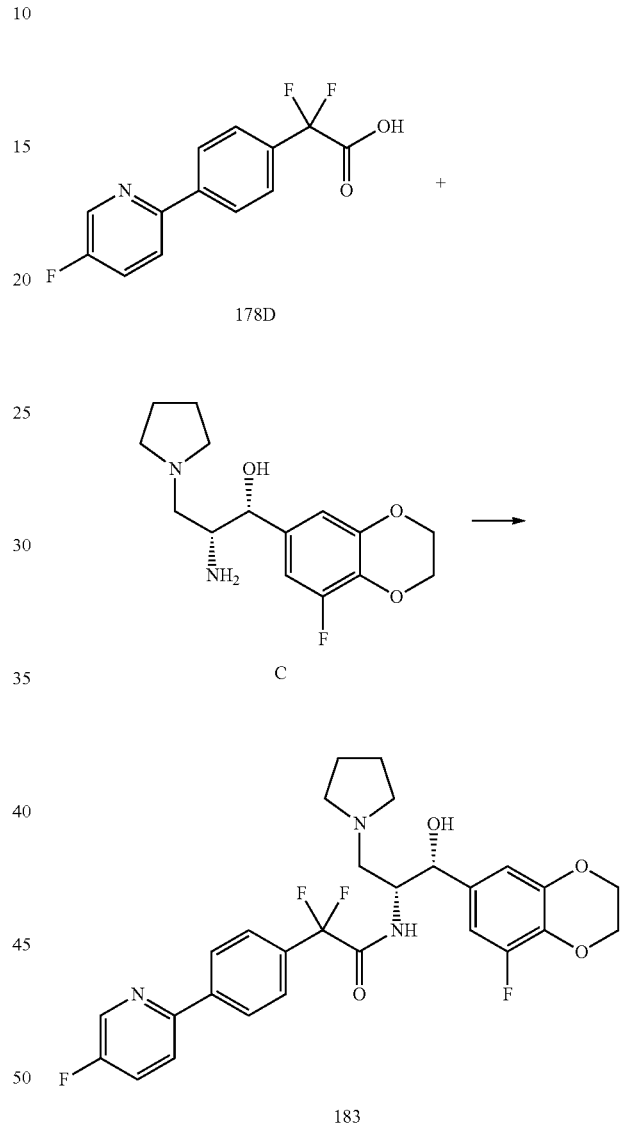

A mixture of Compound 178D (88 mg, 0.33 mmol), Intermediate C (105 mg, 0.34 mmol), EDCI.HCl (96 mg, 0.49 mmol), and HOBt (67 mg, 0.49 mmol) in dichloromethane (15 mL) was stirred at 25° C. for 15 h. Then it was treated with water (20 mL), extracted with dichloromethane (20 mL×3), dried over anhydrous sodium sulfate, concentrated in vacuum and purified with prep-HPLC to obtain Compound 183. LC-MS (m/z): 546 [M+1]⁺; ¹H-NMR (CD₃OD, 400 MHz) δ (ppm) 2.02-2.19 (m, 4H), 3.15-3.31 (m, 2H), 3.52-3.56 (m, 3H), 3.79-3.80 (m, 1H), 4.04-4.08 (m, 4H), 4.56 (d, J=10.4 Hz, 1H), 4.81 (d, J=2.8 Hz, 1H), 6.57-6.68 (m, 2H), 7.48 (d, J=8.4 Hz, 2H), 7.71-7.76 (m, 1H), 8.01-8.07 (m, 3H), 8.59 (d, J=3.2 Hz, 1H).

Example 184

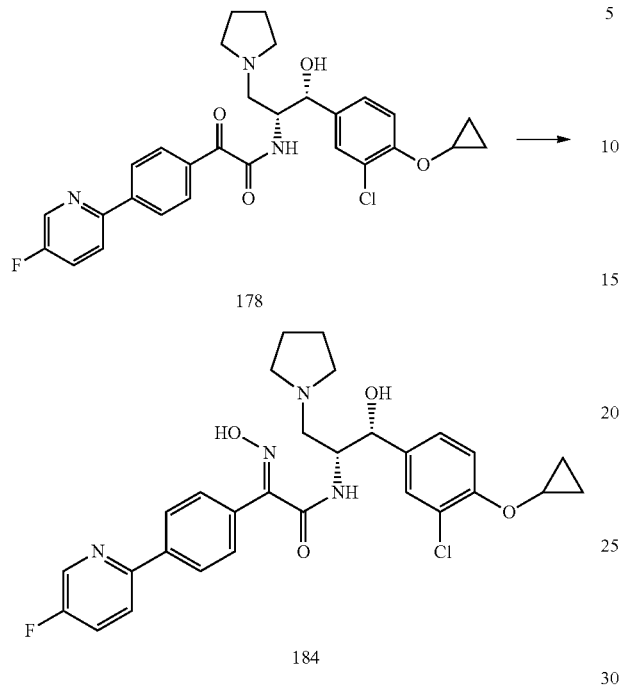

To a solution of Compound 178 (56 mg, 0.086 mmol) in MeOH (20 mL) was added hydroxylamine hydrochloride (120 mg, 1.72 mmol) at 25° C., then the reaction was stirred at 55° C. for 14 h. Then it was purified with prep-HPLC to obtain Compound 184. LC-MS (m/z): 553 [M+1]$^+$; $^1$H-NMR (CD$_3$OD, 400 MHz) major characteristic peaks: δ (ppm) 0.77-0.85 (m, 4H), 2.03-2.06 (m, 2H), 2.20-2.22 (m, 2H), 3.19-3.26 (m, 1H), 3.62-3.92 (m, 5H), 4.60-4.89 (m, 2H), 5.02 (d, J=2.8 Hz, 1H), 7.16-7.51 (m, 5H), 7.51-7.74 (m, 1H), 7.86-7.98 (m, 3H), 8.51-8.54 (m, 1H).

Example 185

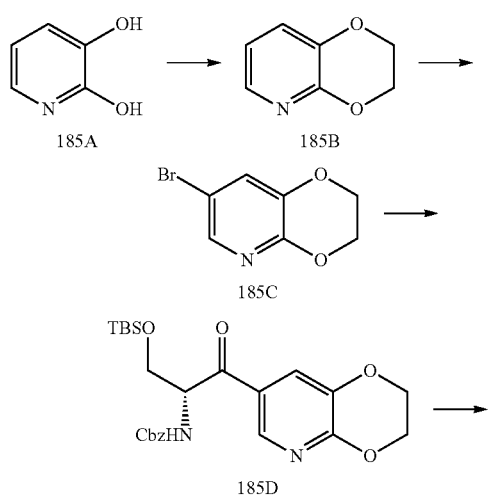

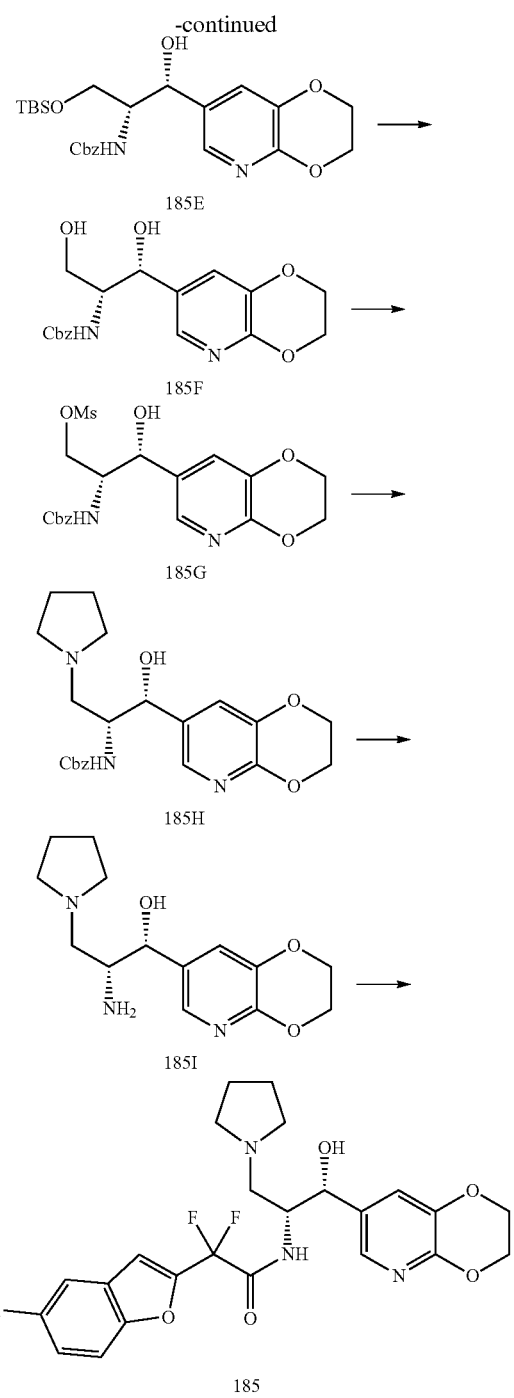

A mixture of Compound 185A (22.2 g, 200 mmol), 1,2-dibromoethane (55.8 g, 300 mmol), and K$_2$CO$_3$ (55.2 g, 600 mmol) in DMSO (270 mL) was stirred at 100° C. for 10 h under nitrogen protection. Then it was cooled to room temperature and extracted with ethyl acetate (100 mL×3). The ethyl acetate layers were combined and washed with water (50 mL×3) and brine (50 mL), dried over sodium sulfate, and concentrated to offer the title Compound 185B.

A mixture of Compound 185B (1.37 g, 10 mmol) and Br$_2$ (1.6 g, 10 mmol) in DCM (27 mL) was stirred at 25° C. for 24 h, cooled to room temperature, quenched by NH$_4$Cl (20 mL), and extracted with DCM (100 mL×3). The DCM layers were combined and washed with water (50 mL×3) and brine (50 mL), dried over sodium sulfate, concentrated and recrystallized from methanol to offer the title Compound 185C.

To a mixture of Compound 185C (3.23 g, 15 mmol) in THF (27 mL) at −65° C. was added by n-BuLi solution (6.45 mL), and the mixture was stirred at −65° C. for 1 h. Then a solution of Compound A4 (1.98 g, 5 mmol) in THF (10 mL) was added. The resultant mixture was stirred for 1 h, quenched by NH₄Cl (20 mL), and extracted with EA (100 mL×3). The EA layers were combined and washed with water (50 mL×3) and brine (50 mL), dried over sodium sulfate, concentrated, and purified with flash column chromatography on silica gel with EA in PE (1/20 to 1/5 v/v) to offer the title Compound 185D.

To a mixture of Compound 185D (1.4 g, 3 mmol) in THF (17 mL) at −90° C. was added L-Selectride (1 M in THF, 6 mL), then it was stirred at −90° C. for 0.5 h, quenched by NH₄Cl (20 mL), and extracted with EA (100 mL×3). The EA layers were combined and washed with water (50 mL×3) and brine (50 mL), dried over sodium sulfate, concentrated, and purified with flash column chromatography on silica gel with EA in PE (1/2 v/v) to offer the title Compound 185E.

A mixture of Compound 185E (1.4 g, 3 mmol) and TBAF·3H₂O (945 mg, 3 mmol) in THF (17 mL) at 20° C. was stirred for 15 h. Then it was diluted by EA (50 mL), washed with water (10 mL×3) and brine (10 mL), dried over sodium sulfate, concentrated, and purified with flash column chromatography on silica gel with methanol in DCM (1/100 to 1/20 v/v) to offer the title Compound 185F.

To a mixture of Compound 185F (800 mg, 2.2 mmol) and TEA (404 mg, 4.4 mmol) in DCM (8 mL) at 20° C. was added MsCl (1.77 mL, 2.2 mmol). The mixture was stirred for 30 min, quenched by water (5 mL), and extracted with DCM (10 mL×3). The combined DCM layers were washed with water (10 mL×3) and brine (10 mL), dried over sodium sulfate, concentrated, and purified with flash column chromatography on silica gel with methanol in DCM (1/100 to 1/50 v/v) to offer the title Compound 185G.

A mixture of Compound 185G (390 mg, 0.9 mmol) and pyrrolidine (632 mg, 9 mmol) in THF (8 mL) at 50° C. was stirred for 13 h then concentrated. The residue was dissolved into EA (50 mL), washed with water (10 mL×3) and brine (10 mL), dried over sodium sulfate, and concentrated to offer the title Compound 185H.

A mixture of Compound 185H (380 mg, 0.9 mmol) and LiOH·H₂O (77 mg, 1.8 mmol) in EtOH (4 mL) was stirred at 100° C. for 13 h then concentrated. The residue was dissolved into DCM (50 mL), washed with water (10 mL×3) and brine (10 mL), dried over sodium sulfate, and concentrated to offer the title Compound 185I.

A mixture of Compound 185I (180 mg, 0.644 mmol), Compound 11E (159 mg, 0.644 mmol), HATU (294 mg, 0.773 mmol) and DIPEA (125 mg, 0.966 mmol) in DCM (4 mL) was stirred at r.t. overnight then concentrated. The residue was dissolved into DCM (50 mL), washed with water (10 mL×3) and brine (10 mL), dried over sodium sulfate, concentrated, and purified with chiral HPLC to offer Compound 185. LC-MS (m/z): 508 [M+1]⁺; ¹H-NMR (CDCl₃, 400 MHz) major characteristic peaks: δ (ppm) 1.75 (m, 4H), 2.61-2.69 (m, 4H), 2.77-2.81 (m, 1H), 2.92-2.97 (m, 1H), 4.03-4.10 (m, 1H), 4.18-4.36 (m, 4H), 5.19 (d, J=7.6 Hz, 1H), 5.27-5.29 (m, 1H), 6.91 (s, 1H), 7.12 (d, J=5.2 Hz, 1H), 7.27-7.30 (m, 1H), 7.37-7.39 (m, 1H), 7.40-7.42 (m, 1H), 7.51 (d, J=1.6 Hz, 1H), 7.83 (d, J=5.2 Hz, 1H).

Example 186

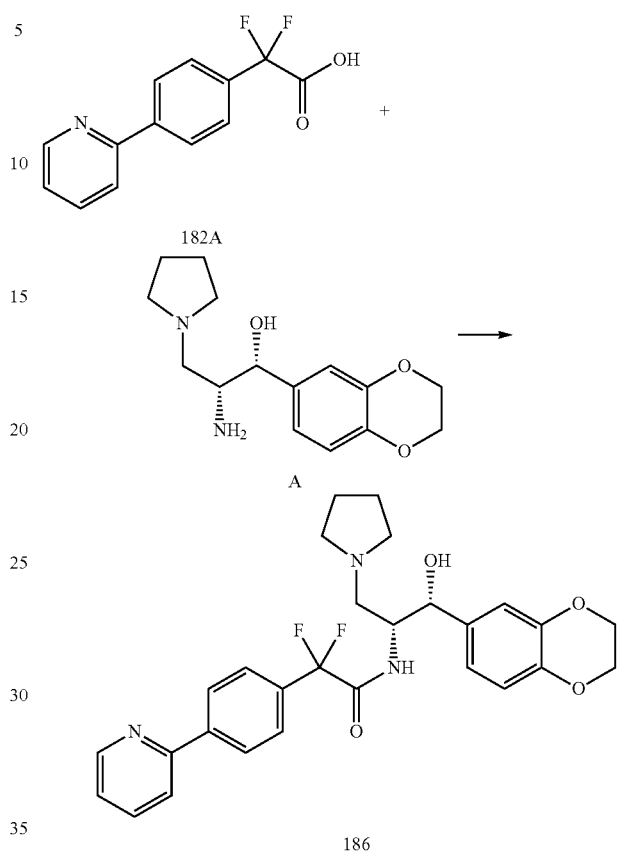

A mixture of Compound 182A (90 mg, 0.36 mmol), EDCI·HCl (103 mg, 0.54 mmol), HOBT (73 mg, 0.54 mmol), and Intermediate A (100 mg, 0.36 mmol) in DCM (5 mL) was stirred for 18 h at 10° C. Then the mixture was diluted by ethyl acetate (50 mL), washed with sat. sodium bicarbonate solution (50 mL×2) and brine (50 mL), and dried over anhydrous sodium sulfate. After evaporation, the crude product was purified with prep-HPLC to furnish Compound 186. LC-MS (m/z): 510 [M+1]⁺; ¹H-NMR (CD₃OD, 400 MHz) major characteristic peaks: δ (ppm) 2.02-2.04 (m, 4H), 3.13-3.20 (m, 2H), 3.49-3.67 (m, 4H), 4.06-4.09 (m, 4H), 4.55-4.57 (m, 1H), 4.81 (d, J=3.2 Hz, 1H), 6.61 (d, J=8.0 Hz, 1H), 6.73 (dd, J=8.4, 2.0 Hz, 1H), 6.77 (d, J=2.0 Hz, 1H), 7.62 (d, J=8.8 Hz, 2H), 7.75 (t, J=6.4 Hz, 1H), 8.04 (d, J=8.4 Hz, 2H), 8.18 (d, J=8.4 Hz, 1H), 8.30-8.32 (m, 1H), 8.80 (d, J=5.2 Hz, 1H).

Example 187

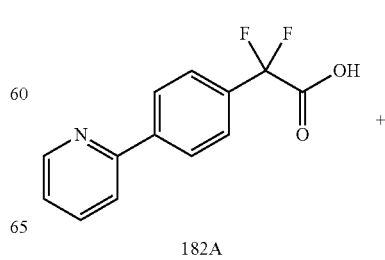

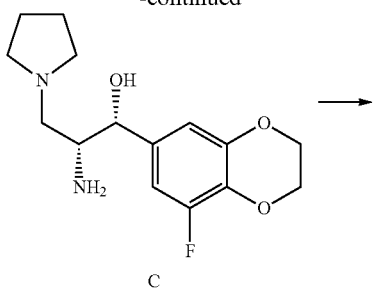

C

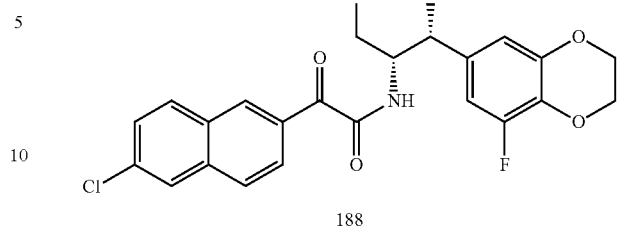

188

To a solution of Compound 151A) (85 mg, 0.37 mmol) and Intermediate H (104 mg, 0.37 mmol) in dichloromethane (6 mL) and DMF (2 mL) was added HATU (208 mg, 0.55 mmol) at 25° C. Then the reaction was stirred at 28° C. for 15 hours. Then the reaction mixture was treated with water (40 mL), extracted with DCM (20 mL×2), washed with brine (10 mL), dried over sodium sulfate, and concentrated. The crude product was purified with prep-HPLC to obtain Compound 188. LC-MS (m/z): 499 [M+1]$^+$; $^1$H-NMR (DMSO-d$_6$, 400 MHz) δ (ppm) 2.08-2.40 (m, 2H), 2.70-3.35 (m, 2H), 3.50-4.10 (m, 3H), 4.24-4.29 (m, 6H), 4.78 (s, 1H), 6.76-6.85 (m, 2H), 7.67-7.70 (m, 1H), 7.87 (d, J=1.6 Hz, 1H), 8.02 (d, J=8.8 Hz, 1H), 8.10 (d, J=8.8 Hz, 1H), 8.20 (d, J=2.0 Hz, 1H), 8.48 (s, 1H), 8.76 (br, 1H).

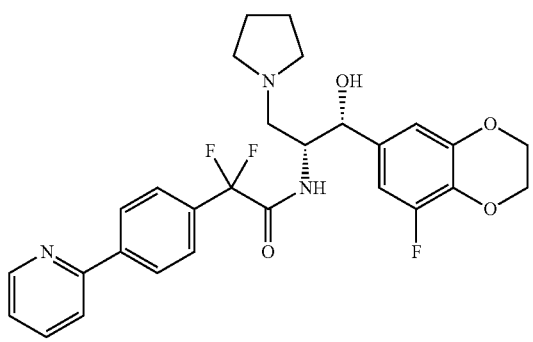

187

A mixture of Compound 182A (90 mg, 0.36 mmol), EDCI.HCl (103 mg, 0.54 mmol), HOBT (73 mg, 0.54 mmol), and Intermediate C (107 mg, 0.36 mmol) in DCM (5 mL) was stirred for 18 h at 10° C. Then the mixture was diluted by ethyl acetate (50 mL), washed with sat. sodium bicarbonate solution (50 mL×2) and brine (50 mL), and dried over anhydrous sodium sulfate. After evaporation, the crude product was purified with prep-HPLC to furnish Compound 187. LC-MS (m/z): 528 [M+1]$^+$; $^1$H-NMR (CD$_3$OD, 400 MHz) major characteristic peaks: δ (ppm) 2.04-2.16 (m, 4H), 3.31-3.32 (m, 2H), 3.52-3.19 (m, 4H), 4.05-4.11 (m, 4H), 4.56-4.59 (m, 1H), 4.81 (d, J=3.2 Hz, 1H), 6.58 (s, 1H), 6.64 (dd, J=11.2, 2.0 Hz, 1H), 7.59 (d, J=8.4 Hz, 2H), 7.64-7.67 (m, 1H), 8.04 (d, J=8.0 Hz, 2H), 8.14 (d, J=8.0 Hz, 1H), 8.20-8.23 (m, 1H), 8.76 (d, J=9.0 Hz, 1H).

Example 188

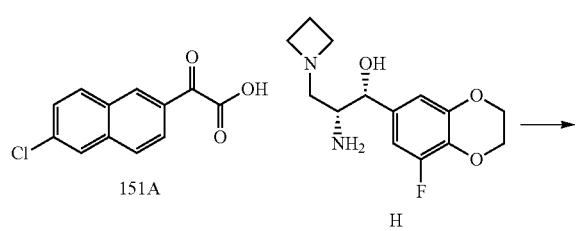

Example 189

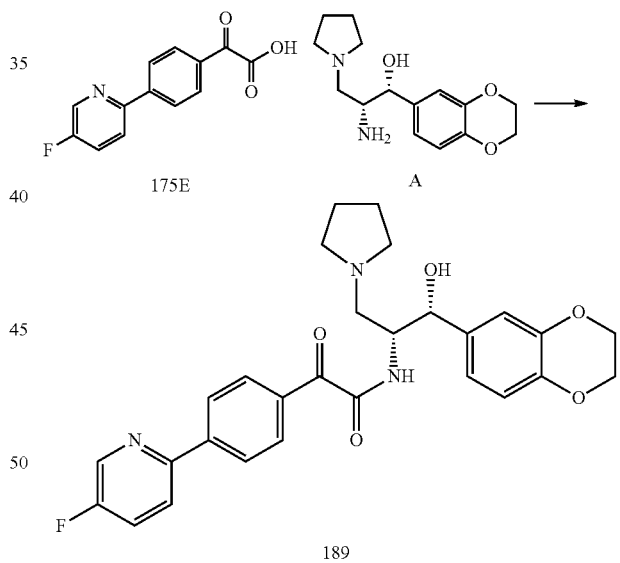

189

A mixture of Compound 175E (100 mg, 0.408 mmol) and Intermediate A (114 mg, 0.408 mmol) and HATU (155 mg, 0.612 mmol) in dichloromethane (4 mL) and DMF (2 mL) was stirred at 25° C. for 15 h. Then it was treated with water (20 mL), extracted with dichloromethane (20 mL×3), dried over anhydrous sodium sulfate, concentrated in vacuum and purified with prep-HPLC to obtain Compound 189. LC-MS (m/z): 506 [M+1]$^+$; $^1$H-NMR (CD$_3$OD, 400 MHz) δ (ppm) 2.03-2.24 (m, 6H), 3.12-3.25 (m, 3H), 3.60-3.71 (m, 2H), 3.82-3.95 (m, 1H), 4.19-4.28 (m, 2H), 4.55-4.58 (m, 1H), 4.93 (d, J=2.8 Hz, 1H), 6.85-6.92 (m, 3H), 7.61-7.90 (m, 2H), 8.00 (s, 4H), 8.59 (d, J=2.8 Hz, 1H).

Example 190

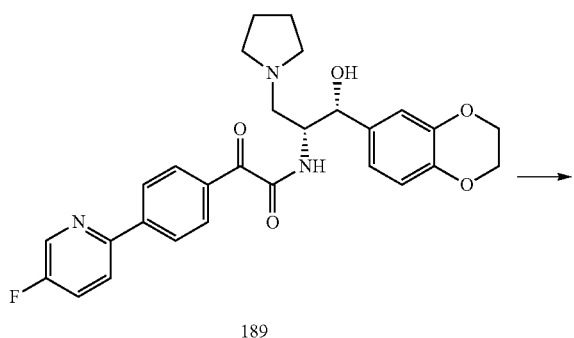

189

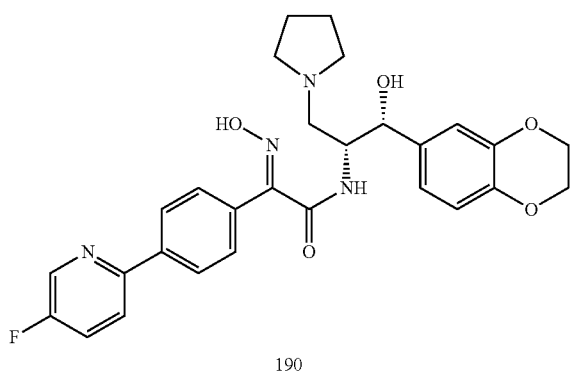

190

To a solution of 189 (40 mg, 0.065 mmol) in MeOH (18 mL) was added hydroxylamine hydrochloride (90 mg, 1.29 mmol) at 25° C., then the reaction was stirred at 55° C. for 14 h. Then it was purified with prep-HPLC to obtain Compound 190. LC-MS (m/z): 521 [M+1]$^+$; $^1$H-NMR (CD$_3$OD, 400 MHz) major characteristic peaks: δ (ppm) 1.91-2.10 (m, 4H), 2.56-3.17 (m, 1H), 3.17-3.77 (m, 4H), 4.12-4.19 (m, 4H), 4.46-4.71 (m, 2H), 4.83-4.84 (m, 1H), 6.70-6.90 (m, 3H), 7.19-7.34 (m, 2H), 7.57-7.63 (m, 1H), 7.82-7.85 (m, 3H), 8.47-8.50 (m, 1H).

Example 191

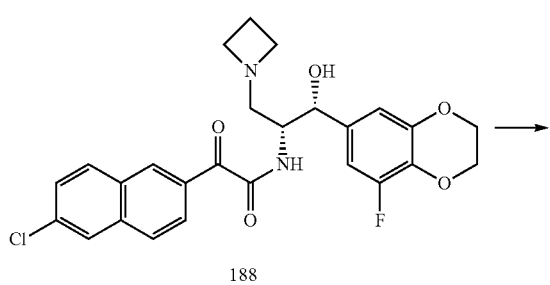

188

-continued

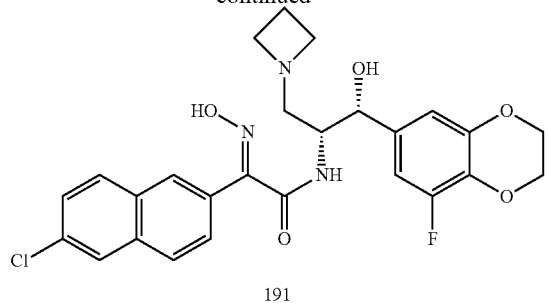

191

To a solution of 188 (30 mg, 0.049 mmol) in MeOH (15 mL) was added hydroxylamine hydrochloride (80 mg, 0.98 mmol) at 30° C., then the reaction was stirred at 55° C. for 4 h. Then it was purified with prep-HPLC to obtain Compound 191. LC-MS (m/z): 514 [M+1]$^+$; $^1$H-NMR (CD$_3$OD, 400 MHz) major characteristic peaks: δ (ppm) 2.40-2.71 (m, 2H), 3.55-3.64 (m, 2H), 4.02-4.50 (m, 9H), 4.63-4.83 (m, 1H), 6.78-6.85 (m, 2H), 7.47-7.51 (m, 2H), 7.68-7.90 (m, 4H).

Example 192

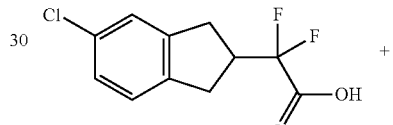

63D

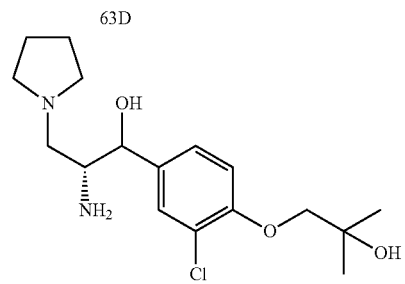

V

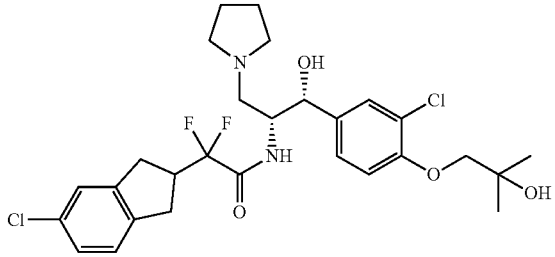

192

To a solution of Intermediate V (100 mg, 0.29 mmol) and Compound 63D (72 mg, 0.29 mmol) in DMF (10 mL) was added EDCI.HCl (84 mg, 0.44 mmol), and HOBt (59 mg, 0.44 mmol) under nitrogen. The mixture was stirred at 25° C. overnight. TLC and LC-MS showed the starting material was consumed completely, sat. sodium bicarbonate (5 mL) was added to the mixture and then extracted with EA (50 mL×3). The combined organic layers were washed with water (5 mL×3) and brine (5 mL), dried over anhydrous sodium sulfate, and concentrated to offer the crude product. The crude product was purified with prep-HPLC to offer Compound 192. LC-MS (m/z): 571 [M+1]+; $^1$H-NMR (CD$_3$OD, 400 MHz) major characteristic peaks: δ (ppm) 1.31-1.34 (m, 6H), 2.00-2.03 (m, 3H), 2.14-2.17 (m, 2H), 2.55-2.61 (m, 2H), 2.64-2.72 (m, 1H), 2.78-2.98 (m, 2H), 3.15-3.25 (m, 2H), 3.51-3.55 (m, 1H), 3.60-3.66 (m, 2H), 3.74-3.79 (m, 3H), 4.62-4.65 (m, 1H), 4.92 (d, J=2.8 Hz, 1H), 7.02 (dd, J=1.2, 8.8 Hz, 1H), 7.08-7.15 (m, 3H), 7.29 (dd, J=1.6, 8.4 Hz, 1H), 7.48 (d, J=2.4 Hz, 1H).
Example 193
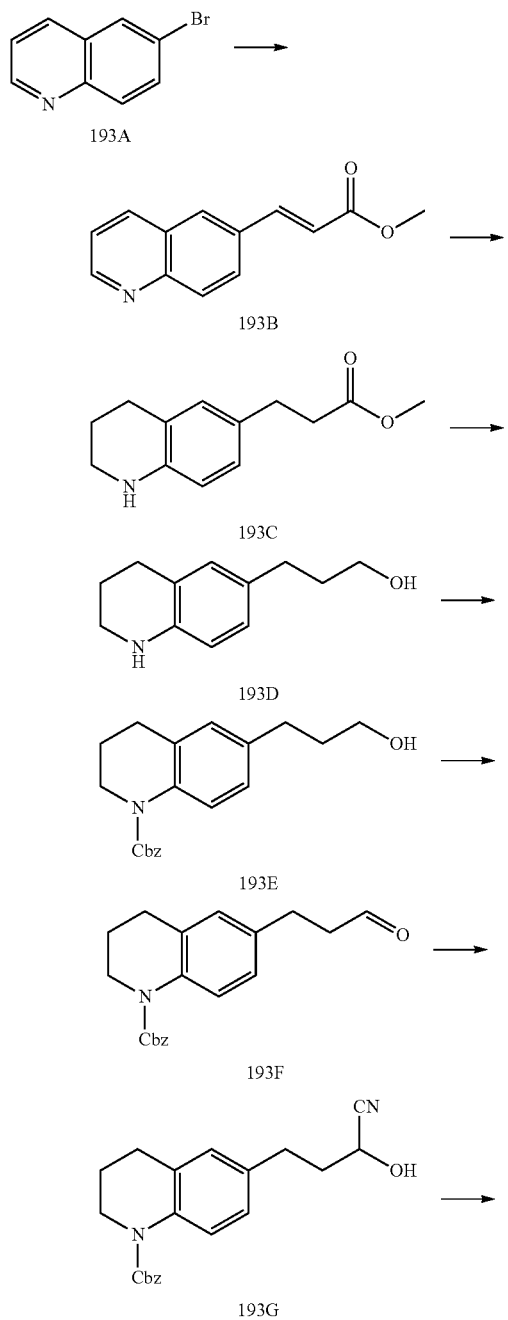
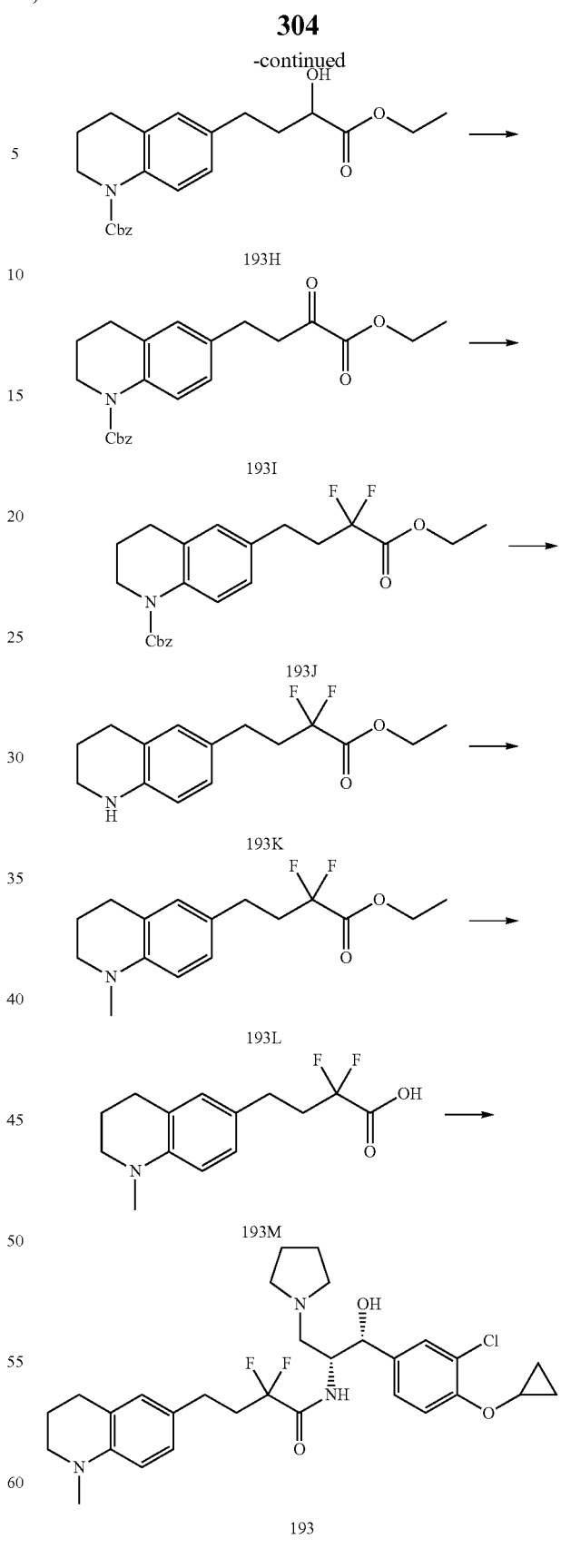
A mixture of Compound 193A (13 g, 62 mmol), methyl acrylate (16.0 g, 187 mmol), Pd(PPh$_3$)$_2$Cl$_2$ (2.0 g, 3.0 mmol), and K$_2$CO$_3$ (22 g, 156 mmol) in DMF (100 mL) was stirred at 100° C. for 12 h, then cooled to room temperature and filtered. The filtrate was treated with water (50 mL), extracted with DCM (100 mL×2), washed with water (100 mL×3) and brine (100 mL), dried over sodium sulfate, concentrated, and purified with flash column chromatography on silica gel (20% ethyl acetate in petroleum) to furnish Compound 193B.

To a solution of Compound 193B (11.5 g, 54 mmol) in MeOH (100 mL) was added Pd/C (1.1 g), then the mixture was stirred at room temperature for 12 h under $H_2$, then filtered. The filtrate was concentrated to furnish the crude Compound 193C.

To a solution of $AlLiH_4$ (1.56 g, 41 mmol) in THF (100 mL) was added Compound 193C (9.0 g, 41 mmol) in THF (20 mL) dropwise at −78° C. under nitrogen, then the mixture was stirred at −78° C. for 2 h and quenched with $Na_2SO_4 \cdot 10H_2O$. Silica gel was added and the resultant mixture was filtered. The filtrate was concentrated to furnish the crude Compound 193D.

To a solution of Compound 193D (8 g, 42 mmol) in THF (80 mL) was added $K_2CO_3$ (5.8 g, 42 mmol), water (25 mL), and CbzCl (7.1 mL) under ice-cooling, and the resulting mixture was stirred at 25° C. for 12 h. EA (200 mL) was added. The organic layer was separated, dried over sodium sulfate, concentrated, and purified with flash column chromatography on silica gel (20% ethyl acetate in petroleum) to furnish Compound 193E.

To a solution of Compound 193E (12.2 g, 37.5 mmol) in DCM (100 mL) was added DMP (16.0 g, 37.5 mmol) at 0° C., then the mixture was stirred at room temperature for 2 h, then filtered. The filtrate was concentrated and the resulting residue was purified with flash column chromatography on silica gel (20% ethyl acetate in petroleum) to furnish Compound 193F.

Compound 193F (9.8 g, 30 mmol) was added to a solution of $Na_2S_2O_5$ (5.8 g, 30 mmol) in water (150 mL), then the mixture was stirred for 2 h at room temperature. And after the addition of NaCN (3 g, 61 mmol) the mixture was stirred for 15 h, diluted with EA (50 mL), extracted with EA (100 mL×2), washed with sat. sodium bicarbonate (100 mL×2) and brine (100 mL), dried over sodium sulfate, concentrated, and purified with flash column chromatography on silica gel (20% ethyl acetate in petroleum) to furnish Compound 193G.

To a solution of Compound 193G (10 g, 28 mmol) in EtOH (150 mL) cooled to 0° C. was bubbled a gentle stream of HCl gas (dried over con. $H_2SO_4$) for 5 h. Then the mixture was treated with water slowly at 0° C., stirred at room temperature for 2 h, then extracted with DCM (100 mL×2), washed with brine (100 mL), dried over sodium sulfate, concentrated, and purified with flash column chromatography on silica gel (20% ethyl acetate in petroleum) to furnish Compound 193H.

To a solution of Compound 193H (845 mg, 2.13 mmol) in DCM (20 mL) was added DMP (1.1 g, 2.55 mmol) at 0° C., then the mixture was stirred at room temperature for 2 h, then filtered. The filtrate was concentrated and the resulting residue was purified with flash column chromatography on silica gel (20% ethyl acetate in petroleum) to furnish Compound 193I.

To a solution of Compound 193I (730 mg, 1.84 mmol) in DCM (20 mL) was added DAST (1.5 g, 9.24 mmol), then the mixture was stirred at room temperature for 12 h, poured into ice water, extracted with DCM (50 mL×2), washed with brine (50 mL), dried over sodium sulfate, concentrated, and purified with flash column chromatography on silica gel (20% ethyl acetate in petroleum) to furnish Compound 193J.

Compound 193J (730 mg, 1.75 mmol) was dissolved in ethanol (20 mL), then $Pd(OH)_2$ (100 mg) was added, then the mixture was stirred at room temperature under $H_2$ overnight, then filtered and evaporated to furnish the product Compound 193K.

To a solution of Compound 193K (350 mg, 1.24 mmol) in $CH_3CN$ (5 mL) was added $CH_3I$ (526 mg, 3.71 mmol), then the mixture was stirred at 70° C. for 2 h, then cooled to room temperature, evaporated and purified with flash column chromatography on silica gel (20% ethyl acetate in petroleum) to furnish Compound 193L.

To a solution of Compound 193L (200 mg, 0.67 mmol) in THF (10 mL) was added LiOH (85 mg, 2.02 mmol) in water (2 mL), then the mixture was stirred at room temperature for 2 h, then evaporated to remove solvent. The mixture was treated with water (50 mL), adjusted to pH 2 with diluted HCl, then extracted with EA (50 mL×2), washed with brine (50 mL), dried over sodium sulfate, and concentrated to furnish the Compound 193M.

A mixture of Compound 193M (96 mg, 0.36 mmol), Intermediate G (111 mg, 0.36 mmol), EDCI.HCl (103 mg, 0.54 mmol), and HOBt (73 mg, 0.54 mmol) in DCM (10 mL) was stirred at room temperature overnight. The mixture was treated with water (50 mL), extracted with DCM (50 mL×2), washed with water (50 mL×2) and brine (50 mL), dried over sodium sulfate, concentrated, and purified with prep-HPLC to offer Compound 193. LC-MS (m/z): 562 $[M+1]^+$; $^1$H-NMR ($CDCl_3$, 400 MHz) major characteristic peaks: δ (ppm) 0.66-0.75 (m, 4H), 2.13 (s, 8H), 2.24-2.31 (m, 1H), 2.41-2.49 (m, 1H), 2.87-2.90 (m, 4H), 3.13 (s, 3H), 3.39-3.64 (m, 5H), 3.76 (s, 2H), 4.50 (s, 1H), 5.05 (s, 1H), 6.90 (s, 1H), 6.99 (d, J=8.0 Hz, 1H), 7.19 (s, 2H), 7.27 (s, 1H), 7.29 (s, 1H), 7.69 (d, J=8.8 Hz, 1H), 11.62 (s, 1H).

Example 194

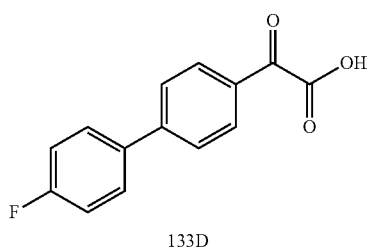

133D

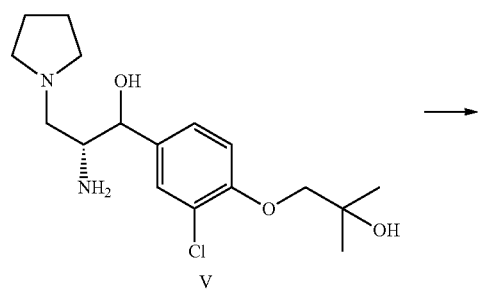

V

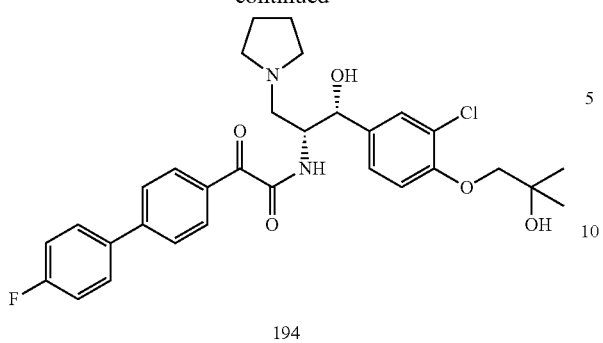

194

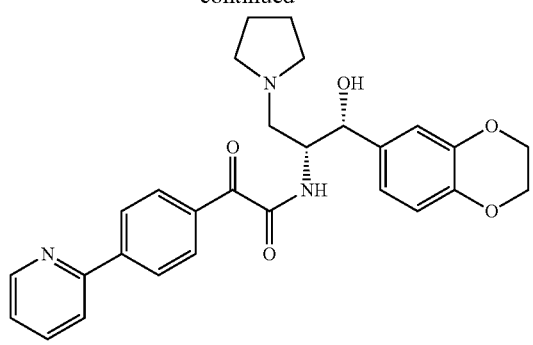

195

To a solution of Intermediate V (100 mg, 0.29 mmol) in DMF (10 mL) was added HATU (167 mg, 0.44 mmol). After stirring for two hours at 25° C., Compound 133D (71 mg, 0.29 mmol) was added and the resultant mixture was stirred overnight at 25° C. TLC and LC-MS showed the starting material was consumed completely, and sat. sodium bicarbonate (5 mL) was added to the mixture which was extracted with ethyl acetate (50 mL×3). The combined organic layers were washed with water (5 mL×3) and brine (5 mL), dried over anhydrous sodium sulfate, and concentrated to offer the crude product. The crude product was purified with prep-HPLC to offer Compound 194. LC-MS (m/z): 569 [M+1]$^+$; $^1$H-NMR (CD$_3$OD, 400 MHz) major characteristic peaks: δ (ppm) 1.27-1.31 (m, 6H), 2.02-2.07 (m, 2H), 2.20-2.23 (m, 2H), 3.19-3.24 (m, 1H), 3.46-3.56 (m, 1H), 3.60-3.83 (m, 5H), 4.56-4.57 (m, 1H), 4.69-4.72 (m, 1H), 4.98 (d, J=2.4 Hz, 1H), 7.06 (d, J=8.4 Hz, 1H), 7.22 (t, J=8.4 Hz, 2H), 7.35 (dd, J=2.0, 8.4 Hz, 1H), 7.50 (d, J=2.0 Hz, 1H), 7.64-7.67 (m, 3H), 7.71-7.74 (m, 3H).

Example 195

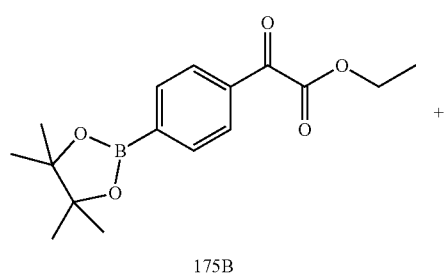

175B

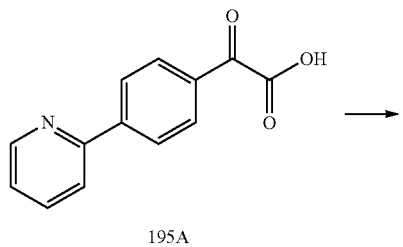

195A

A mixture of Compound 175B (608 mg, 2 mmol), 2-bromopyridine (314 mg, 2 mmol), Pd(dppf)Cl$_2$ (82 mg, 0.1 mmol), and Na$_2$CO$_3$ (636 mg, 6 mmol) in dioxane (15 mL) and water (2 mL) was stirred at 100° C. for 3 h and concentrated. The mixture was treated with water (50 mL) and extracted with DCM (50 mL×3). The aqueous layer was acidified with 1 M HCl and extracted with DCM (50 mL×3). The aqueous layer was purified with prep-HPLC to offer Compound 195A.

A solution of Compound 195A (100 mg, 0.44 mmol), Intermediate A (122 mg, 0.44 mmol), and HATU (335 mg, 0.88 mmol) in DMF (10 mL) was stirred at 25° C. for 16 h. Then it was treated with EA (50 mL), washed with water (20 mL×3) and brine (20 mL×1), dried over anhydrous sodium sulfate, concentrated, and purified with prep-HPLC to obtain Compound 195. LC-MS (m/z): 488 [M+1]$^+$; $^1$H-NMR (CDCl$_3$, 400 MHz) major characteristic peaks: δ (ppm) 1.75 (s, 4H), 2.64 (m, 4H), 2.81-2.94 (m, 2H), 4.15 (s, 4H), 4.27 (s, 1H), 4.99 (s, 1H), 6.77 (m, 3H), 7.31 (m, 1H), 7.72 (s, 2H), 8.00 (m, 2H), 8.26 (m, 2H), 8.66 (m, 1H).

Example 196

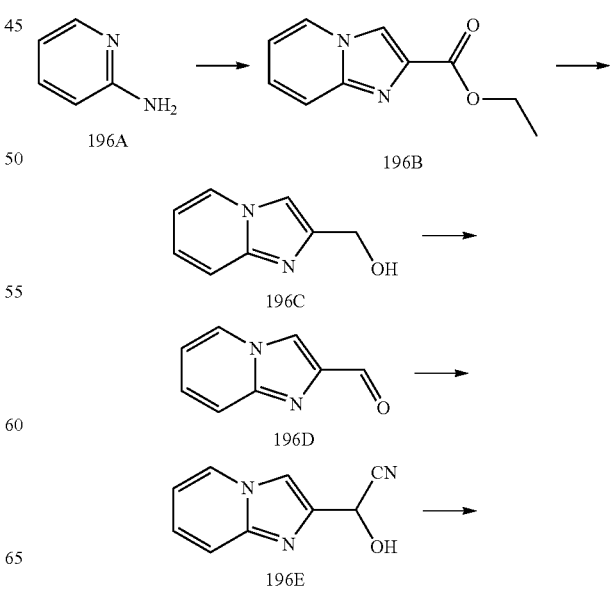

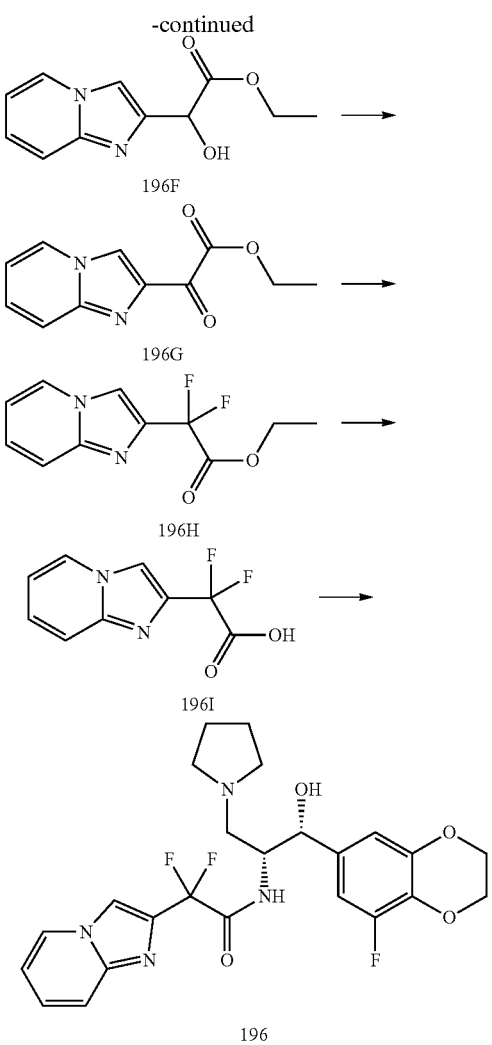

A mixture of Compound 196A (10 g, 106 mmol) and ethyl 3-bromo-2-oxopropanoate (22.8 g, 117 mmol) in THF (300 mL) was stirred at r.t. for 1 h, then heated to 80° C. overnight, cooled to room temperature, diluted with water (50 mL), adjusted to pH>9 with $Na_2CO_3$, and extracted with ethyl acetate (100 mL×3). The ethyl acetate layers were combined and washed with brine (100 mL), dried over sodium sulfate, concentrated, and purified with flash column chromatography on silica gel (ethyl acetate in petroleum ether, 33% v/v) to offer Compound 196B.

To a suspension of $AlLiH_4$ (4.2 g, 111.3 mmol) in THF (200 mL) was added Compound 196B (10.7 g, 55.6 mmol) in THF (50 mL) dropwise at 0° C. under nitrogen. Then the mixture was stirred at 0° C. for 30 min, quenched with $Na_2SO_4 \cdot 10H_2O$ and filtered. The filtrate was concentrated to furnish the crude Compound 196C.

To a solution of Compound 196C (6.9 g, 46.6 mmol) in DCM (140 mL) was added DMP (23.7 g, 55.9 mmol) at 0° C., then the mixture was stirred at room temperature for 2 h, then filtered. The filtrate was concentrated and the resulting residue was purified with flash column chromatography on silica gel (ethyl acetate in petroleum ether, 33% v/v) to furnish Compound 196D.

Compound 196D (2.5 g, 17.1 mmol) was added to a solution of $Na_2S_2O_5$ (3.25 g, 17.1 mol) in water (300 mL), then the mixture was stirred for 2 h at room temperature. And after the addition of NaCN (1.68 g, 34.2 mol), it was stirred again for 15 h, diluted with water (50 mL), stirred for 30 min, and filtered. The solid was collected, washed with water (50 mL), and dried to offer Compound 196E.

To a solution of Compound 196E (2.8 g, 16.2 mmol) in EtOH (80 mL) at 0° C. was bubbled a gentle stream of HCl gas (dried over con. $H_2SO_4$) for 5 h. Then the mixture was treated with ice-water slowly at 0° C., stirred at room temperature for 2 h, adjusted to pH>7 with sodium bicarbonate, extracted with DCM (100 mL×2), washed with brine (100 mL), dried over sodium sulfate, and concentrated to furnish Compound 196F.

To a solution of Compound 196F (1.7 g, 7.72 mmol) in DCM (30 mL) was added DMP (3.93 g, 9.26 mmol), then the mixture was stirred at 0° C. for 2 h, then filtered. The filtrate was concentrated and the resulting residue was purified with flash column chromatography on silica gel (ethyl acetate in petroleum ether, 50% v/v) to furnish Compound 196G.

To a solution of Compound 196G (1.68 g, 7.72 mmol) in DCM (60 mL) was added DAST (6.22 g, 38.6 mmol), then the mixture was stirred at room temperature overnight, poured into ice water, extracted with DCM (100 mL×2), washed with brine (50 mL), dried over sodium sulfate, concentrated, and purified with flash column chromatography on silica gel (ethyl acetate in petroleum ether, 33% v/v) to furnish Compound 196H.

To a solution of Compound 196H (960 mg, 4.0 mmol) in THF (20 mL) and water (2 mL) was added LiOH (252 mg, 6.0 mmol), then the mixture was stirred at room temperature overnight, then evaporated to remove solvent. The mixture was treated with water (50 mL), adjusted to pH 2 with diluted HCl, and purified with prep-HPLC to furnish the Compound 196I.

A mixture of Compound 196I (100 mg, 0.471 mmol), Intermediate C (140 mg, 0.471 mmol), and HATU (215 mg, 0.565 mmol) in DCM (2 mL) was stirred at room temperature overnight and concentrated. The residue was dissolved into DCM (50 mL), washed with water (50 mL) and brine (10 mL), dried over sodium sulfate, concentrated, and purified with chiral HPLC to offer Compound 196. LC-MS (m/z): 490 [M+1]$^+$; $^1$H-NMR (DMSO-d$_6$, 400 MHz) major characteristic peaks: δ (ppm) 1.82-2.01 (m, 4H), 3.05-3.11 (m, 2H), 3.31-3.38 (m, 1H), 3.44-3.52 (m, 3H), 4.19-4.23 (m, 4H), 4.35-4.41 (m, 1H), 4.66-4.67 (m, 1H), 6.62 (s, 1H), 6.69-6.73 (m, 1H), 7.03-7.07 (m, 1H), 7.39-7.43 (m, 1H), 7.59-7.61 (m, 1H), 8.26 (s, 1H), 8.59 (d, J=6.8 Hz, 1H), 8.68-8.70 (m, 1H), 9.41 (brs, 1H).

Example 197

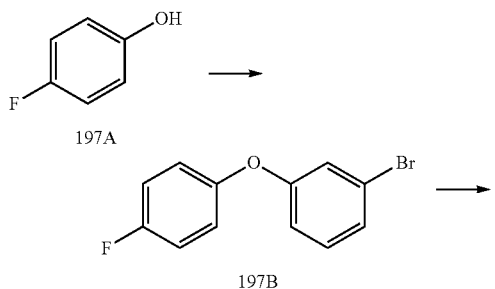

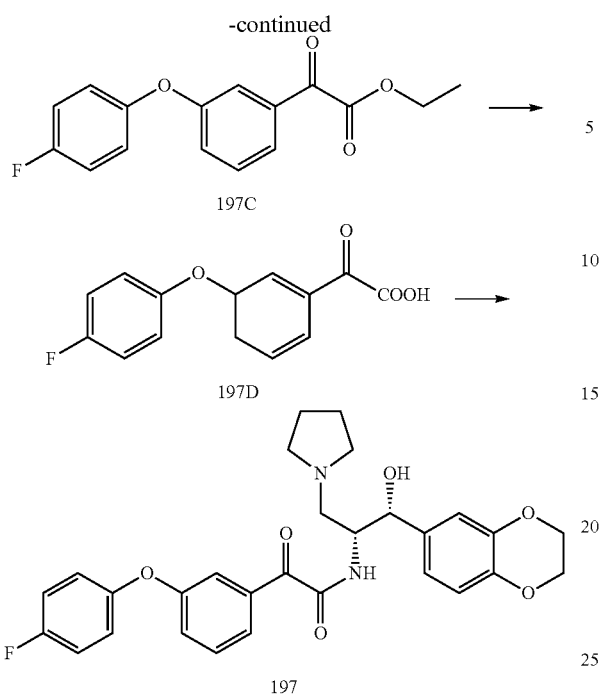

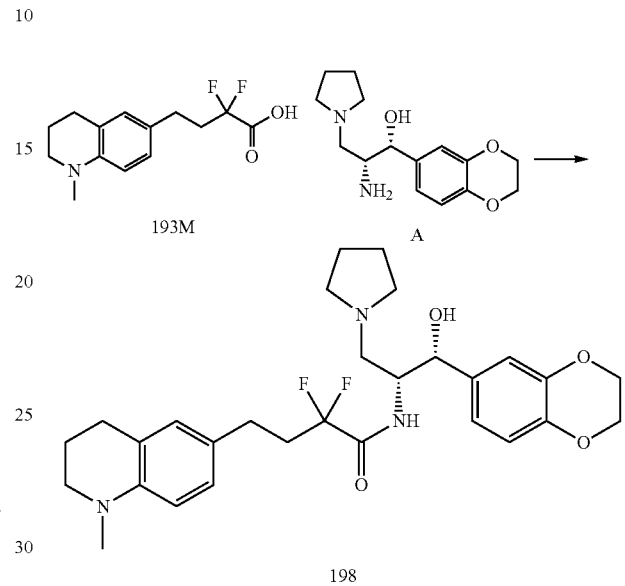

An aqueous solution of KOH (4.9 g, 87.5 mmol) in water (10 mL) was added to a stirred solution of 4-fluorophenol 197A (8.4 g, 75 mmol) in methanol (25 mL). When the addition was complete, the mixture was evaporated in vacuum and the residual solid was dissolved in 1-methyl-2-pyrrolidinone (30 mL) and 3-fluorobromobenzene (13 g, 75 mmol) was added and the mixture was refluxed for 24 hours, then cooled to room temperature, poured into water (150 mL) and extracted with ether (30 mL×2). The combined extracts were dried over sodium sulfate and concentrated. The residue was purified with flash column chromatography on silica gel (ethyl acetate in petroleum ether, from 10% to 50% v/v) to furnish Compound 197B.

To a solution of Compound 197B (2.66 g, 10 mmol) in THF (30 mL) was added dropwise n-BuLi solution (2.5 M, 4 mL, 10 mmol) at −78° C. under nitrogen. The mixture was stirred at −78° C. for 0.5 h, and then the mixture was added to a solution of diethyl oxalate (3 g, 20 mmol) in THF (20 mL) at −78° C. The mixture was stirred at room temperature overnight. The mixture was quenched with saturated aqueous NH$_4$Cl solution (40 mL). The reaction mixture was extracted with EA (50 mL×3), dried over anhydrous sodium sulfate, and concentrated. The residue was purified with flash column chromatography on silica gel (ethyl acetate in petroleum ether, from 10% to 50% v/v) to furnish Compound 197C.

Lithium hydroxide (420 mg, 10 mmol) was added to a solution of Compound 197C (1.44 mg, 5 mmol) in EtOH (20 mL) and water (5 mL). The reaction mixture was stirred at room temperature for 2 h. The reaction mixture was added 1 N HCl to adjust to pH 7 and concentrated in vacuum. The residue was extracted with EA (50 mL×3), dried over anhydrous sodium sulfate, and concentrated to furnish Compound 197D.

A mixture of Compound 197D (262 mg, 1 mmol), Intermediate A (278 mg, 1 mmol), and HATU (760 mg, 2 mmol) in DMF (20 mL) was stirred at 25° C. for 16 h. Then it was diluted with DCM (70 mL), washed with water (50 mL×3) and brine (50×2 mL), dried over anhydrous sodium sulfate, concentrated, and purified with prep-HPLC to obtain Compound 197. LC-MS (m/z): 521 [M+1]$^+$; $^1$H-NMR (CDCl$_3$, 400 MHz) major characteristic peaks: δ (ppm) 1.79-1.81 (m, 4H), 2.70-2.75 (m, 4H), 2.83-3.02 (m, 2H), 4.22 (s, 4H), 4.23-4.27 (m, 1H), 5.04 (s, 1H), 6.81-6.86 (m, 3H), 6.87-6.98 (m, 4H), 6.98-7.05 (m, 1H), 7.27 (m, 1H), 7.35-7.42 (t, J=4.8 Hz, 1H), 7.77 (s, 1H), 7.95-7.97 (d, J=4.2 Hz, 1H).

Example 198

A mixture of Compound 193M (80 mg, 0.3 mmol), Intermediate A (83 mg, 0.3 mmol), EDCI.HCl (86 mg, 0.45 mmol), and HOBt (61 mg, 0.45 mmol) in DCM (10 mL) was stirred at 25° C. overnight. Then the reaction mixture was concentrated to remove DCM. The residue was purified with prep-HPLC to offer Compound 198. LC-MS (m/z): 530 [M+1]$^+$; $^1$H-NMR (CDCl$_3$, 400 MHz) major characteristic peaks: δ (ppm) 2.13 (s, 8H), 2.30-2.37 (m, 1H), 2.45-2.53 (m, 1H), 2.85-2.88 (m, 3H), 2.91 (s, 1H), 3.10 (s, 3H), 3.43-3.46 (m, 2H), 3.79 (s, 2H), 4.00-4.09 (m, 5H), 4.26 (s, 1H), 4.45-4.48 (m, 1H), 5.01 (s, 1H), 6.80 (s, 2H), 6.86-6.90 (m, 1H), 6.98-7.01 (m, 1H), 7.21-7.24 (m, 1H), 7.61 (t, J=8.0 Hz, 1H), 11.89 (s, 1H).

Example 199

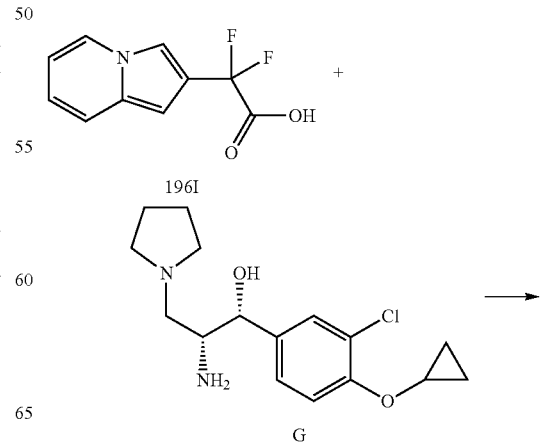

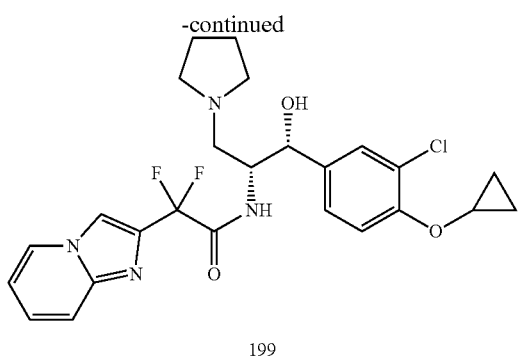

199

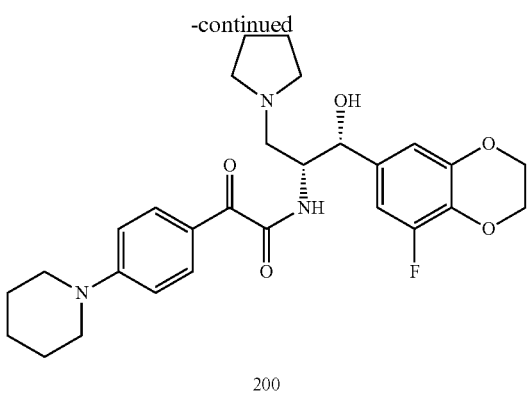

200

A mixture of Compound 196I (100 mg, 0.471 mmol), Intermediate G (146 mg, 0.471 mmol), and HATU (215 mg, 0.565 mmol) in DCM (2 mL) was stirred at room temperature overnight and concentrated. The residue was dissolved into DCM (50 mL), washed with water (50 mL) and brine (10 mL), dried over sodium sulfate, concentrated, and purified with chiral HPLC to offer Compound 199. LC-MS (m/z): 505 [M+1]$^+$; $^1$H-NMR (DMSO-d$_6$, 400 MHz) major characteristic peaks: δ (ppm) 0.61-0.65 (m, 2H), 0.77-0.82 (m, 2H), 1.82-2.00 (m, 4H), 3.06-3.14 (m, 2H), 3.35-3.42 (m, 1H), 3.49-3.53 (m, 3H), 3.79-3.84 (m, 1H), 4.38-4.45 (m, 1H), 4.75-4.76 (m, 1H), 7.04-7.08 (m, 1H), 7.15-7.21 (m, 2H), 7.30 (d, J=1.6 Hz, 1H), 7.39-7.44 (m, 1H), 7.62-7.64 (m, 1H), 8.23 (s, 1H), 8.59 (d, J=7.2 Hz, 1H), 8.69-8.71 (m, 1H), 9.52 (brs, 1H).

Example 200

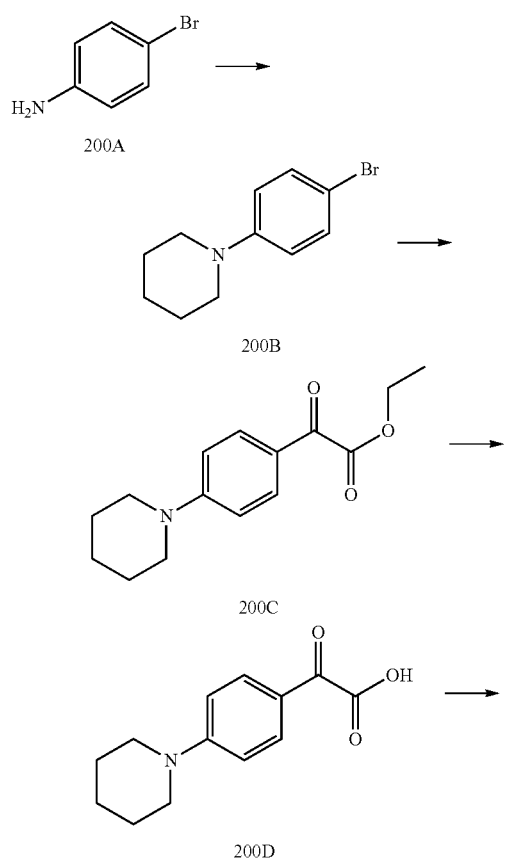

Compound 200A (1.72 g, 10.0 mmol), 1,5-dibromopentane (2.52 g, 11.0 mmol), and K$_2$CO$_3$ (1.51 g, 11.0 mmol) were taken in water (5 mL) and heated at 100° C. for 20 min. in a microwave oven. The reaction mixture was cooled to room temperature and extracted with ethyl acetate (30 mL×2). The combined organic extracts were dried over sodium sulfate, evaporated, and purified with flash column chromatography on silica gel (petroleum ether in ethyl acetate, 10% v/v) to offer Compound 200B.

To a solution of Compound 200B (240 mg, 1.0 mmol) in THF (25 mL) was added dropwise n-BuLi (2.5 M in hexane, 0.48 mL) at −60° C. under nitrogen atmosphere. The reaction mixture was stirred for 30 min. at the same temperature. The resulting mixture was added to the solution of diethyl oxalate (292 mg, 2.0 mmol) in THF (25 mL) at −60° C. The reaction mixture was stirred for 2 hours at −60° C., quenched with sat NH$_4$Cl, and extracted with ethyl acetate (50 mL×2). The combined organic phases were washed with brine (50 mL), dried over sodium sulfate, evaporated, and purified with prep-TLC (petroleum ether in ethyl acetate, 20% v/v) to yield Compound 200C.

To a solution of Compound 200C (97 mg, 0.37 mmol) in MeOH (5 mL) was added LiOH.H$_2$O (18 mg, 0.42 mmol) and water (0.5 mL). The reaction mixture was stirred overnight at 15° C., neutralized with 1 N HCl, and evaporated. The residue was dissolved in water (5 mL), extracted with ethyl acetate (10 mL×2), dried over sodium sulfate, filtered, and evaporated to offer Compound 200D.

To a solution of Compound 200D (58 mg, 0.25 mmol) in CH$_2$Cl$_2$ (5 mL) was added Intermediate C (74 mg, 0.25 mmol) and HATU (142 mg, 0.375 mmol). The reaction mixture was stirred overnight at 15° C., evaporated and purified with prep-HPLC to offer Compound 200. LC-MS: (m/z) 512 [M+1]$^+$; $^1$H-NMR (CD$_3$OD, 400 MHz) major characteristic peaks: δ (ppm) 1.71 (br, 6H), 1.95-2.07 (m, 4H), 2.18-2.21 (m, 2H), 3.52-3.53 (m, 4H), 3.64-3.71 (m, 4H), 4.21-4.30 (m, 5H), 4.88-4.89 (m, 2H), 6.76-6.82 (m, 2H), 6.91-6.93 (m, 2H), 7.57-7.63 (m, 2H).

Example 201

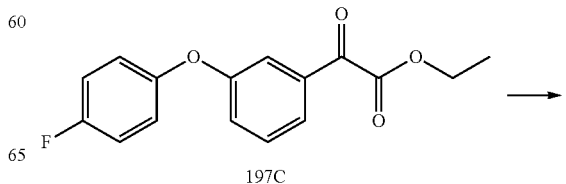

197C

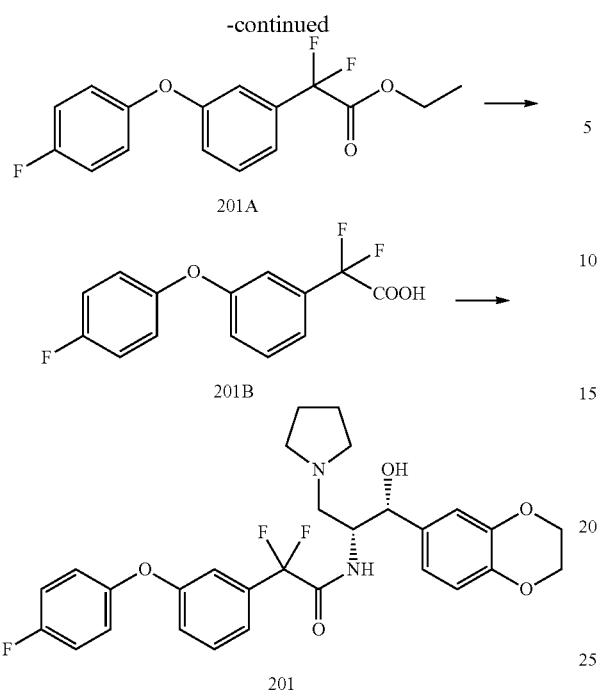

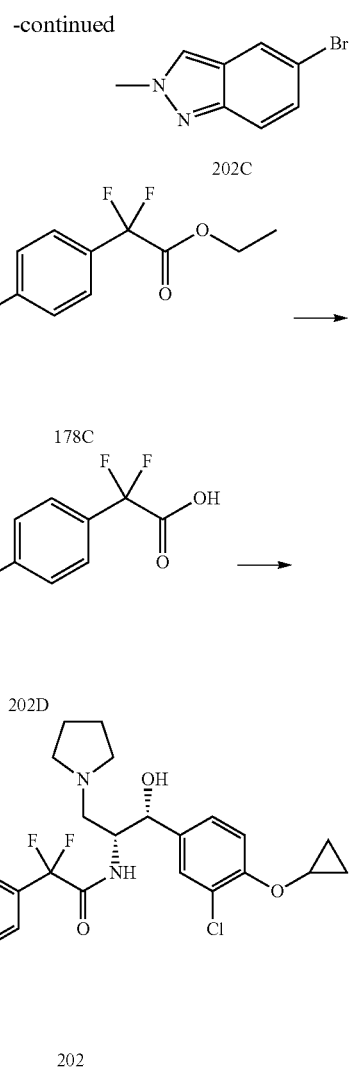

To a solution of Compound 197C (2.89 g, 10 mmol) in DCM (120 mL) was added dropwise DAST (4 mL) at room temperature. The mixture was stirred at room temperature overnight. Then it was quenched with ice, extracted with DCM (30 mL×3), washed with water (50 mL×3) and brine (50×2 mL), dried over anhydrous sodium sulfate, and evaporated to obtain Compound 201A.

Lithium hydroxide (420 mg, 10 mmol) was added to a solution of Compound 201A (1.55 g, 5 mmol) in EtOH (20 mL) and water (5 mL). The reaction mixture was stirred at room temperature for 2 h. The reaction mixture was added 1 N HCl to adjust to pH 7 and concentrated in vacuum. The residue was extracted with EA (50 mL×3), dried over anhydrous sodium sulfate, and concentrated to furnish Compound 201B.

A mixture of Compound 201B (141 mg, 0.5 mmol), Intermediate A (139 mg, 0.5 mmol), HATU (380 mg, 1 mmol) in DMF (5 mL) was stirred at 25° C. for 16 h. Then it was diluted with DCM (70 mL), washed with water (50 mL×3) and brine (50×2 mL), dried over anhydrous sodium sulfate, concentrated, and purified with prep-HPLC to obtain Compound 201. LC-MS (m/z): 543 [M+1]$^+$; $^1$H-NMR (CDCl$_3$, 400 MHz) major characteristic peaks: δ (ppm) 1.71-1.80 (m, 4H), 2.64-2.69 (m, 4H), 2.94 (d, J=4.4 Hz, 2H), 4.14 (m, 1H), 4.22 (m, 4H), 5.02 (s, 1H), 6.71-6.73 (m, 1H), 6.78-6.82 (m, 3H), 6.98-7.07 (m, 7H), 7.30-7.32 (m, 1H).

Example 202

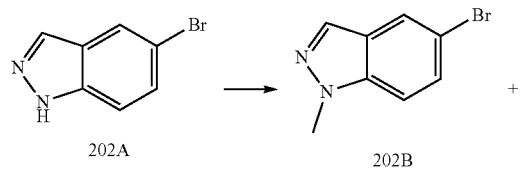

To a solution of 5-bromo-1H-indazole, 202A, (4.92 g, 25.0 mmol) in THF (300 mL) at 0° C. was added NaH (1.10 g, 27.5 mmol). The reaction solution was stirred at this temperature for 1 hour before methyl iodide (5.32 g, 37.5 mmol) was added at 0° C. The reaction was allowed to warm to room temperature slowly, stirred for 2 hours, and quenched with water and concentrated in vacuo. The residue was diluted with water and extracted with dichloromethane (80 mL×2). The organic layers were combined, dried over anhydrous sodium sulfate, and concentrated. The crude product was purified with flash column chromatography on silica gel (ethyl acetate in petroleum ether, 10% v/v) to give Compound 202B and Compound 202C.

A mixture of Compound 178C (153 mg, 0.47 mmol), 202B (100 mg, 0.47 mmol), Pd(dppf)$_2$Cl$_2$ (20 mg, 0.02 mmol), and K$_2$CO$_3$ (195 mg, 1.41 mmol) in dioxane (3 mL) and water (3 mL) was stirred under nitrogen at 100° C. for 3 h. The reaction mixture was cooled to room temperature, and diluted with ethyl acetate (50 mL). The mixture was filtered through celite, then the filtrate was treated with water (40 mL), extracted with ethyl acetate (50 mL×2). The water layer was purified with flash chromatography to furnish the Compound 202D.

A mixture of Compound 202D (90 mg, 0.30 mmol), EDCI.HCl (86 mg, 0.45 mmol), HOBt (61 mg, 0.45 mmol), and Intermediate G (93 mg, 0.30 mmol) in DCM (5 mL) was stirred for 18 h at 10° C. Then the mixture was diluted by ethyl acetate (50 mL), washed with water (50 mL×2) and brine (50 mL), and dried over anhydrous sodium sulfate. After evaporation, the crude product was purified with prep-HPLC to furnish Compound 202. LC-MS (m/z): 595 [M+1]⁺; ¹H-NMR (CD₃OD, 400 MHz) major characteristic peaks: δ (ppm) 0.49-0.51 (m, 4H), 2.03-2.17 (m, 4H), 3.16-3.31 (m, 2H), 3.51-3.74 (m, 5H), 4.11 (s, 3H), 4.64 (d, J=10.4 Hz, 1H), 7.03 (d, J=8.8 Hz, 1H), 7.12 (dd, J=8.8, 1.2 Hz, 1H), 7.36-7.38 (m, 3H), 7.65-7.71 (m, 3H), 7.79 (dd, J=8.8, 1.6 Hz, 1H), 8.08-8.09 (m, 2H).

Example 203

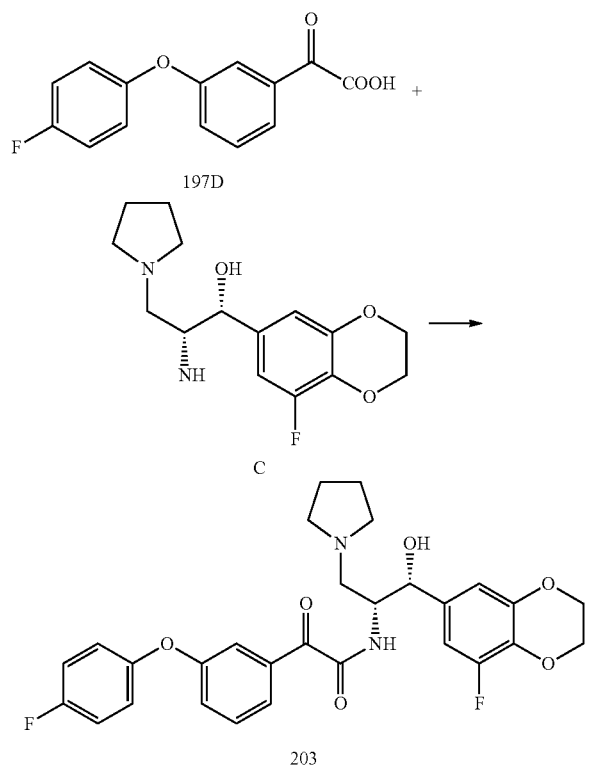

A mixture of Compound 197D (131 mg, 0.5 mmol), Intermediate C (154 mg, 0.5 mmol), HATU (380 mg, 1 mmol) in DMF (5 mL) was stirred at 25° C. for 16 h. Then it was diluted with DCM (20 mL), washed with water (50 mL×3) and brine (50×2 mL), dried over anhydrous sodium sulfate, concentrated, and purified with prep-HPLC to obtain Compound 203. LC-MS (m/z): 539 [M+1]⁺; ¹H-NMR (CDCl₃, 400 MHz) major characteristic peaks: δ (ppm) 2.08-2.19 (m, 4H), 2.87-3.04 (m, 4H), 3.45-3.56 (m, 2H), 3.87 (m, 1H) 4.20-4.28 (m, 4H), 4.47 (m, 1H), 5.05 (s, 1H), 6.71-6.76 (m, 2H), 6.87-6.98 (m, 4H), 6.98-7.05 (m, 1H), 7.27 (m, 1H), 7.35-7.42 (m, 1H), 7.65 (s, 1H), 7.90-7.93 (m, 1H), 11.77 s, 1H).

Example 204

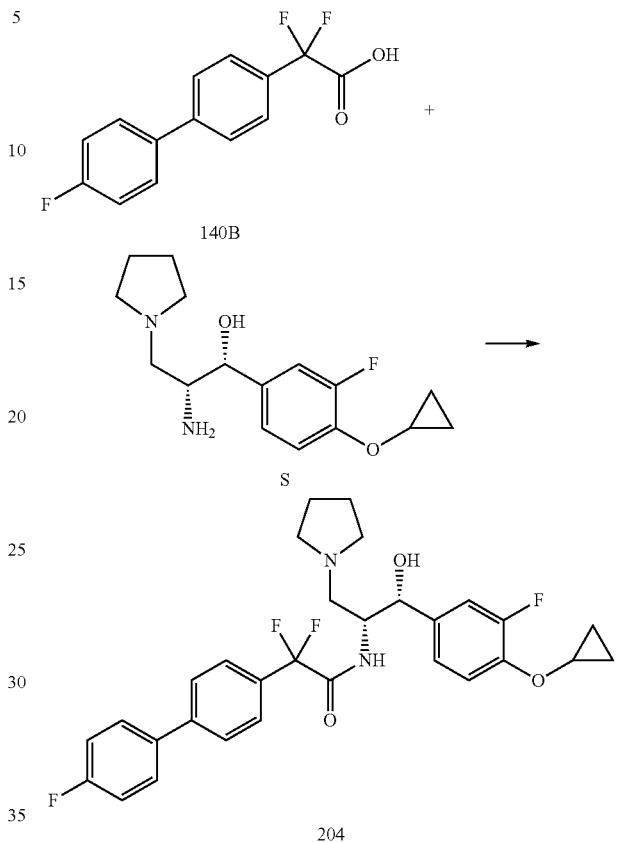

A mixture of Intermediate S (88 mg, 0.30 mmol), Compound 140B (78 mg, 0.30 mmol), EDCl.HCl (86 mg, 0.45 mmol), and HOBt (60 mg, 0.45 mmol) in dichloromethane (10 mL) was stirred at 10° C. for 15 h. Then it was treated with water (20 mL), extracted with dichloromethane (20 mL×3), dried over anhydrous sodium sulfate, concentrated in vacuum, and purified with prep-HPLC to obtain Compound 204. LC-MS (m/z): 543 [M+1]⁺; ¹H-NMR (CDCl₃, 400 MHz) δ (ppm) 0.49-0.62 (m, 4H), 2.04 (s, 2H), 2.18 (s, 2H), 3.17 (s, 1H), 3.27 (s, 1H), 3.54-3.71 (m, 4H), 3.78 (s, 1H), 4.58 (d, J=12 Hz, 1H), 4.89 (s, 1H), 6.95 (d, J=8 Hz, 1H), 7.04 (t, J=8 Hz, 2H), 7.22 (t, J=8 Hz, 2H), 7.39 (d, J=8 Hz, 2H), 7.63 (d, J=8 Hz, 2H), 7.72 (t, J=8 Hz, 2H).

Example 205

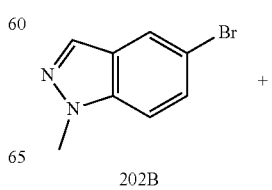

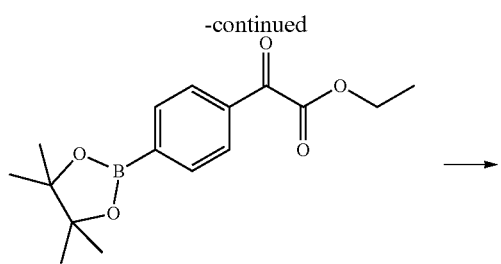

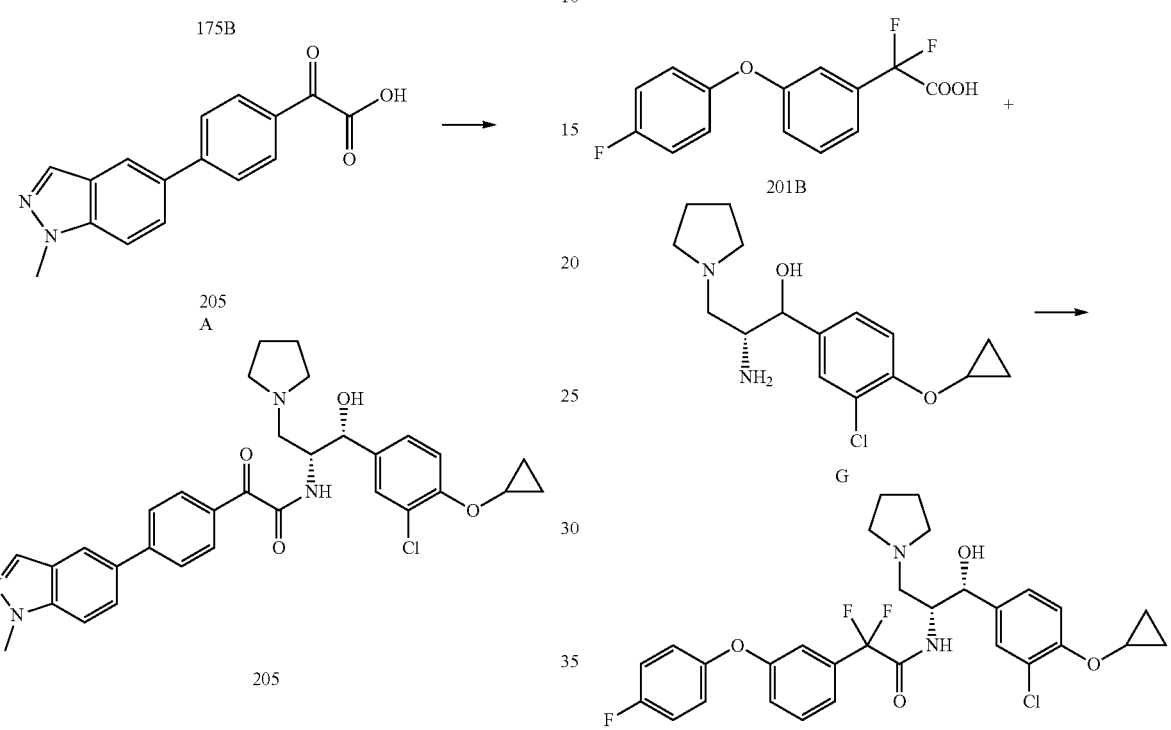

A mixture of Compound 175B (288 mg, 0.95 mmol), 202B (200 mg, 0.95 mmol), Pd(dppf)Cl$_2$ (40 mg, 0.05 mmol), and K$_2$CO$_3$ (393 mg, 2.85 mmol) in dioxane (5 mL) and water (5 mL) was stirred under nitrogen at 90° C. for 3 h. The reaction mixture was cooled to room temperature, and diluted with ethyl acetate (50 mL). The mixture was filtered through celite, then the filtrate was treated with water (40 mL), extracted with ethyl acetate (50 mL×2). The water layer was adjusted to pH 3 by aqueous HCl solution (3 N), extracted with ethyl acetate (50 mL×2) and the ethyl acetate layer was washed with water (50 mL×2), dried over sodium sulfate, filtered, and concentrated to furnish the Compound 205A.

A mixture of Compound 205A (120 mg, 0.43 mmol), HATU (247 mg, 0.65 mmol), and Intermediate G (133 mg, 0.43 mmol) in DMF (5 mL) was stirred for 18 h at 10° C. Then the mixture was purified with prep-HPLC to furnish Compound 205. LC-MS (m/z): 573 [M+1]$^+$; $^1$H-NMR (CD$_3$OD, 400 MHz) major characteristic peaks: δ (ppm) 0.71-0.83 (m, 4H), 2.05-2.23 (m, 4H), 3.24-3.34 (m, 2H), 3.59-3.88 (m, 5H), 4.12 (s, 3H), 4.72-4.75 (m, 1H), 5.02 (d, J=2.4 Hz, 1H), 7.40 (s, 2H), 7.50 (s, 1H), 7.67-7.75 (m, 5H), 7.81 (dd, J=8.8, 1.2 Hz, 1H), 8.12-8.13 (m, 2H).

Example 206

A mixture of Compound 133D (141 mg, 0.5 mmol), Intermediate G (155 mg, 0.5 mmol), and HATU (380 mg, 1 mmol) in DMF (5 mL) was stirred at 25° C. overnight. The reaction mixture was diluted with DCM (70 mL), washed with water (30 mL) and brine (30 mL), dried over anhydrous sodium sulfate, and concentrated. The residue was purified with prep-HPLC to furnish Compound 206. LC-MS (ESI) m/z: 575 [M+H]$^+$; $^1$H-NMR (CD$_3$OD, 400 MHz): δ (ppm) 0.66-0.81 (m, 4H), 2.00-2.15 (m, 4H), 3.12-3.23 (m, 2H), 3.51-3.65 (m, 3H), 3.73-3.77 (m, 2H), 4.54 (m, 1H), 4.87 (s, 1H), 7.02-7.07 (m, 5H), 7.10-7.15 (m, 4H), 7.30 (s, 1H), 7.38 (m, 1H).

Example 207

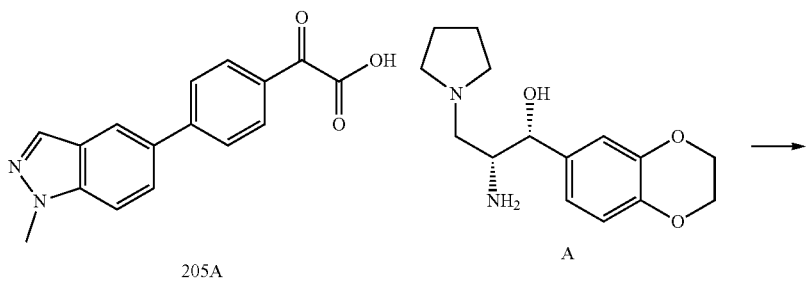

-continued

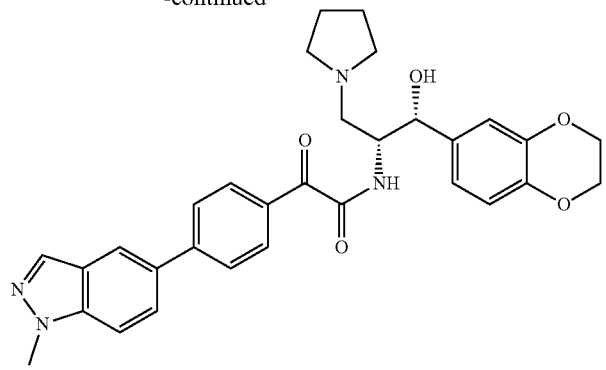

207

A mixture of Compound 205A (144 mg, 0.51 mmol), HATU (293 mg, 0.77 mmol), and Intermediate A (142 mg, 0.51 mmol) in DMF (5 mL) was stirred at 10° C. for 18 h. The reaction mixture was diluted with ethyl acetate (50 mL), washed with water (30 mL) and brine (30 mL), dried over anhydrous sodium sulfate, evaporated, and purified with prep-HPLC to yield Compound 207. LC-MS (ESI) m/z: 541 [M+H]$^+$; $^1$H-NMR (CD$_3$OD, 400 MHz): δ (ppm) 2.01-2.24 (m, 4H), 3.19-3.31 (m, 2H), 3.52-3.56 (m, 1H), 3.68-3.72 (m, 2H), 3.81-3.88 (m, 1H), 4.10-4.21 (m, 7H), 4.65-4.69 (m, 1H), 4.87 (s, 1H), 6.85 (d, J=8.4 Hz, 1H), 6.91-6.94 (m, 1H), 6.97 (d, J=2.0 Hz, 1H), 7.69 (d, J=8.8 Hz, 1H), 7.79-7.83 (m, 3H), 7.87-7.89 (m, 2H), 8.12-8.13 (m, 2H).

A mixture of Intermediate S (118 mg, 0.40 mmol), Compound 133D (97 mg, 0.40 mmol), and HATU (228 mg, 0.60 mmol) in dichloromethane (10 mL) was stirred at 30° C. for 15 h. Then it was treated with water (20 mL), extracted with dichloromethane (20 mL×3), dried over anhydrous sodium sulfate, concentrated in vacuum, and purified with prep-HPLC to obtain Compound 208. LC-MS (m/z): 521 [M+1]$^+$; $^1$H-NMR (CD$_3$OD, 400 MHz) δ (ppm) 0.67-0.82 (m, 4H), 2.05 (s, 2H), 2.21 (s, 2H), 3.10-3.27 (m, 2H), 3.56-3.60 (m, 1H), 3.68-3.74 (m, 2H), 3.80-3.88 (m, 2H), 4.70 (d, J=8 Hz, 1H), 4.98 (s, 1H), 7.19-7.27 (m, 4H), 7.37 (t, J=8 Hz, 1H), 7.68 (d, J=8 Hz, 2H), 7.72-7.78 (m, 4H).

Example 208

Example 209

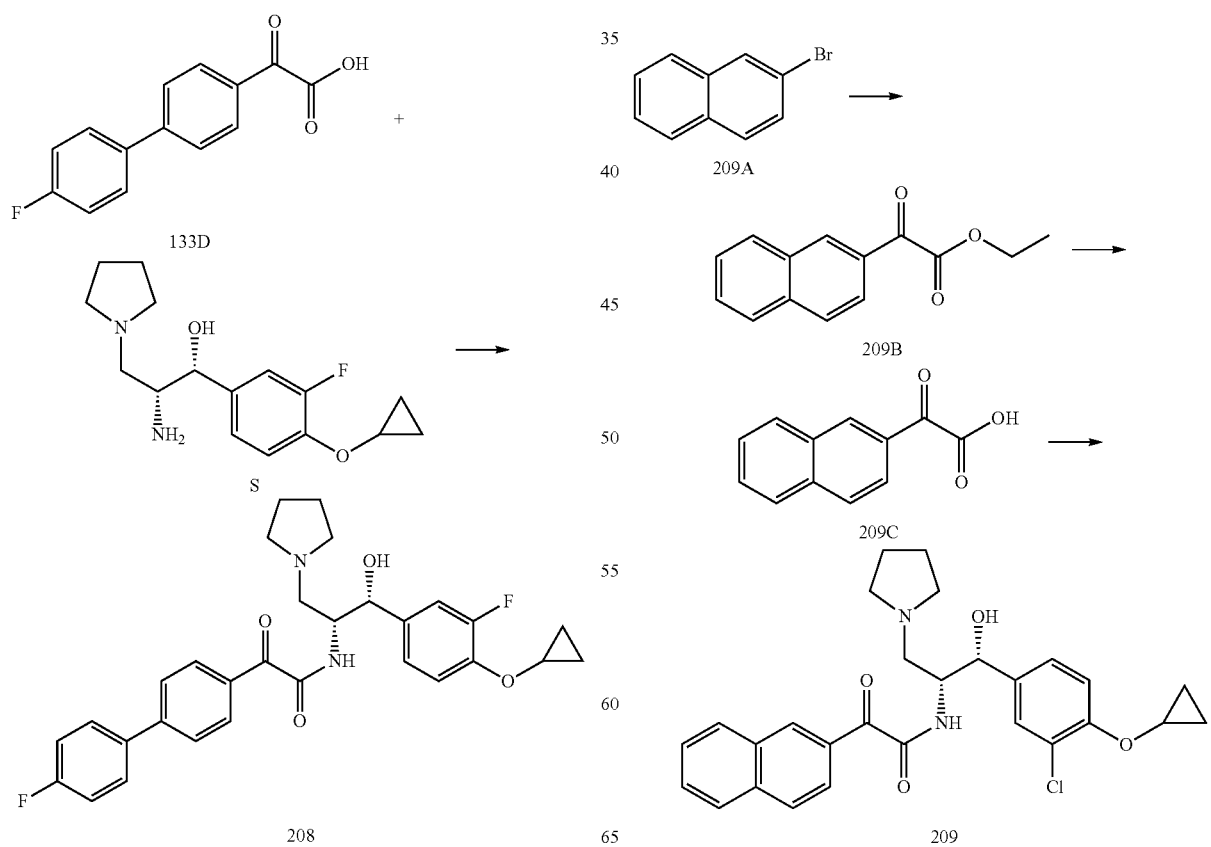

A mixture of Compound 209A (1.0 g, 4.85 mmol), magnesium chips (0.17 g, 7.0 mmol) and THF (15 mL) was stirred at 50° C. for 1 h, and diethyl oxalate (3 mL) was added. The mixture was stirred at 60° C. for 3 h, and saturated NH₄Cl solution (10 mL) was added. It was extracted with ethyl acetate (50 mL×2), washed with brine (50 mL), dried over anhydrous sodium sulfate, and concentrated. The crude product was purified flash with column chromatography on silica gel (10% ethyl acetate in petroleum ether) to afford Compound 209B.

To a solution of Compound 209B (1.4 g, 6.1 mmol) in THF (15 mL) was added LiOH (390 mg, 9.0 mmol) in water (15 mL) at −10° C., and the mixture was stirred at this temperature for 5 h. The reaction mixture was treated with ice water (20 mL) and extracted with ethyl acetate (50 mL). The water layer was adjusted to pH 2 with 1 M HCl and extracted with ethyl acetate (50 mL×2). The combined organic layers were washed with brine (50 mL), dried over anhydrous sodium sulfate, and concentrated. The resulting solid was washed with petroleum ether and filtered to furnish the crude Compound 209C.

A mixture of Compound 209C (160 mg, 0.8 mmol), HATU (608 mg, 1.6 mmol), DMF (6.5 mL), and Intermediate G (298 mg, 0.96 mmol) in DCM (8 mL) was stirred at room temperature overnight. The reaction mixture was treated with water (20 mL), extracted with DCM (50 mL×2), washed with brine (50 mL), dried over anhydrous sodium sulfate, and concentrated. The crude product was purified with prep-HPLC to afford Compound 209. LC-MS (ESI) m/z: 493 [M+H]⁺; ¹H-NMR (CD₃OD, 400 MHz): δ (ppm) 0.5-0.75 (m, 4H), 2.06-2.21 (m, 4H), 3.26-3.30 (m, 1H), 3.58-3.82 (m, 6H), 4.73 (d, J=8.0 Hz, 1H), 5.0 (s, 1H), 7.30 (d, J=8.8 Hz, 1H), 7.40 (d, J=8.8 Hz, 1H), 7.51 (s, 1H), 7.57-7.71 (m, 2H), 7.84-7.95 (m, 4H), 8.26 (s, 1H).

Example 210

A mixture of Compound 201B (141 mg, 0.5 mmol), Intermediate C (148 mg, 0.5 mmol), and HATU (380 mg, 1 mmol) in DMF (5 mL) was stirred at 25° C. for 16 h. The mixture was diluted with DCM (70 mL), and washed with water (30 mL) and brine (30 mL), dried over anhydrous sodium sulfate, and concentrated. The residue was purified with prep-HPLC to yield Compound 210. LC-MS (ESI) m/z: 561 [M+H]⁺; ¹H-NMR (CD₃OD, 400 MHz): δ (ppm) 2.00-2.15 (m, 4H), 3.14-3.26 (m, 2H), 3.50-3.64 (m, 3H), 3.75 (m, 1H), 4.21-4.23 (m, 4H), 4.54 (m, 1H), 4.79 (s, 1H), 6.60-6.63 (m, 2H), 7.05-7.09 (m, 5H), 7.15-7.17 (m, 2H), 7.34 (t, J=8.0 Hz, 1H).

Example 211

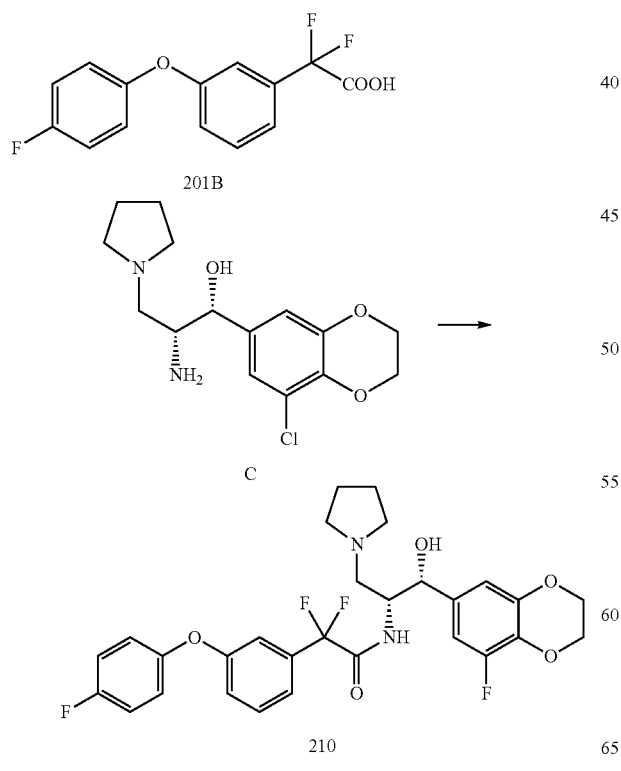

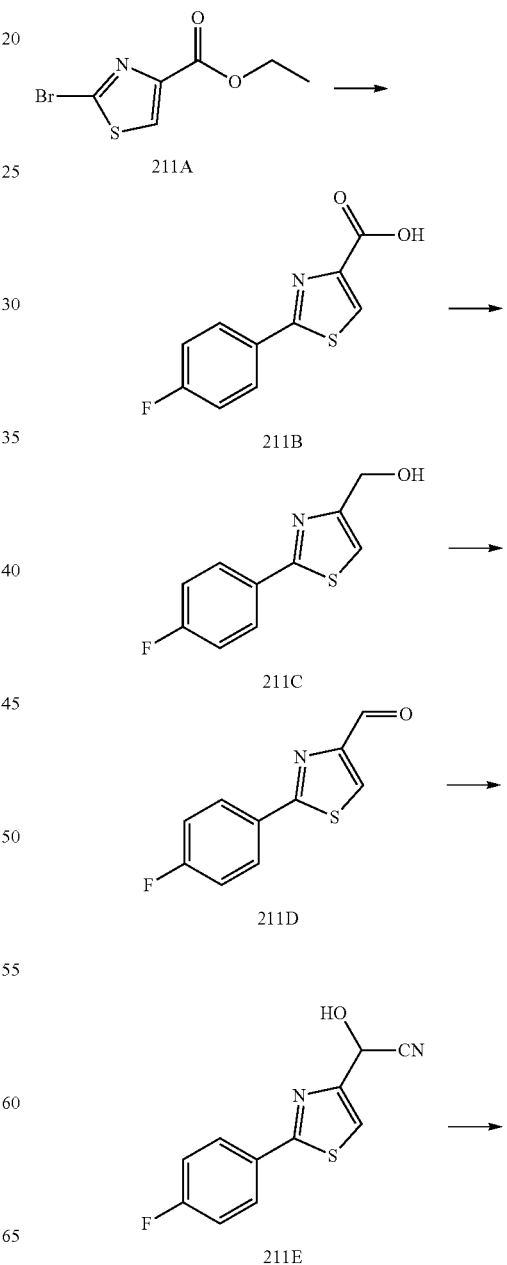

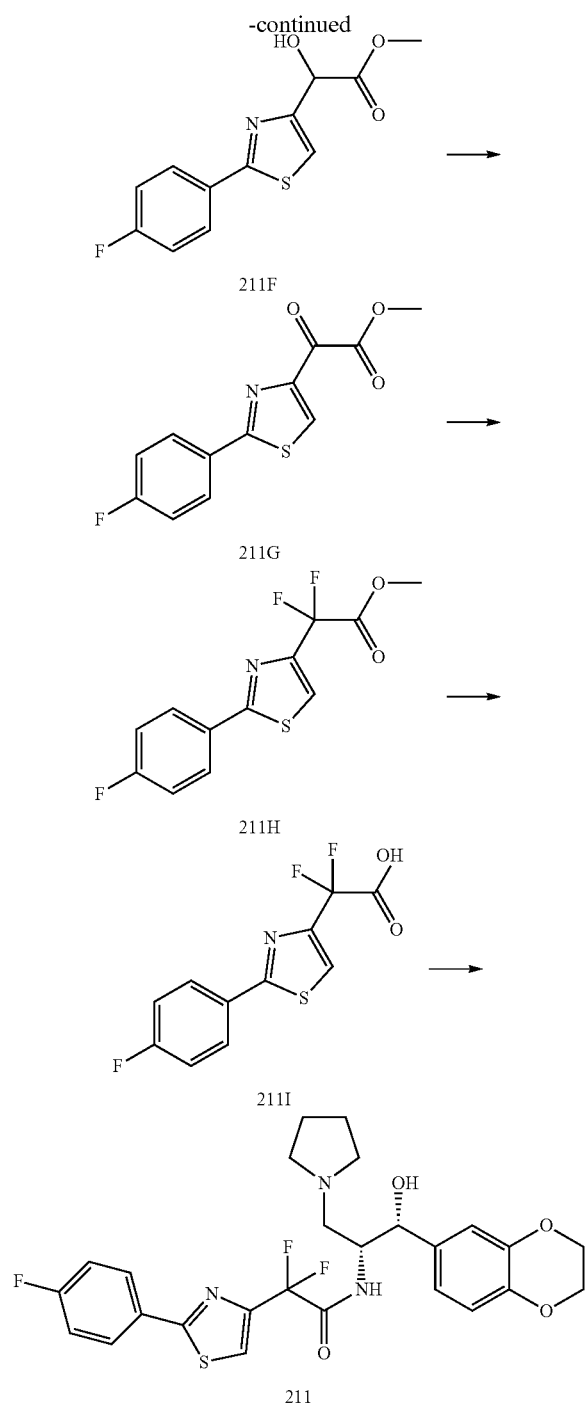

A mixture of Compound 211A (10.00 g, 42.37 mmol), 4-fluorophenylboronic acid (5.51 g, 42.37 mol), PdCl$_2$(PPh$_3$)$_2$ (1.49 g, 2.12 mmol), and sodium bicarbonate (10.68 g, 127.11 mmol) in dioxane (150 mL) and water (30 mL) was stirred at 90° C. for 16 h. It was adjusted to pH 1 with aqueous HCl solution (6 N, 10 mL). The mixture was extracted with dichloromethane (100 mL×3). The combined organic phases were washed with water (200 mL) and brine (200 mL), dried over anhydrous sodium sulfate, concentrated, and purified with flash column chromatography on silica gel (methanol in dichloromethane, from 0% to 8% v/v) to yield Compound 211B.

To a solution of Compound 211B (2.00 g, 7.97 mmol) in THF (50 mL) was added LiAlH$_4$ (303 mg, 7.97 mmol) carefully. The mixture was stirred at 25° C. for 16 h. The reaction mixture was quenched slowly with ice water (4 mL), filtered, and concentrated. The residue was purified with flash column chromatography on silica gel (ethyl acetate in petroleum ether, from 0% to 50% v/v) to afford Compound 211C.

To a solution of Compound 211C (4.30 g, 20.57 mmol) in DCM (100 mL) was added Dess-Martin periodinane (9.60 g, 22.63 mmol) carefully. The mixture was stirred at 25° C. for 16 h. The mixture was filtered to remove the solid and concentrated. The residue was purified with flash column chromatography on silica gel (ethyl acetate in petroleum ether, from 0% to 20% v/v) to afford Compound 211D.

To a solution of Compound 211D (1.80 g, 3.69 mmol) and NaCN (352 mg, 17.39 mmol) in methanol (20 mL) was added AcOH (222 mg, 3.69 mmol) carefully. The mixture was stirred at 25° C. for 16 h, quenched with ice water to form a solid, filtered, and dried to afford Compound 211E.

A mixture of Compound 211E (1.20 g, 5.13 mmol) in methanol (20 mL) under HCl gas was stirred at 20° C. for 16 h. The reaction mixture was quenched with ice water and extracted with dichloromethane (50 mL×3). The combined organic phases were washed with water (150 mL) and brine (150 mL), dried over anhydrous sodium sulfate, and evaporated to furnish Compound 211F.

To a solution of Compound 211F (1.20 g, 4.49 mmol) in DCM (20 mL) was added Dess-Martin periodinane (1.91 g, 4.49 mmol) carefully. The mixture was stirred at 25° C. for 16 h. The mixture was filtered to remove the solid. The filtrate was concentrated and purified with flash column chromatography on silica gel (ethyl acetate in petroleum ether, from 0% to 30% v/v) to yield Compound 211G.

To a solution of Compound 211G (1.00 g, 3.80 mmol) in DCM (10 mL) was added dropwise DAST (3.06 g, 19.00 mmol). The mixture was stirred at 25° C. for 16 h and concentrated. The residue was purified with flash column chromatography on silica gel (ethyl acetate in petroleum ether, from 0% to 15% v/v) to furnish Compound 211H.

A solution of Compound 211H (900 mg, 3.14 mmol) and aqueous LiOH H$_2$O solution (1 N, 4.7 mL, 4.70 mmol) in THF (10 mL) was stirred at 25° C. for 2 h. The mixture was adjusted to pH 1 with aqueous HCl solution (6 N, 5 mL), diluted with ice water (50 mL) to form a solid, filtered, and dried to yield Compound 211I.

A mixture of Compound 211I (100 mg, 0.37 mmol), Intermediate A (102 mg, 0.37 mmol), EDCI (106 mg, 0.56 mmol), and HOBt (76 mg, 0.56 mmol) in dichloromethane (5 mL) and triethylamine (0.2 mL) was stirred at 25° C. for 16 h. The reaction mixture was diluted with ethyl acetate (100 mL), washed with water (30 mL) and brine (30 mL), dried over anhydrous sodium sulfate, concentrated, and purified with prep-HPLC to furnish Compound 211. LC-MS (ESI) m/z: 534 [M+H]$^+$; $^1$H-NMR (CD$_3$OD, 400 MHz): δ (ppm) 1.92-2.13 (m, 4H), 3.12-3.22 (m, 2H), 3.55-3.65 (m, 3H), 3.72-3.78 (m, 1H), 4.12 (s, 4H), 4.50-4.55 (m, 1H), 4.80 (s, 1H), 6.64 (d, J=8.4 Hz, 1H), 6.75-6.81 (m, 2H), 7.26 (t, J=8.8 Hz, 2H), 7.85 (s, 1H), 8.04-8.08 (m, 2H).

Example 212

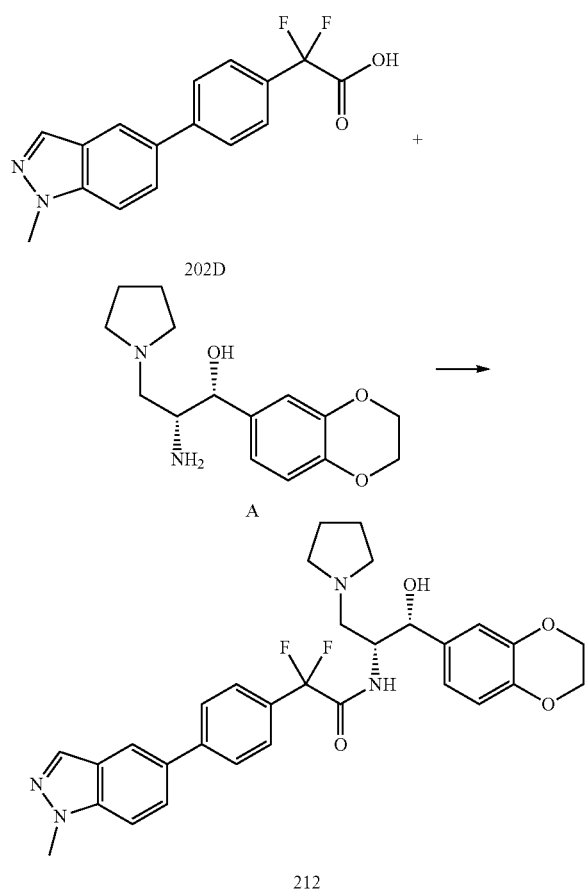

A mixture of Compound 202D (50 mg, 0.16 mmol), EDCI (48 mg, 0.25 mmol), HOBt (34 mg, 0.25 mmol), and Intermediate A (28 mg, 0.26 mmol) in DCM (5 mL) was stirred at 10° C. for 18 h. The mixture was diluted with ethyl acetate (50 mL), washed with water (50 mL×2) and brine (50 mL), and dried over anhydrous sodium sulfate. After evaporation, the crude product was purified with prep-HPLC to afford Compound 212. LC-MS (ESI) m/z: 563 [M+H]$^+$; $^1$H-NMR (CD$_3$OD, 400 MHz): δ (ppm) 2.02-2.18 (m, 4H), 3.14-3.24 (m, 2H), 3.53-3.65 (m, 3H), 3.77-3.84 (m, 1H), 4.06 (s, 4H), 4.12 (s, 3H), 4.55-4.57 (m, 1H), 4.82 (d, J=3.2 Hz, 1H), 6.65 (d, J=8.4 Hz, 1H), 6.74 (dd, J=8.4, 2.0 Hz, 2H), 6.77 (d, J=2.0 Hz, 1H), 7.45 (d, J=8.8 Hz, 1H), 7.68 (d, J=8.8 Hz, 1H), 7.75 (d, J=8.4 Hz, 2H), 7.80 (dd, J=8.8, 1.6 Hz, 1H), 8.08-8.09 (m, 1H), 8.10 (d, J=1.2 Hz, 1H).

Example 213

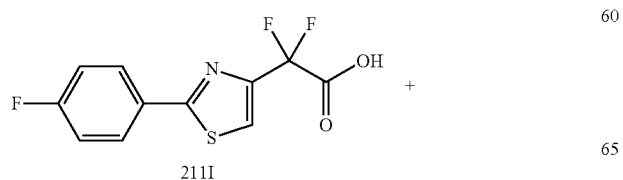

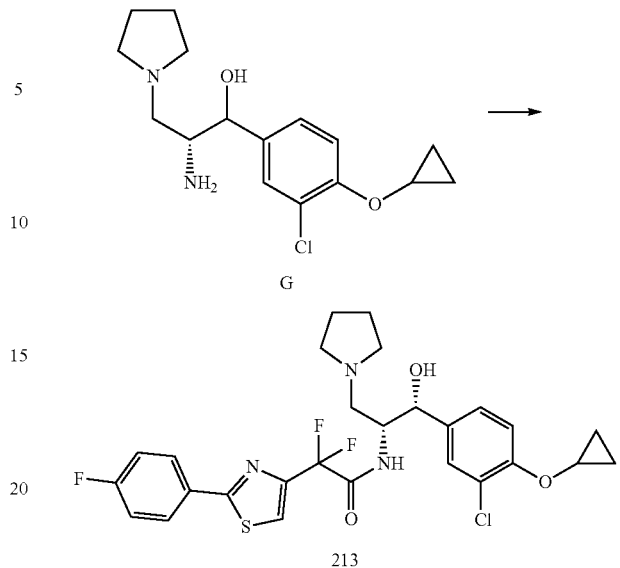

A mixture of Compound 211I (100 mg, 0.37 mmol), Intermediate G (115 mg, 0.37 mmol), HOBt (76 mg, 0.56 mmol), and EDCI (106 mg, 0.56 mmol) in dichloromethane (5 mL) and triethylamine (0.2 mL) was stirred at ambient temperature for 16 hours. The reaction mixture was diluted with ethyl acetate (120 mL), washed with water (100 mL) and brine (100 mL), dried over anhydrous sodium sulfate, concentrated, and purified with prep-HPLC to afford Compound 213. LC-MS (ESI) m/z: 566 [M+H]$^+$; $^1$H-NMR (CD$_3$OD, 400 MHz): δ (ppm) 0.62-0.75 (m, 4H), 1.96-2.14 (m, 4H), 3.13-3.26 (m, 2H), 3.60-3.67 (m, 4H), 3.73-3.78 (m, 1H), 4.54-4.58 (m, 1H), 4.88 (s, 1H), 7.14 (d, J=8.4 Hz, 1H), 7.24-7.29 (m, 3H), 7.34 (s, 1H), 7.85 (s, 1H), 8.04-8.08 (m, 2H).

Example 214

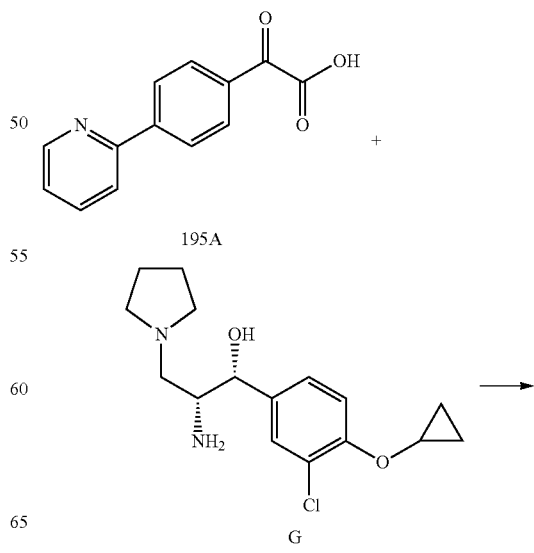

-continued

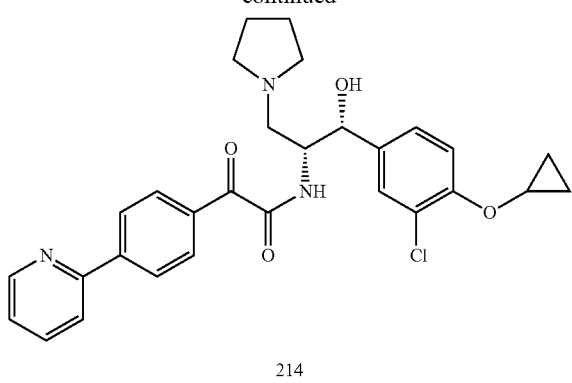

214

A mixture of Compound 195A (150 mg, 0.66 mmol), Intermediate G (205 mg, 0.66 mmol), HATU (500 mg, 1.32 mmol), and DIPEA (0.2 mL) in DMF (20 mL) was stirred at 25° C. for 16 h. The reaction mixture was diluted with ethyl acetate (50 mL), washed with water (20 mL×3) and brine (20 mL), dried over anhydrous sodium sulfate, concentrated, and purified with prep-HPLC and chiral HPLC to furnish the desired product, which was further purified with prep-HPLC to yield Compound 214. LC-MS (ESI) m/z: 520 [M+H]$^+$; $^1$H-NMR (CD$_3$OD, 400 MHz): δ (ppm) 0.62-0.81 (m, 4H), 2.05-2.23 (m, 4H), 3.15-3.28 (m, 2H), 3.58-3.85 (m, 5H), 4.69-4.72 (m, 1H), 4.99 (m, 1H), 7.09-8.06 (m, 10H), 8.72 (m, 1H).

Example 215

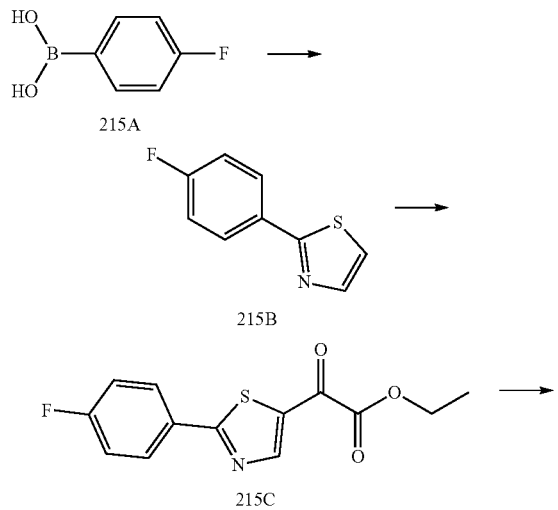

-continued

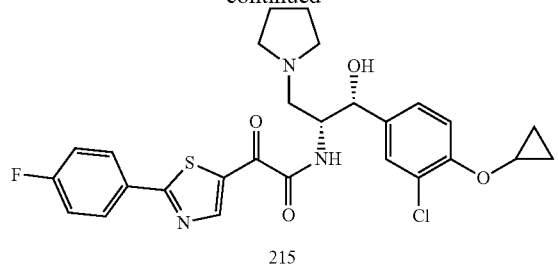

215

A mixture of Compound 215A (2.05 g, 14.6 mmol), 2-bromothiazole (2 g, 12.2 mmol), K$_2$CO$_3$ (3.12 g, 24.4 mmol) and Pd(PPh$_3$)$_2$Cl$_2$ (856 mg, 1.22 mmol) in dioxane (40 mL) and water (4 mL) was stirred at 80° C. for 2 h. The mixture was cooled to room temperature, diluted with water (50 mL), extracted with ethyl acetate (100 mL). The ethyl acetate layer was washed with water (100 mL×3) and brine (100 mL), dried over anhydrous sodium sulfate, concentrated, and purified with flash column chromatography on silica gel (ethyl acetate in petroleum ether, 10% v/v) to afford Compound 215B.

To a solution of Compound 215B (1.4 g, 7.8 mmol) in THF (30 mL) was added n-BuLi (3.4 mL, 8.6 mmol) dropwise at −78° C. The mixture was stirred for 15 min and diethyl oxalate (2.28 g, 15.6 mmol) was added at −78° C. The mixture was stirred for 1 h. The reaction mixture was diluted with ethyl acetate (100 mL), washed with water (50 mL×3) and brine (50 mL), dried over anhydrous sodium sulfate, and concentrated to afford Compound 215C.

To a solution of Compound 215C (400 mg, 1.43 mmol) in THF (10 mL) and water (1 mL) was added LiOH (90 mg, 2.15 mmol). The mixture was stirred at room temperature overnight, diluted with water (50 mL), and extracted with ethyl acetate (50 mL). The aqueous layer was adjusted to pH 2 with 1 M HCl. The precipitate was collected with filtration and dried to furnish Compound 215D.

To a mixture of Compound 215D (97 mg, 0.386 mmol) in DCM (2 mL) was added HATU (176 mg, 0.463 mmol) and Intermediate G (120 mg, 0.386 mmol). The mixture was stirred at room temperature overnight. The mixture was treated with water (50 mL), extracted with DCM (50 mL×2), dried over anhydrous sodium sulfate, and concentrated. The crude product was purified with prep-HPLC to afford Compound 215. LC-MS (ESI) m/z: 544 [M+H]$^+$; $^1$H-NMR (DMSO-d$_6$, 400 MHz): δ (ppm) 0.61-0.66 (m, 2H), 0.76-0.82 (m, 2H), 1.80-1.88 (m, 2H), 1.96-2.03 (m, 2H), 3.09-3.17 (m, 2H), 3.30-3.37 (m, 1H), 3.47-3.60 (m, 3H), 3.87-3.91 (m, 1H), 4.41-4.47 (m, 1H), 4.79-4.80 (m, 1H), 6.02-6.07 (m, 1H), 7.28-7.45 (m, 5H), 8.14-8.18 (m, 2H), 8.63 (d, J=9.2 Hz, 1H), 8.81 (s, 1H), 9.10-9.18 (m, 1H).

Example 216

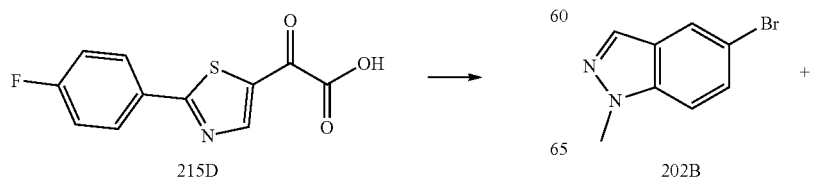

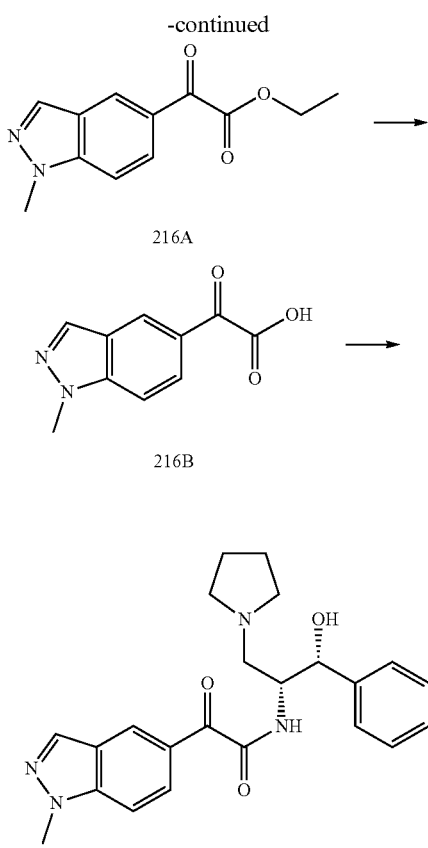

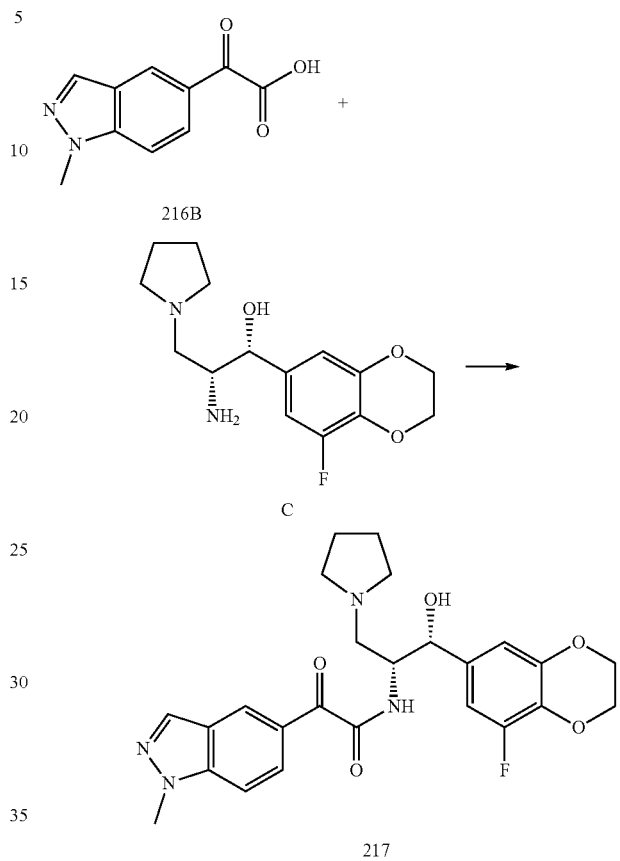

To a solution of Compound 202B (400 mg, 1.89 mmol) in THF (10 mL) was added n-BuLi (2.5 N, 0.76 mL) under nitrogen at −78° C., and the resultant mixture was stirred for 30 min. And then diethyl oxalate (0.65 mL, 4.73 mmol) was added to above mixture, and the resultant mixture was stirred at −78° C. for 1 h. The mixture was quenched with saturated aqueous NH$_4$Cl solution (10 mL), and extracted with ethyl acetate (50 mL×2), washed with saturated aqueous sodium bicarbonate solution (50 mL×2) and brine (50 mL), dried over anhydrous sodium sulfate, and concentrated to furnish Compound 216A.

To a solution of Compound 216A (490 mg, 2.11 mmol) in methanol (5 mL) was added a solution of LiOH H$_2$O (177 mg, 4.22 mmol) in water (5 mL), and the mixture was stirred at room temperature overnight. The crude product was purified with reverse phase chromatography using eluent (methanol in water, from 0% to 7% v/v) to furnish Compound 216B.

A mixture of Compound 216B (100 mg, 0.49 mmol), HATU (279 mg, 0.74 mmol), and Intermediate A (136 mg, 0.49 mmol) in DMF (5 mL) was stirred at 10° C. for 18 h. The mixture was purified with prep-HPLC to afford Compound 216. LC-MS (ESI) m/z: 465 [M+H]$^+$; $^1$H-NMR (CD$_3$OD, 400 MHz): δ (ppm) 2.03-2.07 (m, 2H), 2.18-2.22 (m, 2H), 3.22-3.27 (m, 2H), 3.54-3.58 (m, 1H), 3.67-3.73 (m, 2H), 3.79-3.85 (m, 1H), 4.03-4.24 (m, 7H), 4.68-4.71 (m, 1H), 4.92 (s, 1H), 6.84 (d, J=8.0 Hz, 1H), 6.93 (dd, J=8.4, 2.0 Hz, 1H), 6.97 (d, J=1.6 Hz, 1H), 7.63 (d, J=9.2 Hz, 1H), 7.96 (dd, J=8.8, 1.6 Hz, 1H), 8.11 (s, 1H), 8.20 (s, 1H).

Example 217

A mixture of Compound 216B (100 mg, 0.49 mmol), HATU (279 mg, 0.74 mmol), and Intermediate C (138 mg, 0.49 mmol) in DMF (5 mL) was stirred at 10° C. for 18 h. The mixture was purified with prep-HPLC to afford Compound 217. LC-MS (ESI) m/z: 483 [M+H]$^+$; $^1$H-NMR (CD$_3$OD, 400 MHz): δ (ppm) 2.03-2.07 (m, 2H), 2.20-2.22 (m, 2H), 3.20-3.29 (m, 2H), 3.55-3.59 (m, 1H), 3.67-3.73 (m, 2H), 3.78-3.84 (m, 1H), 4.08-4.13 (m, 4H), 4.20-4.31 (m, 3H), 4.68-4.71 (m, 1H), 4.90 (d, J=2.4 Hz, 1H), 6.82-6.86 (m, 2H), 7.63 (d, J=8.8 Hz, 1H), 7.96 (dd, J=8.8, 1.6 Hz, 1H), 8.17 (s, 1H), 8.19 (s, 1H).

Example 218

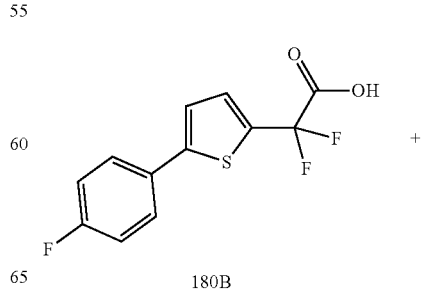

180B

-continued

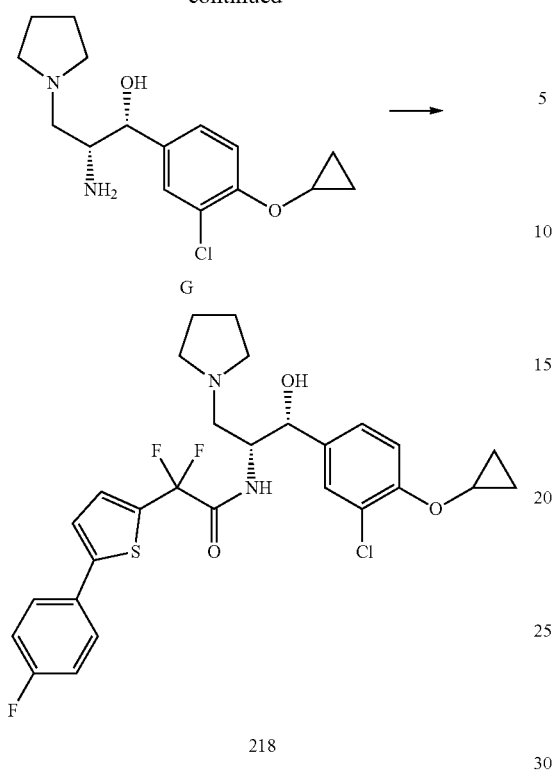

218

-continued

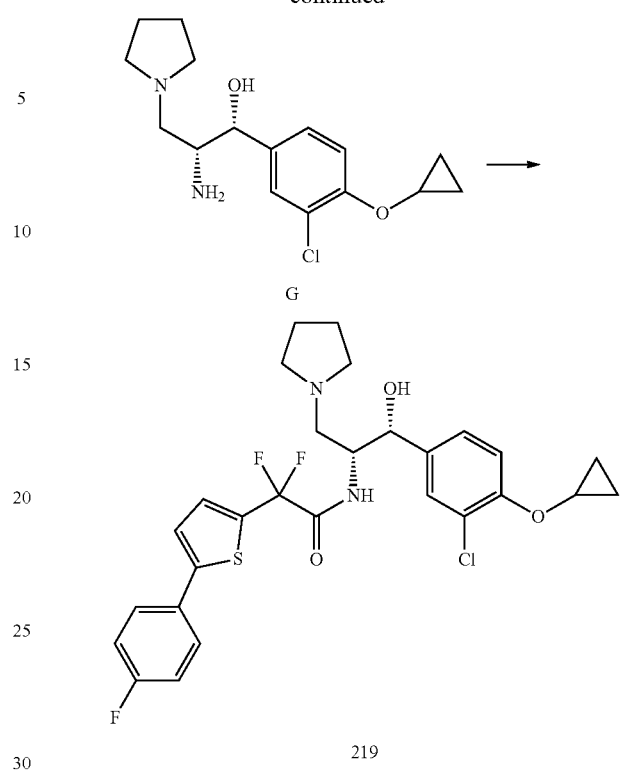

219

To a solution of Compound 180B (88 mg, 0.32 mmol) in DMF (10 mL) was added EDCI (93 mg, 0.48 mmol), HOBt (65 mg, 0.48 mmol) and Intermediate G (100 mg, 0.32 mmol). The mixture was stirred at 25° C. overnight. The reaction mixture was quenched with saturated sodium bicarbonate solution (5 mL) and extracted with ethyl acetate (50 mL×3). The combined organic phases were washed with water (5 mL) and brine (5 mL), dried over anhydrous sodium sulfate, filtered, and concentrated. The crude product was purified with prep-HPLC to furnish Compound 218. LC-MS (ESI) m/z: 565 [M+H]$^+$; $^1$H-NMR (CD$_3$OD, 400 MHz): δ (ppm) 0.54-0.56 (m, 2H), 0.63-0.64 (m, 2H), 2.03-2.05 (m, 2H), 2.16-2.18 (m, 2H), 3.18-3.26 (m, 2H), 3.54-3.59 (m, 2H), 3.66-3.72 (m, 2H), 3.78-3.79 (m, 1H), 4.61-4.64 (m, 1H), 4.91 (s, 1H), 7.05 (d, J=3.2 Hz, 1H), 7.10 (d, J=8.4 Hz, 1H), 7.17-7.21 (m, 3H), 7.24 (d, J=3.6 Hz, 1H), 7.34 (d, J=1.2 Hz, 1H), 7.67-7.70 (m, 2H).

Example 219

To a solution of Intermediate G (136 mg, 0.44 mmol) in DMF (10 mL) was added Compound 174E (110 mg, 0.44 mmol), HATU (251 mg, 0.66 mmol), and DIPEA (114 mg, 0.88 mmol). The mixture was stirred at 25° C. overnight. The reaction mixture was quenched with saturated sodium bicarbonate solution (5 mL) and extracted with ethyl acetate (50 mL×3). The combined organic phases were washed with water (5 mL) and brine (5 mL), dried over anhydrous sodium sulfate, filtered, and concentrated. The crude product was purified with prep-HPLC to afford Compound 219. LC-MS (ESI) m/z: 543 [M+H]$^+$; $^1$H-NMR (CD$_3$OD, 400 MHz): δ (ppm) 0.62-0.66 (m, 2H), 0.73-0.78 (m, 2H), 2.00-2.04 (m, 2H), 2.16-2.19 (m, 2H), 3.19-3.28 (m, 2H), 3.48-3.52 (m, 1H), 3.65-3.79 (m, 4H), 4.52-4.54 (m, 1H), 4.91 (s, 1H), 7.22 (t, J=8.8 Hz, 2H), 7.32 (s, 2H), 7.41 (s, 1H), 7.48 (t, J=2.4 Hz, 1H), 7.78-7.82 (m, 2H), 8.11 (d, J=4.4 Hz, 1H).

Example 220

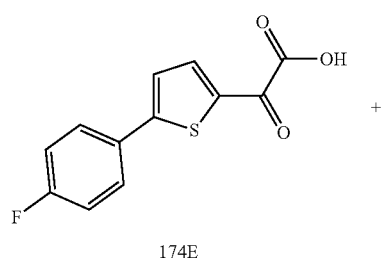

174E

+

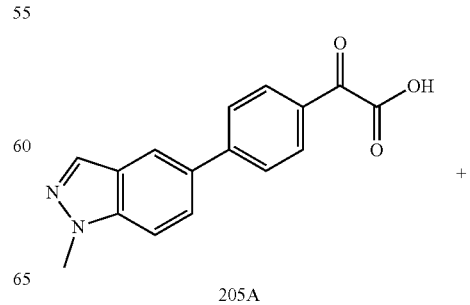

205A

+

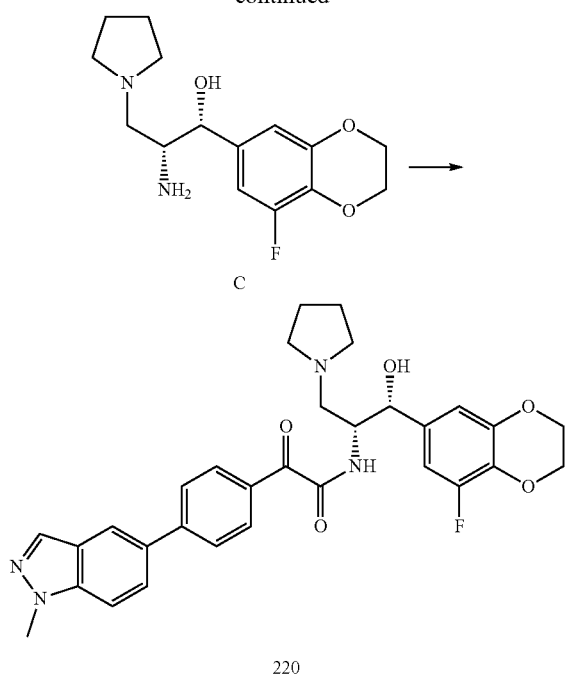

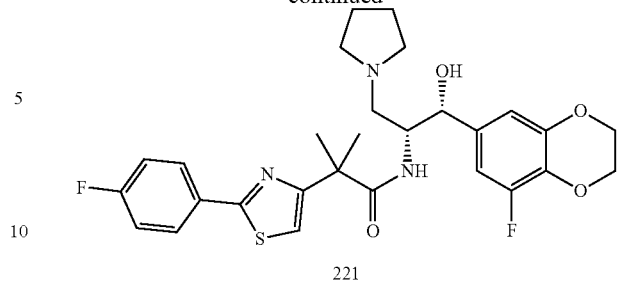

A mixture of Compound 205A (56 mg, 0.20 mmol), Intermediate C (59 mg, 0.20 mmol), and HATU (119 mg, 0.30 mmol) in DMF (10 mL) was stirred at 10° C. for 2 h. The reaction mixture was treated with water (10 mL), extracted with dichloromethane (20 mL×3), dried over anhydrous sodium sulfate, concentrated in vacuo, and purified with prep-HPLC to yield Compound 220. LC-MS (ESI) m/z: 559 [M+H]$^+$; $^1$H-NMR (DMSO-d$_6$, 400 MHz): δ (ppm) 1.88 (s, 2H), 2.03 (s, 2H), 3.09-3.21 (m, 2H), 3.45 (d, J=8 Hz, 2H), 3.56 (s, 2H), 4.09 (s, 3H), 4.28 (s, 4H), 4.51 (s, 1H), 4.78 (s, 1H), 6.81 (t, J=16 Hz, 2H), 7.80 (q, J=12 Hz, 2H), 7.91 (dd, J=12, 4 Hz, 4H), 8.17 (s, 2H), 8.74 (d, J=8 Hz, 1H).

Example 221

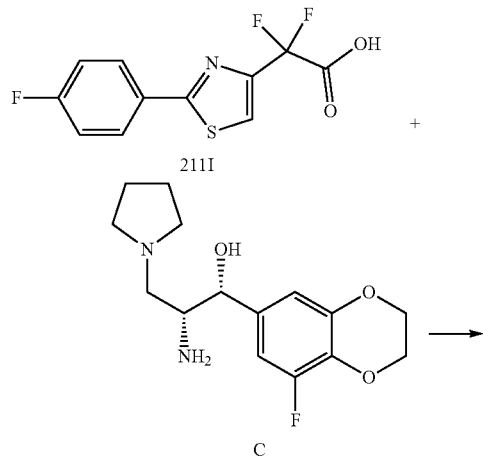

A mixture of Compound 211I (100 mg, 0.37 mmol), Intermediate C (110 mg, 0.37 mmol), HOBt (76 mg, 0.56 mmol), and EDCI (106 mg, 0.56 mmol) in dichloromethane (5 mL) and triethylamine (0.2 mL) was stirred at ambient temperature for 16 hours. The reaction mixture was diluted with ethyl acetate (120 mL), washed with water (100 mL) and brine (100 mL), dried over anhydrous sodium sulfate, concentrated, and purified with prep-HPLC to afford Compound 221. LC-MS (ESI) m/z: 552 [M+H]$^+$; $^1$H-NMR (CD$_3$OD, 400 MHz): δ (ppm) 1.95-2.14 (m, 4H), 3.14-3.31 (m, 2H), 3.58-3.64 (m, 3H), 3.72-3.78 (m, 1H), 4.17 (s, 4H), 4.52-4.56 (m, 1H), 4.82 (s, 1H), 6.85-6.70 (m, 2H), 7.24-7.29 (m, 2H), 7.91 (s, 1H), 8.05-8.09 (m, 2H).

Example 222

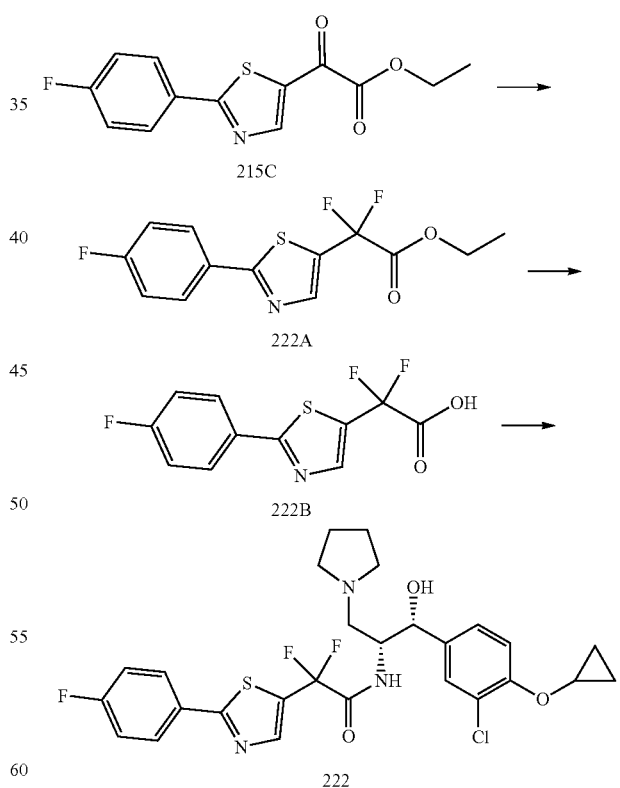

To a solution of Compound 215C (1.0 g, 3.58 mmol) in DCM (20 mL) was added DAST (2.89 g, 17.9 mmol) and the mixture was stirred at 30° C. overnight. The mixture was diluted with DCM (100 mL), washed with water (50 mL×3) and brine (50 mL), dried over anhydrous sodium sulfate, concentrated, and purified with flash column chromatography on silica gel (ethyl acetate in petroleum ether, 10% v/v) to afford Compound 222A.

To a solution of Compound 222A (1.04 g, 3.45 mmol) in THF (20 mL) and water (2 mL) was added LiOH (217 mg, 5.18 mmol). The mixture was stirred at room temperature overnight, diluted with water (50 mL), and adjusted to pH 2 with 1M HCl. The precipitate was collected with filtration and dried to furnish Compound 222B.

To a mixture of Compound 222B (100 mg, 0.366 mmol) in DCM (2 mL) was added HATU (167 mg, 0.44 mmol) and Intermediate G (114 mg, 0.366 mmol). The mixture was stirred at room temperature overnight. The mixture was treated with water (50 mL), extracted with DCM (50 mL×2), dried over anhydrous sodium sulfate, and concentrated. The crude product was purified with prep-HPLC to afford Compound 222. LC-MS (ESI) m/z: 566 [M+H]+; 1H-NMR (DMSO-d6, 400 MHz): δ (ppm) 0.51-0.53 (m, 2H), 0.66-0.67 (m, 2H), 1.85-1.90 (m, 2H), 1.98-2.02 (m, 2H), 3.10-3.21 (m, 2H), 3.42-3.53 (m, 4H), 3.63-3.67 (m, 1H), 4.45-4.51 (m, 1H), 4.80 (s, 1H), 5.98-6.01 (m, 1H), 7.14-7.18 (m, 2H), 7.26 (s, 1H), 7.39-7.43 (m, 2H), 7.94 (s, 1H), 8.02-8.05 (m, 2H), 8.89 (d, J=9.2 Hz, 1H), 9.38-9.47 (m, 1H).

Example 223

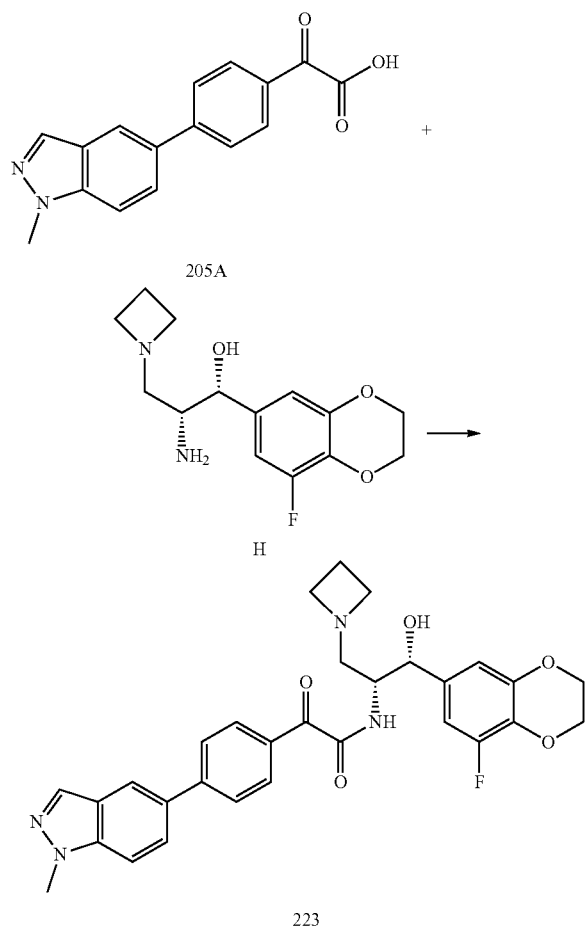

223

A mixture of Compound 205A (56 mg, 0.20 mmol), Intermediate H (56 mg, 0.20 mmol), and HATU (119 mg, 0.30 mmol) in DMF (10 mL) was stirred at 10° C. for 2 h. The reaction mixture was treated with water (10 mL), extracted with dichloromethane (20 mL×3), dried over anhydrous sodium sulfate, concentrated in vacuo, and purified with prep-HPLC to yield Compound 223. LC-MS (ESI) m/z: 545 [M+H]+; 1H-NMR (DMSO-d6, 400 MHz): δ (ppm) 2.26 (s, 1H), 2.42 (t, J=8 Hz, 1H), 3.44-3.48 (m, 2H), 4.09 (s, 3H), 4.19-4.43 (m, 9H), 4.74 (s, 1H), 6.80 (t, J=16 Hz, 2H), 7.81-7.87 (m, 6H), 8.17 (s, 2H), 8.74 (d, 2H), 9.63 (brs, 2H).

Example 224

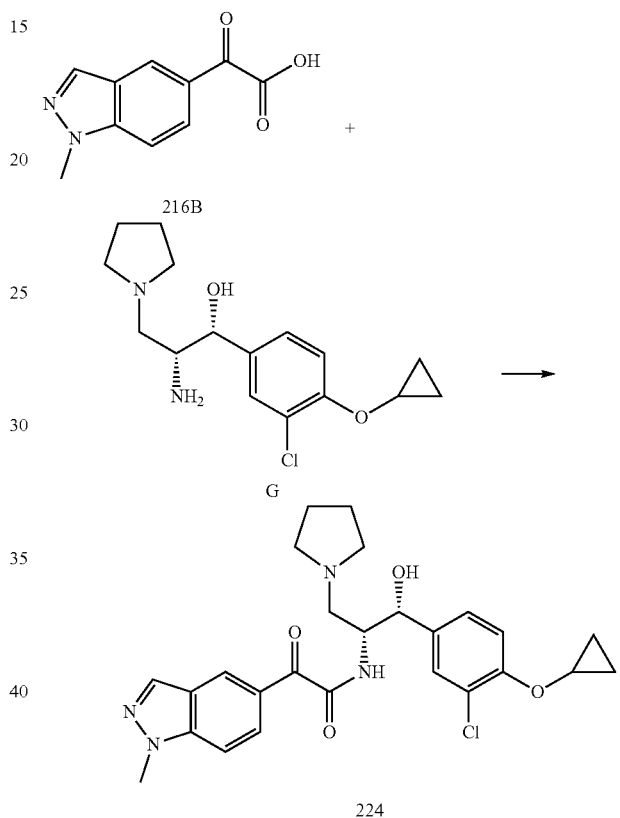

224

A mixture of Compound 216B (100 mg, 0.49 mmol), HATU (279 mg, 0.74 mmol), and Intermediate G (152 mg, 0.49 mmol) in DMF (5 mL) was stirred at 10° C. for 18 h. The mixture was purified with prep-HPLC to afford Compound 224. LC-MS (ESI) m/z: 497 [M+H]+; 1H-NMR (CD3OD, 400 MHz): δ (ppm) 0.59-0.83 (m, 4H), 2.04-2.23 (m, 4H), 3.24-3.27 (m, 1H), 3.34-3.35 (m, 1H), 3.59-3.82 (m, 5H), 4.11 (s, 3H), 4.73-4.77 (m, 1H), 5.01 (s, 1H), 7.34 (d, J=8.8 Hz, 1H), 7.40 (dd, J=8.4, 1.6 Hz, 1H), 7.49 (d, J=2.0 Hz, 1H), 7.59 (d, J=8.8 Hz, 1H), 7.89 (d, J=8.8 Hz, 1H), 7.99 (s, 1H), 8.15 (s, 1H).

Example 225

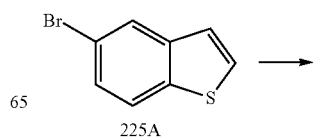

225A

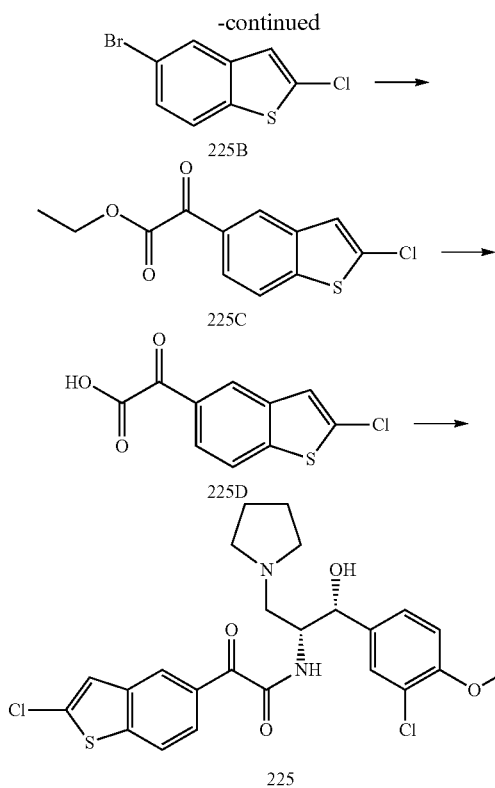

To a mixture of LDA (2 N, 8.3 mL, 16.5 mmol) in tetrahydrofuran (10 mL) under nitrogen was added Compound 225A (3.2 g, 15.0 mmol) in tetrahydrofuran (5 mL) slowly at −78° C. It was stirred at −78° C. for 1 h, and the mixture was added to a solution of carbon tetrachloride (5.5 mL, 56.6 mmol) in tetrahydrofuran (15 mL) at −78° C. The resultant mixture was stirred at −78° C. for 1.5 h, quenched with ammonium chloride solution (50 mL), warmed to room temperature, and extracted with DCM (100 mL×2). The combined organic phases were washed with water (50 mL) and brine (50 mL), dried over anhydrous sodium sulfate, filtered, and concentrated. The residue was purified with flash column chromatography on silica gel (petroleum ether, 100% v/v) to furnish Compound 225B.

A solution of Compound 225B (1.2 g, 5 mmol) in THF (10 mL) under nitrogen was added n-BuLi (2.4 N, 2.5 mL, 6 mmol) at −78° C. The mixture was stirred at −78° C. for 30 min. To the above mixture was added diethyl oxalate (5 mL). The resultant solution was stirred at −78° C. for 15 min, quenched with saturated aqueous $NH_4Cl$ solution (10 mL), and extracted with ethyl acetate (50 mL×2). The combined organic phases were washed with water (50 mL) and brine (50 mL), dried over anhydrous sodium sulfate, filtered, and concentrated. The residue was purified with flash column chromatography on silica gel (petroleum ether, 100% v/v) to afford Compound 225C.

To a solution of Compound 225C (268 mg, 1 mmol) in MeOH (5 mL) was added a solution of LiOH·$H_2O$ (126 mg, 3 mmol) in water (2 mL). The mixture was stirred at room temperature overnight. The solution was concentrated to remove methanol, adjusted to pH 2 with HCl (6 N, 2 mL), and extracted with ethyl acetate (50 mL×2). The combined organic phases were washed with water (50 mL) and brine (50 mL), dried over anhydrous sodium sulfate, filtered, and concentrated. The residue was purified with flash column chromatography on silica gel (ethyl acetate in petroleum ether, from 10% to 20% v/v) to furnish Compound 225D.

A mixture of Compound 225D (125 mg, 0.5 mmol), HATU (342 mg, 0.9 mmol), and Intermediate G (162 mg, 0.5 mmol) in DMF (2 mL) and DCM (5 mL) was stirred at 25° C. overnight. The mixture was concentrated, and purified with prep-HPLC to yield Compound 225. LC-MS (ESI) m/z: 533 [M+H]$^+$; $^1$H-NMR (CD$_3$OD, 400 MHz): δ (ppm) 0.65-0.090 (m, 4H), 1.97-2.23 (m, 4H), 3.12-3.27 (m, 1H), 3.58-3.62 (m, 1H), 3.69-3.85 (m, 5H), 4.60-4.63 (m, 1H), 5.01 (s, 1H), 7.37-7.52 (m, 4H), 7.52 (s, 1H), 7.68 (d, J=8.0 Hz, 1H), 7.84 (d, J=8.0 Hz, 1H).

Example 226

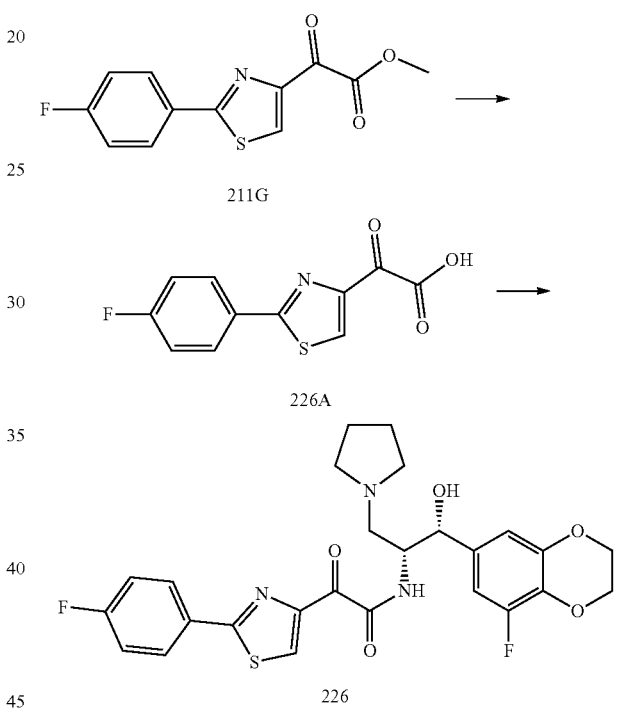

A solution of Compound 211G (500 mg, 1.89 mmol) and LiOH·$H_2O$ (119 mg, 2.83 mmol) in THF (10 mL) and water (2 mL) was stirred at −10° C. for 1 h. It was diluted with ice water (20 mL) and adjusted to pH 1 with diluted hydrochloric acid (6 M) to form a solid. The mixture was filtered and the resulting solid was dried to yield Compound 226A.

A mixture of Compound 226A (100 mg, 0.40 mmol), Intermediate C (118 mg, 0.40 mmol), and HATU (228 mg, 0.60 mmol) in DMF (3 mL) was stirred at room temperature for 16 h. It was diluted with ethyl acetate (120 mL), washed with water (100 mL) and brine (100 mL), dried over anhydrous sodium sulfate, concentrated, and purified with prep-HPLC to afford Compound 226. LC-MS (ESI) m/z: 530 [M+H]$^+$; $^1$H-NMR (DMSO-d$_6$, 400 MHz): δ (ppm) 1.84 (brs, 2H), 1.99 (brs, 2H), 3.08-3.16 (m, 2H), 3.38-3.54 (m, 4H), 4.25 (s, 4H), 4.45 (t, J=6.0 Hz, 1H), 4.76 (s, 1H), 6.14 (brs, 1H), 6.74 (s, 1H), 6.81 (d, J=11.6 Hz, 1H), 7.40 (t, J=8.8 Hz, 2H), 8.08-8.12 (m, 2H), 8.80 (d, J=9.6 Hz, 1H), 8.96 (s, 1H), 9.37 (brs, 1H).

Example 227

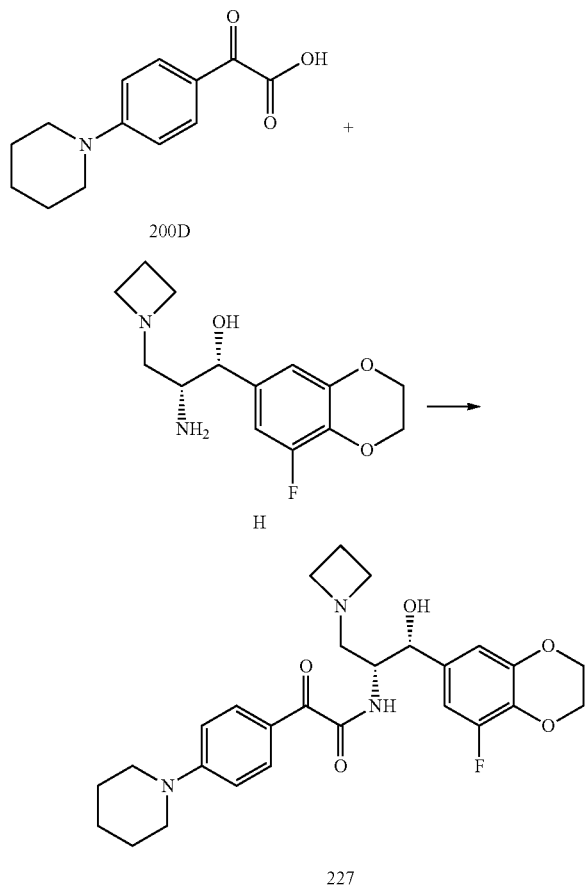

A mixture of Compound 200D (46 mg, 0.20 mmol), Intermediate H (63 mg, 0.20 mmol), and HATU (119 mg, 0.30 mmol) in DMF (10 mL) was stirred at 10° C. for 3 h. The reaction mixture was treated with water (10 mL), extracted with dichloromethane (20 mL×3), dried over anhydrous sodium sulfate, concentrated in vacuo, and purified with prep-HPLC to yield Compound 227. LC-MS (ESI) m/z: 498 [M+H]$^+$; $^1$H-NMR (CDCl$_3$, 400 MHz): δ (ppm) 1.22 (s, 2H), 1.66 (s, 6H), 3.44-3.48 (m, 5H), 3.67 (d, J=12 Hz, 1H), 4.15-4.33 (m, 9H), 4.90 (s, 1H), 6.69 (d, J=12 Hz, 2H), 6.76 (d, J=8 Hz, 2H), 7.67 (d, J=8 Hz, 2H).

Example 228

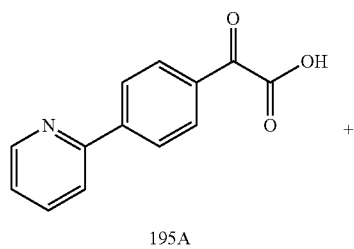

195A

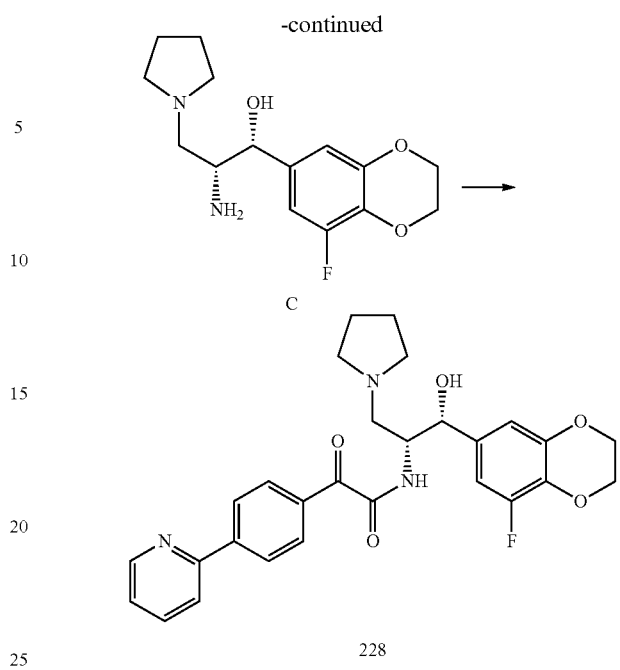

A mixture of Compound 195A (100 mg, 0.44 mmol), Intermediate C (130 mg, 0.44 mmol), and HATU (335 mg, 0.88 mmol) in DMF (10 mL) was stirred at room temperature overnight. The reaction mixture was diluted with ethyl acetate (50 mL), washed with water (20 mL×3) and brine (20 mL), dried over anhydrous sodium sulfate, concentrated, and purified with prep-HPLC to yield Compound 228. LC-MS (ESI) m/z: 506 [M+H]$^+$; $^1$H-NMR (DMSO-d$_6$, 400 MHz): δ (ppm) 1.73-1.75 (m, 4H), 2.54-2.68 (m, 6H), 4.31-4.33 (m, 5H), 4.76-4.77 (s, 1H), 5.69 (s, 1H), 6.75 (s, 1H), 6.81 (d, J=10.4 Hz, 1H), 7.45-7.46 (m, 1H), 7.83-7.98 (m, 3H), 8.07-8.08 (m, 1H), 8.19-8.20 (m, 2H), 8.63-8.64 (m, 1H), 8.74-8.75 (m, 1H).

Example 229

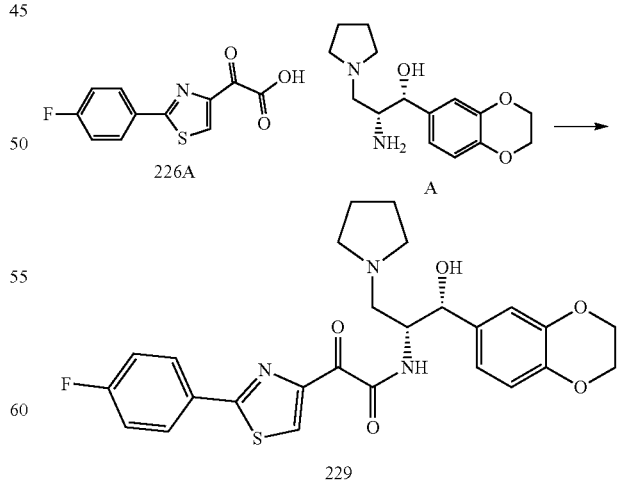

A mixture of Compound 226A (100 mg, 0.40 mmol), Intermediate A (111 mg, 0.40 mmol), and HATU (228 mg, 0.60 mmol) in DMF (3 mL) was stirred at room temperature for 16 h. It was diluted with ethyl acetate (120 mL), washed with water (100 mL) and brine (100 mL), dried over anhydrous sodium sulfate, concentrated, and purified with prep-HPLC to afford Compound 229. LC-MS (ESI) m/z: 512 [M+H]$^+$; $^1$H-NMR (DMSO-d$_6$, 400 MHz): δ (ppm) 1.83 (brs, 2H), 1.99 (brs, 2H), 3.06-3.17 (m, 2H), 3.37-3.53 (m, 4H), 4.18 (s, 4H), 4.43 (t, J=11.2 Hz, 1H), 4.74 (s, 1H), 5.99 (brs, 1H), 6.77-6.87 (m, 3H), 7.40 (t, J=8.8 Hz, 2H), 8.08-8.12 (m, 2H), 8.80 (d, J=9.6 Hz, 1H), 8.95 (s, 1H), 9.24 (brs, 1H).

Example 230

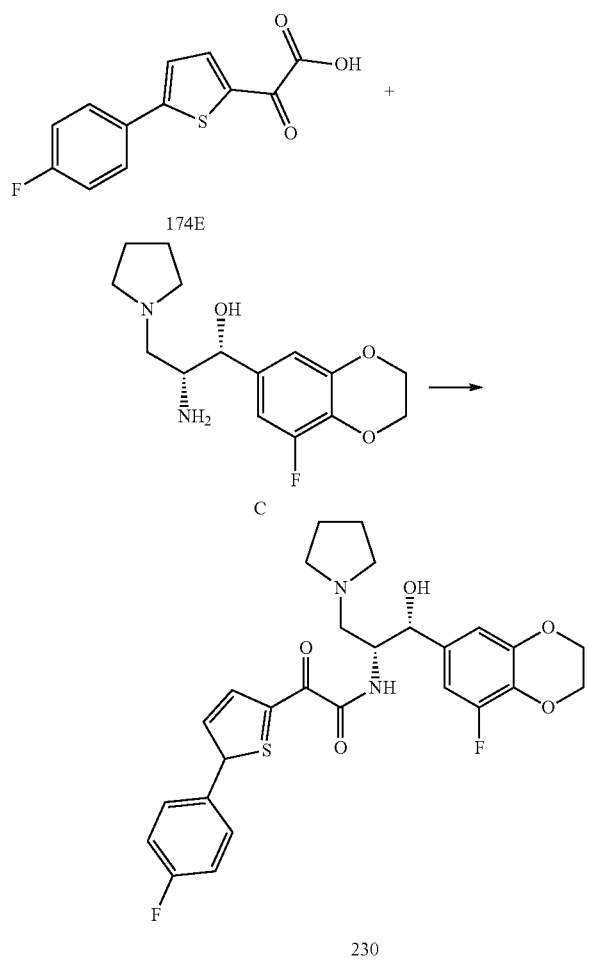

To a solution of Compound 174E (62 mg, 0.25 mmol) in DMF (5 mL) was added Intermediate C (74 mg, 0.25 mmol) and HATU (141 mg, 0.37 mmol). The reaction mixture was stirred at 25° C. for 16 h. The mixture was purified with prep-HPLC to yield Compound 230. LC-MS (m/z) 529 [M+H]$^+$; $^1$H-NMR (CDCl$_3$, 400 MHz): δ (ppm) 2.14-2.17 (m, 4H), 2.77-2.87 (m, 2H), 3.11-3.14 (m, 2H), 3.49-3.51 (m, 1H), 3.82-3.92 (m, 3H), 4.15-4.19 (m, 3H), 4.89 (brs, 1H), 5.16 (s, 1H), 6.70-6.74 (m, 2H), 7.07-7.11 (m, 2H), 7.24-7.25 (m, 1H), 7.59-7.63 (m, 2H), 8.03-8.06 (m, 1H), 8.16-8.17 (m, 1H), 9.70 (brs, 1H).

Example 231

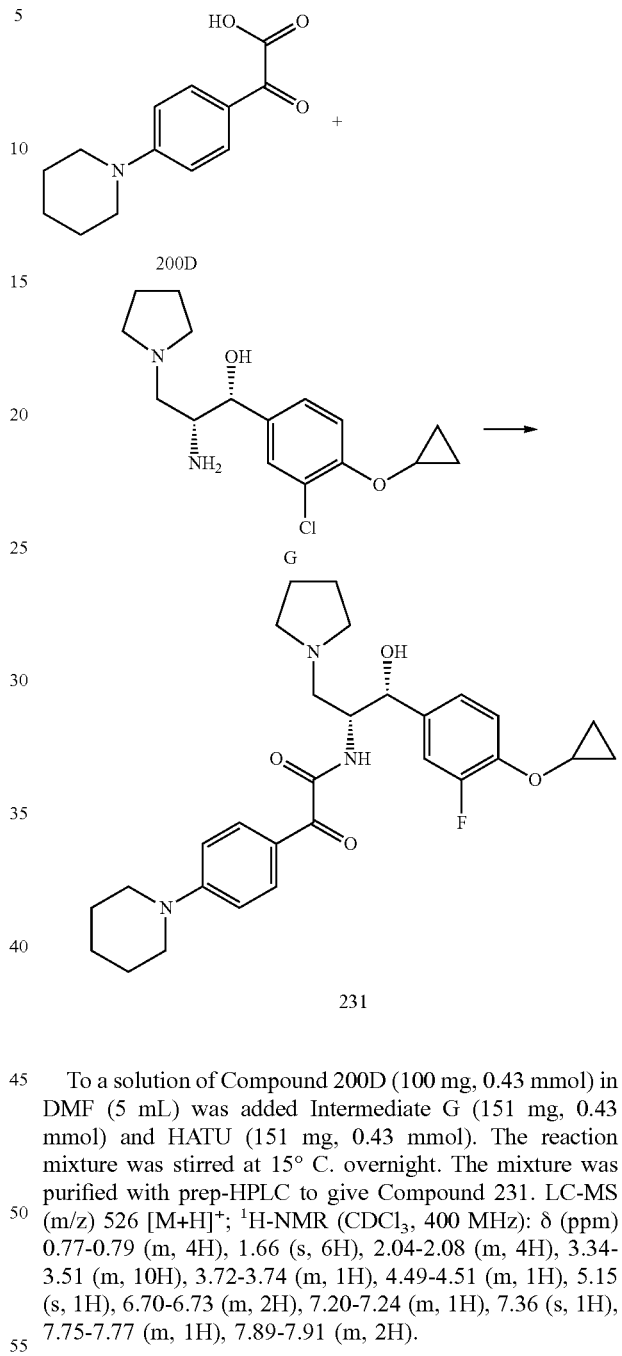

To a solution of Compound 200D (100 mg, 0.43 mmol) in DMF (5 mL) was added Intermediate G (151 mg, 0.43 mmol) and HATU (151 mg, 0.43 mmol). The reaction mixture was stirred at 15° C. overnight. The mixture was purified with prep-HPLC to give Compound 231. LC-MS (m/z) 526 [M+H]$^+$; $^1$H-NMR (CDCl$_3$, 400 MHz): δ (ppm) 0.77-0.79 (m, 4H), 1.66 (s, 6H), 2.04-2.08 (m, 4H), 3.34-3.51 (m, 10H), 3.72-3.74 (m, 1H), 4.49-4.51 (m, 1H), 5.15 (s, 1H), 6.70-6.73 (m, 2H), 7.20-7.24 (m, 1H), 7.36 (s, 1H), 7.75-7.77 (m, 1H), 7.89-7.91 (m, 2H).

Example 232

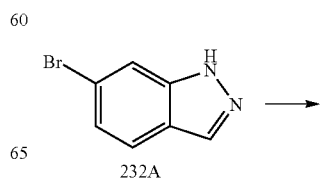

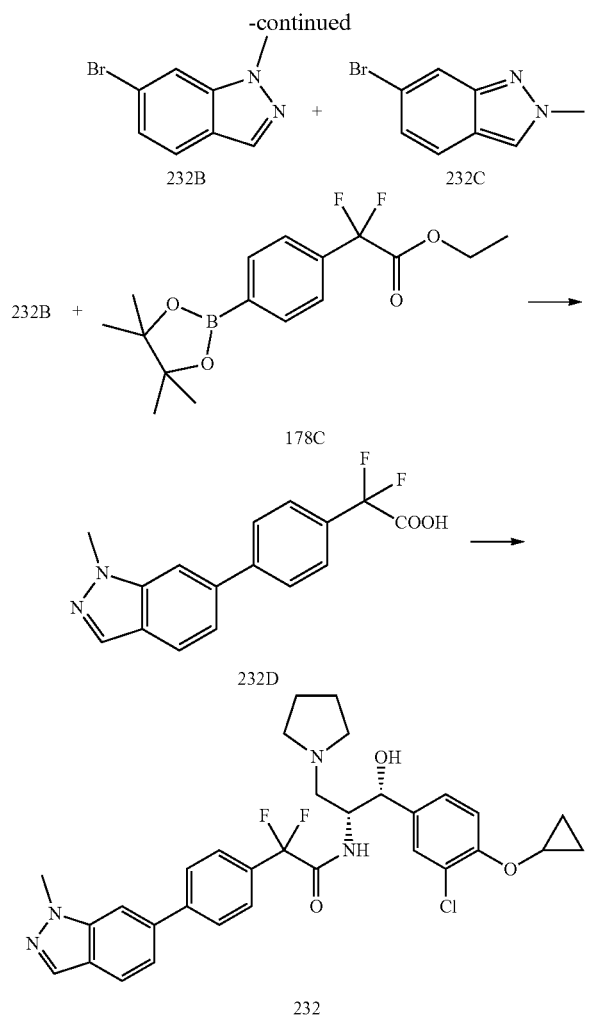

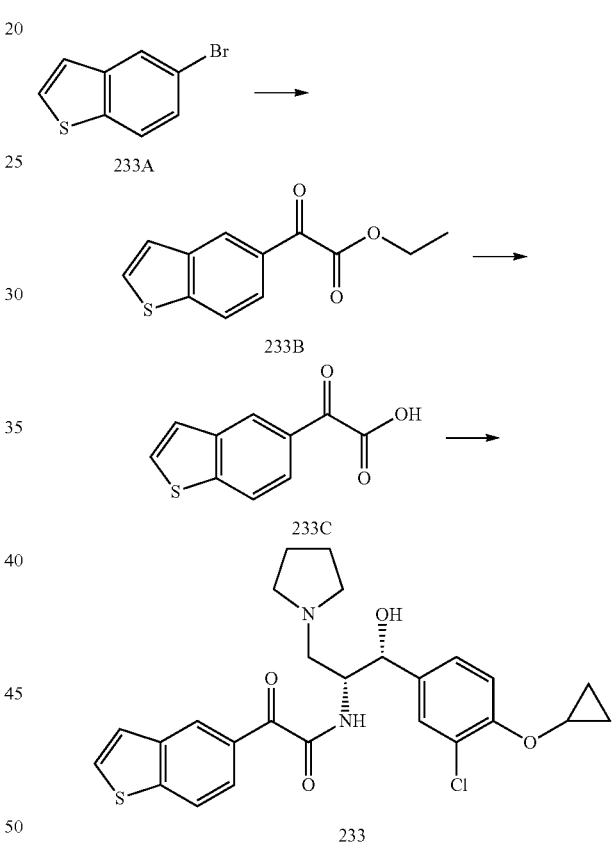

A mixture of Compound 232D (100 mg, 0.33 mmol), EDCI (95 mg, 0.5 mmol), HOBt (68 mg, 0.5 mmol), and Intermediate G (102 mg, 0.33 mmol) in dichloromethane (5 mL) was stirred at 10° C. for 18 h. The mixture was diluted with ethyl acetate (50 mL), washed with water (50 mL×2) and brine (50 mL), and dried over anhydrous sodium sulfate. After evaporation, the crude product was purified with prep-HPLC to furnish Compound 232. LC-MS (ESI) m/z: 595 [M+H]$^+$; $^1$H-NMR (CD$_3$OD, 400 MHz): δ (ppm) 0.33-0.41 (m, 4H), 1.95-2.08 (m, 4H), 3.08-3.17 (m, 2H), 3.38-3.64 (m, 4H), 3.70-3.72 (m, 1H), 4.05 (s, 3H), 4.54-4.56 (m, 1H), 4.82 (d, J=2.4 Hz, 1H), 6.94 (d, J=8.4 Hz, 1H), 7.02 (dd, J=8.8, 1.6 Hz, 1H), 7.28-7.30 (m, 3H), 7.42 (d, J=9.2 Hz, 1H), 7.66 (d, J=7.6 Hz, 2H), 7.75-7.77 (m, 2H), 7.95 (s, 1H).

Example 233

To Compound 232A (10 g, 50.8 mmol) in THF (50 mL) was added sodium hydride (60% in mineral, 2.2 g, 55.8 mmol) with ice bath cooling. The mixture was stirred at room temperature for 30 min. Methyl iodide (4.74 mL, 76.1 mmol) was added at room temperature. The reaction mixture was stirred at room temperature for 1 h, quenched with saturated aqueous ammonium chloride solution (30 mL), and extracted with ethyl acetate (100 mL×3). The combined organic layers were washed with brine (200 mL), dried over anhydrous sodium sulfate, and concentrated. Purification with flash column chromatography on silica gel (ethyl acetate in petroleum ether, 10% to 30% v/v) gave Compound 232B and Compound 232C.

A mixture of Compound 232B (600 mg, 2.84 mmol), Compound 178B (926 mg, 2.84 mmol), Pd(dppf)Cl$_2$ (116 mg, 0.14 mmol), and K$_2$CO$_3$ (1.18 g, 8.52 mmol) in dioxane (5 mL) and water (5 mL) was stirred under nitrogen at 100° C. for 3 h. The reaction mixture was cooled to room temperature and filtered through celite. The filtrate was diluted with water (50 mL) and extracted with ethyl acetate (50 mL×2), and then the organic layer was discarded off. The aqueous layer was acidified to pH 3 with aqueous HCl solution (1 N) and extracted with ethyl acetate (100 mL×2). The combined organic layers were washed with water (50 mL×2) and brine (50 mL), dried over anhydrous sodium sulfate, and concentrated to give Compound 232D.

To a solution of Compound 233A (1.0 g, 4.7 mmol) in THF (30 mL) was added magnesium chips (0.23 g, 9.4 mmol) at room temperature. The mixture was stirred at 50° C. for 2 h, and then diethyl oxalate (3 mL) was added in one portion. The mixture was stirred at 60° C. for 3 h. The solution was quenched with saturated NH$_4$Cl solution and extracted with ethyl acetate (50 mL×2). The combined organic phases were washed with water (15 mL) and brine (15 mL), dried over anhydrous sodium sulfate, filtered, and concentrated. The crude product was purified with flash column chromatography on silica gel (ethyl acetate in petroleum ether, 10% v/v) to give Compound 233B.

To a solution of Compound 233B (1.4 g, 6.1 mmol) in THF (15 mL) was added LiOH H$_2$O (390 mg, 9.0 mmol) in water (15 mL) at −10° C., and the mixture was stirred at this temperature for 5 hours. The reaction mixture was treated with ice water (20 mL) and extracted with ethyl acetate (50 mL). The water layer was adjusted to pH 2 with diluted HCl and extracted with ethyl acetate (50 mL×2). The combined organic layers were washed with brine (50 mL), dried over anhydrous sodium sulfate, and concentrated. The resulting solid was washed with petroleum ether and filtered off to furnish the crude Compound 233C.

A mixture of Compound 233C (160 mg, (0.8 mmol), HATU (608 mg, 1.6 mmol), DMF (6.5 mL) and Intermediate G (298 mg, 0.96 mmol) in DCM (8 mL) was stirred at room temperature overnight. The reaction mixture was treated with water (20 mL), extracted with DCM 50 mL×2), washed with brine (50 mL), dried over anhydrous sodium sulfate, and concentrated. The crude product was purified with prep-HPLC to give Compound 233. LC-MS (ESI) m/z: 499.1 [M+H]$^+$; $^1$H-NMR (CD$_3$OD, 400 MHz): δ (ppm) 0.61-0.79 (m, 4H), 2.01-2.23 (m, 4H), 3.21-3.30 (m, 1H), 3.58-3.86 (m, 6H), 4.73 (d, J=10.8 Hz, 1H), 5.00 (s, 1H), 7.32 (d, J=8.4 Hz, 1H), 7.39 (d, J=8.8 Hz, 1H), 7.47 (d, J=5.2 Hz, 1H), 7.50 (d, J=1.2 Hz, 1H), 7.73-7.75 (m, 2H), 7.98 (d, J=8.4 Hz, 1H), 8.15 (s, 1H).

Example 234

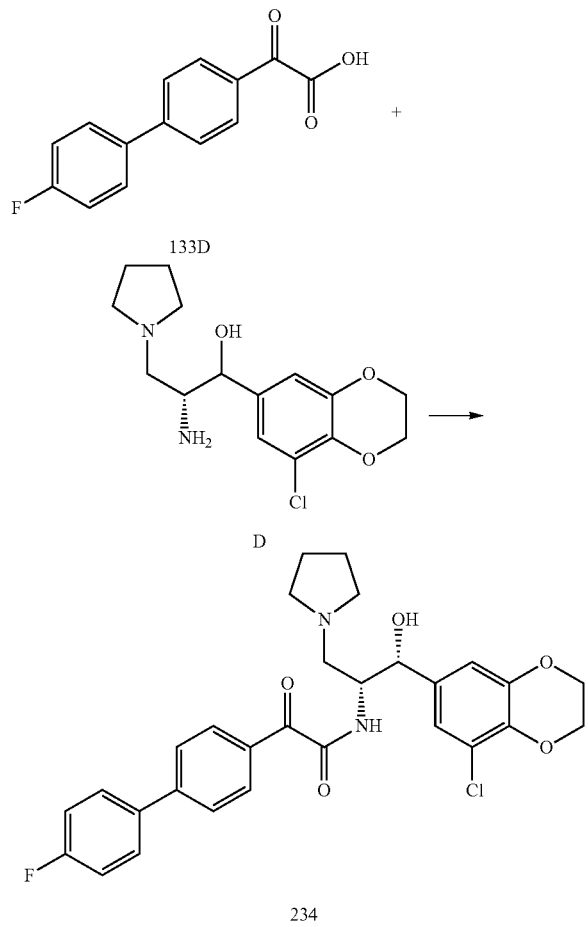

234

A mixture of Compound 133D (156 mg, 0.50 mmol), Intermediate D (100 mg, 0.45 mmol), and HATU (285 mg, 0.75 mmol) in dichloromethane (10 mL) was stirred at 10° C. for 15 h. And then it was treated with water (10 mL) and extracted with dichloromethane (10 mL×3 mL). The organic layers were washed with water (20 mL×3), dried over anhydrous sodium sulfate, concentrated in vacuo, and purified with prep-HPLC to furnish Compound 234. LC-MS (ESI) m/z: 539 [M+H]$^+$; $^1$H-NMR (CDCl$_3$, 400 MHz): δ (ppm) 2.09 (s, 4H), 3.06 (s, 2H), 3.46 (s, 1H), 3.73 (t, J=12 Hz, 1H), 3.89 (s, 2H), 4.10-4.19 (m, 4H), 4.43 (s, 1H), 4.99 (s, 1H), 6.76 (s, 1H), 6.92 (s, 1H), 7.08 (t, J=8 Hz, 2H), 7.50 (t, J=8 Hz, 4H), 7.67 (d, J=8 Hz, 2H), 7.80 (d, J=8 Hz, 2H), 8.50 (s, 1H).

Example 235

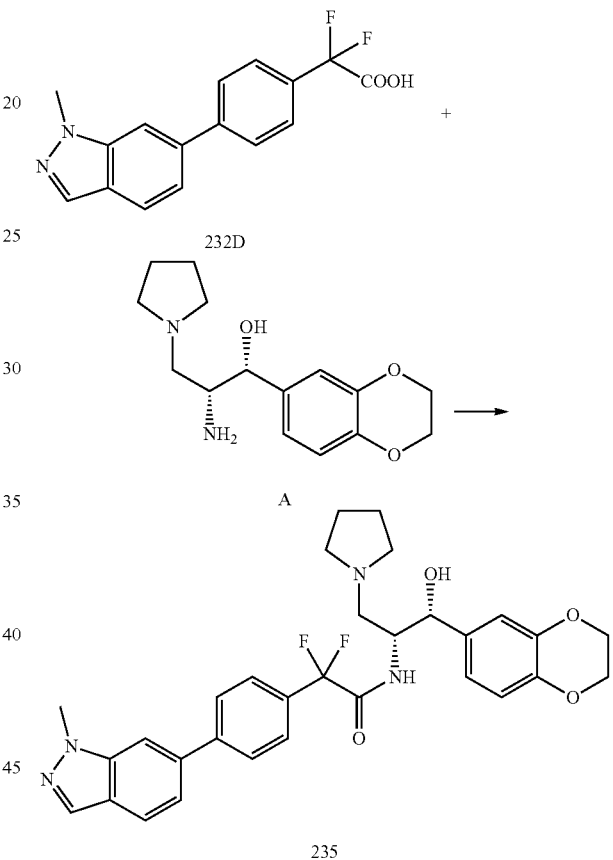

A mixture of Compound 232D (100 mg, 0.33 mmol), EDCI (95 mg, 0.5 mmol), HOBt (68 mg, 0.5 mmol), and Intermediate A (92 mg, 0.33 mmol) in dichloromethane (5 mL) was stirred at 10° C. for 18 h. The mixture was diluted with ethyl acetate (50 mL), washed with water (50 mL×2) and brine (50 mL), and dried over anhydrous sodium sulfate. After evaporation, the crude product was purified with prep-HPLC to furnish Compound 235. LC-MS (ESI) m/z: 563 [M+H]$^+$; $^1$H-NMR (CD$_3$OD, 400 MHz): δ (ppm) 2.03-2.17 (m, 4H), 3.15-3.24 (m, 2H), 3.53-3.67 (m, 3H), 3.80-3.82 (m, 1H), 4.07 (s, 4H), 4.15 (s, 3H), 4.56-4.58 (m, 1H), 4.83 (d, J=3.2 Hz, 1H), 6.64 (d, J=8.4 Hz, 1H), 6.72-6.79 (m, 2H), 7.47-7.53 (m, 3H), 7.81 (d, J=8.0 Hz, 2H), 7.86-7.88 (m, 2H), 8.05 (s, 1H).

Example 236

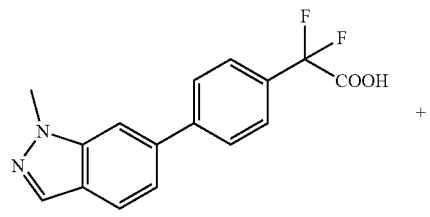

232D

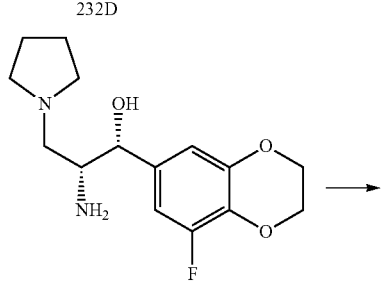

C

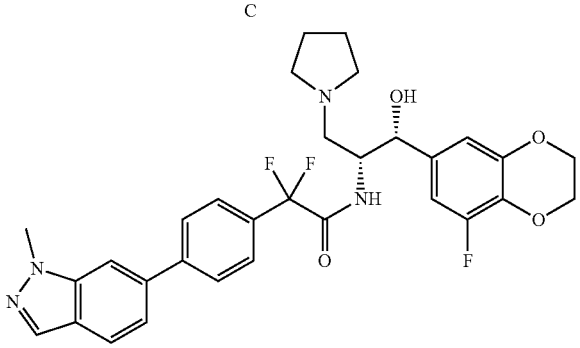

236

A mixture of Compound 232D (100 mg, 0.33 mmol), EDCI (95 mg, 0.5 mmol), HOBt (68 mg, 0.5 mmol), and Intermediate C (98 mg, 0.33 mmol) in dichloromethane (5 mL) was stirred at 10° C. for 18 h. The mixture was diluted with ethyl acetate (50 mL), washed with water (50 mL×2) and brine (50 mL), and dried over anhydrous sodium sulfate. After evaporation, the crude product was purified with prep-HPLC to furnish Compound 236. LC-MS (ESI) m/z: 581 [M+H]$^+$; $^1$H-NMR (CD$_3$OD, 400 MHz): δ (ppm) 2.03-2.18 (m, 4H), 3.17-3.27 (m, 2H), 3.53-3.81 (m, 4H), 4.01-4.07 (m, 4H), 4.15 (s, 3H), 4.59-4.62 (m, 1H), 4.84 (d, J=2.8 Hz, 1H), 6.59 (s, 1H), 6.68 (dd, J=11.6, 2.0 Hz, 1H), 7.48 (d, J=8.0 Hz, 2H), 7.52 (d, J=8.8 Hz, 1H), 7.79 (d, J=8.4 Hz, 2H), 7.86-7.88 (m, 2H), 8.05 (s, 1H).

Example 237

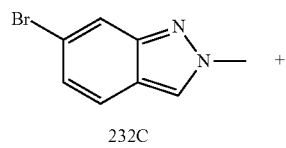

232C

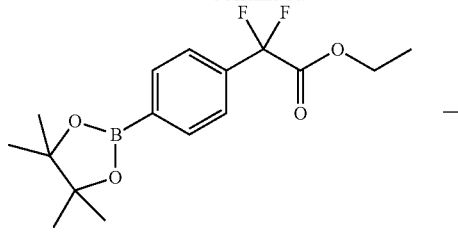

178C

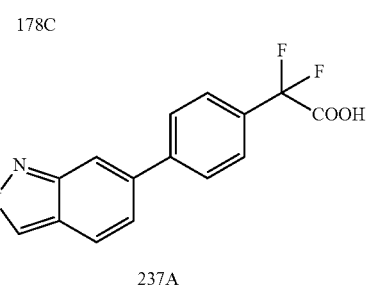

237A

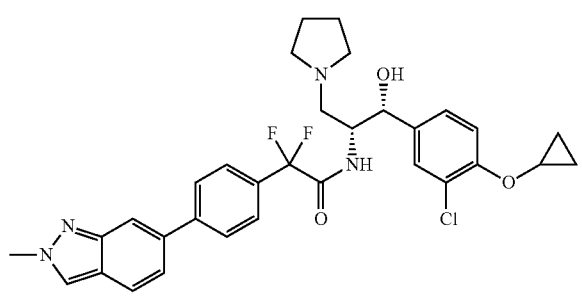

237

A mixture of Compound 232C (200 mg, 0.95 mmol), Compound 178C (310 mg, 0.95 mmol), Pd(dppf)Cl$_2$ (39 mg, 0.05 mmol), and K$_2$CO$_3$ (393 mg, 2.85 mmol) in dioxane (3 mL) and water (3 mL) was stirred under nitrogen at 100° C. for 4 h. The reaction mixture was cooled to room temperature and filtered through celite. The filtrate was treated with water (50 mL) and extracted with ethyl acetate (50 mL×2). The aqueous layer was acidified to pH 3 with aqueous HCl solution (1 N) and extracted with ethyl acetate (100 mL×2). The combined organic layers were washed with water (50 mL×2) and brine (50 mL), dried over anhydrous sodium sulfate, and concentrated to give Compound 237A.

A mixture of Compound 237A (100 mg, 0.33 mmol), EDCI (95 mg, 0.5 mmol), HOBt (68 mg, 0.5 mmol), and Intermediate G (102 mg, 0.33 mmol) in dichloromethane (5 mL) was stirred at 10° C. for 18 h. The mixture was diluted with ethyl acetate (50 mL), washed with water (50 mL×2) and brine (50 mL), and dried over anhydrous sodium sulfate. After evaporation, the crude product was purified with prep-HPLC to furnish Compound 237. LC-MS (ESI) m/z: 595 [M+H]$^+$; $^1$H-NMR (CD$_3$OD, 400 MHz): δ (ppm) 0.45-0.54 (m, 4H), 2.04-2.18 (m, 4H), 3.17-3.32 (m, 2H), 3.49-3.81 (m, 5H), 4.26 (s, 3H), 4.62-4.64 (m, 1H), 4.90 (s, 1H), 7.03 (d, J=8.4 Hz, 1H), 7.11 (dd, J=8.4, 1.6 Hz, 1H), 7.37-7.40 (m, 3H), 7.47 (d, J=8.8 Hz, 1H), 7.74 (d, J=8.0 Hz, 2H), 7.82 (d, J=8.8 Hz, 1H), 7.90 (s, 1H), 8.25 (s, 1H).

Example 238

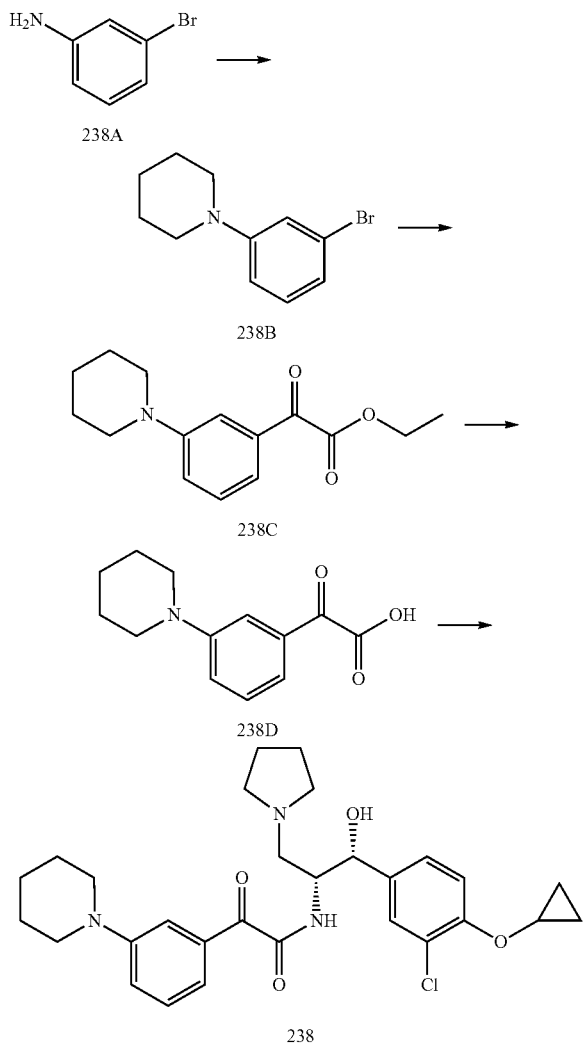

A mixture of Compound 238A (1.72 g, 10 mmol), 1,5-dibromopentane (2.75 g, 12 mmol), sodium dodecyl sulfate (SDS, cat. 40 mg), and sodium bicarbonate (1 g, 12 mmol) in water (20 mL) was heated at 100° C. for 1.5 hours. The reaction mixture was treated with water (20 mL) and extracted with ethyl acetate (50 mL×3). The extraction was washed with water (50 mL), dried over anhydrous sodium sulfate, concentrated, and purified with flash column chromatography on silica gel (ethyl acetate in petroleum ether, from 0% to 1% v/v) to give Compound 238B.

To a solution of Compound 238B (2.4 g, 10 mmol) in dry THF (50 mL) was added dropwise LDA (2.0 M, 5.0 mL, 12.0 mmol) under nitrogen at −70° C. After stirring for 30 min., diethyl oxalate (2.19 g, 15.0 mmol) was added quickly. The mixture was stirred at −70° C. for about an hour. It was quenched with saturated ammonium chloride (10 mL) solution and extracted with ethyl acetate (50 mL×3). The combined organic phases were washed with water (5 mL) and brine (5 mL), dried over anhydrous sodium sulfate, filtered, and concentrated to give a residue. The crude product was purified with flash column chromatography on silica gel (ethyl acetate in petroleum ether, from 0% to 10% v/v) to afford Compound 238C.

To a solution of Compound 238C (261 mg, 1 mmol) in methanol (5 mL) was added dropwise lithium hydroxide (1 N, 2 mL, 2 mmol). The reaction mixture was stirred at room temperature for 2 h. After the reaction mixture was concentrated, HCl (2 N, 1 mL) was added to adjust pH 7, followed by extraction with ethyl acetate (50 mL×3). The combined organic phases were washed with water (5 mL) and brine (5 mL), dried over anhydrous sodium sulfate, filtered, and concentrated to furnish Compound 238D.

To a solution of Compound 238D (100 mg, 0.429 mmol) in dichloromethane (3 mL) was added Intermediate G (130 mg, 0.429 mmol) and HATU (196 mg, 0.515 mmol). The mixture was stirred at room temperature for 2 h. It was concentrated and the resulting residue was purified with prep-HPLC to furnish Compound 238. LC-MS (ESI) m/z: 526 [M+H]$^+$; $^1$H-NMR (CDCl$_3$, 400 MHz): δ (ppm) 0.79-0.83 (m, 4H), 1.57-1.61 (m, 2H), 1.67-1.72 (m, 5H), 1.85-1.87 (m, 4H), 2.71-2.92 (m, 4H), 2.96-3.07 (m, 2H), 3.17-3.19 (m, 4H), 3.75-3.78 (m, 1H), 4.31-4.32 (m, 1H), 5.14 (d, J=1.6 Hz, 1H), 7.16-7.23 (m, 2H), 7.24-7.37 (m, 3H), 7.58-7.60 (m, 1H), 7.76-7.78 (m, 1H).

Example 239

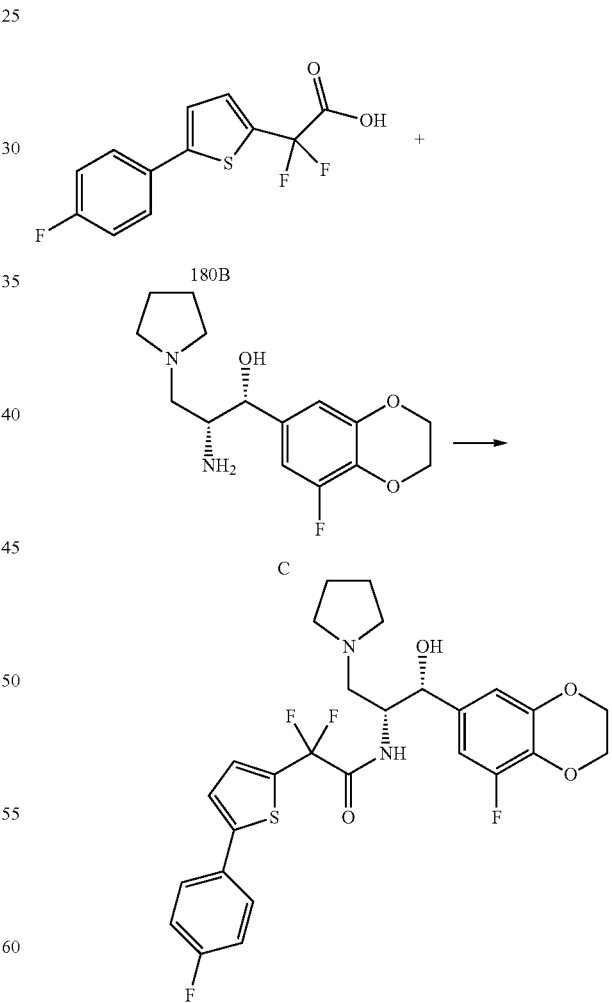

To a solution of Compound 180B (68 mg, 0.25 mmol) in DMF (5 mL) was added Intermediate C (74 mg, 0.25 mmol)

and HATU (142 mg, 0.37 mmol). The reaction mixture was stirred at 25° C. for 16 h. The mixture was purified with prep-HPLC to yield Compound 239. LC-MS (m/z) 551 [M+H]$^+$; $^1$H-NMR (CDCl$_3$, 400 MHz): δ (ppm) 2.15-2.18 (m, 4H), 2.94-2.97 (m, 1H), 3.06-3.10 (m, 1H), 3.50-3.53 (m, 2H), 3.82-3.88 (m, 2H), 4.08-4.10 (m, 3H), 4.16-4.23 (m, 1H), 4.39-4.42 (m, 1H), 5.08 (brs, 1H), 6.59-6.67 (m, 2H), 7.08-7.11 (m, 3H), 7.51-7.55 (m, 3H).

Example 240

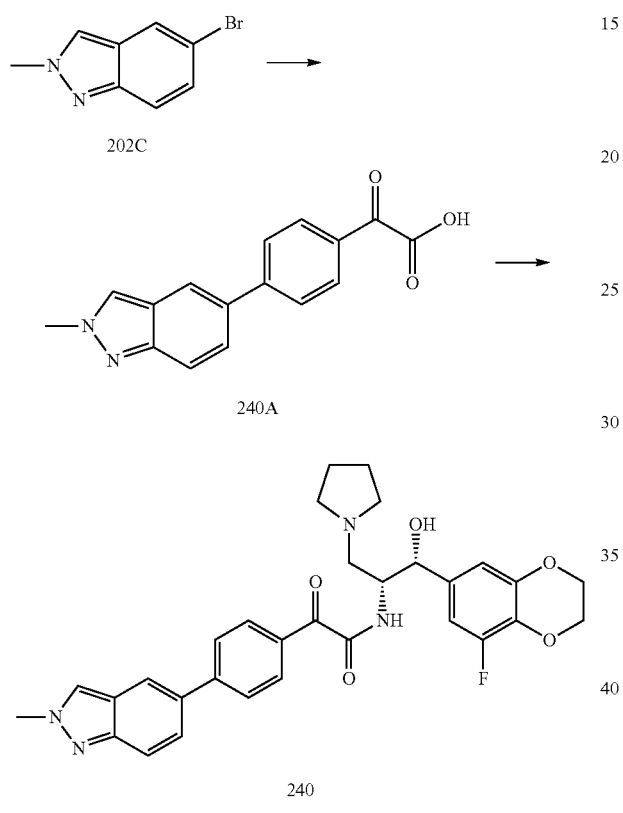

To a solution of Compound 202C (158 mg, 0.75 mmol) in 1,4-dioxane (15 mL) was added ethyl 178C (250 mg, 0.825 mmol), Pd(dppf)Cl$_2$ (30 mg, 0.0375 mmol), potassium carbonate (310 mg, 2.25 mmol) and water (1 mL) under nitrogen. The reaction mixture was stirred at 100° C. for 2 hours. The resulting mixture was cooled to 25° C. The precipitated solid was filtered and dried to afford Compound 240A.

To a solution of Compound 240A (68 mg, 0.24 mmol) in DMF (3 mL) was added Intermediate C (71 mg, 0.24 mmol) and HATU (137 mg, 0.36 mmol). The reaction mixture was stirred at 10° C. overnight. The mixture was purified with prep-HPLC to yield the product Compound 240. LC-MS (m/z) 559 [M+H]$^+$; $^1$H-NMR (CDCl$_3$, 400 MHz): δ (ppm) 2.15-2.22 (m, 4H), 2.94-2.95 (m, 2H), 3.08-3.09 (m, 2H), 3.49-3.50 (m, 1H), 3.56-3.57 (m, 1H), 3.91-3.94 (m, 2H), 4.23-4.27 (m, 5H), 4.49-4.52 (m, 1H), 5.12-5.13 (m, 1H), 6.73-6.78 (m, 2H), 7.58-7.61 (m, 1H), 7.69-7.71 (m, 2H), 7.79-7.81 (m, 1H), 7.85-7.90 (m, 2H), 7.99 (s, 1H), 8.19-8.21 (m, 2H).

Example 241

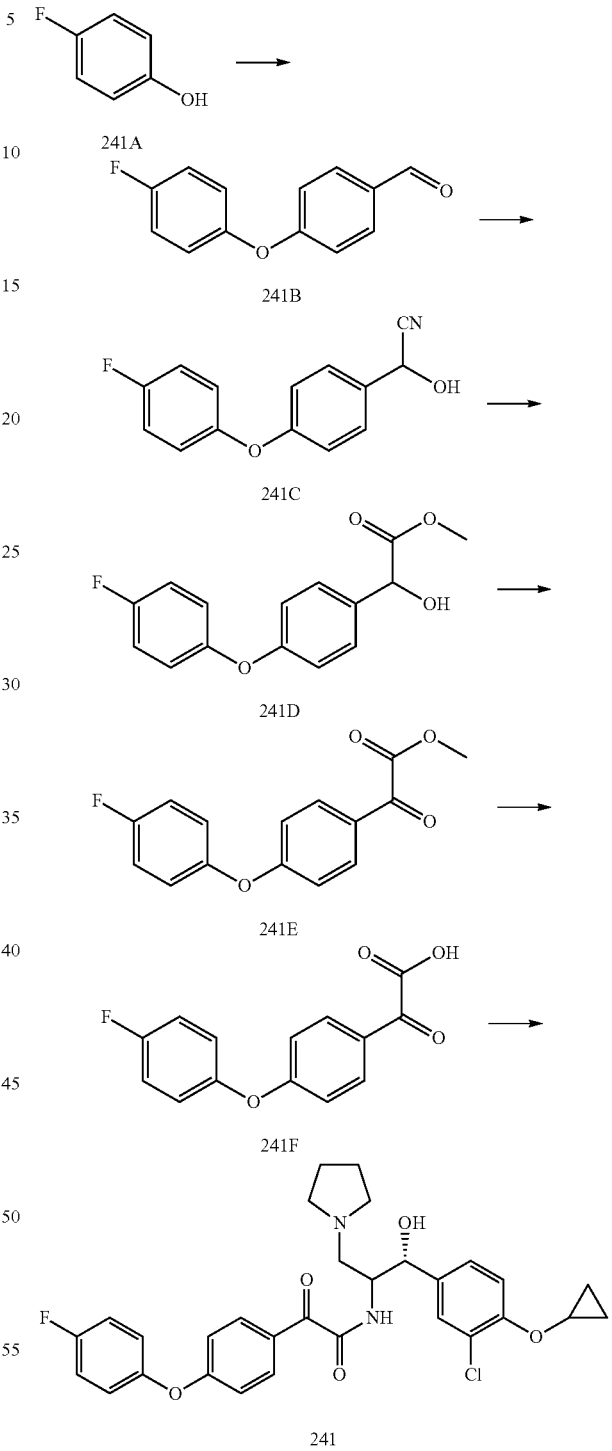

To a solution of Compound 241A (3.1 g, 27.6 mmol) and potassium carbonate (4.15 g, 30.0 mmol) in DMF (50 mL) was added 4-bromobenzaldehyde (5.0 g, 27.6 mmol). The reaction mixture was stirred at 130° C. for 12 h. The reaction was quenched with water (50 mL) and extracted with dichloromethane (150 mL×3). The combined organic layers were washed with brine (150 mL), dried over anhydrous sodium sulfate, filtered, and evaporated. The remaining residue was purified with flash column chromatography on silica gel (ethyl acetate in petroleum ether, from 0% to 10% v/v) to furnish Compound 241B.

A mixture of Compound 241B (1.9 g, 8.8 mmol), and sodium metabisulfite (3.3 g, 17.6 mmol) in water (40 mL) was pre-stirred for 1 h, and then NaCN (431.2 mg, 8.8 mmol) was added into the above-mentioned mixture, and the whole reaction solution was stirred at room temperature for 12 h. The reaction was treated with water (100 mL) and extracted with ethyl acetate (100 mL×3). The combined organic layers were washed with brine (100 mL), dried over anhydrous sodium sulfate, filtered, and evaporated. The crude product was purified with flash column chromatography on silica gel (ethyl acetate in petroleum ether, from 0% to 30% v/v) to give Compound 241C.

To a solution of Compound 241C (1.0 g, 27.6 mmol) in methanol (50 mL) was bubbled with HCl (gas), which was prepared with condensed $H_2SO_4$ and NaCl. After 4 h later, the reaction was quenched with water (50 mL) and extracted with dichloromethane (150 mL×3). The combined organic layers were washed with brine (150 mL), dried over anhydrous sodium sulfate, filtered, and evaporated. The remaining residue was purified with flash column chromatography on silica gel (ethyl acetate in petroleum ether, from 0% to 30% v/v) to afford Compound 241D.

To a solution of Compound 241D (170 mg, 0.62 mmol) in dichloromethane (15 mL) was added Dess-Martin periodinane (313 mg, 0.74 mmol). The reaction was stirred at 0° C. for 0.5 h. The reaction was treated with water (50 mL) and extracted with dichloromethane (150 mL×3). The combined organic layers were washed with brine (150 mL), dried over anhydrous sodium sulfate, filtered, and evaporated. The remaining residue was purified with flash column chromatography on silica gel (ethyl acetate in petroleum ether, 3% v/v) to furnish Compound 241E.

To a solution of Compound 241E (160 mg, 0.58 mmol) in methanol (15 mL) was added LiOH solution (1 N, 0.6 mL, 0.60 mmol). The reaction was stirred at 0° C. for 0.5 h. The reaction was quenched with water (50 mL) and neutralized to pH 1 with HCl (1 M). The mixture was extracted with dichloromethane (150 mL×3). The combined organic layers were washed with brine (150 mL), dried over anhydrous sodium sulfate, filtered, and evaporated to afford Compound 241F.

To a solution of Compound 241F (100 mg, 0.38 mmol) in a mixture of dichloromethane (14 mL) and DMF (2 mL) was added Intermediate G (119 mg, 0.38 mmol) and HATU (175 mg, 0.46 mmol). The mixture was stirred at room temperature for 12 h. The reaction was quenched with water (50 mL) and extracted with dichloromethane (150 mL×3). The combined organic layers were washed with brine (150 mL), dried over anhydrous sodium sulfate, filtered, and evaporated. The remaining residue was purification with prep-HPLC to give Compound 241. LC-MS (ESI) m/z: 553 [M+H]+; 1H-NMR (CDCl3, 400 MHz): δ (ppm) 0.65-0.82 (m, 4H), 2.14 (s, 4H), 2.66-2.96 (m, 4H), 3.51-3.90 (m, 4H), 4.54 (s, 1H), 5.12 (s, 1H), 6.88 (d, J=8.6 Hz, 2H), 7.00-7.12 (m, 4H), 7.16-7.26 (m, 2H), 7.34-7.37 (m, 1H), 7.97-8.03 (m, 3H), 11.60 (s, 1H).

Example 242

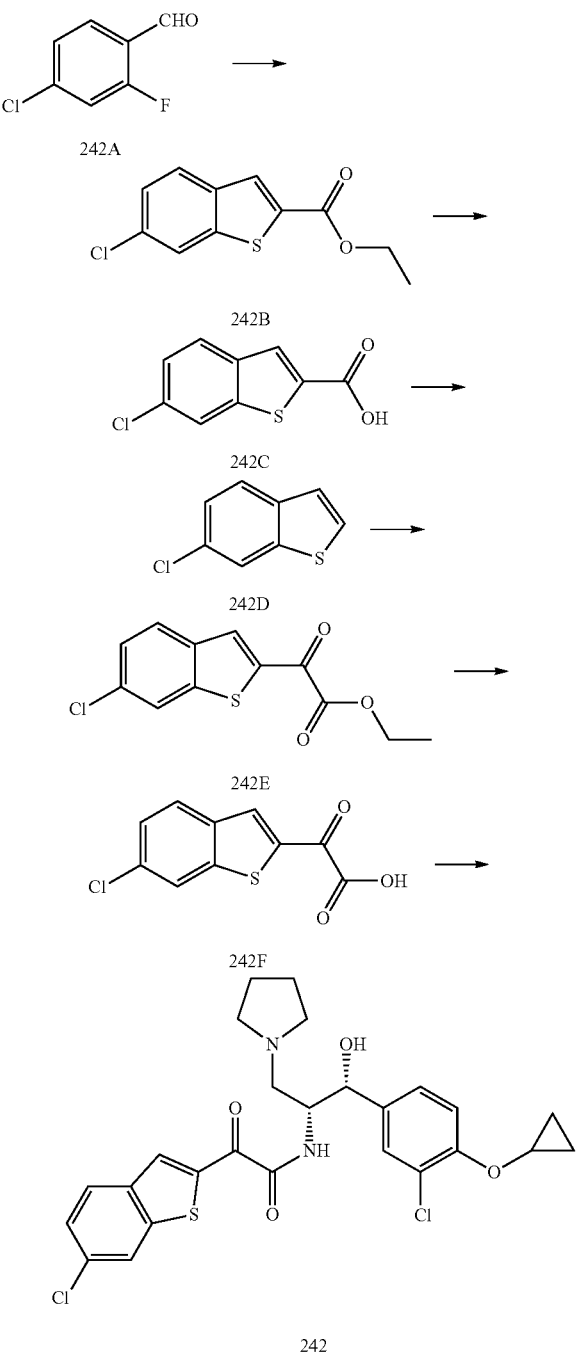

Compound 242A (2.44 g, 15.4 mmol) and potassium carbonate (2.76 g, 20.0 mmol) were suspended in dry DMF (15 mL) and the resulting mixture was cooled to 0° C. Ethyl thioglycolate (1.7 mL, 15.5 mmol) was added in portions over 1 h and the reaction mixture was warmed slowly to room temperature and stirred at 25° C. for 16 h. The reaction was heated at 60° C. for 5.5 h before cooling and adding water (30 mL). The resulting mixture was stirred at room temperature for 30 min and filtered. The residue was washed with water (5 mL×2) and dried to afford the Compound 242B.

Compound 242B (500 mg, 2.08 mmol) was dissolved in hot ethanol (12 mL) and a solution of potassium hydroxide (642 mg, 11.5 mmol) in water (12 mL) was added to the mixture. The suspension was heated at reflux for 1.5 h during which time it mostly dissolved. After cooling slightly aqueous HCl solution (6 N, 5 mL) was added dropwise. Ethanol was evaporated in vacuo and the residual solid was filtered. The filtered cake was washed with water (20 mL) and dried to give Compound 242C.

Compound 242C (420 mg, 1.98 mmol) and copper powder (63 mg, 0.99 mmol) were suspended in quinoline (10 mL) and the resulting mixture was heated at 185° C. for 2 h. After cooling down to room temperature, ethyl acetate (25 mL) was added and the suspension was filtered. The filtered cake was washed with ethyl acetate (5 mL×2) and the combined organic layers were washed with aqueous HCl solution (2 N, 10 mL×2). After drying over anhydrous sodium sulfate, the solution was filtered and evaporated in vacuo to give a residue. The crude product was purified with flash column chromatography on silica gel (ethyl acetate in petroleum ether, from 0% to 10% v/v) to afford Compound 242D.

To a solution of Compound 242D (310 mg, 1.85 mmol) in dry THF (20 mL) was added dropwise n-BuLi (2.4 M solution in hexane, 1.2 mL, 2.78 mmol) under nitrogen at −78° C. After stirring for 30 min, diethyl oxalate (808 mg, 5.54 mmol) was added quickly. The mixture was stirred at −78° C. for about an hour. The resulting mixture was quenched with saturated aqueous NH₄Cl solution (5 mL), extracted with ethyl acetate (50 mL×3), washed with water (5 mL) and brine (5 mL), dried over anhydrous sodium sulfate, filtered, and concentrated to yield a crude compound. The crude product was purified with flash column chromatography on silica gel (ethyl acetate in petroleum ether, 10% v/v) to furnish Compound 242E.

To a solution of Compound 242E (150 mg, 0.56 mmol) in THF (10 mL) was added dropwise a solution of LiOH H₂O (25 mg, 0.62 mmol) in water (2.5 mL) at −30° C. The mixture was stirred at −30° C. for half an hour. The reaction solution was adjusted to pH 3 with aqueous HCl solution (1 N, 2.5 mL) and separated. The organic layer was dried directly over anhydrous sodium sulfate, filtered, and concentrated to afford Compound 242F.

To a solution of Intermediate G (129 mg, 0.42 mmol) in DMF (10 mL) was added Compound 242F (100 mg, 0.42 mmol), HATU (237 mg, 0.62 mmol), and N, N-diisopropylethylamine (107 mg, 0.83 mmol) under nitrogen. The mixture was stirred at 25° C. overnight. The resulting mixture was quenched with saturated aqueous sodium bicarbonate solution (5 mL) and extracted with ethyl acetate (50 mL×3). The combined organic phases were washed with water (5 mL) and brine (5 mL), dried over anhydrous sodium sulfate, filtered, and concentrated to afford a crude compound. The crude product was purified with prep-HPLC to furnish Compound 242. LC-MS (ESI) m/z: 533 [M+H]⁺; ¹H-NMR (CD₃OD, 400 MHz): δ (ppm) 0.58-0.70 (m, 2H), 0.73-0.79 (m, 2H), 2.01-2.04 (m, 2H), 2.16-2.21 (m, 2H), 3.20-3.26 (m, 2H), 3.49-3.53 (m, 1H), 3.70-3.76 (m, 4H), 4.58-4.60 (m, 1H), 4.91 (d, J=2.8 Hz, 1H), 7.32-7.34 (m, 2H), 7.44 (d, J=1.6 Hz, 1H), 7.47 (dd, J=8.8, 2.0 Hz, 1H), 7.97 (d, J=8.4 Hz, 1H), 8.04 (s, 1H), 8.38 (s, 1H).

Example 243

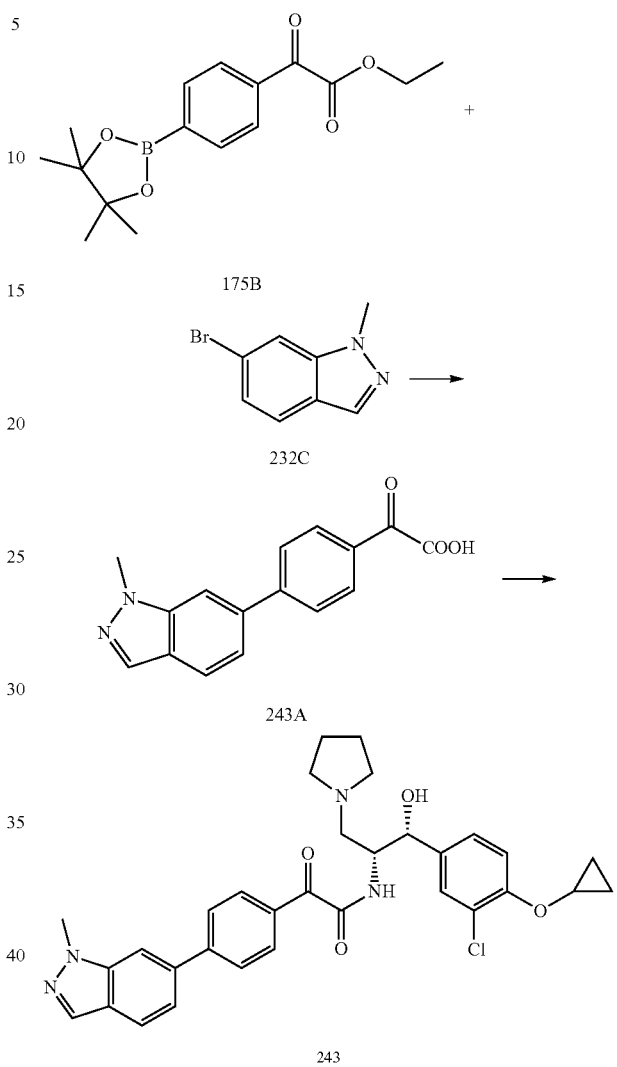

A mixture of Compound 232C (600 mg, 2.84 mmol), Compound 175B (863 mg, 2.84 mmol), Pd(dppf)Cl₂ (116 mg, 0.14 mmol), and K₂CO₃ (1.18 g, 8.52 mmol) in dioxane (5 mL) and water (5 mL) was stirred under nitrogen at 100° C. for 3 h. The reaction mixture was cooled to room temperature and filtered through celite. The filtrate was treated with water (50 mL) and extracted with ethyl acetate (50 mL×2). The aqueous layer was acidified to pH 3 with aqueous HCl solution (1 N) and filtered. The cake was washed with water (20 mL) and dried in vacuo to give Compound 243A.

A mixture of Compound 243A (100 mg, 0.36 mmol), HATU (205 mg, 0.54 mmol), and Intermediate A (112 mg, 0.36 mmol) in DMF (5 mL) was stirred at 10° C. for 18 h. The mixture was purified with prep-HPLC to furnish Compound 243. LC-MS (ESI) m/z: 573 [M+H]⁺; ¹H-NMR (CD₃OD, 400 MHz): δ (ppm) 0.72-0.82 (m, 4H), 2.07-2.08 (m, 2H), 2.23-2.24 (m, 2H), 3.31-3.32 (m, 2H), 3.60-3.63 (m, 1H), 3.71-3.77 (m, 2H), 3.83-3.89 (m, 2H), 4.15-4.16 (m, 3H), 4.72-4.76 (m, 1H), 5.02 (s, 1H), 7.41 (s, 2H), 7.50

(s, 1H), 7.53-7.55 (m, 1H), 7.70-7.72 (m, 2H), 7.79-7.81 (m, 2H), 7.88-7.89 (m, 2H), 8.07 (s, 1H).

Example 244

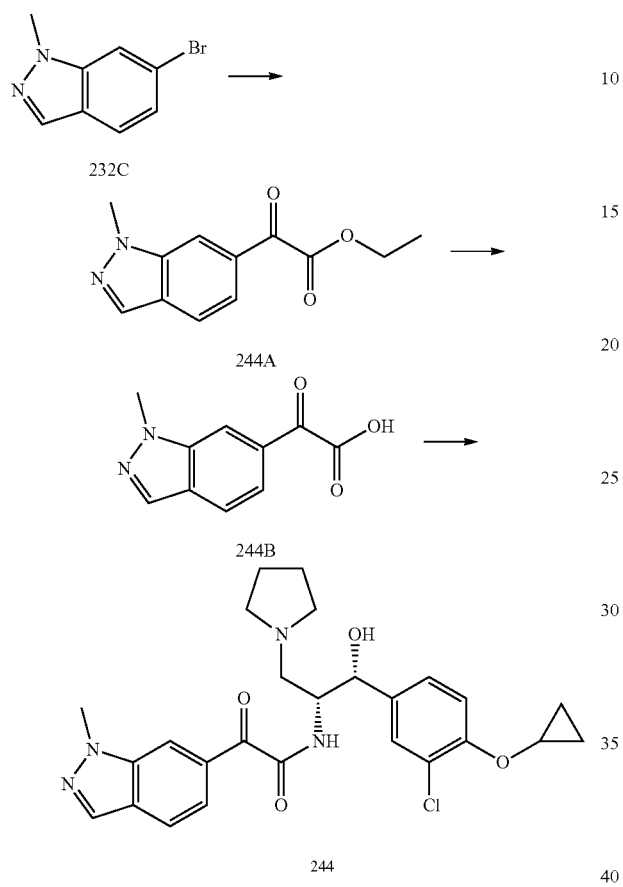

To a solution of Compound 232C (800 mg, 3.79 mmol) in dry THF (10 mL) was added n-BuLi (2.5 N solution in hexane, 1.53 mL) under nitrogen at −78° C. The resulting solution was stirred at −78° C. for 30 min and transferred into a stirred solution of diethyl oxalate (1.39 g, 9.5 mmol) in dry THF (5 mL) at −78° C. The solution was stirred at −78° C. for 1 h, quenched with addition of saturated NH$_4$Cl solution (10 mL), poured into water (100 mL), and extracted with ethyl acetate (50 mL×2). The combined organic layers were washed with brine (100 mL), dried over anhydrous sodium sulfate, and concentrated in vacuo to give a solid. This solid was triturated with methanol and filtered. The filtrate was concentrated to give the desired Compound 244A which was used for the next step without further purification.

To a solution of Compound 244A (500 mg, 2.16 mmol) in methanol (10 mL) was added a solution of LiOH.H$_2$O (200 mg, 4.32 mmol) in water (5 mL). The mixture was stirred at room temperature overnight and purified with reverse phase chromatography using eluent (methanol in water, from 0% to 7% v/v) to furnish Compound 244B.

A mixture of Compound 244B (70 mg, 0.34 mmol), HATU (194 mg, 0.51 mmol), and Intermediate G (105 mg, 0.34 mmol) in DMF (5 mL) was stirred at 10° C. for 18 h. The mixture was purified with prep-HPLC to afford Compound 244. LC-MS (ESI) m/z: 497 [M+H]$^+$; $^1$H-NMR (DMSO-d$_6$, 400 MHz): δ (ppm) 0.62-0.82 (m, 4H), 1.88-1.91 (m, 2H), 2.03-2.05 (m, 2H), 3.13-3.20 (m, 2H), 3.47-3.59 (m, 4H), 3.89-3.90 (m, 1H), 4.14 (s, 3H), 4.54-4.56 (m, 1H), 4.86 (d, J=2.8 Hz, 1H), 7.33-7.39 (m, 2H), 7.45-7.49 (m, 2H), 7.84 (d, J=8.8 Hz, 1H), 8.21 (s, 1H), 8.27 (s, 1H), 8.83 (d, J=9.2 Hz, 1H), 9.32 (brs, 1H).

Example 245

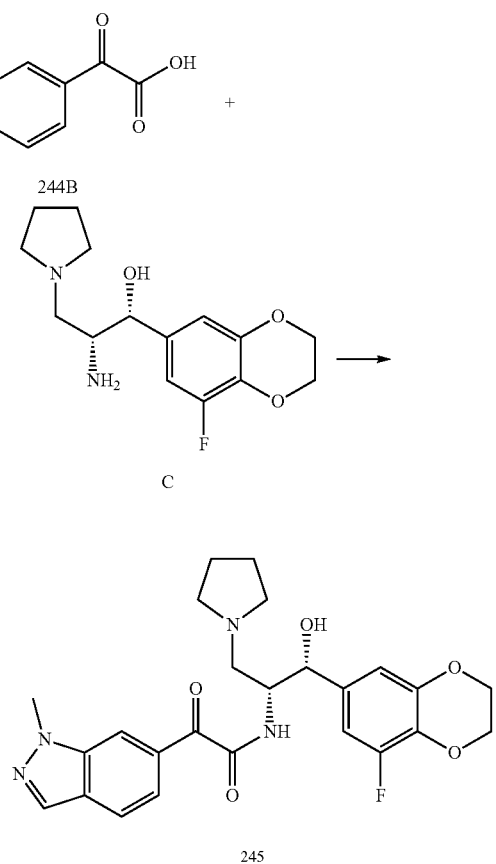

A mixture of Compound 244B (60 mg, 0.29 mmol), HATU (167 mg, 0.44 mmol), and Intermediate C (86 mg, 0.29 mmol) in DMF (5 mL) was stirred at 10° C. for 18 h. The mixture was purified with prep-HPLC to afford Compound 245. LC-MS (ESI) m/z: 483 [M+H]$^+$; $^1$H-NMR (DMSO-d$_6$, 400 MHz): δ (ppm) 1.87-2.04 (m, 4H), 3.08-3.21 (m, 2H), 3.43-3.46 (m, 2H), 3.54-3.57 (m, 2H), 4.12 (s, 3H), 4.22-4.32 (m, 4H), 4.48-4.55 (m, 1H), 4.77 (d, J=2.8 Hz, 1H), 6.77 (s, 1H), 6.84 (dd, J=11.6, 1.6 Hz, 1H), 7.51 (dd, J=8.4, 0.8 Hz, 1H), 7.86 (d, J=8.8 Hz, 1H), 8.21 (s, 1H), 8.31 (s, 1H), 8.81 (d, J=9.2 Hz, 1H), 9.31 (brs, 1H).

Example 246

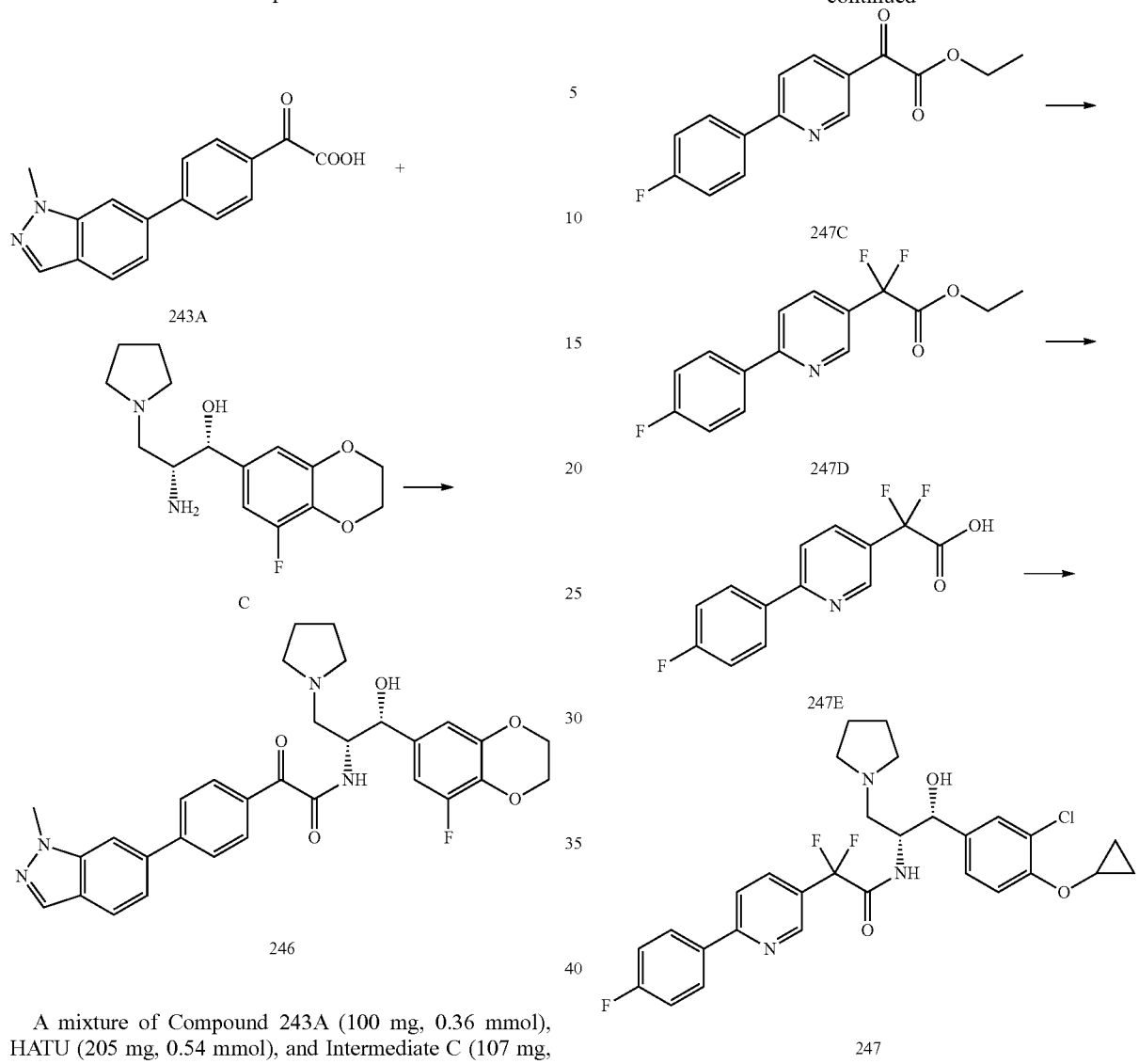

A mixture of Compound 243A (100 mg, 0.36 mmol), HATU (205 mg, 0.54 mmol), and Intermediate C (107 mg, 0.36 mmol) in DMF (5 mL) was stirred at 10° C. for 18 h. The mixture was purified with prep-HPLC to furnish Compound 246. LC-MS (ESI) m/z: 559 [M+H]$^+$; $^1$H-NMR (DMSO-d$_6$, 400 MHz): δ (ppm) 1.73-1.74 (m, 4H), 2.54-2.61 (m, 5H), 2.66-2.71 (m, 1H), 4.13 (s, 3H), 4.27-4.31 (m, 5H), 4.78 (d, J=2.8 Hz, 1H), 6.76 (s, 1H), 6.83 (dd, J=11.2, 1.2 Hz, 1H), 7.52 (dd, J=8.4, 1.2 Hz, 1H), 7.79-7.92 (m, 5H), 8.05 (s, 1H), 8.11 (s, 1H), 8.66 (d, J=9.6 Hz, 1H).

Example 247

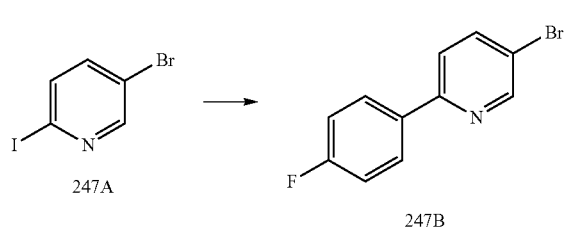

A mixture of Compound 247A (14.2 g, 50 mmol), Compound (4-fluorophenyl)boronic acid (7.7 g, 55 mmol), Pd(dppf)Cl$_2$ (2.05 g, 2.5 mmol) and K$_2$CO$_3$ (20.7 g, 150 mmol) in dioxane (600 mL) and water (80 mL) was heated to reflux for 2 h. Ethyl acetate (500 mL) was added. The organic layers were washed with water (50 mL), saturated sodium bicarbonate solution (100 mL) and brine (100 mL), dried over anhydrous sodium sulfate, and concentrated to give a crude compound. The crude product was purified with flash column chromatography on silica gel (ethyl acetate in petroleum ether, from 5% to 10% v/v) to furnish Compound 247B.

To a solution of Compound 247B (2.51 g, 10 mmol) in THF (20 mL) was added n-BuLi (4.4 mL, 2.4 M in hexane, 11 mmol) dropwise under nitrogen at −76° C. The reaction mixture was stirred at −76° C. for 15 minutes. The reaction was added to a solution of diethyl oxalate (4.7 mL, 35 mmol) in THF (10 mL) under nitrogen at −60° C. for 30 minutes. The reaction mixture was quenched with saturated NH$_4$Cl solution (10 mL) and water (50 mL) and extracted with ethyl acetate (50 mL×3). The combined organic layers were washed with brine (25 mL), dried over anhydrous sodium sulfate, filtered, and evaporated to give a crude compound. The crude product was purified with flash column chromatography on silica gel (ethyl acetate in petroleum ether, from 5% to 10% v/v) to furnish Compound 247C.

To a solution of Compound 247C (445 mg, 1.64 mmol) in dry dichloromethane (10 mL) was added DAST (0.55 mL, 4.09 mmol). The mixture was stirred at 25° C. for 14 hours. After the reaction was completed, dichloromethane (35 mL) was added. The organic layer was washed with water (20 mL), saturated sodium bicarbonate solution (20 mL) and brine (20 mL), dried over anhydrous sodium sulfate, and concentrated to give a crude compound. The crude product was purified with flash column chromatography on silica gel (ethyl acetate in petroleum ether, from 10% to 20% v/v) to furnish Compound 247D.

To a solution of Compound 247D (458 mg, 1.57 mmol) in THF/water/MeOH (9 mL, 1:1:1, v/v) was added LiOH.H$_2$O (98 mg, 2.35 mmol). The mixture was stirred at 28° C. for 1 h. After the reaction was completed, it was adjusted to pH 6 with 2 N HCl. The reaction mixture was concentrated in vacuo. The crude product was in lyophilization to furnish Compound 247E.

A mixture of Compound 247E (88 mg, 0.33 mmol), Intermediate G (128 mg, 0.41 mmol), EDCI.HCl (96 mg, 0.49 mmol), and HOBt (67 mg, 0.49 mmol) in dichloromethane (15 mL) and DMF (2 mL) was stirred at 25° C. for 5 h. It was treated with water (20 mL), extracted with dichloromethane (20 mL×3), dried over anhydrous sodium sulfate, concentrated in vacuo, and purified with prep-HPLC to furnish Compound 247. LC-MS (ESI) m/z: 560 [M+H]$^+$; $^1$H-NMR (CD$_3$OD, 400 MHz): δ (ppm) 0.65-0.68 (m, 4H), 2.12-2.15 (m, 4H), 3.00-3.02 (m, 2H), 3.38-3.45 (m, 2H), 3.53-3.62 (m, 2H), 3.75-3.82 (m, 2H), 4.50-4.52 (m, 1H), 4.94-4.96 (d, J=2.8 Hz, 1H), 7.07 (s, 2H), 7.20 (t, J=8.8 Hz, 2H), 7.32-7.34 (m, 1H), 7.65-7.71 (m, 2H), 8.00-8.04 (m, 2H), 8.68 (s, 1H).

Example 248

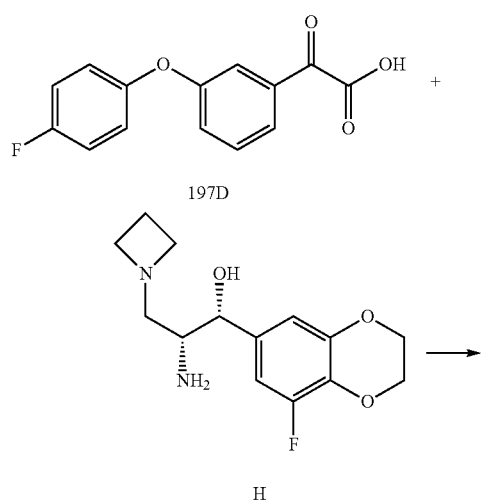

A mixture of Compound 197D (52 mg, 0.20 mmol), Intermediate H (63 mg, 0.20 mmol), and HATU (119 mg, 0.30 mmol) in DMF (5 mL) was stirred at 10° C. for 3 h. The mixture was purified with prep-HPLC to furnish Compound 248. LC-MS (ESI) m/z: 525 [M+H]$^+$; $^1$H-NMR (CDCl$_3$, 400 MHz): δ (ppm) 2.34-2.46 (m, 1H), 2.55-2.66 (m, 1H), 3.34 (s, 1H), 3.41-3.47 (m, 1H), 3.56 (dd, J=8, 12 Hz, 1H), 4.07-4.15 (s, 5H), 4.22-4.29 (m, 3H), 4.85 (s, 1H), 6.62-6.63 (m, 2H), 6.66-7.02 (m, 4H), 7.13 (d, J=8 Hz, 1H), 7.31 (t, J=8 Hz, 1H), 7.52 (t, J=8 Hz, 2H).

Example 249

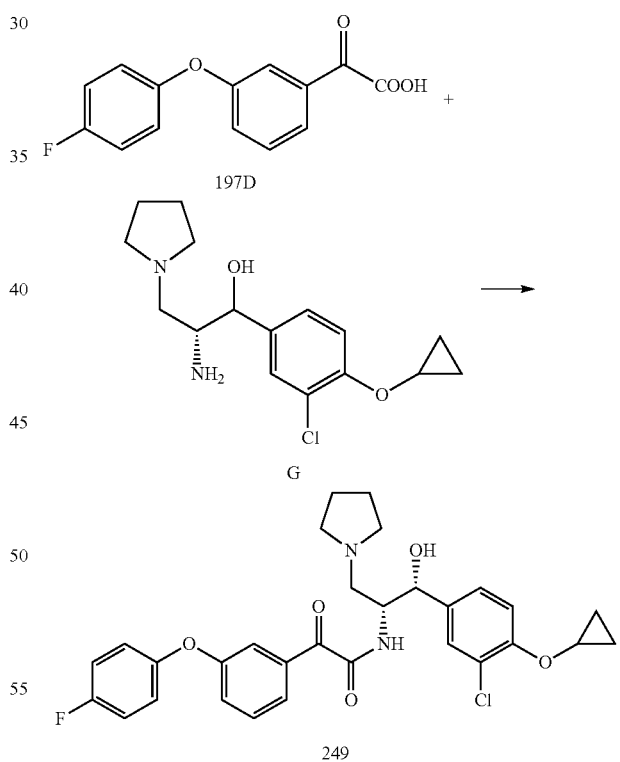

To a mixture of Compound 197D (130 mg, 0.5 mmol) and intermediate G (148 mg, 0.5 mmol) in DMF (5 mL) was added HATU (380 mg, 1 mmol). The reaction mixture was stirred at room temperature overnight. The resulting solution was washed with brine (30 mL), dried over anhydrous sodium sulfate, filtered, and concentrated. The residue was purified with reverse phase chromatography using eluent (methanol in water, from 10% to 50% v/v) to furnish Compound 249. LC-MS (ESI) m/z: 553 [M+H]+; 1H-NMR (DMSO-d6, 400 MHz): δ (ppm) 0.67-0.68 (m, 2H), 0.81-0.82 (m, 2H), 1.63-1.69 (m, 4H), 2.462-2.468 (m, 2H), 2.56-2.63 (m, 4H), 3.91-3.92 (m, 1H), 4.21-4.25 (m, 1H), 4.80 (s, 1H), 5.69 (s, 1H), 7.11-7.13 (m, 2H), 7.27-7.54 (m, 9H), 8.64-8.66 (d, J=8.6 Hz, 1H).

Example 250

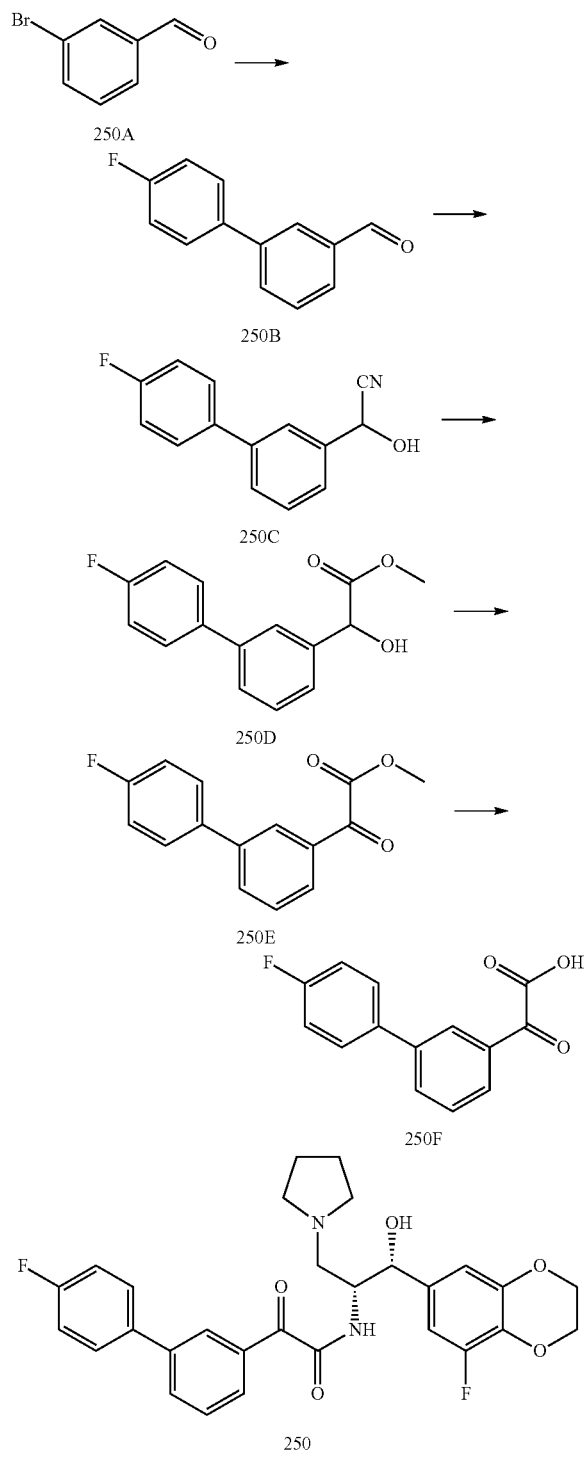

A mixture of Compound 250A (5.0 g, 27 mmol), 4-fluorophenylboronic acid (4.92 g, 35.13 mmol), [1,1'-bis(diphenylphosphino)ferrocene]dichloropalladium(II) (1.19 g, 1.62 mmol), potassium carbonate (11.2 g, 81.07 mmol), water (38 mL) and 1,4-dioxane (38 mL) was stirred under nitrogen atmosphere at 120° C. for 6 h. After cooling, water (20 mL) was added, and the mixture was extracted with ethyl acetate (100 mL×3). The combined organic layers were washed until neutral and dried over anhydrous sodium sulfate. After removal of the solvent in vacuo, the crude product was purified with flash column chromatography on silica gel (ethyl acetate in petroleum ether, from 5% to 10% v/v) to furnish Compound 250B.

To a solution of Compound 250B (3.0 g, 14.98 mmol) in water (40 mL) was added sodium metabisulfite (2.85 g, 14.98 mmol). The reaction mixture was stirred at room temperature for 1 h. After that, NaCN (1.47 g, 29.97 mmol) was added carefully. The mixture was stirred for 12 h and treated with ethyl acetate (100 mL). The resulting biphasic mixture was transferred to a separatory funnel. The layers were separated and the organic phase was washed with water (20 mL) and brine (20 mL). The organic phase was dried over anhydrous sodium sulfate, filtered, and concentrated in vacuo to afford the crude product, which was purified with flash column chromatography on silica gel (ethyl acetate in petroleum ether, from 20% to 40% v/v)) to furnish Compound 250C.

To a solution of Compound 250C (2.5 g, 11 mmol) in methanol (25 mL) at 0° C. was bubbled a gentle stream of HCl (gas) (dried over con. H2SO4) for 6 h. The reaction mixture was diluted with water (20 mL) and stirred at room temperature for 2 h. An aqueous solution of NaOH (2 M) was added dropwise into the reaction mixture until the pH was adjusted to 7. The mixture was extracted with dichloromethane (50 mL×3) and washed with water (50 mL) and brine (50 mL). The combined organic phases were dried over anhydrous sodium sulfate, filtered, and concentrated to give the crude product. The crude compound was purified with flash column chromatography on silica gel (ethyl acetate in petroleum ether, from 15% to 20% v/v) to furnish Compound 250D.

To a solution of Compound 250D (2.3 g, 8.84 mmol) in dichloromethane (30 mL) was added 1,2-benziodoxol-3(1H)-one (2.41 g, 9.72 mmol) at 0° C. The mixture was stirred at this temperature for 4 h. After that, the reaction solution was quenched with saturated ammonium chloride solution (10 mL) and extracted with ethyl acetate (30 mL×3). The organic phase was washed with water (20 mL) and brine (20 mL), dried over anhydrous sodium sulfate, filtered, and concentrated to furnish the crude product. The crude oil was purified with flash column chromatography on silica gel (ethyl acetate in petroleum ether, from 5% to 10% v/v) to furnish Compound 250E.

To a solution of Compound 250E (1.80 g, 6.97 mmol) in THF (20 mL) was added LiOH.H2O (335 mg, 7.98 mmol) in water (14 mL) at 0° C. The mixture was stirred at room temperature for 1 h. The reaction mixture was treated with ice water (10 mL) and extracted with ethyl acetate (50 mL). The water layer was adjusted to pH 2 with diluted HCl and extracted with ethyl acetate (50 mL×2). The combined organic layers were washed with brine (50 mL), dried over anhydrous sodium sulfate, and concentrated. The resulting solid was washed with petroleum ether and filtered off to afford Compound 250F.

A mixture of Compound 250F (110 mg, 0.45 mmol), Intermediate C (146 mg, 0.49 mmol), and HATU (205 mg, 0.54 mmol) in dichloromethane (3 mL) and DMF (3 mL)

was stirred at 0° C. for 4 h. The mixture was concentrated in vacuo and the resulting residue was purified with prep-HPLC to furnish the crude product as a white solid. The crude solid was further purified with prep-TLC on silica gel (ethyl acetate in petroleum ether, 30% v/v) to furnish Compound 250. LC-MS (ESI) m/z: 523 [M+H]$^+$; $^1$H-NMR (CDCl$_3$, 400 MHz): δ (ppm) 1.82-1.85 (m, 4H), 2.72-2.78 (m, 4H), 2.99-3.03 (m, 2H), 4.23-4.31 (m, 5H), 5.05 (d, J=2.1, 1H), 6.70 (s, 1H), 6.74 (dd, J=11.3, 1.9 Hz, 1H), 7.15 (t, J=8.7 Hz, 3H), 7.42-7.59 (m, 3H), 7.79 (d, J=8.3, 1H), 8.20 (d, J=6.7, 1H), 8.44 (s, 1H). Chiral separation condition: n-hexane (0.1% DEA):EtOH (0.1% DEA)=30:60, column: OD-H (250*4.6 mm 5 μm), retention time: 4.09 mm.

Example 251

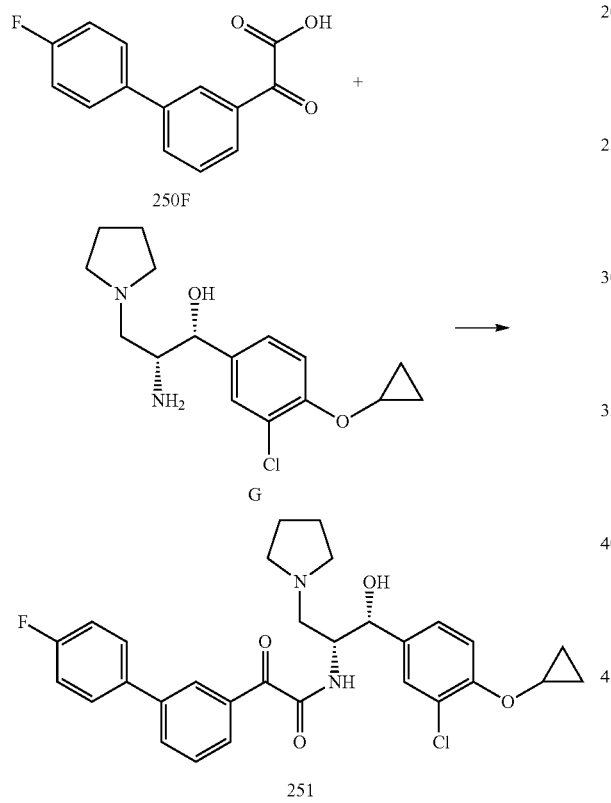

A mixture of Compound 250F (130 mg, 0.53 mmol), Intermediate G (182 mg, 0.58 mmol), and HATU (304 mg, 0.79 mmol) in dichloromethane (3 mL) and DMF (3 mL) was stirred at 0° C. for 4 h. The mixture was concentrated in vacuo and purified with prep-HPLC to furnish the crude product as a yellow solid. The crude solid was further purified with prep-TLC on silica gel (ethyl acetate in petroleum ether, 30% v/v) to furnish Compound 251. LC-MS (ESI) m/z: 537 [M+H]$^+$; $^1$H-NMR (CDCl$_3$, 400 MHz): δ (ppm) 0.71 (dd, J=10.7, 4.5 Hz, 4H), 1.89 (s, 1H), 2.08 (s, 4H), 3.12 (s, 2H), 3.48-3.71 (m, 2H), 3.83-3.94 (m, 3H), 4.55 (s, 1H), 5.07 (s, 1H), 7.08-7.12 (m, 2H), 7.15-7.23 (m, 2H), 7.35 (d, J=1.8 Hz, 1H), 7.38-7.49 (m, 3H), 7.71 (d, J=7.9 Hz, 1H), 7.81 (d, J=7.8 Hz, 1H), 7.94 (d, J=9.6 Hz, 1H), 8.12 (s, 1H).

Example 252

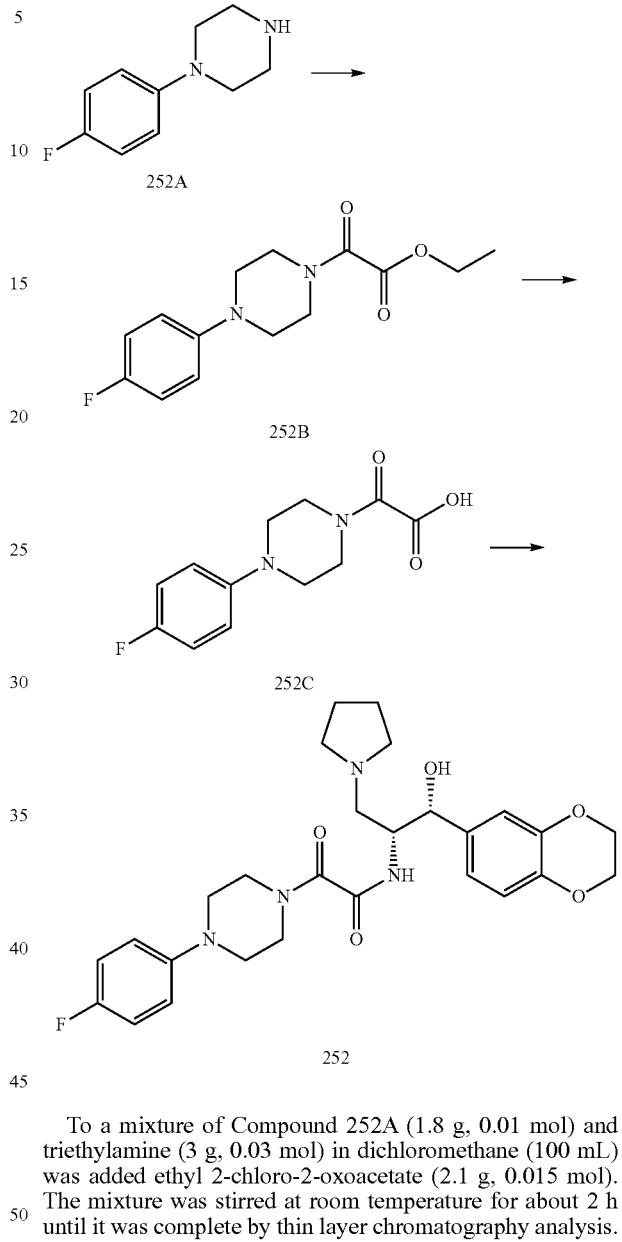

To a mixture of Compound 252A (1.8 g, 0.01 mol) and triethylamine (3 g, 0.03 mol) in dichloromethane (100 mL) was added ethyl 2-chloro-2-oxoacetate (2.1 g, 0.015 mol). The mixture was stirred at room temperature for about 2 h until it was complete by thin layer chromatography analysis. The resulting mixture was washed with brine (100 mL), dried over anhydrous sodium sulfate, filtered, and concentrated. The residue was purified with flash column chromatography on silica gel (ethyl acetate in petroleum ether, from 10% to 50% v/v) to furnish Compound 252B.

To a solution of Compound 252B (2.8 g, 0.01 mol) in ethanol/water (40 mL/10 mL) was added LiOH H$_2$O (840 mg, 0.02 mol). The mixture was stirred at room temperature for about 2 h until it was complete by thin layer chromatography analysis. The reaction mixture was acidified to pH 2 with aqueous HCl solution (1.0 N, 40 mL) and extracted with ethyl acetate (30 mL×2). The combined organic layers were washed with brine (100 mL), dried over anhydrous sodium sulfate, filtered, and concentrated to afford Compound 252C.

To a mixture of Compound 252C (126 mg, 0.5 mmol) and Intermediate A (139 mg, 0.5 mmol) in DMF (5 mL) was added HATU (380 mg, 1 mmol). The reaction mixture was stirred at room temperature overnight. The resulting solution was washed with brine (30 mL), dried over anhydrous sodium sulfate, filtered, and concentrated. The residue was purified with reverse phase chromatography using eluent (methanol in water, from 10% to 55% v/v) to furnish Compound 252. LC-MS (ESI) m/z: 513 [M+H]$^+$; $^1$H-NMR (CD$_3$OD, 400 MHz): δ (ppm) 1.83-1.84 (m, 4H), 2.68-2.72 (m, 5H), 2.88-2.94 (m, 2H), 3.03-3.06 (m, 2H), 3.09-3.14 (m, 1H), 3.33-3.37 (m, 2H), 3.58-0.366 (m, 1H), 3.75-3.81 (m, 1H), 4.20-4.21 (m, 4H), 4.37-4.39 (m, 1H), 4.84-4.85 (m, 1H), 6.79-6.81 (m, 1H), 6.86-6.88 (m, 1H), 6.96 (s, 1H), 7.01-7.04 (m, 4H);

Example 253

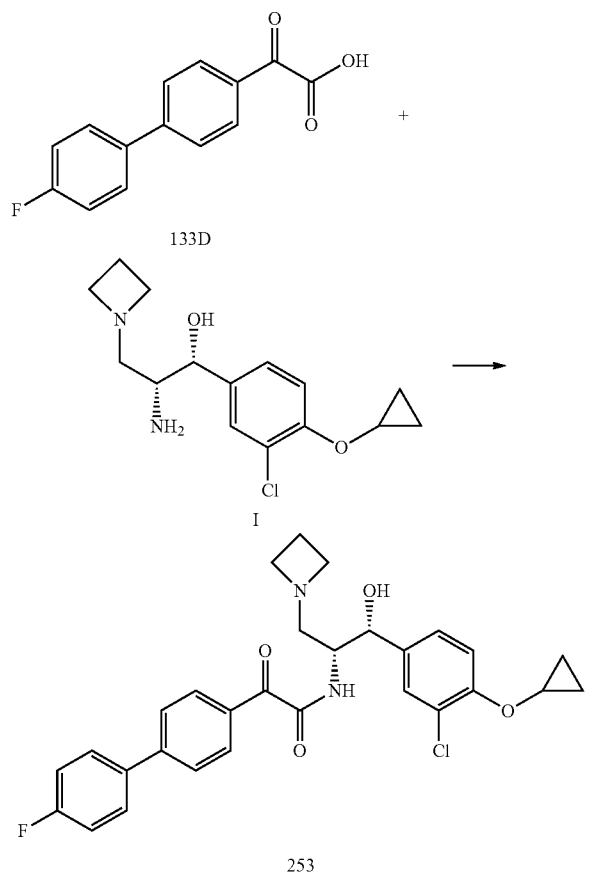

A mixture of Compound 133D (146 mg, 0.60 mmol), EDCI (193 mg, 0.90 mmol), HOBt (119 mg, 0.9 mmol) and Intermediate I (178 mg, 0.60 mmol) in DCM (20 mL) was stirred at room temperature overnight. The reaction mixture was treated with water (50 mL), extracted with DCM (50 mL×2), washed with brine (50 mL), dried over anhydrous sodium sulfate, and concentrated. The crude product was purified with prep-HPLC to give Compound 253. LC-MS (ESI) m/z: 523.1 [M+H]$^+$, $^1$H-NMR (CD$_3$OD, 400 MHz): δ (ppm) 0.71-0.84 (m, 4H), 2.45-2.66 (m, 2H), 3.57-3.67 (m, 2H), 3.84-3.86 (m, 1H), 4.21-4.36 (m, 5H), 4.55-4.57 (m, 1H), 4.98 (d, J=2.4 Hz, 1H), 7.21-7.28 (m, 2H), 7.35-7.40 (m, 2H), 7.52 (s, 1H), 7.64-7.67 (m, 4H), 7.73-7.77 (m, 2H).

Example 254

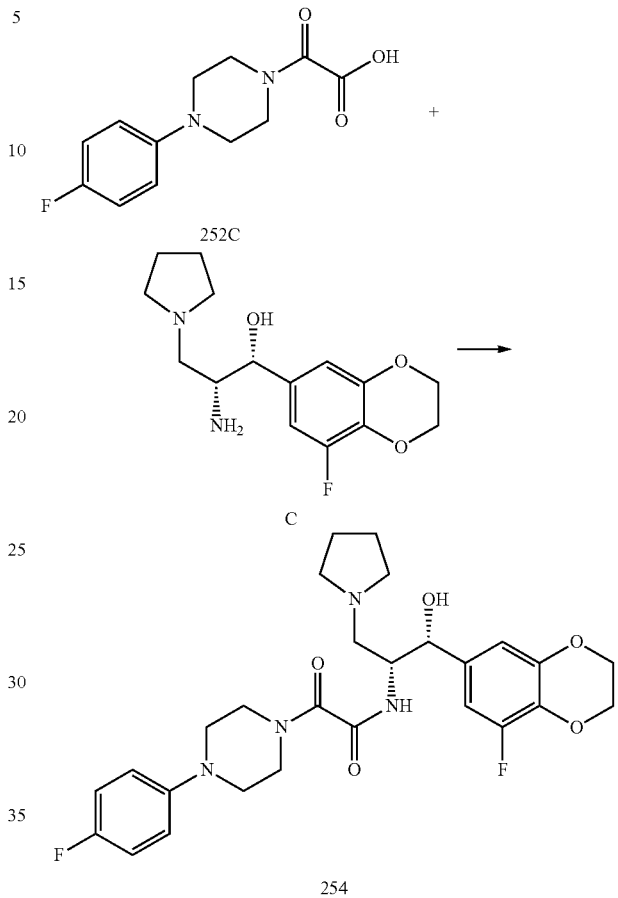

To a mixture of Compound 252C (126 mg, 0.5 mmol) and Intermediate C (150 mg, 0.5 mmol) in DMF (5 mL) was added HATU (380 mg, 1 mmol). The reaction mixture was stirred at room temperature overnight. The resulting solution was washed with brine (30 mL), dried over anhydrous sodium sulfate, filtered, and concentrated. The resulting residue was purified with reverse phase chromatography using eluent (methanol in water, from 10% to 55% v/v) to furnish Compound 254. LC-MS (ESI) m/z: 531 [M+H]$^+$; $^1$H-NMR (DMSO-d$_6$, 400 MHz): δ (ppm) 1.86-2.01 (m, 4H), 2.87-3.84 (m, 14H), 4.27 (s, 4H), 4.40-4.43 (m, 1H), 4.47 (s, 1H), 6.73 (s, 1H), 6.80-6.81 (m, 1H), 6.83-6.85 (m, 2H), 7.06-7.18 (m, 2H), 8.68 (d, J=9.6 Hz, 1H), 9.83 (brs, 1H).

Example 255

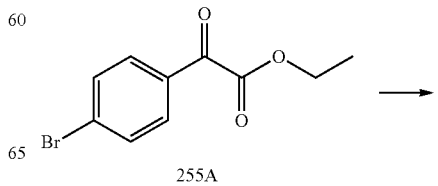

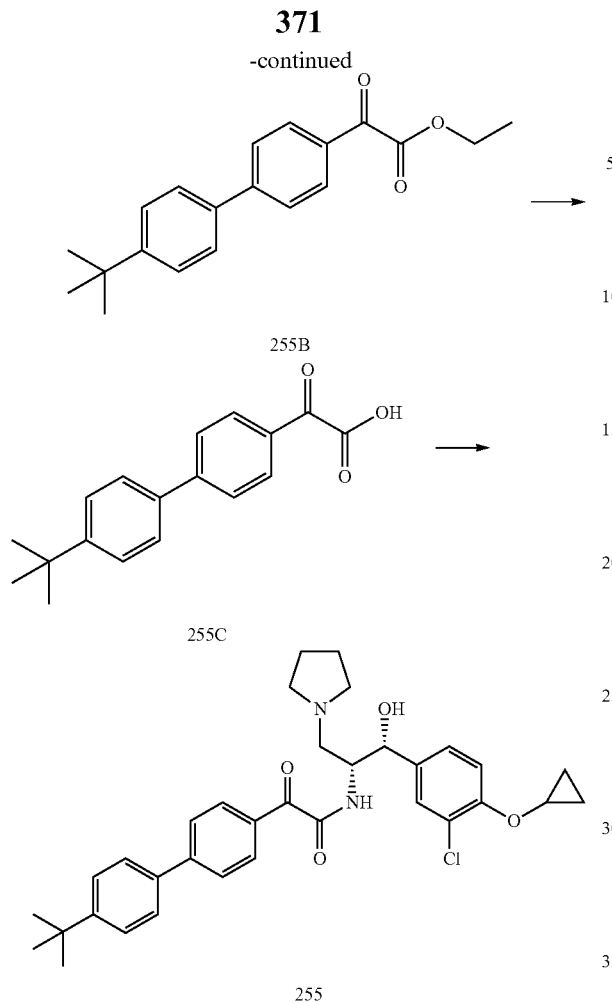

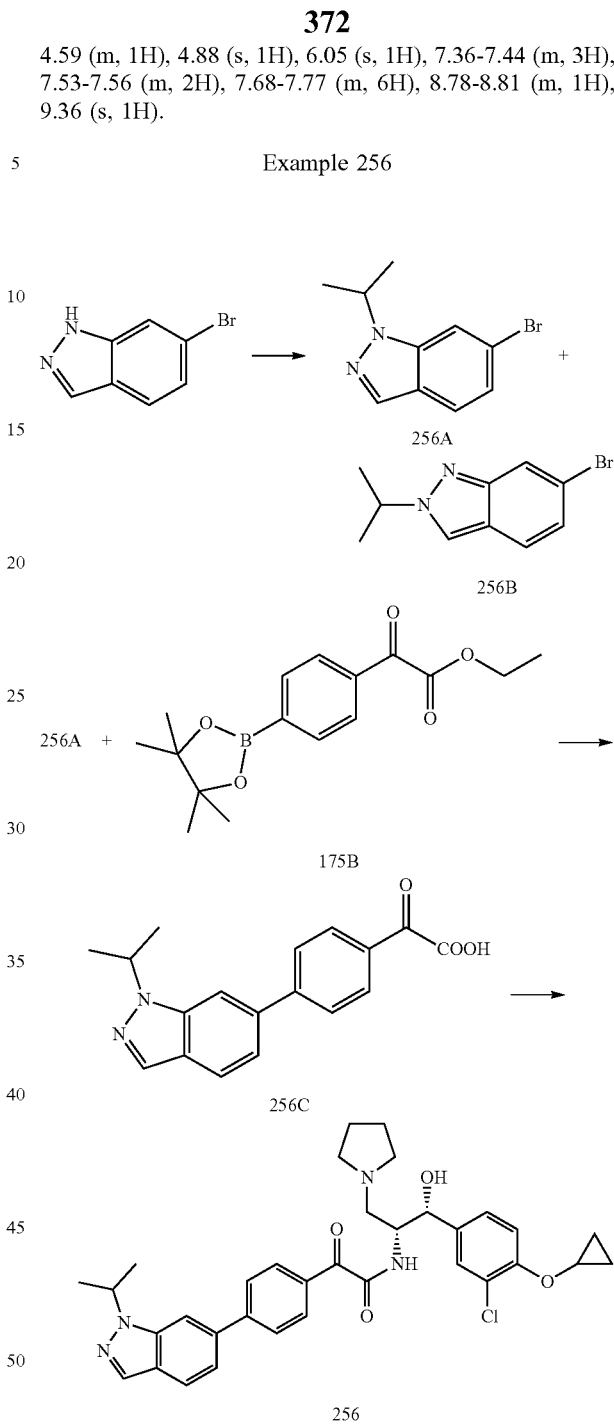

4.59 (m, 1H), 4.88 (s, 1H), 6.05 (s, 1H), 7.36-7.44 (m, 3H), 7.53-7.56 (m, 2H), 7.68-7.77 (m, 6H), 8.78-8.81 (m, 1H), 9.36 (s, 1H).

Example 256

A mixture of Compound 255A (0.72 g, 2.8 mmol), $K_3PO_4$ (1.78 g, 8.4 mmol), (4-(tert-butyl)phenyl)boronic acid (0.5 g, 2.8 mmol), and $Pd(dppf)Cl_2$ (20 mg, 0.28 mmol) in toluene (10 mL) was stirred under nitrogen at 100° C. for 16 h. The mixture was cooled to 25° C., diluted with ethyl acetate (50 mL), washed with water (20 mL×2) and brine (20 mL), dried over anhydrous sodium sulfate, concentrated, and purified with flash column chromatography on silica gel (ethyl acetate in petroleum ether, from 0% to 10% v/v) to afford Compound 255B.

A mixture of Compound 255B (0.45 g, 1.5 mmol) and $LiOH·H_2O$ (0.09 g, 2.2 mmol) in THF (5 mL) and water (2 mL) was stirred at 0° C. for 2 h. The mixture was diluted with ethyl acetate (30 mL), washed with water (10 mL×2) and brine (10 mL), dried over anhydrous sodium sulfate, concentrated, and purified with reverse phase chromatography using eluent (methanol in water, from 0% to 100% v/v) to afford Compound 255C.

A mixture of Compound 255C (0.1 g, 0.35 mmol), HATU (0.2 g, 0.5 mmol), and Intermediate G in dichloromethane (5 mL) was stirred at 25° C. for 16 h. The mixture was diluted with ethyl acetate (30 mL), washed with water (10 mL×2) and brine (10 mL), dried over anhydrous sodium sulfate, concentrated, and purified with prep-HPLC to furnish Compound 255. LC-MS (ESI) m/z: 575 [M+H]$^+$; $^1$H-NMR (DMSO-$d_6$, 400 MHz): δ (ppm) 0.67-0.68 (m, 2H), 0.82-0.83 (m, 2H), 1.33 (s, 9H), 1.88-1.90 (m, 2H), 2.04 (s, 2H), 3.13-3.23 (m, 2H), 3.48-3.56 (m, 4H), 3.93 (s, 1H), 4.54-

To 6-bromoindazole (3.2 g, 16.2 mmol) in DMF (30 mL) was added sodium hydride (60% in mineral, 712 mg, 17.8 mmol) with ice bath cooling. The mixture was stirred at room temperature for 30 min. Compound 2-iodopropane (8.3 g 48.6 mmol) was added at room temperature. The reaction mixture was stirred at room temperature for 1 h, quenched with saturated aqueous ammonium chloride solution (30 mL), and extracted with ethyl acetate (100 mL×3). The combined organic layers were washed with brine (200 mL), dried over anhydrous sodium sulfate, and concentrated. Purification with flash column chromatography on silica gel (ethyl acetate in petroleum ether, from 0% to 1% v/v) gave Compound 256A and Compound 256B.

A mixture of Compound 256A (1.0 g, 4.2 mmol), Compound 175B (1.28 g, 4.2 mmol), Pd(dppf)Cl$_2$ (171 mg, 0.21 mmol), and K$_2$CO$_3$ (1.74 g, 12.6 mmol) in dioxane (20 mL) and water (20 mL) was stirred under nitrogen at 100° C. for 3.5 h. The reaction mixture was cooled to room temperature and filtered through celite. The filtrate was diluted with water (100 mL) and extracted with ethyl acetate (100 mL×2). The aqueous layer was acidified to pH 3 with aqueous HCl solution (1 N) and extracted with ethyl acetate (100 mL×2). The combined organic layers were washed with water (100 mL×2) and brine (100 mL), dried over anhydrous sodium sulfate, and concentrated to give Compound 256C.

A mixture of Compound 256C (100 mg, 0.32 mmol), HATU (182 mg, 0.48 mmol), and Intermediate G (99 mg, 0.32 mmol) in DMF (5 mL) was stirred for 18 h at 10° C. The mixture was diluted with ethyl acetate (50 mL), washed with water (50 mL×2) and brine (50 mL), and dried over anhydrous sodium sulfate. After evaporation, the crude product was purified with prep-HPLC to furnish Compound 256. LC-MS (ESI) m/z: 601 [M+H]$^+$; $^1$H-NMR (DMSO-d$_6$, 400 MHz): δ (ppm) 0.63-0.85 (m, 4H), 1.52 (dd, J=6.4, 1.6 Hz, 6H), 1.89-2.05 (m, 4H), 3.13-3.25 (m, 2H), 3.41-3.58 (m, 4H), 3.93-3.98 (m, 1H), 4.57-4.62 (m, 1H), 4.91 (s, 1H), 5.12-5.18 (m, 1H), 6.10 (s, 1H), 7.37 (dd, J=8.4, 1.6 Hz, 1H), 7.43-7.48 (m, 2H), 7.52 (dd, J=8.4, 1.2 Hz, 1H), 7.78 (d, J=8.4 Hz, 2H), 7.89 (d, J=8.8 Hz, 3H), 8.09 (s, 1H), 8.14 (s, 1H), 8.84 (d, J=9.6 Hz, 1H), 9.59 (brs, 1H).

Example 257

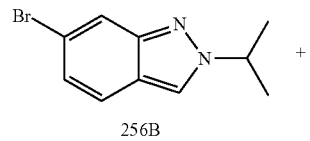

256B

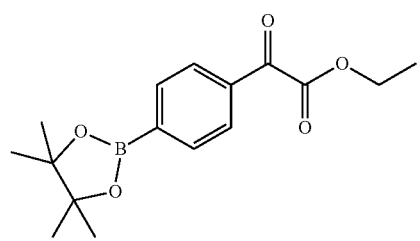

175B

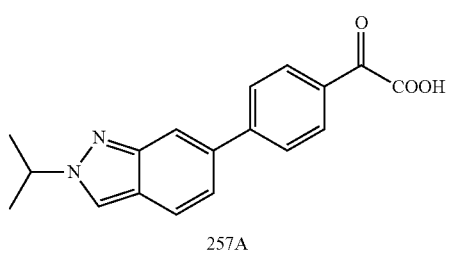

257A

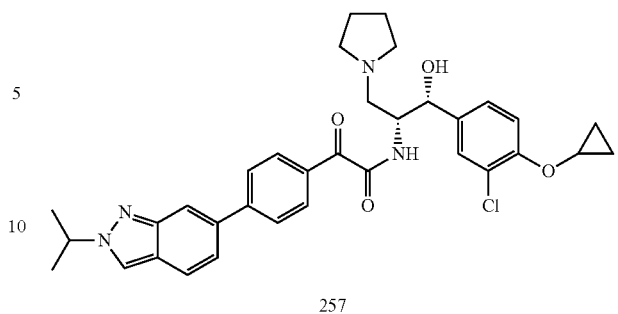

257

A mixture of Compound 175B (500 mg, 2.1 mmol), Compound 256B (638 mg, 2.1 mmol), Pd(dppf)Cl$_2$ (92 mg, 0.11 mmol), and K$_2$CO$_3$ (869 mg, 6.3 mmol) in dioxane (10 mL) and water (10 mL) was stirred under nitrogen at 100° C. for 3.5 h. The reaction mixture was cooled to room temperature and filtered through celite. The filtrate was diluted with water (100 mL) and extracted with ethyl acetate (100 mL×2). The aqueous layer was acidified to pH 3 with aqueous HCl solution (1 N) and extracted with ethyl acetate (100 mL×2). The combined organic layers were washed with water (100 mL×2) and brine (100 mL), dried over anhydrous sodium sulfate, and concentrated to give Compound 257A.

A mixture of Compound 257A (100 mg, 0.32 mmol), HATU (182 mg, 0.48 mmol), and Intermediate G (99 mg, 0.32 mmol) in DMF (5 mL) was stirred at 10° C. for 18 h. The mixture was diluted with ethyl acetate (50 mL), washed with water (50 mL×2) and brine (50 mL), and dried over anhydrous sodium sulfate. After evaporation, the crude product was purified with prep-HPLC to furnish Compound 257. LC-MS (ESI) m/z: 601 [M+H]$^+$; $^1$H-NMR (DMSO-d$_6$, 400 MHz): δ (ppm) 0.68-0.84 (m, 4H), 1.58 (d, J=6.4 Hz, 6H), 1.89-2.04 (m, 4H), 3.09-3.22 (m, 2H), 3.43-3.58 (m, 4H), 3.93-3.97 (m, 1H), 4.56-4.61 (m, 1H), 4.84-4.92 (m, 2H), 6.08-609 (m, 1H), 7.35-7.38 (m, 1H), 7.41-7.46 (m, 3H), 7.75-7.77 (m, 2H), 7.82-7.85 (m, 3H), 8.01 (s, 1H), 8.48 (s, 1H), 8.83 (d, J=10.0 Hz, 1H), 9.65 (brs, 1H).

Example 258

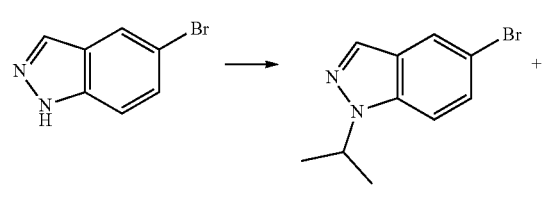

258A

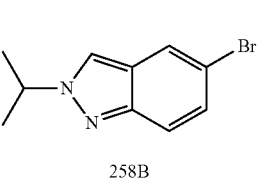

258B

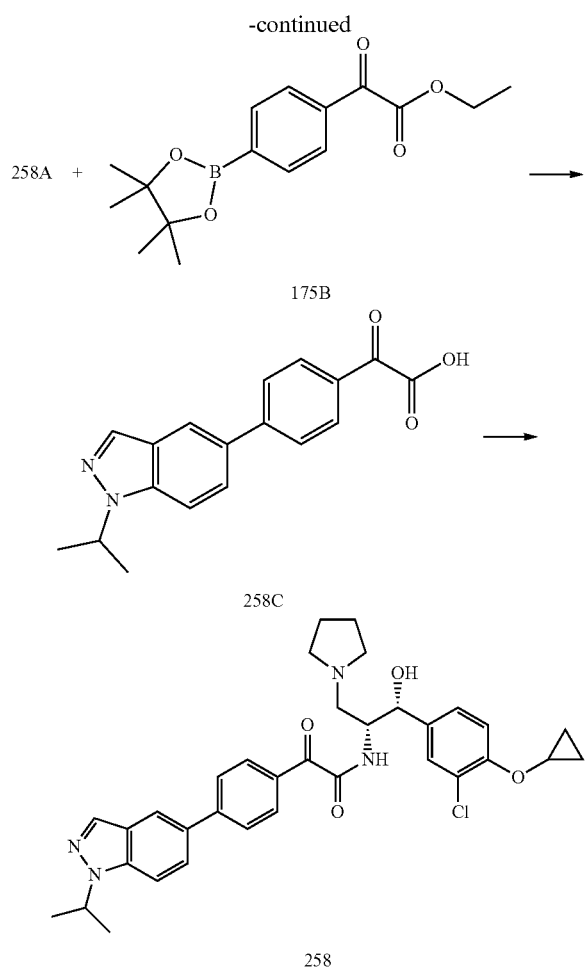

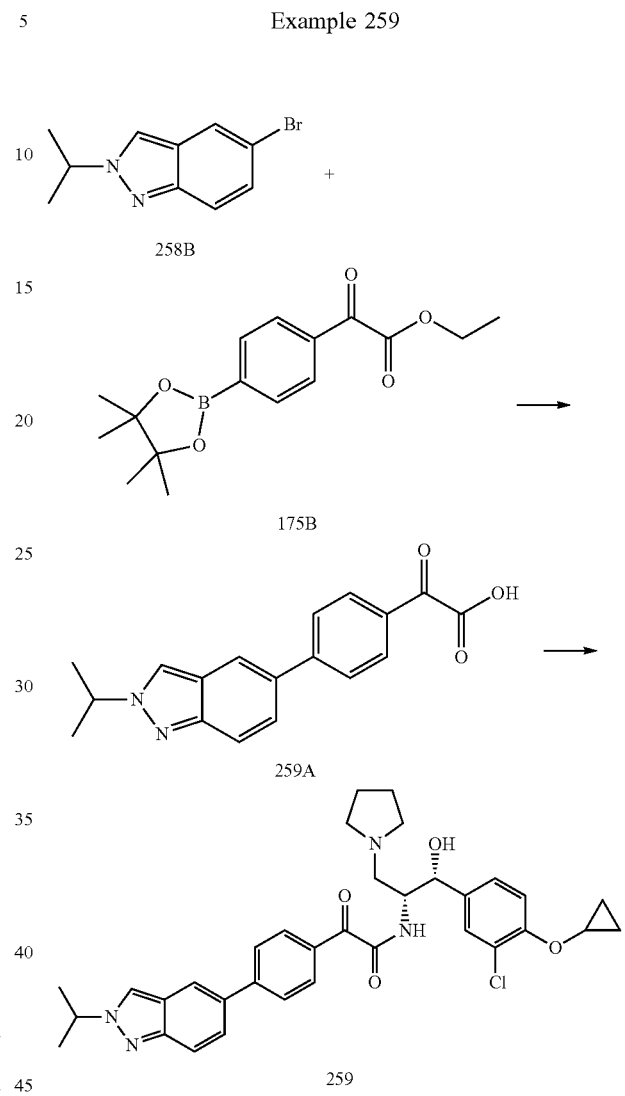

5.20-5.21 (m, 1H), 5.47-5.50 (m, 1H), 7.42-7.44 (m, 2H), 7.51-7.52 (m, 1H), 7.79-7.83 (m, 4H), 7.97-7.99 (m, 2H), 8.12-8.16 (m, 2H), 8.19-8.21 (m, 1H), 8.94 (brs, 1H).

Example 259

To a solution of 5-bromo-1H-indazole (5.91 g, 30 mmol) in anhydrous DMF (100 mL) was added 2-bromopropane (8.67 g, 70.5 mmol) and cesium carbonate (29.2 g, 90 mmol) at room temperature. After stirring the reaction mixture at room temperature for 3 h, 2 N hydrochloric acid was added until a neutral pH was reached. The aqueous layer was extracted with ethyl acetate (100 mL×2). The combined organic extracts were washed with brine (100 mL×2) and dried over anhydrous sodium sulfate. After filtration, the solvent was removed in vacuo and the residue was purified with flash column chromatography on silica gel to give Compound 258A and Compound 258B.

To a solution of Compound 258A (180 mg, 0.75 mmol) in 1,4-dioxane (15 mL) was added Compound 175B (250 mg, 0.825 mmol), Pd(dppf)Cl$_2$ (30 mg, 0.0375 mmol), potassium carbonate (310 mg, 2.25 mmol) and water (1 mL) under nitrogen. The reaction mixture was stirred at 100° C. for 2 hours. The resulting mixture was cooled to 25° C. The precipitated solid was filtered and dried to afford Compound 258C.

To a solution of Compound 258C (45 mg, 0.146 mmol) in DMF (3 mL) was added Intermediate G (45 mg, 0.146 mmol) and HATU (83 mg, 0.219 mmol). The reaction mixture was stirred at 20° C. for 10 h. The mixture was purified with prep-HPLC to yield the product Compound 258. LC-MS (m/z) 601 [M+H]$^+$; $^1$H-NMR (Acetone-d$_6$, 400 MHz): δ (ppm) 0.71-0.72 (m, 2H), 0.82-0.84 (m, 2H), 1.57 (s, 3H), 1.58 (s, 3H), 2.05-2.25 (m, 4H), 3.45-3.60 (m, 2H), 3.82-4.15 (m, 5H), 4.92-4.97 (m, 1H), 5.02-5.09 (m, 1H), To a solution of Compound 258B (180 mg, 0.75 mmol) in 1,4-dioxane (15 mL) was added Compound 175B (250 mg, 0.825 mmol), Pd(dppf)Cl$_2$ (30 mg, 0.0375 mmol), potassium carbonate (310 mg, 2.25 mmol) and water (1 mL) under nitrogen. The reaction mixture was stirred at 100° C. for 2 hours. The resulting mixture was cooled to 25° C. The precipitated solid was filtered and dried to afford Compound 259A.

To a solution of Compound 259A (74 mg, 0.24 mmol) in DMF (3 mL) was added Intermediate G (74 mg, 0.24 mmol) and HATU (136 mg, 0.36 mmol). The reaction mixture was stirred at 20° C. for 10 h. The mixture was purified with prep-HPLC to yield the product Compound 259. LC-MS (m/z) 601 [M+H]$^+$; $^1$H-NMR (acetone-d$_6$, 400 MHz): δ (ppm) 0.70-0.72 (m, 2H), 0.79-0.84 (m, 2H), 1.68 (s, 3H), 1.70 (s, 3H), 2.05-2.13 (m, 2H), 2.26-2.28 (m, 2H), 3.43-3.56 (m, 2H), 3.85-3.91 (m, 3H), 4.06-4.09 (m, 2H), 4.93-5.01 (m, 2H), 5.20-5.21 (m, 1H), 7.39-7.46 (m, 2H), 7.51-7.52 (m, 1H), 7.75-7.82 (m, 4H), 7.97-7.99 (m, 2H), 8.16-8.21 (m, 2H), 8.58-8.59 (m, 1H), 8.82 (brs, 1H).

Example 260

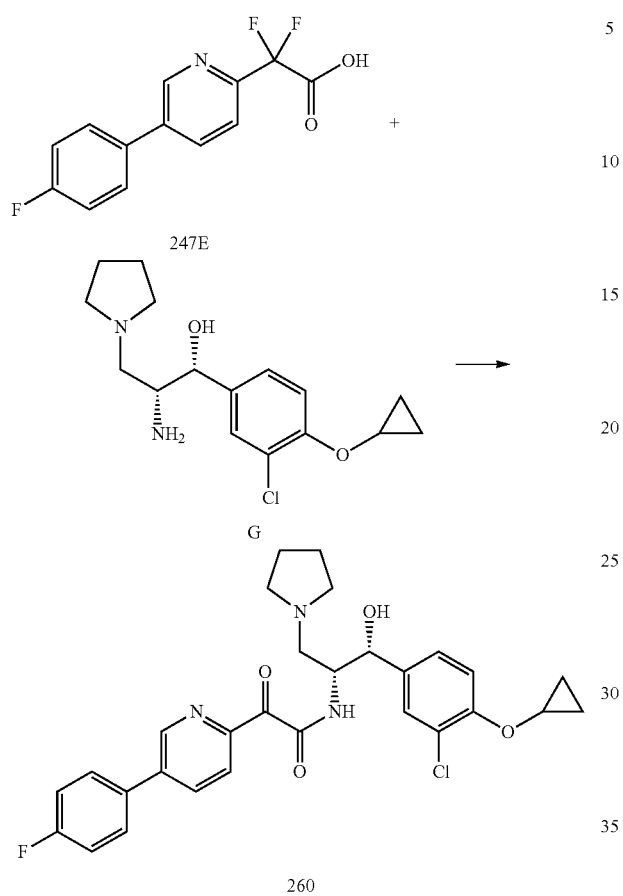

To a mixture of Compound 247E (100 mg, 0.3 mmol) in THF (10 mL) and DMF (2 mL) was added EDCI (106 mg, 0.55 mmol), HOBt (74 mg, 0.55 mmol) and Intermediate G (115 mg, 0.37 mmol). The mixture was stirred at 25° C. for 15 hours. It was diluted with water (20 mL) and extracted with ethyl acetate (20 mL×3). The combined organic layers were washed with brine (25 mL), dried over anhydrous sodium sulfate, and concentrated to give a crude compound. The crude product was purified with prep-HPLC to afford Compound 260. LC-MS (ESI) m/z: 538 [M+H]$^+$; $^1$H-NMR (CD$_3$OD, 400 MHz): δ (ppm) 0.61-0.75 (m, 4H), 2.06-2.20 (m, 4H), 3.22-3.28 (m, 2H), 3.56-3.80 (m, 5H), 4.61-4.64 (m, 1H), 4.94 (s, 1H), 7.21-7.31 (m, 4H), 7.41 (d, J=1.6 Hz, 1H), 7.72 (d, J=8.0 Hz, 1H), 7.77-7.80 (m, 2H), 8.19 (dd, J=8.0, 2.0 Hz, 1H), 8.82 (s, 1H).

Example 261

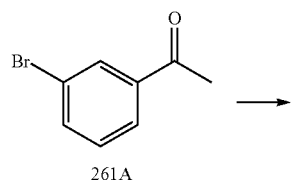

261A

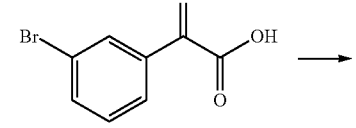

261B

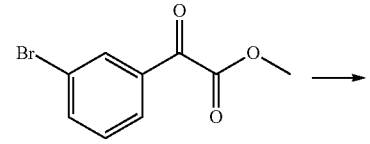

261C

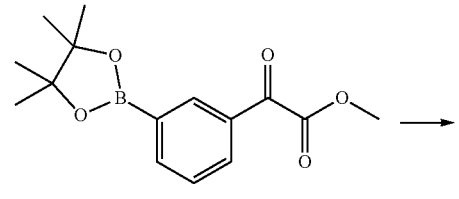

261D

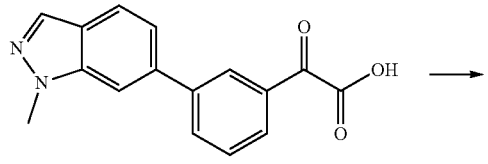

261E

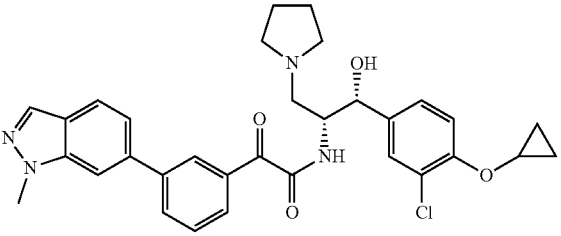

261

A suspension of Compound 261A (6.00 g, 30.15 mmol) and SeO$_2$ (5.02 g, 45.22 mmol) in pyridine (50 mL) was stirred at 100° C. for 16 h. It was filtered to remove the resultant solid and the filtrate was evaporated to remove pyridine. The residue was dissolved in aqueous NaOH solution (5% w/w, 200 mL) and extracted with diethyl ether (100 mL×2). The aqueous was adjusted to pH 1 with con. HCl to form a solid, which was filtered and dried to afford Compound 261B.

A mixture of Compound 261B (3.00 g, 13.22 mmol) and concentrated H$_2$SO$_4$ (1 mL) in methanol (50 mL) was stirred at 80° C. for 16. After evaporation, the residue was diluted with ethyl acetate (200 mL), washed with water (200 mL) and brine (200 mL), dried over anhydrous sodium sulfate, and purified with flash column chromatography on silica gel (ethyl acetate in petroleum ether, from 0% to 10% v/v) to furnish Compound 261C.

A mixture of Compound 261C (1.58 g, 6.53 mmol), 4,4,4',4',5,5,5',5'-octamethyl-2,2'-bi(1,3,2-dioxaborolane) (1.82 g, 7.18 mmol), KOAc (1.92 g, 19.59 mmol), and PdCl$_2$(PPh$_3$)$_2$ (229 mg, 0.33 mmol) in dioxane (50 mL) was stirred under nitrogen at 90° C. for 16 h. It was diluted with ethyl acetate (150 mL), washed with water (200 mL) and brine (200 mL), dried over anhydrous sodium sulfate, and evaporated to afford Compound 261D.

A mixture of Compound 261D (500 mg, 1.72 mmol), 6-bromo-1-methyl-1H-indazole (364 mg, 1.72 mmol), K₂CO₃ (475 mg, 3.44 mmol), and Pd(dppf)Cl₂ (70 mg, 0.09 mmol) in dioxane (10 mL) and water (2 mL) was stirred under nitrogen at 85° C. for 16 h. The mixture was cooled down to room temperature and purified with reverse phase chromatography using eluent (methanol in water, from 0% to 100% v/v) to give Compound 261E.

A mixture of Compound 261E (100 mg, 0.36 mmol), Intermediate G (111 mg, 0.36 mmol), and HATU (207 mg, 0.54 mmol) in DMF (5 mL) was stirred at room temperature for 16 h. It was diluted with ethyl acetate (120 mL), washed with water (100 mL) and brine (100 mL), dried over anhydrous sodium sulfate, concentrated, and purified with prep-HPLC to yield Compound 261. LC-MS (ESI) m/z: 573 [M+H]⁺; ¹H-NMR (DMSO-d₆, 400 MHz): δ (ppm) 0.63-0.78 (m, 4H), 1.87-2.03 (m, 4H), 3.15 (brs, 2H), 3.49-3.84 (m, 4H), 4.12 (s, 4H), 4.54 (s, 1H), 4.86 (s, 1H), 6.09 (s, 1H), 7.34-7.68 (m, 6H), 7.86-8.31 (m, 5H), 8.81 (s, 1H), 9.42 (s, 1H).

Example 262

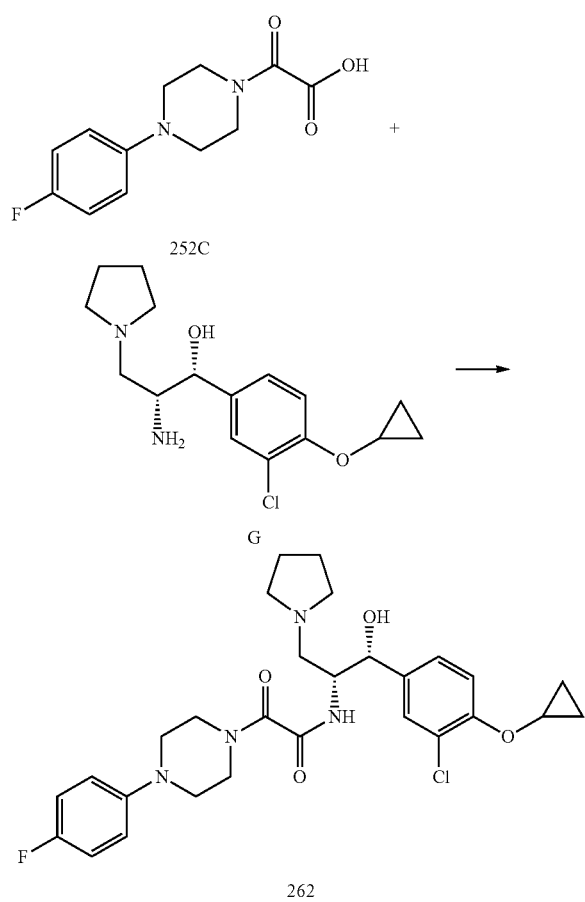

To a mixture of Compound 252C (126 mg, 0.5 mmol) and Intermediate G (160 mg, 0.5 mmol) in DMF (5 mL) was added HATU (380 mg, 1 mmol). The reaction mixture was stirred at room temperature overnight. The resulting solution was diluted with dichloromethane (50 mL), washed with brine (30 mL), dried over anhydrous sodium sulfate, filtered, and concentrated. The resulting residue was purified with reverse phase chromatography using eluent (methanol in water, from 10% to 55% v/v) to furnish Compound 262. LC-MS (ESI) m/z: 545 [M+H]⁺; ¹H-NMR (DMSO-d₆, 400 MHz): δ (ppm) 0.64-0.65 (m, 2H), 0.81-0.82 (m, 2H), 1.86-2.01 (m, 4H), 2.80-3.65 (m, 14H), 3.91-3.93 (m, 1H), 4.47-4.48 (m, 1H), 4.87-4.88 (m, 1H), 6.04 (br s, 1H), 6.94-6.96 (m, 2H), 7.13-7.18 (m, 2H), 7.68-7.84 (m, 3H), 8.69 (d, J=9.6 Hz, 1H), 10.10 (brs, 1H).

Example 263

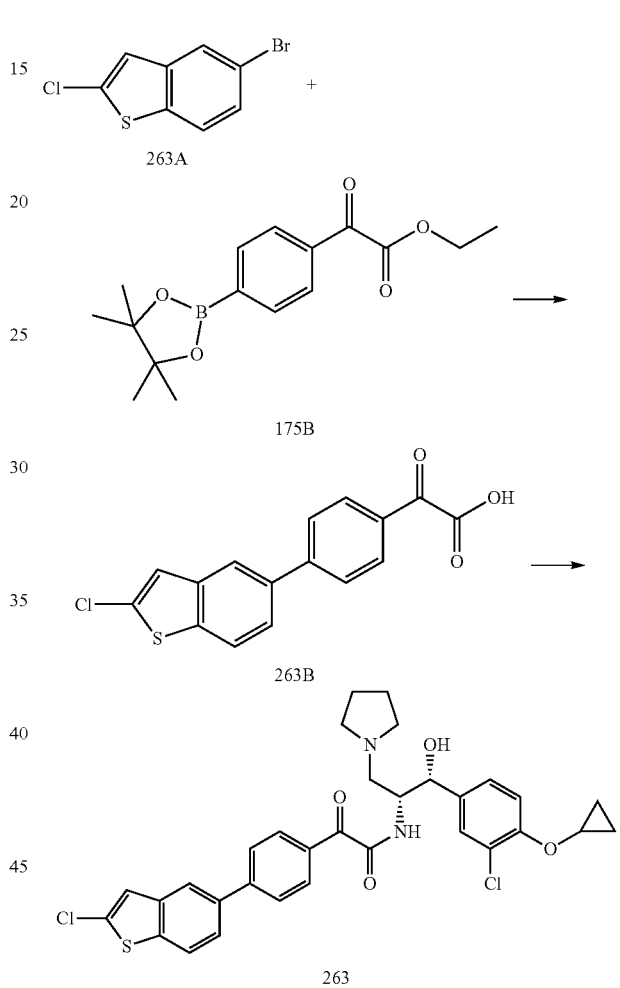

A mixture of Compound 263A (492 mg, 2 mmol), Compound 175B (669 mg, 2.2 mmol), K₂CO₃ (828 mg, 6 mmol), and Pd(dppf)Cl₂ (50 mg, 0.07 mmol) in dioxane (20 mL) and water (4 mL) was stirred under nitrogen at 100° C. overnight. The solution was cooled to room temperature and adjusted to pH 6 with aqueous hydrochloric acid solution (6 N, 1 mL). The solution was extracted with ethyl acetate (100 mL×3). The organic layer was washed with water (50 mL) and brine (50 mL), dried over anhydrous sodium sulfate, filtered, and evaporated to afford Compound 263B.

A mixture of Compound 263B (156 mg, 0.5 mmol), HATU (342 mg, 0.9 mmol), and Intermediate G (155 mg, 0.5 mmol) in dichloromethane (10 mL) and DMF (4 mL) was stirred at 25° C. overnight. The solution was extracted with ethyl acetate (50 mL×2). The combined organic phases were washed with water (50 mL) and brine (50 mL), dried over anhydrous sodium sulfate, filtered, and concentrated to give a residue. The crude product was purified with prep-HPLC to afford Compound 263. LC-MS (ESI) m/z: 609 [M+H]$^+$; $^1$H-NMR (CD$_3$OD, 400 MHz): δ (ppm) 0.66-0.85 (m, 4H), 2.05-2.25 (m, 4H), 3.42-3.90 (m, 7H), 4.71-4.74 (m, 1H), 5.00 (s, 1H), 7.38-7.39 (m, 2H), 7.42 (s, 1H), 7.47-7.52 (m, 1H), 7.73-7.76 (m, 5H), 7.93-7.95 (m, 1H), 8.08-8.09 (m, 1H).

Example 264

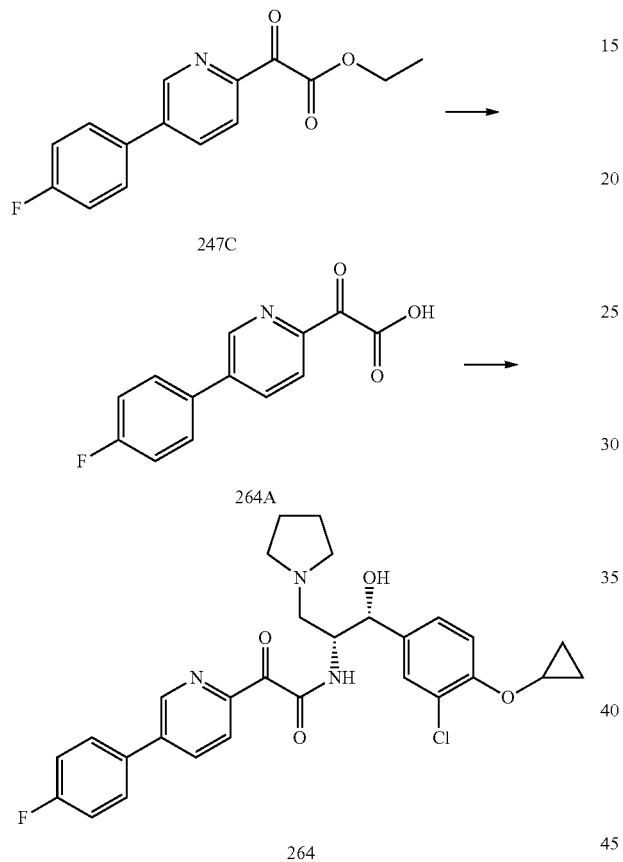

Example 265

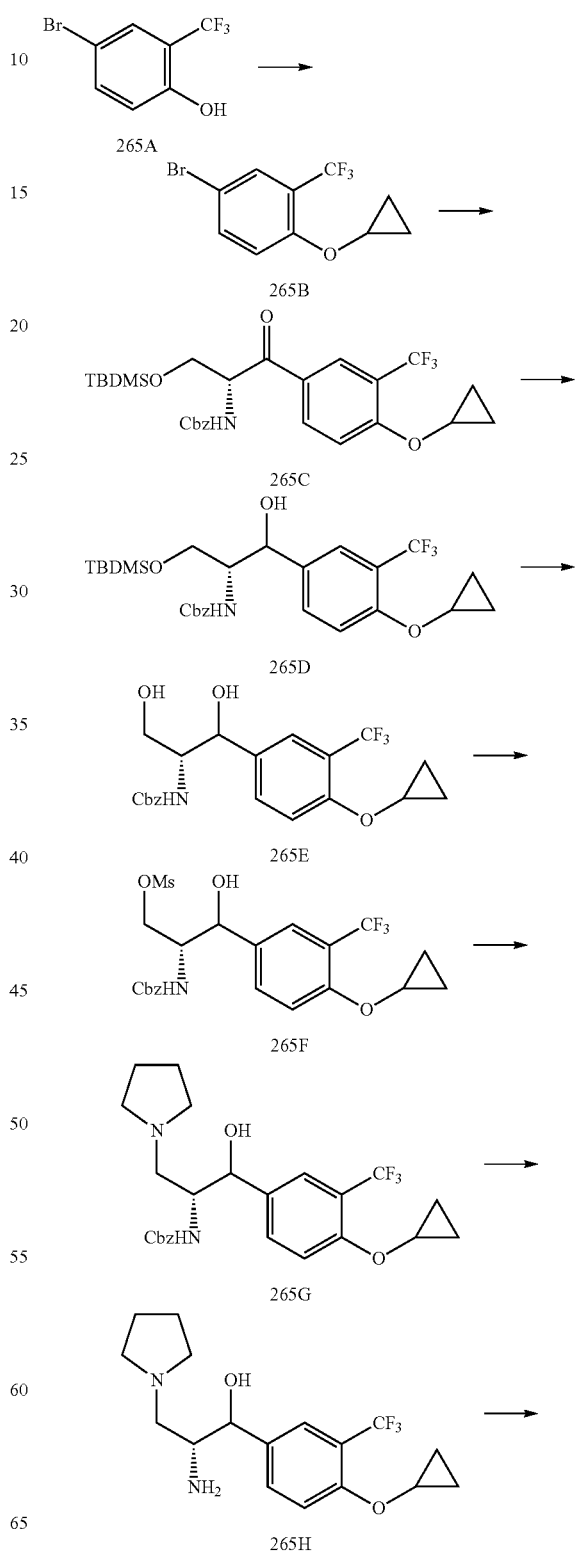

To a solution of Compound 247C (500 mg, 1.82 mmol) in methanol/water (10 mL, 1:1, v/v) was added LiOH.H$_2$O (153 mg, 3.64 mmol). The reaction mixture was stirred at 15° C. for 18 h. After the reaction was completed, it was adjusted to pH 6 with aqueous HCl solution (3 N) and concentrated in vacuo to give a crude compound. The crude product was lyophilized to furnish Compound 264A.

To a mixture of Compound 264A (90 mg, 0.37 mmol) in dichloromethane (5 mL) was added HATU (213 mg, 0.55 mmol) and Intermediate G (115 mg, 0.37 mmol). The mixture was stirred at 15° C. for 18 h. It was treated with water (20 mL) and extracted with ethyl acetate (50 mL×3). The combined organic layers were washed with water (50 mL), dried over anhydrous sodium sulfate, and concentrated to give a crude compound. The crude product was purified with prep-HPLC to afford Compound 264. LC-MS (ESI) m/z: 538 [M+H]$^+$; $^1$H-NMR (DMSO-d$_6$, 400 MHz): δ (ppm) 0.65-0.84 (m, 4H), 1.87-2.08 (m, 4H), 3.10-3.26 (m, 3H), 3.62-3.72 (m, 3H), 3.91-3.95 (m, 1H), 4.50-4.55 (m, 1H), 4.88 (d, J=2.8 Hz, 1H), 6.09 (brs, 1H), 7.36-7.49 (m, 5H), 7.91-7.94 (m, 2H), 8.06 (d, J=8.4 Hz, 1H), 8.33 (dd, J=8.0, 2.0 Hz, 1H), 8.99 (d, J=2.0 Hz, 1H), 9.13 (d, J=9.2 Hz, 1H), 9.53 (brs, 1H).

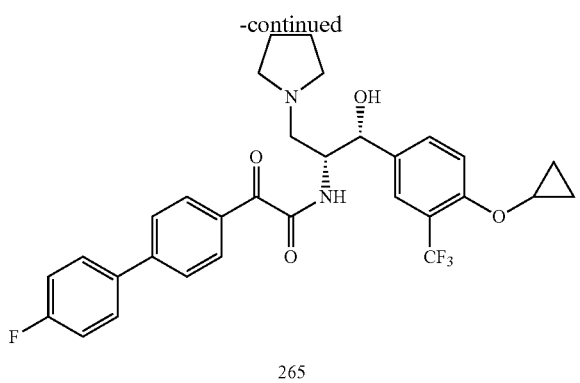

265

To a solution of Compound 265A (11.6 g, 48 mmol) in 1-methyl-2-pyrrolidinone (150 mL) was added cesium carbonate (33 g, 87 mmol) and bromocyclopropane (16.5 mL, 1999 mmol). The mixture was stirred for 24 h while keeping inner temperature between 145° C. and 155° C. After the reaction was cooled to ambient temperature, the dark solution was diluted with water (400 mL) and extracted with a mixture of ethyl acetate in petroleum ether (15% v/v) (300 mL×3). The combined organic phases were washed with brine (150 mL×4), dried over anhydrous sodium sulfate, filtered, and concentrated to afford the crude product as a brown oil. The crude product was purified with flash column chromatography on silica gel (petroleum ether) to furnish Compound 265B.

To a solution of Compound 265B (6.79 g, 8.1 mmol) in dry THF (200 mL) maintained at −70° C. was added n-BuLi (2.5 Min hexane, 9.76 mL) dropwise under nitrogen atmosphere over a period of 20 minutes. After the reaction was stirred at −70° C. for 40 minutes, Intermediate A4 (3.2 g, 8.1 mmol) dissolved in dry THF (20 mL) was added slowly to the cold solution at a rate that maintained the internal temperature between −70° C. and −50° C. After the addition was complete, the solution was left to stir for 1 h. The reaction was quenched with saturated ammonium chloride solution (400 mL) and extracted with ethyl acetate (300 mL×3). The organic phase was washed with water (200 mL) and brine (200 mL), dried over anhydrous sodium sulfate, filtered, and concentrated to furnish the crude Compound 265C. The crude product was purified with flash column chromatography on silica gel (ethyl acetate in petroleum ether, from 5% to 10% v/v) to furnish Compound 265C.

To a solution of Compound 265C (5.95 g, 110 mmol) in dry THF (70 mL) was added L-Selectride (1.0 Min THF, 23.7 mL) dropwise under nitrogen atmosphere while keeping the temperature at −90° C. After the addition was complete, the solution was allowed to stir at this temperature for 1 h. The reaction was quenched with saturated ammonium chloride solution (50 mL), extracted with ethyl acetate (100 mL×2), washed with water (100 mL) and brine (100 mL), dried over anhydrous sodium sulfate, filtered, and concentrated to furnish a crude compound. The crude product was purified with flash column chromatography on silica gel (ethyl acetate in petroleum ether, 10% v/v) to give Compound 265D.

To a solution of Compound 265D (5.4 g, 10 mmol) in THF (100 mL) was added tetrabutylammonium fluoride (1.31 g, 5.0 mmol) at 0° C. The mixture was stirred at room temperature for 12 h. After that, the reaction mixture was evaporated to remove tetrahydrofuran. The mixture was treated with water (50 mL) and extracted with ethyl acetate (150 mL×3). The combined organic phases were washed with water (150 mL) and brine (150 mL), dried over anhydrous sodium sulfate, filtered, and concentrated to furnish a crude compound. The crude product was purified with flash column chromatography on silica gel (ethyl acetate in petroleum ether, 20% v/v) to furnish Compound 265E.

To a solution of Compound 265E (1.18 g, 2.78 mmol) dissolved in THF (50 mL) was added triethylamine (866 mg, 8.5 mmol). The mixture was cooled to −30° C., and then methanesulfonyl chloride (389 mg, 3.41 mmol) was added dropwise over a period of 15 minutes. After the addition was complete, the reaction was stirred at −30° C. for 1.5 h, diluted with water (50 mL), and extracted with ethyl acetate (150 mL×2). The combined organic layers were washed with brine (150 mL), dried over anhydrous sodium sulfate, filtered, and concentrated to furnish Compound 265F.

To a solution of Compound 265F (1.0 g, 1.98 mmol) in THF (30 mL) was added pyrrolidine (2.3 g, 32 mmol). The reaction mixture was allowed to heat to 50° C. for 16 h. The mixture was diluted with water (100 mL), extracted with ethyl acetate (150 mL×2), washed with brine (50 mL), dried over anhydrous sodium sulfate, filtered, and concentrated to furnish a crude compound. The crude product was purified with flash column chromatography on silica gel (methanol in dichloromethane, 5% v/v) to give Compound 265G.

To a solution of Compound 265G (100 mg, 0.21 mmol) in ethanol (8 mL) and water (2 mL) was added LiOH.H$_2$O (56 mg, 1.33 mmol). The mixture was heated to 80° C. and stirred for 16 h. And then it was diluted with water (15 mL) and extracted with dichloromethane (50 mL×2). The combined organic phases were washed with water (50 mL) and brine (50 mL), dried over anhydrous sodium sulfate, filtered, and concentrated to furnish Compound 265H.

A mixture of Compound 265H (100 mg, (0.21 mmol), HATU (95 mg, 0.25 mmol), and Intermediate C (40.8 mg, 0.17 mmol) in DCM (15 mL) was stirred at room temperature overnight. The reaction mixture was treated with water (20 mL), extracted with DCM (50 mL×2), washed with brine (50 mL), dried over anhydrous sodium sulfate, and concentrated. The crude product was purified with prep-HPLC to give Compound 265. LC-MS (ESI) m/z: 571.2 [M+H]$^+$; $^1$H-NMR (CD$_3$OD, 400 MHz): δ (ppm) 0.66-0.82 (m, 4H), 2.04-2.23 (m, 4H), 3.23-3.26 (m, 1H), 3.60-3.89 (m, 6H), 4.72-4.76 (m, 1H), 5.06 (d, J=2.4 Hz, 1H), 7.22-7.26 (m, 2H), 7.47 (d, J=8.8 Hz, 1H), 7.65 (s, 1H), 7.67-7.77 (m, 8H).

Example 266

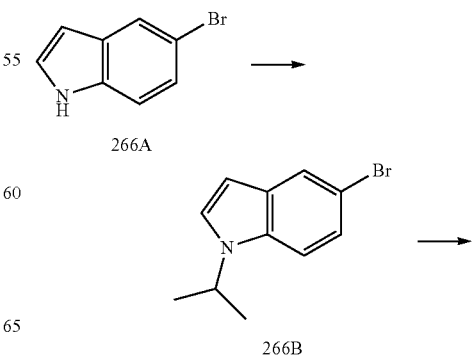

385

-continued

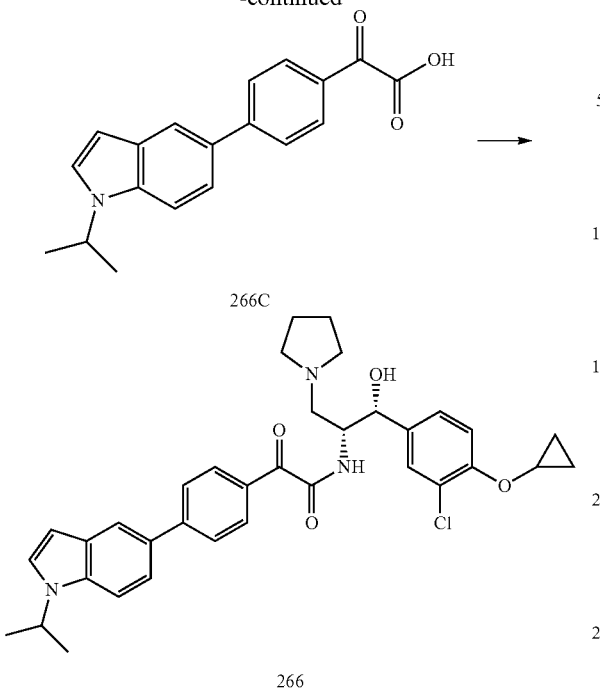

266C

266

To a solution of Compound 266A (1.96 g, 10 mmol) in DMF (50 mL) was added sodium hydride (60% suspend in oil, 800 mg, 20 mmol) at 0° C. The mixture was stirred at 0° C. for 0.5 h and 2-iodopropane (2.55 g, 15 mmol) was added at 0° C. The resultant mixture was stirred at room temperature overnight, diluted with ethyl acetate (100 mL), washed with water (50 mL×3) and brine (50 mL), dried over anhydrous sodium sulfate, concentrated, and purified with flash column chromatography on silica gel (ethyl acetate in petroleum ether, 10% v/v) to give Compound 266B.

A mixture of Compound 266B (500 mg, 2.1 mmol), Pd(dppf)Cl$_2$ (86 mg, 0.1 mmol), 175B (638 mg, 2.1 mmol), and K$_2$CO$_3$ (668 mg, 6.3 mmol) in dioxane (15 mL) and water (2 mL) was stirred under nitrogen at 100° C. overnight. The mixture was cooled down to room temperature, concentrated, diluted with water (50 mL), and extracted with ethyl acetate (30 mL×3). The aqueous layer was acidified to pH 2 with aqueous HCl solution (1 N) and extracted with dichloromethane (10 mL×3). The dichloromethane layer was dried over anhydrous sodium sulfate and filtered to afford Compound 266C/dichloromethane solution. A solution of Compound 266C in dichloromethane was directly used for the next step without further purification.

To a solution of Compound 266C in dichloromethane (15 mL, from previous step) was added Intermediate G (155 mg, 0.5 mmol) and HATU (380 mg, 1 mmol). The mixture was stirred at room temperature overnight. The mixture was purified with prep-HPLC to furnish Compound 266. LC-MS (ESI) m/z: 600 [M+H]$^+$; $^1$H-NMR (DMSO-d$_6$, 400 MHz): δ (ppm) 0.67-0.71 (m, 2H), 0.81-0.86 (m, 2H), 1.48 (d, J=6.4 Hz, 6H), 1.88-1.92 (m, 2H), 2.03-2.08 (m, 2H), 3.13-3.24 (m, 2H), 3.43-3.52 (m, 4H), 3.93-3.97 (m, 1H), 4.56-4.61 (m, 1H), 4.79-4.86 (m, 1H), 4.89-4.89 (m, 1H), 6.04 (brs, 1H), 6.56 (d, J=3.6 Hz, 1H), 7.35-7.37 (m, 1H), 7.42-7.46 (m, 2H), 7.52-7.55 (m, 1H), 7.59-7.59 (m, 1H), 7.66-7.68 (m, 1H), 7.72-7.74 (m, 2H), 7.78-7.80 (m, 2H), 7.69 (d, J=1.6 Hz, 1H), 8.79 (d, J=9.2 Hz, 1H), 9.34 (brs, 1H).

386

Example 267

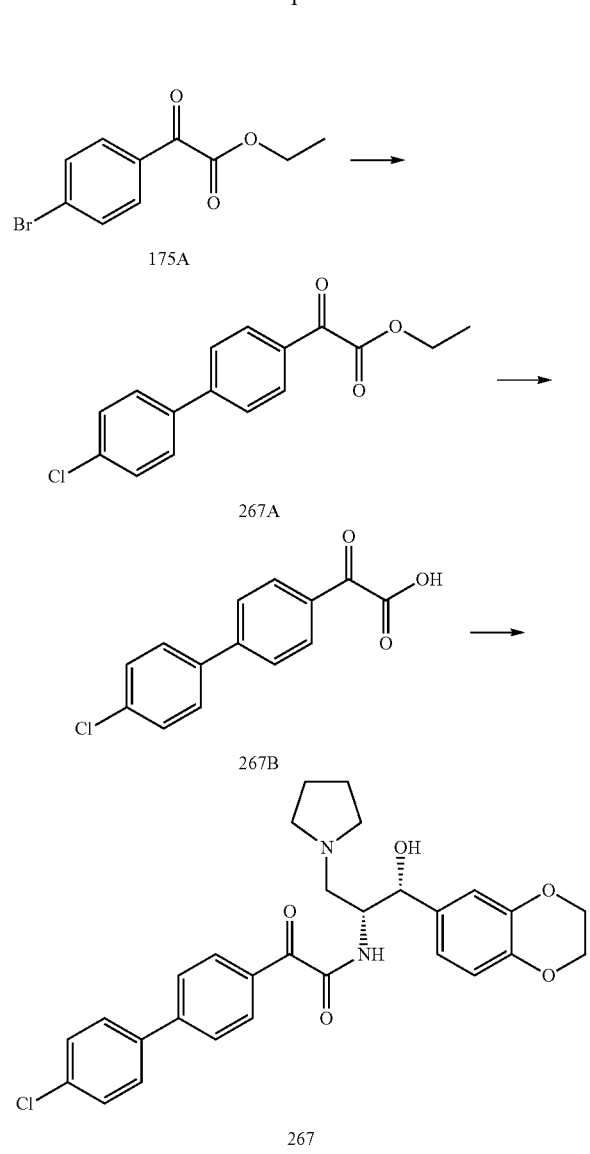

175A

267A

267B

267

To a mixture of Compound 175A (2.56 g, 0.01 mol), 4-chlorophenylboronic acid (2 g, 1.32 mol), and K$_3$PO$_4$ (6.4 g, 0.03 mol) in toluene (80 mL) was added Pd(PPh$_3$)$_4$ (1.156 g, 0.001 mol). The reaction mixture was stirred under nitrogen at 100° C. overnight. The resulting mixture was cooled down to room temperature, washed with brine (100 mL), dried over anhydrous sodium sulfate, filtered, and concentrated. The residue was purified with flash column chromatography on silica gel (ethyl acetate in petroleum ether, from 10% to 50% v/v) to furnish Compound 267A.

To a solution of Compound 267A (2.9 g, 0.01 mol) in ethanol/water (40 mL/10 mL) was added LiOH H$_2$O (840 mg, 0.02 mol). The mixture was stirred at room temperature for about 2 h until completion by thin layer chromatography analysis. The reaction mixture was acidified to pH 2 with aqueous HCl solution (1.0 N, 40 mL) and extracted with ethyl acetate (30 mL×2). The combined organic layers were washed with brine (100 mL), dried over anhydrous sodium sulfate, filtered, and concentrated to afford Compound 267B.

To a mixture of Compound 267B (130 mg, 0.5 mmol) and Intermediate A (139 mg, 0.5 mmol) in DMF (5 mL) was added HATU (380 mg, 1 mmol). The reaction mixture was stirred at room temperature overnight. The resulting solution was washed with brine (30 mL), dried over anhydrous sodium sulfate, filtered, and concentrated. The residue was purified with reverse phase chromatography using eluent (methanol in water, from 10% to 55% v/v) to furnish Compound 267. LC-MS (ESI) m/z: 521 [M+H]$^+$; $^1$H-NMR (DMSO-d$_6$, 400 MHz): δ (ppm) 1.66-1.74 (m, 4H), 2.50-2.70 (m, 6H), 4.21-4.22 (m, 5H), 4.75 (s, 1H), 5.57 (s, 1H), 6.82 (s, 2H), 6.87 (s, 1H), 7.58-7.60 (m, 2H), 7.78-7.83 (m, 6H), 8.61 (d, J=9.6 Hz, 1H).

Example 268

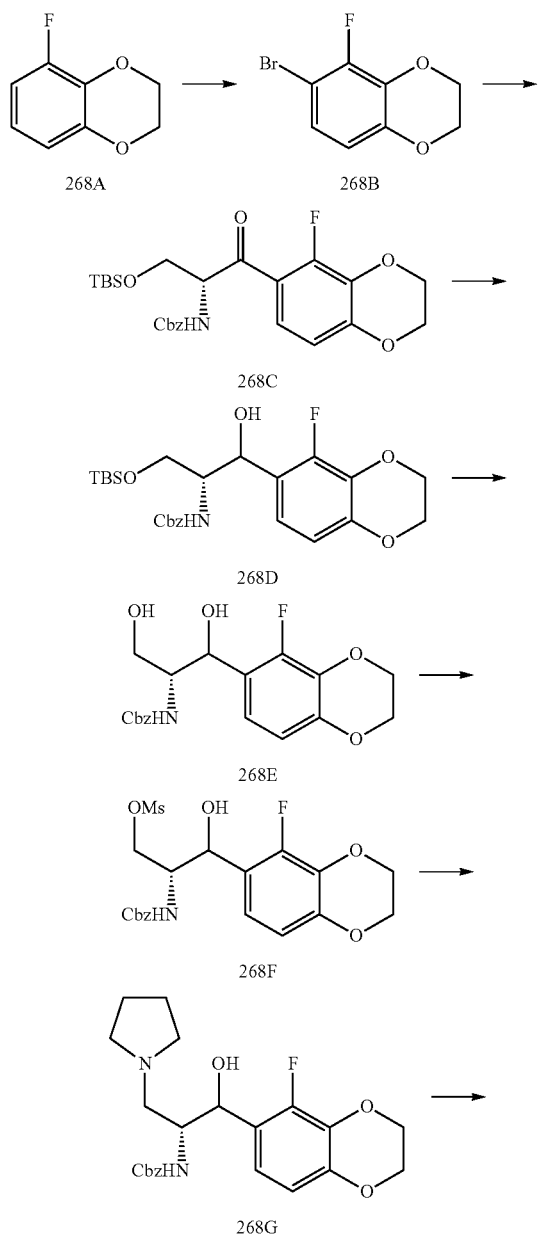

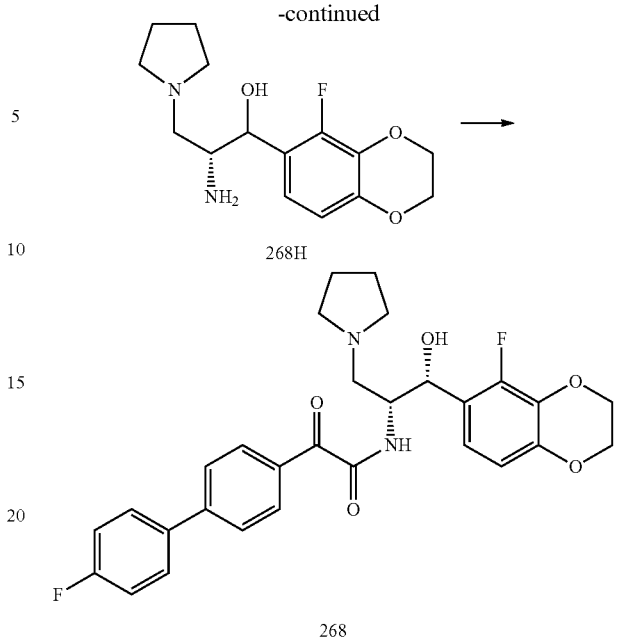

To a solution of Compound 268A (3.35 g, 21.73 mmol) in methanol (10 mL) was added dropwise bromine (1.34 mL, 26.10 mmol) at −10° C. The mixture was stirred room temperature for 5 h. It was quenched with saturated aqueous Na$_2$S$_2$O$_3$ solution (100 mL) and filtered to remove the resultant solid. The filtrate was evaporated and purified with flash column chromatography on silica gel (ethyl acetate in petroleum ether, from 0% to 3% v/v) to afford Compound 268B.

To a solution of Compound 268B (12.00 g, 51.72 mmol) in THF (30 mL) was added dropwise n-BuLi (2.4 M in hexane, 22 mL, 51.72 mmol) under nitrogen at −78° C. The mixture was stirred at −78° C. for 30 min. A solution of Intermediate A4 (6.77 g, 17.11 mmol) in THF (20 mL) was added dropwise under nitrogen at −78° C. The mixture was stirred at −78° C. for 20 min and quenched with saturated aqueous ammonium chloride solution (100 mL). The mixture was diluted with ethyl acetate (300 mL), washed with water (200 mL) and brine (200 mL), dried over anhydrous sodium sulfate, and purified with flash column chromatography on silica gel (ethyl acetate in petroleum ether, from 0% to 10% v/v) to furnish Compound 268C.

To a solution of Compound 268C (7.20 g, 14.72 mmol) in THF (200 mL) was added dropwise L-Selectride (1 M in THF, 29 mL, 29.00 mmol) under nitrogen at −90° C. The mixture was stirred at −90° C. for 1 h and quenched with saturated aqueous ammonium chloride solution (100 mL). It was diluted with ethyl acetate (300 mL), washed with water (200 mL) and brine (200 mL), dried over anhydrous sodium sulfate, and purified with flash column chromatography on silica gel (ethyl acetate in petroleum ether, from 0% to 20% v/v) to afford Compound 268D.

A mixture of Compound 268D (2.00 g, 4.07 mmol) and Bu$_4$NF (641 mg, 2.04 mmol) in THF (20 mL) was stirred at 20° C. for 16 h. It was diluted with ethyl acetate (200 mL), washed with water (200 mL) and brine (200 mL), dried over anhydrous sodium sulfate, and purified with flash column chromatography on silica gel (methanol in dichloromethane, from 0% to 5% v/v) to give Compound 268E.

To a solution of Compound 268E (1.70 g, 4.50 mmol) and triethylamine (909 mg, 9.00 mmol) in THF (20 mL) was added dropwise methanesulfonyl chloride (565 mg, 4.96 mmol) at −15° C. The mixture was stirred at −15° C. for 1 h. It was quenched with saturated ice water (50 mL), diluted with ethyl acetate (200 mL), washed with water (150 mL) and brine (200 mL), dried over anhydrous sodium sulfate, and purified with flash column chromatography on silica gel (ethyl acetate in petroleum ether, from 0% to 80% v/v) to afford Compound 268F.

A solution of Compound 268F (1.50 g, 3.30 mmol) and pyrrolidine (2.34 g, 32.92 mmol) in THF (10 mL) was stirred at 50° C. for 16 h. It was diluted with ethyl acetate (200 mL), washed with water (200 mL) and brine (200 mL), dried over anhydrous sodium sulfate, and purified with reverse phase chromatography using eluent (methanol in water, from 0% to 100% v/v) to furnish Compound 268G.

A mixture of Compound 268G (900 mg, 2.09 mmol) and Pd(OH)$_2$/C (20%, 500 mg) in methanol (10 mL) was stirred under hydrogen at 20° C. for 16 h. It was filtered to remove Pd(OH)$_2$/C and the filtrate was evaporated to give Compound 268H.

A mixture of Compound 268H (100 mg, 0.34 mmol), Compound 133D (82 mg, 0.34 mmol), and HATU (194 mg, 0.51 mmol) in DMF (5 mL) was stirred at room temperature for 16 h. It was diluted with ethyl acetate (120 mL), washed with water (100 mL) and brine (100 mL), dried over anhydrous sodium sulfate, concentrated, and purified with prep-HPLC to yield Compound 268. LC-MS (ESI) m/z: 523 [M+H]$^+$; $^1$H-NMR (DMSO-d$_6$, 400 MHz): δ (ppm) 1.82-2.03 (m, 4H), 3.08-3.19 (m, 2H), 3.47-3.60 (m, 4H), 4.17-4.30 (m, 4H), 4.4-4.54 (m, 1H), 4.80 (d, J=8.0 Hz, 1H), 6.10 (s, 1H), 6.75 (d, J=7.6 Hz, 1H), 6.92 (t, J=8.0 Hz, 1H), 7.37 (t, J=8.8 Hz, 2H), 7.79-7.90 (m, 6H), 9.01 (d, J=8.8 Hz, 1H), 9.41 (s, 1H).

Example 269

-continued

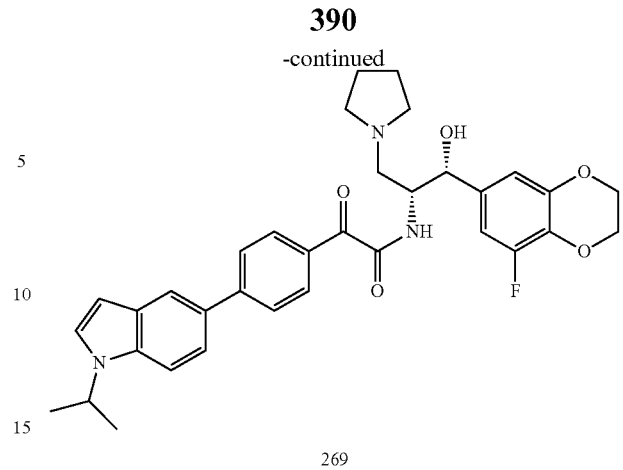

269

To a solution of Compound 266C in dichloromethane (15 mL, from previous step) was added Intermediate C (150 mg, 0.5 mmol) and HATU (380 mg, 1 mmol). The mixture was stirred at room temperature overnight. The mixture was directly purified with prep-HPLC to afford Compound 269. LC-MS (ESI) m/z: 586 [M+H]$^+$; $^1$H-NMR (DMSO-d$_6$, 400 MHz): δ (ppm) 1.48 (d, J=6.8 Hz, 6H), 1.88-1.89 (m, 2H), 2.03-2.03 (m, 2H), 3.12-3.20 (m, 2H), 3.45-3.55 (m, 4H), 4.28-4.30 (m, 4H), 4.51-4.54 (m, 1H), 4.79-4.83 (m, 2H), 6.04-6.05 (m, 1H), 6.57-6.58 (m, 1H), 6.78 (s, 1H), 6.83-6.85 (m, 1H), 7.53-7.55 (m, 1H), 7.58-7.59 (m, 1H), 7.65-7.67 (m, 1H), 7.83-7.89 (m, 4H), 7.96-7.97 (m, 1H), 8.73-8.76 (m, 1H), 9.36 (brs, 1H).

Example 270

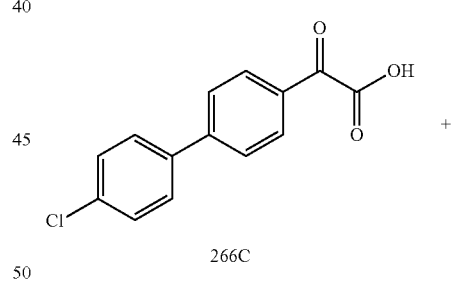

266C

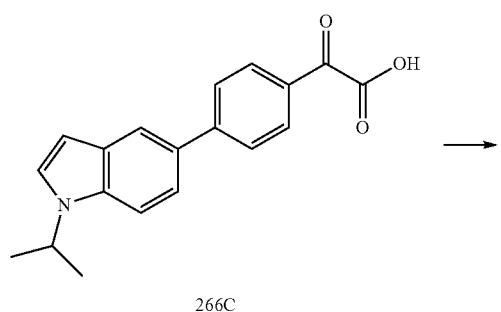

C

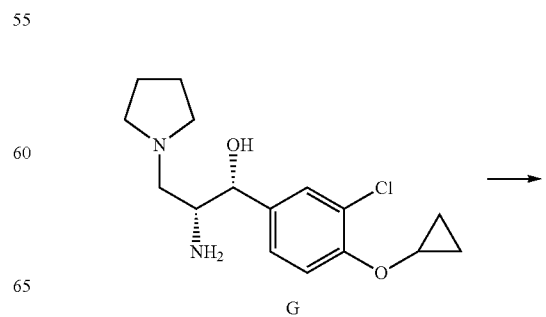

G

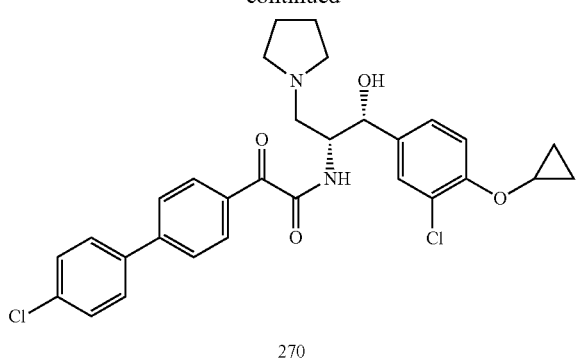

270

To a mixture of Compound 266C (130 mg, 0.5 mmol) and Intermediate G (151 mg, 0.5 mmol) in DMF (5 mL) was added HATU (380 mg, 1 mmol). The reaction mixture was stirred at room temperature overnight. The resulting solution was washed with brine (30 mL), dried over anhydrous sodium sulfate, filtered, and concentrated. The residue was purified with reverse phase chromatography using eluent (methanol in water, from 10% to 55% v/v) to furnish Compound 270. LC-MS (ESI) m/z: 553 [M+H]$^+$; $^1$H-NMR (DMSO-d$_6$, 400 MHz): δ (ppm) 0.66-0.83 (m, 4H), 1.88-2.04 (m, 4H), 3.15-3.20 (m, 2H), 3.49-3.56 (m, 4H), 3.93 (s, 1H), 4.56 (s, 1H), 4.88 (s, 1H), 6.07 (s, 1H), 7.36-7.44 (m, 3H), 7.59-7.62 (m, 2H), 7.77-7.80 (m, 6H), 8.80-8.83 (d, J=10.0 Hz, 1H), 9.48 (s, 1H).

Example 271

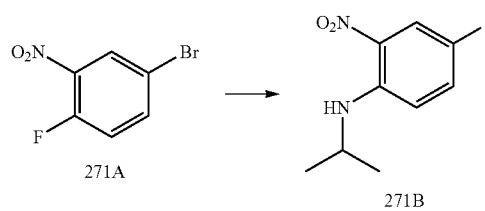

271A

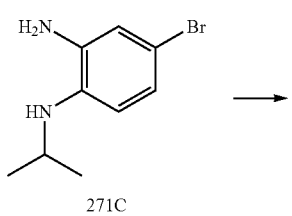

271B

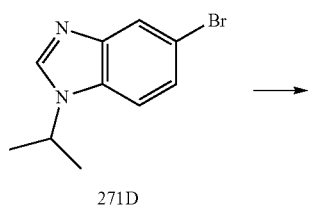

271C

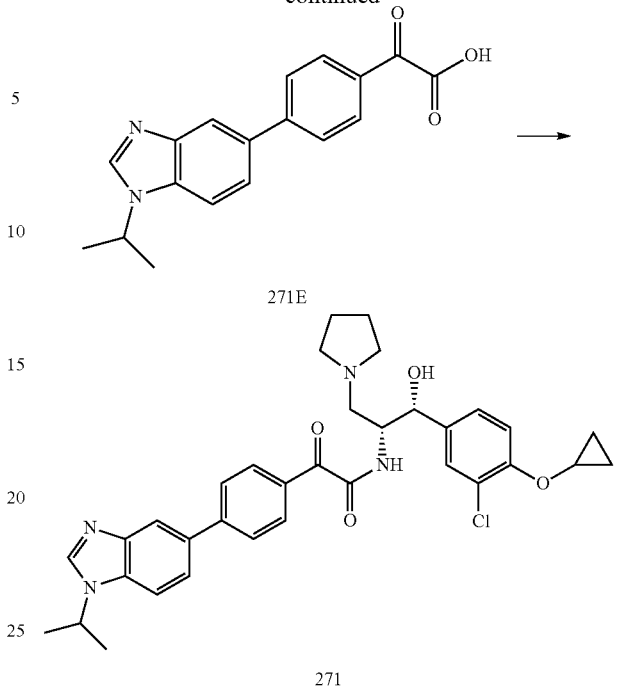

To a solution of Compound 271A (6.6 g, 30 mmol) in dichloromethane (30 mL) was added propan-2-amine (3.54 g, 60 mmol) at 0° C. The mixture was stirred at 40° C. overnight and the mixture was dispersed between water (100 mL) and ethyl acetate (200 mL). After separation, the organic phase was washed with water (10 mL×3) and brine (10 mL), dried over anhydrous sodium sulfate, filtered, and concentrated to afford the Compound 271B.

To a solution of Compound 271B (2.0 g, 7.75 mmol) in ethanol (60 mL) was added stannic chloride (5.25 g, 23.3 mmol). The mixture was stirred at reflux for 4 h. After cooling down to room temperature, aqueous sodium hydroxide solution (4 N, 5 mL) was added dropwise to the mixture and the resulting mixture was filtered. After removal of solvent, the residue was extracted with ethyl acetate (50 mL×3), washed with water (10 mL×2) and brine (10 mL), dried over anhydrous sodium sulfate, filtered, and concentrated. The crude product was purified with flash column chromatography on silica gel (ethyl acetate in petroleum ether, from 0% to 20% v/v) to furnish Compound 271C.

To a solution of Compound 271C (1.3 g, 5.70 mmol) in DMF (30 mL) was added triethoxymethane (4.74 mL, 28.5 mmol) and con. HCl (1.5 mL). The mixture was stirred at 100° C. for 8 h. After cooling down to room temperature, the mixture was poured into water (150 mL) and adjusted to pH 8 with saturated aqueous sodium bicarbonate solution (3.5 mL). The mixture was extracted with ethyl acetate (50 mL×3) and separated. The combined organic phases were washed with water (10 mL×2) and brine (10 mL), dried over anhydrous sodium sulfate, filtered, and concentrated. The crude product was purified with flash column chromatography on silica gel (ethyl acetate in petroleum ether, from 0% to 50% v/v) to yield Compound 271D.

To a solution of Compound 271D (476 mg, 2.0 mmol) in dioxane (30 mL) and water (5 mL) was added K$_2$CO$_3$ (828 mg, 6.0 mmol), Compound 175B (608 mg, 2.0 mmol), and Pd(dppf)Cl$_2$ (146 mg, 0.2 mmol). The mixture was stirred under nitrogen at 100° C. for 2 h. After removal of solvent, the residue was dissolved in ethyl acetate (150 mL), washed with water (5 mL×2) and brine (5 mL), dried over anhydrous sodium sulfate, filtered, and concentrated to yield a crude compound. The crude product was purified with reverse phase chromatography using eluent (methanol in pure water, 50% v/v) to give Compound 271E.

To a solution of Intermediate G (121 mg, 0.39 mmol) in DMF (10 mL) was added Compound 271E (100 mg, 0.32 mmol), HATU (182 mg, 0.48 mmol), and N,N-diisopropylethylamine (124 mg, 0.96 mmol). The mixture was stirred under nitrogen at 25° C. overnight. The resulting mixture was quenched with saturated aqueous sodium bicarbonate solution (5 mL) and extracted with ethyl acetate (50 mL×3). The combined organic phases were washed with water (5 mL) and brine (5 mL), dried over anhydrous sodium sulfate, filtered, and concentrated to afford a crude compound. The crude product was purified with prep-HPLC to furnish Compound 271. LC-MS (ESI) m/z: 601 [M+H]$^+$; $^1$H-NMR (CD$_3$OD, 400 MHz): δ (ppm) 0.68-0.70 (m, 2H), 0.82-0.83 (m, 2H), 1.65 (d, J=6.4 Hz, 6H), 1.90-1.93 (m, 2H), 2.02-2.05 (m, 2H), 3.14-3.24 (m, 2H), 3.50-3.59 (m, 4H), 3.93-3.97 (m, 1H), 4.57-4.60 (m, 1H), 4.92 (d, J=2.4 Hz, 1H), 5.02-5.09 (m, 1H), 7.36-7.46 (m, 3H), 7.81-7.88 (m, 4H), 7.92-7.95 (m, 1H), 8.16-8.19 (m, 2H), 9.54 (s, 1H), 9.84 (brs, 1H).

Example 272

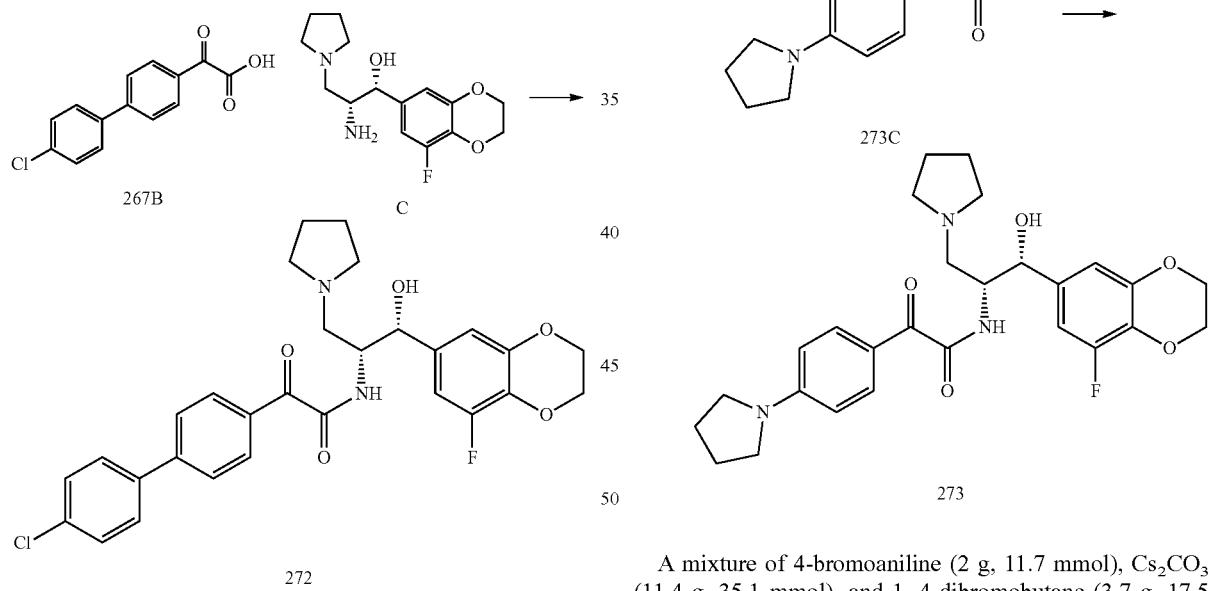

To a mixture of Compound 267B (130 mg, 0.5 mmol) and Intermediate C (143 mg, 0.5 mmol) in DMF (5 mL) was added HATU (380 mg, 1 mmol). The reaction mixture was stirred at room temperature overnight. The resulting solution was washed with brine (30 mL), dried over anhydrous sodium sulfate, filtered, and concentrated. The residue was purified with reverse phase chromatography using eluent (methanol in water, from 10% to 55% v/v) to furnish Compound 272. LC-MS (ESI) m/z: 539 [M+H]$^+$; $^1$H-NMR (DMSO-d$_6$, 400 MHz): δ (ppm) 1.87-2.03 (m, 4H), 3.10-3.18 (m, 2H), 3.42-3.54 (m, 4H), 4.23-4.28 (m, 4H), 4.51 (s, 1H), 4.78 (s, 1H), 6.05 (s, 1H), 6.76 (s, 1H), 6.81 (d, J=11.6 Hz, 1H), 7.59 (m, 2H), 7.79-7.84 (m, 4H), 7.91-7.93 (m, 2H), 8.75 (d, J=10.0 Hz, 1H), 9.37 (s, 1H).

Example 273

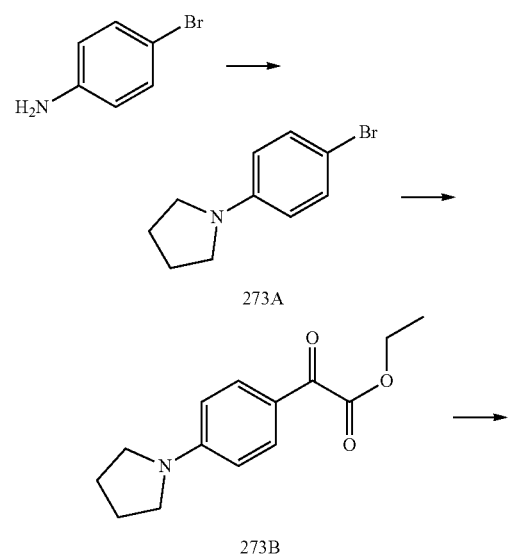

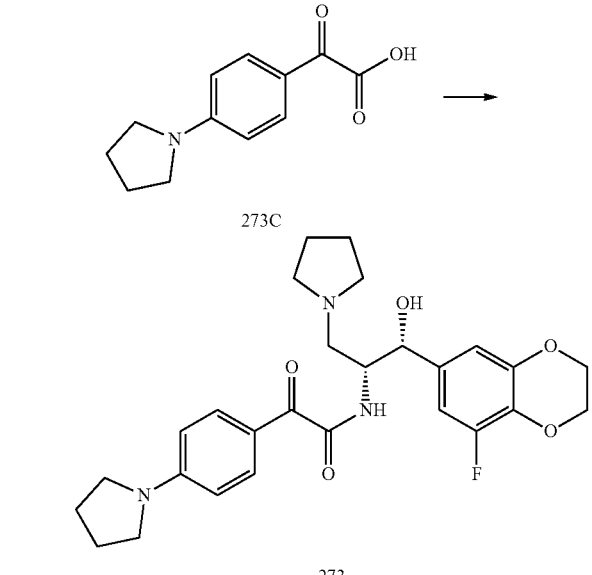

A mixture of 4-bromoaniline (2 g, 11.7 mmol), Cs$_2$CO$_3$ (11.4 g, 35.1 mmol), and 1, 4-dibromobutane (3.7 g, 17.5 mmol) in DMF (40 mL) was stirred under nitrogen at 60° C. for 16 h. The mixture was cooled to room temperature, diluted with ethyl acetate (200 mL), washed with water (50 mL×2) and brine (50 mL), dried over anhydrous sodium sulfate, concentrated, and purified with flash column chromatography on silica gel (ethyl acetate in petroleum ether, from 0% to 10% v/v) to afford Compound 273A.

To a solution of Compound 273A (300 mg, 1.3 mmol) in dry THF (10 mL) was added n-BuLi (2.5 N in hexane, 0.6 mL, 1.5 mmol) under nitrogen at −78° C. The resulting solution was stirred at −78° C. for 30 min and transferred into a stirred solution of diethyl oxalate (0.97 g, 6.6 mmol) in dry THF (5 mL) at this temperature. The solution was stirred at −78° C. for 1 h, quenched with addition of saturated aqueous ammonium chloride solution (10 mL), poured into water (50 mL), and extracted with ethyl acetate (50 mL×2). The combined organic layers were washed with brine (50 mL), dried over anhydrous sodium sulfate, and concentrated in vacuo to give Compound 273B.

A mixture of Compound 273B (0.2 g, 0.8 mmol) and LiOH.H$_2$O (68 mg, 1.6 mmol) in THF (5 mL) and water (2 mL) was stirred at 0° C. for 2 h. The mixture was diluted with ethyl acetate (30 mL), washed with water (10 mL×2) and brine (10 mL), dried over anhydrous sodium sulfate, concentrated, and purified with reverse phase chromatography using eluent (methanol in water, from 0% to 100% v/v) to afford Compound 273C.

A mixture of Compound 273C (74 mg, 0.3 mmol), HATU (200 mg, 0.5 mmol), and Intermediate C (100 mg, 0.3 mmol) in dichloromethane (5 mL) was stirred at 25° C. for 16 h. The mixture was diluted with ethyl acetate (30 mL), washed with water (10 mL×2) and brine (10 mL), dried over anhydrous sodium sulfate, concentrated, and purified with prep-HPLC to furnish Compound 273. LC-MS (ESI) m/z: 498 [M+H]$^+$; $^1$H-NMR (DMSO-d$_6$, 400 MHz): δ (ppm) 1.85 (s, 2H), 1.98 (s, 6H), 3.09-3.17 (m, 2H), 3.41-3.53 (m, 4H), 3.98-4.11 (m, 4H), 4.27 (m, 4H), 4.47 (s, 1H), 4.74 (s, 1H), 6.55 (d, J=9.2 Hz, 2H), 6.72-6.81 (m, 2H), 7.75 (d, J=8.8 Hz, 2H), 8.42 (d, J=9.6 Hz, 1H), 9.28 (s, 1H).

Example 274

(10 mL) was heated under nitrogen atmosphere at 90° C. for 2 h. After cooling, water (5 mL) was added, and the mixture was extracted with ethyl acetate (20 mL×3). The combined organic layers were washed until neutralization and dried over anhydrous sodium sulfate. After removal of the solvent in vacuo, the crude product was purified with flash column chromatography on silica gel (ethyl acetate in petroleum ether, from 10% to 20% v/v) to furnish Compound 274A.

A mixture of Compound 274A (130 mg, 0.44 mmol), Intermediate G (164 mg, 0.53 mmol), and HATU (252 mg, 0.66 mmol) in dichloromethane (10 mL) was stirred under nitrogen atmosphere at 25° C. for 5 h. The mixture was quenched with water (5 mL). The organic layer was washed with brine (50 mL), dried over anhydrous sodium sulfate, filtered, and concentrated in vacuo to afford a crude compound. The crude product was purified with prep-HPLC to furnish Compound 274. LC-MS (ESI) m/z: 587 [M+H]$^+$; $^1$H-NMR (DMSO-d$_6$, 400 MHz): δ (ppm) 0.64-0.68 (m, 2H), 0.79-0.84 (m, 2H), 1.88-1.91 (m, 2H), 1.99-2.04 (m, 2H), 3.14-3.19 (m, 2H), 3.47-3.49 (m, 3H), 3.87-3.95 (m, 1H), 4.55 (t, J=4.0 Hz, 1H), 4.87 (s, 1H), 6.05 (d, J=4.0 Hz, 1H), 7.33-7.44 (m, 3H), 7.85-7.89 (m, 4H), 7.91-7.99 (m, 4H), 8.82 (d, J=9.7 Hz, 1H), 9.34 (brs, 1H).

Example 275

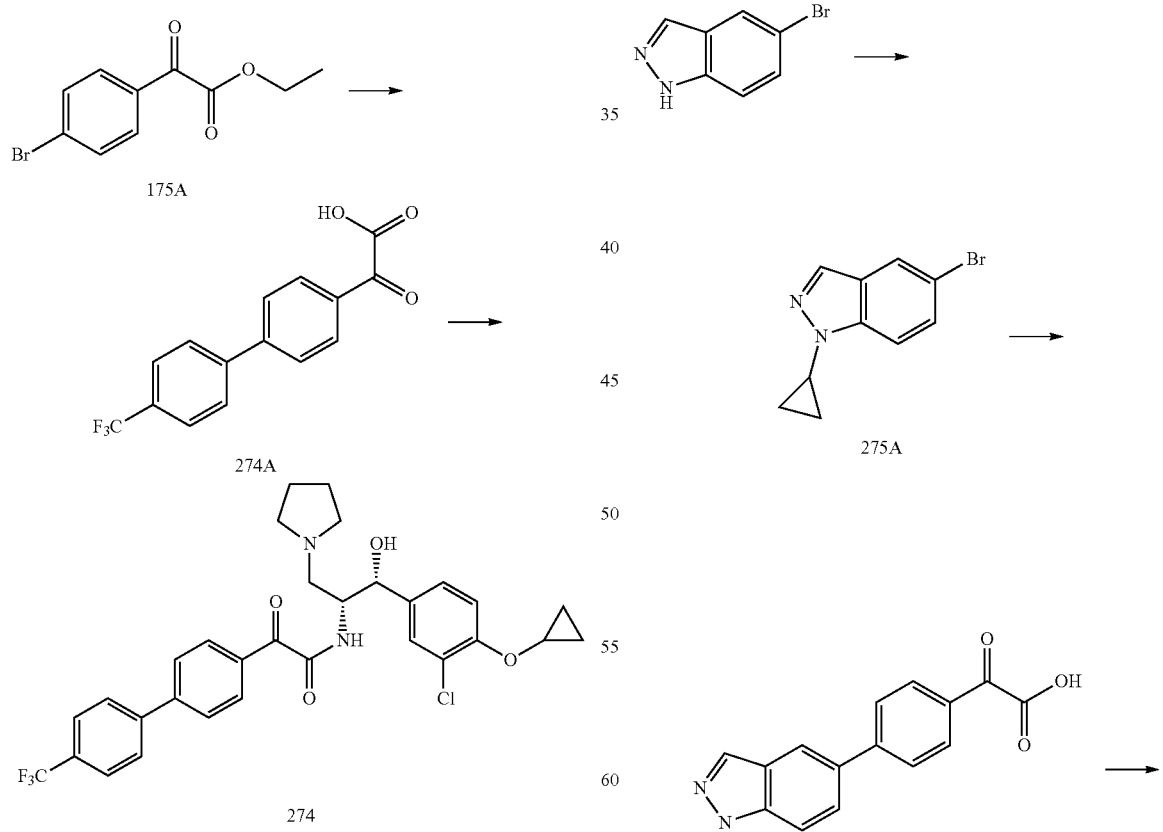

A mixture of (4-(trifluoromethyl)phenyl)boronic acid (500 mg, 2.63 mmol), Compound 175A (615 mg, 2.39 mmol), Pd(dppf)Cl$_2$ (87.5 mg, 0.12 mmol), potassium carbonate (992 mg, 7.18 mmol), water (3 mL), and 1,4-dioxane

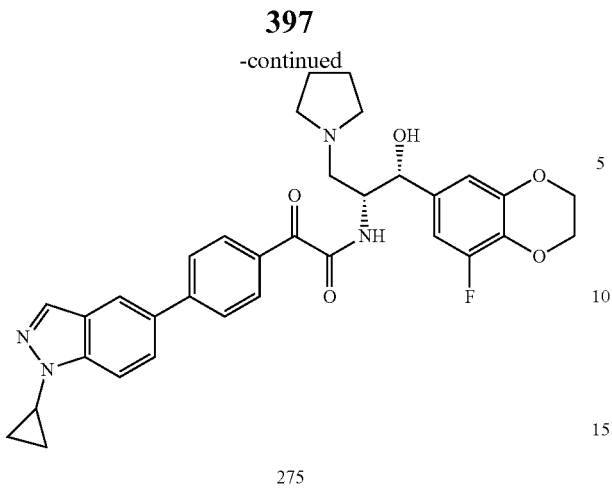

275

To a suspension of 5-bromo-1H-indazole (600 mg, 3.1 mmol) in 1,2-dichloroethane (30 mL) was added cyclopropylboronic acid (532 mg, 6.2 mmol), copper acetate (562 mg, 6.2 mmol), sodium carbonate (658 mg, 6.2 mmol), 2,2'-bipyridine (967 mg, 6.2 mmol) and molecular sieve (2.0 g) at room temperature. The reaction mixture was stirred at room temperature for 48 h. The reaction was quenched with saturated aqueous ammonium chloride solution and extracted with dichloromethane (50 mL×2). The combined organic extracts were washed with brine (100 mL×2) and dried over anhydrous sodium sulfate. After filtration, the solvent was removed in vacuo and the residue was purified with prep-TLC (ethyl acetate in petroleum ether, 10% v/v) to give Compound 275A.

To a solution of Compound 275A (575 mg, 2.43 mmol) in 1,4-dioxane (15 mL) was added 175B (738 mg, 2.43 mmol), Pd(dppf)Cl$_2$ (98 mg, 0.12 mmol), potassium carbonate (1.06 g, 7.29 mmol) and water (1 mL) under nitrogen. The reaction mixture was stirred at 110° C. for 3 hours. The resulting mixture was cooled to 25° C. The precipitated solid was filtered and dried to afford Compound 275B.

To a solution of Compound 275B (60 mg, 0.196 mmol) in DMF (5 mL) was added Intermediate C (58 mg, 0.196 mmol) and HATU (111 mg, 0.294 mmol). The reaction mixture was stirred at 20° C. for 2 h. The mixture was purified with prep-HPLC to yield the product Compound 275. LC-MS (m/z) 585 [M+H]$^+$; $^1$H-NMR (acetone-d$_6$, 400 MHz): δ (ppm) 1.27-1.29 (m, 4H), 2.06-2.13 (m, 2H), 2.28-2.30 (m, 2H), 3.50-3.63 (m, 2H), 4.04-4.11 (m, 5H), 4.23-4.31 (m, 5H), 4.90-4.91 (m, 1H), 5.10-5.11 (m, 1H), 6.82-6.88 (m, 2H), 7.87-7.95 (m, 4H), 8.11-8.14 (m, 3H), 8.24-8.25 (m, 1H), 8.35 (s, 1H).

Example 276

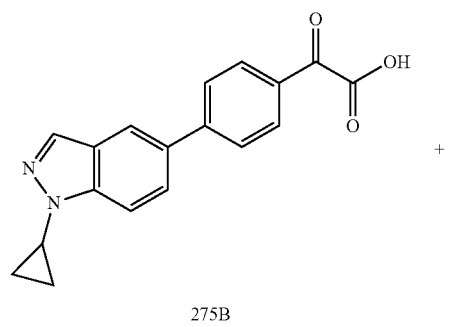

275B

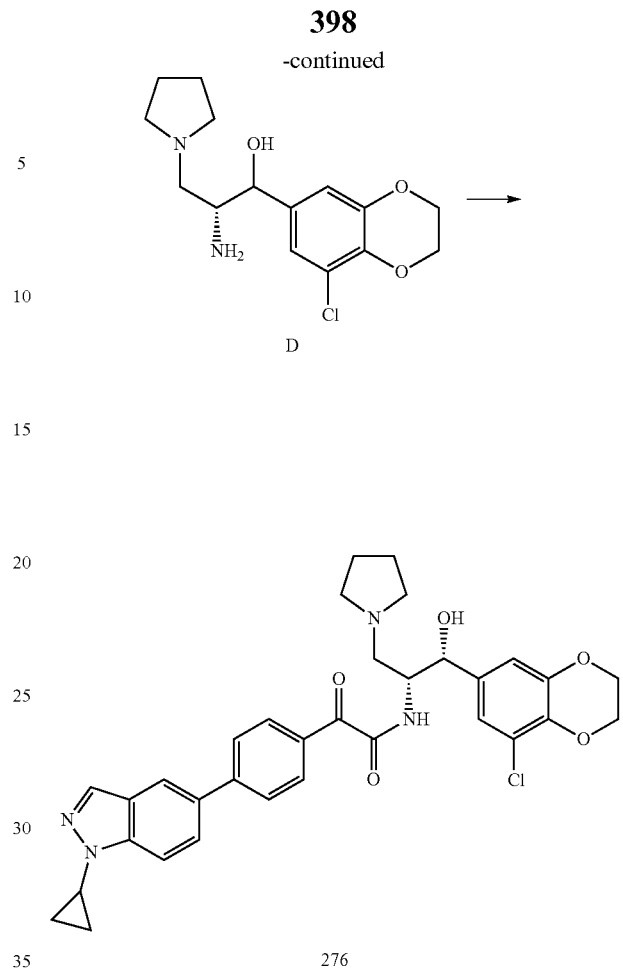

D

276

A mixture of Intermediate D (97 mg, 0.31 mmol), Compound 275B (80 mg, 0.26 mmol), and HATU (150 mg, 0.40 mmol) in DMF (5 mL) was stirred at 10° C. for 1.5 h. And then it was purified with prep-HPLC to yield Compound 276. LC-MS (ESI) m/z: 601 [M+H]$^+$; $^1$H-NMR ((CD$_3$)$_2$CO, 400 MHz): δ (ppm) 1.18-1.19 (m, 4H), 2.03-2.17 (m, 2H), 2.24 (s, 2H), 3.47 (m, 3H), 3.73-3.83 (m, 2H), 3.88-3.99 (m, 3H), 4.20-4.38 (m, 4H), 4.87 (s, 1H), 5.14 (d, J=2.0 Hz, 1H), 6.96 (d, J=2.0 Hz, 1H), 7.09 (d, J=2.0 Hz, 1H), 7.83 (d, J=8.4 Hz, 4H), 8.03 (d, J=9.6 Hz, 3H), 8.15 (d, J=10.4 Hz, 2H), 9.93 (brs, 1H).

Example 277

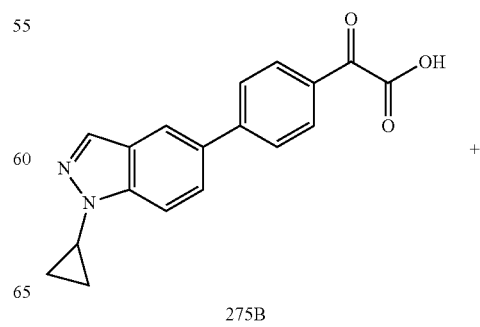

275B

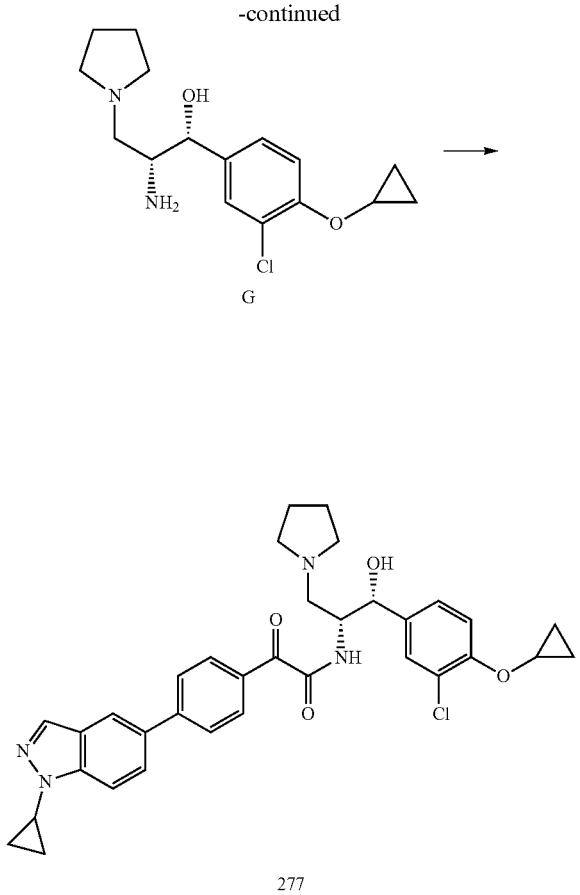

G

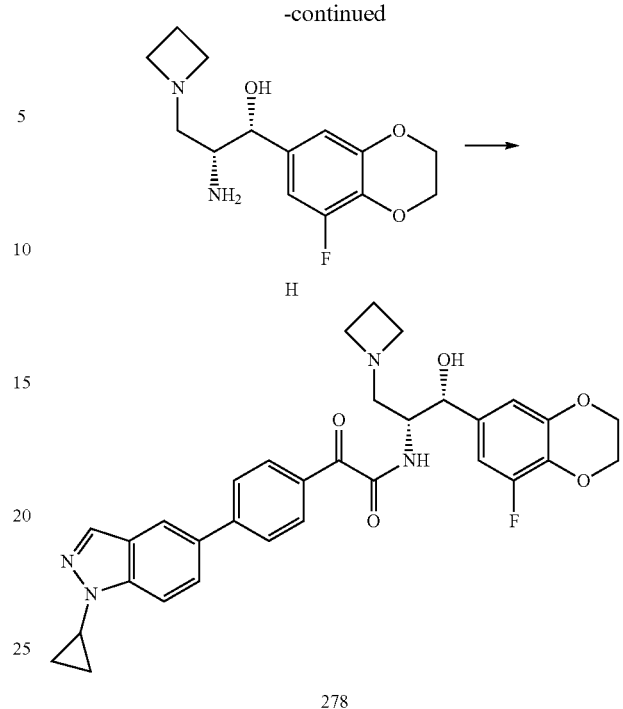

H

278

To a solution of Compound 275B (60 mg, 0.196 mmol) in DMF (5 mL) was added Intermediate H (55 mg, 0.196 mmol) and HATU (111 mg, 0.294 mmol). The reaction mixture was stirred at 20° C. for 2 h. The mixture was purified with prep-HPLC to yield Compound 278. LC-MS (ESI) m/z: 571 [M+H]$^+$; $^1$H-NMR (acetone-d$_6$, 400 MHz): δ (ppm) 1.33-1.37 (m, 4H), 2.60-2.62 (m, 1H), 2.71-2.74 (m, 1H), 3.92-3.95 (m, 3H), 4.27-4.31 (m, 4H), 4.61-4.64 (m, 4H), 4.73-4.74 (m, 1H), 5.10-5.11 (m, 1H), 6.82-6.88 (m, 2H), 7.88-7.90 (m, 2H), 7.98-8.10 (m, 4H), 8.31 (s, 1H), 8.56 (s, 1H).

277

To a solution of Compound 275B (60 mg, 0.196 mmol) in DMF (5 mL) was added Intermediate G (60 mg, 0.196 mmol) and HATU (111 mg, 0.294 mmol). The reaction mixture was stirred at 20° C. for 2 h. The mixture was purified with prep-HPLC to yield Compound 277. LC-MS (m/z) 599 [M+H]$^+$; $^1$H-NMR (acetone-d$_6$, 400 MHz): δ (ppm) 0.69-0.71 (m, 2H), 0.79-0.84 (m, 2H), 1.18-1.20 (m, 4H), 2.06-2.09 (m, 1H), 2.25-2.27 (m, 2H), 3.46-3.55 (m, 2H), 3.77-3.78 (m, 1H), 3.88-3.92 (m, 2H), 3.96-4.08 (m, 4H), 4.90-4.94 (m, 1H), 5.20 (s, 1H), 7.36-7.46 (m, 2H), 7.51-7.52 (m, 1H), 7.80-7.82 (m, 4H), 7.98-8.00 (m, 2H), 8.05 (s, 1H), 8.14 (s, 1H), 8.17-8.20 (m, 1H), 9.14 (brs, 1H).

Example 278

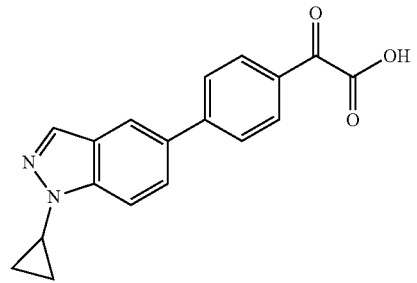

275B

Example 279

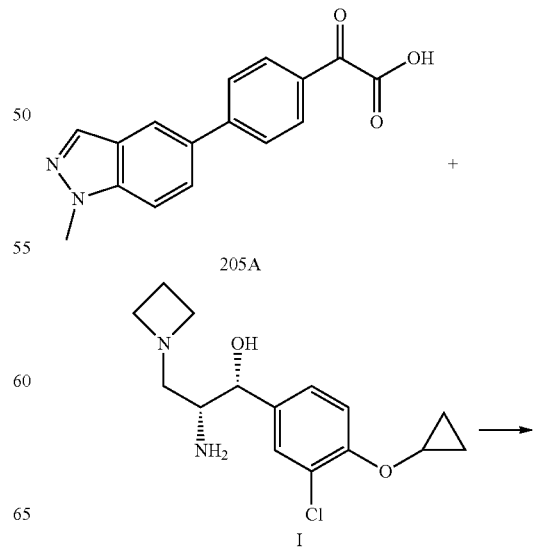

205A

I

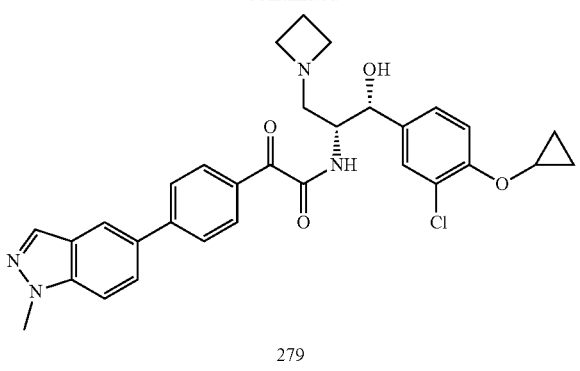

279

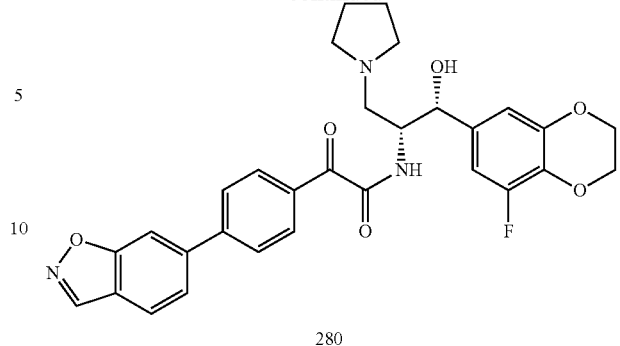

280

To a solution of Compound 205A (70 mg, 0.25 mmol) in DMF (3 mL) was added Intermediate I (74 mg, 0.25 mmol) and HATU (142 mg, 0.375 mmol). The reaction mixture was stirred at 15° C. overnight. The mixture was purified with prep-HPLC to yield Compound 279. LC-MS (m/z) 559 [M+H]$^+$; $^1$H-NMR (acetone-d$_6$, 400 MHz): δ (ppm) 0.70-0.73 (m, 2H), 0.80-0.84 (m, 2H), 2.56-2.57 (m, 1H), 2.71-2.74 (m, 1H), 3.86-3.96 (m, 4H), 4.13 (s, 3H), 4.47-4.60 (m, 4H), 4.77-4.78 (m, 1H), 5.20-5.21 (m, 1H), 7.39-7.45 (m, 2H), 7.50-7.51 (m, 1H), 7.71-7.74 (m, 1H), 7.79-7.82 (m, 3H), 7.93-7.95 (m, 2H), 8.09 (s, 1H), 8.13-8.15 (m, 2H), 9.51 (brs, 1H).

Example 280

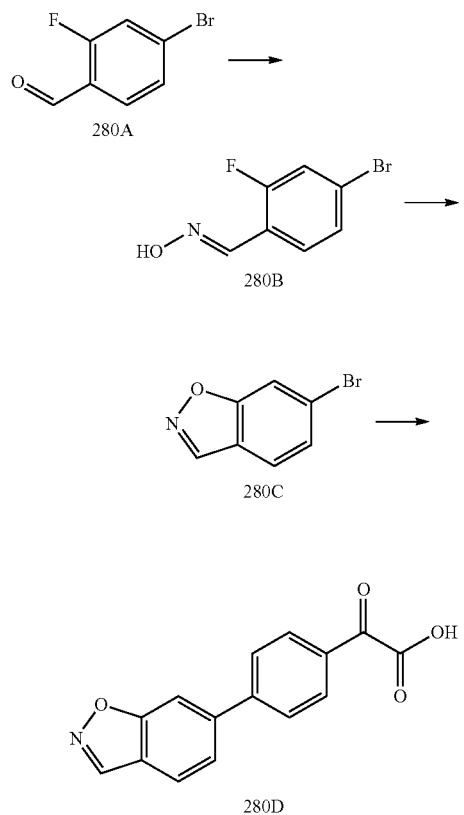

A mixture of Compound 280A (2 g, 10 mmol), hydroxylamine hydrochloride (830 mg, 12 mmol), and sodium acetate (656 mg, 8 mmol) in water (5 mL) and ethanol (20 mL) was stirred under nitrogen at 25° C. for 5 h. The solution was concentrated to dryness. The crude product was washed with water (5 mL) and dried to afford Compound 280B.

To a solution of Compound 280B (717 mg, 3.3 mmol) in DMSO (10 mL) was added potassium carbonate (638 mg, 4.6 mmol) at 25° C. The mixture was stirred at 120° C. overnight. The solution was cooled to room temperature and extracted with ethyl acetate (100 mL×2). The combined organic layers were washed with water (50 mL) and brine (50 mL), dried over anhydrous sodium sulfate, filtered, and evaporated to give Compound 280C.

A mixture of Compound 280C (197 mg, 1 mmol), Compound 175B (334 mg, 1.1 mmol), potassium carbonate (414 mg, 3 mmol), and Pd(dppf)Cl$_2$ (20 mg, 0.04 mmol) in dioxane (10 mL) and water (2 mL) was stirred under nitrogen at 100° C. overnight. The solution was cooled to room temperature, adjusted to pH 4 with aqueous hydrochloric acid solution (6 N, 2 mL), and extracted with ethyl acetate (100 mL×3). The organic layer was washed with water (50 mL) and brine (50 mL), dried over anhydrous sodium sulfate, filtered, and evaporated to afford Compound 280D.

A mixture of Compound 280D (133.5 mg, 0.5 mmol), HATU (342 mg, 0.9 mmol), and Intermediate C (148 mg, 0.5 mmol) in dichloromethane (10 mL) and DMF (4 mL) was stirred at 25° C. overnight. The solution was extracted with ethyl acetate (50 mL×2). The combined organic phases were washed with water (50 mL) and brine (50 mL), dried over anhydrous sodium sulfate, filtered, and concentrated to give a residue. The residue was purified with prep-HPLC to furnish Compound 280. LC-MS (ESI) m/z: 546 [M+H]$^+$; $^1$H-NMR (DMSO-d$_6$, 400 MHz): δ (ppm) 1.84-2.03 (m, 4H), 3.09-3.20 (m, 2H), 3.45-3.53 (m, 4H), 4.22-4.32 (m, 4H), 4.47-4.50 (m, 1H), 4.77 (s, 1H), 6.04 (s, 1H), 6.76-6.84 (m, 2H), 7.29-7.32 (m, 2H), 7.76-7.79 (m, 3H), 7.92-7.94 (m, 2H), 8.76-8.79 (m, 1H), 9.24-9.26 (m, 1H), 11.41 (s, 1H).

Example 281

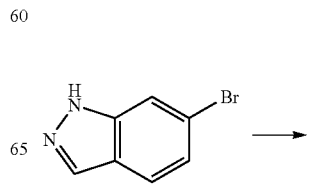

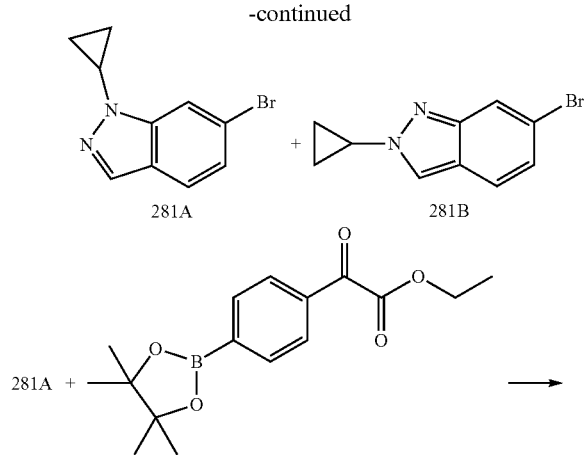

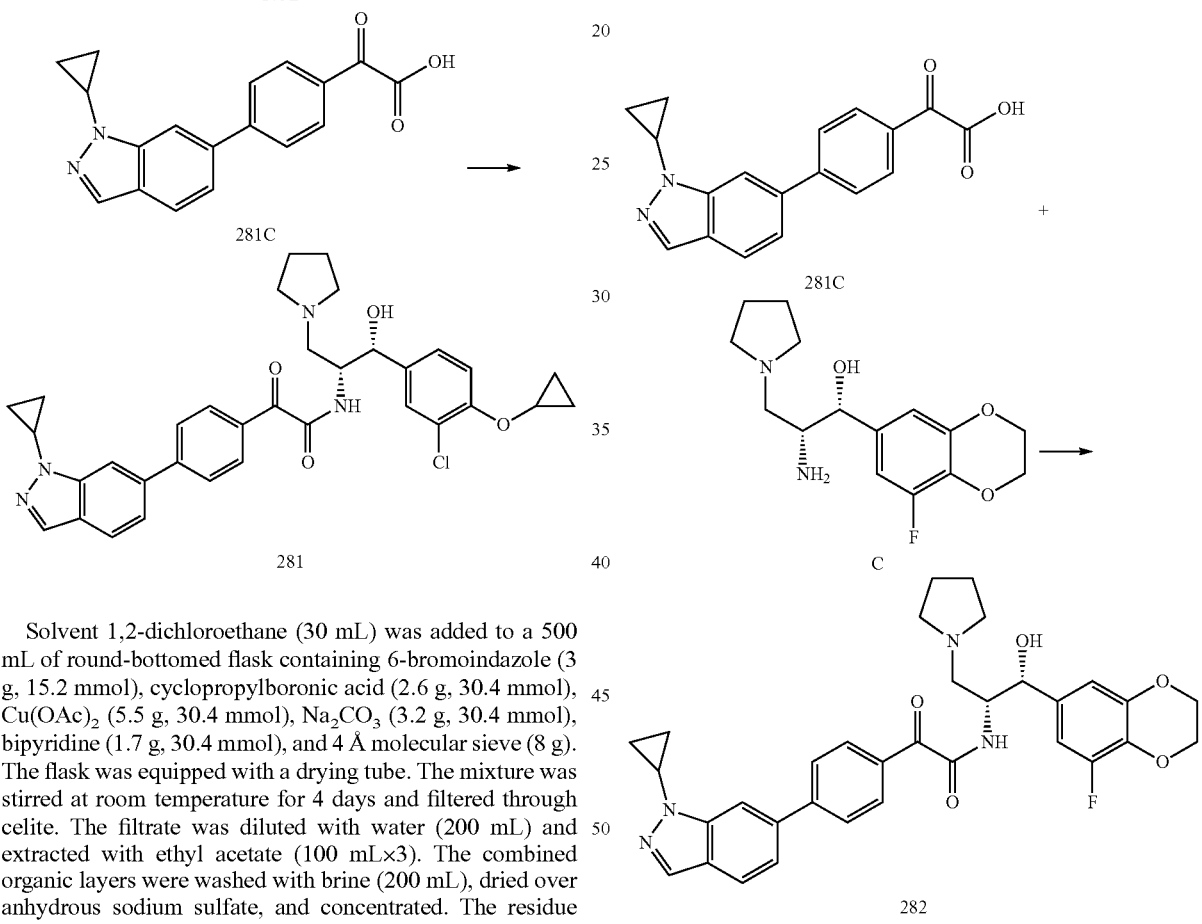

mL×2) and brine (100 mL), dried over anhydrous sodium sulfate, and concentrated to give Compound 281C.

A mixture of Compound 281C (100 mg, 0.33 mmol), HATU (190 mg, 0.50 mmol), and Intermediate G (102 mg, 0.33 mmol) in DMF (5 mL) was stirred at 10° C. for 18 h. The mixture was directly purified with prep-HPLC to furnish Compound 281. LC-MS (ESI) m/z: 599 [M+H]$^+$; $^1$H-NMR (DMSO-d$_6$, 400 MHz): δ (ppm) 0.66-0.85 (m, 4H), 1.17-1.19 (m, 4H), 1.88-2.08 (m, 4H), 3.12-3.25 (m, 2H), 3.48-3.59 (m, 4H), 3.83-3.88 (m, 1H), 3.93-3.98 (m, 1H), 4.56-4.63 (m, 1H), 4.90 (s, 1H), 6.17 (brs, 1H), 7.37 (dd, J=8.8, 2.4 Hz, 1H), 7.43-7.47 (m, 2H), 7.55 (dd, J=8.4, 1.2 Hz, 1H), 7.79 (d, J=8.0 Hz, 2H), 7.88-7.92 (m, 3H), 8.03 (s, 1H), 8.09 (s, 1H), 8.86 (d, J=10.0 Hz, 1H), 9.41 (brs, 1H).

Example 282

Solvent 1,2-dichloroethane (30 mL) was added to a 500 mL of round-bottomed flask containing 6-bromoindazole (3 g, 15.2 mmol), cyclopropylboronic acid (2.6 g, 30.4 mmol), Cu(OAc)$_2$ (5.5 g, 30.4 mmol), Na$_2$CO$_3$ (3.2 g, 30.4 mmol), bipyridine (1.7 g, 30.4 mmol), and 4 Å molecular sieve (8 g). The flask was equipped with a drying tube. The mixture was stirred at room temperature for 4 days and filtered through celite. The filtrate was diluted with water (200 mL) and extracted with ethyl acetate (100 mL×3). The combined organic layers were washed with brine (200 mL), dried over anhydrous sodium sulfate, and concentrated. The residue was purified with flash column chromatography on silica gel (ethyl acetate in petroleum ether, from 0% to 10% v/v) to give Compound 281A and Compound 281B.

A mixture of Compound 281A (600 mg, 2.53 mmol), Compound 175B (769 mg, 2.53 mmol), Pd(dppf)Cl$_2$ (106 mg, 0.13 mmol), and K$_2$CO$_3$ (1.05 g, 7.59 mmol) in dioxane (10 mL) and water (10 mL) was stirred under nitrogen at 100° C. for 3 h. The reaction mixture was cooled to room temperature and filtered through celite. The filtrate was diluted with water (100 mL) and extracted with ethyl acetate (100 mL×2). The organic layers were discarded off. The aqueous layer was acidified to pH 3 with aqueous HCl solution (1 N) and extracted with ethyl acetate (100 mL×2). The combined organic layers were washed with water (100

A mixture of Compound 281C (100 mg, 0.33 mmol), HATU (190 mg, 0.50 mmol), and Intermediate C (98 mg, 0.33 mmol) in DMF (5 mL) was stirred at 10° C. for 18 h. The mixture was directly purified with prep-HPLC to furnish Compound 282. LC-MS (ESI) m/z: 585 [M+H]$^+$; $^1$H-NMR (DMSO-d$_6$, 400 MHz): δ (ppm) 1.17-1.19 (m, 4H), 1.88-2.08 (m, 4H), 3.11-3.22 (m, 2H), 3.46-3.56 (m, 4H), 3.84-3.89 (m, 1H), 4.29-4.31 (m, 4H), 4.52-4.54 (m, 1H), 4.80 (d, J=2.4 Hz, 1H), 6.05 (brs, 1H), 6.79 (s, 1H), 6.84 (d, J=12.0 Hz, 1H), 7.55 (d, J=8.4 Hz, 1H), 7.89-7.94 (m, 5H), 8.04 (s, 1H), 8.09 (s, 1H), 8.79 (d, J=9.2 Hz, 1H), 9.33 (brs, 1H).

Example 283

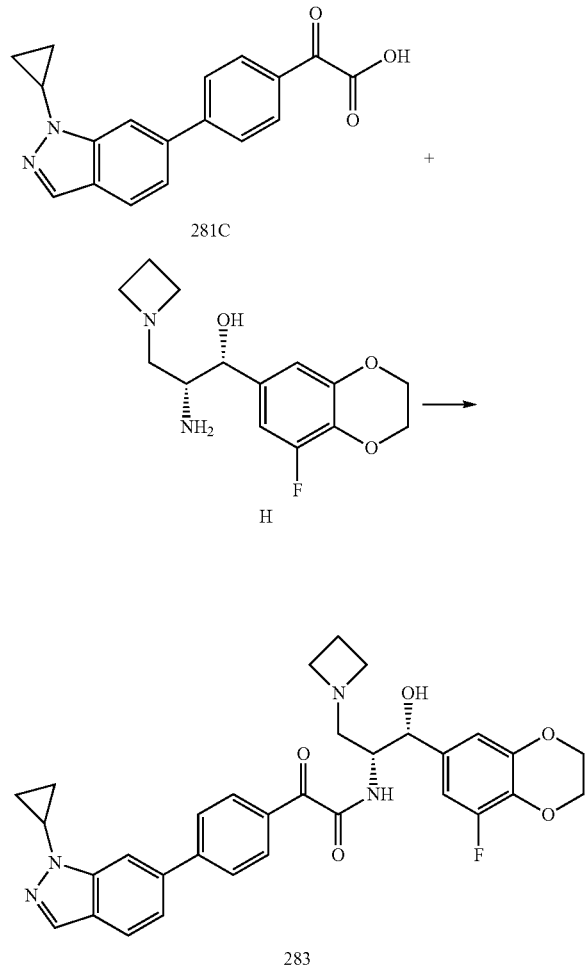

A mixture of Compound 281C (100 mg, 0.33 mmol), HATU (190 mg, 0.50 mmol), and Intermediate H (93 mg, 0.33 mmol) in DMF (5 mL) was stirred at 10° C. for 18 h. The mixture was directly purified with prep-HPLC to furnish Compound 283. LC-MS (ESI) m/z: 571 [M+H]$^+$; $^1$H-NMR (DMSO-d$_6$, 400 MHz): δ (ppm) 1.16-1.18 (m, 4H), 2.26-2.30 (m, 1H), 2.40-2.48 (m, 1H), 3.32-3.39 (m, 1H), 3.49-3.54 (m, 1H), 3.84-3.89 (m, 1H), 4.05-4.40 (m, 9H), 4.76 (d, J=3.2 Hz, 1H), 6.03 (brs, 1H), 6.78 (s, 1H), 6.83 (dd, J=11.2, 1.6 Hz, 1H), 7.55 (dd, J=8.4, 1.2 Hz, 1H), 7.85-7.94 (m, 5H), 8.03 (s, 1H), 8.09 (s, 1H), 8.79 (d, J=9.6 Hz, 1H), 9.65 (brs, 1H).

Example 284

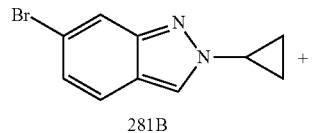

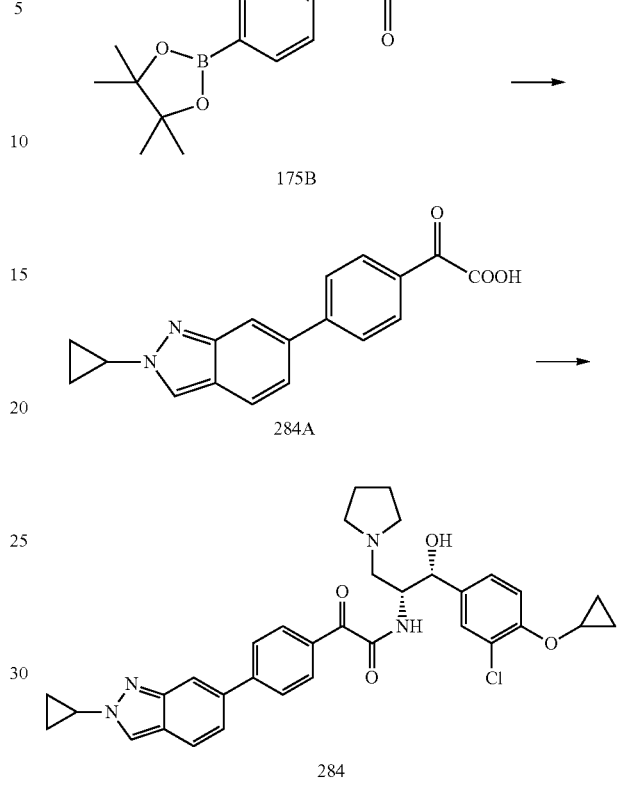

A mixture of Compound 281B (100 mg, 0.42 mmol), Compound 175B (128 mg, 0.42 mmol), Pd(dppf)Cl$_2$ (17 mg, 0.02 mmol), and K$_2$CO$_3$ (174 mg, 1.26 mmol) in dioxane (5 mL) and water (5 mL) was stirred under nitrogen at 100° C. for 3 h. The reaction mixture was cooled to room temperature and filtered through celite. The filtrate was diluted with water (100 mL), extracted with ethyl acetate (100 mL×2), and the organic layer was discarded off. The aqueous layer was acidified to pH 3 with aqueous HCl solution (1 N) and extracted with ethyl acetate (100 mL×2). The combined organic layers were washed with water (100 mL×2) and brine (100 mL), dried over anhydrous sodium sulfate, and concentrated to give Compound 284A.

A mixture of Compound 284A (80 mg, 0.26 mmol), HATU (148 mg, 0.39 mmol), and Intermediate G (81 mg, 0.26 mmol) in DMF (5 mL) was stirred at 10° C. for 18 h. The mixture was directly purified with prep-HPLC to furnish Compound 284. LC-MS (ESI) m/z: 599 [M+H]$^+$; $^1$H-NMR (DMSO-d$_6$, 400 MHz): δ (ppm) 0.67-0.85 (m, 4H), 1.12-1.34 (m, 4H), 1.87-1.92 (m, 4H), 3.11-3.24 (m, 2H), 3.46-3.58 (m, 4H), 3.92-3.96 (m, 1H), 4.18-4.23 (m, 1H), 4.43-4.56 (m, 1H), 4.89 (d, J=2.8 Hz, 1H), 6.05 (brs, 1H), 7.35-7.46 (m, 4H), 7.77 (d, J=8.4 Hz, 2H), 7.81-7.85 (m, 3H), 7.97 (s, 1H), 8.55 (s, 1H), 8.83 (d, J=10.0 Hz, 1H), 9.38 (brs, 1H).

Example 285
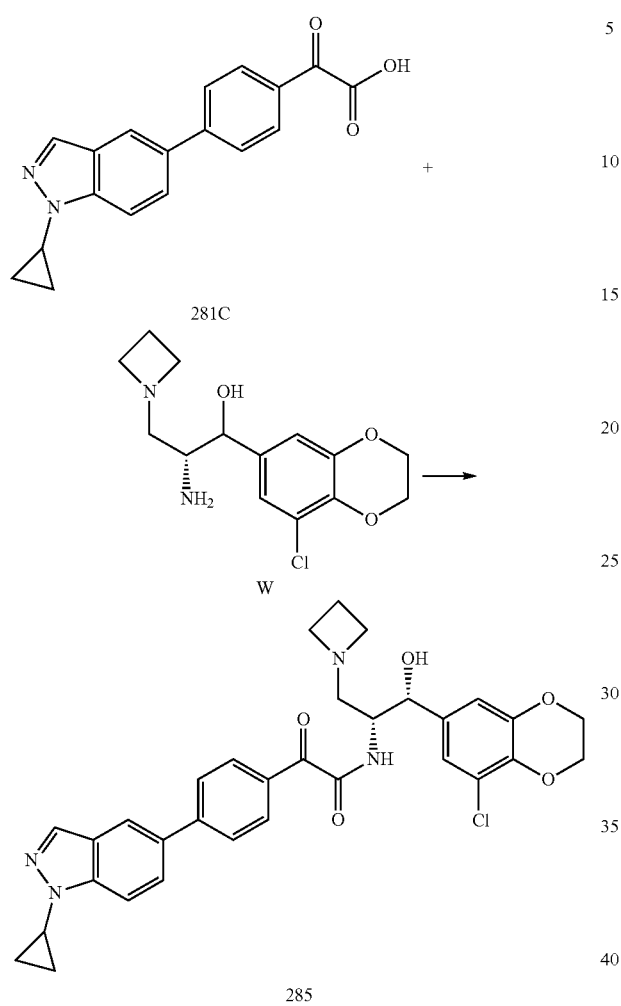
A mixture of Intermediate W (89 mg, 0.30 mmol), Compound 281C (90 mg, 0.30 mmol), and HATU (148 mg, 0.39 mmol) in DMF (4 mL) was stirred at 10° C. for 1.5 h. And then it was purified with prep-HPLC to yield Compound 285. LC-MS (ESI) m/z: 587 [M+H]$^+$; $^1$H-NMR ((CD$_3$)$_2$CO, 400 MHz): δ (ppm) 1.21-1.23 (m, 4H), 2.56-2.65 (m, 1H), 2.69-2.81 (m, 1H), 3.77-3.82 (m, 1H), 3.91-4.05 (m, 2H), 4.21-4.39 (m, 4H), 4.50-4.68 (m, 4H), 4.72-4.78 (m, 1H), 5.11 (d, J=2.8 Hz, 1H), 6.95 (d, J=2.0 Hz, 1H), 7.08 (d, J=2.0 Hz, 1H), 7.85 (d, J=8.8 Hz, 4H), 8.02 (t, J=8.4 Hz, 2H), 8.10 (d, J=9.6 Hz, 1H), 8.14 (s, 1H), 8.18 (s, 1H), 8.86 (brs, 1H).
Example 286
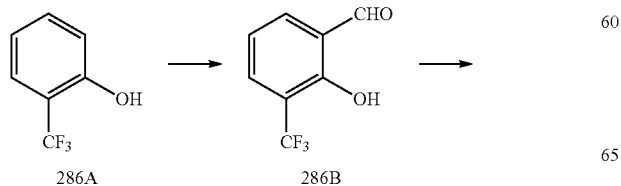
-continued
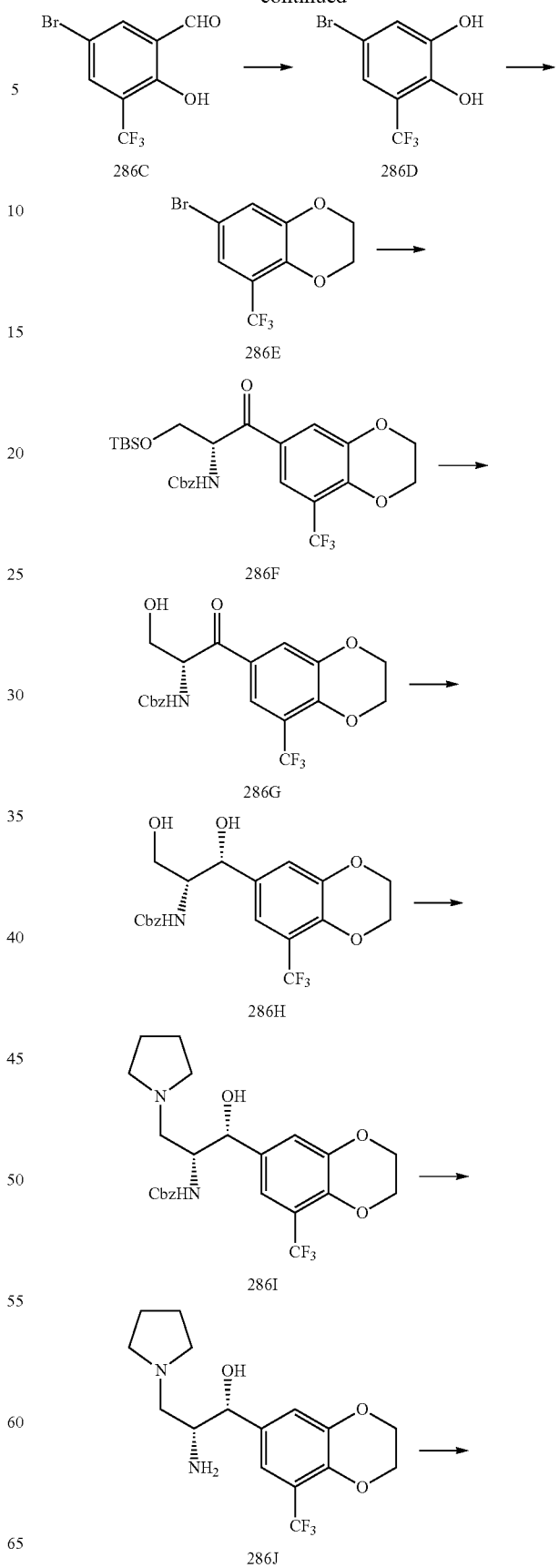

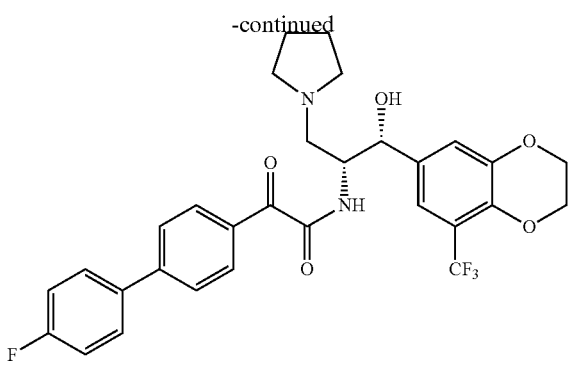

286

To a solution of Compound 286A (5 g, 31 mmol) in 2,2,2-trifluoroacetic acid (50 mL) was added hexamethylenetramine (4.7 g, 33.6 mmol). The reaction solution was heated at reflux overnight. After cooling, the mixture was treated with 50% $H_2SO_4$ (20 mL) at room temperature for 4 h and extracted with ether (50 mL×3). The combined ether phases were washed with aqueous HCl solution (5 M, 50 mL), water (50 mL) and brine (50 mL), dried over anhydrous sodium sulfate, concentrated, and purified with flash column chromatography on silica gel (ethyl acetate in petroleum ether, 10% v/v) to afford Compound 286B.

To a solution of Compound 286B (1 g, 5.3 mmol) in acetonitrile (15 mL) was added NBS (0.88 g, 5.3 mmol) and ammonium formate (32 mg, 0.5 mmol) at 0° C. The mixture was stirred at room temperature for 2 h. The solvent was removed to give yellow solid. The yellow solid was diluted with ethyl acetate (100 mL), washed with brine (100 mL), dried over anhydrous sodium sulfate, and concentrated to yield Compound 286C.

To a solution of Compound 286C (1.3 g, 4.8 mmol) in THF (10 mL) was added dropwise aqueous NaOH solution (0.05 N, 18 mL) at 0° C., and 30% $H_2O_2$ (2.3 mL) was added dropwise. The mixture was stirred at room temperature for 2 h. Other portion of 30% $H_2O_2$ (2.3 mL) was added dropwise. The mixture was stirred for 4 h. It was cooled to 0° C. and aq. NaOH solution (2 N, 2 mL) was added dropwise until pH 10~11. The mixture was stirred at 25° C. for 0.5 h, adjusted to pH 2~3 with concentrated HCl at 0° C., and extracted with dichloromethane (20 mL×3). The organic layers were washed with brine (20 mL×2), dried over anhydrous sodium sulfate, and concentrated to give Compound 286D.

To a mixture of Compound 286D (1.2 g, 4.7 mol) and $K_2CO_3$ (1.9 g, 14.1 mol) in DMF (12 mL) was added 1,2-dibromoethane (4.4 g, 23.5 mol). The mixture was stirred at 80° C. for 4 h. It was cooled down to room temperature and filtered. The cake was washed with ethyl acetate (50 mL). The filtrate was diluted with water (50 mL) and extracted with ethyl acetate (50 mL×3). The organic layer was washed with water (50 mL×5) and brine (50 mL), dried over anhydrous sodium sulfate, concentrated, and purified with flash column chromatography on silica gel (ethyl acetate in petroleum, 5% v/v) to furnish Compound 286E.

To a solution of Compound 286E (0.9 g, 3.2 mmol) in dry THF (10 mL) was added n-BuLi solution (2.5 N in hexane, 1.3 mL) under nitrogen at −60° C. The above mixture was stirred at −60° C. for 0.5 h. A solution of Compound A4 (0.4 g, 1.1 mmol) in THF (4 mL) was added. The resulting mixture was stirred at −60° C. for 0.5 h, quenched with saturated aqueous ammonium chloride solution (20 mL), extracted with ethyl acetate (30 mL×2), washed with brine (30 mL), dried over anhydrous sodium sulfate, and concentrated to give a crude compound. The crude product was purified with flash column chromatography on silica gel (ethyl acetate in petroleum ether, 10% v/v) to yield Compound 286F.

To a solution of Compound 286F (4.8 g, 8.9 mmol) in THF (25 mL) and water (25 mL) was added acetic acid (75 mL). The resulting mixture was stirred at 35° C. for 16 h, diluted with brine (150 mL), and adjusted to pH 8 with saturated aqueous sodium bicarbonate solution (75 mL). The mixture was extracted with ethyl acetate (100 mL×2), washed with brine (100 mL), dried over anhydrous sodium sulfate, concentrated, and purified with flash column chromatography on silica gel (ethyl acetate in petroleum, 20% v/v) to afford Compound 286G.

To a solution of Compound 286G (2 g, 4.7 mmol) in dry THF (60 mL) was added dropwise DIBAL-H (1 N in toluene, 9.4 mL, 9.4 mmol) under nitrogen at −80° C. The resultant mixture was stirred at −80° C. for 30 min and additional DIBAL-H (1 N in toluene, 9.4 mL, 9.4 mmol) was added dropwise again. The mixture was stirred at −80° C. for 1 h and quenched with aqueous HCl solution (2 N, 28 mL) at −20° C. The mixture was extracted with ethyl acetate (200 mL×2), washed with water (200 mL) and brine (100 mL), dried over anhydrous sodium sulfate, and purified with flash column chromatography on silica gel (ethyl acetate in petroleum, 50% v/v) to furnish Compound 286H.

To a solution of Compound 286H (1.5 g, 3.5 mmol) in THF (50 mL) was added triethylamine (1.1 g, 10.5 mmol). The mixture was cooled to −20° C. and MsCl (0.44 g, 3.9 mmol) was added slowly. The mixture was stirred at −20° C. for about half an hour and pyrrolidine (2.1 g, 30 mmol) was added to the mixture. The resulting mixture was stirred at −60° C. for 16 h and cooled to 25° C. The mixture was diluted with ethyl acetate (200 mL), washed with water (50 mL×2) and brine (50 mL), dried over anhydrous sodium sulfate, concentrated, and purified with flash column chromatography on silica gel (methanol in dichloromethane, from 5% to 10% v/v) to give Compound 286I.

To a solution of Compound 286I (0.5 g, 1.2 mmol) in methanol (10 mL) was added $Pd(OH)_2$ (100 mg). The mixture was stirred under hydrogen at room temperature overnight. After removal of $Pd(OH)_2$ by filtration, the filtrate was evaporated to furnish Compound 286J.

A mixture of Compound 286I (0.1 g, 0.28 mmol), HATU (0.16 g, 0.43 mmol), and Intermediate C (70 mg, 0.28 mmol) in DMF (3 mL) was stirred at 25° C. for 16 h. The mixture was diluted with ethyl acetate (30 mL), washed with water (10 mL×2) and brine (10 mL), dried over anhydrous sodium sulfate, concentrated, and purified with prep-HPLC to yield Compound 286. LC-MS (ESI) m/z: 573 [M+H]$^+$; $^1$H-NMR (DMSO-$d_6$, 400 MHz): δ (ppm) 1.88-1.89 (m, 2H), 2.03-2.04 (m, 2H), 3.14-3.20 (m, 2H), 3.52-3.55 (m, 4H), 4.29-4.35 (m, 4H), 4.53-4.56 (m, 1H), 4.87 (s, 1H), 6.10 (d, J=4 Hz, 1H), 7.20-7.23 (m, 2H), 7.35-7.40 (m, 2H), 7.79-7.88 (m, 6H), 8.77-8.79 (m, 1H), 9.30 (s, 1H).

Example 287

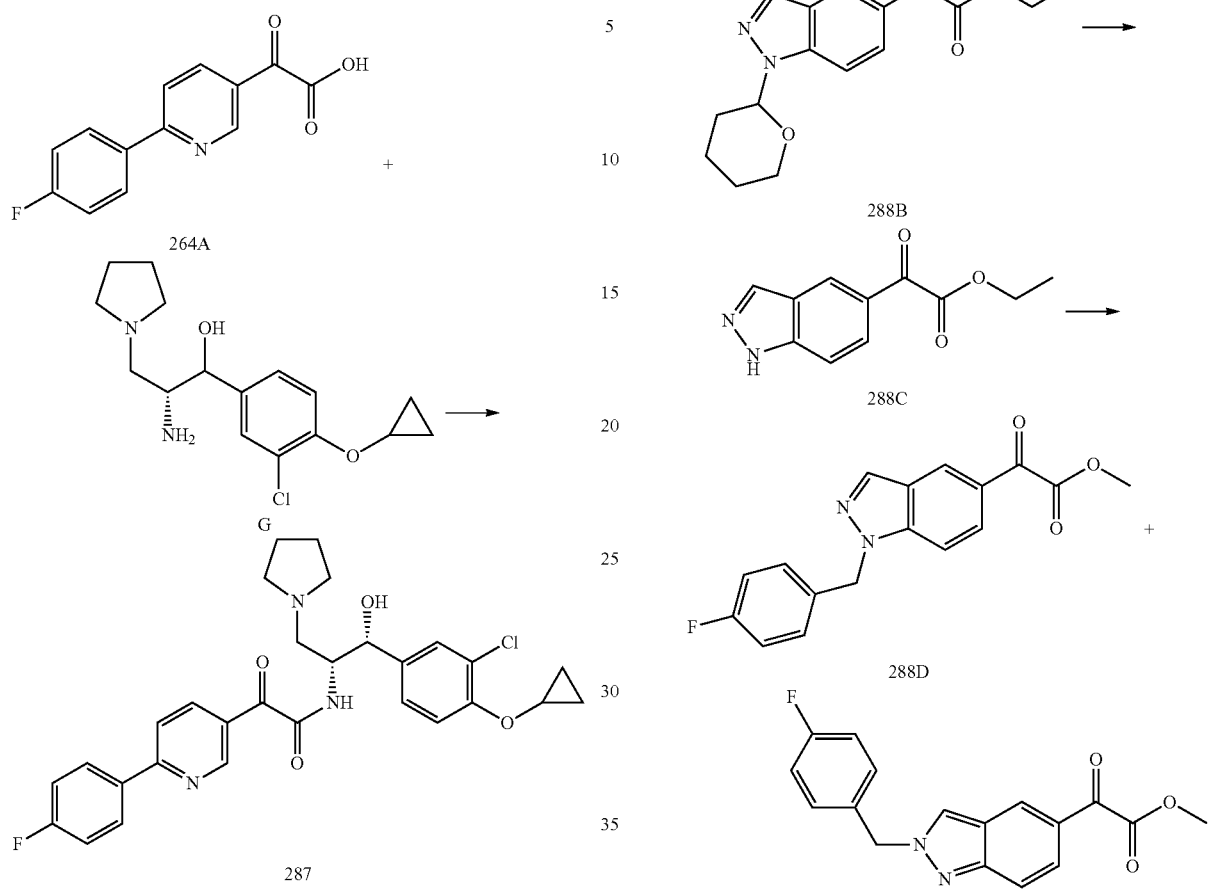

A mixture of Compound 264A (100 mg, 0.40 mmol), Intermediate G (150 mg, 0.48 mmol), and HATU (233 mg, 0.60 mmol) in dichloromethane (2 mL) and DMF (2 mL) was stirred at 25° C. for 15 h. After the reaction was completed, it was poured into water (20 mL) and extracted with dichloromethane (20 mL×3). The combined organic layers were dried over anhydrous sodium sulfate, concentrated in vacuo, and purified with prep-HPLC to afford Compound 287. LC-MS (ESI) m/z: 538 [M+H]$^+$; $^1$H-NMR (DMSO-d$_6$, 400 MHz): δ (ppm) 0.68-0.81 (m, 4H), 1.88-2.04 (m, 5H), 3.01-3.20 (m, 3H), 3.41-3.55 (m, 4H), 4.51-4.53 (m, 1H), 4.86 (s, 1H), 7.32-7.44 (m, 5H), 8.12-8.31 (m, 4H), 8.76-8.81 (m, 1H), 9.01 (s, 1H).

Example 288

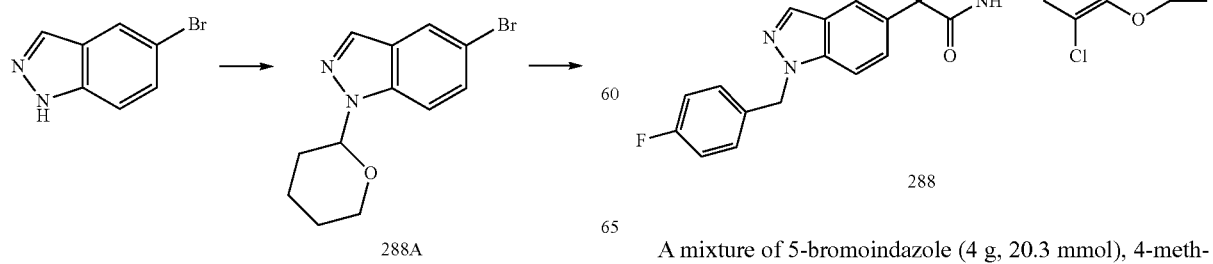

A mixture of 5-bromoindazole (4 g, 20.3 mmol), 4-methylbenzenesulfonic acid (1.9 g, 10.1 mmol), and DHP (3.4 g, 40.6 mmol) in dichloromethane (50 mL) was stirred at room temperature for 18 hours. The reaction mixture was treated with ethyl acetate (500 mL), washed with sodium bicarbonate solution (500 mL×3) and water (500 mL×3), dried over anhydrous sodium sulfate, and concentrated. The crude product was purified with flash column chromatography on silica gel (ethyl acetate in petroleum ether, from 10% to 33% v/v) to furnish Compound 288A.

To a solution of Compound 288A (4.2 g, 14.8 mmol) in dry THF (50 mL) was added dropwise n-BuLi (2.0 M, 7.5 mL, 17.8 mmol) under nitrogen at −70° C. After stirring for 30 min., diethyl oxalate (6.5 g, 44.4 mmol) was added quickly. The mixture was stirred at −70° C. for one hour. It was quenched with saturated ammonium chloride solution (10 mL) and extracted with ethyl acetate (50 mL×3). The combined organic phases were washed with water (5 mL) and brine (5 mL), dried over anhydrous sodium sulfate, filtered, and concentrated to give a residue. The residue was purified with flash column chromatography on silica gel (ethyl acetate in petroleum ether, from 0% to 20% v/v) to afford Compound 288B.

To a solution of Compound 288B (1.4 g, 4.6 mmol) in ethanol (10 mL) was added dropwise 2 N hydrogen chloride (10 mL, 18.5 mmol). The reaction mixture was stirred at room temperature for 8 h. Sodium bicarbonate solution was added to adjust pH 7, followed by extraction with ethyl acetate (50 mL×3). The combined organic phases were washed with water (5 mL) and brine (5 mL), dried over anhydrous sodium sulfate, filtered, and concentrated to furnish Compound 288C.

A mixture of Compound 288C (500 mg, 2.29 mmol), 1-(bromomethyl)-4-fluorobenzene (647 mg, 3.44 mmol), and $Cs_2CO_3$ (897 mg, 2.75 mmol) in 1-methylpyrrolidin-2-one (20 mL) was stirred at room temperature for 18 hours. The reaction mixture was treated with $H_2O$ (50 mL) and ethyl acetate (50 mL), washed with and water (500 mL×3), dried over anhydrous sodium sulfate, and concentrated. The crude product was purified with flash column chromatography on silica gel (ethyl acetate in petroleum ether, from 10% to 33% v/v) to furnish Compound 288D and Compound 288E.

To a solution of Compound 288D (300 mg, 0.91 mmol) in THF (2 mL) was added dropwise 1 N lithium hydroxide (2 mL, 2 mmol). The reaction mixture was stirred at room temperature for 2 h. After the reaction mixture was concentrated, 2 N HCl (1 mL) was added to adjust pH 7, and extracted with ethyl acetate (50 mL×3). The combined organic phases were washed with water (5 mL) and brine (5 mL), dried over anhydrous sodium sulfate, filtered, and concentrated to furnish Compound 288F.

To a solution of Compound 288F (50 mg, 0.167 mmol) in dichloromethane (3 mL) was added Intermediate G (62 mg, 0.201 mmol) and HATU (95 mg, 0.25 mmol). The mixture was stirred at room temperature for 2 h. It was concentrated and the resulting residue was purified with prep-HPLC to afford Compound 288. LC-MS (ESI) m/z: 591 [M+H]$^+$; $^1$H-NMR (CDCl$_3$, 400 MHz): δ (ppm) 0.68-0.91 (m, 4H), 2.11-2.15 (m, 4H), 2.97-3.05 (m, 2H), 3.48-3.50 (m, 1H), 3.65-3.68 (m, 1H), 3.70-3.85 (m, 1H), 3.87-3.91 (m, 2H), 4.53-4.57 (m, 1H), 5.01-5.06 (m, 1H), 5.56 (s, 2H), 6.96-7.00 (m, 2H), 7.13-7.19 (m, 3H), 7.20-7.23 (m, 1H), 7.28-7.31 (m, 1H), 7.38 (s, 1H), 7.93-7.95 (m, 1H), 8.11-8.13 (m, 2H), 8.58 (s, 1H), 11.48 (brs, 1H).

Example 289

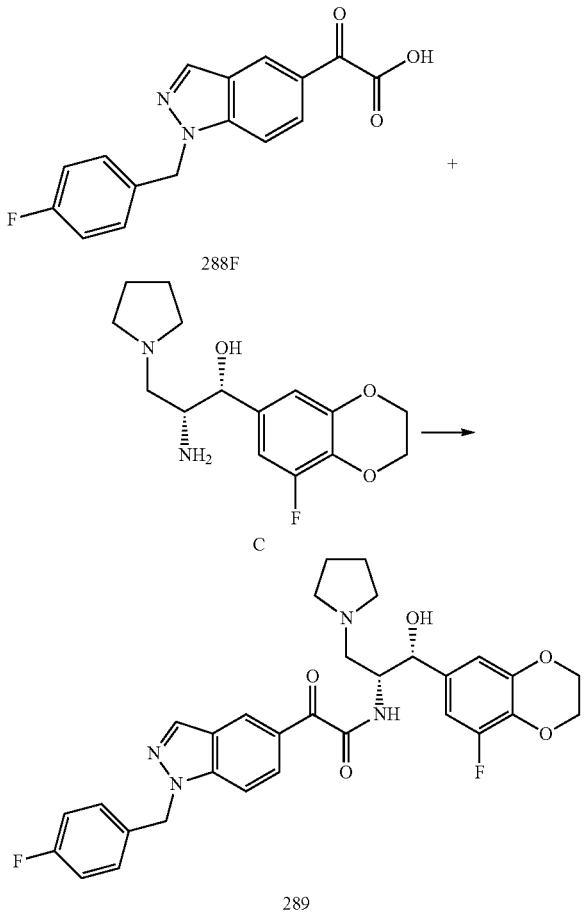

To a solution of Compound 288F (50 mg, 0.167 mmol) in dichloromethane (3 mL) was added Intermediate C (59 mg, 0.201 mmol) and HATU (95 mg, 0.25 mmol). The mixture was stirred at room temperature for 2 hours. It was concentrated and the resulting residue was purified with prep-HPLC to afford Compound 289. LC-MS (ESI) m/z: 577 [M+H]$^+$; $^1$H-NMR (CDCl$_3$, 400 MHz): δ (ppm) 2.18-2.19 (m, 4H), 3.01-3.05 (m, 2H), 3.49-3.51 (m, 1H), 3.71-3.79 (m, 2H), 3.96-4.02 (m, 2H), 4.18-4.22 (m, 4H), 4.45-4.47 (m, 1H), 5.10 (d, J=3.2 Hz, 1H), 5.56 (s, 2H), 6.72-6.73 (m, 2H), 6.97-7.03 (m, 2H), 7.16-7.19 (m, 2H), 7.35-7.37 (m, 1H), 7.68-7.70 (m, 1H), 8.02-8.04 (m, 1H), 8.18 (s, 1H), 8.73 (s, 1H).

Example 290

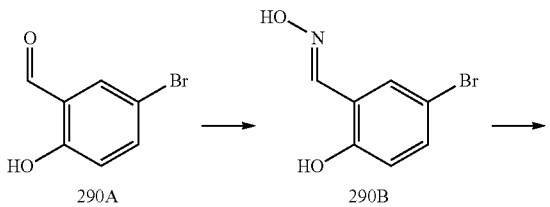

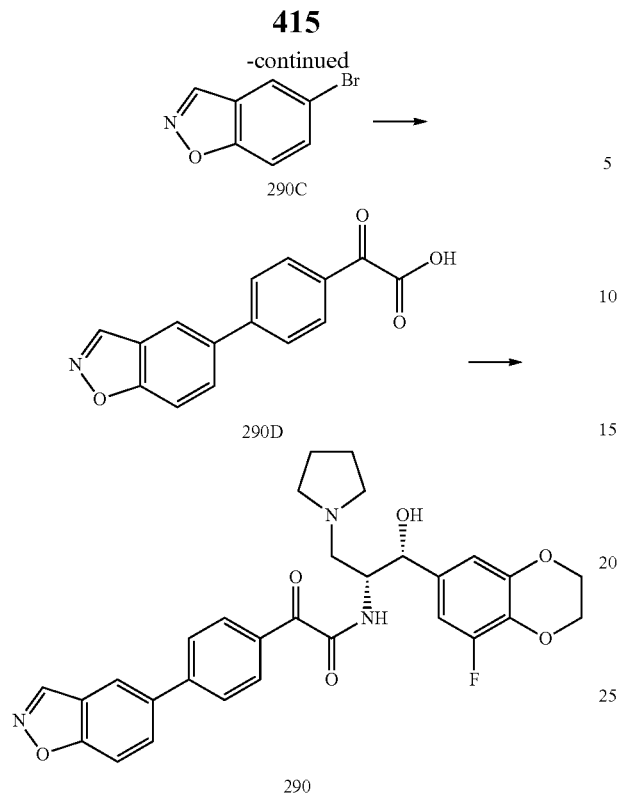

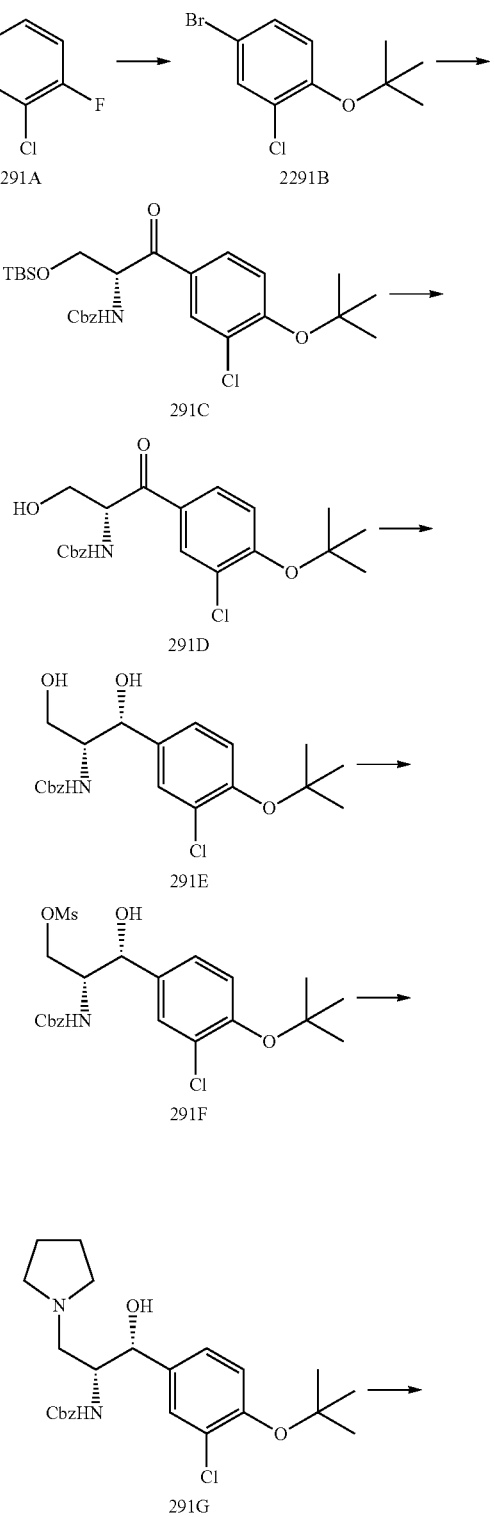

A mixture of Compound 290A (2 g, 9.85 mmol) and aminooxysulfonic acid (1.67 g, 14.78 mmol) in ethanol (50 mL) was stirred at room temperature for 2 h. The mixture was diluted with DCM (200 mL), washed with water (200 mL×2) and brine (100 mL), dried over anhydrous sodium sulfate, and concentrated to afford Compound 290B.

To a solution of $PPh_3$ (3.44 g, 13.12 mmol) in DCM (40 mL) was added DDQ (2.98 g, 13.12 mmol) in portions at room temperature and the resultant mixture was stirred for 5 min. Compound 290B (1.89 g, 8.75 mmol) was added. The reaction mixture was stirred for 5 min, diluted with DCM (100 mL), and filtered. The filtrate was washed with water (100 mL×2) and brine (50 mL), dried over anhydrous sodium sulfate, concentrated, and purified with flash column chromatography on silica gel (ethyl acetate in petroleum ether, 10% v/v) to give Compound 290C.

A mixture of Compound 290C (198 mg, 1 mmol), Compound 175B (456 mg, 1.5 mmol), $Pd(PPh_3)_2Cl_2$ (70 mg, 0.1 mmol), and $K_2CO_3$ (256 mg, 2 mmol) in dioxane (5 mL) and water (0.5 mL) was stirred at 80° C. for 2 h. The mixture was cooled down and filtered. The precipitate was dissolved in water and filtered. The filtrate was purified with reverse phase chromatography using eluent (methanol in water, from 0% to 100% v/v) to yield Compound 290D.

A mixture of Compound 290D (100 mg, 0.374 mmol), Intermediate C (111 mg, 0.374 mmol), and HATU (171 mg, 0.449 mmol) in DCM (3 mL) was stirred at room temperature overnight. The mixture was diluted with DCM (100 mL), washed with water (50 mL×2) and brine (50 mL), dried over anhydrous sodium sulfate, and concentrated. The crude product was purified with prep-HPLC to give Compound 290. LC-MS (ESI) m/z: 546 [M+H]$^+$; $^1$H-NMR (acetone-d$_6$, 400 MHz): δ (ppm) 2.09-2.22 (m, 4H), 3.27-3.40 (m, 3H), 3.72-3.77 (m, 2H), 3.87-3.96 (m, 2H), 4.26-4.33 (m, 4H), 4.77-4.82 (m, 1H), 5.12-5.13 (m, 1H), 6.84-6.90 (m, 2H), 7.36 (dd, J=1.2 Hz, J$_2$=8.0 Hz, 1H), 7.44 (d, J=1.6 Hz, 1H), 7.72-7.78 (m, 3H), 8.05 (d, J=8.8 Hz, 2H), 8.18-8.20 (m, 1H).

Example 291

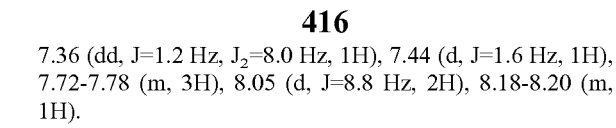

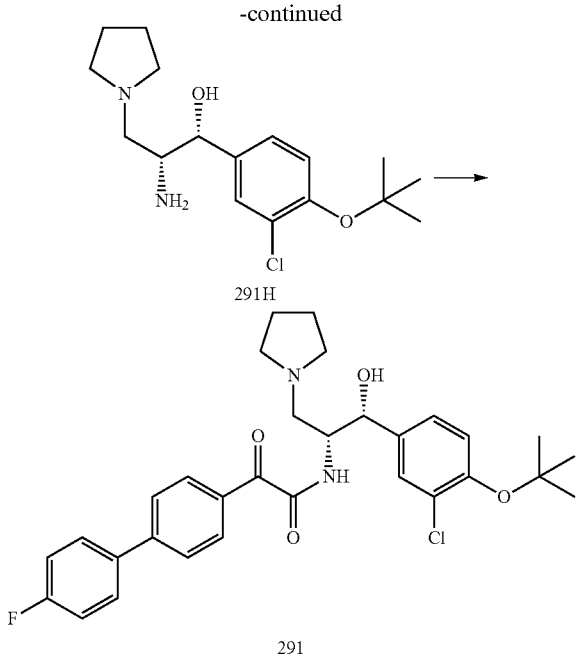

291H

291

To a solution of Compound 291A (10.00 g, 47.85 mmol) in DMF (100 mL) was added t-BuOK (8.04 mL, 71.77 mmol) at room temperature. The mixture was stirred room temperature for 2 h and quenched with water (100 mL). The mixture was diluted with ethylacetate (300 mL), washed with water (200 mL) and brine (200 mL), dried over anhydrous sodium sulfate, and purified with flash column chromatography on silica gel (ethyl acetate in petroleum ether, from 0% to 5% v/v) to afford Compound 291B.

To a solution of Compound 291B (11.00 g, 0.042 mol) in THF (30 mL) was added dropwise n-BuLi solution (2.5 Min hexane, 16.8 mL, 0.042 mol) under nitrogen at −68° C. The mixture was stirred at −78° C. for 30 min and a solution of Compound A4 (5.50 g, 13.89 mmol) in THF (20 mL) was added dropwise under nitrogen at −78° C. The mixture was stirred at −78° C. for 20 min and quenched with saturated aqueous ammonium chloride solution (100 mL). The mixture was diluted with ethyl acetate (300 mL), washed with water (200 mL) and brine (200 mL), dried over anhydrous sodium sulfate, and purified with flash column chromatography on silica gel (ethyl acetate in petroleum ether, from 0% to 10% v/v) to furnish Compound 291C.

A solution of Compound 291C (6.00 g, 11.56 mmol) in THF (40 mL), AcOH (120 mL), and water (40 mL) was stirred at 25° C. for 48 h. The mixture was evaporated to remove solvent, diluted with ethyl acetate (300 mL), washed with water (200 mL) and brine (200 mL), dried over anhydrous sodium sulfate, and purified with flash column chromatography on silica gel (ethyl acetate in petroleum ether, from 0% to 50% v/v) to afford Compound 291D.

To a solution of Compound 291D (3.20 g, 7.90 mmol) in THF (20 mL) was added dropwise DIBAL-H solution (1 Min toluene, 15.8 mL, 15.80 mmol) under nitrogen at −80° C. After 30 min, additional DIBAL-H solution (1 Min toluene, 15.8 mL, 15.80 mmol) was added dropwise under nitrogen at −80° C. The mixture was stirred under nitrogen at −80° C. for 2 h and quenched with saturated aqueous ammonium chloride solution (200 mL) at −20° C. The mixture was diluted with ethyl acetate (200 mL), washed with water (200 mL) and brine (200 mL), dried over anhydrous sodium sulfate, and purified with flash column chromatography on silica gel (methanol in dichloromethane, from 0% to 5% v/v) to give Compound 291E.

To a solution of Compound 291E (1.10 g, 2.70 mmol) and triethylamine (818 mg, 8.10 mmol) in THF (10 mL) was added dropwise methanesulfonyl chloride (370 mg, 3.24 mmol) at −15° C. The mixture was stirred at −15° C. for 1 h. It was quenched with saturated ice water (50 mL), diluted with ethyl acetate (200 mL), washed with water (150 mL) and brine (200 mL), dried over anhydrous sodium sulfate, and evaporated to afford Compound 291F. The target compound was directly used for the next step without further purification.

A solution of Compound 291F (1.10 g, 2.27 mmol) and pyrrolidine (1.68 g, 22.68 mmol) in THF (10 mL) was stirred at 50° C. for 16 h. The mixture was cooled down to room temperature and diluted with ethyl acetate (200 mL). The organic layer was washed with water (200 mL) and brine (200 mL), dried over anhydrous sodium sulfate, and purified with flash column chromatography on silica gel (methanol in dichloromethane, from 0% to 8% v/v) to furnish Compound 291G.

A mixture of Compound 291G (300 mg, 0.65 mmol) and LiOH.H$_2$O (356 mg, 6.52 mmol) in methanol (10 mL) and water (2 mL) was stirred at 80° C. for 16 h. It was diluted with ethyl acetate (200 mL), washed with water (200 mL) and brine (200 mL), dried over anhydrous sodium sulfate, and purified with reverse phase chromatography using eluent (methanol in water, from 0% to 100% v/v) to furnish Compound 291H.

A mixture of Compound 291H (110 mg, 0.34 mmol), Intermediate C (82 mg, 0.34 mmol), and HATU (190 mg, 0.51 mmol) in DMF (5 mL) was stirred at room temperature for 16 h. It was diluted with ethyl acetate (120 mL), washed with water (100 mL) and brine (100 mL), dried over anhydrous sodium sulfate, and purified with prep-HPLC to afford Compound 291. LC-MS (ESI) m/z: 553 [M+H]$^+$; $^1$H-NMR (DMSO-d$_6$, 400 MHz): δ (ppm) 1.33 (s, 9H), 1.84-1.93 (m, 2H), 2.00-2.06 (m, 2H), 3.11-3.24 (m, 2H), 3.49-3.53 (m, 4H), 4.52-4.57 (m, 1H), 4.91 (s, 1H), 6.08 (s, 1H), 7.21 (d, J=8.4 Hz, 1H), 7.27-7.30 (m, 1H), 7.37 (t, J=8.8 Hz, 2H), 7.47 (s, 1H), 7.78-7.85 (m, 6H), 8.79 (d, J=9.2 Hz, 1H), 7.43 (s, 1H).

Example 292

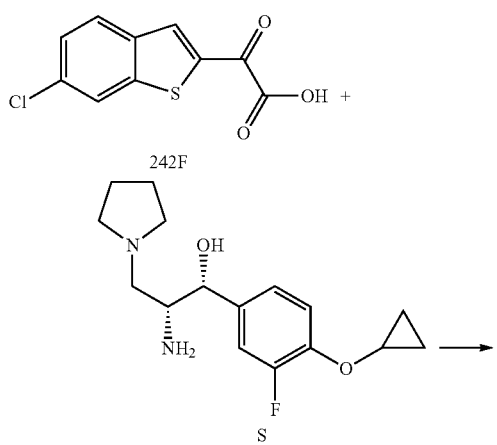

242F

S

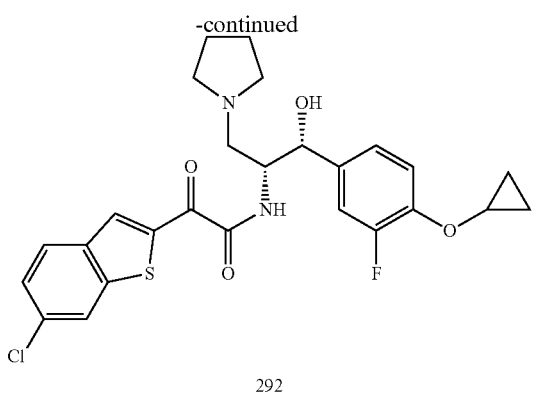

292

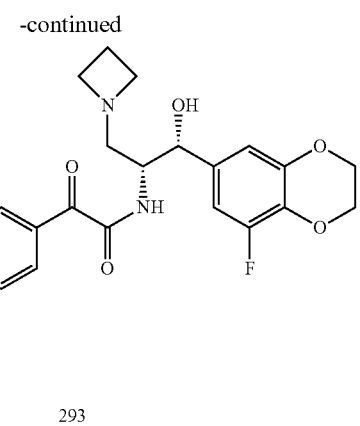

293

To a solution of Compound S (118 mg, 0.40 mmol) in DMF (10 mL) was added Compound 242F (80 mg, 0.33 mmol), HATU (190 mg, 0.50 mmol), and N,N-diisopropylethylamine (129 mg, 1.0 mmol). The mixture was stirred under nitrogen at 25° C. overnight. The resulting mixture was quenched with saturated aqueous sodium bicarbonate solution (5 mL) and extracted with ethyl acetate (50 mL×3). The combined organic phases were washed with water (5 mL) and brine (5 mL), dried over anhydrous sodium sulfate, filtered, and concentrated to afford a crude compound. The crude product was purified with prep-HPLC to furnish Compound 292. LC-MS (ESI) m/z: 517 [M+H]$^+$; $^1$H-NMR (DMSO-$d_6$ 400 MHz): δ (ppm) 0.64-0.76 (m, 4H), 1.84-2.00 (m, 4H), 3.09-3.17 (m, 2H), 3.33-3.38 (m, 1H), 3.50-3.56 (m, 3H), 3.86-3.90 (m, 1H), 4.43-4.48 (m, 1H), 4.79 (s, 1H), 6.06 (s, 1H), 7.14-7.20 (m, 2H), 7.35 (t, J=8.8 Hz, 1H), 7.55 (dd, J=8.8, 2.0 Hz, 1H), 8.13 (d, J=8.4 Hz, 1H), 8.30 (d, J=2.0 Hz, 1H), 8.58 (s, 1H), 8.63 (d, J=10.0 Hz, 1H), 9.06 (s, 1H).

A mixture of Compound 255C (50 mg, 0.18 mmol), HATU (100 mg, 0.27 mmol), and Intermediate H (50 mg, 0.18 mmol) in DMF (3 mL) was stirred at 25° C. for 16 h. The mixture was diluted with ethyl acetate (30 mL), washed with water (10 mL×2) and brine (10 mL), dried over anhydrous sodium sulfate, concentrated, and purified with prep-HPLC to furnish Compound 293. LC-MS (ESI) m/z: 547 [M+H]$^+$; $^1$H-NMR (DMSO-$d_6$, 400 MHz): δ (ppm) 1.33 (s, 9H), 2.26-2.45 (m, 2H), 3.36-3.48 (m, 2H), 4.07-4.30 (m, 9H), 4.74 (s, 1H), 6.02 (s, 1H), 6.76-6.84 (m, 2H), 7.54-7.56 (m, 2H), 7.69-7.71 (m, 2H), 7.78-7.84 (m, 4H), 8.75 (d, J=9.6 Hz, 1H), 9.67 (s, 1H).

Example 294

Example 293

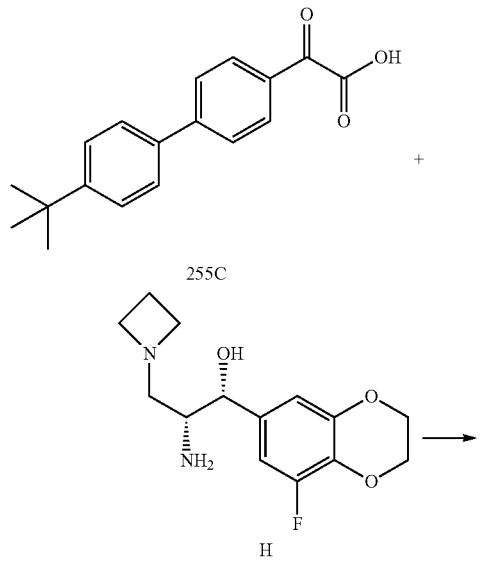

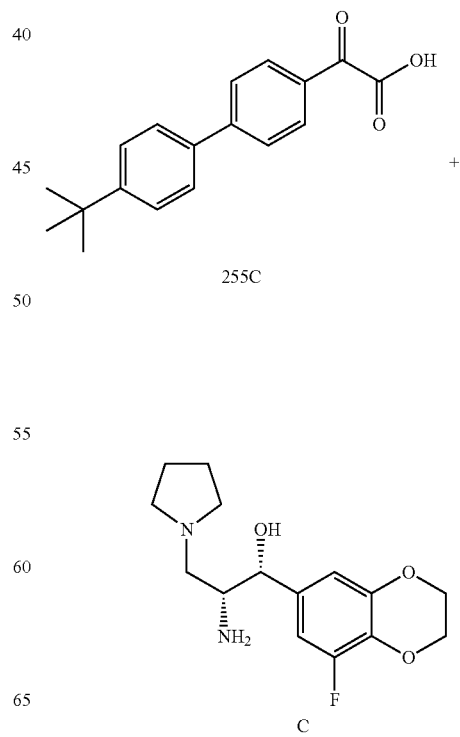

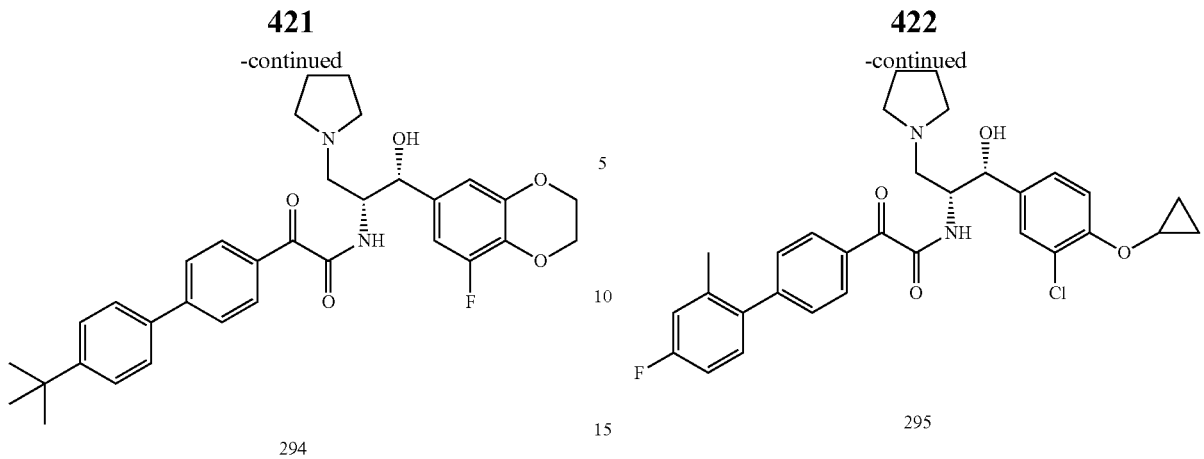

294

295

A mixture of Compound 255C (50 mg, 0.18 mmol), HATU (100 mg, 0.27 mmol), and Intermediate C (53 mg, 0.18 mmol) in DMF (3 mL) was stirred at 25° C. for 16 h. The mixture was diluted with ethyl acetate (30 mL), washed with water (10 mL×2) and brine (10 mL), dried over anhydrous sodium sulfate, concentrated, and purified with prep-HPLC to furnish Compound 294. LC-MS (ESI) m/z: 561 [M+H]$^+$; $^1$H-NMR (DMSO-d$_6$, 400 MHz): δ (ppm) 1.33 (s, 9H), 1.87-2.03 (m, 4H), 3.12-3.19 (m, 2H), 3.46-3.55 (m, 4H), 4.26-4.30 (m, 4H), 4.51-4.52 (m, 1H), 4.79 (s, 1H), 6.06 (s, 1H), 6.77-6.84 (m, 2H), 7.54-7.56 (m, 2H), 7.71-7.89 (m, 6H), 8.76 (d, J=9.6 Hz, 1H), 9.44 (s, 1H).

Example 295

To a solution of Compound 295A (752 mg, 4 mmol) in 1,4-dioxane (32 mL) and water (4 mL) was added Compound 175B (1.4 g, 4.4 mmol), Pd(dppf)Cl$_2$ (164 mg, 0.2 mmol), and potassium carbonate (1.66 g, 12 mmol) under nitrogen at 20° C. The reaction mixture was stirred at 110° C. for 3 hours. The resulting mixture was cooled to 20° C. It was adjusted to pH 5 with 2 N HCl and extracted with ethyl acetate (40 mL×3). The combined organic layers were concentrated in vacuo without dryness to give the crude Compound 295B.

To a solution of Compound 295B (78 mg, 0.3 mmol) in DMF (3 mL) and dichloromethane (4 mL) was added Intermediate G (112 mg, 0.36 mmol) and HATU (171 mg, 0.45 mmol). The reaction mixture was stirred at 25° C. for 3 hours. The mixture was purified with prep-HPLC to yield the product Compound 295. LC-MS (m/z) 551 [M+H]$^+$; $^1$H-NMR (DMSO-d$_6$, 400 MHz): δ (ppm) 0.74-0.90 (m, 4H), 1.93-2.01 (m, 5H), 2.27 (s, 3H), 2.95-3.10 (m, 2H), 3.11-3.3.15 (m, 1H), 3.61-3.65 (m, 3H), 4.00-4.02 (m, 1H), 4.76-4.79 (m, 1H), 5.52 (d, J=10.4 Hz, 1H), 7.13-7.17 (m, 1H), 7.20-7.24 (m, 1H), 7.28-7.32 (m, 1H), 7.48 (d, J=8.8 Hz, 2H), 7.55 (s, 2H), 7.69 (s, 1H), 8.16 (d, J=8.4 Hz, 2H), 9.73 (brs, 1H).

Example 296

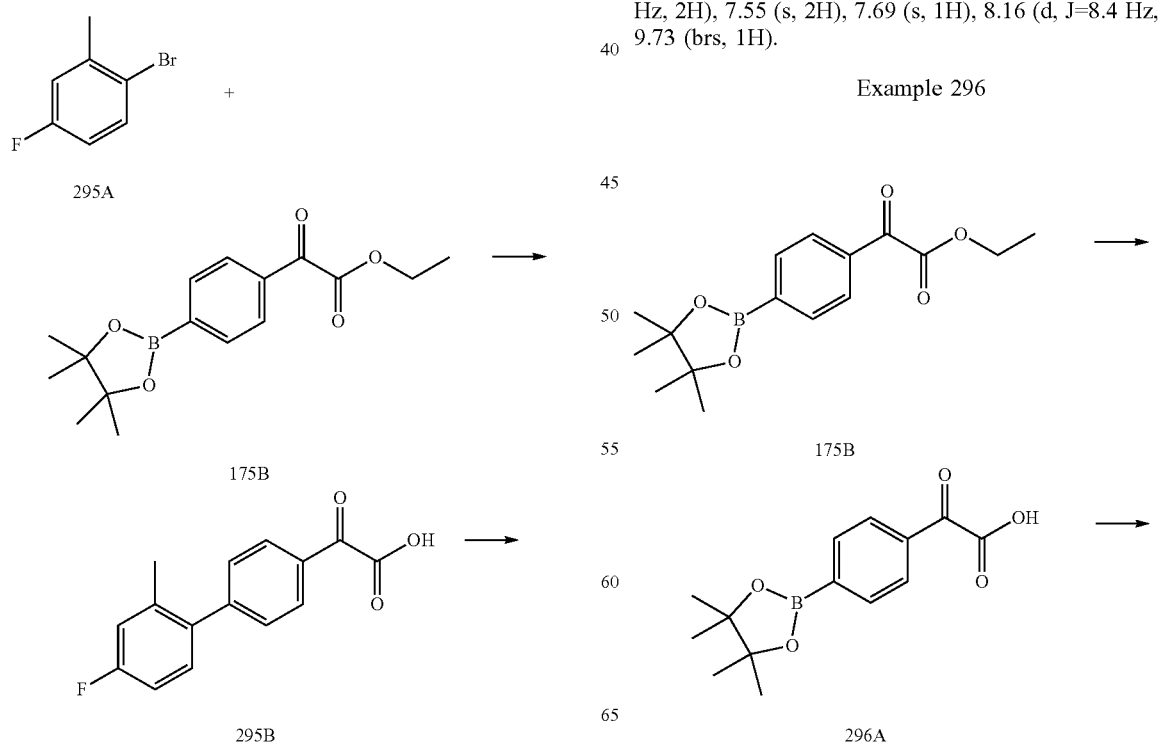

295A

175B

295B

175B

296A

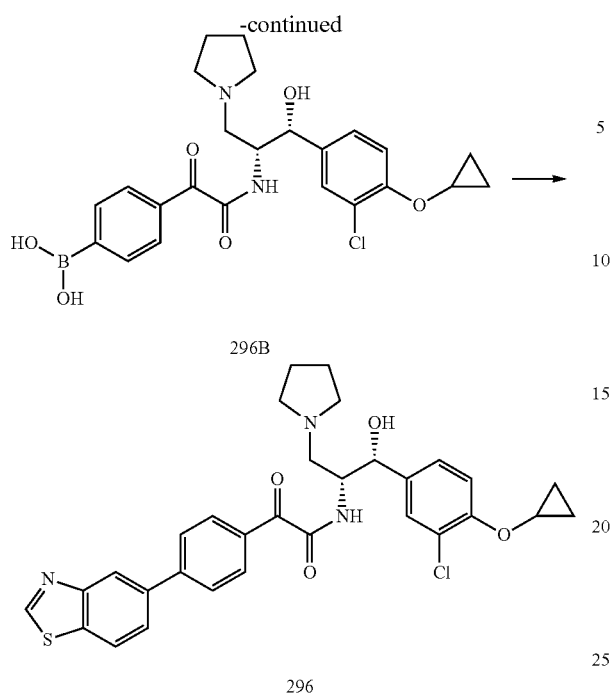

296B

296

To a solution of Compound 175B (600 mg, 1.97 mmol) in THF (20 mL) was added LiOH.H₂O (124 mg, 2.96 mmol) dissolved in water (3 mL) at 0° C. The mixture was stirred at room temperature for 4 h. The reaction mixture was treated with water (10 mL) and extracted with ethyl acetate (10 mL). The water layer was adjusted to pH 6 with diluted HCl and extracted with ethyl acetate (25 mL×2). The combined organic layers were washed with brine (15 mL), dried over anhydrous sodium sulfate, and concentrated to afford Compound 296A, which was used for the next step without further purification.

A mixture of Compound 296A (480 mg, 1.74 mmol), Intermediate G (594 mg, 1.91 mmol), and HATU (991 mg, 2.61 mmol) in dichloromethane (20 mL) was stirred at 25° C. for 10 h. The mixture was quenched with water (10 mL). The organic layer was washed with brine (50 mL), dried over anhydrous sodium sulfate, filtered, and concentrated in vacuo to afford a crude compound. The crude product was purified with prep-HPLC to furnish Compound 296B.

A mixture of 5-bromobenzo[d]thiazole (35 mg, 0.16 mmol), Compound 296B (104 mg, 0.22 mmol), [1,1'-bis (diphenylphosphino)ferrocene]dichloropalladium(II) (6 mg, 8.2 mol), potassium carbonate (68 mg, 0.49 mmol), water (0.5 mL), and 1,4-dioxane (2 mL) was heated under nitrogen atmosphere at 100° C. for 1 h. After cooling, water (5 mL) was added, and the mixture was extracted with ethyl acetate (10 mL×3). The combined organic layers were washed with brine (5 mL). The combined organic layers were dried over anhydrous sodium sulfate, filtered, and concentrated to afford the crude product as a black oil. The oil was purified with prep-HPLC to furnish Compound 296. LC-MS (ESI) m/z: 576 [M+H]⁺; ¹H-NMR ((CD₃)₂CO, 400 MHz): δ (ppm) 0.71-0.73 (m, 2H), 0.81-0.84 (m, 2H), 2.09-2.13 (m, 2H), 2.28 (s, 2H), 3.55 (s, 1H), 3.89-3.90 (m, 2H), 4.05-4.08 (m, 4H), 4.94 (s, 1H), 5.21 (d, J=2 Hz, 1H), 7.42-7.43 (m, 2H), 7.51 (d, J=1.6 Hz, 1H), 7.91 (dd, J=8.5, 3.0 Hz, 4H), 8.03 (d, J=8.5 Hz, 2H), 8.21 (d, J=9.7 Hz, 1H), 8.31 (d, J=8.5 Hz, 1H), 8.45 (d, J=1.5 Hz, 1H), 9.37 (s, 1H).

Example 297

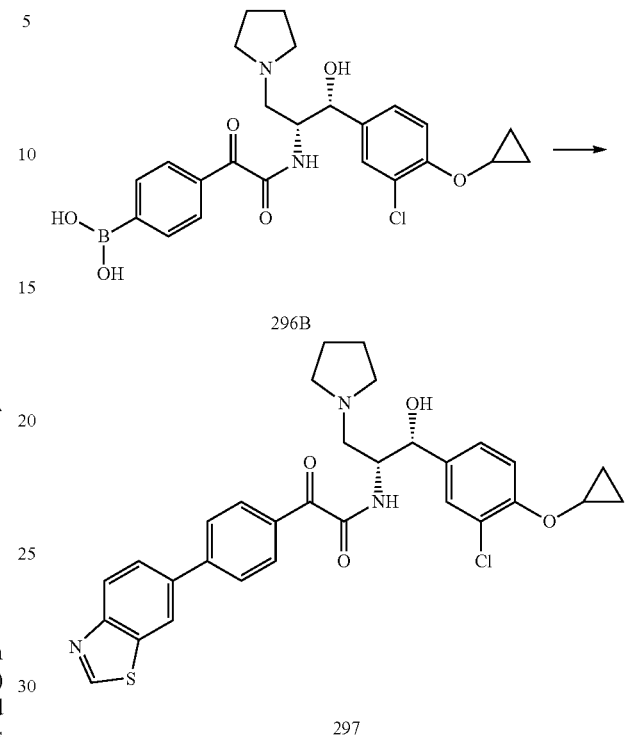

296B

297

A mixture of 6-bromobenzo[d]thiazole (30 mg, 0.14 mmol), Compound 296B (90 mg, 0.18 mmol), [1,1'-bis (diphenylphosphino)ferrocene]dichloropalladium(II) (6 mg, 8.2 μmol), potassium carbonate (58 mg, 0.42 mmol), water (0.5 mL), and 1,4-dioxane (2 mL) was heated under nitrogen atmosphere at 100° C. for 1 h. After cooling, water (5 mL) was added, and the mixture was extracted with ethyl acetate (10 mL×3). The combined organic layers were washed with brine (5 mL). The combined organic layers were dried over anhydrous sodium sulfate, filtered, and concentrated to afford the crude product as a black oil. The oil was purified with prep-HPLC to furnish Compound 297. LC-MS (ESI) m/z: 576 [M+H]⁺; ¹H-NMR ((CD₃)₂CO, 400 MHz): δ (ppm) 0.60-0.86 (m, 4H), 2.06-2.38 (m, 4H), 3.27 (s, 1H), 3.52-3.64 (m, 2H), 3.89-3.91 (m, 2H), 4.01 (d, J=5.7 Hz, 1H), 4.06-4.16 (m, 2H), 4.92-4.97 (m, 1H), 5.20 (d, J=2.1 Hz, 1H), 7.35-7.45 (m, 2H), 7.49 (d, J=1.7 Hz, 1H), 7.83-7.90 (m, 2H), 7.95 (dd, J=8.6, 1.8 Hz, 1H), 8.03 (d, J=8.6 Hz, 2H), 8.19-8.23 (m, 2H), 8.55 (d, J=1.6 Hz, 1H), 9.36 (s, 1H).

Example 298

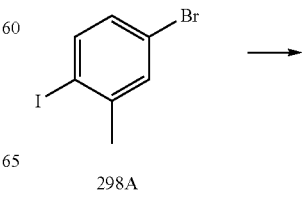

298A

-continued

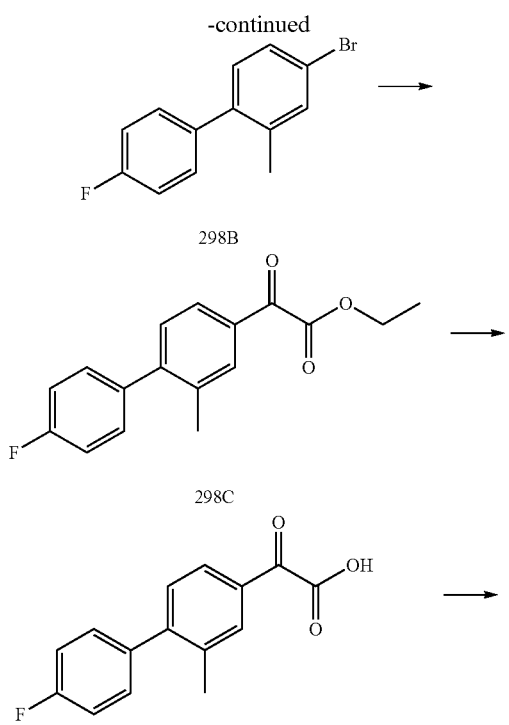

298B

298C

298D

298

To a mixture of Compound 298A (2.96 g, 0.01 mol), 4-fluorophenylboronic acid (2 g, 1.32 mol), and K₃PO₄ (6.4 g, 0.03 mol) in 1,2-dimethoxyethane (80 mL) was added Pd(dppf)Cl₂ (733 mg, 1.0 mmol). The reaction mixture was stirred under nitrogen at room temperature overnight. The resulting mixture washed with brine (100 mL), dried over anhydrous sodium sulfate, filtered, and concentrated. The residue was purified with flash column chromatography on silica gel (ethyl acetate in petroleum ether, from 10% to 50% v/v) to furnish Compound 298B.

To a solution of Compound 298B (2.64 g, 10 mmol) in THF (30 mL) was added dropwise n-BuLi solution (2.5 M in hexane, 4 mL, 10 mmol) under nitrogen at −78° C. The mixture was stirred at −78° C. for 0.5 h and the solution was added to a solution of diethyl oxalate (3 g, 20 mmol) in THF (20 mL) under nitrogen at −78° C. The mixture was stirred at room temperature overnight and quenched with saturated aqueous ammonium chloride solution (40 mL). The reaction mixture was extracted with ethyl acetate (50 mL×3), washed with water (100 mL) and brine (100 mL), dried over anhydrous sodium sulfate, and concentrated. The residue was purified with flash column chromatography on silica gel (ethyl acetate in petroleum ether, from 10% to 50% v/v) to give Compound 298C.

To a solution of Compound 298C (2.8 g, 0.01 mol) in ethanol/water (40 mL/10 mL) was added LiOH H₂O (840 mg, 0.02 mol). The mixture was stirred at room temperature for about 2 h until completion by thin layer chromatography analysis. The reaction mixture was acidified to pH 2 with aqueous HCl solution (1.0 N, 40 mL) and extracted with ethyl acetate (30 mL×2). The combined organic layers were washed with brine (100 mL), dried over anhydrous sodium sulfate, filtered, and concentrated to afford Compound 298D.

To a mixture of Compound 298D (126 mg, 0.5 mmol) and Intermediate G (155 mg, 0.5 mmol) in DMF (5 mL) was added HATU (380 mg, 1 mmol). The reaction mixture was stirred at room temperature overnight. The resulting solution was washed with brine (30 mL), dried over anhydrous sodium sulfate, filtered, and concentrated. The residue was purified with prep-HPLC to furnish Compound 298. LC-MS (ESI) m/z: 551 [M+H]⁺; ¹H-NMR (DMSO-d₆, 400 MHz): δ (ppm) 0.62-0.87 (m, 4H), 1.88-2.04 (m, 4H), 2.26 (s, 3H), 3.13-3.21 (m, 2H), 3.50-3.56 (m, 4H), 3.88-3.89 (m, 1H), 4.54-4.56 (m, 1H), 4.87 (s, 1H), 6.05 (s, 1H), 7.27-7.45 (m, 8H), 7.53 (d, J=6.8 Hz, 1H), 7.76 (s, 1H), 8.80 (d, J=9.2 Hz, 1H), 9.40 (s, 1H).

Example 299

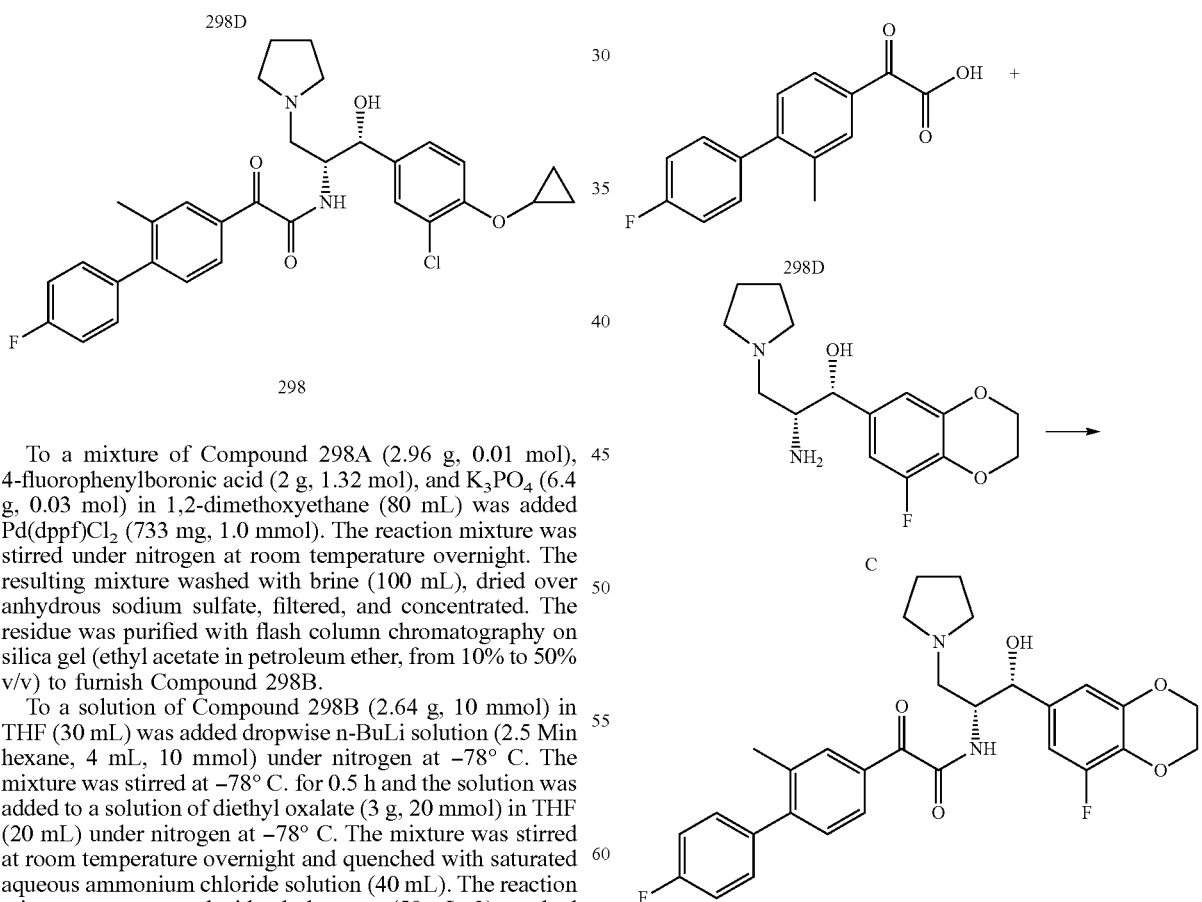

299

To a mixture of Compound 298D (130 mg, 0.5 mmol) and Intermediate C (143 mg, 0.5 mmol) in DMF (5 mL) was added HATU (380 mg, 1 mmol). The reaction mixture was stirred at room temperature overnight. The resulting solution was washed with brine (30 mL), dried over anhydrous sodium sulfate, filtered, and concentrated. The residue was purified with prep-HPLC to furnish Compound 299. LC-MS (ESI) m/z: 537 [M+H]$^+$; $^1$H-NMR (DMSO-d$_6$, 400 MHz): δ (ppm) 1.86-2.04 (m, 4H), 2.27 (s, 3H), 3.11-3.18 (m, 2H), 3.42-3.54 (m, 4H), 4.23-4.28 (m, 4H), 4.49 (s, 1H), 4.77 (s, 1H), 6.04 (s, 1H), 6.75 (s, 1H), 6.81-6.84 (m, 1H), 7.31-7.35 (m, 3H), 7.42-7.46 (m, 2H), 7.65 (d, J=7.6 Hz, 1H), 7.80 (s, 1H), 8.75 (d, J=9.6 Hz, 1H), 9.30 (s, 1H).

Example 300

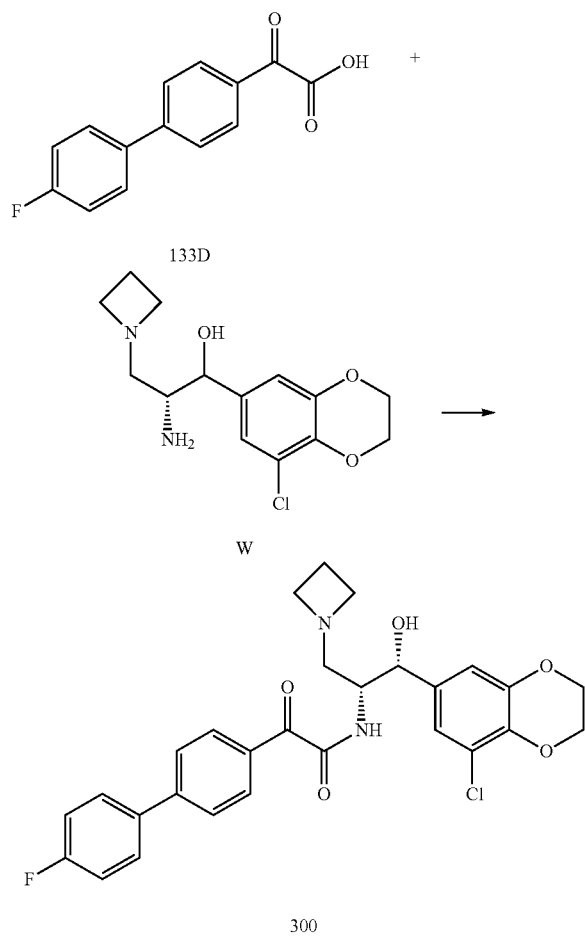

A mixture of Compound 133D (110 mg, 0.37 mmol), Intermediate W (90 mg, 0.37 mmol), and HATU (182 mg, 0.48 mmol) in dichloromethane (10 mL) was stirred at 10° C. for 15 h. And then it was treated with water (10 mL) and extracted with dichloromethane (10 mL×3 mL). The organic layers were washed with water (20 mL×3), dried over anhydrous sodium sulfate, concentrated in vacuo, and purified with prep-HPLC to yield Compound 300. LC-MS (ESI) m/z: 525 [M+H]$^+$; $^1$H-NMR ((CD$_3$)$_2$CO, 400 MHz): δ (ppm) 2.58 (s, 1H), 2.70-2.77 (m, 1H), 3.88-4.01 (m, 2H), 4.22-4.38 (m, 4H), 4.49-4.64 (m, 4H), 4.71-4.77 (m, 1H), 5.12 (s, 1H), 5.47 (s, 1H), 6.94 (d, J=1.6 Hz, 1H), 7.07 (d, J=2.0 Hz, 1H), 7.30 (t, J=8.8 Hz, 2H), 7.77-7.84 (m, 4H), 7.99 (d, J=8.4 Hz, 2H), 8.11 (d, J=9.6 Hz, 1H), 9.19 (s, 1H).

Example 301

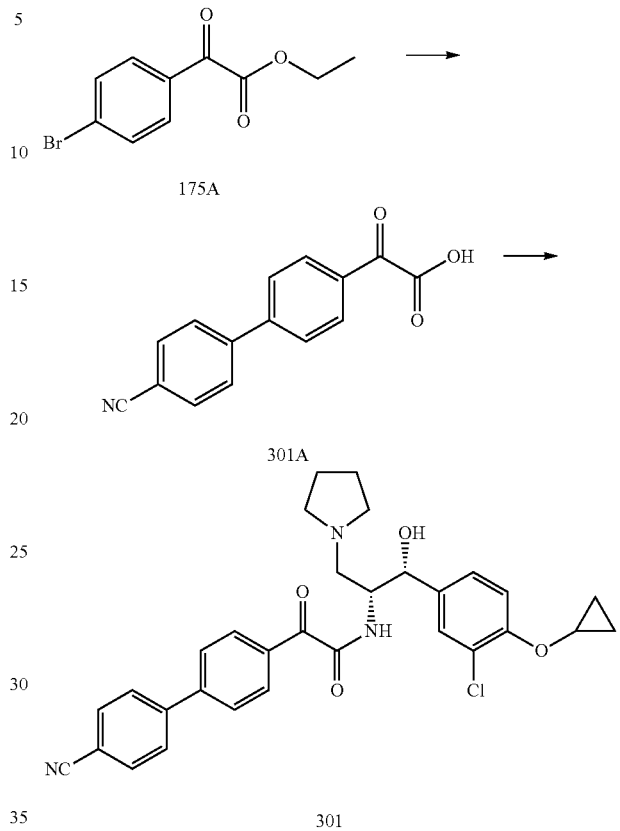

A mixture of Compound 175A (512 mg, 2 mmol), 4-cyanophenylboronic acid (294 mg, 2 mmol), potassium carbonate (828 mg, 6 mmol), and Pd(dppf)Cl$_2$ (40 mg, 0.08 mmol) in dioxane (20 mL) and water (4 mL) was stirred under nitrogen at 100° C. overnight. The solution was cooled down to room temperature, adjusted to pH 4 with aqueous hydrochloric acid solution (6 N, 2 mL), and extracted with ethyl acetate (100 mL×3). The combined organic layers were washed with water (50 mL) and brine (50 mL), dried over anhydrous sodium sulfate, filtered, and evaporated to afford Compound 301A.

A mixture of Compound 301A (100 mg, 0.4 mmol), HATU (273 mg, 0.72 mmol), and Intermediate G (124 mg, 0.4 mmol) in dichloromethane (10 mL) and DMF (2 mL) was stirred at 25° C. overnight. The solution was extracted with ethyl acetate (50 mL×2). The combined organic phases were washed with water (50 mL) and brine (50 mL), dried over anhydrous sodium sulfate, filtered, and concentrated to give a residue. The residue was purified with prep-HPLC to furnish Compound 301. LC-MS (ESI) m/z: 544 [M+H]$^+$; $^1$H-NMR (DMSO-d$_6$, 400 MHz): δ (ppm) 0.66-0.82 (m, 4H), 1.88-2.02 (m, 4H), 3.12-3.21 (m, 2H), 3.47-3.64 (m, 4H), 3.88-3.93 (m, 1H), 4.53-4.61 (m, 1H), 4.87 (s, 1H), 6.05 (s, 1H), 7.33-7.43 (m, 3H), 7.85-7.86 (m, 3H), 7.95-8.03 (m, 5H), 8.81-8.83 (m, 1H), 9.39 (s, 1H).

Example 302

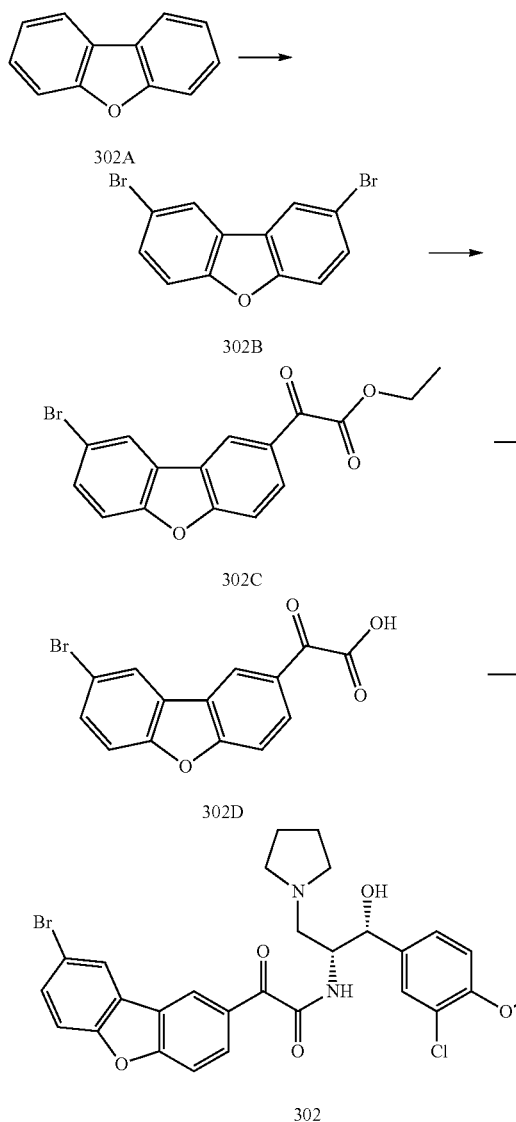

To a solution of Compound 302A (1 g, 0.59 mmol) in CHCl$_3$ (6 mL) was added bromine (0.68 mL, 13.26 mmol) at 0° C. The mixture was stirred at 25° C. for 48 h. It was poured into aq. Na$_2$S$_2$O$_3$ (50 mL) and extracted with ethyl acetate (20 mL×3). The combined organic layers were washed with brine (30 mL), dried over anhydrous sodium sulfate, and concentrated in vacuo to furnish the crude product. It was recrystallized from methanol to give Compound 302B.

To a solution of Compound 302B (324 mg, 1 mmol) in THF (20 mL) was added n-BuLi (2.5 M, 0.4 mL, 1.06 mmol) under nitrogen at −60° C. It was stirred at −60° C. for 0.5 h. And then a solution of diethyl oxalate (0.4 mL, 3 mmol) in THF (5 mL) was added. The mixture was stirred at −60° C. for 0.5 h, quenched with saturated ammonium chloride solution (200 mL), extracted with ethyl acetate (20 mL×3), washed with brine (20 mL), dried over anhydrous sodium sulfate, and purified with flash column chromatography on silica gel (ethyl acetate in petroleum ether, 5% v/v) to furnish Compound 302C.

To a solution of Compound 302C (39 mg, 0.11 mmol) in THF/water (6 mL, 5:1, v/v) was added LiOH H$_2$O (52 mg, 0.12 mmol). The mixture was stirred at 0° C. for 1 h. After the reaction was completed, water (20 mL) was added. It was extracted with ethyl acetate (20 mL). The water was adjusted to pH 2. It was extracted with ethyl acetate (20 mL×3). The combined organic layers were dried over anhydrous sodium sulfate and concentrated in vacuo to give the crude Compound 302D.

A mixture of Compound 302D (35 mg, 0.11 mmol), Intermediate G (43 mg, 0.14 mmol), and HATU (54 mg, 0.14 mmol) in DMF (4 mL) was stirred at 10° C. for 3 h. And then it was purified with prep-HPLC to give Compound 302. LC-MS (ESI) m/z: 611 [M+H]$^+$; $^1$H-NMR ((CD$_3$)$_2$CO, 400 MHz): δ (ppm) 0.58-0.83 (m, 4H), 2.07-2.16 (m, 2H), 2.24 (s, 2H), 3.45 (s, 2H), 3.80-3.85 (m, 2H), 3.96 (s, 3H), 4.90 (s, 1H), 5.20 (s, 1H), 7.36 (d, J=8.0 Hz, 1H), 7.44 (dd, J=8.4 Hz, J$_2$=1.6 Hz, 1H), 7.53 (d, J=2.0 Hz, 1H), 7.69-7.77 (m, 3H), 8.17 (dd, J=8.4 Hz, J$_2$=1.6 Hz, 1H), 8.23 (d, J=9.6 Hz, 1H), 8.43 (d, J=2 Hz, 1H), 8.84 (d, J=1.2 Hz, 1H), 10.19 (brs, 1H).

Example 303

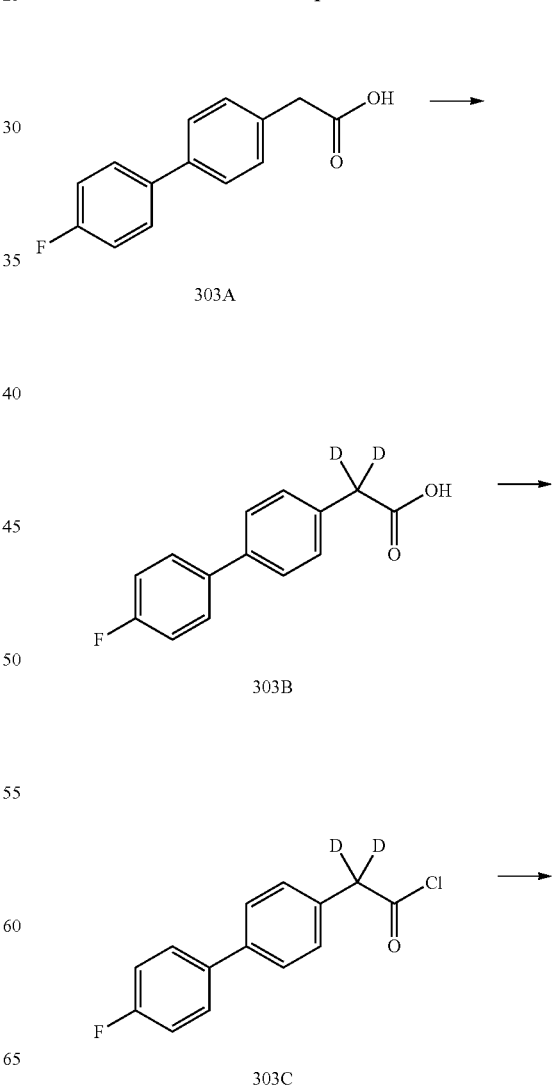

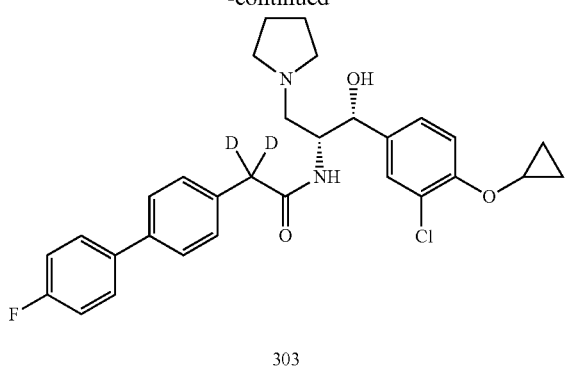

303

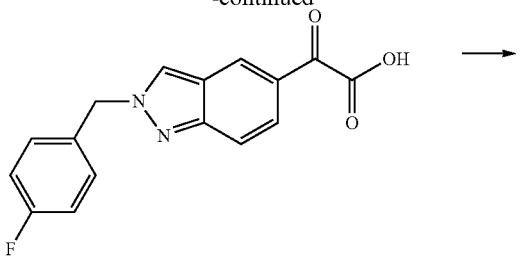

304A

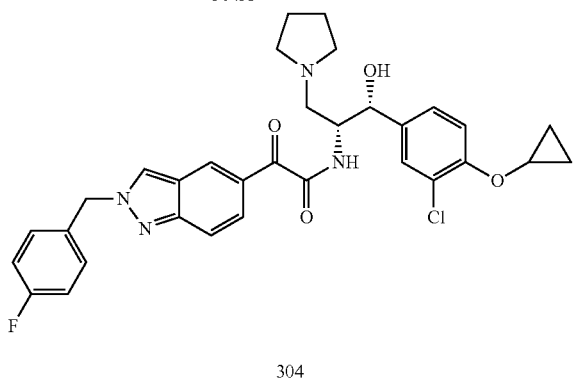

304

A mixture of Compound 303A (191 mg, 0.83 mmol), K₂CO₃ (456 mg, 3.3 mmol), and D₂O (12 mL) was stirred at 110° C. overnight. The mixture was acidified with the addition of 1 M HCl, extracted with DCM (20 mL×2), dried over anhydrous sodium sulfate, and concentrated to furnish Compound 303B.

A mixture of Compound 303B (145 mg, 0.63 mmol) in SOCl₂ (4.5 mL) was stirred at 25° C. for 2 h. The mixture was concentrated to give Compound 303C (160 mg, yield 100%) as a yellow oil, which was directly used for the next step without further purification.

A solution of Intermediate G (200 mg, 0.63 mmol) in CD₃OD was evaporated to dryness and the residue was dissolved CDCl₃ (8 mL). The solution was added to Compound 303C (200 mg, 0.63 mmol). The mixture was stirred at 25° C. for 0.5 h. The reaction mixture was treated with water (20 mL), extracted with DCM (50 mL×2), washed with brine (50 mL), dried over anhydrous sodium sulfate, and concentrated. The crude product was purified with prep-HPLC to give Compound 303. LC-MS (ESI) m/z: 525.2 [M+H]⁺; ¹H-NMR (CD₃OD, 400 MHz): δ (ppm) 0.57-0.66 (m, 4H), 2.02-2.23 (m, 4H), 3.13-3.30 (m, 2H), 3.48-3.68 (m, 4H), 3.80-3.88 (m, 1H), 4.51-4.54 (m, 1H), 4.87 (d, J=2.4 Hz, 1H), 7.06-7.20 (m, 6H), 7.42-7.49 (m, 3H), 7.62-7.66 (m, 2H).

Example 304

To a solution of Compound 288E (150 mg, 0.45 mmol) in THF (1 mL) was added dropwise 1 N lithium hydroxide (1 mL, 1 mmol). The reaction mixture was stirred at room temperature for 2 h. After the reaction mixture was concentrated, 2 N HCl (1 mL) added to adjust pH 7, and extracted with ethyl acetate (50 mL×3). The combined organic phases were washed with water (5 mL) and brine (5 mL), dried over anhydrous sodium sulfate, filtered, and concentrated to furnish Compound 304A.

To a solution of Compound 304A (50 mg, 0.167 mmol) in dichloromethane (3 mL) was added Intermediate G (62 mg, 0.201 mmol) and HATU (95 mg, 0.25 mmol). The mixture was stirred at room temperature for 2 h. It was concentrated and the resulting residue was purified with prep-HPLC to afford Compound 304. LC-MS (ESI) m/z: 591 [M+H]⁺; ¹H-NMR (CDCl₃, 400 MHz): δ (ppm) 0.74-0.76 (m, 4H), 2.13-2.15 (m, 4H), 3.01-3.05 (m, 1H), 3.50-3.58 (m, 1H), 3.59-3.81 (m, 3H), 3.87-4.01 (m, 2H), 4.53-4.57 (m, 1H), 5.11-5.16 (m, 1H), 5.56 (s, 2H), 7.05-7.09 (m, 2H), 7.21-7.23 (m, 1H), 7.27-7.33 (m, 3H), 7.36-7.37 (m, 1H), 7.66-7.68 (s, 1H), 7.79-7.80 (m, 1H), 8.12 (s, 2H), 8.58 (s, 1H).

Example 305

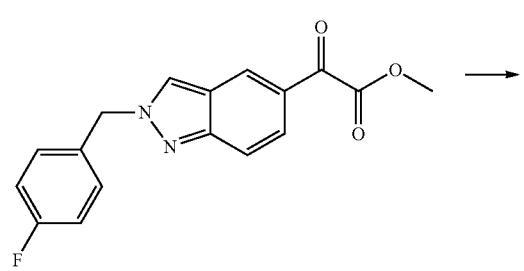

2088E

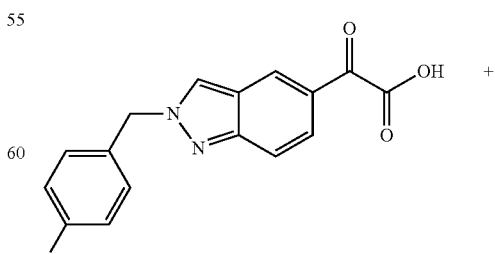

304A

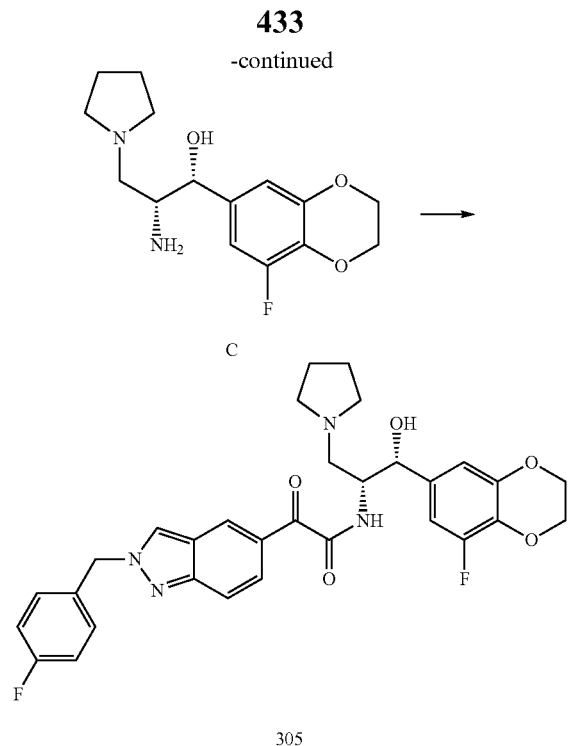

To a solution of Compound 304A (50 mg, 0.167 mmol) in dichloromethane (3 mL) was added Intermediate C (59 mg, 0.201 mmol) and HATU (95 mg, 0.25 mmol). The mixture was stirred at room temperature for 2 h. It was purified with prep-HPLC and prep-TLC to afford Compound 305. LC-MS (ESI) m/z: 577 [M+H]$^+$; $^1$H-NMR (CDCl$_3$, 400 MHz): δ (ppm) 1.82-1.85 (m, 4H), 2.75-2.84 (m, 4H), 3.01-3.04 (m, 2H), 4.16-4.33 (m, 5H), 5.03 (d, J=1.6 Hz, 1H), 5.57 (s, 2H), 6.69-6.74 (m, 2H), 7.04-7.09 (m, 2H), 7.26-7.32 (m, 2H), 7.42-7.45 (m, 1H), 7.69 (d, J=8.8 Hz, 1H), 7.92 (d, J=8.8 Hz, 1H), 8.09 (s, 1H), 8.93 (s, 1H).

Example 306

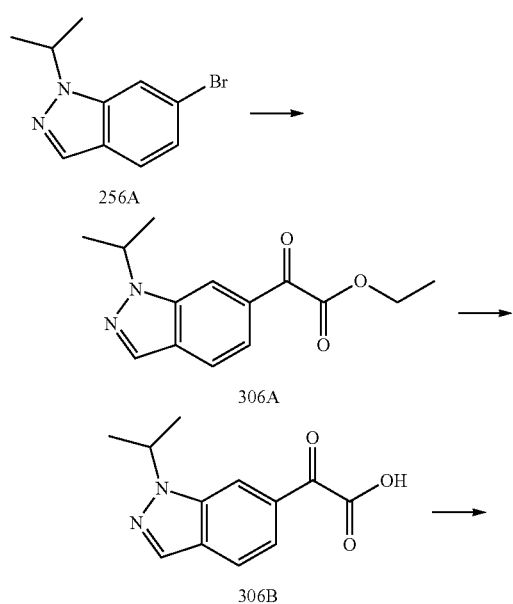

To a solution of Compound 256A (640 mg, 2.69 mmol) in dry THF (10 mL) was added dropwise n-BuLi solution (2.5 M in hexane, 1.1 mL, 2.72 mmol) under nitrogen at −78° C. The mixture was stirred at −78° C. for 30 min and diethyl oxalate (0.91 mL, 6.73 mmol) was added quickly to the above mixture. The mixture was stirred at −78° C. for 30 min, quenched with saturated aqueous ammonium chloride solution (10 mL), and extracted with ethyl acetate (80 mL×2). The combined organic extracts were dried over anhydrous sodium sulfate, filtered, and concentrated in vacuo. The crude product was purified with flash column chromatography on silica gel (ethyl acetate in petroleum ether, from 0% to 5% v/v) to furnish Compound 306A.

To a solution of Compound 306A (490 mg, 2.11 mmol) in methanol (5 mL) was added LiOH H$_2$O (177 mg, 4.22 mmol) in water (5 mL) and the mixture was stirred at room temperature overnight. After completion of the reaction, the mixture was adjusted to pH 6 with aqueous HCl solution (3 N) and concentrated in vacuo. The residue was in lyophilization to afford Compound 306B.

A mixture of Compound 306B (70 mg, 0.30 mmol), HATU (171 mg, 0.45 mmol), and Intermediate G (93 mg, 0.30 mmol) in DMF (5 mL) was stirred at 10° C. for 18 h. The mixture was directly purified with prep-HPLC to yield Compound 306. LC-MS (ESI) m/z: 525 [M+H]$^+$; $^1$H-NMR (DMSO-d$_6$, 400 MHz): δ (ppm) 0.59-0.81 (m, 4H), 1.47 (d, J=6.4 Hz, 3H), 1.52 (d, J=6.8 Hz, 3H), 1.87-2.04 (m, 4H), 3.06-3.22 (m, 2H), 3.47-3.56 (m, 4H), 3.87-3.91 (m, 1H), 4.54-4.56 (m, 1H), 4.86 (d, J=2.8 Hz, 1H), 5.01-5.05 (m, 1H), 6.07 (brs, 1H), 7.33-7.39 (m, 2H), 7.45-7.48 (m, 2H), 7.83 (d, J=8.8 Hz, 1H), 8.23 (s, 1H), 8.35 (s, 1H), 8.81 (d, J=9.6 Hz, 1H), 9.34 (brs, 1H).

Example 307

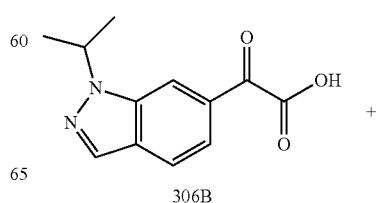

-continued

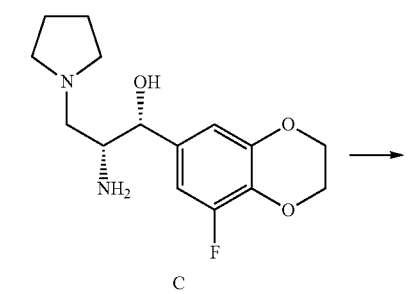

C

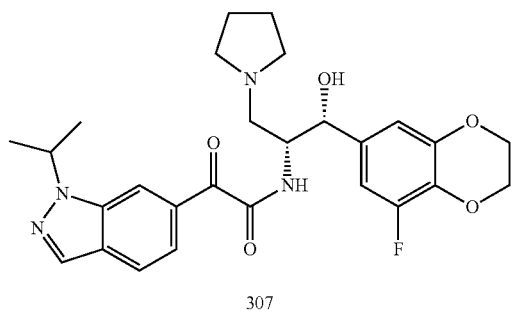

307

A mixture of Compound 306B (70 mg, 0.30 mmol), HATU (171 mg, 0.45 mmol), and Intermediate C (93 mg, 0.30 mmol) in DMF (5 mL) was stirred at 10° C. for 18 h. The mixture was directly purified with prep-HPLC to afford Compound 307. LC-MS (ESI) m/z: 511 [M+H]$^+$; $^1$H-NMR (DMSO-d$_6$, 400 MHz): δ (ppm) 1.49 (d, J=6.8 Hz, 3H), 1.52 (d, J=6.8 Hz, 3H), 1.87-1.89 (m, 2H), 2.02-2.04 (m, 2H), 3.10-3.21 (m, 2H), 3.43-3.55 (m, 4H), 4.21-4.31 (m, 4H), 4.48-4.55 (m, 1H), 4.77 (d, J=3.2 Hz, 1H), 5.02-5.08 (m, 1H), 6.77 (s, 1H), 6.84 (dd, J=11.6, 1.6 Hz, 1H), 7.50 (dd, J=8.4, 1.2 Hz, 1H), 7.86 (d, J=8.8 Hz, 1H), 8.24 (s, 1H), 8.38 (s, 1H), 8.79 (d, J=9.6 Hz, 1H), 9.30 (brs, 1H).

Example 308

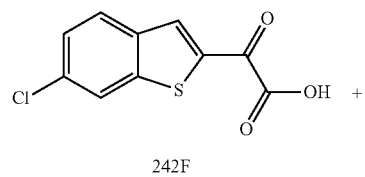

242F

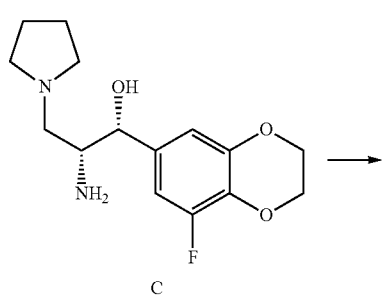

C

-continued

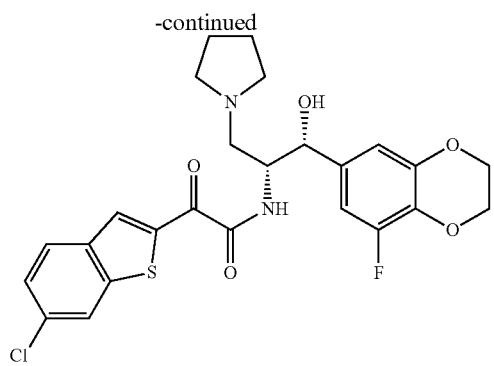

308

To a solution of Intermediate C (118 mg, 0.40 mmol) in DMF (10 mL) was added Compound 242F (80 mg, 0.33 mmol), HATU (190 mg, 0.50 mmol), and N,N-diisopropylethylamine (129 mg, 1.0 mmol). The mixture was stirred under nitrogen at 25° C. overnight. The resulting mixture was quenched with saturated aqueous sodium bicarbonate solution (5 mL) and extracted with ethyl acetate (50 mL×3). The combined organic phases were washed with water (5 mL) and brine (5 mL), dried over anhydrous sodium sulfate, filtered, and concentrated to afford a crude compound. The crude product was purified with prep-HPLC to furnish Compound 308. LC-MS (ESI) m/z: 519 [M+H]$^+$; $^1$H-NMR (CD$_3$OD, 400 MHz): δ (ppm) 2.00-2.04 (m, 2H), 2.15-2.18 (m, 2H), 3.19-3.29 (m, 2H), 3.46-3.50 (m, 1H), 3.67-3.81 (m, 3H), 4.11-4.23 (m, 4H), 4.29-4.35 (m, 2H), 4.54-4.57 (m, 1H), 4.85 (d, J=3.2 Hz, 1H), 6.76-6.81 (m, 2H), 7.46 (dd, J=8.8, 2.0 Hz, 1H), 7.98 (d, J=8.8 Hz, 1H), 8.04 (d, J=1.6 Hz, 1H), 8.48 (s, 1H).

Example 309

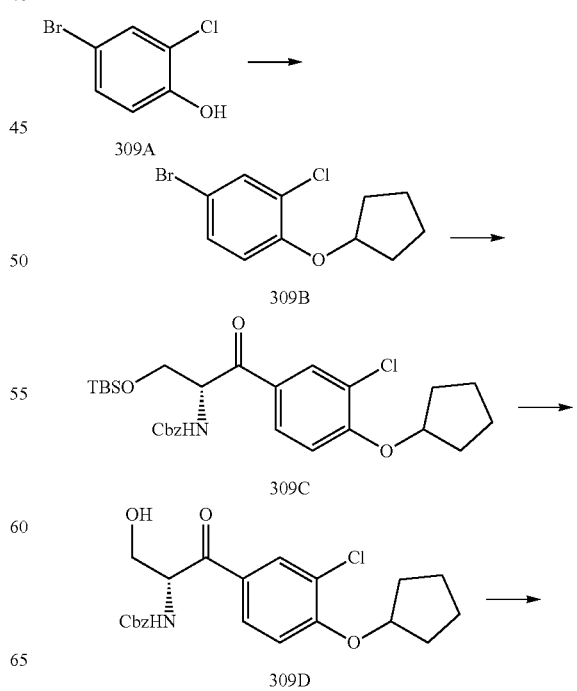

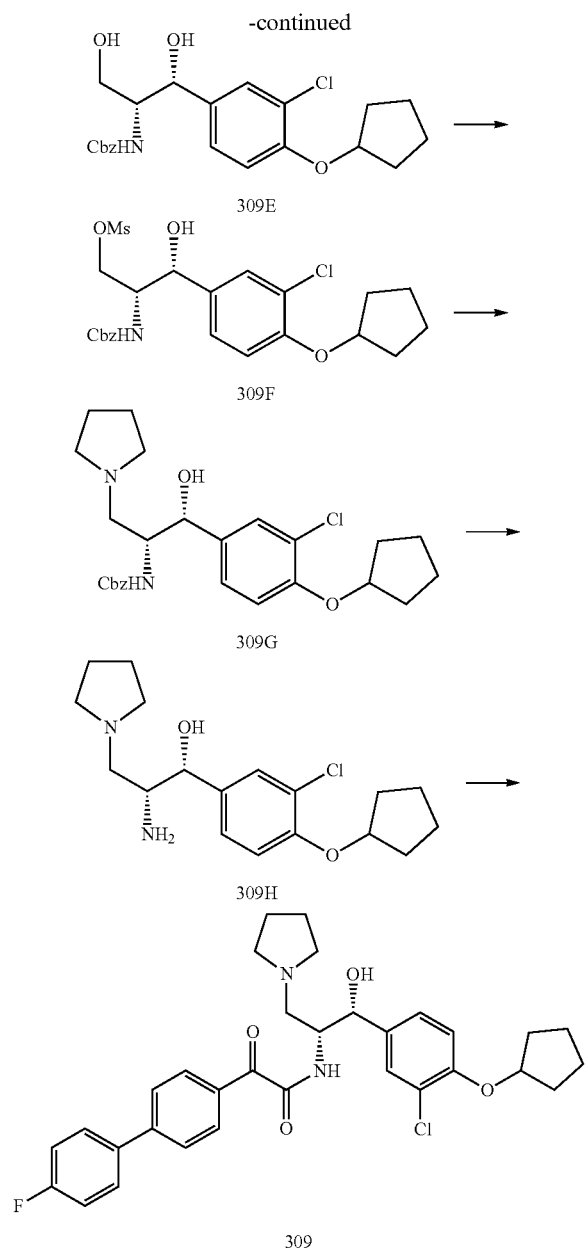

stirred for 40 minutes at −70° C., Compound A4 (18.5 g, 46.7 mmol) dissolved in dry THF (50 mL) was added slowly to the cold solution at a rate that maintained the internal temperature between-70° C. and −50° C. After the addition was complete, the solution was left to stir for 1 h. The reaction was quenched with saturated ammonium chloride solution (400 mL), extracted with ethyl acetate (400 mL×3), washed with water (200 mL) and brine (200 mL), dried over anhydrous sodium sulfate, filtered, and concentrated to furnish the crude Compound (3). The crude product was purified with flash column chromatography on silica gel (ethyl acetate in petroleum ether, from 5% to 20% v/v) to furnish Compound 309C.

A solution of Compound 309C (14.1 g, 26.5 mmol) in a mixture of tetrahydrofuran water and glacial acetic acid (450 mL, 1/1/3, v/v/v) was stirred at 25° C. for 30 h. After that, the reaction mixture was concentrated under reduced pressure to remove excess solvent. The reaction the residue was poured into ice water (20 g) and adjusted pH 7~8 with aqueous sodium hydroxide (1 N) and saturated aqueous sodium bicarbonate solution. The solution was extracted with ethyl acetate (100 mL×3). The combined organic phases were washed with brine (50 mL), dried over anhydrous sodium sulfate, filtered, and concentrated to afford the crude target compound, which was further purified with flash column chromatography on silica gel (ethyl acetate in petroleum ether, from 30% to 50% v/v) to give Compound 309D.

To a solution of Compound 309D (10.0 g, 24.0 mmol) in dry THF (500 mL) maintained at −78° C. was added diisobutylaluminum hydride (1.0 Min toluene, 96 mL) dropwise under nitrogen atmosphere over a period of 15 minutes. After the reaction was stirred at −70° C. for 1 h, a solution of HCl (2 N, 100 mL) was added to the mixture slowly. The reaction mixture was extracted with ethyl acetate (100 mL×3), dried over anhydrous sodium sulfate, filtered, and concentrated to afford the crude target compound, which was further purified with flash column chromatography on silica gel (ethyl acetate in petroleum ether, from 50% to 150% v/v) to furnish Compound 309E.

To a solution of Compound 309E (9.25 g, 24.0 mmol) dissolved in tetrahydrofuran (300 mL) was added triethylamine (7.3 g, 72.0 mmol). The mixture was cooled to −30° C., and then methanesulfonyl chloride (3 g, 26.4 mmol) was added dropwise over a period of 15 minutes. After the addition was complete, the reaction was stirred at −30° C. for 1.5 h, diluted with water (150 mL), and extracted with ethyl acetate (150 mL×2). The combined organic layers were washed with brine (100 mL), dried over anhydrous sodium sulfate, filtered, and concentrated to afford crude Compound 309F, which was directly used for the next step without further purification.

To a solution of Compound 309F 11.2 g, purity 70%) in tetrahydrofuran (50 mL) was added pyrrolidine (13.5 g, 190 mmol). The reaction mixture was allowed to heat to 50° C. for 16 h. The mixture was diluted with water (100 mL), extracted with ethyl acetate (250 mL×2), washed with brine (50 mL), dried over anhydrous sodium sulfate, filtered, and concentrated to furnish a crude compound. The crude product was purified with flash column chromatography on silica gel (methanol in dichloromethane, 5% v/v) to give Compound 309G.

To a solution of Compound 309G (800 mg, 1.69 mmol) in ethanol (12 mL) and water (2 mL) was added LiOH H₂O (284 mg, 6.76 mmol). The mixture was heated to 80° C. and stirred for 16 h. The reaction mixture was diluted with water (15 mL) and extracted with dichloromethane (50 mL×2).

To a solution of Compound 309A (31.7 g, 154 mmol) in 1-methyl-2-pyrrolidinone (300 mL) was added cesium carbonate (100.4 g, 308 mmol) and bromocyclopentane (68.4 g, 462 mmol). The mixture was stirred for 24 h while keeping inner temperature between 145° C. and 155° C. After the reaction was cooled to ambient temperature, the dark solution was diluted with water (400 mL) and extracted with a mixture of ethyl acetate in petroleum ether (15% v/v) (300 mL×3). The combined organic phases were washed with brine (150 mL×4), dried over anhydrous sodium sulfate, filtered, and concentrated to afford the crude product as a brown oil. The crude product was purified with flash column chromatography on silica gel (petroleum ether) to furnish Compound 309B.

To a solution of Compound 309B (32 g, 116.8 mmol) in dry THF (360 mL) maintained at −70° C. was added n-BuLi (2.5 Min hexane, 46.7 mL) dropwise under nitrogen atmosphere over a period of 20 minutes. After the reaction was The combined organic phases were washed with water (50 mL) and brine (50 mL), dried over anhydrous sodium sulfate, filtered, and concentrated to furnish Compound 309H, which was directly used for the next step without further purification.

To a solution of Compound 309H (200 mg, 0.6 mmol), Intermediate C (146 mg, 0.6 mmol), and HATU (456 mg, 1.2 mmol) in N,N-dimethylformamide (3 mL) was stirred at room temperature for 1 h. The reaction solution was purified with prep-HPLC to furnish Compound 309. LC-MS (ESI) m/z: 565 [M+H]$^+$; $^1$H-NMR (DMSO-d$_6$, 400 MHz): δ (ppm) 1.55-1.74 (m, 6H), 1.87-202 (m, 6H), 3.05-3.54 (m, 6H), 4.51-4.91 (m, 3H), 6.01 (d, J=4.4 Hz, 1H), 7.12 (d, J=8.8 Hz, 1H), 7.29 (dd, J=8.8, 2.0 Hz, 1H), 7.33-7.42 (m, 3H), 7.70-7.81 (m, 6H), 8.81 (d, J=10.0 Hz, 1H), 9.34 (s, 1H).

Example 310

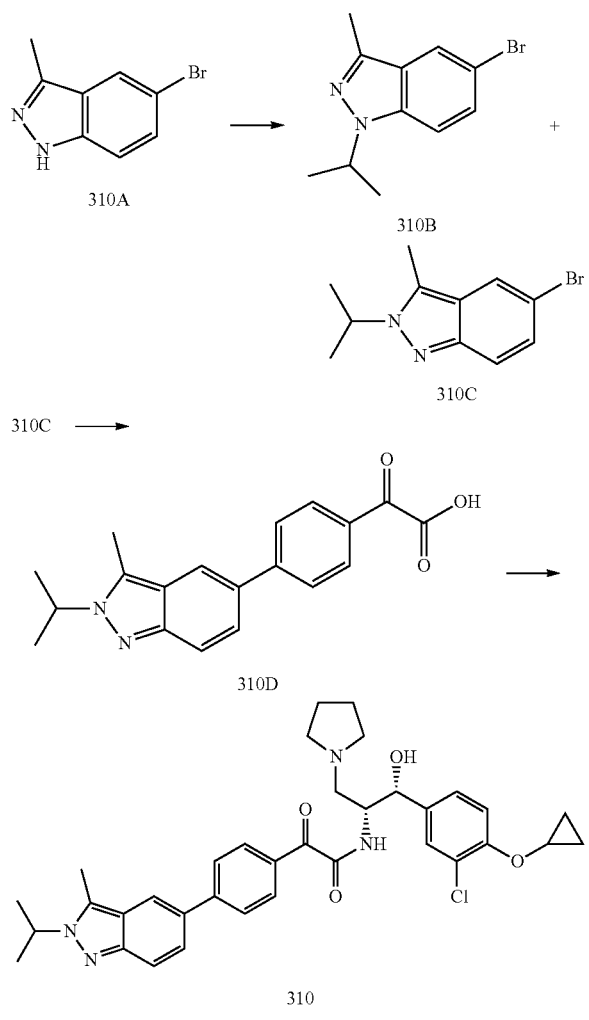

A mixture of Compound 310A (2.11 g, 10 mmol), 2-bromopropane (2.46 g, 20 mmol), and K$_2$CO$_3$ in DMF (40 mL) was stirred at 100° C. overnight. The mixture was diluted with ethyl acetate (200 mL), washed with water (200 mL×4) and brine (100 mL), dried over anhydrous sodium sulfate, concentrated, and purified with flash column chromatography on silica gel (ethyl acetate in petroleum ether, 33% v/v) to afford Compound 310B and Compound 310C.

A mixture of Compound 310C (330 mg, 1.3 mmol), Compound 175B (594 mg, 1.96 mmol), Pd(PPh$_3$)$_2$Cl$_2$ (91 mg, 0.13 mmol), and K$_2$CO$_3$ (333 mg, 2.6 mmol) in dioxane (6 mL) and water (0.6 mL) was stirred at 80° C. for 2 h. The mixture was cooled down and filtered. The precipitate was dissolved in water and washed with ethyl acetate (50 mL). The aqueous layer was adjusted to pH 2 with concentrated HCl and extracted with ethyl acetate (200 mL). The organic layer was dried over anhydrous sodium sulfate and concentrated to yield Compound 310D.

A mixture of Compound 310D (100 mg, 0.31 mmol), Intermediate C (96 mg, 0.31 mmol), and HATU (177 mg, 0.465 mmol) in DCM (2 mL) was stirred at room temperature overnight. The mixture was diluted with DCM (100 mL), washed with water (50 mL×2) and brine (50 mL), dried over anhydrous sodium sulfate, and concentrated. The crude product was purified with prep-HPLC to give Compound 310. LC-MS (ESI) m/z: 615 [M+H]$^+$; $^1$H-NMR (DMSO-d$_6$, 400 MHz): δ (ppm) 0.64-0.70 (m, 2H), 0.79-0.85 (m, 2H), 1.52 (d, J=6.4 Hz, 6H), 1.86-1.92 (m, 2H), 2.01-2.06 (m, 2H), 2.71 (s, 3H), 3.09-3.24 (m, 2H), 3.46-3.59 (m, 4H), 3.93-3.98 (m, 1H), 4.56-4.60 (m, 1H), 4.86-4.91 (m, 2H), 6.04-6.08 (m, 1H), 7.35-7.46 (m, 3H), 7.60-7.62 (m, 1H), 7.67-7.69 (m, 1H), 7.74-7.76 (m, 2H), 7.81-7.84 (m, 2H), 8.13 (s, 1H), 8.81 (d, J=10.0 Hz, 1H), 9.43 (brs, 1H).

Example 311

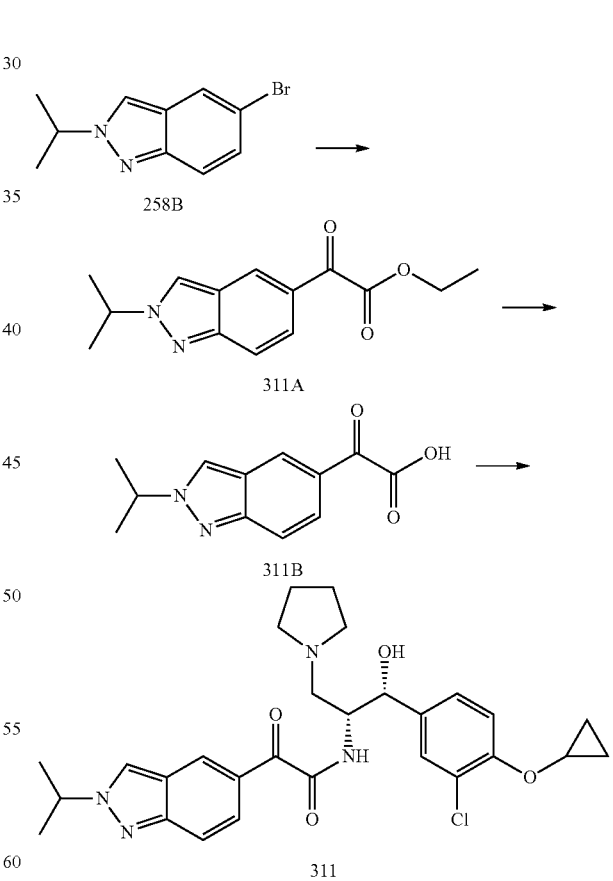

To a solution of Compound 256B (717 mg, 3.0 mmol) in THF (20 mL) was added dropwise n-BuLi (1.2 mL, 2.5 M in hexane, 3.0 mmol) under nitrogen atmosphere at −60° C. The reaction mixture was stirred at the same temperature for 30 minutes. Compound diethyl oxalate (1.31 g, 9.0 mmol)

was added. The resulting mixture was stirred at −60° C. for an additional 30 minutes. The reaction mixture was quenched with saturated ammonium chloride solution (30 mL) and extracted with ethyl acetate (40 mL×2). The combined organic phases were dried over anhydrous sodium sulfate, filtered, evaporated, and purified with flash column chromatography on silica gel (ethyl acetate in petroleum ether, 10% v/v) to give Compound 311A.

To a solution of Compound 311A (20 mg, 0.077 mmol) in MeOH (2 mL) was added LiOH.H$_2$O (4 mg, 0.095 mmol) and water (1.0 mL). The reaction mixture was stirred at 15° C. for 4 h. The reaction mixture was neutralized with HCl (1 N). The resulting mixture was evaporated. The residue was dissolved in water (3 mL). The mixture was extracted with ethyl acetate (5 mL×2), dried over anhydrous sodium sulfate, filtered, and evaporated to give Compound 311B.

To a solution of Compound 311B (17 mg, 0.073 mmol) in DMF (3 mL) was added Intermediate G (22 mg, 0.073 mmol) and HATU (28 mg, 0.073 mmol). The reaction mixture was stirred at 20° C. for 2 h. The mixture was purified with prep-HPLC to yield Compound 311. LC-MS (m/z) 525 [M+H]$^+$; $^1$H-NMR (DMSO-d$_6$, 400 MHz): δ (ppm) 0.62-0.66 (m, 2H), 0.80-0.81 (m, 2H), 1.57 (d, J=10.8 Hz, 6H), 1.87-1.89 (m, 2H), 2.01-2.03 (m, 2H), 3.11-3.22 (m, 2H), 3.47-3.55 (m, 4H), 3.90-3.93 (m, 1H), 4.55-4.60 (m, 2H), 4.85-4.91 (m, 2H), 7.35-7.44 (m, 3H), 7.64-7.67 (m, 2H), 8.27 (s, 1H), 8.64 (s, 1H), 8.71-8.74 (m, 1H), 9.39 (brs, 1H).

Example 312

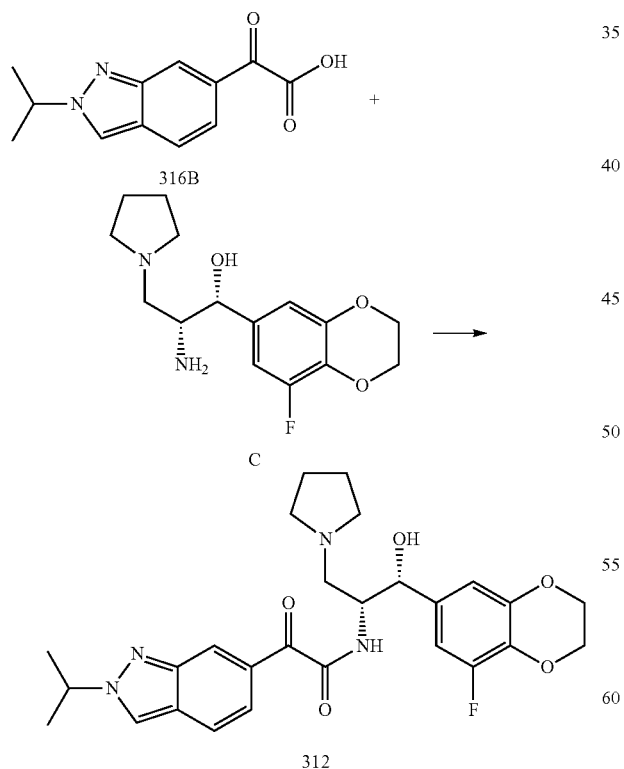

312

A mixture of Compound 316B (70 mg, 0.30 mmol), HATU (171 mg, 0.45 mmol), and Intermediate C (93 mg, 0.30 mmol) in DMF (5 mL) was stirred at 10° C. for 18 h. The mixture was directly purified with prep-HPLC to afford Compound 312. LC-MS (ESI) m/z: 511 [M+H]$^+$; $^1$H-NMR (DMSO-d$_6$, 400 MHz): δ (ppm) 1.57 (d, J=6.8 Hz, 6H), 1.88-2.04 (m, 4H), 3.10-3.20 (m, 2H), 3.43-3.56 (m, 4H), 4.24-4.30 (m, 4H), 4.51-4.55 (m, 1H), 4.77 (d, J=2.4 Hz, 1H), 4.86-4.96 (m, 1H), 6.76 (s, 1H), 6.82 (dd, J=11.6, 2.0 Hz, 1H), 7.45 (dd, J=8.4, 1.2 Hz, 1H), 7.80 (d, J=8.8 Hz, 1H), 8.29 (m, 1H), 8.56 (s, 1H), 8.71 (d, J=9.6 Hz, 1H), 9.29 (brs, 1H).

Example 313

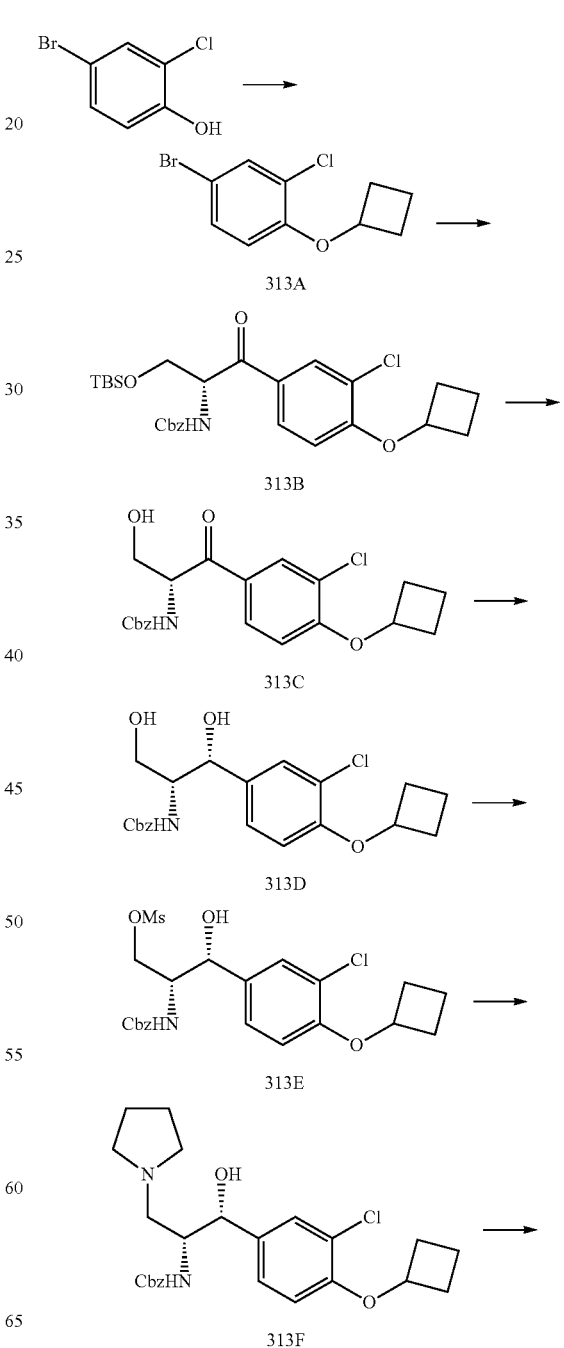

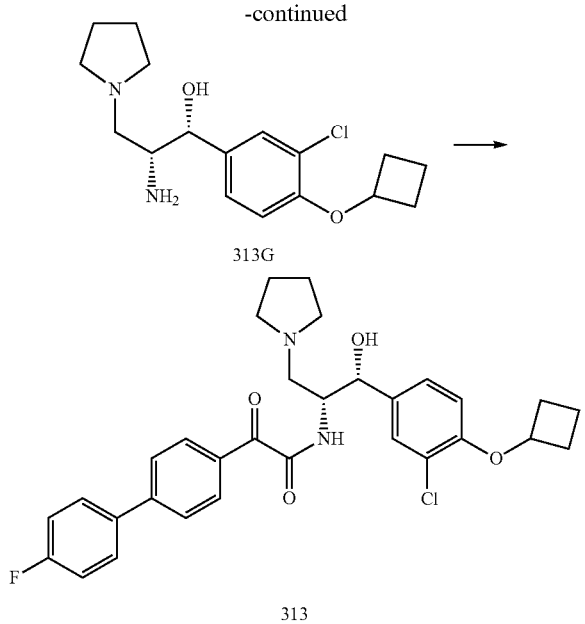

To a solution of 4-bromo-2-chlorophenol (5.0 g, 24 mmol) in 1-methyl-2-pyrrolidinone (70 mL) was added cesium carbonate (15.6 g, 48 mmol) and bromocyclobutane (9.7 g, 72 mmol). The mixture was stirred for 24 h while keeping inner temperature between 145° C. and 155° C. After the reaction mixture was cooled to ambient temperature, the dark solution was diluted with water (100 mL) and extracted with a mixture of ethyl acetate in petroleum ether (15% v/v) (100 mL×3). The combined organic phases were washed with brine (150 mL×4), dried over anhydrous sodium sulfate, filtered, and concentrated to afford the crude product as a brown oil. The crude product was purified with flash column chromatography on silica gel (petroleum ether) to furnish Compound 313A.

To a solution of Compound 313A (15.6 g, 60 mmol) in dry THF (500 mL) maintained at −70° C. was added n-BuLi (60 mmol, 2.4 M in hexane, 25 mL) dropwise under nitrogen atmosphere over a period of 20 minutes. After the reaction mixture was stirred at −70° C. for 40 minutes, Compound A4 (7.9 g, 20 mmol) dissolved in dry THF (50 mL) was added slowly to the cold solution at a rate that maintained the internal temperature between −70° C. and −50° C. After the addition was complete, the solution was left to stir for 1 h. The reaction mixture was quenched with saturated ammonium chloride solution (100 mL) and extracted with ethyl acetate (100 mL×3). The organic phase was washed with water (100 mL) and brine (100 mL), dried over anhydrous sodium sulfate, filtered, and concentrated to furnish the crude Compound 313B. The crude product was purified with flash column chromatography on silica gel (ethyl acetate in petroleum ether, from 5% to 10% v/v) to furnish Compound 313B.

A solution of Compound 313B (8.5 g, 16.4 mmol) in a mixture of tetrahydrofuran, water, and glacial acetic acid (250 mL, 1/1/3, v/v/v) was stirred at 25° C. for 72 h. The reaction mixture was concentrated under reduced pressure to remove excess solvent. The residue was poured into ice water (20 g) and adjusted to pH 7~8 with aqueous sodium hydroxide (1 N) and saturated aqueous sodium bicarbonate solution. The mixture was extracted with ethyl acetate (100 mL×3). The combined organic phases were washed with brine (100 mL), dried over anhydrous sodium sulfate, filtered, and concentrated to afford the crude target compound, which was further purified with flash column chromatography on silica gel (ethyl acetate in petroleum ether, from 30% to 50% v/v) to give Compound 313C.

To a solution of Compound 313C (1.2 g, 2.97 mmol) in dry THF (700 mL) maintained at −78° C. was added diisobutylaluminum hydride (1.0 M in toluene, 11.9 mL) dropwise under nitrogen atmosphere over a period of 15 minutes. After the reaction mixture was stirred at −70° C. for 1 h, a solution of HCl (2 N, 20 mL) was added to the mixture slowly. The reaction mixture was extracted with ethyl acetate (30 mL×3), dried over anhydrous sodium sulfate, filtered, and concentrated to afford the crude target compound, which was further purified with flash column chromatography on silica gel (ethyl acetate in petroleum ether, from 50% to 150% v/v) to furnish Compound 313D.

To a solution of Compound 313D (607 mg, 1.50 mmol) dissolved in THF (15 mL) was added triethylamine (454 mg, 4.50 mmol). The mixture was cooled to −30° C., and then methanesulfonyl chloride (188 mg, 1.65 mmol) was added dropwise over a period of 15 minutes. After the addition was complete, the reaction mixture was stirred at −30° C. for 1.5 h, diluted with water (30 mL), and extracted with ethyl acetate (30 mL×2). The combined organic layers were washed with brine (30 mL), dried over anhydrous sodium sulfate, filtered, and concentrated to afford Compound 313E, which was directly used for the next step without further purification.

To a solution of Compound 313E (690 mg, 1.42 mmol) in THF (30 mL) was added pyrrolidine (1.0 g, 14.2 mmol). The reaction mixture was allowed to heat to 50° C. for 16 h. The mixture was diluted with water (15 mL), extracted with ethyl acetate (75 mL×2), washed with brine (25 mL), dried over anhydrous sodium sulfate, filtered, and concentrated to furnish a crude compound. The crude product was purified with flash column chromatography on silica gel (methanol in dichloromethane, 5% v/v) to give Compound 313F.

To a solution of Compound 313F (330 mg, 0.72 mmol) in ethanol (6 mL) and water (1 mL) was added LiOH.H$_2$O (121 mg, 2.88 mmol). The mixture was heated to 80° C. and stirred for 10 h. The reaction mixture was diluted with water (10 mL) and extracted with dichloromethane (20 mL×2). The combined organic phases were washed with water (20 mL) and brine (20 mL), dried over anhydrous sodium sulfate, filtered, and concentrated to furnish Compound 313G, which was directly used for the next step without further purification.

To a solution of Compound 313G (75 mg, 0.23 mmol) in dichloromethane (5 mL) was added Intermediate C (56 mg, 0.23 mmol) and 1-[bis(dimethylamino)methylene]-1H-1,2,3-triazolo[4,5-b]pyridinium 3-oxid hexafluorophosphate (131 mg, 0.345 mmol). The reaction mixture was stirred at 20° C. for 5 h. The resulting mixture was washed with brine. The organic phase was dried over anhydrous sodium sulfate, filtered, and concentrated. The crude product was purified with prep-HPLC to yield Compound 313. LC-MS (ESI) m/z: 551 [M+H]$^+$; $^1$H-NMR (DMSO-d$_6$, 400 MHz): δ (ppm) 1.60-1.63 (m, 1H), 1.74-1.77 (m, 1H), 1.89-1.91 (m, 2H), 2.00-2.08 (m, 4H), 2.41-2.45 (m, 2H), 3.15-3.22 (m, 2H), 3.45-3.48 (m, 3H), 3.55-3.56 (m, 2H), 4.55-4.56 (m, 1H), 4.71-4.75 (m, 1H), 4.87 (s, 1H), 6.03 (s, 1H), 6.95-6.98 (m, 1H), 7.26-7.29 (m, 1H), 7.36-7.40 (m, 2H), 7.44-7.45 (m, 1H), 7.73-7.76 (m, 3H), 7.80-7.84 (m, 2H), 8.79-8.81 (m, 1H), 9.47 (brs, 1H).

Example 314

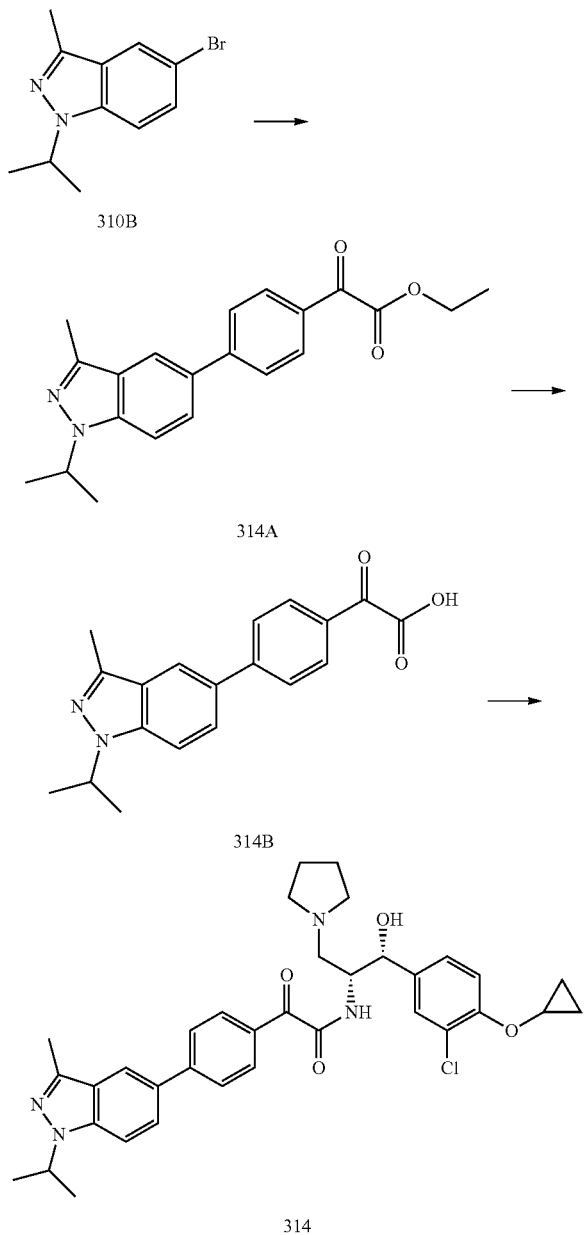

A mixture of Compound 310B (330 mg, 1.3 mmol), Compound 175B (594 mg, 1.96 mmol), Pd(PPh₃)₂Cl₂ (91 mg, 0.13 mmol), and K₂CO₃ (333 mg, 2.6 mmol) in dioxane (6 mL) and water (0.6 mL) was stirred at 80° C. for 2 h. The mixture was cooled down, diluted with ethyl acetate (200 mL), washed with water (200 mL×4) and brine (100 mL), dried over anhydrous sodium sulfate, concentrated, and purified with flash column chromatography on silica gel (ethyl acetate in petroleum ether, 20% v/v) to yield Compound 314A.

A mixture of Compound 314A (240 mg, 0.68 mmol) and LiOH.H₂O (43 mg, 1.03 mmol) in THF (5 mL) and water (0.5 mL) was stirred at room temperature overnight. The mixture was diluted with water (50 mL), adjusted to pH 2 with concentrated HCl, and extracted with ethyl acetate (200 mL). The organic layer was dried over anhydrous sodium sulfate and concentrated to yield Compound 314B.

A mixture of Compound 314B (120 mg, 0.372 mmol), Intermediate G (115 mg, 0.372 mmol), and HATU (211 mg, 0.555 mmol) in dichloromethane (3 mL) was stirred at room temperature overnight. The mixture was diluted with dichloromethane (100 mL), washed with water (50 mL×2) and brine (50 mL), dried over anhydrous sodium sulfate, and concentrated. The crude product was purified with prep-HPLC to give Compound 314. LC-MS (ESI) m/z: 615 [M+H]⁺; ¹H-NMR (DMSO-d₆, 400 MHz): δ (ppm) 0.63-0.70 (m, 2H), 0.79-0.86 (m, 2H), 1.48 (d, J=6.4 Hz, 6H), 1.87-1.93 (m, 2H), 2.02-2.07 (m, 2H), 2.57 (s, 3H), 313-3.24 (m, 2H), 3.49-3.60 (m, 4H), 3.93-3.98 (m, 1H), 4.52-4.61 (m, 1H), 4.89-5.00 (m, 2H), 6.06-6.07 (m, 1H), 7.35-7.46 (m, 3H), 7.73-7.79 (m, 4H), 7.82-7.86 (m, 2H), 8.11 (d, J=7.2 Hz, 1H), 8.81-8.83 (m, 1H), 9.43 (brs, 1H).

Example 315

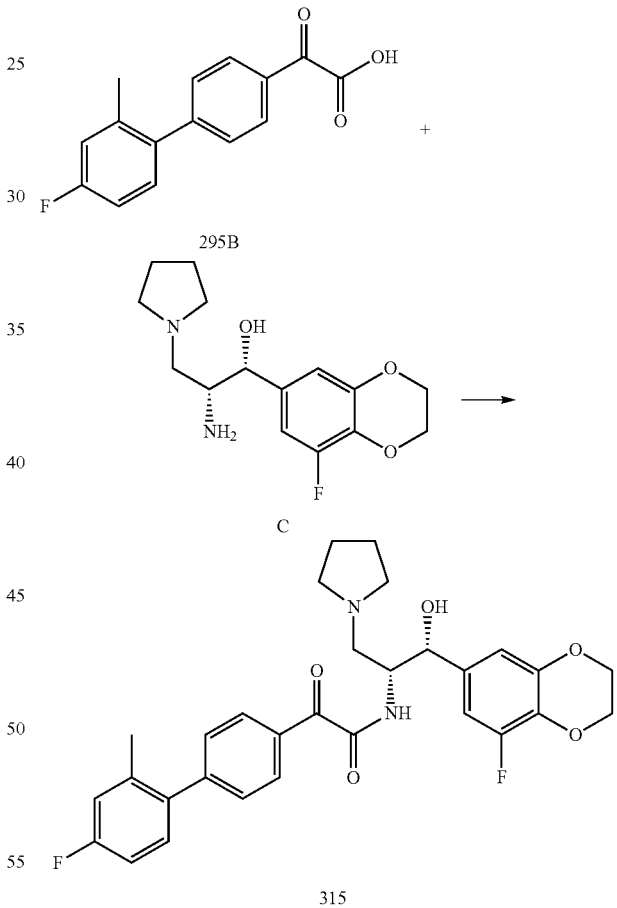

To a solution of Compound 295B (78 mg, 0.3 mmol) in DMF (1.5 mL) and dichloromethane (4 mL) was added Intermediate C (100 mg, 0.33 mmol) and HATU (171 mg, 0.45 mmol). The reaction mixture was stirred at 25° C. for 3 hours. The mixture was purified with prep-HPLC to yield Compound 315. LC-MS (m/z) 537 [M+H]⁺; ¹H-NMR (DMSO-d₆, 400 MHz): δ (ppm) 1.80-1.87 (m, 4H), 2.25 (s, 3H), 3.04-3.15 (m, 2H), 3.44-3.53 (m, 3H), 4.25-4.27 (m, 5H), 4.47-4.52 (m, 1H), 4.76 (s, 1H), 6.05 (s, 1H), 6.76-6.80

(m, 2H), 7.17-7.26 (m, 2H), 7.49 (d, J=8.4 Hz, 2H), 7.88 (d, J=8.4 Hz, 2H), 8.76 (d, J=10 Hz, 1H), 9.30 (brs, 1H).

Example 316

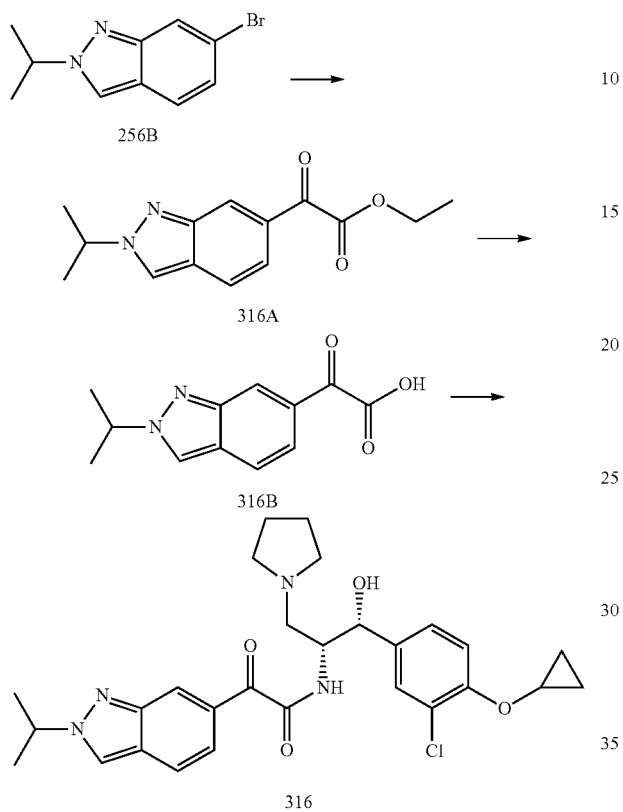

To a solution of Compound 256B (640 mg, 2.69 mmol) in dry THF (10 mL) was added dropwise n-BuLi solution (2.5 Min hexane, 1.1 mL, 2.72 mmol) under nitrogen at −78° C. The mixture was stirred at −78° C. for 30 min and diethyl oxalate (0.91 mL, 6.73 mmol) was added quickly to the above mixture. The mixture was stirred at −78° C. for 30 min, quenched with saturated aqueous ammonium chloride solution (10 mL), and extracted with ethyl acetate (80 mL×2). The combined organic extracts were dried over anhydrous sodium sulfate, filtered, and concentrated in vacuo. The crude product was purified with flash column chromatography on silica gel (ethyl acetate in petroleum ether, from 0% to 20% v/v) to furnish Compound 316A.

To a solution of Compound 316A (180 mg, 0.69 mmol) in methanol (3 mL) was added LiOH H$_2$O (44 mg, 1.04 mmol) in water (3 mL) and the mixture was stirred at room temperature overnight. After completion of the reaction, the mixture was adjusted to pH 3 with aqueous HCl solution (3 N) and concentrated in vacuo. The residue was in lyophilization to afford Compound 316B.

A mixture of Compound 316B (70 mg, 0.30 mmol), HATU (171 mg, 0.45 mmol), and Intermediate G (93 mg, 0.30 mmol) in DMF (5 mL) was stirred at 10° C. for 18 h. The mixture was directly purified with prep-HPLC to yield Compound 316. LC-MS (ESI) m/z: 525 [M+H]$^+$; $^1$H-NMR (CD$_3$OD, 400 MHz): δ (ppm) 0.67-0.81 (m, 4H), 1.67 (d, J=6.8 Hz, 6H), 2.04-2.22 (m, 4H), 3.22-3.28 (m, 2H), 3.55-3.61 (m, 1H), 3.68-3.89 (m, 4H), 4.66-4.69 (m, 1H), 4.87-4.90 (m, 1H), 4.95 (d, J=3.2 Hz, 1H), 7.37 (s, 2H), 7.44-7.47 (m, 2H), 7.75 (d, J=8.8 Hz, 1H), 8.37 (s, 1H), 8.39 (s, 1H).

Example 317

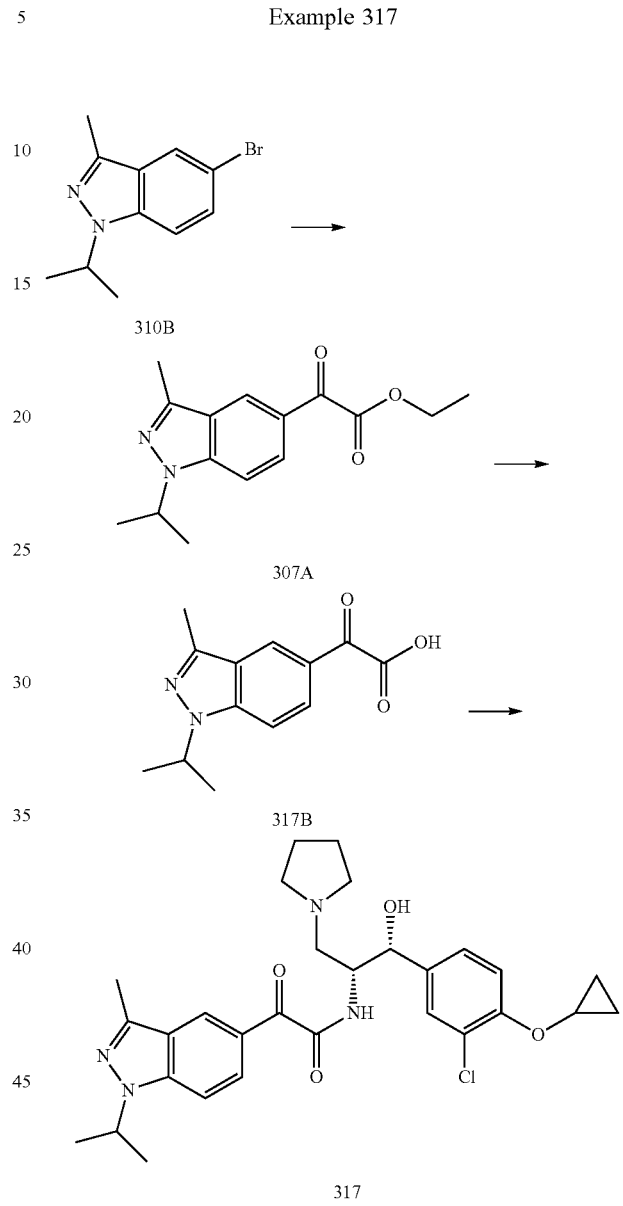

To a solution of Compound 310B (245 mg, 0.97 mmol) in dry THF (12 mL) maintained at −70° C. was added n-BuLi (2.5 Min hexane, 0.4 mL) dropwise under nitrogen atmosphere over a period of 5 minutes. After the reaction mixture was stirred at −70° C. for 40 minutes, diethyl oxalate (355 mg, 2.4 mmol) was added in one portion. The mixture was stirred at 60° C. for 2 hours. The solution was quenched with saturated ammonium chloride solution and extracted with ethyl acetate (50 mL×2). The combined organic phases were washed with water (15 mL) and brine (15 mL), dried over anhydrous sodium sulfate, filtered, and concentrated to give Compound 317A.

To a solution of Compound 317A (260 mg, 0.96 mmol) in THF (9 mL) was added LiOH H$_2$O (70 mg, 1.66 mmol) in water (3 mL) at −5° C., the mixture was stirred at this temperature for 5 hours. The reaction mixture was treated with ice water (20 mL) and extracted with ethyl acetate (50 mL). The water layer was adjusted to pH 2 with diluted HCl and extracted with ethyl acetate (50 mL×2). The combined organic layers were washed with brine (50 mL), dried over anhydrous sodium sulfate, and concentrated. The resulting solid was washed with petroleum ether and filtered to afford the crude Compound 317B.

A mixture of Compound 317B (75 mg, (0.3 mmol), HATU (174 mg, 0.46 mmol), and Intermediate G (113 mg, 0.36 mmol) in dichloromethane (10 mL) was stirred at room temperature overnight. The reaction mixture was treated with water (20 mL), extracted with dichloromethane 50 mL×2), washed with brine (50 mL), dried over anhydrous sodium sulfate, and concentrated. The crude product was purified with prep-HPLC to give Compound 317. LC-MS (ESI) m/z: 539.2 [M+H]$^+$; $^1$H-NMR (CD$_3$OD, 400 MHz): δ (ppm) 0.45-0.75 (m, 4H), 1.53-1.56 (m, 6H), 2.04-2.23 (m, 4H), 2.55 (d, J=4.0 Hz, 3H), 3.21-3.32 (m, 2H), 3.59-3.60 (m, 1H), 3.70-3.77 (m, 4H), 4.67 (d, J=10.8 Hz, 1H), 4.90 (s, 1H), 4.98 (d, J=2.8 Hz, 1H), 7.28 (d, J=8.4 Hz, 1H), 7.37 (dd, J=2.0 Hz, 8.4 Hz, 1H), 7.46 (d, J=2.0 Hz, 1H), 7.52 (d, J=8.8 Hz, 1H), 7.76 (dd, J=1.6 Hz, 9.2 Hz, 1H), 8.36 (d, J=0.8 Hz, 1H).

Example 318

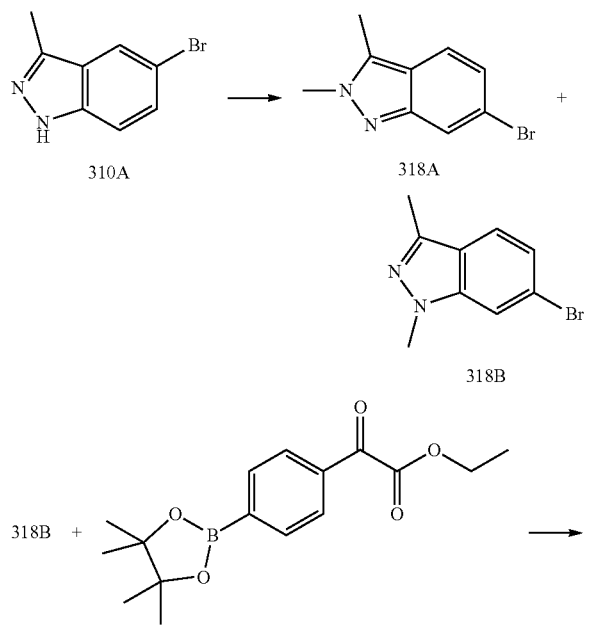

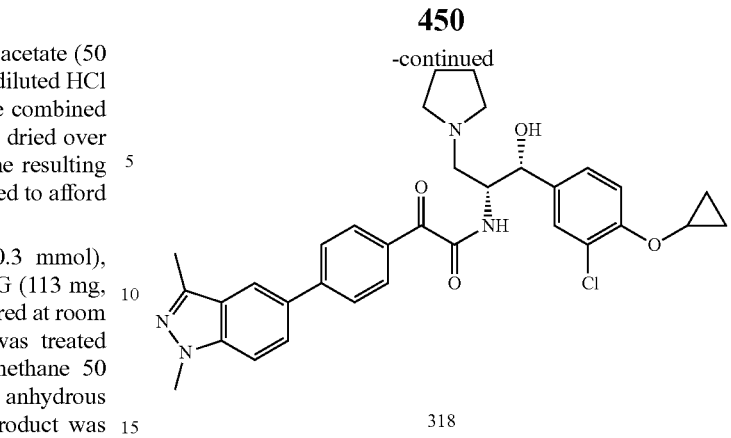

318

To Compound 310A (1.9 g, 9.05 mmol) in DMF (15 mL) was added sodium hydride (60% in mineral, 398 mg, 9.96 mmol) with ice bath cooling. The mixture was stirred for 30 min at room temperature and iodomethane (0.94 mL, 27.15 mmol) was added. The reaction mixture was stirred at room temperature for 3 h, quenched with ammonium chloride solution (30 mL), and extracted with ethyl acetate (100 mL×3). The combined organic layers were washed with brine (200 mL), dried over anhydrous sodium sulfate, concentrated, and purified with flash column chromatography on silica gel (ethyl acetate in petroleum ether, from 0% to 90% v/v) to give Compound 318A and Compound 318B.

A mixture of Compound 318B (225 mg, 1 mmol), Compound 175B (477 mg, 1.57 mmol), Pd(PPh$_3$)$_2$Cl$_2$ (70 mg, 0.1 mmol), and K$_2$CO$_3$ (256 mg, 2 mmol) in dioxane (5 mL) and water (0.5 mL) was stirred at 80° C. for 2 h. The mixture was cooled down and filtered. The precipitate dissolved with water (10 mL) and purified with reverse phase chromatography using eluent (methanol in water, from 0% to 100% v/v) to yield Compound 318C.

A mixture of Compound 318C (70 mg, 0.238 mmol), Intermediate G (74 mg, 0.238 mmol), and HATU (136 mg, 0.357 mmol) in dichloromethane (2 mL) was stirred at room temperature overnight. The mixture was diluted with dichloromethane (100 mL), washed with water (50 mL×2) and brine (50 mL), dried over anhydrous sodium sulfate, and concentrated. The crude product was purified with prep-HPLC to give Compound 318. LC-MS (ESI) m/z: 587 [M+H]$^+$; $^1$H-NMR (DMSO-d$_6$, 400 MHz): δ (ppm) 0.66-0.70 (m, 2H), 0.80-0.85 (m, 2H), 1.87-1.92 (m, 2H), 2.02-2.07 (m, 2H), 2.55 (s, 3H), 3.11-3.24 (m, 2H), 3.49-3.58 (m, 4H), 3.93-3.98 (m, 1H), 4.00 (s, 3H), 4.55-4.62 (m, 1H), 4.89-4.90 (m, 1H), 6.06-6.07 (m, 1H), 7.35-7.46 (m, 3H), 7.70-7.86 (m, 6H), 8.13 (s, 1H), 8.82 (d, J=9.6 Hz, 1H), 9.44 (brs, 1H).

Example 319

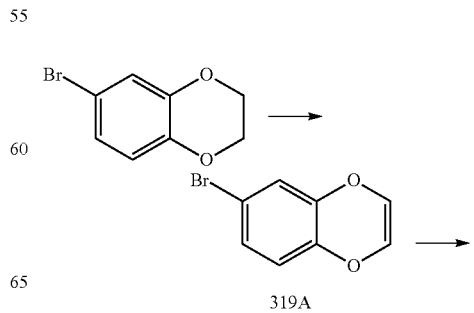

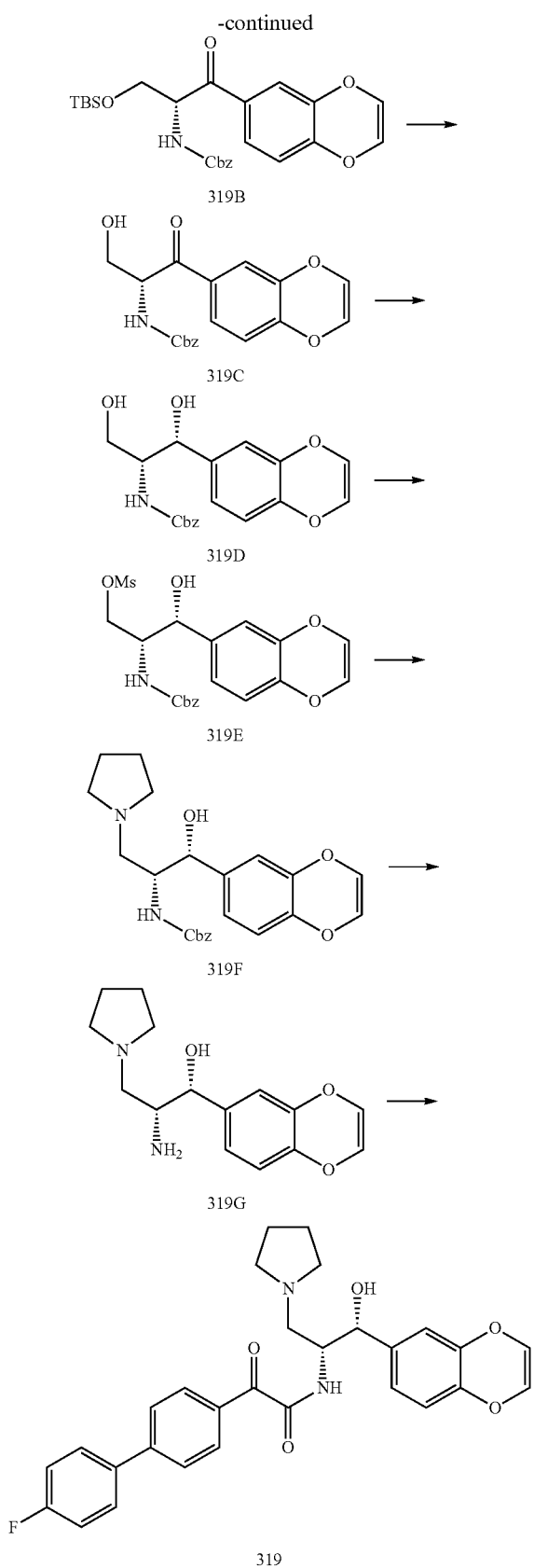

A mixture of 6-bromo-2,3-dihydrobenzo[b][1,4]dioxane (1.07 g, 5 mmol), NBS (2.1 g, 12 mmol), and AIBN (20 mg) in CCl₄ (60 mL) was refluxed under nitrogen for 18 h. The mixture was cooled down to room temperature and filtered. The filtrate was washed with water (50 mL×2) and dried over anhydrous magnesium sulfate. After removal of the solvent, the residue was dissolved in acetone (50 mL) and refluxed under nitrogen for 3 h with NaI (3.75 g, 25 mmol). The mixture was cooled down to room temperature and evaporated. The residue was diluted with water (100 mL) and extracted with dichloromethane (50 mL×3). The organic layer was washed with aqueous $Na_2S_2O_3$ solution (100 mL×2) and brine (100 mL), dried over anhydrous sodium sulfate, concentrated, and purified with flash column chromatography on silica gel (petroleum ether, 100% v/v) to yield Compound 319A.

To a solution of Compound A4 (5.7 g, 26.8 mmol) in THF (120 mL) was added n-BuLi (2.5 Min hexane, 14.4 mL, 36 mmol) under nitrogen at −78° C. The mixture was stirred at −78° C. for 0.5 h and a solution of Compound 319A (3.6 g, 9 mmol) in THF (30 mL) was added. The mixture was stirred at −78° C. for 5 min, quenched with saturated aqueous ammonium chloride solution (100 mL), and extracted with ethyl acetate (200 mL×3). The organic layer was washed with brine (200 mL), dried over anhydrous sodium sulfate, concentrated, and purified with flash column chromatography on silica gel (ethyl acetate in petroleum ether, 9% v/v) to furnish Compound 319B.

A mixture of Compound 319B (100 mg) in AcOH (5 mL), THF (2 mL), and water (2 mL) was stirred at 40° C. overnight. The mixture was cooled down to room temperature, diluted with brine (20 mL), and extracted with ethyl acetate (20 mL×3). The organic layer was adjusted to pH 8 with saturated aqueous sodium bicarbonate solution (30 mL) and separated. The organic layer was dried over anhydrous sodium sulfate, concentrated, and purified with flash column chromatography on silica gel (ethyl acetate in petroleum ether, 50% v/v) to afford Compound 319C.

To a solution of Compound 319C (1.5 g, 4.2 mmol) in THF (30 mL) was added dropwise DIBAL-H (1.5 N in toluene, 12 mL, 17 mmol) under nitrogen at −80° C. The mixture was stirred under nitrogen at −70° C. for 0.5 h, quenched with aqueous hydrogen chloride solution (1 N, 50 mL), and extracted with ethyl acetate (50 mL×3). The organic layer was washed with brine (50 mL), dried over anhydrous sodium sulfate, concentrated, and purified with flash column chromatography on silica gel (ethyl acetate in petroleum ether, 55% v/v) to give Compound 319D.

To a solution of Compound 319D (1.48 g, 4 mmol) and triethylamine (1.2 g, 12 mmol) in THF (30 mL) was added dropwise MsCl (0.52 g, 4.6 mmol) under nitrogen at −20° C. The mixture was stirred under nitrogen at −15° C. for 1 h, quenched with water (100 mL), and extracted with ethyl acetate (50 mL×3). The organic layer was washed with brine (50 mL), dried over anhydrous sodium sulfate, and concentrated to furnish Compound 319E.

To a solution of Compound 319E (1.74 g, 4 mmol) in THF (50 mL) was added pyrrolidine (2.8 g, 40 mmol). The mixture was stirred at 50° C. overnight. The mixture was cooled down to room temperature, diluted with water (100 mL), and extracted with ethyl acetate (50 mL×3). The organic layer was washed with brine (100 mL), dried over anhydrous sodium sulfate, concentrated, and purified with flash column chromatography on silica gel (methanol in dichloromethane, 5% v/v) to afford Compound 319F.

To a solution of Compound 319F (550 mg, 1.34 mmol) in ethanol (20 mL) was added a solution of LiOH H₂O (225 mg, 5.37 mmol) in water (5 mL). The mixture was stirred at 100° C. overnight. After removal of ethanol, the mixture was diluted with water (30 mL) and extracted with ethyl acetate (30 mL×3). The organic layer was washed with brine (100 mL), dried over anhydrous sodium sulfate, and concentrated to furnish Compound 319G.

A mixture of Compound 319G (100 mg, 0.36 mmol), Compound 133D (88 mg, 0.36 mmol), and HATU (275 mg, 0.72 mmol) in DMF (3 mL) was stirred at room temperature overnight. The mixture was directly purified with prep-HPLC to yield Compound 319. LC-MS (ESI) m/z: 503 [M+H]$^+$; $^1$H-NMR (DMSO-d$_6$, 400 MHz): δ (ppm) 1.86-1.93 (m, 2H), 2.02-2.03 (m, 2H), 3.10-3.22 (m, 2H), 3.44-3.47 (m, 2H), 3.53-3.56 (m, 2H), 4.47-4.54 (m, 1H), 4.76 (s, 1H), 5.99 (s, 1H), 6.19 (d, J=4.0 Hz, 1H), 6.22 (d, J=3.6 Hz, 1H), 6.72 (d, J=8.0 Hz, 1H), 6.74 (d, J=2.0 Hz, 1H), 6.89-6.92 (m, 1H), 7.35-7.40 (m, 2H), 7.82-7.90 (m, 6H), 8.79 (d, J=10.0 Hz, 1H), 9.34 (s, 1H).

Example 320

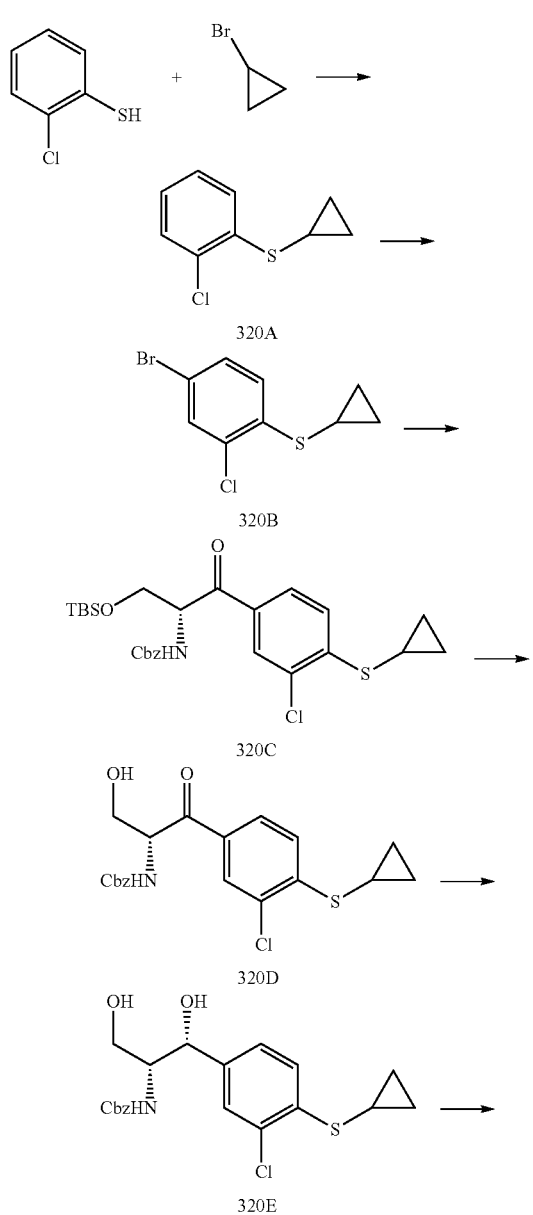

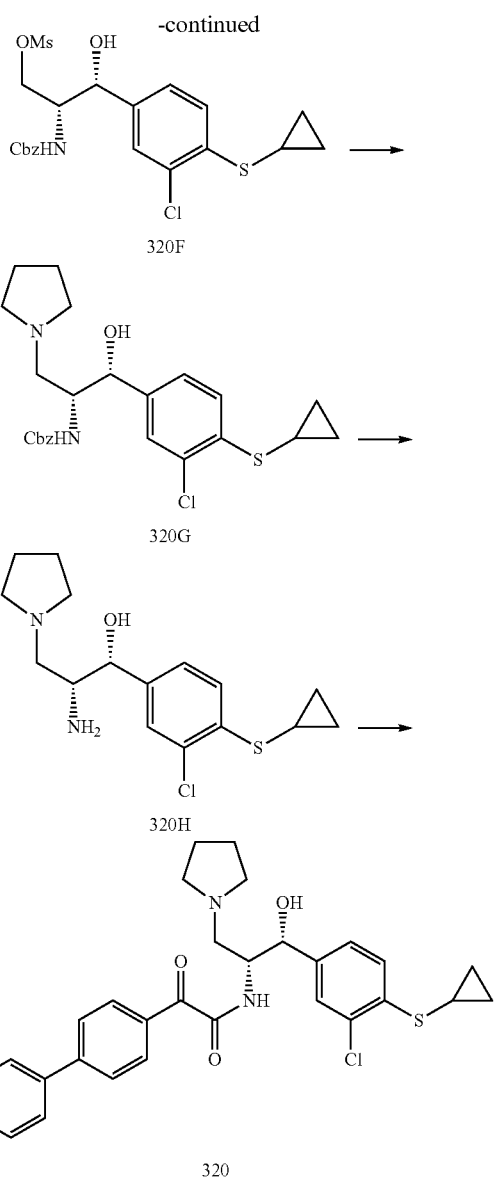

To a solution of 2-chlorobenzenethiol (7.2 g, 50 mmol) in DMSO (20 mL) was added potassium tert-butoxide (6.7 g, 60 mmol) in portions under nitrogen at 5° C. The reaction mixture was stirred at 25° C. for 15 min. To the above solution was added bromocyclopropane (12 g, 100 mmol) in DMSO (10 mL) dropwise. The reaction mixture was stirred under nitrogen at 80° C. After the reaction mixture was cooled to ambient temperature, the dark solution was diluted with water (400 mL) and extracted with a mixture of ethyl acetate (60 mL×3). The combined organic phases were washed with brine (50 mL×2), dried over anhydrous sodium sulfate, filtered, and concentrated to afford the crude product as a brown oil. The crude product was purified with flash column chromatography on silica gel (petroleum ether) to furnish Compound 320A.

To a solution of Compound 320A (36 g, 195.6 mmol) in dry dichloromethane (600 mL) was added Br$_2$ (37.6 g, 235 mmol) at 5° C. dropwise. The reaction mixture was stirred at 25° C. for 22 hours. It was washed with water (200 mL), saturated sodium thiosulfate (200 mL) and brine (200 mL), dried over anhydrous sodium sulfate, filtered, and concentrated to afford the crude product as a brown oil. The crude product was purified with flash column chromatography on silica gel (petroleum ether) to furnish Compound 320B.

To a solution of Compound 320B (23.6 g, 90 mmol) in dry THF (400 mL) maintained at −70° C. was added n-BuLi (2.5 Min hexane, 36.4 mL) dropwise under nitrogen atmosphere over a period of 20 minutes. After the reaction mixture was stirred at −70° C. for 40 minutes, Compound A4 (11.9 g, 30 mmol) dissolved in dry THF (20 mL) was added slowly to the cold solution at a rate that maintained the internal temperature between −70° C. and −50° C. After the addition was complete, the solution was left to stir for 1 h. The reaction mixture was quenched with saturated ammonium chloride solution (200 mL) and extracted with ethyl acetate (200 mL×3). The organic phase was washed with water (100 mL) and brine (100 mL), dried over anhydrous sodium sulfate, filtered, and concentrated to furnish the crude Compound 320C. The crude product was purified with flash column chromatography on silica gel (ethyl acetate in petroleum ether, from 5% to 10% v/v) to furnish the pure Compound 320C.

A solution of Compound 320C (7.0 g, 13.5 mmol) in a mixture of tetrahydrofuran, water, and glacial acetic acid (145 mL, 1/1/3, v/v/v) was stirred at 25° C. for 30 h. The reaction mixture was concentrated under reduced pressure to remove excess solvent. The residue was poured into ice water (20 g) and adjusted to pH 7~8 with aqueous sodium hydroxide (1 N) and saturated aqueous sodium bicarbonate solution. The mixture was extracted with ethyl acetate (60 mL×3). The combined organic phases were washed with brine (50 mL), dried over anhydrous sodium sulfate, filtered, and concentrated to afford the crude target compound, which was further purified with flash column chromatography on silica gel (ethyl acetate in petroleum ether, from 30% to 50% v/v) to give Compound 320D.

To a solution of Compound 320D (2.4 g, 5.9 mmol) in dry THF (50 mL) maintained at −78° C. was added diisobutylaluminum hydride (1.5 Min toluene, 16 mL) dropwise under nitrogen atmosphere over a period of 15 minutes. After the reaction mixture was stirred at −70° C. for 1 h, a solution of HCl (2 N) was added to the mixture slowly. The reaction mixture was extracted with ethyl acetate (20 mL×3), dried over anhydrous sodium sulfate, filtered, and concentrated to afford the crude target compound, which was further purified with flash column chromatography on silica gel (ethyl acetate in petroleum ether, from 50% to 67% v/v) to furnish Compound 320E.

To a solution of Compound 320E (1.69 g, 4.15 mmol) dissolved in THF (30 mL) was added triethylamine (1.26 g, 12.5 mmol). The mixture was cooled to −30° C., and then methanesulfonyl chloride (526 mg, 4.57 mmol) was added dropwise over a period of 15 minutes. After the addition was complete, the reaction mixture was stirred at −30° C. for 1.5 h, diluted with water (50 mL), and extracted with ethyl acetate (50 mL×2). The combined organic layers were washed with brine (50 mL), dried over anhydrous sodium sulfate, filtered, and concentrated to afford Compound 320F, which was directly used for the next step without further purification.

To a solution of Compound 320F (910 mg, 1.88 mmol) in THF (60 mL) was added pyrrolidine (1.33 g, 18.8 mmol). The reaction mixture was allowed to heat to 50° C. for 16 h. The mixture was diluted with water (30 mL), extracted with ethyl acetate (60 mL×2), washed with brine (20 mL), dried over anhydrous sodium sulfate, filtered, and concentrated to furnish a crude compound. The crude product was purified with flash column chromatography on silica gel (methanol in dichloromethane, 7% v/v) to give Compound 320G.

To a solution of Compound 320G (548 mg, 1.19 mmol) in ethanol (14 mL) and water (2 mL) was added LiOH H$_2$O (200 mg, 4.77 mmol). The mixture was heated to 80° C. and stirred for 16 hours. The reaction mixture was diluted with water (10 mL) and extracted with dichloromethane (50 mL×2). The combined organic phases were washed with water (50 mL) and brine (50 mL), dried over anhydrous sodium sulfate, filtered, and concentrated to furnish Compound 320H, which was directly used for the next step without further purification.

To a solution of Compound 320H (100 mg, 0.3 mmol) in dichloromethane (10 mL) was added Compound 133D (56 mg, 0.23 mmol) and HATU (131 mg, 0.35 mmol). The reaction mixture was stirred at 25° C. for 3 hours. The mixture was purified with prep-HPLC to yield Compound 320. LC-MS (m/z) 553 [M+H]$^+$; $^1$H-NMR (DMSO-d$_6$, 400 MHz): δ (ppm) 0.57 (s, 2H), 1.15 (d, J=7.6 Hz, 2H), 1.88-1.90 (m, 2H), 2.04 (s, 2H), 2.24-2.26 (m, 1H), 3.12-3.23 (m, 2H), 3.42-3.56 (m, 4H), 4.59-4.61 (m, 1H), 4.92 (s, 1H), 6.12 (d, J=4.0 Hz, 1H), 7.36-7.46 (m, 4H), 7.61 (d, J=8.4 Hz, 1H), 7.71-7.81 (m, 6H), 8.85 (d, J=10.0 Hz, 1H), 9.36 (s, 1H).

Example 321

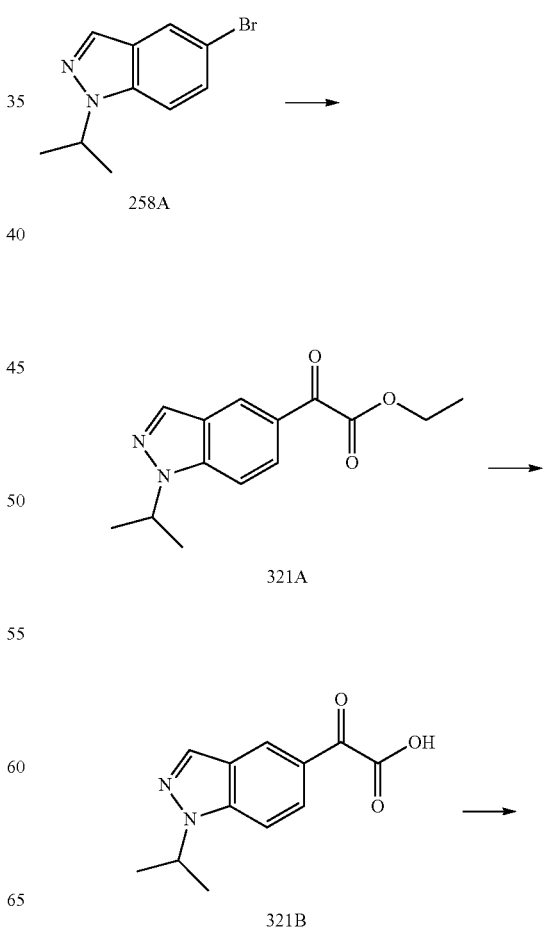

-continued

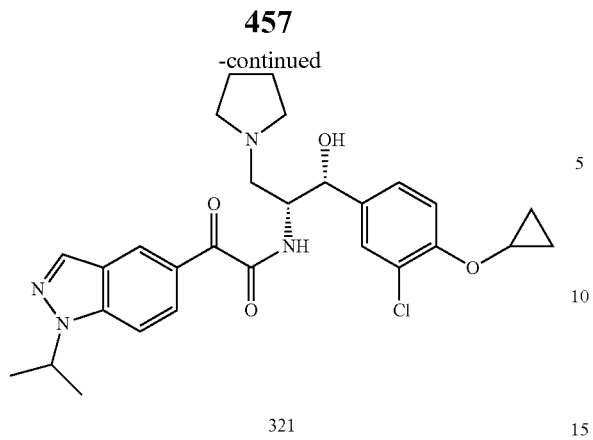

321

To a solution of Compound 258A (960 mg, 4.0 mmol) in THF (30 mL) was added dropwise n-BuLi (1.6 mL, 2.5 Min hexane, 4.0 mmol) under nitrogen atmosphere at −60° C. The reaction mixture was stirred at the same temperature for 30 minutes. Compound diethyl oxalate (1.75 g, 12.0 mmol) was added. The resulting mixture was stirred at −60° C. for an additional 30 minutes. The reaction mixture was quenched with saturated ammonium chloride solution (40 mL) and extracted with ethyl acetate (50 mL×2). The combined organic phases were dried over anhydrous sodium sulfate, filtered, evaporated, and purified with flash column chromatography on silica gel (ethyl acetate in petroleum ether, 10% v/v) to give Compound 321A.

To a solution of Compound 321A (160 mg, 0.61 mmol) in MeOH (5 mL) was added LiOH.H$_2$O (51 mg, 1.22 mmol) and water (1.0 mL). The reaction mixture was stirred at 15° C. for 4 h. The reaction mixture was neutralized with HCl (1 N). The resulting mixture was evaporated. The residue was dissolved in water (5 mL). The mixture was extracted with ethyl acetate (10 mL×2), dried over anhydrous sodium sulfate, filtered, and evaporated to give Compound 321B.

To a solution of Compound 321B (70 mg, 0.30 mmol) in DMF (4 mL) was added Intermediate G (93 mg, 0.30 mmol) and HATU (81 mg, 0.45 mmol). The reaction mixture was stirred at 20° C. for 5 h. The mixture was purified with prep-HPLC to yield Compound 321. LC-MS (m/z) 525 [M+H]$^+$; $^1$H-NMR (acetone-d$_6$, 400 MHz): δ (ppm) 0.57-0.59 (m, 1H), 0.67-0.68 (m, 1H), 0.76-0.81 (m, 2H), 1.57 (d, J=6.8 Hz, 6H), 2.09-2.11 (m, 2H), 2.27 (s, 2H), 3.47-3.51 (m, 2H), 3.82-3.86 (m, 2H), 3.99-4.02 (m, 3H), 4.91-4.92 (m, 1H), 5.04-5.07 (m, 1H), 5.19 (s, 1H), 1.27 (m, 1H), 7.41-7.43 (m, 1H), 7.50 (s, 1H), 7.69-7.71 (m, 1H), 7.93-7.96 (m, 1H), 8.12-8.14 (m, 1H), 8.21 (s, 1H), 8.55 (s, 1H), 9.01 (brs, 1H).

Example 322

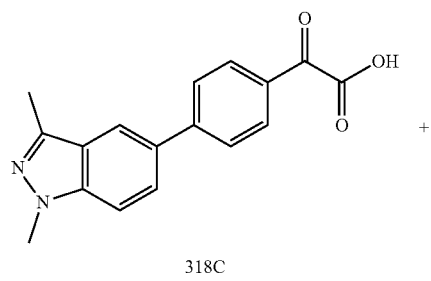

318C

-continued

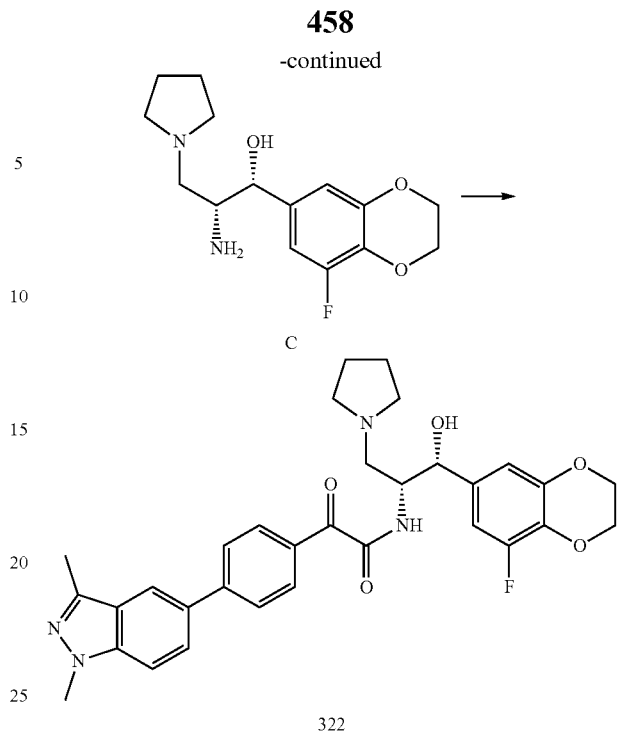

A mixture of Compound 318C (80 mg, 0.272 mmol), Intermediate C (81 mg, 0.272 mmol), and HATU (155 mg, 0.408 mmol) in dichloromethane (2 mL) was stirred at room temperature overnight. The mixture was diluted with dichloromethane (100 mL), washed with water (50 mL×2) and brine (50 mL), dried over anhydrous sodium sulfate, and concentrated. The crude product was purified with prep-HPLC to give Compound 322. LC-MS (ESI) m/z: 573 [M+H]$^+$; $^1$H-NMR (DMSO-d$_6$, 400 MHz): δ (ppm) 1.84-1.93 (m, 2H), 1.99-2.08 (m, 2H), 2.55 (s, 3H), 3.11-3.21 (m, 2H), 3.43-3.56 (m, 4H), 4.00 (s, 3H), 4.25-4.29 (m, 4H), 4.49-4.56 (m, 1H), 4.78-4.80 (m, 1H), 6.05-6.06 (m, 1H), 6.77 (s, 1H), 6.83 (d, J=11.2 Hz, 1H), 7.69-7.72 (m, 1H), 7.79-7.82 (m, 1H), 8.02-8.04 (m, 4H), 8.17 (s, 1H), 8.74 (d, J=10.0 Hz, 1H), 9.40 (brs, 1H).

Example 323

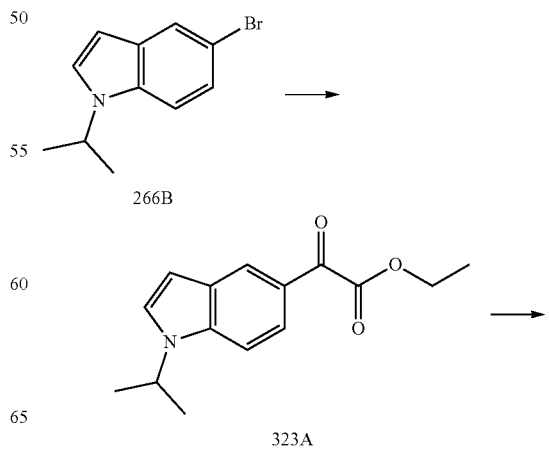

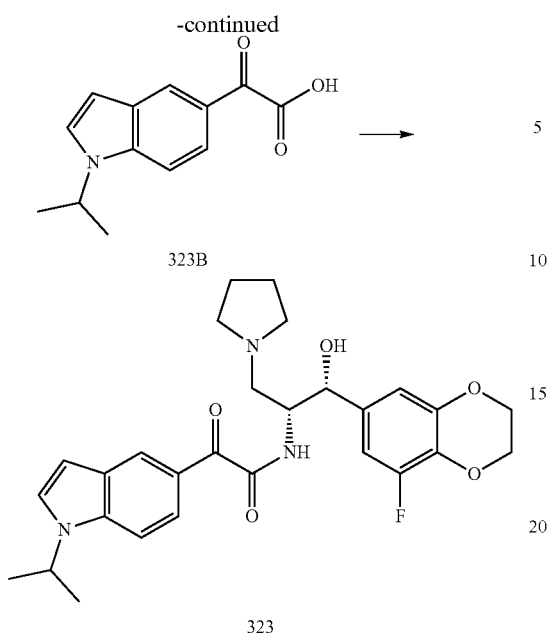

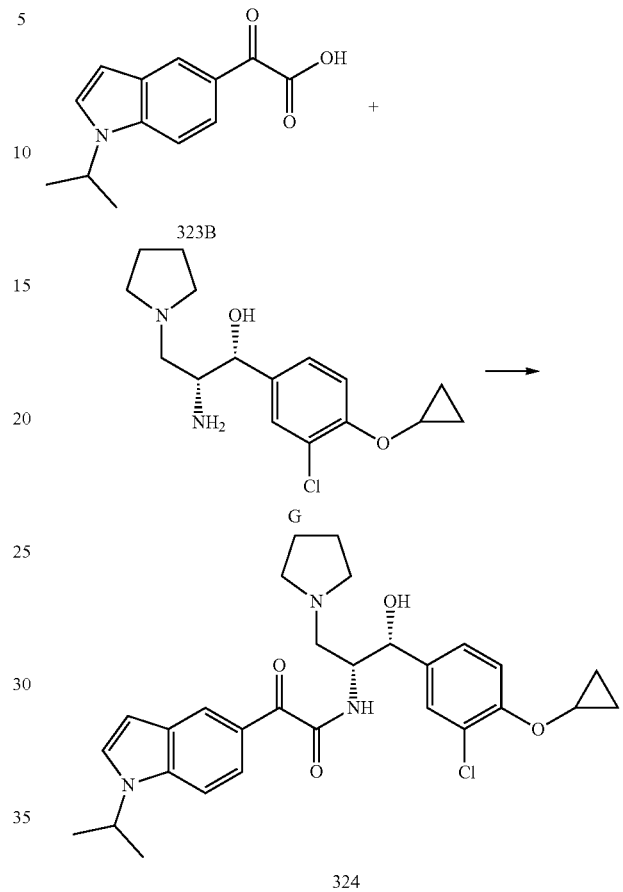

Example 324

To a solution of Compound 266B (1.6 g, 6.7 mmol) in THF (70 mL) was added n-BuLi (2.5 Min hexane, 3.2 mL, 8 mmol) under nitrogen at −78° C. The mixture was stirred at −78° C. for 0.5 h and diethyl oxalate (1.96 g, 13.4 mmol) was added at this temperature. The mixture was stirred at −78° C. for 0.5 h, quenched with saturated aqueous ammonium chloride solution (100 mL), and extracted with ethyl acetate (50 mL×3). The organic layer was washed with brine (100 mL), dried over anhydrous sodium sulfate, concentrated, and purified with flash column chromatography on silica gel (ethyl acetate in petroleum ether, 10% v/v) to yield Compound 323A.

To a solution of Compound 323A (259 mg, 1 mmol) in THF (10 mL) was added a solution of LiOH H$_2$O (84 mg, 2 mmol) in water (3 mL). The mixture was stirred at room temperature overnight. After removal of THF, the mixture was acidified to pH 1 with aqueous HCl solution (1 N) and extracted with dichloromethane (20 mL). The organic layer was dried over anhydrous sodium sulfate and used directly for the next step as a dichloromethane solution.

A mixture of Compound 323B in dichloromethane solution (115 mg, 0.5 mmol), Intermediate C (150 mg, 0.5 mmol), and HATU (380 mg, 1 mmol) in dichloromethane (10 mL) and DMF (3 mL) was stirred at room temperature overnight. The mixture was concentrated and the resulting residue was purified with prep-HPLC to yield Compound 323. LC-MS (ESI) m/z: 510 [M+H]$^+$; $^1$H-NMR (DMSO-d$_6$, 400 MHz): δ (ppm) 1.47 (d, J=6.8 Hz, 6H), 1.87-1.90 (m, 2H), 2.01-2.03 (m, 2H), 3.09-3.21 (m, 2H), 3.37-3.43 (m, 2H), 3.53-3.59 (m, 2H), 4.22-4.32 (m, 4H), 4.52-4.56 (m, 1H), 4.78-4.79 (m, 1H), 4.82-4.87 (m, 1H), 6.00 (s, 1H), 6.65 (d, J=2.8 Hz, 1H), 6.77 (s, 1H), 6.82 (d, J=13.2 Hz, 1H), 7.60-7.69 (m, 3H), 8.10 (s, 1H), 8.67 (d, J=9.6 Hz, 1H), 9.34 (s, 1H).

A mixture of Compound 323B in dichloromethane solution (115 mg, 0.5 mmol), Intermediate G (155 mg, 0.5 mmol), and HATU (380 mg, 1 mmol) in dichloromethane (10 mL) and DMF (3 mL) was stirred at room temperature overnight. The mixture was concentrated and the resulting residue was purified with prep-HPLC to yield Compound 324. LC-MS (ESI) m/z: 524 [M+H]$^+$; $^1$H-NMR (DMSO-d$_6$, 400 MHz): δ (ppm) 0.59-0.69 (m, 2H), 0.80-0.81 (m, 2H), 1.46 (d, J=6.8 Hz, 6H), 1.87-1.89 (m, 2H), 2.03 (s, 2H), 3.12-3.20 (m, 2H), 3.43-3.57 (m, 4H), 3.89-3.90 (m, 1H), 4.57-4.62 (m, 1H), 4.80-4.83 (m, 1H), 4.88 (s, 1H), 6.01 (d, J=4.0 Hz, 1H), 6.62 (d, J=3.2 Hz, 1H), 7.34-7.40 (m, 2H), 7.45 (s, 1H), 7.58 (s, 2H), 7.68 (d, J=3.6 Hz, 1H), 8.04 (s, 1H), 8.68 (d, J=9.2 Hz, 1H), 9.38 (s, 1H).

Example 325

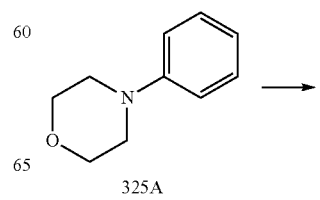

Example 326

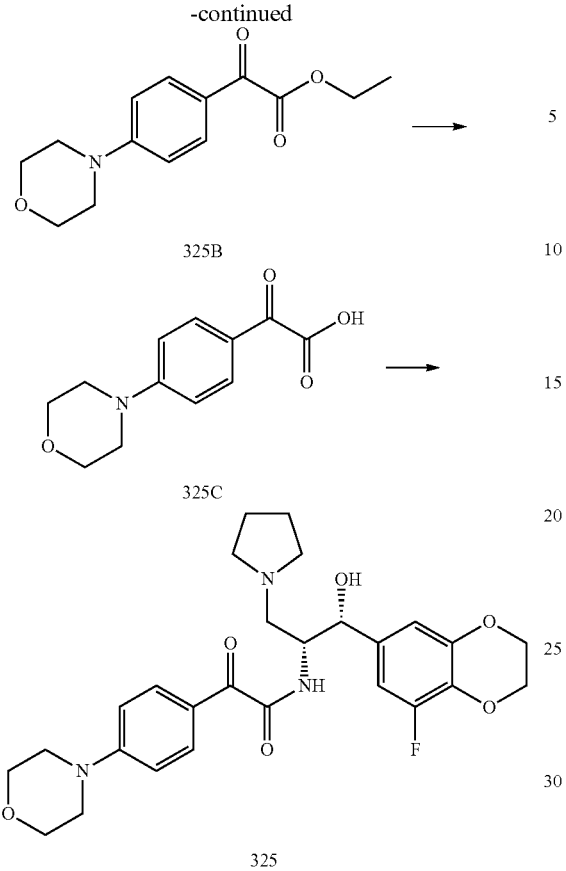

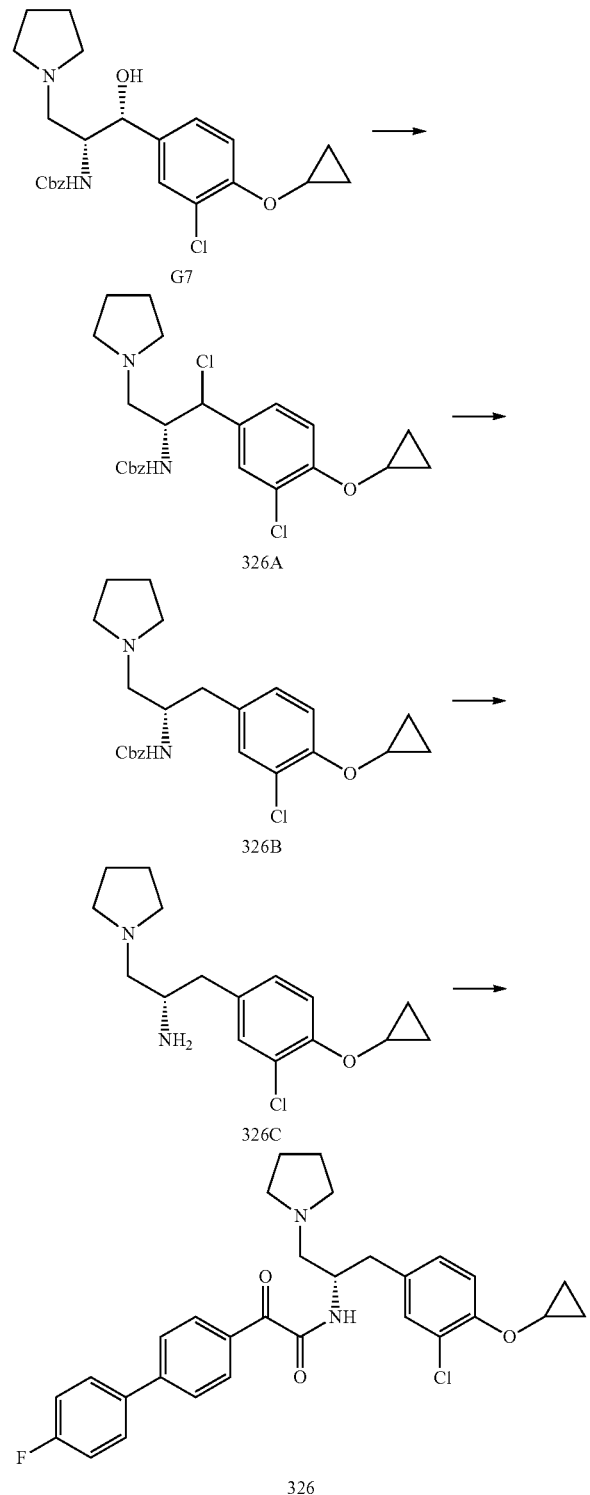

To a solution of Compound 325A (1.63 g, 10.0 mmol) and ethyl 2-chloro-2-oxoacetate (1.49 g, 11.0 mmol) in dichloromethane (50 mL) was added dropwise titanium chloride solution (1 Min dichloromethane, 20 mL, 20.0 mmol) at −10° C. The mixture was stirred for 4 hours while keeping the temperature at −10° C. The mixture was poured into ice water, and then extracted with diethyl ether (50 mL×3). The resulting product was concentrated under reduced pressure and purified with silica gel column chromatography (ethyl acetate in petroleum ether, 30% v/v) to give Compound 325B.

To a solution of Compound 325B (263 mg, 1.00 mmol) in MeOH (5 mL) was added LiOH.H$_2$O (63 mg, 1.50 mmol) and water (1.0 mL). The reaction mixture was stirred at 15° C. for 4 h. The reaction mixture was neutralized with HCl (1 N). The resulting mixture was evaporated. The residue was dissolved in water (5 mL). The mixture was extracted with ethyl acetate (10 mL×2), dried over anhydrous sodium sulfate, filtered, and evaporated to give Compound 325C.

To a solution of Compound 325C (71 mg, 0.31 mmol) in DMF (4 mL) was added Intermediate C (92 mg, 0.31 mmol) and HATU (81 mg, 0.45 mmol). The reaction mixture was stirred at 20° C. for 5 h. The mixture was purified with prep-HPLC to yield Compound 325. LC-MS (m/z) 514 [M+H]$^+$; $^1$H-NMR (acetone-d$_6$, 400 MHz): δ (ppm) 2.06-2.12 (m, 2H), 2.26-2.28 (m, 2H), 3.55-3.64 (m, 5H), 3.82-3.85 (m, 1H), 3.93-4.10 (m, 7H), 4.23-4.31 (m, 5H), 4.80-4.87 (m, 1H), 5.05-5.06 (m, 1H), 6.78-6.84 (m, 2H), 7.33-7.34 (m, 2H), 8.04-8.06 (m, 1H), 8.11-8.14 (m, 2H), 8.56 (brs, 1H).

To a solution of Compound G7 (3.8 g, 8.6 mmol) in dichloromethane (20 mL) was added dropwise SOCl$_2$ (3.05 g, 25.7 mmol) under nitrogen at 0° C. The resulting mixture was stirred at room temperature for 2 h. The mixture was adjusted to pH 8 with sat. sodium bicarbonate solution, extracted with dichloromethane (50 mL×2), washed with brine (50 mL), dried over anhydrous sodium sulfate, concentrated, and purified with flash column chromatography on silica gel (ethyl acetate in petroleum ether, 50% v/v) to furnish Compound 326A.

To a solution of Compound 326A (600 mg, 1.30 mmol) in methanol (20 mL) was added $K_2CO_3$ (89 mg, 0.65 mmol) and Pt/C (60 mg). The resulting mixture was stirred under $H_2$ at 25° C. for 12 h. The mixture was filtered. The filtrate was concentrated and the resulting residue was purified with flash column chromatography on silica gel (ethyl acetate in petroleum ether, 50% v/v) to furnish Compound 326B.

To a solution of Compound 326B (288 mg, 0.67 mmol) in dichloromethane (15 mL) was added $PdCl_2$ (30 mg). The resulting mixture was stirred under $H_2$ at room temperature for 12 h. The mixture was filtered. The filtrate was treated with water (20 mL) and $NH_3.H_2O$ (20 mL). The mixture was stirred at room temperature for 10 min, extracted with dichloromethane (50 mL×2), washed with brine (50 mL), dried over anhydrous sodium sulfate, and concentrated to afford Compound 326C.

A mixture of Compound 326C (90 mg, 0.3 mmol), Intermediate C (75 mg, 0.3 mmol), and HATU (170 mg, 0.47 mmol) in dichloromethane (20 mL) was stirred at room temperature for 4 h. The mixture was treated with water (50 mL), extracted with dichloromethane (20 mL×2), washed with water (20 mL×3) and brine (50 mL), dried over anhydrous sodium sulfate, concentrated, and purified with prep-HPLC to furnish Compound 326. LC-MS (ESI) m/z: 521 [M+H]$^+$; $^1$H-NMR (CDCl$_3$, 400 MHz): δ (ppm) 0.73-0.75 (m, 4H), 2.07 (s, 4H), 2.85-3.05 (m, 4H), 3.19-3.24 (m, 1H), 3.66-3.77 (m, 3H), 3.91 (s, 1H), 4.67 (s, 1H), 7.09-7.11 (m, 3H), 7.14-7.16 (m, 1H), 7.18-7.24 (m, 1H), 7.50-7.54 (m, 4H), 7.85 (d, J=9.2 Hz, 1H), 7.95 (d, J=8.4 Hz, 2H), 8.94 (s, 1H).

Example 327

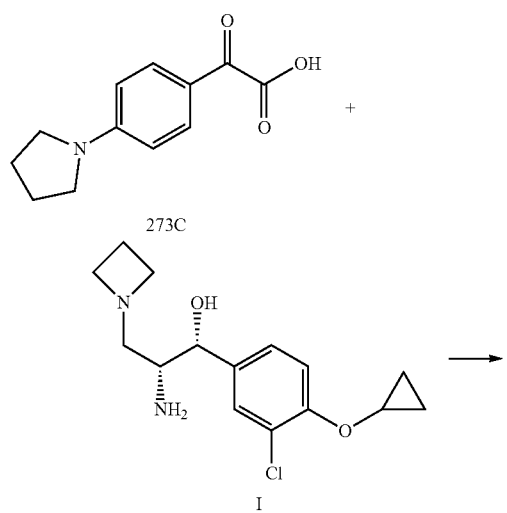

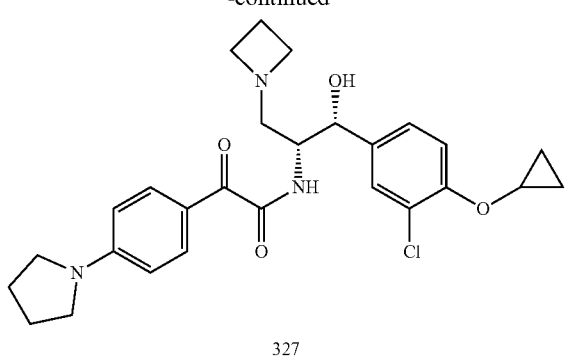

A mixture of Compound 273C (90 mg, 0.41 mmol), HATU (234 mg, 0.62 mmol), and Intermediate I (121 mg, 0.41 mmol) in DMF (3 mL) was stirred at 25° C. for 16 h. The mixture was diluted with ethyl acetate (30 mL), washed with water (10 mL×2) and brine (10 mL), dried over anhydrous sodium sulfate, concentrated, and purified with prep-HPLC to furnish Compound 327. LC-MS (ESI) m/z: 498 [M+H]$^+$; $^1$H-NMR (DMSO-d$_6$, 400 MHz): δ (ppm) 0.67-0.68 (m, 2H), 0.82-0.84 (m, 2H), 1.97-2.00 (m, 4H), 2.25-2.30 (m, 1H), 2.38-2.46 (m, 1H), 3.47-4.19 (m, 11H), 4.35-4.40 (m, 1H), 4.79 (s, 1H), 5.96 (s, 1H), 6.49 (d, J=8.8 Hz, 2H), 7.28-7.31 (m, 1H), 7.38-7.40 (m, 2H), 7.56 (d, J=8.8 Hz, 2H), 8.47 (d, J=9.6 Hz, 1H), 9.62 (s, 1H).

Example 328

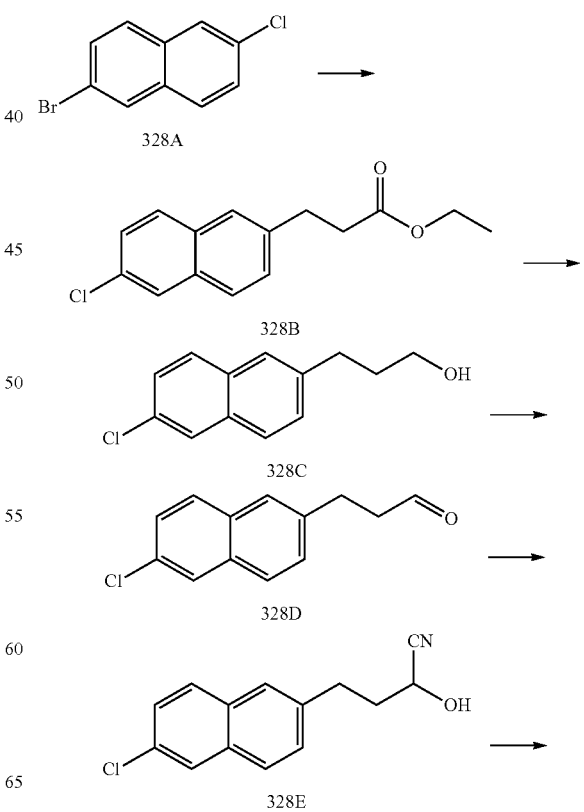

-continued

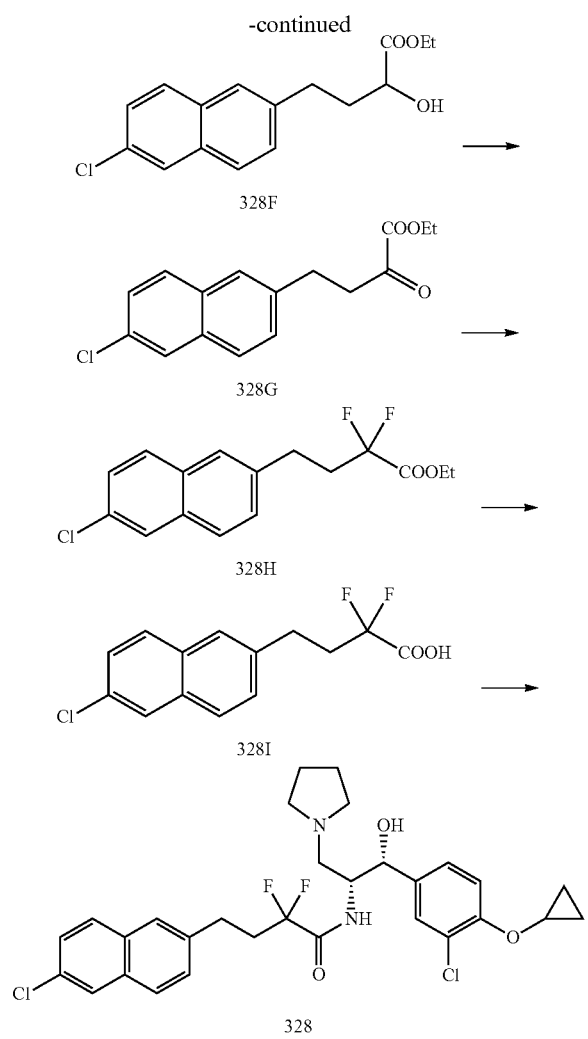

To a mixture of Compound 328A (2.4 g, 10 mmol), 3,3-diethoxyprop-1-ene (4 g, 30 mmol), and TBAC (2.7 g, 10 mmol) in DMF (80 mL) was added Pd(OAc)$_2$ (224 mg, 1 mmol). The reaction mixture was stirred under nitrogen at 90° C. overnight. After the completion of reaction, the resulting mixture was cooled down to room temperature, washed with brine (100 mL), dried over anhydrous sodium sulfate, and concentrated to give a residue. The crude product was purified with flash column chromatography on silica gel (ethyl acetate in petroleum ether, from 10% to 50% v/v) to furnish Compound 328B.

To a solution of Compound 328B (2.64 g, 10 mmol) in anhydrous THF (30 mL) was added lithium aluminum hydride (458 mg, 12 mmol) in portions under nitrogen at 0° C. The mixture was stirred at room temperature for 0.5 h and quenched with addition of water (2 mL). The resulting precipitation was filtered. The filtrate was dried over anhydrous sodium sulfate and evaporated to dryness in vacuo to afford Compound 328C.

To a solution of Compound 328C (2.2 g, 0.01 mol) in dichloromethane (40 mL) was Dess-Martin periodinane (845 mg, 0.02 mol). After 4 hours, the reaction mixture was washed with brine (50 mL), dried over anhydrous sodium sulfate, and concentrated to furnish a residue. The crude product was purified with flash column chromatography on silica gel (ethyl acetate in petroleum ether, from 10% to 50% v/v) to yield Compound 328D.

To a suspension of Compound 328D (218 mg, 1 mmol) and NaCN (74 mg, 1.5 mmol) in methanol (5 mL) was carefully added dropwise AcOH (1 mL). The reaction mixture was stirred at room temperature overnight. After removal of methanol, the residue was dissolved in dichloromethane (40 mL), washed with brine (30 mL), dried over anhydrous sodium sulfate, filtered, and concentrated. The residue was purified with flash column chromatography on silica gel (ethyl acetate in petroleum ether, from 10% to 50% v/v) to furnish Compound 328E.

A solution of Compound 328E (2.5 g, 10 mmol) in methanol (50 mL) was stirred under HCl gas at room temperature for 6 h. The reaction mixture was quenched with water (30 mL) and stirred at room temperature for 1 h. After removal of solvent, the residue was dissolved in ethyl acetate (200 mL), washed with brine (50 mL), dried over anhydrous sodium sulfate, and concentrated to give Compound 328F.

A solution of Compound 328F (2.9 g, 10 mmol) and Dess-Martin periodinane (6.3 g, 15 mmol) in dichloromethane (50 mL) was stirred at room temperature for 2 h. After the completion of reaction, the reaction mixture was washed with brine (50 mL), dried over anhydrous sodium sulfate, and concentrated to give a residue. The crude product was purified with flash column chromatography on silica gel (ethyl acetate in petroleum ether, from 20% to 30% v/v) to afford Compound 328G.

To a solution of Compound 328G (2.9 g, 10 mmol) in dichloromethane (50 mL) was added DAST (3 mL, 41.3 mmol) at room temperature. The mixture was stirred at room temperature overnight. After the completion of the reaction, the reaction mixture was washed with water (50 mL×3) and brine (50 mL), dried over anhydrous sodium sulfate, and concentrated to afford a residue. The crude product was purified with flash column chromatography on silica gel (ethyl acetate in petroleum ether, from 20% to 40% v/v) to give Compound 328H.

A mixture of Compound 328H (3.1 g, 10 mmol) and LiOH H$_2$O (1.2 g, 28.4 mmol) in ethanol/water (40 mL/4 mL) was stirred at room temperature overnight. After the completion of the reaction, the reaction mixture was adjusted to pH 6 with aqueous HCl solution (2 N, 1.5 mL). After removal of solvent, the residue was dissolved in ethyl acetate (200 mL), washed with water (50 mL×3) and brine (50 mL), dried over anhydrous sodium sulfate, and concentrated to furnish Compound 328I.

To a mixture of Compound 328I (142 mg, 0.5 mmol) and Intermediate G (232 mg, 0.75 mmol) in DMF (5 mL) was added HATU (380 mg, 1 mmol). The reaction mixture was stirred at room temperature overnight and the resulting solution was diluted with ethyl acetate (30 mL). The organic layer was washed with brine (30 mL), dried over anhydrous sodium sulfate, filtered, and concentrated. The residue was purified with reverse phase chromatography using eluent (methanol in water, from 10% to 55% v/v) to furnish Compound 328. LC-MS (ESI) m/z: 577 [M+H]$^+$; $^1$H-NMR (CD$_3$OD, 400 MHz): δ (ppm) 0.28-0.29 (m, 2H), 0.41-0.51 (m, 2H), 2.01-2.23 (m, 6H), 2.39-2.65 (m, 2H), 3.18-3.35 (m, 3H), 3.51-3.59 (m, 1H), 3.63-3.84 (m, 3H), 3.61-3.65 (m, 1H), 4.94 (s, 1H), 7.19-7.21 (m, 1H), 7.31-7.38 (m, 2H), 7.42-7.51 (m, 2H), 7.61 (s, 1H), 7.76-7.89 (m, 3H).

Example 329

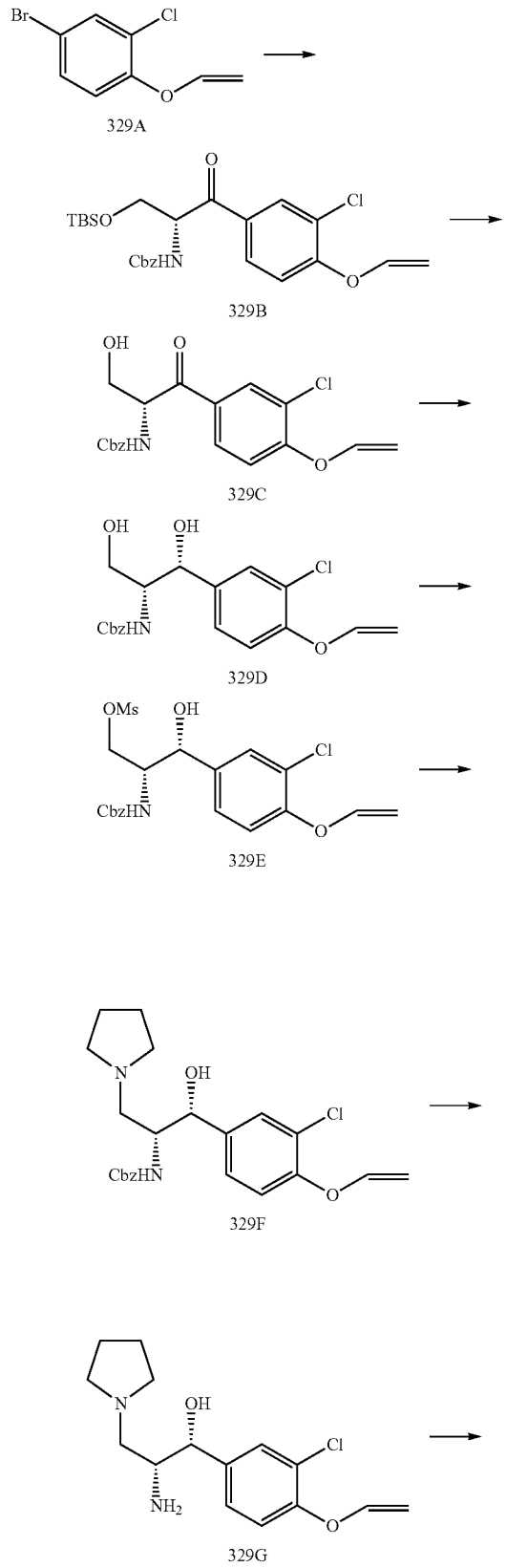

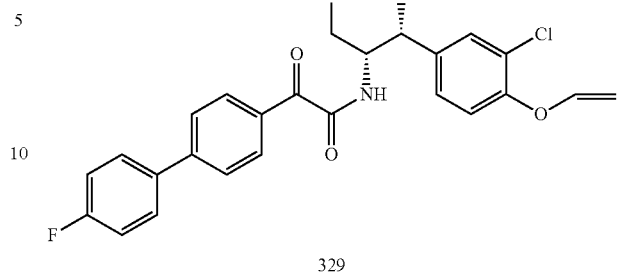

329

To a solution of Compound 329A (19.8 g, 85.4 mmol) in dry THF (600 mL) maintained at −70° C. was added n-BuLi (2.5 M in hexane, 34.5 mL) dropwise under nitrogen atmosphere over a period of 20 minutes. After the reaction mixture was stirred at −70° C. for 40 minutes, Compound A4 (12 g, 30.4 mmol) dissolved in dry THF (50 mL) was added slowly to the cold solution at a rate that maintained the internal temperature between −70° C. and −50° C. After the addition was complete, the solution was left to stir for 1 h. The reaction mixture was quenched with saturated ammonium chloride solution (400 mL) and extracted with ethyl acetate (300 mL×3). The organic phase was washed with water (200 mL) and brine (200 mL), dried over anhydrous sodium sulfate, filtered, and concentrated to furnish the crude Compound 329B. The crude product was purified with flash column chromatography on silica gel (ethyl acetate in petroleum ether, from 5% to 10% v/v) to furnish Compound 329B.

A solution of Compound 329B (7.4 g, 15.1 mmol) in a mixture of tetrahydrofuran, water, and glacial acetic acid (153 mL, 1/1/3, v/v/v) was stirred at 25° C. for 30 h. The reaction mixture was concentrated under reduced pressure to remove excess solvent. The residue was poured into ice water (20 g) and adjusted to pH 7~8 with aqueous sodium hydroxide (1 N) and saturated aqueous sodium bicarbonate solution. The mixture was extracted with ethyl acetate (60 mL×3). The combined organic phases were washed with brine (50 mL), dried over anhydrous sodium sulfate, filtered, and concentrated to afford the crude target compound, which was further purified with flash column chromatography on silica gel (ethyl acetate in petroleum ether, from 30% to 50% v/v) to give Compound 329C.

To a solution of Compound 329C (3.0 g, 8 mmol) in dry THF (140 mL) maintained at −78° C. was added diisobutylaluminum hydride (1.5 M in toluene, 25 mL) dropwise under nitrogen atmosphere over a period of 15 minutes. After the reaction mixture was stirred at −70° C. for 1 h, a solution of HCl (2 N, 40 mL) was added to the mixture slowly. The reaction mixture was extracted with ethyl acetate (30 mL×3), dried over anhydrous sodium sulfate, filtered, and concentrated to afford the crude target compound, which was further purified with flash column chromatography on silica gel (ethyl acetate in petroleum ether, from 50% to 150% v/v) to furnish Compound 329D.

To a solution of Compound 329D (2.30 g, 6.10 mmol) dissolved in THF (100 mL) was added triethylamine (1.90 g, 18.81 mmol). The mixture was cooled to −30° C., and then methanesulfonyl chloride (0.80 g, 6.98 mmol) was added dropwise over a period of 15 minutes. After the addition was complete, the reaction mixture was stirred at −30° C. for 1.5 h, diluted with water (100 mL), and extracted with ethyl acetate (100 mL×2). The combined organic layers were washed with brine (100 mL), dried over anhydrous sodium sulfate, filtered, and concentrated to afford Compound 329E, which was directly used for the next step without further purification.

To a solution of Compound 329E (3.81 g, 6.10 mmol) in THF (100 mL) was added pyrrolidine (11 g, 154 mmol). The reaction mixture was allowed to heat to 50° C. for 16 h. The mixture was diluted with water (100 mL), extracted with ethyl acetate (150 mL×2), washed with brine (100 mL), dried over anhydrous sodium sulfate, filtered, and concentrated to furnish a crude compound. The crude product was purified with flash column chromatography on silica gel (methanol in dichloromethane, 5% v/v) to give Compound 329F.

To a solution of Compound 329F (1.33 g, 3.08 mmol) in ethanol (30 mL) and water (7 mL) was added LiOH.H$_2$O (570 mg, 13.51 mmol). The mixture was heated to 80° C. and stirred for 16 h. The reaction mixture was diluted with water (50 mL) and extracted with dichloromethane (50 mL×2). The combined organic phases were washed with water (50 mL) and brine (50 mL), dried over anhydrous sodium sulfate, filtered, and concentrated to furnish Compound 329G, which was directly used for the next step without further purification.

A mixture of Intermediate C (80 mg, 0.32 mmol), Compound 329G (116 mg, 0.39 mmol), and HATU (187 mg, 0.49 mmol) in dichloromethane (20 mL) was stirred at room temperature overnight. The mixture was diluted with dichloromethane (100 mL), washed with water (50 mL×2) and brine (50 mL), dried over anhydrous sodium sulfate, and concentrated. The crude product was purified with prep-HPLC to give Compound 329. LC-MS (ESI) m/z: 523 [M+H]$^+$; $^1$H-NMR (CD$_3$OD, 400 MHz): δ (ppm) 2.05-2.23 (m, 4H), 3.20-3.37 (m, 2H), 3.60-3.77 (m, 4H), 4.48-4.50 (m, 1H), 4.68-4.74 (m, 2H), 5.04 (s, 1H), 6.73-6.78 (m, 1H), 7.15 (d, J=8.4 Hz, 1H), 7.22-7.27 (m, 2H), 7.42 (dd, J=8.4 Hz, 2.0 Hz, 1H), 7.58 (d, J=1.6 Hz, 1H), 7.65-7.76 (m, 6H).

Example 330

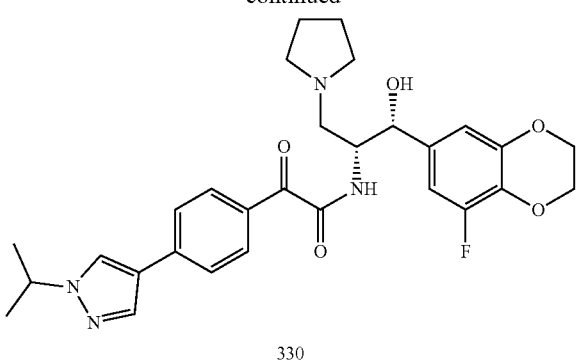

330

To a solution of 4-bromo-1H-pyrazole (2.92 g, 20.0 mmol) in anhydrous DMF (50 mL) was added 2-bromopropane (3.69 g, 30.0 mmol) and potassium carbonate (6.90 g, 50 mmol) at room temperature. The reaction mixture was stirred for 10 h. The mixture was diluted with water (100 mL) and extracted with ethyl acetate (150 mL×3). The combined organic extracts were washed with brine (150 mL×2) and dried over anhydrous sodium sulfate. After filtration, the solvent was removed in vacuo and the residue was purified with flash column chromatography on silica gel to give Compound 330A.

To a solution of Compound 330A (189 mg, 1.0 mmol) in 1,4-dioxane (10 mL) was added Intermediate 175B (304 mg, 1.0 mmol), Pd(dppf)Cl$_2$ (35 mg, 0.05 mmol), sodium carbonate (318 mg, 3.0 mmol), and water (1 mL) under nitrogen. The reaction mixture was stirred at 110° C. for 2 hours. The resulting mixture was cooled to 25° C. The precipitated solid was filtered and dried to afford Compound 330B.

To a solution of Compound 330B (25 mg, 0.10 mmol) in DMF (2 mL) was added Intermediate C (30 mg, 0.10 mmol) and HATU (57 mg, 0.15 mmol). The reaction mixture was stirred at 20° C. for 2 h. The mixture was purified with prep-HPLC to yield Compound 330. LC-MS (ESI) m/z: 537 [M+H]$^+$; $^1$H-NMR (acetone-d$_6$, 400 MHz): δ (ppm) 1.61 (d, J=6.4 Hz, 6H), 2.09-2.12 (m, 1H), 2.25-2.31 (m, 2H), 2.86 (s, 1H), 3.03 (s, 1H), 3.46-3.54 (m, 2H), 3.82-3.85 (m, 1H), 3.95-4.07 (m, 3H), 4.24-4.30 (m, 4H), 5.07-5.08 (m, 1H), 6.81-6.87 (m, 2H), 7.79-7.81 (m, 2H), 8.06-8.10 (m, 3H), 8.30 (s, 1H), 8.56 (s, 1H), 8.69 (brs, 1H).

Example 331

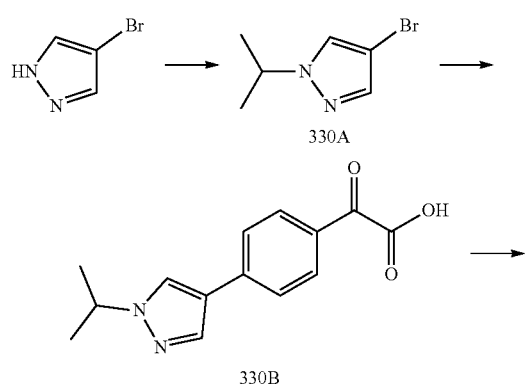

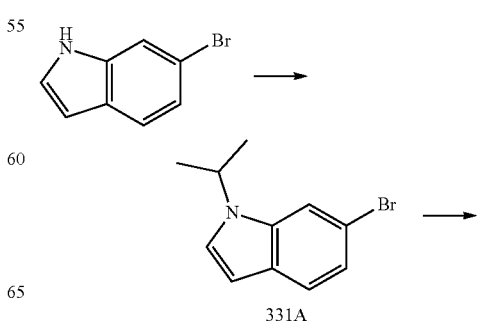

331A

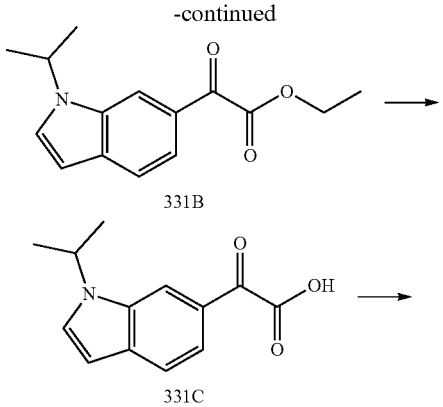

331B

331C

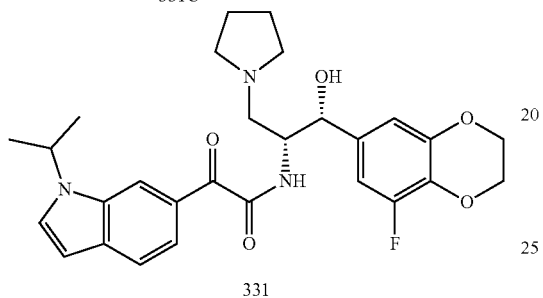

331

To a solution of 6-bromo-1H-indole (6 g, 30 mmol) in DMF (150 mL) was added sodium hydride (60% suspend in oil, 2.4 g, 60 mmol) at 0° C. The mixture was stirred at 0° C. for 0.5 h and 2-iodopropane (7.6 g, 45 mmol) was added at 0° C. The resultant mixture was stirred at room temperature overnight and diluted with ethyl acetate (300 mL). The organic layer was washed with water (100 mL×3) and brine (100 mL), dried over anhydrous sodium sulfate, concentrated, and purified with flash column chromatography on silica gel (ethyl acetate in petroleum ether, 10% v/v) to give Compound 331A.

To a solution of Compound 331A (476 mg, 2 mmol) in THF (20 mL) was added n-BuLi (2.5 Min hexane, 1 mL, 2.4 mmol) under nitrogen at −78° C. The mixture was stirred at −78° C. for 0.5 h and diethyl oxalate (584 mg, 4 mmol) was added at −78° C. The mixture was stirred at −78° C. for 0.5 h, quenched with saturated aqueous ammonium chloride solution (50 mL), and extracted with ethyl acetate (50 mL×3). The organic layer was washed with brine (100 mL), dried over anhydrous sodium sulfate, concentrated, and purified with flash column chromatography on silica gel (ethyl acetate in petroleum ether, 10% v/v) to yield Compound 331B.

To a solution of Compound 331B (368 mg, 1.42 mmol) in THF (10 mL) was added a solution of LiOH H$_2$O (120 mg, 2.84 mmol) in water (3 mL). The mixture was stirred at room temperature overnight. After removal of THF, the mixture was acidified to pH 1 with aqueous HCl solution (1 N) and extracted with dichloromethane (20 mL). The organic layer was dried over anhydrous sodium sulfate and used directly for the next step as a dichloromethane solution.

A mixture of Compound 331C in dichloromethane solution (115 mg, 0.5 mmol), Intermediate C (150 mg, 0.5 mmol), and HATU (380 mg, 1 mmol) in dichloromethane (10 mL) and DMF (3 mL) was stirred at room temperature overnight. The mixture was concentrated and the resulting residue was purified with prep-HPLC to yield Compound 331. LC-MS (ESI) m/z: 510 [M+H]$^+$; $^1$H-NMR (DMSO-d$_6$, 400 MHz): δ (ppm) 1.46 (d, J=6.8 Hz, 3H), 1.50 (d, J=6.4 Hz, 3H), 1.85-1.88 (m, 2H), 2.02-2.03 (m, 2H), 3.09-3.20 (m, 2H), 3.41-3.44 (m, 2H), 3.52-3.56 (m, 2H), 4.23-4.25 (m, 4H), 4.50-4.55 (m, 1H), 4.76-4.81 (m, 2H), 6.02 (s, 1H), 6.60 (d, J=3.2 Hz, 1H), 6.76 (s, 1H), 6.82-6.85 (m, 1H), 7.45-7.47 (m, 1H), 7.61 (d, J=8.4 Hz, 1H), 7.85 (d, J=3.2 Hz, 1H), 8.27 (s, 1H), 8.66 (d, J=9.2 Hz, 1H), 9.33 (s, 1H).

Example 332

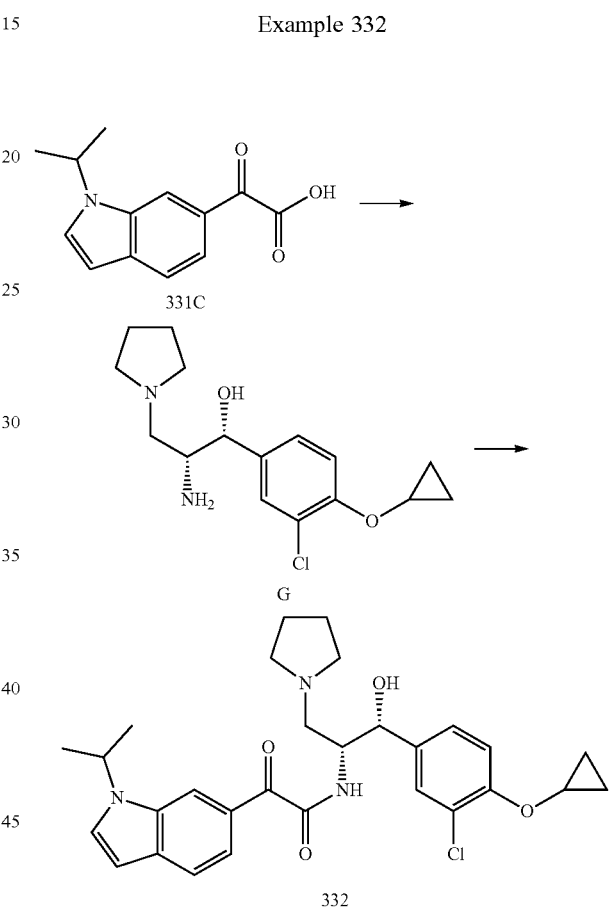

A mixture of Compound 331C in dichloromethane solution (115 mg, 0.5 mmol), Intermediate G (155 mg, 0.5 mmol), and HATU (380 mg, 1 mmol) in dichloromethane (10 mL) and DMF (3 mL) was stirred at room temperature overnight. The mixture was concentrated and the resulting residue was purified with prep-HPLC to yield Compound 332. LC-MS (ESI) m/z: 524 [M+H]$^+$; $^1$H-NMR (DMSO-d$_6$, 400 MHz): δ (ppm) 0.62-0.65 (m, 2H), 0.79-0.81 (m, 2H), 1.45 (d, J=6.8 Hz, 3H), 1.49 (d, J=6.8 Hz, 3H), 1.86-1.88 (m, 2H), 2.00-2.03 (m, 2H), 3.12-3.20 (m, 2H), 3.45-3.47 (m, 4H), 3.87-3.90 (m, 1H), 4.54-4.58 (m, 1H), 4.74-4.80 (m, 1H), 4.85 (s, 1H), 6.05 (s, 1H), 6.59 (d, J=3.2 Hz, 1H), 7.32-7.38 (m, 2H), 7.41-7.45 (m, 2H), 7.58 (d, J=8.8 Hz, 1H), 7.84 (d, J=3.2 Hz, 1H), 8.24 (s, 1H), 8.67 (d, J=9.2 Hz, 1H), 9.39 (s, 1H).

Example 333

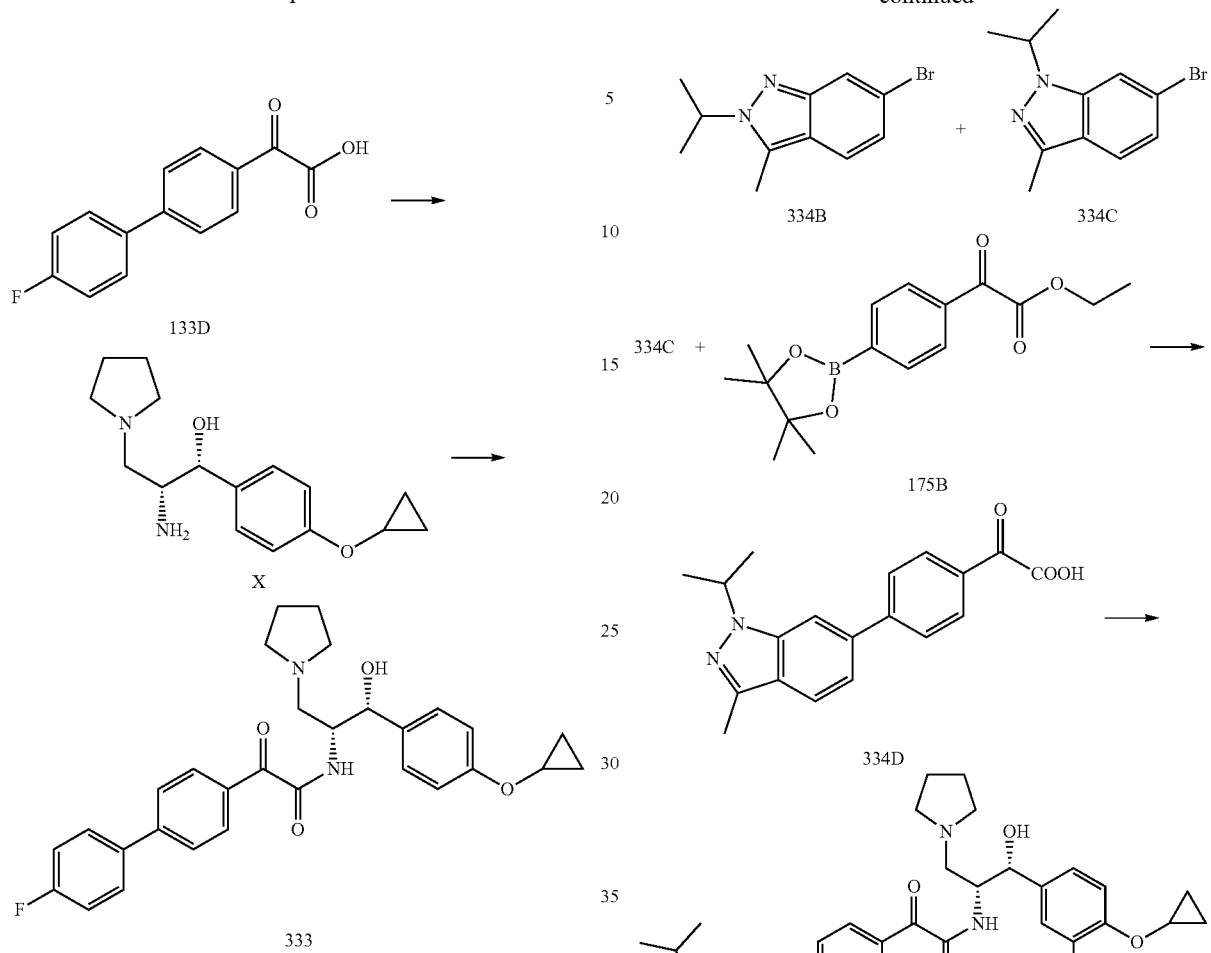

To a solution of Intermediate X (80 mg, 0.29 mmol) in a mixture of dichloromethane (3 mL) and DMF (3 mL) was added Compound 133D (72 mg, 0.29 mmol) and HATU (165 mg, 0.43 mmol). The mixture was stirred at room temperature for 4 h. The reaction mixture was concentrated and the resulting residue was purified with prep-HPLC to furnish Compound 333. LC-MS (ESI) m/z: 503 [M+H]$^+$; $^1$H-NMR (CD$_3$OD, 400 MHz): δ (ppm) 0.64-0.65 (m, 2H), 0.74-0.77 (m, 2H), 1.29 (s, 1H), 2.02-2.07 (m, 2H), 2.17-2.21 (m, 2H), 3.23-3.26 (m, 1H), 3.56 (dd, J=13.3, 2.8 Hz, 1H), 3.67-3.80 (m, 3H), 3.81-3.83 (m, 1H), 4.66-4.70 (m, 1H), 4.98 (d, J=3.1 Hz, 1H), 7.04 (d, J=8.7 Hz, 2H), 7.22-7.26 (m, 2H), 7.38 (d, J=8.6 Hz, 2H), 7.68 (d, J=8.5 Hz, 2H), 7.71-7.75 (m, 2H), 7.78 (d, J=8.5 Hz, 2H).

Example 334

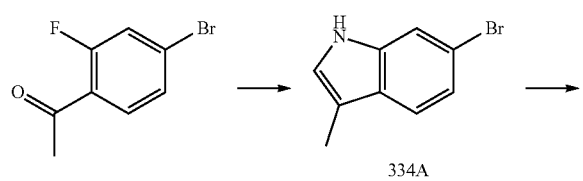

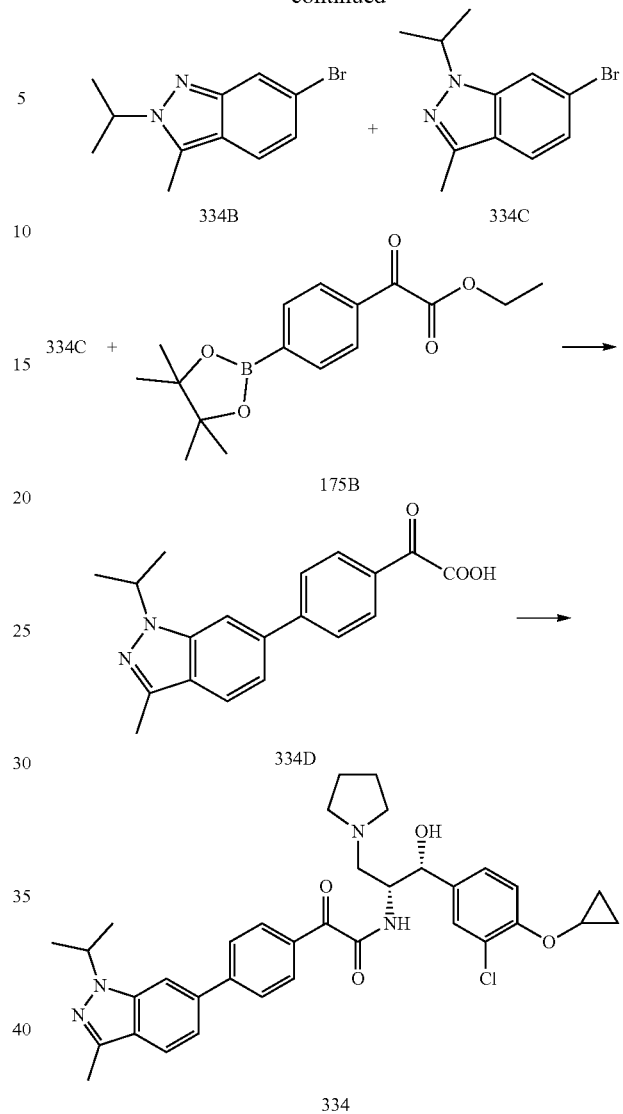

To a solution of 1-(4-bromo-2-fluorophenyl)ethan-1-one (1.0 g, 3.89 mmol) in 1,2-ethanediol (12 mL) was added 80% of hydrazine monohydrate (0.6 mL, 7.78 mmol) at room temperature. The reaction mixture was stirred at 200° C. in a microwave for 4.5 h, cooled down to room temperature, and quenched with water (50 mL). The solid precipitated was filtered, washed with water (20 mL), and dried under vacuo to afford Compound 334A.

To Compound 334A (1.9 g, 9.05 mmol) in DMF (15 mL) was added sodium hydride (60% in mineral, 398 mg, 9.96 mmol) with ice bath cooling. The mixture was stirred at room temperature for 30 min and 2-iodopropane (2.7 mL, 27.15 mmol) was added. The reaction mixture was stirred at room temperature for 1 h, quenched with ammonium chloride solution (30 mL), and extracted with ethyl acetate (100 mL×3). The combined organic layers were washed with brine (200 mL), dried over anhydrous sodium sulfate, concentrated, and purified with flash column chromatography on silica gel (ethyl acetate in petroleum ether, from 0% to 20% v/v) to give Compound 334B and Compound 334C.

A mixture of Compound 334C (400 mg, 1.59 mmol), Compound 175B (483 mg, 1.59 mmol), Pd(dppf)Cl$_2$ (65 mg, 0.08 mmol), and K$_2$CO$_3$ (658 mg, 4.77 mmol) in dioxane (5 mL) and water (5 mL) was stirred under nitrogen at 100° C. for 3 h. The reaction mixture was cooled down to room temperature and filtered through celite. The filtrate was diluted with water (100 mL) and extracted with ethyl acetate (100 mL×2). The aqueous layer was acidified to pH 3 with aqueous HCl solution (1 N) and extracted with dichloromethane (100 mL×3). The combined organic layers were washed with water (50 mL), dried over anhydrous sodium sulfate, and concentrated to yield Compound 334D.

A mixture of Compound 334D (80 mg, 0.25 mmol), HATU (143 mg, 0.37 mmol), and Intermediate G (78 mg, 0.25 mmol) in DMF (5 mL) was stirred at 20° C. for 18 h. The mixture was directly purified with prep-HPLC to furnish Compound 334. LC-MS (ESI) m/z: 615 [M+H]$^+$; $^1$H-NMR (DMSO-d$_6$, 400 MHz): δ (ppm) 0.65-0.85 (m, 4H), 1.48-1.51 (m, 6H), 1.89-2.08 (m, 4H), 2.53 (s, 3H), 3.14-3.25 (m, 2H), 3.45-3.49 (m, 4H), 3.94-3.97 (m, 1H), 4.57-4.62 (m, 1H), 4.92 (s, 1H), 5.03-5.09 (m, 1H), 6.10 (brs, 1H), 7.37-7.49 (m, 4H), 7.77 (d, J=8.4 Hz, 2H), 7.81 (d, J=5.6 Hz, 1H), 7.88 (d, J=8.8 Hz, 2H), 8.01 (s, 1H), 8.86 (d, J=10.0 Hz, 1H), 9.57 (brs, 1H).

Example 335

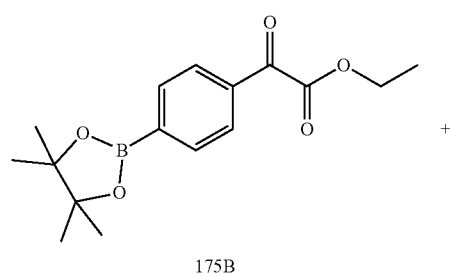

175B

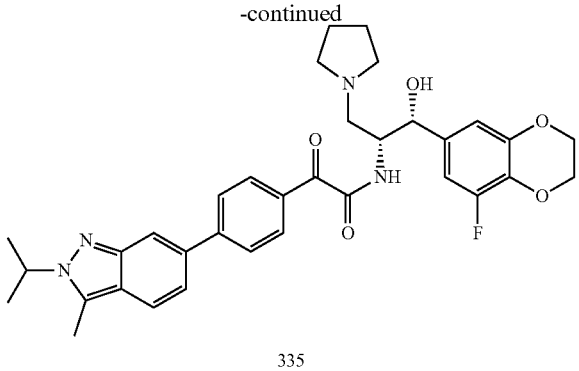

335

A mixture of Compound 334B (460 mg, 1.82 mmol), Compound 175B (553 mg, 1.82 mmol), Pd(dppf)Cl$_2$ (73 mg, 0.09 mmol), and K$_2$CO$_3$ (753 mg, 5.46 mmol) in dioxane (5 mL) and water (5 mL) was stirred under nitrogen at 100° C. for 3 h. The reaction mixture was cooled down to room temperature and filtered through celite. The filtrate was diluted with water (100 mL) and extracted with ethyl acetate (100 mL×2). The aqueous layer was acidified to pH 3 with aqueous HCl solution (1 N) and extracted with dichloromethane (100 mL×3). The combined organic layers were washed with water (100 mL×3), dried over anhydrous sodium sulfate, and concentrated to give Compound 335A.

A mixture of Compound 335A (80 mg, 0.25 mmol), HATU (143 mg, 0.37 mmol), and Intermediate C (74 mg, 0.25 mmol) in DMF (5 mL) was stirred at 20° C. for 18 h. The mixture was directly purified with prep-HPLC to furnish Compound 335. LC-MS (ESI) m/z: 601 [M+H]$^+$; $^1$H-NMR (DMSO-d$_6$, 400 MHz): δ (ppm) 1.52 (d, J=6.4 Hz, 6H), 1.88-2.05 (m, 4H), 2.67 (s, 3H), 3.10-3.22 (m, 2H), 3.43-3.55 (m, 4H), 4.24-4.29 (m, 4H), 4.49-4.54 (m, 1H), 4.78 (d, J=2.8 Hz, 1H), 4.86-4.92 (m, 1H), 5.99 (brs, 1H), 6.77 (s, 1H), 6.84 (dd, J=11.6, 1.6 Hz, 1H), 7.36 (dd, J=8.8, 1.2 Hz, 1H), 7.82 (d, J=8.8 Hz, 1H), 7.88-8.01 (m, 5H), 8.75 (d, J=9.6 Hz, 1H), 9.33 (brs, 1H).

Example 336

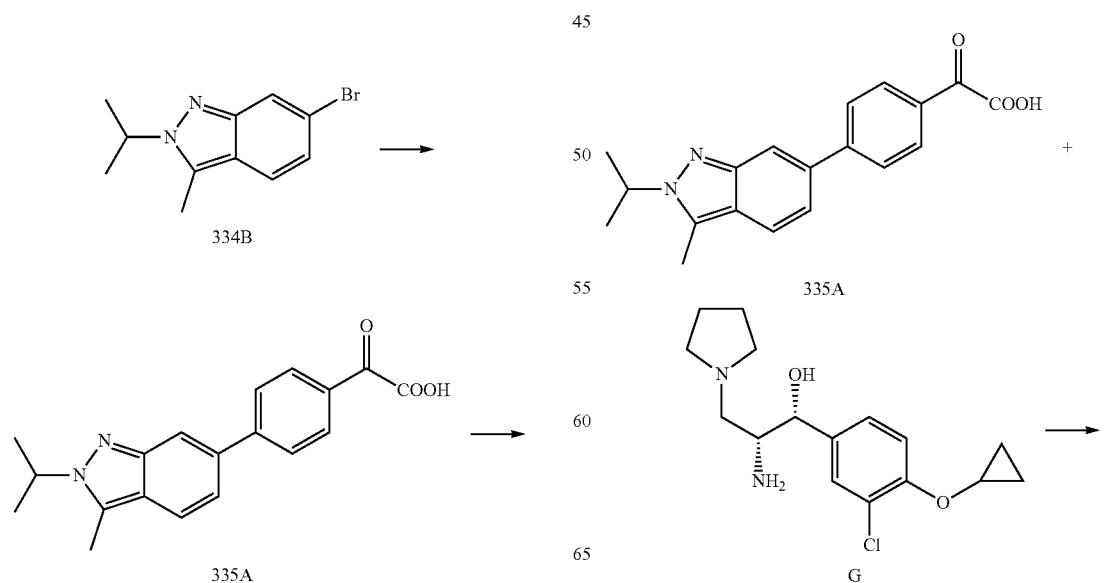

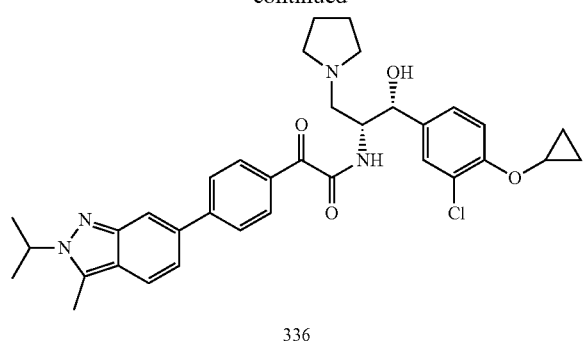

336

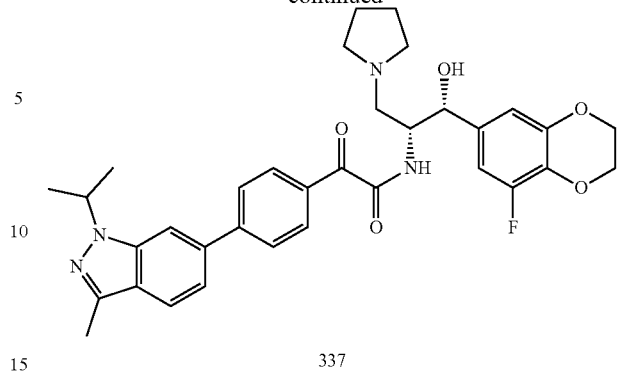

337

A mixture of Compound 335A (80 mg, 0.25 mmol), HATU (143 mg, 0.37 mmol), and Intermediate G (78 mg, 0.25 mmol) in DMF (5 mL) was stirred at 20° C. for 18 h. The mixture was directly purified with prep-HPLC to furnish Compound 336. LC-MS (ESI) m/z: 615 [M+H]⁺; ¹H-NMR (DMSO-d₆, 400 MHz): δ (ppm) 0.69-0.85 (m, 4H), 1.52 (d, J=6.8 Hz, 6H), 1.89-2.08 (m, 4H), 2.67 (s, 3H), 3.11-3.24 (m, 2H), 3.45-3.57 (m, 4H), 3.93-3.97 (m, 1H), 4.55-4.59 (m, 1H), 4.86-4.93 (m, 2H), 5.99 (brs, 1H), 7.36 (d, J=8.8 Hz, 2H), 7.42-7.46 (m, 2H), 7.77 (d, J=8.8 Hz, 2H), 7.80-7.85 (m, 3H), 7.95 (s, 1H), 8.82 (d, J=10.0 Hz, 1H), 9.34 (brs, 1H).

A mixture of Compound 334D (80 mg, 0.25 mmol), HATU (143 mg, 0.37 mmol), and Intermediate C (74 mg, 0.25 mmol) in DMF (5 mL) was stirred at 20° C. for 18 h. The mixture was directly purified with prep-HPLC to furnish Compound 337. LC-MS (ESI) m/z: 601 [M+H]⁺; ¹H-NMR (DMSO-d₆, 400 MHz): δ (ppm) 1.48 (d, J=6.4 Hz, 6H), 1.88-2.08 (m, 4H), 2.53 (s, 3H), 3.11-3.22 (m, 2H), 3.39-3.55 (m, 4H), 4.20-4.29 (m, 4H), 4.51-4.55 (m, 1H), 4.79 (d, J=2.8 Hz, 1H), 5.03-5.09 (m, 1H), 6.03 (brs, 1H), 6.78 (s, 1H), 6.84 (d, J=11.6 Hz, 1H), 7.48 (d, J=8.8 Hz, 1H), 7.82 (d, J=8.4 Hz, 1H), 7.92-7.97 (m, 4H), 8.02 (s, 1H), 8.77 (d, J=9.6 Hz, 1H), 9.31 (brs, 1H).

Example 338

Example 337

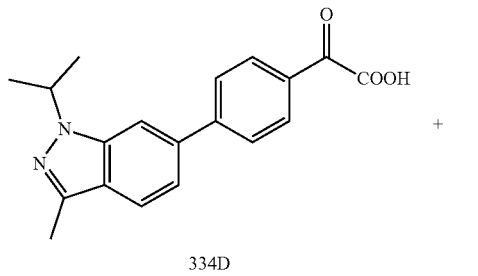

334D

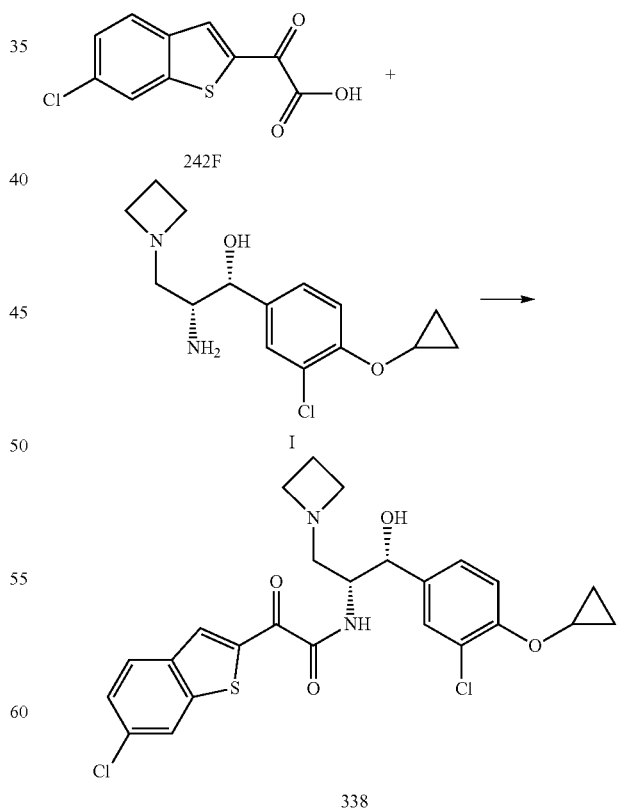

To a solution of Intermediate I (172 mg, 0.58 mmol) in dichloromethane (10 mL) was added Compound 242F (140 mg, 0.58 mmol) and HATU (332 mg, 0.87 mmol). The mixture was stirred under nitrogen at room temperature overnight. The resulting mixture was quenched with saturated aqueous sodium bicarbonate solution (5 mL) and extracted with ethyl acetate (50 mL×3). The combined organic phases were washed with water (5 mL) and brine (5 mL), dried over anhydrous sodium sulfate, filtered, and concentrated to afford a crude compound. The crude product was purified with prep-HPLC to furnish Compound 338. LC-MS (ESI) m/z: 519 [M+H]$^+$; $^1$H-NMR (DMSO-d$_6$, 400 MHz): δ (ppm) 0.62-0.64 (m, 2H), 0.78-0.79 (m, 2H), 2.22-2.28 (m, 1H), 2.33-2.42 (m, 1H), 3.30-3.31 (m, 1H), 3.86-3.90 (m, 1H), 4.02-4.30 (m, 6H), 4.78 (d, J=2.4 Hz, 1H), 6.04 (s, 1H), 7.29 (dd, J=8.8, 2.0 Hz, 1H), 7.37 (d, J=8.4 Hz, 1H), 7.39 (d, J=2.4 Hz, 1H), 7.55 (dd, J=8.4, 2.0 Hz, 1H), 8.11 (d, J=8.8 Hz, 1H), 8.30 (d, J=1.6 Hz, 1H), 8.49 (s, 1H), 8.57 (d, J=10.0 Hz, 1H), 9.49 (s, 1H).

Example 339

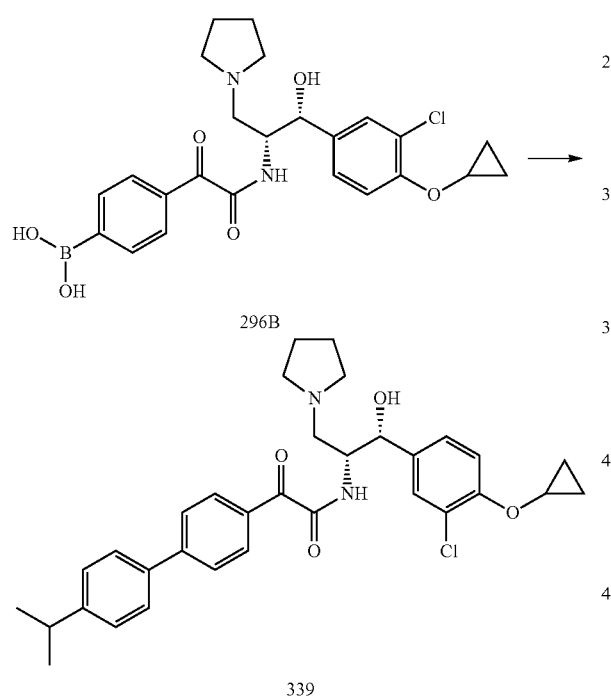

A mixture of 1-bromo-4-isopropylbenzene (44 mg, 0.22 mmol), Compound 296B (110 mg, 0.22 mmol), [1,1′-bis(diphenylphosphino)ferrocene]dichloropalladium(II) (6 mg, 8.2 μmol), sodium carbonate (47 mg, 0.44 mmol), water (0.5 mL), and 1,4-dioxane (5 mL) was stirred under nitrogen atmosphere at 80° C. for 2 h. After cooling, the reaction mixture was treated with water (5 mL), extracted with ethyl acetate (10 mL×3), washed with brine (5 mL), dried over anhydrous sodium sulfate, filtered, and concentrated to afford the crude product as a black oil. The oil was purified with prep-HPLC to furnish Compound 339. LC-MS (ESI) m/z: 561 [M+H]$^+$; $^1$H-NMR (DMSO-d$_6$, 400 MHz): δ (ppm) 0.60-0.66 (m, 2H), 0.76-0.84 (m, 2H), 1.23 (d, J=7.2 Hz, 6H), 1.82-1.92 (m, 2H), 1.97-2.07 (m, 2H), 2.91-3.00 (m, 1H), 3.08-3.27 (m, 2H), 3.41-3.61 (m, 4H), 3.86-3.95 (m, 1H), 4.42-4.61 (m, 1H), 4.85-4.91 (m, 1H), 6.04 (d, J=4.8 Hz, 1H), 7.33-7.44 (m, 5H), 7.64 (d, J=12.4 Hz, 2H), 7.69-7.80 (m, 4H), 8.77 (d, J=10.0 Hz, 1H), 9.34 (s, 1H).

Example 340

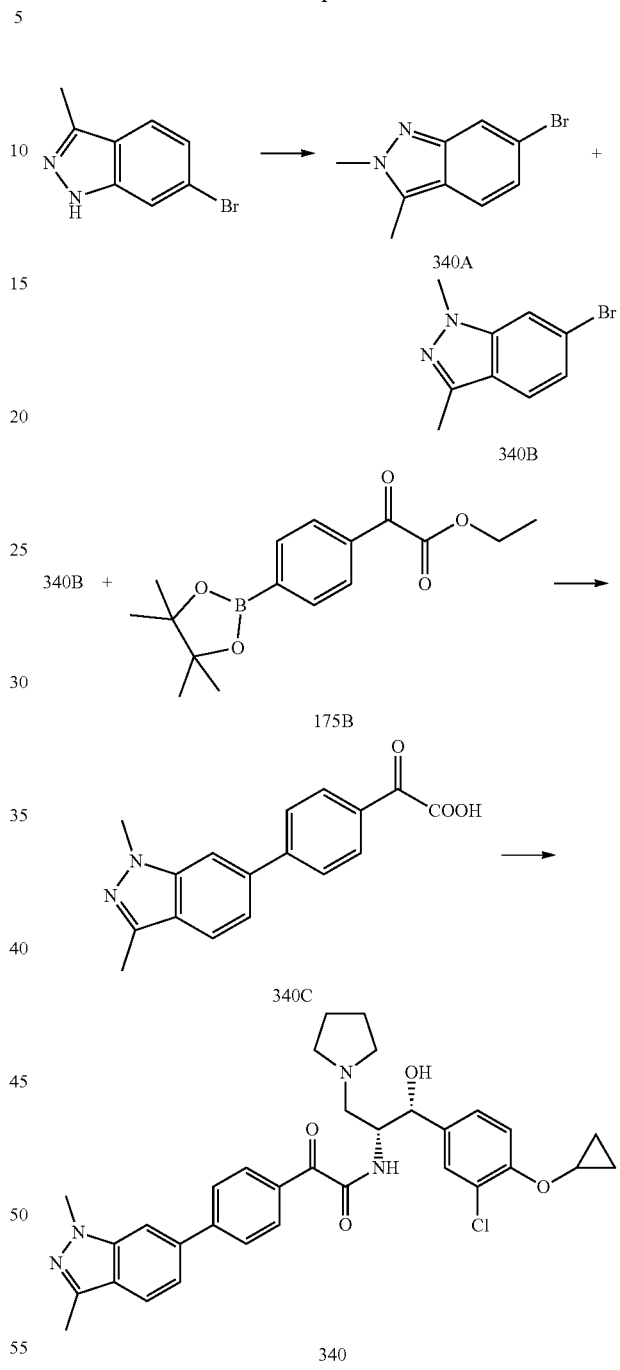

To 6-bromo-3-methyl-1H-indazole (1.9 g, 9.05 mmol) in DMF (15 mL) was added sodium hydride (60% in mineral, 398 mg, 9.96 mmol) with ice bath cooling. The mixture was stirred for 30 min at room temperature and iodomethane (0.94 mL, 27.15 mmol) was added. The reaction mixture was stirred at room temperature for 3 h, quenched with ammonium chloride solution (30 mL), and extracted with ethyl acetate (100 mL×3). The combined organic layers were washed with brine (200 mL), dried over anhydrous sodium sulfate, concentrated, and purified with flash column chromatography on silica gel (ethyl acetate in petroleum ether, from 0% to 90% v/v) to give Compound 340A and Compound 340B.

A mixture of Compound 340B (500 mg, 2.23 mmol), Compound 175B (678 mg, 2.23 mmol), Pd(dppf)Cl$_2$ (90 mg, 0.11 mmol), and K$_2$CO$_3$ (923 mg, 6.69 mmol) in dioxane (10 mL) and water (10 mL) was stirred under nitrogen at 100° C. for 3 h. The reaction mixture was cooled to room temperature and filtered through celite. The filtrate was diluted with water (100 mL) and extracted with ethyl acetate (100 mL×2). The aqueous layer was acidified to pH 3 with aqueous HCl solution (1 N) and extracted with dichloromethane (100 mL×3). The combined organic layers were washed with water (50 mL), dried over anhydrous sodium sulfate, and concentrated to give Compound 340C.

A mixture of Compound 340C (70 mg, 0.24 mmol), HATU (137 mg, 0.36 mmol), and Intermediate G (75 mg, 0.24 mmol) in DMF (5 mL) was stirred at 20° C. for 18 h. The mixture was directly purified with prep-HPLC to furnish Compound 340. LC-MS (ESI) m/z: 587 [M+H]$^+$; $^1$H-NMR (DMSO-d$_6$, 400 MHz): δ (ppm) 0.65-0.87 (m, 4H), 1.85-2.04 (m, 4H), 2.53 (s, 3H), 3.10-3.24 (m, 2H), 3.44-3.58 (m, 4H), 3.93-3.98 (m, 1H), 4.04 (s, 3H), 4.55-4.59 (m, 1H), 4.89 (d, J=2.0 Hz, 1H), 6.06 (brs, 1H), 7.36 (dd, J=8.4, 2.0 Hz, 1H), 7.42-7.50 (m, 3H), 7.80-7.86 (m, 3H), 7.89 (d, J=8.4 Hz, 2H), 7.96 (s, 1H), 8.83 (d, J=9.6 Hz, 1H), 9.35 (brs, 1H).

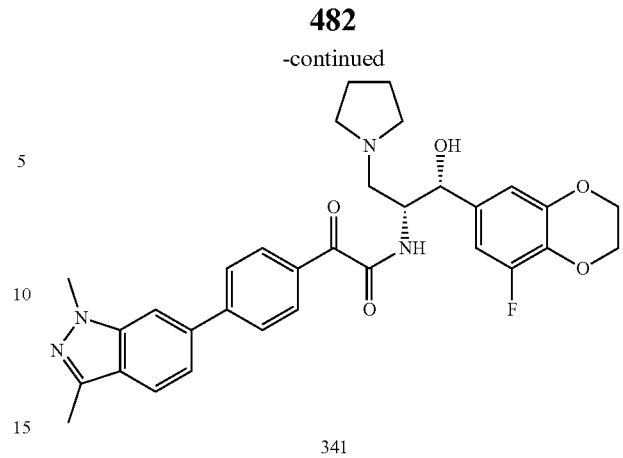

341

A mixture of Compound 340C (70 mg, 0.24 mmol), HATU (137 mg, 0.36 mmol), and Intermediate C (71 mg, 0.24 mmol) in DMF (5 mL) was stirred at 20° C. for 18 h. The mixture was directly purified with prep-HPLC to furnish Compound 341. LC-MS (ESI) m/z: 573 [M+H]$^+$; $^1$H-NMR (DMSO-d$_6$, 400 MHz): δ (ppm) 1.88-2.08 (m, 4H), 2.50 (s, 3H), 3.13-3.19 (m, 2H), 3.50-3.51 (m, 4H), 4.04 (s, 3H), 4.26-4.29 (m, 4H), 4.51-4.53 (m, 1H), 4.79 (d, J=2.4 Hz, 1H), 6.06 (brs, 1H), 6.78 (s, 1H), 6.84 (d, J=10.8 Hz, 1H), 7.49 (d, J=8.4 Hz, 1H), 7.84 (d, J=8.4 Hz, 1H), 7.95-7.97 (m, 5H), 8.77 (d, J=9.6 Hz, 1H), 9.31 (brs, 1H).

Example 342

Example 341

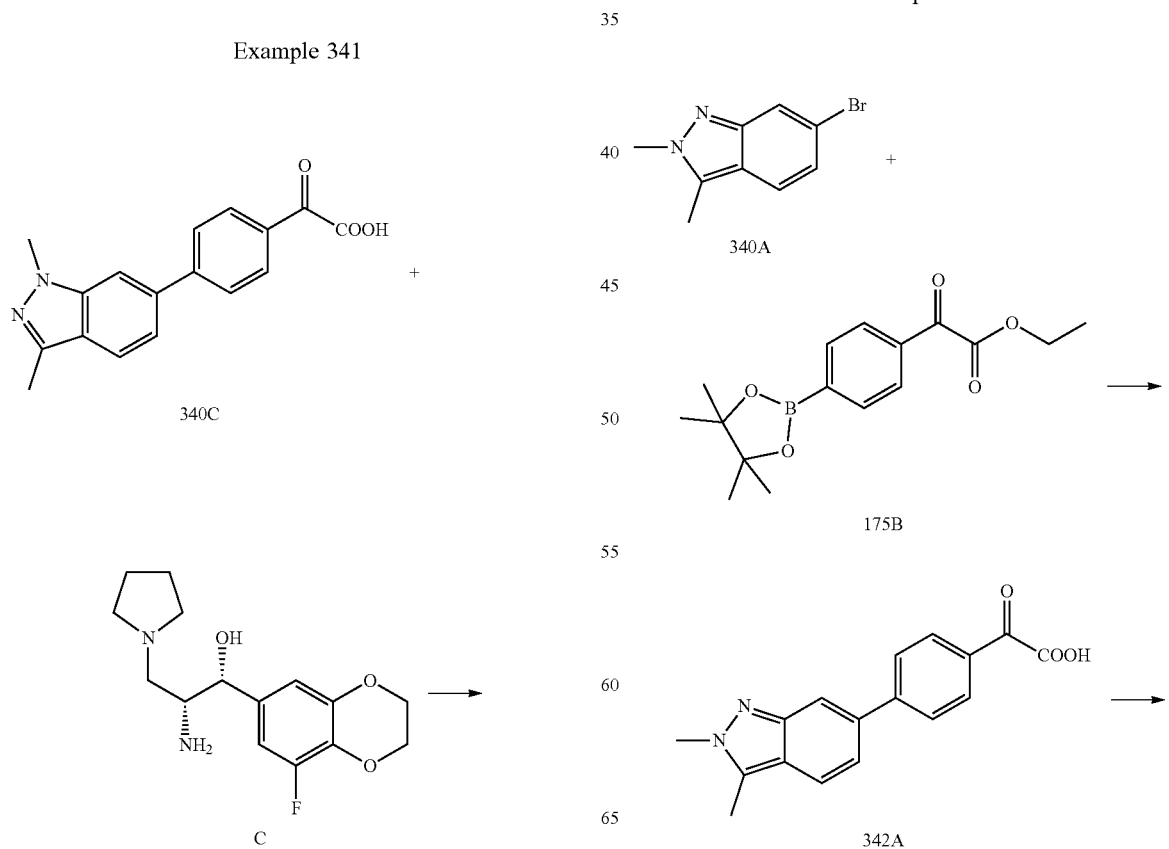

-continued

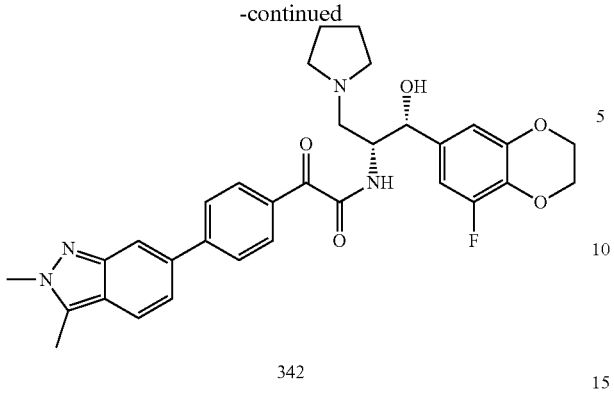

342

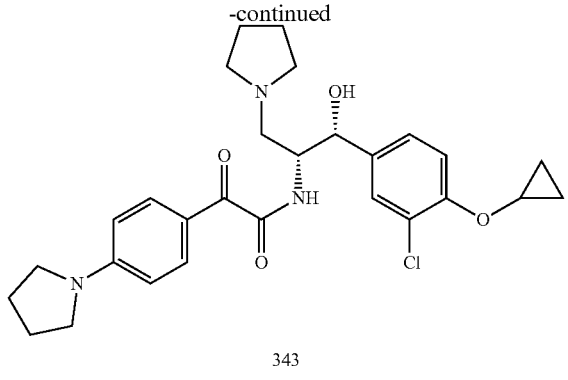

343

A mixture of Compound 340A (500 mg, 2.23 mmol), Compound 175B (678 mg, 2.23 mmol), Pd(dppf)Cl$_2$ (90 mg, 0.11 mmol), and K$_2$CO$_3$ (923 mg, 6.69 mmol) in dioxane (10 mL) and water (10 mL) was stirred under nitrogen at 100° C. for 3 h. The reaction mixture was cooled down to room temperature and filtered through celite. The filtrate was diluted with water (100 mL) and extracted with ethyl acetate (100 mL×2). The aqueous layer was acidified to pH 3 with aqueous HCl solution (1 N) and extracted with dichloromethane (100 mL×3). The combined organic layers were washed with water (50 mL), dried over anhydrous sodium sulfate, and concentrated to give Compound 342A.

A mixture of Compound 342A (70 mg, 0.24 mmol), HATU (137 mg, 0.36 mmol), and Intermediate C (71 mg, 0.24 mmol) in DMF (5 mL) was stirred at 20° C. for 18 h. The mixture was directly purified with prep-HPLC to furnish Compound 342. LC-MS (ESI) m/z: 573 [M+H]$^+$; $^1$H-NMR (DMSO-d$_6$, 400 MHz): δ (ppm) 1.88-2.03 (m, 4H), 2.65 (s, 3H), 3.13-3.21 (m, 2H), 3.41-3.55 (m, 4H), 4.09 (s, 3H), 4.27-4.29 (m, 4H), 4.48-4.53 (m, 1H), 4.78 (d, J=2.0 Hz, 1H), 6.77 (s, 1H), 6.83 (d, J=12.8 Hz, 1H), 7.39 (d, J=8.8 Hz, 1H), 7.82-7.93 (m, 6H), 7.76 (d, J=9.6 Hz, 1H), 9.29 (brs, 1H).

Example 343

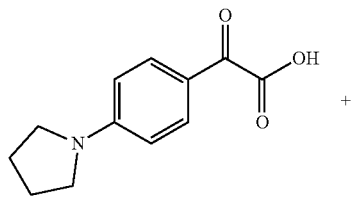

273C

+

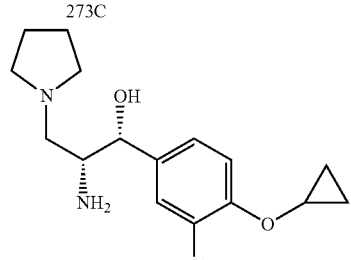

G

A mixture of Compound 273C (90 mg, 0.41 mmol), HATU (234 mg, 0.62 mmol), and Intermediate G (127 mg, 0.41 mmol) in DMF (3 mL) was stirred at 25° C. for 16 h. The mixture was diluted with ethyl acetate (30 mL), washed with water (10 mL×2) and brine (10 mL), dried over anhydrous sodium sulfate, concentrated, and purified with prep-HPLC to furnish Compound 343. LC-MS (ESI) m/z: 512 [M+H]$^+$; $^1$H-NMR (DMSO-d$_6$, 400 MHz): δ (ppm) 0.65-0.67 (m, 2H), 0.82-0.83 (m, 2H), 1.85-1.87 (m, 2H), 1.97-2.01 (m, 6H), 3.09-3.20 (m, 2H), 3.48-3.54 (m, 8H), 3.89-3.94 (m, 1H), 4.50-4.55 (m, 1H), 4.84 (d, J=2.4 Hz, 1H), 5.97-6.04 (m, 1H), 6.51 (d, J=9.2 Hz, 2H), 7.30-7.32 (m, 1H), 7.37-7.41 (m, 2H), 7.64 (d, J=9.2 Hz, 2H), 8.47 (d, J=9.6 Hz, 1H), 9.32 (s, 1H).

Example 344

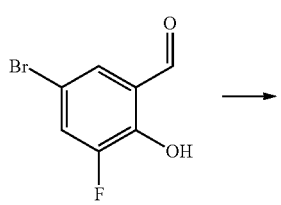

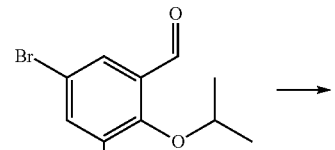

344A

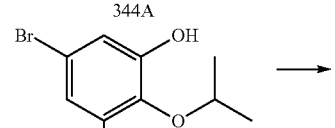

344B

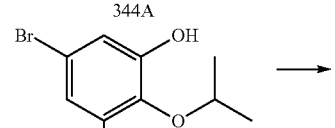

344C

-continued

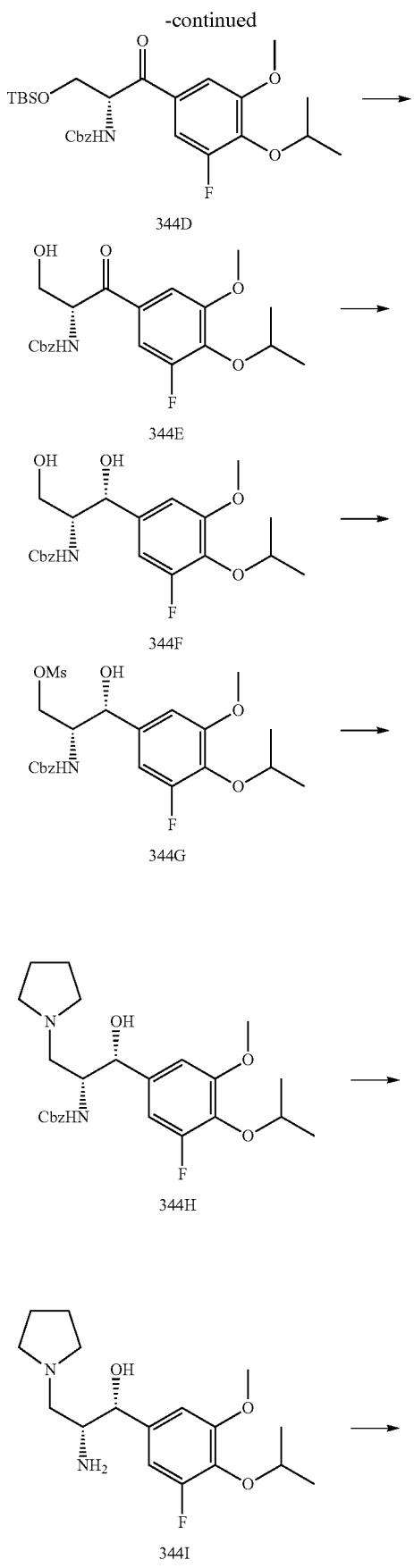

344D

344E

344F

344G

344H

344I

-continued

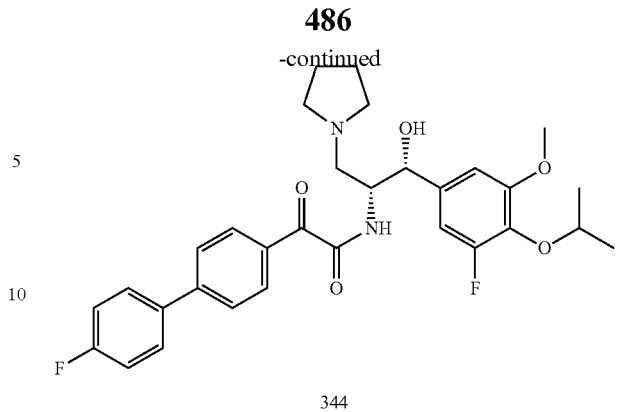

344

To a mixture of 5-bromo-3-fluoro-2-hydroxybenzaldehyde (21.8 g, 100 mol) and K₂CO₃ (110 g, 800 mol) in DMF (400 mL) was added 2-iodopropane (20 mL, 200 mol). The mixture was stirred at 70° C. for 4 h. It was cooled to room temperature and filtered. The cake was washed with ethyl acetate (50 mL). The filtrate was diluted with water (900 mL) and extracted with ethyl acetate (400 mL×3). The organic layer was washed with water (900 mL×5) and brine (900 mL), dried over anhydrous sodium sulfate, concentrated, and purified with flash column chromatography on silica gel on silica (ethyl acetate in petroleum, 10% v/v) to afford Compound 344A.

A mixture of Compound 344A (4.3 g, 16.5 mol) and m-chloroperoxybenzoic acid (5.7 g, 33 mole) in methylene chloride (40 mL) was refluxed under nitrogen overnight. The cooled mixture was filtered and the precipitate was washed with methylene chloride. The combined filtrate and washing were washed with aq. sodium bicarbonate (40 mL×3) and NaCl (40 mL) and concentrated to give a solid. The solid was dissolved in MeOH (27 mL). A solution of 10% NaOH (9 mL) was added with cooling. After stirring for 45 min at room temperature, the mixture was concentrated and 5% NaOH (100 mL) was added. The solution was washed with ether (80 mL×2). The basic solution was acidified with con. HCl and extracted with ether (80 mL×2). The ether extracts were washed with aq. sodium bicarbonate (100 mL×3), dried over MgSO₄, and concentrated to give the crude Compound 344B.

To a mixture of Compound 344B (4.2 g, 17 mol) and K₂CO₃ (3.5 g, 26 mol) in DMF (60 mL) was added iodomethane (1.27 mL, 20 mol). The mixture was stirred at 25° C. overnight. It was filtered. The cake was washed with ethyl acetate (10 mL). The filtrate was diluted with water (120 mL) and extracted with ethyl acetate (40 mL×3). The organic layer was washed with water (100 mL×5) and brine (100 mL), dried over anhydrous sodium sulfate, concentrated, and purified with flash column chromatography on silica gel on silica (ethyl acetate in petroleum, 5% v/v) to afford Compound 344C.

To a solution of Compound 344C (6.37 g, 24 mmol) in THF (70 mL) was added n-BuLi (2.4 M, 10 mL, 24 mmol) under nitrogen at −60° C. It was stirred at −60° C. for 0.5 h. And then it was added a solution of Compound A4 (3.21 g, 8 mmol) in THF (20 mL). The mixture was stirred at −60° C. for 0.5 h, quenched with saturated ammonium chloride solution (50 mL), extracted with ethyl acetate (60 mL×3), washed with brine (100 mL), dried over anhydrous sodium sulfate, and purified with flash column chromatography on silica gel (ethyl acetate in petroleum ether, 10% v/v) to furnish Compound 344D.

487

To a solution of Compound 344D (3.89 g, 7.5 mmol) in THF (30 mL) was added TBAF (1 M, 2.2 mL) which had been adjusted to pH 6-7 with CH₃COOH. The mixture was stirred at 35° C. for 16 h. Water (50 mL) was added. It was extracted with ethyl acetate (50 mL×3). The organic layer was washed with brine (50 mL), dried over anhydrous sodium sulfate, concentrated, and purified with flash column chromatography on silica gel (ethyl acetate in petroleum ether, 30% v/v) to yield Compound 344E.

To a solution of Compound 344E (1.54 g, 3.70 mmol) in dry THF (35 mL) was added DIBAL-H (1.5 M, 5 mL, 7.5 mmol) slowly dropwise under nitrogen at −60° C. It was stirred at −65° C. for 0.5 h. And then DIBAL-H (1.5 M, 5 mL, 7.5 mmol) was added to the reaction. It was stirred at −65° C. for another 0.5 h. A solution of HCl (2 M) was added to quench the reaction. It was extracted with ethyl acetate (50 mL), washed with brine (40 mL×2), dried over anhydrous sodium sulfate, and concentrated to yield a crude product. It was purified with flash column chromatography on silica gel (methanol in dichloromethane, 5% v/v) to yield Compound 344F.

To a solution of Compound 344F (1.04 g, 2.56 mmol) and triethylamine (0.7 mL, 5.12 mmol) in dichloromethane (30 mL) was added MsCl (0.22 mL, 2.81 mmol) at −30° C. and the resultant mixture was stirred at −30° C. for 2 h. It was treated with water (20 mL). The organic layer was washed with water (40 mL×2) and brine (50 mL), dried over anhydrous sodium sulfate, and concentrated to furnish Compound 344G.

To a solution of Compound 344G (1.2 g, 2.5 mmol) in THF (20 mL) was added pyrrolidine (2.3 mL, 25 mmol). The mixture was stirred at 50° C. overnight. It was treated with water (20 mL), extracted with ethyl acetate (10 mL×3), washed with brine (30 mL×1), dried over anhydrous sodium sulfate, and concentrated in vacuo to give a crude product. It was purified with flash column chromatography on silica gel (methanol in dichloromethane, 20% v/v) to yield Compound 344H.

To a solution of Compound 344H (840 mg, 1.8 mmol) in MeOH (30 mL) was added 10% Pd(OH)₂ (150 mg). The solution was stirred under H₂ atmosphere at 25° C. for 24 h. The solution was filtered. The filtrate was concentrated to yield the crude Compound 344I.

A mixture of Compound 344I (72 mg, 0.22 mmol), Compound 133D (49 mg, 0.20 mmol), and HATU (91 mg, 0.24 mmol) in DMF (4 mL) was stirred at 20° C. for 15 h. It was purified with prep-HPLC to give Compound 344. LC-MS (ESI) m/z: 553 [M+H]⁺; ¹H-NMR ((CD₃)₂CO, 400 MHz): δ (ppm) 1.22 (t, J=6.4 Hz, 6H), 2.08-2.17 (m, 2H), 2.25 (s, 2H), 2.49 (s, 3H), 3.74 (s, 3H), 3.85 (s, 1H), 3.90-4.03 (m, 3H), 4.32-4.38 (m, 1H), 4.91 (s, 1H), 5.23 (s, 1H), 6.90 (dd, J=11.2 Hz, J₂=1.6 Hz, 1H), 7.01 (s, 1H), 7.29 (t, J=8.8 Hz, 2H), 7.76 (d, J=8.8 Hz, 2H), 7.80-7.84 (m, 2H), 7.98 (d, J=8.4 Hz, 2H), 8.15 (d, J=10 Hz, 1H), 9.52 (brs, 1H).

Example 345

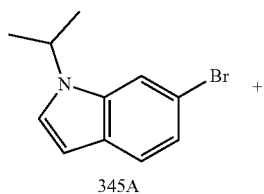

345A

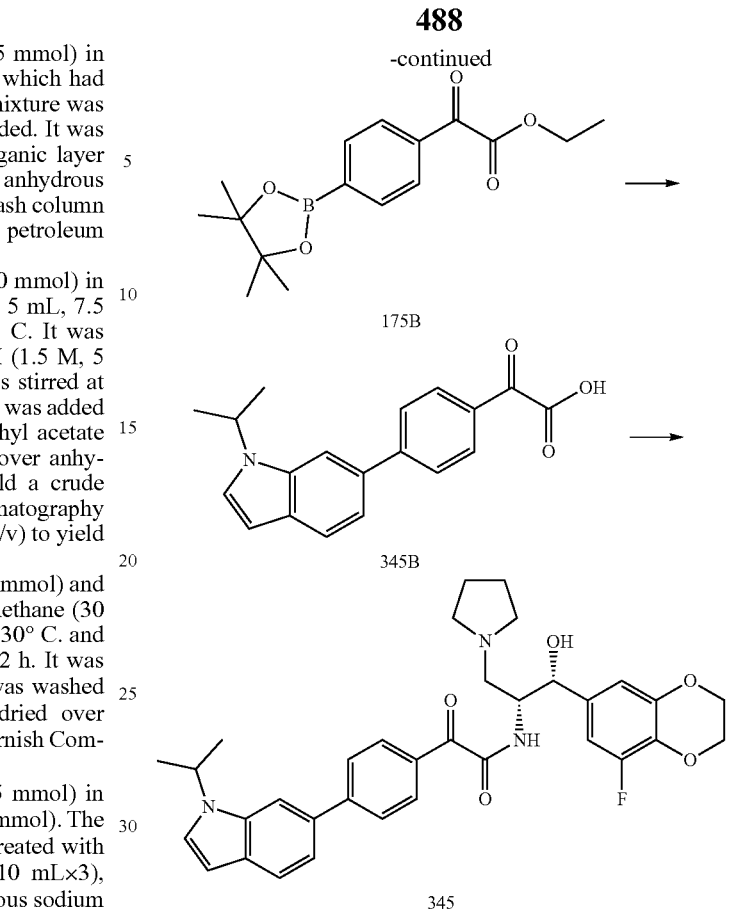

A mixture of Compound 345A (500 mg, 2.1 mmol), Pd(dppf)Cl₂ (86 mg, 0.1 mmol), ethyl 2-oxo-2-(4-(4,4,5,5-tetramethyl-1,3,2-dioxaborolan-2-yl)phenyl)acetate 175B (638 mg, 2.1 mmol), and K₂CO₃ (668 mg, 6.3 mmol) in 1,4-dioxane (15 mL) and water (2 mL) was stirred under nitrogen at 100° C. overnight. The mixture was cooled down to room temperature, concentrated, diluted with water (50 mL), and extracted with ethyl acetate (30 mL×3). The aqueous layer was acidified to pH 2 with aqueous HCl solution (1 N) and extracted with dichloromethane (10 mL×3). The dichloromethane layer was dried over anhydrous sodium sulfate, filtered to afford Compound 345B/dichloromethane solution. The solution of Compound 345B in dichloromethane was directly used for the next step without further purification.

To a solution of Compound 345B in dichloromethane (15 mL, from previous step) and DMF (3 mL) was added Intermediate C (155 mg, 0.5 mmol) and HATU (380 mg, 1 mmol). The mixture was stirred at room temperature overnight. The mixture was concentrated and the resulting residue was purified with prep-HPLC to furnish Compound 345. LC-MS (ESI) m/z: 586 [M+H]⁺; ¹H-NMR (DMSO-d₆, 400 MHz): δ (ppm) 1.49-1.51 (m, 6H), 1.88-1.89 (m, 2H), 2.02-2.03 (m, 2H), 3.12-3.21 (m, 2H), 3.60-3.62 (m, 4H), 4.25-4.29 (m, 4H), 4.50-4.54 (m, 1H), 4.79 (s, 1H), 4.90-4.97 (m, 1H), 6.04 (s, 1H), 6.52-6.52 (m, 1H), 6.78 (s, 1H), 6.82-6.85 (m, 1H), 7.43-7.45 (m, 1H), 7.61-7.62 (m, 1H), 7.66-7.68 (m, 1H), 7.88-7.94 (m, 5H), 8.74-8.76 (m, 1H), 9.32 (brs, 1H).

Example 346

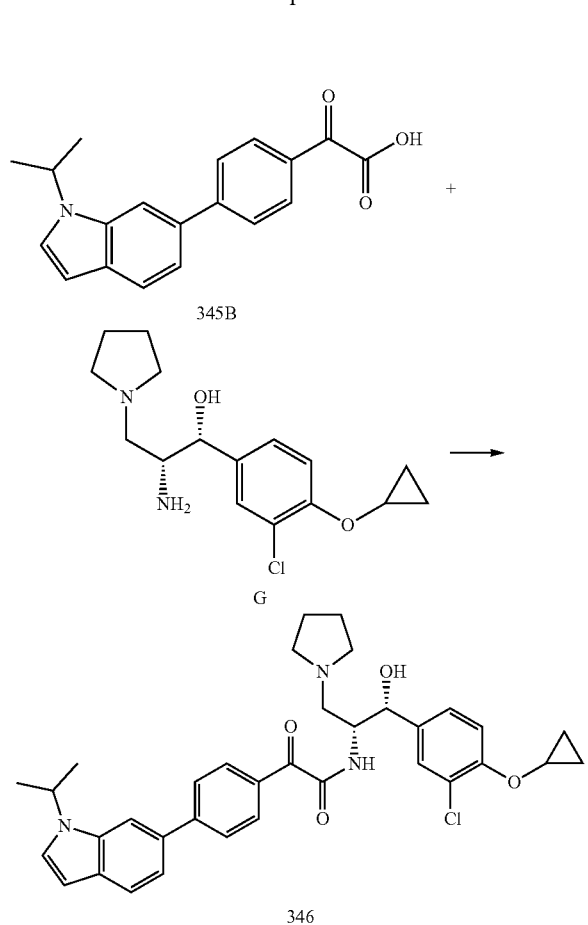

To a solution of Compound 346B in dichloromethane (15 mL, from the previous step) was added Intermediate G (155 mg, 0.5 mmol) and HATU (380 mg, 1 mmol). The mixture was stirred at room temperature overnight. The mixture was concentrated and the resulting residue was purified with prep-HPLC to furnish Compound 346. LC-MS (ESI) m/z: 600 [M+H]+; $^1$H-NMR (DMSO-d$_6$, 400 MHz): δ (ppm) 0.68-0.70 (m, 2H), 0.82-0.83 (m, 2H), 1.49-1.52 (m, 6H), 1.89-1.90 (m, 2H), 2.03-2.04 (m, 2H), 3.13-3.22 (m, 2H), 3.55-3.59 (m, 4H), 3.94-3.98 (m, 1H), 4.57-4.62 (m, 1H), 4.91-4.95 (m, 2H), 6.06-6.07 (m, 1H), 6.52-6.53 (m, 1H), 7.36-7.46 (m, 4H), 7.62-7.73 (m, 4H), 7.84-7.86 (m, 2H), 7.92 (s, 1H), 8.82-8.84 (m, 1H), 9.52 (brs, 1H).

Example 347

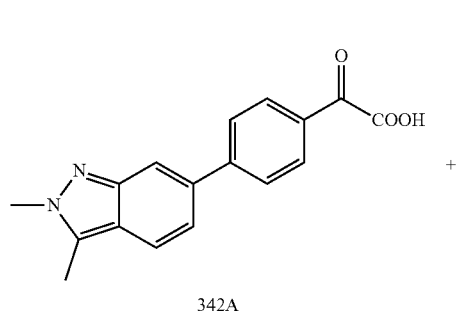

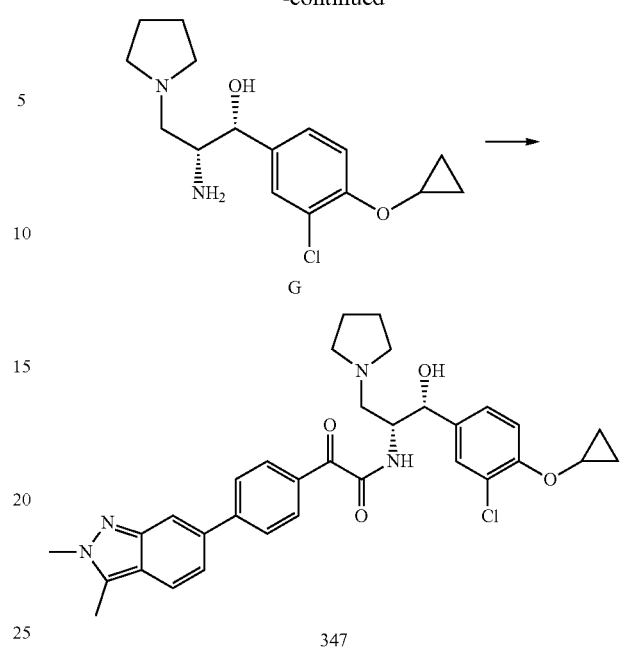

A mixture of Compound 342A (70 mg, 0.24 mmol), HATU (137 mg, 0.36 mmol), DIPEA (0.04 mL, 0.24 mmol), and Intermediate G (75 mg, 0.24 mmol) in DMF (5 mL) was stirred at 25° C. for 2 h. The mixture was directly purified with prep-HPLC to furnish Compound 347. LC-MS (ESI) m/z: 587 [M+H]+; $^1$H-NMR (DMSO-d$_6$, 400 MHz): δ (ppm) 0.68-0.85 (m, 4H), 1.89-2.04 (m, 4H), 2.65 (s, 3H), 3.11-3.24 (m, 2H), 3.47-3.57 (m, 4H), 3.92-3.97 (m, 1H), 4.09 (s, 3H), 4.56-4.60 (m, 1H), 4.88 (s, 1H), 7.35-7.39 (m, 2H), 7.42-7.46 (m, 2H), 7.75-7.84 (m, 5H), 7.89 (s, 1H), 8.82 (d, J=9.6 Hz, 1H), 9.34 (brs, 1H).

Example 348

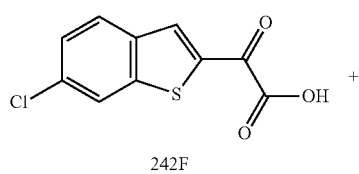

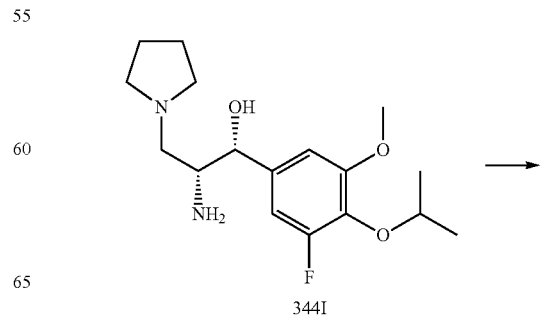

-continued

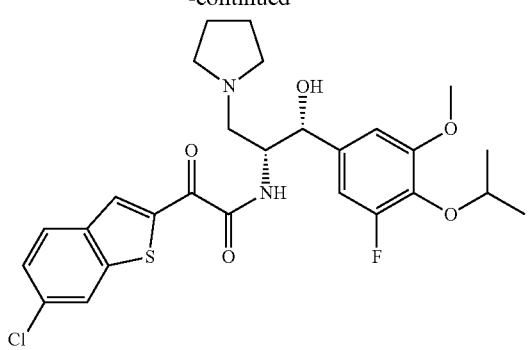

348

A mixture of Compound 344I (72 mg, 0.22 mmol), Compound 242F (48 mg, 0.20 mmol), and HATU (91 mg, 0.24 mmol) in DMF (4 mL) was stirred at 20° C. for 15 h. It was purified with prep-HPLC to give Compound 348. LC-MS (ESI) m/z: 549 [M+H]$^+$; $^1$H-NMR ((CD$_3$)$_2$CO, 400 MHz): δ (ppm) 1.34 (dd, J$_1$=15.2 Hz, J$_2$=10.4 Hz, 6H), 2.22 (s, 2H), 2.97 (s, 3H), 3.45 (s, 2H), 3.78-3.81 (m, 4H), 3.95 (s, 3H), 4.23-4.29 (m, 1H), 4.86 (s, 1H), 5.17 (s, 1H), 6.86 (dd, J$_1$=10.8 Hz, J$_2$=1.6 Hz, 1H), 6.98 (s, 1H), 7.51 (dd, J$_1$=8.8 Hz, J$_2$=2 Hz, 1H), 8.09-8.17 (m, 3H), 8.60 (s, 1H), 9.83 (brs, 1H).

Example 349

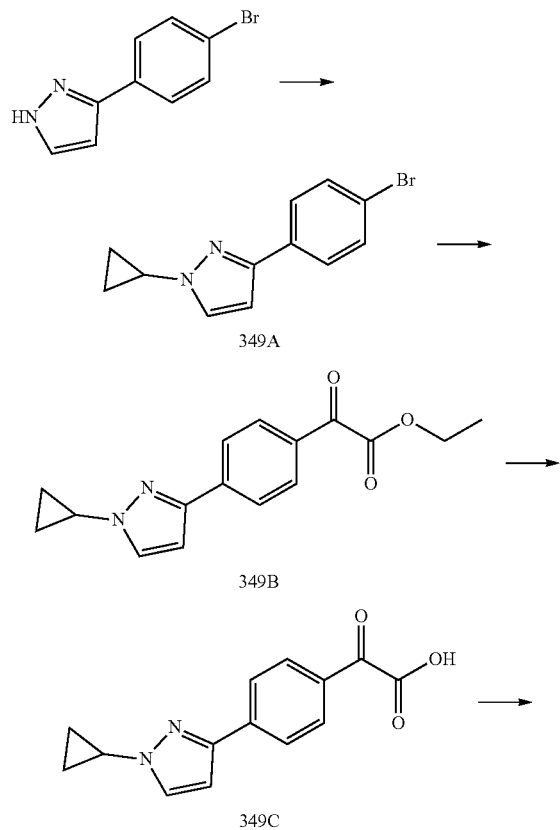

-continued

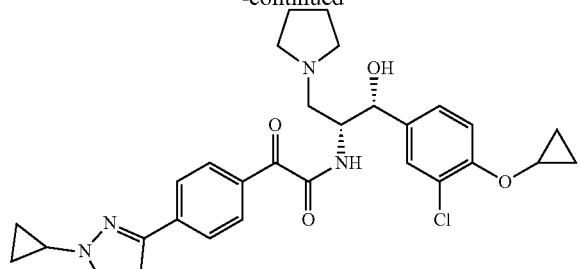

349

A mixture of 3-(4-bromophenyl)-1H-pyrazole (1.0 g, 4.5 mmol), cyclopropylboronic acid (0.8 g, 9 mmol), Cu(OAc)$_2$ (1.6 g, 9 mmol), Na$_2$CO$_3$ (0.9 g, 9 mmol), bipyridine (1.4 g, 9 mmol), and 4 Å molecular sieve powder (5 g) in 1,2-dichloroethane (20 mL) was stirred at 30° C. for 72 h. After filtration, the mixture was diluted with dichloromethane (50 mL), washed with water (30 mL×2) and brine (50 mL), dried over anhydrous sodium sulfate, and concentrated to give a crude compound. The crude product was purified with flash column chromatography on silica gel (ethyl acetate in petroleum ether, from 0% to 10% v/v) to afford Compound 349A.

To a solution of Compound 349A (342 mg, 1.3 mmol) in dry THF (10 mL) was added n-BuLi (2.5 N in hexane, 0.6 mL, 1.5 mmol) under nitrogen at −78° C. The resulting solution was stirred at −78° C. for 30 min and transferred into a stirred solution of diethyl oxalate (0.97 g, 6.6 mmol) in dry THF (5 mL) at this temperature. The solution was stirred at −78° C. for 1 h, quenched with addition of saturated aqueous ammonium chloride solution (10 mL), poured into water (50 mL), and extracted with ethyl acetate (50 mL×2). The combined organic layers were washed with brine (50 mL), dried over anhydrous sodium sulfate, and concentrated in vacuo to give Compound 349B, which was used for the next step without further purification.

A mixture of Compound 349B (0.26 g, 0.9 mmol) and LiOH.H$_2$O (77 mg, 1.8 mmol) in THF (5 mL) and water (2 mL) was stirred at 0° C. for 2 h. The mixture was diluted with ethyl acetate (30 mL), washed with water (10 mL×2) and brine (10 mL), dried over anhydrous sodium sulfate, concentrated, and purified with reverse phase chromatography using eluent (methanol in water, from 0% to 100% v/v) to afford Compound 349C.

A mixture of Compound 349D (77 mg, 0.3 mmol), HATU (200 mg, 0.5 mmol), and Intermediate G (93 mg, 0.3 mmol) in dichloromethane (5 mL) was stirred at 25° C. for 16 h. The mixture was diluted with ethyl acetate (30 mL), washed with water (10 mL×2) and brine (10 mL), dried over anhydrous sodium sulfate, and concentrated to yield a crude compound. The crude product was purified with prep-HPLC to furnish Compound 349. LC-MS (ESI) m/z: 549 [M+H]$^+$; $^1$H-NMR (DMSO-d$_6$, 400 MHz): δ (ppm) 0.69-0.71 (m, 2H), 0.83-0.84 (m, 2H), 1.01-1.03 (m, 2H), 1.11-1.12 (m, 2H), 1.88-1.89 (m, 2H), 2.02-2.04 (m, 2H), 3.12-3.21 (m, 2H), 3.48-3.55 (m, 4H), 3.77-3.84 (m, 1H), 3.92-3.97 (m, 1H), 4.57 (s, 1H), 4.87 (s, 1H), 6.01-6.10 (m, 1H), 6.82-6.83 (m, 1H), 7.35-7.45 (m, 3H), 7.72-7.74 (m, 2H), 7.87-7.91 (m, 3H), 8.77 (d, J=10 Hz, 1H), 9.32 (s, 1H).

Example 350

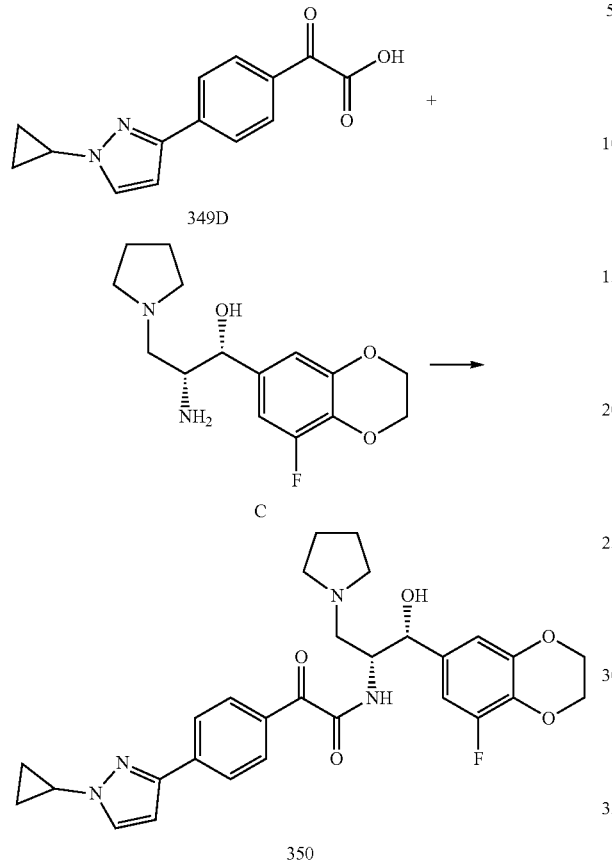

A mixture of Compound 349D (77 mg, 0.3 mmol), HATU (200 mg, 0.5 mmol), and Intermediate C (89 mg, 0.3 mmol) in dichloromethane (5 mL) was stirred at 25° C. for 16 h. The mixture was diluted with ethyl acetate (30 mL), washed with water (10 mL×2) and brine (10 mL), dried over anhydrous sodium sulfate, and concentrated to yield a crude compound. The crude product was purified with prep-HPLC to furnish Compound 350. LC-MS (ESI) m/z: 535 [M+H]$^+$; $^1$H-NMR (DMSO-d$_6$, 400 MHz): δ (ppm) 1.01-1.03 (m, 2H), 1.10-1.11 (m, 2H), 1.87-1.88 (m, 2H), 2.02-2.03 (m, 2H), 3.10-3.20 (m, 2H), 3.43-3.45 (m, 2H), 3.53-3.56 (m, 2H), 3.78-3.83 (m, 1H), 4.27-4.30 (m, 4H), 4.51-4.53 (m, 1H), 4.77 (s, 1H), 6.76-6.85 (m, 3H), 7.83-7.85 (m, 2H), 7.90-7.93 (m, 3H), 8.73 (d, J=9.6 Hz, 1H), 9.29 (s, 1H).

Example 351

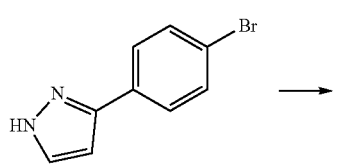

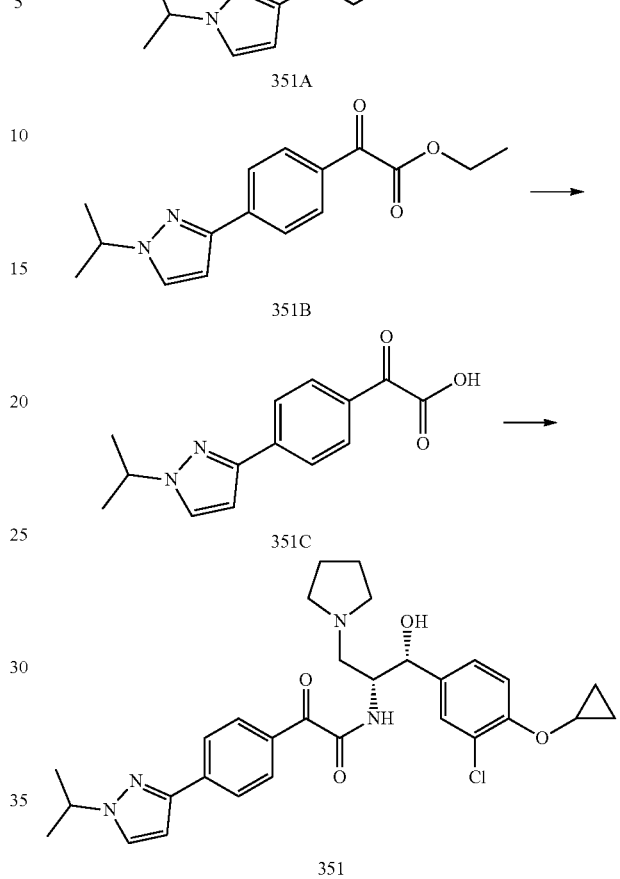

To a solution of 3-(4-bromophenyl)-1H-pyrazole (1.0 g, 4.5 mmol) in DMF (20 mL) was added NaH (198 mg, 5 mmol). The mixture was stirred at 25° C. for 0.5 h and 2-iodopropane (1.53 g, 9 mmol) was added. The mixture was stirred at 25° C. for 2 h. The mixture was diluted with water (30 mL) and extracted with ethyl acetate (50 mL×2). The combined organic layers were washed with brine (50 mL), dried over anhydrous sodium sulfate, and concentrated in vacuo to give a crude compound. The crude product was purified with flash column chromatography on silica gel (ethyl acetate in petroleum ether, from 0% to 10% v/v) to afford Compound 351A.

To a solution of Compound 351A (343 mg, 1.3 mmol) in dry THF (10 mL) was added n-BuLi (2.5 N in hexane, 0.6 mL, 1.5 mmol) under nitrogen at −78° C. The resulting solution was stirred at −78° C. for 30 min and transferred into a stirred solution of diethyl oxalate (0.97 g, 6.6 mmol) in dry THF (5 mL) at this temperature. The solution was stirred at −78° C. for 1 h, quenched with addition of saturated aqueous ammonium chloride solution (10 mL), poured into water (50 mL), and extracted with ethyl acetate (50 mL×2). The combined organic layers were washed with brine (50 mL), dried over anhydrous sodium sulfate, and concentrated in vacuo to give Compound 351B, which was used for the next step without further purification.

A mixture of Compound 351B (0.27 g, 0.9 mmol) and LiOH.H$_2$O (77 mg, 1.8 mmol) in THF (5 mL) and water (2 mL) was stirred at 0° C. for 2 h. The mixture was diluted with ethyl acetate (30 mL), washed with water (10 mL×2) and brine (10 mL), dried over anhydrous sodium sulfate, concentrated, and purified with reverse phase chromatography using eluent (methanol in water, from 0% to 100% v/v) to afford Compound 351C.

A mixture of Compound 351C (77 mg, 0.3 mmol), HATU (200 mg, 0.5 mmol), and Intermediate G (93 mg, 0.3 mmol) in dichloromethane (5 mL) was stirred at 25° C. for 16 h. The mixture was diluted with ethyl acetate (30 mL), washed with water (10 mL×2) and brine (10 mL), dried over anhydrous sodium sulfate, and concentrated to yield a crude compound. The crude product was purified with prep-HPLC to furnish Compound 351. LC-MS (ESI) m/z: 551 [M+H]$^+$; $^1$H-NMR (DMSO-d$_6$, 400 MHz): δ (ppm) 0.70-0.71 (m, 2H), 0.83-0.84 (m, 2H), 1.47 (s, 3H), 1.48 (s, 3H), 1.89-1.90 (m, 2H), 2.04-2.05 (m, 2H), 3.12-3.21 (m, 2H), 3.48-3.51 (m, 4H), 3.94 (s, 1H), 4.56-4.58 (m, 2H), 4.88 (s, 1H), 6.05-6.07 (m, 1H), 6.82-6.83 (m, 1H), 7.35-7.45 (m, 3H), 7.71-7.73 (m, 2H), 7.88-7.90 (m, 3H), 8.78 (d, J=9.2 Hz, 1H), 9.41 (s, 1H).

Example 352

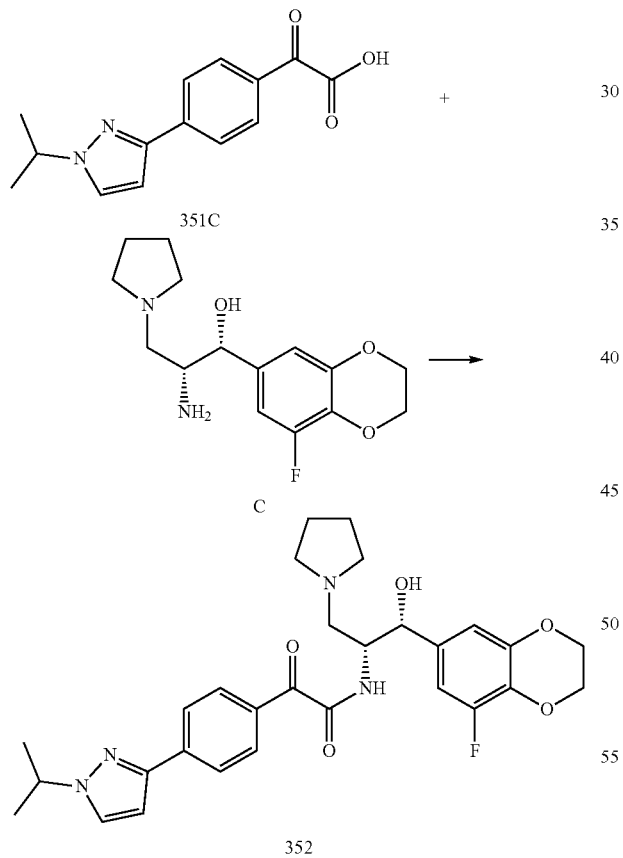

A mixture of Compound 351C (77 mg, 0.3 mmol), HATU (200 mg, 0.5 mmol), and Intermediate C (89 mg, 0.3 mmol) in DMF (5 mL) was stirred at 25° C. for 16 h. The mixture was diluted with ethyl acetate (30 mL), washed with water (10 mL×2) and brine (10 mL), dried over anhydrous sodium sulfate, and concentrated to yield a crude compound. The crude product was purified with prep-HPLC to furnish Compound 352. LC-MS (ESI) m/z: 537 [M+H]$^+$; $^1$H-NMR (DMSO-d$_6$, 400 MHz): δ (ppm) 1.47 (s, 3H), 1.48 (s, 3H), 1.87-1.88 (m, 2H), 2.02-2.03 (m, 2H), 3.12-3.21 (m, 2H), 3.43-3.45 (m, 2H), 3.54-3.56 (m, 2H), 4.27-4.30 (m, 4H), 4.52-4.58 (m, 2H), 4.78 (s, 1H), 6.77-6.85 (m, 3H), 7.83-7.85 (m, 2H), 7.90-7.94 (m, 3H), 8.74 (d, J=9.6 Hz, 1H), 9.29 (s, 1H).

Example 353

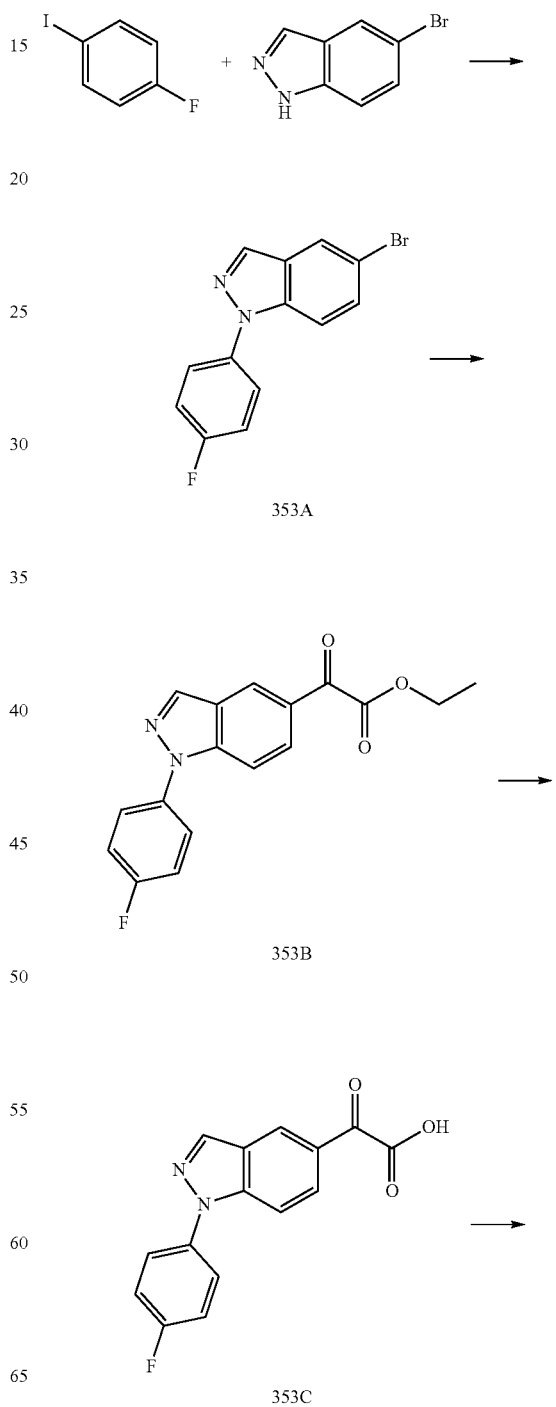

497

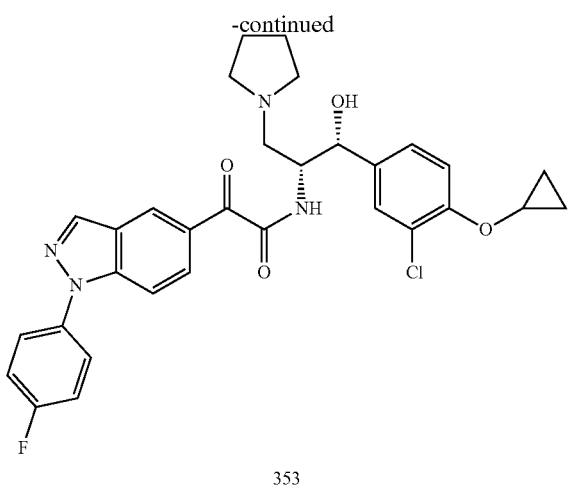

353

A mixture of 1-fluoro-4-iodobenzene (5 g, 23 mmol), 5-bromo-1H-indazole (4.4 g, 23 mmol), CuI (428 mg, 2.3 mmol), L-proline (518 mg, 4.5 mmol), and K₃PO₄ (9.55 g, 45 mmol) in 1,4-dioxane (200 mL) was stirred under nitrogen at reflux for 24 h. The resulting mixture was cooled to room temperature. The mixture was treated with water (200 mL), extracted with ethyl acetate (100 mL×2), washed with sat. sodium bicarbonate (100 mL×2) and brine (100 mL), dried over anhydrous sodium sulfate, concentrated, and purified with flash column chromatography on silica gel (ethyl acetate in petroleum ether, 10% v/v) to furnish Compound 353A.

To a solution of Compound 353A (650 mg, 2.2 mmol) in THF (50 mL) was added dropwise n-BuLi (1.1 mL, 2.7 mmol) under nitrogen at −78° C. The resulting mixture was stirred at −78° C. for 15 min. To the resulting mixture was added diethyl oxalate (1.6 g, 11.2 mmol) as a soon as a quickly. The mixture was stirred at −78° C. for 1 h, quenched with sat. ammonium chloride solution, treated with water (50 mL), extracted with ethyl acetate (50 mL×2), washed with brine (50 mL), dried over anhydrous sodium sulfate, concentrated, and purified with flash column chromatography on silica gel (ethyl acetate in petroleum ether, 10% v/v) to furnish Compound 353B.

To a solution of Compound 353B (130 mg, 0.42 mmol) in THF (5 mL) was added dropwise LiOH.H₂O (35 mg, 0.83 mmol) in water (2 mL) at −20° C. The resulting mixture was stirred at −20° C. for 1 h. The mixture was adjusted pH to 1 with diluted HCl. The resulting mixture was extracted with ethyl acetate (50 mL×2), and then the organic layer was dried over anhydrous sodium sulfate and concentrated to furnish Compound 353C.

A mixture of Compound 353C (100 mg, 0.35 mmol), Intermediate 353G (109 mg, 0.35 mmol), and HATU (210 mg, 0.53 mmol) in DMF (5 mL) was stirred at room temperature for 12 h. The mixture was treated with water (50 mL), extracted with dichloromethane (20 mL×2), washed with water (20 mL×3) and brine (50 mL), dried over anhydrous sodium sulfate, concentrated, and purified with prep-HPLC to furnish Compound 353. LC-MS (ESI) m/z: 577 [M+H]⁺; ¹H-NMR (DMSO-d₆, 400 MHz): δ (ppm) 0.59-0.81 (m, 4H), 1.86-2.05 (m, 4H), 3.13-3.22 (m, 2H), 3.50-3.57 (m, 4H), 3.89-3.92 (m, 1H), 4.56-4.62 (m, 1H), 4.89 (s, 1H), 6.05-6.06 (m, 1H), 7.34-7.51 (m, 5H), 7.79-7.85 (m, 4H), 7.43 (s, 1H), 8.56 (s, 1H), 8.01 (d, J=9.6 Hz, 1H), 9.39 (s, 1H).

498

Example 354

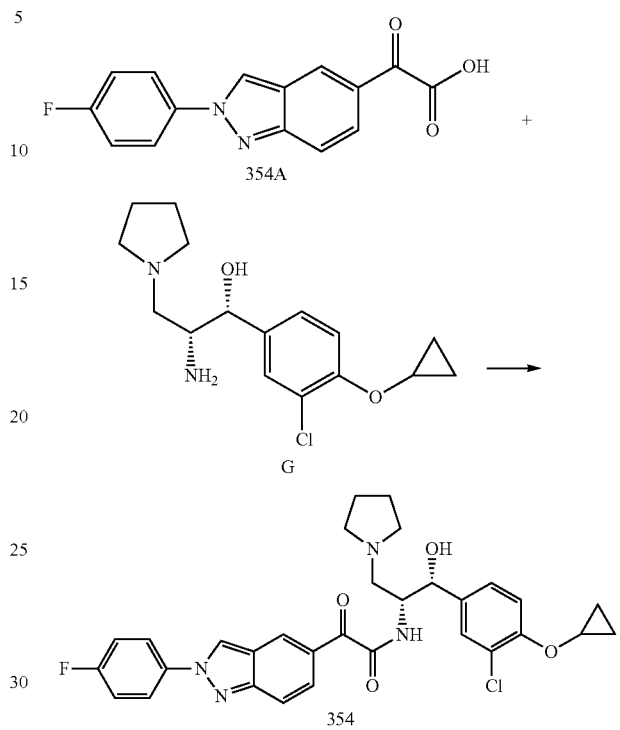

A mixture of Compound 354A (100 mg, 0.35 mmol), Intermediate G (109 mg, 0.35 mmol), and HATU (210 mg, 0.53 mmol) in DMF (5 mL) was stirred at room temperature for 12 h. The mixture was treated with water (50 mL), extracted with dichloromethane (20 mL×2), washed with water (20 mL×3) and brine (50 mL), dried over anhydrous sodium sulfate, concentrated, and purified with prep-HPLC to furnish Compound 354. LC-MS (ESI) m/z: 577 [M+H]⁺; ¹H-NMR (DMSO-d₆, 400 MHz): δ (ppm) 0.61-0.79 (m, 4H), 1.86-2.02 (m, 4H), 3.11-3.18 (m, 2H), 3.45-3.53 (m, 4H), 3.85-3.89 (m, 1H), 4.45-4.50 (m, 1H), 4.81 (s, 1H), 6.01 (s, 1H), 6.93 (d, J=9.2 Hz, 1H), 7.25-7.39 (m, 7H), 7.73-7.76 (m, 1H), 8.27-8.28 (d, J=2.0 Hz, 1H), 8.63 (d, J=9.6 Hz, 1H), 9.21 (s, 1H), 9.30 (s, 1H).

Example 355

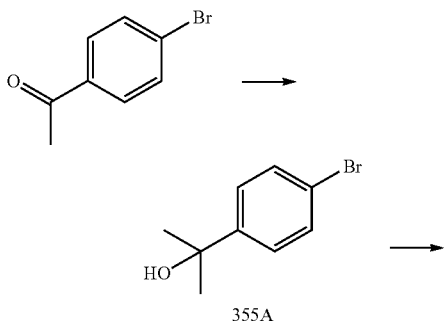

355A

499
-continued

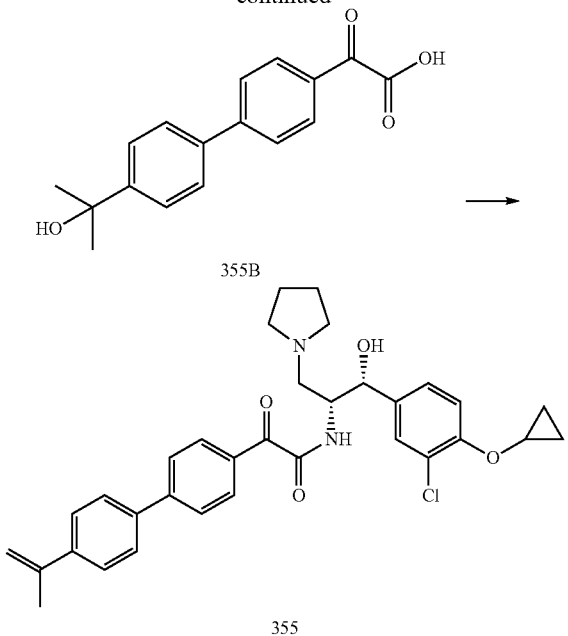

A mixture of 1-(4-bromophenyl)ethan-1-one (2.0 g, 10 mmol) in tetrahydrofuran (30 mL) was maintained at −70° C., and methylmagnesium bromide (3 M, 6.7 mL) was added at −70° C. The reaction mixture was stirred at −78° C. for 0.5 h. The reaction mixture was treated with water (30 mL) and extracted with ethyl acetate (50 mL×2). The combined organic layers were washed with brine (15 mL), dried over anhydrous sodium sulfate, filtered, and concentrated. The remaining residue was purified with flash column chromatography on silica gel (ethyl acetate in petroleum ether, from 10% to 25% v/v) to furnish Compound 355A.

A mixture of Compound 175B (616 mg, 2 mmol), Compound 355A (428 mg, 2 mmol), [1,1'-bis(diphenylphosphino)ferrocene]dichloropalladium(II) (168 mg, 0.2 mol), sodium carbonate (424 mg, 4 mmol), water (0.5 mL), and 1,4-dioxane (5 mL) was stirred under nitrogen atmosphere at 80° C. for 2 h. After cooling, the reaction mixture was treated with water (30 mL), washed with ethyl acetate (30 mL×3), adjusted pH to 2.0 with hydrochloric acid (1 M), extracted with ethyl acetate (20 mL×3), washed with brine (5 mL), dried over anhydrous sodium sulfate, filtered, and concentrated to furnish Compound 355B.

A mixture of Compound 355B (100 mg, 0.35 mmol), Intermediate G (108 mg, 0.35 mmol), and HATU (266 mg, 0.70 mmol) in DMF (3.5 mL) was stirred at 25° C. for 2 h. The mixture was purified with prep-HPLC directly to furnish Compound 355. LC-MS (ESI) m/z: 559 [M+H]$^+$; $^1$H-NMR (CDCl$_3$, 400 MHz): δ (ppm) 0.68-0.76 (m, 2H), 0.77-0.88 (m, 2H), 1.68-1.92 (m, 1H), 2.07-2.21 (m, 2H), 2.22 (s, 3H), 2.23-2.28 (m, 1H), 3.33-3.50 (m, 2H), 3.76-3.97 (m, 6H), 4.84-4.90 (m, 1H), 5.18-5.26 (m, 2H), 5.53 (s, 1H), 7.28-7.43 (m, 2H), 7.45-7.57 (m, 1H), 7.67 (d, J=8.4 Hz, 2H), 7.75-7.81 (m, 4H), 7.92-8.01 (m, 2H), 8.21 (d, J=6.0 Hz, 1H), 10.84 (brs, 1H).

Example 356

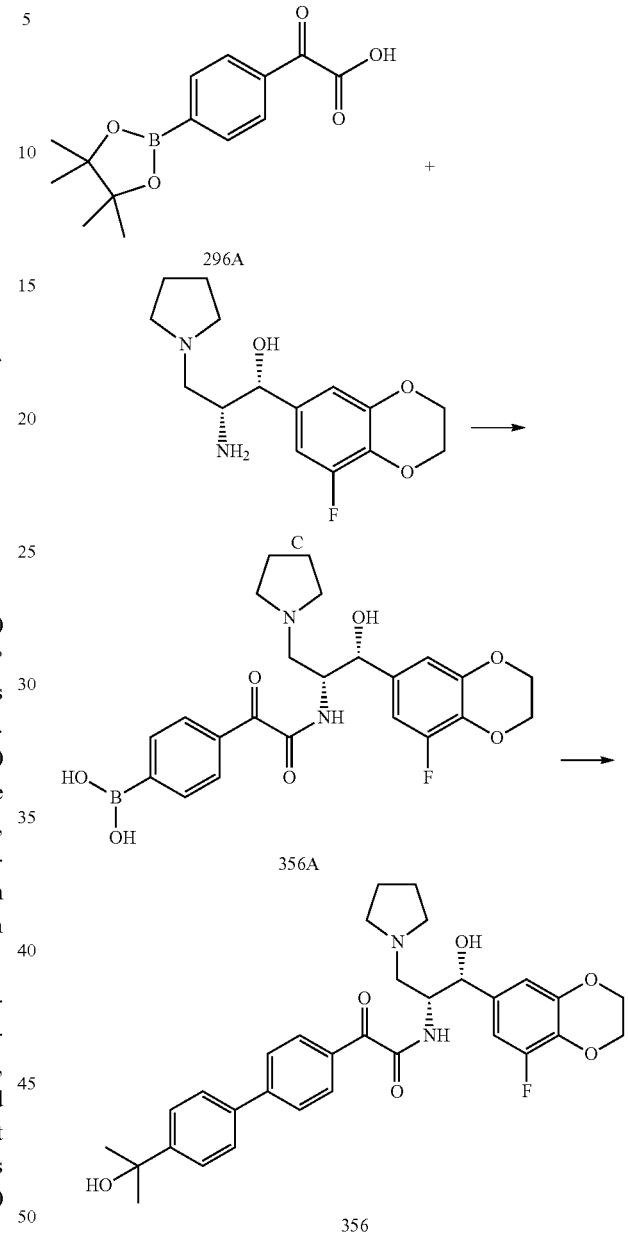

A mixture of Compound 296A (150 mg, 0.54 mmol), Intermediate C (175 mg, 0.59 mmol), and HATU (308 mg, 0.81 mmol) in dichloromethane (5 mL) was stirred at 25° C. overnight. The mixture was quenched with water (10 mL), extracted with dichloromethane (5 mL×2), washed with brine (5 mL), dried over anhydrous sodium sulfate, filtered, and concentrated. The crude product was purified with prep-HPLC to furnish Compound 356A.

A mixture of 2-(4-bromophenyl)propan-2-ol (34 mg, 0.15 mmol), Compound 356A (75 mg, 0.15 mmol), [1,1'-bis(diphenylphosphino)ferrocene]dichloropalladium(II) (7 mg, 8.2 μmol), sodium carbonate (44 mg, 0.30 mmol), water (0.5 mL), and 1,4-dioxane (5 mL) was stirred under nitrogen atmosphere at 80° C. for 2 h. After cooling, the reaction mixture was treated with water (5 mL), extracted with ethyl acetate (10 mL×3), washed with brine (5 mL), dried over anhydrous sodium sulfate, filtered, and concentrated. The residue was purified with prep-HPLC. The solution was adjusted to pH=8.0 with sodium bicarbonate solution, extracted with ethyl acetate (50 mL×2), dried over anhydrous sodium sulfate, filtered, and concentrated to furnish Compound 356. LC-MS (ESI) m/z: 563 [M+H]$^+$; $^1$H-NMR (CDCl$_3$, 400 MHz): δ (ppm) 1.42-1.75 (m, 6H), 1.79-1.86 (m, 4H), 2.74-2.81 (m, 4H), 2.96-3.04 (m, 2H), 4.24-4.31 (m, 6H), 5.05 (d, J=2.4 Hz, 1H), 6.70-6.76 (m, 2H), 7.39 (d, J=8.8 Hz, 1H), 7.75-7.64 (m, 5H), 7.68 (d, J=9.2 Hz, 2H), 8.31 (d, J=8.8 Hz, 2H).

Example 357

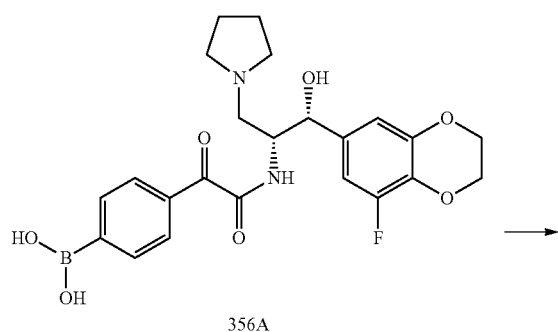

357

A mixture of 1-bromo-4-isopropylbenzene (30 mg, 0.15 mmol), Compound 356A (75 mg, 0.15 mmol), [1,1'-bis (diphenylphosphino)ferrocene]dichloropalladium(II) (7 mg, 8.2 μmol), sodium carbonate (32 mg, 0.30 mmol), water (0.5 mL), and 1,4-dioxane (5 mL) was stirred under nitrogen atmosphere at 80° C. for 2 h. After cooling, the reaction mixture was treated with water (5 mL), extracted with ethyl acetate (10 mL×3), washed with brine (5 mL), dried over anhydrous sodium sulfate, filtered, and concentrated. The residue was purified with prep-HPLC to furnish Compound 357. LC-MS (ESI) m/z: 547 [M+H]$^+$; $^1$H-NMR ((CD$_3$)$_2$CO, 400 MHz): δ (ppm) 1.64 (m, 6H), 2.08-2.11 (m, 3H), 2.17-2.23 (m, 1H), 2.96-3.043 (m, 4H), 3.17-3.82 (m, 4H), 4.21-4.33 (m, 3H), 4.37 (d, 1H), 4.69-5.75 (m, 2H), 6.85-7.07 (m, 2H), 7.35-7.43 (m, 2H), 7.46-7.79 (m, 3H), 7.81-7.87 (m, 1H), 7.89-7.98 (m, 1H), 8.02-8.14 (m, 1H).

Example 358

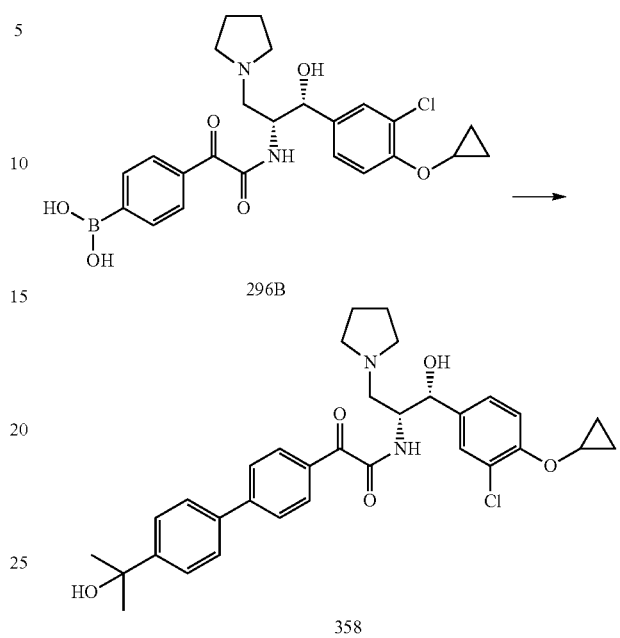

358

A mixture of 2-(4-bromophenyl)propan-2-ol (49 mg, 0.23 mmol), Compound 296B (110 mg, 0.23 mmol), [1,1'-bis (diphenylphosphino)ferrocene]dichloropalladium(II) (8.4 mg, 10 μmol), potassium carbonate (49 mg, 0.46 mmol), water (1 mL), and 1,4-dioxane (5 mL) was heated under nitrogen atmosphere at 100° C. for 2 h. After cooling, water (5 mL) was added, and the mixture was extracted with ethyl acetate (10 mL×3). The combined organic layers were washed with brine (5 mL). The combined organic layers were dried over anhydrous sodium sulfate, filtered, and concentrated to afford the crude product as a black oil. The oil was purified with prep-HPLC. The solution was adjusted to pH=8.0 with sodium bicarbonate solution, extracted with ethyl acetate (50 mL×2), dried over anhydrous sodium sulfate, filtered, and concentrated to furnish Compound 358. LC-MS (ESI) m/z: 577 [M+H]$^+$; $^1$H-NMR (CDCl$_3$, 400 MHz): δ (ppm) 0.76-0.88 (m, 4H), 1.23-1.30 (m, 1H), 1.63 (s, 6H), 1.83-1.88 (m, 4H), 2.01 (s, 1H), 2.73-2.81 (m, 5H), 2.97-3.03 (m, 2H), 3.74-3.79 (m, 1H), 4.33 (d, J=4.4 Hz, 1H), 5.11 (d, J=2.4 Hz, 1H), 7.21-7.28 (m, 1H), 7.35-7.51 (m, 3H), 7.57-7.63 (m, 4H), 7.68 (d, J=7.2 Hz, 2H), 8.26 (d, J=8.8 Hz, 1H).

Example 359

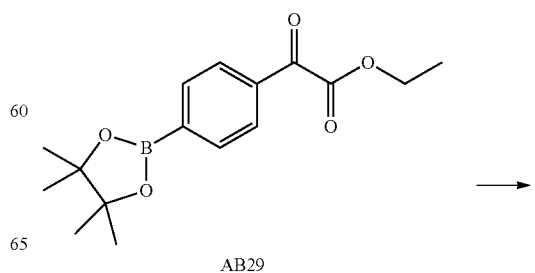

AB29

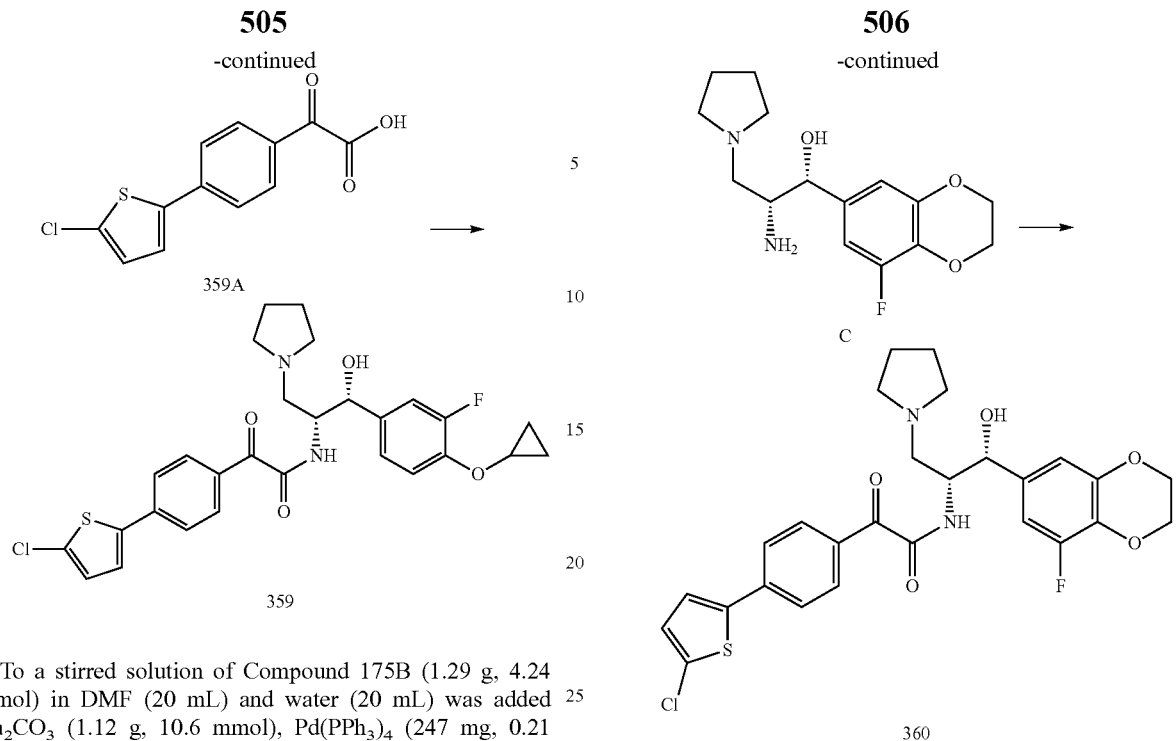

To a stirred solution of Compound 175B (1.29 g, 4.24 mmol) in DMF (20 mL) and water (20 mL) was added Na₂CO₃ (1.12 g, 10.6 mmol), Pd(PPh₃)₄ (247 mg, 0.21 mmol), and 2-bromo-5-chlorothiophene (838 mg, 4.24 mmol). The mixture was stirred under nitrogen at 90° C. for 16 h. The reaction mixture was cooled to room temperature and purified with reverse phase chromatography using eluent (methanol in water (include 0.05% of NH₃.H₂O), from 0% to 40% v/v) to afford Compound 359A.

To a solution of Intermediate S (55 mg, 0.22 mmol) in dichloromethane (10 mL) was added Compound 359A (50 mg, 0.18 mmol) and HATU (107 mg, 0.28 mmol). The mixture was stirred under nitrogen at room temperature overnight. The resulting mixture was quenched with saturated aqueous sodium bicarbonate solution (5 mL) and extracted with ethyl acetate (50 mL×3). The combined organic phases were washed with water (5 mL) and brine (5 mL), dried over anhydrous sodium sulfate, filtered, and concentrated to afford a crude compound. The crude product was purified with prep-HPLC to furnish Compound 359. LC-MS (ESI) m/z: 543 [M+H]⁺; ¹H-NMR (DMSO-d₆, 400 MHz): δ (ppm) 0.68-0.70 (m, 2H), 0.79-0.81 (m, 2H), 1.87-1.90 (m, 2H), 2.02-2.04 (m, 2H), 3.12-3.18 (m, 2H), 3.45-3.55 (m, 4H), 3.92-3.95 (m, 1H), 4.51-4.53 (m, 1H), 4.85 (d, J=2.4 Hz, 1H), 6.05 (d, J=4.4 Hz, 1H), 7.19 (t, J=8.8 Hz, 2H), 7.28 (d, J=4.0 Hz, 1H), 7.39 (t, J=8.8 Hz, 1H), 7.63 (d, J=4.0 Hz, 1H), 7.74 (d, J=8.4 Hz, 2H), 7.83 (d, J=8.4 Hz, 2H), 7.75 (d, J=9.6 Hz, 1H), 9.31 (s, 1H).

Example 360

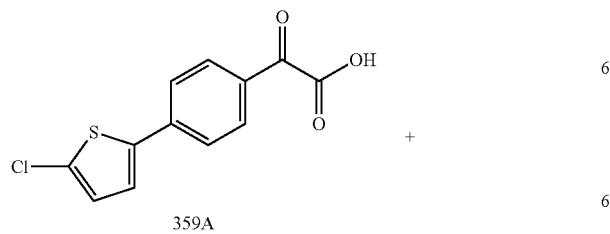

To a solution of Intermediate C (100 mg, 0.34 mmol) in dichloromethane (10 mL) was added Compound 359A (75 mg, 0.28 mmol) and HATU (160 mg, 0.42 mmol). The mixture was stirred under nitrogen at room temperature overnight. The resulting mixture was quenched with saturated aqueous sodium bicarbonate solution (5 mL) and extracted with ethyl acetate (50 mL×3). The combined organic phases were washed with water (5 mL) and brine (5 mL), dried over anhydrous sodium sulfate, filtered, and concentrated to afford a crude compound. The crude product was purified with prep-HPLC to furnish Compound 360. LC-MS (ESI) m/z: 545 [M+H]⁺; ¹H-NMR (DMSO-d₆, 400 MHz): δ (ppm) 1.86-1.88 (m, 2H), 2.01-2.04 (m, 2H), 3.11-3.18 (m, 2H), 3.52-3.54 (m, 4H), 4.28-4.29 (m, 4H), 4.48-4.50 (m, 1H), 4.76 (s, 1H), 6.03 (s, 1H), 6.75 (s, 1H), 6.81 (d, J=11.6 Hz, 1H), 7.27 (d, J=2.0 Hz, 1H), 7.65 (d, J=3.6 Hz, 1H), 7.76 (d, J=8.4 Hz, 2H), 7.87 (d, J=8.4 Hz, 2H), 8.73 (d, J=9.6 Hz, 1H), 9.28 (s, 1H).

Example 361

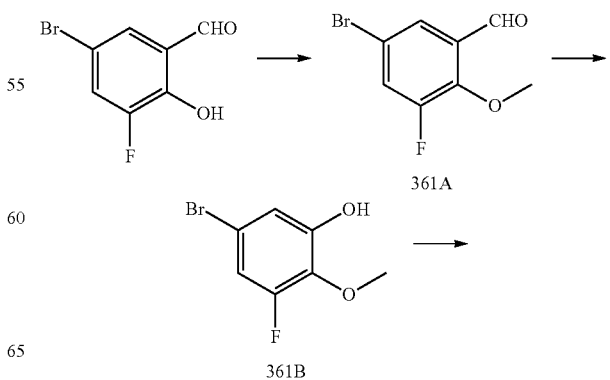

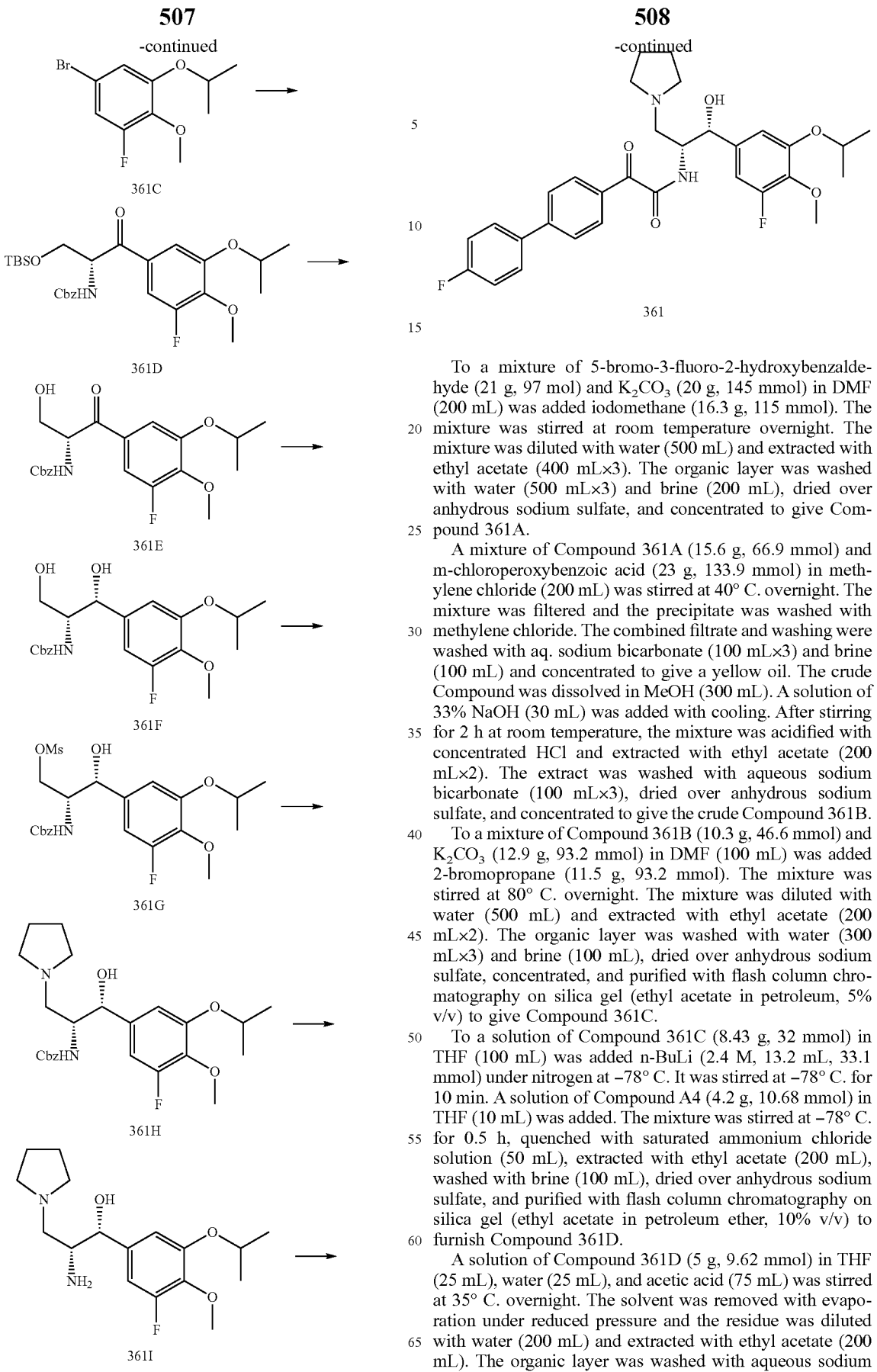

To a mixture of 5-bromo-3-fluoro-2-hydroxybenzaldehyde (21 g, 97 mol) and K$_2$CO$_3$ (20 g, 145 mmol) in DMF (200 mL) was added iodomethane (16.3 g, 115 mmol). The mixture was stirred at room temperature overnight. The mixture was diluted with water (500 mL) and extracted with ethyl acetate (400 mL×3). The organic layer was washed with water (500 mL×3) and brine (200 mL), dried over anhydrous sodium sulfate, and concentrated to give Compound 361A.

A mixture of Compound 361A (15.6 g, 66.9 mmol) and m-chloroperoxybenzoic acid (23 g, 133.9 mmol) in methylene chloride (200 mL) was stirred at 40° C. overnight. The mixture was filtered and the precipitate was washed with methylene chloride. The combined filtrate and washing were washed with aq. sodium bicarbonate (100 mL×3) and brine (100 mL) and concentrated to give a yellow oil. The crude Compound was dissolved in MeOH (300 mL). A solution of 33% NaOH (30 mL) was added with cooling. After stirring for 2 h at room temperature, the mixture was acidified with concentrated HCl and extracted with ethyl acetate (200 mL×2). The extract was washed with aqueous sodium bicarbonate (100 mL×3), dried over anhydrous sodium sulfate, and concentrated to give the crude Compound 361B.

To a mixture of Compound 361B (10.3 g, 46.6 mmol) and K$_2$CO$_3$ (12.9 g, 93.2 mmol) in DMF (100 mL) was added 2-bromopropane (11.5 g, 93.2 mmol). The mixture was stirred at 80° C. overnight. The mixture was diluted with water (500 mL) and extracted with ethyl acetate (200 mL×2). The organic layer was washed with water (300 mL×3) and brine (100 mL), dried over anhydrous sodium sulfate, concentrated, and purified with flash column chromatography on silica gel (ethyl acetate in petroleum, 5% v/v) to give Compound 361C.

To a solution of Compound 361C (8.43 g, 32 mmol) in THF (100 mL) was added n-BuLi (2.4 M, 13.2 mL, 33.1 mmol) under nitrogen at −78° C. It was stirred at −78° C. for 10 min. A solution of Compound A4 (4.2 g, 10.68 mmol) in THF (10 mL) was added. The mixture was stirred at −78° C. for 0.5 h, quenched with saturated ammonium chloride solution (50 mL), extracted with ethyl acetate (200 mL), washed with brine (100 mL), dried over anhydrous sodium sulfate, and purified with flash column chromatography on silica gel (ethyl acetate in petroleum ether, 10% v/v) to furnish Compound 361D.

A solution of Compound 361D (5 g, 9.62 mmol) in THF (25 mL), water (25 mL), and acetic acid (75 mL) was stirred at 35° C. overnight. The solvent was removed with evaporation under reduced pressure and the residue was diluted with water (200 mL) and extracted with ethyl acetate (200 mL). The organic layer was washed with aqueous sodium bicarbonate (100 mL) and brine (100 mL), dried over anhydrous sodium sulfate, concentrated, and purified with flash column chromatography on silica gel (ethyl acetate in petroleum ether, 33% v/v) to yield Compound 361E.

To a solution of Compound 361E (1.6 g, 3.95 mmol) in dry THF (70 mL) was added DIBAL-H (1 M, 15.8 mL, 15.8 mmol) slowly dropwise under nitrogen at −78° C. It was stirred at −78° C. for 1 h. A solution of HCl (2 M, 20 mL) was added to quench the reaction. It was extracted with ethyl acetate (50 mL), washed with brine (40 mL), dried over anhydrous sodium sulfate, and concentrated to yield a crude product. It was purified with flash column chromatography on silica gel (ethyl acetate in petroleum ether, 50% v/v) to give Compound 361F.

To a solution of Compound 361F (1.44 g, 3.53 mmol) and triethylamine (1.07 g, 10.6 mmol) in dichloromethane (30 mL) was added MsCl (445 mg, 3.89 mmol) at −30° C. and the resultant mixture was stirred at −30° C. for 1 h. It was treated with water (100 mL) and dichloromethane (100 mL). The organic layer was washed with water (40 mL×2) and brine (50 mL), dried over anhydrous sodium sulfate, and concentrated to furnish Compound 361G.

To a solution of Compound 361G (1.71 g, 3.6 mmol) in THF (40 mL) was added pyrrolidine (2.61 g, 36 mmol). The mixture was stirred at 50° C. overnight. It was treated with water (100 mL), extracted with ethyl acetate (100 mL×3), washed with brine (100 mL), dried over anhydrous sodium sulfate, and concentrated in vacuo to give a crude product. It was purified with flash column chromatography on silica gel (methanol in dichloromethane, 5% v/v) to give Compound 361H.

To a solution of Compound 361H (1.25 g, 2.71 mmol) in ethanol (24 mL) was added LiOH.H$_2$O (456 mg, 10.86 mmol). The solution was stirred at 80° C. overnight. The mixture was diluted with ethyl acetate (100 mL), washed with water (100 mL) and brine (100 mL), dried over anhydrous sodium sulfate, and concentrated to yield the crude Compound 361I.

A mixture of Compound 361I (100 mg, 0.306 mmol), Intermediate C (69 mg, 0.306 mmol), and HATU (174 mg, 0.459 mmol) in dichloromethane (2 mL) was stirred at room temperature overnight. The mixture was diluted with dichloromethane (50 mL), washed with water (100 mL) and brine (50 mL), dried over anhydrous sodium sulfate, concentrated, and purified with prep-HPLC to give Compound 361. LC-MS (ESI) m/z: 553 [M+H]$^+$; $^1$H-NMR (DMSO-d$_6$, 400 MHz): δ (ppm) 1.17 (d, J=6.0 Hz, 3H), 1.26 (d, J=6.0 Hz, 3H), 1.87-1.93 (m, 2H), 2.01-2.05 (m, 2H), 3.11-3.24 (m, 2H), 3.45-3.57 (m, 4H), 3.77 (s, 3H), 4.49-4.57 (m, 2H), 4.84-4.85 (m, 1H), 6.09 (d, J=4.0 Hz, 1H), 6.85 (d, J=11.6 Hz, 1H), 6.89 (s, 1H), 7.38 (t, J=8.8 Hz, 2H), 7.78-7.87 (m, 6H), 8.77 (d, J=10.0 Hz, 1H), 9.38 (brs, 1H).

Example 362

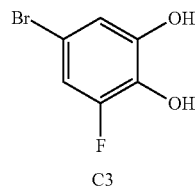

C3

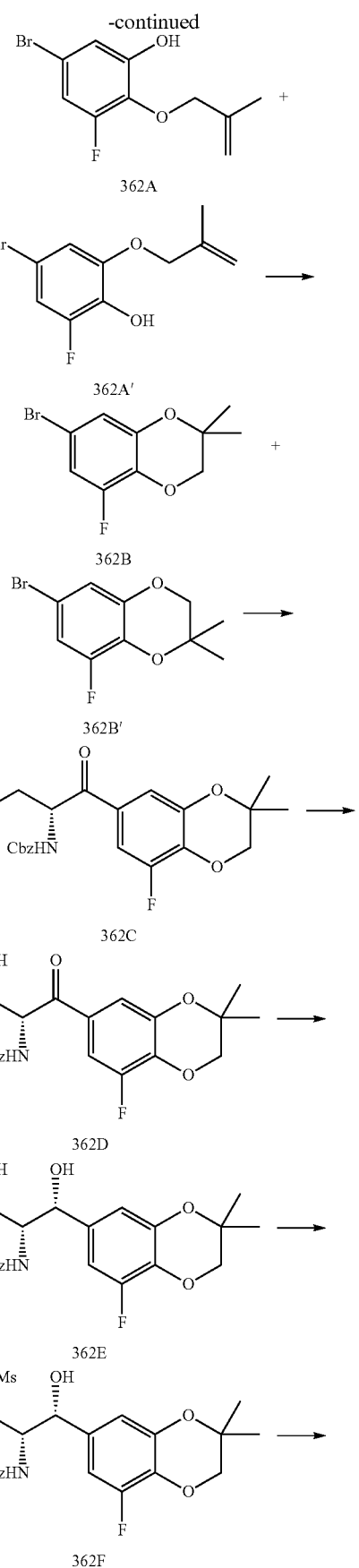

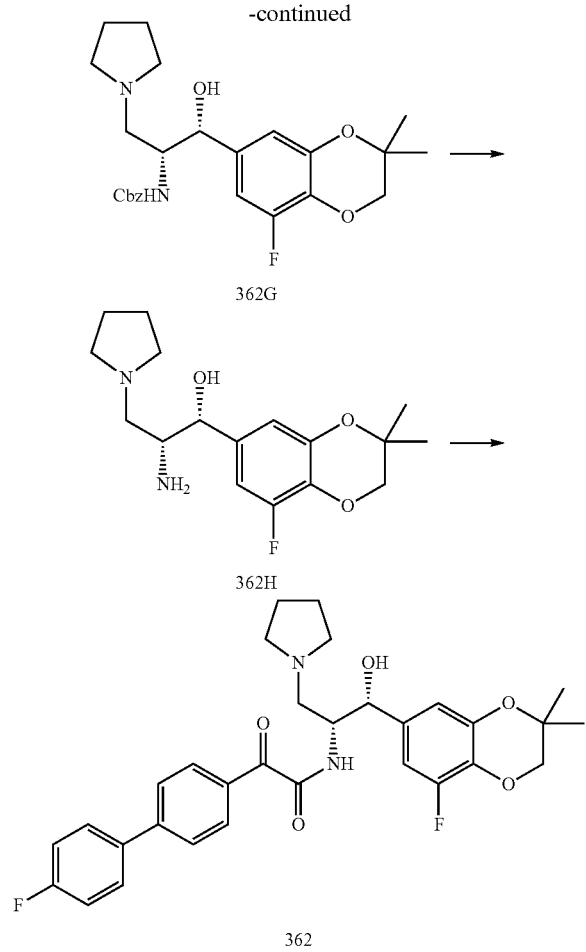

To a mixture of Compound C3 (31 g, 150 mol) and Li$_2$CO$_3$ (22.4 g, 310 mol) in DMF (250 mL) was added 3-bromo-2-methylprop-1-ene (31.9 mL, 310 mol). The mixture was stirred at 55° C. for 48 h, cooled down to room temperature, and filtered. The cake was washed with ethyl acetate (100 mL). The filtrate was diluted with water (500 mL) and extracted with ethyl acetate (200 mL×3). The organic layer was washed with saturated aqueous LiCl solution (100 mL×5), dried over anhydrous sodium sulfate, filtered, and concentrated. The crude product was purified with flash column chromatography on silica gel on silica gel (ethyl acetate in petroleum ether, 5% v/v) to give a mixture of Compound 362A and Compound 362A'.

A solution of Compound 362A and Compound 362A' (23 g, 88.5 mmol) in formic acid (200 mL) was stirred and heated to reflux for 2 h. After removal of the solvent, the residue was diluted with dichloromethane (200 mL). The mixture was carefully adjusted pH to 9 with saturated aqueous sodium bicarbonate solution at 0° C. and extracted with dichloromethane (100 mL×3). The combined organic phases were washed with water (50 mL×2) and brine (50 mL×2), dried over anhydrous sodium sulfate, filtered, and concentrated to afford a crude compound. The crude product was purified with flash column chromatography on silica gel (ethyl acetate in petroleum ether, 10% v/v) to furnish a mixture of Compound 362B and Compound 362B'.

To a solution of Compound 362B and Compound 362B' (3.8 g, 14.6 mmol) in dry THF (80 mL) maintained at −60° C. was dropwise added n-BuLi (2.5 Min hexane, 6.0 mL, 15.1 mmol) under nitrogen atmosphere over a period of 20 minutes. After the reaction mixture was stirred at −60° C. for 40 minutes, a solution of Compound A4 (1.93 g, 4.87 mmol) in dry THF (20 mL) was added slowly. After the completion of addition, the solution was left to stir for 0.5 h at −60° C. The reaction mixture was quenched with saturated aqueous ammonium chloride solution (20 mL) and extracted with ethyl acetate (100 mL×3). The organic phase was washed with brine (20 mL), dried over anhydrous sodium sulfate, filtered, and concentrated to furnish a crude compound. The crude product was purified with flash column chromatography on silica gel (ethyl acetate in petroleum ether, from 5% to 10% v/v) to yield Compound 362C.

A solution of Compound 362C (1.1 g, 2.13 mmol) in a mixture of tetrahydrofuran, water, and glacial acetic acid (25 mL, 1/1/3 v/v/v) was stirred at 35° C. for 16 h. The reaction mixture was concentrated under reduced pressure to remove excess solvent. The residue was poured into ethyl acetate (50 mL) and water (20 mL). The mixture was adjusted to pH 7~8 with saturated aqueous sodium bicarbonate solution and extracted with ethyl acetate (100 mL×3). The combined organic phases were washed with brine (10 mL), dried over anhydrous sodium sulfate, filtered, and concentrated to afford the crude target compound. The crude product was further purified with flash column chromatography on silica gel (ethyl acetate in petroleum ether, 50% v/v) to give Compound 362D.

To a solution of Compound 362D (690 mg, 1.71 mmol) in dry THF (20 mL) maintained at −78° C. was added diisobutylaluminum hydride (1.0 Min toluene, 6.85 mL) dropwise under nitrogen atmosphere over a period of 15 minutes. After the reaction mixture was stirred at −70° C. for 1 h, saturated solution of ammonium chloride solution (10 mL) was added to the mixture slowly. The reaction mixture was extracted with ethyl acetate (50 mL×3), washed with water (10 mL) and brine (10 mL), dried over anhydrous sodium sulfate, filtered, and concentrated to afford the crude target compound. The crude product was further purified with flash column chromatography on silica gel (ethyl acetate in petroleum ether, from 50% to 87% v/v) to furnish Compound 362E.

To a solution of Compound 362E (600 mg, 1.48 mmol) dissolved in dry THF (15 mL) was added triethylamine (0.62 mL, 4.44 mmol). The mixture was cooled to −40° C., and then methanesulfonyl chloride (0.17 mL, 2.22 mmol) was added dropwise. After the addition was complete, the reaction mixture was stirred at −40° C. for 2 h, diluted with water (30 mL), and extracted with ethyl acetate (30 mL×2). The combined organic layers were washed with brine (30 mL), dried over anhydrous sodium sulfate, filtered, and concentrated to afford a crude compound. The crude product was purified with flash column chromatography on silica gel (ethyl acetate in petroleum ether, 50% v/v) to give Compound 362F.

To a solution of Compound 362F (320 mg, 0.66 mmol) in THF (10 mL) was added pyrrolidine (0.55 mL, 6.6 mmol). The reaction mixture was allowed to heat to 50° C. for 16 h. The mixture was diluted with water (10 mL), extracted with ethyl acetate (50 mL×3), washed with water (10 mL) and brine (10 mL), dried over anhydrous sodium sulfate, filtered, and concentrated to furnish a crude compound. The crude product was purified with flash column chromatography on silica gel (methanol in dichloromethane, 8% v/v) to give Compound 362G.

Compound 362G (215 mg, 0.47 mmol) was dissolved in methanol (20 mL), and 20% Pd(OH)$_2$ (45 mg) was added.

The mixture was stirred under hydrogen at room temperature overnight. After filtration, the filtrate was evaporated to give the Compound 362H.

To a solution of Compound 362H (93 mg, 0.29 mmol) in dichloromethane (10 mL) was added Compound 133D (70 mg, 0.29 mmol) and HATU (164 mg, 0.43 mmol). The mixture was stirred under nitrogen at room temperature overnight. The resulting mixture was quenched with saturated aqueous sodium bicarbonate solution (5 mL) and extracted with ethyl acetate (50 mL×3). The combined organic phases were washed with water (5 mL) and brine (5 mL), dried over anhydrous sodium sulfate, filtered, and concentrated to afford a crude compound. The crude product was purified with prep-HPLC to furnish Compound 362. LC-MS (ESI) m/z: 551 [M+H]$^+$; $^1$H-NMR (DMSO-d$_6$, 400 MHz): δ (ppm) 1.23 (s, 3H), 1.28 (s, 3H), 1.88-2.02 (m, 4H), 3.10-3.17 (m, 2H), 3.44-3.54 (m, 4H), 3.98 (s, 2H), 4.50 (s, 1H), 4.77 (s, 1H), 6.01 (d, J=2.8 Hz, 1H), 6.72 (s, 1H), 6.81 (d, J=10.8 Hz, 1H), 7.37 (t, J=8.4 Hz, 2H), 7.80-7.92 (m, 6H), 8.73 (d, J=9.2 Hz, 1H), 9.31 (s, 1H).

Example 363

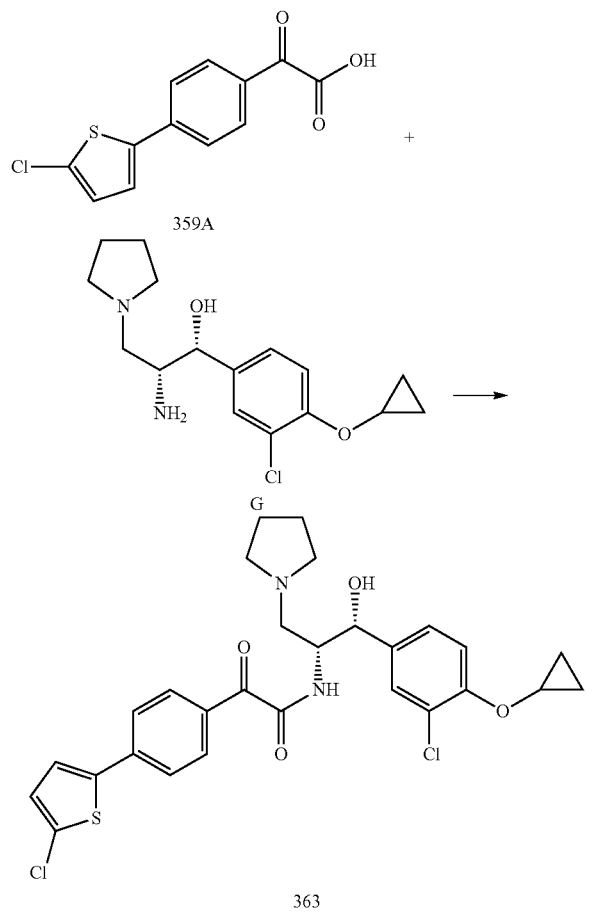

To a solution of Intermediate G (112 mg, 0.36 mmol) in dichloromethane (10 mL) was added Compound 359A (80 mg, 0.30 mmol) and HATU (171 mg, 0.45 mmol). The mixture was stirred under nitrogen at room temperature overnight. The resulting mixture was quenched with saturated aqueous sodium bicarbonate solution (5 mL) and extracted with ethyl acetate (50 mL×3). The combined organic phases were washed with water (5 mL) and brine (5 mL), dried over anhydrous sodium sulfate, filtered, and concentrated to afford a crude compound. The crude product was purified with prep-HPLC to furnish Compound 363. LC-MS (ESI) m/z: 559 [M+H]$^+$; $^1$H-NMR (DMSO-d$_6$, 400 MHz): δ (ppm) 0.68-0.70 (m, 2H), 0.82-0.84 (m, 2H), 1.87-1.91 (m, 2H), 2.02-2.04 (m, 2H), 3.11-3.20 (m, 2H), 3.47-3.55 (m, 4H), 3.92-3.96 (m, 1H), 4.53-4.57 (m, 1H), 4.88 (s, 1H), 6.06 (d, J=3.2 Hz, 1H), 7.27 (d, J=4.0 Hz, 1H), 7.34 (dd, J=8.8, 1.6 Hz, 1H), 7.41 (d, J=8.4 Hz, 1H), 7.43 (d, J=1.6 Hz, 1H), 7.62 (d, J=4.0 Hz, 1H), 7.70-7.76 (m, 4H), 8.78 (d, J=9.6 Hz, 1H), 9.48 (s, 1H).

Example 364

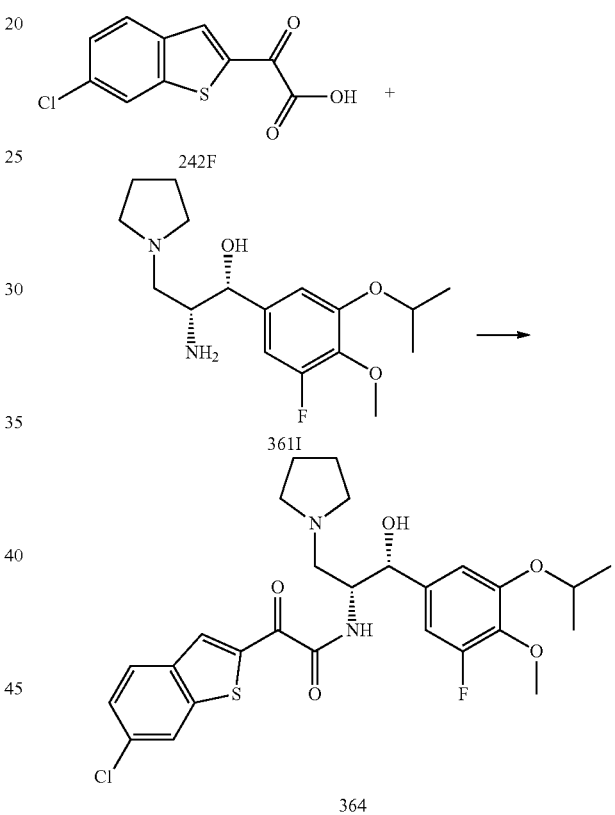

A mixture of Compound 361I (100 mg, 0.306 mmol), Compound 242F (74 mg, 0.306 mmol), and HATU (174 mg, 0.459 mmol) in dichloromethane (2 mL) was stirred at room temperature overnight. The mixture was diluted with dichloromethane (50 mL), washed with water (100 mL) and brine (50 mL), dried over anhydrous sodium sulfate, concentrated, and purified with prep-HPLC to give Compound 364. LC-MS (ESI) m/z: 549 [M+H]$^+$; $^1$H-NMR (DMSO-d$_6$, 400 MHz): δ (ppm) 1.17 (d, J=6.0 Hz, 3H), 1.25 (d, J=6.0 Hz, 3H), 1.81-1.88 (m, 2H), 1.98-2.05 (m, 2H), 3.09-3.20 (m, 2H), 3.40-3.57 (m, 4H), 3.71 (s, 3H), 4.44-4.56 (m, 2H), 4.78-4.80 (m, 1H), 6.10 (d, J=2.0 Hz, 1H), 6.80-6.86 (m, 2H), 7.54 (dd, J$_1$=1.6 Hz, J$_2$=8.4 Hz, 1H), 8.13 (d, J=8.8 Hz, 1H), 8.29 (d, J=2.0 Hz, 1H), 8.55 (s, 1H), 8.60 (d, J=9.6 Hz, 1H), 9.19 (brs, 1H).

Example 365

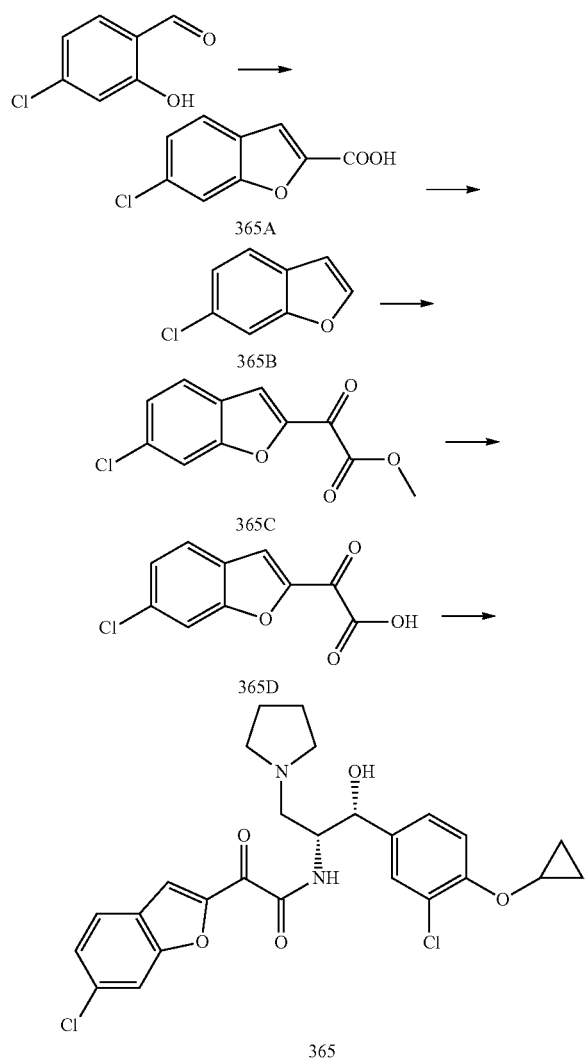

A mixture of 4-chloro-2-hydroxybenzaldehyde (1.56 g, 0.01 mol), diethyl 2-bromomalonate (2.38 g, 0.01 mol), and K$_2$CO$_3$ (1.38 g, 0.01 mol) in 2-butanone (80 mL) was refluxed overnight. After completion of the reaction, the resulting mixture was cooled down to room temperature, poured into water, acidified to pH 2 with dilute aqueous sulfuric acid solution (2 N), and extracted with ether (40 mL×3). After removal of the organic solvent, the residue was dissolved in alcoholic potash (prepared from 20 mL of alcohol and 2 g of solid potassium hydroxide) and refluxed for 2 h. The solvent was concentrated and the residue was dissolved in water (20 mL). The aqueous layer was acidified to pH 2 with dilute aqueous sulfuric acid solution (2 N) and solid was precipitated. The formed solid were collected with filtration, washed with water (20 mL), and dried to afford Compound 365A.

A solution of Compound 365A (1.98 g, 10 mmol) and copper powder (0.4 g) were refluxed in quinoline (20 mL) for 2 h. After cooling down to room temperature, the mixture was diluted with ether (80 mL) and washed with diluted aqueous HCl solution (2 N, 40 mL×3). The organic layer was washed with water (30 mL) and brine (30 mL), dried over anhydrous sodium sulfate, and carefully concentrated at 0° C. to give Compound 365B.

To a solution of Compound 365B (1.53 g, 10 mmol) in THF (30 mL) was added dropwise n-BuLi solution (2.5 M in hexane, 4 mL, 10 mmol) under nitrogen at −78° C. The mixture was stirred at −78° C. for 0.5 h and the above solution was added to a solution of diethyl oxalate (3 g, 20 mmol) in THF (20 mL) under nitrogen at −78° C. The mixture was slowly warmed to room temperature and stirred at room temperature overnight. The mixture was quenched with saturated aqueous ammonium chloride solution (40 mL) and extracted with ethyl acetate (50 mL×3). The combined organic layers were washed with water (100 mL) and brine (100 mL), dried over anhydrous sodium sulfate, and concentrated. The residue was purified with flash column chromatography on silica gel (ethyl acetate in petroleum ether, from 10% to 50% v/v) to furnish Compound 365C.

To a solution of Compound 365C (2.4 g, 10 mmol) in THF/H$_2$O (40 mL/10 mL) was added LiOH H$_2$O (840 mg, 20 mmol). The mixture was stirred at room temperature for about 2 h until completion by thin layer chromatography analysis. The reaction mixture was acidified to pH 2 with diluted aqueous HCl solution (1.0 N, 40 mL) and extracted with ethyl acetate (30 mL×2). The combined organic layers were washed with water (100 mL) and brine (100 mL), dried over anhydrous sodium sulfate, filtered, and concentrated to yield Compound 365D.

To a mixture of Compound 365D (112 mg, 0.5 mmol) and Intermediate G (155 mg, 0.5 mmol) in DMF (5 mL) was added HATU (380 mg, 1 mmol). The reaction mixture was stirred at room temperature overnight. The resulting solution was diluted with ethyl acetate (50 mL), washed with water (30 mL) and brine (30 mL), dried over anhydrous sodium sulfate, filtered, and concentrated. The residue was purified with prep-HPLC to furnish Compound 365. LC-MS (ESI) m/z: 517 [M+H]$^+$; $^1$H-NMR (DMSO-d$_6$, 400 MHz): δ (ppm) 0.63-0.79 (m, 4H), 1.88-1.99 (m, 4H), 3.13-3.21 (m, 2H), 3.38-3.56 (m, 4H), 3.88-3.89 (m, 1H), 4.43-4.45 (m, 1H), 4.78-4.79 (m, 1H), 6.04 (s, 1H), 7.27-7.39 (m, 3H), 7.47-7.49 (m, 1H), 7.93 (d, J=8.4 Hz, 1H), 8.01 (s, 1H), 8.20 (s, 1H), 8.62 (d, J=10.0 Hz, 1H), 9.07 (brs, 1H).

Example 366

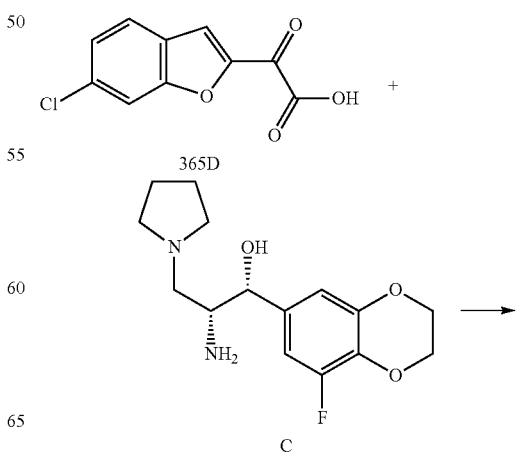

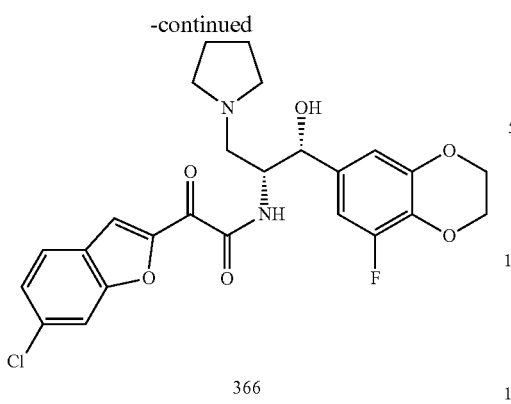

366

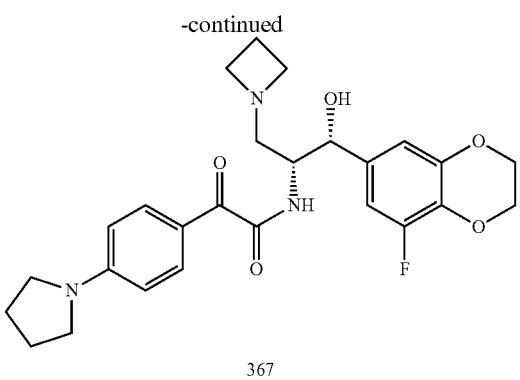

367

To a mixture of Compound 365D (114 mg, 0.5 mmol) and Intermediate C (143 mg, 0.5 mmol) in DMF (5 mL) was added HATU (380 mg, 1 mmol). The reaction mixture was stirred at room temperature overnight. The resulting solution was diluted with ethyl acetate (30 mL), washed with water (30 mL) and brine (30 mL), dried over anhydrous sodium sulfate, filtered, and concentrated. The residue was purified with prep-HPLC to furnish Compound 366. LC-MS (ESI) m/z: 503 [M+H]$^+$; $^1$H-NMR (DMSO-d$_6$, 400 MHz): δ (ppm) 1.84-2.01 (m, 4H), 3.11-3.13 (m, 2H), 3.31-3.54 (m, 4H), 4.23-4.27 (m, 4H), 4.40-4.43 (m, 1H), 4.71 (s, 1H), 6.04 (br s, 1H), 6.72 (s, 1H), 6.77-6.81 (m, 1H), 7.47 (d, J=8.4 Hz, 1H), 7.98 (d, J=8.4 Hz, 1H), 8.02 (s, 1H), 8.26 (s, 1H), 8.60 (d, J=9.6 Hz, 1H), 9.04 (br s, 1H).

A mixture of Compound 273C (66 mg, 0.3 mmol), HATU (200 mg, 0.5 mmol), and Intermediate H (85 mg, 0.3 mmol) in DMF (5 mL) was stirred at 25° C. for 16 h. The mixture was diluted with ethyl acetate (30 mL), washed with water (10 mL×2) and brine (10 mL), dried over anhydrous sodium sulfate, and concentrated to yield a crude compound. The crude product was purified with prep-HPLC to furnish Compound 367. LC-MS (ESI) m/z: 484 [M+H]$^+$; $^1$H-NMR (DMSO-d$_6$, 400 MHz): δ (ppm) 1.97-2.00 (m, 4H), 2.24-2.27 (m, 1H), 2.38-2.43 (m, 1H), 3.31-3.35 (m, 6H), 4.07-4.16 (m, 4H), 4.28-4.33 (m, 5H), 4.72 (s, 1H), 6.00 (s, 1H), 6.52-6.54 (m, 2H), 6.72-6.80 (m, 2H), 7.64-7.66 (m, 2H), 8.43 (d, J=10 Hz, 1H), 9.84 (s, 1H).

Example 368

Example 367

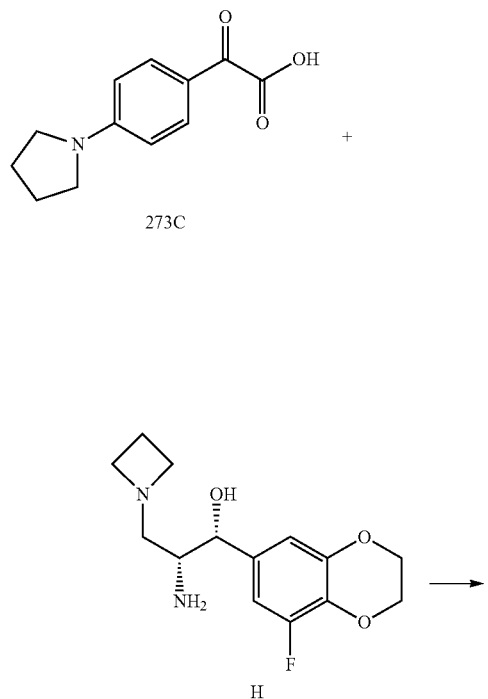

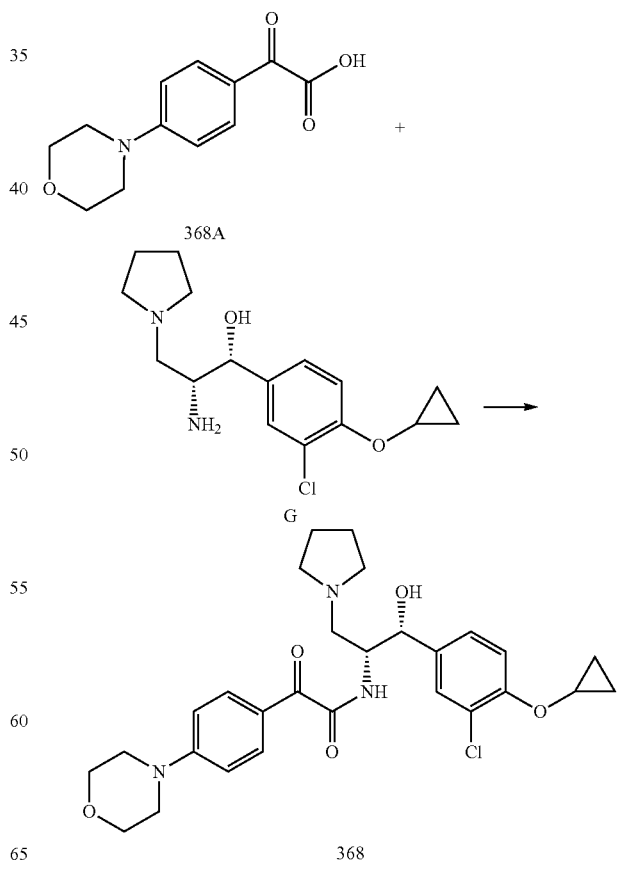

368

A mixture of Intermediate G (177 mg, 0.57 mmol), Compound 368A (117 mg, 0.52 mmol), and HATU (350 mg, 0.92 mmol) in DMF (5 mL) was stirred at room temperature overnight. The mixture was diluted with dichloromethane (100 mL), washed with water (50 mL×2) and brine (50 mL), dried over anhydrous sodium sulfate, and concentrated. The crude product was purified with prep-HPLC to give Compound 368. LC-MS (ESI) m/z: 528.2 [M+H]$^+$; $^1$H-NMR (CD$_3$OD, 400 MHz): δ (ppm) 0.72-0.86 (m, 4H), 2.03-2.23 (m, 4H), 3.21-3.31 (m, 2H), 3.40-3.43 (m, 4H), 3.55-3.58 (m, 1H), 3.68-3.74 (m, 2H), 3.79-3.89 (m, 6H), 4.70-4.73 (m, 1H), 4.98 (d, J=2.8 Hz, 1H), 6.84 (d, J=9.2 Hz, 2H), 7.38 (s, 2H), 7.44-7.47 (m, 3H).

Example 369

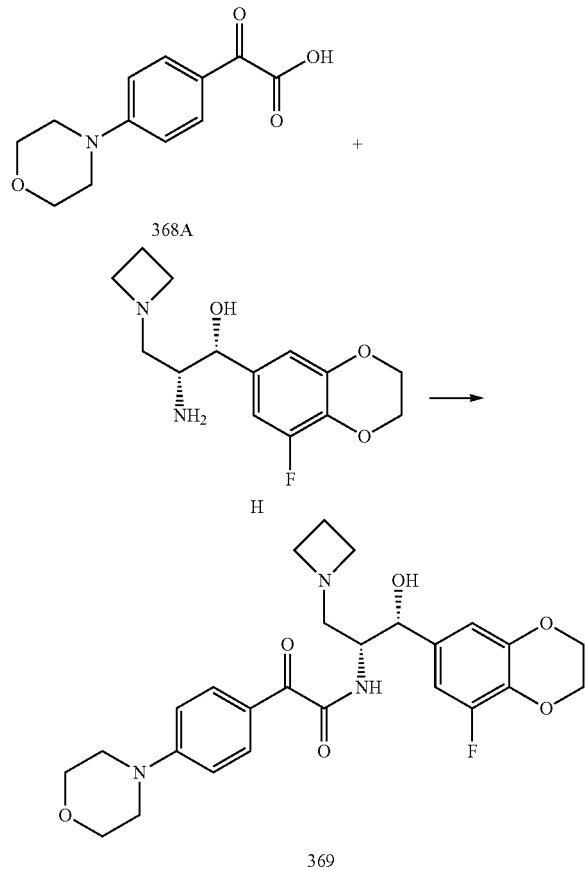

A mixture of Intermediate H (100 mg, 0.42 mmol), Compound 368A (141 mg, 0.50 mmol), and HATU (290 mg, 0.76 mmol) in DMF (5 mL) was stirred at room temperature overnight. The mixture was diluted with dichloromethane (100 mL), washed with water (50 mL×2) and brine (50 mL), dried over anhydrous sodium sulfate, and concentrated. The crude product was purified with prep-HPLC to give Compound 369. LC-MS (ESI) m/z: 500.2 [M+H]$^+$; $^1$H-NMR (CD$_3$OD, 400 MHz): δ (ppm) 2.40-2.68 (m, 2H), 3.40-3.43 (m, 4H), 3.51-3.75 (m, 3H), 3.82-3.85 (m, 4H), 4.06-4.20 (m, 1H), 4.20-4.34 (m, 9H), 4.34-4.49 (m, 1H), 4.86 (d, J=3.2 Hz, 1H), 6.77-6.80 (m, 2H), 6.93 (d, J=9.2 Hz, 2H), 7.64 (d, J=9.2 Hz, 2H).

Example 370

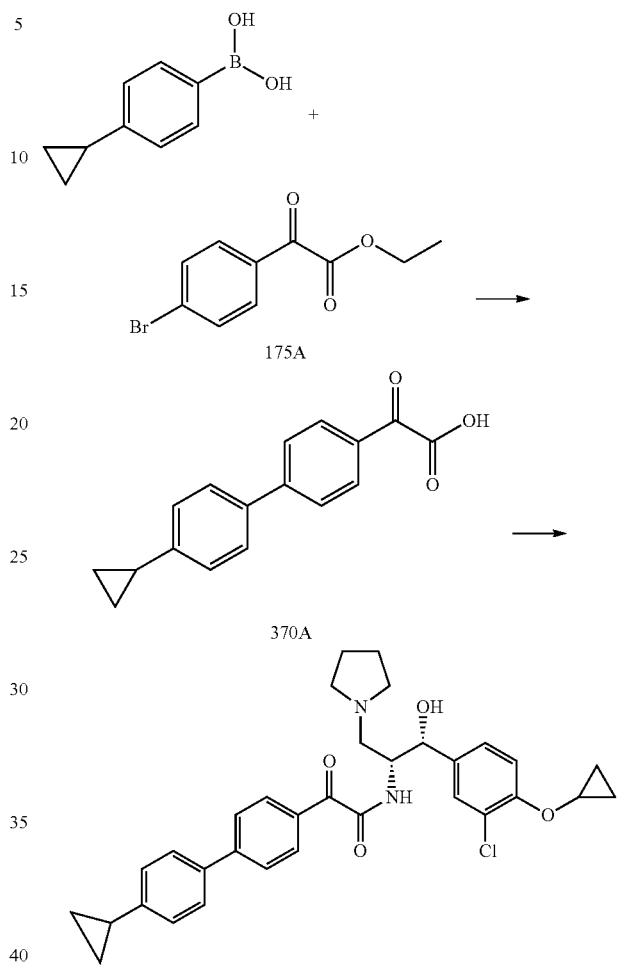

A mixture of Compound 175A (200 mg, 1.23 mmol), ethyl 2-(4-bromophenyl)-2-oxoacetate (316 mg, 1.23 mmol), Pd(dppf)Cl$_2$ (49 mg, 0.06 mmol), and K$_2$CO$_3$ (509 mg, 3.69 mmol) in 1,4-dioxane (10 mL) and water (10 mL) was stirred under nitrogen at 100° C. for 3 h. The reaction mixture was cooled down to room temperature and filtered through celite. The filtrate was diluted with water (100 mL) and extracted with ethyl acetate (100 mL×2). The aqueous layer was acidified to pH 3 with aqueous HCl solution (1 N) and extracted with dichloromethane (100 mL×3). The combined dichloromethane layers were washed with water (50 mL), dried over anhydrous sodium sulfate, and concentrated to give Compound 370A.

A mixture of Compound 370A (65 mg, 0.24 mmol), HATU (137 mg, 0.36 mmol), and Intermediate G (74 mg, 0.24 mmol) in DMF (5 mL) was stirred at 25° C. overnight. The mixture was directly purified with prep-HPLC to furnish Compound 370. LC-MS (ESI) m/z: 559 [M+H]$^+$; $^1$H-NMR (DMSO-d$_6$, 400 MHz): δ (ppm) 0.65-0.85 (m, 6H), 0.99-1.03 (m, 2H), 1.90-2.02 (m, 5H), 3.12-3.19 (m, 2H), 3.41-3.55 (m, 4H), 3.91-3.96 (m, 1H), 4.55-4.59 (m, 1H), 4.91 (s, 1H), 6.07 (s, 1H), 7.22 (d, J=8.4 Hz, 2H), 7.35 (dd, J=8.4, 1.6 Hz, 1H), 7.41 (d, J=8.4 Hz, 1H), 7.45 (d, J=1.6 Hz, 1H), 7.64 (d, J=8.8 Hz, 2H), 7.71-7.74 (m, 4H), 8.80 (d, J=9.6 Hz, 1H), 9.67 (brs, 1H).

Example 371

Example 372

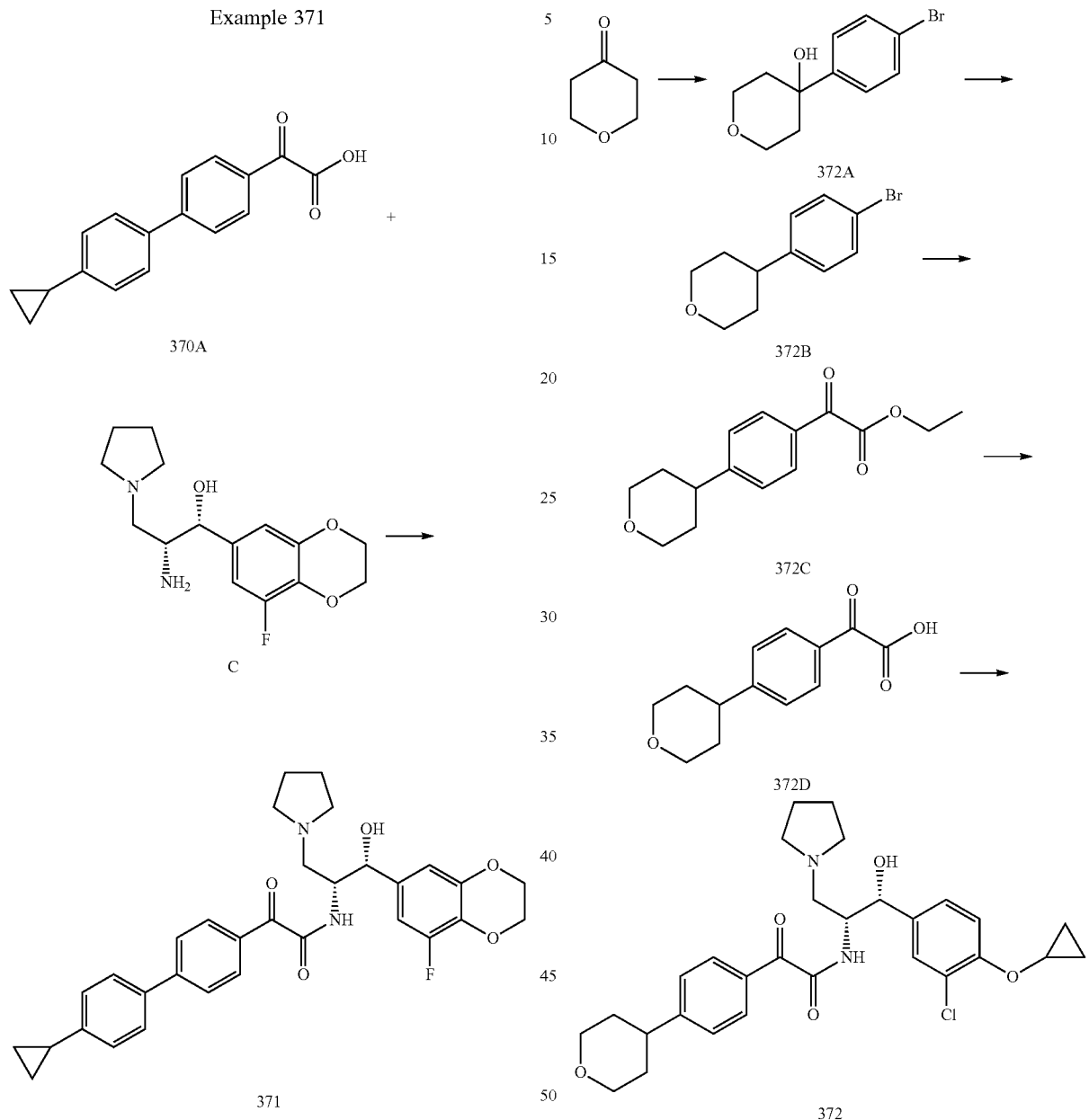

A mixture of Compound 370A (65 mg, 0.24 mmol), HATU (137 mg, 0.36 mmol), and Intermediate C (71 mg, 0.24 mmol) in DMF (5 mL) was stirred at 25° C. overnight. The mixture was directly purified with prep-HPLC to furnish Compound 371. LC-MS (ESI) m/z: 545 [M+H]$^+$; $^1$H-NMR (DMSO-d$_6$, 400 MHz): δ (ppm) 0.72-0.76 (m, 2H), 0.99-1.03 (m, 2H), 1.88-2.02 (m, 5H), 3.11-3.14 (m, 2H), 3.26-3.55 (m, 4H), 4.23-4.29 (m, 4H), 4.49-4.54 (m, 1H), 4.80 (s, 1H), 6.05 (d, J=4.0 Hz, 1H), 6.77 (s, 1H), 6.83 (dd, J=12.0, 1.6 Hz, 1H), 7.22 (d, J=8.4 Hz, 2H), 7.65 (d, J=8.4 Hz, 2H), 7.78 (d, J=8.4 Hz, 2H), 7.87 (d, J=8.4 Hz, 2H), 8.74 (d, J=9.6 Hz, 1H), 9.51 (brs, 1H).

To a solution of tetrahydro-4H-pyran-4-one (380 mg, 3.8 mmol) and 1-bromo-4-iodobenzene (2.4 g, 8.5 mmol) in dry THF (50 mL) was added dropwise n-BuLi (2.5 M solution in hexane, 1.52 mL, 3.8 mmol) under nitrogen at −78° C. over a period of 15 min. The resulting solution was allowed to warm slowly to room temperature and stirred for 3.5 h. The resulting mixture was quenched with saturated aqueous ammonium chloride solution (10 mL) and extracted with ethyl acetate (50 mL×3). The organic layer was washed with water (10 mL) and brine (10 mL), dried over anhydrous sodium sulfate, filtered, and concentrated to yield a crude product. The crude product was purified with flash column chromatography on silica gel (ethyl acetate, 100% v/v) to furnish Compound 372A.

To a solution of Compound 372A (620 mg, 2.42 mmol) in dry dichloromethane (10 mL) was added triethylsilane (0.43 mL, 2.71 mmol). Trifluoroacetic acid (1.83 mL, 24.2 mmol) was added dropwise. After one hour at −78° C., the mixture was warmed to room temperature and stirred for 3 h. The resulting mixture was quenched with aqueous NaOH solution (1 N, 5 mL) and extracted with dichloromethane (50 mL×3). The organic layer was washed with water (10 mL) and brine (10 mL), dried over anhydrous sodium sulfate, filtered, and concentrated to yield a crude product. The crude product was purified with flash column chromatography on silica gel (ethyl acetate in petroleum ether, 80% v/v) to afford Compound 372B.

To a solution of Compound 372B (295 mg, 1.23 mmol) in dry THF (20 mL) was added dropwise n-BuLi (2.5 M solution in hexane, 0.74 mL, 1.84 mmol) under nitrogen at −78° C. After stirring for 30 min, diethyl oxalate (449 mg, 3.07 mmol) was added in one portion. The mixture was stirred at −78° C. for about an hour. The resulting mixture was quenched with saturated aqueous ammonium chloride solution (10 mL) and extracted with ethyl acetate (50 mL×3). The organic layer was washed with water (5 mL) and brine (5 mL), dried over anhydrous sodium sulfate, filtered, and concentrated to yield a crude product. The crude product was purified with flash column chromatography on silica gel (ethyl acetate in petroleum ether, 10% v/v) to furnish Compound 372C.

To a solution of Compound 372C (155 mg, 0.59 mmol) in THF (10 mL) was added dropwise a solution of LiOH.H$_2$O (50 mg, 1.18 mmol) in water (3 mL). The mixture was stirred at room temperature for 3 h. The reaction solution was adjusted to pH 3 with aqueous HCl solution (1 N, 1.5 mL) and separated. The organic layer was dried directly over anhydrous sodium sulfate, filtered, and concentrated to afford Compound 372D.

To a solution of Intermediate G (87 mg, 0.28 mmol) in dichloromethane (10 mL) was added Compound 372D (55 mg, 0.23 mmol) and HATU (134 mg, 0.35 mmol) under nitrogen. The mixture was stirred at room temperature overnight. The resulting mixture was diluted with saturated aqueous sodium bicarbonate solution (5 mL) and extracted with dichloromethane (50 mL×3). The combined organic phases were washed with water (5 mL) and brine (5 mL), dried over anhydrous sodium sulfate, filtered, and concentrated to afford a crude product. The crude product was purified with prep-HPLC to furnish Compound 372. LC-MS (ESI) m/z: 527 [M+H]$^+$; $^1$H-NMR (DMSO-d$_6$, 400 MHz): δ (ppm) 0.68-0.84 (m, 4H), 1.62-1.69 (m, 4H), 1.87-2.03 (m, 4H), 2.83-2.91 (m, 1H), 3.11-3.20 (m, 2H), 3.44-3.54 (m, 6H), 3.95-3.97 (m, 3H), 4.53-4.58 (m, 1H), 4.87 (s, 1H), 6.05 (d, J=4.0 Hz, 1H), 7.34-7.42 (m, 5H), 7.62 (d, J=8.4 Hz, 2H), 8.76 (d, J=9.6 Hz, 1H), 9.51 (s, 1H).

Example 373

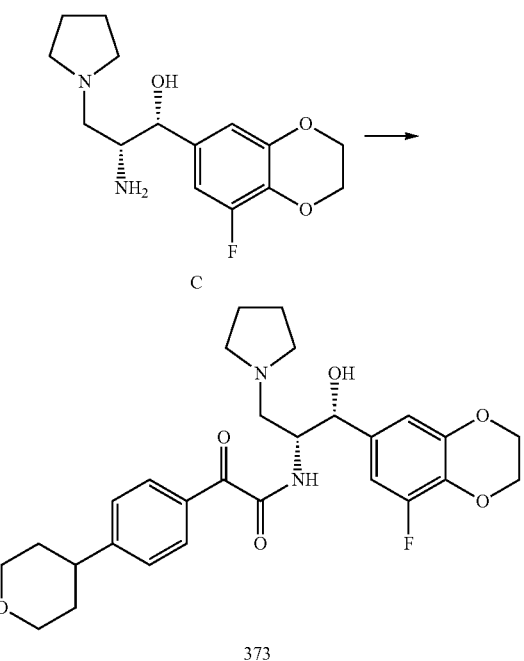

To a solution of Intermediate C (83 mg, 0.28 mmol) in dichloromethane (10 mL) was added Compound 372D (55 mg, 0.23 mmol) and HATU (134 mg, 0.35 mmol) under nitrogen. The mixture was stirred at room temperature overnight. The resulting mixture was diluted with saturated aqueous sodium bicarbonate solution (5 mL) and extracted with dichloromethane (50 mL×3). The combined organic phases were washed with water (5 mL) and brine (5 mL), dried over anhydrous sodium sulfate, filtered, and concentrated to afford a crude product. The crude product was purified with prep-HPLC to furnish Compound 373. LC-MS (ESI) m/z: 513 [M+H]$^+$; $^1$H-NMR (DMSO-d$_6$, 400 MHz): δ (ppm) 1.66-1.71 (m, 4H), 1.87-2.02 (m, 4H), 2.85-2.91 (m, 1H), 3.10-3.16 (m, 2H), 3.48-3.54 (m, 6H), 3.95-3.98 (m, 2H), 4.26-4.29 (m, 4H), 4.47-4.52 (m, 1H), 4.77 (s, 1H), 6.03 (d, J=2.4 Hz, 1H), 6.75 (s, 1H), 6.81 (dd, J=11.2, 1.6 Hz, 1H), 7.40 (d, J=8.4 Hz, 2H), 7.74 (d, J=8.4 Hz, 2H), 8.70 (d, J=9.6 Hz, 1H), 9.42 (s, 1H).

Example 374

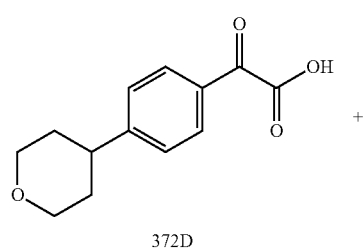 +

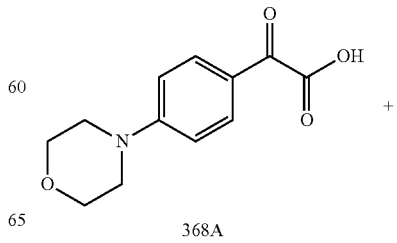 +

525
-continued

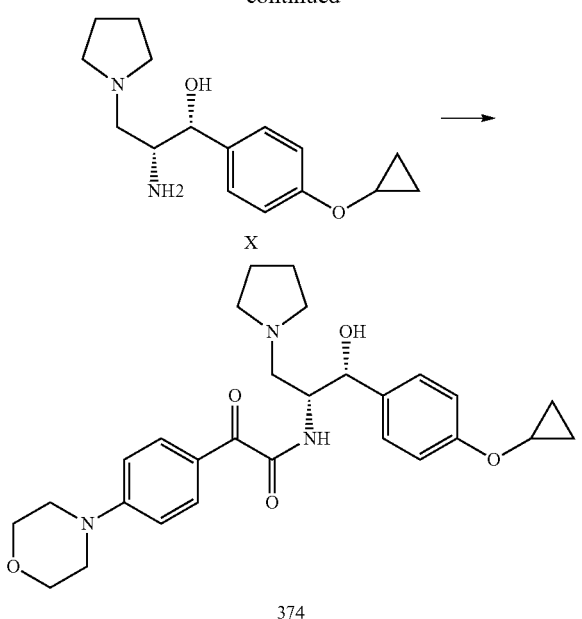

374

A mixture of Intermediate X (77 mg, 0.34 mmol), Compound 368A (55 mg, 0.24 mmol), and HATU (175 mg, 0.46 mmol) in DMF (5 mL) was stirred at room temperature overnight. The mixture was diluted with dichloromethane (100 mL), washed with water (50 mL×2) and brine (50 mL), dried over anhydrous sodium sulfate, and concentrated. The crude product was purified with prep-HPLC to give Compound 374. LC-MS (ESI) m/z: 494.2 [M+H]$^+$; $^1$H-NMR (CD$_3$OD, 400 MHz): δ (ppm) 0.68-0.69 (m, 2H), 0.77-0.81 (m, 2H), 2.05-2.22 (m, 5H), 3.20-3.30 (m, 2H), 3.40-3.42 (m, 4H), 3.53-3.60 (m, 1H), 3.66-3.72 (m, 2H), 3.76-3.85 (m, 7H), 4.66-4.69 (m, 1H), 4.97 (d, J=2.8 Hz, 1H), 6.88 (d, J=9.2 Hz, 2H), 7.04 (d, J=8.4 Hz, 2H), 7.37 (d, J=8.4 Hz, 2H), 7.60 (d, J=9.2 Hz, 2H).

Example 375

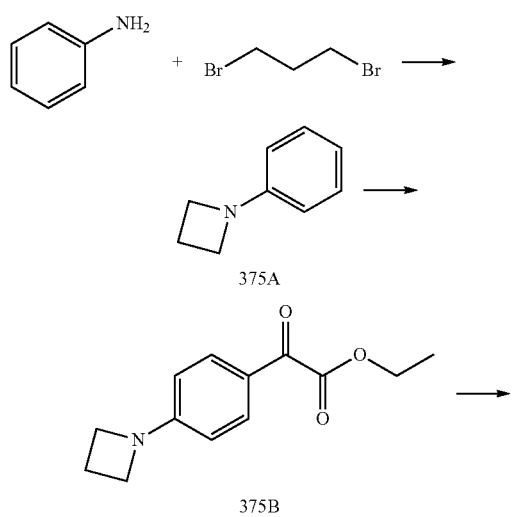

526
-continued

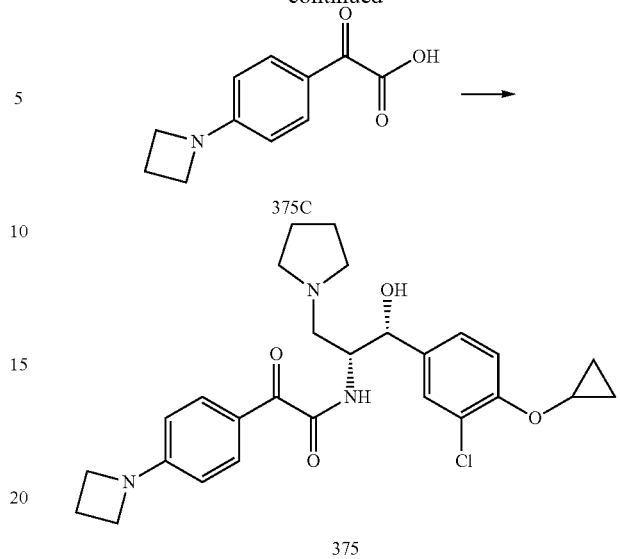

375

To a solution of aniline (9.3 g, 100 mmol) in DMF (350 mL) was added cesium carbonate (100 g, 306 mmol) and 1,3-dibromopropane (27 g, 135 mmol). The mixture was stirred for 24 h while keeping inner temperature between 60° C. and 65° C. After the reaction mixture was cooled to ambient temperature, the dark solution was diluted with water (400 mL) and extracted with ethyl acetate (300 mL×3). The combined organic phases were washed with brine (150 mL×4), dried over anhydrous sodium sulfate, filtered, and concentrated to afford the crude product as a brown oil. The crude product was purified with flash column chromatography on silica gel (petroleum ether) to furnish Compound 375A.

To a solution of compound 375A (900 mg, 6.8 mmol) and aluminum trichloride (5.0 g, 37.9 mmol) in dichloromethane (30 mL) was added dropwise ethyl 2-chloro-2-oxoacetate (1.06 g, 8.0 mmol) at 0° C. The mixture was stirred for 4 hours while keeping the temperature at 0° C. The mixture was poured into ice water and extracted with ethyl acetate (50 mL×3). The resulting product was concentrated under reduced pressure, and the resultant residue was purified with silica gel column chromatography (ethyl acetate in petroleum ether, 30% v/v) to give Compound 375B.

To a solution of Compound 375B (333 mg, 1.00 mmol) in MeOH (10 mL) was added LiOH.H$_2$O (90 mg, 2.14 mmol) and water (2 mL). The reaction mixture was stirred at 15° C. for 4 h. The reaction mixture was neutralized with HCl (1 N). The resulting mixture was evaporated. The residue was dissolved in water (5 mL). The mixture was extracted with ethyl acetate (10 mL×2), dried over anhydrous sodium sulfate, filtered, and evaporated to give Compound 375C.

A mixture of Intermediate G (203 mg, 0.65 mmol), Compound 375C (110 mg, 0.53 mmol), and HATU (350 mg, 0.92 mmol) in DMF (5 mL) was stirred at room temperature overnight. The mixture was diluted with dichloromethane (150 mL), washed with water (100 mL×2) and brine (100 mL), dried over anhydrous sodium sulfate, and concentrated. The crude product was purified with prep-HPLC to give Compound 375. LC-MS (ESI) m/z: 498.2 [M+H]$^+$; $^1$H-NMR (CD$_3$OD, 400 MHz): δ (ppm) 0.69-0.87 (m, 4H), 1.90-2.26 (m, 4H), 3.01-3.27 (m, 2H), 3.43-3.68 (m, 4H), 3.70-3.95 (m, 2H), 4.19-4.42 (m, 2H), 4.77 (s, 1H), 4.98-5.17 (m, 2H), 5.53-5.92 (m, 1H), 6.96-7.31 (m, 5H), 7.36-7.57 (m, 3H).

Example 376

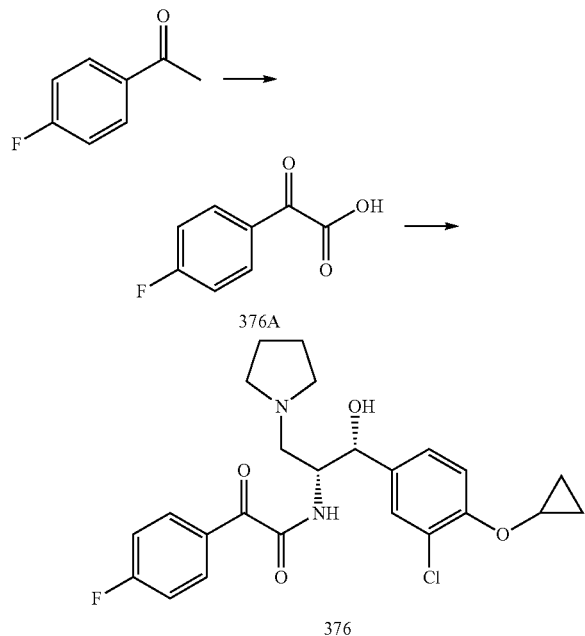

376

A mixture of 1-(4-fluorophenyl)ethan-1-one (5.00 g, 36.20 mmol) and SeO$_2$ (6.06 g, 54.30 mmol) in pyridine (20 mL) was stirred at 70° C. for 16 h. After filtration to remove the resultant solid, the filtrate was evaporated to give a residue. The crude product was dissolved in aqueous sodium hydroxide solution (1 M, 20 mL) and water (50 mL) and extracted with diethyl ether (160 mL) to remove by-product. The aqueous solution was adjusted to pH 1 with concentrated hydrochloride acid (4 mL) and extracted with dichloromethane (100 mL×3). The organic layer was washed with brine (50 mL), dried over anhydrous sodium sulfate, and evaporated to afford Compound 376A.

A mixture of Compound 376A (54 mg, 0.32 mmol), Intermediate G (100 mg, 0.32 mmol), and HATU (183 mg, 0.48 mmol) in dichloromethane (3 mL) was stirred at 20° C. for 16 h. The mixture was diluted with ethyl acetate (100 mL), washed with water (100 mL) and brine (100 mL), dried over anhydrous sodium sulfate, and evaporated to give a residue. The crude product was purified with prep-HPLC to afford Compound 376. LC-MS (ESI) m/z: 461 [M+H]$^+$; $^1$H-NMR (DMSO-d$_6$, 400 MHz): δ (ppm) 0.66-0.83 (m, 4H), 1.86-2.02 (m, 4H), 3.12-3.18 (m, 2H), 3.46-3.53 (m, 4H), 3.89-3.95 (m, 1H), 4.48-4.55 (m, 1H), 4.85 (s, 1H), 6.08 (s, 1H), 7.30-7.42 (m, 5H), 7.89 (t, J=8.8 Hz, 2H), 8.74 (d, J=9.6 Hz, 1H), 9.57 (s, 1H).

Example 377

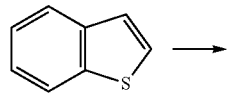

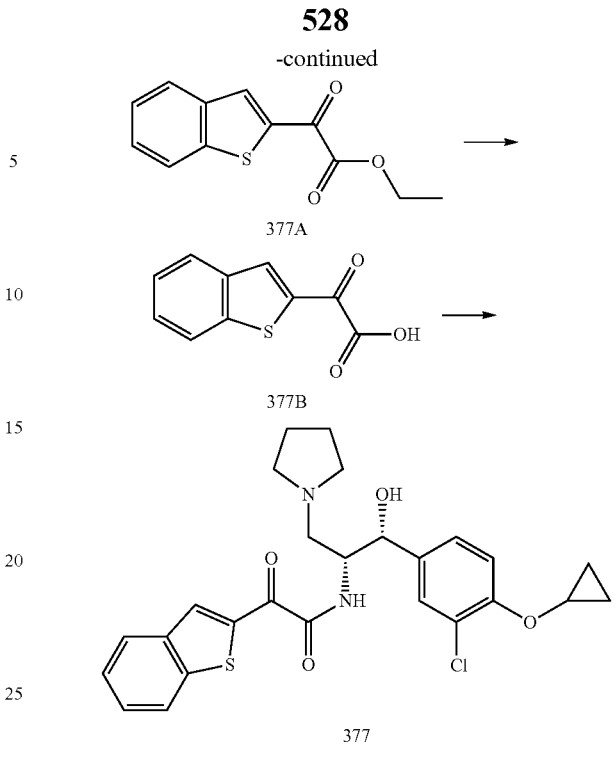

377

To a solution of benzo[b]thiophene (1 g, 7.5 mmol) in THF (25 mL) was added dropwise n-BuLi (3.6 mL, 8.9 mmol) under nitrogen at −78° C. The resulting mixture was stirred at −78° C. for 15 min. To the resulting mixture was added diethyl oxalate (3.3 g, 8.9 mmol) quickly. The mixture was stirred for 1 h at −78° C., quenched with sat. ammonium chloride solution, treated with water (50 mL), extracted with ethyl acetate (50 mL×2), washed with brine (50 mL), dried over anhydrous sodium sulfate, concentrated, and purified with flash column chromatography on silica gel (petroleum ether) to furnish Compound 377A.

To a solution of Compound 377A (1.5 g, 6.4 mmol) in THF (50 mL) was added dropwise LiOH.H$_2$O (538 mg, 12.8 mmol) in water (4 mL) at −20° C. The resulting mixture was stirred at −20° C. for 1 h. The mixture was adjusted to pH 1 with diluted HCl. The resulting mixture was extracted with ethyl acetate (50 mL×2). The organic layer was concentrated, treated with petroleum ether (50 mL), and stirred for 30 min. The yellow solid was formed and filtered to furnish Compound 377B.

A mixture of Compound 377B (100 mg, 0.48 mmol), Intermediate G (150 mg, 0.48 mmol), and HATU (277 mg, 0.73 mmol) in DMF (5 mL) was stirred at room temperature for 12 h. The mixture was treated with water (10 mL), extracted with dichloromethane (20 mL×2), washed with water (20 mL×3) and brine (50 mL), dried over anhydrous sodium sulfate, concentrated, and purified with prep-HPLC to furnish Compound 377. LC-MS (ESI) m/z: 499 [M+H]$^+$; $^1$H-NMR (acetone-d$_6$, 400 MHz): δ (ppm) 0.60-0.81 (m, 4H), 2.23 (s, 2H), 2.93 (s, 3H), 3.50 (s, 2H), 3.81-3.85 (m, 2H), 4.00-4.06 (m, 3H), 4.86 (t, J=7.2 Hz, 1H), 5.15 (d, J=2.8 Hz, 1H), 7.33-7.41 (m, 2H), 7.47-7.53 (m, 2H), 7.61 (t, J=7.2 Hz, 1H), 8.04-8.09 (m, 2H), 8.14-8.19 (m, 1H), 8.64 (s, 1H), 9.52 (s, 1H).

Example 378

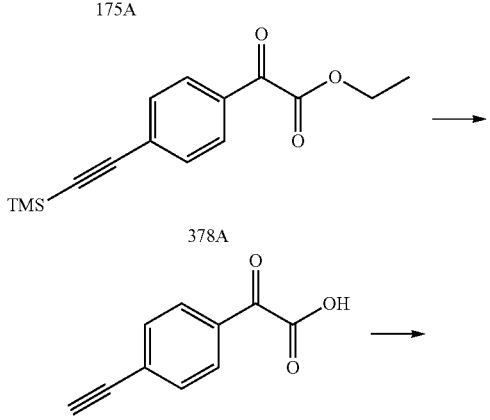

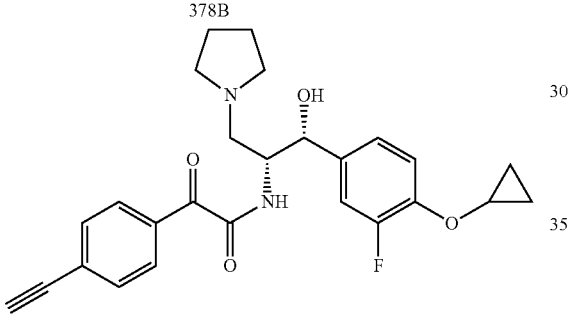

To a solution of compound 175A (2.57 g, 10.0 mmol), CuI (190 mg, 1.0 mmol), and Pd(PPh$_3$)$_2$Cl$_2$ (210 mg, 0.3 mmol) in triethylamine (80 mL) was added dropwise ethynyltrimethylsilane (1.17 g, 12.0 mmol) under nitrogen atmosphere at room temperature. The reaction mixture was stirred at 90° C. for 30 minutes. Solids were collected with filtration and washed with acetate ethyl (80 mL×2). The filtrate was concentrated under reduced pressure to give a residue, which was purified with flash column chromatography on silica gel (ethyl acetate in petroleum ether, 5% v/v) to yield compound 378A.

To a solution of Compound 378A (500 mg, 1.8 mmol) in THF (5 mL) was added LiOH.H$_2$O (113 mg, 2.7 mmol) in water (2.0 mL). The resulting mixture was stirred at room temperature for 2 h, evaporated, treated with water (5 mL), and adjusted to pH 2 with diluted HCl. The mixture was extracted with ethyl acetate (10 mL×3), washed with brine (10 mL), dried over anhydrous sodium sulfate, and concentrated to afford the Compound 378B.

To a solution of Compound 378B (34 mg, 0.2 mmol) in DMF (3 mL) was added Intermediate S (59 mg, 0.2 mmol) and HATU (114 mg, 0.3 mmol). The reaction mixture was stirred at room temperature for 4 h. The mixture was purified with prep-HPLC to give Compound 378. LC-MS (ESI) m/z: 451 [M+H]$^+$; $^1$H-NMR (acetone-d$_6$, 400 MHz): δ (ppm) 0.68-0.70 (m, 2H), 0.79-0.81 (m, 2H), 2.04-2.09 (m, 4H), 3.60-3.63 (m, 3H), 3.88-3.93 (m, 5H), 4.00 (s, 1H), 4.81-4.83 (m, 1H), 5.15 (d, J=2.8 Hz, 1H), 7.23-7.25 (m, 2H), 7.33-7.35 (m, 1H), 7.58 (d, J=8.4 Hz, 2H), 7.98 (d, J=8.4 Hz, 2H), 8.15-8.18 (m, 1H), 9.31 (brs, 1H).

Example 379

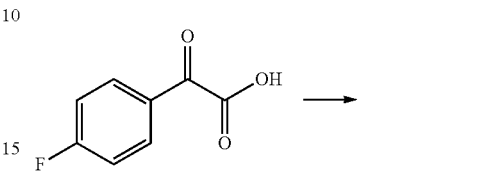

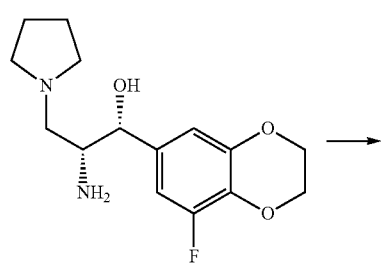

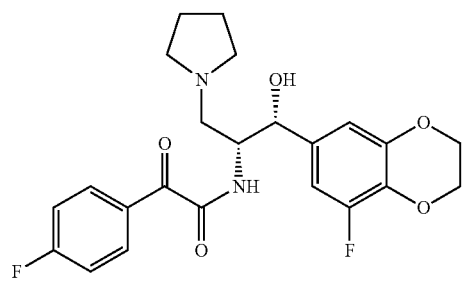

A mixture of Compound 376A (54 mg, 0.32 mmol), Intermediate C (95 mg, 0.32 mmol), and HATU (183 mg, 0.48 mmol) in dichloromethane (3 mL) was stirred at 20° C. for 16 h. The mixture was diluted with ethyl acetate (100 mL), washed with water (100 mL) and brine (100 mL), dried over anhydrous sodium sulfate, and evaporated to give a residue. The crude product was purified with prep-HPLC to afford Compound 379. LC-MS (ESI) m/z: 447 [M+H]$^+$; $^1$H-NMR (DMSO-d$_6$, 400 MHz): δ (ppm) 1.83-2.04 (m, 4H), 3.07-3.19 (m, 2H), 3.41-3.47 (m, 4H), 4.27 (s, 4H), 4.42-4.50 (m, 1H), 4.75 (s, 1H), 6.04 (s, 1H), 6.74 (s, 1H), 6.80 (d, J=10.4 Hz, 1H), 7.36 (t, J=8.8 Hz, 2H), 7.93-7-98 (m, 2H), 8.70 (d, J=9.6 Hz, 1H), 9.40 (s, 1H).

Example 380

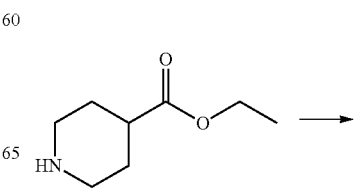

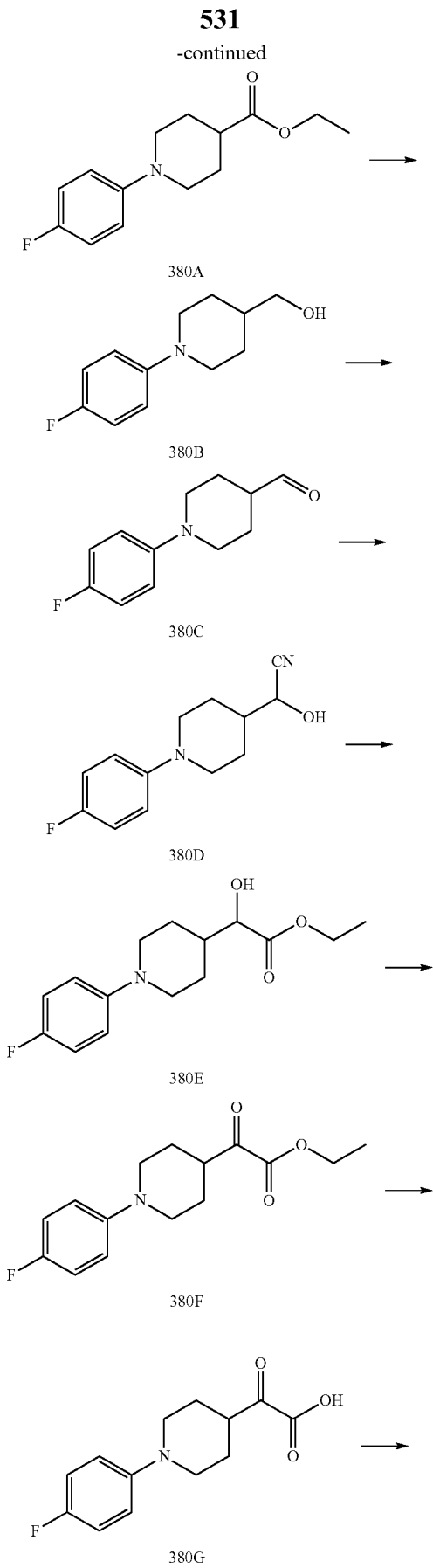

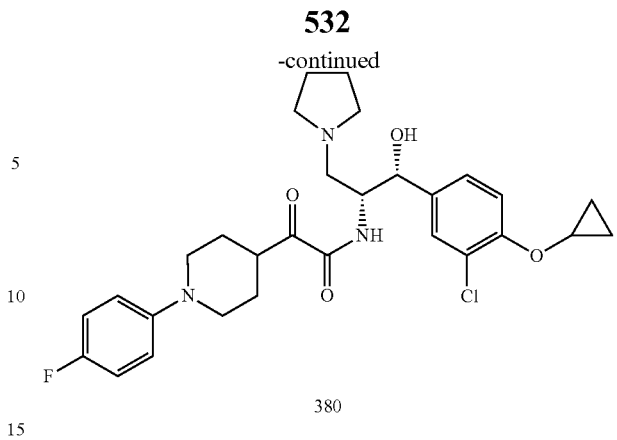

A mixture of ethyl piperidine-4-carboxylate (10 g, 64 mmol), 1-fluoro-4-iodobenzene (14 g, 64 mmol), K$_2$CO$_3$ (17.6 g, 127 mmol), and L-proline (1.46 g, 12.7 mmol) in DMSO (50 mL) was stirred under nitrogen at 85° C. for 12 h. The resulting mixture was added NH$_3$.H$_2$O (50 mL), extracted with ethyl acetate (100 mL×2), washed with water (100 mL×3) and brine (100 mL), dried over anhydrous sodium sulfate, concentrated, and purified with flash column chromatography on silica gel (ethyl acetate in petroleum ether, 10% v/v) to furnish Compound 380A.

To a solution of AlLiH$_4$ (1.2 g, 31 mmol) in THF (100 mL) was added Compound 380A (7.9 g, 31 mmol) in THF (50 mL) dropwise under nitrogen at −78° C. The resulting mixture was stirred at −78° C. for 1.5 h, quenched with Na$_2$SO$_4$.10H$_2$O. The mixture was treated with silica gel and filtered. The filtrate was concentrated and the resulting residue was purified with flash column chromatography on silica gel (ethyl acetate in petroleum ether, 20% v/v) to afford Compound 380B.

To a cooled −78° C. solution of oxalyl chloride (9.1 g, 72 mmol) in dichloromethane (150 mL) was added dropwise DMSO (7.5 g, 96 mmol), maintaining the internal temperature below −40° C. After 30 min, Compound 380B (5 g, 24 mmol) in dichloromethane (10 mL) was added dropwise to the reaction mixture. The reaction mixture was stirred at −78° C. for 45 min, triethylamine (12 g, 120 mmol) was added dropwise, and the mixture was warmed to room temperature stirred for 2 h. The mixture was treated with water (100 mL), extracted with dichloromethane (50 mL×2), washed with water (50 mL×2), dried over anhydrous sodium sulfate, concentrated, and purified with flash column chromatography on silica gel (ethyl acetate in petroleum ether, 20% v/v) to furnish Compound 380C.

Compound 380C (3.3 g, 16 mol) was added to a solution of Na$_2$S$_2$O$_5$ (3 g, 16 mol) in water (100 mL). The mixture was stirred for 2 h at room temperature. After the addition of NaCN (1.6 g, 32 mmol) the resulting mixture was stirred for 15 h, diluted with ethyl acetate (50 mL), extracted with ethyl acetate (100 mL×2), washed with sat. sodium bicarbonate (100 mL×2) and brine (100 mL), dried over anhydrous sodium sulfate, and concentrated to afford the crude Compound 380D.

To a solution of Compound 380D (3.7 g, 15.8 mmol) in ethanol (80 mL) cooled to 0° C. was bubbled a gentle stream of HCl gas (dried over con. H$_2$SO$_4$) for 5 h. The mixture was treated with water slowly at 0° C., stirred at room temperature for 2 h, adjusted to pH 8 with NaOH (1 M), extracted with dichloromethane (50 mL×2), washed with brine (100 mL), dried over anhydrous sodium sulfate, and concentrated to give Compound 380E.

To a cooled −78° C. solution of oxalyl chloride (3.66 g, 28.8 mmol) in dichloromethane (50 mL) was added dropwise DMSO (3 g, 38.4 mmol), maintaining the internal temperature below −40° C. After 30 min, Compound 380E (2.7 g, 9.6 mmol) in dichloromethane (10 mL) was added dropwise to the reaction mixture. The reaction mixture was stirred at −78° C. for 45 min, triethylamine (4.85 g, 48 mmol) was added dropwise, and the mixture was warmed to room temperature stirred for 2 h. The mixture was treated with water (100 mL), extracted with dichloromethane (50 mL×2), washed with water (50 mL×2), dried over anhydrous sodium sulfate, concentrated, and purified with flash column chromatography on silica gel (ethyl acetate in petroleum ether, 20% v/v) to furnish Compound 380F.

To a solution of Compound 380F (878 mg, 3.14 mmol) in THF (20 mL) was added LiOH.H₂O (264 mg, 6.29 mmol) in water (2 mL) at −30° C. The resulting mixture was stirred at −30° C. for 2 h, evaporated, treated with water, adjusted to pH 2 with diluted HCl, and lyophilized. The solid was purified with reverse phase chromatography using eluent (acetonitrile in water, from 1% to 100% v/v) to furnish Compound 380G.

A mixture of Compound 380G (300 mg, 1.19 mmol), Intermediate G (370 mg, 1.19 mmol), and HATU (681 mg, 0.73 mmol) in DMF (15 mL) was stirred at room temperature for 12 h. The mixture was treated with water (10 mL), extracted with dichloromethane (20 mL×2), washed with water (20 mL×3) and brine (50 mL), dried over anhydrous sodium sulfate, concentrated, and purified with reverse phase chromatography eluting with (acetonitrile in water, from 1% to 100% v/v) to furnish Compound 380. LC-MS (ESI) m/z: 544 [M+H]⁺; ¹H-NMR (acetone-d₆, 400 MHz): δ (ppm) 0.69-0.84 (m, 4H), 1.68 (s, 1H), 1.92-2.13 (m, 9H), 3.15-3.37 (m, 4H), 3.62-3.69 (m, 3H), 3.82-3.89 (m, 4H), 4.65-4.68 (m, 1H), 5.09 (s, 1H), 7.14-7.19 (m, 1H), 7.34-7.40 (m, 5H), 7.79-7.81 (m, 1H), 8.21 (s, 1H), 11.31 (s, 1H).

Example 381

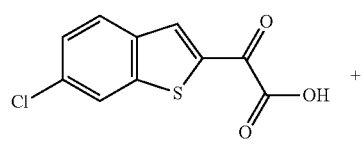

242F

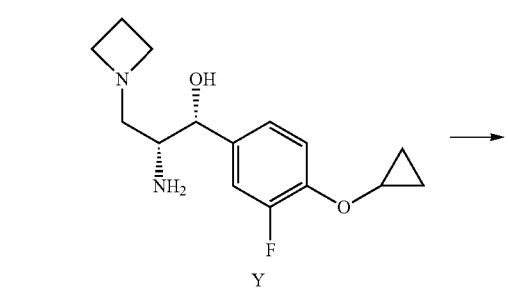

Y

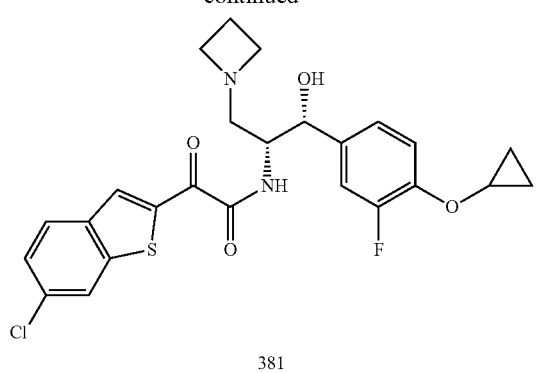

381

A mixture of Intermediate Y (70 mg, 0.25 mmol), HATU (143 mg, 0.37 mmol), and Compound 242F (60 mg, 0.25 mmol) in DMF (5 mL) was stirred at 25° C. overnight. The mixture was directly purified with prep-HPLC to furnish Compound 381. LC-MS (ESI) m/z: 503 [M+H]⁺; ¹H-NMR (DMSO-d₆, 400 MHz): δ (ppm) 0.61-0.79 (m, 4H), 2.24-2.42 (m, 2H), 3.33-3.49 (m, 2H), 3.82-3.91 (m, 1H), 4.02-4.33 (m, 5H), 4.77 (d, J=4.0 Hz, 1H), 6.03 (brs, 1H), 7.13-7.20 (m, 2H), 7.36 (t, J=8.4 Hz, 1H), 7.56 (dd, J=8.4, 2.0 Hz, 1H), 8.12 (d, J=8.0 Hz, 1H), 8.30 (d, J=2.0 Hz, 1H), 8.52 (s, 1H), 8.56 (d, J=10.0 Hz, 1H), 9.44 (brs, 1H).

Example 382

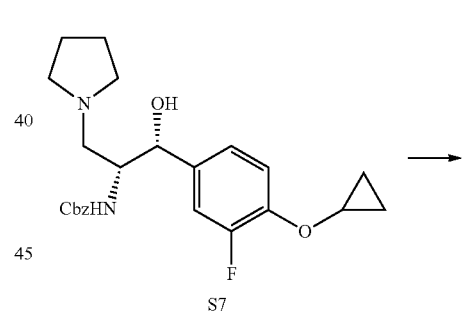

S7

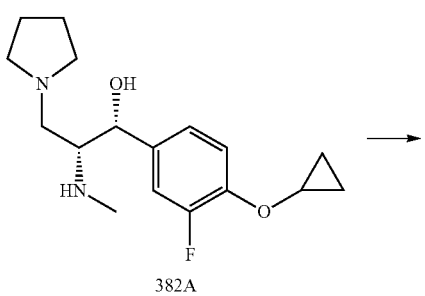

382A

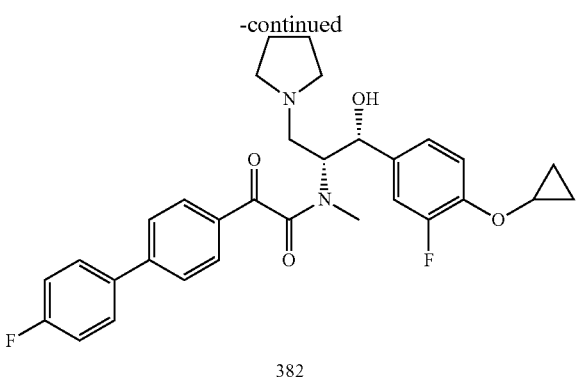

382

To a solution of AlLiH₄ (76 mg, 2 mmol) in THF (15 mL) was added Intermediate S7 (430 mg, 1 mmol) in THF (5 mL) dropwise under nitrogen atmosphere. The resulting mixture was stirred at 60° C. for 3 h and quenched with aqueous Na₂SO₄ solution. The filtrate was concentrated to afford a crude product, which was purified by prep-HPLC to give Compound 382A (240 mg, yield 78%). LC-MS (ESI) m/z: 309 [M+H]⁺; ¹H-NMR (CDCl₃, 400 MHz): δ (ppm) 0.75-0.85 (m, 4H), 1.76-1.79 (m, 4H), 2.34 (s, 3H), 2.43-2.59 (m, 6H), 2.87-2.91 (m, 1H), 3.77-3.82 (m, 1H), 4.63-4.69 (m, 1H), 7.02-7.12 (m, 2H), 7.22-7.26 (m, 1H).

A mixture of Compound 382A (92 mg, 0.33 mmol), Compound 133D (73 mg, 0.30 mmol), and HATU (137 mg, 0.36 mmol) in DMF (4 mL) was stirred at 25° C. for 4 h. Then it was purified by prep-HPLC to give Compound 382 (70 mg, yield 36%) as a white solid. LC-MS (ESI) m/z: 535 [M+H]⁺; ¹H-NMR ((CD₃)₂CO, 400 MHz): δ (ppm) 0.61-0.90 (m, 4H), 2.06-2.25 (m, 4H), 3.08-3.27 (m, 3H), 3.45 (s, 2H), 3.71-4.46 (m, 5H), 5.08-5.38 (m, 1H), 5.57-5.72 (m, 1H), 6.88-7.85 (m, 11H), 9.20-9.95 (m, 1H).

Example 383

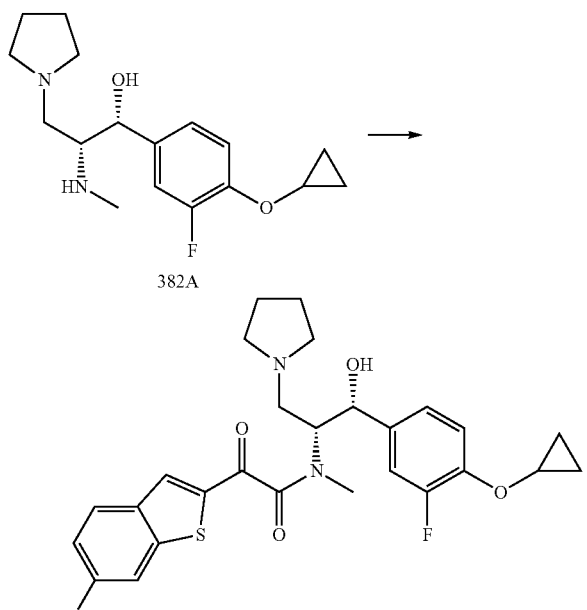

383

A mixture of Compound 382A (140 mg, 0.45 mmol), Compound 242F (98 mg, 0.40 mmol), and HATU (182 mg, 0.48 mmol) in DMF (3 mL) was stirred at 25° C. for 15 h. It was purified by prep-HPLC to give Compound 383 (88 mg, yield 34%) as a white solid. LC-MS (ESI) m/z: 531 [M+H]⁺; ¹H-NMR (DMSO-d, 400 MHz): δ (ppm) 0.30-0.84 (m, 4H), 1.88-2.04 (m, 4H), 2.99-3.29 (m, 6H), 3.55-3.69 (m, 2H), 3.81-4.08 (m, 2H), 4.31-4.78 (m, 1H), 4.95-5.15 (m, 1H), 6.04-6.19 (m, 1H), 6.90-7.71 (s, 5H), 7.86-8.12 (m, 1H), 8.26-8.32 (m, 1H), 9.38-9.53 (m, 1H).

BIOLOGICAL EXAMPLES

The following describes ways in which the compounds described herein were tested to measure in vitro activity in enzymatic and cell-based assays. A person of ordinary skill in the art would know that variations in the assay conditions could be used to determine the activity of the compounds.

Assay 1: GCS Enzymatic Assay

This assay was modified based on the study by Larsen et al. (*J. Lipid Res.* 2011, 53, 282). Madin-Darby canine kidney (MDCK) cell lysate was prepared using M-PER Mammalian Protein Extraction Reagent (Thermal Scientific) in the presence of a protease inhibitor cocktail (Roche). Protein concentration was determined using BCA assay kit (Pierce). Sixty micrograms of MDCK cell lysate was incubated with various concentrations of a compound described herein from 0.001 μM-10 μM, respectively, in 100 mM Tris buffer (pH 7.5) containing 10 mM MgCl₂, 1 mM dithiothreitol, 1 mM EGTA, 2 mM NAD, 100 μM UDP-glucose, 10 μM C6-NBD-Ceramide (Matreya LLC, Pleasant Gap, Pa.), 35 μM dioleoylphosphatidylcholine and 5 μM sulfatide (Sigma) in a final reaction volume of 100 μL at 37° C. for 1 hour. 0.1% DMSO was used as mock treatment or control. The reaction was terminated by adding 100 μL acetonitrile solution and subjected to LC/MS analysis.

The quantitative analysis of NBD-Ceramide and glucosylceramide was performed on a Shimadzu ultra-fast liquid chromatography (Shimadzu, Japan) coupled with API 4000 triple quadrupole mass spectrometer (Applied Biosystems, Concord, Ontario, Canada). Sample separation was conducted on a Waters Xbridge™ BEH130 C18, 100 mm×4.6 mm i.d, 3.5 μm (Milford, Mass., USA). The mobile phase consisted of water and acetonitrile supplemented with 0.1% formic acid (v/v). The flow rate was 1.0 mL/min. The initial mobile phase was 20% acetonitrile and was ramped in a linear fashion to 50% acetonitrile in 0.4 min. From 0.4 to 1.5 min, the gradient was ramped to 98% acetonitrile, and then was held at 100% until 8.0 min. Acetonitrile was reset to 20% in 1.5 min, and maintained until 10.0 min. The total run time was 10.0 min. The MS/MS detection was performed in ESI positive mode. The mass transition of NBD-Ceramide was m/z 576.36-558.40 under the collision energy of 15 V, and the mass transition of glucosylceramide was m/z 738.35-558.40 under 21V collision energy. The cell lysate was diluted with equal volume of acetonitrile. Aliquots of 50 μL diluted samples were added to 1.5 mL tubes, and 100 μL of acetonitrile containing internal standard (100 ng/mL tolbutamide) were added for protein precipitation. The mixture were vortexed and then centrifuged at 13000 rpm for 10 min. 70 μL of supernatant were mixed with 140 μL of H₂O and the final solution were injected for LC/MS/MS analysis and IC₅₀'s and/or percent inhibitions calculated.

Assay 2: K562 Cell-Based Assay

This assay was modified based on the study by Gupta et al. (*J. Lipid Res.* 2010, 51, 866). K562 cells were seeded into 12-well plates at 3×10⁵ cells/well/mL in RPMI-1640 medium with 5% FBS and incubated at 37° C. for 24 h. One µL of a compound described herein at desired concentration (10 mM, 1 mM, 0.1 mM, 0.01 mM, 0.001 mM and 0.0001 mM in DMSO) or DMSO was added into corresponding well and mixed. Cells were incubated at 37° C. for 4 h. Then 100 µL of RPMI-1640 medium containing 110 µM of NBD-Ceramide, 11% BSA, 5% FBS, and corresponding concentration of a compound described herein was added into each well and mixed. Cells were incubated for additional 0.5 h at 37° C., followed by washing the cells with ice-cold PBS (pH 7.4) twice with centrifugation and resuspended with 50 µL cold PBS+1% Triton X-100. The cell lysate was sonicated for 15 min before adding equal volume of methanol for LCMS analysis. A small aliquot of cell lysate was used to determine protein concentration by BCA assay kit.

The HPLC equipment and methods used in Assay 1 were used in this assay as well and $IC_{50}$'s were calculated.

Assay 3: NCI/ADR-Res Cell-Based Assay

NCI/ADR-RES cells were seeded into 12-well plates (4×10⁵ cells/well) in RPMI-1640 medium with 10% FBS and incubated at 37° C. for 24 h. Before treatment with a compound described herein, cell culture media were removed and replaced with 1 mL per well RPMI-1640 medium containing 5% FBS and a compound as described herein at desired concentrations (10 µM, 1 µM, 0.1 µM, 0.01 µM, 0.001 µM, and 0.0001 µM), respectively, or 0.1% DMSO only. Cells were cultured for 4 hours at 37° C. followed by replacing the media with RPMI-1640 containing 1% BSA and 10 µM of C6-NBD-Ceramide in the present of a compound described herein, and incubated for additional 0.5 hour at 37° C. Cells were then washed twice with ice-cold PBS (pH 7.4), scraped with 50 µL cold PBS+1% Triton X-100. The cell lysate was sonicated for 15 min before adding equal volume of methanol for LCMS analysis. A small aliquot of cell lysate was used to determine protein concentration by BCA assay kit.

The HPLC equipment and methods used in Assay 1 were used in this assay as well and $IC_{50}$'s and % inhibition were calculated.

Using the above assays, the following compounds were tested. In the tables below, "nt" means that the compound was not tested in the assay. Either $IC_{50}$ or % inhibition data are included in the tables. The % inhibition data is identified by an asterix ("*"). For $IC_{50}$ data, "A" means the compound had an $IC_{50}$ of greater than zero but less than or equal to about 50 nM and "B" means the compound had an $IC_{50}$ is greater than about 50 but less than or equal to about 5000 nM. For % inhibition data, "A*" means the compound had a % inhibition of a percent inhibition of greater than or equal to about 50% and "B*" means the compound had a % inhibition of greater than or equal to about 3% but less than about 50%.

TABLE 1

The data provided is the $IC_{50}$ (nM) generated from Assay 1, except as otherwise noted by *, which is % inhibition, also generated from Assay 1.

| Cmpd No. | Name | Data |
|---|---|---|
| 1 | 2-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide | A |
| 2 | 2-(2,3-dihydrobenzo[b][1,4]dioxin-6-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide | B |
| 3 | 2-(5-chlorobenzo[b]thiophen-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide | A |
| 4 | 2-(5-chlorobenzo[b]thiophen-2-yl)-2,2-difluoro-N-((2R)-1-(3-fluoro-4-methoxyphenyl)-1-hydroxy-3-(pyrrolidin-1-yl)propan-2-yl)acetamide | B* |
| 5A | 2-(2,3-dihydro-1H-inden-2-yl)-2,2-difluoro-N-((2R)-1-(3-fluoro-4-methoxyphenyl)-1-hydroxy-3-(pyrrolidin-1-yl)propan-2-yl)acetamide | B |
| 5 | 2-(2,3-dihydro-1H-inden-2-yl)-2,2-difluoro-N-((1S,2R)-1-(3-fluoro-4-methoxyphenyl)-1-hydroxy-3-(pyrrolidin-1-yl)propan-2-yl)acetamide | A |
| 5B | 2-(2,3-dihydro-1H-inden-2-yl)-2,2-difluoro-N-((1R,2R)-1-(3-fluoro-4-methoxyphenyl)-1-hydroxy-3-(pyrrolidin-1-yl)propan-2-yl)acetamide | B* |
| 6 | 2-(5-chlorobenzo[d]thiazol-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide | B* |
| 7 | 2-(5,6-dichloro-2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide | A |
| 8 | 2-(2,3-dihydro-1H-inden-2-yl)-2,2-difluoro-N-((1R,2R)-1-(2-fluoro-5-methoxyphenyl)-1-hydroxy-3-(pyrrolidin-1-yl)propan-2-yl)acetamide | B* |
| 8J | 2-(2,3-dihydro-1H-inden-2-yl)-2,2-difluoro-N-((1S,2R)-1-(2-fluoro-5-methoxyphenyl)-1-hydroxy-3-(pyrrolidin-1-yl)propan-2-yl)acetamide | B* |
| 10 | 2-(5-chloro-1-methyl-1H-benzo[d]imidazol-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide | B* |
| 11 | 2-(5-chlorobenzofuran-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide | A |

TABLE 1-continued

The data provided is the IC$_{50}$ (nM) generated from Assay 1, except as otherwise noted by *, which is % inhibition, also generated from Assay 1.

| Cmpd No. | Name | Data |
|---|---|---|
| 12B | 2-(2,3-dihydro-1H-inden-2-yl)-2,2-difluoro-N-((1S,2R)-1-(7-fluoro-2,3-dihydrobenzo[b][1,4]dioxin-6-yl)-1-hydroxy-3-(pyrrolidin-1-yl)propan-2-yl)acetamide | B |
| 13 | 2-(7,8-dihydro-6H-cyclopenta[g]quinoxalin-7-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide | B |
| 14 | 2-(5-chloro-1-methyl-1H-indol-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide | A |
| 15 | 2-(5,7-dichlorobenzofuran-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide | A |
| 16 | N-((1R,2R)-1-(2,3-dihydrobenzo[b][1,4]dioxin-6-yl)-1-hydroxy-3-(pyrrolidin-1-yl)propan-2-yl)-2,2-difluoro-4-(3-(pyridin-2-yl)phenyl)butanamide | A |
| 17 | N-((1R,2R)-1-(2,3-dihydrobenzo[b][1,4]dioxin-6-yl)-1-hydroxy-3-(pyrrolidin-1-yl)propan-2-yl)-2,2-difluoro-3-(naphthalen-2-yl)propanamide | B |
| 18 | 2-(5,6-dichlorobenzofuran-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide | B* |
| 19 | 2-(4,5-dichlorobenzofuran-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide | A |
| 20 | N-((1R,2R)-1-(2,3-dihydrobenzo[b][1,4]dioxin-6-yl)-1-hydroxy-3-(pyrrolidin-1-yl)propan-2-yl)-2,2-difluoro-3-(3-(pyridin-2-yl)phenyl)propanamide | B* |
| 21 | N-((1R,2R)-1-(2,3-dihydrobenzo[b][1,4]dioxin-6-yl)-1-hydroxy-3-(pyrrolidin-1-yl)propan-2-yl)-2,2-difluoro-2-(5-iluoro-2,3-dihydro-1H-inden-2-yl)acetamide | A |
| 22 | N-((1R,2R)-1-(2,3-dihydrobenzo[b][1,4]dioxin-6-yl)-1-hydroxy-3-(pyrrolidin-1-yl)propan-2-yl)-2,2-difluoro-4-(naphthalen-2-yl)butanamide | A |
| 22K | N-((1S,2R)-1-(2,3-dihydrobenzo[b][1,4]dioxin-6-yl)-1-hydroxy-3-(pyrrolidin-1-yl)propan-2-yl)-2,2-difluoro-4-(naphthalen-2-yl)butanamide | B* |
| 23 | 2-(benzofuran-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide | A |
| 24 | N-((1R,2R)-1-(2,3-dihydrobenzo[b][1,4]dioxin-6-yl)-1-hydroxy-3-(pyrrolidin-1-yl)propan-2-yl)-2,2-difluoro-2-(5-fluorobenzofuran-2-yl)acetamide | A |
| 25 | (E)-4-(4-chlorophenyl)-N-((1R,2R)-1-(2,3-dihydrobenzo[b][1,4]dioxin-6-yl)-1-hydroxy-3-(pyrrolidin-1-yl)propan-2-yl)-2,2-difluorobut-3-enamide | B* |
| 26 | N-((1R,2R)-3-(3-amino-8-azabicyclo[3.2.1]octan-8-yl)-1-(2,3-dihydrobenzo[b][1,4]dioxin-6-yl)-1-hydroxypropan-2-yl)-2-(5-chlorobenzofuran-2-yl)-2,2-difluoroacetamide | B* |
| 28 | N-((1R,2R)-1-(2,3-dihydrobenzo[b][1,4]dioxin-6-yl)-1-hydroxy-3-(pyrrolidin-1-yl)propan-2-yl)-2,2-difluoro-2-(5-fluorobenzo[b]thiophen-2-yl)acetamide | A |
| 30 | N-((1R,2R)-1-(2,3-dihydrobenzo[b][1,4]dioxin-6-yl)-1-hydroxy-3-(pyrrolidin-1-yl)propan-2-yl)-2,2-difluoro-2-(5-(trifluoromethyl)benzofuran-2-yl)acetamide | A |
| 31 | 2-(5-bromobenzofuran-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide | A |
| 32C | N-((1S,2R)-3-(azetidin-1-yl)-1-(2,3-dihydrobenzo[b][1,4]dioxin-6-yl)-1-hydroxypropan-2-yl)-2-(5-chlorobenzofuran-2-yl)-2,2-difluoroacetamide | B* |
| 32D | N-((1R,2R)-3-(azetidin-1-yl)-1-(2,3-dihydrobenzo[b][1,4]dioxin-6-yl)-1-hydroxypropan-2-yl)-2-(5-chlorobenzofuran-2-yl)-2,2-difluoroacetamide | A |
| 33A | 2-(5-chlorobenzofuran-2-yl)-2,2-difluoro-N-((1S,2R)-1-(7-fluoro-2,3-dihydrobenzo[b][1,4]dioxin-6-yl)-1-hydroxy-3-(pyrrolidin-1-yl)propan-2-yl)acetamide | B* |
| 33 | 2-(5-chlorobenzofuran-2-yl)-2,2-difluoro-N-((1R,2R)-1-(7-fluoro-2,3-dihydrobenzo[b][1,4]dioxin-6-yl)-1-hydroxy-3-(pyrrolidin-1-yl)propan-2-yl)acetamide | B* |
| 34G | 2-(5-chlorobenzofuran-2-yl)-2,2-difluoro-N-((1S,2R)-1-hydroxy-3-(pyrrolidin-1-yl)-1-(quinolin-6-yl)propan-2-yl)acetamide | B* |
| 34 | 2-(5-chlorobenzofuran-2-yl)-2,2-difluoro-N-((1R,2R)-1-hydroxy-3-(pyrrolidin-1-yl)-1-(quinolin-6-yl)propan-2-yl)acetamide | A* |

TABLE 1-continued

The data provided is the IC$_{50}$ (nM) generated from Assay 1, except as otherwise noted by *, which is % inhibition, also generated from Assay 1.

| Cmpd No. | Name | Data |
|---|---|---|
| 36C | 2-(5-chlorobenzofuran-2-yl)-N-((1S,2R)-1-(2,3-dihydrobenzo[b][1,4]dioxin-6-yl)-3-(3,3-dimethylpyrrolidin-1-yl)-1-hydroxypropan-2-yl)-2,2-difluoroacetamide | B* |
| 37G | 2-(5-chlorobenzofuran-2-yl)-2,2-difluoro-N-((1S,2R)-1-hydroxy-3-(pyrrolidin-1-yl)-1-(4-(trifluoromethoxy)phenyl)propan-2-yl)acetamide | B* |
| 37 | 2-(5-chlorobenzofuran-2-yl)-2,2-difluoro-N-((1R,2R)-1-hydroxy-3-(pyrrolidin-1-yl)-1-(4-(trifluoromethoxy)phenyl)propan-2-yl)acetamide | B* |
| 38 | 2-(5-chlorobenzofuran-2-yl)-N-((1R,2R)-1-(2,3-dihydrobenzo[b][1,4]dioxin-6-yl)-3-((S)-3-fluoropyrrolidin-1-yl)-1-hydroxypropan-2-yl)-2,2-difluoroacetamide | B* |
| 39 | 2-(5-chlorobenzofuran-2-yl)-N-((1R,2R)-1-(2,3-dihydrobenzo[b][1,4]dioxin-6-yl)-1-hydroxy-3-((R)-2-methylpyrrolidin-1-yl)propan-2-yl)-2,2-difluoroacetamide | A |
| 40 | 2-(5-chlorobenzofuran-2-yl)-N-((1R,2R)-1-(2,3-dihydrobenzo[b][1,4]dioxin-6-yl)-1-hydroxy-3-((S)-2-methylpyrrolidin-1-yl)propan-2-yl)-2,2-difluoroacetamide | A |
| 41 | 2-(5-chlorobenzofuran-2-yl)-N-((1R,2R)-3-(3,3-difluoropyrrolidin-1-yl)-1-(2,3-dihydrobenzo[b][1,4]dioxin-6-yl)-1-hydroxypropan-2-yl)-2,2-difluoroacetamide | B* |
| 44H | N-((1S,2R)-1-(3-chloro-4-cyclopropoxyphenyl)-1-hydroxy-3-(pyrrolidin-1-yl)propan-2-yl)-2-(5-chlorobenzofuran-2-yl)-2,2-difluoroacetamide | B* |
| 44 | N-((1R,2R)-1-(3-chloro-4-cyclopropoxyphenyl)-1-hydroxy-3-(pyrrolidin-1-yl)propan-2-yl)-2-(5-chlorobenzofuran-2-yl)-2,2-difluoroacetamide | A |
| 46 | 2-(5-chlorobenzofuran-2-yl)-N-((1R,2R)-1-(2,3-dihydrobenzo[b][1,4]dioxin-6-yl)-3-((R)-3-fluoropyrrolidin-1-yl)-1-hydroxypropan-2-yl)-2,2-difluoroacetamide | B |
| 47 | N-((1R,2R)-1-(3-chloro-4-((tetrahydrofuran-3-yl)oxy)phenyl)-1-hydroxy-3-(pyrrolidin-1-yl)propan-2-yl)-2-(5-chlorobenzofuran-2-yl)-2,2-difluoroacetamide | A |
| 48 | 2-(5-chlorobenzofuran-2-yl)-N-((1R,2R)-1-(2,3-dihydrobenzo[b][1,4]dioxin-6-yl)-1-hydroxy-3-(2-azaspiro[3.3]heptan-2-yl)propan-2-yl)-2,2-difluoroacetamide | B* |
| 49 | 2-(5-chlorobenzofuran-2-yl)-2,2-difluoro-N-((1R,2R)-1-hydroxy-1-(1-methyl-1H-indazol-5-yl)-3-(pyrrolidin-1-yl)propan-2-yl)acetamide | B |
| 50 | N-((1R,2R)-1-(2,3-dihydrobenzo[b][1,4]dioxin-6-yl)-1-hydroxy-3-(pyrrolidin-1-yl)propan-2-yl)-2,2-difluoro-2-(5-(pyridin-2-yl)-2,3-dihydro-1H-inden-2-yl)acetamide | A |
| 51 | N-((1R,2R)-3-(2-azabicyclo[2.2.1]heptan-2-yl)-1-(2,3-dihydrobenzo[b][1,4]dioxin-6-yl)-1-hydroxypropan-2-yl)-2-(5-chlorobenzofuran-2-yl)-2,2-difluoroacetamide | A |
| 52 | N-((1R,2R)-1-(3-chloro-4-cyclopropoxyphenyl)-1-hydroxy-3-(pyrrolidin-1-yl)propan-2-yl)-2,2-difluoro-4-(naphthalen-2-yl)butanamide | A |
| 53 | N-((1R,2R)-3-(7-azabicyclo[2.2.1]heptan-7-yl)-1-(2,3-dihydrobenzo[b][1,4]dioxin-6-yl)-1-hydroxypropan-2-yl)-2-(5-chlorobenzofuran-2-yl)-2,2-difluoroacetamide | A |
| 54 | 2-(5-chlorobenzofuran-2-yl)-2,2-difluoro-N-((1R,2R)-1-hydroxy-1-(1-methyl-1H-indazol-6-yl)-3-(pyrrolidin-1-yl)propan-2-yl)acetamide | B* |
| 54G | 2-(5-chlorobenzofuran-2-yl)-2,2-difluoro-N-((1S,2R)-1-hydroxy-1-(1-methyl-1H-indazol-6-yl)-3-(pyrrolidin-1-yl)propan-2-yl)acetamide | B* |
| 56 | 2-(5-chlorobenzofuran-2-yl)-2,2-difluoro-N-((1R,2R)-1-hydroxy-1-(6-methoxypyridin-3-yl)-3-(pyrrolidin-1-yl)propan-2-yl)acetamide | A |
| 57B | N-[2-(2H,3H-benzo[e]1,4-dioxan-6-yl)(1R)-2-hydroxy-1-(pyrrolidinylmethyl)ethyl]-2-(5-chlorobenzo[d]furan-2-yl)-2,2-difluoroacetamide | A |
| 57 | 2-(5-chlorobenzofuran-2-yl)-N-((1R,2R)-1-(2,3-dihydrobenzo[b][1,4]dioxin-6-yl)-1-deutero-1-hydroxy-3-(pyrrolidin-1-yl)propan-2-yl)-2,2-difluoroacetamide | A |
| 57C | 2-(5-chlorobenzofuran-2-yl)-N-((1S,2R)-1-(2,3-dihydrobenzo[b][1,4]dioxin-6-yl)-1-deutero-1-hydroxy-3-(pyrrolidin-1-yl)propan-2-yl)-2,2-difluoroacetamide | B* |
| 59 | 2-(5-chlorobenzofuran-2-yl)-N-((1R,2R)-1-(3-(difluoromethyl)-4-methoxyphenyl)-1-hydroxy-3-(pyrrolidin-1-yl)propan-2-yl)-2,2-difluoroacetamide | B |
| 59I | 2-(5-chlorobenzofuran-2-yl)-N-((1S,2R)-1-(3-(difluoromethyl)-4-methoxyphenyl)-1-hydroxy-3-(pyrrolidin-1-yl)propan-2-yl)-2,2-difluoroacetamide | B* |

TABLE 1-continued

The data provided is the IC$_{50}$ (nM) generated from Assay 1, except as otherwise noted by *, which is % inhibition, also generated from Assay 1.

| Cmpd No. | Name | Data |
|---|---|---|
| 60 | 2-(5-chlorobenzofuran-2-yl)-N-((1R,2R)-1-(2,3-dihydrobenzo[b][1,4]dioxin-6-yl)-1-hydroxy-3-(pyrrolidin-1-yl)propan-2-yl)-2,2-dideutero-acetamide | A |
| 61 | N-((1R,2R)-1-(7-bromo-2,3-dihydrobenzo[b][1,4]dioxin-6-yl)-1-hydroxy-3-(pyrrolidin-1-yl)propan-2-yl)-2-(5-chlorobenzofuran-2-yl)-2,2-difluoroacetamide | B* |
| 62 | 2-(5-chlorobenzofuran-2-yl)-N-((1R,2R)-1-(2,3-dihydrobenzo[b][1,4]dioxin-6-yl)-3-(3,3-dimethylazetidin-1-yl)-1-hydroxypropan-2-yl)-2,2-difluoroacetamide | B* |
| 63 | 2-(5-chloro-2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide | A |
| 64 | 2-(5-chlorobenzofuran-2-yl)-2,2-difluoro-N-((1R,2R)-1-(8-fluoro-2,3-dihydrobenzo[b][1,4]dioxin-6-yl)-1-hydroxy-3-(pyrrolidin-1-yl)propan-2-yl)acetamide | A |
| 65 | N-((1R,2R)-1-(8-chloro-2,3-dihydrobenzo[b][1,4]dioxin-6-yl)-1-hydroxy-3-(pyrrolidin-1-yl)propan-2-yl)-2-(5-chlorobenzofuran-2-yl)-2,2-difluoroacetamide | A |
| 66 | 2-(5-chlorobenzofuran-2-yl)-N-((1R,2R)-1-(2,3-dihydrobenzo[b][1,4]dioxin-6-yl)-1-hydroxy-3-(3-methylazetidin-1-yl)propan-2-yl)-2,2-difluoroacetamide | A |
| 67 | 2-(5-chloro-2,3-dihydro-1H-inden-2-yl)-N-((1R,2R)-1-(3-chloro-4-cyclopropoxyphenyl)-1-hydroxy-3-(pyrrolidin-1-yl)propan-2-yl)-2,2-difluoroacetamide | A |
| 68G | 2-(5-chlorobenzofuran-2-yl)-N-((1R,2R)-1-(5-chlorobenzofuran-2-yl)-1-hydroxy-3-(pyrrolidin-1-yl)propan-2-yl)-2,2-difluoroacetamide | B* |
| 68 | 2-(5-chlorobenzofuran-2-yl)-N-((1S,2R)-1-(5-chlorobenzofuran-2-yl)-1-hydroxy-3-(pyrrolidin-1-yl)propan-2-yl)-2,2-difluoroacetamide | B* |
| 69 | N-((1R,2R)-1-(3-chloro-4-cyclopropoxyphenyl)-1-hydroxy-3-(pyrrolidin-1-yl)propan-2-yl)-2,2-difluoro-2-(5-(trifluoromethyl)benzofuran-2-yl)acetamide | A |
| 69A | N-((1S,2R)-1-(3-chloro-4-cyclopropoxyphenyl)-1-hydroxy-3-(pyrrolidin-1-yl)propan-2-yl)-2,2-difluoro-2-(5-(trifluoromethyl)benzofuran-2-yl)acetamide | B |
| 70 | 2-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)-2-oxoacetamide | A |
| 71 | 2-(5-chlorobenzofuran-2-yl)-N-((1R,2R)-1-(2,3-dihydrobenzo[b][1,4]dioxin-6-yl)-1-hydroxy-3-(pyrrolidin-1-yl)propan-2-yl)-2-oxoacetamide | A |
| 72 | (E)-2-(5-chlorobenzofuran-2-yl)-N-((1R,2R)-1-(2,3-dihydrobenzo[b][1,4]dioxin-6-yl)-1-hydroxy-3-(pyrrolidin-1-yl)propan-2-yl)-2-(hydroxyimino)acetamide | A |
| 73 | N-((1R,2R)-1-(2,3-dihydrobenzo[b][1,4]dioxin-6-yl)-1-hydroxy-3-(pyrrolidin-1-yl)propan-2-yl)-2-oxo-2-(5-(pyridin-2-yl)-2,3-dihydro-1H-inden-2-yl)acetamide | A |
| 74 | 2-(5-chloro-2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)-2-oxoacetamide | A |

TABLE 2

The data provided is the IC$_{50}$ (nM) generated from Assay 1, except as otherwise noted by *, which is % inhibition, also generated from Assay 1.

| Cmpd No. | Name | Data |
|---|---|---|
| 77 | N-((1R,2R)-1-(2,3-dihydrobenzo[b][1,4]dioxin-6-yl)-1-hydroxy-3-(pyrrolidin-1-yl)propan-2-yl)-2-oxo-2-(4,5,6,7-tetrahydro-2H-isoindol-1-yl)acetamide | B* |
| 78 | N-((1R,2R)-3-(azetidin-1-yl)-1-(2,3-dihydrobenzo[b][1,4]dioxin-6-yl)-1-hydroxypropan-2-yl)-2-(5-chlorobenzofuran-2-yl)-2-oxoacetamide | A |
| 79 | N-((1R,2R)-1-(3-chloro-4-cyclopropoxyphenyl)-1-hydroxy-3-(pyrrolidin-1-yl)propan-2-yl)-2-(5-chlorobenzofuran-2-yl)-2-oxoacetamide | A |
| 80 | 2-(5-chlorobenzofuran-2-yl)-2,2-difluoro-N-((1S,2R)-1-hydroxy-1-(6-isopropoxypyridin-3-yl)-3-(pyrrolidin-1-yl)propan-2-yl)acetamide | B |
| 82 | N-((1R,2R)-1-(3-chloro-4-cyclopropoxyphenyl)-1-hydroxy-3-(pyrrolidin-1-yl)propan-2-yl)-2,2-difluoro-4-(6-fluoronaphthalen-2-yl)butanamide | A |

TABLE 2-continued

The data provided is the IC$_{50}$ (nM) generated from Assay 1, except as otherwise noted by *, which is % inhibition, also generated from Assay 1.

| Cmpd No. | Name | Data |
|---|---|---|
| 83 | N-((1R,2R)-3-(azetidin-1-yl)-1-(8-fluoro-2,3-dihydrobenzo[b][1,4]dioxin-6-yl)-1-hydroxypropan-2-yl)-2-(5-chlorobenzofuran-2-yl)-2,2-difluoroacetamide | A |
| 84 | N-((1R,2R)-1-(2,3-dihydrobenzo[b][1,4]dioxin-6-yl)-1-hydroxy-3-(pyrrolidin-1-yl)propan-2-yl)-2,2-difluoro-4-(6-fluoronaphthalen-2-yl)butanamide | A |
| 85 | 2-(5-chlorobenzofuran-2-yl)-2,2-difluoro-N-((1R,2R)-1-hydroxy-3-(pyrrolidin-1-yl)-1-(6-(2,2,2-trifluoroethoxy)pyridin-3-yl)propan-2-yl)acetamide | A |
| 86 | N-((1R,2R)-3-(azetidin-1-yl)-1-(8-fluoro-2,3-dihydrobenzo[b][1,4]dioxin-6-yl)-1-hydroxypropan-2-yl)-2,2-difluoro-4-(6-fluoronaphthalen-2-yl)butanamide | A |
| 87 | 2,2-difluoro-N-((1R,2R)-1-(8-fluoro-2,3-dihydrobenzo[b][1,4]dioxin-6-yl)-1-hydroxy-3-(pyrrolidin-1-yl)propan-2-yl)-4-(6-fluoronaphthalen-2-yl)butanamide | A |
| 88 | 2,2-difluoro-4-(6-fluoronaphthalen-2-yl)-N-((1R,2R)-1-hydroxy-3-(pyrrolidin-1-yl)-1-(6-(2,2,2-trifluoroethoxy)pyridin-3-yl)propan-2-yl)butanamide | A* |
| 89 | N-((1R,2R)-3-(azetidin-1-yl)-1-(8-fluoro-2,3-dihydrobenzo[b][1,4]dioxin-6-yl)-1-hydroxypropan-2-yl)-2-(5-chlorobenzofuran-2-yl)-2-oxoacetamide | A |
| 90 | N-((1R,2R)-1-(2,3-dihydrobenzo[b][1,4]dioxin-6-yl)-1-hydroxy-3-(pyrrolidin-1-yl)propan-2-yl)-4-(6-fluoronaphthalen-2-yl)-2-oxobutanamide | A |
| 91 | 2-(5-chloro-2,3-dihydro-1H-inden-2-yl)-2,2-difluoro-N-((1R,2R)-1-hydroxy-3-(pyrrolidin-1-yl)-1-(6-(2,2,2-trifluoroethoxy)pyridin-3-yl)propan-2-yl)acetamide | B* |
| 92 | N-((1R,2R)-3-(azetidin-1-yl)-1-(8-fluoro-2,3-dihydrobenzo[b][1,4]dioxin-6-yl)-1-hydroxypropan-2-yl)-2-(5-chloro-2,3-dihydro-1H-inden-2-yl)-2,2-difluoroacetamide | A |
| 93 | 2-(5-chloro-2,3-dihydro-1H-inden-2-yl)-2,2-difluoro-N-((1R,2R)-1-(8-fluoro-2,3-dihydrobenzo[b][1,4]dioxin-6-yl)-1-hydroxy-3-(pyrrolidin-1-yl)propan-2-yl)acetamide | A |
| 94 | N-((1R,2R)-1-(3-chloro-4-isopropoxyphenyl)-1-hydroxy-3-(pyrrolidin-1-yl)propan-2-yl)-2-(5-chlorobenzofuran-2-yl)-2,2-difluoroacetamide | A |
| 95 | 2-(5-chlorobenzofuran-2-yl)-N-((1R,2R)-1-(8-fluoro-2,3-dihydrobenzo[b][1,4]dioxin-6-yl)-1-hydroxy-3-(pyrrolidin-1-yl)propan-2-yl)-2-oxoacetamide | A |
| 96 | N-((1R,2R)-1-(2,3-dihydrobenzo[b][1,4]dioxin-6-yl)-1-hydroxy-3-(3-methylazetidin-1-yl)propan-2-yl)-2,2-difluoro-4-(6-fluoronaphthalen-2-yl)butanamide | A* |
| 97 | 2,2-difluoro-4-(6-fluoronaphthalen-2-yl)-N-((1R,2R)-1-hydroxy-1-(6-isopropoxypyridin-3-yl)-3-(pyrrolidin-1-yl)propan-2-yl)butanamide | A* |
| 98 | N-((1R,2R)-3-(azetidin-1-yl)-1-(8-fluoro-2,3-dihydrobenzo[b][1,4]dioxin-6-yl)-1-hydroxypropan-2-yl)-2-(5-chlorobenzofuran-2-yl)-2-(hydroxyimino)acetamide | A |
| 99 | 2-(5-chlorobenzofuran-2-yl)-N-((1R,2R)-1-(6-cyclopropoxypyridin-3-yl)-1-hydroxy-3-(pyrrolidin-1-yl)propan-2-yl)-2,2-difluoroacetamide | A |
| 100 | 2-(5-chlorobenzofuran-2-yl)-N-((1R,2R)-1-(2,3-dihydrobenzo[b][1,4]dioxin-6-yl)-1-hydroxy-3-(3-methylazetidin-1-yl)propan-2-yl)-2-oxoacetamide | B* |
| 101 | N-((1R,2R)-1-(6-cyclopropoxypyridin-3-yl)-1-hydroxy-3-(pyrrolidin-1-yl)propan-2-yl)-2,2-difluoro-4-(6-fluoronaphthalen-2-yl)butanamide | A |
| 102 | (E)-2-(5-chlorobenzofuran-2-yl)-N-((1R,2R)-1-(2,3-dihydrobenzo[b][1,4]dioxin-6-yl)-1-hydroxy-3-(3-methylazetidin-1-yl)propan-2-yl)-2-(hydroxyimino)acetamide | A |
| 103 | 2-(5-chlorobenzofuran-2-yl)-2,2-difluoro-N-((1S,2R)-1-hydroxy-1-(2-isopropoxypyridin-4-yl)-3-(pyrrolidin-1-yl)propan-2-yl)acetamide | B* |
| 104 | (E)-2-(5-chlorobenzofuran-2-yl)-N-((1R,2R)-1-(8-fluoro-2,3-dihydrobenzo[b][1,4]dioxin-6-yl)-1-hydroxy-3-(pyrrolidin-1-yl)propan-2-yl)-2-(hydroxyimino)acetamide | A |
| 105 | N-((1R,2R)-1-(3-chloro-4-((tetrahydro-2H-pyran-4-yl)oxy)phenyl)-1-hydroxy-3-(pyrrolidin-1-yl)propan-2-yl)-2-(5-chlorobenzofuran-2-yl)-2,2-difluoroacetamide | A |
| 106 | (E)-N-((1R,2R)-1-(2,3-dihydrobenzo[b][1,4]dioxin-6-yl)-1-hydroxy-3-(pyrrolidin-1-yl)propan-2-yl)-4-(6-fluoronaphthalen-2-yl)-2-(hydroxyimino)butanamide | A |
| 107 | 2,2-difluoro-N-((1R,2R)-1-hydroxy-1-(6-isopropoxypyridin-3-yl)-3-(pyrrolidin-1-yl)propan-2-yl)-4-(naphthalen-2-yl)butanamide | A |

TABLE 2-continued

The data provided is the IC$_{50}$ (nM) generated from Assay 1, except as otherwise noted by *, which is % inhibition, also generated from Assay 1.

| Cmpd No. | Name | Data |
|---|---|---|
| 108 | 2,2-difluoro-N-((1R,2R)-1-hydroxy-3-(pyrrolidin-1-yl)-1-(6-(2,2,2-trifluoroethoxy)pyridin-3-yl)propan-2-yl)-4-(naphthalen-2-yl)butanamide | B |
| 109 | 2,2-difluoro-N-((1R,2R)-1-(8-fluoro-2,3-dihydrobenzo[b][1,4]dioxin-6-yl)-1-hydroxy-3-(pyrrolidin-1-yl)propan-2-yl)-4-(naphthalen-2-yl)butanamide | A |
| 110 | N-((1R,2R)-1-(3-chloro-4-((tetrahydro-2H-pyran-4-yl)oxy)phenyl)-1-hydroxy-3-(pyrrolidin-1-yl)propan-2-yl)-2,2-difluoro-4-(naphthalen-2-yl)butanamide | A |
| 111 | N-((1R,2R)-1-(8-fluoro-2,3-dihydrobenzo[b][1,4]dioxin-6-yl)-1-hydroxy-3-(pyrrolidin-1-yl)propan-2-yl)-4-(6-fluoronaphthalen-2-yl)-2-oxobutanamide | A |
| 112 | (E)-N-((1R,2R)-1-(3-chloro-4-cyclopropoxyphenyl)-1-hydroxy-3-(pyrrolidin-1-yl)propan-2-yl)-4-(6-fluoronaphthalen-2-yl)-2-(hydroxyimino)butanamide | A |
| 113 | N-((1S,2R)-3-(azetidin-1-yl)-1-(8-fluoro-2,3-dihydrobenzo[b][1,4]dioxin-6-yl)-1-hydroxypropan-2-yl)-2,2-difluoro-4-(naphthalen-2-yl)butanamide | B* |
| 114 | 2,2-difluoro-4-(6-fluoronaphthalen-2-yl)-N-((1R,2R)-1-hydroxy-1-(2-isopropoxypyridin-4-yl)-3-(pyrrolidin-1-yl)propan-2-yl)butanamide | A* |
| 115 | (E)-N-((1R,2R)-1-(8-fluoro-2,3-dihydrobenzo[b][1,4]dioxin-6-yl)-1-hydroxy-3-(pyrrolidin-1-yl)propan-2-yl)-4-(6-fluoronaphthalen-2-yl)-2-(hydroxyimino)butanamide | A |
| 116 | 2-(5-chloro-2,3-dihydro-1H-inden-2-yl)-N-((1R,2R)-1-(3-chloro-4-((tetrahydro-2H-pyran-4-yl)oxy)phenyl)-1-hydroxy-3-(pyrrolidin-1-yl)propan-2-yl)-2,2-difluoroacetamide | A |
| 117 | N-((1S,2R)-1-(2,2-dimethylchroman-6-yl)-1-hydroxy-3-(pyrrolidin-1-yl)propan-2-yl)-2,2-difluoro-4-(naphthalen-2-yl)butanamide | B* |
| 118 | (E)-N-((1R,2R)-3-(azetidin-1-yl)-1-(8-fluoro-2,3-dihydrobenzo[b][1,4]dioxin-6-yl)-1-hydroxypropan-2-yl)-4-(6-fluoronaphthalen-2-yl)-2-(hydroxyimino)butanamide | B |
| 119 | 2-(5-chlorobenzofuran-2-yl)-N-((1R,2R)-1-(2,2-dimethylchroman-6-yl)-1-hydroxy-3-(pyrrolidin-1-yl)propan-2-yl)-2,2-difluoroacetamide | A* |
| 120 | N-((1R,2R)-1-(6-cyclopropoxypyridin-3-yl)-1-hydroxy-3-(pyrrolidin-1-yl)propan-2-yl)-2,2-difluoro-4-(naphthalen-2-yl)butanamide | A* |
| 121 | N-((1R,2R)-1-(3-chloro-4-((1-methylpiperidin-4-yl)oxy)phenyl)-1-hydroxy-3-(pyrrolidin-1-yl)propan-2-yl)-2,2-difluoro-4-(naphthalen-2-yl)butanamide | B* |
| 122 | N-((1R,2R)-3-(azetidin-1-yl)-1-(3-chloro-4-cyclopropoxyphenyl)-1-hydroxypropan-2-yl)-2-(5-chlorobenzofuran-2-yl)-2-oxoacetamide | A* |
| 123 | N-((1R,2R)-1-(3-chloro-4-((1-methylpiperidin-4-yl)oxy)phenyl)-1-hydroxy-3-(pyrrolidin-1-yl)propan-2-yl)-2-(5-chlorobenzofuran-2-yl)-2,2-difluoroacetamide | A* |
| 124 | N-((1S,2R)-1-(3-chloro-4-morpholinophenyl)-1-hydroxy-3-(pyrrolidin-1-yl)propan-2-yl)-2,2-difluoro-4-(naphthalen-2-yl)butanamide | B* |
| 125 | N-((1R,2R)-1-(4-cyclopropoxy-3-fluorophenyl)-1-hydroxy-3-(pyrrolidin-1-yl)propan-2-yl)-2,2-difluoro-4-(naphthalen-2-yl)butanamide | A |
| 126 | 2-(5-chlorobenzofuran-2-yl)-N-((1R,2R)-1-(4-cyclopropoxy-3-fluorophenyl)-1-hydroxy-3-(pyrrolidin-1-yl)propan-2-yl)-2,2-difluoroacetamide | A |
| 127 | N-((1R,2R)-1-(3-chloro-4-morpholinophenyl)-1-hydroxy-3-(pyrrolidin-1-yl)propan-2-yl)-2-(5-chlorobenzofuran-2-yl)-2,2-difluoroacetamide | B |
| 128 | N-((1R,2R)-1-(4-(2-(azetidin-1-yl)ethoxy)-3-chlorophenyl)-1-hydroxy-3-(pyrrolidin-1-yl)propan-2-yl)-2-(5-chlorobenzofuran-2-yl)-2,2-difluoroacetamide | A |
| 129 | N-((1R,2R)-1-(3-chloro-4-(oxetan-3-yloxy)phenyl)-1-hydroxy-3-(pyrrolidin-1-yl)propan-2-yl)-2,2-difluoro-4-(naphthalen-2-yl)butanamide | A |
| 130 | N-((1R,2R)-1-(3-chloro-4-(oxetan-3-yloxy)phenyl)-1-hydroxy-3-(pyrrolidin-1-yl)propan-2-yl)-2-(5-chlorobenzofuran-2-yl)-2,2-difluoroacetamide | A |
| 131 | N-((1R,2R)-1-(4-(2-(azetidin-1-yl)ethoxy)-3-chlorophenyl)-1-hydroxy-3-(pyrrolidin-1-yl)propan-2-yl)-2,2-difluoro-4-(naphthalen-2-yl)butanamide | A* |
| 132 | 2-(6-chloronaphthalen-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide | A |
| 133 | N-((1R,2R)-1-(8-fluoro-2,3-dihydrobenzo[b][1,4]dioxin-6-yl)-1-hydroxy-3-(pyrrolidin-1-yl)propan-2-yl)-2-(4'-fluoro-[1,1'-biphenyl]-4-yl)-2-oxoacetamide | A |

TABLE 2-continued

The data provided is the IC$_{50}$ (nM) generated from Assay 1, except as otherwise noted by *, which is % inhibition, also generated from Assay 1.

| Cmpd No. | Name | Data |
|---|---|---|
| 134 | N-((1R,2R)-3-(azetidin-1-yl)-1-(3-chloro-4-cyclopropoxyphenyl)-1-hydroxypropan-2-yl)-2,2-difluoro-4-(6-fluoronaphthalen-2-yl)butanamide | A* |
| 135 | 2-(6-chloronaphthalen-2-yl)-2,2-difluoro-N-((1R,2R)-1-(8-fluoro-2,3-dihydrobenzo[b][1,4]dioxin-6-yl)-1-hydroxy-3-(pyrrolidin-1-yl)propan-2-yl)acetamide | A |
| 136 | (E)-N-((1R,2R)-1-(3-chloro-4-cyclopropoxyphenyl)-1-hydroxy-3-(pyrrolidin-1-yl)propan-2-yl)-2-(5-chlorobenzofuran-2-yl)-2-(hydroxyimino)acetamide | A |
| 137 | (E)-N-((1R,2R)-3-(azetidin-1-yl)-1-(3-chloro-4-cyclopropoxyphenyl)-1-hydroxypropan-2-yl)-4-(6-fluoronaphthalen-2-yl)-2-(hydroxyimino)butanamide | B* |
| 138 | (E)-N-((1R,2R)-1-(8-fluoro-2,3-dihydrobenzo[b][1,4]dioxin-6-yl)-1-hydroxy-3-(pyrrolidin-1-yl)propan-2-yl)-2-(4'-fluoro-[1,1'-biphenyl]-4-yl)-2-(hydroxyimino)acetamide | A |
| 139 | N-((1R,2R)-1-(3-chloro-4-cyclopropoxyphenyl)-1-hydroxy-3-(pyrrolidin-1-yl)propan-2-yl)-2-(6-chloronaphthalen-2-yl)-2,2-difluoroacetamide | A* |
| 140 | 2,2-difluoro-N-((1R,2R)-1-(8-fluoro-2,3-dihydrobenzo[b][1,4]dioxin-6-yl)-1-hydroxy-3-(pyrrolidin-1-yl)propan-2-yl)-2-(4'-fluoro-[1,1'-biphenyl]-4-yl)acetamide | A |
| 141 | (E)-N-((1R,2R)-3-(azetidin-1-yl)-1-(8-fluoro-2,3-dihydrobenzo[b][1,4]dioxin-6-yl)-1-hydroxypropan-2-yl)-2-(hydroxyimino)-4-(naphthalen-2-yl)butanamide | A |
| 142 | (E)-N-((1R,2R)-1-(3-chloro-4-cyclopropoxyphenyl)-1-hydroxy-3-(pyrrolidin-1-yl)propan-2-yl)-2-(hydroxyimino)-4-(naphthalen-2-yl)butanamide | A |
| 143 | N-((1R,2R)-1-(8-fluoro-2,3-dihydrobenzo[b][1,4]dioxin-6-yl)-1-hydroxy-3-(pyrrolidin-1-yl)propan-2-yl)-4-(naphthalen-2-yl)-2-oxobutanamide | A |
| 144 | N-((1R,2R)-3-(azetidin-1-yl)-1-(2,3-dihydrobenzo[b][1,4]dioxin-6-yl)-1-hydroxypropan-2-yl)-2,2-difluoro-4-(naphthalen-2-yl)butanamide | A |
| 145 | N-((1R,2R)-3-(azetidin-1-yl)-1-(8-fluoro-2,3-dihydrobenzo[b][1,4]dioxin-6-yl)-1-hydroxypropan-2-yl)-4-(naphthalen-2-yl)-2-oxobutanamide | A* |
| 146 | N-((1R,2R)-1-(3-chloro-4-((tetrahydro-2H-pyran-4-yl)oxy)phenyl)-1-hydroxy-3-(pyrrolidin-1-yl)propan-2-yl)-2-(6-chloronaphthalen-2-yl)-2,2-difluoroacetamide | A |
| 147 | N-((1R,2R)-1-(3-chloro-4-cyclopropoxyphenyl)-1-hydroxy-3-(pyrrolidin-1-yl)propan-2-yl)-4-(naphthalen-2-yl)-2-oxobutanamide | A* |
| 148 | (E)-N-((1R,2R)-1-(8-fluoro-2,3-dihydrobenzo[b][1,4]dioxin-6-yl)-1-hydroxy-3-(pyrrolidin-1-yl)propan-2-yl)-2-(hydroxyimino)-4-(naphthalen-2-yl)butanamide | A |
| 149 | N-((1R,2R)-1-(3-chloro-4-cyclopropoxyphenyl)-1-hydroxy-3-(pyrrolidin-1-yl)propan-2-yl)-2-(4'-fluoro-[1,1'-biphenyl]-4-yl)-2-oxoacetamide | A |
| 150 | N-((1R,2R)-3-(azetidin-1-yl)-1-(8-fluoro-2,3-dihydrobenzo[b][1,4]dioxin-6-yl)-1-hydroxypropan-2-yl)-2-(4'-fluoro-[1,1'-biphenyl]-4-yl)-2-oxoacetamide | A |
| 151 | 2-(6-chloronaphthalen-2-yl)-N-((1R,2R)-1-(8-fluoro-2,3-dihydrobenzo[b][1,4]dioxin-6-yl)-1-hydroxy-3-(pyrrolidin-1-yl)propan-2-yl)-2-oxoacetamide | A |
| 152 | N-((1R,2R)-1-(3-chloro-4-((tetrahydro-2H-pyran-4-yl)oxy)phenyl)-1-hydroxy-3-(pyrrolidin-1-yl)propan-2-yl)-2-(4'-fluoro-[1,1'-biphenyl]-4-yl)-2-oxoacetamide | A |
| 153 | (E)-N-((1R,2R)-1-(3-chloro-4-cyclopropoxyphenyl)-1-hydroxy-3-(pyrrolidin-1-yl)propan-2-yl)-2-(4'-fluoro-[1,1'-biphenyl]-4-yl)-2-(hydroxyimino)acetamide | A |
| 154 | N-((1R,2R)-3-(azetidin-1-yl)-1-(3-chloro-4-cyclopropoxyphenyl)-1-hydroxypropan-2-yl)-4-(6-fluoronaphthalen-2-yl)-2-oxobutanamide | B* |
| 155 | (E)-N-((1R,2R)-3-(azetidin-1-yl)-1-(8-fluoro-2,3-dihydrobenzo[b][1,4]dioxin-6-yl)-1-hydroxypropan-2-yl)-2-(4'-fluoro-[1,1'-biphenyl]-4-yl)-2-(hydroxyimino)acetamide | A |
| 156 | 2-(7-chloronaphthalen-2-yl)-N-((1R,2R)-1-(8-fluoro-2,3-dihydrobenzo[b][1,4]dioxin-6-yl)-1-hydroxy-3-(pyrrolidin-1-yl)propan-2-yl)-2-oxoacetamide | A |
| 157 | N-((1R,2R)-3-(azetidin-1-yl)-1-(8-fluoro-2,3-dihydrobenzo[b][1,4]dioxin-6-yl)-1-hydroxypropan-2-yl)-2,2-difluoro-2-(4'-fluoro-[1,1'-biphenyl]-4-yl)acetamide | A |
| 158 | (E)-2-(6-chloronaphthalen-2-yl)-N-((1R,2R)-1-(8-fluoro-2,3-dihydrobenzo[b][1,4]dioxin-6-yl)-1-hydroxy-3-(pyrrolidin-1-yl)propan-2-yl)-2-(hydroxyimino)acetamide | A |

TABLE 2-continued

The data provided is the IC$_{50}$ (nM) generated from Assay 1, except as otherwise noted by *, which is % inhibition, also generated from Assay 1.

| Cmpd No. | Name | Data |
| --- | --- | --- |
| 159 | N-((1R,2R)-1-(3-chloro-4-cyclopropoxyphenyl)-1-hydroxy-3-(pyrrolidin-1-yl)propan-2-yl)-2,2-difluoro-2-(4'-fluoro-[1,1'-biphenyl]-4-yl)acetamide | A |
| 160 | N-((1R,2R)-1-(2,3-dihydrobenzo[b][1,4]dioxin-6-yl)-1-hydroxy-3-(pyrrolidin-1-yl)propan-2-yl)-2,2-difluoro-2-(4'-fluoro-[1,1'-biphenyl]-4-yl)acetamide | A |
| 161 | N-((1R,2R)-3-(azetidin-1-yl)-1-(2,3-dihydrobenzo[b][1,4]dioxin-6-yl)-1-hydroxypropan-2-yl)-2,2-difluoro-2-(4'-fluoro-[1,1'-biphenyl]-4-yl)acetamide | A |
| 162 | N-((1R,2R)-3-(azetidin-1-yl)-1-(3-chloro-4-cyclopropoxyphenyl)-1-hydroxypropan-2-yl)-2,2-difluoro-2-(4'-fluoro-[1,1'-biphenyl]-4-yl)acetamide | A* |
| 163 | N-((1R,2R)-1-(3-chloro-4-((tetrahydro-2H-pyran-4-yl)oxy)phenyl)-1-hydroxy-3-(pyrrolidin-1-yl)propan-2-yl)-2,2-difluoro-2-(4'-fluoro-[1,1'-biphenyl]-4-yl)acetamide | A |
| 164 | (E)-N-((1R,2R)-3-(azetidin-1-yl)-1-(3-chloro-4-cyclopropoxyphenyl)-1-hydroxypropan-2-yl)-2-(hydroxyimino)-4-(naphthalen-2-yl)butanamide | A* |
| 165 | N-((1R,2R)-1-(2,3-dihydrobenzo[b][1,4]dioxin-6-yl)-1-hydroxy-3-(pyrrolidin-1-yl)propan-2-yl)-2,2-difluoro-4-(5,6,7,8-tetrahydronaphthalen-2-yl)butanamide | A |
| 166 | N-((1R,2R)-1-(3-chloro-4-cyclopropoxyphenyl)-1-hydroxy-3-(pyrrolidin-1-yl)propan-2-yl)-2,2-difluoro-4-(5,6,7,8-tetrahydronaphthalen-2-yl)butanamide | A |
| 167 | 2,2-difluoro-N-((1R,2R)-1-(8-fluoro-2,3-dihydrobenzo[b][1,4]dioxin-6-yl)-1-hydroxy-3-(pyrrolidin-1-yl)propan-2-yl)-4-(5,6,7,8-tetrahydronaphthalen-2-yl)butanamide | A |
| 168 | N-((1S,2R)-1-(3-chloro-4-(2-hydroxy-2-methylpropoxy)phenyl)-1-hydroxy-3-(pyrrolidin-1-yl)propan-2-yl)-2-(5-chlorobenzofuran-2-yl)-2,2-difluoroacetamide | B* |
| 169 | (E)-N-((1R,2R)-3-(azetidin-1-yl)-1-(3-chloro-4-cyclopropoxyphenyl)-1-hydroxypropan-2-yl)-2-(5-chlorobenzofuran-2-yl)-2-(hydroxyimino)acetamide | A* |
| 170 | N-((1R,2R)-3-(azetidin-1-yl)-1-(3-chloro-4-cyclopropoxyphenyl)-1-hydroxypropan-2-yl)-4-(naphthalen-2-yl)-2-oxobutanamide | B* |
| 171 | N-((1R,2R)-3-(azetidin-1-yl)-1-(3-chloro-4-cyclopropoxyphenyl)-1-hydroxypropan-2-yl)-2,2-difluoro-4-(naphthalen-2-yl)butanamide | A |
| 172 | N-((1R,2R)-1-(3-chloro-4-cyclopropoxyphenyl)-1-hydroxy-3-(pyrrolidin-1-yl)propan-2-yl)-2-(6-chloronaphthalen-2-yl)-2-oxoacetamide | A |
| 173 | (E)-N-((1R,2R)-1-(3-chloro-4-cyclopropoxyphenyl)-1-hydroxy-3-(pyrrolidin-1-yl)propan-2-yl)-2-(6-chloronaphthalen-2-yl)-2-(hydroxyimino)acetamide | A |
| 174 | N-((1R,2R)-1-(2,3-dihydrobenzo[b][1,4]dioxin-6-yl)-1-hydroxy-3-(pyrrolidin-1-yl)propan-2-yl)-2-(5-(4-fluorophenyl)thiophen-2-yl)-2-oxoacetamide | A |
| 175 | N-((1R,2R)-1-(3-chloro-4-cyclopropoxyphenyl)-1-hydroxy-3-(pyrrolidin-1-yl)propan-2-yl)-2-(4-(5-fluoropyridin-2-yl)phenyl)-2-oxoacetamide | A |
| 176 | N-((1R,2R)-1-(8-fluoro-2,3-dihydrobenzo[b][1,4]dioxin-6-yl)-1-hydroxy-3-(pyrrolidin-1-yl)propan-2-yl)-2-(4-(5-fluoropyridin-2-yl)phenyl)-2-oxoacetamide | A |
| 177 | (E)-N-((1R,2R)-1-(3-chloro-4-((tetrahydro-2H-pyran-4-yl)oxy)phenyl)-1-hydroxy-3-(pyrrolidin-1-yl)propan-2-yl)-2-(4'-fluoro-[1,1'-biphenyl]-4-yl)-2-(hydroxyimino)acetamide | A |
| 178 | N-((1R,2R)-1-(3-chloro-4-cyclopropoxyphenyl)-1-hydroxy-3-(pyrrolidin-1-yl)propan-2-yl)-2,2-difluoro-2-(4-(5-fluoropyridin-2-yl)phenyl)acetamide | A* |
| 179 | N-((1R,2R)-1-(2,3-dihydrobenzo[b][1,4]dioxin-6-yl)-1-hydroxy-3-(pyrrolidin-1-yl)propan-2-yl)-2,2-difluoro-2-(4-(5-fluoropyridin-2-yl)phenyl)acetamide | A* |
| 180 | N-((1R,2R)-1-(2,3-dihydrobenzo[b][1,4]dioxin-6-yl)-1-hydroxy-3-(pyrrolidin-1-yl)propan-2-yl)-2,2-difluoro-2-(5-(4-fluorophenyl)thiophen-2-yl)acetamide | A* |
| 181 | (Z)-N-((1R,2R)-1-(2,3-dihydrobenzo[b][1,4]dioxin-6-yl)-1-hydroxy-3-(pyrrolidin-1-yl)propan-2-yl)-2-(5-(4-fluorophenyl)thiophen-2-yl)-2-(hydroxyimino)acetamide | A |
| 182 | N-((1R,2R)-1-(3-chloro-4-cyclopropoxyphenyl)-1-hydroxy-3-(pyrrolidin-1-yl)propan-2-yl)-2,2-difluoro-2-(4-(pyridin-2-yl)phenyl)acetamide | A |
| 183 | 2,2-difluoro-N-((1R,2R)-1-(8-fluoro-2,3-dihydrobenzo[b][1,4]dioxin-6-yl)-1-hydroxy-3-(pyrrolidin-1-yl)propan-2-yl)-2-(4-(5-fluoropyridin-2-yl)phenyl)acetamide | A |

TABLE 2-continued

The data provided is the IC$_{50}$ (nM) generated from Assay 1, except as otherwise noted by *, which is % inhibition, also generated from Assay 1.

| Cmpd No. | Name | Data |
|---|---|---|
| 184 | (E)-N-((1R,2R)-1-(3-chloro-4-cyclopropoxyphenyl)-1-hydroxy-3-(pyrrolidin-1-yl)propan-2-yl)-2-(4-(5-fluoropyridin-2-yl)phenyl)-2-(hydroxyimino)acetamide | A |
| 185 | 2-(5-chlorobenzofuran-2-yl)-N-((1R,2R)-1-(2,3-dihydro-[1,4]dioxino[2,3-b]pyridin-7-yl)-1-hydroxy-3-(pyrrolidin-1-yl)propan-2-yl)-2,2-difluoroacetamide | B* |
| 186 | N-((1R,2R)-1-(2,3-dihydrobenzo[b][1,4]dioxin-6-yl)-1-hydroxy-3-(pyrrolidin-1-yl)propan-2-yl)-2,2-difluoro-2-(4-(pyridin-2-yl)phenyl)acetamide | A* |
| 187 | 2,2-difluoro-N-((1R,2R)-1-(8-fluoro-2,3-dihydrobenzo[b][1,4]dioxin-6-yl)-1-hydroxy-3-(pyrrolidin-1-yl)propan-2-yl)-2-(4-(pyridin-2-yl)phenyl)acetamide | A |
| 188 | N-((1R,2R)-3-(azetidin-1-yl)-1-(8-fluoro-2,3-dihydrobenzo[b][1,4]dioxin-6-yl)-1-hydroxypropan-2-yl)-2-(6-chloronaphthalen-2-yl)-2-oxoacetamide | A* |
| 189 | N-((1R,2R)-1-(2,3-dihydrobenzo[b][1,4]dioxin-6-yl)-1-hydroxy-3-(pyrrolidin-1-yl)propan-2-yl)-2-(4-(5-fluoropyridin-2-yl)phenyl)-2-oxoacetamide | A* |
| 190 | (E)-N-((1R,2R)-1-(2,3-dihydrobenzo[b][1,4]dioxin-6-yl)-1-hydroxy-3-(pyrrolidin-1-yl)propan-2-yl)-2-(4-(5-fluoropyridin-2-yl)phenyl)-2-(hydroxyimino)acetamide | A* |
| 191 | (E)-N-((1R,2R)-3-(azetidin-1-yl)-1-(8-fluoro-2,3-dihydrobenzo[b][1,4]dioxin-6-yl)-1-hydroxypropan-2-yl)-2-(6-chloronaphthalen-2-yl)-2-(hydroxyimino)acetamide | A |
| 192 | 2-(5-chloro-2,3-dihydro-1H-inden-2-yl)-N-((1R,2R)-1-(3-chloro-4-(2-hydroxy-2-methylpropoxy)phenyl)-1-hydroxy-3-(pyrrolidin-1-yl)propan-2-yl)-2,2-difluoroacetamide | A* |
| 193 | N-((1R,2R)-1-(3-chloro-4-cyclopropoxyphenyl)-1-hydroxy-3-(pyrrolidin-1-yl)propan-2-yl)-2,2-difluoro-4-(1-methyl-1,2,3,4-tetrahydroquinolin-6-yl)butanamide | A* |
| 194 | N-((1R,2R)-1-(3-chloro-4-(2-hydroxy-2-methylpropoxy)phenyl)-1-hydroxy-3-(pyrrolidin-1-yl)propan-2-yl)-2-(4'-fluoro-[1,1'-biphenyl]-4-yl)-2-oxoacetamide | A |
| 195 | N-((1R,2R)-1-(2,3-dihydrobenzo[b][1,4]dioxin-6-yl)-1-hydroxy-3-(pyrrolidin-1-yl)propan-2-yl)-2-oxo-2-(4-(pyridin-2-yl)phenyl)acetamide | A* |
| 196 | 2,2-difluoro-N-((1R,2R)-1-(8-fluoro-2,3-dihydrobenzo[b][1,4]dioxin-6-yl)-1-hydroxy-3-(pyrrolidin-1-yl)propan-2-yl)-2-(imidazo[1,2-a]pyridin-2-yl)acetamide | B* |
| 197 | N-((1R,2R)-1-(2,3-dihydrobenzo[b][1,4]dioxin-6-yl)-1-hydroxy-3-(pyrrolidin-1-yl)propan-2-yl)-2-(3-(4-fluorophenoxy)phenyl)-2-oxoacetamide | A |
| 198 | N-((1R,2R)-1-(2,3-dihydrobenzo[b][1,4]dioxin-6-yl)-1-hydroxy-3-(pyrrolidin-1-yl)propan-2-yl)-2,2-difluoro-4-(1-methyl-1,2,3,4-tetrahydroquinolin-6-yl)butanamide | A* |
| 199 | N-((1R,2R)-1-(3-chloro-4-cyclopropoxyphenyl)-1-hydroxy-3-(pyrrolidin-1-yl)propan-2-yl)-2,2-difluoro-2-(imidazo[1,2-a]pyridin-2-yl)acetamide | B* |
| 200 | N-((2R)-1-(8-fluoro-2,3-dihydrobenzo[b][1,4]dioxin-6-yl)-1-hydroxy-3-(pyrrolidin-1-yl)propan-2-yl)-2-oxo-2-(4-(piperidin-1-yl)phenyl)acetamide | A |
| 201 | N-((1R,2R)-1-(2,3-dihydrobenzo[b][1,4]dioxin-6-yl)-1-hydroxy-3-(pyrrolidin-1-yl)propan-2-yl)-2,2-difluoro-2-(3-(4-fluorophenoxy)phenyl)acetamide | A* |
| 202 | N-((1R,2R)-1-(3-chloro-4-cyclopropoxyphenyl)-1-hydroxy-3-(pyrrolidin-1-yl)propan-2-yl)-2,2-difluoro-2-(4-(1-methyl-1H-indazol-5-yl)phenyl)acetamide | A |
| 203 | N-((1R,2R)-1-(8-fluoro-2,3-dihydrobenzo[b][1,4]dioxin-6-yl)-1-hydroxy-3-(pyrrolidin-1-yl)propan-2-yl)-2-(3-(4-fluorophenoxy)phenyl)-2-oxoacetamide | A |
| 204 | N-((1R,2R)-1-(4-cyclopropoxy-3-fluorophenyl)-1-hydroxy-3-(pyrrolidin-1-yl)propan-2-yl)-2,2-difluoro-2-(4'-fluoro-[1,1'-biphenyl]-4-yl)acetamide | A |
| 205 | N-((1R,2R)-1-(3-chloro-4-cyclopropoxyphenyl)-1-hydroxy-3-(pyrrolidin-1-yl)propan-2-yl)-2-(4-(1-methyl-1H-indazol-5-yl)phenyl)-2-oxoacetamide | A |
| 206 | N-((1R,2R)-1-(3-chloro-4-cyclopropoxyphenyl)-1-hydroxy-3-(pyrrolidin-1-yl)propan-2-yl)-2,2-difluoro-2-(3-(4-fluorophenoxy)phenyl)acetamide | A* |
| 207 | N-((1R,2R)-1-(2,3-dihydrobenzo[b][1,4]dioxin-6-yl)-1-hydroxy-3-(pyrrolidin-1-yl)propan-2-yl)-2-(4-(1-methyl-1H-indazol-5-yl)phenyl)-2-oxoacetamide | A |
| 208 | N-((1R,2R)-1-(4-cyclopropoxy-3-fluorophenyl)-1-hydroxy-3-(pyrrolidin-1-yl)propan-2-yl)-2-(4'-fluoro-[1,1'-biphenyl]-4-yl)-2-oxoacetamide | A |

TABLE 2-continued

The data provided is the IC$_{50}$ (nM) generated from Assay 1, except as otherwise noted by *, which is % inhibition, also generated from Assay 1.

| Cmpd No. | Name | Data |
| --- | --- | --- |
| 209 | N-((1R,2R)-1-(3-chloro-4-cyclopropoxyphenyl)-1-hydroxy-3-(pyrrolidin-1-yl)propan-2-yl)-2-(naphthalen-2-yl)-2-oxoacetamide | A |
| 210 | 2,2-difluoro-N-((1R,2R)-1-(8-fluoro-2,3-dihydrobenzo[b][1,4]dioxin-6-yl)-1-hydroxy-3-(pyrrolidin-1-yl)propan-2-yl)-2-(3-(4-fluorophenoxy)phenyl)acetamide | A |
| 211 | N-((1R,2R)-1-(2,3-dihydrobenzo[b][1,4]dioxin-6-yl)-1-hydroxy-3-(pyrrolidin-1-yl)propan-2-yl)-2,2-difluoro-2-(2-(4-fluorophenyl)thiazol-4-yl)acetamide | B* |
| 212 | N-((1R,2R)-1-(2,3-dihydrobenzo[b][1,4]dioxin-6-yl)-1-hydroxy-3-(pyrrolidin-1-yl)propan-2-yl)-2,2-difluoro-2-(4-(1-methyl-1H-indazol-5-yl)phenyl)acetamide | A |
| 213 | N-((1R,2R)-1-(3-chloro-4-cyclopropoxyphenyl)-1-hydroxy-3-(pyrrolidin-1-yl)propan-2-yl)-2,2-difluoro-2-(2-(4-fluorophenyl)thiazol-4-yl)acetamide | B* |
| 214 | N-((1R,2R)-1-(3-chloro-4-cyclopropoxyphenyl)-1-hydroxy-3-(pyrrolidin-1-yl)propan-2-yl)-2-oxo-2-(4-(pyridin-2-yl)phenyl)acetamide | A |
| 215 | N-((1R,2R)-1-(3-chloro-4-cyclopropoxyphenyl)-1-hydroxy-3-(pyrrolidin-1-yl)propan-2-yl)-2-(2-(4-fluorophenyl)thiazol-5-yl)-2-oxoacetamide | B* |
| 216 | N-((1R,2R)-1-(2,3-dihydrobenzo[b][1,4]dioxin-6-yl)-1-hydroxy-3-(pyrrolidin-1-yl)propan-2-yl)-2-(1-methyl-1H-indazol-5-yl)-2-oxoacetamide | A |
| 217 | N-((1R,2R)-1-(8-fluoro-2,3-dihydrobenzo[b][1,4]dioxin-6-yl)-1-hydroxy-3-(pyrrolidin-1-yl)propan-2-yl)-2-(1-methyl-1H-indazol-5-yl)-2-oxoacetamide | A |
| 218 | N-((1R,2R)-1-(3-chloro-4-cyclopropoxyphenyl)-1-hydroxy-3-(pyrrolidin-1-yl)propan-2-yl)-2,2-difluoro-2-(5-(4-fluorophenyl)thiophen-2-yl)acetamide | B* |
| 219 | N-((1R,2R)-1-(3-chloro-4-cyclopropoxyphenyl)-1-hydroxy-3-(pyrrolidin-1-yl)propan-2-yl)-2-(5-(4-fluorophenyl)thiophen-2-yl)-2-oxoacetamide | A* |
| 220 | N-((1R,2R)-1-(8-fluoro-2,3-dihydrobenzo[b][1,4]dioxin-6-yl)-1-hydroxy-3-(pyrrolidin-1-yl)propan-2-yl)-2-(4-(1-methyl-1H-indazol-5-yl)phenyl)-2-oxoacetamide | A |
| 221 | 2,2-difluoro-N-((1R,2R)-1-(8-fluoro-2,3-dihydrobenzo[b][1,4]dioxin-6-yl)-1-hydroxy-3-(pyrrolidin-1-yl)propan-2-yl)-2-(2-(4-fluorophenyl)thiazol-4-yl)acetamide | A* |
| 222 | N-((1R,2R)-1-(3-chloro-4-cyclopropoxyphenyl)-1-hydroxy-3-(pyrrolidin-1-yl)propan-2-yl)-2,2-difluoro-2-(2-(4-fluorophenyl)thiazol-5-yl)acetamide | B* |
| 223 | N-((1R,2R)-3-(azetidin-1-yl)-1-(8-fluoro-2,3-dihydrobenzo[b][1,4]dioxin-6-yl)-1-hydroxypropan-2-yl)-2-(4-(1-methyl-1H-indazol-5-yl)phenyl)-2-oxoacetamide | A |
| 224 | N-((1R,2R)-1-(3-chloro-4-cyclopropoxyphenyl)-1-hydroxy-3-(pyrrolidin-1-yl)propan-2-yl)-2-(1-methyl-1H-indazol-5-yl)-2-oxoacetamide | A* |
| 225 | N-((1R,2R)-1-(3-chloro-4-cyclopropoxyphenyl)-1-hydroxy-3-(pyrrolidin-1-yl)propan-2-yl)-2-(2-chlorobenzo[b]thiophen-5-yl)-2-oxoacetamide | B* |
| 226 | N-((1R,2R)-1-(8-fluoro-2,3-dihydrobenzo[b][1,4]dioxin-6-yl)-1-hydroxy-3-(pyrrolidin-1-yl)propan-2-yl)-2-(2-(4-fluorophenyl)thiazol-4-yl)-2-oxoacetamide | B* |
| 227 | N-((1R,2R)-3-(azetidin-1-yl)-1-(8-fluoro-2,3-dihydrobenzo[b][1,4]dioxin-6-yl)-1-hydroxypropan-2-yl)-2-oxo-2-(4-(piperidin-1-yl)phenyl)acetamide | A |
| 228 | N-((1R,2R)-1-(8-fluoro-2,3-dihydrobenzo[b][1,4]dioxin-6-yl)-1-hydroxy-3-(pyrrolidin-1-yl)propan-2-yl)-2-oxo-2-(4-(pyridin-2-yl)phenyl)acetamide | A |
| 229 | N-((1R,2R)-1-(2,3-dihydrobenzo[b][1,4]dioxin-6-yl)-1-hydroxy-3-(pyrrolidin-1-yl)propan-2-yl)-2-(2-(4-fluorophenyl)thiazol-4-yl)-2-oxoacetamide | B* |
| 230 | N-((1R,2R)-1-(8-fluoro-2,3-dihydrobenzo[b][1,4]dioxin-6-yl)-1-hydroxy-3-(pyrrolidin-1-yl)propan-2-yl)-2-(5-(4-fluorophenyl)thiophen-2-yl)-2-oxoacetamide | A |
| 231 | N-((1R,2R)-1-(3-chloro-4-cyclopropoxyphenyl)-1-hydroxy-3-(pyrrolidin-1-yl)propan-2-yl)-2-oxo-2-(4-(piperidin-1-yl)phenyl)acetamide | A |
| 232 | N-((1R,2R)-1-(3-chloro-4-cyclopropoxyphenyl)-1-hydroxy-3-(pyrrolidin-1-yl)propan-2-yl)-2,2-difluoro-2-(4-(1-methyl-1H-indazol-6-yl)phenyl)acetamide | A |
| 233 | 2-(benzo[b]thiophen-5-yl)-N-((1R,2R)-1-(3-chloro-4-cyclopropoxyphenyl)-1-hydroxy-3-(pyrrolidin-1-yl)propan-2-yl)-2-oxoacetamide | A |

TABLE 2-continued

The data provided is the IC$_{50}$ (nM) generated from Assay 1, except as otherwise noted by *, which is % inhibition, also generated from Assay 1.

| Cmpd No. | Name | Data |
|---|---|---|
| 234 | N-((1R,2R)-1-(8-chloro-2,3-dihydrobenzo[b][1,4]dioxin-6-yl)-1-hydroxy-3-(pyrrolidin-1-yl)propan-2-yl)-2-(4'-fluoro-[1,1'-biphenyl]-4-yl)-2-oxoacetamide | A |
| 235 | N-((1R,2R)-1-(2,3-dihydrobenzo[b][1,4]dioxin-6-yl)-1-hydroxy-3-(pyrrolidin-1-yl)propan-2-yl)-2,2-difluoro-2-(4-(1-methyl-1H-indazol-6-yl)phenyl)acetamide | A |
| 236 | 2,2-difluoro-N-((1R,2R)-1-(8-fluoro-2,3-dihydrobenzo[b][1,4]dioxin-6-yl)-1-hydroxy-3-(pyrrolidin-1-yl)propan-2-yl)-2-(4-(1-methyl-1H-indazol-6-yl)phenyl)acetamide | A |
| 237 | N-((1R,2R)-1-(3-chloro-4-cyclopropoxyphenyl)-1-hydroxy-3-(pyrrolidin-1-yl)propan-2-yl)-2,2-difluoro-2-(4-(2-methyl-2H-indazol-6-yl)phenyl)acetamide | A |
| 238 | N-((2R)-1-(3-chloro-4-cyclopropoxyphenyl)-1-hydroxy-3-(pyrrolidin-1-yl)propan-2-yl)-2-oxo-2-(3-(piperidin-1-yl)phenyl)acetamide | B* |
| 239 | 2,2-difluoro-N-((1R,2R)-1-(8-fluoro-2,3-dihydrobenzo[b][1,4]dioxin-6-yl)-1-hydroxy-3-(pyrrolidin-1-yl)propan-2-yl)-2-(5-(4-fluorophenyl)thiophen-2-yl)acetamide | A |
| 240 | N-((1R,2R)-1-(8-fluoro-2,3-dihydrobenzo[b][1,4]dioxin-6-yl)-1-hydroxy-3-(pyrrolidin-1-yl)propan-2-yl)-2-(4-(2-methyl-2H-indazol-5-yl)phenyl)-2-oxoacetamide | A |
| 241 | N-((1R,2R)-1-(3-chloro-4-cyclopropoxyphenyl)-1-hydroxy-3-(pyrrolidin-1-yl)propan-2-yl)-2-(4-(4-fluorophenoxy)phenyl)-2-oxoacetamide | A |
| 242 | N-((1R,2R)-1-(3-chloro-4-cyclopropoxyphenyl)-1-hydroxy-3-(pyrrolidin-1-yl)propan-2-yl)-2-(6-chlorobenzo[b]thiophen-2-yl)-2-oxoacetamide | A |
| 243 | N-((1R,2R)-1-(3-chloro-4-cyclopropoxyphenyl)-1-hydroxy-3-(pyrrolidin-1-yl)propan-2-yl)-2-(4-(1-methyl-1H-indazol-6-yl)phenyl)-2-oxoacetamide | A |
| 244 | N-((1R,2R)-1-(3-chloro-4-cyclopropoxyphenyl)-1-hydroxy-3-(pyrrolidin-1-yl)propan-2-yl)-2-(1-methyl-1H-indazol-6-yl)-2-oxoacetamide | A |
| 245 | N-((1R,2R)-1-(8-fluoro-2,3-dihydrobenzo[b][1,4]dioxin-6-yl)-1-hydroxy-3-(pyrrolidin-1-yl)propan-2-yl)-2-(1-methyl-1H-indazol-6-yl)-2-oxoacetamide | A* |
| 246 | N-((1R,2R)-1-(8-fluoro-2,3-dihydrobenzo[b][1,4]dioxin-6-yl)-1-hydroxy-3-(pyrrolidin-1-yl)propan-2-yl)-2-(4-(1-methyl-1H-indazol-6-yl)phenyl)-2-oxoacetamide | A |
| 247 | N-((1R,2R)-1-(3-chloro-4-cyclopropoxyphenyl)-1-hydroxy-3-(pyrrolidin-1-yl)propan-2-yl)-2,2-difluoro-2-(6-(4-fluorophenyl)pyridin-3-yl)acetamide | A* |
| 248 | N-((1R,2R)-3-(azetidin-1-yl)-1-(8-fluoro-2,3-dihydrobenzo[b][1,4]dioxin-6-yl)-1-hydroxypropan-2-yl)-2-(3-(4-fluorophenoxy)phenyl)-2-oxoacetamide | A |
| 249 | N-((1R,2R)-1-(3-chloro-4-cyclopropoxyphenyl)-1-hydroxy-3-(pyrrolidin-1-yl)propan-2-yl)-2-(3-(4-fluorophenoxy)phenyl)-2-oxoacetamide | A |
| 250 | N-((1R,2R)-1-(8-fluoro-2,3-dihydrobenzo[b][1,4]dioxin-6-yl)-1-hydroxy-3-(pyrrolidin-1-yl)propan-2-yl)-2-(4'-fluoro-[1,1'-biphenyl]-3-yl)-2-oxoacetamide | A |
| 251 | N-((1R,2R)-1-(3-chloro-4-cyclopropoxyphenyl)-1-hydroxy-3-(pyrrolidin-1-yl)propan-2-yl)-2-(4'-fluoro-[1,1'-biphenyl]-3-yl)-2-oxoacetamide | A |
| 252 | N-((1R,2R)-1-(2,3-dihydrobenzo[b][1,4]dioxin-6-yl)-1-hydroxy-3-(pyrrolidin-1-yl)propan-2-yl)-2-(4-(4-fluorophenyl)piperazin-1-yl)-2-oxoacetamide | A* |
| 253 | N-((1R,2R)-3-(azetidin-1-yl)-1-(3-chloro-4-cyclopropoxyphenyl)-1-hydroxypropan-2-yl)-2-(4'-fluoro-[1,1'-biphenyl]-4-yl)-2-oxoacetamide | A |
| 254 | N-((1R,2R)-1-(8-fluoro-2,3-dihydrobenzo[b][1,4]dioxin-6-yl)-1-hydroxy-3-(pyrrolidin-1-yl)propan-2-yl)-2-(4-(4-fluorophenyl)piperazin-1-yl)-2-oxoacetamide | A |
| 255 | 2-(4'-(tert-butyl)-[1,1'-biphenyl]-4-yl)-N-((1R,2R)-1-(3-chloro-4-cyclopropoxyphenyl)-1-hydroxy-3-(pyrrolidin-1-yl)propan-2-yl)-2-oxoacetamide | A |
| 256 | N-((1R,2R)-1-(3-chloro-4-cyclopropoxyphenyl)-1-hydroxy-3-(pyrrolidin-1-yl)propan-2-yl)-2-(4-(1-isopropyl-1H-indazol-6-yl)phenyl)-2-oxoacetamide | A |
| 257 | N-((1R,2R)-1-(3-chloro-4-cyclopropoxyphenyl)-1-hydroxy-3-(pyrrolidin-1-yl)propan-2-yl)-2-(4-(2-isopropyl-2H-indazol-6-yl)phenyl)-2-oxoacetamide | A |
| 258 | N-((1R,2R)-1-(3-chloro-4-cyclopropoxyphenyl)-1-hydroxy-3-(pyrrolidin-1-yl)propan-2-yl)-2-(4-(1-isopropyl-1H-indazol-5-yl)phenyl)-2-oxoacetamide | A |

TABLE 2-continued

The data provided is the IC$_{50}$ (nM) generated from Assay 1, except as otherwise noted by *, which is % inhibition, also generated from Assay 1.

| Cmpd No. | Name | Data |
|---|---|---|
| 259 | N-((1R,2R)-1-(3-chloro-4-cyclopropoxyphenyl)-1-hydroxy-3-(pyrrolidin-1-yl)propan-2-yl)-2-(4-(2-isopropyl-2H-indazol-5-yl)phenyl)-2-oxoacetamide | A |
| 260 | N-((1R,2R)-1-(3-chloro-4-cyclopropoxyphenyl)-1-hydroxy-3-(pyrrolidin-1-yl)propan-2-yl)-2,2-difluoro-2-(5-(4-fluorophenyl)pyridin-2-yl)acetamide | A |
| 261 | N-((1R,2R)-1-(3-chloro-4-cyclopropoxyphenyl)-1-hydroxy-3-(pyrrolidin-1-yl)propan-2-yl)-2-(3-(1-methyl-1H-indazol-6-yl)phenyl)-2-oxoacetamide | A* |
| 262 | N-((1R,2R)-1-(3-chloro-4-cyclopropoxyphenyl)-1-hydroxy-3-(pyrrolidin-1-yl)propan-2-yl)-2-(4-(4-fluorophenyl)piperazin-1-yl)-2-oxoacetamide | B* |
| 263 | N-((1R,2R)-1-(3-chloro-4-cyclopropoxyphenyl)-1-hydroxy-3-(pyrrolidin-1-yl)propan-2-yl)-2-(4-(2-chlorobenzo[b]thiophen-5-yl)phenyl)-2-oxoacetamide | A |
| 264 | N-((1R,2R)-1-(3-chloro-4-cyclopropoxyphenyl)-1-hydroxy-3-(pyrrolidin-1-yl)propan-2-yl)-2-(5-(4-fluorophenyl)pyridin-2-yl)-2-oxoacetamide | A |
| 265 | N-((1R,2R)-1-(4-cyclopropoxy-3-(trifluoromethyl)phenyl)-1-hydroxy-3-(pyrrolidin-1-yl)propan-2-yl)-2-(4'-fluoro-[1,1'-biphenyl]-4-yl)-2-oxoacetamide | B* |
| 266 | N-((1R,2R)-1-(3-chloro-4-cyclopropoxyphenyl)-1-hydroxy-3-(pyrrolidin-1-yl)propan-2-yl)-2-(4-(1-isopropyl-1H-indol-5-yl)phenyl)-2-oxoacetamide | A |
| 267 | 2-(4'-chloro-[1,1'biphenyl]-4-yl)-N-((1R,2R)-1-(2,3-dihydrobenzo[b][1,4]dioxin-6-yl)-1-hydroxy-3-(pyrrolidin-1-yl)propan-2-yl)-2-oxoacetamide | A |
| 268 | N-((1R,2R)-1-(5-fluoro-2,3-dihydrobenzo[b][1,4]dioxin-6-yl)-1-hydroxy-3-(pyrrolidin-1-yl)propan-2-yl)-2-(4'-fluoro-[1,1'-biphenyl]-4-yl)-2-oxoacetamide | A |
| 269 | N-((1R,2R)-1-(8-fluoro-2,3-dihydrobenzo[b][1,4]dioxin-6-yl)-1-hydroxy-3-(pyrrolidin-1-yl)propan-2-yl)-2-(4-(1-isopropyl-1H-indol-5-yl)phenyl)-2-oxoacetamide | A |
| 270 | N-((1R,2R)-1-(3-chloro-4-cyclopropoxyphenyl)-1-hydroxy-3-(pyrrolidin-1-yl)propan-2-yl)-2-(4'-chloro-[1,1'-biphenyl]-4-yl)-2-oxoacetamide | A |
| 271 | N-((1R,2R)-1-(3-chloro-4-cyclopropoxyphenyl)-1-hydroxy-3-(pyrrolidin-1-yl)propan-2-yl)-2-(4-(1-isopropyl-1H-benzo[d]imidazol-5-yl)phenyl)-2-oxoacetamide | A |
| 272 | 2-(4'-chloro-[1,1'biphenyl]-4-yl)-N-((1R,2R)-1-(8-fluoro-2,3-dihydrobenzo[b][1,4]dioxin-6-yl)-1-hydroxy-3-(pyrrolidin-1-yl)propan-2-yl)-2-oxoacetamide | A |
| 273 | N-((1R,2R)-1-(8-fluoro-2,3-dihydrobenzo[b][1,4]dioxin-6-yl)-1-hydroxy-3-(pyrrolidin-1-yl)propan-2-yl)-2-oxo-2-(4-(pyrrolidin-1-yl)phenyl)acetamide | A |
| 274 | N-((1R,2R)-1-(3-chloro-4-cyclopropoxyphenyl)-1-hydroxy-3-(pyrrolidin-1-yl)propan-2-yl)-2-oxo-2-(4'-(trifluoromethyl)-[1,1'-biphenyl]-4-yl)acetamide | A |
| 275 | 2-(4-(1-cyclopropyl-1H-indazol-5-yl)phenyl)-N-((1R,2R)-1-(8-fluoro-2,3-dihydrobenzo[b][1,4]dioxin-6-yl)-1-hydroxy-3-(pyrrolidin-1-yl)propan-2-yl)-2-oxoacetamide | A |
| 276 | N-((1R,2R)-1-(8-chloro-2,3-dihydrobenzo[b][1,4]dioxin-6-yl)-1-hydroxy-3-(pyrrolidin-1-yl)propan-2-yl)-2-(4-(1-cyclopropyl-1H-indazol-5-yl)phenyl)-2-oxoacetamide | A |
| 277 | N-((1R,2R)-1-(3-chloro-4-cyclopropoxyphenyl)-1-hydroxy-3-(pyrrolidin-1-yl)propan-2-yl)-2-(4-(1-cyclopropyl-1H-indazol-5-yl)phenyl)-2-oxoacetamide | A |
| 278 | N-((1R,2R)-3-(azetidin-1-yl)-1-(8-fluoro-2,3-dihydrobenzo[b][1,4]dioxin-6-yl)-1-hydroxypropan-2-yl)-2-(4-(1-cyclopropyl-1H-indazol-5-yl)phenyl)-2-oxoacetamide | A |
| 279 | N-((1R,2R)-3-(azetidin-1-yl)-1-(3-chloro-4-cyclopropoxyphenyl)-1-hydroxypropan-2-yl)-2-(4-(1-methyl-1H-indazol-5-yl)phenyl)-2-oxoacetamide | A |
| 280 | 2-(4-(benzo[d]isoxazol-6-yl)phenyl)-N-((1R,2R)-1-(8-fluoro-2,3-dihydrobenzo[b][1,4]dioxin-6-yl)-1-hydroxy-3-(pyrrolidin-1-yl)propan-2-yl)-2-oxoacetamide | A |
| 281 | N-((1R,2R)-1-(3-chloro-4-cyclopropoxyphenyl)-1-hydroxy-3-(pyrrolidin-1-yl)propan-2-yl)-2-(4-(1-cyclopropyl-1H-indazol-6-yl)phenyl)-2-oxoacetamide | A |
| 282 | 2-(4-(1-cyclopropyl-1H-indazol-6-yl)phenyl)-N-((1R,2R)-1-(8-fluoro-2,3-dihydrobenzo[b][1,4]dioxin-6-yl)-1-hydroxy-3-(pyrrolidin-1-yl)propan-2-yl)-2-oxoacetamide | A |
| 283 | N-((1R,2R)-3-(azetidin-1-yl)-1-(8-fluoro-2,3-dihydrobenzo[b][1,4]dioxin-6-yl)-1-hydroxypropan-2-yl)-2-(4-(1-cyclopropyl-1H-indazol-6-yl)phenyl)-2-oxoacetamide | A |

TABLE 2-continued

The data provided is the IC$_{50}$ (nM) generated from Assay 1, except as otherwise noted by *, which is % inhibition, also generated from Assay 1.

| Cmpd No. | Name | Data |
|---|---|---|
| 284 | N-((1R,2R)-1-(3-chloro-4-cyclopropoxyphenyl)-1-hydroxy-3-(pyrrolidin-1-yl)propan-2-yl)-2-(4-(2-cyclopropyl-2H-indazol-6-yl)phenyl)-2-oxoacetamide | A |
| 285 | N-((1R,2R)-3-(azetidin-1-yl)-1-(8-chloro-2,3-dihydrobenzo[b][1,4]dioxin-6-yl)-1-hydroxypropan-2-yl)-2-(4-(1-cyclopropyl-1H-indazol-5-yl)phenyl)-2-oxoacetamide | A |
| 286 | 2-(4'-fluoro-[1,1'-biphenyl]-4-yl)-N-((1R,2R)-1-hydroxy-3-(pyrrolidin-1-yl)-1-(8-(trifluoromethyl)-2,3-dihydrobenzo[b][1,4]dioxin-6-yl)propan-2-yl)-2-oxoacetamide | B |
| 287 | N-((1R,2R)-1-(3-chloro-4-cyclopropoxyphenyl)-1-hydroxy-3-(pyrrolidin-1-yl)propan-2-yl)-2-(6-(4-fluorophenyl)pyridin-3-yl)-2-oxoacetamide | A |
| 288 | N-((1R,2R)-1-(3-chloro-4-cyclopropoxyphenyl)-1-hydroxy-3-(pyrrolidin-1-yl)propan-2-yl)-2-(1-(4-fluorobenzyl)-1H-indazol-5-yl)-2-oxoacetamide | A |
| 289 | N-((1R,2R)-1-(8-fluoro-2,3-dihydrobenzo[b][1,4]dioxin-6-yl)-1-hydroxy-3-(pyrrolidin-1-yl)propan-2-yl)-2-(1-(4-fluorobenzyl)-1H-indazol-5-yl)-2-oxoacetamide | A |
| 290 | 2-(4-(benzo[d]isoxazol-5-yl)phenyl)-N-((1R,2R)-1-(8-fluoro-2,3-dihydrobenzo[b][1,4]dioxin-6-yl)-1-hydroxy-3-(pyrrolidin-1-yl)propan-2-yl)-2-oxoacetamide | A |
| 291 | N-((1R,2R)-1-(4-(tert-butoxy)-3-chlorophenyl)-1-hydroxy-3-(pyrrolidin-1-yl)propan-2-yl)-2-(4'-fluoro-[1,1'-biphenyl]-4-yl)-2-oxoacetamide | B |
| 292 | 2-(6-chlorobenzo[b]thiophen-2-yl)-N-((1R,2R)-1-(4-cyclopropoxy-3-fluorophenyl)-1-hydroxy-3-(pyrrolidin-1-yl)propan-2-yl)-2-oxoacetamide | A |
| 293 | N-((1R,2R)-3-(azetidin-1-yl)-1-(8-fluoro-2,3-dihydrobenzo[b][1,4]dioxin-6-yl)-1-hydroxypropan-2-yl)-2-(4'-(tert-butyl)-[1,1'-biphenyl]-4-yl)-2-oxoacetamide | A |
| 294 | 2-(4'-(tert-butyl)-[1,1'-biphenyl]-4-yl)-N-((1R,2R)-1-(8-fluoro-2,3-dihydrobenzo[b][1,4]dioxin-6-yl)-1-hydroxy-3-(pyrrolidin-1-yl)propan-2-yl)-2-oxoacetamide | A |
| 295 | N-((1R,2R)-1-(3-chloro-4-cyclopropoxyphenyl)-1-hydroxy-3-(pyrrolidin-1-yl)propan-2-yl)-2-(4'-fluoro-2'-methyl-[1,1'-biphenyl]-4-yl)-2-oxoacetamide | B |
| 296 | 2-(4-(benzo[d]thiazol-5-yl)phenyl)-N-((1R,2R)-1-(3-chloro-4-cyclopropoxyphenyl)-1-hydroxy-3-(pyrrolidin-1-yl)propan-2-yl)-2-oxoacetamide | A |
| 297 | 2-(4-(benzo[d]thiazol-6-yl)phenyl)-N-((1R,2R)-1-(3-chloro-4-cyclopropoxyphenyl)-1-hydroxy-3-(pyrrolidin-1-yl)propan-2-yl)-2-oxoacetamide | A |
| 298 | N-((1R,2R)-1-(3-chloro-4-cyclopropoxyphenyl)-1-hydroxy-3-(pyrrolidin-1-yl)propan-2-yl)-2-(4'-fluoro-2-methyl-[1,1'-biphenyl]-4-yl)-2-oxoacetamide | A |
| 299 | N-((1R,2R)-1-(8-fluoro-2,3-dihydrobenzo[b][1,4]dioxin-6-yl)-1-hydroxy-3-(pyrrolidin-1-yl)propan-2-yl)-2-(4'-fluoro-2-methyl-[1,1'-biphenyl]-4-yl)-2-oxoacetamide | A |
| 300 | N-((1R,2R)-3-(azetidin-1-yl)-1-(8-chloro-2,3-dihydrobenzo[b][1,4]dioxin-6-yl)-1-hydroxypropan-2-yl)-2-(4'-fluoro-[1,1'-biphenyl]-4-yl)-2-oxoacetamide | A |
| 301 | N-((1R,2R)-1-(3-chloro-4-cyclopropoxyphenyl)-1-hydroxy-3-(pyrrolidin-1-yl)propan-2-yl)-2-(4'-cyano-[1,1'-biphenyl]-4-yl)-2-oxoacetamide | A |
| 302 | 2-(8-bromodibenzo[b,d]furan-2-yl)-N-((1R,2R)-1-(3-chloro-4-cyclopropoxyphenyl)-1-hydroxy-3-(pyrrolidin-1-yl)propan-2-yl)-2-oxoacetamide | A |
| 303 | N-[(1R,2R)-2-(3-chloro-4-cyclopropoxyphenyl)-2-hydroxy-1-(pyrrolidinylmethyl)ethyl]-2-[4-(4-fluorophenyl)phenyl]acetamide | A |
| 304 | N-((1R,2R)-1-(3-chloro-4-cyclopropoxyphenyl)-1-hydroxy-3-(pyrrolidin-1-yl)propan-2-yl)-2-(2-(4-fluorobenzyl)-2H-indazol-5-yl)-2-oxoacetamide | A |
| 305 | N-((1R,2R)-1-(8-fluoro-2,3-dihydrobenzo[b][1,4]dioxin-6-yl)-1-hydroxy-3-(pyrrolidin-1-yl)propan-2-yl)-2-(2-(4-fluorobenzyl)-2H-indazol-5-yl)-2-oxoacetamide | A |
| 306 | N-((1R,2R)-1-(3-chloro-4-cyclopropoxyphenyl)-1-hydroxy-3-(pyrrolidin-1-yl)propan-2-yl)-2-(1-isopropyl-1H-indazol-6-yl)-2-oxoacetamide | A |
| 307 | N-((1R,2R)-1-(8-fluoro-2,3-dihydrobenzo[b][1,4]dioxin-6-yl)-1-hydroxy-3-(pyrrolidin-1-yl)propan-2-yl)-2-(1-isopropyl-1H-indazol-6-yl)-2-oxoacetamide | A |
| 308 | 2-(6-chlorobenzo[b]thiophen-2-yl)-N-((1R,2R)-1-(8-fluoro-2,3-dihydrobenzo[b][1,4]dioxin-6-yl)-1-hydroxy-3-(pyrrolidin-1-yl)propan-2-yl)-2-oxoacetamide | A |

TABLE 2-continued

The data provided is the IC$_{50}$ (nM) generated from Assay 1, except as otherwise noted by *, which is % inhibition, also generated from Assay 1.

| Cmpd No. | Name | Data |
|---|---|---|
| 309 | N-((1R,2R)-1-(3-chloro-4-(cyclopentyloxy)phenyl)-1-hydroxy-3-(pyrrolidin-1-yl)propan-2-yl)-2-(4'-fluoro-[1,1'-biphenyl]-4-yl)-2-oxoacetamide | A |
| 310 | N-((1R,2R)-1-(3-chloro-4-cyclopropoxyphenyl)-1-hydroxy-3-(pyrrolidin-1-yl)propan-2-yl)-2-(4-(2-isopropyl-3-methyl-2H-indazol-5-yl)phenyl)-2-oxoacetamide | A |
| 311 | N-((1R,2R)-1-(3-chloro-4-cyclopropoxyphenyl)-1-hydroxy-3-(pyrrolidin-1-yl)propan-2-yl)-2-(2-isopropyl-2H-indazol-5-yl)-2-oxoacetamide | A |
| 312 | N-((1R,2R)-1-(8-fluoro-2,3-dihydrobenzo[b][1,4]dioxin-6-yl)-1-hydroxy-3-(pyrrolidin-1-yl)propan-2-yl)-2-(2-isopropyl-2H-indazol-6-yl)-2-oxoacetamide | A |
| 313 | N-((1R,2R)-1-(3-chloro-4-cyclobutoxyphenyl)-1-hydroxy-3-(pyrrolidin-1-yl)propan-2-yl)-2-(4'-fluoro-[1,1'-biphenyl]-4-yl)-2-oxoacetamide | A |
| 314 | N-((1R,2R)-1-(3-chloro-4-cyclopropoxyphenyl)-1-hydroxy-3-(pyrrolidin-1-yl)propan-2-yl)-2-(4-(1-isopropyl-3-methyl-1H-indazol-5-yl)phenyl)-2-oxoacetamide | A |
| 315 | 2-(4'-fluoro-2'-methyl-[1,1'-biphenyl]-4-yl)-N-((1R,2R)-1-(8-fluoro-2,3-dihydrobenzo[b][1,4]dioxin-6-yl)-1-hydroxy-3-(pyrrolidin-1-yl)propan-2-yl)-2-oxoacetamide | A |
| 316 | N-((1R,2R)-1-(3-chloro-4-cyclopropoxyphenyl)-1-hydroxy-3-(pyrrolidin-1-yl)propan-2-yl)-2-(2-isopropyl-2H-indazol-6-yl)-2-oxoacetamide | A |
| 317 | N-((1R,2R)-1-(3-chloro-4-cyclopropoxyphenyl)-1-hydroxy-3-(pyrrolidin-1-yl)propan-2-yl)-2-(1-isopropyl-3-methyl-1H-indazol-5-yl)-2-oxoacetamide | A |
| 318 | N-((1R,2R)-1-(3-chloro-4-cyclopropoxyphenyl)-1-hydroxy-3-(pyrrolidin-1-yl)propan-2-yl)-2-(4-(1,3-dimethyl-1H-indazol-5-yl)phenyl)-2-oxoacetamide | A |
| 319 | N-((1R,2R)-1-(benzo[b][1,4]dioxin-6-yl)-1-hydroxy-3-(pyrrolidin-1-yl)propan-2-yl)-2-(4'-fluoro-[1,1'-biphenyl]-4-yl)-2-oxoacetamide | A |
| 320 | N-((1R,2R)-1-(3-chloro-4-(cyclopropylthio)phenyl)-1-hydroxy-3-(pyrrolidin-1-yl)propan-2-yl)-2-(4'-fluoro-[1,1'-biphenyl]-4-yl)-2-oxoacetamide | A |
| 321 | N-((1R,2R)-1-(3-chloro-4-cyclopropoxyphenyl)-1-hydroxy-3-(pyrrolidin-1-yl)propan-2-yl)-2-(1-isopropyl-1H-indazol-5-yl)-2-oxoacetamide | A |
| 322 | 2-(4-(1,3-dimethyl-1H-indazol-5-yl)phenyl)-N-((1R,2R)-1-(8-fluoro-2,3-dihydrobenzo[b][1,4]dioxin-6-yl)-1-hydroxy-3-(pyrrolidin-1-yl)propan-2-yl)-2-oxoacetamide | A |
| 323 | N-((1R,2R)-1-(8-fluoro-2,3-dihydrobenzo[b][1,4]dioxin-6-yl)-1-hydroxy-3-(pyrrolidin-1-yl)propan-2-yl)-2-(1-isopropyl-1H-indol-5-yl)-2-oxoacetamide | A |
| 324 | N-((1R,2R)-1-(3-chloro-4-cyclopropoxyphenyl)-1-hydroxy-3-(pyrrolidin-1-yl)propan-2-yl)-2-(1-isopropyl-1H-indol-5-yl)-2-oxoacetamide | A |
| 325 | N-((1R,2R)-1-(8-fluoro-2,3-dihydrobenzo[b][1,4]dioxin-6-yl)-1-hydroxy-3-(pyrrolidin-1-yl)propan-2-yl)-2-(4-morpholinophenyl)-2-oxoacetamide | A |
| 326 | (S)-N-(1-(3-chloro-4-cyclopropoxyphenyl)-3-(pyrrolidin-1-yl)propan-2-yl)-2-(4'-fluoro-[1,1'-biphenyl]-4-yl)-2-oxoacetamide | B |
| 327 | N-((1R,2R)-3-(azetidin-1-yl)-1-(3-chloro-4-cyclopropoxyphenyl)-1-hydroxypropan-2-yl)-2-oxo-2-(4-(pyrrolidin-1-yl)phenyl)acetamide | A |
| 328 | N-((1R,2R)-1-(3-chloro-4-cyclopropoxyphenyl)-1-hydroxy-3-(pyrrolidin-1-yl)propan-2-yl)-4-(6-chloronaphthalen-2-yl)-2,2-difluorobutanamide | A |
| 329 | N-((1R,2R)-1-(3-chloro-4-(vinyloxy)phenyl)-1-hydroxy-3-(pyrrolidin-1-yl)propan-2-yl)-2-(4'-fluoro-[1,1'-biphenyl]-4-yl)-2-oxoacetamide | A |
| 330 | N-((1R,2R)-1-(8-fluoro-2,3-dihydrobenzo[b][1,4]dioxin-6-yl)-1-hydroxy-3-(pyrrolidin-1-yl)propan-2-yl)-2-(4-(1-isopropyl-1H-pyrazol-4-yl)phenyl)-2-oxoacetamide | A |
| 331 | N-((1R,2R)-1-(8-fluoro-2,3-dihydrobenzo[b][1,4]dioxin-6-yl)-1-hydroxy-3-(pyrrolidin-1-yl)propan-2-yl)-2-(1-isopropyl-1H-indol-6-yl)-2-oxoacetamide | A |
| 332 | N-((1R,2R)-1-(3-chloro-4-cyclopropoxyphenyl)-1-hydroxy-3-(pyrrolidin-1-yl)propan-2-yl)-2-(1-isopropyl-1H-indol-6-yl)-2-oxoacetamide | A |
| 333 | N-((1R,2R)-1-(4-cyclopropoxyphenyl)-1-hydroxy-3-(pyrrolidin-1-yl)propan-2-yl)-2-(4'-fluoro-[1,1'-biphenyl]-4-yl)-2-oxoacetamide | A |
| 334 | N-((1R,2R)-1-(3-chloro-4-cyclopropoxyphenyl)-1-hydroxy-3-(pyrrolidin-1-yl)propan-2-yl)-2-(4-(1-isopropyl-3-methyl-1H-indazol-6-yl)phenyl)-2-oxoacetamide | A |

TABLE 2-continued

The data provided is the IC$_{50}$ (nM) generated from Assay 1, except as otherwise noted by *, which is % inhibition, also generated from Assay 1.

| Cmpd No. | Name | Data |
|---|---|---|
| 335 | N-((1R,2R)-1-(8-fluoro-2,3-dihydrobenzo[b][1,4]dioxin-6-yl)-1-hydroxy-3-(pyrrolidin-1-yl)propan-2-yl)-2-(4-(2-isopropyl-3-methyl-2H-indazol-6-yl)phenyl)-2-oxoacetamide | A |
| 336 | N-((1R,2R)-1-(3-chloro-4-cyclopropoxyphenyl)-1-hydroxy-3-(pyrrolidin-1-yl)propan-2-yl)-2-(4-(2-isopropyl-3-methyl-2H-indazol-6-yl)phenyl)-2-oxoacetamide | A |
| 337 | N-((1R,2R)-1-(8-fluoro-2,3-dihydrobenzo[b][1,4]dioxin-6-yl)-1-hydroxy-3-(pyrrolidin-1-yl)propan-2-yl)-2-(4-(1-isopropyl-3-methyl-1H-indazol-6-yl)phenyl)-2-oxoacetamide | A |
| 338 | N-((1R,2R)-3-(azetidin-1-yl)-1-(3-chloro-4-cyclopropoxyphenyl)-1-hydroxypropan-2-yl)-2-(6-chlorobenzo[b]thiophen-2-yl)-2-oxoacetamide | A |
| 339 | N-((1R,2R)-1-(3-chloro-4-cyclopropoxyphenyl)-1-hydroxy-3-(pyrrolidin-1-yl)propan-2-yl)-2-(4'-isopropyl-[1,1'-biphenyl]-4-yl)-2-oxoacetamide | A |
| 340 | N-((1R,2R)-1-(3-chloro-4-cyclopropoxyphenyl)-1-hydroxy-3-(pyrrolidin-1-yl)propan-2-yl)-2-(4-(1,3-dimethyl-1H-indazol-6-yl)phenyl)-2-oxoacetamide | A |
| 341 | 2-(4-(1,3-dimethyl-1H-indazol-6-yl)phenyl)-N-((1R,2R)-1-(8-fluoro-2,3-dihydrobenzo[b][1,4]dioxin-6-yl)-1-hydroxy-3-(pyrrolidin-1-yl)propan-2-yl)-2-oxoacetamide | A |
| 342 | 2-(4-(2,3-dimethyl-2H-indazol-6-yl)phenyl)-N-((1R,2R)-1-(8-fluoro-2,3-dihydrobenzo[b][1,4]dioxin-6-yl)-1-hydroxy-3-(pyrrolidin-1-yl)propan-2-yl)-2-oxoacetamide | A |
| 343 | N-((1R,2R)-1-(3-chloro-4-cyclopropoxyphenyl)-1-hydroxy-3-(pyrrolidin-1-yl)propan-2-yl)-2-oxo-2-(4-(pyrrolidin-1-yl)phenyl)acetamide | A |
| 344 | N-((1R,2R)-1-(3-fluoro-4-isopropoxy-5-methoxyphenyl)-1-hydroxy-3-(pyrrolidin-1-yl)propan-2-yl)-2-(4'-fluoro-[1,1'-biphenyl]-4-yl)-2-oxoacetamide | A |
| 345 | N-((1R,2R)-1-(8-fluoro-2,3-dihydrobenzo[b][1,4]dioxin-6-yl)-1-hydroxy-3-(pyrrolidin-1-yl)propan-2-yl)-2-(4-(1-isopropyl-1H-indol-6-yl)phenyl)-2-oxoacetamide | A |
| 346 | N-((1R,2R)-1-(3-chloro-4-cyclopropoxyphenyl)-1-hydroxy-3-(pyrrolidin-1-yl)propan-2-yl)-2-(4-(1-isopropyl-1H-indol-6-yl)phenyl)-2-oxoacetamide | A |
| 347 | N-((1R,2R)-1-(3-chloro-4-cyclopropoxyphenyl)-1-hydroxy-3-(pyrrolidin-1-yl)propan-2-yl)-2-(4-(2,3-dimethyl-2H-indazol-6-yl)phenyl)-2-oxoacetamide | A |
| 348 | 2-(6-chlorobenzo[b]thiophen-2-yl)-N-((1R,2R)-1-(3-fluoro-4-isopropoxy-5-methoxyphenyl)-1-hydroxy-3-(pyrrolidin-1-yl)propan-2-yl)-2-oxoacetamide | B |
| 349 | N-((1R,2R)-1-(3-chloro-4-cyclopropoxyphenyl)-1-hydroxy-3-(pyrrolidin-1-yl)propan-2-yl)-2-(4-(1-cyclopropyl-1H-pyrazol-3-yl)phenyl)-2-oxoacetamide | A |
| 350 | 2-(4-(1-cyclopropyl-1H-pyrazol-3-yl)phenyl)-N-((1R,2R)-1-(8-fluoro-2,3-dihydrobenzo[b][1,4]dioxin-6-yl)-1-hydroxy-3-(pyrrolidin-1-yl)propan-2-yl)-2-oxoacetamide | A |
| 351 | N-((1R,2R)-1-(3-chloro-4-cyclopropoxyphenyl)-1-hydroxy-3-(pyrrolidin-1-yl)propan-2-yl)-2-(4-(1-isopropyl-1H-pyrazol-3-yl)phenyl)-2-oxoacetamide | A |
| 352 | N-((1R,2R)-1-(8-fluoro-2,3-dihydrobenzo[b][1,4]dioxin-6-yl)-1-hydroxy-3-(pyrrolidin-1-yl)propan-2-yl)-2-(4-(1-isopropyl-1H-pyrazol-3-yl)phenyl)-2-oxoacetamide | A |
| 353 | N-((1R,2R)-1-(3-chloro-4-cyclopropoxyphenyl)-1-hydroxy-3-(pyrrolidin-1-yl)propan-2-yl)-2-(1-(4-fluorophenyl)-1H-indazol-5-yl)-2-oxoacetamide | A |
| 354 | N-((1R,2R)-1-(3-chloro-4-cyclopropoxyphenyl)-1-hydroxy-3-(pyrrolidin-1-yl)propan-2-yl)-2-(2-(4-fluorophenyl)-2H-indazol-5-yl)-2-oxoacetamide | A |
| 355 | N-((1R,2R)-1-(3-chloro-4-cyclopropoxyphenyl)-1-hydroxy-3-(pyrrolidin-1-yl)propan-2-yl)-2-oxo-2-(4'-(prop-1-en-2-yl)-[1,1'-biphenyl]-4-yl)acetamide | A |
| 356 | N-((1R,2R)-1-(8-fluoro-2,3-dihydrobenzo[b][1,4]dioxin-6-yl)-1-hydroxy-3-(pyrrolidin-1-yl)propan-2-yl)-2-(4'-(2-hydroxypropan-2-yl)-[1,1'-biphenyl]-4-yl)-2-oxoacetamide | A |
| 357 | N-((1R,2R)-1-(8-fluoro-2,3-dihydrobenzo[b][1,4]dioxin-6-yl)-1-hydroxy-3-(pyrrolidin-1-yl)propan-2-yl)-2-(4'-isopropyl-[1,1'-biphenyl]-4-yl)-2-oxoacetamide | A |
| 358 | N-((1R,2R)-1-(3-chloro-4-cyclopropoxyphenyl)-1-hydroxy-3-(pyrrolidin-1-yl)propan-2-yl)-2-(4'-(2-hydroxypropan-2-yl)-[1,1'-biphenyl]-4-yl)-2-oxoacetamide | A |
| 359 | 2-(4-(5-chlorothiophen-2-yl)phenyl)-N-((1R,2R)-1-(4-cyclopropoxy-3-fluorophenyl)-1-hydroxy-3-(pyrrolidin-1-yl)propan-2-yl)-2-oxoacetamide | A |

TABLE 2-continued

The data provided is the IC$_{50}$ (nM) generated from Assay 1, except as otherwise noted by *, which is % inhibition, also generated from Assay 1.

| Cmpd No. | Name | Data |
|---|---|---|
| 360 | 2-(4-(5-chlorothiophen-2-yl)phenyl)-N-((1R,2R)-1-(8-fluoro-2,3-dihydrobenzo[b][1,4]dioxin-6-yl)-1-hydroxy-3-(pyrrolidin-1-yl)propan-2-yl)-2-oxoacetamide | A |
| 361 | N-((1R,2R)-1-(3-fluoro-5-isopropoxy-4-methoxyphenyl)-1-hydroxy-3-(pyrrolidin-1-yl)propan-2-yl)-2-(4'-fluoro-[1,1'-biphenyl]-4-yl)-2-oxoacetamide | B |
| 362 | N-((1R,2R)-1-(8-fluoro-3,3-dimethyl-2,3-dihydrobenzo[b][1,4]dioxin-6-yl)-1-hydroxy-3-(pyrrolidin-1-yl)propan-2-yl)-2-(4'-fluoro-[1,1'-biphenyl]-4-yl)-2-oxoacetamide | A |
| 363 | N-((1R,2R)-1-(3-chloro-4-cyclopropoxyphenyl)-1-hydroxy-3-(pyrrolidin-1-yl)propan-2-yl)-2-(4-(5-chlorothiophen-2-yl)phenyl)-2-oxoacetamide | A |
| 364 | 2-(6-chlorobenzo[b]thiophen-2-yl)-N-((1R,2R)-1-(3-fluoro-5-isopropoxy-4-methoxyphenyl)-1-hydroxy-3-(pyrrolidin-1-yl)propan-2-yl)-2-oxoacetamide | B |
| 365 | N-((1R,2R)-1-(3-chloro-4-cyclopropoxyphenyl)-1-hydroxy-3-(pyrrolidin-1-yl)propan-2-yl)-2-(6-chlorobenzofuran-2-yl)-2-oxoacetamide | A |
| 366 | 2-(6-chlorobenzofuran-2-yl)-N-((1R,2R)-1-(8-fluoro-2,3-dihydrobenzo[b][1,4]dioxin-6-yl)-1-hydroxy-3-(pyrrolidin-1-yl)propan-2-yl)-2-oxoacetamide | A |
| 367 | N-((1R,2R)-3-(azetidin-1-yl)-1-(8-fluoro-2,3-dihydrobenzo[b][1,4]dioxin-6-yl)-1-hydroxypropan-2-yl)-2-oxo-2-(4-(pyrrolidin-1-yl)phenyl)acetamide | nt |
| 368 | N-((1R,2R)-1-(3-chloro-4-cyclopropoxyphenyl)-1-hydroxy-3-(pyrrolidin-1-yl)propan-2-yl)-2-(4-morpholinophenyl)-2-oxoacetamide | A |
| 369 | N-((1R,2R)-3-(azetidin-1-yl)-1-(8-fluoro-2,3-dihydrobenzo[b][1,4]dioxin-6-yl)-1-hydroxypropan-2-yl)-2-(4-morpholinophenyl)-2-oxoacetamide | A |
| 370 | N-((1R,2R)-1-(3-chloro-4-cyclopropoxyphenyl)-1-hydroxy-3-(pyrrolidin-1-yl)propan-2-yl)-2-(4'-cyclopropyl-[1,1'-biphenyl]-4-yl)-2-oxoacetamide | A |
| 371 | 2-(4'-cyclopropyl-[1,1'-biphenyl]-4-yl)-N-((1R,2R)-1-(8-fluoro-2,3-dihydrobenzo[b][1,4]dioxin-6-yl)-1-hydroxy-3-(pyrrolidin-1-yl)propan-2-yl)-2-oxoacetamide | A |
| 372 | N-((1R,2R)-1-(3-chloro-4-cyclopropoxyphenyl)-1-hydroxy-3-(pyrrolidin-1-yl)propan-2-yl)-2-oxo-2-(4-(tetrahydro-2H-pyran-4-yl)phenyl)acetamide | A |
| 373 | N-((1R,2R)-1-(8-fluoro-2,3-dihydrobenzo[b][1,4]dioxin-6-yl)-1-hydroxy-3-(pyrrolidin-1-yl)propan-2-yl)-2-oxo-2-(4-(tetrahydro-2H-pyran-4-yl)phenyl)acetamide | A |
| 374 | N-((1R,2R)-1-(4-cyclopropoxyphenyl)-1-hydroxy-3-(pyrrolidin-1-yl)propan-2-yl)-2-(4-morpholinophenyl)-2-oxoacetamide | B |
| 375 | 2-(4-(azetidin-1-yl)phenyl)-N-((1R,2R)-1-(3-chloro-4-cyclopropoxyphenyl)-1-hydroxy-3-(pyrrolidin-1-yl)propan-2-yl)-2-oxoacetamide | B |
| 376 | N-((1R,2R)-1-(3-chloro-4-cyclopropoxyphenyl)-1-hydroxy-3-(pyrrolidin-1-yl)propan-2-yl)-2-(4-fluorophenyl)-2-oxoacetamide | A |
| 377 | 2-(benzo[b]thiophen-2-yl)-N-((1R,2R)-1-(3-chloro-4-cyclopropoxyphenyl)-1-hydroxy-3-(pyrrolidin-1-yl)propan-2-yl)-2-oxoacetamide | A |
| 378 | N-((1R,2R)-1-(4-cyclopropoxy-3-fluorophenyl)-1-hydroxy-3-(pyrrolidin-1-yl)propan-2-yl)-2-(4-ethynylphenyl)-2-oxoacetamide | A |
| 379 | N-((1R,2R)-1-(8-fluoro-2,3-dihydrobenzo[b][1,4]dioxin-6-yl)-1-hydroxy-3-(pyrrolidin-1-yl)propan-2-yl)-2-(4-fluorophenyl)-2-oxoacetamide | A |
| 380 | N-((1R,2R)-1-(3-chloro-4-cyclopropoxyphenyl)-1-hydroxy-3-(pyrrolidin-1-yl)propan-2-yl)-2-(1-(4-fluorophenyl)piperidin-4-yl)-2-oxoacetamide | B |
| 381 | N-((1R,2R)-3-(azetidin-1-yl)-1-(4-cyclopropoxy-3-fluorophenyl)-1-hydroxypropan-2-yl)-2-(6-chlorobenzo[b]thiophen-2-yl)-2-oxoacetamide | A |
| 382 | N-((1R,2R)-1-(4-cyclopropoxy-3-fluorophenyl)-1-hydroxy-3-(pyrrolidin-1-yl)propan-2-yl)-2-(4'-fluoro-[1,1'-biphenyl]-4-yl)-N-methyl-2-oxoacetamide | A |
| 383 | 2-(6-chlorobenzo[b]thiophen-2-yl)-N-((1R,2R)-1-(4-cyclopropoxy-3-fluorophenyl)-1-hydroxy-3-(pyrrolidin-1-yl)propan-2-yl)-N-methyl-2-oxoacetamide | A |

TABLE 3

The data provided is the IC$_{50}$ (nM) generated from Assay 1, except as otherwise noted by *, which is % inhibition, also generated from Assay 1.

| Ex | Structure | Name | Data |
|---|---|---|---|
| 384 | 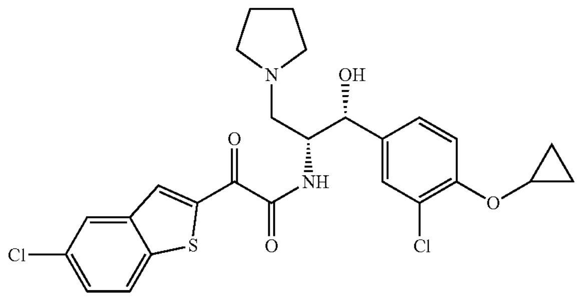 [SMILES: O=C(N[C@H](CN1CCCC1)[C@H](O)c1ccc(OC2CC2)c(Cl)c1)C(=O)c1cc2cc(Cl)ccc2s1] | N-((1R,2R)-1-(3-chloro-4-cyclopropoxyphenyl)-1-hydroxy-3-(pyrrolidin-1-yl)propan-2-yl)-2-(5-chlorobenzo[b]thiophen-2-yl)-2-oxoacetamide | A |
| 385 | 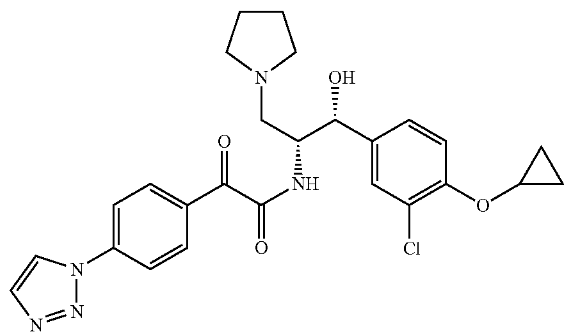 [SMILES: O=C(N[C@H](CN1CCCC1)[C@H](O)c1ccc(OC2CC2)c(Cl)c1)C(=O)c1ccc(-n2ccnn2)cc1] | 2-(4-(1H-1,2,3-triazol-1-yl)phenyl)-N-((1R,2R)-1-(3-chloro-4-cyclopropoxyphenyl)-1-hydroxy-3-(pyrrolidin-1-yl)propan-2-yl)-2-oxoacetamide | B |
| 386 | 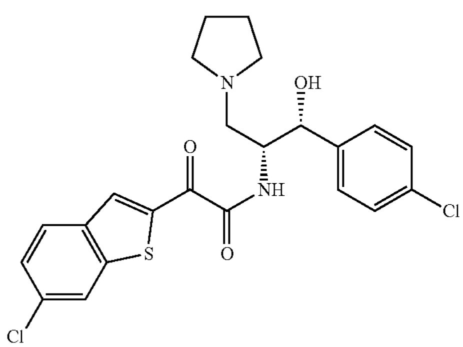 [SMILES: O=C(N[C@H](CN1CCCC1)[C@H](O)c1ccc(Cl)cc1)C(=O)c1cc2ccc(Cl)cc2s1] | 2-(6-chlorobenzo[b]thiophen-2-yl)-N-((1R,2R)-1-(4-chlorophenyl)-1-hydroxy-3-(pyrrolidin-1-yl)propan-2-yl)-2-oxoacetamide | B |
| 387 | 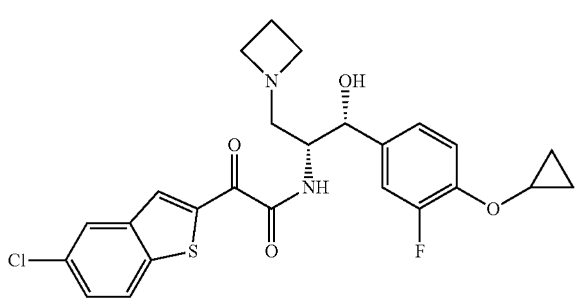 [SMILES: O=C(N[C@H](CN1CCC1)[C@H](O)c1ccc(OC2CC2)c(F)c1)C(=O)c1cc2cc(Cl)ccc2s1] | N-((1R,2R)-3-(azetidin-1-yl)-1-(4-cyclopropoxy-3-fluorophenyl)-1-hydroxypropan-2-yl)-2-(5-chlorobenzo[b]thiophen-2-yl)-2-oxoacetamide | A |

| Ex | Structure | Name | Data |
|---|---|---|---|
| 388 | 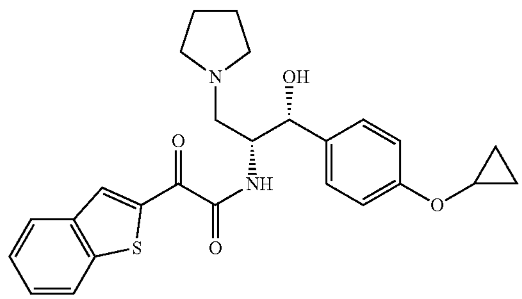 [SMILES: O=C(N[C@H](CN1CCCC1)[C@H](O)c1ccc(OC2CC2)cc1)C(=O)c1cc2ccccc2s1] | 2-(benzo[b]thiophen-2-yl)-N-((1R,2R)-1-(4-cyclopropoxyphenyl)-1-hydroxy-3-(pyrrolidin-1-yl)propan-2-yl)-2-oxoacetamide | A |
| 389 | 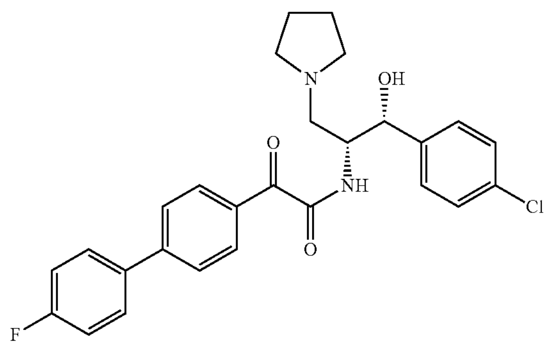 [SMILES: O=C(N[C@H](CN1CCCC1)[C@H](O)c1ccc(Cl)cc1)C(=O)c1ccc(-c2ccc(F)cc2)cc1] | N-((1R,2R)-1-(4-chlorophenyl)-1-hydroxy-3-(pyrrolidin-1-yl)propan-2-yl)-2-(4'-fluoro-[1,1'-biphenyl]-4-yl)-2-oxoacetamide | B |
| 390 | 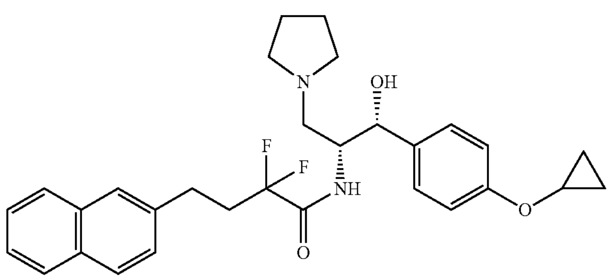 [SMILES: O=C(N[C@H](CN1CCCC1)[C@H](O)c1ccc(OC2CC2)cc1)C(F)(F)CCc1ccc2ccccc2c1] | N-((1R,2R)-1-(4-cyclopropoxyphenyl)-1-hydroxy-3-(pyrrolidin-1-yl)propan-2-yl)-2,2-difluoro-4-(naphthalen-2-yl)butanamide | A |
| 391 | 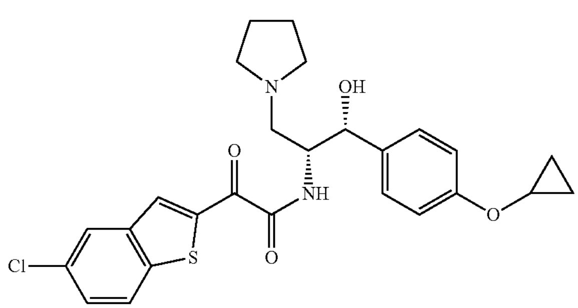 [SMILES: O=C(N[C@H](CN1CCCC1)[C@H](O)c1ccc(OC2CC2)cc1)C(=O)c1cc2cc(Cl)ccc2s1] | 2-(5-chlorobenzo[b]thiophen-2-yl)-N-((1R,2R)-1-(4-cyclopropoxyphenyl)-1-hydroxy-3-(pyrrolidin-1-yl)propan-2-yl)-2-oxoacetamide | A |

TABLE 3-continued

The data provided is the IC$_{50}$ (nM) generated from Assay 1, except as otherwise noted by *, which is % inhibition, also generated from Assay 1.

| Ex | Structure | Name | Data |
|----|-----------|------|------|
| 392 | 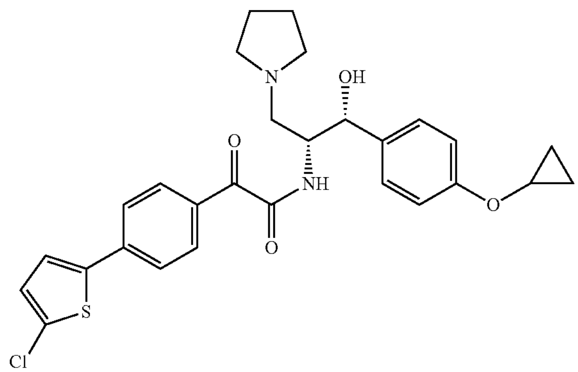 [SMILES: O=C(N[C@H](CN1CCCC1)[C@H](O)c1ccc(OC2CC2)cc1)C(=O)c1ccc(-c2ccc(Cl)s2)cc1] | 2-(4-(5-chlorothiophen-2-yl)phenyl)-N-((1R,2R)-1-(4-cyclopropoxyphenyl)-1-hydroxy-3-(pyrrolidin-1-yl)propan-2-yl)-2-oxoacetamide | A |
| 393 | 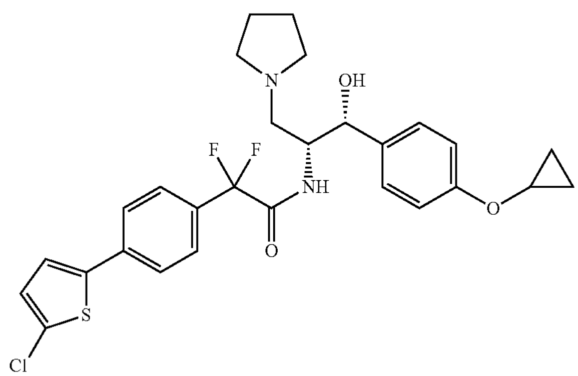 [SMILES: O=C(N[C@H](CN1CCCC1)[C@H](O)c1ccc(OC2CC2)cc1)C(F)(F)c1ccc(-c2ccc(Cl)s2)cc1] | 2-(4-(5-chlorothiophen-2-yl)phenyl)-N-((1R,2R)-1-(4-cyclopropoxyphenyl)-1-hydroxy-3-(pyrrolidin-1-yl)propan-2-yl)-2,2-difluoroacetamide | A |
| 394 | 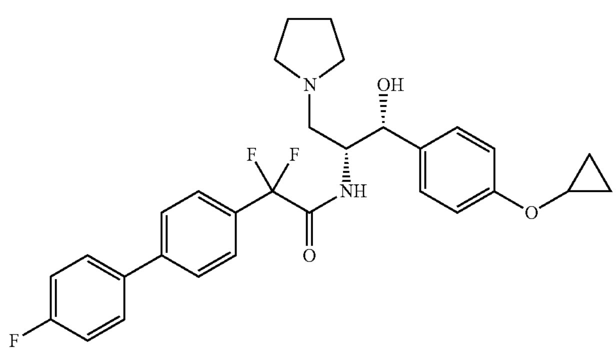 [SMILES: O=C(N[C@H](CN1CCCC1)[C@H](O)c1ccc(OC2CC2)cc1)C(F)(F)c1ccc(-c2ccc(F)cc2)cc1] | N-((1R,2R)-1-(4-cyclopropoxyphenyl)-1-hydroxy-3-(pyrrolidin-1-yl)propan-2-yl)-2,2-difluoro-2-(4'-fluoro-[1,1'-biphenyl]-4-yl)acetamide | A |
| 395 | 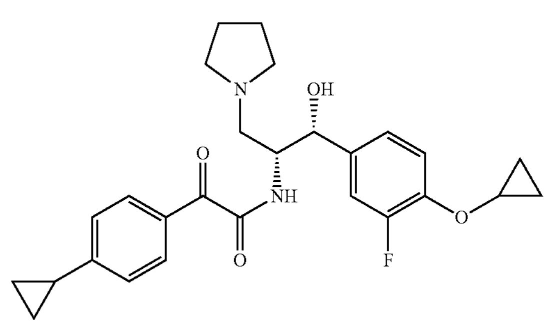 [SMILES: O=C(N[C@H](CN1CCCC1)[C@H](O)c1ccc(OC2CC2)c(F)c1)C(=O)c1ccc(C2CC2)cc1] | N-((1R,2R)-1-(4-cyclopropoxy-3-fluorophenyl)-1-hydroxy-3-(pyrrolidin-1-yl)propan-2-yl)-2-(4-cyclopropylphenyl)-2-oxoacetamide | A |

TABLE 3-continued

The data provided is the IC$_{50}$ (nM) generated from Assay 1, except as otherwise noted by *, which is % inhibition, also generated from Assay 1.

| Ex | Structure | Name | Data |
|---|---|---|---|
| 396 | 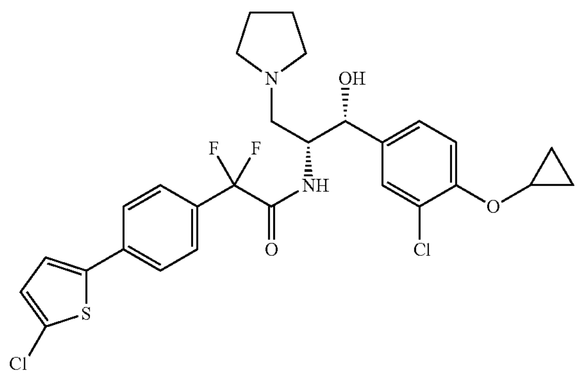 [SMILES: O=C(N[C@H](CN1CCCC1)[C@H](O)c1ccc(OC2CC2)c(Cl)c1)C(F)(F)c1ccc(-c2ccc(Cl)s2)cc1] | N-((1R,2R)-1-(3-chloro-4-cyclopropoxyphenyl)-1-hydroxy-3-(pyrrolidin-1-yl)propan-2-yl)-2-(4-(5-chlorothiophen-2-yl)phenyl)-2,2-difluoroacetamide | A |
| 397 | 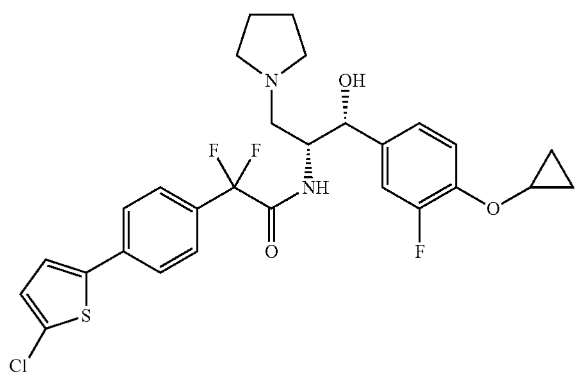 [SMILES: O=C(N[C@H](CN1CCCC1)[C@H](O)c1ccc(OC2CC2)c(F)c1)C(F)(F)c1ccc(-c2ccc(Cl)s2)cc1] | 2-(4-(5-chlorothiophen-2-yl)phenyl)-N-((1R,2R)-1-(4-cyclopropoxy-3-fluorophenyl)-1-hydroxy-3-(pyrrolidin-1-yl)propan-2-yl)-2,2-difluoroacetamide | A |
| 398 | 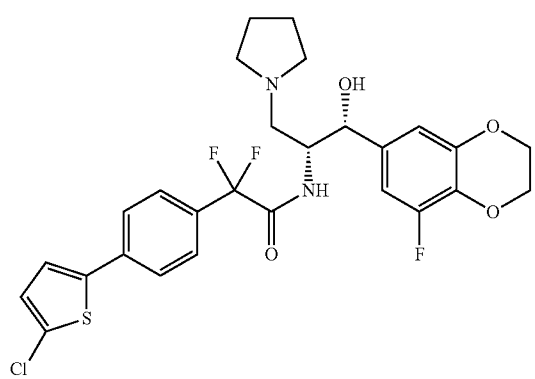 [SMILES: O=C(N[C@H](CN1CCCC1)[C@H](O)c1cc(F)c2c(c1)OCCO2)C(F)(F)c1ccc(-c2ccc(Cl)s2)cc1] | 2-(4-(5-chlorothiophen-2-yl)phenyl)-2,2-difluoro-N-((1R,2R)-1-(8-fluoro-2,3-dihydrobenzo[b][1,4]dioxin-6-yl)-1-hydroxy-3-(pyrrolidin-1-yl)propan-2-yl)acetamide | A |
| 399 | 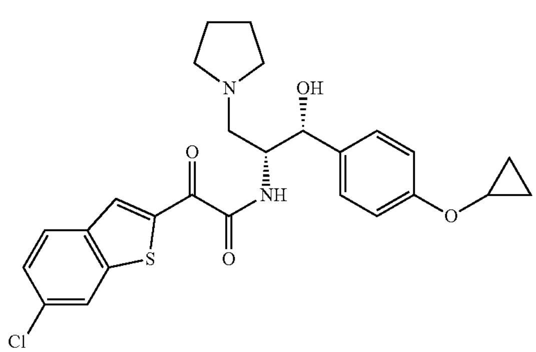 [SMILES: O=C(N[C@H](CN1CCCC1)[C@H](O)c1ccc(OC2CC2)cc1)C(=O)c1cc2ccc(Cl)cc2s1] | 2-(6-chlorobenzo[b]thiophen-2-yl)-N-((1R,2R)-1-(4-cyclopropoxyphenyl)-1-hydroxy-3-(pyrrolidin-1-yl)propan-2-yl)-2-oxoacetamide | A |

US 10,927,092 B2

TABLE 3-continued

The data provided is the IC$_{50}$ (nM) generated from Assay 1, except as otherwise noted by *, which is % inhibition, also generated from Assay 1.

| Ex | Structure | Name | Data |
|---|---|---|---|
| 400 | 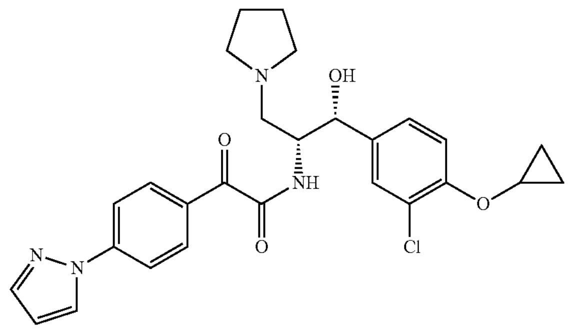 [SMILES: O=C(N[C@H](CN1CCCC1)[C@H](O)c1ccc(OC2CC2)c(Cl)c1)C(=O)c1ccc(-n2cccn2)cc1] | 2-(4-(1H-pyrazol-1-yl)phenyl)-N-((1R,2R)-1-(3-chloro-4-cyclopropoxyphenyl)-1-hydroxy-3-(pyrrolidin-1-yl)propan-2-yl)-2-oxoacetamide | A |
| 401 | 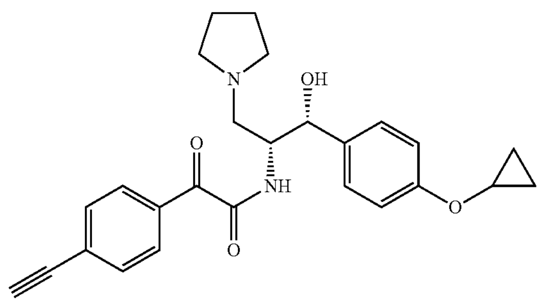 [SMILES: C#Cc1ccc(C(=O)C(=O)N[C@H](CN2CCCC2)[C@H](O)c2ccc(OC3CC3)cc2)cc1] | N-((1R,2R)-1-(4-cyclopropoxyphenyl)-1-hydroxy-3-(pyrrolidin-1-yl)propan-2-yl)-2-(4-ethynylphenyl)-2-oxoacetamide | B |
| 402 | 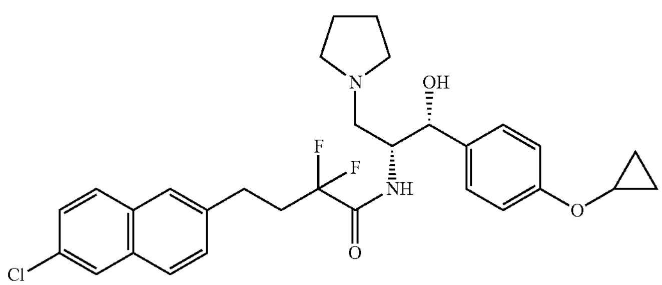 [SMILES: O=C(N[C@H](CN1CCCC1)[C@H](O)c1ccc(OC2CC2)cc1)C(F)(F)CCc1ccc2cc(Cl)ccc2c1] | 4-(6-chloronaphthalen-2-yl)-N-((1R,2R)-1-(4-cyclopropoxyphenyl)-1-hydroxy-3-(pyrrolidin-1-yl)propan-2-yl)-2,2-difluorobutanamide | B |
| 403 | 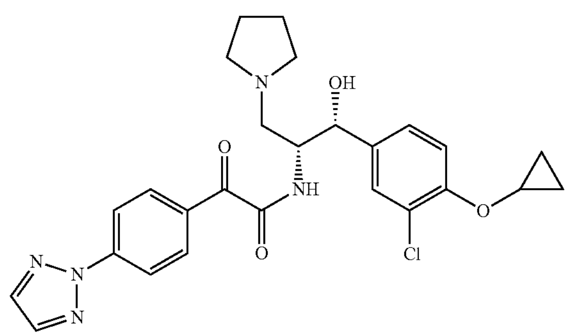 [SMILES: O=C(N[C@H](CN1CCCC1)[C@H](O)c1ccc(OC2CC2)c(Cl)c1)C(=O)c1ccc(-n2nccn2)cc1] | 2-(4-(2H-1,2,3-triazol-2-yl)phenyl)-N-((1R,2R)-1-(3-chloro-4-cyclopropoxyphenyl)-1-hydroxy-3-(pyrrolidin-1-yl)propan-2-yl)-2-oxoacetamide | A |

TABLE 3-continued

The data provided is the IC$_{50}$ (nM) generated from Assay 1, except as otherwise noted by *, which is % inhibition, also generated from Assay 1.

| Ex | Structure | Name | Data |
|---|---|---|---|
| 404 | 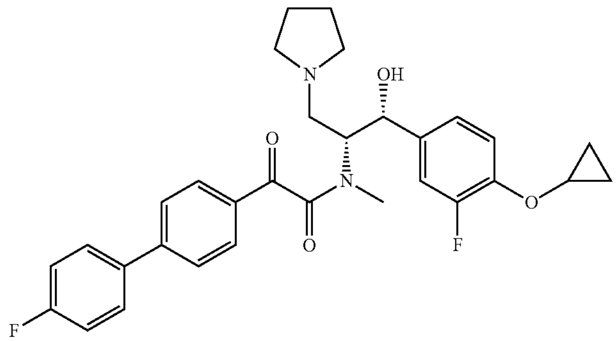 [SMILES: CN(C(=O)C(=O)c1ccc(-c2ccc(F)cc2)cc1)[C@H](CN1CCCC1)[C@H](O)c1ccc(OC2CC2)c(F)c1] | N-((1R,2R)-1-(4-cyclopropoxy-3-fluorophenyl)-1-hydroxy-3-(pyrrolidin-1-yl)propan-2-yl)-2-(4'-fluoro-[1,1'-biphenyl]-4-yl)-N-methyl-2-oxoacetamide | A |
| 405 | 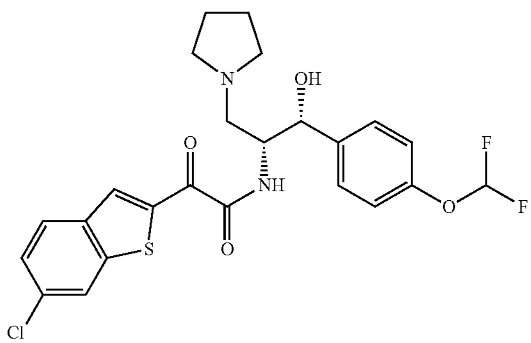 [SMILES: O=C(N[C@H](CN1CCCC1)[C@H](O)c1ccc(OC(F)F)cc1)C(=O)c1cc2ccc(Cl)cc2s1] | 2-(6-chlorobenzo[b]thiophen-2-yl)-N-((1R,2R)-1-(4-(difluoromethoxy)phenyl)-1-hydroxy-3-(pyrrolidin-1-yl)propan-2-yl)-2-oxoacetamide | B |
| 406 | 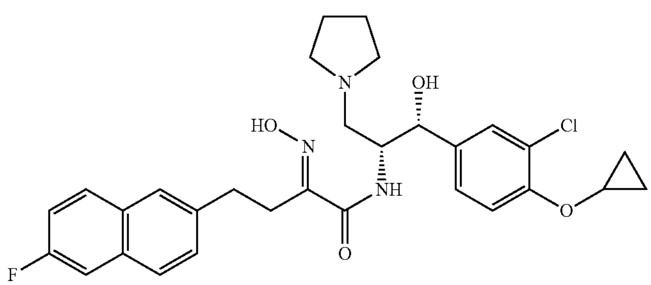 [SMILES: O=C(N[C@H](CN1CCCC1)[C@H](O)c1ccc(OC2CC2)c(Cl)c1)/C(CCc1ccc2cc(F)ccc2c1)=N/O] | (E)-N-((1R,2R)-1-(3-chloro-4-cyclopropoxyphenyl)-1-hydroxy-3-(pyrrolidin-1-yl)propan-2-yl)-4-(6-fluoronaphthalen-2-yl)-2-(hydroxyimino)butanamide | A* |
| 407 | 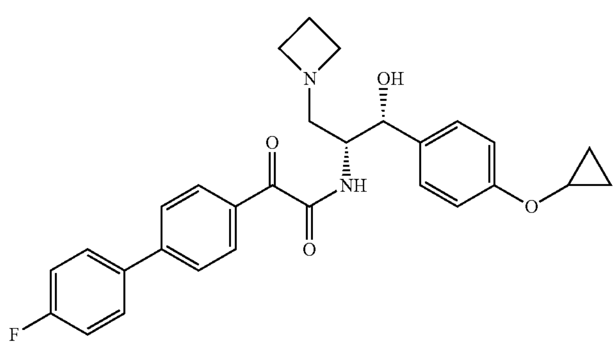 [SMILES: O=C(N[C@H](CN1CCC1)[C@H](O)c1ccc(OC2CC2)cc1)C(=O)c1ccc(-c2ccc(F)cc2)cc1] | N-((1R,2R)-3-(azetidin-1-yl)-1-(4-cyclopropoxyphenyl)-1-hydroxypropan-2-yl)-2-(4'-fluoro-[1,1'-biphenyl]-4-yl)-2-oxoacetamide | nt |

TABLE 3-continued

The data provided is the IC₅₀ (nM) generated from Assay 1, except as otherwise noted by *, which is % inhibition, also generated from Assay 1.

| Ex | Structure | Name | Data |
|---|---|---|---|
| 408 | 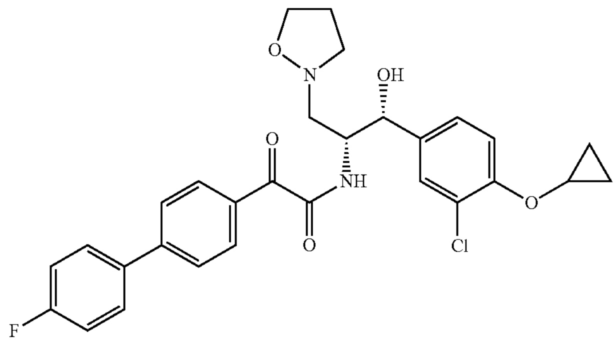 [SMILES: O=C(N[C@H](CN1CCCO1)[C@H](O)c1ccc(OC2CC2)c(Cl)c1)C(=O)c1ccc(-c2ccc(F)cc2)cc1] | N-((1R,2R)-1-(3-chloro-4-cyclopropoxyphenyl)-1-hydroxy-3-(isoxazolidin-2-yl)propan-2-yl)-2-(4'-fluoro-[1,1'-biphenyl]-4-yl)-2-oxoacetamide | nt |
| 409 | 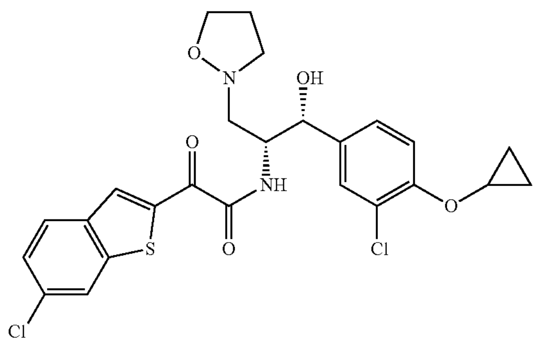 [SMILES: O=C(N[C@H](CN1CCCO1)[C@H](O)c1ccc(OC2CC2)c(Cl)c1)C(=O)c1cc2ccc(Cl)cc2s1] | N-((1R,2R)-1-(3-chloro-4-cyclopropoxyphenyl)-1-hydroxy-3-(isoxazolidin-2-yl)propan-2-yl)-2-(6-chlorobenzo[b]thiophen-2-yl)-2-oxoacetamide | nt |
| 410 | 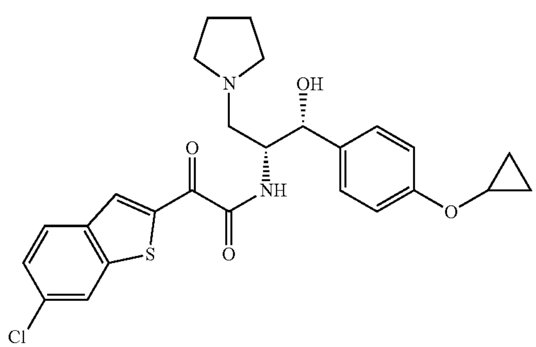 [SMILES: O=C(N[C@H](CN1CCCC1)[C@H](O)c1ccc(OC2CC2)cc1)C(=O)c1cc2ccc(Cl)cc2s1] | 2-(6-chlorobenzo[b]thiophen-2-yl)-N-((1R,2R)-1-(4-cyclopropoxyphenyl)-1-hydroxy-3-(pyrrolidin-1-yl)propan-2-yl)-2-oxoacetamide | nt |
| 411 | 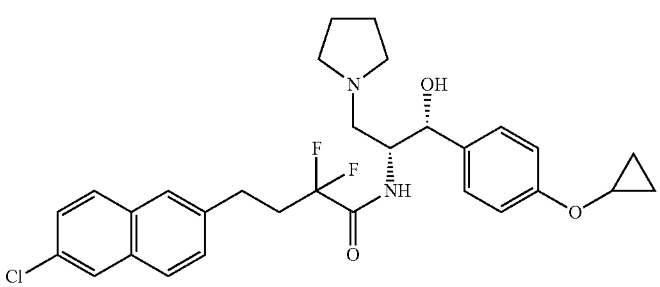 [SMILES: O=C(N[C@H](CN1CCCC1)[C@H](O)c1ccc(OC2CC2)cc1)C(F)(F)CCc1ccc2cc(Cl)ccc2c1] | 4-(6-chloronaphthalen-2-yl)-N-((1R,2R)-1-(4-cyclopropoxyphenyl)-1-hydroxy-3-(pyrrolidin-1-yl)propan-2-yl)-2,2-difluorobutanamide | nt |

TABLE 3-continued

The data provided is the IC$_{50}$ (nM) generated from Assay 1, except as otherwise noted by *, which is % inhibition, also generated from Assay 1.

| Ex | Structure | Name | Data |
|---|---|---|---|
| 412 | 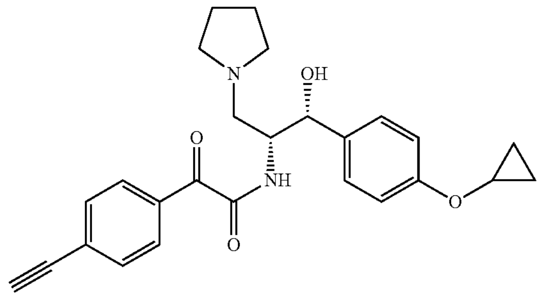 [SMILES: C#Cc1ccc(C(=O)C(=O)N[C@H](CN2CCCC2)[C@H](O)c2ccc(OC3CC3)cc2)cc1] | N-((1R,2R)-1-(4-cyclopropoxyphenyl)-1-hydroxy-3-(pyrrolidin-1-yl)propan-2-yl)-2-(4-ethynylphenyl)-2-oxoacetamide | nt |
| 413 | 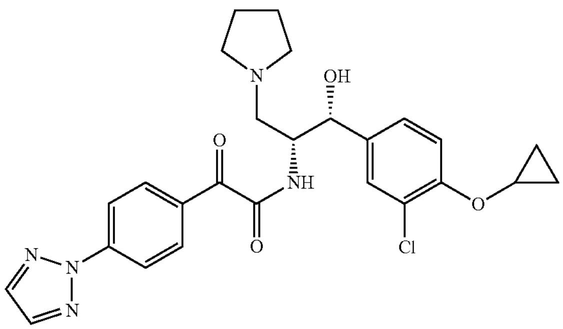 | 2-(4-(2H-1,2,3-triazol-2-yl)phenyl)-N-((1R,2R)-1-(3-chloro-4-cyclopropoxyphenyl)-1-hydroxy-3-(pyrrolidin-1-yl)propan-2-yl)-2-oxoacetamide | nt |
| 414 | 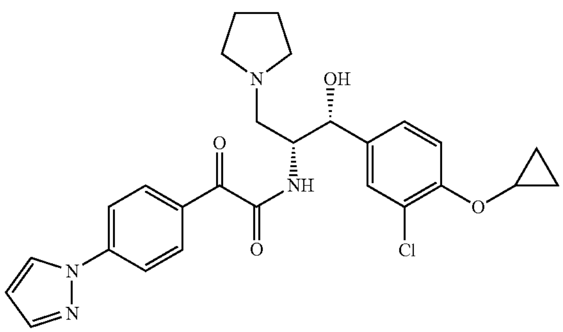 | 2-(4-(1H-pyrazol-1-yl)phenyl)-N-((1R,2R)-1-(3-chloro-4-cyclopropoxyphenyl)-1-hydroxy-3-(pyrrolidin-1-yl)propan-2-yl)-2-oxoacetamide | nt |
| 415 | 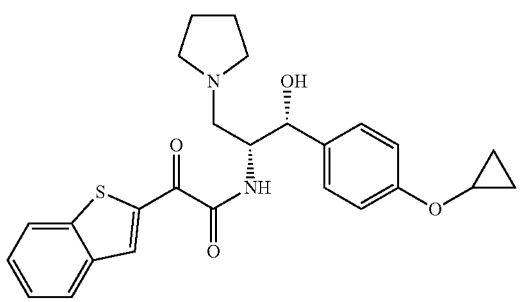 [SMILES: O=C(N[C@H](CN1CCCC1)[C@H](O)c1ccc(OC2CC2)cc1)C(=O)c1cc2ccccc2s1] | 2-(benzo[b]thiophen-2-yl)-N-((1R,2R)-1-(4-cyclopropoxyphenyl)-1-hydroxy-3-(pyrrolidin-1-yl)propan-2-yl)-2-oxoacetamide | nt |
| 416 | 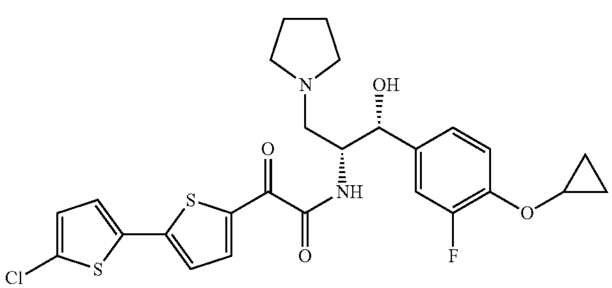 [SMILES: O=C(N[C@H](CN1CCCC1)[C@H](O)c1ccc(OC2CC2)c(F)c1)C(=O)c1ccc(-c2ccc(Cl)s2)s1] | 2-(5'-chloro-[2,2'-bithiophen]-5-yl)-N-((1R,2R)-1-(4-cyclopropoxy-3-fluorophenyl)-1-hydroxy-3-(pyrrolidin-1-yl)propan-2-yl)-2-oxoacetamide | nt |

TABLE 3-continued

The data provided is the IC$_{50}$ (nM) generated from Assay 1, except as otherwise noted by *, which is % inhibition, also generated from Assay 1.

| Ex | Structure | Name | Data |
|---|---|---|---|
| 417 | 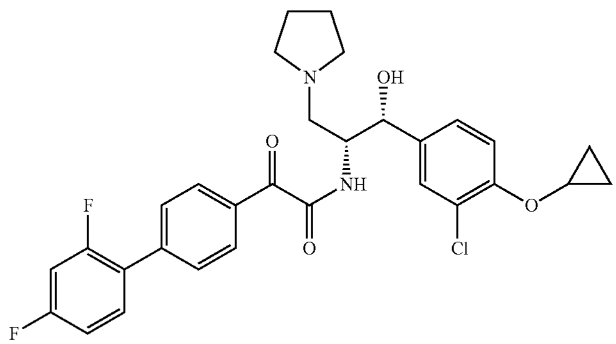 [SMILES: O=C(N[C@H](CN1CCCC1)[C@H](O)c1ccc(OC2CC2)c(Cl)c1)C(=O)c1ccc(-c2ccc(F)cc2F)cc1] | N-((1R,2R)-1-(3-chloro-4-cyclopropoxyphenyl)-1-hydroxy-3-(pyrrolidin-1-yl)propan-2-yl)-2-(2',4'-difluoro-[1,1'-biphenyl]-4-yl)-2-oxoacetamide | nt |
| 418 | 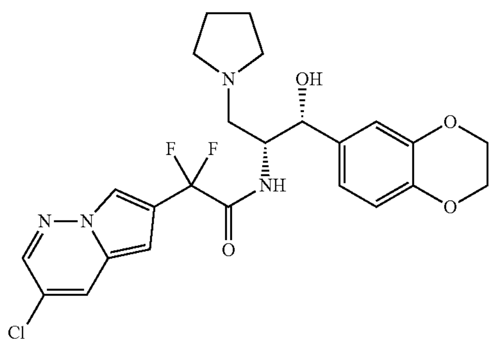 [SMILES: O=C(N[C@H](CN1CCCC1)[C@H](O)c1ccc2c(c1)OCCO2)C(F)(F)c1cc2cc(Cl)cnn2c1] | 2-(3-chloropyrrolo[1,2-b]pyridazin-6-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide | nt |
| 419 | 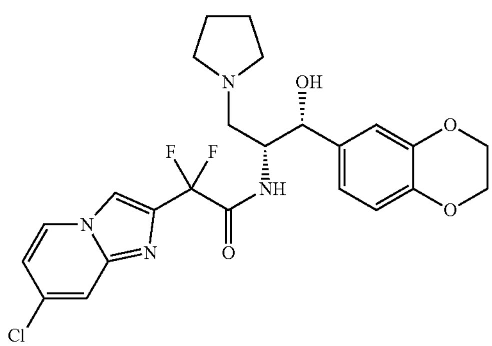 [SMILES: O=C(N[C@H](CN1CCCC1)[C@H](O)c1ccc2c(c1)OCCO2)C(F)(F)c1cn2ccc(Cl)cc2n1] | 2-(7-chloroimidazo[1,2-a]pyridin-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide | nt |
| 420 | 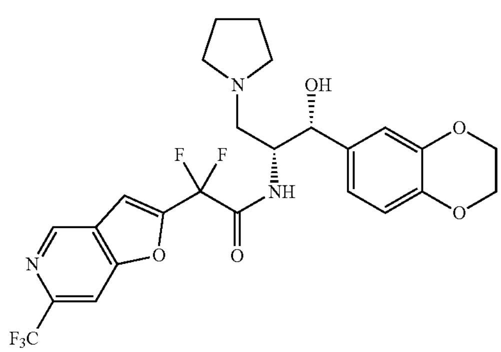 [SMILES: O=C(N[C@H](CN1CCCC1)[C@H](O)c1ccc2c(c1)OCCO2)C(F)(F)c1cc2cnc(C(F)(F)F)cc2o1] | N-((1R,2R)-1-(2,3-dihydrobenzo[b][1,4]dioxin-6-yl)-1-hydroxy-3-(pyrrolidin-1-yl)propan-2-yl)-2,2-difluoro-2-(6-(trifluoromethyl)furo[3,2-c]pyridin-2-yl)acetamide | nt |

TABLE 3-continued

The data provided is the IC$_{50}$ (nM) generated from Assay 1, except as otherwise noted by *, which is % inhibition, also generated from Assay 1.

| Ex | Structure | Name | Data |
|---|---|---|---|
| 421 | 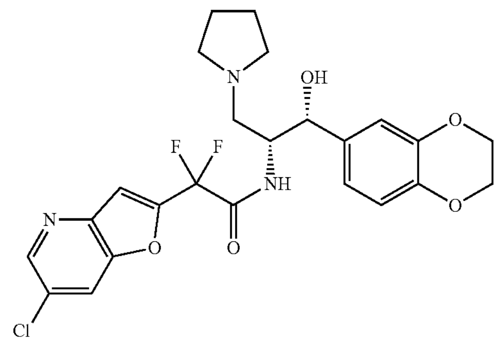 [SMILES: O=C(N[C@H](CN1CCCC1)[C@H](O)c1ccc2c(c1)OCCO2)C(F)(F)c1cc2ncc(Cl)cc2o1] | 2-(6-chlorofuro[3,2-b]pyridin-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide | nt |
| 422 | 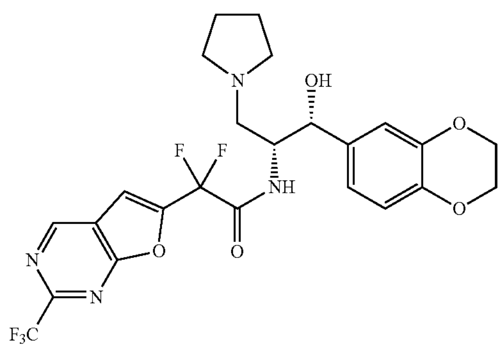 [SMILES: O=C(N[C@H](CN1CCCC1)[C@H](O)c1ccc2c(c1)OCCO2)C(F)(F)c1cc2cnc(C(F)(F)F)nc2o1] | N-((1R,2R)-1-(2,3-dihydrobenzo[b][1,4]dioxin-6-yl)-1-hydroxy-3-(pyrrolidin-1-yl)propan-2-yl)-2,2-difluoro-2-(2-(trifluoromethyl)furo[2,3-d]pyrimidin-6-yl)acetamide | nt |
| 423 | 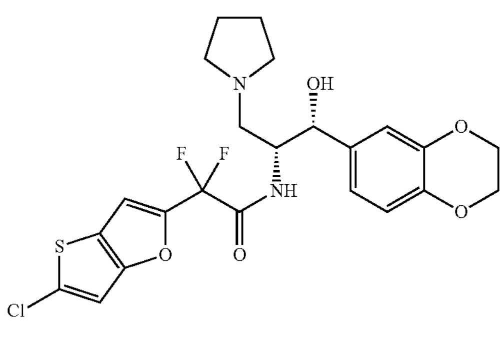 [SMILES: O=C(N[C@H](CN1CCCC1)[C@H](O)c1ccc2c(c1)OCCO2)C(F)(F)c1cc2sc(Cl)cc2o1] | 2-(5-chlorothieno[3,2-b]furan-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide | nt |
| 424 | 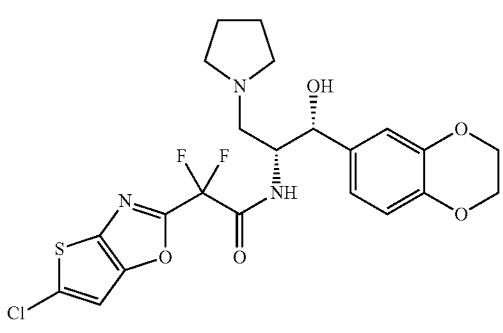 [SMILES: O=C(N[C@H](CN1CCCC1)[C@H](O)c1ccc2c(c1)OCCO2)C(F)(F)c1nc2sc(Cl)cc2o1] | 2-(5-chlorothieno[2,3-d]oxazol-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide | nt |

TABLE 3-continued

The data provided is the IC$_{50}$ (nM) generated from Assay 1, except as otherwise noted by *, which is % inhibition, also generated from Assay 1.

| Ex | Structure | Name | Data |
|---|---|---|---|
| 425 | 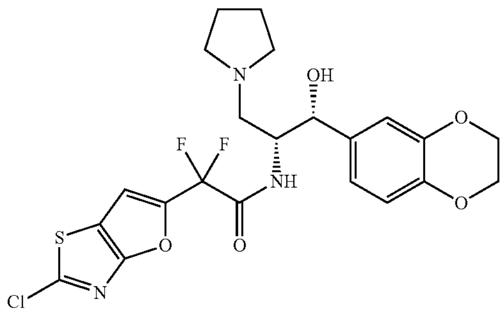 | 2-(2-chlorofuro[2,3-d]thiazol-5-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide | nt |
| 426 | 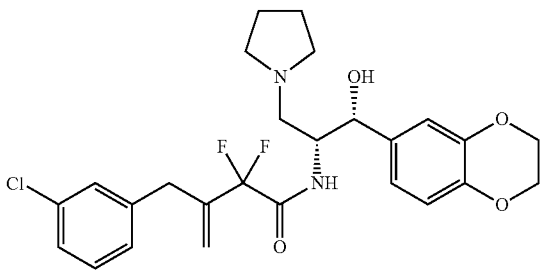 [SMILES: C=C(Cc1cccc(Cl)c1)C(F)(F)C(=O)N[C@H](CN1CCCC1)[C@H](O)c1ccc2c(c1)OCCO2] | 3-(3-chlorobenzyl)-N-((1R,2R)-1-(2,3-dihydrobenzo[b][1,4]dioxin-6-yl)-1-hydroxy-3-(pyrrolidin-1-yl)propan-2-yl)-2,2-difluorobut-3-enamide | nt |
| 427 | 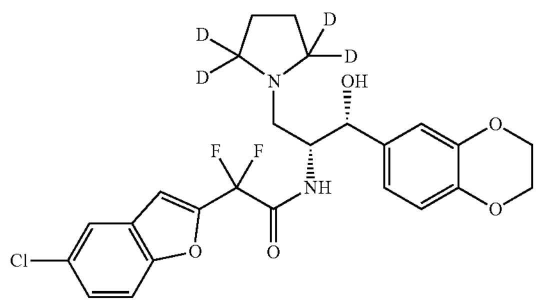 [SMILES: [2H]C1([2H])CCC([2H])([2H])N1C[C@@H](NC(=O)C(F)(F)c1cc2cc(Cl)ccc2o1)[C@H](O)c1ccc2c(c1)OCCO2] | 2-(5-chlorobenzofuran-2-yl)-N-((1R,2R)-1-(2,3-dihydrobenzo[b][1,4]dioxin-6-yl)-1-hydroxy-3-(2,2,5,5-tetradeuteropyrrolidin-1-yl)propan-2-yl)-2,2-difluoroacetamide | nt |
| 428 | 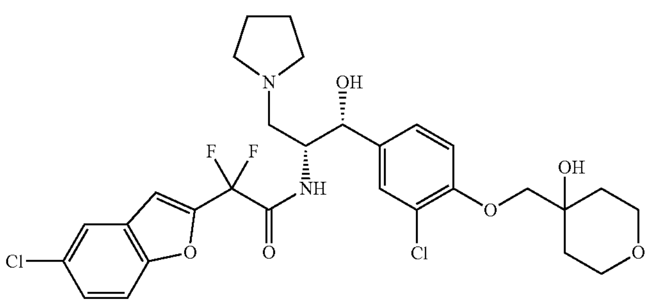 [SMILES: O=C(N[C@H](CN1CCCC1)[C@H](O)c1ccc(OCC2(O)CCOCC2)c(Cl)c1)C(F)(F)c1cc2cc(Cl)ccc2o1] | N-((1R,2R)-1-(3-chloro-4-((4-hydroxytetrahydro-2H-pyran-4-yl)methoxy)phenyl)-1-hydroxy-3-(pyrrolidin-1-yl)propan-2-yl)-2-(5-chlorobenzofuran-2-yl)-2,2-difluoroacetamide | nt |
| 429 | 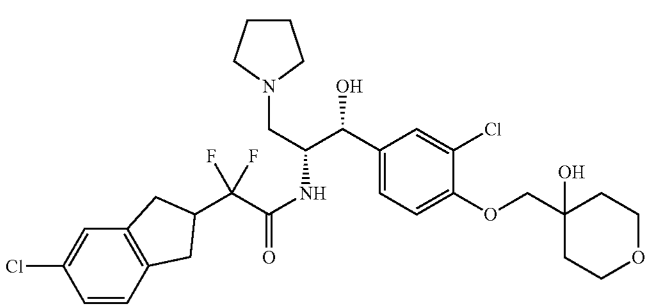 [SMILES: O=C(N[C@H](CN1CCCC1)[C@H](O)c1ccc(OCC2(O)CCOCC2)c(Cl)c1)C(F)(F)C1Cc2ccc(Cl)cc2C1] | 2-(5-chloro-2,3-dihydro-1H-inden-2-yl)-N-((1R,2R)-1-(3-chloro-4-((4-hydroxytetrahydro-2H-pyran-4-yl)methoxy)phenyl)-1-hydroxy-3-(pyrrolidin-1-yl)propan-2-yl)-2,2-difluoroacetamide | nt |

TABLE 3-continued

The data provided is the IC$_{50}$ (nM) generated from Assay 1, except as otherwise noted by *, which is % inhibition, also generated from Assay 1.

| Ex | Structure | Name | Data |
|---|---|---|---|
| 430 | 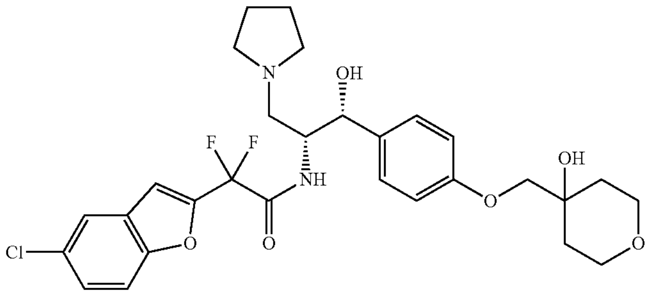 | 2-(5-chlorobenzofuran-2-yl)-2,2-difluoro-N-((1R,2R)-1-hydroxy-1-(4-((4-hydroxytetrahydro-2H-pyran-4-yl)methoxy)phenyl)-3-(pyrrolidin-1-yl)propan-2-yl)acetamide | nt |
| 431 | 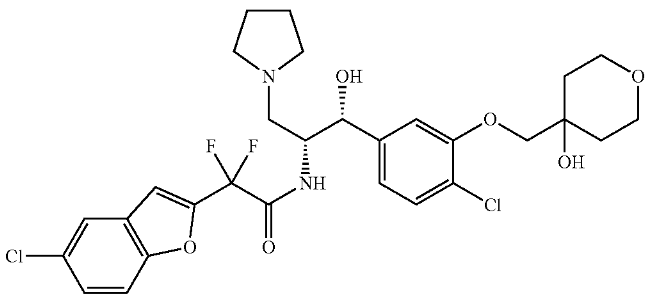 [SMILES: O=C(N[C@H](CN1CCCC1)[C@H](O)c1ccc(Cl)c(OCC2(O)CCOCC2)c1)C(F)(F)c1cc2cc(Cl)ccc2o1] | N-((1R,2R)-1-(4-chloro-3-((4-hydroxytetrahydro-2H-pyran-4-yl)methoxy)phenyl)-1-hydroxy-3-(pyrrolidin-1-yl)propan-2-yl)-2-(5-chlorobenzofuran-2-yl)-2,2-difluoroacetamide | nt |
| 432 | 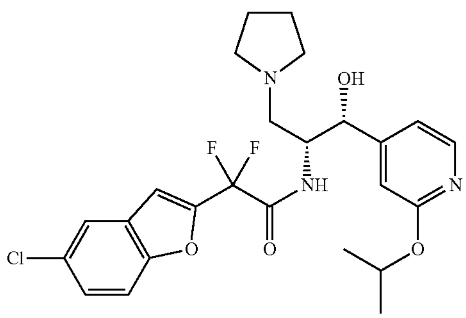 [SMILES: CC(C)Oc1cc([C@@H](O)[C@@H](CN2CCCC2)NC(=O)C(F)(F)c2cc3cc(Cl)ccc3o2)ccn1] | 2-(5-chlorobenzofuran-2-yl)-2,2-difluoro-N-((1R,2R)-1-hydroxy-1-(2-isopropoxypyridin-4-yl)-3-(pyrrolidin-1-yl)propan-2-yl)acetamide | nt |
| 433 | 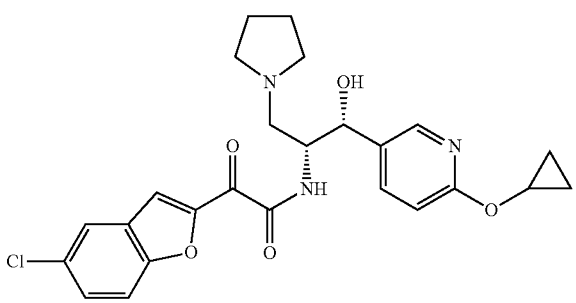 [SMILES: O=C(N[C@H](CN1CCCC1)[C@H](O)c1ccc(OC2CC2)nc1)C(=O)c1cc2cc(Cl)ccc2o1] | 2-(5-chlorobenzofuran-2-yl)-N-((1R,2R)-1-(6-cyclopropoxypyridin-3-yl)-1-hydroxy-3-(pyrrolidin-1-yl)propan-2-yl)-2-oxoacetamide | nt |
| 434 | 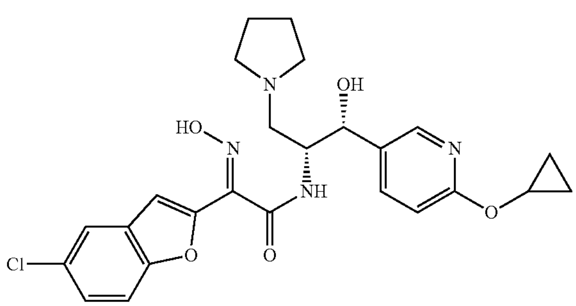 [SMILES: O=C(N[C@H](CN1CCCC1)[C@H](O)c1ccc(OC2CC2)nc1)/C(=N/O)c1cc2cc(Cl)ccc2o1] | (E)-2-(5-chlorobenzofuran-2-yl)-N-((1R,2R)-1-(6-cyclopropoxypyridin-3-yl)-1-hydroxy-3-(pyrrolidin-1-yl)propan-2-yl)-2-(hydroxyimino)acetamide | nt |

TABLE 3-continued

The data provided is the IC$_{50}$ (nM) generated from Assay 1, except as otherwise noted by *, which is % inhibition, also generated from Assay 1.

| Ex | Structure | Name | Data |
|---|---|---|---|
| 435 | 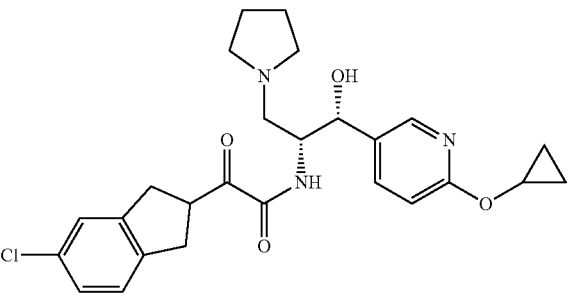 [SMILES: O=C(N[C@H](CN1CCCC1)[C@H](O)c1ccc(OC2CC2)nc1)C(=O)C1Cc2ccc(Cl)cc2C1] | 2-(5-chloro-2,3-dihydro-1H-inden-2-yl)-N-((1R,2R)-1-(6-cyclopropoxypyridin-3-yl)-1-hydroxy-3-(pyrrolidin-1-yl)propan-2-yl)-2-oxoacetamide | nt |
| 436 | 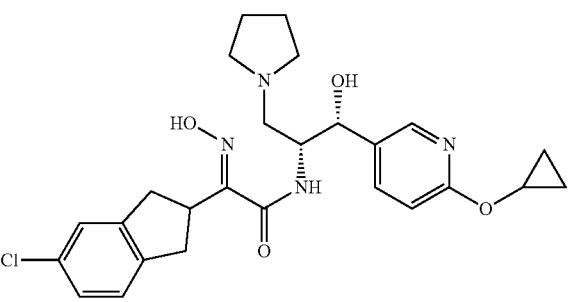 [SMILES: O=C(N[C@H](CN1CCCC1)[C@H](O)c1ccc(OC2CC2)nc1)/C(=N/O)C1Cc2ccc(Cl)cc2C1] | (E)-2-(5-chloro-2,3-dihydro-1H-inden-2-yl)-N-((1R,2R)-1-(6-cyclopropoxypyridin-3-yl)-1-hydroxy-3-(pyrrolidin-1-yl)propan-2-yl)-2-(hydroxyimino)acetamide | nt |
| 437 | 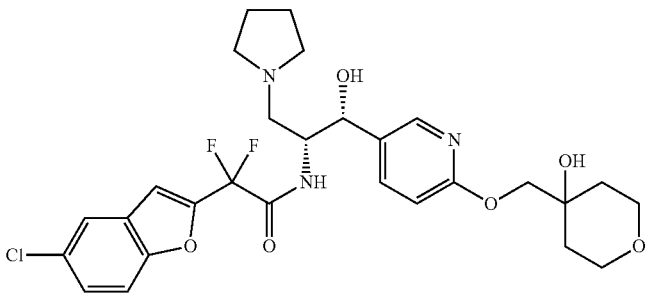 [SMILES: O=C(N[C@H](CN1CCCC1)[C@H](O)c1ccc(OCC2(O)CCOCC2)nc1)C(F)(F)c1cc2cc(Cl)ccc2o1] | 2-(5-chlorobenzofuran-2-yl)-2,2-difluoro-N-((1R,2R)-1-hydroxy-1-(6-((4-hydroxytetrahydro-2H-pyran-4-yl)methoxy)pyridin-3-yl)-3-(pyrrolidin-1-yl)propan-2-yl)acetamide | nt |
| 438 | 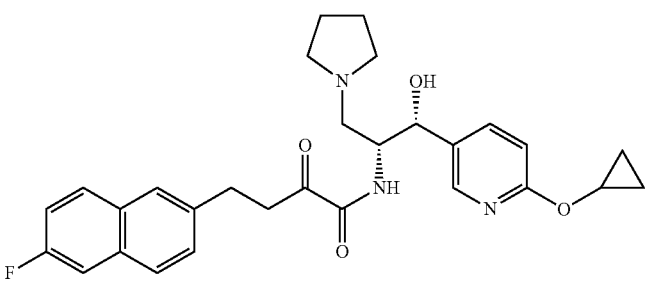 [SMILES: O=C(CCc1ccc2cc(F)ccc2c1)C(=O)N[C@H](CN1CCCC1)[C@H](O)c1ccc(OC2CC2)nc1] | N-((1R,2R)-1-(6-cyclopropoxypyridin-3-yl)-1-hydroxy-3-(pyrrolidin-1-yl)propan-2-yl)-4-(6-fluoronaphthalen-2-yl)-2-oxobutanamide | nt |
| 439 | 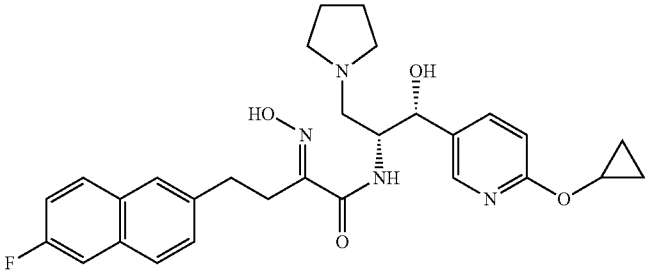 [SMILES: O=C(N[C@H](CN1CCCC1)[C@H](O)c1ccc(OC2CC2)nc1)/C(CCc1ccc2cc(F)ccc2c1)=N/O] | (E)-N-((1R,2R)-1-(6-cyclopropoxypyridin-3-yl)-1-hydroxy-3-(pyrrolidin-1-yl)propan-2-yl)-4-(6-fluoronaphthalen-2-yl)-2-(hydroxyimino)butanamide | nt |

TABLE 3-continued

The data provided is the IC$_{50}$ (nM) generated from Assay 1, except as otherwise noted by *, which is % inhibition, also generated from Assay 1.

| Ex | Structure | Name | Data |
|---|---|---|---|
| 440 | 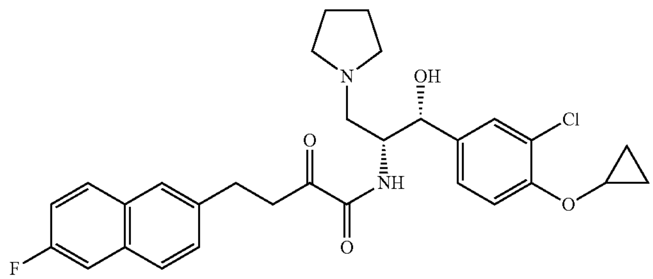 | N-((1R,2R)-1-(3-chloro-4-cyclopropoxyphenyl)-1-hydroxy-3-(pyrrolidin-1-yl)propan-2-yl)-4-(6-fluoronaphthalen-2-yl)-2-oxobutanamide | nt |
| 442 | 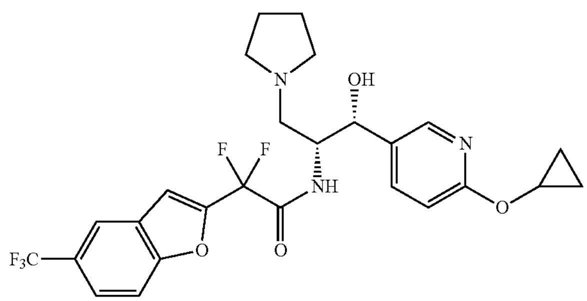 [SMILES: O=C(N[C@H](CN1CCCC1)[C@H](O)c1ccc(OC2CC2)nc1)C(F)(F)c1cc2cc(C(F)(F)F)ccc2o1] | N-((1R,2R)-1-(6-cyclopropoxypyridin-3-yl)-1-hydroxy-3-(pyrrolidin-1-yl)propan-2-yl)-2,2-difluoro-2-(5-(trifluoromethyl)benzofuran-2-yl)acetamide | nt |
| 443 | 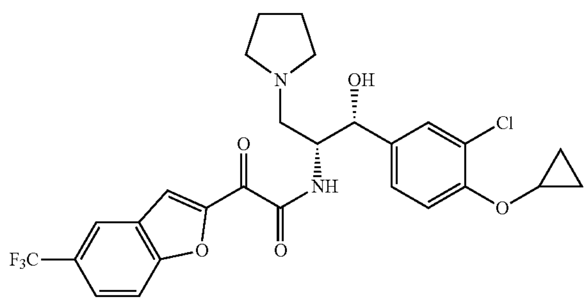 [SMILES: O=C(N[C@H](CN1CCCC1)[C@H](O)c1ccc(OC2CC2)c(Cl)c1)C(=O)c1cc2cc(C(F)(F)F)ccc2o1] | N-((1R,2R)-1-(3-chloro-4-cyclopropoxyphenyl)-1-hydroxy-3-(pyrrolidin-1-yl)propan-2-yl)-2-oxo-2-(5-(trifluoromethyl)benzofuran-2-yl)acetamide | nt |
| 444 | 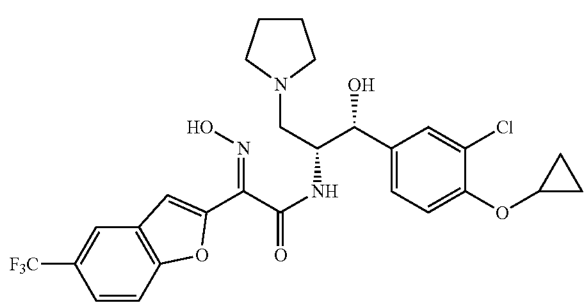 [SMILES: O=C(N[C@H](CN1CCCC1)[C@H](O)c1ccc(OC2CC2)c(Cl)c1)/C(=N/O)c1cc2cc(C(F)(F)F)ccc2o1] | (E)-N-((1R,2R)-1-(3-chloro-4-cyclopropoxyphenyl)-1-hydroxy-3-(pyrrolidin-1-yl)propan-2-yl)-2-(hydroxyimino)-2-(5-(trifluoromethyl)benzofuran-2-yl)acetamide | nt |
| 445 | 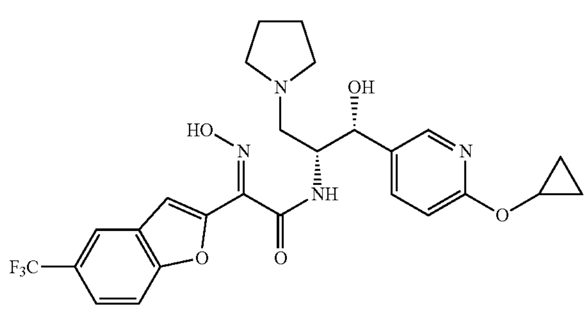 [SMILES: O=C(N[C@H](CN1CCCC1)[C@H](O)c1ccc(OC2CC2)nc1)/C(=N/O)c1cc2cc(C(F)(F)F)ccc2o1] | (E)-N-((1R,2R)-1-(6-cyclopropoxypyridin-3-yl)-1-hydroxy-3-(pyrrolidin-1-yl)propan-2-yl)-2-(hydroxyimino)-2-(5-(trifluoromethyl)benzofuran-2-yl)acetamide | nt |

TABLE 3-continued

The data provided is the IC$_{50}$ (nM) generated from Assay 1, except as otherwise noted by *, which is % inhibition, also generated from Assay 1.

| Ex | Structure | Name | Data |
|---|---|---|---|
| 446 | 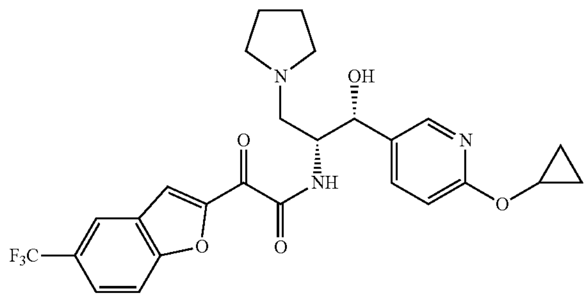 [SMILES: O=C(N[C@H](CN1CCCC1)[C@H](O)c1ccc(OC2CC2)nc1)C(=O)c1cc2cc(C(F)(F)F)ccc2o1] | N-((1R,2R)-1-(6-cyclopropoxypyridin-3-yl)-1-hydroxy-3-(pyrrolidin-1-yl)propan-2-yl)-2-oxo-2-(5-(trifluoromethyl)benzofuran-2-yl)acetamide | nt |
| 447 | 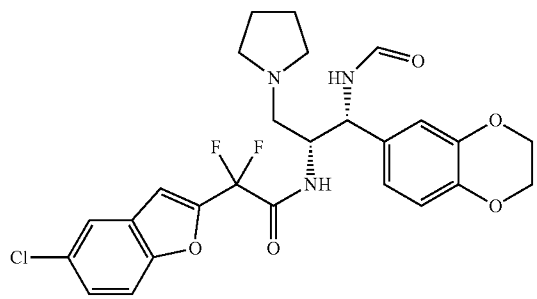 [SMILES: O=CN[C@H](c1ccc2c(c1)OCCO2)[C@@H](CN1CCCC1)NC(=O)C(F)(F)c1cc2cc(Cl)ccc2o1] | 2-(5-chlorobenzofuran-2-yl)-N-((1R,2R)-1-(2,3-dihydrobenzo[b][1,4]dioxin-6-yl)-1-formamido-3-(pyrrolidin-1-yl)propan-2-yl)-2,2-difluoroacetamide | nt |
| 448 | 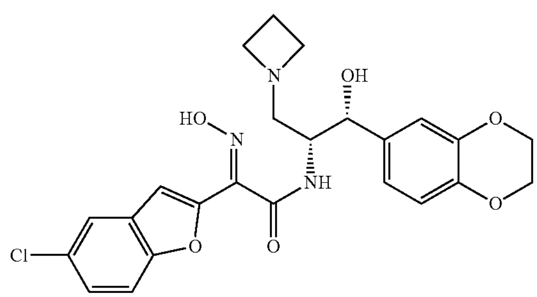 [SMILES: O=C(N[C@H](CN1CCC1)[C@H](O)c1ccc2c(c1)OCCO2)/C(=N/O)c1cc2cc(Cl)ccc2o1] | (E)-N-((1R,2R)-3-(azetidin-1-yl)-1-(2,3-dihydrobenzo[b][1,4]dioxin-6-yl)-1-hydroxypropan-2-yl)-2-(5-chlorobenzofuran-2-yl)-2-(hydroxyimino)acetamide | nt |
| 449 | 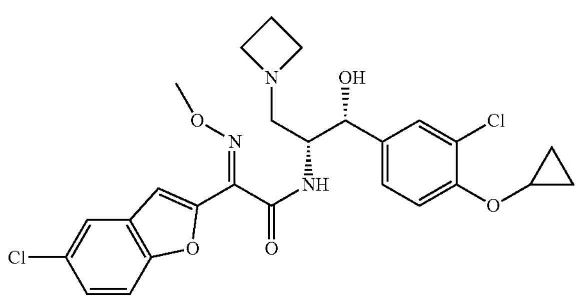 [SMILES: CO/N=C(/C(=O)N[C@H](CN1CCC1)[C@H](O)c1ccc(OC2CC2)c(Cl)c1)c1cc2cc(Cl)ccc2o1] | (E)-N-((1R,2R)-3-(azetidin-1-yl)-1-(3-chloro-4-cyclopropoxyphenyl)-1-hydroxypropan-2-yl)-2-(5-chlorobenzofuran-2-yl)-2-(methoxyimino)acetamide | nt |
| 450 | 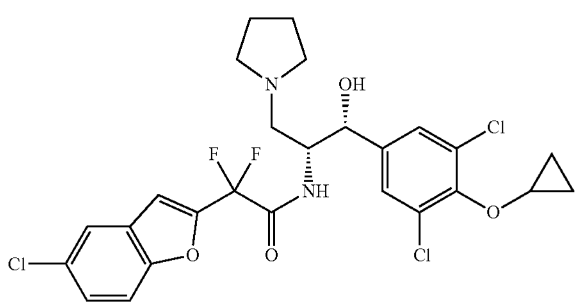 [SMILES: O=C(N[C@H](CN1CCCC1)[C@H](O)c1cc(Cl)c(OC2CC2)c(Cl)c1)C(F)(F)c1cc2cc(Cl)ccc2o1] | 2-(5-chlorobenzofuran-2-yl)-N-((1R,2R)-1-(3,5-dichloro-4-cyclopropoxyphenyl)-1-hydroxy-3-(pyrrolidin-1-yl)propan-2-yl)-2,2-difluoroacetamide | nt |

TABLE 3-continued

The data provided is the IC$_{50}$ (nM) generated from Assay 1, except as otherwise noted by *, which is % inhibition, also generated from Assay 1.

| Ex | Structure | Name | Data |
|---|---|---|---|
| 451 | 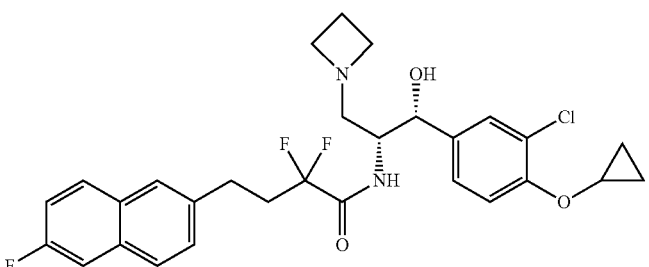 | N-((1R,2R)-3-(azetidin-1-yl)-1-(3-chloro-4-cyclopropoxyphenyl)-1-hydroxypropan-2-yl)-2,2-difluoro-4-(6-fluoronaphthalen-2-yl)butanamide | nt |
| 452 | 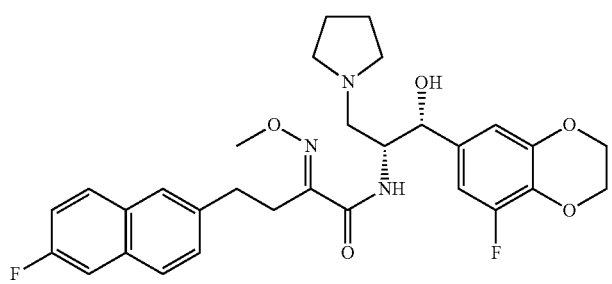 [SMILES: CO/N=C(\CCc1ccc2cc(F)ccc2c1)C(=O)N[C@H](CN1CCCC1)[C@H](O)c1cc(F)c2c(c1)OCCO2] | (E)-N-((1R,2R)-1-(8-fluoro-2,3-dihydrobenzo[b][1,4]dioxin-6-yl)-1-hydroxy-3-(pyrrolidin-1-yl)propan-2-yl)-4-(6-fluoronaphthalen-2-yl)-2-(methoxyimino)butanamide | nt |
| 453 | 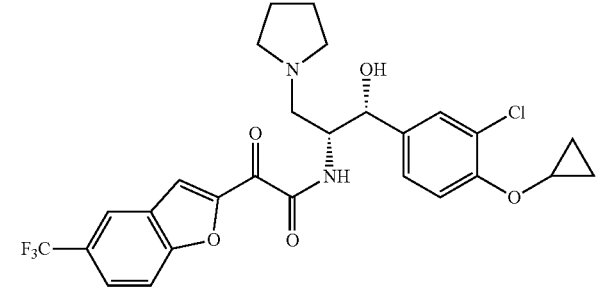 [SMILES: O=C(N[C@H](CN1CCCC1)[C@H](O)c1ccc(OC2CC2)c(Cl)c1)C(=O)c1cc2cc(C(F)(F)F)ccc2o1] | N-((1R,2R)-1-(3-chloro-4-cyclopropoxyphenyl)-1-hydroxy-3-(pyrrolidin-1-yl)propan-2-yl)-2-oxo-2-(5-(trifluoromethyl)benzofuran-2-yl)acetamide | nt |
| 454 | 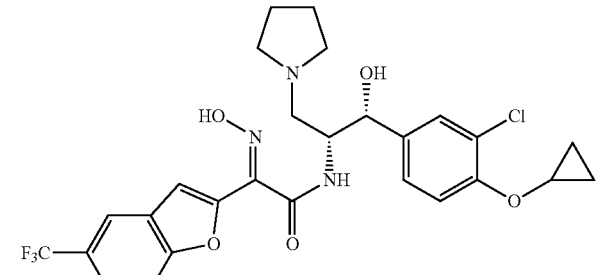 | (E)-N-((1R,2R)-1-(3-chloro-4-cyclopropoxyphenyl)-1-hydroxy-3-(pyrrolidin-1-yl)propan-2-yl)-2-(hydroxyimino)-2-(5-(trifluoromethyl)benzofuran-2-yl)acetamide | nt |
| 455 | 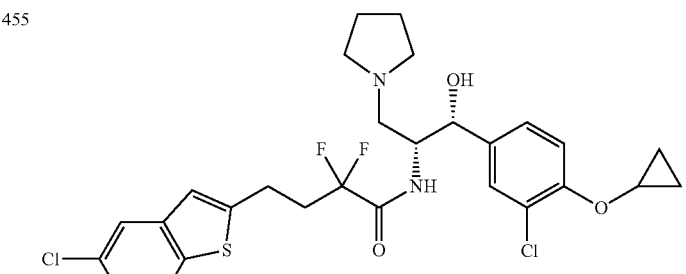 | N-((1R,2R)-1-(3-chloro-4-cyclopropoxyphenyl)-1-hydroxy-3-(pyrrolidin-1-yl)propan-2-yl)-4-(5-chlorobenzo[b]thiophen-2-yl)-2,2-difluorobutanamide | nt |

TABLE 3-continued

The data provided is the IC$_{50}$ (nM) generated from Assay 1, except as otherwise noted by *, which is % inhibition, also generated from Assay 1.

| Ex | Structure | Name | Data |
|----|-----------|------|------|
| 456 | 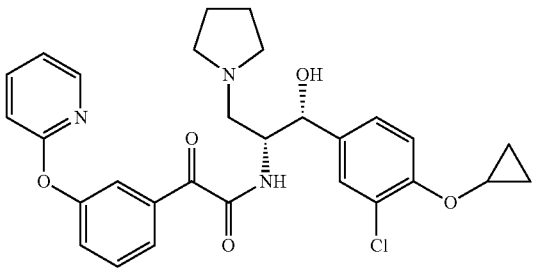 [SMILES: O=C(N[C@H](CN1CCCC1)[C@H](O)c1ccc(OC2CC2)c(Cl)c1)C(=O)c1cccc(Oc2ccccn2)c1] | N-((1R,2R)-1-(3-chloro-4-cyclopropoxyphenyl)-1-hydroxy-3-(pyrrolidin-1-yl)propan-2-yl)-2-oxo-2-(3-(pyridin-2-yloxy)phenyl)acetamide | nt |
| 457 | 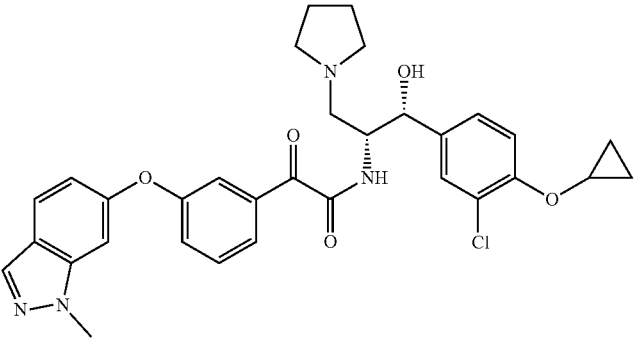 [SMILES: Cn1ncc2ccc(Oc3cccc(C(=O)C(=O)N[C@H](CN4CCCC4)[C@H](O)c4ccc(OC5CC5)c(Cl)c4)c3)cc21] | N-((1R,2R)-1-(3-chloro-4-cyclopropoxyphenyl)-1-hydroxy-3-(pyrrolidin-1-yl)propan-2-yl)-2-(3-((1-methyl-1H-indazol-6-yl)oxy)phenyl)-2-oxoacetamide | nt |
| 458 | 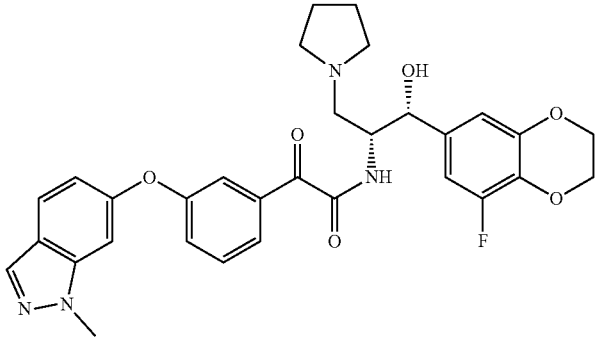 [SMILES: Cn1ncc2ccc(Oc3cccc(C(=O)C(=O)N[C@H](CN4CCCC4)[C@H](O)c4cc(F)c5c(c4)OCCO5)c3)cc21] | N-((1R,2R)-1-(8-fluoro-2,3-dihydrobenzo[b][1,4]dioxin-6-yl)-1-hydroxy-3-(pyrrolidin-1-yl)propan-2-yl)-2-(3-((1-methyl-1H-indazol-6-yl)oxy)phenyl)-2-oxoacetamide | nt |
| 459 | 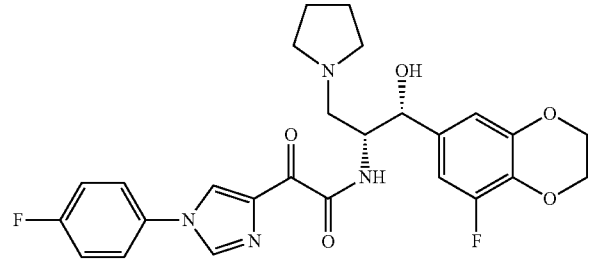 [SMILES: O=C(N[C@H](CN1CCCC1)[C@H](O)c1cc(F)c2c(c1)OCCO2)C(=O)c1cn(-c2ccc(F)cc2)cn1] | N-((1R,2R)-1-(8-fluoro-2,3-dihydrobenzo[b][1,4]dioxin-6-yl)-1-hydroxy-3-(pyrrolidin-1-yl)propan-2-yl)-2-(1-(4-fluorophenyl)-1H-imidazol-4-yl)-2-oxoacetamide | nt |
| 460 | 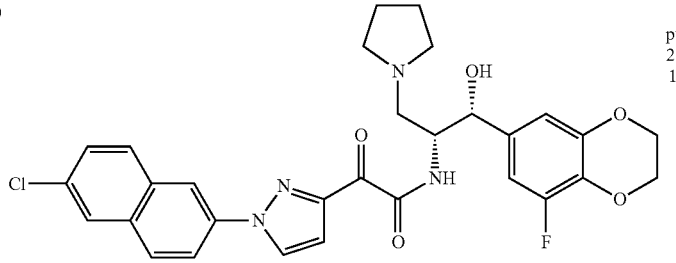 | 2-(1-(6-chloronaphthalen-2-yl)-1H-pyrazol-3-yl)-N-((1R,2R)-1-(8-fluoro-2,3-dihydrobenzo[b][1,4]dioxin-6-yl)-1-hydroxy-3-(pyrrolidin-1-yl)propan-2-yl)-2-oxoacetamide | nt |

TABLE 3-continued

The data provided is the IC$_{50}$ (nM) generated from Assay 1, except as otherwise noted by *, which is % inhibition, also generated from Assay 1.

| Ex | Structure | Name | Data |
|---|---|---|---|
| 461 | 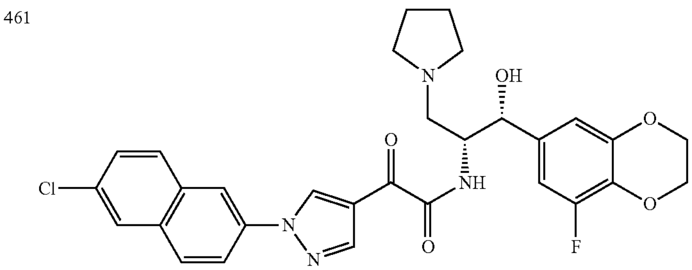 | 2-(1-(6-chloronaphthalen-2-yl)-1H-pyrazol-4-yl)-N-((1R,2R)-1-(8-fluoro-2,3-dihydrobenzo[b][1,4]dioxin-6-yl)-1-hydroxy-3-(pyrrolidin-1-yl)propan-2-yl)-2-oxoacetamide | nt |
| 462 | 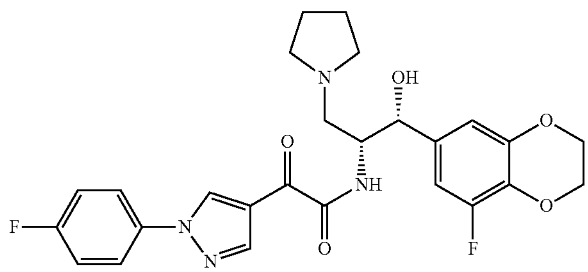 [SMILES: O=C(N[C@H](CN1CCCC1)[C@H](O)c1cc(F)c2c(c1)OCCO2)C(=O)c1cnn(-c2ccc(F)cc2)c1] | N-((1R,2R)-1-(8-fluoro-2,3-dihydrobenzo[b][1,4]dioxin-6-yl)-1-hydroxy-3-(pyrrolidin-1-yl)propan-2-yl)-2-(1-(4-fluorophenyl)-1H-pyrazol-4-yl)-2-oxoacetamide | nt |
| 463 | 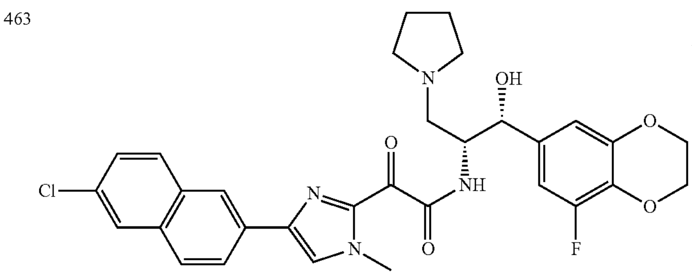 | 2-(4-(6-chloronaphthalen-2-yl)-1-methyl-1H-imidazol-2-yl)-N-((1R,2R)-1-(8-fluoro-2,3-dihydrobenzo[b][1,4]dioxin-6-yl)-1-hydroxy-3-(pyrrolidin-1-yl)propan-2-yl)-2-oxoacetamide | nt |
| 464 | 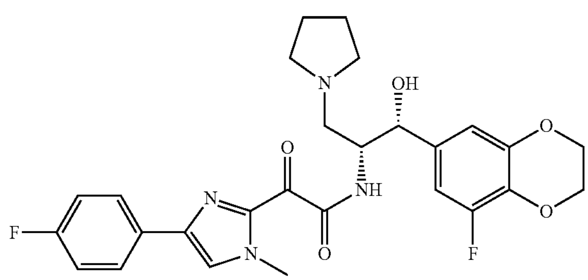 [SMILES: Cn1cc(-c2ccc(F)cc2)nc1C(=O)C(=O)N[C@H](CN1CCCC1)[C@H](O)c1cc(F)c2c(c1)OCCO2] | N-((1R,2R)-1-(8-fluoro-2,3-dihydrobenzo[b][1,4]dioxin-6-yl)-1-hydroxy-3-(pyrrolidin-1-yl)propan-2-yl)-2-(4-(4-fluorophenyl)-1-methyl-1H-imidazol-2-yl)-2-oxoacetamide | nt |
| 465 | 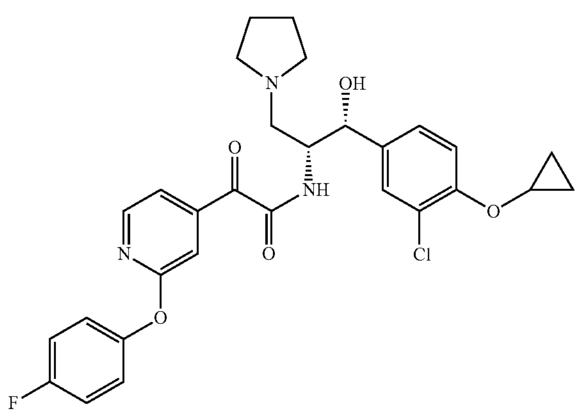 [SMILES: O=C(N[C@H](CN1CCCC1)[C@H](O)c1ccc(OC2CC2)c(Cl)c1)C(=O)c1ccnc(Oc2ccc(F)cc2)c1] | N-((1R,2R)-1-(3-chloro-4-cyclopropoxyphenyl)-1-hydroxy-3-(pyrrolidin-1-yl)propan-2-yl)-2-(2-(4-fluorophenoxy)pyridin-4-yl)-2-oxoacetamide | nt |

TABLE 3-continued

The data provided is the IC$_{50}$ (nM) generated from Assay 1, except as otherwise noted by *, which is % inhibition, also generated from Assay 1.

| Ex | Structure | Name | Data |
|---|---|---|---|
| 466 | 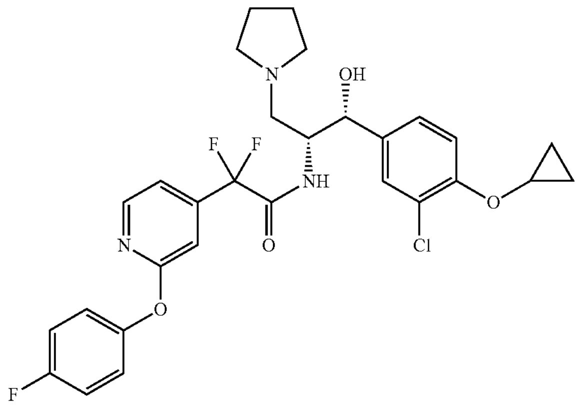 [SMILES: O=C(N[C@H](CN1CCCC1)[C@H](O)c1ccc(OC2CC2)c(Cl)c1)C(F)(F)c1ccnc(Oc2ccc(F)cc2)c1] | N-((1R,2R)-1-(3-chloro-4-cyclopropoxyphenyl)-1-hydroxy-3-(pyrrolidin-1-yl)propan-2-yl)-2,2-difluoro-2-(2-(4-fluorophenoxy)pyridin-4-yl)acetamide | nt |
| 467 | 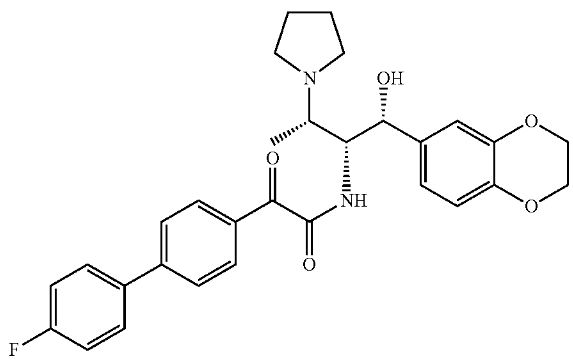 [SMILES: C[C@@H]([C@@H](NC(=O)C(=O)c1ccc(-c2ccc(F)cc2)cc1)[C@H](O)c1ccc2c(c1)OCCO2)N1CCCC1] | N-((1R,2R,3S)-1-(2,3-dihydrobenzo[b][1,4]dioxin-6-yl)-1-hydroxy-3-(pyrrolidin-1-yl)butan-2-yl)-2-(4'-fluoro-[1,1'-biphenyl]-4-yl)-2-oxoacetamide | nt |
| 468 | 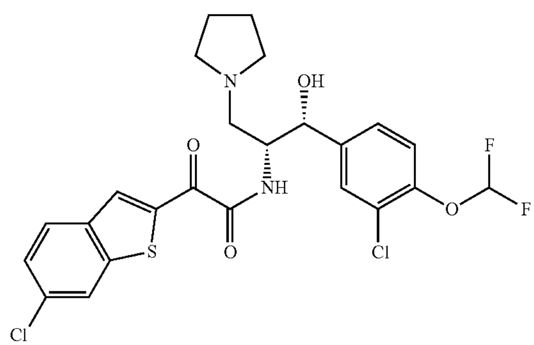 [SMILES: O=C(N[C@H](CN1CCCC1)[C@H](O)c1ccc(OC(F)F)c(Cl)c1)C(=O)c1cc2ccc(Cl)cc2s1] | N-((1R,2R)-1-(3-chloro-4-(difluoromethoxy)phenyl)-1-hydroxy-3-(pyrrolidin-1-yl)propan-2-yl)-2-(6-chlorobenzo[b]thiophen-2-yl)-2-oxoacetamide | nt |
| 469 | 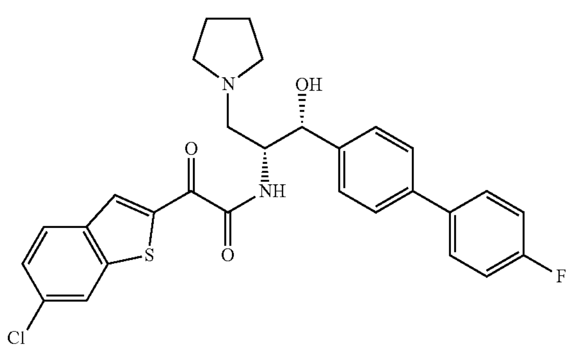 [SMILES: O=C(N[C@H](CN1CCCC1)[C@H](O)c1ccc(-c2ccc(F)cc2)cc1)C(=O)c1cc2ccc(Cl)cc2s1] | 2-(6-chlorobenzo[b]thiophen-2-yl)-N-((1R,2R)-1-(4'-fluoro-[1,1'-biphenyl]-4-yl)-1-hydroxy-3-(pyrrolidin-1-yl)propan-2-yl)-2-oxoacetamide | nt |

… TABLE 3-continued

The data provided is the IC$_{50}$ (nM) generated from Assay 1, except as otherwise noted by *, which is % inhibition, also generated from Assay 1.

| Ex | Structure | Name | Data |
|---|---|---|---|
| 470 | 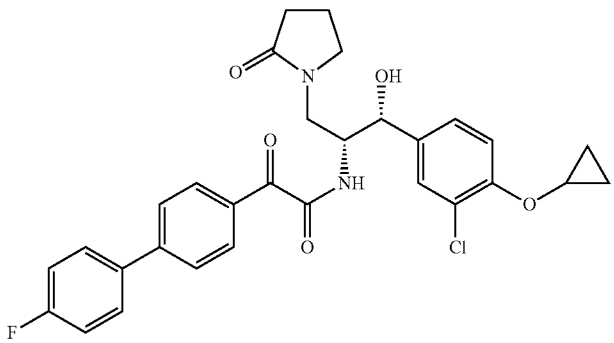 [SMILES: O=C(N[C@H](CN1CCCC1=O)[C@H](O)c1ccc(OC2CC2)c(Cl)c1)C(=O)c1ccc(-c2ccc(F)cc2)cc1] | N-((1R,2R)-1-(3-chloro-4-cyclopropoxyphenyl)-1-hydroxy-3-(2-oxopyrrolidin-1-yl)propan-2-yl)-2-(4'-fluoro-[1,1'-biphenyl]-4-yl)-2-oxoacetamide | nt |
| 471 | 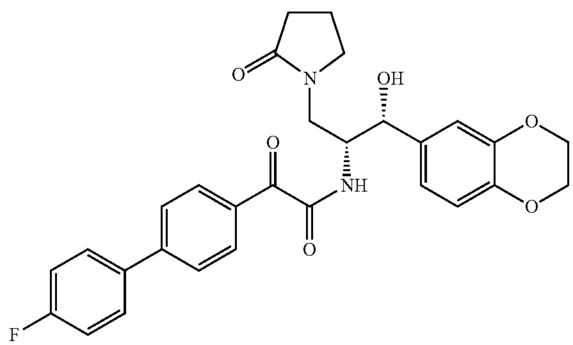 [SMILES: O=C(N[C@H](CN1CCCC1=O)[C@H](O)c1ccc2c(c1)OCCO2)C(=O)c1ccc(-c2ccc(F)cc2)cc1] | N-((1R,2R)-1-(2,3-dihydrobenzo[b][1,4]dioxin-6-yl)-1-hydroxy-3-(2-oxopyrrolidin-1-yl)propan-2-yl)-2-(4'-fluoro-[1,1'-biphenyl]-4-yl)-2-oxoacetamide | nt |
| 472 | 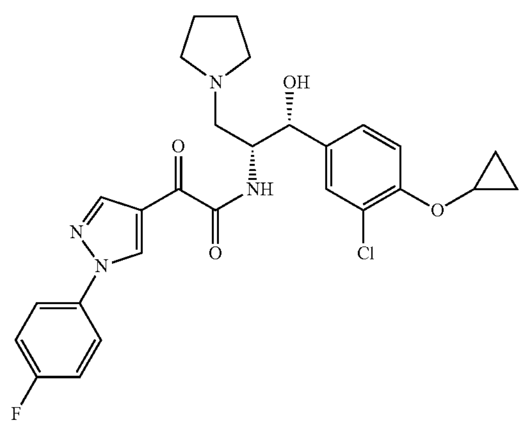 [SMILES: O=C(N[C@H](CN1CCCC1)[C@H](O)c1ccc(OC2CC2)c(Cl)c1)C(=O)c1cnn(-c2ccc(F)cc2)c1] | N-((1R,2R)-1-(3-chloro-4-cyclopropoxyphenyl)-1-hydroxy-3-(pyrrolidin-1-yl)propan-2-yl)-2-(1-(4-fluorophenyl)-1H-pyrazol-4-yl)-2-oxoacetamide | nt |
| 473 | 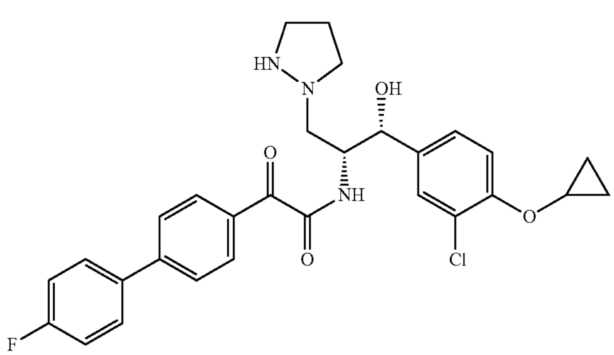 [SMILES: O=C(N[C@H](CN1CCCN1)[C@H](O)c1ccc(OC2CC2)c(Cl)c1)C(=O)c1ccc(-c2ccc(F)cc2)cc1] | N-((1R,2R)-1-(3-chloro-4-cyclopropoxyphenyl)-1-hydroxy-3-(pyrazolidin-1-yl)propan-2-yl)-2-(4'-fluoro-[1,1'-biphenyl]-4-yl)-2-oxoacetamide | nt |

TABLE 3-continued

The data provided is the IC$_{50}$ (nM) generated from Assay 1, except as otherwise noted by *, which is % inhibition, also generated from Assay 1.

| Ex | Structure | Name | Data |
|----|-----------|------|------|
| 474 | 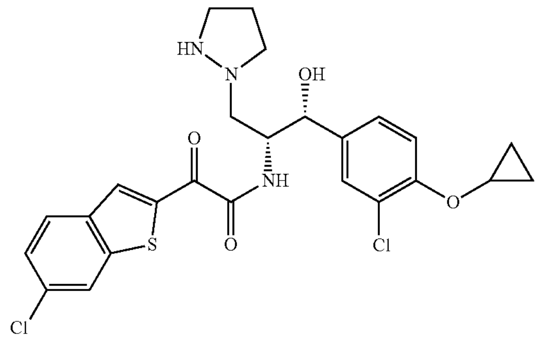 [SMILES: O=C(N[C@H](CN1CCCN1)[C@H](O)c1ccc(OC2CC2)c(Cl)c1)C(=O)c1cc2ccc(Cl)cc2s1] | N-((1R,2R)-1-(3-chloro-4-cyclopropoxyphenyl)-1-hydroxy-3-(pyrazolidin-1-yl)propan-2-yl)-2-(6-chlorobenzo[b]thiophen-2-yl)-2-oxoacetamide | nt |
| 475 | 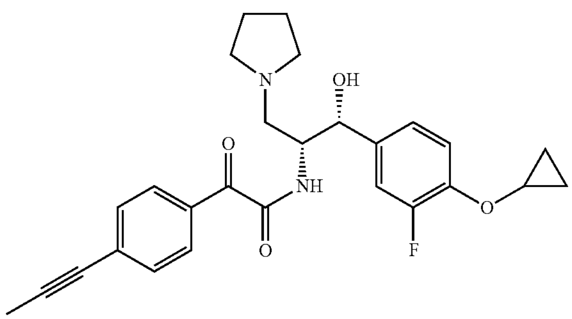 [SMILES: CC#Cc1ccc(C(=O)C(=O)N[C@H](CN2CCCC2)[C@H](O)c2ccc(OC3CC3)c(F)c2)cc1] | N-((1R,2R)-1-(4-cyclopropoxy-3-fluorophenyl)-1-hydroxy-3-(pyrrolidin-1-yl)propan-2-yl)-2-oxo-2-(4-(prop-1-yn-1-yl)phenyl)acetamide | nt |
| 476 | 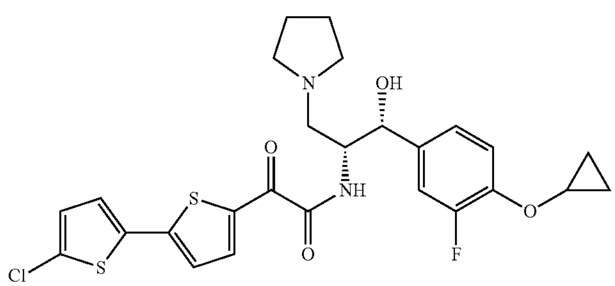 [SMILES: O=C(N[C@H](CN1CCCC1)[C@H](O)c1ccc(OC2CC2)c(F)c1)C(=O)c1ccc(-c2ccc(Cl)s2)s1] | 2-(5'-chloro-[2,2'-bithiophen]-5-yl)-N-((1R,2R)-1-(4-cyclopropoxy-3-fluorophenyl)-1-hydroxy-3-(pyrrolidin-1-yl)propan-2-yl)-2-oxoacetamide | nt |
| 477 | 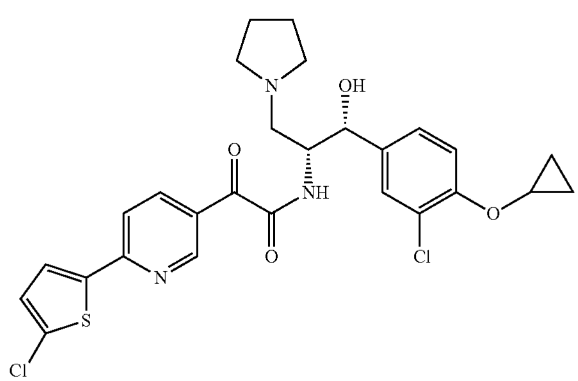 [SMILES: O=C(N[C@H](CN1CCCC1)[C@H](O)c1ccc(OC2CC2)c(Cl)c1)C(=O)c1ccc(-c2ccc(Cl)s2)nc1] | N-((1R,2R)-1-(3-chloro-4-cyclopropoxyphenyl)-1-hydroxy-3-(pyrrolidin-1-yl)propan-2-yl)-2-(6-(5-chlorothiophen-2-yl)pyridin-3-yl)-2-oxoacetamide | nt |

TABLE 3-continued

The data provided is the IC$_{50}$ (nM) generated from Assay 1, except as otherwise noted by *, which is % inhibition, also generated from Assay 1.

| Ex | Structure | Name | Data |
|---|---|---|---|
| 478 | 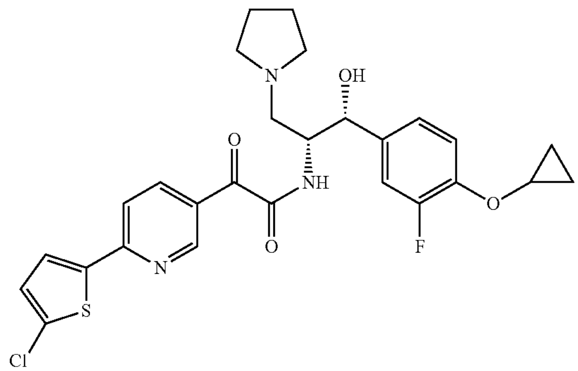 [SMILES: O=C(N[C@H](CN1CCCC1)[C@H](O)c1ccc(OC2CC2)c(F)c1)C(=O)c1ccc(-c2ccc(Cl)s2)nc1] | 2-(6-(5-chlorothiophen-2-yl)pyridin-3-yl)-N-((1R,2R)-1-(4-cyclopropoxy-3-fluorophenyl)-1-hydroxy-3-(pyrrolidin-1-yl)propan-2-yl)-2-oxoacetamide | nt |

Sandhoff Disease Mouse Model

The murine model of Sandhoff disease is a knock out (KO) of the HEXB gene, which codes for beta-hexosaminidase in mice, as it does in humans. This KO mouse displays a phenotype closely resembling that seen in humans, although at a more advanced age, compared to humans. At ~3 months of age, the animals develop tremor and increased limb tone, which is worse in the hind legs. These manifestations become progressively more severe until 4-5 months of age, when the animals become moribund and rapidly lose weight. The motor phenotype has been quantified by activity monitor, bar-crossing, and inverted screen tests (Jayakumar M et al *Blood* 2001, 97, 327-329; Cachon-Gonzalez et al *PNAS* 2006, 103(27), 1037-10378). Histologically, the mouse neurons appear to be distended by lysosomal storage material, and signs of neuroinflammation are present. Biochemically, levels of beta-hexosaminidase are absent, and accumulations of gangliosides GM2, GA2, as well as sialic acid, can be demonstrated (Cachon-Gonzalez et al 2006; Arthur et al *Neurochem Res* 2013, DOI 10.1007/s11064-013-0992-5).

To evaluate the potential efficacy of different BioMarin substrate reduction compounds in Sandhoff disease, homozygous male mice are mated with heterozygous females. All pups (approximately 50% KO and 50% het) in a litter are treated by daily IP or SC injection with the same test (or control) article for 14 days, beginning at 3 days old. The chosen route of administration is determined based on pharmacokinetic/pharmacodynamic properties of the compound to be tested. At the end of the dosing period, pups are deeply anesthetized using isoflurane through nose cones (4% for induction and 1.5% for maintenance), blood is collected by cardiac puncture method, then the mice are euthanized. Brains and livers are collected and snap frozen. These tissues are used for analysis of experimental endpoints (GM2 and sialic acid in brain, GA2 and sialic acid in liver). An additional tissue sample (tail tip or toe) is collected and snap frozen, then sent for genotyping.

I(f) tested compounds are found which have a marked effect on the experimental endpoints, an additional experiment is performed looking at effects on activity, inverted screen, and bar crossing tests, as well as average survival time, compared to vehicle-treated mice.

Polycystic Kidney Disease Mouse Model

To jck mice is administered a compound of the invention ad libitum in food (standard chow) from 26-64 days of age. Control jck mice are fed a control diet from 26-64 days of age. At 63 days of age, the animals are transferred to metabolic cages for 24 hour urine collection. At 64 days of age, animals are sacrificed, weighed, and blood is collected by heart puncture for serum isolation. Kidneys are isolated, bisected, and weighed and half of each kidney is fixed in 4% paraformaldehyde in PBS overnight for paraffin embedding and hematoxylin and eosin staining. Kidney weight to body weight ratio is used to determine activity of the compound. Cyst volume is measured by quantitating the percentage of cystic area in histological sections of kidneys from the treated and control animals and multiplied by the kidney/body weight ratio. Kidney function is assessed by measuring blood urea nitrogen (BUN) levels in serum samples derived from animals at sacrifice. BUN levels are elevated in untreated controls while the treated animals demonstrated a significant reduction of BUN levels.

Other objects, features and advantages of the compounds, methods and compositions described herein will become apparent from the following description. It should be understood, however, that the description and the specific examples, while indicating specific embodiments, are given by way of illustration only, since various changes and modifications within the spirit and scope of the present description will become apparent from this detailed description.

All publications including patents, patent applications and published patent applications cited herein are hereby incorporated by reference for all purposes.

We claim:
1. A compound of Formula I:

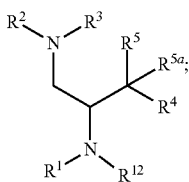

Formula I wherein

R¹ is —C(O)C(R⁶)(R⁶ᵃ)R¹ᵃ or —C(O)C(R⁶)(R⁶ᵃ)—X¹—R¹ᵃ;

X¹ is alkylene, alkenylene, or cycloalkylene;

R¹ᵃ is
(a) benzofuranyl, optionally substituted with 1, 2, or 3 R⁷ groups, or
(b) phenyl substituted with one substituent selected from pyridinyl, indazolyl, benzothiophenyl, benzoisoxazolyl, benzothiazolyl, pyrazolyl, and triazolyl, wherein the substituent is optionally further substituted with 1, 2 or 3 R⁷ᵃ groups;

R² and R³ together with the nitrogen to which they are attached form a 3-10 membered heterocycloalkyl ring, optionally substituted with 1, 2, 3, 4, 5, 6, 7, or 8 R⁸;

R⁴ is aryl or heteroaryl each of which is optionally substituted with 1, 2, 3, or 4 R⁹ groups;

R⁵ is —OH, and R⁵ᵃ is hydrogen;

R⁶ and R⁶ᵃ are halo; R⁶ and R⁶ᵃ are deuterium; or R⁶ and R⁶ᵃ together with the carbon to which they are attached form C(═NOH) or C(O);

each R⁷, when present, is independently nitro, cyano, amino, alkylamino, dialkylamino, halo, haloalkyl, alkyl, alkenyl, alkynyl, hydroxy, alkoxy, haloalkoxy, alkoxycarbonyl, aminocarbonyl, alkylaminocarbonyl, dialkylaminocarbonyl, cycloalkyl, heterocycloalkyl, phenyl, phenylalkyl, phenyloxy, heteroaryl, heteroarylalkyl, or heteroaryloxy; where the phenyl and the heteroaryl, either alone or as part of another group, are independently optionally substituted with 1, 2 or 3 R⁷ᵃ;

each R⁷ᵃ, when present, is independently selected from cyano, halo, alkyl, alkenyl, haloalkyl, hydroxyalkyl, and cycloalkyl;

each R⁸, when present, is independently deuterium, amino, alkylamino, dialkylamino, alkyl, hydroxy, alkoxy, halo, haloalkyl, or cycloalkyl; or two R⁸ together with the carbon to which they are attached form C(O);

each R⁹, when present, is independently cyano, nitro, amino, alkylamino, dialkylamino, halo, haloalkyl, alkyl, hydroxy, alkoxy, alkenyloxy, hydroxyalkyloxy, haloalkoxy, cycloalkylthio, cycloalkyloxy, cycloalkylalkyloxy, heterocycloalkyl, heterocycloalkyloxy, heterocycloalkylalkyloxy, or phenyl; where the heterocycloalkyl and the phenyl, either alone or as part of another group, are independently optionally substituted with 1 or 2 R⁹ᵃ;

each R⁹ᵃ, when present, is independently selected from alkyl, hydroxy, alkoxy, halo, haloalkyl, haloalkoxy, alkoxycarbonyl, amino, alkylamino, and dialkylamino; and R¹² is hydrogen or C₁₋₅ alkyl;

optionally a tautomer, a single stereoisomer or mixture of stereoisomers thereof and additionally optionally a pharmaceutically acceptable salt thereof.

2. The compound of claim 1, wherein the compound of Formula I is according to Formula I(b) or Formula I(c):

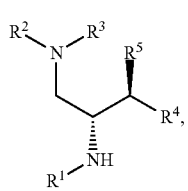

Formula I(b)

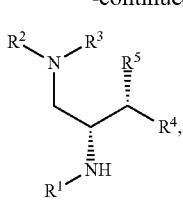

Formula I(c)

optionally as a tautomer, a single stereoisomer or mixture of stereoisomers thereof and additionally optionally as a pharmaceutically acceptable salt thereof.

3. The compound of claim 1, wherein R² and R³ together with the nitrogen to which they are attached form a 4-5 membered monocyclic heterocycloalkyl ring or a 7-8 membered bicyclic heterocycloalkyl; each of which is optionally substituted with 1 or 2 R⁸; optionally as a tautomer, a single stereoisomer or mixture of stereoisomers thereof and additionally optionally as a pharmaceutically acceptable salt thereof.

4. The compound of claim 1, wherein R⁴ is aryl which is optionally substituted with 1, 2, or 3 R⁹ groups; optionally as a tautomer, a single stereoisomer or mixture of stereoisomers thereof and additionally optionally as a pharmaceutically acceptable salt thereof.

5. The compound of claim 4, wherein each R⁹, when present, is independently halo, alkoxy, alkenyloxy, hydroxyalkyloxy, haloalkoxy, cycloalkylthio, cycloalkyloxy, cycloalkylalkyloxy, heterocycloalkyloxy, or heterocycloalkylalkyloxy; optionally as a tautomer, a single stereoisomer or mixture of stereoisomers thereof and additionally optionally as a pharmaceutically acceptable salt thereof.

6. The compound of claim 1, wherein R⁴ is heteroaryl which is optionally substituted with 1, 2, or 3 R⁹ groups; optionally as a tautomer, a single stereoisomer or mixture of stereoisomers thereof and additionally optionally as a pharmaceutically acceptable salt thereof.

7. The compound of claim 6, wherein R⁴ is 2,3-dihydrobenzo[b][1,4]dioxin-6-yl optionally substituted with a halo; optionally as a tautomer, a single stereoisomer or mixture of stereoisomers thereof and additionally optionally as a pharmaceutically acceptable salt thereof.

8. The compound of claim 1, wherein X¹ is C₁₋₃ alkylene; optionally as a tautomer, a single stereoisomer or mixture of stereoisomers thereof and additionally optionally as a pharmaceutically acceptable salt thereof.

9. The compound of claim 1, wherein R⁶ and R⁶ᵃ together with the carbon to which they are attached form C(O) or C(═NOH); optionally as a tautomer, a single stereoisomer or mixture of stereoisomers thereof and additionally optionally as a pharmaceutically acceptable salt thereof.

10. The compound of claim 1, wherein R⁶ and R⁶ᵃ are halo; optionally as a tautomer, a single stereoisomer or mixture of stereoisomers thereof and additionally optionally as a pharmaceutically acceptable salt thereof.

11. The compound of claim 1 wherein:

R¹ is —C(O)C(R⁶)(R⁶ᵃ)R¹ᵃ or —C(O)C(R⁶)(R⁶ᵃ)—X¹—R¹ᵃ;

X¹ is alkylene, alkenylene, or cycloalkylene;

R¹ᵃ is
(a) benzofuranyl, optionally substituted with 1, 2, or 3 R⁷ groups, or
(b) phenyl substituted with one substituent selected from pyridinyl, indazolyl, benzothiophenyl, benzoisoxazolyl, benzothiazolyl, pyrazolyl, and triazolyl, wherein the substituent is optionally further substituted with 1, 2 or 3 $R^{7a}$ groups;

$R^2$ and $R^3$ together with the nitrogen to which they are attached form a 4-5 membered monocyclic heterocycloalkyl ring or a 7-8 membered bicyclic heterocycloalkyl; each of which is optionally substituted with 1 or 2 $R^8$;

$R^4$ is aryl or heteroaryl each of which is optionally substituted with 1, 2, or 3 $R^9$ groups;

$R^5$ is —OH, and $R^{5a}$ is hydrogen;

$R^6$ and $R^{6a}$ are halo; or $R^6$ and $R^{6a}$ together with the carbon to which they are attached form C(=NOH) or C(O);

each $R^7$, when present, is independently nitro, cyano, halo, haloalkyl, alkyl, alkenyl, alkynyl, cycloalkyl, heterocycloalkyl, phenyl, phenylalkyl, phenyloxy, heteroaryl, heteroarylalkyl, or heteroaryloxy; where the phenyl and the heteroaryl, either alone or as part of another group, are independently optionally substituted with 1, 2 or 3 $R^{7a}$;

each $R^{7a}$, when present, is independently selected from cyano, halo, alkyl, alkenyl, haloalkyl, hydroxyalkyl, and cycloalkyl;

each $R^8$, when present, is independently amino, alkylamino, dialkylamino, alkyl, halo, or cycloalkyl; or two $R^8$ together with the carbon to which they are attached form C(O);

each $R^9$, when present, is independently cyano, nitro, amino, alkylamino, dialkylamino, halo, haloalkyl, alkyl, hydroxy, alkoxy, alkenyloxy, hydroxyalkyloxy, haloalkoxy, cycloalkylthio, cycloalkyloxy, cycloalkylalkyloxy, heterocycloalkyl, heterocycloalkyloxy, heterocycloalkylalkyloxy, or phenyl; where the heterocycloalkyl and the phenyl, either alone or as part of another group, are independently optionally substituted with 1 or 2 $R^{9a}$;

each $R^{9a}$, when present, is independently selected from alkyl, hydroxy, alkoxy, halo, haloalkyl, haloalkoxy, alkoxycarbonyl, amino, alkylamino, and dialkylamino; and $R^{12}$ is hydrogen or $CH_3$;

optionally a tautomer, a single stereoisomer or mixture of stereoisomers thereof and additionally optionally a pharmaceutically acceptable salt thereof.

12. The compound of claim 1 wherein:
$R^1$ is —C(O)C($R^6$)($R^{6a}$)$R^{1a}$ or —C(O)C($R^6$)($R^{6a}$)—$X^1$—$R^{1a}$;
$X^1$ is alkylene;
$R^{1a}$ is
(a) benzofuranyl, optionally substituted with 1, 2, or 3 $R^7$ groups, or
(b) phenyl substituted with one substituent selected from pyridinyl, indazolyl, benzothiophenyl, benzoisoxazolyl, benzothiazolyl, pyrazolyl, and triazolyl, wherein the substituent is optionally further substituted with 1, 2 or 3 $R^{7a}$ groups;

$R^2$ and $R^3$ together with the nitrogen to which they are attached form a 4-5 membered monocyclic heterocycloalkyl ring or a 7-8 membered bicyclic heterocycloalkyl; each of which is optionally substituted with 1 or 2 $R^8$;

$R^4$ is aryl or heteroaryl each of which is optionally substituted with 1, 2, or 3 $R^9$ groups;

$R^5$ is —OH, and $R^{5a}$ is hydrogen;

$R^6$ and $R^{6a}$ are halo; or $R^6$ and $R^{6a}$ together with the carbon to which they are attached form or C(O);

each $R^7$, when present, is independently nitro, cyano, halo, haloalkyl, alkyl, alkenyl, alkynyl, cycloalkyl, heterocycloalkyl, phenyl, phenylalkyl, phenyloxy, heteroaryl, heteroarylalkyl, or heteroaryloxy; where the phenyl and the heteroaryl, either alone or as part of another group, are independently optionally substituted with 1, 2 or 3 $R^{7a}$;

each $R^{7a}$, when present, is independently selected from cyano, halo, alkyl, alkenyl, haloalkyl, hydroxyalkyl, and cycloalkyl;

each $R^8$, when present, is independently amino, alkylamino, dialkylamino, alkyl, or halo;

each $R^9$, when present, is independently amino, alkylamino, dialkylamino, halo, haloalkyl, alkyl, hydroxy, alkoxy, alkenyloxy, hydroxyalkyloxy, haloalkoxy, cycloalkylthio, cycloalkyloxy, cycloalkylalkyloxy, heterocycloalkyl, heterocycloalkyloxy, heterocycloalkylalkyloxy, or phenyl; where the heterocycloalkyl and the phenyl, either alone or as part of another group, are independently optionally substituted with 1 or 2 $R^{9a}$;

each $R^{9a}$, when present, is independently selected from alkyl and halo; and $R^{12}$ is hydrogen or $CH_3$;

optionally a tautomer, a single stereoisomer or mixture of stereoisomers thereof and additionally optionally a pharmaceutically acceptable salt thereof.

13. A compound selected from the group consisting of:
2-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide;
2-(2,3-dihydrobenzo[b][1,4]dioxin-6-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide;
2-(5-chlorobenzo[b]thiophen-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide;
2-(5-chlorobenzo[b]thiophen-2-yl)-2,2-difluoro-N-((2R)-1-(3-fluoro-4-methoxyphenyl)-1-hydroxy-3-(pyrrolidin-1-yl)propan-2-yl)acetamide;
2-(2,3-dihydro-1H-inden-2-yl)-2,2-difluoro-N-((2R)-1-(3-fluoro-4-methoxyphenyl)-1-hydroxy-3-(pyrrolidin-1-yl)propan-2-yl)acetamide;
2-(2,3-dihydro-1H-inden-2-yl)-2,2-difluoro-N-((1S,2R)-1-(3-fluoro-4-methoxyphenyl)-1-hydroxy-3-(pyrrolidin-1-yl)propan-2-yl)acetamide;
2-(2,3-dihydro-1H-inden-2-yl)-2,2-difluoro-N-((1R,2R)-1-(3-fluoro-4-methoxyphenyl)-1-hydroxy-3-(pyrrolidin-1-yl)propan-2-yl)acetamide;
2-(5-chlorobenzo[d]thiazol-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide;
2-(5,6-dichloro-2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide;
2-(2,3-dihydro-1H-inden-2-yl)-2,2-difluoro-N-((1R,2R)-1-(2-fluoro-5-methoxyphenyl)-1-hydroxy-3-(pyrrolidin-1-yl)propan-2-yl)acetamide;
2-(2,3-dihydro-1H-inden-2-yl)-2,2-difluoro-N-((1S,2R)-1-(2-fluoro-5-methoxyphenyl)-1-hydroxy-3-(pyrrolidin-1-yl)propan-2-yl)acetamide;
2-(5-chloro-1-methyl-1H-benzo[d]imidazol-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide;
2-(5-chlorobenzofuran-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide;

2-(2,3-dihydro-1H-inden-2-yl)-2,2-difluoro-N-((1S,2R)-1-(7-fluoro-2,3-dihydrobenzo[b][1,4]dioxin-6-yl)-1-hydroxy-3-(pyrrolidin-1-yl)propan-2-yl)acetamide;

2-(7,8-dihydro-6H-cyclopenta[g]quinoxalin-7-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide;

2-(5-chloro-1-methyl-1H-indol-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide;

2-(5,7-dichlorobenzofuran-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide;

N-((1R,2R)-1-(2,3-dihydrobenzo[b][1,4]dioxin-6-yl)-1-hydroxy-3-(pyrrolidin-1-yl)propan-2-yl)-2,2-difluoro-4-(3-(pyridin-2-yl)phenyl)butanamide;

N-((1R,2R)-1-(2,3-dihydrobenzo[b][1,4]dioxin-6-yl)-1-hydroxy-3-(pyrrolidin-1-yl)propan-2-yl)-2,2-difluoro-3-(naphthalen-2-yl)propanamide;

2-(5,6-dichlorobenzofuran-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide;

2-(4,5-dichlorobenzofuran-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide;

N-((1R,2R)-1-(2,3-dihydrobenzo[b][1,4]dioxin-6-yl)-1-hydroxy-3-(pyrrolidin-1-yl)propan-2-yl)-2,2-difluoro-3-(3-(pyridin-2-yl)phenyl)propanamide;

N-((1R,2R)-1-(2,3-dihydrobenzo[b][1,4]dioxin-6-yl)-1-hydroxy-3-(pyrrolidin-1-yl)propan-2-yl)-2,2-difluoro-2-(5-fluoro-2,3-dihydro-1H-inden-2-yl)acetamide;

N-((1R,2R)-1-(2,3-dihydrobenzo[b][1,4]dioxin-6-yl)-1-hydroxy-3-(pyrrolidin-1-yl)propan-2-yl)-2,2-difluoro-4-(naphthalen-2-yl)butanamide;

N-((1S,2R)-1-(2,3-dihydrobenzo[b][1,4]dioxin-6-yl)-1-hydroxy-3-(pyrrolidin-1-yl)propan-2-yl)-2,2-difluoro-4-(naphthalen-2-yl)butanamide;

2-(benzofuran-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide;

N-((1R,2R)-1-(2,3-dihydrobenzo[b][1,4]dioxin-6-yl)-1-hydroxy-3-(pyrrolidin-1-yl)propan-2-yl)-2,2-difluoro-2-(5-fluorobenzofuran-2-yl)acetamide;

(E)-4-(4-chlorophenyl)-N-((1R,2R)-1-(2,3-dihydrobenzo[b][1,4]dioxin-6-yl)-1-hydroxy-3-(pyrrolidin-1-yl)propan-2-yl)-2,2-difluorobut-3-enamide;

N-((1R,2R)-3-(3-amino-8-azabicyclo[3.2.1]octan-8-yl)-1-(2,3-dihydrobenzo[b][1,4]dioxin-6-yl)-1-hydroxypropan-2-yl)-2-(5-chlorobenzofuran-2-yl)-2,2-difluoroacetamide;

N-((1R,2R)-1-(2,3-dihydrobenzo[b][1,4]dioxin-6-yl)-1-hydroxy-3-(pyrrolidin-1-yl)propan-2-yl)-2,2-difluoro-2-(5-fluorobenzo[b]thiophen-2-yl)acetamide;

N-((1R,2R)-1-(2,3-dihydrobenzo[b][1,4]dioxin-6-yl)-1-hydroxy-3-(pyrrolidin-1-yl)propan-2-yl)-2,2-difluoro-2-(5-(trifluoromethyl)benzofuran-2-yl)acetamide;

2-(5-bromobenzofuran-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide;

N-((1S,2R)-3-(azetidin-1-yl)-1-(2,3-dihydrobenzo[b][1,4]dioxin-6-yl)-1-hydroxypropan-2-yl)-2-(5-chlorobenzofuran-2-yl)-2,2-difluoroacetamide;

N-((1R,2R)-3-(azetidin-1-yl)-1-(2,3-dihydrobenzo[b][1,4]dioxin-6-yl)-1-hydroxypropan-2-yl)-2-(5-chlorobenzofuran-2-yl)-2,2-difluoroacetamide;

2-(5-chlorobenzofuran-2-yl)-2,2-difluoro-N-((1S,2R)-1-(7-fluoro-2,3-dihydrobenzo[b][1,4]dioxin-6-yl)-1-hydroxy-3-(pyrrolidin-1-yl)propan-2-yl)acetamide;

2-(5-chlorobenzofuran-2-yl)-2,2-difluoro-N-((1R,2R)-1-(7-fluoro-2,3-dihydrobenzo[b][1,4]dioxin-6-yl)-1-hydroxy-3-(pyrrolidin-1-yl)propan-2-yl)acetamide;

2-(5-chlorobenzofuran-2-yl)-2,2-difluoro-N-((1S,2R)-1-hydroxy-3-(pyrrolidin-1-yl)-1-(quinolin-6-yl)propan-2-yl)acetamide;

2-(5-chlorobenzofuran-2-yl)-2,2-difluoro-N-((1R,2R)-1-hydroxy-3-(pyrrolidin-1-yl)-1-(quinolin-6-yl)propan-2-yl)acetamide;

2-(5-chlorobenzofuran-2-yl)-N-((1S,2R)-1-(2,3-dihydrobenzo[b][1,4]dioxin-6-yl)-3-(3,3-dimethylpyrrolidin-1-yl)-1-hydroxypropan-2-yl)-2,2-difluoroacetamide;

2-(5-chlorobenzofuran-2-yl)-2,2-difluoro-N-((1S,2R)-1-hydroxy-3-(pyrrolidin-1-yl)-1-(4-(trifluoromethoxy)phenyl)propan-2-yl)acetamide;

2-(5-chlorobenzofuran-2-yl)-2,2-difluoro-N-((1R,2R)-1-hydroxy-3-(pyrrolidin-1-yl)-1-(4-(trifluoromethoxy)phenyl)propan-2-yl)acetamide;

2-(5-chlorobenzofuran-2-yl)-N-((1R,2R)-1-(2,3-dihydrobenzo[b][1,4]dioxin-6-yl)-3-((S)-3-fluoropyrrolidin-1-yl)-1-hydroxypropan-2-yl)-2,2-difluoroacetamide;

2-(5-chlorobenzofuran-2-yl)-N-((1R,2R)-1-(2,3-dihydrobenzo[b][1,4]dioxin-6-yl)-1-hydroxy-3-((R)-2-methylpyrrolidin-1-yl)propan-2-yl)-2,2-difluoroacetamide;

2-(5-chlorobenzofuran-2-yl)-N-((1R,2R)-1-(2,3-dihydrobenzo[b][1,4]dioxin-6-yl)-1-hydroxy-3-((S)-2-methylpyrrolidin-1-yl)propan-2-yl)-2,2-difluoroacetamide;

2-(5-chlorobenzofuran-2-yl)-N-((1R,2R)-3-(3,3-difluoropyrrolidin-1-yl)-1-(2,3-dihydrobenzo[b][1,4]dioxin-6-yl)-1-hydroxypropan-2-yl)-2,2-difluoroacetamide;

2-(5-chlorobenzofuran-2-yl)-N-((1R,2R)-1-(2,3-dihydrobenzo[b][1,4]dioxin-6-yl)-3-((R)-3-fluoropyrrolidin-1-yl)-1-hydroxypropan-2-yl)-2,2-difluoroacetamide;

N-((1R,2R)-1-(3-chloro-4-((tetrahydrofuran-3-yl)oxy)phenyl)-1-hydroxy-3-(pyrrolidin-1-yl)propan-2-yl)-2-(5-chlorobenzofuran-2-yl)-2,2-difluoroacetamide;

2-(5-chlorobenzofuran-2-yl)-N-((1R,2R)-1-(2,3-dihydrobenzo[b][1,4]dioxin-6-yl)-1-hydroxy-3-(2-azaspiro[3.3]heptan-2-yl)propan-2-yl)-2,2-difluoroacetamide;

2-(5-chlorobenzofuran-2-yl)-2,2-difluoro-N-((1R,2R)-1-hydroxy-1-(1-methyl-1H-indazol-5-yl)-3-(pyrrolidin-1-yl)propan-2-yl)acetamide;

N-((1R,2R)-1-(2,3-dihydrobenzo[b][1,4]dioxin-6-yl)-1-hydroxy-3-(pyrrolidin-1-yl)propan-2-yl)-2,2-difluoro-2-(5-(pyridin-2-yl)-2,3-dihydro-1H-inden-2-yl)acetamide;

N-((1R,2R)-3-(2-azabicyclo[2.2.1]heptan-2-yl)-1-(2,3-dihydrobenzo[b][1,4]dioxin-6-yl)-1-hydroxypropan-2-yl)-2-(5-chlorobenzofuran-2-yl)-2,2-difluoroacetamide;

N-((1R,2R)-3-(7-azabicyclo[2.2.1]heptan-7-yl)-1-(2,3-dihydrobenzo[b][1,4]dioxin-6-yl)-1-hydroxypropan-2-yl)-2-(5-chlorobenzofuran-2-yl)-2,2-difluoroacetamide;

2-(5-chlorobenzofuran-2-yl)-2,2-difluoro-N-((1R,2R)-1-hydroxy-1-(1-methyl-1H-indazol-6-yl)-3-(pyrrolidin-1-yl)propan-2-yl)acetamide;

2-(5-chlorobenzofuran-2-yl)-2,2-difluoro-N-((1S,2R)-1-hydroxy-1-(1-methyl-1H-indazol-6-yl)-3-(pyrrolidin-1-yl)propan-2-yl)acetamide;

2-(5-chlorobenzofuran-2-yl)-2,2-difluoro-N-((1R,2R)-1-hydroxy-1-(6-methoxypyridin-3-yl)-3-(pyrrolidin-1-yl)propan-2-yl)acetamide;

N-[2-(2H,3H-benzo[e]1,4-dioxan-6-yl)(1R)-2-hydroxy-1-(pyrrolidinylmethyl)ethyl]-2-(5-chlorobenzo[d]furan-2-yl)-2,2-difluoroacetamide;
2-(5-chlorobenzofuran-2-yl)-N-((1R,2R)-1-(2,3-dihydrobenzo[b][1,4]dioxin-6-yl)-1-deutero-1-hydroxy-3-(pyrrolidin-1-yl)propan-2-yl)-2,2-difluoroacetamide;
2-(5-chlorobenzofuran-2-yl)-N-((1S,2R)-1-(2,3-dihydrobenzo[b][1,4]dioxin-6-yl)-1-deutero-1-hydroxy-3-(pyrrolidin-1-yl)propan-2-yl)-2,2-difluoroacetamide;
2-(5-chlorobenzofuran-2-yl)-N-((1R,2R)-1-(3-(difluoromethyl)-4-methoxyphenyl)-1-hydroxy-3-(pyrrolidin-1-yl)propan-2-yl)-2,2-difluoroacetamide;
2-(5-chlorobenzofuran-2-yl)-N-((1S,2R)-1-(3-(difluoromethyl)-4-methoxyphenyl)-1-hydroxy-3-(pyrrolidin-1-yl)propan-2-yl)-2,2-difluoroacetamide;
2-(5-chlorobenzofuran-2-yl)-N-((1R,2R)-1-(2,3-dihydrobenzo[b][1,4]dioxin-6-yl)-1-hydroxy-3-(pyrrolidin-1-yl)propan-2-yl)-2,2-dideutero-acetamide;
N-((1R,2R)-1-(7-bromo-2,3-dihydrobenzo[b][1,4]dioxin-6-yl)-1-hydroxy-3-(pyrrolidin-1-yl)propan-2-yl)-2-(5-chlorobenzofuran-2-yl)-2,2-difluoroacetamide;
2-(5-chlorobenzofuran-2-yl)-N-((1R,2R)-1-(2,3-dihydrobenzo[b][1,4]dioxin-6-yl)-3-(3,3-dimethylazetidin-1-yl)-1-hydroxypropan-2-yl)-2,2-difluoroacetamide;
2-(5-chloro-2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide;
2-(5-chlorobenzofuran-2-yl)-2,2-difluoro-N-((1R,2R)-1-(8-fluoro-2,3-dihydrobenzo[b][1,4]dioxin-6-yl)-1-hydroxy-3-(pyrrolidin-1-yl)propan-2-yl)acetamide;
N-((1R,2R)-1-(8-chloro-2,3-dihydrobenzo[b][1,4]dioxin-6-yl)-1-hydroxy-3-(pyrrolidin-1-yl)propan-2-yl)-2-(5-chlorobenzofuran-2-yl)-2,2-difluoroacetamide;
2-(5-chlorobenzofuran-2-yl)-N-((1R,2R)-1-(2,3-dihydrobenzo[b][1,4]dioxin-6-yl)-1-hydroxy-3-(3-methylazetidin-1-yl)propan-2-yl)-2,2-difluoroacetamide;
2-(5-chlorobenzofuran-2-yl)-N-((1R,2R)-1-(5-chlorobenzofuran-2-yl)-1-hydroxy-3-(pyrrolidin-1-yl)propan-2-yl)-2,2-difluoroacetamide;
2-(5-chlorobenzofuran-2-yl)-N-((1S,2R)-1-(5-chlorobenzofuran-2-yl)-1-hydroxy-3-(pyrrolidin-1-yl)propan-2-yl)-2,2-difluoroacetamide;
2-(2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)-2-oxoacetamide;
2-(5-chlorobenzofuran-2-yl)-N-((1R,2R)-1-(2,3-dihydrobenzo[b][1,4]dioxin-6-yl)-1-hydroxy-3-(pyrrolidin-1-yl)propan-2-yl)-2-oxoacetamide;
(E)-2-(5-chlorobenzofuran-2-yl)-N-((1R,2R)-1-(2,3-dihydrobenzo[b][1,4]dioxin-6-yl)-1-hydroxy-3-(pyrrolidin-1-yl)propan-2-yl)-2-(hydroxyimino)acetamide;
N-((1R,2R)-1-(2,3-dihydrobenzo[b][1,4]dioxin-6-yl)-1-hydroxy-3-(pyrrolidin-1-yl)propan-2-yl)-2-oxo-2-(5-(pyridin-2-yl)-2,3-dihydro-1H-inden-2-yl)acetamide; and
2-(5-chloro-2,3-dihydro-1H-inden-2-yl)-N-((1R,2R)-1-(2,3-dihydrobenzo[b][1,4]dioxin-6-yl)-1-hydroxy-3-(pyrrolidin-1-yl)propan-2-yl)-2-oxoacetamide;
2-(6-chlorobenzo[b]thiophen-2-yl)-N-((1R,2R)-1-(4-chlorophenyl)-1-hydroxy-3-(pyrrolidin-1-yl)propan-2-yl)-2-oxoacetamide;
2-(benzo[b]thiophen-2-yl)-N-((1R,2R)-1-(4-cyclopropoxyphenyl)-1-hydroxy-3-(pyrrolidin-1-yl)propan-2-yl)-2-oxoacetamide;
N-((1R,2R)-1-(4-chlorophenyl)-1-hydroxy-3-(pyrrolidin-1-yl)propan-2-yl)-2-(4'-fluoro-[1,1'-biphenyl]-4-yl)-2-oxoacetamide;
N-((1R,2R)-1-(4-cyclopropoxyphenyl)-1-hydroxy-3-(pyrrolidin-1-yl)propan-2-yl)-2,2-difluoro-4-(naphthalen-2-yl)butanamide;
2-(5-chlorobenzo[b]thiophen-2-yl)-N-((1R,2R)-1-(4-cyclopropoxyphenyl)-1-hydroxy-3-(pyrrolidin-1-yl)propan-2-yl)-2-oxoacetamide;
2-(4-(5-chlorothiophen-2-yl)phenyl)-N-((1R,2R)-1-(4-cyclopropoxyphenyl)-1-hydroxy-3-(pyrrolidin-1-yl)propan-2-yl)-2-oxoacetamide;
2-(4-(5-chlorothiophen-2-yl)phenyl)-N-((1R,2R)-1-(4-cyclopropoxyphenyl)-1-hydroxy-3-(pyrrolidin-1-yl)propan-2-yl)-2,2-difluoroacetamide;
N-((1R,2R)-1-(4-cyclopropoxyphenyl)-1-hydroxy-3-(pyrrolidin-1-yl)propan-2-yl)-2,2-difluoro-2-(4'-fluoro-[1,1'-biphenyl]-4-yl)acetamide;
2-(4-(5-chlorothiophen-2-yl)phenyl)-2,2-difluoro-N-((1R,2R)-1-(8-fluoro-2,3-dihydrobenzo[b][1,4]dioxin-6-yl)-1-hydroxy-3-(pyrrolidin-1-yl)propan-2-yl)acetamide;
2-(6-chlorobenzo[b]thiophen-2-yl)-N-((1R,2R)-1-(4-cyclopropoxyphenyl)-1-hydroxy-3-(pyrrolidin-1-yl)propan-2-yl)-2-oxoacetamide;
N-((1R,2R)-1-(4-cyclopropoxyphenyl)-1-hydroxy-3-(pyrrolidin-1-yl)propan-2-yl)-2-(4-ethynylphenyl)-2-oxoacetamide;
4-(6-chloronaphthalen-2-yl)-N-((1R,2R)-1-(4-cyclopropoxyphenyl)-1-hydroxy-3-(pyrrolidin-1-yl)propan-2-yl)-2,2-difluorobutanamide;
2-(6-chlorobenzo[b]thiophen-2-yl)-N-((1R,2R)-1-(4-(difluoromethoxy)phenyl)-1-hydroxy-3-(pyrrolidin-1-yl)propan-2-yl)-2-oxoacetamide;
N-((1R,2R)-3-(azetidin-1-yl)-1-(4-cyclopropoxyphenyl)-1-hydroxypropan-2-yl)-2-(4'-fluoro-[1,1'-biphenyl]-4-yl)-2-oxoacetamide;
2-(3-chloropyrrolo[1,2-b]pyridazin-6-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide;
2-(7-chloroimidazo[1,2-a]pyridin-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide;
N-((1R,2R)-1-(2,3-dihydrobenzo[b][1,4]dioxin-6-yl)-1-hydroxy-3-(pyrrolidin-1-yl)propan-2-yl)-2,2-difluoro-2-(6-(trifluoromethyl)furo[3,2-c]pyridin-2-yl)acetamide;
2-(6-chlorofuro[3,2-b]pyridin-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide;
N-((1R,2R)-1-(2,3-dihydrobenzo[b][1,4]dioxin-6-yl)-1-hydroxy-3-(pyrrolidin-1-yl)propan-2-yl)-2,2-difluoro-2-(2-(trifluoromethyl)furo[2,3-d]pyrimidin-6-yl)acetamide;
2-(5-chlorothieno[3,2-b]furan-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide;
2-(5-chlorothieno[2,3-d]oxazol-2-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide;
2-(2-chlorofuro[2,3-d]thiazol-5-yl)-N-((1R,2R)-1-(2,3-dihydrobenzo[b][1,4]dioxin-6-yl)-1-hydroxy-3-(pyrrolidin-1-yl)propan-2-yl)-2,2-difluoroacetamide;
3-(3-chlorobenzyl)-N-((1R,2R)-1-(2,3-dihydrobenzo[b][1,4]dioxin-6-yl)-1-hydroxy-3-(pyrrolidin-1-yl)propan-2-yl)-2,2-difluorobut-3-enamide;
2-(5-chlorobenzofuran-2-yl)-N-((1R,2R)-1-(2,3-dihydrobenzo[b][1,4]dioxin-6-yl)-1-hydroxy-3-(2,2,5,5-tetradeuteropyrrolidin-1-yl)propan-2-yl)-2,2-difluoroacetamide;

N-((1R,2R)-1-(3-chloro-4-((4-hydroxytetrahydro-2H-pyran-4-yl)methoxy)phenyl)-1-hydroxy-3-(pyrrolidin-1-yl)propan-2-yl)-2-(5-chlorobenzofuran-2-yl)-2,2-difluoroacetamide;

2-(5-chloro-2,3-dihydro-1H-inden-2-yl)-N-((1R,2R)-1-(3-chloro-4-((4-hydroxytetrahydro-2H-pyran-4-yl)methoxy)phenyl)-1-hydroxy-3-(pyrrolidin-1-yl)propan-2-yl)-2,2-difluoroacetamide;

2-(5-chlorobenzofuran-2-yl)-2,2-difluoro-N-((1R,2R)-1-hydroxy-1-(4-((4-hydroxytetrahydro-2H-pyran-4-yl)methoxy)phenyl)-3-(pyrrolidin-1-yl)propan-2-yl)acetamide;

N-((1R,2R)-1-(4-chloro-3-((4-hydroxytetrahydro-2H-pyran-4-yl)methoxy)phenyl)-1-hydroxy-3-(pyrrolidin-1-yl)propan-2-yl)-2-(5-chlorobenzofuran-2-yl)-2,2-difluoroacetamide;

2-(5-chlorobenzofuran-2-yl)-2,2-difluoro-N-((1R,2R)-1-hydroxy-1-(2-isopropoxypyridin-4-yl)-3-(pyrrolidin-1-yl)propan-2-yl)acetamide;

2-(5-chlorobenzofuran-2-yl)-N-((1R,2R)-1-(6-cyclopropoxypyridin-3-yl)-1-hydroxy-3-(pyrrolidin-1-yl)propan-2-yl)-2-oxoacetamide;

(E)-2-(5-chlorobenzofuran-2-yl)-N-((1R,2R)-1-(6-cyclopropoxypyridin-3-yl)-1-hydroxy-3-(pyrrolidin-1-yl)propan-2-yl)-2-(hydroxyimino)acetamide;

2-(5-chloro-2,3-dihydro-1H-inden-2-yl)-N-((1R,2R)-1-(6-cyclopropoxypyridin-3-yl)-1-hydroxy-3-(pyrrolidin-1-yl)propan-2-yl)-2-oxoacetamide;

(E)-2-(5-chloro-2,3-dihydro-1H-inden-2-yl)-N-((1R,2R)-1-(6-cyclopropoxypyridin-3-yl)-1-hydroxy-3-(pyrrolidin-1-yl)propan-2-yl)-2-(hydroxyimino)acetamide;

2-(5-chlorobenzofuran-2-yl)-2,2-difluoro-N-((1R,2R)-1-hydroxy-1-(6-((4-hydroxytetrahydro-2H-pyran-4-yl)methoxy)pyridin-3-yl)-3-(pyrrolidin-1-yl)propan-2-yl)acetamide;

N-((1R,2R)-1-(6-cyclopropoxypyridin-3-yl)-1-hydroxy-3-(pyrrolidin-1-yl)propan-2-yl)-4-(6-fluoronaphthalen-2-yl)-2-oxobutanamide;

(E)-N-((1R,2R)-1-(6-cyclopropoxypyridin-3-yl)-1-hydroxy-3-(pyrrolidin-1-yl)propan-2-yl)-4-(6-fluoronaphthalen-2-yl)-2-(hydroxyimino)butanamide;

N-((1R,2R)-1-(6-cyclopropoxypyridin-3-yl)-1-hydroxy-3-(pyrrolidin-1-yl)propan-2-yl)-2,2-difluoro-2-(5-(trifluoromethyl)benzofuran-2-yl)acetamide;

(E)-N-((1R,2R)-1-(6-cyclopropoxypyridin-3-yl)-1-hydroxy-3-(pyrrolidin-1-yl)propan-2-yl)-2-(hydroxyimino)-2-(5-(trifluoromethyl)benzofuran-2-yl)acetamide;

N-((1R,2R)-1-(6-cyclopropoxypyridin-3-yl)-1-hydroxy-3-(pyrrolidin-1-yl)propan-2-yl)-2-oxo-2-(5-(trifluoromethyl)benzofuran-2-yl)acetamide;

2-(5-chlorobenzofuran-2-yl)-N-((1R,2R)-1-(2,3-dihydrobenzo[b][1,4]dioxin-6-yl)-1-formamido-3-(pyrrolidin-1-yl)propan-2-yl)-2,2-difluoroacetamide;

(E)-N-((1R,2R)-3-(azetidin-1-yl)-1-(2,3-dihydrobenzo[b][1,4]dioxin-6-yl)-1-hydroxypropan-2-yl)-2-(5-chlorobenzofuran-2-yl)-2-(hydroxyimino)acetamide;

2-(5-chlorobenzofuran-2-yl)-N-((1R,2R)-1-(3,5-dichloro-4-cyclopropoxyphenyl)-1-hydroxy-3-(pyrrolidin-1-yl)propan-2-yl)-2,2-difluoroacetamide;

(E)-N-((1R,2R)-1-(8-fluoro-2,3-dihydrobenzo[b][1,4]dioxin-6-yl)-1-hydroxy-3-(pyrrolidin-1-yl)propan-2-yl)-4-(6-fluoronaphthalen-2-yl)-2-(methoxyimino)butanamide;

N-((1R,2R)-1-(8-fluoro-2,3-dihydrobenzo[b][1,4]dioxin-6-yl)-1-hydroxy-3-(pyrrolidin-1-yl)propan-2-yl)-2-(3-((1-methyl-1H-indazol-6-yl)oxy)phenyl)-2-oxoacetamide;

N-((1R,2R)-1-(8-fluoro-2,3-dihydrobenzo[b][1,4]dioxin-6-yl)-1-hydroxy-3-(pyrrolidin-1-yl)propan-2-yl)-2-(1-(4-fluorophenyl)-1H-imidazol-4-yl)-2-oxoacetamide;

2-(1-(6-chloronaphthalen-2-yl)-1H-pyrazol-3-yl)-N-((1R,2R)-1-(8-fluoro-2,3-dihydrobenzo[b][1,4]dioxin-6-yl)-1-hydroxy-3-(pyrrolidin-1-yl)propan-2-yl)-2-oxoacetamide;

2-(1-(6-chloronaphthalen-2-yl)-1H-pyrazol-4-yl)-N-((1R,2R)-1-(8-fluoro-2,3-dihydrobenzo[b][1,4]dioxin-6-yl)-1-hydroxy-3-(pyrrolidin-1-yl)propan-2-yl)-2-oxoacetamide;

N-((1R,2R)-1-(8-fluoro-2,3-dihydrobenzo[b][1,4]dioxin-6-yl)-1-hydroxy-3-(pyrrolidin-1-yl)propan-2-yl)-2-(1-(4-fluorophenyl)-1H-pyrazol-4-yl)-2-oxoacetamide;

2-(4-(6-chloronaphthalen-2-yl)-1-methyl-1H-imidazol-2-yl)-N-((1R,2R)-1-(8-fluoro-2,3-dihydrobenzo[b][1,4]dioxin-6-yl)-1-hydroxy-3-(pyrrolidin-1-yl)propan-2-yl)-2-oxoacetamide;

N-((1R,2R)-1-(8-fluoro-2,3-dihydrobenzo[b][1,4]dioxin-6-yl)-1-hydroxy-3-(pyrrolidin-1-yl)propan-2-yl)-2-(4-(4-fluorophenyl)-1-methyl-1H-imidazol-2-yl)-2-oxoacetamide;

N-((1R,2R,3S)-1-(2,3-dihydrobenzo[b][1,4]dioxin-6-yl)-1-hydroxy-3-(pyrrolidin-1-yl)butan-2-yl)-2-(4'-fluoro-[1,1'-biphenyl]-4-yl)-2-oxoacetamide;

N-((1R,2R)-1-(3-chloro-4-(difluoromethoxy)phenyl)-1-hydroxy-3-(pyrrolidin-1-yl)propan-2-yl)-2-(6-chlorobenzo[b]thiophen-2-yl)-2-oxoacetamide;

2-(6-chlorobenzo[b]thiophen-2-yl)-N-((1R,2R)-1-(4'-fluoro-[1,1'-biphenyl]-4-yl)-1-hydroxy-3-(pyrrolidin-1-yl)propan-2-yl)-2-oxoacetamide; and N-((1R,2R)-1-(2,3-dihydrobenzo[b][1,4]dioxin-6-yl)-1-hydroxy-3-(2-oxopyrrolidin-1-yl)propan-2-yl)-2-(4'-fluoro-[1,1'-biphenyl]-4-yl)-2-oxoacetamide; and optionally as a tautomer, a single stereoisomer or mixture of stereoisomers thereof and additionally optionally as a pharmaceutically acceptable salt thereof.

14. A pharmaceutical composition, comprising: i) a compound of claim 1 optionally as a tautomer, a single stereoisomer or mixture of stereoisomers thereof and additionally optionally as a pharmaceutically acceptable salt thereof, and ii) a pharmaceutically acceptable excipient or pharmaceutically acceptable carrier.

\* \* \* \* \*